Figure 2:
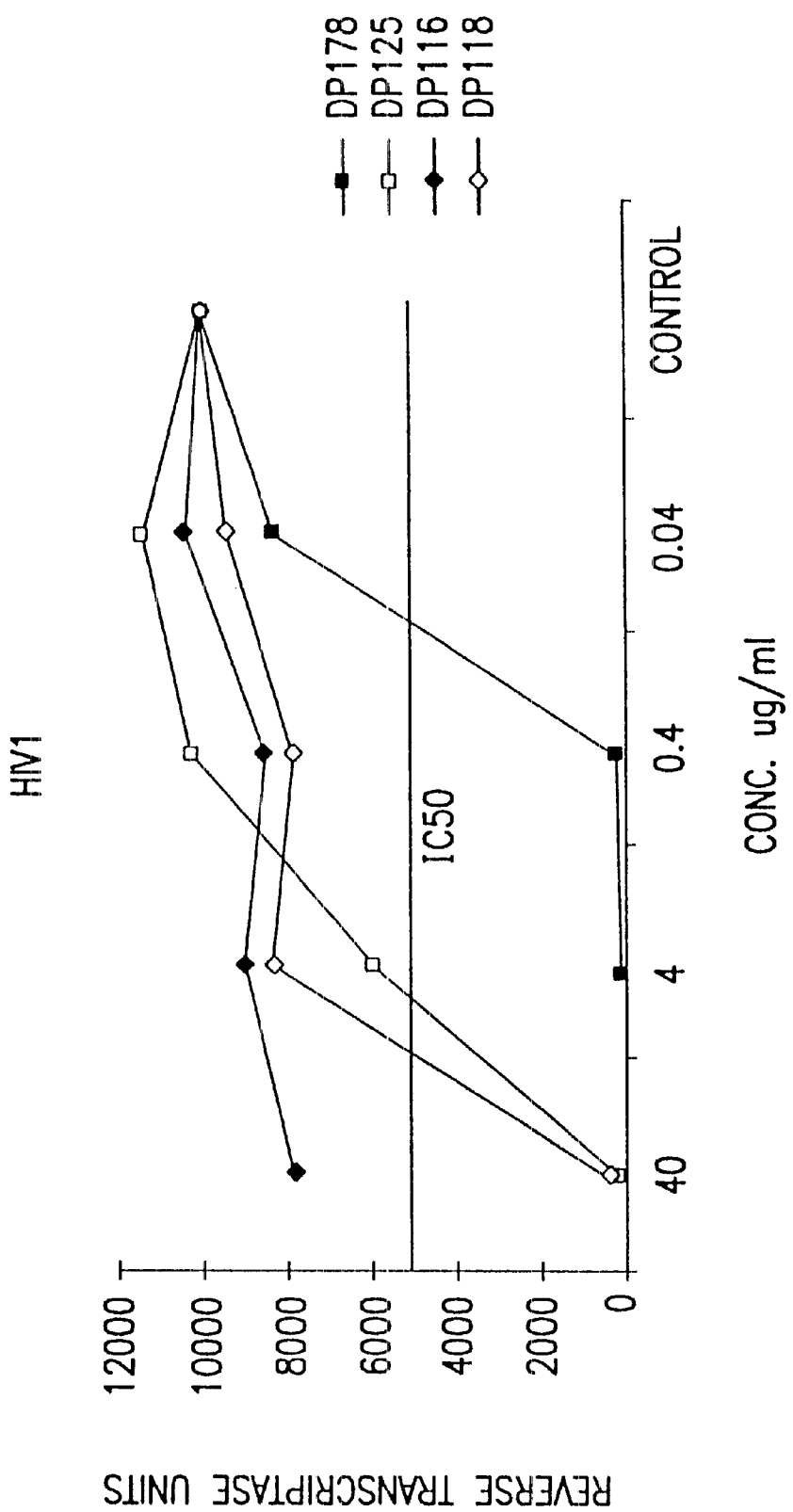

US006479055B1

(12) United States Patent
Bolognesi et al.

(10) Patent No.: US 6,479,055 B1
(45) Date of Patent: *Nov. 12, 2002

(54) METHODS FOR INHIBITION OF MEMBRANE FUSION-ASSOCIATED EVENTS, INCLUDING RESPIRATORY SYNCYTIAL VIRUS TRANSMISSION

(75) Inventors: Dani Paul Bolognesi; Thomas James Matthews; Carl T. Wild, all of Durham; Shawn O'Lin Barney, Cary; Dennis Michael Lambert, Cary; Stephen Robert Petteway, Cary; Alphonse J. Langlois, Durham, all of NC (US)

(73) Assignee: Trimeris, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/470,896

(22) Filed: Jun. 6, 1995

Related U.S. Application Data

(63) Continuation-in-part of application No. 08/360,107, filed on Dec. 20, 1994, now Pat. No. 6,017,536, which is a continuation-in-part of application No. 08/255,208, filed on Jun. 7, 1994, which is a continuation-in-part of application No. 08/073,028, filed on Jun. 7, 1993, now Pat. No. 5,464,933.

(51) Int. Cl.[7] .............................................. A61K 39/145

(52) U.S. Cl. ................................ 424/211.1; 424/186.1; 530/324

(58) Field of Search .... 435/5, 240.2; 424/184.1–189.1, 424/204.1–211.1, 225.1, 227.1, 230.1; 514/1, 2; 530/324, 350, 826

(56) References Cited

U.S. PATENT DOCUMENTS 5,141,867 A * 8/1992 Ivanoff et al. ........... 435/252.3

FOREIGN PATENT DOCUMENTS

| | | |
|---|---|---|
| EP | EP 0323157 | 12/1988 |
| WO | WO 9007119 | 6/1990 |
| WO | WO 9109872 | 7/1991 |
| WO | WO 9222654 | 12/1992 |

OTHER PUBLICATIONS

White "Membrane Fusion". *Science*, vol. 258 (Nov. 6, 1992), pp. 917–924.*

Schödel et al. "Structure of Hepatitis B Virus Core and e–Antigen. A Single Precore Amino Acid Prevents Nucleocapsid Assembly" *Journal of Biological Chemistry*, vol. 268, No. 2 (Jan. 15, 1993), pp. 1332–1337. QP501.J7.*

Cheng et al. "Screening for Nasopharyngeal Carcinoma with an ELISA Using the Epstein–Barr Virus Nuclear Antigen, EBNA 1: a Complementary Test to the IgA/VCA Immunofluorescence Assay" *Journal of Virological Methods*, vol. 42, No. 1(Apr. 1993), pp. 45–51. QR3556.*

Jemmerson "Effects of Conformation, Amino Acid Sequence, and Carrier Coupling on the Immunological Recognition of Peptide and Protein Antigens" in: Zegers et al., *Immunological Recognition of Peptides in Medicine and Biology* (New York, CRC, 1995), pp. 213–225.*

Collins et al. "Nucleotide Sequence of the Gene Encoding the Fusion (F) Glycoprotein of Human Respiratory Syncytial Virus", *Proceedings of the National Academy of Sciences*, vol. 81 (Dec. 1984), pp. 7683–7687.*

Moscona et al. "Fusion Properties of Cells Infected with Human Parainfluenza Virus Type 3: Receptor Requirements for Viral Spread and Virus–Mediated Membrane Fusion", *Journal of Virology*, vol. 66, No. 11 (Nov. 1992), pp. 6280–6287. QR355.J65.*

Wildner et al. "Database screening for molecular mimicry", Immunology Today vol. 18, No. 5(May 1997), pp. 251–252.*

Baum et al. "Also . . . ", Immunology Today, vol. 18, No. 5(May 1997), pp. 252–253.*

Wild et al., "A synthetic peptide inhibitor of human immunodeficiency virus replication: Correlation between solution structure and viral inhibition", Proc. Natl. Acad. Sci. USA vol. 89(1992), pp. 10537–10541.*

Bousse et al., "A single amino acid change enhances the fusion promotion activity of human parainfluenza virus type 1 hemagglutinin–neuraminidase glycoprotein", Virology, vol. 209 (1995), pp. 654–657.*

Geysen et al., "Cognitive features of continuous antigenic determinants", J. Molecular Recognition vol. 1(1988), pp. 33–41. Benet et al., "Pharmacokinetics: The dynamics of drug absorption, distribution, and elimination", in The Pharmacological Basis of Therapeutics, Goodman et al., eds., Pergamon Press, New York, 1990, pp. 1–33.*

Yarchoan et al. "Correlations between the in vitro and in vivo activity of anit–HIV agents: Implications for future drug development", Journal of Enzyme Inhibition, vol. 6, No. 1(1992), pp. 99–111.*

Gait et al. "Progress in anti–HIV structure–based drug design", Trends in Biotechnology, vol. 13, No. 10(Oct. 1995), pp. 430–438.*

Wild et al., 1992, "A synthetic peptide inhibitor of human immunodeficiency virus replication: Correlation between solution structure and viral inhibition", Proc. Natl. Acad. Sci. USA 89:10537–10541.

(List continued on next page.)

*Primary Examiner*—Jeffrey Stucker
(74) *Attorney, Agent, or Firm*—Pennie & Edmonds LLP

(57) ABSTRACT

The present invention relates to peptides which exhibit potent anti-viral activity. In particular, the invention relates to methods of using such peptides as inhibitory of respiratory syncytial virus ("RSV") transmission to uninfected cells. The peptides used in the methods of the invention are homologs of the DP-178 and DP-107 peptides, peptides corresponding to amino acid residues 638 to 673, and to amino acid residues 558 to 595, respectively, of the HIV-$1_{LAI}$ transmembrane protein (TM) gp41.

44 Claims, 83 Drawing Sheets-

OTHER PUBLICATIONS

Mitsuya et al., 1991, "Targeted therapy of human immunodeficiency virus–related disease", FASEB J. 5:2369–2381.

Hammarskjold and Rekosh, 1989, "The molecular biology of the human immunodeficiency virus", Biochem. Biophys. Acta 989:269–280.

Guyader et al., 1987, "Genome organization and transactivation of the human immunodeficiency virus type 2", Nature 326:662–669.

Clavel et al., 1986, "Isolation of a new human retrovirus from west african patients with AIDS", Science 233:343–346.

Maddon et al., 1986, "The T4 gene encodes the AIDS virus receptor and is expressed in the immune system and the brain", Cell 47:333–348.

McDougal et al., 1986, "Binding of HTLV–III/LAV to T4+ T cells by a complex of the 110k viral protein and the T4 molecule", Science 231:382–385.

Barin et al., 1985, "Virus envelope protein of HTLV–III represents major target antigen for antibodies in AIDS patients", Science 228:1094–1096.

Dalgleish et al., 1984, "The CD4 (T4) antigen is an essential component of the receptor for the AIDS retrovirus", Nature 312:763–767.

Gallo et al., 1984, "Frequent detection and isolation of cytopathic retroviruses (HTLV–III) from patients with AIDS and at risk for AIDS", Science 224:500–503.

Klatzmann et al., 1984, "T–lymphocyte T4 molecule behaves as the receptor for human retrovirus LAV", Nature 312:767–768.

Teich et al., 1984, Pathogeneis of lentivirus, in "RNA Tumor Viruses", Weiss et al., eds., CSH–Press, pp. 949–956.

Barre–Sinoussi et al., 1983, "Isolation of a T–lymphotropic retrovirus from a patient at risk for acquired immune deficiency syndrome (AIDS)", Science 220:868–870.

Chen, 1994, "Functional role of the zipper motif region of human immunodeficiency virus type 1 transmembrane protein gp41", J. Virology 68:2002–2010.

Carr and Kim, 1993, "Aspring loaded mechanism for the conformational change of influenza hemagglutinin", Cell 73:823–832.

Songyang et al., 1993, "SH2 domains recognize specific phosphopeptide sequences", Cell 72:767–778.

Lam et al., 1991, "The new type of synthetic peptide library for identifying ligand–binding activity", Nature 354:82–84.

Lupas et al., "Predicting coiled coils from protein sequences", Science 252:1162–1165.

Xu et al., 1991, "Epitope mapping of two immunodominant domains of gp41, the transmembrane protein of human immunodeficiency virus type 1, using ten human monoclonal antibodies", J. Virology 65:4832–4838.

Chambers et al., 1990, "Heptad repeat sequences are located adjacent to hydrophobic regions in several types of virus fusion glycoproteins", J. Gen. Virology 71:3075–3080.

Malim et al., 1988, "Immunodeficiency virus rev trans–activator modulates the expression of the viral regulatory genes", Nature 355:181–183.

Suzuki et al., 1995, "Viral Interleukin 10 (IL–10), the Human Herpes Virus 4 Cellular IL–10 Homologue, Induces Local Anergy to Allogenic and Syngeneic Tumors", J of Experimental Medicine 182:477–486.

Wild et al., 1994, "Propensity for a Leucine Zipper–Like Domain of Human Immunodeficiency Virus Type 1 gp41 to Form Oligomers Correlates With a Role in Virus–Induced Fusion Rather Than Assembly of the Glycoprotein Complex", Proc. Natl. Acad. Sci. USA 91:12676–80.

Bousse et al., 1994, "Regions on the Hemagglutinin–Neuraminidase Proteins of Human Parainfluenza Virus Type–1 and Sendai Virus Important for Membrane Fusion", Virology 204:506–514.

Wang et al., 1993, "Ion Channel Activity of Influenza A Virus M2 Protein: Characterization of the Amantidine Block", J of Virology 67:5585–94.

Lazinski et al., 1993, "Relating Structure to Function in the Hepatitis Delta Virus Antigen", J of Virology 67:2672–80.

White, J.M., 1992, "Membrane Fusion", Science 258:917–924.

Daar et al., 1990, "High concentrations of recombinant soluble CD4 are required to neutralize primary human immunodeficiency virus type 1 isolates", Proc. Natl. Acad. Sci. USA 87:6574–6579.

Erickson et al., 1990, "Design, Activity, and 2.8 Å Crystal Structure of a $C_2$ Symmetric Inhibitor Complexed to HIV–1 Protease", Science 249:527–533.

Smith et al., 1987, "Blocking of HIV–1 Infectivity by a Soluble, Secreted Form of the CD4 Antigen", Science 238:1704–1707.

Collins et al., 1984, "Nucleotide Sequence of the Gene Encoding the Fusion (F) Glycoprotein of Human Respiratory Syncytial Virus", Proc. Natl. Acad. Sci. USA 81:7683–87.

* cited by examiner

| | |
|---|---|
| HIV1LAI (DP-178; SEQ ID:1) | YTSLIHSLIEESQNQQEKNEQELLELDKWASLWNWF |
| HIV1SF2 (DP-185; SEQ ID:3) | YTNTIYNLLEESQNQQEKNEQELLELDKWASLWNWF |
| HIV1RF (SEQ ID:4) | YTGIIYNLLEESQNQQEKNEQELLELDKWANLWNWF |
| HIV1MN (SEQ ID:5) | YTSLIYSLLEKSQTQQEKNEQELLELDKWASLWNWF |
| HIV2ROD (SEQ ID:6) | LEANISKSLEQAQIQQEKNMYELQKLNSWDIFGNWF |
| HIV2NIHZ (SEQ ID:7) | LEANISQSLEQAQIQQEKNMYELQKLNSWDVFTNWL |
| DP180 (SEQ ID:2) | SSESFTLLEQWNNWKLQLAEQWLEQINEKHYLEDIS |
| DP118 (SEQ ID:10) | QQLLDVVKRQQEMLRLTVWGTKNLQARVTAIEKYLKDQ |
| DP125 (SEQ ID:8) | CGGNNLLRAIEAQQHLLQLTVWGIKQLQARILAVERYLKDQ |
| DP116 (SEQ ID:9) | LQARILAVERYLKDQQQ |

FIG.1

Number of Syncytia/well: concentration in μg/ml (micrograms/ml)

| DP178 | 10 | 5 | 1 | 0.2 | 0.1 | 0.05 | 0.025 | 0.0125 | Control |
|---|---|---|---|---|---|---|---|---|---|
| *Syncytia* | | | | | | | | | |
| HIV1LAI | 0 | 0 | 0 | 0 | 0 | 0 | 0 | 0 | 67 |
| HIV1MN | 0 | 0 | 0 | 0 | 0 | ND | ND | ND | 34 |
| HIV1RF | 0 | 0 | 0 | 0 | 0 | ND | ND | ND | 65 |
| HIV1SF2 | 0 | 0 | 0 | 0 | 0 | ND | ND | ND | 58 |

| DP125 | 10 | 5 | 1 | 0.2 | 0.1 | 0.05 | 0.025 | 0.0125 | Control |
|---|---|---|---|---|---|---|---|---|---|
| *Syncytia* | | | | | | | | | |
| HIV1LAI | 0 | 0 | 54 | 69 | 80 | 75 | 79 | 82 | 67 |
| HIV1MN | 0 | 0 | 30 | 36 | ND | ND | ND | ND | 34 |
| HIV1RF | 0 | 0 | 67 | 63 | ND | ND | ND | ND | 65 |
| HIV1SF2 | 0 | 0 | 9 | 66 | ND | ND | ND | ND | 58 |

| DP116 | 10 | 5 | 1 | 0.2 | 0.1 | 0.05 | 0.025 | 0.0125 | Control |
|---|---|---|---|---|---|---|---|---|---|
| *Syncytia* | | | | | | | | | |
| HIV1LAI | 75 | ND | ND | ND | ND | ND | ND | ND | 67 |
| HIV1MN | 35 | ND | ND | ND | ND | ND | ND | ND | 34 |
| HIV1RF | 81 | ND | ND | ND | ND | ND | ND | ND | 65 |
| HIV1SF2 | 81 | ND | ND | ND | ND | ND | ND | ND | 58 |

FIG.4A

| DP180 | 40 | 20 | 10 | 5 | 2.5 | 1.25 | 0.625 | 0.3125 | Control |
|---|---|---|---|---|---|---|---|---|---|
| *Syncytia* | | | | | | | | | |
| HIV1LAI | 50 | >45 | >45 | >45 | >45 | >45 | >45 | >45 | 58 |
| DP185 | 40 | 20 | 10 | 5 | 2.5 | 1.25 | 0.625 | 0.3125 | Control |
| *Syncytia* | | | | | | | | | |
| HIV1LAI | 0 | 0 | 0 | 0 | 0 | 0 | 0 | ND | 60 |

FIG.4B

HIV1

Number of Syncytia/well: concentration in ng/ml (nanograms/ml)

| DP178 | 20 | 10 | 5 | 2.5 | 1.25 | 0.625 | 0.3125 | Control |
|---|---|---|---|---|---|---|---|---|
| Syncytia HIV1 | 0 | 0 | 0 | 0 | 0 | 14 | 20 | 48 |
| DP116 | 20 | 10 | 5 | 2.5 | 1.25 | 0.625 | 0.3125 | Control |
| Syncytia HIV1 | ND | 48 | ND | ND | ND | ND | ND | ND |

HIV2

Number of Syncytia/well: concentration in µg/ml (micrograms/ml)

| DP178 | 20 | 10 | 5 | 2.5 | 1.25 | 0.625 | 0.3125 | Control |
|---|---|---|---|---|---|---|---|---|
| Syncytia HIV2 | 50 | 54 | 55 | 57 | 63 | 77 | 78 | 76 |
| DP116 | 20 | 10 | 5 | 2.5 | 1.25 | 0.625 | 0.3125 | Control |
| Syncytia HIV2 | ND | 58 | ND | ND | ND | ND | ND | ND |

FIG.5

| Sequence | A | D | A | D | A | D | A | D | A | D | A | Motifs |
|---|---|---|---|---|---|---|---|---|---|---|---|---|
| GCN4 (gcn4 yeast) | M | K Q L | E D K V | E E L L | S K N Y | H L E N E | V A R L | K K L | | | | [LMNV] {CFGIMPTW} |
| C-FOS (fos_human) | T | D T L | Q A E T | D Q L | E D E K S | A L Q T E | I A N L | L K E | | | | [IKLT] {CFGHIMPRVWY} |
| C-JUN (tap1_human) | I | A R L | E E K V | K T L | L K A Q N | S E L A S T | A N M L | R E Q | | | | [AILNV] {CDFGHILPVWY} |
| C-MYC (myo_human) | E | Q K L | I S E E | D L L | E K R R R | E Q L K H K | L E Q L | R N S | | | | [ELR] {ACFGMPVWY} |
| FLU LOOP 36 | I | E K T | N E K F | H Q I | I E K E F | S E V E G R I | I Q D L | L E K Y | A | D | D A | [FILTV] {ACFLMPTVW} |

FIG.12

FIG. 13

| Sequence | Positions | | | | | | | | | | | | | Motifs |
|---|---|---|---|---|---|---|---|---|---|---|---|---|---|---|
| | A | D | A | D | A | D | A | D | A | D | A | D | A | |
| DP-107 (env_hv1bru)L1=D | N | N | L | L | R | A | I | E | A | Q | Q | H | L | [ILQT] {CFIM

FIG. 14

| Sequence | Positions | | | | | | | | | | | | | | | | | | | | | | | | | | | | | | | | | | Parent Motif | Hybrid Motif |
|---|---|---|---|---|---|---|---|---|---|---|---|---|---|---|---|---|---|---|---|---|---|---|---|---|---|---|---|---|---|---|---|---|---|---|---|---|
| | A | D | A | D | A | D | A | D | A | D | | | | | | | | | | | | | | | | | | | | | | | | | | |
| GCN4 (gcn4 yeast) | M K | Q L E D K | V E | E I L L | S K N Y | H L E N E | V A R L | K K L | | | | | | | | | | | | | | | | | | | | | | | | | | | [LMV] {CFGIMPTW} | |
| DP-178 (env_hv1bru)Y1=A | Y T | S L I | H S L | I E E S | Q N Q | Q E K N | E Q E L | L E L D K | | | | | | | | | | | | | | | | | | | | | | | | | | | [EKLQY] {ACFGMPRVWY} | [EKLMNQVY] {C

| Sequence | Positions | | | | | | | | | | | Parent Motif | Hybrid Motif |
|---|---|---|---|---|---|---|---|---|---|---|---|---|---|
| | A | D | A | D | A | D | A | D | A | D | A | | |
| DP-107 (env_hv1bru)L1=0 | I N N L L R A I E A Q Q H L L L Q L T V W G I K Q L Q A R I L A V E R Y L K D Q | | | | | | | | | | | [ILQTV] {CDFIMPST} | |
| DP-107 (env_hv1bru)L2=0 | N N L L R A I E A Q Q H L L L Q L T V W G I K Q L Q A R I L A V E R Y L K D Q | | | | | | | | | | | [EKLNQV] {CFKMPS} | |
| DP-178 (env_hv1bru)Y1=A | Y T S L I H S L I E E S Q N Q Q E K N E Q E L L E L D K W A S L W N W F | | | | | | | | | | | [EFKLQWY] {CFGMPRVY} | |
| DP-178 (env_hv1bru)Y1=0 | Y T S L I H S L I E E S Q N Q Q E K N E Q E L L E L D K W A S L W N W F | | | | | | | | | | | [EFILNQSWY] {CFGMPRVY} | [EFIKLNQSTVWY] {CFMP} |
| FLU LOOP 36 | I E K I T N E K F H Q I E K E F S E V E G R I Q D L E K Y | | | | | | | | | | | [FILTV] {ACFLMPTVW} | |

FIG.16

| Sequence | Positions | | | | | | | | | | | | | | | | | | | Parent Motif | Hybrid Motif |
|---|---|---|---|---|---|---|---|---|---|---|---|---|---|---|---|---|---|---|---|---|---|
| | A | D | A | D | A | D | A | D | A | D | A | D | A | D | A | D | A | D | | |
| GCN4 (gcn4 yeast) | M | K | Q | L | E | D | K | V | E | E | L | L | S | K | N | Y | H | L | E | N | E | V | A | R | L | K | K | L | | | |
| DP-107 (env_hv1bru)L1=D | N | N | L | L | R | A | I | E | A | Q | Q | H | L | L | Q | L | T | V | W | G | I | K | Q | L | Q | A | R | I | L | A | V | E | R | Y | L | K | D | Q | [LMAV] {

| Sequence | Positions | | | | | | | | Parent Motif | Hybrid Motif |
|---|---|---|---|---|---|---|---|---|---|---|
| | A | D | A | D | A | D | A | D | | |
| GCN4 (gcn4_yeast) | M K | Q L E D K V | E E L L | S K N Y | H L E N E V | A R L K K L | | | [LMNV] {CFGIMPTW} | |
| DP-107 (env_hv1bru)L1=D | N N | L L R A I E | A Q Q H | L L Q L T | V W G I K Q | L Q A R I L | A V E R Y L | K D Q | [ILQTV] {CDFIMPST} | |
| DP-107 (env_hv1bru)L2=D | N N | L L R A I E | A Q Q H | L L Q L T | V W G I K Q | L Q A R I L | A V E R Y L | K D Q | [EKLNQV] {CFKMPS} | |
| DP-178 (env_hv1bru)Y1=A | Y T | S L I H S L | I E E S | Q N Q Q E | K N E Q E L | L E L D K W A S L W N W F | | | [EFKLQWY] {CFGMPRVY} | |
| DP-178 (env_hv1bru)Y1=D | | Y T S L I H S L | I E E S | Q N Q Q E | K N E Q E L | L E L D K W A S L W N W F | | | [EFILNQSWY] {CFGMPRVY} | |
|

```
P-[LIV]-{P}(6)-[LIV]
P-{P}(1)-[LIV]-{P}(6)-[LIV]-{P}(6)-[LIV]
P-{P}(2)-[LIV]-{P}(6)-[LIV]-{P}(6)-[LIV]
P-{P}(3)-[LIV]-{P}(6)-[LIV]-{P}(6)-[LIV]
P-{P}(4)-[LIV]-{P}(6)-[LIV]-{P}(6)-[LIV]
P-{P}(5)-[LIV]-{P}(6)-[LIV]-{P}(6)-[LIV]
P-{P}(6)-[LIV]-{P}(6)-[LIV]-{P}(6)-[LIV]
P-{P}(7)-[LIV]-{P}(6)-[LIV]-{P}(6)-[LIV]
P-{P}(8)-[LIV]-{P}(6)-[LIV]-{P}(6)-[LIV]
P-{P}(9)-[LIV]-{P}(6)-[LIV]-{P}(6)-[LIV]
P-{P}(10)-[LIV]-{P}(6)-[LIV]-{P}(6)-[LIV]
P-X(1,12)-[LIV]-{P}(6)-[LIV]-{P}(6)-[LIV]
P-X(13,23)-[LIV]-{P}(6)-[LIV]-{P}(6)-[LIV]
```

FIG. 19

```
Fusion          ▼ALLMOTI5▼
Peptide                                        ▲107x178x4▲
▼.......ELGFLG   A AGSTMGARSM TLTVQARQ   ▲LL SGIVQQQ   DP107-NNL

LRAIEAQQHL LQLTVWGIKQ LQARILAVER YLKDQ-DP107   QLLG▲▼   I WGC

▲107x178x4▲
              ▼ALLMOTI5▼                      *LVS Coiled-Coil*
SGKLICT TAVP  ▼WNASWS NKSLEQIWNN MTWM   *E  ▲WDREINN  DP178-

YTSLIHSL IEESQNQQEK NEQELLELDK*   WASLWNWF-DP178   NI

♦Transmembrane Region♦
TNWLWYIK▲   ♦IF IMIVGGLVGL RIVFAVLSIV   NRVRQGYS▼   PL

✦P23LZIPC✦
SFQTHLPTPR GPDR  ✦PEGIEE EGGERDRDRS IRLVNGSLAL IWDDLRSL✦   CL

▼ALLMOTI5▼           ▲107x178x4▲
F  ▼SYHRLRDLL LIVTRIVELL GRRGW  ▲EALKY WWNLLQYWSQ

ELKNSAVSLL NAT▲   AIAVAEG TDRVIEVVQG A▼   CRAIRHIPR

RIRQGLERIL L
```

FIG. 20

```
        Fusion          ▾ALLMOTI5▾
        Peptide                        ♦107x178x4♦
▾.......FLGFL      LGVGSAIAS GVA    ♦YSKVLHL EGEVNKIKSA
```

```
                                                              ♦P1&12LZIPC♦
LLSTNKAVVS LSNGVSVLTS KVLDLKNYID KQ♦▾ LL     ♦PIVNKQ
```

```
     ♦107x178x4♦
SC ♦SISNIETV I♦  EFQQKNNRLLEITREFSVNAG♦ VTTPVSTMLTNSELLSL
```

```
       ♦P1&12LZIPC♦
                ▾ALLMOTI5▾
INDM  ♦PI  ▾TNDQ KKLMSNNVQI V♦  RQQSYSI♦  MS IIKEEVLAYV
```

```
VQ▾   LPLYGVID TPCWKLHTSP LCTTNTKEGS NICLTRTDRG WYCDNAGSVS
```

```
FFPQAETCKV QSNRVFCDTM NSLTLPSEIN LCNVDIFNPK
```

```
YDCKIMTSKT DVSSSVITSL GAIVSCYGKT KCTASNKNRG
```

```
IIKTFSNGCDYVSNKGMDTV SVGNTLYYVN KQEGKSLYVK G
```

```
           ♦P7, 12, & 23LZIPC♦
                   ♦107x178x4♦                    ▾ALLMOTI5▾
EPHNFYDPLVF ♦PSDE ♦EDASISQVNEKINQSLAF ▾I♦ RKSDELL♦
```

```
              ♦Transmembrane Region♦
IINVNA♦  GK STTN  ♦IMITTI IIVIIVILLS LIAVGLLLY▾  C♦
```

```
KARSTPVTLS KDQLSGINNI AFSN
```

FIG. 21

Fusion
Peptide    ▼ALLMOTI5▼    ♦107x178x4♦
.......FLGFLG    ▼AAGTA MGAAA    ♦TALTVQSQLLLAGILQQQKNLLAAV ♦107x178x4♦
EAQ♦    QQM    ♦LKLTIWGVKNLNARVTALEKYLEDQARLN♦    AWG▼    CA

*LVS Coiled-Coil*
                 ▼ALLMOTI5▼    ♦107x178x4♦
WKQVCHTTVP WQWNNRTPDW    ▼NNMT    *WLE    ♦WERQISYLEGNIT ♦107x178x4♦
TQLEEARAQEEKNLD♦    AYQKLSS*    WSDFWSW▼    FDF    ♦SKWLN    ♦ILK ♦Transmembrane Region♦
IGFLDVLGIIGLRLLYTV♦    YS♦    CIARVRQGYS PLSPQIHIHP WKGQPDNAEG

PGEGGDKRKN SSEPWQKESG TAEWKSNWCK RLTNWCSISS IWLYNS

▼ALLMOTI5▼
▼CLTL LVHLRSAFQY IQYGLGELKA AAQEAVVALA RLAQNAGYQIWL▼

ACRSAYRA IINSPRRVRQ GLEGILN

FIG. 22

Fusion　　　　　　　　　　　　　　　　　　　　　　　　　　　★107x178x4★
Peptide　♥ALLMOTI5♥　　　　　　　　　　　　　　　　　*LVS Coiled-Coil*
......EAG　　♥VVL　AGVALGVATA AQITAGIALIIQ ★*SNLNAQAIQ

SLRTSLEQSNKAIEEIREATQETVIA* YQGVQDY★　VNNEL♥　VP

♥ALLMOTI5♥
　　　　　　　　　　　　　　　　　　　　　　　　　★107x178x4★
　　　　　　　　　　　　　　　　　　　　　　　　+P6 & 12LZIPC+
AMQHMSCELVGQRLGLRLLRYYTELLSIFGPSLRD　+PISA ★♥EISIQALIYAL

GGEIIIKILEKLGYSGSD★　MIAILESRGIKTKI♥　THVDLPGKF IILSISY

+P1 & 12LZIPC+
+PTLSEVKGVIVHRLEAV+ SYNIGSQEWYTTVPRYIATNGYLISNFDESSCVFVS

ESAICSQNSL YPMSPLLQQC IRGDTSSCAR TLVSGTMGNK FILSKGNIVA

NCASILCKCY STSTIINQSP DKLLTFIASD TCPLVEIDGA TIQVGGRQYP

*LVS Coiled-Coil*
　　　　　　　　　♥ALLMOTI5♥
　　　　　　　+P12 & 23LZIPC+
DMVYEGKVAL G　+PAISLD　♥RL*DVGTNLGNALKKLDDAKVLI+

+Transmembrane Region+
DSS+　NQILETVRRS♥*　SFN　　+FGSLLSVPILSCTAL ALLLLIYCC+

K RRYQQTLKQH TKVDPAFKPD LTGTSKSYVR SL

FIG. 23

Fusion ▼ALLMOTI5▼
Peptide                                                   ★107x178x4★
▼........FIGAI IGSVALGVA TAAQITAASA LIQANQNAAN ★ILRLKESITA

TIEAVHEVTDGLSQLAVA★ VG KM▼ QQFVNDQFNNTAQELDCIKITQQV

▼ALLMOTI5▼
GVELNLYLTELTTV FGPQITSPAL ▼TQLTIQALYNAGGNMDYLLTKLGVG

♣P1 & 12LZIPC♣
NNQLSSLIGSGLIT GN▼ ♣PILYDSQT QLLGIQVTLP SVGNLNNMRATYLET

LSVST TKGFASALVP KVVTQVGSVI EELDTSYCIE TDLDLYCTRI VTFPMSPGIY

SCLNGNTSAC MYSKTEGALT TPYMTLKGSV IANCKMTTCR CADPPGIISQ

▼ALLMOTI5▼
★107x178x4★
NYGEAVSLID RHSCN ★▼VLSLD GITLRLSGEF DATYQKNISI LDSQVIVTG

*LVS Coiled-Coil*                                      ◆Trans-
*N LDISTELGNV NNSISNALDK LEESNSKLDK VNVKLTSTSA ◆LIT* YIA membrane Fusion ♥ALLMOTI5♥
Peptide ♠107x178x4♠ *LVS Coiled-Coil*
.......FFGGV ♠IG ♥TIALG *VATSAQITAAVALVEAKQARSDIEKLKE

AIRDTNKAVQSVQSSIGNLIVAIKSVQ* DYVNKE♥♠ IVPSIARLGCEAAG

♥ALLMOTI5♥
♠107x178x4♠
LQLGIALTQH ♠♥YSELTNIFGDNIGSLQEKGIKLQGIASLYRTNITE♥♠

♣P5 & 12LZIPC♣
IFTTSTVDKYDIYDLLFTESIKVRVIDVDLNDYSITLQVRL ♣PLLTRLLNTQIYR

VDSISYNI♣ QNREWYI♣ PLPSHIMTKGAFLGGADVKECIEAFSSYIC

PSDPGFVLNHEMESCLSGNISQCPRTVVKSDIVPRYAFVNGGVVANCITT

TCTCNGIGNRINQPPDQGVKIITHKECNTIGINGMLFNTNKEGTLAFYTP

♥ALLMOTI5♥
♠107x178x4♠
♣P6 & 23LZIPC♣
NDITLNNSVALD ♣PIDI ♠SIELN ♥KAKSDLEESKEWI♣ RRSNQKL♣

♦Transmembrane Region♦
DSIGNWHQSSTT ♦IIIV♠ LIM IIILFIINVT II♦ IIAVKYY♥ R

IQKRNRVDQN DKPYVLTNK

FIG. 25

Fusion
Peptide
.......GLFGAI AGFIENGWEGMIDGWYGFRHQNSEGTG

♠107x178x4♠
♥ALLMOTI5♥
*LVS Coiled-Coil*
*Q  ♥AADLKST  ♠QAAIDQINGKLNRVIEKTNEKFHQIEKEFSEVEGRIQ

DLEKYVEDTKIDL* WSYNAELLVALENQHTI♠ DLT♥ DSEMNKLFEKTR

RQLRENAEEMGNGCFKIYHKCDNACIESIRNGTYDHDVYRDEALNNRFQIKG

VELKSGYKDWILWISFAISCFLLCVVLLGFIMWACQRGNIRCNICI

FIG. 26

FIG. 27A

| | Sequence |
|---|---|
| RSV F2 | YTSVITIELSNIKENKCNGAKVKLIKQELDKYKNAVTELQLLMQST |
| T-142 | YTSVITIELSNIKENKCNGAKVKLIKQELDKYK |
| T-143 | TSVITIELSNIKENKCNGAKVKLIKQELDKYKN |
| T-144 | SVITIELSNIKENKCNGAKVKLIKQELDKYKNA |
| T-145 | VITIELSNIKENKCNGAKVKLIKQELDKYKNAV |
| T-146 | ITIELSNIKENKCNGAKVKLIKQELDKYKNAVT |
| T-147 | TIELSNIKENKCNGAKVKLIKQELDKYKNAVTE |
| T-148 | IELSNIKENKCNGAKVKLIKQELDKYKNAVTEL |
| T-149 | ELSNIKENKCNGAKVKLIKQELDKYKNAVTELQ |
| T-150 | LSNIKENKCNGAKVKLIKQELDKYKNAVTELQL |
| T-151 | SNIKENKCNGAKVKLIKQELDKYKNAVTELQLL |
| T-152 | NIKENKCNGAKVKLIKQELDKYKNAVTELQLLM |
| T-153 | IKENKCNGAKVKLIKQELDKYKNAVTELQLLMQ |
| T-154 | KENKCNGAKVKLIKQELDKYKNAVTELQLLMQS |
| T-155 | ENKCNGAKVKLIKQELDKYKNAVTELQLLMQST |

| RSV F2 | AV | FUSION ARRAY PURIFIED IC50 (XTT) (µg/ml) | CD |
|---|---|---|---|
| T-142 | ++ | 39 | ++ |
| T-143 | ++ | 31 | +++ |
| T-144 | + | 114 | ++ |
| T-145 | ++ | 40 | + |
| T-146 | - | 281 | - |
| T-147 | - | 204 | - |
| T-148 | - | 354 | - |
| T-149 | - | 336 | - |
| T-150 | - | 342 | + |
| T-151 | +/- | 116 | + |
| T-152 | +/- | 117 | ++ |
| T-153 | - | 280 | + |
| T-154 | +/- | 118 | ++ |
| T-155 | - | 253 | + |

FIG.27B

| RSV PEPTIDE# | | AVG. IC50 (XTT) UG/ML |
|---|---|---|
| T-22 | IELSNIKENKCNGTDAKVKLIKQELDKYKNAVTELQLLMQST | >500 |
| T-23 | IELSNIKENKCNGTDAKVKLIKQELDKY | >500 |
| T-24 | ENKCNGTDAKVKLIKQELDKYKNAVTEL | >500 |
| T-25 | DAKVKLIKQELDKYKNAVTELQLLMQST | >500 |
| T-26 | CNGTDAKVKLIKQELDKYKNAVTELQLL | >500 |
| T-27 | SNIKENKCNGTDAKVKLIKQELDKYKNAVTELQLL | >500 |
| T-68 | VSKGYSALRTGWYTSVITIELSNIKEN | 165 |
| T-334 | AFIRKSDELLHNV | 26 |
| T-371 | YTSVITIELSNIKENKUNGTDAKVKLIKQELDKYK | >500 |
| T-372 | TSVITIELSNIKENKUNGTDAKVKLIKQELDKYKN | NOT TESTED |
| T-373 | SVITIELSNIKENKUNGTDAKVKLIKQELDKYKNA | >500 |
| T-374 | SNIKENKUNGTDAKVKLIKQELDKYKNAVTELQLL | >500 |
| T-375 | KENKUNGTDAKVKLIKQELDKYKNAVTELQLLMQS | >500 |
| T-575 | AVSKGYLSALRTGWYTSVITIELSNIKENKUNGTDA | >100 |

FIG.27C

| RSV DP-107-LIKE REGION (F1) | | | | | | | | | | | | | | | | | | | | | |
|---|---|---|---|---|---|---|---|---|---|---|---|---|---|---|---|---|---|---|---|---|---|
| RSV | | | | | | | | | | | | | | | | | | | | | |
| F1-107 | A | S | G | V | A | V | S | K | V | L | H | L

| RSV | AV | FUSION ASSAY PURIFIED IC50 XTT (µg/ml) | CD |
|---|---|---|---|
| F-107 | − | 204 | − |
| T-120 | − | 354 | − |
| T-121 | − | 347 | − |
| T-122 | +/− | 126 | − |
| T-123 | + | 95 | − |
| T-124 | + | 84 | − |
| T-125 | + | 89 | − |
| T-126 | + | 89 | − |
| T-127 | − | 206 | − |
| T-128 | − | 343 | − |
| T-129 | +/− | 177 | − |
| T-130 | − | 118 | − |
| T-131 | +/− | 272 | − |
| T-132 | +/− | 307 | − |
| T-133 | + | 187 | − |
| T-134 | − | 60 | − |
| T-135 | + | 194 | − |
| T-136 | ++ | 99 | − |
| T-137 | + | 38 | − |
| T-138 | − | 86 | +/− |
| T-139 | − | 160 | +/− |
| T-140 | | 204 | +/− |

FIG.27E

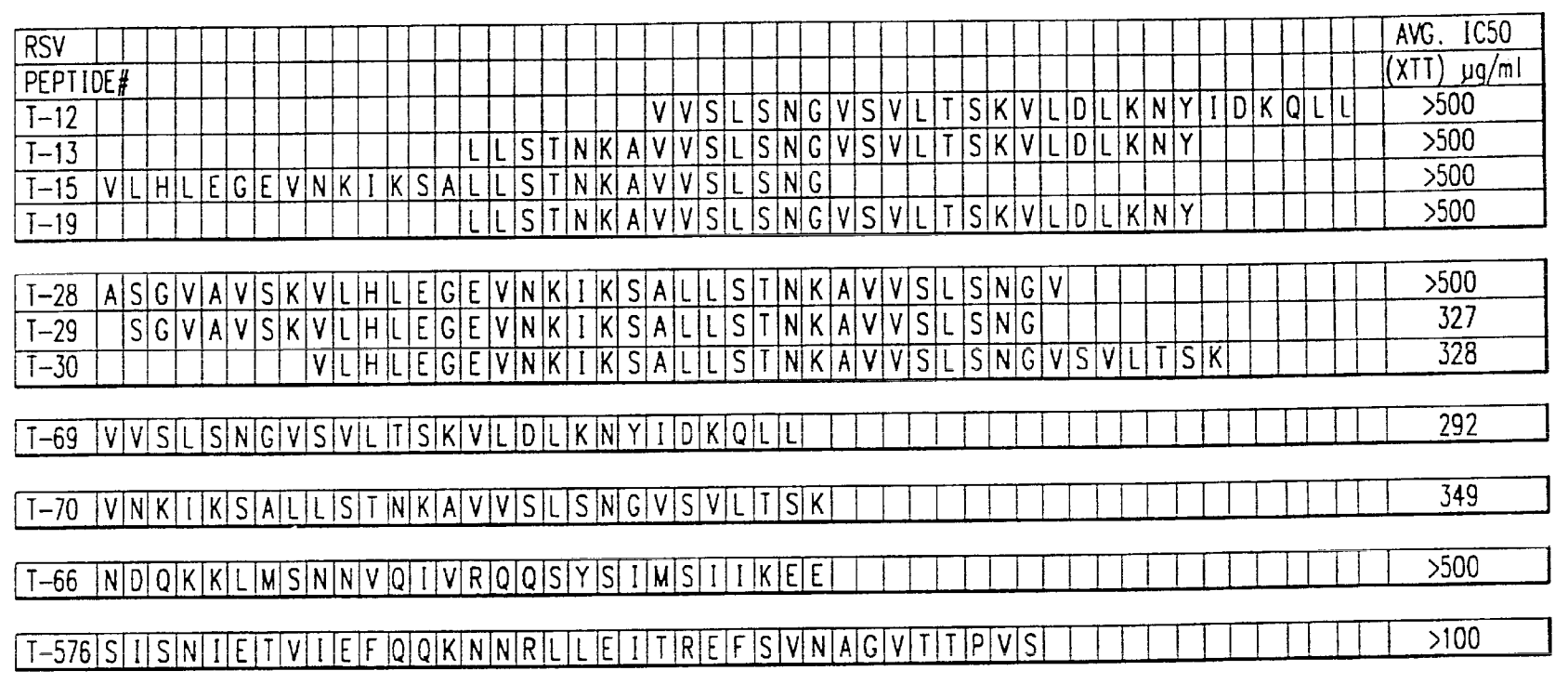

| RSV PEPTIDE # | | | | | | | | | | | | | | | | | | | | | | | | | | | | | | | | | | | AVG. IC50 (XTT) µg/ml |
|---|---|---|---|---|---|---|---|---|---|---|---|---|---|---|---|---|---|---|---|---|---|---|---|---|---|---|---|---|---|---|---|---|---|---|---|
| T-12 | | | | | | | | | | | | | V | V | S | L | S | N

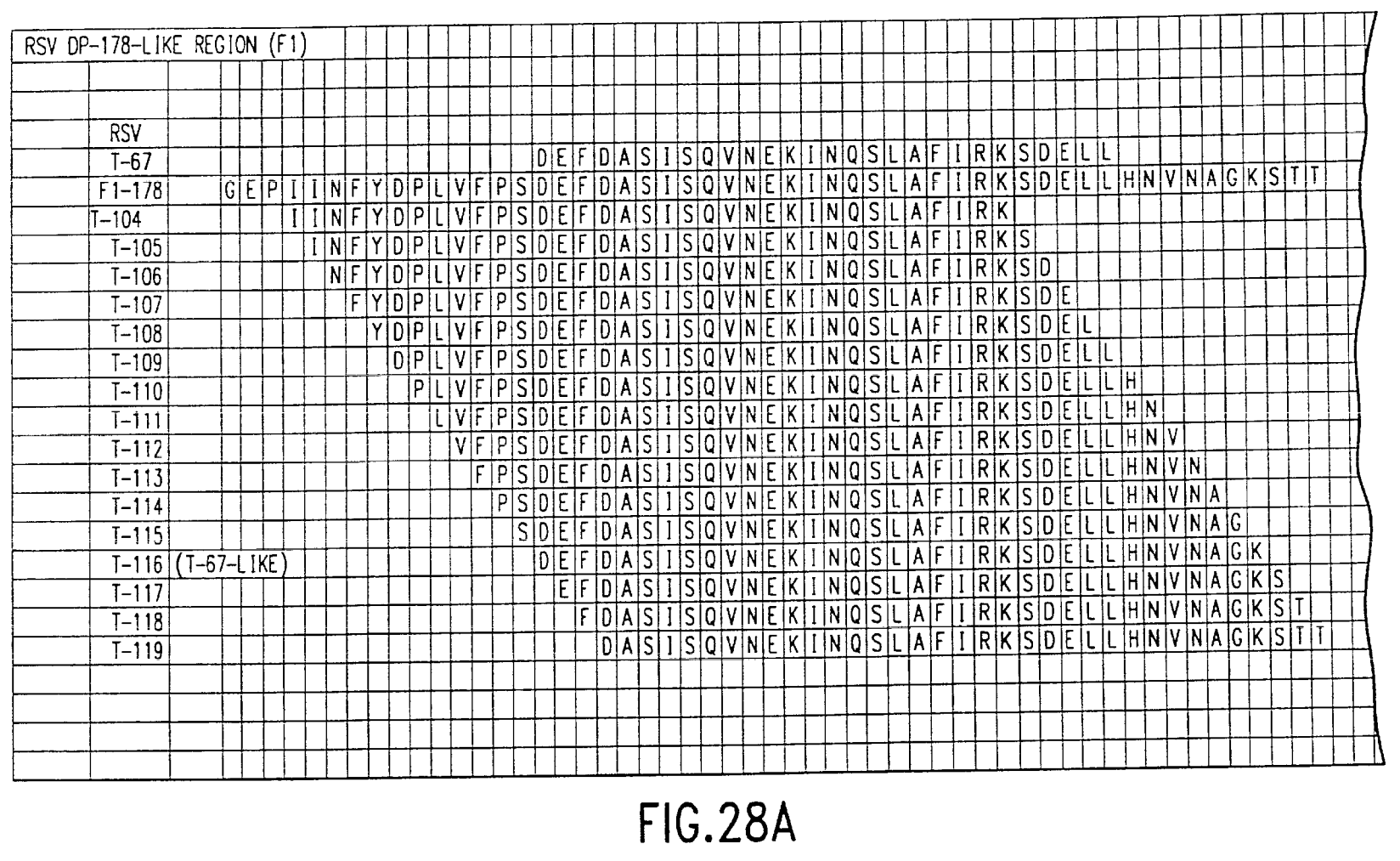

| RSV DP-178-LIKE REGION (F1) | | | | | | | | | | | | |
|---|---|---|---|---|---|---|---|---|---|---|---|---|
| RSV | | | | | | | | | | | | |
| T-67 | G E P | I I N | F Y D | P L V | F P S | D E F | D A S | I

| | | | |
|---|---|---|---|
| | | FUSION ASSAY | |
| | | PURIFIED | |
| | | IC50 | |
| RSV | AV | (μg/ml) (XTT) | CD |
| T-67 | ++ | 37 | +/- |
| F1-178 | | | |
| T-104 | + | 95 | |
| T-105 | + | 86 | |
| T-106 | - | 186 | |
| T-107 | ++ | 20 | |
| T-108 | +++ | 6 | |
| T-109 | +++ | 8 | |
| T-110 | ++ | 30 | |
| T-111 | +++ | 9 | |
| T-112 | +++ | 8 | +/- |
| T-113 | +++ | 6 | +/- |
| T-114 | +++ | 5 | +/- |
| T-115 | +++ | 6 | +/- |
| T-116 | +++ | 9 | +/- |
| T-117 | +++ | 14 | +/- |
| T-118 | +++ | 5 | +/- |
| T-119 | +++ | 6 | +/- |
| | | | |
| | | | |
| | | | |
| | | | |

FIG.28B

FIG. 28C

RSV: PIIINFYDPLVFPSDEFDASIISQVNEKIINQSLAFIRKSDELLHNV

| PEPTIDE# | Sequence | AVG. IC50 (XTT) ug/ml |
|---|---|---|
| T-71 | RMKQLEEDKVEELLSKLAFIRKSDELLHNV | 138 |
| T-384 | | NOT TESTED |
| T-613 | DELLHNVNAGKST | >100 |
| T-614 | KSDELLHNVNAGKST | >100 |
| T-615 | IRKSDELLHNVNAGKST | >100 |
| T-616 | AFIRKSDELLHNVNAGKST | >100 |
| T-617 | FDASIISQVNEKIINQSLAFII | NOT TESTED |
| T-662 | SLAFIRKSDELLHNVNAGKST | >100 |
| T-663 | FDASIISQVNEKIINQSLAFIIRK | NOT TESTED |
| T-665 | FDASIISQVNEKIINQSLAFIIRKSDELLHNVNAGK | 7 |
| T-666 | FDASIISQVNEKIINQSLAFIIRKSDELLHNVNA | 4 |
| T-667 | FDASIISQVNEKIINQSLAFIIRKSDELLHNV | 4 |
| T-668 | FDASIISQVNEKIINQSLAFIIRKSDELLH | 5 |
| T-669 | FDASIISQVNEKIINQSLAFIIRKSDELL | 80 |
| T-670 | FDASIISQVNEKIINQSLAFIIRKSD | >100 |
| T-671 | ASIISQVNEKIINQSLAFIIRKSDELLHNVNAGKST | 8 |
| T-672 | IISQVNEKIINQSLAFIIRKSDELLHNVNAGKST | 6 |
| T-673 | QVNEKIINQSLAFIIRKSDELLHNVNAGKST | 14 |
| T-674 | NEKIINQSLAFIIRKSDELLHNVNAGKST | >100 |
| T-675 | KIINQSLAFIIRKSDELLHNVNAGKST | >100 |
| T-676 | NQSLAFIIRKSDELLHNVNAGKST | >100 |
| T-730 | FDASIISQVNEKIINQSLAFIIRKSDELLHNVNAGKST | NOT TESTED |

FIG. 29A

| HPIV3 DP107-LIKE REGION(F1) | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| HPF3 107 | G | T | I | A | L | G | V | A | T | S | A | Q | I | T | A | A | V | A | L | V | E | A | K | Q | A | R | S | D | I | E | K | L | K | E |
| 157 | | A | L | G | V | A | T | S | A | Q | I | T | A | A | V | A | L | V | E | A | K | Q | A | R | S | D | I | E | K | L | K | E |
| 158 | | | L | G | V | A | T | S | A | Q | I | T | A | A | V | A | L | V | E | A | K | Q | A | R | S | D | I | E | K | L | K | E |
| 159 | | | | G | V | A | T | S | A | Q | I | T | A | A | V | A | L | V | E | A | K | Q | A | R | S | D | I | E | K | L | K | E |
| 160 | | | | | V | A | T | S | A | Q | I | T | A | A | V | A | L | V | E | A | K | Q | A | R | S | D | I | E | K | L | K | E |
| 161 | | | | | | A | T | S | A | Q | I | T | A | A | V | A | L | V | E | A | K | Q | A | R | S | D | I | E | K | L | K | E |
| 162 | | | | | | | T | S | A | Q | I | T | A | A | V | A | L | V | E | A | K | Q | A | R | S | D | I | E | K | L | K | E |
| 163 | | | | | | | | S | A | Q | I | T | A | A | V | A | L | V | E | A | K | Q | A | R | S | D | I | E | K | L | K | E |
| 164 | | | | | | | | | A | Q | I | T | A | A | V | A | L | V | E | A | K | Q | A | R | S | D | I | E | K | L | K | E |
| 165 | | | | | | | | | | Q | I | T | A | A | V | A | L | V | E | A | K | Q | A | R | S | D | I | E | K | L | K | E |
| 166 | | | | | | | | | | | I | T | A | A | V | A | L | V | E | A | K | Q | A | R | S | D | I | E | K | L | K | E |
| 167 | | | | | | | | | | | | T | A | A | V | A | L | V | E | A | K | Q | A | R | S | D | I | E | K | L | K | E |
| 168 | | | | | | | | | | | | | A | A | V | A | L | V | E | A | K | Q | A | R | S | D | I | E | K | L | K | E |
| 169 | | | | | | | | | | | | | | A | V | A | L | V | E | A | K | Q | A | R | S | D | I | E | K | L | K | E |
| 170 | | | | | | | | | | | | | | | V | A | L | V | E | A | K | Q | A | R | S | D | I | E | K | L | K | E |
| 171 | | | | | | | | | | | | | | | | A | L | V | E | A | K | Q | A | R | S | D | I | E | K | L | K | E |
| 172 | | | | | | | | | | | | | | | | | L | V | E | A | K | Q | A | R | S | D | I | E | K | L | K | E |
| 173 | | | | | | | | | | | | | | | | | | V | E | A | K | Q | A | R | S | D | I | E | K | L | K | E |
| 174 | | | | | | | | | | | | | | | | | | | E | A | K | Q | A | R | S | D | I | E | K | L | K | E |
| T-40 | | | | | | | | | | | | | | | | | | | | A | K | Q | A | R | S | D | I | E | K | L | K | E |
| 175 | | | | | | | | | | | | | | | | | | | | | K | Q | A | R | S | D | I | E | K | L | K | E |
| 176 | | | | | | | | | | | | | | | | | | | | | | Q | A | R | S | D | I | E | K | L | K | E |
| 177 | | | | | | | | | | | | | | | | | | | | | | | A | R | S | D | I | E | K | L | K | E |
| 178 | | | | | | | | | | | | | | | | | | | | | | | | R | S | D | I | E | K | L | K | E |
| 179 | | | | | | | | | | | | | | | | | | | | | | | | | S | D | I | E | K | L | K | E |
| 180 | | | | | | | | | | | | | | | | | | | | | | | | | | D | I | E | K | L | K | E |
| 181 | | | | | | | | | | | | | | | | | | | | | | | | | | | I | E | K | L | K | E |
| 182 | | | | | | | | | | | | | | | | | | | | | | | | | | | | E | K | L | K | E |
| 183 | | | | | | | | | | | | | | | | | | | | | | | | | | | | | K | L | K | E |
| 184 | | | | | | | | | | | | | | | | | | | | | | | | | | | | | | L | K | E |
| 185 | | | | | | | | | | | | | | | | | | | | | | | | | | | | | | | K | E |
| 186 | | | | | | | | | | | | | | | | | | | | | | | | | | | | | | | | E |
| 187 | | | | | | | | | | | | | | | | | | | | | | | | | | | | | | | | |
| 188 | | | | | | | | | | | | | | | | | | | | | | | | | | | | | | | | |

| HPIV3 107 | AV | IC50 (UG/ML) | CD |
|---|---|---|---|
| 157 | – | 574* | + |
| 158 | – | 146* | + |
| 159 | – | 707* | + |
| 160 | – | 536* | + |
| 161 | – | 390* | + |
| 162 | – | 403* | + |
| 163 | – | 123* | + |
| 164 | – | 512.067* | +++ |
| 165 | – | 742* | – |
| 166 | – | 540* | – |
| 167 | – | 215* | – |
| 168 | – | 680* | – |
| 169 | – | 137* | – |
| 170 | – | 456* | – |
| 171 | – | 437* | – |
| 172 | + | 63* | – |
| 173 | ++ | 30* | – |
| 174 | + | 56* | ++ |
| T-40 | +/– |  | +++ |
| 175 | +/– | 110* | ++ |
| 176 | – | 197.75* | +++ |
| 177 | – | 350* | + |
| 178 | ++ | 30* | + |
| 179 | – | 295* | – |
| 180 | – | 732* | – |
| 181 | – | 929* | – |
| 182 | – | 707* | – |
| 183 | – | 218.50* | ++ |
| 184 | + | 67.8* | +++ |
| 185 | – | 542* | – |
| 186 | – | 613* | – |
| 187 | – | 152* | – |
| 188 | – | 669* | – |

FIG. 29C

| HPIV-3 DP107-LIKE WALKS | |
|---|---|
| T-42 | ATSAQITAAVALVEAKQARSDIEKLKEA |
| T-43 | AAVALVEAKQARSDIEKLKEAIRDTNKA |
| T-39 | AAVALVEAKQARSDIEKLKEAIRDTNKAVQSVQSS |
| T-38 | AKQARSDIEKLKEAIRDTNKAVQSVQSS |
| T-40 | AKQARSDIEKLKEAIRDTNKAVQSVQSSIGNLIVA |
| T-44 | IEKLKEAIRDTNKAVQSVQSSIGNLIVA |
| T-45 | IRDTNKAVQSVQSSIGNLIVAIKS |
| T-46 | AVQSVQSSIGNLIVAIKS |
| T-582 TRUNCATED 184 | LKEAIRDTNKAVQSVQSSIGNLIVAIKS |

FIG.29D

| | AVG. IC50 | | | | | | | | | | |
|---|---|---|---|---|---|---|---|---|---|---|---|
| | | | 643.000 μg/ml* | 655.000 μg/ml* | 720.000 μg/ml* | 700.000 μg/ml* | 58.798 μg/ml | 225.140 μg/ml | 485.000 μg/ml* | 548.000 μg/ml* | |
| | | | | | | | | | | | |
| V Q D Y | | | | | | | | | | | |
| V Q D Y V N K E I I V | | | | | | | | | | | 137.654 μg/ml* |

FIG. 29E

HPIV3 DP178-LIKE REGION (F1)

| | 1 | 2 | 3 | 4 | 5 | 6 | 7 | 1 | 2 | 3 | 4 | 5 | 6 | 7 | 1 | 2 | 3 | 4 | 5 | 6 | 7 | 1 | 2 | 3 | 4 | 5 | 6 | 7 | 1 | 2 | 3 | 4 | 5 | 6 | 7 | 1 | 2 | 3 | 4 | 5 | 6 | 7 | 1 | 2 | 3 | 4 | 5 | 6 | 7 | 1 | 2 | 3 | 4 | 5 | 6 | 7 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| HPF3 178 | Y | T | P | N | D | I | T | L | N | N | S | V | A | L | D | P | I | D | I | S | I | E | L | N | K | A | K | S | D | L | E | E | S | K | E | W | I | R | R | S | N | Q | K | L | D | S | I | G | N | W | H | Q | S | S | T | T |
| 189 | Y | T | P | N | D | I | T | L | N | N | S | V | A | L | D | P | I | D | I | S | I | E | L | N | K | A | K | S | D | L | E | E | S | K | E | | | | | | | | | | | | | | | | | | | | | |
| 190 | | T | P | N | D | I | T | L | N | N | S | V | A | L | D | P | I | D | I | S | I | E | L | N | K | A | K | S | D | L | E | E | S | K | E | W | | | | | | | | | | | | | | | | | | | | |
| 191 | | | P | N | D | I | T | L | N | N | S | V | A | L | D | P | I | D | I | S | I | E | L | N | K | A | K | S | D | L | E | E | S | K | E | W | I | | | | | | | | | | | | | | | | | | | |
| 192 | | | | N | D | I | T | L | N | N | S | V | A | L | D | P | I | D | I | S | I | E | L | N | K | A | K | S | D | L | E | E | S | K | E | W | I | R | | | | | | | | | | | | | | | | | | |
| 193 | | | | | D | I | T | L | N | N | S | V | A | L | D | P | I | D | I | S | I | E | L | N | K | A | K | S | D | L | E | E | S | K | E | W | I | R | R | | | | | | | | | | | | | | | | | |
| 194 | | | | | | I | T | L | N | N | S | V | A | L | D | P | I | D | I | S | I | E | L | N | K | A | K | S | D | L | E | E | S | K | E | W | I | R | R | S | | | | | | | | | | | | | | | | |
| 195 | | | | | | | T | L | N | N | S | V | A | L | D | P | I | D | I | S | I | E | L | N | K | A | K | S | D | L | E | E | S | K | E | W | I | R | R | S | N | | | | | | | | | | | | | | | |
| 196 | | | | | | | | L | N | N | S | V | A | L | D | P | I | D | I | S | I | E | L | N | K | A | K | S | D | L | E | E | S | K | E | W | I | R | R | S | N | Q | | | | | | | | | | | | | | |
| 197 | | | | | | | | | N | N | S | V | A | L | D | P | I | D | I | S | I | E | L | N | K | A | K | S | D | L | E | E | S | K | E | W | I | R | R | S | N | Q | K | | | | | | | | | | | | | |
| 198 | | | | | | | | | | N | S | V | A | L | D | P | I | D | I | S | I | E | L | N | K | A | K | S | D | L | E | E | S | K | E | W | I | R | R | S | N | Q | K | L | | | | | | | | | | | | |
| 199 | | | | | | | | | | | S | V | A | L | D | P | I | D | I | S | I | E | L | N | K | A | K | S | D | L | E | E | S | K | E | W | I | R | R | S | N | Q | K | L | D | | | | | | | | | | | |
| 200 | | | | | | | | | | | | V | A | L | D | P | I | D | I | S | I | E | L | N | K | A | K | S | D | L | E | E | S | K | E | W | I | R | R | S | N | Q | K | L | D | S | | | | | | | | | | |
| 201 | | | | | | | | | | | | | A | L | D | P | I | D | I | S | I | E | L | N | K | A | K | S | D | L | E | E | S | K | E | W | I | R | R | S | N | Q | K | L | D | S | I | | | | | | | | | |
| 202 | | | | | | | | | | | | | | L | D | P | I | D | I | S | I | E | L | N | K | A | K | S | D | L | E | E | S | K | E | W | I | R | R | S | N | Q | K | L | D | S | I | G | | | | | | | | |
| 203 | | | | | | | | | | | | | | | D | P | I | D | I | S | I | E | L | N | K | A | K | S | D | L | E | E | S | K | E | W | I | R | R | S | N | Q | K | L | D | S | I | G | N | | | | | | | |
| 204 | | | | | | | | | | | | | | | | P | I | D | I | S | I | E | L | N | K | A | K | S | D | L | E | E | S | K | E | W | I | R | R | S | N | Q | K | L | D | S | I | G | N | W | | | | | | |
| 205 | | | | | | | | | | | | | | | | | I | D | I | S | I | E | L | N | K | A | K | S | D | L | E | E | S | K | E | W | I | R | R | S | N | Q | K | L | D | S | I | G | N | W | H | | | | | |
| 206 | | | | | | | | | | | | | | | | | | D | I | S | I | E | L | N | K | A | K | S | D | L | E | E | S | K | E | W | I | R | R | S | N | Q | K | L | D | S | I | G | N | W | H | Q | | | | |
| 207 | | | | | | | | | | | | | | | | | | | I | S | I | E | L | N | K | A | K | S | D | L | E | E | S | K | E | W | I | R | R | S | N | Q | K | L | D | S | I | G | N | W | H | Q | S | | | |
| 208 | | | | | | | | | | | | | | | | | | | | S | I | E | L | N | K | A | K | S | D | L | E | E | S | K | E | W | I | R | R | S | N | Q | K | L | D | S | I | G | N | W | H | Q | S | S | | |
| 209 | | | | | | | | | | | | | | | | | | | | | I | E | L | N | K | A | K | S | D | L | E | E | S | K | E | W | I | R | R | S | N | Q | K | L | D | S | I | G | N | W | H | Q | S | S | T | |
| 210 | | | | | | | | | | | | | | | | | | | | | | E | L | N | K | A | K | S | D | L | E | E | S | K | E | W | I | R | R | S | N | Q | K | L | D | S | I | G | N | W | H | Q | S | S | T | T |

FIG.30A

| HP1V3 178 | AV | IC50 (μg/ml) | CD |
|---|---|---|---|
| 189 | − | 827* | − |
| 190 | − | 775* | − |
| 191 | − | 612* | − |
| 192 | − | 699* | − |
| 193 | − | 525* | − |
| 194 | + | 61* | ++ |
| 195 | + | 49 | + |
| 196 | +++ | 3.1 | ++ |
| 197 | +++ | 71.15 | + |
| 198 | ++++ | 0.325 | + |
| 199 | +++ | 2.3* | ++ |
| 200 | +++ | 1.0* | + |
| 201 | ++++ | 0.224* | + |
| 202 | ++++ | 0.390* | + |
| 203 | ++++ | 0.213 | + |
| 204 | ++++ | 0.174 | + |
| 205 | +++ | 2.0* | + |
| 206 | +++ | 2.0* | + |
| 207 | ++ | 37* | + |
| 208 | +++ | 1.0* | + |
| 209 | +++ | 2.0* | + |
| 210 | | | |

FIG. 30B

| ID | Sequence | Value |
|---|---|---|
| T-269 TRUNCATED 201 | EWIRRSNQKLDSII | 457.500UG/ML |
| T-626 205 MUTANT | IDISIELNKAKSDLEESKEWIKKISNQKLDSIGNWH | 209.589NG/ML |
| T-383 | RMKQLEDKVEELLSKLEWIRRSNQKLDSII | NOT DONE |
| T-577 | DQQIKQYKRLLDRLIIPLIYDGLRQKDVIVSNQESN | 133.793UG/ML* |
| T-578 | YSELTNIFGDNIGSLQEKGIKLQGIASLYRTNIITEII | 107.177UG/ML* |
| T-579 | TSIITLQVRLPLLTRLLNTQIIYRVDSISYNIIQNREWY | NOT DONE |

FIG.30C

FUSION　　　　　　　　　　　　♥ALLMOTI5♥
PEPTIDE　　　　　　　　　　　♣107x178x4♣
.....RNKRGVFVLGFLGFLATAGSAMGAAS ♣♥ XXXXAQSRTLLAGIVQQQQ

LLDVVKRQQELLRLTVWGTKNLQTRVTAIEKYLKDQAQL♣NAWG♥ CAF

♥ALLMOTI5♥
*LVS PREDICTED COILED-COIL
RQVCHTTVPWPNASLTPDW *NND ♥TWQEWERKVDFLEENITALLEEAQIQQ

♣107x178x4♣
EKNMY ♣ELQKLNSWD* VF♥ GNXXXXXXXXXXXXXXXXXXXXXXXXXXX♣

IYIVMLAKLRQGYRPVFSSPPSYFQXTHTQQDPALPTREGKEGDGGEGGGNSSWP

WQIEYIHF

FIG. 31

MTRRRVLSVVVLLAALACRLGAQTPEQPAPPATTVQPTATRQQTSFPFRVCELSSHGDLFRFSSD

♠ 107x178x4♠
IQCPSFGTRENHTEGLLMVFKDNIIPYSF ♣ KVRSYTKIVTNILIYNGWYADSVTNRHE♠

EKFSVDSY ETDQMDTIYQ CYNAVKMTKD GLTRVYVDRD GVNITVNLKP TGGLANGVRR

YASQTELYDA PGWLIWTYRT RTTVNCLITD MMAKSNSPFD FFVTTTGQTV EMSPFYDGKN

KETFHERADS FHVRTNYKIV DYDNRGTNPQ GERRAFLDKG TYTLSWKLEN RTAYCPLQHW

QTFDSTIATE TGKSIHFVTD EGTSSFVTNT TVGIELPDAF KCIEEQVNKT HEKYEAVQD

RYTKGQEAIT YFITSGGLLL AWLPLTPRSL ATVKNLTELT TPTSSPPSSP SPPAPSAARG

STPAAVLRRR RRDAGNATTP VPPTAPGKSL GTLNNPATVQ IQFAYDSLRR QINRMLGDLA

RAWCLEQKRQ NMVLRELTKI NPTTVMSSIY GKAVAAKRLG DVISVSQCVP VNQATVTLRK

SMRVPGSETM CYSRPLVSFS FINDTKTYEG QLGTDNEIFL TKKMTEVCQA TSQYYFQSGN

♣107x178x4♣
EIHVYNDYHH FKTIELDGIA TLQTFISLNT ♣SLIENIDFASLELYSRDEQRASNVFD *LE♣

*LVS PREDICTED COILED COIL*         TM Potential
 GIFREYNFQAQNIAGLRKDLDNAVSN* GRNQ FVDGLGELMDSLGSVG QSITN ♣P12LZIPC♣
TM Potential           TM Potential
LVSTVGGLFSSLVSGFISF FK N ♣PFGGMLILVLVAGVVILVISL♣ TRRTRQMS

QQPVQMLYPG IDELAQQHAS GEGPGINPIS KTELQAIMLA LHEQNQEQKR AAQRAAGPSV

ASRALQAARDRFPGLRRRRY HDPETAAALL GEAETEF

FIG. 32

MMDPNSTSED VKFTPDPYQV PFVQAFDQAT RVYQDLGGPS QAPLPCVLWP VLPEPLPQGQ

LTAYHVSTAP TGSWFSAPQP APENAYQAYA APQLFPVSDI TQNQQTNQAG GEAPQPGDNS

TVQTAAAVVF ACPGANQGQQ LADIGVPQPA PVAAPARRTR KPQQPESLEE CDSELEI

@DNA BINDING@      ♠107x178X4♠     +DIMERIZATION+
@KRY KNRVASRKCRAK  ♠EK@ Q          +LLQHYREVAAAKSSENDRLRLLLKQ♠

MCPSLDVD+ SI IPRTPDVLHE DLLNF

FIG. 33

FUSION
PEPTIDE ♥ALLMOTI5♥ *LVS COILED-COIL*
FAG ♥VVLAGAALGVATAAQITAGIALHQSML*NSQAIDNLRASLETTN

QAIEAIRQAGQEMI*LAVQGVQDYINN♥ ELIPSMNQLSCDLIGQKLGLKLLRYYT

♣P23LZIPC♣
♣P6,12LZIPC♣
♠107X178X4♠
♥ALLMOTI5♥
EILSLFGPSLRD ♣PISA ♠♥EISIQLSYALGGDINKV♣ LEKLGYSGGDL♣

♣P1,12LZIPC♣
LGILES♠ RGIKARI♥ THVDTESYFIVLSIAY ♣PTLSEIKGVIVHRLEGV♣ SY

NIGSQEWYTTVPKYVATQGYLISNFDESSCTFMPEGTVCSQNALYPMSPLLQECL

RGSTKSCARTLVSGSFGNRFILSQGNLIANCASILCKCYTTGTIINQDPDKILTYIAA

♣P23LZIPC♣
♣P12LZIPC♣
♥ALLMOTI5♥
*LVS COILED-COIL*
DHCPVVEVNGVTIQVGSRRYPDAVYLHRIDLGP ♣P ♥IS *LERLDVGTNLGN

♦TRANSMEMBRANE REGION♦
AIAKLEDAKELL♣ ESSDQI*L♣ RSMK ♦GLSSTSIVYILI♥ AVCLGGLIGIP

ALICCC♦ RGRCNKKGEQVGMSRPGLKPDLTGTSKSYVRSL

FIG. 34

Pre S1 and Pre S2

MGQNLSTSNPLGFFPDHQLDPAFRANTANPDWDFNPNKDTWPDANKVGAGAFG

LGFTPPHGGLLGWSPQAQGILQTLPANPPPASTNRQSGRQPTPLSPPLRNTHPQAM

QWNSTTFHQTLQDPRVRGLYFPAGGSSSGTVNPVLTTASPLSSIFSRIGDPALN

MAJOR SURFACE ANTIGEN(HBs)
        FUSION
        PEPTIDE
          ♣P12 & 23LZIPC♣
MENITSG  FLG  ♣PLL VLQAGFFLLTRILTI♣ PQSLDSWWTSLNFLGGTTVCLG

♣P12 & 23LZIPC♣
QNSQSPTSNHSPTSCPPTC  ♣PGYRWMCLRRFIIFLFILLLCLIFLLVLLDYQGML♣

PVCPLIPGSSTTSTGPCRTCMTTAQGTSMYPSCCCTKPSDGNCTCIPIPSSWAFGKF

♦<u>TRANSMEMBRANE REGION</u>♦
LWEWASARFSWLS ♦<u>LLVPFVQWFVGLSPTVWLSVI</u>♦ WMMWYWGPSL

♦<u>TRANSMEMBRANE REGION</u>♦

♦<u>YSILSPFLPLLPIFFCLWVYI</u>♦

FIG. 35

FUSION ♥ ALLMOTI5 ♥ ♣107x 178x4♣
PEPTIDE                    *LVS COILED COIL
AIQLIPLFVG LGI ♥TTAVSTGAAGLGVS ♣IT *QYTKLSHQLISDV

QAISSTIQDLQDQVDSLAEVVLQ* NRRGLDLLTAE♣ QGGI♥

CLALQEKCCFYANKSGIVRDKIKNLQDDLERRRRQLIDNPFWTSFHG

FLPYVMPLLGPLLCLLLVLSFGPIIFNKLMTFIKHQIESIQAKPIQVHYH

TRANSMEMBRANE REGION
RLEQEDSGGSYLTLT......???????????????????????....

FIG. 36

MKAQKGFTLI ELMIVVAIIG ILAAIAPGQ

♠107x178x4♠
♥ALLMOTI5♥
♣♥YQDYTARTQVTRAVSEVSALKTAAESAILEGKEIVSSA♠ T♥

PK DTQYDIGFT

♠107x178x4♠
♥ALLMOTI5♥
♣♥ESTLLDGSGKSQIQVTDNQDGTVELVATLGKSSGS♠ AIKGAVITSR♥

KNDGV WNCKITKTPT AWKPNYAPAN CPKS

FIG. 37

MNTLQKGFTL IELMIVIAIV GILAAVALPA YQDYTARAQV

SEAILLAEGQ KSAVTEYYLN HGIWP

♣<u>107x178x4</u>♣
♥<u>ALLMOTI5</u>♥
♣♥<u>KDNTSAGVASSSSIKGKYVKEVKVENGVVTAT</u>♣

MNSSNVNKEIQGKKLSLWAKRQDGSVKW♥

FCGQP VTRNAKDDTV TADATGNDGK IDTKHLPSTC RDNFDAS

FIG. 38

MKKTLLGSLI LLAFAGNVQA DINTETSGKV TFFGKVVENT

CKVKTEHKNL SVVLNDVGKN SLSTKVNTAM PTPFTITLQN

CDPTTANGTA NKANKVGLYF Y

♣<u>107x178x4</u>♣
♥<u>ALLMOTI5</u>♥
♣♥<u>SWKNVDKENNFTLKNEQTTADYATNVNI</u>♣

QLMESNGTKAISVVGKETE♥

DF MHTNNNGVAL NQTHPNNAHI SGSTQLTTGT NELPLHFIAQ

YYATNKATAG KVQSSVDFQI AYE

FIG. 39

MNKKLLMNFF IVSPLLLATT ATDFTPVP

♣107x178x4♣
♥ALLMOTI5♥
♣♥LSSNQIIKTAKASTNDNIKDLLDWYSSGSDTFTNS♣♥

EVLDNSL GSMRIKNTDG SISLIIFPSP YYSPAFTKGE KV

♣107x178x4♣
♣DLNTKRTKKSQHTSEGTYIHFQISGVT♣

N TEKLPTPIEL PLKVKVHGKD SPLKYG

♣P12LZIPC♣
♣PKFDKKQLAISTLDFEIRHQLTQI♣

HGLYRSSDKT GGYWKITMND GSTYQSDLSK KFEYNTEKPP

INIDEIKTIE AEIN

FIG. 40

♥ALLMOTI5♥
MKKTAFILLL FIALTLTTSP L ♥VNG

♠107x178x4♠
*LVS PREDICTED COILED-COIL*
*S ♠EKSEEINEKDLRKKSELQRNALSNLRQIY* YYNEKAITENKESDD♠

QFLENTLL♥ FKG FFTGHPW

♠107x178x4♠
♠YNDLLVDLGSKDATNKYKGKKVDLYGAY♠

YGYQCAGGTPNKTACMYGGVTLHDN NRLTEEKKVP INLWIDGKQTTV

♣P12LZIPC♣
♣PIDKVKTSKKEVTVQELDL♣ QARHYLHGK FGLYNSDSFGGKVQ

♣P12LZIPC♣
RGLIVF HSSEGSTVSY DLFDAQGQY ♣P DTLLRIYRDN KTINSENLHI♣

DLYLYTT

FIG. 41

♥ALLMOTI5♥
MKKTAFTLLL FIALTLTTSP L ♥VNGS

♠107x178x4♠
♠EKSEEINEKDLRKKSELQGTALGNLKQIYYYNEKAKTENKESHD♠ Q♥

FLQHTILFKG FFTDHSWYND LLVDFDSKDI VDKYKGKKVDLYGAYY

GYQC AGGTPNKTAC MYGGVTLHDN NRLTEEKKVPINL WLDGKQNTV

♠107x178x4♠
♥ALLMOTI5♥
♣P12LZIPC♣
♣P ♥L ♣ETVKTNKKNVTVQELDLQARRYL♣ QEKYNLYN♠

SDVFDGKVQR♥ GLIVF HTSTE

♣P23LZIPC♣
♣PSVNYDLFGAQGQYSNTLLRIYRDNKTINSENMHI♣ DIYLYTS

FIG. 42

MKNITFIFFILLASPLYANGDRLYRADSRPPDEIKRFRSLMPRGNEYFDRGT

♥ALLMOTI5♥
♥QMNINLYDHARGTQTGFVRYDDGYV

♠107x178x4♠
♠STSLSLRSAHLAGQYILSGYSLTIYIVI♠ ANMFNVNDVISVY♥

SP HPYEQEVSAL GGIPYSQIYG WYRVNFGVID ERLHRNREYR

DRYYRNLNIA PAEDGYRLAG FPPDHQAWRE EPWIHHAPQG

CGDSSRTITG DTCNE

♥ALLMOTI5♥
♥ETQNLSTIYLREYQSKVKRQIFSDYQSEVDIYNRIRDEL♥

FIG. 43

MMFSGFNADY EASSSRCSSA SPAGDSLSYY HSPADSFSSM

GSPVNAQDFC TDLAVSSANF IPTVTAISTS PDLQWLVQPA

LVSSVAPSQT RAPHPFGVPA PSAGAYSRAG VVKTMTGGRA

*LVS PREDICTED COILED-COIL*
QSIGRRGKVE QLSPEEEEKR RIRRE *RNKMA AAK

♣107x178x4♣
♥ALLMOTI5♥
♥CRNRRREL ♣<u>TDTLQAETDQLEDEKSALQTEIANLLKEKEKL</u>♥

EFILAAHR* PACKIPDDL GFPEEMSVAS LDLTGGLPEV

ATPESEEAFT LPLLNDPEPK PSVEPVKSIS SMELKTEPFD

DFLFPASSRP SGSETARSVP DMDLSGSFYA LPLLNDPEPK

PSVEPVKSIS SMELKTEPFD DFLFPASSRP SGSETARSVP

DMDLSGSFYA GSSSNEPSSD SLSSPTLLAL

FIG. 44

SGWESYYKTEGDEEAEEEQEENLEASGDYKYSGRDSLIFLVDASKA

MFESQSEDELTPFDMSIQCIQSVYISKHSSDRDLLAVVFYGTEKDKNS

VNFKNIYVLQELDNPGAKRILELDQFKGQQGQKRFQDMMGHGSDY

SLSEVLWVCANLFSDVQFKMSHKRIMLFTNEDNPHGNDSAKASRAR

TKAGDLRDTGIFLDLMHLKKPGGFDISLFYRDHSIAEDED

♣107x178x4♣
♥ALLMOTI5♥
　　*LVS PREDICTED COILED-COIL*

♥LRVH *FEE ♣SSKLEDLLRKVRAKETRKRALSRLKLKLNKDIV* ISV

GIYNLVQKAL♥ KPPPIKLYRETN♣ EPVKTKTRTFNTSTGGLLLPSDTKR

SQIYGSRQIILEKEETEELKRFDDPGLMLMGFKPLVLLKKHHLRPSLFVYPE
ESLVIGS STLFSALLIKCLEKEVAALCRYTPRRNIPPYFVALVPQEEELDDQK
IQVTPPGFQLVFLPFADDKRKMPFTEKIMATPEQVGKMKAIVEKLRFTYRS
DSFENPVLQQHFRNLEALALDLME

♣PI2LZIPC♣
♣PEQAVDLTLPKVEAMNKRL♣ GSLVDEFKELVYPPDYNPEGKVTKR
KHDNEGSGSKRPKVEYSEEELKTHISKGTLGKFTVPMLKEACRAYGLKSG
LKKQELLEALTKHFQD

FIG. 45

GGGALSPQHSAVTQGSIIKNKEGMDAKS

♣107x178x4♣
♥ALLMOTI5♥
♥♣LTAWSRTLVTFKDVFVDFTREEWKLLDT♣ AQQIVYRNV
MLENYKNLVSLGYQLT♥ KPDVILRLEKGEEPWLVEREIHQETHPD
SETAFEIKSSVSSRSIFKDKQSCDIKMEGMARNDLWYLSLEEVWKCR
DQLDKYQENPERHLRHQLIHTGEKPYECKECGKSFSRSSHLIGHQKT
HTGEEPYECKECGKSFSWFSHLVTHQRTHTGDKLYTCNQCGKSFVH
SSRLIRHQRTHTGHKPYECPECGKSFRQSTHLILHQRTHVRVRPYECN
ECGKSYSQRSHLVVHHRIHTGLKPFECKDCGKCFSRSSHLYSHQRTH
TGEKPYECHDCGKSFSQSSALIVHQRIHTGEKPYECCQCGKAFIRKN
DLIKHQRIHVGAETYKCNQCGIIFSQNS

♣P23LZIPC♣
♣PFIVHQIAHTGEQFLTCGNQCGTALVNTSNLIGQTNHI♣ RENAY

FIG. 46

FIG. 47A

| RESIDUE - 438 | P | D | A | V | Y | L | H | R | I | D | L | G | P | P | I | I | S | L | E | R | L | D | V | G | T | N | L | G | N | A | I | I | A | K | L | E | A | K | E | L | L | E | S | S | D | Q | I | L | R | S | M | -488# |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| MEASLES ED. 178-LIKE WALK | | | | | | | | | | | | | | | | | | | | | | | | | | | | | | | | | | | | | | | | | | | | | | | | | | | | | |
| T-252A0 | P | D | A | V | Y | L | H | R | I | D | L | G | P | P | I | I | S | L | E | R | L | D | V | G | T | N | L | G | N | A | I | I | A | K | L | E | | | | | | | | | | | | | | | | |
| T-253A0 | | D | A | V | Y | L | H | R | I | D | L | G | P | P | I | I | S | L | E | R | L | D | V | G | T | N | L | G | N | A | I | I | A | K | L | E | D | | | | | | | | | | | | | | | |
| T-254A0 | | | A | V | Y | L | H | R | I | D | L | G | P | P | I | I | S | L | E | R | L | D | V | G | T | N | L | G | N | A | I | I | A | K | L | E | A | K | | | | | | | | | | | | | | |
| T-255A0 | | | | V | Y | L | H | R | I | D | L | G | P | P | I | I | S | L | E | R | L | D | V | G | T | N | L | G | N | A | I | I | A | K | L | E | A | K | | | | | | | | | | | | | | |
| T-256A0 | | | | | Y | L | H | R | I | D | L | G | P | P | I | I | S | L | E | R | L | D | V | G | T | N | L | G | N | A | I | I | A | K | L | E | A | K | E | | | | | | | | | | | | | |
| T-257B1,C1 | | | | | | | L | H | R | I | D | L | G | P | P | I | I | S | L | E | R | L | D | V | G | T | N | L | G | N | A | I | I | A | K | L | E | A | K | E | L | L | | | | | | | | | | |
| T-258B1 | | | | | | | | H | R | I | D | L | G | P | P | I | I | S | L | E | R | L | D | V | G | T | N | L | G | N | A | I | I | A | K | L | E | A | K | E | L | L | E | | | | | | | | | |
| T-259B1 | | | | | | | | | R | I | D | L | G | P | P | I | I | S | L | E | R | L | D | V | G | T | N | L | G | N | A | I | I | A | K | L | E | A | K | E | L | L | E | S | | | | | | | | |
| T-260B1 | | | | | | | | | | I | D | L | G | P | P | I | I | S | L | E | R | L | D | V | G | T | N | L | G | N | A | I | I | A | K | L | E | A | K | E | L | L | E | S | S | | | | | | | |
| T-261A0 | | | | | | | | | | | D | L | G | P | P | I | I | S | L | E | R | L | D | V | G | T | N | L | G | N | A | I | I | A | K | L | E | A | K | E | L | L | E | S | S | D | | | | | | |
| T-262B1 | | | | | | | | | | | | L | G | P | P | I | I | S | L | E | R | L | D | V | G | T | N | L | G | N | A | I | I | A | K | L | E | A | K | E | L | L | E | S | S | D | Q | | | | | |
| T-263B1 | | | | | | | | | | | | | G | P | P | I | I | S | L | E | R | L | D | V | G | T | N | L | G | N | A | I | I | A | K | L | E | A | K | E | L | L | E | S | S | D | Q | I | | | | |
| T-264B1 | | | | | | | | | | | | | | P | P | I | I | S | L | E | R | L | D | V | G | T | N | L | G | N | A | I | I | A | K | L | E | A | K | E | L | L | E | S | S | D | Q | I | L | | | |
| T-265B1 | | | | | | | | | | | | | | | P | I | I | S | L | E | R | L | D | V | G | T | N | L | G | N | A | I | I | A | K | L | E | A | K | E | L | L | E | S | S | D | Q | I | L | R | | |
| T-266A0 | | | | | | | | | | | | | | | | | | | | | | | | | | | | | | | | | | | | | | | | | | | | | | | | | | | R | S | M |
| T-267A0 | | | | | | | | | | | | | | | | | | | | | | | | | | | | | | | | | | | | | | | | | | | | | | | | | | R | S | |
| T-268A0 | | | | | | | | | | | | | | | | | | | | | | | | | | | | | | | |

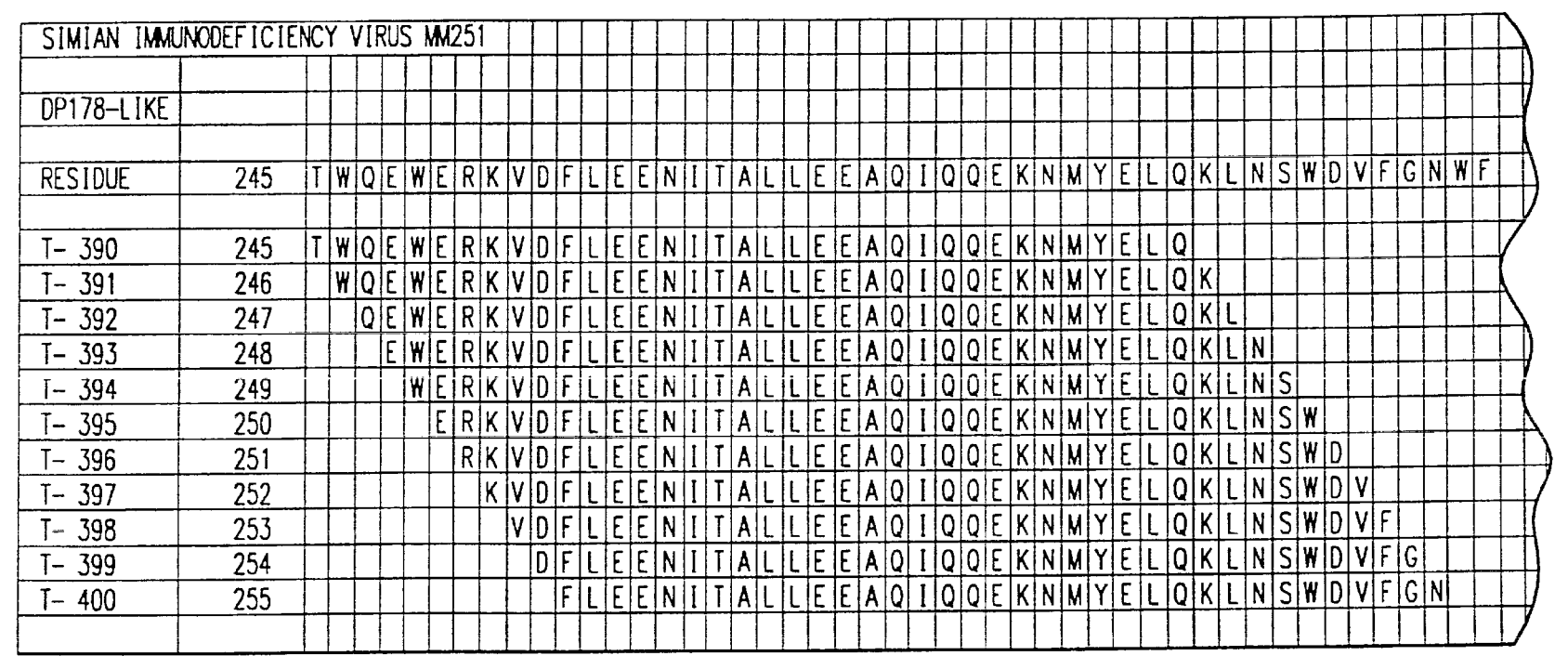

| SIMIAN IMMUNODEFICIENCY VIRUS MM251 | | | | | | | | | | | | | | | | | | |
|---|---|---|---|---|---|---|---|---|---|---|---|---|---|---|---|---|---|---|
| DP178-LIKE | | | | | | | | | | | | | | | | | | |
| RESIDUE | 245 | | | | | | | | | | | | | | | | | |
| T-390 | 245 | T | W | Q | E | W | E | R | K

| | RESIDUE | 47 | | ANTIVIRAL ACTIVITY SIV |
|---|---|---|---|---|
| 291 | | | | |
| 280 | | 35 | T390 | NT |
| 281 | | 35 | T391 | +++ |
| 282 | | 35 | T392 | +++ |
| 283 | | 35 | T393 | +++ |
| 284 | | 35 | T394 | +++ |
| 285 | | 35 | T395 | +++ |
| 286 | | 35 | T396 | +++ |
| 287 | | 35 | T397 | +++ |
| 288 | | 35 | T398 | +++ |
| 289 | | 35 | T399 | +++ |
| 290 | | 35 | T400 | |

| Position | 656 | 657 | 658 | 659 | 660 | 661 | 662 | 663 | 664 | 665 | 666 | 667 | 668 | 669 | 670 | 671 | 672 | 673 | 674 | 675 | 676 | 677 | 678 | Clone | HIV-1/IIIB IC50 ng/ml | HIV-2 NIHZ IC50 ng/ml |
|---|---|---|---|---|---|---|---|---|---|---|---|---|---|---|---|---|---|---|---|---|---|---|---|---|---|---|
| ref | Q | N | Q | E | K | N | E | E | L | L | L | L | E | D | K | W | A | S | L | W | N | W | F | | | |
| | | | | | | | | | | | | | | | | | | | | | | | | T661 | 297* | |
| | Q | N | Q | E | K | N | E | | | | | | | | | | | | | | | | | T660 | 258* | |
| | Q | N | Q | E | K | N | E | | | | | | | | | | | | | | | | | T659 | 2290* | |
| | Q | N | Q | E | K | N | E | | | | | | | | | | | | | | | | | T658 | 191* | |
| | Q | N | Q | E | K | N | E | | | L | | | | | | | | | | | | | | T657 | 128* | |
| | Q | N | Q | E | K | N | E | Q | | L | | L | | | | | | | | | | | | T656 | 5* | |
| | Q | N | Q | E | K | N | E | Q | | L | L | L | L | | | | | | | | | | | T655 | 2300* | |
| | Q | N | Q | E | K | N | E | Q | | L | L | L | L | D | | | | | | | | | | T654 | 1 | |
| | Q | N | Q | E | K | N | E | Q | | L | L | L | L | D | K | W | | | | | | | | T653 | 63* | |
| | Q | N | Q | E | K | N | E | Q | | L | L | L | L | D | K | W | A | S | L | | | | | T652 | 4* | |
| | Q | N | Q | E | K | N | E | Q | E | L | L | L | L | D | | | | | | | | | | T651 | 338* | |
| | Q | N | Q | E | K | N | E | Q | E | L | L | L | L | D | | | | | | | | | | T625 | ND | |
| | Q | N | Q | E | K | N | E | Q | E | L | L | L | L | D | | | | | | | | | | T650 | 44* | |
| | Q | N | Q | E | K | N | E | Q | E | L | L | L | L | D | | | | | | | | | | T649 | 8* | |
| | Q | N | Q | E | K | N | E | Q | E | L | L | L | L | D | K | | | | | W | N | W | | T624 | 2 | |
| | Q | N | Q | E | K | N | E | Q | E | L | L | L | L | D | K | | | | | | | | | T50 | 6 | |
| | Q | N | Q | E | K | N | E | Q | E | L | L | L | L | D | K | | | | | | | | | T648 | 36 | |
| | Q | N | Q | E | K | N | E | Q | E | L | G | G | C | | | | | | | | | | | T647 | 44 | |
| | Q | N | Q | E | K | N | E | Q | E | L | | | | | | | | | | | | | | T711 | ND | |
| | Q | N | Q | E | K | N | E | Q | E | L | | | | | | | | | | | | | | T621 | 229 | |
| | Q | N | Q | E | K | N | E | Q | E | L | | | D | K | W | A | S | | | | | | T646 | 83 | |
| | Q | N | Q | E | K | N | E | Q | E | L | | | D | K | W | A | S | | | | | | T645 | 85 | |
| | Q | N | Q | E | K | N | E | Q | E | L | | | D | K | W | A | S | L | W | | | | T644 | 4960* | |
| | Q | N | Q | E | K | N | E | Q | E | L | | | D | K | W | A | S | | | | | | T643 | 1690* | |
| | Q | N | Q | E | K | N | E | Q | E | L | | | D | K | W | A | S | | | | | | T642 | 1450* | |

HIV-1 BRU 178 CONSTRUCTS, MUTATIONS, TRUNCATIONS

| Construct | TRUNC. Pt. T20 | MUTANTS REMOVED | MUTANTS ADDED | AA# 6 | AA# | Sequence (positions 634–678) |
|---|---|---|---|---|---|---|
| AA# (tens) | | | | 6 | 1///3 5 | |
| AA# (ones) | | | | | W | Y T S L I H S L I I E E S Q N Q Q E K N E Q E L L E L D K W A S L W N W F |
| T4 | X | | | | | Y T S L I H S L I I E E S Q N Q Q E K N E Q E L L E L D K W A S L W N W F |
| T228 | X | X | | | | |
| T700 | | | | | | NO AC- ... Y T S L I H S L I I E E S Q N Q Q E K N E Q E L L E L D K W A S L W N W F |
| T715 | X | | | | | Y T S L I H S L I I E E S Q N Q Q E K N E Q E L L E L D K W A S L W N W F |
| T65/T716 | X | | | | | Y T S L I H S L I I E E S Q N Q Q E K N E Q E L L E L D K W A S L W N W F |
| T714 | X | | | | | T S L I H S L I I E E S Q N Q Q E K N E Q E L L E L D K W A S L W N W F |
| T712 | X | | | | | L I H S L I I E E S Q N Q Q E K N E Q E L L E L D K W A S L W N W F |
| T64 | X | | | | | L I H S L I E E S Q N Q Q E K N E Q E L L E L D K W A S L W N W F |
| T63 | X | | | | | L I I E E S Q N Q Q E K N E Q E L L E L D K W A S L W N W F |
| T62 | X | | | | | E S Q N Q Q E K N E Q E L L E L D K W A S L W N W F |
| T3 | X | | | | | NO AC- E S Q N Q Q E K N E Q E L L E L D K W A S L W N W F |
| T61/T102 | X | | | | | E K N E Q E L L E L D K W A S L W N W F NO |
| T217 | X | | | | | N E Q E L L E L D K W A S L W N W F |
| T218 | X | | | | | E Q E L L E L D K W A S L W N W F |
| T219 | X | | | | | Q E L L E L D K W A S L W N W F |

| | HIV-1/IIIB IC50(ng/ml) |
|---|---|
| T4 | >400000 |
| T228 | >50000 |
| T700 | >100000 |
| T715 | ND |
| T65/T716 | ND |
| T714 | ND |
| T712 | ND |
| T64 | ND |
| T63 | ND |
| T62 | ND |
| T3 | 3000 |
| T61/T102 | 64000 |
| T217 | 40000 |
| T218 | 25000 |
| T219 | 48000 |

FIG.49F

| ID | | | Sequence | | | | | | | | | | | | | | | | | | |
|---|---|---|---|---|---|---|---|---|---|---|---|---|---|---|---|---|---|---|---|---|---|
| T220 | X | | | | | | | | | | | | L | L | E | L | D | K | W | A | S | L | W | N | W | F |
| T221 | X | | | | | | | | | | | E | L | L | E | L | D | K | W | A | S | L | W | N | W | F |
| T234 | X | X | | | | | | | | | | A | L | L | E | L | D | K | W | A | S | L | W | N | W | F |
| T235 | X | X | | | | | | | | | | A | A | L | E | L | D | K | W | A | S | L | W | N | W | F |
| T570 | X | X | | | | | | | | | | A | A | R | L | E | L | D | K | W | A | S | L | W | N | W | F |
| T381 | X | X | | | | | | | | | | A | A | R | L | E | V | K | D | E | L | Q | K | M | R |
| T382 | X | X | | | | | | | | | | A | A | R | E | L | E | L | D | K | W | A | S | L | W | N | W | F |
| T677 | X | X | | | | | | | | | E | A | A | A | R | E | L | E | L | D | K | W | A | S | L | W | N | W | F |
| T376 | X | X | | | | | | | | R | M | K | Q | L | E | D | K | V | E | E | L | L | S | K |
| T589 | X | X | | | | | | | | R | M | K | Q | L | E | D | K | V | E | E | L | L | S | K | | L | E | L | D | K | W | A | S | L | W | N | W | F |
| T377 | X | X | | | | | | | | F | W | N | W | L | S | A | W | K | D | L | E | L | K | S | | L | E | L | D | K | W | A | S | L | W | N | W | F |
| T590 | X | X | | | | | | | | F | W | N | W | L | S | A | W | K | D | L | E | L | K | S | | L | E | L | D | K | W | A | S | L | W | N | W | F |
| T378 | X | X | | | | | | | | | | K | V | E | E | L | L | S | K | N | Y | H | L | E | N | | L | E | L | D | K | W | A | S | L | W | N | W | F |
| T591 | X | X | | | | | | | | | | K | V | E | E | L | L | S | K | N | Y | H | L | E | N | E | L | E | L | D | K | W | A | S | L | W | N | W | F |
| T270 | X | X | | | | | | | | | | | | | F | W | N | W | L | S | A | W | K | D | L | E | I | L | Y | P | G | S | L | E | L | D | K | W | A | S | L | W | N | W | F |
| T271 | X | X | | | | | | | | | | | | | | | | | | | | | CYCLIZED- | | | | C | L | E | L | D | K | W | A | S | L | W | N | W | F | C |
| T272 | X | X | | | | | | | | | | | | | | | | | | | | | | | | | | C | L | E | L | D | K | W | A | S | L | W | N | W | F | C |
| T273 | X | X | | | | | | | | | | | | | | | | | | | | | CYCLIZED- | | | | C | L | E | L | D | K | W | A | S | L | A | N | W | F | C |
| T608 | X | X | | | | | | | | | | | | | | | | | | | | | | | | | | C | L | E | L | D | K | W | A | S | L | A | N | W | F | C |
| T609 | X | X | | | | | | | | | | | | | | | | | | | | | CYCLIZED- | | | | C | L | E | L | D | K | W | A | S | L | W | N | F | F | C |
| T610 | X | X | | | | | | | | | | | | | | | | | | | | | | | | | | | L | E | L | D | K | W | A | S | L | W | N | W | F |
| T611 | X | X | | | | | | | | | | | | | | | | | | | | | | | | | | | L | E | L | D | K | W | A | S | L | A | N | A | F |
| T612 | X | X | | | | | | | | | | | | | | | | | | | | | | | | | | | L | E | L | D | K | W | A | S | L | F | N | F | F |
| T222 | X | X | | | | | | | | | | | | | | | | | | | | | | | | | | | L | E | L | D | K | W | A | S | L | A | N | W | F |
| T223 | X | X | | | | | | | | | | | | | | | | | | | | | | | | | | | L | E | L | D | K | W | A | S | L | W | N | W | A |
| T60/T224 | X | | | | | | | | | | | | | | | | | | | | | | | | | | | L | K | L | D | K | W | A | S | L | W | N | W | F |
| T225 | X | X | | | | | | | | | | | | | | | | | | | | | | | | | | | L | E | L | K | K | W | A | S | L | W | N | W | F |
| T226 | X | X | | | | | | | | | | | | | | | | | | | | | | | | | | | | E | L | L | D | K | W | A | S | L | W | N | W | F |
| T227 | X | X | | | | | | | | | | | | | | | | | | | | | | | | | | | | | | L | D | K | W | A | S | L | W | N | W | F |

FIG. 49G

| | |
|---|---|
| T220 | 59000 |
| T221 | 16000 |
| T234 | >100000 |
| T235 | 53000 |
| T570 | >100000 |
| T381 | 89000 |
| T382 | 190000 |
| T677 | 6310 |
| T376 | >100000 |
| T589 | 745000 |
| T377 | 69000 |
| T590 | 30290 |
| T378 | 95000 |
| T591 | 59000 |
| T270 | >200000 |
| T271 | 16000 |
| T272 | 1000 |
| T273 | >100000 |
| T608 | >100000 |
| T609 | >100000 |
| T610 | >100000 |
| T611 | 70000 |
| T612 | >100000 |
| T222 | 49000 |
| T223 | 57000 |
| T60/T224 | 77000 |
| T225 | >100000 |
| T226 | >100000 |
| T227 | >100000 |

FIG. 49H

FIG. 49I

HIV-1 Bru 178 CONTRUCTS, MUTATIONS

| | Pt. MUTANTS | REMOVED | ADDED | AA# | | | | | | | | | | | | | | | | | | | | | |
|---|---|---|---|---|---|---|---|---|---|---|---|---|---|---|---|---|---|---|---|---|---|---|---|---|---|
| | | | | | 6 | 6 | 6 | 6 | 6 | 6 | 6 | 6 | 6 | 6 | 6 | 6 | 6 | 6 | 6 | 5 | 5 | 5 | 5 | 5 | 5 |
| | | | | | 1 | 3 | \ | \ | 4 | 4 | 4 | 4 | 4 | 4 | 4 | 4 | 4 | 4 | 4 | 5 | 5 | 5 | 5 | 5 | 5 |
| | | | | | 3 | 3 | \ | W | 3 | 4 | 5 | 6 | 7 | 8 | 9 | 0 | 1 | 2 | 3 | 0 | 1 | 2 | 3 | 4 | 5 |
| | | | | | | | W | | Y | T | S | L | I | H | S | L | I | E | E | S | | | | | |
| T595 | | X | | C,G,G | | | | | | | | | | | | | | | | | | | | | |
| T574 | | X | | C13H27CO- | | | | | | Y | T | S | L | I | H | S | L | I | E | E | S | | | | |
| T680 | | X | | FREE TERMINI | | | | | | Y | T | S | L | I | H | S | L | I | E | E | S | | | | |
| T573 | | X | | NO AC- | | | | | | Y | T | S | L | I | H | S | L | I | E | E | S | | | | |
| T84 | | X | | DIG- | | | | | | Y | T | S | L | I | H | S | L | I | E | E | S | | | | |
| T83 | | X | | BIOTIN- | | | | | | Y | T | S | L | I | H | S | L | I | E | E | S | | | | |
| T708 | | X | | BIOTIN-NH(CH2)6CO- | | | | | | Y | T | S | L | I | H | S | L | I | E | E | S | | | | |
| T707 | | X | | BIOTIN-NH(CH2)4CO- | | | | | | Y | T | S | L | I | H | S | L | I | E | E | S | | | | |
| T20 | | | | | | | | | | Y | T | S | L | I | H | S | L | I | E | E | S | | | | |
| T95 | X | | | | | | | | | Y | T | S | L | I | H | S | L | I | E | E | S | | | | |
| T96 | X | | | | | | | | | Y | T | S | L | I | H | S | L | I | E | E | S | | | | |
| T97 | X | | | | | | | | | Y | T | S | L | I | H | S | L | I | E | E | S | | | | |
| T98 | X | | | | | | | | | Y | T | S | L | I | H | S | L | I | E | E | S | | | | |

FIG. 49J

| | | | | | | | | | | | | | | | | | | 7 | | 7 | | | | HIV-1/IIIB IC50 (ng/ml) |
|---|---|---|---|---|---|---|---|---|---|---|---|---|---|---|---|---|---|---|---|---|---|---|---|---|
| 6 | 6 | 6 | 6 | 6 | 6 | 6 | 6 | 6 | 6 | 6 | 6 | 6 | 6 | 6 | 6 | 6 | 6 | 1 | 6 | 7 | | | | |
| 5 | 5 | 5 | 5 | 6 | 6 | 6 | 6 | 6 | 6 | 6 | 6 | 6 | 7 | 7 | 7 | 7 | 7 | \ | 7 | 7 | | | | |
| 6 | 7 | 8 | 9 | 0 | 1 | 2 | 3 | 4 | 5 | 6 | 7 | 8 | 0 | 1 | 2 | 3 | 5 | | 7 | 8 | | | | |
| Q | N | Q | E | K | N | E | Q | E | L | L | D | K | W | A | S | L | W | | N | F | | | | |
| Q | N | Q | E | K | N | E | Q | E | L | L | D | K | W | A | S | L | W | | N | F | T595 | | | 112 |
| Q | N | Q | E | K | N | E | Q | E | L | L | D | K | W | A | S | L | W | | N | F | T574 | | | ND |
| Q | N | Q | E | K | N | E | Q | E | L | L | D | K | W | A | S | L | W | | N | F | I680 | | | 70 |
| Q | N | Q | E | K | N | E | Q | E | L | L | D | K | W | A | S | L | W | | N | F | T573 | | | ND |
| Q | N | Q | E | K | N | E | Q | E | L | L | D | K | W | A | S | L | W | | N | F | T84 | | | ND |
| Q | N | Q | E | K | N | E | Q | E | L | L | D | K | W | A | S | L | W | | N | F | T83 | | | 15 |
| Q | N | Q | E | K | N | E | Q | E | L | L | D | K | W | A | S | L | W | | N | F | T708 | | | ND |
| Q | N | Q | E | K | N | E | Q | E | L | L | D | K | W | A | S | L | W | | N | F | T707 | | | ND |
| Q | N | Q | E | K | N | E | Q | E | L | L | D | K | W | A | S | L | N | | A | F | T20 | | | 0.6 |
| Q | N | Q | E | K | N | E | Q | E | L | L | D | K | W | A | S | L | W | | N | F | T95 | | | 43 |
| Q | N | Q | E | K | N | E | Q | E | L | L | D | K | W | A | S | A | N | | W | F | T96 | | | 1 |
| Q | N | Q | E | K | N | E | Q | Q | L | L | D | K | W | A | S | L | W | | N | F | T97 | | | 2 |
| Q | N | Q | E | K | N | E | Q | E | L | L | D | K | W | A | S | L | W | | N | F | T98 | | | 10 |

FIG.49K

| | | | | | | | | | | | |
|---|---|---|---|---|---|---|---|---|---|---|---|
| T99 | X | | | | | | | | | | |
| T103 | X | Y | T | S | L | Q | S | L | I | E | S |
| T212 | X | Y | T | S | L | H | S | L | I | E | S |
| T213 | X | Y | T | S | L | H | S | L | I | E | S |
| T214 | X | Y | T | S | L | H | S | L | I | E | S |
| T215 | X | Y | T | S | L | H | S | L | I | Q | S |
| T216 | X | Y | T | S | L | H | S | L | I | Q | S |
| T229 | X | Y | T | S | L | H | S | L | I | E | S |
| T230 | X | Y | T | S | L | H | S | L | I | E | S |
| T231 | X | Y | T | S | L | Q | S | L | I | E | S |
| T379 | X | Y | T | S | L | H | S | L | I | E | S |
| T701 | X | Y | T | S | L | H | S | L | I | E | S |
| T702 | X | Y | T | S | L | H | S | L | I | E | S |
| T703 | X | Y | T | S | L | H | S | L | I | E | S |
| T704 | X | Y | T | S | L | H | S | L | I | E | S |
| T705 | X | Y | T | S | L | H | S | L | I | E | S |
| T706 | X | Y | T | S | L | H | S | L | I | E | S |
| T156 | X | L | L | D | N | F | E | S | T | W | E | Q | S |
| T89 | X | L | L | D | N | F | E | S | T | W | E | Q | S |
| T90 | X | L | S | N | L | L | Q | I | S | N | S | D |

| | | | | | | | | | | | | | | | | | | | | | | ID | Value |
|---|---|---|---|---|---|---|---|---|---|---|---|---|---|---|---|---|---|---|---|---|---|---|---|
| Q | N | Q | E | K | N | Q | E | L | L | E | L | D | K | W | A | S | L | W | N | W | F | T99 | 56 |
| Q | N | Q | E | K | N | Q | E | L | L | E | L | D | K | W | A | S | L | W | N | W | F | T103 | ND |
| Q | N | Q | E | K | N | Q | E | L | L | E | L | D | K | W | A | S | L | W | N | W | F | T212 | 3 |
| Q | N | Q | E | K | N | Q | E | L | L | E | L | D | K | W | A | S | L | W | N | W | F | T213 | 25 |
| Q | N | Q | E | K | N | Q | E | L | L | E | L | N | K | W | A | S | L | W | N | W | F | T214 | 19 |
| Q | N | Q | E | K | N | Q | E | L | L | E | L | D | K | W | A | S | L | W | N | W | F | T215 | 23 |
| Q | N | Q | E | Q | N | Q | E | L | L | Q | L | D | K | W | A | S | L | W | N | W | F | T216 | 1000 |
| Q | N | Q | E | K | N | Q | E | L | L | E | L | D | K | W | E | A | N | A | N | A | A | T229 | >100000 |
| Q | N | Q | E | K | N | Q | E | L | L | Q | L | D | K | W | A | S | L | W | N | W | F | T230 | 6 |
| Q | N | Q | E | K | N | Q | E | L | L | Q | L | D | K | W | A | S | L | W | N | W | F | T231 | 4 |
| Q | N | Q | E | K | L | Q | E | L | L | E | L | D | K | W | A | S | L | F | N | F | F | T379 | 0.3 |
| Q | N | Q | E | K | N | Q | E | L | L | E | L | F | D | W | A | S | L | W | N | W | F | T701 | 3 |
| Q | N | Q | E | K | N | Q | E | L | L | E | L | D | K | W | A | S | L | W | N | W | F | T702 | 36 |
| Q | N | Q | E | K | N | Q | E | L | L | E | L | D | K | P | A | S | P | W | N | W | F | T703 | 0.5 |
| Q | N | Q | E | K | N | Q | E | L | L | E | L | D | K | W | A | S | L | W | N | W | F | T704 | 510 |
| Q | N | Q | E | K | N | Q | E | L | L | E | L | D | K | W | A | S | L | W | N | S | F | T705 | 14 |
| Q | N | Q | E | Q | Q | E | I | S | I | Q | N | L | H | K | S | A | L | Q | E | Y | W | T706 | 68 |
| Q | N | Q | E | Q | Q | E | I | S | I | Q | N | L | H | K | S | A | L | Q | E | Y | W | T156 | 80000 |
| K | W | E | A | L | E | I | E | H | E | K | W | K | L | T | Q | W | Q | S | Y | E | Q | T89 | >100000 |
| E | W | L | E | A | L | E | I | E | H | E | K | W | K | L | T | Q | W | Q | S | Y | E | Q | T90 | >100000 |

FIG.49L

| HIV-1 BRU DP-107 PEPTIDES | | | | 5 | 5 | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | | | | | 1 | 1 | 4 | | | | | | | | | | | | | | | | | | | | | | | | | |
| | | | | | | 0 | 0 | | | | | | | | | | | | | | | | | | | | | | | | | |
| | | | | | v | | | M | T | L | T | V | Q | A | R | Q | L | L | S | Q | I | V | Q | Q | N | N | L | L | R | A | I | E | A | Q | Q | H | L | L | Q | L | T | V | W | G | I | K | Q | L |
| | WALK | TRUNCATION | ADDITION | | | | | | | | | | | | | | | | | | | | | | | | | | | | | |
| T10 | 28-MER | | UNBLOCKED | | | | | M | T | L | T | V | Q | A | R | Q | L | L | S | Q | I | V | Q | Q | N | N | L | L | R | A | I | E | A | Q | Q | H | L | L | Q | L | T | V | W | G | I | K | Q | L |
| T37 | 28-MER | | | | | | | M | T | L | T | V | Q | A | R | Q | L | L | S | Q | I | V | Q | Q | N | N | L | L | R | A | I | E | A | Q | | | | | | | | | | | | | | |
| T48 | 28-MER | | | | | | | | | | | | Q | A | R | Q | L | L | S | Q | I | V | Q | Q | N | N | L | L | R | A | I | E | A | Q | Q | H | L | L | Q | | | | | | | | |
| T36 | 28-MER | | | | | | | | | | | | | | R | Q | L | L | S | Q | I | V | Q | Q | N | N | L | L | R | A | I | E | A | Q | Q | H | L | L | Q | L | T | | | | | | |
| T8 | 28-MER | | UNBLOCKED | | | | | | | | | | | | | | | | | | | V | Q | Q | N | N | L | L | R | A | I | E | A | Q | Q | H | L | L | Q | L | T | V | W | G | I | K | Q | L |
| T33 | 28-MER | | | | | | | | | | | | | | | | | | | | | V | Q | Q | N | N | L | L | R | A | I | E | A | Q | Q | H | L | L | Q | L | T | V | W | G | I | K | Q | L |
| T21 | 38-MER | | BIOTIN | | | | | | | | | | | | | | | | | | | | | | N | N | L | L | R | A | I | E | A | Q | Q | H | L | L | Q | L | T | V | W | G | I | K | Q | L |
| T85 | | | | | | | | | | | | | | | | | | | | | | | | | N | N | L | L | R | A | I | E | A | Q | Q | H | L | L | Q | L | T | V | W | G | I | K | Q | L |
| T1 | | x | | | | | | | | | | | | | | | | | | | | | | | | | | | BIOTIN | | | | | | | | | | | | | | | | | | | |
| T2 | | x | UNBLOCKED | | | | | | | | | | | | | | | | | | | | | | | | | | | | | | | | | | | | | | | | G | I | K | Q | L |
| T7 | | x | UNBLOCKED | | | | | | | | | | | | | | | | | | | | | | | | | | | | | | | | | | | | | | T | V | W | G | I | K | Q | L |
| T34 | | x | | | | | | | | | | | | | | | | | | | | | | | | | | | | | | | | | | | | | Q | L | T | V | W | G | I | K | Q | L |
| T6 | 28-MER | | UNBLOCKED | | | | | | | | | | | | | | | | | | | | | | | | L | L | R | A | I | E | A | Q | Q | H | L | L | Q | L | T | V | W | G | I | K | Q | L |
| T35 | 28-MER | | | | | | | | | | | | | | | | | | | | | | | | | | | L | R | A | I | E | A | Q | Q | H | L | L | Q | L | T | V | W | G | I | K | Q | L |
| T5 | 28-MER | | | | | | | | | | | | | | | | | | | | | | | | | | | | | | | | | | Q | H | L | L | Q | L | T | V | W | G | I | K | Q | L |

FIG.50A

| | | | | | | | | | | | | | | | | | | | | | | |
|---|---|---|---|---|---|---|---|---|---|---|---|---|---|---|---|---|---|---|---|---|---|---|
| | | | | | | | | | | | | | | | | | | | | | | |
| | | | | | | | | | | | | | | | | | | | | 6 | | |
| | | | | | | | | | | | | | | | | | | | | 0 | | |
| | | | | | | | | | | | | | | | | | | | | 2 | | |
| Q | A | R | I | L | A | V | E | R | Y | L | K | D | Q | Q | L | L | G | I | W | G | | |
| | | | | | | | | | | | | | | | | | | | | | | |
| | | | | | | | | | | | | | | | | | | | | | | |
| | | | | | | | | | | | | | | | | | | | | | | HIV/IIIB |
| | | | | | | | | | | | | | | | | | | | | | | IC50(µg/ml) |
| | | | | | | | | | | | | | | | | | | | | | T10 | 50 |
| | | | | | | | | | | | | | | | | | | | | | T37 | 75* |
| | | | | | | | | | | | | | | | | | | | | | T48 | 83* |
| | | | | | | | | | | | | | | | | | | | | | T36 | 45* |
| | | | | | | | | | | | | | | | | | | | | | T8 | 50 |
| | | | | | | | | | | | | | | | | | | | | | T33 | >100* |
| Q | A | R | I | L | A | V | E | R | Y | L | K | D | Q | | | | | | | | T21 | 2 |
| Q | A | R | I | L | A | V | E | R | Y | L | K | D | Q | | | | | | | | T86 | 2 |
| Q | A | R | I | L | A | V | E | R | Y | L | K | D | Q | | | | | | | | T1 | >100 |
| | | | | | | | | | | | | | | | | | | | | | T2 | ND |
| Q | A | R | I | L | A | V | | | | | | | | | | | | | | | T7 | 26 |
| A | R | I | L | A | V | | | | | | | | | | | | | | | | T34 | >100* |
| Q | A | R | I | L | A | V | E | R | Y | L | K | D | Q | | | | | | | | T6 | 44 |
| Q | A | R | I | L | A | V | E | R | Y | L | K | D | Q | | | | | | | | T35 | >100* |
| Q | A | R | I | L | A | V | E | R | Y | L | K | D | Q | Q | L | L | G | I | W | G | T3 | 55 |

FIG.50B

EPSTEIN-BARR VIRUS STRAIN B95.8 BZLF1 TRANSACTIVATOR PROTEIN EB1 OR ZEBRA

| RESIDUE | 173 | 174 | 175 | 176 | 177 | 178 | 179 | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | | 219 | | ACT | RES |
|---|---|---|---|---|---|---|---|---|---|---|---|---|---|---|---|---|---|---|---|---|---|---|---|---|---|---|---|---|---|---|---|---|---|---|---|---|---|---|---|---|
| | S | E | L | E | I | K | R | Y | K | N | R | V | A | S | R | K | C | R | A | K | F | K | Q | L | L | Q | H | Y | R | E | V | A | A | A | K | S | S | E | N | D | R | L | R | L | L | L | | | | |
| T-423 | S | E | L | E | I | K | R | Y | K | N | R | V | A | S | R | K | C | R | A | K | F | K | Q | L | L | Q | H | Y | R | E | V | A | A | A | K | | | | 208 | ++ | 35 |
| T-424 | | E | L | E | I | K | R | Y | K | N | R | V | A | S | R | K | C | R | A | K | F | K | Q | L | L | Q | H | Y | R | E | V | A | A | A | K | S | | | 209 | - | 35 |
| T-425 | | | L | E | I | K | R | Y | K | N | R | V | A | S | R | K | C | R | A | K | F | K | Q | L | L | Q | H | Y | R | E | V | A | A | A | K | S | S | | 210 | - | 35 |
| T-426 | | | | E | I | K | R | Y | K | N | R | V | A | S | R | K | C | R | A | K | F | K | Q | L | L | Q | H | Y | R | E | V | A | A | A | K | S | S | E | 211 | - | 35 |
| T-427 | | | | | I | K | R | Y | K | N | R | V | A | S | R | K | C | R | A | K | F | K | Q | L | L | Q | H | Y | R | E | V | A | A | A | K | S | S | E | N | 212 | - | 35 |
| T-428 | | | | | | K | R | Y | K | N | R | V | A | S | R | K | C | R | A | K | F | K | Q | L | L | Q | H | Y | R | E | V | A | A | A | K | S | S | E | N | D | 213 | - | 35 |
| T-429 | | | | | | | R | Y | K | N | R | V | A | S | R | K | C | R | A | K | F | K | Q | L | L | Q | H | Y | R | E | V | A | A | A | K | S | S | E | N | D | R | 214 | - | 35 |
| T-430 | | | | | | | | Y | K | N | R | V | A | S | R | K | C | R | A | K | F | K | Q | L | L | Q | H | Y | R | E | V | A | A | A | K | S | S | E | N | D | R | L | 215 | - | 35 |
| T-431 | | | | | | | | | K | N | R | V | A | S | R | K | C | R | A | K | F | K | Q | L | L | Q | H | Y | R | E | V | A | A | A | K | S | S | E | N | D | R | L | R | 216 | - | 35 |
| T-432 | | | | | | | | | | N | R | V | A | S | R | K | C | R | A | K | F | K | Q | L | L | Q | H | Y | R | E | V | A | A | A | K | S | S | E | N | D | R | L | R | L | 217 | - | 35 |
| T-433 | | | | | | | | | | | R | V | A | S | R | K | C | R | A | K | F | K | Q | L | L | Q | H | Y | R | E | V | A | A | A | K | S | S | E | N | D | R | L | R | L | L | 218 | - | 35 |
| T-434 | | | | | | | | | | | | V | A | S | R | K | C | R | A | K | F | K | Q | L | L | Q | H | Y | R | E | V | A | A | A | K | S | S | E | N | D | R | L | R | L | L | L | 219 | - | 35 |

FIG.51A

| RESIDUE | | | | | | | | | | | | | | | | | | | | | ACT | RES |
|---|---|---|---|---|---|---|---|---|---|---|---|---|---|---|---|---|---|---|---|---|---|---|
| | | | | | | | | | | | | | | | | | | | | 230 | | 45 |
| T-435 | 185 | A | S | R | K | C | R | A | K | F | K | Q | L | L | Q | H | Y | R | E | V | A | A | A | K | S | S | E | N | D | R | L | R | L | L | L | K | | | | | | | |
| T-435 | 185 | A | S | R | K | C | R | A | K | F | K | Q | L | L | Q | H | Y | R | E | V | A | A | A | K | S | S | E | N | D | R | L | R | L | L | L | K | | | | | 220 | – | 35 |
| T-436 | 186 | | S | R | K | C | R | A | K | F | K | Q | L | L | Q | H | Y | R | E | V | A | A | A | K | S | S | E | N | D | R | L | R | L | L | L | K | Q | | | | 221 | – | 35 |
| T-437 | 187 | | | R | K | C | R | A | K | F | K | Q | L | L | Q | H | Y | R | E | V | A | A | A | K | S | S | E | N | D | R | L | R | L | L | L | K | Q | M | | | 222 | – | 35 |
| T-438 | 188 | | | | K | C | R | A | K | F | K | Q | L | L | Q | H | Y | R | E | V | A | A | A | K | S | S | E | N | D | R | L | R | L | L | L | K | Q | M | C | | 223 | – | 35 |
| T-439 | 189 | | | | | C | R | A | K | F | K | Q | L | L | Q | H | Y | R | E | V | A | A | A | K | S | S | E | N | D | R | L | R | L | L | L | K | Q | M | C | P | 224 | +++ | 35 |
| T-440 | 190 | | | | | | R | A | K | F | K | Q | L | L | Q | H | Y | R | E | V | A | A | A | K | S | S | E | N | D | R | L | R | L | L | L | K | Q | M | C | P | S | 225 | – | 35 |
| T-441 | 191 | | | | | | | A | K | F | K | Q | L | L | Q | H | Y | R | E | V | A | A | A | K | S | S | E | N | D | R | L | R | L | L | L | K | Q | M | C | P | S | L | 226 | + | 35 |
| T-442 | 192 | | | | | | | | K | F | K | Q | L | L | Q | H | Y | R | E | V | A | A | A | K | S | S | E | N | D | R | L | R | L | L | L | K | Q | M | C | P | S | L | D | 227 | – | 35 |
| T-443 | 193 | | | | | | | | | F | K | Q | L | L | Q | H | Y | R | E | V | A | A | A | K | S | S | E | N | D | R | L | R | L | L | L | K | Q | M | C | P | S | L | D | V | 228 | – | 35 |
| T-444 | 194 | | | | | | | | | | K | Q | L | L | Q | H | Y | R | E | V | A | A | A | K | S | S | E | N | D | R | L | R | L | L | L | K | Q | M | C | P | S | L | D | V | D | 229 | + | 35 |
| T-445 | 195 | | | | | | | | | | | Q | L | L | Q | H | Y | R | E | V | A | A | A | K | S | S | E | N | D | R | L | R | L | L | L | K | Q | M | C | P | S | L | D | V | D | S | 230 | + | 35 |
| T-446 | 196 | | | | | | | | | | | | L | L | Q | H | Y | R | E | V | A | A | A | K | S | S | E | N | D | R | L | R | L | L | L | K | Q | M | C | P | S | L | D | V | D | S | I | 231 | – | 35 |

FIG.51B

| RESIDUE | 197 | | | | | | | | | | | | | | | | | | | | 242 | 45 |
|---|---|---|---|---|---|---|---|---|---|---|---|---|---|---|---|---|---|---|---|---|---|---|
| T-447 | | L | Q | H | Y | R | E | V | A | A | K | S | S | E | N | D | R | L | R | L | | |
| T-448 | 197 | | L | Q | H | Y | R | E | V | A | A | K | S | S | E | N | D | R | L | R | L | 232 | 35 |
| T-449 | 198 | | | Q | H | Y | R | E | V | A | A | K | S | S | E | N | D | R | L | R | L | 233 | 35 |
| # | 199 | | | | H | Y | R | E | V | A | A | K | S | S | E | N | D | R | L | R | L | 234 | 35 |
| T-451 | 200 | | | | | Y | R | E | V | A | A | K | S | S | E | N | D | R | L | R | L | 235 | 35 |
| T-452 | 201 | | | | | | R | E | V | A | A | K | S | S | E | N | D | R | L | R | L | 236 | 35 |
| T-453 | 202 | | | | | | | E | V | A | A | K | S | S | E | N | D | R | L | R | L | 237 | 35 |
| T-454 | 203 | | | | | | | | V | A | A | K | S | S | E | N | D | R | L | R | L | 238 | 35 |
| T-455 | 204 | | | | | | | | | A | A | K | S | S | E | N | D | R | L | R | L | 239 | 35 |
| T-456 | 205 | | | | | | | | | | A | A | K | S | S | E | N | D | R | L | R | L | 240 | 35 |
| T-457 | 206 | | | | | | | | | | | A | K | S | S | E | N | D | R | L | R | L | 241 | 35 |
| T-458 | 207 | | | | | | | | | | | | K | S | S | E | N | D | R | L | R | L | 242 | 35 |
| | 208 | | | | | | | | | | | | | S | S | E | N | D | R | L | R | L | 243 | 35 |

| RESIDUE | 209 | | | | | | | | | | | | | | | | | | | | | 246 | 37 |
|---|---|---|---|---|---|---|---|---|---|---|---|---|---|---|---|---|---|---|---|---|---|---|---|
| T-459 | 209 | S | E | N | D | R | L | R | L | L | K | Q | M | C | P | S | L | D | V | D | S | I | I | P R T P D V L H E D L L N F |
| T-460 | 210 | S | E | N | D | R | L | R | L | L | K | Q | M | C | P | S | L | D | V | D | S | I | I | P R T P D V L H E D L L N | 244 | 35 |
| T-461 | 211 | | E | N | D | R | L | R | L | L | K | Q | M | C | P | S | L | D | V | D | S | I | I | P R T P D V L H E D L L N F | 245 | 35 |
| | | | | N | D | R | L | R | L | L | K | Q | M | C | P | S | L | D | V | D | S | I | I | P R T P D V L H E D L L N F | 246 | 35 |

FIG.51C

DOMAIN I:
174 P-L-L-V-L-Q-A-G-F-F-L-L-T-R-I-L-T-I-P-Q-S-L-D-S-W-W-T-S-L-N-F-L-G-G-G-T-T-V-C-L-G-Q-N-S-Q-S-P 220

METHODS FOR INHIBITION OF MEMBRANE FUSION-ASSOCIATED EVENTS, INCLUDING RESPIRATORY SYNCYTIAL VIRUS TRANSMISSION

This is a Continuation-In-Part of application Ser. No. 08/360,107 filed Dec. 20, 1994, now U.S. Pat. No. 6,017,536, which is a Continuation-In-Part of application Ser. No. 08/255,208 filed Jun. 7, 1994, which is a continuation in part of application Ser. No. 08/073,028, now U.S. Pat. No. 5,464,933, each of which is incorporated herein by reference in its entirety.

This invention was made with Government support under Grant No. A1-30411-02 awarded by the National Institutes of Health. The Government has certain rights in the invention.

1. INTRODUCTION

The present invention relates, first, to DP178 (SEQ ID NO:1), a peptide corresponding to amino acids 638 to 673 of the HIV-1$_{LAI}$ transmembrane protein (TM) gp41, and portions or analogs of DP178 (SEQ ID NO:1), which exhibit anti-membrane fusion capability, antiviral activity, such as the ability to inhibit HIV transmission to uninfected CD-4$^+$ cells, or an ability to modulate intracellular processes involving coiled-coil peptide structures. Further, the invention relates to the use of DP178 (SEQ ID NO:1) and DP178 portions and/or analogs as antifusogenic or antiviral compounds or as inhibitors of intracellular events involving coiled-coil peptide structures. The present invention also relates to peptides analogous to DP107 (SEQ ID NO:25), a peptide corresponding to amino acids 558 to 595 of the HIV-1$_{LAI}$ transmembrane protein (TM) gp41, having amino acid sequences present in other viruses, such as enveloped viruses, and/or other organisms, and further relates to the uses of such peptides. These peptides exhibit anti-membrane fusion capability, antiviral activity, or the ability to modulate intracellular processes involving coiled-coil peptide structures. The present invention additionally relates to methods for identifying compounds that disrupt the interaction between DP178 and DP107, and/or between DP107-like and DP178-like peptides. Further, the invention relates to the use of the peptides of the invention as diagnostic agents. For example, a DP178 peptide may be used as an HIV subtype-specific diagnostic. The invention is demonstrated, first, by way of an Example wherein DP178 (SEQ ID:1), and a peptide whose sequence is homologous to DP178 are each shown to be potent, non-cytotoxic inhibitors of HIV-1 transfer to uninfected CD-4$^+$ cells. The invention is further demonstrated by Examples wherein peptides having structural and/or amino acid motif similarity to DP107 and DP178 are identified in a variety of viral and nonviral organisms, and in examples wherein a number of such identified peptides derived from several different viral systems are demonstrated to exhibit antiviral activity.

2. BACKGROUND OF THE INVENTION

2.1 Membrane Fusion Events

Membrane fusion is a ubiquitous cell biological process (for a review, see White, J. M., 1992, Science 258:917–924). Fusion events which mediate cellular housekeeping functions, such as endocytosis, constitutive secretion, and recycling of membrane components, occur continuously in all eukaryotic cells.

Additional fusion events occur in specialized cells. Intracellularly, for example, fusion events are involved in such processes as occur in regulated exocytosis of hormones, enzymes and neurotransmitters. Intercellularly, such fusion events feature prominently in, for example, sperm-egg fusion and myoblast fusion.

Fusion events are also associated with disease states. For example, fusion events are involved in the formation of giant cells during inflammatory reactions, the entry of all enveloped viruses into cells, and, in the case of human immunodeficiency virus (HIV), for example, are responsible for the virally induced cell-cell fusion which leads to cell death.

2.2. The Human Immunodeficiency Virus

The human immunodeficiency virus (HIV) has been implicated as the primary cause of the slowly degenerative immune system disease termed acquired immune deficiency syndrome (AIDS) (Barre-Sinoussi, F. et al., 1983, Science 220:868–870; Gallo, R. et al., 1984, Science 224:500–503). There are at least two distinct types of HIV: HIV-1 (Barre-Sinoussi, F. et al., 1983, Science 220:868–870; Gallo R. et al., 1984, Science 224:500–503) and HIV-2 (Clavel, F. et al., 1986, Science 233:343–346; Guyader, M. et al., 1987, Nature 326:662–669). Further, a large amount of genetic heterogeneity exists within populations of each of these types. Infection of human CD-4$^+$ T-lymphocytes with an HIV virus leads to depletion of the cell type and eventually to opportunistic infections, neurological dysfunctions, neoplastic growth, and ultimately death.

HIV is a member of the lentivirus family of retroviruses (Teich, N. et al., 1984, RNA Tumor Viruses, Weiss, R. et al., eds., CSH-Press, pp. 949–956). Retroviruses are small enveloped viruses that contain a diploid, single-stranded RNA genome, and replicate via a DNA intermediate produced by a virally-encoded reverse transcriptase, an RNA-dependent DNA polymerase (Varmus, H., 1988, Science 240:1427–1439). Other retroviruses include, for example, oncogenic viruses such as human T-cell leukemia viruses (HTLV-I,-II,-III), and feline leukemia virus.

The HIV viral particle consists of a viral core, composed of capsid proteins, that contains the viral RNA genome and those enzymes required for early replicative events. Myristylated Gag protein forms an outer viral shell around the viral core, which is, in turn, surrounded by a lipid membrane enveloped derived from the infected cell membrane. The HIV enveloped surface glycoproteins are synthesized as a single 160 Kd precursor protein which is cleaved by a cellular protease during viral budding into two glycoproteins, gp41 and gp120. gp41 is a transmembrane protein and gp120 is an extracellular protein which remains non-covalently associated with gp41, possibly in a trimeric or multimeric form (Hammarskjold, M. and Rekosh, D., 1989, Biochem. Biophys. Acta 989:269–280).

HIV is targeted to CD-4$^+$ cells because the CD-4 cell surface protein acts as the cellular receptor for the HIV-1 virus (Dalgleish, A. et al., 1984, Nature 312:763–767; Klatzmann et al., 1984, Nature 312:767–768; Maddon et al., 1986, Cell 47:333–348). Viral entry into cells is dependent upon gp120 binding the cellular CD-4$^+$ receptor molecules (McDougal, J. S. et al., 1986, Science 231:382–385; Maddon, P. J. et al., 1986, Cell 47:333–348) and thus explains HIV's tropism for CD-4$^+$ cells, while gp41 anchors the enveloped glycoprotein complex in the viral membrane.

2.3. HIV Treatment

HIV infection is pandemic and HIV associated diseases represent a major world health problem. Although considerable effort is being put into the successful design of effective therapeutics, currently no curative anti-retroviral drugs against AIDS exist. In attempts to develop such drugs, several stages of the HIV life cycle have been considered as targets for therapeutic intervention (Mitsuya, H. et al., 1991, FASEB J. 5:2369–2381). For example, virally encoded reverse transcriptase has been one focus of drug development. A number of reverse-transcriptase-targeted drugs, including 2',3'-dideoxynucleoside analogs such as AZT, ddI, ddc, and d4T have been developed which have been shown to been active against HIV (Mitsuya, H. et al., 1991, Science 249:1533–1544). While beneficial, these nucleoside analogs are not curative, probably due to the rapid appearance of drug resistant HIV mutants (Lander, B. et al., 1989, Science 243:1731–1734). In addition, the drugs often exhibit toxic side effects. such as bone marrow suppression, vomiting, and liver function abnormalities.

Attempts are also being made to develop drugs which can inhibit viral entry into the cell, the earliest stage of HIV infection. Here, the focus has thus far been on CD4, the cell surface receptor for HIV. Recombinant'soluble CD4, for example, has been shown to inhibit infection of CD-4$^+$ T-cells by some HIV-1 strains (Smith, D. H. et al., 1987, Science 238:1704–1707). Certain primary HIV-1 isolates, however, are relatively less sensitive to inhibition by recombinant CD-4 (Daar, E. et al., 1990, Proc. Natl. Acad. Sci. USA 87:6574–6579). In addition, recombinant soluble CD-4 clinical trials have produced inconclusive results (Schooley, R. et al., 1990, Ann. Int. Med. 112:247–253; Kahn, J. O. et al., 1990, Ann. Int. Med. 112:254–261; Yarchoan, R. et al., 1989, Proc. Vth Int. Conf. on AIDS, p. 564, MCP 137).

The late stages of HIV replication, which involve crucial virus-specific secondary processing of certain viral proteins, have also been suggested as possible anti-HIV drug targets. Late stage processing is dependent on the activity of a viral protease, and drugs are being developed which inhibit this protease (Erickson, J., 1990, Science 249:527–533). The clinical outcome of these candidate drugs is still in question.

Attention is also being given to the development of vaccines for the treatment of HIV infection. The HIV-1 enveloped proteins (gp160, gp120, gp41) have been shown to be the major antigens for anti-HIV antibodies present in AIDS patients (Barin, et al., 1985, Science 228:1094–1096). Thus far, therefore, these proteins seem to be the most promising candidates to act as antigens for anti-HIV vaccine development. To this end, several groups have begun to use various portions of gp160, gp120, and/or gp41 as immunogenic targets for the host immune system. See for example, Ivanoff, L. et al., U.S. Pat. No. 5,141,867; Saith, G. et al., WO 92/22,654; Shafferman, A., WO 91/09,872; Formoso, C. et al., WO 90/07,119. Clinical results concerning these candidate vaccines, however, still remain far in the future.

Thus, although a great deal of effort is being directed to the design and testing of anti-retroviral drugs, a truly effective, non-toxic treatment is still needed.

3. SUMMARY OF THE INVENTION

The present invention relates, first, to DP178 (SEQ ID:1), a 36-amino acid synthetic peptide corresponding to amino acids 638 to 673 of the transmembrane protein (TM) gp41 from the HIV-1 isolate LAI (HIV-$1_{LAI}$), which exhibits potent anti-HIV-1 activity. As evidenced by the Example presented below, in Section 6, the DP178 (SEQ ID:1) antiviral activity is so high that, on a weight basis, no other known anti-HIV agent is effective at concentrations as low as those at which DP178 (SEQ ID:1) exhibits its inhibitory effects.

The invention further relates to those portions and analogs of DP178 which also show such antiviral activity, and/or show anti-membrane fusion capability, or an ability to modulate intracellular processes involving coiled-coil peptide structures. The term "DP178 analog" refers to a peptide which contains an amino acid sequence corresponding to the DP178 peptide sequence present within the gp41 protein of HIV-$1_{LAI}$, but found in viruses and/or organisms other than HIV-$1_{LAI}$. Such DP178 analog peptides may, therefore, correspond to DP178-like amino acid sequences present in other viruses, such as, for example, enveloped viruses, such as retroviruses other than HIV-$1_{LAI}$, as well as non-enveloped viruses. Further, such analogous DP178 peptides may also correspond to DP178-like amino acid sequences present in nonviral organisms.

The invention further relates to peptides DP107 (SEQ ID NO:25) analogs. DP107 is a peptide corresponding to amino acids 558–595 of the HIV-$1_{LAI}$ transmembrane protein (TM) gp41. The term "DP107 analog" as used herein refers to a peptide which contains an amino acid sequence corresponding to the DP107 peptide sequence present within the gp41 protein of HIV-$1_{LAI}$, but found in viruses and organisms other than HIV-$1_{LAI}$. Such DP107 analog peptides may, therefore, correspond to DP107-like amino acid sequences present in other viruses,.such as, for for example, enveloped viruses, such as retroviruses other than HIV-$1_{LAI}$, as well as non-enveloped viruses. Further, such DP107 analog peptides may also correspond to DP107-like amino acid sequences present in nonviral organisms.

Further, the peptides of the invention include DP107 analog and DP178 analog peptides having amino acid sequences recognized or identified by the 107×178×4, ALL-MOTI5 and/or PLZIP search motifs described herein.

The peptides of the invention may, for example, exhibit antifusogenic activity, antiviral activity, and/or may have the ability to modulate intracellular processes which involve coiled-coil peptide structures. With respect to the-antiviral activity of the peptides of the invention, such an antiviral activity includes, but is not limited to the inhibition of HIV transmission to uninfected CD-4$^+$ cells. Additionally, the antifusogenic capability, antiviral activity or intracellular modulatory activity of the peptides of the invention merely requires the presence of the peptides of the invention,. and,. specifically, does not require the stimulation of a host immune response directed against such peptides.

The peptides of the invention may be used, for example, as inhibitors of membrane fusion-asociated events, such as, for example, the inhibition of human and non-human retroviral, especially HIV, transmission to uninfected cells. It is further contemplated that the peptides of the invention may be used as modulators of intracellular events involving coiled-coil peptide structures.

The peptides of the invention may, alternatively, be used to identify compounds which may themselves exhibit antifusogenic, antiviral, or intracellular modulatory activity. Additional uses include, for example, the use of the peptides of the invention as organism or viral type and/or subtype-specific diagnostic tools.

The terms "antifusogenic" and "anti-membrane fusion", as used herein, refer to an agent's ability to inhibit or reduce the level of membrane fusion events between two or more moieties. relative to the level of membrane fusion which occurs between said moieties in the absence of the peptide. The moieties may be, for example, cell membranes or viral structures, such as viral envelopes or pili. The term "antiviral", as used herein, refers to the compound's ability to inhibit viral infection of cells, via, for example, cell-cell fusion or free virus infection. Such infection may involve membrane fusion, as occurs in the case of enveloped viruses, or some other fusion event involving a viral structure and a cellular structure (e. g., such as the fusion of a viral pilus and bacterial membrane during bacterial conjugation).

It is also contemplated that the peptides of the invention may exhibit the ability to modulate intracellular events involving coiled-coil peptide structures. "Modulate", as used herein, refers to a stimulatory or inhibitory effect on the intracellular process of interest relative to the level or activity of such a process in the absence of a peptide of the invention.

Embodiments of the invention are demonstrated below wherein an extremely low concentration of DP178 (SEQ ID:1), and very low concentrations of a DP178 homolog (SEQ ID:3) are shown to be potent inhibitors of HIV-1 mediated CD-4$^+$ cell-cell fusion (i.e., syncytial formation) and infection of CD-4$^+$ cells by cell-free virus. Further, it is shown that DP178 (SEQ ID:1) is not toxic to cells, even at concentrations 3 logs higher than the inhibitory DP-178 (SEQ ID:1) concentration.

The present invention is based, in part, on the surprising discovery that the DP107 and DP178 domains of the HIV gp41 protein non-covalently complex with each other, and that their interaction is required for the normal infectivity of the virus. This discovery is described in the Example presented, below, in Section 8. The invention, therefore, further relates to methods for identifying antifusogenic, including antiviral, compounds that disrupt the interaction between DP107 and DP178, and/or between DP107-like and DP178-like peptides.

Additional embodiments of the invention (specifically, the Examples presents in Sections 9–16 and 19–25, below) are demonstrated, below, wherein peptides, from a variety of viral and nonviral sources, having structural and/or amino acid motif similarity to DP107 and DP178 are identified, and search motifs for their identification are described. Further, Examples (in Sections 17, 18, 25–29) are presented wherein a number of the peptides of the invention are demonstrated exhibit substantial antiviral activity or activity predictive of antiviral. activity.

3.1. Definitions

Peptides are defined herein as organic compounds comprising two or more amino Acids covalently joined by peptide bonds. Peptides may be referred to with respect to the number of constituent amino acids, i.e., a dipeptide contains two amino acid residues, a tripeptide contains three, etc. Peptides containing ten or fewer amino acids may be referred to as oligopeptides, while those with more than ten amino acid residues are polypeptides. Such peptides may also include any of the modifications and additional amino and carboxy groups as are described herein.

Peptide sequences defined herein are represented by one-letter symbols for amino acid residues as follows:

A (alanine)
R (arginine)
N (asparagine)
D (aspartic acid)
C (cysteine)
Q (glutamine)
E (glutamic acid)
G (glycine)
H (histidine)
I (isoleucine)
L (leucine)
K (lysine)
M (methionine)
F (phenylalanine)
P (proline)
S (serine)
T (threonine)
W (tryptophan)
Y (tyrosine)
V (valine)

4. BRIEF DESCRIPTION OF THE FIGURES

FIG. 1. Amino acid sequence of DP178 (SEQ ID:1) derived from HIV$_{LAI}$; DP178 homologs derived from HIV-1$_{SF2}$ (DP-185; SEQ ID:3), HIV-1$_{RF}$ (SEQ ID:4), and HIV-1$_{MN}$ (SEQ ID:5); DP178 homologs derived from amino acid sequences of two prototypic HIV-2 isolates, namely, HIV-2$_{rod}$ (SEQ ID:6) and HIV-2$_{NHZ}$ (SEQ ID:7); control peptides: DP-180 (SEQ ID:2), a peptide incorporating the amino acid residues of DP178 in a scrambled sequence;, DP-118 (SEQ ID:10) unrelated to DP178, which inhibits HIV-1 cell free virus infection; DP-125 (SEQ ID:8), unrelated to, DP178, also inhibits HIV-1 cell free virus infection; DP-116 (SEQ ID:9), unrelated to DP178, is negative for inhibition of HIV-1 infection when tested using a cell-free virus infection assay. Throughout the figures, the one letter amino acid code is used.

FIG. 2. Inhibition of HIV-1 cell-free virus infection by synthetic peptides. IC$_{50}$ refers to the concentration of peptide that inhibits RT production from infected cells by 50% compared to the untreated control. Control: the level of RT produced by untreated cell cultures infected with the same level of virus as treated cultures.

Figure 3:
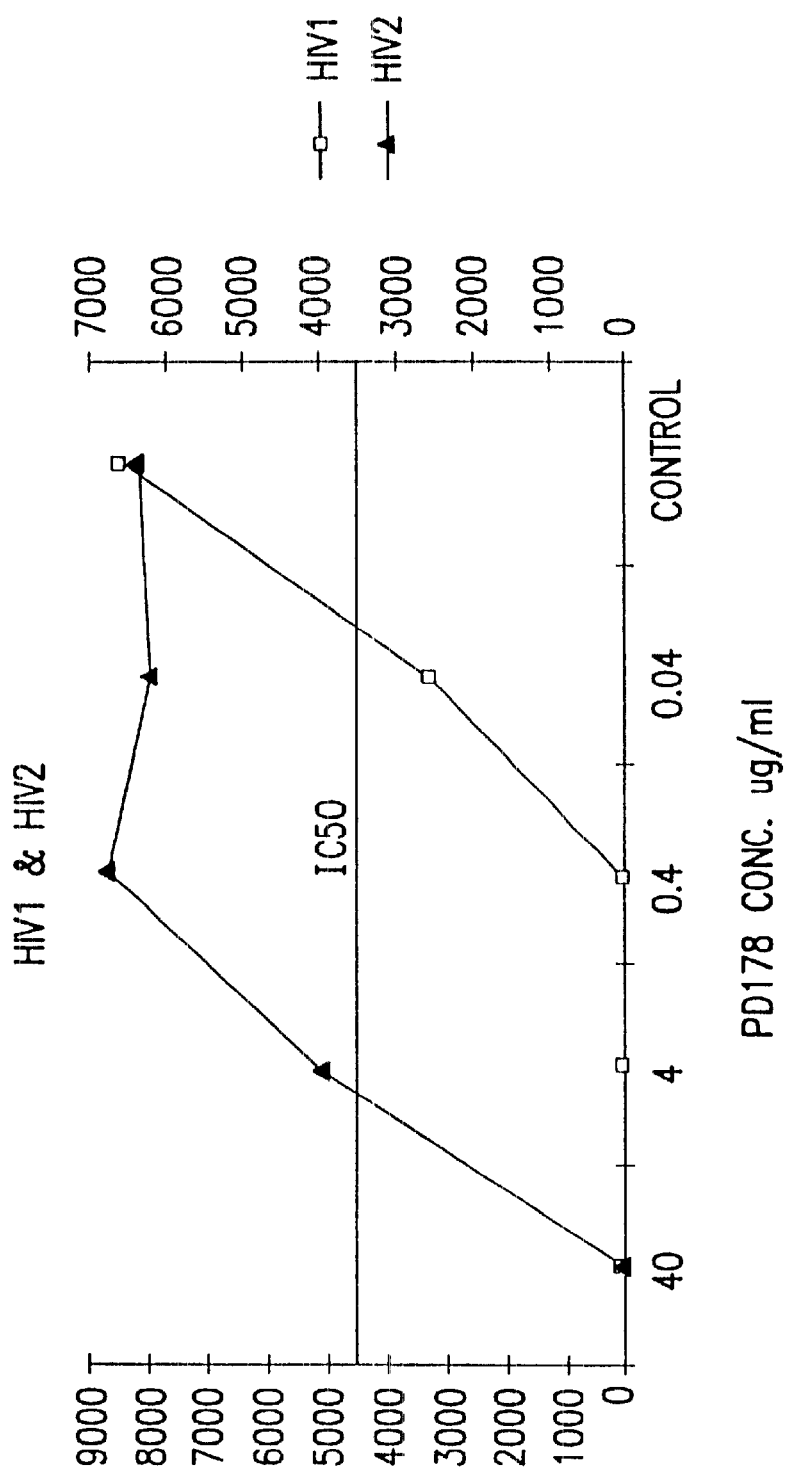

FIG. 3. Inhibition of HIV-1 and HIV-2 cell-free virus infection by the synthetic peptide DP178 (SEQ ID:1). IC$_{50}$: concentration of peptide that inhibits RT production by 50% compared to the untreated control. Control: Level of RT produced by untreated cell cultures infected with the same level of virus as treated cultures.

FIGS. 4A–4B. Fusion Inhibition Assays. FIG .4A: DP178 (SEQ ID:1) inhibition of HIV-1 prototypic isolate-mediated syncytial formation; data represents the number of virus-induced syncytial per cell. FIG. 4B: DP-180 (SEQ ID:2) represents a scrambled control peptide; DP-185 (SEQ ID:3) represents a DP178 homolog derived from HIV-1$_{SF2}$ isolate; Control, refers to the number of syncytial produced in the absence of peptide.

FIG. 5. Fusion inhibition assay: HIV-1 vs. HIV-2. Data represents the number of virus-induced syncytial per well. ND: not done.

Figure 6:
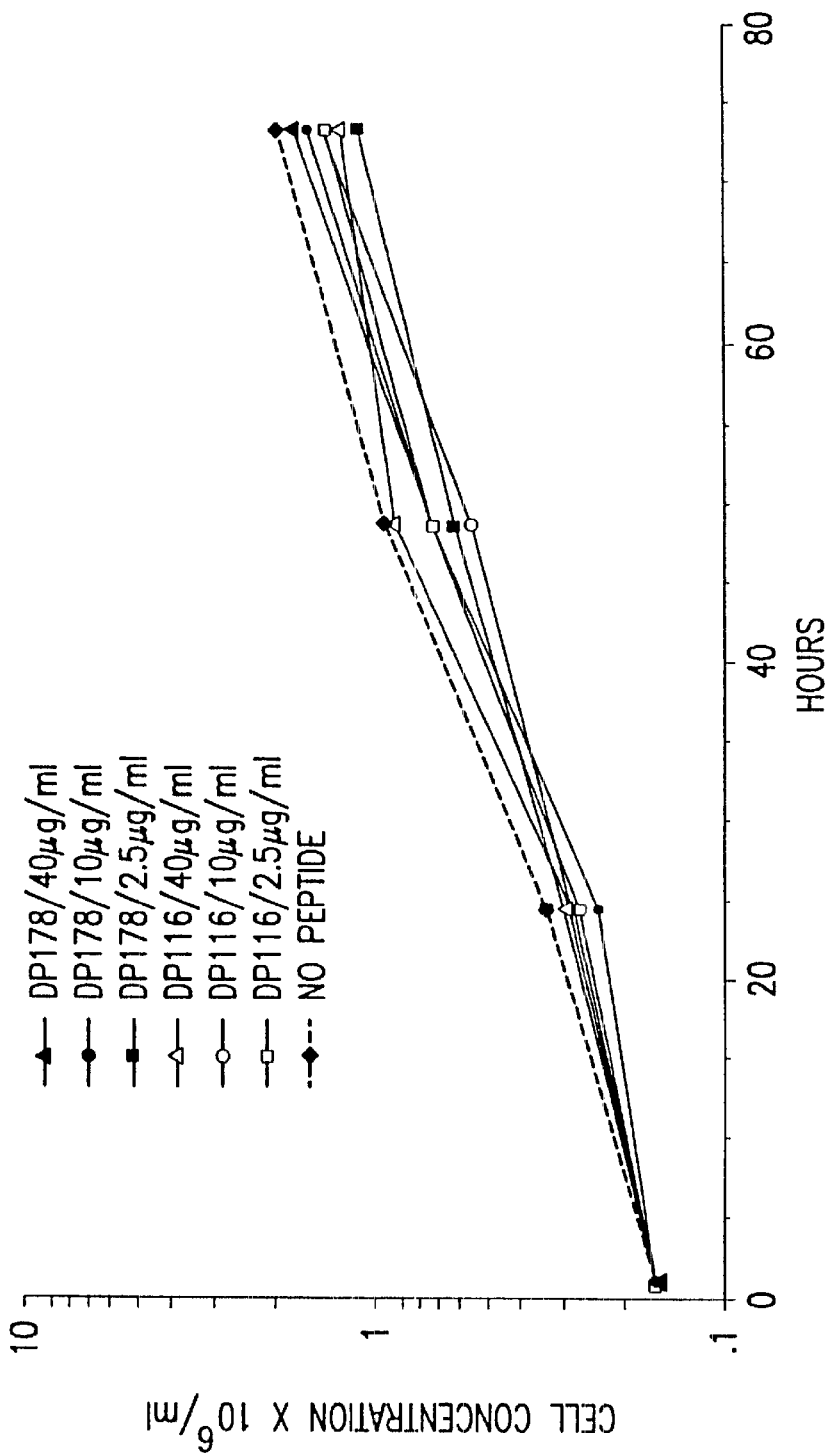

FIG. 6. Cytotoxicity study of DP178 (SEQ ID:1) and DP-116 (SEQ ID:9) on CEM cells. Cell proliferation data is shown.

Figure 7:
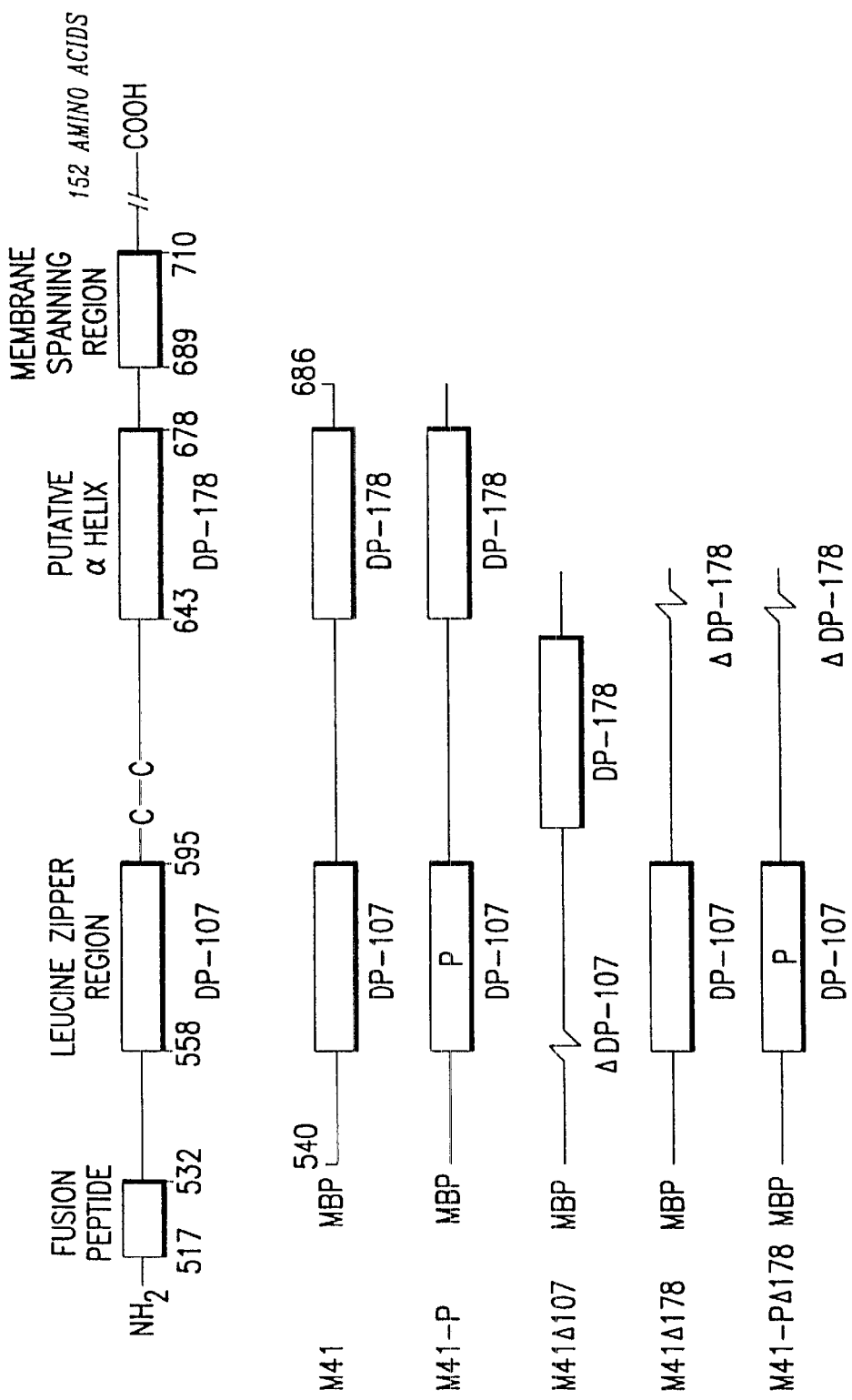

FIG. 7. Schematic representation of HIV-gp41 and maltose binding protein (MBP)-gp41 fusion proteins. DP107 and DP178 are synthetic peptides based on the two putative helices of gp41. The letter P in the DP107 boxes denotes. an Ile to Pro mutation at amino acid number 578. Amino acid residues are numbered according to Meyers et al., "Human Retroviruses and AIDS", 1991, Theoret. Biol. and Biophys. Group, Los Alamos Natl. Lab., Los Alamos, N. Mex. The proteins are more fully described, below, in Section 8.1.1.

Figure 8:
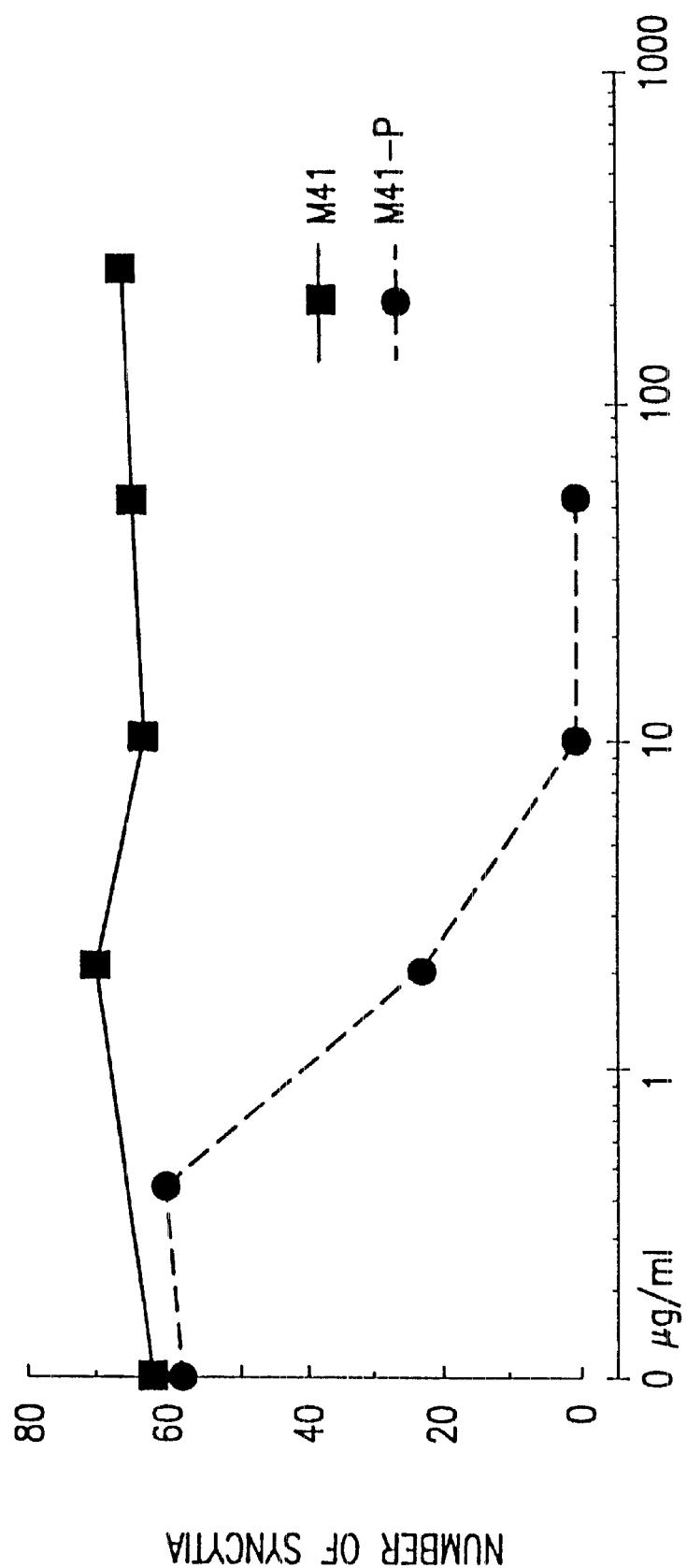

FIG. 8. A point mutation alters the conformation and anti-HIV activity of M41.

Figure 9:
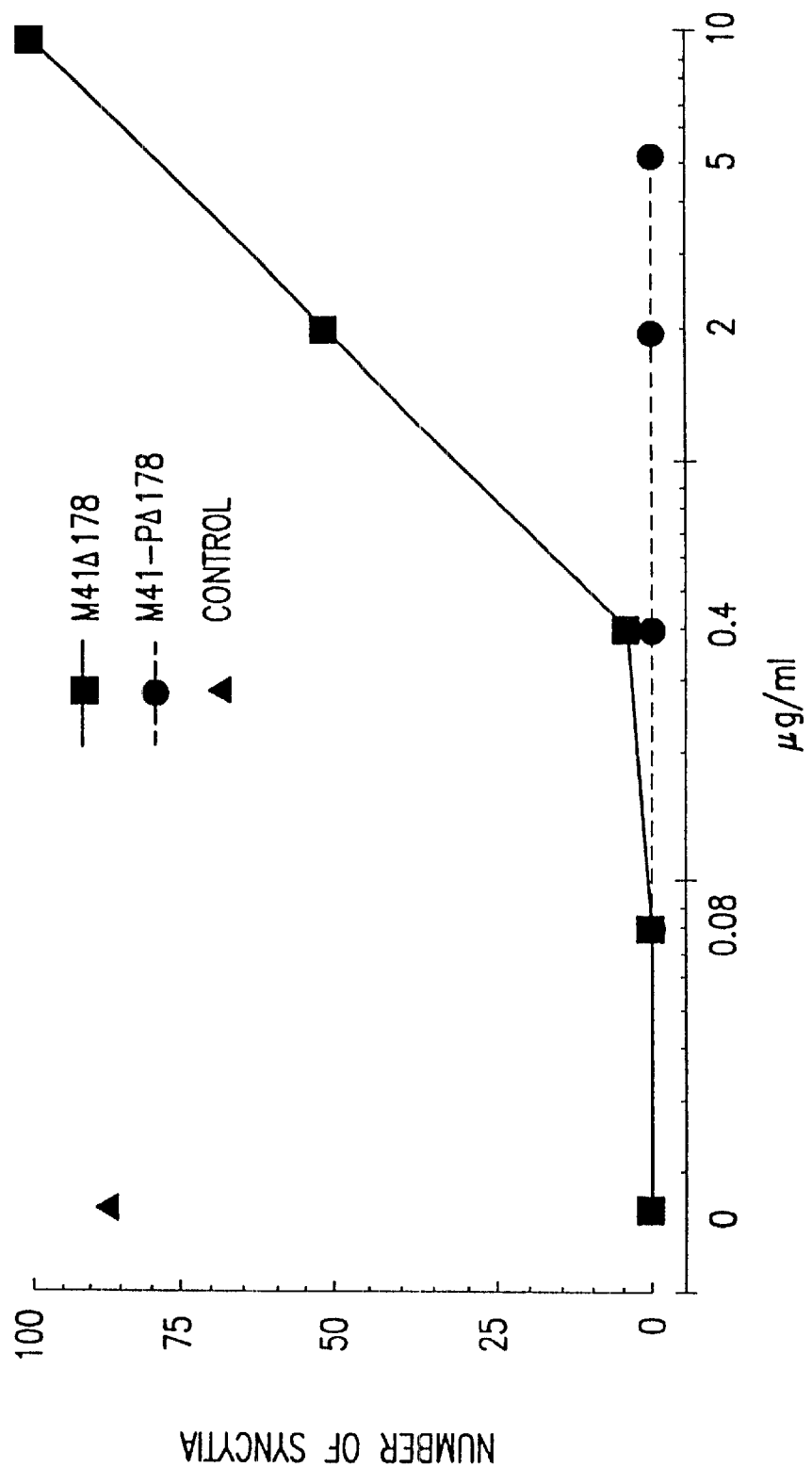

FIG. 9. Abrogation of DP178 anti-HIV activity. Cell fusion assays were carried out in the presence of 10 nM DP178 and various concentrations of M41Δ178 or M41PΔ178.

Figure 10:
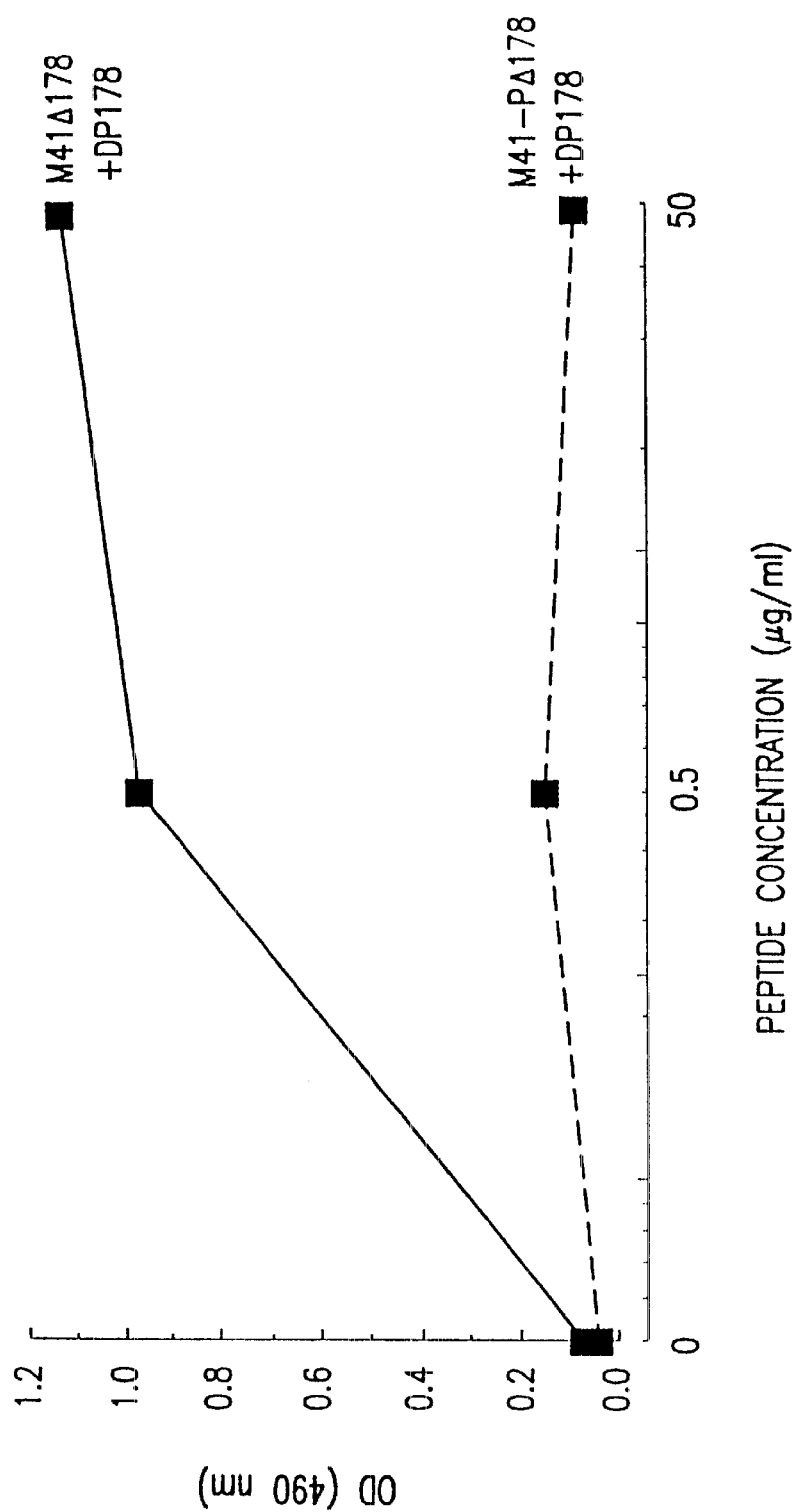

FIG. 10. Binding of DP178 to leucine zipper of gp41 analyzed by FAb-D ELISA.

Figure 11A:
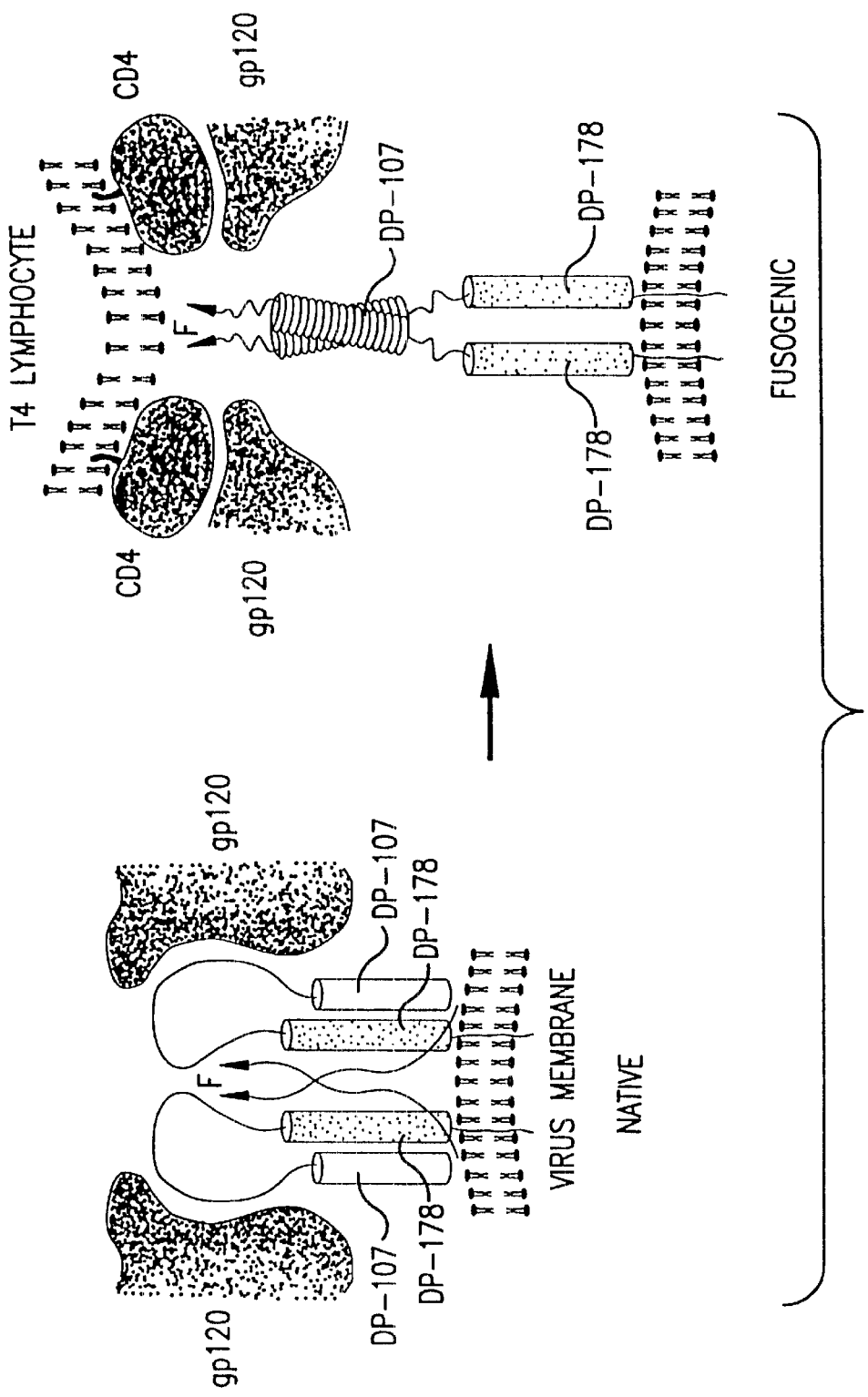
Figure 11B:
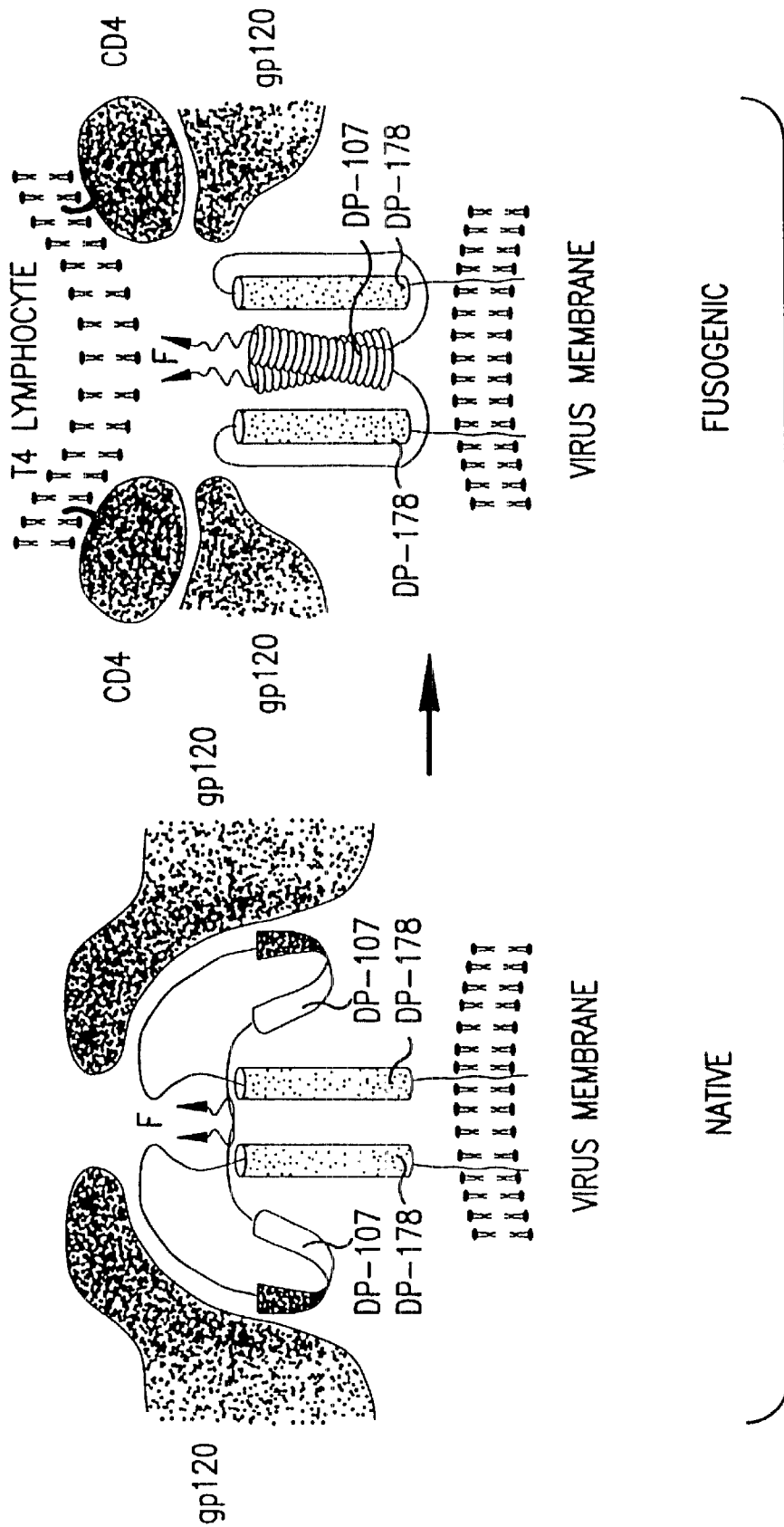

FIGS. 11A–B. Models for a structural transition in the HIV-1 TM protein. Two models are proposed which indicate a structural transition from a native oligomer to a fusogenic state following a trigger event (possibly gp120 binding to CD4). Common features of both models include (1) the native state is held together by noncovalent protein-protein interactions to form the heterodimer of gp120/41 and other interactions, principally though gp41 interactive sites, to form homo-oligomers on-the virus surface of the gp120/41 complexes; (2) shielding of the hydrophobic fusogenic peptide at the N-terminus (F) in the native state; and (3) the leucine zipper domain (DP107) exists as a homo-oligomer coiled coil only:in the fusogenic state. The major differences in the two models include the structural state (native or fusogenic) in which the DP107 and DP178 domains are complexed to each other. In the first model (FIG. 11A) this interaction occurs in the native state and in the second (FIG. 11B), it occurs during the fusogenic state. When triggered, the fusion complex in the model depicted in (A),is generated through formation of coiled-coil interactions in homologous DP107 domains resulting in an extended α-helix. This conformational change positions the fusion peptide for interaction with the cell membrane. In the second model (FIG. 11B), the fusogenic complex is stabilized by the association of the DP178 domain with the DP107 coiled-coil.

FIG. 12. Motif design using heptad repeat positioning of amino acids of known coiled-coils.

FIG. 13. Motif design using proposed heptad repeat positioning of amino acids of DP107 and DP178.

Figure 14:
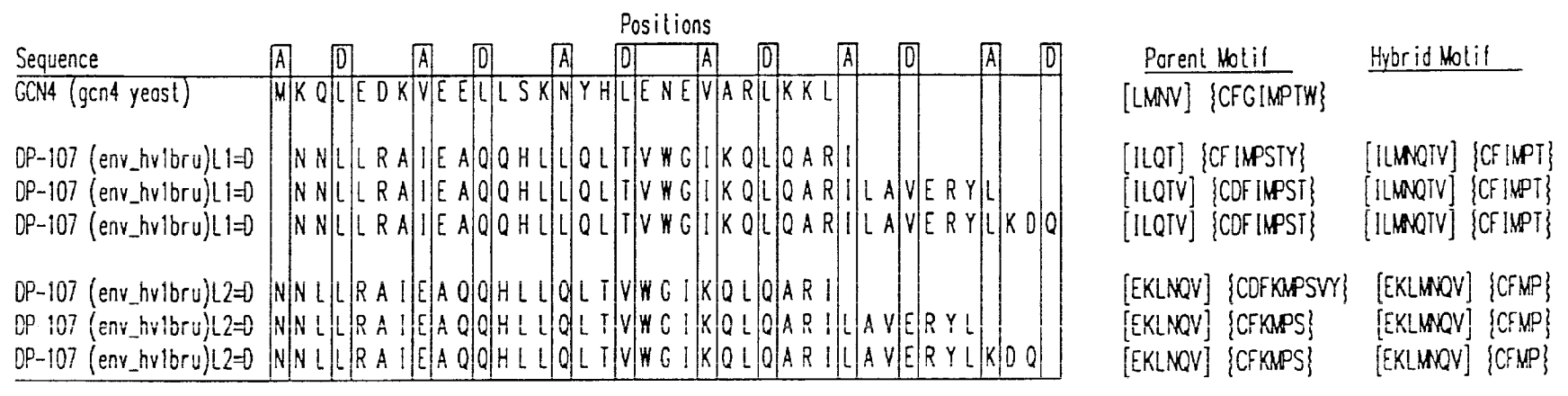

FIG. 14. Hybrid motif design crossing GCN4 and DP107.

FIG. 15. Hybrid motif design crossing GCN4 and DP178.

FIG. 16. Hybrid motif design 107×178×4, crossing DP107 and DP178. This motif was found to be the most consistent at identifying relevant DP107-like and DP178-like peptide regions.

FIG. 17. Hybrid motif design crossing GCN4, DP107, and DP178.

FIG. 18. Hybrid motif design ALLMOTI5 crossing GCN4, DP107, DP178, c-Fos c-Jun, c-Myc, and Flu Loop 36.

FIG. 19. PLZIP motifs designed to identify N-terminal proline-leucine zipper motifs.

FIG. 20. Search results for HIV-1 (BRU isolate) enveloped protein gp41. Sequence search motif designations: Spades (♠): 107×178×4; Hearts (♥) ALLMOTI5; Clubs (♣): PLZIP; Diamonds (♦): transmembrane region (the putative transmembrane domains were identified using a PC/Gene program designed to search for such peptide regions). Asterisk (*): Lupas method. The amino acid sequences identified by each motif are bracketed by the respective characters. Representative sequences chosen based on 107×178×4 searches are underlined and in bold. DP107 and DP178 sequences are marked, and additionally double-underlined and italicized.

FIG. 21. Search results for human respiratory syncytial virus (RSV) strain A2 fusion glycoprotein F1. Sequence search motif designations are as in FIG. 20.

FIG. 22. Search results for simian immunodeficiency virus (SIV) enveloped protein gp41 (AGM3 isolate). Sequence search motif designations are as in FIG. 20.

FIG. 23. Search results for canine distemper virus (strain Onderstepoort) fusion glycoprotein 1. Sequence search motif designations are as in FIG. 20.

FIG. 24. Search results for newcastle disease virus (strain Australia-Victoria/32) fusion glycoprotein. F1. Sequence search motif designations are as in FIG. 20.

FIG. 25. Search results for human parainfluenza 3 virus (strain NIH 47885) fusion glycoprotein F1. Sequence search motif designations are as in FIG. 20.

FIG. 26. Search results for influenza A virus (strain A/AICHI/2/68) hemagglutinin precursor HA2. Sequence search designations are as in FIG. 20.

FIGS. 27A–F. Respiratory Syncytial Virus (RSV) peptide antiviral and circular dichroism data. FIGS. 27A–B: Peptides derived from the F2 DP178/DP107-like region. Antiviral and CD data. FIGS. 27C–D: Peptides derived from the F1 DP107-like region. Peptide and CD data.

Antiviral activity (AV) is represented by the following qualitative symbols:

"–", negative antiviral activity;

"+/–", antiviral activity at greater than 100 µg/ml;

"+", antiviral activity at between 50–100 µg/ml;

"++", antiviral activity at. between 20–50 µg/ml;

"+++", antiviral activity at between 1–20 g/ml;

"++++", antiviral activity at <1 µg/ml.

CD data, referring to the level of helicity is represented by the following qualitative symbol:

"–", no helicity;

"+", 25–50% helicity;

"++", 50–75% helicity;

"+++" 75–100% helicity.

$IC_{50}$ refers to the concentration of peptide necessary to produce only 50% of the number of syncytial relative to infected control cultures containing no peptide. $IC_{50}$ values were obtained using purified peptides only.

FIGS. 28A-C. Respiratory Syncytial Virus (RSV) DP178-like region (F1) peptide antiviral and CD data. Antiviral symbols, CD symbols, and $IC_{50}$ are as in FIGS. 27A–D. $IC_{50}$ values were obtained using purified peptides only.

FIGS. 29A–E. Peptides derived from the HPIV3 F1 DP107-like region.- Peptide antiviral and CD data. Antiviral symbols, CD symbols, and $IC_{50}$ are as in FIGS. 27A–D. Purified peptides were used to obtain $IC_{50}$ values, except where the values are marked by an asterisk (*), in which cases, the $IC_{50}$ values were obtained using a crude peptide preparation.

FIGS. 30A–C. Peptides derived from the HPIV3 F1 DP178-like region. Peptide antiviral and CD data. Antiviral symbols, CD symbols, and $IC_{50}$ are as in FIGS. 27A–D. Purified peptides were used to obtain $IC_{50}$ values, except where the values are marked by an asterisk (*), in which cases, the $IC_{50}$ values were obtained using a crude peptide preparation.

FIG. 31. Motif search results for simian immunodeficiency virus (SIV) isolate MM251, enveloped polyprotein gp41. Sequence search designations are as in FIG. 20.

FIG. 32. Motif search results for Epstein-Barr Virus (Strain B95–8), glycoprotein gp110 precursor (designated gp115). BALF4. Sequence search designations are as in FIG. 20.

FIG. 33. Motif search results for Epstein-Barr Virus (Strain B95-8), BZLF1 trans-activator protein (designated EB1 or Zebra). Sequence search designations are as in FIG. 20. Additionally, "@" refers to a well known DNA binding domain and "+" refers to a well known dimerization domain, as defined by Flemington and Speck (Flemington, E. and Speck, S. H., 1990, Proc. Natl. Acad. Sci. USA 87:9459–9463).

FIG. 34. Motif search results for measles virus (strain Edmonston), fusion glycoprotein F1. Sequence search designations are as in FIG. 20.

FIG. 35. Motif search results for Hepatitis B Virus (Subtype AYW), major surface antigen precursor S. Sequence search designations are as in FIG. 20.

FIG. 36. Motif search results for simian Mason-Pfizer monkey virus, enveloped (TM) protein gp20. Sequence search designations are as in FIG. 20.

FIG. 37. Motif search results for *Pseudomonas aerginosa*, fimbrial protein (Pilin). Sequence search designations are as in FIG. 20.

FIG. 38. Motif search results for *Neisseria gonorrhoeae* fimbrial protein (Pilin). Sequence search designations are as in FIG. 20.

FIG. 39. Motif search results for *Hemophilus influenzae* fimbrial protein. Sequence search designations are as in FIG. 20.

FIG. 40. Motif search results for *Staphylococcus aureus*, toxic shock syndrome toxin-1. Sequence search designations are as in FIG. 20.

FIG. 41. Motif search results for *Staphylococcus aureus* enterotoxin Type E. Sequence search designations are as in FIG. 20.

FIG. 42. Motif search results for *Staphylococcus aureus* enterotoxin A. Sequence search designations are as in FIG. 20.

FIG. 43. Motif search results for *Escherichia coli*, heat labile enterotoxin A. Sequence search designations are as in FIG. 20.

FIG. 44. Motif search results for human c-fos proto-oncoprotein. Sequence search designations are as in FIG. 20.

FIG. 45. Motif search results for human lupus KU autoantigen protein P70. Sequence search designations are as in FIG. 20.

FIG. 46. Motif search results for human, zinc finger protein 10. Sequence search designations are as in FIG. 20.

Figure 47B:
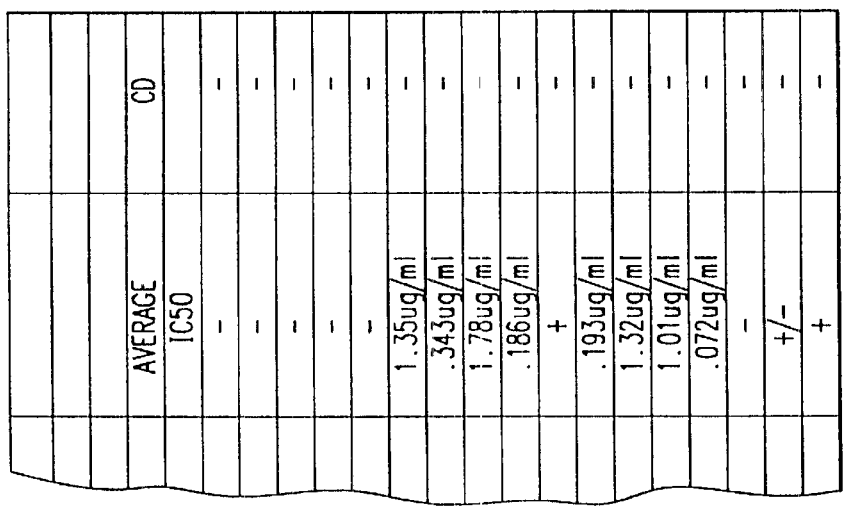

FIGS. 47A–B. Measles virus (MeV) fusion protein DP178-like region antiviral: and CD data. Antiviral symbols, CD symbols, and $IC_{50}$ are as in FIGS. 27A–D. $IC_{50}$ values were obtained using purified peptides.

FIGS. 48A–B. Simian immunodeficiency virus. (SIV) TM (fusion) protein DP178-like region antiviral data. Antiviral symbols are as in FIGS., 27A–D "NT", not tested.

FIGS. 49A–L. DP178-derived peptide antiviral data. The peptides listed herein were derived from the region surrounding the HIV-1 BRU isolate DP178 region (e.g., gp41 amino acid residues 615–717).

Figure 49A:
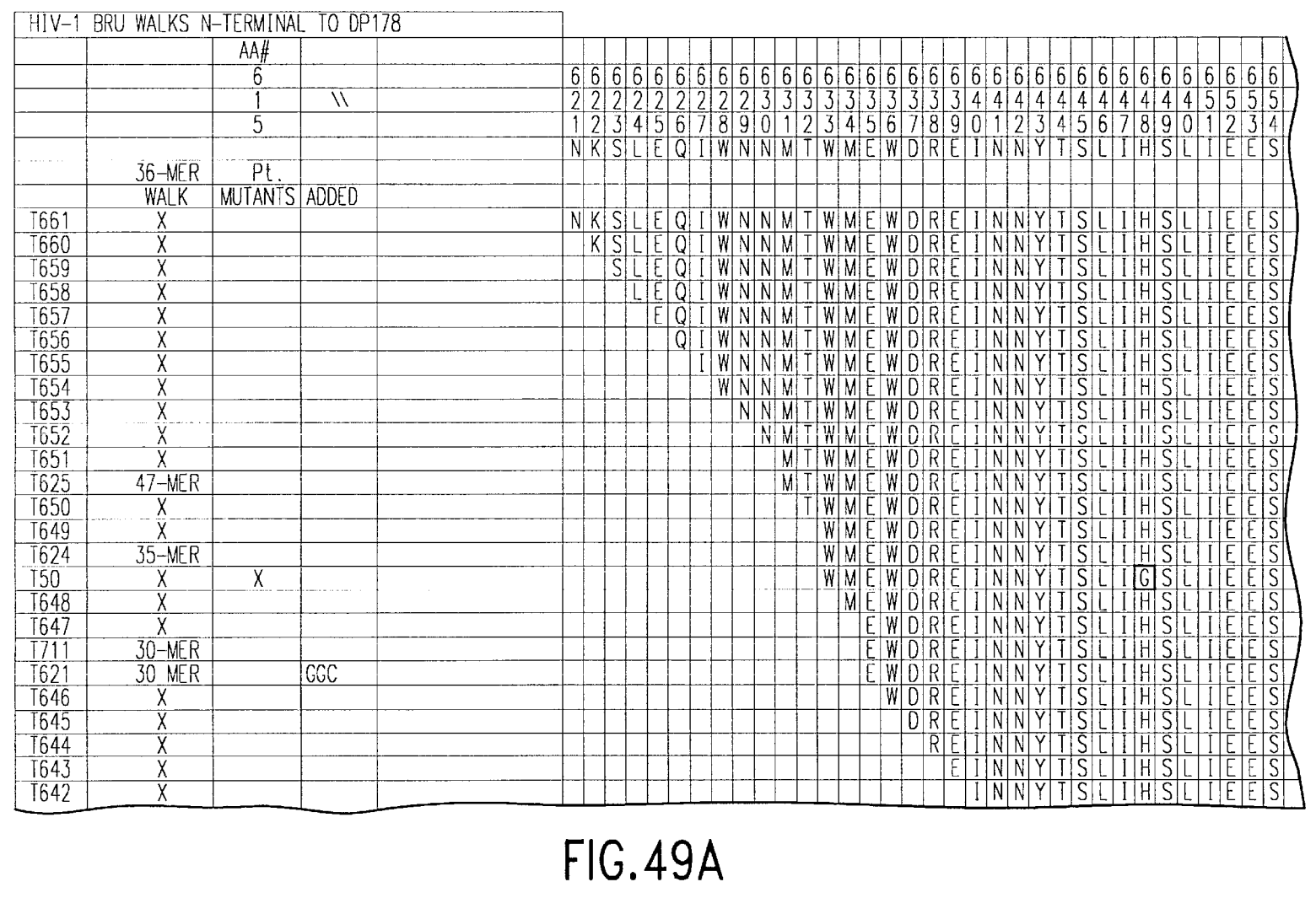
Figure 49C:
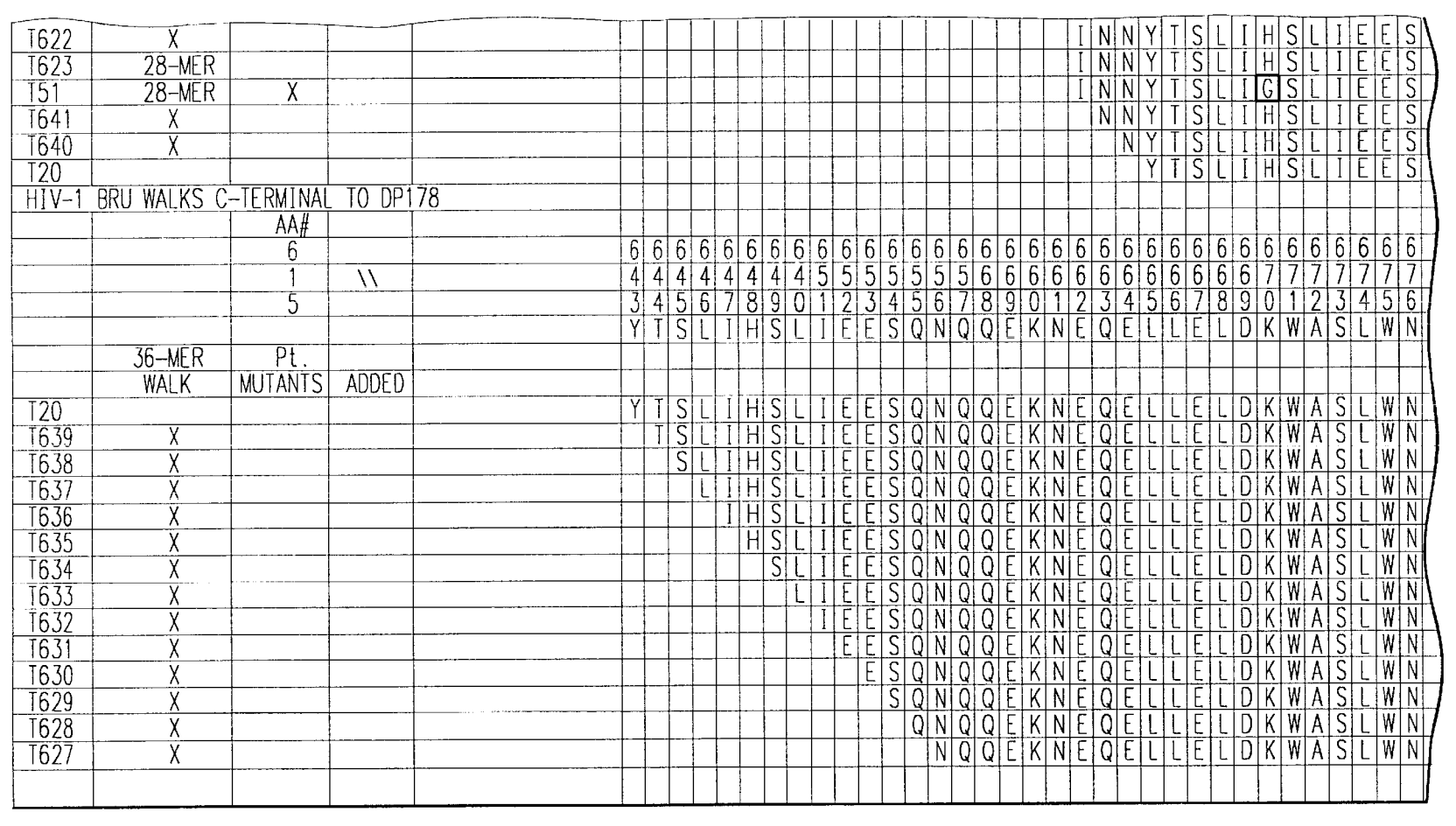
Figure 49D:
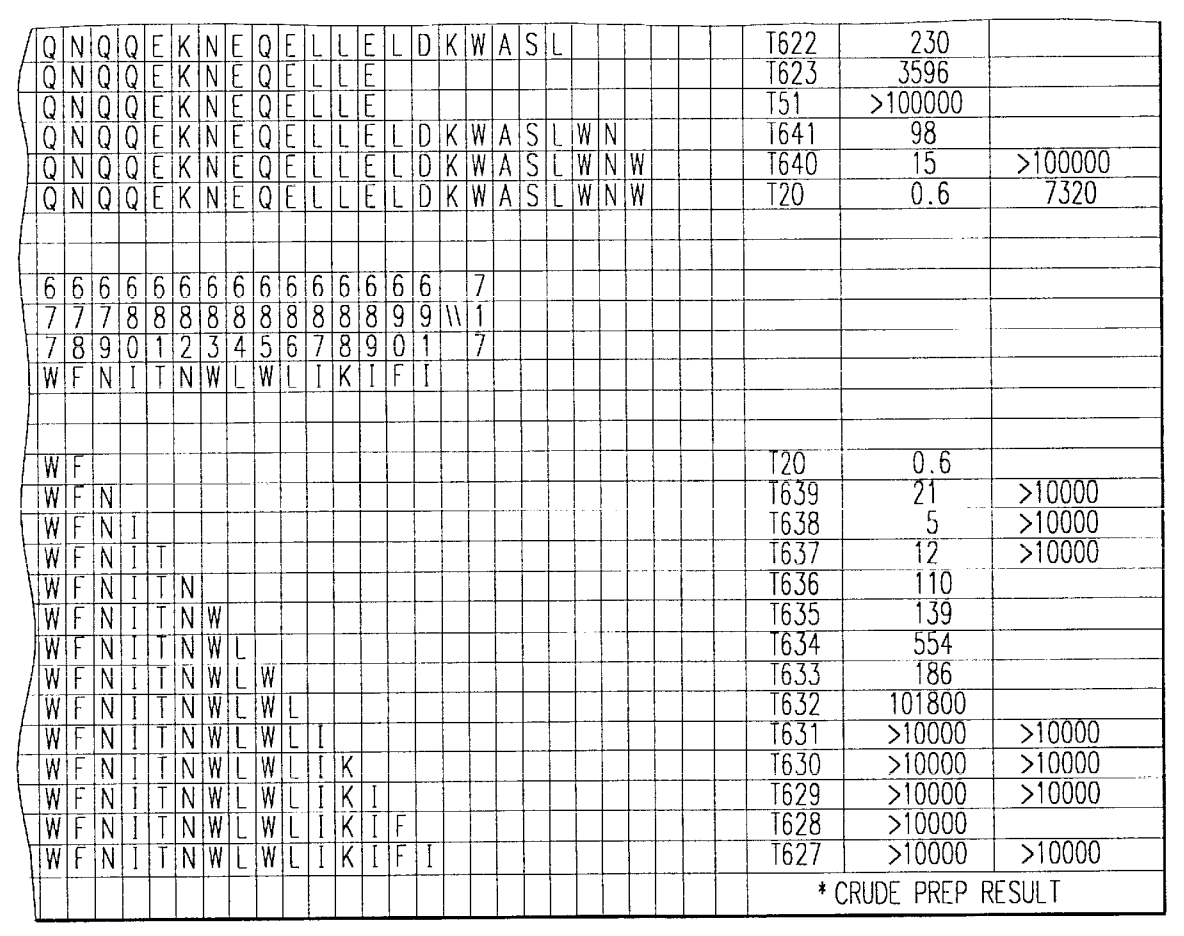

In instances where peptides contained DP178 point mutations, the mutated amino acid residues are shown with a shaded background. In instances in which the test peptide has had an amino and/or carboxy-terminal group added or removed (apart from the standard amido and acetyl- blocking groups found on such peptides), such modifications are indicated. FIG. 49A: The column to the immediate right of the name of the test peptide indicates the size of the test peptide and points out whether the peptide is derived from a one amino acid peptide "walk" across the DP178 region. The next column to the right indicates whether the test peptide contains a point mutation, while the column to its right indicates whether certain amino acid residues have been added to or removed from the DP178-derived amino acid sequence. FIG. 49B: The column to the immediate right of the test peptide name indicates whether the peptide represents a DP178 truncation, the next column to the right points out whether the peptide contains a point mutation, and the column to its right indicates whether the peptide contains amino acids which have been added to or . removed from the DP178 sequence itself. FIG. 49C: The column to the immediate right of the test peptide name indicates whether the test peptide contains a point mutation, while the column to its right indicates whether amino acid residues have been added to or removed from the DP178 sequence itself. $IC_{50}$ is as defined in FIGS. 27A–D, and $IC_{50}$ values were obtained using purified peptides except where marked with an asterisk (*), in which case the $IC_{50}$ was obtained using a crude peptide preparation.

FIGS. 50A–B. DP107 and DP107 gp41 region truncated peptide antiviral data. $IC_{50}$ as defined in FIGS. 27A–D,. and $IC_{50}$ values were obtained using purified peptides except where marked with an asterisk (*) in which case the $IC_{50}$ was obtained using a crude peptide preparation.

FIGS. 51A–C. Epstein-Barr virus Strain B95-8 BZLF1 DP178/DP107 analog region peptide walks and electrophoretic mobility shift assay results. The peptides (T-423 to T-446, FIG. 51A; T-447 to T-461, FIG. 51B) represent one amino acid residue "walks" through the EBV Zebra protein region from amino acid residue 173 to 246.

The amino acid residue within this region which corresponds to the first amino acid residue of each peptide is listed to the left of each peptide, while the amino acid residue within this region which corresponds to the last amino acid residue of each peptide is listed to the right of each peptide. The length of each test peptide is listed at the far right of each line, under the heading "Res".

"ACT" refers to a test peptide's ability to inhibit Zebra binding to its response element. "+" refers to a visible, but incomplete, abrogation of the response element/Zebra homodimer complex; "+++" refers to a complete abrogation of the complex; and "–" represents a lack of complex disruption.

Figure 52B:
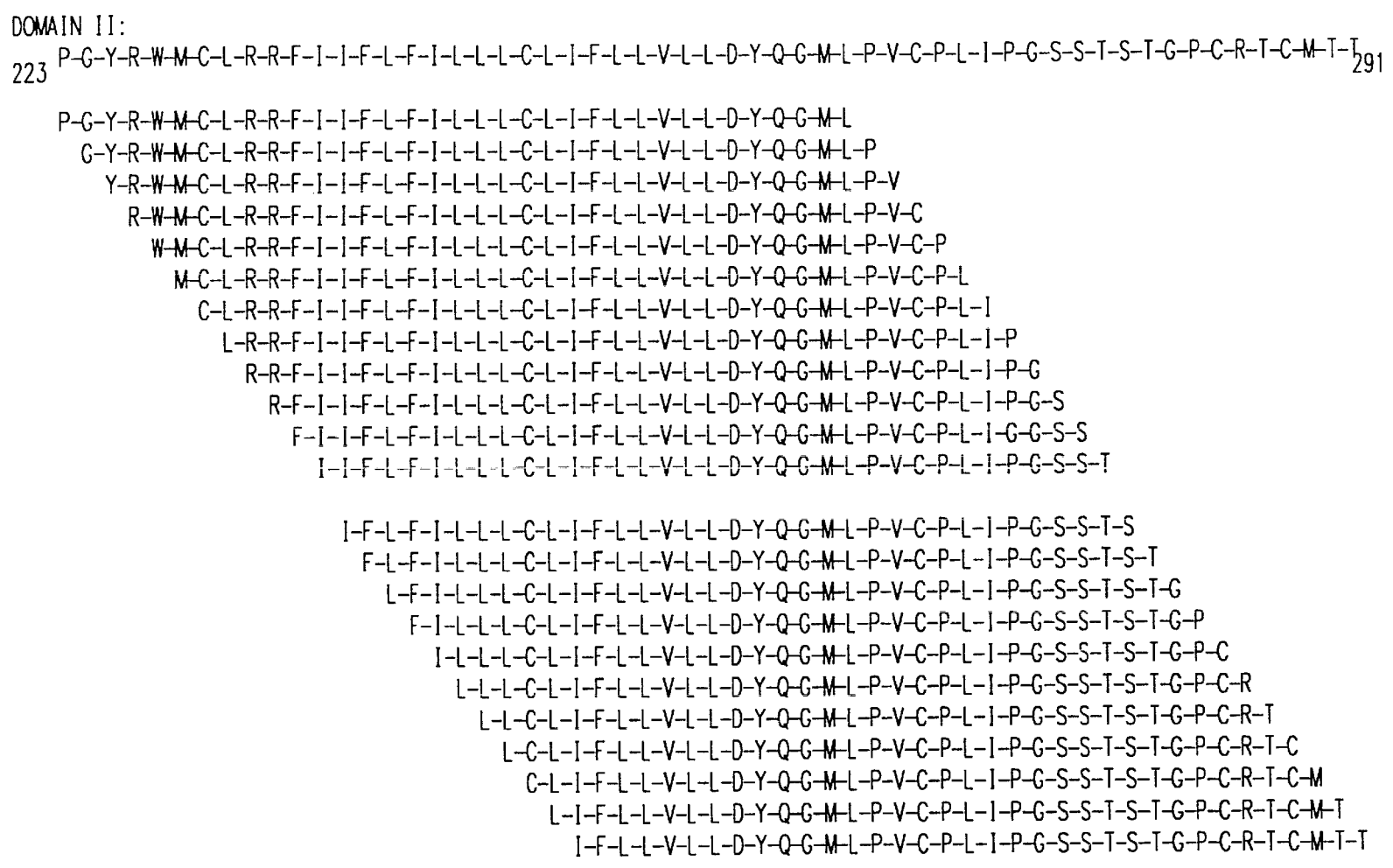

FIGS. 52A–B. Hepatitis B virus subtype AYW major surface antigen precursor S protein DP178/DP107 analog region and peptide walks. 52A depicts Domain I (S protein amino acid residues 174–220), which-contains a potential DP178/DP107 analog region. In addition, peptides are listed which represent one amino acid peptide "walks" through domain I. 52B depicts Domain II (S protein amino acid residues 2.33–291), which contains a second potential DP178/DP107.analog region. In addition, peptides are listed which represent one amino acid peptide "walks" through domain II.

5. DETAILED DESCRIPTION OF THE INVENTION

Described herein are peptides which may exhibit antifusogenic activity, antiviral capability, and/or the ability to modulate intracellular processes involving coiled-coil peptide structures. The peptides described include, first, DP178 (SEQ ID NO:1), a gp41-derived 36 amino acid peptide and. fragments and analogs of DP178.

In addition, the peptides of the invention described herein include peptides which are DP107 analogs. DP107 (SEQ ID NO:25) is a 38 amino acid peptide corresponding to residues 558 to 595 of the HIV-1$_{LAI}$ transmembrane (TM) gp41 protein. Such DP107 analogs may exhibit antifusogenic capability, antiviral activity or an ability to modulate intracellular processes involving coiled-coil structures.

Further, peptides of the invention include DP107 and DP178 are described herein having amino acid sequences recognized by the 107×178×4, ALLMOTI5, and PLZIP search motifs. Such motifs are also discussed.

Also described here are antifusogenic, antiviral, intracellular modulatory, and diagnostic uses of the peptides of the invention. Further, procedures are. described for the use of the peptides of the invention for the identification of compounds exhibiting antifusogenic, antiviral or intracellular modulatory activity.

While not limited to any theory-of operation, the following model is proposed to explain the potent anti-HIV activity of DP178, based, in part, on the experiments described in the Examples, infra. In the HIV protein, gp41, DP178 corresponds to a putative α-helix region located in the C-terminal end of the gp41 ectodomain, and appears to associate with a distal site on gp41 whose interactive structure is influenced by the leucine zipper motif, a coiled-coil structure., referred to as DP107. The association of these two domains may reflect a molecular linkage or "molecular clasp" intimately involved in the fusion process. It is of interest that mutations in the C-terminal α-helix motif of gp41 (i.e., the D178 domain) tend to enhance the fusion ability of gp41, whereas mutations in the leucine zipper region (i.e., the DP107 domain) decrease or abolish the fusion ability of the viral protein. It may be that the leucine zipper motif is involved in membrane fusion while the C-terminal α-helix motif serves as a molecular safety to regulate the availability. of the leucine zipper during virus-induced membrane fusion.

On the basis of the foregoing, two models are proposed of gp41-mediated membrane fusion which are schematically shown in FIGS. 11A–B. The reason for. proposing two models is that the temporal nature of the interaction between the regions defined by DP107 and DP178 cannot, as yet, be pinpointed. Each model envisions two conformations for gp41—one in a "native" state as it might be found. on a resting virion. The other in a "fusogenic" state to reflect conformational changes triggered following binding of gp120 to CD4 and just prior to fusion with the target cell membrane. The strong binding affinity between gp120 and CD4 may actually represent the trigger for the fusion process obviating the need for a pH change such as occurs for viruses that fuse within intracellular vesicles. The two major features of both models are: (1) the leucine zipper sequences (DP107) in each chain of oligomeric enveloped are held apart in the native state and are only allowed access to one another in the fusogenic state so as to form the extremely stable coiled-coils, and (2) association of the DP178 and DP107 sites as they exist in gp41 occur either in the native or fusogenic state. FIG. 11A depicts DP178/DP107 interaction in the native state as a molecular clasp. On the other hand, if one assumes that the most stable form of the enveloped occurs in the fusogenic state, the model in FIG. 11B can be considered.

When synthesized as peptides, both DP107 and P178 are potent inhibitors of HIV infection and fusion, probably by virtue of their ability to form complexes with viral gp41 and interfere with its fusogenic process; e.g., during the structural transition of the viral protein from the native structure to the fusogenic state, the DP178 and DP107 peptides may gain access to their respective binding sites on the viral gp41, and exert a disruptive influence. DP107 peptides which demonstrate anti-HIV activity are described in Applicants' co-pending application Ser. No. 08/264,531, filed Jun. 23, 1994, which is incorporated by reference herein in its entirety.

As shown in the Examples, infra, a truncated recombinant gp41 protein corresponding to the ectodomain of gp41 containing both DP107 and DP178 domains (excluding the fusion peptide, transmembrane region and cytoplasmic domain of gp41) did not inhibit HIV-1 induced fusion. However, when a single mutation was introduced to disrupt the coiled-coil structure of the DP107 domain—a mutation which results in a total loss of biological activity of DP107 peptides—the inactive recombinant protein was transformed to an active inhibitor of HIV-1 induced fusion. This transformation may result from liberation of the potent DP178 domain from a molecular clasp with the leucine zipper, DP107 domain.

For clarity of discussion, the invention will be described primarily for DP178 peptide inhibitors of HIV. However, the principles may be analogously applied to other viruses, both enveloped and nonenveloped, and to other non-viral organisms.

5.1. DP178 and DP178-LIKE Peptides

The DP178 peptide (SEQ ID:1) of the. invention corresponds to amino acid residues 638 to 673 of the transmembrane protein gp41 from the HIV-1$_{LAI}$ isolate, and has the 36 amino acid sequence (reading from amino to carboxy terminus):

NH$_2$—YTSLIHSLIEESQNQQEKNEQELLELDKWASLWNWF—COOH (SEQ ID:1)

In. addition to the full-length DP178 (SEQ ID:1) 36-mer, the peptides of the invention may include truncations of the DP178 (SEQ ID:1) peptide which exhibit antifusogenic activity, antiviral activity and/or the ability to modulate intracellular processes involving coiled-coil peptide structures. Truncations of DP178 (SEQ ID:1) peptides may comprise peptides of between 3 and 36 amino acid residues (i.e., peptides ranging in size from a tripeptide to a 36-mer polypeptide), as shown in Tables I and IA, below. Peptide sequences in these tables are listed from amino (left) to carboxy (right) terminus. "X" may represent an amino group (—NH$_2$) and "Z" may represent a carboxyl (—COOH) group. Alternatively, "X" may represent a hydrophobic group, including but not limited to carbobenzyl, dansyl, or T-butoxycarbonyl; an acetyl group; a 9-fluorenylmethoxycarbonyl (FMOC) group; or a covalently attached macromolecular group, including but not limited to a lipid-fatty acid conjugate, polyethylene glycol, carbohydrate or peptide group. Further, "Z" may represent an amido. group; a T-butoxycarbonyl group; or a covalently attached macromolecular group., including but not limited to a lipid-fatty acid conjugate, polyethylene glycol, carbohydrate or peptide group. A preferred "X" or "Z" macromolecular group is a peptide group.

TABLE I

DP178 (SEQ ID:1) CARBOXY TRUNCATIONS

X-YTS-Z
X-YTSL-Z
X-YTSLI-Z
X-YTSLIH-Z
X-YTSLIHS-Z
X-YTSLIHSL-Z
X-YTSLIHSLI-Z
X-YTSLIHSLIE-Z
X-YTSLIHSLIEE-Z
X-YTSLIHSLIEES-Z
X-YTSLIHSLIEESQ-Z
X-YTSLIHSLIEESQN-Z
X-YTSLIHSLIEESQNQ-Z
X-YTSLIHSLIEESQNQQ-Z
X-YTSLIHSLIEESQNQQE-Z
X-YTSLIHSLIEESQNQQEK-Z
X-YTSLIHSLIEESQNQQEKN-Z
X-YTSLIHSLIEESQNQQEKNE-Z
X-YTSLIHSLIEESQNQQEKNEQ-Z
X-YTSLIHSLIEESQNQQEKNEQE-Z
X-YTSLIHSLIEESQNQQEKNEQEL-Z
X-YTSLIHSLIEESQNQQEKNEQELL-Z
X-YTSLIHSLIEESQNQQEKNEQELLE-Z
X-YTSLIHSLIEESQNQQEKNEQELLEL-Z
X-YTSLIHSLIEESQNQQEKNEQELLELD-Z
X-YTSLIHSLIEESQNQQEKNEQELLELDK-Z
X-YTSLIHSLIEESQNQQEKNEQELLELDKW-Z
X-YTSLIHSLIEESQNQQEKNEQELLELDKWA-Z
X-YTSLIHSLIEESQNQQEKNEQELLELDKWAS-Z

TABLE I-continued

DP178 (SEQ ID:1) CARBOXY TRUNCATIONS

X-YTSLIHSLIEESQNQQEKNEQELLELDKWASL-Z
X-YTSLIHSLIEESQNQQEKNEQELLELDKWASLW-Z
X-YTSLIHSLIEESQNQQEKNEQELLELDKWASLWN-Z
X-YTSLIHSLIEESQNQQEKNEQELLELDKWASLWNW-Z
X-YTSLIHSLIEESQNQQEKNEQELLELDKWASLWNWF-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not lmited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE IA

DP178 (SEQ ID:1) AMINO TRUNCATIONS

X-NWF-Z
X-WNWF-Z
X-LWNWF-Z
X-SLWNWF-Z
X-ASLWNWF-Z
X-WASLWNWF-Z
X-KWASLWNWF-Z
X-DKWASLWNWF-Z
X-LDKWASLWNWF-Z
X-ELDKWASLWNWF-Z
X-LELDKWASLWNWF-Z
X-LLELDKWASLWNWF-Z
X-ELLELDKWASLWNWF-Z
X-QELLELDKWASLWNWF-Z
X-EQELLELDKWASLWNWF-Z
X-NEQELLELDKWASLWNWF-Z
X-KNEQELLELDKWASLWNWF-Z
X-EKNEQELLELDKWASLWNWF-Z
X-QEKNEQELLELDKWASLWNWF-Z
X-QQEKNEQELLELDKWASLWNWF-Z
X-NQQEKNEQELLELDKWASLWNWF-Z
X-QNQQEKNEQELLELDKWASLWNWF-Z
X-SQNQQEKNEQELLELDKWASLWNWF-Z
X-ESQNQQEKNEQELLELDKWASLWNWF-Z
X-EESQNQQEKNEQELLELDKWASLWNWF-Z
X-IEESQNQQEKNEQELLELDKWASLWNWF-Z
X-LIEESQNQQEKNEQELLELDKWASLWNWF-Z
X-SLIEESQNQQEKNEQELLELDKWASLWNWF-Z
X-HSLIEESQNQQEKNEQELLELDKWASLWNWF-Z
X-IHSLIEESQNQQEKNEQELLELDKWASLWNWF-Z
X-LIHSLIEESQNQQEKNEQELLELDKWASLWNWF-Z
X-SLIHSLIEESQNQQEKNEQELLELDKWASLWNWF-Z
X-TSLIHSLIEESQNQQEKNEQELLELDKWASLWNWF-Z
X-YTSLIHSLIEESQNQQEKNEQELLELDKWASLWNWF-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

The peptides of the invention also include DP178-like peptides. "DP178-like", as used herein, refers, first, to DP178 and DP178 truncations which contain one or more amino acid substitutions, insertions and/or deletions. Second, "DP-178-like" refers to peptide sequences identified or recognized by the ALLMOTI5, 107×178×4 and PLZIP search motifs described herein, having structural and/or amino acid motif similarity to DP178. The DP178-like peptides of the invention may exhibit antifusogenic or antiviral activity, or may exhibit the ability to modulate intracellular processes involving coiled-coil peptides. Further, such DP178-like peptides may possess additional advantageous features, such as, for example, increased bioavailability, and/or stability, or reduced host immune recognition.

HIV-1 and HIV-2 enveloped proteins are structurally distinct, but there exists a striking amino acid conservation within the DP178-corresponding regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the DP178 peptides of the invention. Utilizing the DP178 and DP178 analog sequences described herein,.the skilled artisan can readily compile DP178 consensus sequences and ascertain from these, conserved amino acid residues which would represent preferred amino acid substitutions.

The amino acid substitutions may be of a conserved or non-conserved nature. conserved amino acid substitutions consist of replacing one or more amino acids of the DP178 (SEQ ID:1) peptide sequence with amino acids of similar charge, size, and/or hydrophobicity characteristics, such as, for example, a glutamic acid (E) to aspartic acid (D) amino acid substitution. Non-conserved substitutions consist of replacing one or more amino acids of the DP178 (SEQ ID:1) peptide sequence with amino acids possessing dissimilar charge, size, and/or hydrophobicity characteristics, such as, for example, a glutamic acid (E) to valine (V) substitution.

Amino acid insertions may consist of single amino acid residues or stretches of residues. The insertions may be made at the carboxy or amino terminal end of the DP178 or DP178 truncated peptides, as well as at a position internal to the peptide. Such insertions will generally range from 2 to 15 amino acids in length. It is contemplated that insertions made at either the carboxy or amino terminus of the peptide of interest may be of a broader size range, with about 2 to about 50 amino acids being preferred. One or more such insertions may be introduced into. DP178 (SEQ.ID:1) or DP178 truncations, as long as such insertions result in peptides which may still be recognized by the 107×178×4, ALLMOTI5 or PLZIP search motifs described herein, or may, alternatively, exhibit antifusogenic or antiviral activity, or exhibit the ability to modulate intracellular processes involving coiled-coil peptide structures.

Preferred amino or carboxy terminal insertions are peptides ranging from about 2 to about 50 amino acid residues in length, corresponding to gp41 protein regions either amino to or carboxy to the actual DP178 gp41 amino acid sequence, respectively. Thus, a preferred amino terminal or carboxy terminal amino acid insertion would contain gp41 amino acid sequences found immediately amino to or carboxy to the DP178 region of the gp41 protein.

Deletions of DP178 (SEQ ID:1) or DP178 truncations are also within the scope of the invention. Such deletions consist of the removal of one or more amino acids from the DP178 or DP178-like peptide sequence, with the lower limit length of the resulting peptide sequence being 4 to 6 amino acids. Such deletions may involve a single contiguous or greater than one discrete portion of the peptide sequences. One or more such deletions may be introduced into DP178 (SEQ.ID:1) or DP178 truncations, as long as such deletions result in peptides which may still be recognized by the 107×178×4, ALLMOTI5 or PLZIP search motifs described herein, or may, alternatively, exhibit antifusogenic or antiviral activity, or exhibit the ability to modulate intracellular processes involving coiled-coil peptide structures.

DP178 analogs are further described, below, in Section 5.3.

5.2. DP107 and DP107-LIKE Peptides

Further, the peptides of the invention include peptides having amino acid sequences corresponding to DP107 analogs. DP107 is a 38 amino acid peptide which exhibits potent antiviral activity, and corresponds to residues 558 to 595 of HIV-1$_{LAI}$ transmembrane (TM) gp41 protein, as shown here:

NH$_2$—NNLLRAIEAQQHLLQLTVWQIKQLQA-
RILAVERYLkDQ—COOH (SEQ ID:25)

In addition to the full-length DP107 (SEQ ID:25) 38-mer, the peptides of the invention may include truncations of the DP107 (SEQ ID:25) peptide which exhibit antifusogenic activity, antiviral activity and/or the ability to modulate intracellular processes involving coiled-coil peptide structures. Truncations of DP107 (SEQ ID:25) peptides may comprise peptides of between 3 and 38 amino acid residues (i.e., peptides ranging in size from a tripeptide to a 38-mer polypeptide), as shown in Tables II and IIA, below. Peptide sequences in these tables are listed from amino (left) to carboxy (right) terminus. "X" may represent an amino group (—NH$_2$) and "Z" may represent a carboxyl (—COOH) group. Alternatively, "X" may represent a hydrophobic group, including but not limited to carbobenzyl, dansyl, or T-butoxycarbonyl; an acetyl group; a 9-fluorenylmethoxy-carbonyl (FMOC) group; or a covalently attached macromolecular group, including but not limited to a lipid-fatty acid conjugate, polyethylene glycol, carbohydrate or peptide group. Further, "Z" may represent an amido group; a T-butoxycarbonyl group; or a covalently attached macromolecular group, including but not limited to a lipid-fatty acid conjugate, polyethyleneglycol, carbohydrate or peptide group. A preferred "X" or "Z" macromolecular group is a peptide group.

TABLE II

DP107 (SEQ ID:25) CARBOXY TRUNCATIONS

X-NNL-Z
X-NNLL-Z
X-NNLLR-Z
X-NNLLRA-Z
X-NNLLRAI-Z
X-NNLLRAIE-Z
X-NNLLRAIEA-Z
X-NNLLRAIEAQ-Z
X-NNLLRAIEAQQ-Z
X-NNLLRAIEAQQH-Z
X-NNLLRAIEAQQHL-Z
X-NNLLRAIEAQQHLL-Z
X-NNLLRAIEAQQHLLQ-Z
X-NNLLRAIEAQQHLLQL-Z
X-NNLLRAIEAQQHLLQLT-Z
X-NNLLRAIEAQQHLLQLTV-Z
X-NNLLRAIEAQQHLLQLTVW-Z
X-NNLLRAIEAQQHLLQLTVWQ-Z
X-NNLLRAIEAQQHLLQLTVWQI-Z
X-NNLLRAIEAQQHLLQLTVWQIK-Z
X-NNLLRAIEAQQHLLQLTVWQIKQ-Z
X-NNLLRAIEAQQHLLQLTVWQIKQL-Z
X-NNLLRAIEAQQHLLQLTVWQIKQLQ-Z
X-NNLLRAIEAQQHLLQLTVWQIKQLQA-Z
X-NNLLRAIEAQQHLLQLTVWQIKQLQAR-Z
X-NNLLRAIEAQQHLLQLTVWQIKQLQARI-Z
X-NNLLRAIEAQQHLLQLTVWQIKQLQARIL-Z

TABLE II-continued

DP107 (SEQ ID:25) CARBOXY TRUNCATIONS

X-NNLLRAIEAQQHLLQLTVWQIKQLQARILA-Z
X-NNLLRAIEAQQHLLQLTVWQIKQLQARILAV-Z
X-NNLLRAIEAQQHLLQLTVWQIKQLQARILAVE-Z
X-NNLLRAIEAQQHLLQLTVWQIKQLQARILAVER-Z
X-NNLLRAIEAQQHLLQLTVWQIKQLQARILAVERY-Z
X-NNLLRAIEAQQHLLQLTVWQIKQLQARILAVERYL-Z
X-NNLLRAIEAQQHLLQLTVWQIKQLQARILAVERYLK-Z
X-NNLLRAIEAQQHLLQLTVWQIKQLQARILAVERYLKD-Z
X-NNLLRAIEAQQHLLQLTVWQIKQLQARILAVERYLKDQ-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOS) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE IIA

DP178 (SEQ ID:25) AMINO TRUNCATIONS

X-KDQ-Z
X-LKDQ-Z
X-YLKDQ-Z
X-RYLKDQ-Z
X-ERYLKDQ-Z
X-VERYLKDQ-Z
X-AVERYLKDQ-Z
X-LAVERYLKDQ-Z
X-ILAVERYLKDQ-Z
X-RILAVERYLKDQ-Z
X-ARILAVERYLKDQ-Z
X-QARILAVERYLKDQ-Z
X-LQARILAVERYLKDQ-Z
X-QLQARILAVERYLKDQ-Z
X-KQLQARILAVERYLKDQ-Z
X-IKQLQARILAVERYLKDQ-Z
X-QIKQLQARILAVERYLKDQ-Z
X-WQIKQLQARILAVERYLKDQ-Z
X-VWQIKQLQARILAVERYLKDQ-Z
X-TVWQIKQLQARILAVERYLKDQ-Z
X-LTVWQIKQLQARILAVERYLKDQ-Z
X-QLTVWQIKQLQARILAVERYLKDQ-Z
X-LQLTVWQIKQLQARILAVERYLKDQ-Z
X-LLQLTVWQIKQLQARILAVERYLKDQ-Z
X-HLLQLTVWQIKQLQARILAVERYLKDQ-Z
X-QHLLQLTVWQIKQLQARILAVERYLKDQ-Z
X-QQHLLQLTVWQIKQLQARILAVERYLKDQ-Z
X-AQQHLLQLTVWQIKQLQARILAVERYLKDQ-Z
X-EAQQHLLQLTVWQIKQLQARILAVERYLKDQ-Z
X-IEAQQHLLQLTVWQIKQLQARILAVERYLKDQ-Z
X-AIEAQQHLLQLTVWQIKQLQARILAVERYLKDQ-Z
X-RAIEAQQHLLQLTVWQIKQLQARILAVERYLKDQ-Z
X-LRAIEAQQHLLQLTVWQIKQLQARILAVERYLKDQ-Z
X-LLRAIEAQQHLLQLTVWQIKQLQARILAVERYLKDQ-Z
X-NLLRAIEAQQHLLQLTVWQIKQLQARILAVERYLKDQ-Z
X-NNLLRAIEAQQHLLQLTVWQIKQLQARILAVERYLKDQ-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

The peptides of the invention also include DP107-like peptides "DP107-like", as used herein, refers, first, to DP107 and DP107 truncations which contain one or more amino acid substitutions, insertions and/or deletions. Second, "DP-107-like" refers to peptide sequences identified or recognized by the ALLMOTI5, 107×178×4 and PLZIP search motifs described herein, having structural and/or amino acid motif similarity to DP107. The DP107-like peptides of the invention may exhibit antifusogenic or antiviral activity, or may exhibit the ability to modulate intracellular processes involving coiled-coil peptides. Further, such DP107-like peptides may possess additional advantageous features, such as, for example, increased bioavailability, and/or stability, or reduced host immune recognition.

HIV-1 and HIV-2 enveloped proteins are structurally distinct, but there exists a striking amino acid conservation within the DP107-corresponding regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the DP107 peptides of the invention. Utilizing the DP107 and DP107 analog sequences described herein, the skilled artisan can readily compile DP107 consensus sequences and ascertain from these, conserved amino acid residues which would represent preferred amino acid substitutions.

The amino acid substitutions may be of a conserved or non-conserved nature. Conserved amino acid substitutions consist of replacing one or more amino acids,of the DP107 (SEQ ID:25) peptide sequence with amino acids of similar charge, size, and/or hydrophobicity characteristics, such as, for example, a glutamic acid (E) to aspartic acid (D) amino acid substitution. Non-conserved substitutions consist of replacing one or more amino acids of the DP107 (SEQ ID:25) peptide sequence with amino acids possessing dissimilar charge, size, and/or hydrophobicity characteristics, such as, for example, a glutamic acid (E) to valine (V) substitution.

Amino acid insertions may consist of single amino acid residues or stretches of residues. The insertions may be made at the carboxy or amino terminal end of the DP107 or DP107 truncated peptides, as well as at a position internal to the peptide. Such insertions will generally range from 2 to 15 amino acids in length. It is contemplated that insertions made at either the carboxy or amino terminus of the peptide of interest may be of a broader size range, with about 2 to about 50 amino acids being preferred. One or more such insertions may be introduced into DP107 (SEQ.ID:25) or DP107 truncations, as long as such insertions result in peptides which may still be recognized by the 107×178×4, ALLMOTI5 or PLZIP search motifs described herein, or may, alternatively, exhibit antifusogenic or antiviral activity, or exhibit the ability to modulate intracellular processes involving coiled-coil peptide structures.

Preferred amino or carboxy terminal insertions are peptides ranging from about 2 to about 50 amino acid residues in length, corresponding to gp41 protein regions either amino to or carboxy to the actual DP107 gp41 amino acid sequence, respectively. Thus, a preferred amino terminal or carboxy terminal amino acid insertion would contain gp41 amino acid sequences found immediately amino to or carboxy to the DP107 region of the gp41 protein.

Deletions of DP107 (SEQ ID:25) or DP178 truncations are also within the scope of the invention. Such deletions consist of the removal of one or more amino acids from the DP107 or DP107-like peptide sequence, with the lower limit length of the resulting peptide, sequence being 4 to 6 amino acids. Such deletions may involve a single contiguous or greater than one discrete portion of the peptide sequences. One or more such deletions may be introduced into DP107 (SEQ.ID:25) or DP107 truncations, as long as such deletions result in peptides which may still be recognized by the 107×178×4, ALLMOTI5 or PLZIP search motifs described herein, or may, alternatively, exhibit antifusogenic or antiviral activity, or exhibit the ability to modulate intracellular processes involving coiled-coil peptide structures.

DP107 and DP107 truncations are more fully described in Applicants' co-pending U.S. patent application Ser. No. 08/374,666, filed Jan. 27, 1995, and which is incorporated herein by reference in its entirety. DP107 analogs are further described, below, in Section 5.3.

5.3. DP107 and DP178 Analogs

Peptides corresponding to analogs of the DP178, DP178 truncations, DP107 and DP107 truncation sequences of the invention, described, above, in Sections 5.1 and 5.2 may be found in other viruses, including, for example, non-HIV-1$_{LAI}$ enveloped viruses, non-enveloped viruses and other non-viral organisms.

The term "analog", as used herein, refers to a peptide which is recognized or identified via the 107×178×4, ALLMOTI5 and/or PLZIP search strategies discussed below. Further, such peptides may exhibit antifusogenic capability, antiviral activity, or the ability to modulate intracellular processes involving coiled-coil structures.

Such DP178 and DP107 analogs may, for example, correspond to peptide sequences present in TM proteins of enveloped viruses and may, additionally correspond to peptide sequences present in non enveloped and non-viral organisms. Such peptides may exhibit antifusogenic activity, antiviral activity, most particularly antiviral activity which is specific to the virus in which their native sequences are found, or may exhibit an ability to modulate intracellular processes involving coiled-coil peptide structures.

DP178 analogs are peptides whose amino acid sequences are comprised of the amino acid sequences of peptide regions of, for example, other (i.e., other than HIV-1$_{LAI}$) viruses that correspond to the gp41 peptide region from which DP178 (SEQ ID:1) was derived. Such viruses may include, but are not limited to, other HIV-1 isolates and HIV-2 isolates. DP178 analogs derived from the corresponding gp41 peptide region of other (i.e., non HIV-1$_{LAI}$). HIV-1 isolates may include, for example, peptide sequences as shown below.

NH$_2$—YT<u>NTI</u>Y<u>TL</u> LEESQNQQEKNEQELLELDKWASLWNWF—COOH (DP-185; SEQ ID:3);

NH$_2$—YT<u>GI</u>IY<u>NL</u> LEESQNQQEKNEQELLELDKWA<u>N</u>LWNWF—COOH (SEQ ID:4);

NH$_2$—YTSL<u>I</u>YSL<u>LE</u> KSQIQQEKNEQELLELDKWASLWNWF—COOH (SEQ ID:5).

SEQ ID:3 (DP-185), SEQ ID:4, and SEQ ID:5 are derived from HIV-1$_{SF2}$, HIV-1$_{RF}$, and HIV-1$_{MN}$ isolates, respectively. Underlined amino acid residues refer to those residues that differ from the corresponding. position in the DP178 (SEQ ID:1) peptide. One such DP178 analog, DP-185 (SEQ ID:3), is described in the Example presented in Section 6, below, where it is demonstrated that DP-185 (SEQ ID:3) exhibits antiviral activity. The DP178 analogs of the invention may also include truncations, as described above. Further, the analogs of the invention modifications such those described for DP178 analogs in Section 5.1., above. It is preferred that the DP178 analogs of the invention represent peptides whose amino acid sequences correspond to the DP178 region of the gp41 protein, it is also contemplated that the peptides of the invention may, additionally, include amino sequences, ranging from about 2 to about 50 amino acid residues in length, corresponding to gp41 protein regions either amino to or carboxy to the actual DP178 amino acid sequence.

Striking similarities, as shown in FIG. 1, exist within the regions of HIV-1 and HIV-2 isolates which correspond to the DP178 sequence. A DP178 analog derived from the HIV-$2_{NIHZ}$ isolate has the 36 amino acid sequence (reading from amino to carboxy terminus):

NH$_2$—LEANISQSLEQAQIQQEKNMYELQKLN-
SWDVFTNWL—COOH (SEQ ID:7)

Table III and Table IV show some possible truncations of the HIV-$2_{NIHZ}$ DP178 analog, which may comprise peptides of between 3 and 36 amino acid residues (i.e., peptides ranging in size from a tripeptide to a 36-mer polypeptide). Peptide sequences in these tables are listed from amino (left) to carboxy (right) terminus "X" may represent an amino group (—NH$_2$) and "Z" may represent a carboxyl (—COOH) group. Alternatively, "X" may represent a hydrophobic group, including but not limited to carbobenzyl, dansyl, or T-butoxycarbonyl; an acetyl group; a 9-fluorenylmethoxy-carbonyl (FMOC) group; or a covalently attached macromolecular group, including but not limited to a lipid-fatty acid conjugate, Further, "Z" may represent an amido group; a T-butoxycarbonyl group; or a covalently attached macromolecular group, including but not limited to a lipid-fatty acid conjugate, polyethylene glycol, carbohydrate or peptide group. A preferred "X" or "Z" macromolecular group is a peptide group.

TABLE III

HIV-$2_{NIHZ}$ DP178 analog carboxy truncations.

X-LEA-Z
X-LEAN-Z
X-LEANI-Z
X-LEANIS-Z
X-LEANISQ-Z
X-LEANISQS-Z
X-LEANISQSL-Z
X-LEANISQSLE-Z
X-LEANISQSLEQ-Z
X-LEANISQSLEQA-Z
X-LEANISQSLEQAQ-Z
X-LEANISQSLEQAQI-Z
X-LEANISQSLEQAQIQ-Z
X-LEANISQSLEQAQIQQ-Z
X-LEANISQSLEQAQIQQE-Z
X-LEANISQSLEQAQIQQEK-Z
X-LEANISQSLEQAQIQQEKN-Z
X-LEANISQSLEQAQIQQEKNM-Z
X-LEANISQSLEQAQIQQEKNMY-Z
X-LEANISQSLEQAQIQQEKNMYE-Z
X-LEANISQSLEQAQIQQEKNMYEL-Z
X-LEANISQSLEQAQIQQEKNMYELQ-Z
X-LEANISQSLEQAQIQQEKNMYELQK-Z
X-LEANISQSLEQAQIQQEKNMYELQKL-Z
X-LEANISQSLEQAQIQQEKNMYELQKLN-Z
X-LEANISQSLEQAQIQQEKNMYELQKLNS-Z
X-LEANISQSLEQAQIQQEKNMYELQKLNSW-Z
X-LEANISQSLEQAQIQQEKNMYELQKLNSWD-Z
X-LEANISQSLEQAQIQQEKNMYELQKLNSWDV-Z
X-LEANISQSLEQAQIQQEKNMYELQKLNSWDVF-Z
X-LEANISQSLEQAQIQQEKNMYELQKLNSWDVFT-Z
X-LEANISQSLEQAQIQQEKNMYELQKLNSWDVFTN-Z

TABLE III-continued

HIV-$2_{NIHZ}$ DP178 analog carboxy truncations.

X-LEANISQSLEQAQIQQEKNMYELQKLNSWDVFTNW-Z
X-LEANISQSLEQAQIQQEKNMYELQKLNSWDVFTNWL-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not lmited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE IV

HIV-$2_{NIHZ}$ DP178 analog amino truncations.

X-NWL-Z
X-TNWL-Z
X-FTNWL-Z
X-VFTNWL-Z
X-DVFTNWL-Z
X-WDVFTNWL-Z
X-SWDVFTNWL-Z
X-NSWDVFTNWL-Z
X-LNSWDVFTNWL-Z
X-KLNSWDVFTNWL-Z
X-QKLNSWDVFTNWL-Z
X-LQKLNSWDVFTNWL-Z
X-ELQKLNSWDVFTNWL-Z
X-YELQKLNSWDVFTNWL-Z
X-MYELQKLNSWDVFTNWL-Z
X-NMYELQKLNSWDVFTNWL-Z
X-KNMYELQKLNSWDVFTNWL-Z
X-EKNMYELQKLNSWDVFTNWL-Z
X-QEKNMYELQKLNSWDVFTNWL-Z
X-QQEKNMYELQKLNSWDVFTNWL-Z
X-IQQEKNMYELQKLNSWDVFTNWL-Z
X-QIQQEKNMYELQKLNSWDVFTNWL-Z
X-AQIQQEKNMYELQKLNSWDVFTNWL-Z
X-QAQIQQEKNMYELQKLNSWDVFTNWL-Z
X-EQAQIQQEKNMYELQKLNSWDVFTNWL-Z
X-LEQAQIQQEKNMYELQKLNSWDVFTNWL-Z
X-SLEQAQIQQEKNMYELQKLNSWDVFTNWL-Z
X-QSLEQAQIQQEKNMYELQKLNSWDVFTNWL-Z
X-SQSLEQAQIQQEKNMYELQKLNSWDVFTNWL-Z
X-ISQSLEQAQIQQEKNMYELQKLNSWDVFTNWL-Z
X-NISQSLEQAQIQQEKNMYELQKLNSWDVFTNWL-Z
X-ANISQSLEQAQIQQEKNMYELQKLNSWDVFTNWL-Z
X-EANISQSLEQAQIQQEKNMYELQKLNSWDVFTNWL-Z
X-LEANISQSLEQAQIQQEKNMYELQKLNSWDVFTNWL-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not lmited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

DP178 and DP107 analogs are recognized or identified, for example, by utilizing one or more of the 107×178×4, ALLMOTI5 or PLZIP computer-assisted search strategies described and demonstrated, below, in the Examples presented in Sections 9 through 16 and 19 through 25. The search strategy identifies additional peptide regions which are predicted to have structural and/or amino acid sequence features similar to those of DP107 and/or DP178 .

The search strategies are described fully, below, in the Example presented in Section 9. While this search strategy is based, in part, on a primary amino acid motif deduced from DP107 and DP178, it is not based solely on searching for primary amino acid sequence homologies, as such protein sequence homologies exist within, but not between major groups of viruses. For example, primary amino acid sequence homology is high within the TM protein of different strains of HIV-1 or within the TM protein of different isolates of simian immunodeficiency virus (SIV). Primary amino acid sequence homology between HIV-1 and SIV, however, is low enough so as not to be useful. It is not possible, therefore, to find peptide regions similar to DP107 or DP178 within other viruses, or within non-viral organisms, whether structurally, or otherwise, based on primary sequence homology, alone.

Further, while it would be potentially useful to identify primary sequence arrangements of amino acids based on, for example, the physical chemical characteristics of different classes of amino acids rather than based on the specific amino acids themselves, such search strategies have, until now, proven inadequate. For example, a computer algorithm designed by Lupas et al. to identify coiled-coil propensities of regions within proteins (Lupas, A., et al., 1991 Science 252:1162–1164) is inadequate for identifying protein regions analogous to DP107 or DP178.

Specifically, analysis of-HIV-1 gp160 (containing both gp120 and gp41) using the Lupas algorithm does not identify the coiled-coil region within DP107. It does, however, identify a region within DP178 beginning eight amino acids N-terminal to the start of DP178 and ending eight amino acids from the C-terminus. The DP107 peptide has been shown experimentally to form. a stable coiled coil. A search based on the Lupas search algorithm, therefore, would not have identified the DP107 coiled-coil region. Conversely, the Lupas algorithm identified the DP178 region as a potential coiled-coil motif. However, the peptide derived from the DP178 region failed to form a coiled coil in solution.

A possible explanation for the inability of the Lupas search algorithm to accurately identify coiled-coil sequences within the HIV-1 TM, is that the Lupas algorithm is based on the structure of coiled coils from proteins that are not structurally or functionally similar to the TM proteins of viruses, antiviral peptides (e.g. DP107 and DP178) of which are an object of this invention.

The computer search strategy of the invention, as demonstrated in the Examples presented below, in Sections 9 through 16 and 19 through 25, successfully identifies regions of proteins similar to DP107 or DP178. This search strategy was:designed to be used with a commercially-available sequence database package, preferably PC/Gene.

A series of search motifs, the 107×178×4, ALLMOTI5 and PLZIP motifs, were designed and engineered to range in stringency from strict to broad, as discussed in this Section and in Section 9, with 107×178×4 being preferred. The sequences identified via such search motifs, such as those listed in Tables V-XIV, below, potentially exhibit antifusogenic, such as antiviral, activity, may additionally be useful in the identification of antifusogenic, such as antiviral, compounds, and are intended to be within the scope of the invention.

Coiled-coiled sequences are thought to consist of heptad amino acid repeats. For ease of description, the amino acid positions within the heptad repeats are sometimes referred to as A through G, with the first position being A, the second B, etc. The motifs used to identify DP107-like and DP178-like sequences herein are designed to specifically search for and identify such heptad repeats. In the descriptions of each of the motifs described, below, amino acids enclosed by brackets, i.e., [ ], designate the only amino acid residues that are acceptable at the given position, while amino acids enclosed by braces, i.e., { }, designate the only amino acids which are unacceptable at the given heptad position. When a set of bracketed or braced amino acids is followed by a number in parentheses i.e., ( ), it refers to the number of subsequent amino acid positions for which the designated set of amino acids hold, e.g, a (2) means "for the next two heptad amino acid positions".

The ALLMOTI5 is written as follows:
{CDGHP}-{CFP} (2)-{CDGHP}-{CFP} (3)-
{CDGHP}-{CFP} (2)-{CDGHP}-{CFP} (3)-
{CDGHP}-{CFP} (2)-{CDGHP}-{CFP} (3)-
{CDGHP}-{CFP} (2)-{CDGHP}-{CFP} (3)-
{CDGHP}-{CFP} (2)-{CDGHP}-{CFP} (3)-

Translating this motif, it would read: "at the first (A) position of the heptad, any amino acid residue except C, D, G,. H, or P is acceptable, at the next two (B,C) amino acid positions, any amino acid residue except C, F, or P is acceptable, at the fourth heptad position (D), any amino acid residue except C, D, G, H, or P is acceptable, at the next three (E, F, G) amino acid positions, any amino acid residue except C, F, or P is acceptable. This motif is designed to search for five consecutive heptad repeats (thus the repeat of the first line five times), meaning that it searches for 35-mer sized peptides. It may also be designed to search for 28-mers, by only repeating the initial motif four times. With respect to the ALLMOTI5 motif, a 35-mer search is preferred. Those viral (non-bacteriophage) sequences identified via such an ALLMOTI5 motif are listed in Table V, below, at the end of this Section. The viral sequences listed in Table V potentially exhibit antiviral activity, may be useful in the the identification of antiviral compounds, and are intended to be within the scope of the invention. In those instances wherein a single gene exhibits greater than one sequence. recognized by the ALLMOTI5 search motif, the amino a acid residue numbers of these sequences are listed under "Area 2", Area 3", etc. This convention is used for each of the Tables listed, below, at the end of this Section.

The 107×178×4 motif is written as follows:
[EFIKLNQSTVWY]-{CFMP} (2)-[EFIKLNQSTVWY]-{CFMP} (3)-
[EFIKLNQSTVWY]-{CFMP} (2)-[EFIKLNQSTVWY]-{CFMP} (3)-
[EFIKLNQSTVWY]-{CFMP} (2)-[EFIKLNQSTVWY]-{CFMP} (3)-
[EFIKLNQSTVWY]-{CFMP} (2)-[EFIKLNQSTVWY]-{CFMP} (3)-

Translating this motif, it would read: "at the first (A) position of the heptad, only amino acid residue E, F, I, K, L, N, Q, S, T, V, W, or Y is acceptable, at the next two (B,C) amino acid 30 positions, any amino acid residue except C, F, M or P is acceptable, at the fourth position (D), only amino acid residue E, F, I, K, L, N, Q, S, T, V, W, or Y is acceptable, at the next three (E, F, G) amino acid positions, any amino acid residue except C, F, M or P is acceptable. This motif is designed to search for four consecutive heptad repeats (thus the repeat of the first line four times), meaning that it searches for 28-mer sized peptides. It may also be designed to search for 35-mers, by repeating the initial motif five times. With respect to the 107×178×4 motif, a 28-mer search is preferred.

Those viral (non-bacteriophage) sequences identified via such a 107×178×4 motif are listed in Table VI, below, at the end of this Section, with those viral (non-bacteriophage) sequences listed in Table VII, below at the end of this Section, being preferred.

The 107×178×4 search motif was also utilized to identify non-viral procaryotic protein sequences, as listed in Table VIII, below, at the end of this Section. Further, this search motif was used to reveal a number of human proteins. The results of this human protein 107×178×4 search is listed in Table IX, below, at the end of this Section. The sequences listed in Tables VIII and IX, therefore, reveal peptides which may be useful as antifusogenic compounds or in the identification of antifusogenic compounds, and are intended to be within the scope of the invention.

The PLZIP series of motifs are as listed in FIG. 19. These motifs are designed to identify leucine zipper coiled-coil like heptads wherein at least one proline residue is present at some predefined distance N-terminal to the repeat. These PLZIP motifs find regions of proteins with similarities to HIV-1 DP178 generally located just N-terminal to the transmembrane anchor. These motifs may be translated according to the same convention described above. Each. line depicted in FIG. 19 represents a single, complete search motif. "X" in these motifs refers to any-amino acid residue. In instances wherein a motif contains two numbers within parentheses, this refers to a variable number of amino acid residues. For example, X (1,12) is translated to "the next one to twelve amino. acid residues,. inclusive, may be any amino acid".

Tables X through XIV, below, at the end of this Section, list sequences identified via searches conducted with such PLZIP motifs. Specifically, Table X lists viral sequences identified via PCTLZIP, P1CTLZIP and P2CTLZIP search motifs, Table XI lists viral sequences identified via P3CTLZIP, P4CTLZIP, P5CTLZIP and P6CTLZIP search motifs, Table XII lsts viral sequences identified via P7CTLZIP, P8CTLZIP and P9CTLZIP search motifs, Table XIII lists viral sequences identified via P12LZIPC searches and Table XIV lists viral. sequences identified via P23TLZIPC search motifs. The viral sequences listed in these tables represent peptides which potentially exhibit. antiviral activity, may be useful in the identification of antiviral compounds, and are intended to be within the scope of the invention.

The Examples presented in Sections 17, 18, 26 and 27 below, demonstrate that viral sequences identified via the motif searches described herein identify substantial antiviral characteristics. Specifically, the Example presented in Section 17 describes peptides. with anti-respiratory syncytial virus activity, the Example presented in Section 18 describes peptides with anti-parainfluenza virus activity, the Example presented in Section 26 describes peptides with anti-measles virus activity and the Example presented in Section 27 describes peptides with anti-simian immunodeficiency virus activity.

The DP107 and DP178 analogs may, further, contain any of the additional groups described for DP178, above, in Section 5.1. For example, these peptides may include any of the additional amino-terminal groups as described above for "X" groups, and may also include any of the carboxy-terminal groups as described, above, for "Z" groups.

Additionally, truncations of the identified DP107 and DP178 peptides are among the peptides of the invention. Further, such DP107 and DP178 analogs and DP107/DP178 analog truncations may exhibit one or more amino acid substitutions, insertion, and/or deletions. The DP178 analog amino acid substitutions, insertions and deletions, are as described, above, for DP178-like peptides in Section 5.1. The DP-107 analog amino acid substitutions, insertions and deletions are also as described, above, for DP107-like peptides in Section 5.2.

Tables XV through XXII, below, present representative examples of such DP107/DP178 truncations. Specifically,- Table XV presents Respiratory Syncytial Virus F1 region DP107 analog carboxy truncations, Table XVI presents Respiratory Syncytial Virus F1 region DP107 analog amino truncations, Table XVII presents Respiratory Syncytial Virus F1 region DP178 analog carboxy truncations, Table XVIII presents Respiratory Syncytial Virus F1 region DP178 analog amino truncations, Table XIX presents Human Parainfluenza Virus 3 F1 region DP178 analog carboxy truncations, Table XX presents Human Parainfluenza Virus 3F1 region DP178 analog amino truncations, Table XXI presents Human Parainfluenza Virus 3 F1 region DP107 analog carboxy truncations and Table XXII presents Human Parainfluenza Virus 3 F1 region DP107 analog amino truncations. Further, Table XXIII, below,.presents DP107/DP178 analogs and analog truncations which exhibit substantial-antiviral activity. These antiviral peptides are grouped according to the specific virus which they inhibit, including respiratory syncytial virus, human parainfluenza virus 3, simian immunodeficiency virus and measles virus.

TABLE V

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| P170K_TRVPS | POTENTIAL 170 KD PROTEIN | TOBACCO RATTLE VIRUS (STRAIN PSG) | 113–153 | | | | | | | |
| P194K_TRVSY | POTENTIAL 194 KD PROTEIN | TOBACCO RATTLE VIRUS (STRAIN SYM) | 144–178 | 214–248 | 391–446 | 644–678 | 1045–1079 | 1135–1176 | 1335–1376 | 1618–1656 |
| P55KD_HSV6U | 55 8 KD PROTEIN | HERPES SIMPLEX VIRUS (TYPE 6/STRAIN UGANDA-1102) | 228–262 | | | | | | | |
| PAANT_HDVAM | DELTA ANTIGEN | HEPATITIS DELTA VIRUS (ISOLATE AMERICAN) | 3–48 | 100–144 | | | | | | |
| PAANT_HDVD3 | DELTA ANTIGEN | HEPATITIS DELTA VIRUS (ISOLATE D380) | 7–48 | 100–144 | | | | | | |
| PAANT_HDVTT | DELTA ANTIGEN (ALPHA ANTIGEN) | HEPATITIS DELTA VIRUS (ISOLATE ITALIAN) | 3–48 | 100–144 | | | | | | |
| PAANT_HDVL1 | DELTA ANTIGEN | HEPATITIS DELTA VIRUS (ISOLATE LEBANON-1) | 3–48 | 100–144 | | | | | | |
| PAANT_HDVM1 | DELTA ANTIGEN | HEPATITIS DELTA VIRUS (ISOLATE JAPANESE M-1) | 3–48 | 100–144 | | | | | | |
| PAANT_HDVM2 | DELTA ANTIGEN | HEPATITIS DELTA VIRUS (ISOLATE JAPANESE M-2) | 3–48 | 100–144 | | | | | | |
| PAANT_HDVNA | DELTA ANTIGEN | HEPATITIS DELTA VIRUS (ISOLATE NAURU) | 3–48 | 100–144 | | | | | | |
| PAANT_HDVS1 | DELTA ANTIGEN | HEPATITIS DELTA VIRUS (ISOLATE JAPANESE S-1) | 1–49 | 100–144 | | | | | | |
| PAANT_HDVS2 | DELTA ANTIGEN | HEPATITIS DELTA VIRUS (ISOLATE JAPANESE S-2) | 1–49 | 100–144 | | | | | | |
| PAANT_HDVWO | DELTA ANTIGEN | HEPATITIS DELTA VIRUS (ISOLATE WOODCHUCK) | 3–48 | 100–144 | | | | | | |
| PAT3H_FOWPM | ANTITHROMBIN-III HOMOLOG | FOWLPOX VIRUS (ISOLATE HP-438) | 71–110 | | | | | | | |
| PAT11_VACCV | 94 KD A-TYPE INCLUSION PROTEIN | VACCINIA VIRUS (STRAIN WR) | 14–57 | 420–564 | 570–625 | | | | | |
| PAT11_VARV | 81 KD A-TYPE INCLUSION PROTEIN | VARIOLA VIRUS | 425–525 | 531–565 | 571–628 | | | | | |
| PAT12_HSV11 | ALPHA TRANS-INDUCING FACTOR | HERPES SIMPLEX VIRUS (TYPE 1) | 304–345 | 304–345 | | | | | | |
| PAT12_HSV1F | ALPHA TRANS-INDUCING FACTOR | HERPES SIMPLEX VIRUS (TYPE 1) | 102–139 | 304–345 | | | | | | |
| PAT12_HSVEB | ALPHA TRANS-INDUCING FACTOR | EQUINE HERPESVIRUS TYPE 1 (STRAIN AB4P) | 101–147 | 268–331 | | | | | | |
| PAT12_VACCC | PUTATIVE A-TYPE INCLUSION PROTEIN | VACCINIA VIRUS (STRAIN COPENHAGEN) | 79–124 | 219–263 | | | | | | |
| PAT12_VACCV | PUTATIVE A-TYPE INCLUSION PROTEIN | VACCINIA VIRUS | 79–124 | | | | | | | |
| PAT12_VZVD | ALPHA TRANS-INDUCING FACTOR | VARICELLA-ZOSTER VIRUS (STRAIN DUMAS) | 298–361 | 395–429 | | | | | | |
| PAT13_VACCV | PUTATIVE A-TYPE INCLUSION PROTEIN | VACCINIA VIRUS | 51–95 | | | | | | | |
| PATIN_HSV23 | ALPHA TRANS-INDUCING PROTEIN (VMW65) | HERPES SIMPLEX VIRUS (TYPE 2) | 178–219 | 324–381 | | | | | | |
| PATIN_HSV2H | ALPHA TRANS-INDUCING PROTEIN (VMW65) | HERPES SIMPLEX VIRUS (TYPE 2) | 177–222 | 324–381 | | | | | | |
| PATIN_HSVBP | ALPHA TRANS-INDUCING PROTEIN | BOVINE HERPESVIRUS TYPE 1 | 195–256 | | | | | | | |
| PATIN_HSVEB | ALPHA TRANS-INDUCING PROTEIN | EQUINE HERPESVIRUS TYPE 1 | 241–289 | | | | | | | |
| PATIN_VZVD | ALPHA TRANS-INDUCING PROTEIN ( | VARICELLA-ZOSTER VIRUS (STRAIN DUMAS) | 206–252 | | | | | | | |
| PATI_COWPX | A-TYPE INCLUSION PROTEIN | COWPOX VIRUS | 14–57 | 426–526 | 532–566 | 572–629 | 803–989 | 1106–1150 | | |
| PBDL2_EBV | PROTEIN BDLF2 | EPSTEIN-BARR VIRUS (STRAIN B95-8) | 90–131 | | | | | | | |
| PBRL1_EBV | TRANSCRIPTION ACTIVATOR BRLF1 | EPSTEIN-BARR VIRUS (STRAIN B95-8) | 150–187 | | | | | | | |
| PCOA1_POVBA | COAT PROTEIN VP1 | POLYOMAVIRUS BK | 107–141 | | | | | | | |
| PCOA1_POVBK | COAT PROTEIN VP1 | POLYOMAVIRUS BK | 107–141 | | | | | | | |
| PCOA1_POVHA | COAT PROTEIN VP1 | HAMSTER POLYOMAVIRUS | 159–195 | | | | | | | |
| PCOA1_SV40 | COAT PROTEIN VP1 | SIMIAN VIRUS 40 | 109–143 | | | | | | | |
| PCOA2_BFDV | COAT PROTEIN VP2 | BUDGERIGAR FLEDGLING DISEASE VIRUS | 141–213 | | | | | | | |
| PCOA2_POVBA | COAT PROTEIN VP2 | POLYOMAVIRUS BK (STRAIN AS) | 14–64 | 317–351 | | | | | | |
| PCOA2_POVBK | COAT PROTEIN VP2 | POLYOMAVIRUS BK | 14–64 | 317–351 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PCOA2_POVBO | COAT PROTEIN VP2 | BOVINE POLYOMAVIRUS | 35–76 | 153–216 | | | | | | |
| PCOA2_POVHA | COAT PROTEIN VP2 | HAMSTER POLYOMAVIRUS | 7–48 | 174–208 | | | | | | |
| PCOA2_POVIC | COAT PROTEIN VP2 | POLYOMAVIRUS JC | 14–64 | 233–267 | | | | | | |
| PCOA2_POVLY | COAT PROTEIN VP2 | LYMPHOTROPIC POLYOMAVIRUS | 14–78 | 156–206 | | | | | | |
| PCOA2_POVM3 | COAT PROTEIN VP2 | MOUSE POLYOMAVIRUS (STRAIN 3) | 5–72 | 137–185 | | | | | | |
| PCOA2_POVMA | COAT PROTEIN VP2 | MOUSE POLYOMAVIRUS | 5–72 | 137–185 | | | | | | |
| PCOA2_POVMC | COAT PROTEIN VP2 | MOUSE POLYOMAVIRUS | 5–72 | 137–185 | | | | | | |
| PCOA2_POVMK | COAT PROTEIN VP2 | MOUSE POLYOMAVIRUS | 15–56 | 177–211 | | | | | | |
| PCOA2_SV40 | COAT PROTEIN VP2 | SIMIAN VIRUS 40 | 14–62 | 228–262 | 318–352 | | | | | |
| PCOAT_ABMVW | COAT PROTEIN | ABUTIL ON MOSAIC VIRUS (ISOLATE WEST INDIA | 180–214 | | | | | | | |
| PCOAT_ACLSV | COAT PROTEIN | APPLE CHLOROTIC LEAF SPOT VIRUS | 154–188 | | | | | | | |
| PCOAT_AEDEV | COAT PROTEIN VP1 | AEDES DENSONUCLEOSIS VIRUS | 243–284 | | | | | | | |
| PCOAT_AMCV | COAT PROTEIN | ARTICHOKE MOTTLED CRINKLE VIRUS | 36–70 | 100–134 | | | | | | |
| PCOAT_BLRV | COAT PROTEIN | BEAN LEAFROLL VIRUS | 89–123 | | | | | | | |
| PCOAT_BMV | COAT PROTEIN | BROME MOSAIC VIRUS | 36–73 | | | | | | | |
| PCOAT_BYDV1 | COAT PROTEIN | BARLEY YELLOW DWARF VIRUS | 163–197 | | | | | | | |
| PCOAT_BYDVM | COAT PROTEIN | BARLEY YELLOW DWARF VIRUS | 163–197 | | | | | | | |
| PCOAT_BYDVP | COAT PROTEIN | BARLEY YELLOW DWARF VIRUS | 164–198 | | | | | | | |
| PCOAT_BYDVR | COAT PROTEIN | BARLEY YELLOW DWARF VIRUS | 164–198 | | | | | | | |
| PCOAT_CAMVC | COAT PROTEIN | CAULIFLOWER MOSAIC VIRUS (STRAIN | 56–90 | 186–223 | | | | | | |
| PCOAT_CAMVD | COAT PROTEIN | CAULIFLOWER MOSAIC VIRUS | 53–91 | 187–224 | | | | | | |
| PCOAT_CAMVE | COAT PROTEIN | CAULIFLOWER MOSAIC VIRUS | 56–90 | 186–223 | | | | | | |
| PCOAT_CAMVN | COAT PROTEIN | CAULIFLOWER MOSAIC VIRUS | 56–90 | 185–222 | | | | | | |
| PCOAT_CAMVS | COAT PROTEIN | CAULIFLOWER MOSAIC VIRUS | 53–91 | 187–224 | | | | | | |
| PCOAT_CARMV | COAT PROTEIN | CARNATION MOTTLE VIRUS | 13–51 | | | | | | | |
| PCOAT_CCMV | COAT PROTEIN | COWPEA CHLOROTIC MOTTLE VIRUS | 141–178 | | | | | | | |
| PCOAT_CERV | PROBABLE COAT PROTEIN | CARNATION ETCHED RING VIRUS | 192–226 | | | | | | | |
| PCOAT_CHVP1 | MAJOR CAPSID PROTEIN | PARAMECIUM BURSARIA CHLORELLA VIRUS 1 | 393–435 | | | | | | | |
| PCOAT_CLVK | COAT PROTEIN | CASSAVA LATENT VIRUS | 197–231 | | | | | | | |
| PCOAT_CLVN | COAT PROTEIN | CASSAVA LATENT VIRUS | 197–231 | | | | | | | |
| PCOAT_CMVFC | COAT PROTEIN | CUCUMBER MOSAIC VIRUS | 153–187 | | | | | | | |
| PCOAT_CMVI | COAT PROTEIN | CUCUMBER MOSAIC VIRUS | 153–187 | | | | | | | |
| PCOAT_CMVP6 | COAT PROTEIN | CUCUMBER MOSAIC VIRUS | 153–187 | | | | | | | |
| PCOAT_CMVQ | COAT PROTEIN | CUCUMBER MOSAIC VIRUS | 153–187 | | | | | | | |
| PCOAT_CMVWL | COAT PROTEIN | CUCUMBER MOSAIC VIRUS | 153–187 | | | | | | | |
| PCOAT_CMVY | COAT PROTEIN | CUCUMBER MOSAIC VIRUS | 153–187 | | | | | | | |
| PCOAT_CNV | COAT PROTEIN | CUCUMBER NECROSIS VIRUS | 328–365 | | | | | | | |
| PCOAT_CSMV | COAT PROTEIN | CHLORIS STRIATE MOSAIC VIRUS | 184–218 | | | | | | | |
| PCOAT_CTV36 | COAT PROTEIN | CITRUS TRISTEZA VIRUS | 79–120 | | | | | | | |
| PCOAT_CYMV | COAT PROTEIN | CLOVER YELLOW MOSAIC VIRUS | 162–204 | | | | | | | |
| PCOAT_EPMV | COAT PROTEIN | EGGPLANT MOSAIC VIRUS | 40–74 | | | | | | | |
| PCOAT_FCVC6 | COAT PROTEIN | FELINE CALICIVIRUS | 432–466 | 566–600 | | | | | | |
| PCOAT_FCVF4 | COAT PROTEIN | FELINE CALICIVIRUS | 502–550 | 566–600 | | | | | | |
| PCOAT_FCVF9 | COAT PROTEIN | FELINE CALICIVIRUS | 519–553 | 569–603 | | | | | | |
| PCOAT_FMVD | PROBABLE COAT PROTEIN | FIGWORT MOSAIC VIRUS | 144–199 | 206–247 | 449–483 | | | | | |
| PCOAT_FXMV | COAT PROTEIN | FOXTAIL MOSAIC VIRUS | 168–220 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PCOAT_IRV1 | CAPSID PROTEIN | TIPULA IRIDESCENT VIRUS | 90–124 | | | | | | | |
| PCOAT_IRV22 | CAPSID PROTEIN | SIMULIUM IRIDESCENT VIRUS | 90–124 | | | | | | | |
| PCOAT_IRV6 | CAPSID PROTEIN | CHILO IRIDESCENT VIRUS | 51–85 | | | | | | | |
| PCOAT_LSV | COAT PROTEIN | LILY SYMPTOMLESS VIRUS | 32–70 | 255–289 | | | | | | |
| PCOAT_MSTV | COAT PROTEIN | MAIZE STRIPE VIRUS | 7–76 | 84–121 | | | | | | |
| PCOAT_MSVK | COAT PROTEIN | MAIZE STREAK VIRUS | 187–221 | | | | | | | |
| PCOAT_MSVN | COAT PROTEIN | MAIZE STREAK VIRUS | 187–221 | | | | | | | |
| PCOAT_MSVS | COAT PROTEIN | MAIZE STREAK VIRUS | 187–221 | | | | | | | |
| PCOAT_ORSV | COAT PROTEIN | ODONTOGLOSSUM RINGSPOT VIRUS | 105–139 | | | | | | | |
| PCOAT_PAVBO | COAT PROTEIN VP2 | BOVINE PARVOVIRUS | 380–414 | 444–480 | | | | | | |
| PCOAT_PAVC7 | COAT PROTEIN VP1 | CANINE PARVOVIRUS | 497–531 | | | | | | | |
| PCOAT_PEBV | COAT PROTEIN | PEA EARLY BROWNING VIRUS | 73–114 | | | | | | | |
| PCOAT_POPMV | COAT PROTEIN | POPLAR MOSAIC VIRUS | 36–81 | | | | | | | |
| PCOAT_PPMVS | COAT PROTEIN | PEPPER MILD MOTTLE VIRUS | 104–138 | | | | | | | |
| PCOAT_PVSP | COAT PROTEIN | POTATO VIRUS | 38–72 | 251–292 | | | | | | |
| PCOAT_PYMVV | COAT PROTEIN | POTATO YELLOW MOSAIC VIRUS | 190–224 | | | | | | | |
| PCOAT_RBDV | COAT PROTEIN | RASPBERRY BUSHY DWARF VIRUS | 10–44 | 140–199 | | | | | | |
| PCOAT_RCNMV | COAT PROTEIN | RED CLOVER NECROTIC MOSAIC VIRUS | 272–306 | | | | | | | |
| PCOAT_RSV | COAT PROTEIN | RICE STRIPE VIRUS | 34–68 | 83–120 | 259–309 | | | | | |
| PCOAT_SLCV | COAT PROTEIN | SQUASH LEAF CURL VIRUS | 190–224 | | | | | | | |
| PCOAT_SMWLM | COAT PROTEIN | SATELLITE MAIZE WHITE LINE MOSAIC VIRUS | 66–100 | | | | | | | |
| PCOAT_SOCMV | COAT PROTEIN | SOYBEAN CHLOROTIC MOTTLE VIRUS | 128–166 | | | | | | | |
| PCOAT_STNV1 | COAT PROTEIN | SATELLITE TOBACCO NECROSIS VIRUS 1 | 2–50 | | | | | | | |
| PCOAT_STNV2 | COAT PROTEIN | SATELLITE TOBACCO NECROSIS VIRUS 2 | 38–72 | | | | | | | |
| PCOAT_TAMV | GENOME POLYPROTEIN | TAMARILLO MOSAIC VIRUS | 7–55 | | | | | | | |
| PCOAT_TAV | COAT PROTEIN | TOMATO ASPERMY VIRUS | 14–48 | | | | | | | |
| PCOAT_TBSVB | COAT PROTEIN | TOMATO BUSHY STUNT VIRUS | 1–37 | 43–77 | | | | | | |
| PCOAT_TBSVC | COAT PROTEIN | TOMATO BUSHY STUNT VIRUS | 44–78 | 100–134 | | | | | | |
| PCOAT_TCV | COAT PROTEIN | TURNIP CRINKLE VIRUS | 12–46 | | | | | | | |
| PCOAT_TGMV | COAT PROTEIN | TOMATO GOLDEN MOSAIC VIRUS | 186–220 | | | | | | | |
| PCOAT_TMGMV | COAT PROTEIN | TOBACCO MILD GREEN MOSAIC VIRUS | 103–137 | | | | | | | |
| PCOAT_TMV | COAT PROTEIN | TOBACCO MOSAIC VIRUS | 103–137 | | | | | | | |
| PCOAT_TMV06 | COAT PROTEIN | TOBACCO MOSAIC VIRUS | 103–137 | | | | | | | |
| PCOAT_TMVCO | COAT PROTEIN | TOBACCO MOSAIC VIRUS | 76–138 | | | | | | | |
| PCOAT_TMVDA | COAT PROTEIN | TOBACCO MOSAIC VIRUS | 103–137 | | | | | | | |
| PCOAT_TMVER | COAT PROTEIN | TOBACCO MOSAIC VIRUS | 103–137 | | | | | | | |
| PCOAT_TMVHR | COAT PROTEIN | TOBACCO MOSAIC VIRUS | 103–137 | | | | | | | |
| PCOAT_TMVO | COAT PROTEIN | TOBACCO MOSAIC VIRUS | 103–137 | | | | | | | |
| PCOAT_TMVOM | COAT PROTEIN | TOBACCO MOSAIC VIRUS | 103–137 | | | | | | | |
| PCOAT_TMVTO | COAT PROTEIN | TOBACCO MOSAIC VIRUS | 103–137 | | | | | | | |
| PCOAT_TRVCA | COAT PROTEIN | TOBACCO RATTLE VIRUS | 71–109 | | | | | | | |
| PCOAT_TRVTC | COAT PROTEIN | TOBACCO RATTLE VIRUS | 69–103 | | | | | | | |
| PCOAT_TYDVA | COAT PROTEIN | TOBACCO YELLOW DWARF VIRUS | 2–36 | | | | | | | |
| PCOAT_TYMV | COAT PROTEIN | TURNIP YELLOW MOSAIC VIRUS | 41–75 | | | | | | | |
| PCOAT_TYMVA | COAT PROTEIN | TURNIP YELLOW MOSAIC VIRUS | 41–75 | | | | | | | |
| PCOAT_WCMVO | COAT PROTEIN | WHITE CLOVER MOSAIC VIRUS | 163–197 | | | | | | | |
| PCORA_HPBGS | CORE ANTIGEN | GROUND SQUIRREL HEPATITIS VIRUS | 94–135 | | | | | | | |

TABLE V-continued

ALLMOT5 SEARCH RESULTS SUMMARY FOR ALL VIRAL (NON-BACTERIOPHAGE) PROTEINS

| PCGENE FILE NAME | ALLMOT5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PCORA_HPBV9 | CORE ANTIGEN | HEPATITIS B VIRUS | 111–149 | | | | | | | |
| PCORA_WHV1 | CORE ANTIGEN | WOODCHUCK HEPATITIS VIRUS 1 | 62–106 | | | | | | | |
| PCORA_WHV8 | CORE ANTIGEN | WOODCHUCK HEPATITIS VIRUS 8 | 62–106 | | | | | | | |
| PD250_ASFB7 | PROTEIN D250R | AFRICAN SWINE FEVER VIRUS | 198–232 | | | | | | | |
| PDNB2_ADE02 | EARLY E2A DNA-BINDING PROTEIN | HUMAN ADENOVIRUS TYPE 2 | 291–336 | | | | | | | |
| PDNB2_ADE05 | EARLY E2A DNA-BINDING PROTEIN | HUMAN ADENOVIRUS TYPE 5 | 291–336 | | | | | | | |
| PDNB1_EBV | MAJOR DNA-BINDING PROTEIN | EPSTEIN-BARR VIRUS | 25–252 | 718–752 | 974–1009 | 1027–1068 | | | | |
| PDNB1_HCMVA | MAJOR DNA-BINDING PROTEIN | HUMAN CYTOMEGALOVIRUS | 338–372 | 1013–1070 | | | | | | |
| PDNB1_HSV11 | MAJOR DNA-BINDING PROTEIN | HERPES SIMPLEX VIRUS | 557–595 | 599–640 | 769–803 | 1079–1140 | | | | |
| PDNB1_HSV1F | MAJOR DNA-BINDING PROTEIN | HERPES SIMPLEX VIRUS | 557–595 | 599–640 | 769–803 | 1079–1140 | | | | |
| PDNB1_HSV1K | MAJOR DNA-BINDING PROTEIN | HERPES SIMPLEX VIRUS | 557–595 | 599–640 | 769–803 | 1079–1140 | | | | |
| PDNB1_HSVB2 | MAJOR DNA-BINDING PROTEIN | BOVINE HERPESVIRUS TYPE 2 | 552–591 | 599–633 | 1048–1131 | | | | | |
| PDNB1_HSVE1 | MAJOR DNA-BINDING PROTEIN | EQUINE HERPESVIRUS TYPE 1 | 273–314 | 1107–1148 | | | | | | |
| PDNB1_HSVEB | MAJOR DNA-BINDING PROTEIN | EQUINE HERPESVIRUS TYPE 1 | 617–658 | | | | | | | |
| PDNB1_HSVSA | MAJOR DNA-BINDING PROTEIN | HERPESVIRUS SAIMIRI | 222–259 | 330–367 | 506–557 | 873–907 | | | | |
| PDNB1_MCMVS | MAJOR DNA-BINDING PROTEIN | MURINE CYTOMEGALOVIRUS | 584–618 | 987–1125 | | | | | | |
| PDNB1_SCMVC | MAJOR DNA-BINDING PROTEIN | SIMIAN CYTOMEGALOVIRUS | 525–562 | 1043–1077 | | | | | | |
| PDNB1_VZVD | MAJOR DNA-BINDING PROTEIN | VARICELLA-ZOSTER VIRUS | 613–650 | | | | | | | |
| PDNL1_ASFM2 | DNA LIGASE | AFRICAN SWINE FEVER VIRUS | 72–106 | | | | | | | |
| PDNL1_VACCC | DNA LIGASE | VACCINIA VIRUS | 395–436 | | | | | | | |
| PDNL1_VACCV | DNA LIGASE | VACCINIA VIRUS | 395–436 | | | | | | | |
| PDNL1_VARV | DNA LIGASE | VARIOLA VIRUS | 395–436 | | | | | | | |
| PDPOL_ADE02 | DNA POLYMERASE | HUMAN ADENOVIRUS TYPE 2 | 667–743 | | | | | | | |
| PDPOL_ADE05 | DNA POLYMERASE | HUMAN ADENOVIRUS TYPE 5 | 667–743 | | | | | | | |
| PDPOL_ADE07 | DNA POLYMERASE | HUMAN ADENOVIRUS TYPE 7 | 733–809 | | | | | | | |
| PDPOL_ADE12 | DNA POLYMERASE | HUMAN ADENOVIRUS TYPE 12 | 665–741 | | | | | | | |
| PDPOL_CBEPV | DNA POLYMERASE | CHORISTONEURA BIENNIS ENTOMOPOXVIRUS | 23–64 | 202–240 | | | | | | |
| PDPOL_CHVN2 | DNA POLYMERASE | CHLORELLA VIRUS NY-2A | 247–284 | | | | | | | |
| PDPOL_CHVP1 | DNA POLYMERASE | PARAMECIUM BURSARIA CHLORELLA VIRUS 1 | 247–284 | | | | | | | |
| PDPOL_FOWPV | DNA POLYMERASE | FOWLPOX VIRUS | 17–51 | 80–114 | 371–412 | | | | | |
| PDPOL_HCMVA | DNA POLYMERASE | HUMAN CYTOMEGALOVIRUS (STRAIN AD169) | 753–787 | 1033–1074 | | | | | | |
| PDPOL_HPBDB | DNA POLYMERASE | DUCK HEPATITIS B VIRUS | 5–39 | | | | | | | |
| PDPOL_HPBDC | DNA POLYMERASE | DUCK HEPATITIS B VIRUS (STRAIN CHINA) | 5–39 | | | | | | | |
| PDPOL_HPBDW | DNA POLYMERASE | DUCK HEPATITIS B VIRUS (WHITE SHANGHAI DUCK ISOLATE S3 | 5–39 | 297–338 | | | | | | |
| PDPOL_HPBGS | DNA POLYMERASE | GROUND SQUIRREL HEPATITIS VIRUS | 291–325 | 224–265 | 557–595 | | | | | |
| PDPOL_HPBHE | DNA POLYMERASE | HERON HEPATITIS B VIRUS | 5–39 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PDPOL_HPBVY | DNA POLYMERASE | HEPATITIS B VIRUS (SUBTYPE AYW) | 201–235 | | | | | | | |
| PDPOL_HPBVZ | DNA POLYMERASE | HEPATITIS B VIRUS (SUBTYPE ADYW) | 201–235 | | | | | | | |
| PDPOL_HSV11 | DNA POLYMERASE | HERPES SIMPLEX VIRUS (TYPE 1/STRAIN 17) | 511–559 | | | | | | | |
| PDPOL_HSV1A | DNA POLYMERASE | HERPES SIMPLEX VIRUS (TYPE 1/STRAIN ANGELOTTI) | 511–559 | | | | | | | |
| PDPOL_HSV1K | DNA POLYMERASE | HERPES SIMPLEX VIRUS (TYPE 1/STRAIN KOS) | 511–559 | | | | | | | |
| PDPOL_HSV1S | DNA POLYMERASE | HERPES SIMPLEX VIRUS (TYPE 1/STRAIN SC16) | 511–559 | | | | | | | |
| PDPOL_HSV21 | DNA POLYMERASE | HERPES SIMPLEX VIRUS (TYPE 2/STRAIN 186) | 512–560 | | | | | | | |
| PDPOL_HSVEB | DNA POLYMERASE | EQUINE HERPESVIRUS TYPE 1 (STRAIN AB4P) | 494–528 | | | | | | | |
| PDPOL_HSV11 | DNA POLYMERASE | ICTALURID HERPESVIRUS 1 (CHANNEL CATFISH VIRUS) | 33–67 | 328–366 | 401–435 | 706–749 | 808–858 | | | |
| PDPOL_NPVAC | DNA POLYMERASE | AUTOGRAPHA CALIFORNICA NUCLEAR POLYHEDROSIS VIRUS | 595–646 | | | | | | | |
| PDPOL_VACCC | DNA POLYMERASE | VACCINIA VIRUS (STRAIN COPENHAGEN) | 627–683 | 770–818 | 828–862 | | | | | |
| PDPOL_VACCV | DNA POLYMERASE | VACCINIA VIRUS (STRAIN WR) | 627–683 | 770–818 | 828–862 | | | | | |
| PDPOL_VARV | DNA POLYMERASE | VARIOLA VIRUS | 626–682 | 769–817 | 827–861 | | | | | |
| PDPOL_VZVD | DNA POLYMERASE | VARICELLA-ZOSTER VIRUS (STRAIN DUMAS) | 473–533 | | | | | | | |
| PDPOL_WHV1 | DNA POLYMERASE | WOODCHUCK HEPATITIS VIRUS 1 | 285–326 | | | | | | | |
| PDPOL_WHV59 | DNA POLYMERASE | WOODCHUCK HEPATITIS VIRUS 59 | 290–331 | | | | | | | |
| PDPOL_WHV7 | DNA POLYMERASE | WOODCHUCK HEPATITIS VIRUS 7 | 290–331 | | | | | | | |
| PDPOL_WHV8 | DNA POLYMERASE | WOODCHUCK HEPATITIS VIRUS 8 | 289–330 | | | | | | | |
| PDPOL_WHV81 | DNA POLYMERASE | WOODCHUCK HEPATITIS VIRUS 8 (INFECTIOUS CLONE) | 290–331 | | | | | | | |
| PDPOM_HPBVY | DNA POLYMERASE | HEPATITIS B VIRUS (SUBTYPE AYW) | 201–235 | | | | | | | |
| PDUT_HSVEB | DEOXYURIDINE 5'-TRIPHOSPHATE NUCLEOTIDOHY | EQUINE HERPESVIRUS TYPE 1 (STRAIN AB4P) | 135–169 | | | | | | | |
| PDUT_HSVSA | DEOXYURIDINE 5'-TRIPHOSPHATE NUCLEOTIDOHY | HERPESVIRUS SAIMIRI (STRAIN 11) | 179–223 | | | | | | | |
| PE1A_ADE41 | EARLY E1A 27 KD PROTEIN | HUMAN ADENOVIRUS TYPE 41 | 107–141 | | | | | | | |
| PE1BL_ADE40 | E1B PROTEIN, LARGE T-ANTIGEN | HUMAN ADENOVIRUS TYPE 40 | 102–166 | | | | | | | |
| PE1BS_ADE02 | E1B PROTEIN, SMALL T-ANTIGEN | HUMAN ADENOVIRUS TYPE 2 | 103–137 | | | | | | | |
| PE1BS_ADE05 | E1B PROTEIN, SMALL T-ANTIGEN | HUMAN ADENOVIRUS TYPE 5 | 103–137 | | | | | | | |
| PE1BS_ADE12 | E1B PROTEIN, SMALL T-ANTIGEN | HUMAN ADENOVIRUS TYPE 12 | 96–131 | | | | | | | |
| PE1BS_ADE40 | E1B PROTEIN, SMALL T-ANTIGEN | HUMAN ADENOVIRUS TYPE 40 | 100–134 | | | | | | | |
| PE1BS_ADE41 | E1B PROTEIN, SMALL T-ANTIGEN | HUMAN ADENOVIRUS TYPE 41 | 100–134 | | | | | | | |
| PE1BS_ADEM1 | E1B PROTEIN, SMALL T-ANTIGEN | MOUSE ADENOVIRUS TYPE 1 | 119–173 | | | | | | | |
| PE314_ADE02 | EARLY E3B 14 KD PROTEIN | HUMAN ADENOVIRUS TYPE 2 | 2–39 | | | | | | | |
| PE314_ADE03 | EARLY E3 15.3 KD PROTEIN | HUMAN ADENOVIRUS TYPE 3 | 8–49 | | | | | | | |
| PE314_ADE05 | EARLY E3 14.5 KD PROTEIN | HUMAN ADENOVIRUS TYPE 5 | 2–39 | | | | | | | |
| PE314_ADE07 | EARLY E3 15.3 KD PROTEIN | HUMAN ADENOVIRUS TYPE 7 | 7–48 | | | | | | | |
| PE320_ADE35 | EARLY E3 20.3 KD GLYCOPROTEIN | HUMAN ADENOVIRUS TYPE 35 | 70–107 | | | | | | | |
| PE321_ADE35 | EARLY E3 20.6 KD GLYCOPROTEIN | HUMAN ADENOVIRUS TYPE 35 | 125–169 | | | | | | | |
| PE411_ADE02 | PROBABLE EARLY E4 11 KD PROTEIN | HUMAN ADENOVIRUS TYPE 2 | 10–44 | | | | | | | |
| PE411_ADE05 | PROBABLE EARLY E4 11 KD PROTEIN | HUMAN ADENOVIRUS TYPE 5 | 10–44 | | | | | | | |
| PEAR_EBV | EARLY ANTIGEN PROTEIN R | EPSTEIN-BARR VIRUS (STRAIN B95-8) | 123–157 | | | | | | | |
| PEBN4_EBV | EBNA-4 NUCLEAR PROTEIN | EPSTEIN-BARR VIRUS (STRAIN B95-8) | 487–521 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PEFT1_VARV | EARLY TRANSCRIPTION FACTOR 70 KD SUBUNIT | VARIOLA VIRUS | 23–71 | 307–341 | | | | | | |
| PENV1_FRSFV | ENV POLYPROTEIN PRECURSOR | FRIEND SPLEEN FOCUS-FORMING VIRUS | 341–375 | | | | | | | |
| PENV2_FRSFV | ENV POLYPROTEIN PRECURSOR | FRIEND SPLEEN FOCUS-FORMING VIRUS | 341–378 | | | | | | | |
| PENV_AVIRE | ENV POLYPROTEIN | AVIAN RETICULOENDOTHELIOSIS VIRUS | 420–472 | | | | | | | |
| PENV_AVISN | ENV POLYPROTEIN | AVIAN SPLEEN NECROSIS VIRUS | 426–478 | | | | | | | |
| PENV_BAEVM | ENV POLYPROTEIN | BABOON ENDOGENOUS VIRUS (STRAIN M7) | 390–456 | | | | | | | |
| PENV_BIV06 | ENV POLYPROTEIN PRECURSOR | BOVINE IMMUNODEFICIENCY VIRUS (ISOLATE 106) | 10–44 | 88–122 | 221–255 | 530–610 | 635–691 | | | |
| PENV_BIV27 | ENV POLYPROTEIN PRECURSOR | BOVINE IMMUNODEFICIENCY VIRUS (ISOLATE 127) | 10–44 | 88–122 | 159–193 | 250–284 | 559–639 | 664–724 | | |
| PENV_BLVAF | ENV POLYPROTEIN | BOVINE LEUKEMIA VIRUS (AMERICAN ISOLATE FLK) | 304–379 | | | | | | | |
| PENV_BLVAU | ENV POLYPROTEIN | BOVINE LEUKEMIA VIRUS (AUSTRALIAN ISOLATE) | 304–379 | | | | | | | |
| PENV_BLVAV | ENV POLYPROTEIN | BOVINE LEUKEMIA VIRUS (AMERICAN ISOLATE VDM) | 304–379 | | | | | | | |
| PENV_BLVB2 | ENV POLYPROTEIN | BOVINE LEUKEMIA VIRUS (BELGIUM ISOLATE LB285) | 304–379 | | | | | | | |
| PENV_BLVB5 | ENV POLYPROTEIN | BOVINE LEUKEMIA VIRUS (BELGIUM ISOLATE LB59) | 304–379 | | | | | | | |
| PENV_BLVJ | ENV POLYPROTEIN | BOVINE LEUKEMIA VIRUS (JAPANESE ISOLATE BLV-1) | 304–379 | | | | | | | |
| PENV_CAEVC | ENV POLYPROTEIN PRECURSOR | CAPRINE ARTHRITIS ENCEPHALITIS VIRUS (STRAIN CORK) | 157–196 | 615–720 | 751–785 | 847–895 | | | | |
| PENV_CAEVG | ENV POLYPROTEIN PRECURSOR | CAPRINE ARTHRITIS ENCEPHALITIS VIRUS (STRAIN G63) | 154–193 | 613–718 | 749–783 | 845–893 | | | | |
| PENV_EIAV1 | ENV POLYPROTEIN PRECURSOR | EQUINE INFECTIOUS ANEMIA VIRUS (CLONE P3.2-1) | 39–76 | 436–525 | 559–593 | 668–716 | | | | |
| PENV_EIAV2 | ENV POLYPROTEIN PRECURSOR | EQUINE INFECTIOUS ANEMIA VIRUS (CLONE P3.2-2) | 39–76 | 436–525 | 559–593 | 658–692 | | | | |
| PENV_EIAV3 | ENV POLYPROTEIN PRECURSOR | EQUINE INFECTIOUS ANEMIA VIRUS (CLONE P3.2-3) | 39–76 | 436–525 | 559–593 | 658–716 | | | | |
| PENV_EIAV5 | ENV POLYPROTEIN PRECURSOR | EQUINE INFECTIOUS ANEMIA VIRUS (CLONE P3.2-5) | 38–76 | 437–526 | 560–594 | 659–693 | | | | |
| PENV_EIAV9 | ENV POLYPROTEIN PRECURSOR | EQUINE INFECTIOUS ANEMIA VIRUS (CLONE 1369) | 39–76 | 436–525 | 559–593 | 658–716 | | | | |
| PENV_EIAVC | ENV POLYPROTEIN PRECURSOR | EQUINE INFECTIOUS ANEMIA VIRUS (CLONE CL22) | 39–76 | 436–525 | 559–593 | 658–716 | | | | |
| PENV_EIAVW | ENV POLYPROTEIN PRECURSOR | EQUINE INFECTIOUS ANEMIA VIRUS (STRAIN WSU5) | 39–76 | 436–525 | 559–593 | 658–716 | | | | |
| PENV_EIAVY | ENV POLYPROTEIN PRECURSOR | EQUINE INFECTIOUS ANEMIA VIRUS (ISOLATE WYOMING) | 39–76 | 436–525 | 559–593 | 658–716 | | | | |
| PENV_FENV1 | ENV POLYPROTEIN PRECURSOR | FELINE ENDOGENOUS VIRUS ECE1 | 503–555 | 567–604 | | | | | | |
| PENV_FIVPE | ENVELOPE POLYPROTEIN PRECURSOR | FELINE IMMUNODEFICIENCY VIRUS (ISOLATE PETALUMA) | 610–690 | 715–756 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PENV_FIVSD | ENVELOPE POLYPROTEIN PRECURSOR | FELINE IMMUNODEFICIENCY VIRUS (ISOLATE SAN DIEGO) | 601–688 | 713–754 | | | | | | |
| PENV_FIVT2 | ENVELOPE POLYPROTEIN PRECURSOR | FELINE IMMUNODEFICIENCY VIRUS (ISOLATE TM2) | 60–122 | 609–689 | 714–755 | | | | | |
| PENV_FLVC6 | ENV POLYPROTEIN PRECURSOR | FELINE LEUKEMIA PROVIRUS (CLONE CFE-6) | 497–549 | 561–595 | | | | | | |
| PENV_FLVGL | ENV POLYPROTEIN PRECURSOR | FELINE LEUKEMIA VIRUS (STRAIN A/GLASGOW-1) | 478–530 | 542–576 | | | | | | |
| PENV_FLVLB | ENV POLYPROTEIN PRECURSOR | FELINE LEUKEMIA VIRUS (STRAIN LAMBDA-B1) | 498–550 | 562–596 | | | | | | |
| PENV_FLVSA | ENV POLYPROTEIN PRECURSOR | FELINE LEUKEMIA VIRUS (STRAIN SARMA) | 475–527 | 539–573 | | | | | | |
| PENV_FOAMV | ENV POLYPROTEIN | HUMAN SPUMARETROVIRUS | 1–41 | 154–205 | 321–355 | 563–693 | 866–903 | | | |
| PENV_FSVGA | ENV POLYPROTEIN PRECURSOR | FELINE SARCOMA VIRUS (STRAIN GARDNER-ARNSTEIN) | 498–550 | 562–596 | | | | | | |
| PENV_FSVGB | ENV POLYPROTEIN PRECURSOR | FELINE SARCOMA VIRUS (STRAIN GA) | 478–530 | 542–576 | | | | | | |
| PENV_FSVSM | ENV POLYPROTEIN PRECURSOR | FELINE SARCOMA VIRUS (STRAIN SM) | 481–524 | 545–579 | | | | | | |
| PENV_FSVST | ENV POLYPROTEIN PRECURSOR | FELINE SARCOMA VIRUS (STRAIN SNYDER-THEILEN) | 498–532 | | | | | | | |
| PENV_GALV | ENV POLYPROTEIN PRECURSOR | GIBBON APE LEUKEMIA VIRUS | 523–575 | 587–621 | | | | | | |
| PENV_HTL1A | ENV POLYPROTEIN | HUMAN T-CELL LEUKEMIA VIRUS TYPE 1 (STRAIN ATK) | 321–383 | | | | | | | |
| PENV_HTL1C | ENV POLYPROTEIN | HUMAN T-CELL LEUKEMIA VIRUS TYPE 1 (CARIBBEAN ISOLATE) | 316–383 | | | | | | | |
| PENV_HTL1M | ENV POLYPROTEIN | HUMAN T-CELL LEUKEMIA VIRUS TYPE 1 (ISOLATE MT-2) | 321–383 | | | | | | | |
| PENV_HTLV2 | ENV POLYPROTEIN PRECURSOR | HUMAN T-CELL LEUKEMIA VIRUS TYPE II | 317–377 | | | | | | | |
| PENV_HV1A2 | ENVELOPE POLYPROTEIN GP160 PRECURSOR | HUMAN IMMUNODEFICIENCY VIRUS TYPE 1 (ARV2/SF2 ISOLATE) | 497–593 | 612–711 | 766–845 | | | | | |
| PENV_HV1B1 | ENVELOPE POLYPROTEIN GP160 PRECURSOR | HUMAN IMMUNODEFICIENCY VIRUS TYPE 1 (BH10 ISOLATE) | 505–594 | 610–712 | 767–843 | | | | | |
| PENV_HV1B8 | ENVELOPE POLYPROTEIN GP160 PRECURSOR | HUMAN IMMUNODEFICIENCY VIRUS TYPE 1 (BH8 ISOLATE) | 500–589 | 605–707 | 762–838 | | | | | |
| PENV_HV1BN | ENVELOPE POLYPROTEIN GP160 PRECURSOR (CONT | HUMAN IMMUNODEFICIENCY VIRUS TYPE 1 (BRAIN ISOLATE) | 331–365 | 501–590 | 609–708 | 763–831 | | | | |
| PENV_HV1BR | ENVELOPE POLYPROTEIN GP160 PRECURSOR | HUMAN IMMUNODEFICIENCY VIRUS TYPE 1 (BRU ISOLATE) | 510–599 | 615–717 | 772–841 | | | | | |
| PENV_HV1C4 | ENVELOPE POLYPROTEIN GP160 PRECURSOR | HUMAN IMMUNODEFICIENCY VIRUS TYPE 1 (CDC-451 ISOLATE) | 342–376 | 510–606 | 626–724 | 779–855 | | | | |
| PENV_HV1EL | ENVELOPE POLYPROTEIN GP160 PRECURSOR | HUMAN IMMUNODEFICIENCY VIRUS TYPE 1 (ELI ISOLATE) | 255–296 | 502–591 | 607–709 | 768–829 | | | | |
| PENV_HV1H2 | ENVELOPE POLYPROTEIN GP160 PRECURSOR | HUMAN IMMUNODEFICIENCY VIRUS TYPE 1 (HXB2 ISOLATE) | 505–594 | 610–712 | 767–836 | | | | | |
| PENV_HV1H3 | ENVELOPE POLYPROTEIN GP160 PRECURSOR | HUMAN IMMUNODEFICIENCY VIRUS TYPE 1 (HXB3 ISOLATE) | 505–594 | 610–712 | 767–843 | | | | | |
| PENV_HV1J3 | ENVELOPE POLYPROTEIN GP160 PRECURSOR | HUMAN IMMUNODEFICIENCY VIRUS TYPE 1 (JH3 ISOLATE) | 343–377 | 517–605 | 622–723 | 778–843 | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PENV_HV1JR | ENVELOPE POLYPROTEIN GP160 PRECURSOR | HUMAN IMMUNODEFICIENCY VIRUS TYPE 1 (JRCSF ISOLATE) | 329–363 | 497–586 | 603–704 | 759–835 | | | | |
| PENV_HV1KB | ENVELOPE POLYPROTEIN GP160 PRECURSOR | HUMAN IMMUNODEFICIENCY VIRUS TYPE 1 (STRAIN KB-1-GP32) | 88–122 | 338–372 | 511–545 | 555–599 | 618–677 | 681–718 | 772–848 | |
| PENV_HV1MA | ENVELOPE POLYPROTEIN GP160 PRECURSOR | HUMAN IMMUNODEFICIENCY VIRUS TYPE 1 (MAL ISOLATE) | 259–300 | 507–596 | 617–714 | 770–825 | | | | |
| PENV_HV1MF | ENVELOPE POLYPROTEIN GP160 PRECURSOR | HUMAN IMMUNODEFICIENCY VIRUS TYPE 1 (MFA ISOLATE) | 503–592 | 622–710 | 765–841 | | | | | |
| PENV_HV1MN | ENVELOPE POLYPROTEIN GP160 PRECURSOR | HUMAN IMMUNODEFICIENCY VIRUS TYPE 1 (MN ISOLATE) | 336–370 | 506–595 | 617–713 | 774–841 | | | | |
| PENV_HV1N5 | ENVELOPE POLYPROTEIN GP160 PRECURSOR | HUMAN IMMUNODEFICIENCY VIRUS TYPE 1 (NEW YORK-5 ISOL | 326–360 | | | | | | | |
| PENV_HV1ND | ENVELOPE POLYPROTEIN GP160 PRECURSOR | HUMAN IMMUNODEFICIENCY VIRUS TYPE 1 (NDK ISOLATE) | 249–290 | 495–584 | 601–702 | 757–825 | | | | |
| PENV_HV1OY | ENVELOPE POLYPROTEIN GP160 PRECURSOR | HUMAN IMMUNODEFICIENCY VIRUS TYPE 1 (OY1 ISOLATE) | 336–370 | 497–593 | 610–711 | 766–842 | | | | |
| PENV_HV1PV | ENVELOPE POLYPROTEIN GP160 PRECURSOR | HUMAN IMMUNODEFICIENCY VIRUS TYPE 1 (PV22 ISOLATE) | 505–594 | 610–712 | 767–843 | | | | | |
| PENV_HV1RH | ENVELOPE POLYPROTEIN GP160 PRECURSOR | HUMAN IMMUNODEFICIENCY VIRUS TYPE 1 (RF/HAT ISOLATE) | 344–378 | 507–603 | 619–721 | 776–852 | | | | |
| PENV_HV1S1 | ENVELOPE POLYPROTEIN GP160 PRECURSOR | HUMAN IMMUNODEFICIENCY VIRUS TYPE 1 (SF162 ISOLATE) | 496–585 | 602–703 | 758–830 | | | | | |
| PENV_HV1S3 | ENVELOPE POLYPROTEIN GP160 PRECURSOR | HUMAN IMMUNODEFICIENCY VIRUS TYPE 1 (SF33 ISOLATE) | 332–366 | 494–590 | 607–708 | 763–837 | | | | |
| PENV_HV1SC | ENVELOPE POLYPROTEIN GP160 PRECURSOR | HUMAN IMMUNODEFICIENCY VIRUS TYPE 1 (SC ISOLATE) | 331–365 | 498–594 | 611–712 | 767–834 | | | | |
| PENV_HV1W1 | ENVELOPE POLYPROTEIN GP160 PRECURSOR | HUMAN IMMUNODEFICIENCY VIRUS TYPE 1 (WMJ1 ISOLATE) | 331–365 | 498–594 | 611–712 | 767–836 | | | | |
| PENV_HV1W2 | ENVELOPE POLYPROTEIN GP160 PRECURSOR | HUMAN IMMUNODEFICIENCY VIRUS TYPE 1 (WMJ2 ISOLATE) | 327–361 | 489–584 | 602–703 | 758–827 | | | | |
| PENV_HV1Z2 | ENVELOPE POLYPROTEIN GP160 PRECURSOR | HUMAN IMMUNODEFICIENCY VIRUS TYPE 1 (Z2/CDC-Z34 ISOLAT | 255–296 | 502–591 | 610–709 | 764–831 | | | | |
| PENV_HV1Z3 | ENVELOPE POLYPROTEIN GP160 PRECURSOR | HUMAN IMMUNODEFICIENCY VIRUS TYPE 1 (ZAIRE 3 ISOLATE) | 251–292 | | | | | | | |
| PENV_HV1Z6 | ENVELOPE POLYPROTEIN GP160 PRECURSOR | HUMAN IMMUNODEFICIENCY VIRUS TYPE 1 (ZAIRE 6 ISOLATE) | 256–297 | 504–593 | 609–711 | 766–840 | | | | |
| PENV_HV1Z8 | ENVELOPE POLYPROTEIN GP160 PRECURSOR | HUMAN IMMUNODEFICIENCY VIRUS TYPE 1 (Z-84 ISOLATE) | 266–307 | 512–601 | 617–675 | 682–719 | 774–831 | | | |
| PENV_HV1ZH | ENVELOPE POLYPROTEIN GP160 PRECURSOR | HUMAN IMMUNODEFICIENCY VIRUS TYPE 1 (ZAIRE HZ321 ISOLA | 522–594 | 612–671 | 675–712 | 777–839 | | | | |
| PENV_HV2BE | ENVELOPE POLYPROTEIN GP160 PRECURSOR | HUMAN IMMUNODEFICIENCY VIRUS TYPE 2 (ISOLATE BEN) | 447–481 | 510–595 | 617–680 | | | | | |
| PENV_HV2CA | ENVELOPE POLYPROTEIN GP160 PRECURSOR | HUMAN IMMUNODEFICIENCY VIRUS TYPE 2 (ISOLATE CAM2) | 512–597 | 619–709 | | | | | | |
| PENV_HV2D1 | ENVELOPE POLYPROTEIN GP160 PRECURSOR | HUMAN IMMUNODEFICIENCY VIRUS TYPE 2 (ISOLATE D194) | 501–586 | 608–698 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PENV_HV2G1 | ENVELOPE POLYPROTEIN GP160 PRECURSOR | HUMAN IMMUNODEFICIENCY VIRUS TYPE 2 (ISOLATE GHANA-1) | 439–473 | 502–587 | 609–699 | | | | | |
| PENV_HV2NZ | ENVELOPE POLYPROTEIN GP160 PRECURSOR | HUMAN IMMUNODEFICIENCY VIRUS TYPE 2 (ISOLATE NIH-Z) | 488–587 | 609–699 | | | | | | |
| PENV_HV2RO | ENVELOPE POLYPROTEIN GP160 PRECURSOR | HUMAN IMMUNODEFICIENCY VIRUS TYPE 2 (ISOLATE ROD) | 511–596 | 618–708 | | | | | | |
| PENV_HV2S2 | ENVELOPE POLYPROTEIN GP160 PRECURSOR | HUMAN IMMUNODEFICIENCY VIRUS TYPE 2 (ISOLATE ST/24.1C# | 442–476 | 505–590 | 612–702 | | | | | |
| PENV_HV2SB | ENVELOPE POLYPROTEIN GP160 PRECURSOR | HUMAN IMMUNODEFICIENCY VIRUS TYPE 2 (ISOLATE SBL/ISY) | 526–588 | 614–700 | | | | | | |
| PENV_HV2ST | ENVELOPE POLYPROTEIN GP160 PRECURSOR | HUMAN IMMUNODEFICIENCY VIRUS TYPE 2 (ISOLATE ST) | 442–476 | 505–590 | 612–702 | | | | | |
| PENV_IPMAE | ENV POLYPROTEIN PRECURSOR | MOUSE INTRACISTERNAL A-PARITCLE | 367–422 | 465–527 | | | | | | |
| PENV_JSRV | ENV POLYPROTEIN PRECURSOR | SHEEP PULMONARY ADENOMATOSIS VIRUS | 403–455 | 571–605 | | | | | | |
| PENV_MCFF | ENV POLYPROTEIN PRECURSOR | MINK CELL FOCUS-FORMING MURINE LEUKEMIA VIRUS | 473–525 | 537–571 | | | | | | |
| PENV_MCFF3 | ENV POLYPROTEIN PRECURSOR (COAT POLYPROTE | MINK CELL FOCUS-FORMING MURINE LEUKEMIA VIRUS (ISOLA | 474–526 | 538–572 | | | | | | |
| PENV_MLVAV | ENV POLYPROTEIN PRECURSOR | AKV MURINE LEUKEMIA VIRUS | 503–555 | 567–601 | | | | | | |
| PENV_MLVCB | ENV POLYPROTEIN PRECURSOR | CAS-BR-E MURINE LEUKEMIA VIRUS | 498–550 | 562–596 | | | | | | |
| PENV_MLVF5 | ENV POLYPROTEIN PRECURSOR | FRIEND MURINE LEUKEMIA VIRUS (ISOLATE 57) | 520–564 | 576–610 | | | | | | |
| PENV_MLVFF | ENV POLYPROTEIN PRECURSOR | FRIEND MURINE LEUKEMIA VIRUS (ISOLATE FB29) | 520–564 | 576–610 | | | | | | |
| PENV_MLVFP | ENV POLYPROTEIN PRECURSOR | FRIEND MURINE LEUKEMIA VIRUS (ISOLATE PVC-211) | 520–564 | 576–610 | | | | | | |
| PENV_MLVHO | ENV POLYPROTEIN PRECURSOR | HOMO1V MURINE LEUKEMIA VIRUS | 504–551 | 563–597 | | | | | | |
| PENV_MLVKI | ENV POLYPROTEIN PRECURSOR | KIRSTEN MURINE LEUKEMIA VIRUS | 40–92 | 104–138 | | | | | | |
| PENV_MLVMO | ENV POLYPROTEIN PRECURSOR | MOLONEY MURINE LEUKEMIA VIRUS | 502–554 | 566–600 | | | | | | |
| PENV_MLVRD | ENV POLYPROTEIN PRECURSOR | RADIATION MURINE LEUKEMIA VIRUS | 497–549 | 561–595 | | | | | | |
| PENV_MLVRK | ENV POLYPROTEIN PRECURSOR | RADIATION MURINE LEUKEMIA VIRUS (STRAIN KAPLAN) | 497–549 | 561–595 | | | | | | |
| PENV_MMTVB | ENV POLYPROTEIN | MOUSE MAMMARY TUMOR VIRUS (STRAIN BR6) | 477–539 | 556–612 | | | | | | |
| PENV_MMTVG | ENV POLYPROTEIN | MOUSE MAMMARY TUMOR VIRUS (STRAIN GR) | 477–539 | 556–612 | | | | | | |
| PENV_MPMV | ENV POLYPROTEIN | SIMIAN MASON-PFIZER VIRUS | 408–474 | | | | | | | |
| PENV_MSVFB | ENV POLYPROTEIN | FBJ MURINE OSTEOSARCOMA VIRUS | 43–95 | 107–141 | | | | | | |
| PENV_OMVVS | ENV POLYPROTEIN PRECURSOR | OVINE LENTIVIRUS (STRAIN SA-OMVV) | 22–64 | 185–223 | 664–746 | 780–816 | | | | |
| PENV_RMCFV | ENV POLYPROTEIN PRECURSOR | RAUSCHER MINK CELL FOCUS-INDUCING VIRUS | 484–528 | 540–574 | | | | | | |
| PENV_RSFFV | ENV POLYPROTEIN PRECURSOR | RAUSCHER SPLEEN FOCUS-FORMING VIRUS | 342–376 | | | | | | | |
| PENV_SFV1 | ENV POLYPROTEIN | SIMIAN FOAMY VIRUS (TYPE 1) | 1–41 | 101–140 | 154–205 | 321–355 | 563–651 | 658–693 | 866–904 | |
| PENV_SFV3L | ENV POLYPROTEIN | SIMIAN FOAMY VIRUS (TYPE 3/ STRAIN LK3) | 5–46 | 158–209 | 319–357 | 560–706 | 863–901 | | | |
| PENV_SIVA1 | ENVELOPE POLYPROTEIN GP160 PRECURSOR | SIMIAN IMMUNODEFICIENCY VIRUS (AGM155 ISOLATE) | 269–310 | 551–623 | 643–693 | | | | | |
| PENV_SIVAG | ENVELOPE POLYPROTEIN GP160 PRECURSOR | SIMIAN IMMUNODEFICIENCY VIRUS (AGM3 ISOLATE) | 556–628 | 651–699 | 808–852 | | | | | |
| PENV_SIVAI | ENVELOPE POLYPROTEIN GP160 PRECURSOR | SIMIAN IMMUNODEFICIENCY VIRUS (ISOLATE AGM/CLONE GR1 | 257–291 | 336–370 | 535–607 | 627–684 | 792–840 | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PENV_SIVAT | ENVELOPE POLYPROTEIN GP160 PRECURSOR | SIMIAN IMMUNODEFICIENCY VIRUS (TYO-1 ISOLATE) | 264–298 | 549–621 | 644–692 | 796–833 | | | | |
| PENV_SIVCZ | ENVELOPE POLYPROTEIN GP160 PRECURSOR | CHIMPANZEE IMMUNODEFICIENCY VIRUS (SIV(CPZ)) | 253–291 | 330–365 | 512–584 | 669–703 | 803–837 | | | |
| PENV_SIVGB | ENVELOPE POLYPROTEIN GP160 PRECURSOR | SIMIAN IMMUNODEFICIENCY VIRUS (ISOLATE GB1) | 566–654 | 677–725 | | | | | | |
| PENV_SIVM1 | ENVELOPE POLYPROTEIN GP160 PRECURSOR | SIMIAN IMMUNODEFICIENCY VIRUS (MM142-83 ISOLATE) | 114–151 | 465–506 | 528–613 | 635–725 | 809–864 | | | |
| PENV_SIVM2 | ENVELOPE POLYPROTEIN GP160 PRECURSOR | SIMIAN IMMUNODEFICIENCY VIRUS (MM251 ISOLATE) | 71–109 | 161–219 | 245–286 | | | | | |
| PENV_SIVMX | ENVELOPE POLYPROTEIN GP160 PRECURSOR | SIMIAN IMMUNODEFICIENCY VIRUS (K6W ISOLATE) | 464–505 | 540–612 | 638–724 | | | | | |
| PENV_SIVML | ENVELOPE POLYPROTEIN GP160 PRECURSOR | SIMIAN IMMUNODEFICIENCY VIRUS (K78 ISOLATE) | 464–505 | 540–612 | 638–724 | | | | | |
| PENV_SIVS4 | ENVELOPE POLYPROTEIN GP160 PRECURSOR | SIMIAN IMMUNODEFICIENCY VIRUS (F236/SMH4 ISOLATE) | 466–509 | 517–616 | 638–728 | 812–853 | | | | |
| PENV_SIVSP | ENVELOPE POLYPROTEIN GP160 PRECURSOR | SIMIAN IMMUNODEFICIENCY VIRUS (PBJ/BC13 ISOLATE) | 470–513 | 521–620 | 642–732 | 811–848 | | | | |
| PENV_SMRVH | ENV POLYPROTEIN PRECURSOR | SQUIRREL MONKEY RETROVIRUS (SMRV-H) | 400–466 | | | | | | | |
| PENV_SRV1 | ENV POLYPROTEIN | SIMIAN RETROVIRUS SRV-1 | 409–475 | | | | | | | |
| PENV_VILV | ENV POLYPROTEIN PRECURSOR | VISNA LENTIVIRUS (STRAIN 1514) | 21–62 | 184–222 | 637–740 | 773–809 | | | | |
| PENV_VILV1 | ENV POLYPROTEIN PRECURSOR | VISNA LENTIVIRUS (STRAIN 1514/CLONE LV1-1KS1) | 21–62 | 184–222 | 643–746 | 780–816 | | | | |
| PENV_VILV2 | ENV POLYPROTEIN PRECURSOR | VISNA LENTIVIRUS (STRAIN 1514/CLONE LV1-1KS2) | 21–62 | 184–222 | 645–748 | 782–818 | | | | |
| PERBA_AVIER | ERBA ONCOGENE PROTEIN | AVIAN ERYTHROBLASTOSIS VIRUS (STRAIN ES4) | 106–140 | | | | | | | |
| PETF1_FOWP1 | EARLY TRANSCRIPTION FACTOR 70 KD SUBUNIT | FOWLPOX VIRUS (STRAIN F.P-1) | 190–224 | 553–587 | | | | | | |
| PETF1_SFVKA | EARLY TRANSCRIPTION FACTOR 70 KD SUBUNIT | SHOPE FIBROMA VIRUS (STRAIN KASZA) | 37–71 | 267–340 | 550–587 | | | | | |
| PETF1_VACCC | EARLY TRANSCRIPTION FACTOR 70 KD SUBUNIT | VACCINIA VIRUS (STRAIN COPENHAGEN) | 23–71 | 307–341 | | | | | | |
| PETF1_VACCV | EARLY TRANSCRIPTION FACTOR 70 KD SUBUNIT | VACCINIA VIRUS (STRAIN WR) | 23–71 | 307–341 | | | | | | |
| PETF2_VACCC | EARLY TRANSCRIPTION FACTOR 82 KD SUBUNIT | VACCINIA VIRUS (STRAIN COPENHAGEN) | 52–97 | 174–208 | | | | | | |
| PETF2_VARV | EARLY TRANSCRIPTION FACTOR 82 KD SUBUNIT | VARIOLA VIRUS | 52–97 | 174–208 | | | | | | |
| PEXON_HCMVA | ALKALINE EXONUCLEASE | HUMAN CYTOMEGALOVIRUS (STRAIN AD169) | 80–114 | | | | | | | |
| PEXON_HSVEB | ALKALINE EXONUCLEASE | EQUINE HERPESVIRUS TYPE 1 (STRAIN AB4P) | 89–141 | | | | | | | |
| PEXON_PRVN3 | ALKALINE EXONUCLEASE | PSEUDORABIES VIRUS (STRAIN NIA-3) | 82–120 | | | | | | | |
| PEXON_VZVD | ALKALINE EXONUCLEASE | VARICELLA-ZOSTER VIRUS (STRAIN DUMAS) | 109–157 | 342–383 | | | | | | |
| PFIB2_ADE40 | 41.4 KD FIBER PROTEIN | HUMAN ADENOVIRUS TYPE 40 | 182–237 | | | | | | | |
| PFIB2_ADE41 | 41.4 KD FIBER PROTEIN | HUMAN ADENOVIRUS TYPE 41 | 182–223 | | | | | | | |
| PFIBP_ADE03 | FIBER PROTEIN | HUMAN ADENOVIRUS TYPE 3 | 156–194 | | | | | | | |
| PFIBP_ADE07 | FIBER PROTEIN | HUMAN ADENOVIRUS TYPE 7 | 176–210 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PFIBP_ADE40 | FIBER PROTEIN | HUMAN ADENOVIRUS TYPE 40 | 303–352 | | | | | | | |
| PFIBP_ADE41 | FIBER PROTEIN | HUMAN ADENOVIRUS TYPE 41 | 320–366 | | | | | | | |
| PFIBP_ADEB3 | FIBER PROTEIN | BOVINE ADENOVIRUS TYPE 3 | 181–215 | 585–626 | | | | | | |
| PFOSX_MSVFR | V-FOS/FOX TRANSFORMING PROTEIN | FBR MURINE OSTEOSARCOMA VIRUS | 131–169 | | | | | | | |
| PFOS_AVINK | P55-V-FOS TRANSFORMING PROTEIN | AVIAN RETROVIRUS NK24 | 109–152 | | | | | | | |
| PFOS_MSVFB | P55-V-FOS TRANSFORMING PROTEIN | FBJ MURINE OSTEOSARCOMA VIRUS | 155–193 | | | | | | | |
| PGAGC_AVISC | P47(GAG-CRK) PROTEIN | AVIAN SARCOMA VIRUS (STRAIN CT10) | 57–101 | | | | | | | |
| PGAG_AVEV1 | GAG POLYPROTEIN | AVIAN ENDOGENOUS VIRUS EV-1 | 57–94 | | | | | | | |
| PGAG_AVEV2 | GAG POLYPROTEIN | AVIAN ENDOGENOUS ROUS-ASSOCIATED VIRUS-0 | 6–43 | | | | | | | |
| PGAG_AVIMC | GAG POLYPROTEIN | AVIAN MYELOCYTOMATOSIS VIRUS MC29 | 57–94 | | | | | | | |
| PGAG_AVIMD | GAG POLYPROTEIN | AVIAN MYELOCYTOMATOSIS VIRUS HBI | 57–94 | | | | | | | |
| PGAG_AVISU | CORE PROTEIN P19 | AVIAN SARCOMA VIRUS (STRAIN UR2) | 57–94 | | | | | | | |
| PGAG_AVISY | GAG POLYPROTEIN | AVIAN SARCOMA VIRUS (STRAIN Y73) | 57–94 | | | | | | | |
| PGAG_BIV06 | GAG POLYPROTEIN (P53) | BOVINE IMMUNODEFICIENCY VIRUS (ISOLATE 106) | 1–41 | | | | | | | |
| PGAG_EIAVY | GAG POLYPROTEIN | EQUINE INFECTIOUS ANEMIA VIRUS (CLONE CL22) | 61–118 | | | | | | | |
| PGAG_FIVPE | GAG POLYPROTEIN | FELINE IMMUNODEFICIENCY VIRUS (ISOLATE PETALUMA) | 76–110 | | | | | | | |
| PGAG_FIVSD | GAG POLYPROTEIN | FELINE IMMUNODEFICIENCY VIRUS (ISOLATE SAN DIEGO) | 76–110 | | | | | | | |
| PGAG_FIVT2 | GAG POLYPROTEIN | FELINE IMMUNODEFICIENCY VIRUS (ISOLATE TM2) | 76–110 | | | | | | | |
| PGAG_FLV | GAG POLYPROTEIN | FELINE LEUKEMIA VIRUS | 496–537 | | | | | | | |
| PGAG_FOAMV | GAG POLYPROTEIN | HUMAN SPUMARETROVIRUS | 130–186 | 391–425 | 439–480 | 607–655 | | | | |
| PGAG_FSVMD | GAG POLYPROTEIN | FELINE SARCOMA VIRUS (STRAIN MCDONOUGH) | 499–534 | | | | | | | |
| PGAG_FUJSV | GAG POLYPROTEIN | FUJINAMI SARCOMA VIRUS | 57–94 | | | | | | | |
| PGAG_GALV | GAG POLYPROTEIN | GIBBON APE LEUKEMIA VIRUS | 393–444 | | | | | | | |
| PGAG_HV1A2 | GAG POLYPROTEIN | HUMAN IMMUNODEFICIENCY VIRUS TYPE 1 (ARV2/SF2 ISOLATE) | 87–133 | 294–328 | | | | | | |
| PGAG_HV1B1 | GAG POLYPROTEIN | HUMAN IMMUNODEFICIENCY VIRUS TYPE 1 (BH10 ISOLATE) | 90–131 | 292–326 | | | | | | |
| PGAG_HV1B5 | GAG POLYPROTEIN | HUMAN IMMUNODEFICIENCY VIRUS TYPE 1 (BH5 ISOLATE) | 90–131 | 292–326 | | | | | | |
| PGAG_HV1BR | GAG POLYPROTEIN | HUMAN IMMUNODEFICIENCY VIRUS TYPE 1 (BRU ISOLATE) | 90–131 | 292–326 | | | | | | |
| PGAG_HV1C4 | GAG POLYPROTEIN | HUMAN IMMUNODEFICIENCY VIRUS TYPE 1 (CDC-451 ISOLATE) | 90–131 | 292–326 | | | | | | |
| PGAG_HV1EL | GAG POLYPROTEIN | HUMAN IMMUNODEFICIENCY VIRUS TYPE 1 (ELI ISOLATE) | 93–131 | 292–326 | | | | | | |
| PGAG_HV1H2 | GAG POLYPROTEIN | HUMAN IMMUNODEFICIENCY VIRUS TYPE 1 (HXB2 ISOLATE) | 90–131 | 292–326 | | | | | | |
| PGAG_HV1J3 | GAG POLYPROTEIN | HUMAN IMMUNODEFICIENCY VIRUS TYPE 1 (JH3 ISOLATE) | 87–131 | 292–326 | | | | | | |
| PGAG_HV1JR | GAG POLYPROTEIN | HUMAN IMMUNODEFICIENCY VIRUS TYPE 1 (JRCSF ISOLATE) | 87–131 | 292–326 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PGAG_HV1MA | GAG POLYPROTEIN | HUMAN IMMUNODEFICIENCY VIRUS TYPE 1 (MAL ISOLATE) | 90–137 | | | | | | | |
| PGAG_HV1MN | GAG POLYPROTEIN | HUMAN IMMUNODEFICIENCY VIRUS TYPE 1 (MN ISOLATE) | 87–134 | 295–329 | | | | | | |
| PGAG_HV1N5 | GAG POLYPROTEIN | HUMAN IMMUNODEFICIENCY VIRUS TYPE 1 (NEW YORK-5 ISOL) | 90–131 | 292–326 | | | | | | |
| PGAG_HV1ND | GAG POLYPROTEIN | HUMAN IMMUNODEFICIENCY VIRUS TYPE 1 (NDK ISOLATE) | 87–128 | 289–323 | | | | | | |
| PGAG_HV1OY | GAG POLYPROTEIN | HUMAN IMMUNODEFICIENCY VIRUS TYPE 1 (OYI ISOLATE) | 90–131 | 292–326 | | | | | | |
| PGAG_HV1PV | GAG POLYPROTEIN | HUMAN IMMUNODEFICIENCY VIRUS TYPE 1 (PV22 ISOLATE) | 90–131 | 292–326 | | | | | | |
| PGAG_HV1RH | GAG POLYPROTEIN | HUMAN IMMUNODEFICIENCY VIRUS TYPE 1 (RF/HAT ISOLATE) | 90–131 | 292–326 | | | | | | |
| PGAG_HV1U4 | GAG POLYPROTEIN | HUMAN IMMUNODEFICIENCY VIRUS TYPE 1 (STRAIN UGANDAN) | 87–127 | | | | | | | |
| PGAG_HV1W2 | GAG POLYPROTEIN | HUMAN IMMUNODEFICIENCY VIRUS TYPE 1 (WMJ2 ISOLATE) | 292–326 | | | | | | | |
| PGAG_HV1Z2 | GAG POLYPROTEIN | HUMAN IMMUNODEFICIENCY VIRUS TYPE 1 (Z2/CDC-Z34 ISOLAT | 87–132 | 293–327 | | | | | | |
| PGAG_HV2SB | GAG POLYPROTEIN | HUMAN IMMUNODEFICIENCY VIRUS TYPE 2 (ISOLATE SBL/ISY) | 292–326 | 293–327 | | | | | | |
| PGAG_IPHA | RETROVIRUS-RELATED GAG POLYPROTEIN | HAMSTER INTRACISTERNAL A-PARTICLE | 93–127 | 320–357 | | | | | | |
| PGAG_IPMA | RETROVIRUS-RELATED GAG POLYPROTEIN | MOUSE INTRACISTERNAL A-PARTICLE | 67–103 | | | | | | | |
| PGAG_IPMAE | RETROVIRUS-RELATED GAG POLYPROTEIN | MOUSE INTRACISTERNAL A-PARTICLE | 89–133 | 138–172 | | | | | | |
| PGAG_JSRV | GAG POLYPROTEIN | SHEEP PULMONARY ADENOMATOSIS VIRUS | 470–504 | | | | | | | |
| PGAG_MMTVB | GAG POLYPROTEIN | MOUSE MAMMARY TUMOR VIRUS (STRAIN BR6) | 83–151 | 156–190 | | | | | | |
| PGAG_MMTVG | GAG POLYPROTEIN | MOUSE MAMMARY TUMOR VIRUS (STRAIN GR) | 83–151 | 156–190 | | | | | | |
| PGAG_MPMV | GAG POLYPROTEIN | SIMIAN MASON-PFIZER VIRUS | 222–260 | | | | | | | |
| PGAG_RSVP | GAG POLYPROTEIN | ROUS SARCOMA VIRUS (STRAIN PRAGUE C) | 57–94 | 490–531 | | | | | | |
| PGAG_SCVLA | MAJOR COAT PROTEIN | SACCHAROMYCES CEREVISIAE VIRUS L-A (SCV-L-A) | 102–139 | | | | | | | |
| PGAG_SFV1 | GAG POLYPROTEIN | SIMIAN FOAMY VIRUS (TYPE 1) | 128–177 | 378–416 | 583–634 | | | | | |
| PGAG_SFV3L | GAG POLYPROTEIN | SIMIAN FOAMY VIRUS (TYPE 3/ STRAIN LK3) | 373–407 | 435–522 | 591–632 | | | | | |
| PGAG_SIVA1 | GAG POLYPROTEIN | SIMIAN IMMUNODEFICIENCY VIRUS (AGM155 ISOLATE) | 302–336 | | | | | | | |
| PGAG_SIVAG | GAG POLYPROTEIN | SIMIAN IMMUNODEFICIENCY VIRUS (AGM3 ISOLATE) | 306–340 | | | | | | | |
| PGAG_SIVAI | GAG POLYPROTEIN | SIMIAN IMMUNODEFICIENCY VIRUS (ISOLATE AGM/CLONE GR1 | 183–217 | 473–507 | | | | | | |
| PGAG_SIVAT | GAG POLYPROTEIN | SIMIAN IMMUNODEFICIENCY VIRUS (TYO-1 ISOLATE) | 302–336 | | | | | | | |
| PGAG_SIVCZ | GAG POLYPROTEIN | CHIMPANZEE IMMUNODEFICIENCY VIRUS (SIV(CPZ) | 301–335 | | | | | | | |
| PGAG_SIVGB | GAG POLYPROTEIN | SIMIAN IMMUNODEFICIENCY VIRUS (ISOLATE GB1) | 163–204 | 223–267 | 283–317 | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PGAG_SMSAV | GAG POLYPROTEIN | SIMIAN SARCOMA VIRUS | 394–431 | | | | | | | |
| PHEL1_HSV11 | PROBABLE HELICASE | HERPES SIMPLEX VIRUS (TYPE 1/STRAIN 17) | 172–206 | 769–820 | | | | | | |
| PHEL1_HSV2H | PROBABLE HELICASE | HERPES SIMPLEX VIRUS (TYPE 2/STRAIN HG52) | 468–502 | 670–721 | | | | | | |
| PHEL1_HSVSA | PROBABLE HELICASE | HERPESVIRUS SAIMIRI (STRAIN 11) | 158–203 | 413–449 | 599–633 | | | | | |
| PHEL1_VZVD | PROBABLE HELICASE | VARICELLA-ZOSTER VIRUS (STRAIN DUMAS) | 445–517 | 782–821 | | | | | | |
| PHEMA_CVBF | HEMAGGLUTININ-ESTERASE PRECURSOR | BOVINE CORONAVIRUS (STRAIN F15) | 208–242 | | | | | | | |
| PHEMA_CVBLY | HEMAGGLUTININ-ESTERASE PRECURSOR | BOVINE CORONAVIRUS (STRAIN LY-138) | 208–242 | | | | | | | |
| PHEMA_CVBM | HEMAGGLUTININ-ESTERASE PRECURSOR | BOVINE CORONAVIRUS (STRAIN MEBUS) | 208–242 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PHEMA_IADH5 | HEMAGGLUTININ PRECURSOR | INFLUENZA A VIRUS (STRAIN A/DUCK/HOKKAIDO/21/82) | 364–440 | | | | | | | |
| PHEMA_IADH6 | HEMAGGLUTININ PRECURSOR | INFLUENZA A VIRUS (STRAIN A/DUCK/HOKKAIDO/9/85) | 364–440 | | | | | | | |
| PHEMA_IADH7 | HEMAGGLUTININ PRECURSOR | INFLUENZA A VIRUS (STRAIN A/DUCK/HOKKAIDO/10/85) | 364–440 | | | | | | | |
| PHEMA_IADIR | HEMAGGLUTININ PRECURSOR | INFLUENZA A VIRUS (STRAIN A/DUCK/IRELAND/113/83) | 379–471 | 506–551 | | | | | | |
| PHEMA_IADM1 | HEMAGGLUTININ PRECURSOR | INFLUENZA A VIRUS (STRAIN A/DUCK/MEMPHIS/546/76) | 21–55 | | | | | | | |
| PHEMA_IADM2 | HEMAGGLUTININ PRECURSOR | INFLUENZA A VIRUS (STRAIN A/DUCK/MEMPHIS/928/74) | 380–456 | | | | | | | |
| PHEMA_IADNY | HEMAGGLUTININ PRECURSOR | INFLUENZA A VIRUS (STRAIN A/DUCK/NEW YORK/12/78) | 21–55 | | | | | | | |
| PHEMA_IADNZ | HEMAGGLUTININ PRECURSOR | INFLUENZA A VIRUS (STRAIN A/DUCK/NEW ZEALAND/31/76) | 378–454 | | | | | | | |
| PHEMA_IADU1 | HEMAGGLUTININ PRECURSOR | INFLUENZA A VIRUS (STRAIN A/DUCK/UKRAINE/1/60) | 21–55 | | | | | | | |
| PHEMA_IADU3 | HEMAGGLUTININ PRECURSOR | INFLUENZA A VIRUS (STRAIN A/DUCK/UKRAINE/1/63) | 380–456 | | | | | | | |
| PHEMA_IAEN7 | HEMAGGLUTININ PRECURSOR | INFLUENZA A VIRUS (STRAIN A/ENGLAND/321/77) | 377–477 | | | | | | | |
| PHEMA_IAFPR | HEMAGGLUTININ PRECURSOR | INFLUENZA A VIRUS (STRAIN A/FOWL PLAGUE VIRUS/ROSTOCK) | 378–454 | | | | | | | |
| PHEMA_IAGRE | HEMAGGLUTININ PRECURSOR | INFLUENZA A VIRUS (STRAIN A/GREY TEAL/AUSTRALIA/2/79) | 378–473 | | | | | | | |
| PHEMA_IAGU2 | HEMAGGLUTININ PRECURSOR | INFLUENZA A VIRUS (STRAIN A/GULL/MARYLAND/704/77) | 377–476 | | | | | | | |
| PHEMA_IAGUA | HEMAGGLUTININ PRECURSOR | INFLUENZA A VIRUS (STRAIN A/GULL/ASTRAKHAN/227/84) | 379–455 | | | | | | | |
| PHEMA_IAHAL | HEMAGGLUTININ PRECURSOR | INFLUENZA A VIRUS (STRAIN A/EQUINE/ALGIERS/72) | 112–146 | 360–484 | 503–537 | | | | | |
| PHEMA_IAHC6 | HEMAGGLUTININ PRECURSOR | INFLUENZA A VIRUS (STRAIN A/EQUINE/CAMBRIDGE/1/63) | 112–146 | 360–484 | 503–537 | | | | | |
| PHEMA_IAHC7 | HEMAGGLUTININ PRECURSOR | INFLUENZA A VIRUS (STRAIN A/EQUINE/CAMBRIDGE/1/73) | 360–484 | 503–537 | | | | | | |
| PHEMA_IAHCD | HEMAGGLUTININ PRECURSOR | INFLUENZA A VIRUS (STRAIN A/EQUINE/C.DETROIT/1/64) | 360–484 | 503–537 | | | | | | |
| PHEMA_IAHDE | HEMAGGLUTININ PRECURSOR | INFLUENZA A VIRUS (STRAIN A/EQUINE/DETROIT/1/64) | 379–455 | | | | | | | |
| PHEMA_IAHFO | HEMAGGLUTININ PRECURSOR | INFLUENZA A VIRUS (STRAIN A/EQUINE/FONTAINEBLEAU/76) | 379–455 | | | | | | | |
| PHEMA_IAHK6 | HEMAGGLUTININ PRECURSOR | INFLUENZA A VIRUS (STRAIN A/EQUINE/KENTUCKY/2/86) | 379–455 | | | | | | | |
| PHEMA_IAHK7 | HEMAGGLUTININ PRECURSOR | INFLUENZA A VIRUS (STRAIN A/EQUINE/KENTUCKY/1/87) | | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PHEMA_IAHLE | HEMAGGLUTININ PRECURSOR | INFLUENZA A VIRUS (STRAI TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PHEMA_IANT6 | HEMAGGLUTININ PRECURSOR | INFLUENZA A VIRUS (STRAIN A/NT/60/68) | 380-

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PHEMA_IAZUK | HEMAGGLUTININ PRECURSOR | INFLUENZA A VIRUS (STRAIN A/SWINE/UKKEL/1/84 | 380-456 | | | | | | | |
| PHEMA_INBBE | HEMAGGLUTININ PRECURSOR | INFLUENZA B VIRUS (STRAIN B/BEIJING/1/87 | 388-473 | | | | | | | |
| PHEMA

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | ARE TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PHEMA_PI3HX | HEMAGGLUTININ-NEURAMINIDASE | HUMAN PARAINFLUENZA 3 VIRUS (STRAIN WASH/1511/73) | 13–110 | 394–428 | | | | | | |
| PHEMA_PI4HA | HEMAGGLUTININ-NEURAMINIDASE | HUMAN PARAINFLUENZA 4A VIRUS (STRAIN TOSHIBA) | 54–88 | | | | | | | |
| PHEMA TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PIBMP_FMVD | INCLUSION BODY MATRIX PROTEIN | FIGWORT MOSAIC VIRUS (STRAIN DXS) | 1–51 | 372–406 | | | | | | |
| PIBMP_SOCMV | INCLUSION BODY MATRIX PROTEIN | | 1–48 | 132–179 | | | | | | |
| PIC18_HCMVA | PROBABLE PROCESSING AND TRANSPORT PROTEIN | HUMAN CYTOMEGALOVIRUS (STRAIN AD169) | 53–98 | 290–324 | 498–532 | | | | | |
| PIC18_HSV11 | PROCESSING AND TRANSPORT PROTEIN | HERPES SIMPLEX VIRUS (TYPE 1/STRAIN 17) | 331–365 | | | | | | | |
| PIC18_HSV1A | PROCESSING AND TRANSPORT PROTEIN | HERPES SIMPLEX VIRUS (TYPE 1/STRAIN ANGELOTTI) | 331–365 | | | | | | | |
| PIC18_HSV1F | PROCESSING AND TRANSPORT PROTEIN | HERPES SIMPLEX VIRUS (TYPE 1/STRAIN F) | 324–362 | | | | | | | |
| PIC18_HSVB2 | PROBABLE PROCESSING AND TRANSPORT PROTEIN | BOVINE HERPESVIRUS TYPE 2 (STRAIN BMV) | 466–500 | | | | | | | |
| PIC18_HSVEB | PROBABLE PROCESSING AND TRANSPORT PROTEIN | HERPESVIRUS TYPE 1 (ISOLATE HVS25A) | 341–375 | | | | | | | |
| PIC18_HSVSA | PROBABLE PROCESSING AND TRANSPORT PROTEIN | HERPESVIRUS SAIMIRI (STRAIN 11) | 58–99 | 361–395 | | | | | | |
| PIC18_MCMVS | PROBABLE PROCESSING AND TRANSPORT PROTEIN | MURINE CYTOMEGALOVIRUS (STRAIN SMITH) | 60–112 | 290–340 | 647–691 | | | | | |
| PIC18_PRVIF | PROBABLE PROCESSING AND TRANSPORT PROTEIN | PSEUDORABIES VIRUS (STRAIN INDIANA-FUNKHAUSER/BECKE | 299–333 | 303–337 | | | | | | |
| PICP0_HSVBJ | TRANS-ACTING TRANSCRIPTIONAL PROTEIN ICP0 | BOVINE HERPESVIRUS TYPE 1 (STRAIN JURA) | 190–224 | | | | | | | |
| PICP0_HSVBK | TRANS-ACTING TRANSCRIPTIONAL PROTEIN ICP0 | BOVINE HERPESVIRUS TYPE 1 (STRAIN K22) | 190–224 | | | | | | | |
| PICP4_HSVMG | TRANS-ACTING TRANSCRIPTIONAL ACTIVATOR PR | MAREK'S DISEASE HERPESVIRUS (STRAIN GA) | 1022–1056 | | | | | | | |
| PICP4_HSVVD | TRANS-ACTING TRANSCRIPTIONAL PROTEIN ICP4 | VARICELLA-ZOSTER VIRUS (STRAIN DUMAS) | 920–954 | | | | | | | |
| PIE63_HCMVA | TRANSCRIPTIONAL REGULATOR IE63 HOMOLOG | HUMAN CYTOMEGALOVIRUS (STRAIN AD169) | 207–241 | | | | | | | |
| PIE63_HSV11 | TRANSCRIPTIONAL REGULATOR IE63 HOMOLOG | HERPES SIMPLEX VIRUS (TYPE 1/STRAIN 17) | 241–275 | | | | | | | |
| PIE63_HSVEB | TRANSCRIPTIONAL REGULATOR IE63 HOMOLOG | EQUINE HERPESVIRUS TYPE 1 (STRAIN AB4P) | 282–316 | | | | | | | |
| PIE63_VZVD | TRANSCRIPTIONAL REGULATOR IE63 HOMOLOG | VARICELLA-ZOSTER VIRUS (STRAIN DUMAS) | 195–229 | 258–306 | | | | | | |
| PIE68_HSVE4 | IMMEDIATE-EARLY PROTEIN IE68 | EQUINE HERPESVIRUS TYPE 4 (STRAIN 1942) | 87–121 | | | | | | | |
| PIE68_HSVEB | IMMEDIATE-EARLY PROTEIN IE68 | EQUINE HERPESVIRUS TYPE 1 (STRAIN AB4P) | 99–133 | | | | | | | |
| PIE68_HSVSA | IMMEDIATE-EARLY PROTEIN | HERPESVIRUS SAIMIRI (STRAIN 11) | 48–85 | | | | | | | |
| PIR05_HCMVA | HYPOTHETICAL PROTEIN IRL5 | HUMAN CYTOMEGALOVIRUS (STRAIN AD169) | 13–47 | | | | | | | |
| PIR12_HCMVA | HYPOTHETICAL PROTEIN IRL12 | HUMAN CYTOMEGALOVIRUS (STRAIN AD169) | 74–162 | | | | | | | |
| PKABL_FSVHY | TYROSINE-PROTEIN KINASE TRANSFORMING PROT | FELINE SARCOMA VIRUS (STRAIN HARDY-ZUCKERMAN 2) | 280–314 | | | | | | | |
| PKABL_MLVAB | TYROSINE-PROTEIN KINASE TRANSFORMING PROT | ABELSON MURINE LEUKEMIA VIRUS | 217–251 | | | | | | | |
| PKAKT_MLVAT | AKT KINASE TRANSFORMING PROTEIN | AKT8 MURINE LEUKEMIA VIRUS | 172–227 | 263–304 | | | | | | |
| PKFES_FSVGA | TYROSINE-PROTEIN KINASE TRANSFORMING PROT | FELINE SARCOMA VIRUS (STRAIN GARDNER-ARNSTEIN) | 23–64 | 104–178 | | | | | | |
| PKFGR_FSVGR | TYROSINE-PROTEIN KINASE TRANSFORMING PROT | FELINE SARCOMA VIRUS (STRAIN GARDNER-RASHEED) | 218–252 | | | | | | | |

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PKFMS_FSVMD | FMS TYROSINE KINASE TRANSFORMING PROTEIN | FELINE SARCOMA VIRUS (STRAIN MCDONOUGH) | 313–362 | 638–679 | 812–849 | | | | | |
| PKPS_AVISP | TYROSINE-PROTEIN KINASE TRANSFORMING PROT | AVIAN SARCOMA VIRUS (STRAIN PRCII) | 65–99 | | | | | | | |
| PKPS_FUJSV | TYROSINE-PROTEIN KINASE TRANSFORMING PROT | FUJINAMI SARCOMA VIRUS | 65–99 | 152–251 | 348–398 | | | | | |
| PKITH_AMEPV | THYMIDINE KINASE | AMSACTA MOOREI ENTOMOPOXVIRUS | 47–81 | | | | | | | |
| PKITH_CAPVK | THYMIDINE KINASE | CAPRIPOXVIRUS (STRAIN KS-1) | 38–82 | | | | | | | |
| PKITH_EBV | THYMIDINE KINASE | EPSTEIN-BARR VIRUS (STRAIN B95-8) | 228–262 | 431–472 | | | | | | |
| PKITH_HSV11 | THYMIDINE KINASE | HERPES SIMPLEX VIRUS (TYPE 1/STRAIN 17) | 90–124 | | | | | | | |
| PKITH_HSV1C | THYMIDINE KINASE | HERPES SIMPLEX VIRUS (TYPE 1/STRAIN CL101) | 90–124 | | | | | | | |
| PKITH_HSV1E | THYMIDINE KINASE | HERPES SIMPLEX VIRUS (TYPE 1/STRAIN HFEM) | 90–124 | | | | | | | |
| PKITH_HSV1K | THYMIDINE KINASE | HERPES SIMPLEX VIRUS (TYPE 1/STRAIN KOS) | 90–124 | | | | | | | |
| PKITH_HSV1S | THYMIDINE KINASE | HERPES SIMPLEX VIRUS (TYPE 1/STRAIN SC16) | 90–124 | | | | | | | |
| PKITH_HSV23 | THYMIDINE KINASE | HERPES SIMPLEX VIRUS (TYPE 1/STRAIN 333) | 91–125 | | | | | | | |
| PKITH_HSVBM | THYMIDINE KINASE | BOVINE HERPES VIRUS TYPE 3 (STRAIN WC11) | 616–665 | | | | | | | |
| PKITH_HSVE4 | THYMIDINE KINASE | EQUINE HERPESVIRUS TYPE 4 (STRAIN 1942) | 19–53 | 178–219 | | | | | | |
| PKITH_HSVEB | THYMIDINE KINASE | EQUINE HERPESVIRUS TYPE 1 (STRAIN AB4P) | 19–53 | 178–230 | | | | | | |
| PKITH_HSVF | THYMIDINE KINASE | FELINE HERPESVIRUS (FELID HERPESVIRUS 1) | 180–214 | | | | | | | |
| PKITH_HSVMR | THYMIDINE KINASE | MARMOSET HERPESVIRUS | 52–86 | | | | | | | |
| PKITH_HSVSA | THYMIDINE KINASE | HERPESVIRUS SAIMIRI (STRAIN 11) | 337–389 | | | | | | | |
| PKITH_PRVN3 | THYMIDINE KINASE | PSEUDORABIES VIRUS (STRAIN NIA-3) | 161–202 | | | | | | | |
| PKMIL_AVIMH | MIL SERINE/THREONINE-PROTEIN KINASE TRANSF | AVIAN RETROVIRUS MH2 | 69–103 | | | | | | | |
| PKR15_HSV11 | GENE 15 PROTEIN KINASE | ICTALURID HERPESVIRUS 1 | 190–224 | | | | | | | |
| PKR2_HSV11 | PROBABLE SERINE/THREONINE-PROTEIN KINASE | HERPES SIMPLEX VIRUS (TYPE 1/STRAIN 17) | 57–91 | 281–315 | | | | | | |
| PKR74_HSV11 | GENE 74 PROTEIN KINASE | ICTALURID HERPESVIRUS 1 | 487–528 | 597–631 | | | | | | |
| PKRAF_MSV36 | RAF SERINE/THREONINE-PROTEIN KINASE TRANSF | MURINE SARCOMA VIRUS 3611 | 11–45 | | | | | | | |
| PKRB1_VACCC | 30 KD PROTEIN KINASE HOMOLOG | VACCINIA VIRUS (STRAIN COPENHAGEN) | 127–168 | | | | | | | |
| PKRB1_VACCV | 30 KD PROTEIN KINASE HOMOLOG | VACCINIA VIRUS (STRAIN WR) | 127–168 | | | | | | | |
| PKRB1_VARV | 30 KD PROTEIN KINASE HOMOLOG | VARIOLA VIRUS | 123–171 | | | | | | | |
| PKRB2_VACCC | POSSIBLE PROTEIN KINASE B12 | VACCINIA VIRUS (STRAIN COPENHAGEN) | 147–181 | | | | | | | |
| PKRB2_VACCV | POSSIBLE PROTEIN KINASE B12 | VACCINIA VIRUS (STRAIN WR) | 147–181 | | | | | | | |
| PKRF1_VACCC | POSSIBLE PROTEIN KINASE F10 | VACCINIA VIRUS (STRAIN COPENHAGEN) | 169–203 | | | | | | | |
| PKRF1_VACCP | POSSIBLE PROTEIN KINASE F10 | VACCINIA VIRUS (STRAIN L-IVP) | 136–170 | | | | | | | |
| PKRF1_VARV | POSSIBLE PROTEIN KINASE F10 | VARIOLA VIRUS | 169–203 | | | | | | | |
| PKROS_AVISU | ROS TYROSINE KINASE TRANSFORMING PROTEIN | AVIAN SARCOMA VIRUS (STRAIN UR2) | 111–145 | | | | | | | |
| PKRYK_AVIR3 | TYROSINE-PROTEIN KINASE TRANSFORMING PROT | AVIAN RETROVIRUS RPL30 | 15–66 | | | | | | | |
| PKTHY_VACCV | THYMIDYLATE KINASE | VACCINIA VIRUS (STRAIN WR) (STRAIN COPENHAGEN) | 135–169 | | | | | | | |
| PKYES_AVISY | TYROSINE-PROTEIN KINASE TRANSFORMING PROT | AVIAN SARCOMA VIRUS (STRAIN Y73) | 174–233 | | | | | | | |
| PL100_ADE02 | LATE 100 KD PROTEIN | HUMAN ADENOVIRUS TYPE 2 | 441–475 | | | | | | | |
| PL100_ADE05 | LATE 100 KD PROTEIN | HUMAN ADENOVIRUS TYPE 5 | 223–264 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PL100_ADE40 | LATE 100 KD PROTEIN | HUMAN ADENOVIRUS TYPE 40 | 191–232 | 408–442 | | | | | | |
| PL100_ADE41 | LATE 100 KD PROTEIN | HUMAN ADENOVIRUS TYPE 41 | 199–233 | | | | | | | |
| PL52_ADE02 | LATE L1 52 KD PROTEIN | HUMAN ADENOVIRUS TYPE 2 | 238–284 | 301–349 | | | | | | |
| PL52_ADE05 | LATE L1 52 KD PROTEIN | HUMAN ADENOVIRUS TYPE 5 | 238–284 | 301–349 | | | | | | |
| PLMP2_EBV | GENE TERMINAL PROTEIN | EPSTEIN-BARR VIRUS (STRAIN B95-8) | 144–179 | 294–338 | | | | | | |
| PMCEL_SFVKA | MRNA CAPPING ENZYME | SHOPE FIBROMA VIRUS (STRAIN KASZA) | 54–152 | 622–656 | | | | | | |
| PMCEL_VACCC | MRNA CAPPING ENZYME | VACCINIA VIRUS (STRAIN COPENHAGEN) | 1–41 | 623–657 | | | | | | |
| PMCEL_VACCV | MRNA CAPPING ENZYME | VACCINIA VIRUS (STRAIN WR) | 1–41 | 623–657 | | | | | | |
| PMCEL_VARV | MRNA CAPPING ENZYME | VARIOLA VIRUS | 1–39 | 623–657 | | | | | | |
| PMCES_VACCC | MRNA CAPPING ENZYME | VACCINIA VIRUS (STRAIN COPENHAGEN) | 72–137 | 245–286 | | | | | | |
| PMCES_VACCV | MRNA CAPPING ENZYME | VACCINIA VIRUS (STRAIN WR) | 72–137 | 245–286 | | | | | | |
| PMCES_VARV | MRNA CAPPING ENZYME | VARIOLA VIRUS | 72–137 | 245–286 | | | | | | |
| PMCE_ASFB7 | MRNA CAPPING ENZYME | AFRICAN SWINE FEVER VIRUS (STRAIN BA71V) | 116–157 | 279–313 | 738–772 | | | | | |
| PMOVP_ORSV | MOVEMENT PROTEIN | ODONTOGLOSSUM RINGSPOT VIRUS | 53–90 | | | | | | | |
| PMOVP_PPMVS | MOVEMENT PROTEIN | PEPPER MILD MOTTLE VIRUS (STRAIN SPAIN) | 26–66 | | | | | | | |
| PMOVP_TMGMV | MOVEMENT PROTEIN | TOBACCO MILD GREEN MOSAIC VIRUS (TMV STRAIN U2) | 29–66 | | | | | | | |
| PMOVP_TMVTO | MOVEMENT PROTEIN | TOBACCO MOSAIC VIRUS (STRAIN TOMATO/L) | 32–66 | | | | | | | |
| PMOVP_TOMVA | MOVEMENT PROTEIN | TOMATO MOSAIC VIRUS (STRAIN LIIA) | 32–80 | | | | | | | |
| PMOVP_TOMVL | MOVEMENT PROTEIN | TOMATO MOSAIC VIRUS (STRAIN LII) | 32–80 | | | | | | | |
| PMTC1_CHVN1 | MODIFICATION METHYLASE CVIBI | CHLORELLA VIRUS NC-1A | 222–256 | | | | | | | |
| PMTC2_CHVP1 | MODIFICATION METHYLASE CVIAII | PARAMECIUM BURSARIA CHLORELLA VIRUS 1 | 116–164 | | | | | | | |
| PMYC_AVIM2 | MYC TRANSFORMING PROTEIN | AVIAN MYELOCYTOMATOSIS VIRUS CMII | 229–266 | 375–419 | | | | | | |
| PMYC_AVIMC | MYC TRANSFORMING PROTEIN | AVIAN MYELOCYTOMATOSIS VIRUS MC29 | 230–267 | 376–420 | | | | | | |
| PMYC_AVIMD | MYC TRANSFORMING PROTEIN | AVIAN MYELOCYTOMATOSIS VIRUS HBI | 230–267 | 376–420 | | | | | | |
| PMYC_AVIME | MYC TRANSFORMING PROTEIN | AVIAN RETROVIRUS MH2E21 | 377–421 | | | | | | | |
| PMYC_AVIOK | MYC TRANSFORMING PROTEIN | AVIAN RETROVIRUS OK10 | 224–261 | 370–414 | | | | | | |
| PMYC_FLV | MYC TRANSFORMING PROTEIN | FELINE LEUKEMIA VIRUS | 393–437 | | | | | | | |
| PMYC_FLVTT | MYC TRANSFORMING PROTEIN | FELINE LEUKEMIA PROVIRUS FTT | 393–437 | | | | | | | |
| PNCA2_CVMA5 | NUCLEOCAPSID PROTEIN | MURINE CORONAVIRUS MHV (STRAIN A59) | 12–46 | | | | | | | |
| PNCAP_AINOV | NUCLEOCAPSID PROTEIN | AINO VIRUS | 177–211 | | | | | | | |
| PNCAP_BEV | NUCLEOCAPSID PROTEIN | BERNE VIRUS | 46–83 | 122–156 | | | | | | |
| PNCAP_BRSVA | NUCLEOCAPSID PROTEIN | BOVINE RESPIRATOR SYNCYTIAL VIRUS (STRAIN A51908) | 62–108 | 163–200 | 248–303 | 343–383 | | | | |
| PNCAP_BUNGE | NUCLEOCAPSID PROTEIN | BUNYAVIRUS GERMISTON | 176–228 | | | | | | | |
| PNCAP_BUNLC | NUCLEOCAPSID PROTEIN | BUNYAVIRUS LA CROSSE | 176–229 | | | | | | | |
| PNCAP_BUNSH | NUCLEOCAPSID PROTEIN | BUNYAVIRUS SNOWSHOE HARE | 176–229 | | | | | | | |
| PNCAP_BUNYW | NUCLEOCAPSID PROTEIN | BUNYAMWERA VIRUS | 175–228 | | | | | | | |
| PNCAP_CCHFV | NUCLEOCAPSID PROTEIN | CRIMEAN-CONGO HEMORRHAGIC FEVER VIRUS (ISOLATE C6803 | 223–306 | 427–461 | | | | | | |
| PNCAP_CDVO | NUCLEOCAPSID PROTEIN | CANINE DISTEMPER VIRUS (STRAIN ONDERSTEPOORT) | 137–174 | 179–217 | 354–402 | | | | | |
| PNCAP_CHAV | NUCLEOCAPSID PROTEIN | CHANDIPURA VIRUS (STRAIN 1653514) | 40–84 | 321–369 | | | | | | |
| PNCAP_CVBF | NUCLEOCAPSID PROTEIN | BOVINE CORONAVIRUS (STRAIN F15) | 349–383 | | | | | | | |
| PNCAP_CVBM | NUCLEOCAPSID PROTEIN | BOVINE CORONAVIRUS (STRAIN MEBUS) | 349–383 | | | | | | | |
| PNCAP_CVCAE | NUCLEOCAPSID PROTEIN | CANINE ENTERIC CORONAVIRUS (STRAIN K378) | 165–227 | | | | | | | |
| PNCAP_CVHOC | NUCLEOCAPSID PROTEIN | HUMAN CORONAVIRUS (STRAIN OC43) | 349–383 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PNCAP_CVMJH | NUCLEOCAPSID PROTEIN | MURINE CORONAVIRUS MHV (STRAIN JHM) | 12–46 | | | | | | | |
| PNCAP_CVPFS | NUCLEOCAPSID PROTEIN | PORCINE TRANSMISSIBLE GASTROENTERITIS CORONAVIRUS (S | 149–206 | | | | | | | |
| PNCAP_CVPPU | NUCLEOCAPSID PROTEIN | PORCINE TRANSMISSIBLE GASTROENTERITIS CORONAVIRUS (S | 165–227 | | | | | | | |
| PNCAP_CVPR8 | NUCLEOCAPSID PROTEIN | PORCINE RESPIRATORY CORONAVIRUS (STRAIN 86/137004/BRIT | 149–228 | | | | | | | |
| PNCAP_CVPRM | NUCLEOCAPSID PROTEIN | PORCINE RESPIRATORY CORONAVIRUS (STRAIN RM4) | 149–228 | | | | | | | |
| PNCAP_CVRSD | NUCLEOCAPSID PROTEIN | RAT CORONAVIRUS (STRAIN 681) | 12–46 | | | | | | | |
| PNCAP_CVTKE | NUCLEOCAPSID PROTEIN | TURKEY ENTERIC CORONAVIRUS | 349–383 | | | | | | | |
| PNCAP_DUGBV | NUCLEOCAPSID PROTEIN | DUGBE VIRUS | 230–306 | | | | | | | |
| PNCAP_FIPV | NUCLEOCAPSID PROTEIN | FELINE INFECTIOUS PERITONITIS VIRUS (STRAIN 79-1146) | 151–206 | | | | | | | |
| PNCAP_HANTV | NUCLEOCAPSID PROTEIN | HANTAAN VIRUS (STRAIN 76-118) | 1–35 | 40–74 | 333–381 | | | | | |
| PNCAP_HAZVJ | NUCLEOCAPSID PROTEIN | HAZARA VIRUS (ISOLATE JC280) | 233–297 | | | | | | | |
| PNCAP_HRSV1 | NUCLEOCAPSID PROTEIN | HUMAN RESPIRATORY SYNCYTIAL VIRUS (SUBGROUP B/STRAI | 62–145 | 163–200 | 248–303 | 343–380 | | | | |
| PNCAP_HRSVA | NUCLEOCAPSID PROTEIN | HUMAN RESPIRATORY SYNCYTIAL VIRUS (STRAIN A2) | 62–145 | 163–200 | 248–303 | 343–380 | | | | |
| PNCAP_IBVG | NUCLEOCAPSID PROTEIN | AVIAN INFECTIOUS BRONCHITIS VIRUS (STRAIN GRAY) | 186–227 | | | | | | | |
| PNCAP_IBVK | NUCLEOCAPSID PROTEIN | AVIAN INFECTIOUS BRONCHITIS VIRUS (STRAIN KB8523) | 186–220 | | | | | | | |
| PNCAP_JUNIN | NUCLEOCAPSID PROTEIN | JUNIN ARENAVIRUS | 96–151 | | | | | | | |
| PNCAP_LASSG | NUCLEOCAPSID PROTEIN | LASSA VIRUS (STRAIN GA391) | 65–113 | 126–174 | | | | | | |
| PNCAP_LASSJ | NUCLEOCAPSID PROTEIN | LASSA VIRUS (STRAIN JOSIAH) | 65–113 | 122–174 | 467–504 | | | | | |
| PNCAP_LDV | NUCLEOCAPSID PROTEIN | LACTATE DEHYDROGENASE-ELEVATING VIRUS( | 3–40 | | | | | | | |
| PNCAP_LYCVA | NUCLEOCAPSID PROTEIN | LYMPHOCYTIC CHORIOMENINGITIS VIRUS (STRAIN ARMSTRON | 45–117 | 460–497 | | | | | | |
| PNCAP_LYCVW | NUCLEOCAPSID PROTEIN | LYMPHOCYTIC CHORIOMENINGITIS VIRUS (STRAIN WE) | 45–79 | 83–117 | 460–497 | | | | | |
| PNCAP_MAGV | NUCLEOCAPSID PROTEIN | MAGUARI VIRUS | 175–228 | | | | | | | |
| PNCAP_MEASE | NUCLEOCAPSID PROTEIN | MEASLES VIRUS (STRAIN EDMONSTON) | 188–226 | 363–411 | | | | | | |
| PNCAP_MEASH | NUCLEOCAPSID PROTEIN | MEASLES VIRUS (STRAIN HALLE) | 188–226 | 363–411 | | | | | | |
| PNCAP_MEASI | NUCLEOCAPSID PROTEIN | MEASLES VIRUS (STRAIN IP-3-CA) | 188–226 | 363–411 | | | | | | |
| PNCAP_MEASY | NUCLEOCAPSID PROTEIN | MEASLES VIRUS (STRAIN YAMAGATA-1) | 188–226 | 363–411 | | | | | | |
| PNCAP_MOPEI | NUCLEOCAPSID PROTEIN | MOPEIA VIRUS | 65–106 | 471–505 | | | | | | |
| PNCAP_MUMP1 | NUCLEOCAPSID PROTEIN | MUMPS VIRUS (STRAIN SBL-1) | 214–255 | 500–534 | | | | | | |
| PNCAP_MUMPM | NUCLEOCAPSID PROTEIN | MUMPS VIRUS (STRAIN MIYAHARA VACCINE) | 214–255 | | | | | | | |
| PNCAP_PHV | NUCLEOCAPSID PROTEIN | PROSPECT HILL VIRUS | 1–35 | 40–74 | 337–392 | | | | | |
| PNCAP_P11HC | NUCLEOCAPSID PROTEIN | HUMAN PARAINFLUENZA 1 VIRUS (STRAIN C39) | 212–272 | 441–510 | | | | | | |
| PNCAP_P11HW | NUCLEOCAPSID PROTEIN | HUMAN PARAINFLUENZA 1 VIRUS (STRAIN WASHINGTON/1957) | 212–272 | 441–510 | | | | | | |
| PNCAP_P12HT | NUCLEOCAPSID PROTEIN | HUMAN PARAINFLUENZA 1 VIRUS (STRAIN TOSHIBA) | 214–266 | 344–378 | | | | | | |
| PNCAP_P13B | NUCLEOCAPSID PROTEIN | BOVINE PARAINFLUENZA 3 VIRUS | 200–403 | 446–490 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PNCAP_P13H4 | NUCLEOCAPSID PROTEIN | HUMAN PARAINFLUENZA 3 VIRUS (STRAIN NIH 47885) | 87–135 | 208–266 | 344–403 | 440–491 | | | | |
| PNCAP_P14HA | NUCLEOCAPSID PROTEIN | HUMAN PARAINFLUENZA 4A VIRUS (STRAIN TOSHIBA) | 58–94 | 191–267 | | | | | | |
| PNCAP_P14HB | NUCLEOCAPSID PROTEIN | HUMAN PARAINFLUENZA 4B VIRUS (STRAIN 68-333) | 58–94 | 191–267 | | | | | | |
| PNCAP_PIARV | NUCLEOCAPSID PROTEIN | PICHINDE ARENAVIRUS | 65–112 | | | | | | | |
| PNCAP_PIRYV | NUCLEOCAPSID PROTEIN | PIRY VIRUS | 71–116 | 325–359 | | | | | | |
| PNCAP_PUUMH | NUCLEOCAPSID PROTEIN | PUUMALA VIRUS (STRAIN HALLNAS B1) | 1–35 | 40–75 | 337–392 | | | | | |
| PNCAP_PUUMS | NUCLEOCAPSID PROTEIN | PUUMALA VIRUS (STRAIN SOTKAMO) | 1–35 | 40–75 | 337–385 | | | | | |
| PNCAP_PVM | NUCLEOCAPSID PROTEIN | PNEUMONIA VIRUS OF MICE | 93–141 | 248–303 | 344–388 | | | | | |
| PNCAP_RABVA | NUCLEOCAPSID PROTEIN | RABIES VIRUS (STRAIN AVO1) | 133–167 | | | | | | | |
| PNCAP_SEND5 | NUCLEOCAPSID PROTEIN | SENDAI VIRUS (STRAIN Z/HOST MUTANTS) | 212–272 | 345–404 | | | | | | |
| PNCAP_SENDE | NUCLEOCAPSID PROTEIN | SENDAI VIRUS (STRAIN ENDERS) | 212–272 | 345–404 | | | | | | |
| PNCAP_SENDZ | NUCLEOCAPSID PROTEIN | SENDAI VIRUS (STRAIN Z) | 212–272 | 345–408 | | | | | | |
| PNCAP_SEOUS | NUCLEOCAPSID PROTEIN | SEOUL VIRUS (STRAIN SR-11) | 1–35 | 40–74 | 333–381 | | | | | |
| PNCAP_SV41 | NUCLEOCAPSID PROTEIN | SIMIAN VIRUS 41 | 215–267 | 372–406 | 418–466 | | | | | |
| PNCAP_SYNV | NUCLEOCAPSID PROTEIN | SONCHUS YELLOW NET VIRUS | 332–366 | | | | | | | |
| PNCAP_TACV | NUCLEOCAPSID PROTEIN | TACARIBE VIRUS | 50–84 | 230–264 | | | | | | |
| PNCAP_TOSV | NUCLEOCAPSID PROTEIN | TOSCANA VIRUS | 215–249 | | | | | | | |
| PNCAP_TSWVB | NUCLEOCAPSID PROTEIN | TOMATO SPOTTED WILT VIRUS (BRAZILIAN ISOLATE CPNH1/BR | 79–120 | | | | | | | |
| PNCAP_TSWVH | NUCLEOCAPSID PROTEIN | TOMATO SPOTTED WILT VIRUS (HAWAIIAN ISOLATE) | 79–120 | | | | | | | |
| PNCAP_TSWVL | NUCLEOCAPSID PROTEIN | TOMATO SPOTTED WILT VIRUS (STRAIN L3) | 79–120 | | | | | | | |
| PNCAP_UUK | NUCLEOCAPSID PROTEIN | UUKUNIEMI VIRUS | 51–102 | | | | | | | |
| PNCAP_VHSV0 | NUCLEOCAPSID PROTEIN | VIRAL HEMORRHAGIC SEPTICEMIA VIRUS (STRAIN 07-71) | 249–325 | | | | | | | |
| PNCAP_VHSVM | NUCLEOCAPSID PROTEIN | VIRAL HEMORRHAGIC SEPTICEMIA VIRUS (STRAIN MAKAH) | 142–180 | 249–325 | | | | | | |
| PNCAP_VSVIG | NUCLEOCAPSID PROTEIN | VESICULAR STOMATITIS VIRUS (SEROTYPE INDIANA/STRAIN G | 42–108 | | | | | | | |
| PNCAP_VSVJO | NUCLEOCAPSID PROTEIN | VESICULAR STOMATITIS VIRUS (SEROTYPE NEW JERSEY/STRA | 67–115 | | | | | | | |
| PNCAP_VSVSJ | NUCLEOCAPSID PROTEIN | VESICULAR STOMATITIS VIRUS (STRAIN SAN JUAN) | 42–115 | | | | | | | |
| PNEF_HV2BE | NEGATIVE FACTOR | HUMAN IMMUNODEFICIENCY VIRUS TYPE 2 (ISOLATE BEN) | 7–48 | | | | | | | |
| PNEF_HV2D1 | NEGATIVE FACTOR | HUMAN IMMUNODEFICIENCY VIRUS TYPE 2 (ISOLATE D194) | 7–41 | | | | | | | |
| PNEF_HV2RO | NEGATIVE FACTOR | HUMAN IMMUNODEFICIENCY VIRUS TYPE 2 (ISOLATE ROD) | 112–160 | | | | | | | |
| PNEF_HV2SB | NEGATIVE FACTOR | HUMAN IMMUNODEFICIENCY VIRUS TYPE 2 (ISOLATE SBLISY) | 109–150 | | | | | | | |
| PNEF_HV2ST | NEGATIVE FACTOR | HUMAN IMMUNODEFICIENCY VIRUS TYPE 2 (ISOLATE ST) | 108–149 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PNEF_SIVAI | NEGATIVE FACTOR | SIMIAN IMMUNODEFICIENCY VIRUS (ISOLATE AGM/CLONE GR1) | 96–140 | | | | | | | |
| PNEF_SIVS4 | NEGATIVE FACTOR | SIMIAN IMMUNODEFICIENCY VIRUS (F236/SMH4 ISOLATE) | 9–43 | 233–267 | | | | | | |
| PNRAM_IABDA | NEURAMINIDASE | INFLUENZA A VIRUS (STRAIN A/BLACK DUCK/AUSTRALIA/702/78) | 47–81 | | | | | | | |
| PNRAM_IACAO | NEURAMINIDASE | INFLUENZA A VIRUS (STRAIN A/CAMEL/MONGOLIA/82) | 33–74 | | | | | | | |
| PNRAM_IACHI | NEURAMINIDASE | INFLUENZA A VIRUS (STRAIN A/CHILE/1/83) | 50–91 | | | | | | | |
| PNRAM_IACKQ | NEURAMINIDASE | INFLUENZA A VIRUS (STRAIN A/CHICKEN/PENNSYLVANIA/1370/) | 349–383 | | | | | | | |
| PNRAM_IACKR | NEURAMINIDASE | INFLUENZA A VIRUS (STRAIN A/CHICKEN/PENNSYLVANIA/8125/) | 349–383 | | | | | | | |
| PNRAM_IADGE | NEURAMINIDASE | INFLUENZA A VIRUS (STRAIN A/DUCK/GERMANY/49) | 14–48 | | | | | | | |
| PNRAM_IAFPW | NEURAMINIDASE | INFLUENZA A VIRUS (STRAIN A/FOWL PLAGUE VIRUS/WEYBRID) | 14–48 | 194–229 | | | | | | |
| PNRAM_IAHCO | NEURAMINIDASE | INFLUENZA A VIRUS (STRAIN A/) | 10–47 | 193–227 | | | | | | |
| PNRAM_IAHK1 | NEURAMINIDASE | INFLUENZA A VIRUS (STRAIN A/EQUINE/COR/16/74) | 5–44 | 361–402 | | | | | | |
| PNRAM_IAKIE | NEURAMINIDASE | INFLUENZA A VIRUS (STRAIN A/EQUINE/KENTUCKY/1/81) | 50–91 | | | | | | | |
| PNRAM_IALEN | NEURAMINIDASE | INFLUENZA A VIRUS (STRAIN A/KIEV/59/79) | 50–91 | | | | | | | |
| PNRAM_IAME1 | NEURAMINIDASE | INFLUENZA A VIRUS (STRAIN A/LENINGRAD/54/1) | 50–88 | | | | | | | |
| PNRAM_IARUE | NEURAMINIDASE | INFLUENZA A VIRUS (STRAIN A/MEMPHIS/1/71H-A/BELLAMY/42N) | 49–91 | | | | | | | |
| PNRAM_IASH2 | NEURAMINIDASE | INFLUENZA A VIRUS (STRAIN A/RUDDY TURNSTONE/NEW JERSE) | 10–44 | | | | | | | |
| PNRAM_IATKR | NEURAMINIDASE | INFLUENZA A VIRUS (STRAIN A/SHEARWATER/AUSTRALIA/72) | 7–41 | | | | | | | |
| PNRAM_IATRA | NEURAMINIDASE | INFLUENZA A VIRUS (STRAIN A/TURKEY/OREGON/71) | 49–83 | | | | | | | |
| PNRAM_IAUSS | NEURAMINIDASE | INFLUENZA A VIRUS (STRAIN A/TERN/AUSTRALIA/G70C/75) | 50–91 | | | | | | | |
| PNRAM_IAWHM | NEURAMINIDASE | INFLUENZA A VIRUS (STRAIN A/USSR/90/77) | 49–91 | | | | | | | |
| PNRAM_INBBE | NEURAMINIDASE | INFLUENZA B VIRUS (STRAIN B/WHALE/MAINE/1/84) | 5–46 | 348–382 | | | | | | |
| PNRAM_INBHK | NEURAMINIDASE | INFLUENZA B VIRUS (STRAIN B/BEIJING/1/87) | 5–46 | 349–383 | | | | | | |
| PNRAM_INBLE | NEURAMINIDASE | INFLUENZA B VIRUS (STRAIN B/HONG KONG/8/73) | 5–46 | 349–383 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PNRAM_INBLN | NEURAMINIDASE | INFLUENZA B VIRUS (STRAIN B/ LENINGRAD/179/86),STRAIN B/M | 5–39 | 348–382 | | | | | | |
| PNRAM_INBMD | NEURAMINIDASE | INFLUENZA B VIRUS (STRAIN B/ MARYLAND/59) | 5–39 | 349–383 | | | | | | |
| PNRAM_INBMF | NEURAMINIDASE | INFLUENZA B VIRUS (STRAIN B/ MEMPHIS/3/89) | 5–46 | 348–382 | | | | | | |
| PNRAM_INBOR | NEURAMINIDASE | INFLUENZA B VIRUS (STRAIN B/ OREGON/5/80) | 5–46 | 349–383 | | | | | | |
| PNRAM_INBSI | NEURAMINIDASE | INFLUENZA B VIRUS (STRAIN B/ SINGAPORE/222/79) | 5–39 | 349–383 | | | | | | |
| PNRAM_INBUS | NEURAMINIDASE | INFLUENZA B VIRUS (STRAIN B/ USSR/100/83) | 5–39 | 349–383 | | | | | | |
| PNRAM_INBVI | NEURAMINIDASE | INFLUENZA B VIRUS (STRAIN B/ VICTORIA/3/85 | 5–39 | 348–382 | | | | | | |
| PNS2_SIDEV | PROBABLE STRUCTURAL PROTEIN PRECURSOR | BOMBYX DENSONUCLEOSIS VIRUS | 790–828 | | | | | | | |
| PNSS_INSVN | NON-STRUCTURAL PROTEIN | IMPATIENS NECROTIC SPOT VIRUS (STRAIN NL-07) | 95–129 | 204–238 | | | | | | |
| PNSS_TSWVB | NON-STRUCTURAL PROTEIN | TOMATO SPOTTED WILT VIRUS (BRAZILIAN ISOLATE CPNH1/BR | 3–37 | | | | | | | |
| PNSS_TSWVL | NON-STRUCTURAL PROTEIN | TOMATO SPOTTED WILT VIRUS (STRAIN L3) | 3–37 | | | | | | | |
| PNTP1_AMEPV | NUCLEOSIDE TRIPHOSPHATASE I | AMSACTA MOOREI ENTOMOPOXVIRUS | 28–69 | 110–144 | | | | | | |
| PNTP1_CBEPV | NUCLEOSIDE TRIPHOSPHATASE I | CHORISTONEURA BIENNIS ENTOMOPOXVIRUS | 122–169 | 415–449 | 514–555 | | | | | |
| PNTP1_VACCC | NUCLEOSIDE TRIPHOSPHATASE I | VACCINIA VIRUS (STRAIN COPENHAGEN) | 56–90 | 248–289 | 549–599 | | | | | |
| PNTP1_VACCV | NUCLEOSIDE TRIPHOSPHATASE I | VACCINIA VIRUS (STRAIN WR) | 56–90 | 248–289 | 549–599 | | | | | |
| PNTP1_VARV | NUCLEOSIDE TRIPHOSPHATASE I | VARIOLA VIRUS | 154–195 | 455–505 | | | | | | |
| PP100_HSV6U | MAJOR ANTIGENIC STRUCTURAL PROTEIN | HERPES SIMPLEX VIRUS (TYPE 6/ STRAIN UGANDA-1102) | 189–223 | 689–735 | | | | | | |
| PPAP1_VACCC | POLY(A) POLYMERASE CATALYTIC SUBUNIT | VACCINIA VIRUS (STRAIN COPENHAGEN) | 121–180 | | | | | | | |
| PPAP1_VACCV | POLY(A) POLYMERASE CATALYTIC SUBUNIT | VACCINIA VIRUS (STRAIN WR) | 121–180 | | | | | | | |
| PPAP1_VARV | POLY(A) POLYMERASE CATALYTIC SUBUNIT | VARIOLA VIRUS | 121–180 | | | | | | | |
| PPAP2_CAPVK | POLY(A) POLYMERASE REGULATORY SUBUNIT | CAPRIPOXVIRUS (STRAIN KS-1) | 112–146 | | | | | | | |
| PPAP2_FOWPV | POLY(A) POLYMERASE REGULATORY SUBUNIT | FOWLPOX VIRUS | 95–154 | | | | | | | |
| PPAP2_VACCC | POLY(A) POLYMERASE REGULATORY SUBUNIT | VACCINIA VIRUS (STRAIN COPENHAGEN) | 203–249 | | | | | | | |
| PPAP2_VACCV | POLY(A) POLYMERASE REGULATORY SUBUNIT | VACCINIA VIRUS (STRAIN WR) | 203–249 | | | | | | | |
| PPAP2_VARV | POLY(A) POLYMERASE REGULATORY SUBUNIT | VARIOLA VIRUS | 203–249 | | | | | | | |
| PPE12_NPVAC | 12.1 KD PROTEIN IN PE 5'REGION | AUTOGRAPHA CALIFORNICA NUCLEAR POLYHEDROSIS VIRUS | 15–56 | 60–105 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPE12_NPVOP | 11.5 KD PROTEIN IN P26 5'REGION | ORGYIA PSEUDOTSUGATA MULTICAPSID POLYHEDROSIS VIRUS | 11–98 | | | | | | | |
| PPE38_NPVAC | MAJOR IMMEDIATE EARLY PROTEIN | AUTOGRAPHA CALIFORNICA NUCLEAR POLYHEDROSIS VIRUS | 19–77 | 197–249 | | | | | | |
| PPE38_NPVOP | MAJOR IMMEDIATE EARLY PROTEIN | ORGYIA PSEUDOTSUGATA MULTICAPSID POLYHEDROSIS VIRUS | 190–240 | | | | | | | |
| PPE48_NPVAC | 48.3 KD PROTEIN IN PE-P26 INTERGENIC REGION | AUTOGRAPHA CALIFORNICA NUCLEAR POLYHEDROSIS VIRUS | 4–42 | 48–89 | 97–131 | | | | | |
| PPE48_NPVOC | 47.3 KD PROTEIN IN PE-P26 INTERGENIC REGION | ORGYIA PSEUDOTSUGATA MULTICAPSID POLYHEDROSIS VIRUS | 47–82 | 165–199 | | | | | | |
| PPIV2_ADE07 | MATURATION PROTEIN | HUMAN ADENOVIRUS TYPE 7 | 414–448 | | | | | | | |
| PPIV6_ADE02 | PROTEIN VI PRECURSOR | HUMAN ADENOVIRUS TYPE 2 | 37–71 | | | | | | | |
| PPIV6_ADE05 | PROTEIN VI PRECURSOR | HUMAN ADENOVIRUS TYPE 5 | 37–71 | | | | | | | |
| PPOL1_BAYMG | GENOME POLYPROTEIN 1 | BARLEY YELLOW MOSAIC VIRUS (GERMAN ISOLATE) | 329–363 | 743–777 | 957–991 | 1265–1299 | 2229–2266 | 2309–2352 | 2368–2404 | |
| PPOL1_BAYMJ | GENOME POLYPROTEIN 1 | BARLEY YELLOW MOSAIC VIRUS (JAPANESE STRAIN 11-1) | 329–363 | 671–705 | 743–777 | 957–994 | 1265–1299 | 2227–2264 | 2307–2350 | 2366 |
| PPOL1_GCMV | RNA1 POLYPROTEIN | HUNGARIAN GRAPEVINE CHROME MOSAIC VIRUS | 120–161 | 165–216 | 230–273 | 377–415 | | | | |
| PPOL1_GFLV | RNA1 POLYPROTEIN | GRAPEVINE FANLEAF VIRUS | 170–212 | 480–519 | 636–677 | 691–725 | 1157–1196 | 1378–1412 | 1906–1943 | |
| PPOL1_TBRVS | RNA1 POLYPROTEIN | TOMATO BLACK RING VIRUS (STRAIN S) | 223–270 | 929–977 | | | | | | |
| PPOL1_TRSVR | RNA1 POLYPROTEIN | TOMATO RINGSPOT VIRUS (ISOLATE RASPBERRY) | 161–206 | | | | | | | |
| PPOL2_BAYMG | GENOME POLYPROTEIN 2 | BARLEY YELLOW MOSAIC VIRUS (GERMAN ISOLATE) | 240–281 | 669–732 | 739–773 | 787–828 | | | | |
| PPOL2_BAYMJ | GENOME POLYPROTEIN 2 | BARLEY YELLOW MOSAIC VIRUS (JAPANESE STRAIN II-1) | 669–732 | 739–773 | 787–828 | | | | | |
| PPOL2_GFLV | RNA2 POLYPROTEIN | GRAPEVINE FANLEAF VIRUS | 365–406 | 542–602 | | | | | | |
| PPOL2_TBRVS | RNA2 POLYPROTEIN | TOMATO BLACK RING VIRUS (STRAIN S) | 4–38 | | | | | | | |
| PPOL2_TRSVR | RNA2 POLYPROTEIN | TOMATO RINGSPOT VIRUS (ISOLATE RASPBERRY) | 158–206 | 334–368 | | | | | | |
| PPOLG_BOVEV | GENOME POLYPROTEIN | BOVINE ENTEROVIRUS (STRAIN VG-5-27) | 849–886 | 1008–1064 | 1382–1416 | 1459–1507 | 1576–1617 | | | |
| PPOLG_BVDVN | GENOME POLYPROTEIN | BOVINE VIRAL DIARRHEA VIRUS (ISOLATE NADL) | 244–289 | 446–491 | 629–663 | 1033–1074 | 1303–1344 | 1392–1443 | 1869–1910 | 2226–2260 |
| PPOLG_BVDVS | GENOME POLYPROTEIN | BOVINE VIRAL DIARRHEA VIRUS (STRAIN SD-1) | 245–289 | 446–491 | 629–663 | 1033–1074 | 1303–1344 | 1392–1443 | 1779–1820 | 2136–2170 |
| PPOLG_BYMV | GENOME POLYPROTEIN | BEAN YELLOW MOSAIC VIRUS | 96–130 | | | | | | | |
| PPOLG_COXA2 | GENOME POLYPROTEIN | COXSACKIEVIRUS A21 (STRAIN COE) | 9–43 | 562–596 | 664–698 | 1045–1100 | 1498–1546 | 1607–1648 | 1805–1839 | 1901–1946 |
| PPOLG_COXA9 | GENOME POLYPROTEIN | COXSACKIEVIRUS A9 (STRAIN GRIGGS) | 15–49 | 1040–1086 | 1895–1940 | | | | | |
| PPOLG_COXB1 | GENOME POLYPROTEIN | COXSACKIEVIRUS B1 | 15–49 | 1021–1067 | 1876–1921 | | | | | |
| PPOLG_COXB3 | GENOME POLYPROTEIN | COXSACKIEVIRUS B3 | 15–49 | 1024–1070 | 1879–1924 | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOLG_COXB4 | GENOME POLYPROTEIN | COXSACKIEVIRUS B4 | 15–49 | 642–681 | 1022–1068 | 1877–1922 | | | | |
| PPOLG_COXB5 | GENOME POLYPROTEIN | COXSACKIEVIRUS B5 | 15–49 | 1024–1070 | 1879–1924 | | | | | |
| PPOLG_CYVV | GENOME POLYPROTEIN | CLOVER YELLOW VEIN VIRUS | 120–154 | | | | | | | |
| PPOLG_DEN18 | GENOME POLYPROTEIN | DENGUE VIRUS TYPE 1 (STRAIN 836-1) | 74–108 | | | | | | | |
| PPOLG_DEN1A | GENOME POLYPROTEIN | DENGUE VIRUS TYPE 1 (STRAIN AHF 82-80) | 74–108 | | | | | | | |
| PPOLG_DEN1C | GENOME POLYPROTEIN | DENGUE VIRUS TYPE 1 (STRAIN CV1636/77) | 74–108 | | | | | | | |
| PPOLG_DEN1S | GENOME POLYPROTEIN | DENGUE VIRUS TYPE 1 (STRAIN SINGAPORE S275/90) | 74–108 | 832–873 | 960–994 | 1142–1179 | 1386–1420 | 1614–1648 | 2518–2554 | 2946–3016 |
| PPOLG_DEN1W | GENOME POLYPROTEIN | DENGUE VIRUS TYPE 1 (STRAIN WESTERN PACIFIC) | 74–108 | 833–874 | 961–995 | 1143–1180 | | | | |
| PPOLG_DEN21 | GENOME POLYPROTEIN | DENGUE VIRUS TYPE 2 (ISOLATE MALAYSIA M1) | 448–492 | | | | | | | |
| PPOLG_DEN22 | GENOME POLYPROTEIN | DENGUE VIRUS TYPE 2 (ISOLATE MALAYSIA M2) | 448–495 | | | | | | | |
| PPOLG_DEN26 | GENOME POLYPROTEIN | DENGUE VIRUS TYPE 2 (STRAIN 16681) | 74–108 | 728–777 | 961–995 | 1146–1180 | 1246–1280 | 1418–1452 | 1615–1649 | 2517–2551 |
| PPOLG_DEN27 | GENOME POLYPROTEIN | DENGUE VIRUS TYPE 2 (STRAIN 16681-PDK53) | 74–108 | 728–777 | 961–995 | 1146–1180 | 1246–1280 | 1418–1452 | 1615–1649 | 2485–2551 |
| PPOLG_DEN2D | GENOME POLYPROTEIN | DENGUE VIRUS TYPE 2 (STRAIN D2-04) | 728–777 | | | | | | | |
| PPOLG_DEN2H | GENOME POLYPROTEIN | DENGUE VIRUS TYPE 2 (STRAIN TH-36) | 497–546 | | | | | | | |
| PPOLG_DEN2J | GENOME POLYPROTEIN | DENGUE VIRUS TYPE 2 (STRAIN JAMAICA) | 74–108 | 728–777 | 961–995 | 1146–1180 | 1246–1280 | 1418–1452 | 1615–1649 | 2517–2551 |
| PPOLG_DEN2N | GENOME POLYPROTEIN | DENGUE VIRUS TYPE 2 (STRAIN NEW GUINEA C) | 213–247 | 398–432 | | | | | | |
| PPOLG_DEN2P | GENOME POLYPROTEIN | DENGUE VIRUS TYPE 2 (STRAIN PR159/S1) | 74–108 | 728–777 | 832–875 | 961–995 | 1146–1180 | 1246–1280 | 1418–1452 | 1615–1649 |
| PPOLG_DEN2T | GENOME POLYPROTEIN | DENGUE VIRUS TYPE 2 (STRAIN TONGA 1974) | 448–497 | 552–595 | 681–715 | 866–900 | 966–1000 | 1205–1239 | | |
| PPOLG_DEN2U | GENOME POLYPROTEIN | DENGUE VIRUS TYPE 2 (STRAIN PUO-218) | 614–663 | | | | | | | |
| PPOLG_DEN3 | GENOME POLYPROTEIN | DENGUE VIRUS TYPE 3 | 830–872 | 959–993 | 1385–1419 | 2224–2258 | 2480–2521 | 2704–2738 | 2940–2978 | 2980–3014 |
| PPOLG_DEN4 | GENOME POLYPROTEIN | DENGUE VIRUS TYPE 4 | 957–993 | 1380–1414 | 2514–2555 | 2701–2735 | 2941–2975 | 2977–3011 | | |
| PPOLG_EC11G | GENOME POLYPROTEIN | ECHOVIRUS 11 (STRAIN GREGORY) | 213–259 | 1079–1113 | | | | | | |
| PPOLG_EMCV | GENOME POLYPROTEIN | ENCEPHALOMYOCARDITIS VIRUS | 1074–1115 | 1472–1518 | 1522–1570 | 1665–1706 | 1789–1823 | | | |
| PPOLG_EMCVB | GENOME POLYPROTEIN | ENCEPHALOMYOCARDITIS VIRUS (STRAIN EMC-B NONDIABETO | 145–179 | 1076–1117 | 1474–1520 | 1524–1572 | 1667–1708 | | | |
| PPOLG_EMCVD | GENOME POLYPROTEIN | ENCEPHALOMYOCARDITIS VIRUS (STRAIN EMC-D-DIABETOGEN | 145–179 | 1076–1117 | 1474–1520 | 1524–1572 | 1667–1708 | | | |
| PPOLG_ENMG3 | GENOME POLYPROTEIN | MENGO ENCEPHALOMYOCARDITIS VIRUS (STRAIN 37A) | 145–179 | | | | | | | |
| PPOLG_ENMGO | GENOME POLYPROTEIN | MENGO ENCEPHALOMYOCARDITIS VIRUS | 78–112 | | | | | | | |
| PPOLG_FMDV1 | GENOME POLYPROTEIN | FOOT-AND-MOUTH DISEASE VIRUS (STRAIN A10-61) | 221–255 | 294–328 | 578–612 | 1103–1153 | 1493–1528 | 2165–2200 | | |
| PPOLG_FMDVA | GENOME POLYPROTEIN | FOOT-AND-MOUTH DISEASE VIRUS (STRAIN A12) | 220–254 | 293–327 | 577–611 | 1103–1164 | 1493–1528 | 2164–2199 | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOLG_FMDVO | GENOME POLYPROTEIN | FOOT-AND-MOUTH DISEASE VIRUS (STRAINS O1K AND O1BFS) | 221–255 | 1103–1153 | 1493–1528 | 2164–2199 | | | | |
| PPOLG_FMDVS | GENOME POLYPROTEIN | FOOT-AND-MOUTH DISEASE VIRUS (STRAIN C1-SANTA PAU [C-S | 87–128 | 693–728 | | | | | | |
| PPOLG_FMDVT | GENOME POLYPROTEIN | FOOT-AND-MOUTH DISEASE VIRUS (STRAIN C1) | 221–255 | 283–317 | 577–611 | | | | | |
| PPOLG_HCV1 | GENOME POLYPROTEIN | HEPATITIS C VIRUS (ISOLATE 1) | 364–398 | | | | | | | |
| PPOLG_HCVA | GENOME POLYPROTEIN | HOG CHOLERA VIRUS (STRAIN ALFORT) | 440–493 | 626–660 | 695–729 | 1033–1070 | 1190–1235 | 1307–1343 | 1779–1820 | 2136–2170 |
| | | | 2466–2500 | 2525–2559 | 2667–2708 | 3057–3098 | 3152–3193 | 3406–3440 | | |
| PPOLG_HCVB | GENOME POLYPROTEIN | HOG CHOLERA VIRUS (STRAIN BRESCIA) | 440–493 | 626–660 | 695–729 | 1033–1070 | 1173–1235 | 1779–1820 | 2136–2170 | 2388–2436 |
| PPOLG_HCVBK | | | 2466–2500 | 2525–2559 | 2667–2708 | 3057–3098 | 3152–3195 | 3406–3440 | 3521–3562 | |
| PPOLG_HCVE0 | GENOME POLYPROTEIN | HEPATITIS C VIRUS (ISOLATE BK) | 357–398 | 2328–2365 | | | | | | |
| PPOLG_HCVH | GENOME POLYPROTEIN | HEPATITIS C VIRUS (ISOLATE EC10) | 65–99 | | | | | | | |
| PPOLG_HCVH4 | GENOME POLYPROTEIN | HEPATITIS C VIRUS (ISOLATE H) | 364–398 | | | | | | | |
| PPOLG_HCVH7 | GENOME POLYPROTEIN | HEPATITIS C VIRUS (ISOLATE HCV-476) | 364–398 | | | | | | | |
| PPOLG_HCVH8 | GENOME POLYPROTEIN | HEPATITIS C VIRUS (ISOLATE HCT27) | 236–270 | | | | | | | |
| PPOLG_HCVHK | GENOME POLYPROTEIN | HEPATITIS C VIRUS (ISOLATE HCT18) | 248–282 | | | | | | | |
| PPOLG_HCVJ2 | GENOME POLYPROTEIN | HEPATITIS C VIRUS (ISOLATE HCV-KF) | 357–398 | | | | | | | |
| PPOLG_HCVJ5 | GENOME POLYPROTEIN | HEPATITIS C VIRUS (ISOLATE HC-J2) | 357–398 | | | | | | | |
| PPOLG_HCVJ6 | GENOME POLYPROTEIN | HEPATITIS C VIRUS (ISOLATE HC-J5) | 364–398 | | | | | | | |
| PPOLG_HCVJ7 | GENOME POLYPROTEIN | HEPATITIS C VIRUS (ISOLATE HC-J6) | 364–401 | 1716–1750 | 2082–2116 | | | | | |
| PPOLG_HCVJ8 | GENOME POLYPROTEIN | HEPATITIS C VIRUS (ISOLATE HC-J7) | 364–398 | | | | | | | |
| PPOLG_HCVJA | GENOME POLYPROTEIN | HEPATITIS C VIRUS (ISOLATE HC-J8) | 364–398 | 1716–1750 | 2082–2116 | 2468–2502 | 2538–2572 | | | |
| PPOLG_HCVJT | GENOME POLYPROTEIN | HEPATITIS C VIRUS (ISOLATE JAPANESE) | 357–405 | 2331–2365 | | | | | | |
| PPOLG_HCVTW | GENOME POLYPROTEIN | HEPATITIS C VIRUS (ISOLATE HC-JT) | 357–391 | 2331–2365 | | | | | | |
| PPOLG_HPAV2 | GENOME POLYPROTEIN | HEPATITIS C VIRUS (ISOLATE TAIWAN) | 357–398 | 2328–2365 | 2444–2503 | | | | | |
| PPOLG_HPAV4 | GENOME POLYPROTEIN | HEPATITIS A VIRUS (STRAIN 24A) | 2–43 | 101–135 | 203–237 | 870–904 | 1021–1055 | 1117–1151 | | |
| PPOLG_HPAV8 | GENOME POLYPROTEIN | HEPATITIS A VIRUS (STRAIN 43C) | 2–43 | 101–135 | 203–237 | 870–904 | 1021–1055 | 1117–1151 | | |
| PPOLG_HPAVC | GENOME POLYPROTEIN | HEPATITIS A VIRUS (STRAIN 18F) | 2–43 | 101–135 | 203–237 | 870–904 | 1021–1055 | 1117–1151 | | |
| PPOLG_HPAVG | GENOME POLYPROTEIN | HEPATITIS A VIRUS (STRAIN CR326) | 2–43 | 101–135 | 203–237 | | | | | |
| PPOLG_HPAVH | GENOME POLYPROTEIN | HEPATITIS A VIRUS (STRAIN GA76) | 80–114 | 182–216 | | | | | | |
| PPOLG_HPAVL | GENOME POLYPROTEIN | HEPATITIS A VIRUS (STRAIN HM-175) | 2–43 | 101–135 | 203–237 | 870–904 | 1021–1055 | 1103–1151 | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOLG_HPAVM | GENOME POLYPROTEIN | HEPATITIS A VIRUS (STRAIN LA) | 2–43 | 101–135 | 203–237 | 870–904 | 1021–1055 | 1103–1151 | | |
| PPOLG_HPAVS | GENOME POLYPROTEIN | HEPATITIS A VIRUS (STRAIN MBB) | 2–43 | 101–135 | 203–237 | 870–904 | 1021–1055 | 1103–1158 | | |
| PPOLG_HPAVT | GENOME POLYPROTEIN | SIMIAN HEPATITIS A VIRUS (STRAIN AGM-27) | 6–47 | 105–139 | 207–241 | 849–908 | 1025–1059 | 1115–1155 | 1158–1198 | |
| PPOLG_HRV14 | GENOME POLYPROTEIN | SIMIAN HEPATITIS A VIRUS (STRAIN CY-145) | 2–43 | 101–135 | 203–237 | | | | | |
| PPOLG_HRV1A | GENOME POLYPROTEIN | HUMAN RHINOVIRUS 14 (HRV-14) | 1020–1054 | 1393–1427 | 1479–1513 | 1877–1920 | | | | |
| PPOLG_HRV1B | GENOME POLYPROTEIN | HUMAN RHINOVIRUS 1A (HRV-1A) | 362–396 | | | | | | | |
| PPOLG_HRV2 | GENOME POLYPROTEIN | HUMAN RHINOVIRUS 1B (HRV-1B) | 387–421 | 863–904 | 1133–1168 | | | | | |
| PPOLG_HRV89 | GENOME POLYPROTEIN | HUMAN RHINOVIRUS 2 (HRV-2) | 856–897 | 1126–1169 | 1552–1593 | | | | | |
| PPOLG_HUEV7 | GENOME POLYPROTEIN | HUMAN RHINOVIRUS 89 (HRV-89) | 1566–1607 | | | | | | | |
| PPOLG_IBDVO | GENOME POLYPROTEIN | HUMAN ENTEROVIRUS 70 (STRAIN J670/71) | 359–397 | 876–917 | 1032–1088 | 1403–1441 | 1896–1934 | | | |
| PPOLG_JAEV1 | STRUCTURAL POLYPROTEIN | AVIAN INFECTIOUS BURSAL DISEASE VIRUS (STRAIN OH) | 134–168 | 250–291 | 475–524 | | | | | |
| PPOLG_JAEV5 | GENOME POLYPROTEIN | JAPANESE ENCEPHALITIS VIRUS (STRAIN SA-14) | 74–122 | 211–256 | 539–576 | 980–1014 | 1409–1450 | 2463–2497 | 2739–2777 | 2782–2823 |
| | | | 3322–3359 | 3387–3428 | | | | | | |
| PPOLG_JAEVJ | GENOME POLYPROTEIN | JAPANESE ENCEPHALITIS VIRUS (STRAIN SA(V)) | 74–122 | 211–256 | 539–576 | 980–1014 | 1409–1450 | 2463–2497 | 2739–2777 | 2782–2823 |
| | | | 3322–3359 | 3387–3428 | | | | | | |
| PPOLG_JAEVN | GENOME POLYPROTEIN | JAPANESE ENCEPHALITIS VIRUS (STRAIN JAOARS982) | 74–128 | 211–256 | 539–576 | 980–1014 | 1409–1450 | 2463–2497 | 2739–2777 | 2782–2823 |
| | | | 3322–3359 | 3387–3428 | | | | | | |
| PPOLG_KUNJM | GENOME POLYPROTEIN | JAPANESE ENCEPHALITIS VIRUS (STRAIN NAKAYAMA) | 7–48 | 138–183 | 467–504 | 908–942 | 1337–1378 | | | |
| PPOLG_LANVT | GENOME POLYPROTEIN | KUNJIN VIRUS (STRAIN MRM61C) | 74–108 | 207–251 | 851–885 | 2464–2498 | 2528–2579 | 2740–2778 | 3325–3359 | 3389–3423 |
| PPOLG_LANVY | GENOME POLYPROTEIN | LANGAT VIRUS (STRAIN TP21) | 68–102 | 431–465 | 962–996 | 1431–1472 | 1932–1966 | 2536–2591 | 2967–3001 | 3003–3037 |
| | | | 3102–3145 | | | | | | | |
| PPOLG_LIV | GENOME POLYPROTEIN | LANGAT VIRUS (STRAIN YELANTSEV) | 68–102 | 431–465 | | | | | | |
| PPOLG_LIVSB | GENOME POLYPROTEIN | LOUPING ILL VIRUS (LI) | 68–123 | 231–272 | 431–465 | | | | | |
| PPOLG_MCFA | GENOME POLYPROTEIN | LOUPING ILL VIRUS (STRAIN SB 526) | 151–185 | | | | | | | |
| PPOLG_MVEV | GENOME POLYPROTEIN | MOSQUITO CELL FUSING AGENT (CFA FLAVIVIRUS) | 80–114 | 908–942 | 2049–2087 | 2630–2689 | 3036–3095 | 3290–3341 | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOLG_OMV | GENOME POLYPROTEIN | MURRAY VALLEY ENCEPHALITIS VIRUS | 67–115 | 209–253 | 853–887 | 979–1013 | 1408–1449 | | | |
| PPOLG_PEMVC | GENOME POLYPROTEIN | ORNITHOGALUM MOSAIC VIRUS | 418–515 | 946–984 | 1072–1106 | | | | | |
| PPOLG_POL1M | GENOME POLYPROTEIN | PEPPER MOTTLE VIRUS (CALIFORNIA ISOLATE) | 55–100 | 207–248 | 377–411 | 704–738 | 827–862 | 877–947 | 1021–1055 | 1167–1201 |
| | | | 1488–1529 | 1787–1821 | 1948–1982 | 2202–2236 | 2258–2310 | 2805–2839 | 3003–3037 | |
| PPOLG_POL1S | GENOME POLYPROTEIN | POLIOVIRUS TYPE 1 (STRAIN MAHONEY) | 9–43 | 1046–1101 | 1414–1448 | 1500–1548 | 1806–1840 | 1902–1947 | | |
| PPOLG_POL2L | GENOME POLYPROTEIN | POLIOVIRUS TYPE 1 (STRAIN SABIN) | 9–43 | 899–933 | 1047–1102 | 1415–1449 | 1501–1549 | 1610–1651 | 1808–1842 | 1904–1949 |
| PPOLG_POL2W | GENOME POLYPROTEIN | POLIOVIRUS TYPE 2 (STRAIN LANSING) | 9–43 | 897–831 | 1045–1100 | 1413–1447 | 1502–1547 | 1608–1649 | 1806–1840 | 1902–1947 |
| PPOLG_POL32 | GENOME POLYPROTEIN | POLIOVIRUS TYPE 2 (STRAIN W-2) | 9–43 | 897–831 | 1045–1100 | 1413–1447 | 1502–1547 | 1608–1649 | 1806–1840 | 1902–1947 |
| PPOLG_POL3L | GENOME POLYPROTEIN | POLIOVIRUS TYPE 3 (STRAIN 23127) | 9–43 | 896–930 | 1044–1098 | 1412–1446 | 1498–1546 | 1607–1648 | 1805–1839 | 1901–1946 |
| PPOLG_PPVD | GENOME POLYPROTEIN | POLIOVIRUS TYPE 3 (STRAINS P3/LEON/37 AND P3/LEON 12A[1]B) | 9–43 | 896–930 | 1044–1099 | 1412–1446 | 1498–1546 | 1607–1648 | 1805–1839 | 1901–1946 |
| PPOLG_PPVEA | GENOME POLYPROTEIN | PLUM POX POTYVIRUS (STRAIN D) | 164–208 | 441–503 | 728–769 | 815–867 | 921–955 | 1741–1782 | | |
| PPOLG_PPVNA | GENOME POLYPROTEIN | PLUM POX POTYVIRUS (STRAIN EL AMAR) | 116–157 | 784–818 | 1146–1197 | | | | | |
| PPOLG_PPVRA | GENOME POLYPROTEIN | PLUM POX POTYVIRUS (ISOLATE NAT) | 164–208 | 403–437 | 440–502 | 727–768 | 814–873 | 920–954 | 1740–1781 | |
| PPOLG_PRSVH | GENOME POLYPROTEIN | PLUM POX POTYVIRUS (STRAIN RANKOVIC) | 164–208 | 403–437 | 440–502 | 727–768 | 814–866 | 920–954 | 1740–1781 | |
| PPOLG_PRSVP | GENOME POLYPROTEIN | PAPAYA RINGSPOT VIRUS (STRAIN P/MUTANT HA) | 68–102 | 434–468 | | | | | | |
| PPOLG_PRSVW | GENOME POLYPROTEIN | PAPAYA RINGSPOT VIRUS (STRAIN P/MUTANT HA 5-1) | 325–359 | | | | | | | |
| PPOLG_PSBMV | GENOME POLYPROTEIN | PAPAYA RINGSPOT VIRUS (STRAIN W) | 325–359 | | | | | | | |
| PPOLG_PVYC | GENOME POLYPROTEIN | PEA SEED-BORNE MOSAIC (STRAIN DPD1) | 253–315 | 355–389 | 529–589 | 935–976 | 984–1018 | 1080–1177 | 1588–1627 | 1808–1860 |
| | | | 1971–2015 | 2379–2413 | 2712–2746 | 2870–2907 | | | | |
| PPOLG_PVYHU | GENOME POLYPROTEIN | POTATO VIRUS Y (STRAIN C) | 131–196 | 701–735 | 802–856 | | | | | |
| PPOLG_PVYN | GENOME POLYPROTEIN | POTATO VIRUS Y (STRAIN HUNGARIAN) | 144–181 | 701–735 | 802–863 | 901–949 | 1401–1441 | 1492–1526 | 1728–1772 | 1777–1818 |
| | | | 2272–2306 | | | | | | | |
| PPOLG_PVYO | GENOME POLYPROTEIN | POTATO VIRUS Y (STRAIN N) | 140–196 | 211–245 | 701–735 | 802–863 | 1401–1441 | 1492–1526 | 1728–1772 | 1777–1818 |
| | | | 1929–1970 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOLG_PWVSE | GENOME POLYPROTEIN | POTATO VIRUS Y (STRAIN O) | 140–196 | 211–245 | 701–735 | 802–856 | | | | |
| PPOLG_PWVTB | GENOME POLYPROTEIN | PASSIONFRUIT WOODINESS VIRUS (STRAIN SEVERE) | 203–237 | | | | | | | |
| PPOLG_PYFV1 | GENOME POLYPROTEIN | PASSIONFRUIT WOODINESS VIRUS (STRAIN TIP BRIGHT) | 203–237 | | | | | | | |
| PPOLG_STEVM | GENOME POLYPROTEIN | PARSNIP YELLOW FLECK VIRUS (ISOLATE P-121) | 194–228 | 1111–1172 | 1379–1413 | 1858–1899 | 1950–1991 | 2703–2737 | | |
| PPOLG_SVDVH | GENOME POLYPROTEIN | ST. LOUIS ENCEPHALITIS VIRUS (STRAIN MS1-7) | 106–143 | 673–707 | 739–773 | 975–1009 | 1404–1438 | | | |
| PPOLG_SVDVU | GENOME POLYPROTEIN | SWINE VESICULAR DISEASE VIRUS (STRAIN H/3 '76) | 15–49 | 1024–1070 | 1779–1813 | 1890–1924 | | | | |
| PPOLG_TBEVS | GENOME POLYPROTEIN | SWINE VESICULAR DISEASE VIRUS (STRAIN UKG/27/72) | 15–49 | 1024–1070 | 1890–1924 | | | | | |
| PPOLG_TBEVW | GENOME POLYPROTEIN | TICK-BORNE ENCEPHALITIS VIRUS (STRAIN SOFJIN) | 68–140 | 231–272 | 431–465 | 1158–1192 | 1431–1472 | 1929–1966 | 2182–2216 | 2535–2590 |
| | | | 2965–2999 | 3051–3092 | 3100–3143 | | | | | |
| PPOLG_TEV | GENOME POLYPROTEIN | TICK-BORNE ENCEPHALITIS VIRUS (WESTERN SUBTYPE) | 68–140 | 231–272 | 431–465 | 1158–1192 | 1431–1492 | 1932–1966 | 2536–2591 | 2967–3001 |
| | | | 3003–3037 | 3053–3094 | 3102–3145 | | | | | |
| PPOLG_TMEVB | THEILER'S MURINE ENCEPHALOMYELITIS VIRUS (S | TOBACCO ETCH VIRUS | 73–124 | 166–222 | 540–584 | 720–782 | 828–925 | 1148–1192 | 1416–1460 | 1494–1535 |
| | | | 1668–1702 | 1747–1781 | 1792–1826 | 2395–2434 | 2787–2821 | | | |
| PPOLG_TMEVD | GENOME POLYPROTEIN | THEILER'S MURINE ENCEPHALOMYELITIS VIRUS (STRAIN BEAN | 1306–1340 | 1483–1518 | 1601–1635 | | | | | |
| PPOLG_TMEVG | GENOME POLYPROTEIN | THEILER'S MURINE ENCEPHALOMYELITIS VIRUS (STRAIN DA) | 1304–1338 | 1481–1516 | 1599–1663 | | | | | |
| PPOLG_TUMV | GENOME POLYPROTEIN | THEILER'S MURINE ENCEPHALOMYELITIS VIRUS (STRAIN GDVII) | 1306–1340 | 1483–1518 | 1601–1635 | | | | | |
| PPOLG_TVMV | GENOME POLYPROTEIN | TURNIP MOSAIC VIRUS | 216–259 | 314–362 | 494–528 | 768–839 | 1443–1477 | | | |
| PPOLG_WMV2 | GENOME POLYPROTEIN | TOBACCO VEIN MOTTLING VIRUS | 34–68 | 408–449 | 667–704 | 761–813 | 851–885 | 969–1017 | 1031–1072 | 1643–1677 |
| | | | 1686–1725 | 2316–2374 | 2701–2749 | 2814–2848 | | | | |
| PPOLG_WNV | GENOME POLYPROTEIN | WATERMELON MOSAIC VIRUS II | 68–105 | 202–236 | | | | | | |
| PPOLG_YEFV1 | GENOME POLYPROTEIN | WEST NILE VIRUS | 74–108 | 207–251 | 847–881 | 973–1007 | 1413–1447 | 2461–2495 | 2525–2576 | 2737–2775 |
| | | | 3320–3357 | 3385–3426 | | | | | | |
| PPOLG_YEFV2 | GENOME POLYPROTEIN | YELLOW FEVER VIRUS (STRAIN 17D) | 418–452 | 525–563 | 728–768 | 1388–1444 | 2231–2276 | 2477–2565 | 2958–2996 | 3097–3143 |
| PPOLG_YEFV8 | GENOME POLYPROTEIN | YELLOW FEVER VIRUS (STRAIN PASTEUR 17D-204) | 418–452 | 525–563 | 728–768 | 1388–1444 | 2231–2276 | 2477–2565 | 2958–2996 | 3097–3143 |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOLH_POL1M | GENOME POLYPROTEIN | YELLOW FEVER VIRUS (STRAIN 1899/81) | 75–116 | 418–452 | 525–563 | 728–768 | | | | |
| PPOLH_EEVVT | GENOME POLYPROTEIN | POLIOVIRUS TYPE 1 (STRAIN MAHONEY) | 9–43 | 1047–1102 | 1415–1449 | 1501–1549 | 1610–1651 | 1808–1842 | 1904–1949 | |
| PPOLN_FCVC6 | NONSTRUCTURAL POLYPROTEIN | VENEZUELAN EQUINE ENCEPHALITIS VIRUS (STRAIN TRINIDAD | 345–382 | 898–932 | 1945–1979 | | | | | |
| PPOLN_FCVF9 | NON-STRUCTURAL POLYPROTEIN | FELINE CALICIVIRUS (STRAIN CFI/68 FIV) | 510–544 | 369–410 | 986–1020 | 1023–1061 | | | | |
| PPOLN_HEVBU | NON-STRUCTURAL POLYPROTEIN | FELINE CALICIVIRUS (STRAIN F9) | 4–45 | | | | | | | |
| PPOLN_HEVME | NON-STRUCTURAL POLYPROTEIN | HEPATITIS E VIRUS (STRAIN BURMA) | 338–379 | 1139–1177 | | | | | | |
| PPOLN_HEVMY | NON-STRUCTURAL POLYPROTEIN | HEPATITIS E VIRUS (STRAIN MEXICO) | 338–379 | 1139–1184 | | | | | | |
| PPOLN_HEVPA | NON-STRUCTURAL POLYPROTEIN | HEPATITIS E VIRUS (STRAIN MYANMAR) | 338–379 | | | | | | | |
| PPOLN_MIDDV | NON-STRUCTURAL POLYPROTEIN | HEPATITIS E VIRUS (STRAIN PAKISTAN) | 337–378 | 1138–1176 | | | | | | |
| PPOLN_ONNVG | NONSTRUCTURAL POLYPROTEIN | MIDDELBURG VIRUS | 922–977 | 1942–1986 | 2444–2502 | | | | | |
| PPOLN_RHDV | NONSTRUCTURAL POLYPROTEIN | O'NYONG-NYONG VIRUS (STRAIN GULU) | 899–933 | 306–347 | 409–457 | | | | | |
| PPOLN_RRVN | NON-STRUCTURAL POLYPROTEIN | RABBIT HEMORRHAGIC DISEASE VIRUS | 188–234 | 1928–1962 | 2414–2467 | 1657–1716 | | | | |
| PPOLN_RRVT | NONSTRUCTURAL POLYPROTEIN | ROSS RIVER VIRUS (STRAIN NB5092) | 895–929 | 1083–1136 | | | | | | |
| PPOLN_RUBVT | NONSTRUCTURAL POLYPROTEIN | ROSS RIVER VIRUS (STRAIN T48) | 597–631 | 1551–1585 | 1730–1767 | 1862–1896 | | | | |
| PPOLN_SFV | NONSTRUCTURAL POLYPROTEIN | RUBELLA VIRUS (STRAIN THERIEN) | 1506–1540 | 2358–2392 | | | | | | |
| PPOLN_SINDO | NONSTRUCTURAL POLYPROTEIN | SEMLIKI FOREST VIRUS | 1094–1128 | 1491–1525 | 1961–1996 | 2444–2478 | | | | |
| PPOLN_SINDV | NONSTRUCTURAL POLYPROTEIN | SINDBIS VIRUS (SUBTYPE OCKELBO/STRAIN EDSBYN 82-5) | 919–971 | 1959–1994 | 2442–2476 | | | | | |
| PPOLN_EMPV | NONSTRUCTURAL POLYPROTEIN | SINDBIS VIRUS (STRAIN HRSP) | 1491–1525 | 1127–1161 | | | | | | |
| PPOLR_EEEV | RNA REPLICASE POLYPROTEIN | EGGPLANT MOSAIC VIRUS | 899–933 | | | | | | | |
| PPOLS_EEEV3 | STRUCTURAL POLYPROTEIN | EASTERN EQUINE ENCEPHALITIS VIRUS | 372–406 | 914–951 | | | | | | |
| PPOLS_EEEV8 | STRUCTURAL POLYPROTEIN | EASTERN EQUINE ENCEPHALITIS VIRUS (STRAIN VA33[TEN BRO | 373–407 | 915–952 | | | | | | |
| PPOLS_EEVVT | STRUCTURAL POLYPROTEIN | VENEZUELAN EQUINE ENCEPHALITIS VIRUS (STRAIN TC-83) | 1216–1250 | | | | | | | |
| PPOLS_IBDV5 | STRUCTURAL POLYPROTEIN | VENEZUELAN EQUINE ENCEPHALITIS VIRUS (STRAIN TRINIDAD | 1216–1250 | | | | | | | |
| PPOLS_IBDVA | STRUCTURAL POLYPROTEIN | AVIAN INFECTIOUS BURSAL DISEASE VIRUS (STRAIN 52/70) | 134–168 | 231–286 | 470–523 | | | | | |
| PPOLS_IBDVC | STRUCTURAL POLYPROTEIN | AVIAN INFECTIOUS BURSAL DISEASE VIRUS (STRAIN AUSTRALI | 134–168 | 231–286 | 470–523 | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOLS_IBDVE | STRUCTURAL POLYPROTEIN | AVIAN INFECTIOUS BURSAL DISEASE VIRUS (STRAIN CU-1) | 134–168 | 231–286 | 470–523 | | | | | |
| PPOLS_IBDVP | NONSTRUCTURAL PROTEIN VP4 | AVIAN INFECTIOUS BURSAL DISEASE VIRUS (STRAIN E) | 134–168 | 231–286 | 304–340 | | | | | |
| PPOLS_IBDVS | STRUCTURAL POLYPROTEIN | AVIAN INFECTIOUS BURSAL DISEASE VIRUS (STRAIN PBG-98) | 115–149 | 212–267 | 451–504 | | | | | |
| PPOLS_IPNVJ | STRUCTURAL POLYPROTEIN | AVIAN INFECTIOUS BURSAL DISEASE VIRUS (STRAIN STC) | 134–168 | 249–283 | 470–523 | | | | | |
| PPOLS_IPNVN | STRUCTURAL POLYPROTEIN | INFECTIOUS PANCREATIC NECROSIS VIRUS (SEROTYPE JASPER) | 69–103 | 723–785 | | | | | | |
| PPOLS_ONNVG | STRUCTURAL POLYPROTEIN | INFECTIOUS PANCREATIC NECROSIS VIRUS (STRAIN N1) | 716–786 | | | | | | | |
| PPOLS_RRV2 | STRUCTURAL POLYPROTEIN | O'NYONG-NYONG VIRUS (STRAIN GULU) | 1204–1238 | | | | | | | |
| PPOLS_RRVN | STRUCTURAL POLYPROTEIN | ROSS RIVER VIRUS (STRAIN 213970) | 35–69 | | | | | | | |
| PPOLS_RRVT | STRUCTURAL POLYPROTEIN | ROSS RIVER VIRUS (STRAIN NB5092) | 369–403 | 939–973 | | | | | | |
| PPOLS_RUBVH | STRUCTURAL POLYPROTEIN | ROSS RIVER VIRUS (STRAIN T48) | 939–973 | | | | | | | |
| PPOLS_RUBVR | STRUCTURAL POLYPROTEIN | RUBELLA VIRUS (VACCINE STRAIN HPV77) | 999–1036 | | | | | | | |
| PPOLS_RUBVT | STRUCTURAL POLYPROTEIN | RUBELLA VIRUS (VACCINE STRAIN RA27/3) | 999–1036 | | | | | | | |
| PPOLS_SINDO | STRUCTURAL POLYPROTEIN | RUBELLA VIRUS (STRAIN THERIEN) | 999–1036 | | | | | | | |
| PPOLS_SINDV | STRUCTURAL POLYPROTEIN | SINDBIS VIRUS (SUBTYPE OCKELBO/STRAIN EDSBYN 82-5) | 362–396 | | | | | | | |
| PPOLS_SINDW | STRUCTURAL POLYPROTEIN | SINDBIS VIRUS (STRAINS HRSP AND HRLP) | 362–396 | | | | | | | |
| PPOLS_WEEV | STRUCTURAL POLYPROTEIN | SINDBIS VIRUS (WILD TYPE SB DERIVED FROM STRAIN AR339) | 34–68 | | | | | | | |
| PPOL_BAEVM | STRUCTURAL POLYPROTEIN | WESTERN EQUINE ENCEPHALITIS VIRUS | 913–947 | | | | | | | |
| PPOL_BLVAU | POL POLYPROTEIN | BABOON ENDOGENOUS VIRUS (STRAIN M7) | 42–80 | 676–743 | 794–832 | 1001–1042 | | | | |
| PPOL_BLVJ | POL POLYPROTEIN | BOVINE LEUKEMIA VIRUS (AUSTRALIAN ISOLATE) | 625–673 | | | | | | | |
| PPOL_CAEVC | POL POLYPROTEIN | BOVINE LEUKEMIA VIRUS (JAPANESE ISOLATE BLV-1) | 625–673 | | | | | | | |
| PPOL_CAMVD | POL POLYPROTEIN | CAPRINE ARTHRITIS ENCEPHALITIS VIRUS (STRAIN CORK) | 879–934 | | | | | | | |
| PPOL_COYMV | ENZYMATIC POLYPROTEIN | CAULIFLOWER MOSAIC VIRUS (STRAIN D/H) | 177–211 | | | | | | | |
| PPOL_EIAV9 | PUTATIVE POLYPROTEIN | COMMELINA YELLOW MOTTLE VIRUS | 87–121 | 333–367 | 447–498 | 838–876 | 896–930 | 1310–1351 | | |
| PPOL_EIAVC | POL POLYPROTEIN | EQUINE INFECTIOUS ANEMIA VIRUS (CLONE 1369) | 513–566 | 1022–1056 | | | | | | |
| PPOL_EIAVY | POL POLYPROTEIN | EQUINE INFECTIOUS ANEMIA VIRUS (CLONE CL22) | 513–566 | 1022–1056 | | | | | | |
| PPOL_FENV1 | POL POLYPROTEIN | EQUINE INFECTIOUS ANEMIA VIRUS (ISOLATE WYOMING) | 512–565 | 1021–1055 | | | | | | |
| PPOL_FIVPE | POL POLYPROTEIN | FELINE ENDOGENOUS VIRUS ECE1 | 533–600 | 623–659 | 858–899 | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOL_FIVSD | POL POLYPROTEIN | FELINE IMMUNODEFICIENCY VIRUS (ISOLATE PETALUMA) | 429–473 | 606–663 | | | | | | |
| PPOL_FIVT2 | POL POLYPROTEIN | FELINE IMMUNODEFICIENCY VIRUS (ISOLATE SAN DIEGO) | 428–473 | 606–642 | | | | | | |
| PPOL_FMVD | POL POLYPROTEIN | FELINE IMMUNODEFICIENCY VIRUS (ISOLATE TM2) | 428–472 | 595–662 | | | | | | |
| PPOL_FOAMV | ENZYMATIC POLYPROTEIN | FIGWORT MOSAIC VIRUS (STRAIN DXS) | 403–437 | | | | | | | |
| PPOL_GALV | POL POLYPROTEIN | HUMAN SPUMARETROVIRUS (FOAMY VIRUS) | 140–174 | 217–256 | 285–326 | | | | | |
| PPOL_HTL1A | POL POLYPROTEIN | GIBBON APE LEUKEMIA VIRUS | 528–562 | 673–740 | | | | | | |
| PPOL_HTL1C | POL POLYPROTEIN | HUMAN T-CELL LEUKEMIA VIRUS TYPE I (STRAIN ATK) | 670–711 | | | | | | | |
| PPOL_HV1A2 | POL POLYPROTEIN | HUMAN T-CELL LEUKEMIA VIRUS TYPE I (CARIBBEAN ISOLATE) | 670–711 | | | | | | | |
| PPOL_HV1B1 | POL POLYPROTEIN | HUMAN IMMUNODEFICIENCY VIRUS TYPE 1 (ARV2/SF2 ISOLATE) | 501–537 | 606–664 | | | | | | |
| PPOL_HV1B5 | POL POLYPROTEIN | HUMAN IMMUNODEFICIENCY VIRUS TYPE 1 (BH10 ISOLATE) | 513–549 | 639–676 | | | | | | |
| PPOL_HV1BR | POL POLYPROTEIN | HUMAN IMMUNODEFICIENCY VIRUS TYPE 1 (BH5 ISOLATE) | 513–549 | 618–676 | | | | | | |
| PPOL_HV1EL | POL POLYPROTEIN | HUMAN IMMUNODEFICIENCY VIRUS TYPE 1 (BRU ISOLATE) | 513–549 | 618–676 | | | | | | |
| PPOL_HV1H2 | POL POLYPROTEIN | HUMAN IMMUNODEFICIENCY VIRUS TYPE 1 (ELI ISOLATE) | 500–536 | 626–663 | | | | | | |
| PPOL_HV1JR | POL POLYPROTEIN | HUMAN IMMUNODEFICIENCY VIRUS TYPE 1 (HXB2 ISOLATE) | 501–537 | 606–664 | | | | | | |
| PPOL_HV1MA | POL POLYPROTEIN | HUMAN IMMUNODEFICIENCY VIRUS TYPE 1 (JRCSF ISOLATE) | 505–541 | 610–668 | | | | | | |
| PPOL_HV1MN | POL POLYPROTEIN | HUMAN IMMUNODEFICIENCY VIRUS TYPE 1 (MAL ISOLATE) | 476–536 | 601–663 | | | | | | |
| PPOL_HV1N5 | POL POLYPROTEIN | HUMAN IMMUNODEFICIENCY VIRUS TYPE 1 (MN ISOLATE) | 504–540 | 609–667 | | | | | | |
| PPOL_HV1ND | POL POLYPROTEIN | HUMAN IMMUNODEFICIENCY VIRUS TYPE 1 (NEW YORK-5 ISOL | 501–537 | 627–664 | | | | | | |
| PPOL_HV1OY | POL POLYPROTEIN | HUMAN IMMUNODEFICIENCY VIRUS TYPE 1 (NDK ISOLATE) | 500–536 | 626–663 | | | | | | |
| PPOL_HV1PV | POL POLYPROTEIN | HUMAN IMMUNODEFICIENCY VIRUS TYPE 1 (OYI ISOLATE) | 501–537 | 606–664 | | | | | | |
| PPOL_HV1RH | POL POLYPROTEIN | HUMAN IMMUNODEFICIENCY VIRUS TYPE 1 (PV22 ISOLATE) | 513–549 | 693–676 | | | | | | |
| PPOL_HV1U4 | POL POLYPROTEIN | HUMAN IMMUNODEFICIENCY VIRUS TYPE 1 (RF/HAT ISOLATE) | 500–536 | 605–663 | | | | | | |
| PPOL_HV1Z2 | POL POLYPROTEIN | HUMAN IMMUNODEFICIENCY VIRUS TYPE 1 (STRAIN UGANDAN | 500–536 | 601–663 | | | | | | |
| PPOL_HV2BE | POL POLYPROTEIN | HUMAN IMMUNODEFICIENCY VIRUS TYPE 1 (Z2/CDC-Z34 ISOLA | 500–536 | 626–663 | | | | | | |
| PPOL_HV2CA | POL POLYPROTEIN | HUMAN IMMUNODEFICIENCY VIRUS TYPE 2 (ISOLATE BEN) | 49–83 | 484–582 | 653–687 | 817–851 | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOL_HV2D1 | POL POLYPROTEIN | HUMAN IMMUNODEFICIENCY VIRUS TYPE 2 (ISOLATE CAM2) | 356–390 | 464–562 | 632–666 | | | | | |
| PPOL_HV2D2 | POL POLYPROTEIN | HUMAN IMMUNODEFICIENCY VIRUS TYPE 2 (ISOLATE D194) | 502–600 | 671–705 | | | | | | |
| PPOL_HV2G1 | POL POLYPROTEIN | HUMAN IMMUNODEFICIENCY VIRUS TYPE 2 (ISOLATE D205,7) | 376–410 | 484–526 | 529–577 | 653–687 | | | | |
| PPOL_HV2NZ | POL POLYPROTEIN | HUMAN IMMUNODEFICIENCY VIRUS TYPE 2 (ISOLATE GHANA-1) | 464–562 | 633–667 | | | | | | |
| PPOL_HV2RO | POL POLYPROTEIN | HUMAN IMMUNODEFICIENCY VIRUS TYPE 2 (ISOLATE NIH-Z) | 44–78 | 356–390 | 464–529 | 633–667 | | | | |
| PPOL_HV2SB | POL POLYPROTEIN | HUMAN IMMUNODEFICIENCY VIRUS TYPE 2 (ISOLATE ROD) | 357–391 | 465–563 | 634–668 | | | | | |
| PPOL_HV2ST | POL POLYPROTEIN | HUMAN IMMUNODEFICIENCY VIRUS TYPE 2 (ISOLATE SBL/ISY) | 46–80 | 473–562 | 633–667 | | | | | |
| PPOL_IPHA | POL POLYPROTEIN | HUMAN IMMUNODEFICIENCY VIRUS TYPE 2 (ISOLATE ST) | 484–518 | 522–577 | 653–687 | | | | | |
| PPOL_ISRV | PUTATIVE POL POLYPROTEIN | HAMSTER INTRACISTERNAL A-PARTICLE | 462–503 | | | | | | | |
| PPOL_MLVAK | POL POLYPROTEIN | SHEEP PULMONARY ADENOMATOSIS VIRUS | 190–231 | | | | | | | |
| PPOL_MLVAV | POL POLYPROTEIN | AKR MURINE LEUKEMIA VIRUS | 325–392 | | | | | | | |
| PPOL_MLVF5 | POL POLYPROTEIN | AKV MURINE LEUKEMIA VIRUS | 677–744 | | | | | | | |
| PPOL_MLVFF | POL POLYPROTEIN | FRIEND MURINE LEUKEMIA VIRUS (ISOLATE 57) | 682–749 | | | | | | | |
| PPOL_MLVFP | POL POLYPROTEIN | FRIEND MURINE LEUKEMIA VIRUS (ISOLATE FB29) | 682–749 | | | | | | | |
| PPOL_MLVMO | POL POLYPROTEIN | FRIEND MURINE LEUKEMIA VIRUS (ISOLATE PVC-211) | 682–749 | | | | | | | |
| PPOL_MLVRD | POL POLYPROTEIN | MOLONEY MURINE LEUKEMIA VIRUS | 677–744 | | | | | | | |
| PPOL_MLVRK | POL POLYPROTEIN | RADIATION MURINE LEUKEMIA VIRUS | 677–744 | | | | | | | |
| PPOL_MPMV | POL POLYPROTEIN | RADIATION MURINE LEUKEMIA VIRUS (STRAIN KAPLAN) | 62–129 | | | | | | | |
| PPOL_OMVVS | POL POLYPROTEIN | SIMIAN MASON-PFIZER VIRUS | 470–504 | 578–613 | | | | | | |
| PPOL_RSVP | POL POLYPROTEIN | OVINE LENTIVIRUS (STRAIN SA-OMVV) | 470–505 | 855–910 | | | | | | |
| PPOL_RTBV | POL POLYPROTEIN | ROUS SARCOMA VIRUS (STRAIN PRAGUE C) | 646–684 | | | | | | | |
| PPOL_RTBVP | POLYPROTEIN | RICE TUNGRO BACILLIFORM VIRUS | 7–44 | 59–96 | 101–135 | 176–236 | 325–362 | 433–474 | 1005–1039 | 1405–1439 |
| PPOL_SFV1 | POLYPROTEIN | RICE TUNGRO BACILLIFORM VIRUS (ISOLATE PHILIPPINES) | 7–44 | 59–96 | 101–135 | 176–236 | 325–362 | 433–474 | 1005–1039 | 1405–1439 |
| PPOL_SFV3L | POL POLYPROTEIN | SIMIAN FOAMY VIRUS (TYPE 1) | 349–383 | 427–464 | 494–535 | | | | | |
| PPOL_SIVA1 | POL POLYPROTEIN | SIMIAN FOAMY VIRUS (TYPE 3/STRAIN LK3) | 124–165 | 429–467 | 496–530 | | | | | |
| PPOL_SIVA2 | POL POLYPROTEIN | SIMIAN IMMUNODEFICIENCY VIRUS (AGM155 ISOLATE) | 351–385 | 637–678 | 737–771 | 938–979 | | | | |
| PPOL_SIVAG | POL POLYPROTEIN | SIMIAN IMMUNODEFICIENCY VIRUS (AGM266 ISOLATE) | 45–86 | | | | | | | |
| PPOL_SIVAI | POL POLYPROTEIN | SIMIAN IMMUNODEFICIENCY VIRUS (AGM3 ISOLATE) | 477–516 | 642–683 | 742–783 | 942–983 | 1020–1054 | | | |
| PPOL_SIVAT | POL POLYPROTEIN | SIMIAN IMMUNODEFICIENCY VIRUS (ISOLATE AGM/CLONE GR1) | 175–209 | 476–515 | 641–700 | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPOL_SIVCZ | POL POLYPROTEIN | SIMIAN IMMUNODEFICIENCY VIRUS (TYO-1 ISOLATE) | 657–698 | 757–798 | | | | | | |
| PPOL_SIVGB | POL POLYPROTEIN | CHIMPANZEE IMMUNODEFICIENCY VIRUS (S1V(CPZ)) | 527–561 | 626–688 | | | | | | |
| PPOL_SIVM1 | POL POLYPROTEIN | SIMIAN IMMUNODEFICIENCY VIRUS (ISOLATE GB1) | 9–57 | 446–483 | 629–673 | 793–827 | 912–946 | | | |
| PPOL_SIVMK | POL POLYPROTEIN | SIMIAN IMMUNODEFICIENCY VIRUS (MM142-83 ISOLATE) | 485–519 | 654–688 | | | | | | |
| PPOL_SIVS4 | POL POLYPROTEIN | SIMIAN IMMUNODEFICIENCY VIRUS (K6W ISOLATE) | 485–519 | 654–688 | | | | | | |
| PPOL_SIVSP | POL POLYPROTEIN | SIMIAN IMMUNODEFICIENCY VIRUS (F236/SMH4 ISOLATE) | 448–482 | 617–651 | | | | | | |
| PPOL_SOCMV | POL POLYPROTEIN | SIMIAN IMMUNODEFICIENCY VIRUS (PBJ/BC13 ISOLATE) | 451–485 | 620–654 | | | | | | |
| PPOL_SRV1 | ENZYMATIC POLYPROTEIN | SOYBEAN CHLOROTIC MOTTLE VIRUS | 247–295 | 372–416 | | | | | | |
| PPOL_VIL V | POL POLYPROTEIN | SIMIAN RETROVIRUS SRV-1 | 470–504 | 578–613 | | | | | | |
| PPOL_VIL V1 | POL POLYPROTEIN | VISNA LENTIVIRUS (STRAIN 1514) | 489–524 | 874–929 | | | | | | |
| PPOL_VIL V2 | POL POLYPROTEIN | VISNA LENTIVIRUS (STRAIN 1514/ CLONE LV1-1KS1) | 489–524 | 874–929 | | | | | | |
| PPP15_HCMVA | POL POLYPROTEIN | VISNA LENTIVIRUS (STRAIN 1514/ CLONE LV1-1KS2) | 489–524 | 874–929 | | | | | | |
| PPR73_MMTVB | LARGE STRUCTURAL PHOSPHOPROTEIN PP150 | HUMAN CYTOMEGALOVIRUS (STRAIN AD169) | 116–150 | 187–221 | | | | | | |
| PPR73_MMTVC | PROTEIN PR73 | MOUSE MAMMARY TUMOR VIRUS (STRAIN BR6) | 152–200 | | | | | | | |
| PPR73_MMTVG | PROTEIN PR73 | MOUSE MAMMARY TUMOR VIRUS (STRAIN C3H) | 20–79 | | | | | | | |
| PPR7L_MMTVG | PROTEIN PR73 | MOUSE MAMMARY TUMOR VIRUS (STRAIN GR) | 61–95 | 142–201 | | | | | | |
| PPR7R_MMTVG | PROTEIN PR73 | MOUSE MAMMARY TUMOR VIRUS (STRAIN GR) | 145–204 | 270–311 | | | | | | |
| PPYHD_CPVBM | PROTEIN PR73 | MOUSE MAMMARY TUMOR VIRUS (STRAIN GR) | 141–200 | 266–307 | | | | | | |
| PPYHD_NPVAC | POLYHEDRIN PRECURSOR | BOMBYX MORI CYTOPLASMIC POLYHEDROSIS VIRUS | 13–85 | | | | | | | |
| PPYHD_NPVAS | POLYHEDRIN | AUTOGRAPHA CALIFORNICA NUCLEAR POLYHEDROSIS VIRUS | 13–47 | | | | | | | |
| PPYHD_NPVBM | POLYHEDRIN | AGROTIS SEGETUM NUCLEAR POLYHEDROSIS VIRUS | 14–48 | | | | | | | |
| PPYHD_NPVBS | POLYHEDRIN | BOMBYX MORI NUCLEAR POLYHEDROSIS VIRUS | 12–54 | | | | | | | |
| PPYHD_NPVLD | POLYHEDRIN | BUZURA SUPPRESSARIA NUCLEAR POLYHEDROSIS VIRUS | 14–48 | | | | | | | |
| PPYHD_NPVMB | POLYHEDRIN | LYMANTRIA DISPAR MULTICAPSID NUCLEAR POLYHEDROSIS VIRUS | 14–48 | | | | | | | |
| PPYHD_NPVOP | POLYHEDRIN | MAMESTRA BRASSICAE NUCLEAR POLYHEDROSIS VIRUS | 14–48 | | | | | | | |
| PPYHD_NPVOS | POLYHEDRIN | ORGYIA PSEUDOTSUGATA MULTICAPSID POLYHEDROSIS VIRUS | 13–47 | | | | | | | |
| PPYHD_NPVPF | POLYHEDRIN | ORGYIA PSEUDOTSUGATA SINGLE CAPSID NUCLEAR POLYHED | 14–48 | | | | | | | |
| PPYHD_NPVSE | POLYHEDRIN | PANOLIS FLAMMEA MULTIPLE NUCLEOCAPSID POLYHEDROSIS | 14–48 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PPYHD_NPVSF | POLYHEDRIN | SPODOPTERA EXIGUA NUCLEAR POLYHEDROSIS VIRUS (STRAIN | 14–48 | | | | | | | |
| PPYHD_NPVSL | POLYHEDRIN | SPODOPTERA FRUGIPERDA NUCLEAR POLYHEDROSIS VIRUS | 14–48 | | | | | | | |
| PRASK_MSVKI | POLYHEDRIN | SPODOPTERA LITTORALIS NUCLEAR POLYHEDROSIS VIRUS | 17–51 | | | | | | | |
| PREV_BIV27 | TRANSFORMING PROTEIN 21 | KIRSTEN MURINE SARCOMA VIRUS | 142–176 | | | | | | | |
| PREV_EIAV9 | REV PROTEIN | BOVINE IMMUNODEFICIENCY VIRUS (ISOLATE 127) | 77–115 | | | | | | | |
| PREV_EIAVC | REV PROTEIN | EQUINE INFECTIOUS ANEMIA VIRUS (CLONE 1369) | 51–89 | | | | | | | |
| PREV_EIAVY | REV PROTEIN | EQUINE INFECTIOUS ANEMIA VIRUS (CLONE CL22) | 51–89 | | | | | | | |
| PREV_HVI12 | REV PROTEIN | EQUINE INFECTIOUS ANEMIA VIRUS (ISOLATE WYOMING) | 81–119 | | | | | | | |
| PREV_HV1A2 | REV PROTEIN | HUMAN IMMUNODEFICIENCY VIRUS TYPE 1 (CLONE 12) | 35–69 | | | | | | | |
| PREV_HV1B1 | REV PROTEIN | HUMAN IMMUNODEFICIENCY VIRUS TYPE 1 (ARV2/SF2 ISOLATE | 32–69 | | | | | | | |
| PREV_HV1B8 | REV PROTEIN | HUMAN IMMUNODEFICIENCY VIRUS TYPE 1 (BH10 ISOLATE) | 35–69 | | | | | | | |
| PREV_HV1BN | REV PROTEIN | HUMAN IMMUNODEFICIENCY VIRUS TYPE 1 (BH8 ISOLATE) | 25–59 | | | | | | | |
| PREV_HV1BR | REV PROTEIN | HUMAN IMMUNODEFICIENCY VIRUS TYPE 1 (BRAIN ISOLATE) | 22–59 | | | | | | | |
| PREV_HV1EL | REV PROTEIN | HUMAN IMMUNODEFICIENCY VIRUS TYPE 1 (BRU ISOLATE) | 35–69 | | | | | | | |
| PREV_HV1H2 | REV PROTEIN | HUMAN IMMUNODEFICIENCY VIRUS TYPE 1 (ELI ISOLATE) | 32–66 | | | | | | | |
| PREV_HV1I3 | REV PROTEIN | HUMAN IMMUNODEFICIENCY VIRUS TYPE 1 (HXB2 ISOLATE) | 35–69 | | | | | | | |
| PREV_HV1JR | REV PROTEIN | HUMAN IMMUNODEFICIENCY VIRUS TYPE 1 (JH3 ISOLATE) | 29–63 | | | | | | | |
| PREV_HV1MA | REV PROTEIN | HUMAN IMMUNODEFICIENCY VIRUS TYPE 1 (JRCSF ISOLATE) | 31–66 | | | | | | | |
| PREV_HV1MN | REV PROTEIN | HUMAN IMMUNODEFICIENCY VIRUS TYPE 1 (MAL ISOLATE) | 31–66 | | | | | | | |
| PREV_HV1OY | REV PROTEIN | HUMAN IMMUNODEFICIENCY VIRUS TYPE 1 (MN ISOLATE) | 31–66 | | | | | | | |
| PREV_HV1PV | REV PROTEIN | HUMAN IMMUNODEFICIENCY VIRUS TYPE 1 (OYI ISOLATE) | 32–69 | | | | | | | |
| PREV_HV1S3 | REV PROTEIN | HUMAN IMMUNODEFICIENCY VIRUS TYPE 1 (PV22 ISOLATE) AN | 35–69 | | | | | | | |
| PREV_HV1SC | REV PROTEIN | HUMAN IMMUNODEFICIENCY VIRUS TYPE 1 (SF33 ISOLATE) | 35–69 | | | | | | | |
| PREV_SIVA1 | REV PROTEIN | HUMAN IMMUNODEFICIENCY VIRUS TYPE 1 (SC ISOLATE) | 32–69 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PREV_SIVAG | REV PROTEIN | SIMIAN IMMUNODEFICIENCY VIRUS (AGM155 ISOLATE) | 26–77 | | | | | | | |
| PREV_SIVAI | REV PROTEIN | SIMIAN IMMUNODEFICIENCY VIRUS (AGM3 ISOLATE) | 26–77 | | | | | | | |
| PREV_SIVAT | REV PROTEIN | SIMIAN IMMUNODEFICIENCY VIRUS (ISOLATE AGM/CLONE GR1) | 29–77 | | | | | | | |
| PREV_SIVCZ | REV PROTEIN | SIMIAN IMMUNODEFICIENCY VIRUS (TYO-1 ISOLATE) | 28–75 | | | | | | | |
| PREV_VILV | REV PROTEIN | VISNA LENTIVIRUS (STRAIN 1514) | 33–67 | | | | | | | |
| PRIR1_ASFM2 | REV PROTEIN | CHIMPANZEE IMMUNODEFICIENCY VIRUS | 21–62 | | | | | | | |
| PRIR1_EBV | RIBONUCLEOSIDE-DIPHOSPHATE REDUCTASE LAR | AFRICAN SWINE FEVER VIRUS (ISOLATE MALAWI LIL 20/1) | 7–41 | 88–133 | 635–683 | | | | | |
| PRIR1_HCMVA | RIBONUCLEOSIDE-DIPHOSPHATE REDUCTASE LAR | EPSTEIN-BARR VIRUS (STRAIN B95-8) | 213–247 | 689–723 | | | | | | |
| PRIR1_HSVEB | RIBONUCLEOSIDE-DIPHOSPHATE REDUCTASE LAR | HUMAN CYTOMEGALOVIRUS (STRAIN AD169) | 632–668 | | | | | | | |
| PRIR1_HSVSA | RIBONUCLEOSIDE-DIPHOSPHATE REDUCTASE LAR | EQUINE HERPESVIRUS TYPE 1 (STRAIN AB4P) | 76–110 | | | | | | | |
| PRIR1_VACCC | RIBONUCLEOSIDE-DIPHOSPHATE REDUCTASE LAR | HERPESVIRUS SAIMIRI (STRAIN 11) | 324–365 | | | | | | | |
| PRIR1_VACCV | RIBONUCLEOSIDE-DIPHOSPHATE REDUCTASE LAR | VACCINIA VIRUS (STRAIN COPENHAGEN) | 367–402 | | | | | | | |
| PRIR1_VARV | RIBONUCLEOSIDE-DIPHOSPHATE REDUCTASE LAR | VACCINIA VIRUS (STRAIN WR) | 367–402 | | | | | | | |
| PRIR1_VZVD | RIBONUCLEOSIDE-DIPHOSPHATE REDUCTASE LAR | VARIOLA VIRUS | 367–402 | | | | | | | |
| PRIR2_EBV | RIBONUCLEOSIDE-DIPHOSPHATE REDUCTASE LAR | VARICELLA-ZOSTER VIRUS (STRAIN DUMAS) | 223–257 | | | | | | | |
| PRIR2_HSVB3 | RIBONUCLEOSIDE-DIPHOSPHATE REDUCTASE SMA | EPSTEIN-BARR VIRUS (STRAIN B95-8) | 89–137 | | | | | | | |
| PRIR2_HSVEB | RIBONUCLEOSIDE-DIPHOSPHATE REDUCTASE SMA | BOVINE HERPESVIRUS TYPE 1 (STRAIN 34) | 101–135 | | | | | | | |
| PRIR2_HSVSA | RIBONUCLEOSIDE-DIPHOSPHATE REDUCTASE SMA | EQUINE HERPESVIRUS TYPE 1 (STRAIN AB4P) | 106–140 | | | | | | | |
| PRIR2_SFVKA | RIBONUCLEOSIDE-DIPHOSPHATE REDUCTASE SMA | HERPESVIRUS SAIMIRI (STRAIN 11) | 125–159 | | | | | | | |
| PRIR2_VACCC | RIBONUCLEOSIDE-DIPHOSPHATE REDUCTASE SMA | SHOPE FIBROMA VIRUS (STRAIN KASZA) | 98–132 | | | | | | | |
| PRIR2_VACCP | RIBONUCLEOSIDE-DIPHOSPHATE REDUCTASE SMA | VACCINIA VIRUS (STRAIN COPENHAGEN) | 98–132 | | | | | | | |
| PRIR2_VACCV | RIBONUCLEOSIDE-DIPHOSPHATE REDUCTASE SMA | VACCINIA VIRUS (STRAIN L-1VP) | 98–132 | | | | | | | |
| PRIR2_VARV | RIBONUCLEOSIDE-DIPHOSPHATE REDUCTASE SMA | VACCINIA VIRUS (STRAIN WR) | 98–132 | | | | | | | |
| PRL1_HSV2H | RIBONUCLEOSIDE-DIPHOSPHATE REDUCTASE SMA | VARIOLA VIRUS | 98–132 | | | | | | | |
| PRP94_VACCV | NEUROVIRULENCE FACTOR | HERPES SIMPLEX VIRUS (TYPE 2/STRAIN HG52) | 171–212 | | | | | | | |

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRP94_VARV | RNA-POLYMERASE-ASSOCIATED TRANSCRIPTION S | VACCINIA VIRUS (STRAIN WR), AND (STRAIN COPENHAGEN | 116–150 | 465–540 | 757–791 | | | | | |
| PRPO1_VACCC | RNA-POLYMERASE-ASSOCIATED TRANSCRIPTION S | VARIOLA VIRUS | 41–75 | 116–150 | 465–540 | 757–791 | | | | |
| PRPO1_VACCV | DNA-DIRECTED RNA POLYMERASE 147 KD POLYPE | VACCINIA VIRUS (STRAIN COPENHAGEN) | 243–291 | 622–656 | 754–791 | 954–988 | 1006–1057 | | | |
| PRPO1_VARV | DNA-DIRECTED RNA POLYPE 147 KD POLYPE | VACCINIA VIRUS (STRAIN WR) | 243–291 | 622–656 | 754–791 | 954–988 | 1024–1058 | | | |
| PRPO2_CAPVK | DNA-DIRECTED RNA POLYMERASE 147 KD POLYPE | VARIOLA VIRUS | 243–291 | 622–656 | 754–791 | 954–988 | 1006–1057 | | | |
| PRPO2_COWPX | DNA-DIRECTED RNA POLYMERASE 132 KD POLYPE | CAPRIPOXVIRUS (STRAIN KS-1) | 19–60 | 114–155 | 589–630 | | | | | |
| PRPO2_VACCV | DNA-DIRECTED RNA POLYMERASE 132 KD POLYPE | COWPOX VIRUS | 211–245 | 359–400 | 833–874 | | | | | |
| PRPO2_VARV | DNA-DIRECTED RNA POLYMERASE 132 KD POLYPE | VACCINIA VIRUS (STRAIN WR), AND (STRAIN COPENHAGEN) | 211–245 | 359–400 | 833–874 | | | | | |
| PRPO4_VACCV | DNA-DIRECTED RNA POLYMERASE 132 KD POLYPE | VARIOLA VIRUS | 211–245 | 359–400 | 833–874 | | | | | |
| PRPO4_VARV | DNA-DIRECTED RNA POLYMERASE 35 KD POLYPEP | VACCINIA VIRUS (STRAIN COPENHAGEN) | 62–116 | | | | | | | |
| PRPO5_VACCC | DNA-DIRECTED RNA POLYMERASE 35 KD POLYPEP | VACCINIA VIRUS (STRAIN WR) | 62–116 | | | | | | | |
| PRPO5_VARV | DNA-DIRECTED RNA POLYMERASE 35 KD POLYPEP | VARIOLA VIRUS | 62–116 | | | | | | | |
| PRPO6_VACCV | DNA-DIRECTED RNA POLYMERASE 30 KD POLYPEP | VACCINIA VIRUS (STRAIN COPENHAGEN) | 1–71 | | | | | | | |
| PRPO6_VARV | DNA-DIRECTED RNA POLYMERASE 30 KD POLYPEP | VACCINIA VIRUS (STRAIN WR) | 1–71 | | | | | | | |
| PRPO7_VACCV | DNA-DIRECTED RNA POLYMERASE 30 KD POLYPEP | VARIOLA VIRUS | 1–71 | | | | | | | |
| PRPO7_VARV | DNA-DIRECTED RNA POLYMERASE 22 KD POLYPEP | VACCINIA VIRUS (STRAIN WR), AND (STRAIN COPENHAGEN) | 25–59 | | | | | | | |
| PRPOA_LELV | DNA-DIRECTED RNA POLYMERASE 22 KD POLYPEP | VARIOLA VIRUS | 25–59 | | | | | | | |
| PRPOL_EAV | DNA-DIRECTED RNA POLYMERASE 19 KD POLYPEP | VACCINIA VIRUS (STRAIN WR), AND (STRAIN COPENHAGEN) | 43–93 | | | | | | | |
| PRRP1_IAANN | DNA-DIRECTED RNA POLYMERASE 19 KD POLYPEP | VARIOLA VIRUS | 43–93 | | | | | | | |
| PRRP1_IABEI | RNA-DIRECTED RNA POLYMERASE | LELYSTAD VIRUS | 1533–1567 1083–1117 | 1721–1758 1477–1518 | 1958–1992 1633–1673 | 2109–2157 | | | | |
| PRRP1_IADUN | RNA-DIRECTED RNA POLYMERASE SUBUNIT P1 | EQUINE ARTERITIS VIRUS | 171–242 | 279–313 | | | | | | |
| PRRP1_IABEI | RNA-DIRECTED RNA POLYMERASE SUBUNIT P1 | INFLUENZA A VIRUS (STRAIN A/ANN ARBOR/6/60) | | | | | | | | |
| PRRP1_IADUN | RNA-DIRECTED RNA POLYMERASE SUBUNIT P1 | INFLUENZA A VIRUS (STRAIN A/BEIJING/11/56) | 171–242 | 279–313 | 350–391 | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRRP1_IAGU2 | RNA-DIRECTED RNA POLYMERASE SUBUNIT P1 | INFLUENZA A VIRUS (STRAIN A/DUNEDIN/4/73) | 171–242 | 279–313 | | | | | | |
| PRRP1_IAHLO | RNA-DIRECTED RNA POLYMERASE SUBUNIT P1 | INFLUENZA A VIRUS (STRAIN A/GULL/MARYLAND/704/77) | 171–242 | 279–313 | | | | | | |
| PRRP1_IAHTE | RNA-DIRECTED RNA POLYMERASE SUBUNIT P1 | INFLUENZA A VIRUS (STRAIN A/EQUINE/LONDON/1416/73) | 168–242 | 279–313 | | | | | | |
| PRRP1_IAKIE | RNA-DIRECTED RNA POLYMERASE SUBUNIT P1 | INFLUENZA A VIRUS (STRAIN A/EQUINE/TENNESSEE/5/86) | 168–242 | 279–313 | | | | | | |
| PRRP1_IAKOR | RNA-DIRECTED RNA POLYMERASE SUBUNIT P1 | INFLUENZA A VIRUS (STRAIN A/KIEV/59/79) | 171–242 | 279–313 | | | | | | |
| PRRP1_IALE1 | RNA-DIRECTED RNA POLYMERASE SUBUNIT P1 | INFLUENZA A VIRUS (STRAIN A/KOREA/426/68) | 171–242 | 279–313 | | | | | | |
| PRRP1_IALE2 | RNA-DIRECTED RNA POLYMERASE SUBUNIT P1 | INFLUENZA A VIRUS (STRAIN A/LENINGRAD/134/57) | 171–242 | 279–313 | | | | | | |
| PRRP1_IALE3 | RNA-DIRECTED RNA POLYMERASE SUBUNIT P1 | INFLUENZA A VIRUS (STRAIN A/LENINGRAD/134/17/57) | 171–242 | 279–313 | | | | | | |
| PRRP1_IAMAN | RNA-DIRECTED RNA POLYMERASE SUBUNIT P1 | INFLUENZA A VIRUS (STRAIN A/LENINGRAD/134/47/57) | 171–242 | 279–313 | | | | | | |
| PRRP1_IAME8 | RNA-DIRECTED RNA POLYMERASE SUBUNIT P1 | INFLUENZA A VIRUS (STRAIN A/MALLARD/NEW YORK/6750/78) | 171–242 | 279–313 | | | | | | |
| PRRP1_IANT6 | RNA-DIRECTED RNA POLYMERASE SUBUNIT P1 | INFLUENZA A VIRUS (STRAIN A/MEMPHIS/8/88) | 171–242 | 279–313 | | | | | | |
| PRRP1_IAPUE | RNA-DIRECTED RNA POLYMERASE SUBUNIT P1 | INFLUENZA A VIRUS (STRAIN A/NT/60/68) | 171–242 | 279–313 | | | | | | |
| PRRP1_IASIN | RNA-DIRECTED RNA POLYMERASE SUBUNIT P1 | INFLUENZA A VIRUS (STRAIN A/PUERTO RICO/8/34) | 168–242 | 279–313 | | | | | | |
| PRRP1_IATKM | RNA-DIRECTED RNA POLYMERASE SUBUNIT P1 | INFLUENZA A VIRUS (STRAIN A/SINGAPORE/1/57) | 171–242 | 279–313 | | | | | | |
| PRRP1_IAVI7 | RNA-DIRECTED RNA POLYMERASE SUBUNIT P1 | INFLUENZA A VIRUS (STRAIN A/TURKEY/MINNESOTA/833/80) | 171–242 | 279–313 | | | | | | |
| PRRP1_IAWIL | RNA-DIRECTED RNA POLYMERASE SUBUNIT P1 | INFLUENZA A VIRUS (STRAIN A/VICTORIA/3/75) | 171–242 | 279–313 | | | | | | |
| PRRP1_IAWIS | RNA-DIRECTED RNA POLYMERASE SUBUNIT P1 | INFLUENZA A VIRUS (STRAIN A/WILSON-SMITH/33) | 168–242 | 279–313 | | | | | | |
| PRRP1_IAZH3 | RNA-DIRECTED RNA POLYMERASE SUBUNIT P1 | INFLUENZA A VIRUS (STRAIN A/WISCONSIN/3 523/88) | 168–242 | 279–313 | | | | | | |
| PRRP1_IAZON | RNA-DIRECTED RNA POLYMERASE SUBUNIT P1 | INFLUENZA A VIRUS (STRAIN A/SWINE/HONG KONG/126/82) | 187–242 | 279–313 | | | | | | |
| PRRP1_IAZTF | RNA-DIRECTED RNA POLYMERASE SUBUNIT P1 | INFLUENZA A VIRUS (STRAIN A/SWINE/ONTARIO/2/81) | 171–242 | 279–313 | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRRP1_INCJJ | RNA-DIRECTED RNA POLYMERASE SUBUNIT P1 | INFLUENZA B VIRUS (STRAIN B/LEE/40) | 208–249 | | | | | | | |
| PRRP2_IAANN | RNA-DIRECTED RNA POLYMERASE SUBUNIT P1 | INFLUENZA C VIRUS (STRAIN C/JJ/50) | 305–384 | 648-686 | 707–752 | | | | | |
| PRRP2_IADH2 | RNA-DIRECTED RNA POLYMERASE SUBUNIT P2 | INFLUENZA A VIRUS (STRAIN A/ANN ARBOR/6/60) | 110–144 | 177–218 | | | | | | |
| PRRP2_IAFPR | RNA-DIRECTED RNA POLYMERASE SUBUNIT P2 | INFLUENZA A VIRUS (STRAIN A/DUCK/HOKKAIDO/8/80) | 110–144 | 177–218 | | | | | | |
| PRRP2_IAGU2 | RNA-DIRECTED RNA POLYMERASE SUBUNIT P2 | INFLUENZA A VIRUS (STRAIN A/FOWL PLAGUE VIRUS/ROSTOCK | 110–144 | 177–218 | | | | | | |
| PRRP2_IAHLO | RNA-DIRECTED RNA POLYMERASE SUBUNIT P2 | INFLUENZA A VIRUS (STRAIN A/GULL/MARYLAND/704/77) | 110–144 | 177–218 | | | | | | |
| PRRP2_IAHTE | RNA-DIRECTED RNA POLYMERASE SUBUNIT P2 | INFLUENZA A VIRUS (STRAIN A/EQUINE/LONDON/14 16/73) | 110–144 | 177–218 | | | | | | |
| PRRP2_IAKOR | RNA-DIRECTED RNA POLYMERASE SUBUNIT P2 | INFLUENZA A VIRUS (STRAIN A/EQUINE/TENNESSEE/5/86) | 110–144 | 177–218 | | | | | | |
| PRRP2_IALE1 | RNA-DIRECTED RNA POLYMERASE SUBUNIT P2 | INFLUENZA A VIRUS (STRAIN A/KOREA/426/68) | 110–144 | 177–218 | | | | | | |
| PRRP2_IALE2 | RNA-DIRECTED RNA POLYMERASE SUBUNIT P2 | INFLUENZA A VIRUS (STRAIN A/LENINGRAD/134/57) | 110–144 | 177–218 | | | | | | |
| PRRP2_IAMAN | RNA-DIRECTED RNA POLYMERASE SUBUNIT P2 | INFLUENZA A VIRUS (STRAIN A/LENINGRAD/134/17/57) | 110–144 | 177–218 | | | | | | |
| PRRP2_IANT6 | RNA-DIRECTED RNA POLYMERASE SUBUNIT P2 | INFLUENZA A VIRUS (STRAIN A/MALLARD/NEW YORK/6750/78) | 110–144 | 177–218 | | | | | | |
| PRRP2_IAPI0 | RNA-DIRECTED RNA POLYMERASE SUBUNIT P2 | INFLUENZA A VIRUS (STRAIN A/NT/60/68) | 110–144 | 177–218 | | | | | | |
| PRRP2_IAPUE | RNA-DIRECTED RNA POLYMERASE SUBUNIT P2 | INFLUENZA A VIRUS (STRAIN A/PINTAIL/ALBERTA/1 19/79) | 110–144 | 177–218 | | | | | | |
| PRRP2_IARUD | RNA-DIRECTED RNA POLYMERASE SUBUNIT P2 | INFLUENZA A VIRUS (STRAIN A/PUERTO RICO/8/34) | 110–144 | 177–218 | | | | | | |
| PRRP2_IASIN | RNA-DIRECTED RNA POLYMERASE SUBUNIT P2 | INFLUENZA A VIRUS (STRAIN A/RUDDY TURNSTONE/NEW JERS | 110–144 | 177–218 | | | | | | |
| PRRP2_IATKM | RNA-DIRECTED RNA POLYMERASE SUBUNIT P2 | INFLUENZA A VIRUS (STRAIN A/SINGAPORE/1/57) | 110–144 | 177–218 | | | | | | |
| PRRP2_IAVI7 | RNA-DIRECTED RNA POLYMERASE SUBUNIT P2 | INFLUENZA A VIRUS (STRAIN A/TURKEY/MINNESOTA/833/80) | 110–144 | 177–218 | | | | | | |
| PRRP2_IAWIL | RNA-DIRECTED RNA POLYMERASE SUBUNIT P2 | INFLUENZA A VIRUS (STRAIN A/VICTORIA/3/75) | 110–144 | 177–218 | | | | | | |
| PRRP2_IAZH2 | RNA-DIRECTED RNA POLYMERASE SUBUNIT P2 | INFLUENZA A VIRUS (STRAIN A/WILSON-SMITH/33) | 110–144 | 177–218 | | | | | | |
| PRRP2_IAZH3 | RNA-DIRECTED RNA POLYMERASE SUBUNIT P2 | INFLUENZA A VIRUS (STRAIN A/SWINE/HONG KONG/81/78) | 110–144 | 177–218 | | | | | | |
| PRRP2_IAZI1 | RNA-DIRECTED RNA POLYMERASE SUBUNIT P2 | INFLUENZA A VIRUS (STRAIN A/SWINE/HONG KONG/126/82) | 110–144 | 177–218 | | | | | | |
| PRRP2_IAZTF | RNA-DIRECTED RNA POLYMERASE SUBUNIT P2 | INFLUENZA A VIRUS (STRAIN A/SWINE/IOWA/15/30 | 110–144 | 177–218 | | | | | | |

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRRP2_INBAC | RNA-DIRECTED RNA POLYMERASE SUBUNIT P2 | INFLUENZA A VIRUS (STRAIN A/SWINE/TENNESSEE/26/77) | 110–144 | 177–218 | | | | | | |
| PRRP2_INBAD | RNA-DIRECTED RNA POLYMERASE SUBUNIT P2 | INFLUENZA B VIRUS (STRAIN B/ANN ARBOR/1/66 [COLD-ADAPTE | 111–196 | 349–390 | | | | | | |
| PRRP2_INBSI | RNA-DIRECTED RNA POLYMERASE SUBUNIT P2 | INFLUENZA B VIRUS (STRAIN B/ANN ARBOR/1/66 [WILD-TYPE]) | 111–196 | 349–390 | | | | | | |
| PRRP2_IAANN | RNA-DIRECTED RNA POLYMERASE SUBUNIT P2 | INFLUENZA B VIRUS (STRAIN B/SINGAPORE/222/79) | 111–196 | 349–383 | | | | | | |
| PRRP3_IABUD | RNA-DIRECTED RNA POLYMERASE SUBUNIT P3 | INFLUENZA A VIRUS (STRAIN A/ANN ARBOR/6/60) | 1–42 | 363–402 | 473–514 | 707–755 | | | | |
| PRRP3_IACHI | RNA-DIRECTED RNA POLYMERASE SUBUNIT P3 | INFLUENZA A VIRUS (STRAIN A/BUDGERIGAR/HOKKAIDO/1/77) | 1–42 | 363–402 | 473–514 | 518–567 | 707–755 | | | |
| PRRP3_IAFPR | RNA-DIRECTED RNA POLYMERASE SUBUNIT P3 | INFLUENZA A VIRUS (STRAIN A/CHILE/1/83) | 1–42 | 363–402 | 473–514 | 707–755 | | | | |
| PRRP3_IAFPW | RNA-DIRECTED RNA POLYMERASE SUBUNIT P3 | INFLUENZA A FOWL PLAGUE VIRUS/ROSTOCK | 1–42 | 363–402 | 473–514 | 707–755 | | | | |
| PRRP3_IAGU2 | RNA-DIRECTED RNA POLYMERASE SUBUNIT P3 | INFLUENZA A FOWL PLAGUE VIRUS/WEYBRID | 1–42 | 363–402 | 473–514 | 707–755 | | | | |
| PRRP3_IAGUA | RNA-DIRECTED RNA POLYMERASE SUBUNIT P3 | INFLUENZA A VIRUS (STRAIN A/GULL/MARYLAND/704/77 | 1–42 | 363–402 | 473–514 | 707–755 | | | | |
| PRRP3_IAHK6 | RNA-DIRECTED RNA POLYMERASE SUBUNIT P3 | INFLUENZA A VIRUS (STRAIN A/GULL/ASTRAKHAN/227/84) | 7–41 | 363–402 | 473–514 | 707–755 | | | | |
| PRRP3_IAHLO | RNA-DIRECTED RNA POLYMERASE SUBUNIT P3 | INFLUENZA A VIRUS (STRAIN A/EQUINE/KENTUCKY/2/860) | 1–42 | 363–402 | 473–514 | 707–755 | | | | |
| PRRP3_IAHPR | RNA-DIRECTED RNA POLYMERASE SUBUNIT P3 | INFLUENZA A VIRUS (STRAIN A/EQUINE/LONDON/1416/73) | 1–42 | 363–402 | 473–514 | 707–755 | | | | |
| PRRP3_IAKIE | RNA-DIRECTED RNA POLYMERASE SUBUNIT P3 | INFLUENZA A VIRUS (STRAIN A/EQUINE/PRAGUE/1/56) | 1–42 | 363–402 | 473–514 | 721–755 | | | | |
| PRRP3_IAKOR | RNA-DIRECTED RNA POLYMERASE SUBUNIT P3 | INFLUENZA A VIRUS (STRAIN A/KIEV/59/79) | 1–42 | 363–402 | 473–514 | 707–755 | | | | |
| PRRP3_IALEI | RNA-DIRECTED RNA POLYMERASE SUBUNIT P3 | INFLUENZA A VIRUS (STRAIN A/KOREA/426/68) | 1–42 | 363–402 | 473–514 | 707–755 | | | | |
| PRRP3_IALE2 | RNA-DIRECTED RNA POLYMERASE SUBUNIT P3 | INFLUENZA A VIRUS (STRAIN A/LENINGRAD/134/57) | 1–42 | 363–402 | 473–514 | 707–755 | | | | |
| PRRP3_IALE3 | RNA-DIRECTED RNA POLYMERASE SUBUNIT P3 | INFLUENZA A VIRUS (STRAIN A/LENINGRAD/134/17/57) | 1–42 | 363–402 | 473–514 | 707–755 | | | | |
| PRRP3_IAMAN | RNA-DIRECTED RNA POLYMERASE SUBUNIT P3 | INFLUENZA A VIRUS (STRAIN A/LENINGRAD/134/47/57) | 1–42 | 363–402 | 473–514 | 707–755 | | | | |
| PRRP3_IAME8 | RNA-DIRECTED RNA POLYMERASE SUBUNIT P3 | INFLUENZA A VIRUS (STRAIN A/MALLARD/NEW YORK/6750/78) | 363–402 | 473–514 | 707–755 | | | | | |
| PRRP3_IANT6 | RNA-DIRECTED RNA POLYMERASE SUBUNIT P3 | INFLUENZA A VIRUS (STRAIN A/MEMPHIS/8/88) | 7–41 | 363–402 | 473–514 | 707–755 | | | | |
| PRRP3_IAPUE | RNA-DIRECTED RNA POLYMERASE SUBUNIT P3 | INFLUENZA A VIRUS (STRAIN A/NT/60/68) | 1–42 | 363–402 | 473–514 | 707–755 | | | | |
| PRRP3_IARUD | RNA-DIRECTED RNA POLYMERASE SUBUNIT P3 | INFLUENZA A VIRUS (STRAIN A/PUERTO RICO/8/34) | 1–42 | 363–402 | 473–514 | 707–755 | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRRP3_IASE2 | RNA-DIRECTED RNA POLYMERASE SUBUNIT P3 | INFLUENZA A VIRUS (STRAIN A/RUDDY TURNSTONE/NEW JERSE | 1–42 | 363–402 | 473–514 | 707–755 | | | | |
| PRRP3_IASIN | RNA-DIRECTED RNA POLYMERASE SUBUNIT P3 | INFLUENZA A VIRUS (STRAIN A/SEAL/MASSACHUSETTS/133/82) | 1–42 | 363–402 | 473–514 | 707–755 | | | | |
| PRRP3_IATKM | RNA-DIRECTED RNA POLYMERASE SUBUNIT P3 | INFLUENZA A VIRUS (STRAIN A/SINGAPORE/1/57) | 1–42 | 363–402 | 473–514 | 707–755 | | | | |
| PRRP3_IAVI7 | RNA-DIRECTED RNA POLYMERASE SUBUNIT P3 | INFLUENZA A VIRUS (STRAIN A/TURKEY/MINNESOTA/833/80) | 1–42 | 363–402 | 473–514 | 707–755 | | | | |
| PRRP3_IAWIL | RNA-DIRECTED RNA POLYMERASE SUBUNIT P3 | INFLUENZA A VIRUS (STRAIN A/VICTORIA/3/75) | 1–42 | 363–402 | 473–514 | 707–755 | | | | |
| PRRP3_IAZI1 | RNA-DIRECTED RNA POLYMERASE SUBUNIT P3 | INFLUENZA A VIRUS (STRAIN A/WILSON-SMITH/33) | 1–42 | 363–402 | 473–514 | 707–755 | | | | |
| PRRP3_IAZTE | RNA-DIRECTED RNA POLYMERASE SUBUNIT P3 | INFLUENZA A VIRUS (STRAIN A/SWINE/IOWA/15/30) | 1–42 | 363–402 | 473–514 | 707–755 | | | | |
| PRRP3_INBAC | RNA-DIRECTED RNA POLYMERASE SUBUNIT P3 | INFLUENZA A VIRUS (STRAIN A/SWINE/TENNESSEE/24/77) | 7–41 | 363–402 | 473–514 | 707–755 | | | | |
| PRRP3_INBAD | RNA-DIRECTED RNA POLYMERASE SUBUNIT P3 | INFLUENZA B VIRUS (STRAIN B/ANN ARBOR/1/66 [COLD-ADAPTE | 458–533 | | | | | | | |
| PRRP3_INCBE | RNA-DIRECTED RNA POLYMERASE SUBUNIT P3 | INFLUENZA B VIRUS (STRAIN B/ANN ARBOR/1/66 [WILD-TYPE]) | 458–533 | | | | | | | |
| PRRP3_INCJ | RNA-DIRECTED RNA POLYMERASE SUBUNIT P3 | INFLUENZA C VIRUS (STRAIN C/BERLIN/1/85) | 235–269 | 275–309 | | | | | | |
| PRRP3_THOGV | RNA-DIRECTED RNA POLYMERASE SUBUNIT P3 | INFLUENZA C VIRUS (STRAIN C/JJ/50) | 235–269 | 275–316 | | | | | | |
| PRRPA_CVH22 | RNA-DIRECTED RNA POLYMERASE SUBUNIT P3 | THOGOTO VIRUS | 343–401 | | | | | | | |
| PRRPA_CVMJH | RNA-DIRECTED RNA POLYMERASE | HUMAN CORONAVIRUS (STRAIN 229E) | 358–392 | 495–571 | 1742–1776 2769–2803 | 1971–2008 3586–3620 | 3664–3724 3821–3855 | 3912–3946 4075–4121 | 4319–4353 | |
| PRRPB_BEV | RNA-DIRECTED RNA POLYMERASE | MURINE CORONAVIRUS MHV (STRAIN JHM) | 617–651 | 1364–1398 617–651 | 943–1009 | | | | | |
| PRRPB_CVMA5 | RNA-DIRECTED RNA POLYMERASE | BERNE VIRUS | 20–64 | | | | | | | |
| PRRPB_CVMJH | RNA-DIRECTED RNA POLYMERASE | MURINE CORONAVIRUS MHV (STRAIN A59) | 1129–1170 | 1303–1337 | 1453–1494 | 1692–1726 | 2629–2670 | | | |
| PRRPB_IBVB | RNA-DIRECTED RNA POLYMERASE | MURINE CORONAVIRUS MHV (STRAIN JHM) | 1129–1170 | 1303–1337 | 1453–1494 | 1690–1724 | 2627–2668 | | | |
| PRRPB_IBVK | RNA-DIRECTED RNA POLYMERASE | AVIAN INFECTIOUS BRONCHITIS VIRUS (STRAIN BEAUDETTE) | 499–550 | 650–695 | 1460–1494 | 1509–1548 | 2246–2287 | | | |
| PRRPL_BTV10 | RNA-DIRECTED RNA POLYMERASE | AVIAN INFECTIOUS BRONCHITIS VIRUS (STRAIN KB8523) | 115–156 | | | | | | | |
| PRRPL_BUNYW | RNA-DIRECTED RNA POLYMERASE | BLUETONGUE VIRUS (SEROTYPE 10/ISOLATE USA) | 308–342 | 705–748 | 825–903 | 1021–1076 | 1114–1201 | | | |
| PRRPL_CDVO | RNA POLYMERASE | BUNYAMWERA VIRUS | 2–36 | 80–114 | 308–363 | 371–412 | 1704–1741 | 1802–1861 | 1889–1935 | |
| PRRPL_HANTV | RNA POLYMERASE BETA SUBUNIT | CANINE DISTEMPER VIRUS (STRAIN ONDERSTEPOORT) | 20–54 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRRPL_HRSVA | RNA POLYMERASE | HANTAAN VIRUS (STRAIN 76-118) | 98–139 | 174–208 | 372–431 | 557–591 | 655–696 | 731–783 | 905–949 | 1276–1310 |
| | | | 1419–1453 | 1742–1776 | 1993–2027 | | | | | |
| PRRPL_MABVM | RNA POLYMERASE BETA SUBUNIT | HUMAN RESPIRATORY SYNCYTIAL VIRUS (STRAIN A2 | 87–188 | 827–861 | 1131–1179 | 1185–1220 | 1465–1517 | | | |
| PRRPL_MABVP | RNA-DIRECTED RNA POLYMERASE | MARBURG VIRUS (STRAIN MUSOKE) | 597–631 | 1046–1092 | 1490–1552 | 1804–1838 | 2029–2063 | 2194–2266 | | |
| PRRPL_MEASE | RNA-DIRECTED RNA POLYMERASE | MARBURG VIRUS (STRAIN POPP) | 597–631 | 1046–1092 | 1490–1552 | | | | | |
| PRRPL_MUMPM | RNA POLYMERASE BETA SUBUNIT | MEASLES VIRUS (STRAIN EDMONSTON) | 197–231 | 790–824 | 869–903 | 1064–1109 | 1283–1317 | 2121–2155 | | |
| PRRPL_NDVB | RNA POLYMERASE BETA SUBUNIT | MUMPS VIRUS (STRAIN MIYAHARA VACCINE) | 164–214 | 220–254 | 267–304 | 576–627 | 752–807 | 1231–1286 | 1447–1481 | 1487–1531 |
| | | | 1566–1600 | 2191–2225 | | | | | | |
| PRRPL_PI2HT | RNA POLYMERASE BETA SUBUNIT | NEWCASTLE DISEASE VIRUS (STRAIN BEAUDETTE C/45) | 167–208 | 230–295 | 1969–2013 | 2043–2077 | 2108–2142 | | | |
| PRRPL_PI3H4 | RNA POLYMERASE BETA SUBUNIT | HUMAN PARAINFLUENZA 2 VIRUS (STRAIN TOSHIBA) | 136–170 | 575–628 | 750–785 | 1226–1284 | 1316–1357 | 1417–1479 | 1564–1630 | 1687–1721 |
| | | | 1901–1955 | | | | | | | |
| PRRPL_PUUMH | RNA POLYMERASE BETA SUBUNIT | HUMAN PARAINFLUENZA 3 VIRUS (STRAIN NIH 47885) | 48–91 | 107–163 | 540–574 | 747–781 | 1064–1129 | 1293–1356 | 1499–1536 | 1994–2036 |
| PRRPL_RABVP | RNA-DIRECTED RNA POLYMERASE | PUUMALA VIRUS (STRAIN HALLNAS B1) | 98–132 | 381–415 | 444–488 | 557–591 | 655–696 | 731–783 | 922–976 | 1119–1153 |
| | | | 1742–1776 | 1940–1975 | 1993–2032 | | | | | |
| PRRPL_RABVS | RNA POLYMERASE BETA SUBUNIT | RABIES VIRUS (STRAIN PV) | 73–114 | 197–231 | 696–730 | 1174–1222 | 1522–1580 | 1584–1618 | 2068–2123 | |
| PRRPL_RDV | RNA POLYMERASE BETA SUBUNIT | RABIES VIRUS (STRAIN SAD B19) | 73–114 | 197–231 | 696–730 | 749–783 | 1174–1222 | 1522–1580 | 1584–2123 | |
| PRRPL_RVFVZ | RNA-DIRECTED RNA POLYMERASE | RICE DWARF VIRUS | 17–61 | 534–575 | 844–878 | 918–985 | 1037–1071 | | | |
| PRRPL_SEND5 | RNA-DIRECTED RNA POLYMERASE | RIFT VALLEY FEVER VIRUS (STRAIN ZH-548 M12) | 398–439 | 641–678 | 832–887 | 1081–1115 | 1653–1687 | 1819–1870 | | |
| PRRPL_SENDE | RNA POLYMERASE BETA SUBUNIT | SENDAI VIRUS (STRAIN Z/HOST MUTANTS) | 309–343 | 540–600 | 612–656 | 747–781 | 1064–1119 | 1239–1280 | 1499–1536 | 2000–2034 |
| | | | 2146–2216 | | | | | | | |
| PRRPL_SENDZ | RNA POLYMERASE BETA SUBUNIT | SENDAI VIRUS (STRAIN ENDERS) | 129–163 | 360–420 | 432–476 | 567–601 | 884–939 | 1059–1100 | 1319–1356 | 1820–1854 |
| | | | 1966–2036 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRRPL_SEOU8 | RNA POLYMERASE BETA SUBUNIT | SENDAI VIRUS (STRAIN Z) | 309–343 2146–2216 | 540–600 | 612–656 | 747–781 | 1064–1119 | 1239–1280 | 1499–1536 | 2000–2034 |
| PRRPL_SV5WR | RNA-DIRECTED RNA POLYMERASE | SEOUL VIRUS (STRAIN 80-39) | 98–139 | 174–208 | 557–591 | 655–696 | 731–765 | 1742–1776 | 1947–1981 | 1993–2027 |
| PRRPL_SYNV | RNA POLYMERASE BETA SUBUNIT | SIMIAN VIRUS 5 (STRAIN 21004-WR) | 547–627 | 747–781 | 1225–1280 | 1319–1353 | 1592–1626 | 1676–1715 | 2024–2058 | |
| PRRPL_TSWVB | RNA POLYMERASE BETA SUBUNIT | SONCHUS YELLOW NET VIRUS | 760–794 | 825–859 | 977–1014 | 1089–1137 | 1978–2032 | 2059–2107 | | |
| PRRPL_UUK | RNA-DIRECTED RNA POLYMERASE | TOMATO SPOTTED WILT VIRUS (BRAZILIAN ISOLATE CPNH1/BR | 46–101 | 399–433 | 539–573 | 589–634 | 1119–1153 | 1195–1236 | 1321–1379 | 1538–1572 |
| PRRPL_UUK | RNA POLYMERASE | UUKUNIEMI VIRUS | 1684–1725 | 1857–1898 | 2073–2127 | 2156–2200 | 2206–2247 | 2315–2368 | 2378–2419 | 2809–2843 |
| PRRPL_VSVIH | RNA POLYMERASE | | 127–183 | 282–323 | 836–874 | 1030–1071 | 1481–1515 | 2015–2049 | 2061–2098 | |
| PRRPL_VSVIO | RNA POLYMERASE BETA SUBUNIT | VESICULAR STOMATITIS VIRUS (SEROTYPE NEW JERSEY/STRA | 319–358 | 674–715 | 720–763 | 1522–1567 | 1802–1836 | | | |
| PRRPL_VSVSJ | RNA POLYMERASE BETA SUBUNIT | VESICULAR STOMATITIS VIRUS (SEROTYPE NEW JERSEY/STRA | 319–358 | 674–715 | 720–763 | 1802–1836 | | | | |
| PRRPO_ACLSV | RNA POLYMERASE BETA SUBUNIT | VESICULAR STOMATITIS VIRUS (STRAIN SAN JUAN) | 674–715 | 720–763 | 1019–1074 | 1742–1799 | 2066–2107 | | | |
| PRRPO_BWYVF | RNA-DIRECTED RNA POLYMERASE | APPLE CHLOROTIC LEAF SPOT VIRUS | 228–262 | 557–596 | 916–950 | 1235–1269 | | | | |
| PRRPO_BYDV1 | PUTATIVE RNA-DIRECTED RNA POLYMERASE | BEET WESTERN YELLOWS VIRUS (ISOLATE FL-1) | 304–341 | | | | | | | |
| PRRPO_BYDVP | PUTATIVE RNA-DIRECTED RNA POLYMERASE | BARLEY YELLOW DWARF VIRUS (ISOLATE MAV-PS1) | 234–285 | | | | | | | |
| PRRPO_BYDVR | PUTATIVE RNA-DIRECTED RNA POLYMERASE | BARLEY YELLOW DWARF VIRUS (ISOLATE PAV) | 234–285 | | | | | | | |
| PRRPO_CARMV | PUTATIVE RNA-DIRECTED RNA POLYMERASE | BARLEY YELLOW DWARF VIRUS (ISOLATE P-PAV) | 234–285 | | | | | | | |
| PRRPO_CGMVS | PROBABLE RNA-DIRECTED RNA POLYMERASE | CARNATION MOTTLE VIRUS | 93–131 | | | | | | | |
| PRRPO_IBDVS | PUTATIVE RNA-DIRECTED RNA POLYMERASE | CUCUMBER GREEN MOTTLE MOSAIC VIRUS (WATERMELON STR | 7–41 | 387–428 | 446–480 | 726–767 | 1445–1479 | | | |
| PRRPO_IBDVA | PUTATIVE RNA-DIRECTED RNA POLYMERASE | AVIAN INFECTIOUS BURSAL DISEASE VIRUS (STRAIN 52/70) | 384–432 | 446–484 | | | | | | |
| PRRPO_IPNVJ | PUTATIVE RNA-DIRECTED RNA POLYMERASE | AVIAN INFECTIOUS BURSAL DISEASE VIRUS (STRAIN AUSTRALI | 144–185 | 266–307 | 709–757 | 771–809 | | | | |
| PRRPO_IPNVS | PUTATIVE RNA-DIRECTED RNA POLYMERASE | INFECTIOUS PANCREATIC NECROSIS VIRUS (SEROTYPE JASPER) | 147–181 | 268–407 | 501–535 | 750–802 | | | | |
| PRRPO_LYCVA | PUTATIVE RNA-DIRECTED RNA POLYMERASE | INFECTIOUS PANCREATIC NECROSIS VIRUS (SEROTYPE SP) | 147–181 | 366–407 | 501–535 | 753–802 | | | | |
| PRRPO_LYCVW | RNA POLYMERASE | LYMPHOCYTIC CHORIOMENINGITIS VIRUS (STRAIN ARMSTRON | 301–346 | 805–886 | 926–960 | 1509–1543 | 2090–2124 | | | |

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRRPO_MCMV | RNA POLYMERASE | LYMPHOCYTIC CHORIOMENINGITIS VIRUS (STRAIN WE) | 301–345 | | | | | | | |
| PRRPO_PEAMV | PROBABLE RNA-DIRECTED RNA POLYMERASE | MAIZE CHLOROTIC MOTTLE VIRUS | 181–215 | 697–731 | | | | | | |
| PRRPO_PLRV1 | RNA-DIRECTED RNA POLYMERASE | PEA ENATION MOSAIC VIRUS | 321–358 | 423–457 | | | | | | |
| PRRPO_PLRVW | PUTATIVE RNA-DIRECTED RNA POLYMERASE | POTATO LEAFROLL VIRUS (STRAIN 1) | 336–373 | 423–457 | | | | | | |
| PRRPO_PPMVS | PUTATIVE RNA-DIRECTED RNA POLYMERASE | POTATO LEAFROLL VIRUS (STRAIN WAGENINGEN) | 336–373 | | | | | | | |
| PRRPO_RCNMV | PUTATIVE RNA-DIRECTED RNA POLYMERASE | PEPPER MILD MOTTLE VIRUS (STRAIN SPAIN) | 321–362 | 402–454 | 627–661 | 862–896 | | | | |
| PRRPO_REOVD | PUTATIVE RNA-DIRECTED RNA POLYMERASE | RED CLOVER NECROTIC MOSAIC VIRUS | 666–700 | | | | | | | |
| PRRPO_REOVJ | RNA-DIRECTED RNA POLYMERASE | REOVIRUS (TYPE 3/STRAIN DEARING) | 310–361 | | | | | | | |
| PRRPO_REOVL | RNA-DIRECTED RNA POLYMERASE | REOVIRUS (TYPE 2/STRAIN D5/JONES) | 310–344 | | | | | | | |
| PRRPO_ROTBR | RNA-DIRECTED RNA POLYMERASE | REOVIRUS (TYPE 1/STRAIN LANG) | 310–361 | | | | | | | |
| PRRPO_ROTBU | RNA-DIRECTED RNA POLYMERASE SUBUNIT VP1 | BOVINE ROTAVIRUS (STRAIN RF) | 60–96 | 133–167 | 204–245 | 535–569 | 579–631 | 639–686 | 690–724 | 771–805 |
| PRRPO_ROTPC | RNA-DIRECTED RNA POLYMERASE SUBUNIT VP1 | BOVINE ROTAVIRUS (STRAIN UK) | 60–96 | 133–167 | 204–245 | 535–569 | 579–631 | 639–686 | 690–724 | 771–805 |
| PRRPO_ROTPG | RNA-DIRECTED RNA POLYMERASE SUBUNIT VP1 | PORCINE ROTAVIRUS (GROUP C/STRAIN COWDEN) | 3–44 | 255–299 | 335–397 | 476–510 | 518–620 | 966–1007 | | |
| PRRPO_ROTS1 | RNA-DIRECTED RNA POLYMERASE SUBUNIT VP1 | PORCINE ROTAVIRUS (STRAIN GOTTFRIED) | 62–96 | 133–167 | 336–377 | 581–631 | 636–686 | 690–724 | 771–842 | |
| PRRPO_SBMV | RNA-DIRECTED RNA POLYMERASE SUBUNIT VP1 | SIMIAN 11 ROTAVIRUS (STRAIN SA11) | 60–96 | 133–167 | 535–569 | 579–631 | 639–686 | 690–724 | 771–805 | |
| PRRPO_SCVLA | PROBABLE RNA-DIRECTED RNA POLYMERASE | SOUTHERN BEAN MOSAIC VIRUS | 628–665 | | | | | | | |
| PRRPO_TACV | RNA-DIRECTED RNA POLYMERASE | SACCHAROMYCES CEREVISIAE VIRUS L-A | 100–134 | 147–191 | | | | | | |
| PRRPO_TMGMV | RNA POLYMERASE | TACARIBE VIRUS | 155–204 | 220–278 | 375–416 | 484–518 | 891–925 | 1030–1081 | 1285–1319 | 1981–2015 |
| PRRPO_TMV | PUTATIVE RNA-DIRECTED RNA POLYMERASE | TOBACCO MILD GREEN MOSAIC VIRUS (TMV STRAIN U2) | 401–449 | 682–720 | 765–818 | | | | | |
| PRRPO_TMVKR | PUTATIVE RNA-DIRECTED RNA POLYMERASE | TOBACCO MOSAIC VIRUS (VULGARE) | 3–37 | 401–453 | 665–699 | | | | | |
| PRRPO_TMVTO | PUTATIVE RNA-DIRECTED RNA POLYMERASE | TOBACCO MOSAIC VIRUS (STRAIN KOREAN) | 3–37 | 401–453 | 665–699 | | | | | |
| PRRPO_TNVD | PUTATIVE RNA-DIRECTED RNA POLYMERASE | TOBACCO MOSAIC VIRUS (STRAIN TOMATO/L) | 3–37 | 401–453 | 860–894 | | | | | |
| PRRPP_BRSVA | RNA-DIRECTED RNA POLYMERASE | TOBACCO NECROSIS VIRUS (STRAIN D) | 102–144 | | | | | | | |
| PRRPP_CDVO | RNA POLYMERASE ALPHA SUBUNIT | BOVINE RESPIRATORY SYNCYTIAL VIRUS (STRAIN A51908) | 99–158 | 160–216 | | | | | | |
| PRRPP_HRSV | RNA POLYMERASE ALPHA SUBUNIT | CANINE DISTEMPER VIRUS (STRAIN ONDERSTEPOORT) | 312–373 | | | | | | | |
| PRRPP_HRSV1 | RNA POLYMERASE ALPHA SUBUNIT | HUMAN RESPIRATORY SYNCYTIAL VIRUS | 99–158 | 160–216 | | | | | | |
| PRRPP_HRSVA | RNA POLYMERASE ALPHA SUBUNIT | HUMAN RESPIRATORY SYNCYTIAL VIRUS (SUBGROUP B/STRAI | 99–158 | 160–216 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRRPP_HRSVL | RNA POLYMERASE ALPHA SUBUNIT | HUMAN RESPIRATORY SYNCYTIAL VIRUS (STRAIN A2) | 99–158 | 160–216 | | | | | | |
| PRRPP_MEASE | RNA POLYMERASE ALPHA SUBUNIT | HUMAN RESPIRATORY SYNCYTIAL VIRUS (SUBGROUP A/STRAI | 99–158 | 160–216 | | | | | | |
| PRRPP_MEASI | RNA POLYMERASE ALPHA SUBUNIT | MEASLES VIRUS (STRAIN EDMONSTON) | 315–374 | 460–495 | | | | | | |
| PRRPP_MEASY | RNA POLYMERASE ALPHA SUBUNIT | MEASLES VIRUS (STRAIN IP-3-CA) | 315–374 | 460–495 | | | | | | |
| PRRPP_MUMP1 | RNA POLYMERASE ALPHA SUBUNIT | MEASLES VIRUS (STRAIN YAMAGATA-1) | 315–374 | 460–495 | | | | | | |
| PRRPP_MUMPE | RNA POLYMERASE ALPHA SUBUNIT | MUMPS VIRUS (STRAIN SBL-1) | 149–183 | 213–275 | | | | | | |
| PRRPP_MUMPM | RNA POLYMERASE ALPHA SUBUNIT | MUMPS VIRUS (STRAIN ENDERS) | 214–276 | | | | | | | |
| PRRPP_NDVA | RNA POLYMERASE ALPHA SUBUNIT | MUMPS VIRUS (STRAIN MIYAHARA VACCINE) | 214–276 | | | | | | | |
| PRRPP_NDVB | RNA POLYMERASE ALPHA SUBUNIT | NEWCASTLE DISEASE VIRUS (STRAIN AUSTRALIA-VICTORIA/32) | 100–134 | | | | | | | |
| PRRPP_PI1HB | RNA POLYMERASE ALPHA SUBUNIT | NEWCASTLE DISEASE VIRUS (STRAIN BEAUDETTE C/45) | 100–138 | | | | | | | |
| PRRPP_PI1HC | RNA POLYMERASE ALPHA SUBUNIT | HUMAN PARAINFLUENZA 1 VIRUS (STRAIN C35) | 80–114 | 313–364 | 375–437 | | | | | |
| PRRPP_PI1HD | RNA POLYMERASE ALPHA SUBUNIT | HUMAN PARAINFLUENZA 1 VIRUS (STRAIN C39) | 80–114 | 313–364 | 375–437 | | | | | |
| PRRPP_PI1HE | RNA POLYMERASE ALPHA SUBUNIT | HUMAN PARAINFLUENZA 1 VIRUS (STRAIN C1-5/73) | 80–114 | 313–364 | 375–437 | | | | | |
| PRRPP_PI2H | RNA POLYMERASE ALPHA SUBUNIT | HUMAN PARAINFLUENZA 1 VIRUS (STRAIN C1-14/830) | 66–114 | 237–271 | 313–364 | 375–437 | | | | |
| PRRPP_PI2HT | RNA POLYMERASE ALPHA SUBUNIT | HUMAN PARAINFLUENZA 2 VIRUS | 218–281 | | | | | | | |
| PRRPP_PI3B | RNA POLYMERASE ALPHA SUBUNIT | HUMAN PARAINFLUENZA 2 VIRUS (STRAIN TOSHIBA) | 218–281 | | | | | | | |
| PRRPP_PI3H4 | RNA POLYMERASE ALPHA SUBUNIT | BOVINE PARAINFLUENZA 3 VIRUS | 31–130 | 414–470 | | | | | | |
| PRRPP_PI4HA | RNA POLYMERASE ALPHA SUBUNIT | HUMAN PARAINFLUENZA 3 VIRUS (STRAIN NIH 47885) | 410–499 | | | | | | | |
| PRRPP_PI4HB | RNA POLYMERASE ALPHA SUBUNIT | HUMAN PARAINFLUENZA 4A VIRUS (STRAIN TOSHIBA) | 4–38 | 222–285 | | | | | | |
| PRRPP_PIRYV | RNA POLYMERASE ALPHA SUBUNIT | HUMAN PARAINFLUENZA 4B VIRUS (STRAIN 68-333) | 222–285 | | | | | | | |
| PRRPP_RABVA | RNA POLYMERASE ALPHA SUBUNIT | PIRY VIRUS | 137–174 | | | | | | | |
| PRRPP_RABVC | RNA POLYMERASE ALPHA SUBUNIT | RABIES VIRUS (STRAIN AVO1) | 93–127 | | | | | | | |
| PRRPP_RABVE | RNA POLYMERASE ALPHA SUBUNIT | RABIES VIRUS (STRAIN CVS-11) | 93–127 | | | | | | | |
| PRRPP_RABVP | RNA POLYMERASE ALPHA SUBUNIT | RABIES VIRUS (STRAIN ERA), AND (STRAIN PM) | 93–127 | | | | | | | |
| PRRPP_RABVS | RNA POLYMERASE ALPHA SUBUNIT | RABIES VIRUS (STRAIN PV) | 93–127 | | | | | | | |
| PRRPP_SEND5 | RNA POLYMERASE ALPHA SUBUNIT | RABIES VIRUS (STRAIN SAD B19 | 93–127 | | | | | | | |
| PRRPP_SEND6 | RNA POLYMERASE ALPHA SUBUNIT | SENDAI VIRUS (STRAIN Z/HOST MUTANTS) | 313–364 | 375–447 | | | | | | |
| PRRPP_SENDF | RNA POLYMERASE ALPHA SUBUNIT | SENDAI VIRUS (STRAIN 6/94) | 323–364 | 375–447 | | | | | | |
| PRRPP_SENDH | RNA POLYMERASE ALPHA SUBUNIT | SENDAI VIRUS (STRAIN FUSHIMI) | 313–364 | 375–447 | | | | | | |
| PRRPP_SENDZ | RNA POLYMERASE ALPHA SUBUNIT | SENDAI VIRUS (STRAIN HARRIS) | 313–364 | 375–447 | | | | | | |
| PRRPP_SV5 | RNA POLYMERASE ALPHA SUBUNIT | SENDAI VIRUS (STRAIN Z) | 313–364 | 375–447 | | | | | | |
| PRRPP_SYNV | RNA POLYMERASE ALPHA SUBUNIT | SIMIAN VIRUS 5 (STRAIN W3) | 205–278 | | | | | | | |
| PRRPP_VSVIG | RNA POLYMERASE ALPHA SUBUNIT | SONCHUS YELLOW NET VIRUS | 138–173 | 233–281 | | | | | | |
| PRRPP_VSVIM | RNA POLYMERASE ALPHA SUBUNIT | VESICULAR STOMATITIS VIRUS (SEROTYPE INDIANA/STRAIN G | 3–43 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PRRPP_VSVJM | RNA POLYMERASE ALPHA SUBUNIT | VESICULAR STOMATITIS VIRUS (SEROTYPE INDIANA/STRAIN M | 3–43 | | | | | | | |
| PRRPP_VSVJO | RNA POLYMERASE ALPHA SUBUNIT | VESICULAR STOMATITIS VIRUS (SEROTYPE NEW JERSEY/STRA | 3–37 | | | | | | | |
| PRRPP_VSVSJ | RNA POLYMERASE ALPHA SUBUNIT | VESICULAR STOMATITIS VIRUS (SEROTYPE NEW JERSEY/STRA | 3–37 | | | | | | | |
| PSPHR_AMEPV | RNA POLYMERASE ALPHA SUBUNIT | VESICULAR STOMATITIS VIRUS (STRAIN SAN JUAN) | 3–43 | | | | | | | |
| PSP12_VACCV | SPHEROIDIN | AMSACTA MOOREI ENTOMOPOXVIRUS | 223–264 | 361–395 | | | | | | |
| PSP12_VARV | SERINE PROTEINASE INHIBITOR | VACCINIA VIRUS (STRAIN WR) | 21–86 | | | | | | | |
| PSP13_VACCC | SERINE PROTEINASE INHIBITOR 2 | VARIOLA VIRUS | 21–86 | | | | | | | |
| PSP13_VACCV | SERINE PROTEINASE INHIBITOR 3 | VACCINIA VIRUS (STRAIN COPENHAGEN) | 118–167 | 225–266 | | | | | | |
| PSP13_VARV | SERINE PROTEINASE INHIBITOR 3 | VACCINIA VIRUS (STRAIN WR) | 118–167 | 225–266 | | | | | | |
| PSPIA_VACCC | SERINE PROTEINASE INHIBITOR 3 | VARIOLA VIRUS | 122–171 | 229–270 | | | | | | |
| PT2C2_CHVP1 | SERINE PROTEINASE INHIBITOR 2 HOMOLOG FIRST | VACCINIA VIRUS (STRAIN COPENHAGEN) | 11–65 | | | | | | | |
| PTAA2_VACCV | TYPE II RESTRICTION ENZYME CVIAII | PARAMECIUM BURSARIA CHLORELLA VIRUS 1 | 48–85 | | | | | | | |
| PTAG8_FOWPV | TRANS-ACTIVATOR PROTEIN A2 | VACCINIA VIRUS (STRAIN WR, COPENHAGEN, AND VARIOLA VI | 95–133 | 173–207 | | | | | | |
| PTAG8_VACCV | TRANS-ACTIVATOR PROTEIN FP0 | FOWLPOX VIRUS | 3–51 | | | | | | | |
| PTAG8_VARV | TRANS-ACTIVATOR PROTEIN GK1 | VACCINIA VIRUS (STRAIN WR), (STRAIN COPENHAGEN) | 3–51 | | | | | | | |
| PTALA_BFDV | TRANS-ACTIVATOR PROTEIN GK1 | VARIOLA VIRUS | 3–51 | | | | | | | |
| PTALA_POVBO | LARGE T ANTIGEN | BUDGERIGAR FLEDGLING DISEASE VIRUS | 291–325 | 464–498 | | | | | | |
| PTALA_POVHA | LARGE T ANTIGEN | BOVINE POLYOMAVIRUS | 303–337 | 495–537 | | | | | | |
| PTALA_POVJC | LARGE T ANTIGEN | HAMSTER POLYOMAVIRUS | 464–501 | 587–621 | | | | | | |
| PTALA_POVLY | LARGE T ANTIGEN | POLYOMAVIRUS JC | 153–187 | 589–623 | | | | | | |
| PTALA_POVM3 | LARGE T ANTIGEN | LYMPHOTROPIC POLYOMAVIRUS | 3–41 | 206–258 | 437–478 | | | | | |
| PTALA_POVMA | LARGE T ANTIGEN | MOUSE POLYOMAVIRUS (STRAIN 3) | 509–544 | | | | | | | |
| PTALA_POVMC | LARGE T ANTIGEN | MOUSE POLYOMAVIRUS (STRAIN A2) | 507–542 | | | | | | | |
| PTAMI_POVHA | LARGE T ANTIGEN | MOUSE POLYOMAVIRUS (STRAIN CRAWFORD SMALL-PLAQUE) | 504–539 | | | | | | | |
| PTAMI_POVM3 | MIDDLE T ANTIGEN | HAMSTER POLYOMAVIRUS | 339–378 | | | | | | | |
| PTAMI_POVMA | MIDDLE T ANTIGEN | MOUSE POLYOMAVIRUS (STRAIN 3) | 211–245 | 388–422 | | | | | | |
| PTAMI_POVMC | MIDDLE T ANTIGEN | MOUSE POLYOMAVIRUS (STRAIN A2) | 192–226 | 369–403 | | | | | | |
| PTASM_POVBO | MIDDLE T ANTIGEN | MOUSE POLYOMAVIRUS (STRAIN CRAWFORD SMALL-PLAQUE) | 192–226 | 369–403 | | | | | | |
| PTASM_POVLY | SMALL T ANTIGEN | BOVINE POLYOMAVIRUS | 41–85 | | | | | | | |
| PTATR_NPVAC | SMALL T ANTIGEN | LYMPHOTROPIC POLYOMAVIRUS | 3–41 | | | | | | | |
| PTATR_NPVBM | TRANS-ACTIVATING TRANSCRIPTIONAL REGULAT | AUTOGRAPHA CALIFORNICA NUCLEAR POLYHEDROSIS VIRUS | 408–442 | 46–480 | 489–523 | | | | | |
| PTATR_NPVOP | TRANS-ACTIVATING TRANSCRIPTIONAL REGULAT | BOMBYX MORI NUCLEAR POLYHEDROSIS VIRUS | 413–447 | 451–485 | 494–528 | | | | | |
| PTAT_SIVA1 | TRANS-ACTIVATING TRANSCRIPTIONAL REGULAT | ORGYIA PSEUDOTSUGATA MULTICAPSID POLYHEDROSIS VIRUS | 391–455 | 511–554 | | | | | | |
| PTAT_SIVAI | TAT PROTEIN | SIMIAN IMMUNODEFICIENCY VIRUS (AGM155 ISOLATE) | 73–109 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PTAT_VILV | TAT PROTEIN | SIMIAN IMMUNODEFICIENCY VIRUS (ISOLATE AGM/CLONE GR1) | 137–185 | | | | | | | |
| PTAT_VILV1 | TRANS-ACTIVATING TRANSCRIPTIONAL REGULAT | VISNA LENTIVIRUS (STRAIN 1514) | 28–74 | | | | | | | |
| PTAT_VILV2 | TRANS-ACTIVATING TRANSCRIPTIONAL REGULAT | VISNA LENTIVIRUS (STRAIN 1514/CLONE LV1-1KS1) | 40–74 | | | | | | | |
| PTCB_FIV | TRANS-ACTIVATING TRANSCRIPTIONAL REGULAT | VISNA LENTIVIRUS (STRAIN 1514/CLONE LV1-1KS2) | 40–74 | | | | | | | |
| PTEGP_HSV11 | T-CELL RECEPTOR BETA CHAIN PRECURSOR | FELINE LEUKEMIA VIRUS | 279–321 | | | | | | | |
| PTEGP_HSVEA | TEGUMENT PHOSPHOPROTEIN US9 | HERPES SIMPLEX VIRUS (TYPE 1/STRAIN 17) | 27–61 | | | | | | | |
| PTEGP_HSVEB | NONSENSE | | | | | | | | | |
| PTEGP_HSVEK | NONSENSE | | | | | | | | | |
| PTEGP_HSVSB | NONSENSE | | | | | | | | | |
| PTEGU_EBV | NONSENSE | | | | | | | | | |
| PTEGU_HCMVA | LARGE TEGUMENT PROTEIN | EPSTEIN-BARR VIRUS (STRAIN B95-8) | 768–802 | 821–855 | 938–972 | 1101–1138 | 1208–1242 | 1479–1516 | 1700–1753 | 1809–1867 |
| | | | 1870–1916 | 1920–1954 | 3108–3149 | | | | | |
| | | | 34–71 | 215–249 | 543–581 | | | | | |
| PTEGU_HSV11 | PROBABLE LARGE TEGUMENT PROTEIN | HUMAN CYTOMEGALOVIRUS (STRAIN AD169) | 1237–1296 | 2200–2235 | | 700–738 | 868–909 | 936–977 | 1004–1038 | 1163–1200 |
| PTEGU_HSV6G | LARGE TEGUMENT PROTEIN | HERPES SIMPLEX VIRUS (TYPE 1/STRAIN 17) | 731–765 | 801–842 | 1022–1059 | 1223–1269 | 1275–1309 | 1315–1370 | 1520–1531 | 1609–1669 |
| | | | 1673–1714 | 1749–1783 | 1820–1854 | 2670–2704 | | | | |
| PTEGU_HSVEB | LARGE TEGUMENT PROTEIN | HERPES SIMPLEX VIRUS (TYPE 6/STRAIN GS) | 30–71 | 224–262 | 567–608 | 712–757 | 951–1000 | 1091–1181 | 1192–1233 | 1357–1400 |
| PTEGU_HSVSA | LARGE TEGUMENT PROTEIN | EQUINE HERPESVIRUS TYPE 1 (STRAIN AB4P) | 560–597 | 635–683 | 794–848 | 908–956 | 1108–1151 | 1155–1246 | 1399–1458 | 1487–1549 |
| | | | 1619–1657 | 1661–1695 | 1702–1736 | 1806–1843 | 1947–1981 | | | |
| PTEGU_VZVD | PROBABLE LARGE TEGUMENT PROTEIN | HERPESVIRUS SAIMIRI (STRAIN 11) | 520–558 | 560–598 | 615–652 | 672–710 | 777–822 | 846–898 | 948–986 | 1287–1332 |
| | | | 1434–1502 | | | | | | | |
| PTERM_ADE02 | LARGE TEGUMENT PROTEIN | VARICELLA-ZOSTER VIRUS (STRAIN DUMAS) | 657–696 | 713–747 | 804–841 | 933–972 | 1117–1158 | 1415–1471 | 1528–1562 | 1572–1620 |
| | | | 1633–1705 | 1719–1756 | 1945–1986 | 2727–2761 | | | | |
| PTERM_ADE05 | DNA TERMINAL PROTEIN | HUMAN ADENOVIRUS TYPE 2 | 490–572 | | | | | | | |
| PTERM_ADE07 | DNA TERMINAL PROTEIN | HUMAN ADENOVIRUS TYPE 5 | 490–592 | | | | | | | |
| PTERM_ADE12 | DNA TERMINAL PROTEIN | HUMAN ADENOVIRUS TYPE 7 | 491–559 | | | | | | | |
| PIJUN_AVIS1 | DNA TERMINAL PROTEIN | HUMAN ADENOVIRUS TYPE 12 | 443–491 | | | | | | | |
| PTMAF_AVIS4 | TRANSFORMING PROTEIN JUN | AVIAN SARCOMA VIRUS (STRAIN 17) | 210–284 | 497–538 | | | | | | |

TABLE V-continued

ALLMOT5 SEARCH RESULTS SUMMARY FOR ALL VIRAL (NON-BACTERIOPHAGE) PROTEINS

| PCGENE FILE NAME | ALLMOT5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PTOP1_SFVKA | TRANSFORMING PROTEIN MAF | AVIAN MUSCULOAPONEUROTIC FIBROSARCOMA VIRUS AS42 | 247–288 | 295–340 | | | | | | |
| PTOP2_ASFB7 | DNA TOPOISOMERASE | SHOPE FIBROMA VIRUS (STRAIN KASZA) | 127–183 | 269–310 | 601–642 | 945–979 | 1038–1093 | 1123–1162 | | |
| PTOP2_ASFM2 | DNA TOPOISOMERASE II | AFRICAN SWINE FEVER VIRUS (STRAIN BA71V) | 146–180 | 481–515 | | | | | | |
| PTSIS_SMSAV | DNA TOPOISOMERASE II | AFRICAN SWINE FEVER VIRUS (ISOLATE MALAWI LIL 20/1) | 146–180 | 480–514 | 600–641 | 902–936 | 944–978 | 1038–1091 | 1122–1161 | |
| PTYSY_VZVD | PDGF-RELATED TRANSFORMING PROTEIN P28-SIS | SIMIAN SARCOMA VIRUS | 16–71 | | | | | | | |
| PUBIL_NPVOP | THYMIDYLATE SYNTHASE | VARICELLA-ZOSTER VIRUS (STRAIN DUMAS) | 215–260 | | | | | | | |
| PUL01_HCMVA | UBIQUITIN-LIKE PROTEIN | ORGYIA PSEUDOTSUGATA MULTICAPSID POLYHEDROSIS VIRUS | 43–80 | | | | | | | |
| PUL03_HSV13 | HYPOTHETICAL PROTEIN UL1 | HUMAN CYTOMEGALOVIRUS (STRAIN AD169) | 169–203 | | | | | | | |
| PUL03_HSV2H | PROTEIN UL3 | HERPES SIMPLEX VIRUS (TYPE 1/STRAIN 17) | 94–128 | | | | | | | |
| PUL03_HSVEB | PROTEIN UL3 | HERPES SIMPLEX VIRUS (TYPE 2/STRAIN HG52) | 92–126 | | | | | | | |
| PUL04_HSV11 | GENE 60 PROTEIN | EQUINE HERPESVIRUS TYPE 1 (STRAIN AB4P) | 70–104 | | | | | | | |
| PUL06_EBV | PROTEIN UL4 | HERPES SIMPLEX VIRUS (TYPE 1/STRAIN 17) | 102–136 | | | | | | | |
| PUL06_HCMVA | VIRION PROTEIN BBRF1 | EPSTEIN-BARR VIRUS (STRAIN B95-8) | 104–145 | 313–347 | 376–410 | | | | | |
| PUL06_HSV11 | HYPOTHETICAL PROTEIN UL6 | HUMAN CYTOMEGALOVIRUS (STRAIN AD169) | 216–250 | | | | | | | |
| PUL06_HSVEB | VIRION PROTEIN UL6 | HERPES SIMPLEX VIRUS (TYPE 1/STRAIN 17) | 36–94 | 103–141 | 294–329 | 337–371 | | | | |
| PUL06_HSVSA | VIRION GENE 56 PROTEIN | EQUINE HERPESVIRUS TYPE 1 (STRAIN AB4P) | 62–170 | 357–413 | 448–503 | | | | | |
| PUL06_VZVD | VIRION GENE 43 PROTEIN | HERPESVIRUS SAIMIRI (STRAIN 11) | 90–140 | 151–194 | 302–336 | 364–405 | 416–479 | | | |
| PUL08_HCMVA | VIRION GENE 54 PROTEIN | VARICELLA-ZOSTER VIRUS (STRAIN DUMAS) | 87–131 | 350–409 | 704–738 | | | | | |
| PUL09_HSVEB | HYPOTHETICAL PROTEIN UL8 | HUMAN CYTOMEGALOVIRUS (STRAIN AD169) | 6–50 | | | | | | | |
| PUL09_VZVD | ORIGIN OF REPLICATION BINDING PROTEIN | EQUINE HERPESVIRUS TYPE 1 (STRAIN AB4P) | 174–208 | | | | | | | |
| PUL11_HSVEB | ORIGIN OF REPLICATION BINDING PROTEIN | VARICELLA-ZOSTER VIRUS (STRAIN DUMAS) | 122–163 | | | | | | | |
| PUL13_HCMVA | NONSENSE | | | | | | | | | |
| PUL14_HCMVA | HYPOTHETICAL PROTEIN UL13 | HUMAN CYTOMEGALOVIRUS (STRAIN AD169) | 47–81 | 185–227 | | | | | | |
| PUL14_HSVEB | HYPOTHETICAL PROTEIN UL14 | HUMAN CYTOMEGALOVIRUS (STRAIN AD169) | 305–343 | | | | | | | |
| PUL14_PRVN3 | HYPOTHETICAL GENE 48 PROTEIN | EQUINE HERPESVIRUS TYPE 1 (STRAIN AB4P) | 52–96 | 246–283 | | | | | | |
| PUL14_VZVD | UL14 PROTEIN HOMOLOG | PSEUDORABIES VIRUS (STRAIN NIA-3) | 43–95 | | | | | | | |
| PUL16_HSVEB | HYPOTHETICAL GENE 46 PROTEIN | VARICELLA-ZOSTER VIRUS (STRAIN DUMAS) | 61–103 | | | | | | | |
| PUL17_HSV6U | GENE 46 PROTEIN | EQUINE HERPESVIRUS TYPE 1 (STRAIN AB4P) | 266–300 | | | | | | | |
| PUL21_HSVEB | PROTEIN 10R | HERPES SIMPLEX VIRUS (TYPE 6/STRAIN UGANDA-1102) | 239–280 | | | | | | | |
| PUL23_HCMVA | GENE 40 PROTEIN | EQUINE HERPESVIRUS TYPE 1 (STRAIN AB4P) | 44–78 | 421–474 | | | | | | |
| PUL24_HCMVA | HYPOTHETICAL PROTEIN UL23 | HUMAN CYTOMEGALOVIRUS (STRAIN AD169) | 213–253 | | | | | | | |
| PUL24_IIITVT | HYPOTHETICAL PROTEIN UL24 | HUMAN CYTOMEGALOVIRUS (STRAIN AD169) | 5–39 | | | | | | | |
| PUL25_HCMVA | PROTEIN UL24 HOMOLOG | INFECTIOUS LARYNGOTRACHEITIS VIRUS (STRAIN THORNE V88) | 161–195 | | | | | | | |
| PUL25_HSV11 | HYPOTHETICAL PROTEIN UL25 | HUMAN CYTOMEGALOVIRUS (STRAIN AD169) | 255–341 | 351–399 | | | | | | |
| PUL25_HSVEB | VIRION PROTEIN UL25 | HERPES SIMPLEX VIRUS (TYPE 1/STRAIN 17) | 370–411 | | | | | | | |
| PUL25_HSVSA | VIRION PROTEIN UL25 | EQUINE HERPESVIRUS TYPE 1 (STRAIN AB4P) | 364–413 | | | | | | | |
| PUL25_IIITVT | VIRION GENE 19 PROTEIN | HERPESVIRUS SAIMIRI (STRAIN 11) | 29–92 | 183–231 | 365–406 | | | | | |
| PUL25_VZVD | 64.1 KD VIRION PROTEIN | INFECTIOUS LARYNGOTRACHEITIS VIRUS (STRAIN THORNE V88) | 38–84 | 165–206 | | | | | | |
| PUL31_HCMVA | VIRION GENE 34 PROTEIN | VARICELLA-ZOSTER VIRUS (STRAIN DUMAS) | 340–388 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PUL31_HSVEB | HYPOTHETICAL PROTEIN UL31 | HUMAN CYTOMEGALOVIRUS (STRAIN AD169) | 244–285 | | | | | | | |
| PUL31_VZVD | GENE 29 PROTEIN | EQUINE HERPESVIRUS TYPE 1 (STRAIN AB4P) | 153–187 | | | | | | | |
| PUL32_HSVEB | GENE 27 PROTEIN | VARICELLA-ZOSTER VIRUS (STRAIN DUMAS) | 163–197 | | | | | | | |
| PUL32_VZVD | MAJOR ENVELOPE GLYCOPROTEIN 300 | EQUINE HERPESVIRUS TYPE 1 (STRAIN AB4P) (STRAIN AB1) | 342–376 | | | | | | | |
| PUL33_HCMVA | PROBABLE MAJOR ENVELOPE GLYCOPROTEIN 26 | VARICELLA-ZOSTER VIRUS (STRAIN DUMAS) | 72–106 | 296–344 | | | | | | |
| PUL33_VZVD | G-PROTEIN COUPLED RECEPTOR HOMOLOG UL33 | HUMAN CYTOMEGALOVIRUS (STRAIN AD169) | 94–135 | 309–352 | | | | | | |
| PUL34_EBV | GENE 25 PROTEIN | VARICELLA-ZOSTER VIRUS (STRAIN DUMAS) | 29–63 | | | | | | | |
| PUL34_HCMVA | BFRF1 PROTEIN | EPSTEIN-BARR VIRUS (STRAIN B95-8) | 159–200 | | | | | | | |
| PUL34_HSV11 | HYPOTHETICAL PROTEIN UL34 | HUMAN CYTOMEGALOVIRUS (STRAIN AD169) | 113–147 | | | | | | | |
| PUL35_HCMVA | VIRION PROTEIN UL34 | HERPES SIMPLEX VIRUS (TYPE 1/STRAIN 17) | 187–221 | | | | | | | |
| PUL37_EBV | HYPOTHETICAL PROTEIN UL35 | HUMAN CYTOMEGALOVIRUS (STRAIN AD169) | 231–268 | | | | | | | |
| PUL37_HSV11 | PROTEIN BOLF1 | EPSTEIN-BARR VIRUS (STRAIN B95-8) | 708–742 | | | | | | | |
| PUL37_HSVEB | PROTEIN UL37 | HERPES SIMPLEX VIRUS (TYPE 1/STRAIN 17) | 853–891 | | | | | | | |
| PUL37_HSVSA | GENE 23 PROTEIN | EQUINEHERPES VIRUS TYPE 1 (STRAIN AB4P) | 82–137 | 311–345 | 614–648 | 715–750 | 781–822 | | | |
| PUL37_VZVD | GENE 63 PROTEIN | HERPESVIRUS SAIMIRI (STRAIN 11) | 6–65 | 682–741 | | | | | | |
| PUL38_HCMVA | GENE 21 PROTEIN | VARICELLA-ZOSTER VIRUS (STRAIN DUMAS) | 719–753 | 786–827 | | | | | | |
| PUL41_VZVD | HYPOTHETICAL PROTEIN UL38 | HUMAN CYTOMEGALOVIRUS (STRAIN AD169) | 10–51 | | | | | | | |
| PUL42_HSV11 | HOST SHUTOFF VIRION PROTEIN | VARICELLA-ZOSTER VIRUS (STRAIN DUMAS) | 330–366 | | | | | | | |
| PUL42_VZVD | DNA-BINDING PROTEIN UL42 | HERPES SIMPLEX VIRUS (TYPE 1/STRAIN 17) | 134–168 | 221–263 | | | | | | |
| PUL43_HCMVA | DNA-BINDING GENE 18 PROTEIN | HUMAN CYTOMEGALOVIRUS (STRAIN AD169) | 138–172 | | | | | | | |
| PUL43_HSVE4 | HYPOTHETICAL PROTEIN UL43 | EQUINE HERPESVIRUS TYPE 4 (STRAIN 1942) | 72–109 | | | | | | | |
| PUL43_VZVD | MEMBRANE PROTEIN UL43 HOMOLOG | VARICELLA-ZOSTER VIRUS (STRAIN DUMAS) | 27–68 | | | | | | | |
| PUL45_HSV1K | GENE 15 MEMBRANE PROTEIN | VARICELLA-ZOSTER VIRUS (STRAIN DUMAS) | 312–363 | | | | | | | |
| PUL45_HSV1M | PROTEIN UL45 | HERPES SIMPLEX VIRUS (TYPE 1/STRAIN KOS) | 96–137 | | | | | | | |
| PUL45_HCMVA | PROTEIN UL45 | HERPES SIMPLEX VIRUS (TYPE 1/STRAIN MP) | 96–137 | | | | | | | |
| PUL47_HCMVA | PROTEIN UL47 | HUMAN CYTOMEGALOVIRUS (STRAIN AD169) | 114–165 | 448–485 | 745–856 | | | | | |
| PUL47_HSV11 | VIRION PROTEIN UL47 | HERPES SIMPLEX VIRUS (TYPE 1/STRAIN 17) | 473–518 | | | | | | | |
| PUL47_HSV1F | VIRION PROTEIN UL47 | HERPES SIMPLEX VIRUS (TYPE 1/STRAIN F) | 473–518 | | | | | | | |
| PUL47_HSVBP | 80.7 KD ALPHA TRANS-INDUCING PROTEIN | BOVINE HERPESVIRUS TYPE 1 (STRAIN P8-2) | 561–612 | | | | | | | |
| PUL47_HSVE4 | 97 KD ALPHA TRANS-INDUCING PROTEIN | EQUINE HERPESVIRUS TYPE 4 (STRAIN 1942) | 183–246 | 582–620 | 825–866 | | | | | |
| PUL47_HSVEB | 97 KD ALPHA TRANS-INDUCING PROTEIN | EQUINE HERPESVIRUS TYPE 1 (STRAIN AB4P) | 219–253 | 371–412 | 817–866 | | | | | |
| PUL47_VZVD | ALPHA TRANS-INDUCING FACTOR 91.8 KD PROTEIN | VARICELLA-ZOSTER VIRUS (STRAIN DUMAS) | 84–135 | 156–209 | 664–701 | | | | | |
| PUL50_HCMVA | PROTEIN UL50 | HUMAN CYTOMEGALOVIRUS (STRAIN AD169) | 155–189 | | | | | | | |
| PUL51_HSVE4 | PROTEIN UL51 | HERPES SIMPLEX VIRUS (TYPE 1/STRAIN 17) | 118–169 | | | | | | | |
| PUL51_HSVEB | GENE 8 PROTEIN | EQUINE HERPESVIRUS TYPE 4 (STRAIN 1942) | 121–162 | | | | | | | |
| PUL51_VZVD | GENE 8 PROTEIN | EQUINE HERPESVIRUS TYPE 1 (STRAIN AB4P) | 120–161 | | | | | | | |
| PUL52_EBV | GENE 7 PROTEIN | VARICELLA-ZOSTER VIRUS (STRAIN DUMAS) | 122–163 | | | | | | | |
| PUL52_HSV11 | PROBABLE DNA REPLICATION PROTEIN BSLF1 | EPSTEIN-BARR VIRUS (STRAIN B95-8) | 188–255 | | | | | | | |
| PUL52_HSVEB | DNA REPLICATION PROTEIN UL52 | HERPES SIMPLEX VIRUS (TYPE 1/STRAIN 17) | 189–223 | | | | | | | |
| PUL52_HSVSA | DNA REPLICATION PROTEIN UL52 | EQUINE HERPESVIRUS TYPE 1 (STRAIN AB4P) | 141–182 | 929–970 | | | | | | |
| PUL52_VZVD | PROBABLE DNA REPLICATION GENE 56 PROTEIN | HERPESVIRUS SAIMIRI (STRAIN 11) | 445–483 | | | | | | | |

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PUL53_HCMVA | PROBABLE DNA REPLICATION GENE 6 PROTEIN | VARICELLA-ZOSTER VIRUS (STRAIN DUMAS) | 301–342 | | | | | | | |
| PUL55_HSV2H | PROTEIN UL53 | HERPES SIMPLEX VIRUS (TYPE 2/STRAIN HG52) | 12–48 | | | | | | | |
| PUL64_HCMVA | PROTEIN UL55 | HUMAN CYTOMEGALOVIRUS (STRAIN AD169) | 151–185 | | | | | | | |
| PUL70_HCMVA | HYPOTHETICAL PROTEIN UL64 | HUMAN CYTOMEGALOVIRUS (STRAIN AD169) | 32–73 | | | | | | | |
| PUL74_HCMVA | PROBABLE DNA REPLICATION PROTEIN UL70 | HUMAN CYTOMEGALOVIRUS (STRAIN AD169) | 39–99 | | | | | | | |
| PUL87_HSV6U | HYPOTHETICAL PROTEIN UL74 | HUMAN CYTOMEGALOVIRUS (STRAIN AD169) | 43–79 | | | | | | | |
| PUL87_HSVSA | HYPOTHETICAL PROTEIN 5R | HERPES SIMPLEX VIRUS (TYPE 6/STRAIN UGANDA-1102) | 729–770 | | | | | | | |
| PUL88_HCMVA | HYPOTHETICAL GENE 24 PROTEIN | HERPESVIRUS SAIMIRI (STRAIN 11) | 366–400 | 582–616 | | | | | | |
| PUL91_HSVSA | HYPOTHETICAL PROTEIN UL88 | HUMAN CYTOMEGALOVIRUS (STRAIN AD169) | 357–391 | | | | | | | |
| PUL92_EBV | HYPOTHETICAL GENE 30 PROTEIN | HERPESVIRUS SAIMIRI (STRAIN 11) | 24–58 | | | | | | | |
| PUL92_HCMVA | HYPOTHETICAL PROTEIN BDLF4 | EPSTEIN-BARR VIRUS (STRAIN B95-8) | 107–144 | 188–222 | | | | | | |
| PUL92_HSV6U | HYPOTHETICAL PROTEIN UL92 | HUMAN CYTOMEGALOVIRUS (STRAIN AD169) | 79–116 | | | | | | | |
| PUL92_HSVSA | HYPOTHETICAL PROTEIN 9R | HERPES SIMPLEX VIRUS (TYPE 6/STRAIN UGANDA-1102) | 101–145 | 174–216 | | | | | | |
| PUL93_HCMVA | HYPOTHETICAL GENE 31 PROTEIN | HERPESVIRUS SAIMIRI (STRAIN 11) | 88–122 | | | | | | | |
| PUL95_HCMVA | PROTEIN UL93 | HUMAN CYTOMEGALOVIRUS (STRAIN AD169) | 23–57 | 299–384 | | | | | | |
| PUL95_HSV6U | HYPOTHETICAL PROTEIN UL95 | HUMAN CYTOMEGALOVIRUS (STRAIN AD169) | 34–71 | 259–293 | | | | | | |
| PUL96_HCMVA | HYPOTHETICAL PROTEIN 13R | HERPES SIMPLEX VIRUS (TYPE 6/STRAIN UGANDA-1102) | 73–151 | 233–270 | | | | | | |
| PUL96_HSV6U | HYPOTHETICAL PROTEIN UL96 | HUMAN CYTOMEGALOVIRUS (STRAIN AD169) | 51–103 | | | | | | | |
| PUL96_HSVSA | HYPOTHETICAL PROTEIN 14R | HERPES SIMPLEX VIRUS (TYPE 6/STRAIN UGANDA-1102) | 53–113 | | | | | | | |
| PULA2_HCMVA | HYPOTHETICAL GENE 35 PROTEIN | HERPESVIRUS SAIMIRI (STRAIN 11) | 45–100 | | | | | | | |
| PULA4_HCMVA | HYPOTHETICAL PROTEIN UL102 | HUMAN CYTOMEGALOVIRUS (STRAIN AD169) | 6–40 | 758–792 | | | | | | |
| PULD0_HCMVA | VIRION PROTEIN UL104 | HUMAN CYTOMEGALOVIRUS (STRAIN AD169) | 1–56 | 130–171 | | | | | | |
| PUNG_HSV11 | HYPOTHETICAL PROTEIN UL130 | HUMAN CYTOMEGALOVIRUS (STRAIN AD169) | 84–125 | | | | | | | |
| PUNG_HSV23 | URACIL-DNA GLYCOSYLASE | HERPES SIMPLEX VIRUS (TYPE 1/STRAIN 17) | 227–268 | | | | | | | |
| PUNG_HSV2H | URACIL-DNA GLYCOSYLASE | HERPES SIMPLEX VIRUS (TYPE 2/STRAIN 333) | 188–229 | | | | | | | |
| PUNG_HSVSA | URACIL-DNA GLYCOSYLASE | HERPES SIMPLEX VIRUS (TYPE 2/STRAIN HG52) | 148–189 | | | | | | | |
| PUNG_SFVKA | URACIL-DNA GLYCOSYLASE | HERPESVIRUS SAIMIRI (STRAIN 11) | 135–176 | | | | | | | |
| PUS02_HSVEB | SHOPE FIBROMA VIRUS (STRAIN KASZA) | | 81–115 | | | | | | | |
| PUS02_HSVEK | GENE 68 PROTEIN | EQUINE HERPESVIRUS TYPE 1 (STRAIN AB4P) | 79–120 | | | | | | | |
| PUS07_HCMVA | US1 PROTEIN | EQUINE HERPESVIRUS TYPE 1 (STRAIN KENTUCKY A) | 86–120 | | | | | | | |
| PUS11_HCMVA | HYPOTHETICAL PROTEIN HXLF5 | | 2–36 | | | | | | | |
| PUS14_HCMVA | HYPOTHETICAL PROTEIN HXLF1 | HUMAN CYTOMEGALOVIRUS (STRAIN AD169) | 3–51 | | | | | | | |
| PUS18_HCMVA | HYPOTHETICAL PROTEIN HVLF4 | HUMAN CYTOMEGALOVIRUS (STRAIN AD169) | 187–225 | | | | | | | |
| PUS23_HCMVA | MEMBRANE PROTEIN HWLF5 | HUMAN CYTOMEGALOVIRUS (STRAIN AD169) | 294–335 | 535–578 | 330–364 | 439–492 | 541–575 | | | |
| PUS24_HCMVA | HYPOTHETICAL PROTEIN HHLF7 | HUMAN CYTOMEGALOVIRUS (STRAIN AD169) | 135–172 | | | | | | | |
| PUS26_HCMVA | HYPOTHETICAL PROTEIN HHLF6 | HUMAN CYTOMEGALOVIRUS (STRAIN AD169) | 535–584 | | | | | | | |
| PUS27_HCMVA | HYPOTHETICAL PROTEIN HHLF5 | HUMAN CYTOMEGALOVIRUS (STRAIN AD169) | 6–40 | | | | | | | |
| PUS30_HCMVA | G-PROTEIN COUPLED RECEPTOR HOMOLOG US27 | HUMAN CYTOMEGALOVIRUS (STRAIN AD169) | | | | | | | | |
| PV125_AMVLE | HYPOTHETICAL PROTEIN HHRF5 | HUMAN CYTOMEGALOVIRUS (STRAIN AD169) | 135–169 | 274–312 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PV143_NPVAC | 125 KD PROTEIN | ALFALFA MOSAIC VIRUS | 18–52 | 326-367 | 591-649 | | | | | |
| PV16K_TRVPS | HELICASE | (STRAIN 425/ISOLATE LEIDEN AUTOGRAPHA CALIFORNICA NUCLEAR POLYHEDROSIS VIRUS | 313–350 | 1114–1150 | 1179–1213 | | | | | |
| PV16K_TRVSY | 16 KD PROTEIN | TOBACCO RATTLE VIRUS (STRAIN PSG) | 75–117 | | | | | | | |
| PV1A_BBMV | 16 KD PROTEIN | TOBACCO RATTLE VIRUS (STRAIN SYM) | 75–117 | | | | | | | |
| PV1A_BMV | 1A PROTEIN | BROAD BEAN MOTTLE VIRUS | 21–55 | 349-405 | 492–526 | 710–751 | 837–884 | 890–924 | | |
| PV1A_CCMV | 1A PROTEIN | BROME MOSAIC VIRUS | 4–66 | 348–411 | | | | | | |
| PV1A_CMVFN | 1A PROTEIN | COWPEA CHLOROTIC MOTTLE VIRUS | 4–53 | 242–276 | 348–389 | 487–526 | | | | |
| PV1A_CMVO | 1A PROTEIN | CUCUMBER MOSAIC VIRUS (STRAIN FNY) | 11–66 | 393–434 | 584–619 | 868–916 | | | | |
| PV1A_CMVQ | 1A PROTEIN | CUCUMBER MOSAIC VIRUS (STRAIN O) | 11–66 | 393–434 | 584–619 | 868–916 | | | | |
| PV1A_PSVJ | 1A PROTEIN | CUCUMBER MOSAIC VIRUS (STRAIN Q) | 11–66 | 393–434 | | | | | | |
| PV1A_TAV | 1A PROTEIN | PEANUT STUNT VIRUS (STRAIN J) | 4–66 | | | | | | | |
| PV23K_HSVTH | 1A PROTEIN | TOMATO ASPERMY VIRUS | 11–59 | 392–433 | 857–923 | | | | | |
| PV24K_BDV | 23.5 KD PROTEIN | TURKEY HERPESVIRUS (STRAIN H2) | 177–211 | | | | | | | |
| PV25K_NPVAC | 24 KD ANTIGEN | BORNA DISEASE VIRUS | 63–121 | 130–171 | | | | | | |
| PV28K_PLRV1 | 25 KD PROTEIN | AUTOGRAPHA CALIFORNICA NUCLEAR POLYHEDROSIS VIRUS | 4–50 | | | | | | | |
| PV28K_PLRVW | 28 KD PROTEIN | POTATO LEAFROLL VIRUS (STRAIN 1) | 116–150 | | | | | | | |
| PV290_ASFL5 | 28 KD PROTEIN | POTATO LEAFROLL VIRUS (STRAIN WAGENINGEN) | 116–150 | | | | | | | |
| PV29K_PEBV | LIS 290 PROTEIN | AFRICAN SWINE FEVER VIRUS (STRAIN LIS57) | 138–183 | | | | | | | |
| PV29K_TRVSY | 29.6 KD PROTEIN | EARLY BROWNING VIRUS | 115–192 | | | | | | | |
| PV29K_TRVTC | 29 KD PROTEIN | TOBACCO RATTLE VIRUS (STRAIN SYM), AND (STRAIN PSG) | 167–201 | | | | | | | |
| PV2A_CCMV | 29 KD PROTEIN | TOBACCO RATTLE VIRUS (STRAIN TCM) | 45–79 | | | | | | | |
| PV2A_CMVFN | 2A PROTEIN | COWPEA CHLOROTIC MOTTLE VIRUS | 768–806 | | | | | | | |
| PV2A_PSVJ | 2A PROTEIN | CUCUMBER MOSAIC VIRUS (STRAIN FNY) | 386–420 | | | | | | | |
| PV2A_TAV | 2A PROTEIN | PEANUT STUNT VIRUS (STRAIN J) | 717–751 | | | | | | | |
| PV30K_TRVTC | 2A PROTEIN | TOMATO ASPERMY VIRUS | 722–756 | | | | | | | |
| PV360_ASFB7 | 29.1 KD PROTEIN | TOBACCO RATTLE VIRUS (STRAIN TCM) | 105–218 | | | | | | | |
| PV362_ASFB7 | K360 PROTEIN | AFRICAN SWINE FEVER VIRUS (STRAIN BA71V) | 53–87 | 151–192 | | | | | | |
| PV363_ASFB7 | K362 PROTEIN | AFRICAN SWINE FEVER VIRUS (STRAIN BA71V) | 54–102 | 161–212 | 290–324 | | | | | |
| PV3A_BMV | D363 PROTEIN | AFRICAN SWINE FEVER VIRUS (STRAIN BA71V) | 153–199 | | | | | | | |
| PV3A_CMVFN | 3A PROTEIN | BROME MOSAIC VIRUS | 11–45 | | | | | | | |
| PV3A_CMVM | 3A PROTEIN | CUCUMBER MOSAIC VIRUS (STRAIN FNY) | 215–255 | | | | | | | |
| PV3A_CMVO | 3A PROTEIN | CUCUMBER MOSAIC VIRUS (STRAIN M) | 215–255 | | | | | | | |
| PV3A_CMVY | 3A PROTEIN | CUCUMBER MOSAIC VIRUS (STRAIN O) | 215–255 | | | | | | | |
| PV51K_ACLSV | 3A PROTEIN | CUCUMBER MOSAIC VIRUS (STRAIN Y) | 215–255 | | | | | | | |
| PV51K_BWYVF | 50.8 KD PROTEIN | APPLE CHLOROTIC LEAF SPOT VIRUS | 72–106 | | | | | | | |
| PV51K_BWYVG | 51 KD PROTEIN | BEET WESTERN YELLOWS VIRUS (ISOLATE FL-1) | 113–147 | 196–233 | 404–451 | | | | | |
| PV56K_PLRV1 | 51 KD PROTEIN | BEET WESTERN YELLOWS VIRUS (ISOLATE GB1) | 113–147 | 196–233 | 407–451 | | | | | |
| PV56K_PLRVW | 56 KD PROTEIN | POTATO LEAFROLL VIRUS (STRAIN 1) | 47–81 | 438–472 | | | | | | |
| PV58K_BSMV | 56 KD PROTEIN | POTATO LEAFROLL VIRUS (STRAIN WAGENINGEN) | 47–81 | 438–475 | | | | | | |
| PV66K_BWYVF | 58 KD PROTEIN | BARLEY STRIPE MOSAIC VIRUS | 128–162 | 323–371 | | | | | | |
| PV70K_PLRV1 | 66.2 KD PROTEIN | BEET WESTERN YELLOWS VIRUS (ISOLATE FL-1) | 480–521 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PV70K_PLRVW | 69.7 KD PROTEIN | POTATO LEAFROLL VIRUS (STRAIN 1) | 98–144 | 514–548 | | | | | | |
| PV90K_AMVLE | 69.7 KD PROTEIN | POTATO LEAFROLL VIRUS | 98–144 | 409–443 | 514–548 | | | | | |
| PVA04_VACCC | 90 KD PROTEIN | ALFALFA MOSAIC VIRUS (STRAIN WAGENINGEN) | 107–141 | | | | | | | |
| | | ALFALFA MOSAIC VIRUS (STRAIN 425/ISOLATE LEIDEN) | | | | | | | | |
| PVA04_VACCV | PROTEIN A4 | VACCINIA VIRUS (STRAIN COPENHAGEN) | 32–66 | 231–275 | | | | | | |
| PVA04_VARV | PROTEIN A4 | VACCINIA VIRUS (STRAIN WR) | 32–66 | 231–275 | | | | | | |
| PVA06_VACCC | PROTEIN A4 | VARIOLA VIRUS | 22–66 | 210–265 | | | | | | |
| PVA06_VACCV | PROTEIN A6 | VACCINIA VIRUS (STRAIN COPENHAGEN) | 97–213 | 314–355 | | | | | | |
| PVA06_VARV | PROTEIN A6 | VACCINIA VIRUS (STRAIN WR) | 96–212 | 313–354 | | | | | | |
| PVA08_VACCC | PROTEIN A6 | VARIOLA VIRUS | 97–213 | 313–358 | | | | | | |
| PVA08_VACCC | PROTEIN A8 | VACCINIA VIRUS (STRAIN COPENHAGEN) | 176–236 | | | | | | | |
| PVA09_VACCC | PROTEIN A8 | VARIOLA VIRUS | 176–236 | | | | | | | |
| PVA09_VARV | PROTEIN A9 | VACCINIA VIRUS (STRAIN COPENHAGEN) | 46–81 | | | | | | | |
| PVA11_VACCC | PROTEIN A9 | VARIOLA VIRUS | 46–95 | | | | | | | |
| PVA11_VARV | PROTEIN A11 | VACCINIA VIRUS (STRAIN COPENHAGEN) | 97–134 | 141–175 | 219–283 | | | | | |
| PVA12_VARV | PROTEIN A11 | VARIOLA VIRUS | 98–176 | 220–284 | | | | | | |
| PVA12_VARV | PROTEIN A12 | VACCINIA VIRUS (STRAIN COPENHAGEN) | 114–148 | | | | | | | |
| PVA18_VACCC | PROTEIN A12 | VARIOLA VIRUS | 111–152 | | | | | | | |
| PVA18_VACCV | 56 KD ABORTIVE LATE PROTEIN | VACCINIA VIRUS (STRAIN COPENHAGEN) | 433–467 | | | | | | | |
| PVA18_VARV | 56 KD ABORTIVE LATE PROTEIN | VACCINIA VIRUS (STRAIN WR) | 307–341 | 433–467 | | | | | | |
| PVA20_VACCC | 56 KD ABORTIVE LATE PROTEIN | VARIOLA VIRUS | 307–341 | 433–467 | | | | | | |
| PVA20_VARV | PROTEIN A20 | VACCINIA VIRUS (STRAIN COPENHAGEN) | 1–67 | | | | | | | |
| PVA22_VACCC | PROTEIN A20 | VARIOLA VIRUS | 1–67 | | | | | | | |
| PVA22_VARV | PROTEIN A22 | VACCINIA VIRUS (STRAIN COPENHAGEN) | 28–69 | | | | | | | |
| PVA23_VACCC | PROTEIN A22 | VARIOLA VIRUS | 39–80 | | | | | | | |
| PVA23_VARV | PROTEIN A23 | VACCINIA VIRUS (STRAIN COPENHAGEN) | 95–143 | 173–207 | 255–289 | 344–382 | | | | |
| PVA31_VARV | PROTEIN A23 | VARIOLA VIRUS | 95–143 | 173–207 | 255–289 | 344–382 | | | | |
| PVA32_VACCC | PROTEIN A31 | VACCINIA VIRUS (STRAIN WR) | 88–126 | | | | | | | |
| PVA32_VARV | PROTEIN A32 | VACCINIA VIRUS (STRAIN WR), AND (STRAIN COPENHAGEN) | | | | | | | | |
| PVA33_VARV | PROTEIN A32 | VARIOLA VIRUS | 217–251 | | | | | | | |
| PVA36_VACCV | PROTEIN A33 | VARIOLA VIRUS | 63–97 | | | | | | | |
| PVA36_VARV | PROTEIN A36 PRECURSOR | VACCINIA VIRUS (STRAIN WR), AND (STRAIN COPENHAGEN) | 26–67 | 109–155 | | | | | | |
| PVA37_VACCC | PROTEIN A36 PRECURSOR | VARIOLA VIRUS | 26–67 | | | | | | | |
| PVA37_VACCC | PROTEIN A37 | VACCINIA VIRUS (STRAIN COPENHAGEN) | 24–65 | | | | | | | |
| PVA38_VACCC | PROTEIN A37 | VACCINIA VIRUS (STRAIN WR) | 24–65 | | | | | | | |
| PVA38_VARV | PROTEIN A38 | VACCINIA VIRUS (STRAIN COPENHAGEN) | 44–91 | | | | | | | |
| PVA38_VARV | PROTEIN A38 | VACCINIA VIRUS (STRAIN WR) | 44–91 | | | | | | | |
| PVA39_VACCC | PROTEIN A38 | VARIOLA VIRUS | 44–91 | | | | | | | |
| PVA39_VACCC | PROTEIN A39 | VACCINIA VIRUS (STRAIN COPENHAGEN) | 37–71 | | | | | | | |
| PVA46_VACCC | PROTEIN A39 | VACCINIA VIRUS (STRAIN WR) | 75–109 | | | | | | | |
| PVA46_VACCV | PROTEIN A46 | VACCINIA VIRUS (STRAIN COPENHAGEN) | 81–126 | | | | | | | |
| PVA46_VARV | PROTEIN A46 | VACCINIA VIRUS (STRAIN WR) | 81–126 | | | | | | | |
| PVA47_VACCC | PROTEIN A46 | VARIOLA VIRUS | 81–126 | | | | | | | |
| PVA47_VACCV | PROTEIN A47 | VACCINIA VIRUS (STRAIN COPENHAGEN) | 62–96 | 143–184 | | | | | | |

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVA47_VARV | PROTEIN A47 | VACCINIA VIRUS (STRAIN WR) | 62–96 | 143–184 | | | | | | |
| PVA49_VACCC | PROTEIN A47 | VARIOLA VIRUS | 62–96 | 143–184 | | | | | | |
| PVA49_VACCV | PROTEIN A49 | VACCINIA VIRUS (STRAIN COPENHAGEN) | 3–40 | 126–160 | | | | | | |
| PVA49_VARV | PROTEIN A49 | VACCINIA VIRUS (STRAIN WR) | 3–40 | 126–160 | | | | | | |
| PVA52_VACCC | PROTEIN A49 | VARIOLA VIRUS | 3–40 | 126–160 | | | | | | |
| PVA52_VACCV | PROTEIN A52 | VACCINIA VIRUS (STRAIN COPENHAGEN) | 91–132 | | | | | | | |
| PVA57_VACCC | PROTEIN A52 | VACCINIA VIRUS (STRAIN WR) | 91–132 | | | | | | | |
| PVAL1_MSVK | GUANYLATE KINASE HOMOLOG | VACCINIA VIRUS (STRAIN COPENHAGEN) | 134–168 | | | | | | | |
| PVAL1_MSVN | GUANYLATE KINASE HOMOLOG | VACCINIA VIRUS (STRAIN WR) | 134–168 | | | | | | | |
| PVAL1_MSVS | AL1 PROTEIN | MAIZE STREAK VIRUS (KENYAN ISOLATE) | 230–269 | | | | | | | |
| PVAL1_SLCV | AL1 PROTEIN | MAIZE STREAK VIRUS (NIGERIAN ISOLATE) | 228–262 | | | | | | | |
| PVAL1_TYDVA | AL1 PROTEIN | MAIZE STREAK VIRUS (SOUTH-AFRICAN ISOLATE) | 228–262 | | | | | | | |
| PVAL1_TYDVA | AL1 PROTEIN | SQUASH LEAF CURL VIRUS | 117–151 | | | | | | | |
| PVAL3_ABMVW | AL1 PROTEIN | TOBACCO YELLOW DWARF VIRUS (STRAIN AUSTRALIA) | 191–225 | | | | | | | |
| PVAL3_BGMV | AL3 PROTEIN | ABUTILON MOSAIC VIRUS (ISOLATE WEST INDIA) | 44–78 | 83–124 | | | | | | |
| PVAL3_PYMVV | AL3 PROTEIN | BEAN GOLDEN MOSAIC VIRUS | 44–78 | 83–124 | | | | | | |
| PVAL3_SLCV | AL3 PROTEIN | POTATO YELLOW MOSAIC VIRUS (ISOLATE VENEZUELA) | 30–78 | 87–121 | | | | | | |
| PVAL3_TGMV | AL3 PROTEIN | SQUASH LEAF CURL VIRUS | 46–80 | 91–125 | | | | | | |
| PVAT_CAMVC | AL3 PROTEIN | TOMATO GOLDEN MOSAIC VIRUS | 44–78 | | | | | | | |
| PVAT_CAMVD | APHID TRANSMISSION PROTEIN | CAULIFLOWER MOSAIC VIRUS (STRAIN CM-1841) | 22–70 | 84–127 | | | | | | |
| PVAT_CAMVE | APHID TRANSMISSION PROTEIN | CAULIFLOWER MOSAIC VIRUS (STRAIN D/H) | 22–70 | | | | | | | |
| PVAT_CAMVN | APHID TRANSMISSION PROTEIN | CAULIFLOWER MOSAIC VIRUS (STRAIN BBC) | 22–70 | 93–127 | | | | | | |
| PVAT_CAMVP | APHID TRANSMISSION PROTEIN | CAULIFLOWER MOSAIC VIRUS (STRAIN NY8153) | 22–70 | 93–127 | | | | | | |
| PVAT_CAMVS | APHID TRANSMISSION PROTEIN | CAULIFLOWER MOSAIC VIRUS (STRAIN PV147) | 22–70 | 93–127 | | | | | | |
| PVAT_CAMVW | APHID TRANSMISSION PROTEIN | CAULIFLOWER MOSAIC VIRUS (STRAIN STRASBOURG) | 22–70 | 93–130 | | | | | | |
| PVAT_CERV | APHID TRANSMISSION PROTEIN | CAULIFLOWER MOSAIC VIRUS (STRAIN W260) | 36–70 | | | | | | | |
| PVB03_VACCC | PROTEIN B3 | CARNATION ETCHED RING VIRUS | 99–138 | | | | | | | |
| PVB04_VACCC | PROTEIN B4 | VACCINIA VIRUS (STRAIN WR) | 108–142 | | | | | | | |
| PVB04_VACCV | PROTEIN B4 | VACCINIA VIRUS (STRAIN COPENHAGEN) | 89–123 | 321–372 | 496–530 | | | | | |
| PVB04_VARV | PROTEIN B4 | VACCINIA VIRUS (STRAIN WR) | 89–123 | 321–372 | | | | | | |
| PVB05_VACC0 | PLAQUE-SIZE/HOST RANGE PROTEIN PRECURSOR | VARIOLA VIRUS | 89–123 | 321–372 | 496–530 | | | | | |
| PVB05_VACCC | PLAQUE-SIZE/HOST RANGE PROTEIN PRECURSOR | VACCINIA VIRUS (STRAIN LC16MO) | 254–298 | | | | | | | |
| PVB05_VACCL | PLAQUE-SIZE/HOST RANGE PROTEIN PRECURSOR | VACCINIA VIRUS (STRAIN COPENHAGEN) | 254–298 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVB05_VACCV | PLAQUE-SIZE/HOST RANGE PROTEIN PRECURSOR | VACCINIA VIRUS (STRAIN LISTER) | 254–298 | | | | | | | |
| PVB07_VACCV | PLAQUE-SIZE/HOST RANGE PROTEIN PRECURSOR | VACCINIA VIRUS (STRAIN WR) | 254–298 | | | | | | | |
| PVB08_VACCC | PROTEIN B7 PRECURSOR | VACCINIA VIRUS (STRAIN WR), AND (STRAIN COPENHAGEN) | 28–62 | | | | | | | |
| PVB08_VACCV | PROTEIN B8 PRECURSOR | VACCINIA VIRUS (STRAIN COPENHAGEN) | 26–60 | | | | | | | |
| PVB18_VACCC | PROTEIN B8 PRECURSOR | VACCINIA VIRUS (STRAIN WR) | 26–60 | | | | | | | |
| PVB18_VACCV | PROTEIN B18 | VACCINIA VIRUS (STRAIN COPENHAGEN) | 337–375 | 491–532 | | | | | | |
| PVB18_VARV | PROTEIN B18 | VACCINIA VIRUS (STRAIN WR) | 337–375 | 491–532 | | | | | | |
| PVB19_VACCC | PROTEIN B18 | VACCINIA VIRUS | 337–378 | 491–532 | | | | | | |
| PVB19_VACCD | SURFACE ANTIGEN S PRECURSOR | VACCINIA VIRUS (STRAIN COPENHAGEN) | 87–121 | | | | | | | |
| PVB19_VACCV | SURFACE ANTIGEN S PRECURSOR | VACCINIA VIRUS (STRAIN DAIREN I) | 85–119 | | | | | | | |
| PVB20_VACCC | SURFACE ANTIGEN S PRECURSOR | VACCINIA VIRUS (STRAIN WR) | 85–119 | | | | | | | |
| PVB21_VACCV | PROTEIN B20 | VACCINIA VIRUS (STRAIN COPENHAGEN) | 48–85 | | | | | | | |
| PVBL1_BGMV | PROTEIN B21 | VACCINIA VIRUS (STRAIN WR) | 61–95 | | | | | | | |
| PVBL1_SLCV | BL1 PROTEIN | BEAN GOLDEN MOSAIC VIRUS | 159–193 | | | | | | | |
| PVBL1_TGMV | BL1 PROTEIN | SQUASH LEAF CURL VIRUS | 159–193 | | | | | | | |
| PVBR1_BGMV | BL1 PROTEIN | TOMATO GOLDEN MOSAIC VIRUS | 159–193 | | | | | | | |
| PVBR1_SLCV | BR1 PROTEIN | BEAN GOLDEN MOSAIC VIRUS | 172–206 | | | | | | | |
| PVBR1_TGMV | BR1 PROTEIN | SQUASH LEAF CURL VIRUS | 20–61 | | | | | | | |
| PVC02_VACCC | BR1 PROTEIN | TOMATO GOLDEN MOSAIC VIRUS | 25–59 | | | | | | | |
| PVC02_VACCV | PROTEIN C2 | VACCINIA VIRUS (STRAIN COPENHAGEN) | 37–82 | 262–302 | 391–442 | | | | | |
| PVC04_SFVKA | PROTEIN C2 | VACCINIA VIRUS (STRAIN WR) | 37–82 | 262–302 | 391–442 | | | | | |
| PVC04_VACCC | PROTEIN C4 | SHOPE FIBROMA VIRUS (STRAIN KASZA) | 175–223 | 374–408 | | | | | | |
| PVC04_VACCV | PROTEIN C4 | VACCINIA VIRUS (STRAIN COPENHAGEN) | 12–46 | | | | | | | |
| PVC04_VARV | PROTEIN C4 | VACCINIA VIRUS (STRAIN WR) | 12–46 | | | | | | | |
| PVC05_SFVKA | PROTEIN C4 | VARIOLA VIRUS | 12–46 | | | | | | | |
| PVC05_VACCC | HYPOTHETICAL PROTEIN C5 | SHOPE FIBROMA VIRUS (STRAIN KASZA) | 82–125 | | | | | | | |
| PVC05_VACCV | PROTEIN C5 | VACCINIA VIRUS (STRAIN COPENHAGEN) | 31–68 | | | | | | | |
| PVC05_VARV | PROTEIN C5 | VACCINIA VIRUS (STRAIN WR) | 31–68 | | | | | | | |
| PVC08_SFVKA | PROTEIN C5 | VARIOLA VIRUS | 32–70 | 73–121 | | | | | | |
| PVC09_SFVKA | HYPOTHETICAL PROTEIN C8 | SHOPE FIBROMA VIRUS (STRAIN KASZA) | 45–86 | | | | | | | |
| PVC09_VACCC | HYPOTHETICAL PROTEIN C9 | SHOPE FIBROMA VIRUS (STRAIN KASZA) | 63–106 | | | | | | | |
| PVC09_VACCV | PROTEIN C9 | VACCINIA VIRUS (STRAIN COPENHAGEN) | 82–116 | 168–226 | 289–325 | 575–612 | | | | |
| PVC10_VACCC | PROTEIN C9 | VACCINIA VIRUS (STRAIN WR) | 82–116 | 168–226 | 289–323 | 575–612 | | | | |
| PVC10_VACCV | PROTEIN C10 | VACCINIA VIRUS (STRAIN COPENHAGEN) | 136–180 | | | | | | | |
| PVC10_VARV | PROTEIN C10 | VACCINIA VIRUS (STRAIN WR) | 136–176 | | | | | | | |
| PVC12_SFVKA | PROTEIN C10 | VARIOLA VIRUS | 136–170 | | | | | | | |
| PVC13_SFVKA | HYPOTHETICAL PROTEIN C12 | SHOPE FIBROMA VIRUS (STRAIN KASZA) | 2–36 | | | | | | | |
| PVC16_VACCC | PROTEIN C13 | SHOPE FIBROMA VIRUS (STRAIN KASZA) | 3–66 | 137–182 | 189–240 | | | | | |
| PVC17_VACCC | PROTEIN C16/B22 | VACCINIA VIRUS (STRAIN COPENHAGEN) | 142–176 | | | | | | | |
| PVC18_VACCC | PROTEIN C17/B23 | VACCINIA VIRUS (STRAIN COPENHAGEN) | 100–155 | 325–359 | | | | | | |
| PVC19_SFVKA | PROTEIN C18/B24 | VACCINIA VIRUS (STRAIN COPENHAGEN) | 40–98 | | | | | | | |
| PVC19_VACCC | PROTEIN C19 | SHOPE FIBROMA VIRUS (STRAIN KASZA) | 56–97 | | | | | | | |
| PVCAP_EBV | PROTEIN C19/B25 | VACCINIA VIRUS (STRAIN COPENHAGEN) | 218–252 | | | | | | | |
| PVCAP_HCMVA | MAJOR CAPSID PROTEIN | EPSTEIN-BARR VIRUS (STRAIN B95-8) | 150–184 | 670–709 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVCAP_HSV11 | MAJOR CAPSID PROTEIN | HUMAN CYTOMEGALOVIRUS (STRAIN AD169) | 136–174 | 191–225 | 260–294 | | | | | |
| PVCAP_HSV6U | MAJOR CAPSID PROTEIN | HERPES SIMPLEX VIRUS (TYPE 1/STRAIN 17) | 116–175 | 308–356 | | | | | | |
| PVCAP_HSVEB | MAJOR CAPSID PROTEIN | HERPES SIMPLEX VIRUS | 136–174 | 230–266 | 311–382 | | | | | |
| PVCAP_HSVSA | MAJOR CAPSID PROTEIN | EQUINE HERPESVIRUS TYPE 1 (STRAIN AB4P) | 150–184 | 304–352 | | | | | | |
| PVCAP_PRVIS | MAJOR CAPSID PROTEIN | HERPESVIRUS SAIMIRI (STRAIN 11) | 479–520 | 673–714 | 755–799 | | | | | |
| PVCAP_VZVD | MAJOR CAPSID PROTEIN | PSEUDORABIES VIRUS (STRAIN INDIANA S) | 105–160 | 292–326 | | | | | | |
| PVCG3_NPVAC | MAJOR CAPSID PROTEIN | VARICELLA-ZOSTER VIRUS (STRAIN DUMAS) | 128–198 | 316–350 | | | | | | |
| PVD05_FOWP1 | DNA-BINDING PROTEIN | AUTOGRAPHA CALIFORNICA NUCLEAR POLYHEDROSIS VIRUS | 110–248 | | | | | | | |
| PVD05_VACCC | 92.6 KD PROTEIN | FOWLPOX VIRUS (STRAIN FP-1) | 145–181 | | | | | | | |
| PVD05_VACCV | PROTEIN D5 | VACCINIA VIRUS (STRAIN COPENHAGEN) | 123–157 | | | | | | | |
| PVD05_VARV | PROTEIN D5 | VACCINIA VIRUS (STRAIN WR) | 123–157 | | | | | | | |
| PVD09_VACCC | PROTEIN D5 | VARIOLA VIRUS | 123–157 | | | | | | | |
| PVD09_VACCV | PROTEIN D9 | VACCINIA VIRUS (STRAIN COPENHAGEN) | 126–160 | | | | | | | |
| PVD09_VARV | PROTEIN D9 | VACCINIA VIRUS (STRAIN WR) | 126–160 | | | | | | | |
| PVD10_FOWP1 | PROTEIN D9 | VARIOLA VIRUS | 126–160 | | | | | | | |
| PVD10_SFVKA | PROTEIN D10 | FOWLPOX VIRUS (STRAIN FP-1) | 65–99 | 188–222 | | | | | | |
| PVD10_VARV | PROTEIN D10 | SHOPE FIBROMA VIRUS (STRAIN KASZA) | 4–52 | | | | | | | |
| PVDBP_CAMVC | PROTEIN D10 | VARIOLA VIRUS | 67–105 | | | | | | | |
| PVDBP_CAMVD | DNA-BINDING PROTEIN | CAULIFLOWER MOSAIC VIRUS (STRAIN CM-1841) | 1–35 | | | | | | | |
| PVDBP_CAMVE | DNA-BINDING PROTEIN | CAULIFLOWER MOSAIC VIRUS (STRAIN D/H) | 1–35 | | | | | | | |
| PVDBP_CAMVN | DNA-BINDING PROTEIN | CAULIFLOWER MOSAIC VIRUS (STRAIN BBC) | 1–35 | | | | | | | |
| PVDBP_CAMVS | DNA-BINDING PROTEIN | CAULIFLOWER MOSAIC VIRUS (STRAIN NY8153) | 1–35 | | | | | | | |
| PVE02_VACCC | DNA-BINDING PROTEIN | CAULIFLOWER MOSAIC VIRUS (STRAIN STRASBOURG) | 1–35 | | | | | | | |
| PVE02_VACCV | PROTEIN E2 | VACCINIA VIRUS (STRAIN COPENHAGEN) | 282–336 | | | | | | | |
| PVE02_VARV | PROTEIN E2 | VACCINIA VIRUS (STRAIN WR) | 282–336 | | | | | | | |
| PVE03_VACCC | PROTEIN E2 | VARIOLA VIRUS | 282–336 | | | | | | | |
| PVE03_VACCV | PROTEIN E3 | VACCINIA VIRUS (STRAIN COPENHAGEN) | 17–61 | | | | | | | |
| PVE03_VARV | PROTEIN E3 | VACCINIA VIRUS (STRAIN WR) | 17–61 | | | | | | | |
| PVE05_VACCC | PROTEIN E3 | VARIOLA VIRUS | 17–61 | | | | | | | |
| PVE05_VACCD | PROTEIN E5 | VACCINIA VIRUS (STRAIN COPENHAGEN) | 28–93 | | | | | | | |
| PVE05_VACCV | PROTEIN E5 | VACCINIA VIRUS (STRAIN DAIREN 1) | 38–103 | | | | | | | |
| PVE05_VARV | PROTEIN E5 | VACCINIA VIRUS (STRAIN WR) | 38–103 | | | | | | | |
| PVE06_VACCC | PROTEIN E5 | VARIOLA VIRUS | 38–103 | | | | | | | |
| PVE06_VACCV | PROTEIN E6 | VACCINIA VIRUS (STRAIN COPENHAGEN) | 105–139 | 232–266 | | | | | | |
| PVE06_VARV | PROTEIN E6 | VACCINIA VIRUS (STRAIN WR) | 105–139 | 232–266 | | | | | | |
| PVE18_NPVAC | PROTEIN E6 | VARIOLA VIRUS | 105–139 | 367–401 | | | | | | |
| PVE1_HPV1A | EARLY 18.5 KD PROTEIN | AUTOGRAPHA CALIFORNICA NUCLEAR POLYHEDROSIS VIRUS | 112–163 | | | | | | | |
| PVE1_HPV31 | E1 PROTEIN | HUMAN PAPILLOMAVIRUS TYPE 1A | 137–171 | | | | | | | |
| PVE1_HPV33 | E1 PROTEIN | HUMAN PAPILLOMAVIRUS TYPE 31 | 56–90 | | | | | | | |
| PVE1_HPV35 | E1 PROTEIN | HUMAN PAPILLOMAVIRUS TYPE 33 | 33–67 | 133–167 | | | | | | |
| PVE1_HPV39 | E1 PROTEIN | HUMAN PAPILLOMAVIRUS TYPE 35 | 56–90 | | | | | | | |
| PVE1_HPV41 | E1 PROTEIN | HUMAN PAPILLOMAVIRUS TYPE 39 | 59–96 | | | | | | | |
| PVE1_HPV42 | E1 PROTEIN | HUMAN PAPILLOMAVIRUS TYPE 41 | 55–89 | 312–346 | | | | | | |
| PVE1_HPV58 | E1 PROTEIN | HUMAN PAPILLOMAVIRUS TYPE 42 | 25–87 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVE1_HPV6B | E1 PROTEIN | HUMAN PAPILLOMAVIRUS TYPE 58 | 33–67 | 119–174 | | | | | | |
| PVE1_PAPVE | E1 PROTEIN | HUMAN PAPILLOMAVIRUS TYPE 6B | 265–299 | | | | | | | |
| PVE26_NPVAC | E1 PROTEIN | EUROPEAN ELK PAPILLOMAVIRUS | 176–210 | | | | | | | |
| PVE2_CRPVK | EARLY 25.9 KD PROTEIN | AUTOGRAPHA CALIFORNICA NUCLEAR POLYHEDROSIS VIRUS | 72–117 | | | | | | | |
| PVE2_HPV05 | PROBABLE E2 PROTEIN | COTTONTAIL RABBIT (SHOPE) PAPILLOMAVIRUS (STRAIN KANS) | 3–44 | | | | | | | |
| PVE2_HPV08 | PROBABLE E2 PROTEIN | HUMAN PAPILLOMAVIRUS TYPE 5 | 5–57 | 276–310 | 342–383 | 437–471 | | | | |
| PVE2_HPV16 | PROBABLE E2 PROTEIN | HUMAN PAPILLOMAVIRUS TYPE 8 | 5–55 | 148–182 | | | | | | |
| PVE2_HPV18 | E2 PROTEIN | HUMAN PAPILLOMAVIRUS TYPE 16 | 61–105 | 315–349 | | | | | | |
| PVE2_HPV1A | E2 PROTEIN | HUMAN PAPILLOMAVIRUS TYPE 18 | 65–100 | | | | | | | |
| PVE2_HPV2A | E2 PROTEIN | HUMAN PAPILLOMAVIRUS TYPE 1A | 3–37 | 159–193 | | | | | | |
| PVE2_HPV31 | E2 PROTEIN | HUMAN PAPILLOMAVIRUS TYPE 2A | 13–47 | 159–193 | | | | | | |
| PVE2_HPV33 | E2 PROTEIN | HUMAN PAPILLOMAVIRUS TYPE 31 | 61–105 | | | | | | | |
| PVE2_HPV35 | E2 PROTEIN | HUMAN PAPILLOMAVIRUS TYPE 33 | 63–101 | 297–331 | | | | | | |
| PVE2_HPV39 | E2 PROTEIN | HUMAN PAPILLOMAVIRUS TYPE 35 | 62–106 | 158–192 | | | | | | |
| PVE2_HPV41 | E2 PROTEIN | HUMAN PAPILLOMAVIRUS TYPE 39 | 74–110 | 323–357 | | | | | | |
| PVE2_HPV47 | E2 PROTEIN | HUMAN PAPILLOMAVIRUS TYPE 41 | 6–54 | | | | | | | |
| PVE2_HPV51 | E2 PROTEIN | HUMAN PAPILLOMAVIRUS TYPE 47 | 5–55 | 148–182 | | | | | | |
| PVE2_HPV57 | E2 PROTEIN | HUMAN PAPILLOMAVIRUS TYPE 51 | 154–191 | | | | | | | |
| PVE2_HPV58 | E2 PROTEIN | HUMAN PAPILLOMAVIRUS TYPE 57 | 13–47 | 179–213 | | | | | | |
| PVE2_HPV5B | E2 PROTEIN | HUMAN PAPILLOMAVIRUS TYPE 58 | 2–36 | | | | | | | |
| PVE2_PAPVD | PROBABLE E2 PROTEIN | HUMAN PAPILLOMAVIRUS TYPE 5B | 5–57 | | | | | | | |
| PVE2_PAPVE | PROBABLE E2 PROTEIN | DEER PAPILLOMAVIRUS | 107–141 | | | | | | | |
| PVE2_PCPV1 | PROBABLE E2 PROTEIN | EUROPEAN ELK PAPILLOMAVIRUS | 113–150 | | | | | | | |
| PVE2_RHPV1 | E2 PROTEIN | PYGMY CHIMPANZEE PAPILLOMAVIRUS TYPE 1 | 318–361 | | | | | | | |
| PVE39_NPVAC | E2 PROTEIN | RHESUS PAPILLOMAVIRUS TYPE 1 | 62–106 | 307–341 | | | | | | |
| PVE39_NPVOP | EARLY 39 KD PROTEIN | AUTOGRAPHA CALIFORNICA NUCLEAR POLYHEDROSIS VIRUS | 20–57 | | | | | | | |
| PVE4_HPV18 | EARLY 39 KD PROTEIN | ORGYIA PSEUDOTSUGATA MULTICAPSID POLYHEDROSIS VIRUS | 119–156 | | | | | | | |
| PVE4_HPV41 | PROBABLE E4 PROTEIN | HUMAN PAPILLOMAVIRUS TYPE 18 | 42–86 | | | | | | | |
| PVE5_HPV5B | PROBABLE E4 PROTEIN | HUMAN PAPILLOMAVIRUS TYPE 41 | 63–97 | | | | | | | |
| PVEF_GVTN | PROBABLE E5 PROTEIN | HUMAN PAPILLOMAVIRUS TYPE 5B | 3–40 | 96–130 | | | | | | |
| PVENV_BEV | VIRAL ENHANCING FACTOR (VEF) (104 KD GLYCOP | TRICHOPLUSIA N1 GRANULOSIS VIRUS (TNGV) | 681–719 | | | | | | | |
| PVENV_DHVII | ENVELOPE PROTEIN | BERNE VIRUS (BEV) | 195–229 | | | | | | | |
| PVENV_MCV1 | ENVELOPE GLYCOPROTEIN PRECURSOR | DHORI VIRUS (STRAIN INDIAN/1313/61) (DHO) | 318–366 | | | | | | | |
| PVENV_MCV2 | MAJOR ENVELOPE PROTEIN (43 KD PROTEIN) (P43K) | MOLLUSCUM CONTAGIOSUM VIRUS SUBTYPE 1 (MCVI) | 252–286 | | | | | | | |
| PVENV_THOGV | MAJOR ENVELOPE PROTEIN (43 KD PROTEIN) (P43K) | MOLLUSCUM CONTAGIOSUM VIRUS SUBTYPE 2 (MCVII) | 252–286 | | | | | | | |
| PVENV_VACCC | ENVELOPE GLYCOPROTEIN PRECURSOR (SURFACE | THOGOTO VIRUS (THO) | 313–354 | | | | | | | |
| PVENV_VACCI | MAJOR ENVELOPE PROTEIN (37 KD PROTEIN) (P37K) | VACCINIA VIRUS (STRAIN COPENHAGEN) | 257–295 | | | | | | | |

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVENV_VACCP | MAJOR ENVELOPE PROTEIN (37 KD PROTEIN) (P37K) | VACCINIA VIRUS (STRAIN 1HD-J) | 257–295 | | | | | | | |
| PVENV_VACCV | MAJOR ENVELOPE PROTEIN (37 KD PROTEIN) (P37K) | VACCINIA VIRUS (STRAIN L-IVP) | 257–295 | | | | | | | |
| PVENV_VARV | MAJOR ENVELOPE PROTEIN (37 KD PROTEIN) (P37K) | VACCINIA VIRUS (STRAIN WR) | 257–295 | | | | | | | |
| PVENV_VARV | MAJOR ENVELOPE PROTEIN (37 KD PROTEIN) (P37K) | VARIOLA VIRUS | 257–295 | | | | | | | |
| PVETS_NPVAC | ECORJ-T SITE PROTEIN ETS | AUTOGRAPHA CALIFORNICA NUCLEAR POLYHEDROSIS VIRUS ( | 1–53 | | | | | | | |
| PVF01_VACCC | PROTEIN F1 | VACCINIA VIRUS (STRAIN COPENHAGEN), AND VACCINIA VIRUS | 46–80 | 124–158 | | | | | | |
| PVF01_VACCV | PROTEIN F1 | VACCINIA VIRUS (STRAIN WR) | 46–80 | 124–158 | | | | | | |
| PVF03_VACCV | PROTEIN F1 (FRAGMENT) | VACCINIA VIRUS (STRAIN COPENHAGEN) | 71–110 | | | | | | | |
| PVF03_VARV | PROTEIN F3 | VACCINIA VIRUS (STRAIN WR) | 71–110 | | | | | | | |
| PVF05_VACCC | PROTEIN F3 | VACCINIA VIRUS (STRAIN COPENHAGEN) | 81–129 | 282–320 | | | | | | |
| PVF05_VACCP | 36 KD MAJOR MEMBRANE PROTEIN PRECURSOR | VACCINIA VIRUS (STRAIN COPENHAGEN) | 81–129 | 282–320 | | | | | | |
| PVF05_VACCV | 36 KD MAJOR MEMBRANE PROTEIN PRECURSOR | VACCINIA VIRUS (STRAIN L-IVP) | 81–129 | 283–321 | | | | | | |
| PVF05_VARV | 36 KD MAJOR MEMBRANE PROTEIN PRECURSOR | VACCINIA VIRUS (STRAIN WR) | 81–122 | 281–322 | | | | | | |
| PVF06_VARV | 36 KD MAJOR MEMBRANE PROTEIN PRECURSOR | VARIOLA VIRUS | 8–44 | | | | | | | |
| PVF11_VACCC | PROTEIN F6 | VARIOLA VIRUS | 217–258 | 269–315 | | | | | | |
| PVF11_VACCP | PROTEIN F11 | VACCINIA VIRUS (STRAIN COPENHAGEN) | 213–254 | 265–311 | | | | | | |
| PVF11_VARV | PROTEIN F11 | VACCINIA VIRUS (STRAIN L-IVP) | 41–75 | 269–315 | | | | | | |
| PVF12_VACCC | PROTEIN F11 | VARIOLA VIRUS | 1–67 | 102–143 | 199–236 | 350–388 | 544–581 | | | |
| PVF12_VACCP | PROTEIN F12 | VACCINIA VIRUS (STRAIN COPENHAGEN) | 1–67 | 102–143 | 199–236 | 350–388 | 544–581 | | | |
| PVF12_VARV | PROTEIN F12 | VACCINIA VIRUS (STRAIN COPENHAGEN) | 1–67 | 199–236 | 350–388 | 547–581 | | | | |
| PVF16_VACCC | PROTEIN F12 | VACCINIA VIRUS (STRAIN L-IVP) | 155–194 | | | | | | | |
| PVF16_VACCP | PROTEIN F16 | VARIOLA VIRUS | 155–194 | | | | | | | |
| PVF16_VARV | PROTEIN F16 | VACCINIA VIRUS (STRAIN COPENHAGEN) | 155–194 | | | | | | | |
| PVFP3_FOWPV | PROTEIN F16 | VACCINIA VIRUS (STRAIN L-IVP) | 1–43 | | | | | | | |
| PVFP4_FOWPV | PROTEIN FP3 | VARIOLA VIRUS | 139–173 | 239–273 | | | | | | |
| PVFP7_FOWP1 | PROTEIN FP4 | FOWLPOX VIRUS | 23–57 | | | | | | | |
| PVFPL_FOWP1 | PROTEIN FP7 | FOWLPOX VIRUS | 77–111 | | | | | | | |
| PVFUS_VACCV | FPLEFT PROTEIN (FRAGMENT) | FOWLPOX VIRUS (STRAIN FP-1) | 30–64 | | | | | | | |
| PVFUS_VACCV | 14 KD FUSION PROTEIN | VACCINIA VIRUS (STRAIN COPENHAGEN) | 30–64 | | | | | | | |
| PVG01_HSVI1 | 14 KD FUSION PROTEIN | VACCINIA VIRUS (STRAIN WR) | 271–306 | 512–563 | 591–647 | 730–764 | | | | |
| PVG01_VACCC | HYPOTHETICAL GENE 1 PROTEIN | ICTALURID HERPESVIRUS 1 (CHANNEL CATFISH VIRUS) (CCV) | 301–339 | | | | | | | |
| PVG01_VARV | PROTEIN G1 | VACCINIA VIRUS (STRAIN COPENHAGEN) | 240–278 | | | | | | | |
| PVG03_HSVEB | PROTEIN G1 (FRAGMENT) | VACCINIA VIRUS (STRAIN WR) | 301–339 | | | | | | | |
| PVG03_HSVEK | PROTEIN G1 | VARIOLA VIRUS | 143–177 | | | | | | | |
| | GENE 3 PROTEIN | EQUINE HERPESVIRUS TYPE 1 (STRAIN AB4P) (EHV-1) | | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVG03_VARV | GENE 3 PROTEIN (ORF L1) | EQUINE HERPESVIRUS TYPE 1 (STRAIN KENTUCKY A) (EHV-1) | 143–177 | | | | | | | |
| PVG05_VACCC | PROTEIN G3 | VARIOLA VIRUS | 64–98 | | | | | | | |
| PVG05_VARV | PROTEIN G5 | VACCINIA VIRUS (STRAIN COPENHAGEN) | 117–158 | 255–289 | 355–389 | | | | | |
| PVG06_HSVI1 | PROTEIN G5 | VARIOLA VIRUS | 117–158 | 255–289 | 355–389 | | | | | |
| PVG07_HSVI1 | HYPOTHETICAL GENE 6 MEMBRANE PROTEIN | ICTALURID HERPESVIRUS 1 (CHANNEL CATFISH VIRUS) (CCV) | 61–109 | | | | | | | |
| PVG07_VACCC | HYPOTHETICAL GENE 7 MEMBRANE PROTEIN | ICTALURID HERPESVIRUS 1 (CHANNEL CATFISH VIRUS) (CCV) | 69–103 | | | | | | | |
| PVG07_VARV | PROTEIN G7 | VACCINIA VIRUS (STRAIN COPENHAGEN) | 114–175 | 324–358 | | | | | | |
| PVG09_VACCC | PROTEIN G7 | VARIOLA VIRUS | 114–175 | 324–358 | | | | | | |
| PVG09_VACCV | PROTEIN F1 (PROTEIN G9) | VACCINIA VIRUS (STRAIN COPENHAGEN) | 304–338 | | | | | | | |
| PVG09_VARV | PROTEIN F1 (PROTEIN G9) (FRAGMENT) | VACCINIA VIRUS (STRAIN WR) | 304–338 | | | | | | | |
| PVG10_HSVI1 | PROTEIN F1 (PROTEIN G9) | VARIOLA VIRUS | 304–338 | | | | | | | |
| PVG12_SPV1R | HYPOTHETICAL GENE 10 MEMBRANE PROTEIN | ICTALURID HERPESVIRUS 1 (CHANNEL CATFISH VIRUS) (CCV) | 63–97 | | | | | | | |
| PVG16_HSVSA | GENE 12 PROTEIN | SPIROPLASMA VIRUS SPV1-R8A2 B | 11–45 | | | | | | | |
| PVG17_HSVI1 | HYPOTHETICAL GENE 16 PROTEIN | HERPESVIRUS SAIMIRI (STRAIN 11) | 58–95 | | | | | | | |
| PVG18_HSVI1 | HYPOTHETICAL GENE 17 PROTEIN | ICTALURID HERPESVIRUS 1 (CHANNEL CATFISH VIRUS) (CCV) | 92–129 | 177–211 | | | | | | |
| PVG1L_AMEPV | HYPOTHETICAL GENE 18 PROTEIN | ICTALURID HERPESVIRUS 1 (CHANNEL CATFISH VIRUS) (CCV) | 174–208 | 215–256 | | | | | | |
| PVG1_SPV1R | G1L PROTEIN | AMSACTA MOOREI ENTOMOPOXVIRUS (AMEPV) | 407–441 | | | | | | | |
| PVG1_SPV4 | CAPSID PROTEIN | SPIROPLASMA VIRUS SPV1-R8A2 B | 136–170 | 256–297 | 320–357 | | | | | |
| PVG22_HSVI1 | CAPSID PROTEIN | SPIROPLASMA VIRUS 4 (SPV4) | 287–321 | | | | | | | |
| PVG24_HSVI1 | HYPOTHETICAL GENE 22 PROTEIN | ICTALURID HERPESVIRUS 1 (CHANNEL CATFISH VIRUS) (CCV) | 117–158 | 437–629 | 660–892 | 899–1055 | | | | |
| PVG27_HSVI1 | HYPOTHETICAL GENE 24 PROTEIN | ICTALURID HERPESVIRUS 1 (CHANNEL CATFISH VIRUS) (CCV) | 7–72 | 74–108 | | | | | | |
| PVG28_HSVI1 | HYPOTHETICAL GENE 27 PROTEIN | ICTALURID HERPESVIRUS 1 (CHANNEL CATFISH VIRUS) (CCV) | 164–219 | | | | | | | |
| PVG2R_AMEPV | HYPOTHETICAL GENE 28 PROTEIN | ICTALURID HERPESVIRUS 1 (CHANNEL CATFISH VIRUS) (CCV) | 253–290 | | | | | | | |
| PVG2_SPV1R | HYPOTHETICAL G2R PROTEIN | AMSACTA MOOREI ENTOMOPOXVIRUS (AMEPV) | 29–63 | 184–218 | | | | | | |
| PVG2_SPV4 | GENE 2 PROTEIN | SPIROPLASMA VIRUS SPV1-R8A2 B | 222–256 | 285–326 | | | | | | |
| PVG33_HSVI1 | GENE 2 PROTEIN | SPIROPLASMA VIRUS 4 (SPV4) | 255–310 | | | | | | | |
| PVG34_HSVI1 | HYPOTHETICAL GENE 33 PROTEIN | ICTALURID HERPESVIRUS 1 (CHANNEL CATFISH VIRUS) (CCV) | 149–183 | | | | | | | |
| PVG35_HSVI1 | HYPOTHETICAL GENE 34 PROTEIN | ICTALURID HERPESVIRUS 1 (CHANNEL CATFISH VIRUS) (CCV) | 345–379 | | | | | | | |
| PVG37_HSVI1 | HYPOTHETICAL GENE 35 PROTEIN | ICTALURID HERPESVIRUS 1 (CHANNEL CATFISH VIRUS) (CCV) | 17–90 | | | | | | | |
| PVG38_HSVI1 | HYPOTHETICAL GENE 37 PROTEIN | ICTALURID HERPESVIRUS 1 (CHANNEL CATFISH VIRUS) (CCV) | 435–472 | | | | | | | |
| PVG39_HSVI1 | HYPOTHETICAL GENE 38 PROTEIN | ICTALURID HERPESVIRUS 1 (CHANNEL CATFISH VIRUS) (CCV) | 84–118 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVG3_SPV1R | HYPOTHETICAL GENE 39 PROTEIN | ICTALURID HERPESVIRUS 1 (CHANNEL CATFISH VIRUS) (CCV) | 124–158 | 266–300 | | | | | | |
| PVG3_SPV4 | GENE 3 PROTEIN | SPIROPLASMA VIRUS SPV1-R8A2 B | 8–49 | 162–196 | 203–244 | | | | | |
| PVG43_SPV4 | GENE 3 PROTEIN | SPIROPLASMA VIRUS 4 (SPV4) | 6–54 | 87–121 | | | | | | |
| PVG45_HSVSA | HYPOTHETICAL GENE 43 PROTEIN | ICTALURID HERPESVIRUS 1 (CHANNEL CATFISH VIRUS) (CCV) | 116–150 | 262–296 | 324–361 | 643–677 | | | | |
| PVG46_HSVII | HYPOTHETICAL GENE 45 PROTEIN | HERPESVIRUS SAIMIRI (STRAIN 11) | 121–162 | | | | | | | |
| PVG48_HSVII | PROBABLE MAJOR GLYCOPROTEIN | ICTALURID HERPESVIRUS 1 (CHANNEL CATFISH VIRUS) (CCV) | 45–86 | 939–1078 | 1251–1321 | | | | | |
| PVG48_HSVSA | HYPOTHETICAL GENE 48 PROTEIN | ICTALURID HERPESVIRUS 1 (CHANNEL CATFISH VIRUS) (CCV) | 169–207 | | | | | | | |
| PVG49_HSVSA | HYPOTHETICAL GENE 48 PROTEIN | HERPESVIRUS SAIMIRI (STRAIN 11) | 360–417 | 611–666 | 733–767 | | | | | |
| PVG4R_AMEPV | HYPOTHETICAL GENE 49 PROTEIN | HERPESVIRUS SAIMIRI (STRAIN 11) | 68–102 | | | | | | | |
| PVG4_SPV4 | G4R PROTEIN | AMSACTA MOOREI ENTOMOPOXVIRUS (AMEPV) | 4–38 | 328–410 | | | | | | |
| PVG51_HSVII | GENE 4 PROTEIN | SPIROPLASMA VIRUS 4 (SPV4) | 89–130 | | | | | | | |
| PVG51_HSVSA | HYPOTHETICAL GENE 51 MEMBRANE PROTEIN | ICTALURID HERPESVIRUS 1 (CHANNEL CATFISH VIRUS) (CCV) | 34–73 | 89–123 | | | | | | |
| PVG53_HSVII | GENE 51 GLYCOPROTEIN | HERPESVIRUS SAIMIRI (STRAIN 11) | 29–70 | 123–157 | 162–196 | | | | | |
| PVG54_HSVII | HYPOTHETICAL GENE 53 PROTEIN | ICTALURID HERPESVIRUS 1 (CHANNEL CATFISH VIRUS) (CCV) | 67–127 | | | | | | | |
| PVG55_HSVII | HYPOTHETICAL GENE 54 PROTEIN | ICTALURID HERPESVIRUS 1 (CHANNEL CATFISH VIRUS) (CCV) | 355–396 | | | | | | | |
| PVG55_HSVSA | HYPOTHETICAL GENE 55 PROTEIN | ICTALURID HERPESVIRUS 1 (CHANNEL CATFISH VIRUS) (CCV) | 101–135 | | | | | | | |
| PVG56_HSVII | HYPOTHETICAL GENE 55 PROTEIN | HERPESVIRUS SAIMIRI (STRAIN 11) | 126–178 | | | | | | | |
| PVG59_HSVII | HYPOTHETICAL GENE 56 PROTEIN | ICTALURID HERPESVIRUS 1 (CHANNEL CATFISH VIRUS) (CCV) | 151–192 | 578–612 | 644–678 | 750–784 | 846–880 | 1111–1145 | | |
| PVG59_HSVSA | HYPOTHETICAL GENE 59 MEMBRANE PROTEIN | ICTALURID HERPESVIRUS 1 (CHANNEL CATFISH VIRUS) (CCV) | 10–72 | 89–123 | | | | | | |
| PVG5_SPV1R | GENE 59 PROTEIN | ICTALURID HERPESVIRUS 1 (CHANNEL CATFISH VIRUS) (CCV) | 169–209 | | | | | | | |
| PVG61_HSVII | GENE 5 PROTEIN | HERPESVIRUS SAIMIRI (STRAIN 11) | 65–103 | | | | | | | |
| PVG63_HSVII | HYPOTHETICAL GENE 61 PROTEIN | SPIROPLASMA VIRUS SPV1-R8A2 B | 265–299 | | | | | | | |
| PVG65_HSVII | HYPOTHETICAL GENE 63 PROTEIN | ICTALURID HERPESVIRUS 1 (CHANNEL CATFISH VIRUS) (CCV) | 546–584 | | | | | | | |
| PVG66_HSVII | HYPOTHETICAL GENE 65 PROTEIN | ICTALURID HERPESVIRUS 1 (CHANNEL CATFISH VIRUS) (CCV) | 805–839 | 1213–1254 | | | | | | |
| PVG67_HSVII | HYPOTHETICAL GENE 66 PROTEIN | ICTALURID HERPESVIRUS 1 (CHANNEL CATFISH VIRUS) (CCV) | 154–188 | | | | | | | |
| PVG68_HSVII | HYPOTHETICAL GENE 67 PROTEIN | ICTALURID HERPESVIRUS 1 (CHANNEL CATFISH VIRUS) (CCV) | 379–413 | 501–546 | 1321–1369 | 1478–1541 | | | | |
| PVG72_HSVII | HYPOTHETICAL GENE 68 PROTEIN | ICTALURID HERPESVIRUS 1 (CHANNEL CATFISH VIRUS) (CCV) | 245–288 | | | | | | | |
| PVG75_HSVII | HYPOTHETICAL GENE 72 PROTEIN | ICTALURID HERPESVIRUS 1 (CHANNEL CATFISH VIRUS) (CCV) | 447–484 | 723–757 | 912–949 | | | | | |
| PVG8_SPV1R | HYPOTHETICAL GENE 75 PROTEIN | ICTALURID HERPESVIRUS 1 (CHANNEL CATFISH VIRUS) (CCV) | 217–305 | 388–422 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVGF1_1BVB | GENE 8 PROTEIN | SPIROPLASMA VIRUS SPV1-R8A2 B | 5–51 | | | | | | | |
| PVGH3_HCMVA | F1 PROTEIN | AVIAN INFECTIOUS BRONCHITIS VIRUS (STRAIN BEAUDETTE) (I | 142–179 | 1233–1267 | 2119–2156 | 3388–3424 | 3475–3513 | 3517–3556 | 3761–3795 | |
| PVGL1_CVPR8 | GLYCOPROTEIN H301 PRECURSOR | HUMAN CYTOMEGALOVIRUS (STRAIN AD169) | | | | | | | | |
| PVGL2_CVBF | E1 GLYCOPROTEIN PRECURSOR (MATRIX GLYCOP | PORCINE RESPIRATORY CORONAVIRUS (STRAIN 86/137004/BRI | 212–257 | | | | | | | |
| PVGL2_CVBL9 | E2 GLYCOPROTEIN PRECURSOR (SPIKE GLYCOPRO | BOVINE CORONAVIRUS (STRAIN F15 | 642–676 | 850–885 | 993–1088 | 1263–1305 | | | | |
| PVGL2_CVBLY | E2 GLYCOPROTEIN PRECURSOR (SPIKE GLYCOPRO | BOVINE CORONAVIRUS (STRAIN L9) | 850–885 | 993–1109 | 1263–1305 | | | | | |
| PVGL2_CVBM | E2 GLYCOPROTEIN PRECURSOR (SPIKE GLYCOPRO | BOVINE CORONAVIRUS (STRAIN LY-138) | 642–676 | 850–885 | 993–1109 | 1263–1305 | | | | |
| PVGL2_CVBQ | E2 GLYCOPROTEIN PRECURSOR (SPIKE GLYCOPRO | BOVINE CORONAVIRUS (STRAIN MEBUS | 642–676 | 850–885 | 993–1109 | 1263–1305 | | | | |
| PVGL2_CVBV | E2 GLYCOPROTEIN PRECURSOR (SPIKE GLYCOPRO | BOVINE CORONAVIRUS (STRAIN QUEBEC) | 642–676 | 850–885 | 993–1109 | 1263–1305 | | | | |
| PVGL2_CVH22 | E2 GLYCOPROTEIN PRECURSOR (SPIKE GLYCOPRO | BOVINE CORONAVIRUS (STRAIN VACCINE) | 642–676 | 850–885 | 993–1109 | 1263–1305 | | | | |
| PVGL2_CVM4 | E2 GLYCOPROTEIN PRECURSOR (SPIKE GLYCOPRO | HUMAN CORONAVIRUS (STRAIN 229E) | 770–916 | 1055–1112 | | | | | | |
| PVGL2_CVMA5 | E2 GLYCOPROTEIN PRECURSOR (SPIKE GLYCOPRO | MURINE CORONAVIRUS MHV (STRAIN WILD TYPE 4) (MHV-4) | 643–684 | 1001–1117 | 1270–1315 | | | | | |
| PVGL2_CVMJC | E2 GLYCOPROTEIN PRECURSOR (SPIKE GLYCOPRO | MURINE CORONAVIRUS MHV (STRAIN A59) | 591–632 | 949–1079 | 1218–1263 | | | | | |
| PVGL2_CVMJH | E2 GLYCOPROTEIN PRECURSOR (SPIKE GLYCOPRO | MURINE CORONAVIRUS MHV (STRAIN JHMV/VARIANT CL-2) | 643–684 | 1001–1117 | 1270–1315 | | | | | |
| PVGL2_CVPFS | E2 GLYCOPROTEIN PRECURSOR (SPIKE GLYCOPRO | MURINE CORONAVIRUS MHV (STRAIN JHM) | 503–543 | 860–976 | 1129–1174 | | | | | |
| PVGL2_CVPMI | E2 GLYCOPROTEIN PRECURSOR (SPIKE GLYCOPRO | PORCINE TRANSMISSIBLE GASTROENTERITIS CORONAVIRUS (S | 69–110 | 448–482 | 692–733 | 889–923 | 1040–1186 | 1352–1389 | | |
| PVGL2_CVPPR | E2 GLYCOPROTEIN PRECURSOR (SPIKE GLYCOPRO | PORCINE TRANSMISSIBLE GASTROENTERITIS CORONAVIRUS (S | 69–110 | 448–482 | 692–733 | 889–923 | 1040–1186 | 1352–1389 | | |
| PVGL2_CVPPU | E2 GLYCOPROTEIN PRECURSOR (SPIKE GLYCOPRO | PORCINE TRANSMISSIBLE GASTROENTERITIS CORONAVIRUS (S | 70–110 | 446–480 | 690–731 | 887–921 | 1038–1184 | 1350–1387 | | |
| PVGL2_CVPR8 | E2 GLYCOPROTEIN PRECURSOR (SPIKE GLYCOPRO | PORCINE TRANSMISSIBLE GASTROENTERITIS CORONAVIRUS (S | 69–110 | 446–480 | 690–731 | 887–921 | 1038–1184 | 1350–1387 | | |
| PVGL2_CVPRM | E2 GLYCOPROTEIN PRECURSOR (SPIKE GLYCOPRO | PORCINE RESPIRATORY CORONAVIRUS (STRAIN 86/1370004/BRIT | 224–258 | 468–509 | 665–699 | 816–962 | 1128–1165 | | | |
| PVGL2_CVPRT | E2 GLYCOPROTEIN PRECURSOR (SPIKE GLYCOPRO | PORCINE RESPIRATORY CORONAVIRUS (STRAIN RM4) (PRCV) | 224–258 | 468–509 | 665–699 | 816–962 | 1128–1165 | | | |
| PVGL2_EBV | E2 GLYCOPROTEIN PRECURSOR (SPIKE GLYCOPRO | PORCINE TRANSMISSIBLE GASTROENTERITIS CORONAVIRUS (S | 69–110 | 446–480 | 690–731 | 887–921 | 1038–1184 | 1350–1387 | | |
| PVGL2_FIPV | PROBABLE MEMBRANE GLYCOPROTEIN | | 68–102 | | | | | | | |
| PVGL2_IBV6 | E2 GLYCOPROTEIN PRECURSOR | FELINE INFECTIOUS PERITONITIS VIRUS (STRAIN 79-1146) | 189–245 | 451–485 | 695–736 | 892–926 | 1043–1189 | 1355–1392 | | |
| PVGL2_IBVB | E2 GLYCOPROTEIN PRECURSOR | AVIAN INFECTIOUS BRONCHITIS VIRUS (STRAIN 6/82) | 791–905 | 1057–1091 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVGL2_IBVD2 | E2 GLYCOPROTEIN PRECURSOR | AVIAN INFECTIOUS BRONCHITIS VIRUS (STRAIN BEAUDETTE) | 437–478 | 772–904 | 1056–1090 | | | | | |
| PVGL2_IBVK | E2 GLYCOPROTEIN PRECURSOR | AVIAN INFECTIOUS BRONCHITIS VIRUS (STRAIN D274) | 773–905 | 1057–1091 | | | | | | |
| PVGL2_IBVM | E2 GLYCOPROTEIN PRECURSOR | AVIAN INFECTIOUS BRONCHITIS VIRUS (STRAIN KB8523) | 437–478 | 772–904 | 1056–1090 | | | | | |
| PVGLB_HCMVA | E2 GLYCOPROTEIN PRECURSOR | AVIAN INFECTIOUS BRONCHITIS VIRUS (STRAIN M41) | 437–478 | 772–904 | 1056–1090 | | | | | |
| PVGLB_HCMVT | GLYCOPROTEIN B PRECURSOR | HUMAN CYTOMEGALOVIRUS (STRAIN AD169) | 43–88 | 128–162 | | 844–878 | | | | |
| PVGLB_HSV11 | GLYCOPROTEIN B PRECURSOR | HUMAN CYTOMEGALOVIRUS (STRAIN TOWNE) | 22–88 | 128–162 | | 451–485 | 845–879 | | | |
| PVGLB_HSV1F | GLYCOPROTEIN B PRECURSOR | HERPES SIMPLEX VIRUS (TYPE 1/STRAIN 17) | 828–890 | | | | | | | |
| PVGLB_HSV1K | GLYCOPROTEIN B PRECURSOR | HERPES SIMPLEX VIRUS (TYPE 1/STRAIN F) | 827–889 | | | | | | | |
| PVGLB_HSV1P | GLYCOPROTEIN B PRECURSOR | HERPES SIMPLEX VIRUS (TYPE 1/STRAIN KOS) | 827–889 | | | | | | | |
| PVGLB_HSV23 | GLYCOPROTEIN B PRECURSOR | HERPES SIMPLEX VIRUS (TYPE 1/STRAIN PATTON) | 828–890 | | | | | | | |
| PVGLB_HSV2H | GLYCOPROTEIN B PRECURSOR | HERPES SIMPLEX VIRUS (TYPE 2/STRAIN 333) | 828–890 | | | | | | | |
| PVGLB_HSV2S | GLYCOPROTEIN B PRECURSOR | HERPES SIMPLEX VIRUS (TYPE 2/STRAIN HG52) | 828–890 | | | | | | | |
| PVGLB_HSV6U | GLYCOPROTEIN B PRECURSOR | HERPES SIMPLEX VIRUS (TYPE 2/STRAIN SA8) | 817–871 | | | | | | | |
| PVGLB_HSVB1 | GLYCOPROTEIN B | HERPES SIMPLEX VIRUS (TYPE 6/STRAIN UGANDA-1102) | 37–71 | 185–223 | | | | | | |
| PVGLB_HSVB2 | GLYCOPROTEIN 1 PRECURSOR | BOVINE HERPESVIRUS TYPE 1 | 859–913 | | | | | | | |
| PVGLB_HSVBC | GLYCOPROTEIN B-1 PRECURSOR | BOVINE HERPESVIRUS TYPE 2 (STRAIN BMV) | 440–474 | 848–902 | | | | | | |
| PVGLB_HSVE1 | GLYCOPROTEIN 1 PRECURSOR | BOVINE HERPESVIRUS TYPE 1 (STRAIN COOPER) | 863–900 | | | | | | | |
| PVGLB_HSVE4 | GLYCOPROTEIN B PRECURSOR | EQUINE HERPESVIRUS TYPE 1 (ISOLATE HVS25A) | 542–576 | 911–961 | | | | | | |
| PVGLB_HSVEA | GLYCOPROTEIN B PRECURSOR | EQUINE HERPESVIRUS TYPE 4 (STRAIN 1942) | 474–515 | 847–900 | | | | | | |
| PVGLB_HSVEB | GLYCOPROTEIN B PRECURSOR | EQUINE HERPESVIRUS TYPE 1 (STRAIN AB1) | 542–576 | 911–961 | | | | | | |
| PVGLB_HSVEL | GLYCOPROTEIN B PRECURSOR | EQUINE HERPESVIRUS TYPE 1 (STRAIN AB4P) | 542–576 | 911–961 | | | | | | |
| PVGLB_HSVMD | GLYCOPROTEIN B PRECURSOR | EQUINE HERPESVIRUS TYPE 1 (STRAIN KENTUCKY D) | 542–576 | 910–960 | | | | | | |
| PVGLB_HSVSA | GLYCOPROTEIN B PRECURSOR | MAREK'S DISEASE HERPESVIRUS (STRAIN RB-1B) | 390–435 | 649–683 | 787–845 | | | | | |
| PVGLB_MCMVS | GLYCOPROTEIN B PRECURSOR | HERPESVIRUS SAIMIRI (STRAIN 11) | 240–288 | 406–447 | | | | | | |
| PVGLB_PRVIF | GLYCOPROTEIN B PRECURSOR | MURINE CYTOMEGALOVIRUS (STRAIN SMITH) | 206–260 | 427–475 | 693–734 | 744–778 | 860–894 | | | |
| PVGLB_VZVD | GLYCOPROTEIN GII PRECURSOR | PSEUDORABIES VIRUS (STRAIN INDIANA-FUNKHAUSER/BECKE | 847–881 | | | | | | | |
| PVGLC_HSV11 | GLYCOPROTEIN B PRECURSOR | VARICELLA-ZOSTER VIRUS (STRAIN DUMAS) | 92–133 | 596–630 | 809–867 | | | | | |
| PVGLC_HSV1K | GLYCOPROTEIN C PRECURSOR | HERPES SIMPLEX VIRUS (TYPE 1/STRAIN 17) | 469–510 | | | | | | | |
| PVGLC_HSV2 | GLYCOPROTEIN C PRECURSOR | HERPES SIMPLEX VIRUS (TYPE 1/STRAIN KOS) | 469–510 | | | | | | | |
| PVGLC_HSV23 | GLYCOPROTEIN C PRECURSOR | HERPES SIMPLEX VIRUS (TYPE 2) | 442–476 | | | | | | | |
| PVGLC_HSVBC | GLYCOPROTEIN C PRECURSOR | HERPES SIMPLEX VIRUS (TYPE 2/STRAIN 333) | 443–477 | | | | | | | |
| PVGLC_HSVEB | GLYCOPROTEIN GIII PRECURSOR | BOVINE HERPESVIRUS TYPE 1 (STRAIN COOPER) | 235–269 | | | | | | | |
| PVGLC_HSVMB | GLYCOPROTEIN C PRECURSOR | EQUINE HERPESVIRUS TYPE 1 (STRAIN AB4P) AND (STRAIN KEN | 182–218 | | | | | | | |
| PVGLC_HSVMD | SECRETORY GLYCOPROTEIN GP57-65 PRECURSOR | MAREK'S DISEASE HERPESVIRUS (STRAIN BC-1) | 63–97 | | | | | | | |
| PVGLC_HSVMG | SECRETORY GLYCOPROTEIN GP57-65 PRECURSOR | MAREK'S DISEASE HERPESVIRUS (STRAIN RB-1B) | 63–97 | | | | | | | |

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVGLC_HSVMM | SECRETORY GLYCOPROTEIN GP57-65 PRECURSOR | MAREK'S DISEASE HERPESVIRUS (STRAIN GA) | 62–96 | | | | | | | |
| PVGLC_PRVIF | SECRETORY GLYCOPROTEIN GP57-65 PRECURSOR | MAREK'S DISEASE HERPESVIRUS (STRAIN MD5) | 63–97 | | | | | | | |
| PVGLC_VZVD | GLYCOPROTEIN G111 PRECURSOR | PSEUDORABIES VIRUS (STRAIN INDIANA-FUNKHAUSER/BECKE | 183–235 | | | | | | | |
| PVGLC_VZVS | GLYCOPROTEIN GPV | VARICELLA-ZOSTER VIRUS (STRAIN DUMAS) | 280–321 | | | | | | | |
| PVGLD_HSVEA | GLYCOPROTEIN GPV | VARICELLA-ZOSTER VIRUS (STRAIN SCOTT) | 280–321 | | | | | | | |
| PVGLD_HSVEB | GLYCOPROTEIN D PRECURSOR | EQUINE HERPESVIRUS TYPE 1 (STRAIN AB1) | 89–123 | | | | | | | |
| PVGLD_HSVEK | GLYCOPROTEIN D PRECURSOR | EQUINE HERPESVIRUS TYPE 1 (STRAIN AB4P) AND (STRAIN KEN | 139–173 | | | | | | | |
| PVGLE_HSV11 | GLYCOPROTEIN D PRECURSOR | EQUINE HERPESVIRUS TYPE 1 (STRAIN KENTUCKY A) | 139–173 | | | | | | | |
| PVGLE_HSV2 | GLYCOPROTEIN E PRECURSOR | HERPES SIMPLEX VIRUS (TYPE 1/STRAIN 17) | 111–145 | | | | | | | |
| PVGLF_BRSVA | GLYCOPROTEIN E PRECURSOR | HERPES SIMPLEX VIRUS (TYPE 2) | 111–159 | | | | | | | |
| PVGLF_BRSVC | FUSION GLYCOPROTEIN PRECURSOR | BOVINE RESPIRATORY SYNCYTIAL VIRUS (STRAIN A51908) | 146–202 | 504–545 | | | | | | |
| PVGLF_BRSVR | FUSION GLYCOPROTEIN PRECURSOR | BOVINE RESPIRATORY SYNCYTIAL VIRUS (STRAIN COPENHAGE | 146–202 | 267–302 | 506–547 | | | | | |
| PVGLF_CDVO | FUSION GLYCOPROTEIN PRECURSOR | BOVINE RESPIRATORY SYNCYTIAL VIRUS (STRAIN RB94) | 146–202 | 267–302 | 506–554 | | | | | |
| PVGLF_HRSVI | FUSION GLYCOPROTEIN PRECURSOR | CANINE DISTEMPER VIRUS (STRAIN ONDERSTEPOORT) | 228–297 | 340–381 | 568–602 | | | | | |
| PVGLF_HRSVA | FUSION GLYCOPROTEIN PRECURSOR | HUMAN RESPIRATORY SYNCYTIAL VIRUS (SUBGROUP B/STRAI | 116–203 | 267–302 | 506–549 | | | | | |
| PVGLF_HRSVL | FUSION GLYCOPROTEIN PRECURSOR | HUMAN RESPIRATORY SYNCYTIAL VIRUS (STRAIN A2 | 116–202 | 267–302 | 506–549 | | | | | |
| PVGLF_HRSVR | FUSION GLYCOPROTEIN PRECURSOR | HUMAN RESPIRATORY SYNCYTIAL VIRUS (SUBGROUP A/STRAI | 116–202 | 267–302 | 506–547 | | | | | |
| PVGLF_MEASE | FUSION GLYCOPROTEIN PRECURSOR | HUMAN RESPIRATORY SYNCYTIAL VIRUS (STRAIN RSS-2) | 116–202 | 267–302 | 506–549 | | | | | |
| PVGLF_MEASI | FUSION GLYCOPROTEIN PRECURSOR | MEASLES VIRUS (STRAIN EDMONSTON) AND (STRAIN HALLE) | 116–184 | 228–269 | 452–500 | | | | | |
| PVGLF_MEASY | FUSION GLYCOPROTEIN PRECURSOR | MEASLES VIRUS (STRAIN IP-3-CA) | 119–187 | 231–272 | 455–503 | | | | | |
| PVGLF_MUMP1 | FUSION GLYCOPROTEIN PRECURSOR | MEASLES VIRUS (STRAIN YAMAGATA-1) | 116–184 | 228–269 | 452–500 | | | | | |
| PVGLF_MUMPM | FUSION GLYCOPROTEIN PRECURSOR | MUMPS VIRUS (STRAIN SBL-1) | 20–54 | 103–179 | 235–272 | 447–502 | | | | |
| PVGLF_MUMPR | FUSION GLYCOPROTEIN PRECURSOR | MUMPS VIRUS (STRAIN MIYAHARA VACCINE) | 20–54 | 103–179 | 235–272 | 447–502 | | | | |
| PVGLF_MUMPS | FUSION GLYCOPROTEIN PRECURSOR | MUMPS VIRUS (STRAIN RW) | 20–54 | 103–179 | 235–272 | 447–502 | | | | |
| PVGLF_NDVA | FUSION GLYCOPROTEIN PRECURSOR | MUMPS VIRUS (STRAIN SBL) | 20–54 | 103–179 | 235–272 | 447–502 | | | | |
| PVGLF_NDVB | FUSION GLYCOPROTEIN PRECURSOR | NEWCASTLE DISEASE VIRUS (STRAIN AUSTRALIA-VICTORIA/32) | 117–182 | 231–272 | 426–512 | | | | | |
| PVGLF_NDVH3 | FUSION GLYCOPROTEIN PRECURSOR | NEWCASTLE DISEASE VIRUS (STRAIN BEAUDETTE C/45) | 122–182 | 231–272 | 426–517 | | | | | |
| PVGLF_NDVH4 | FUSION GLYCOPROTEIN PRECURSOR | NEWCASTLE DISEASE VIRUS (STRAIN HER/33) | 117–182 | 231–272 | 426–517 | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVGLG_HRSV4 | MAJOR SURFACE GLYCOPROTEIN G | HUMAN RESPIRATORY SYNCYTIAL VIRUS (STRAIN RSB1734 | 30–85 | | | | | | | |
| PVGLG_HRSV5 | MAJOR SURFACE GLYCOPROTEIN G | HUMAN RESPIRATORY SYNCYTIAL VIRUS (STRAIN RSB5857) | 30–107 | | | | | | | |
| PVGLG_HRSV6 | MAJOR SURFACE GLYCOPROTEIN G | HUMAN RESPIRATORY SYNCYTIAL VIRUS (STRAIN RSB6190) | 30–85 | | | | | | | |
| PVGLG_HRSV7 | MAJOR SURFACE GLYCOPROTEIN G | HUMAN RESPIRATORY SYNCYTIAL VIRUS (STRAIN RSB6256) | 30–85 | | | | | | | |
| PVGLG_HRSV8 | MAJOR SURFACE GLYCOPROTEIN G | HUMAN RESPIRATORY SYNCYTIAL VIRUS (STRAIN RSB6614) | 30–85 | | | | | | | |
| PVGLG_HRSVA | MAJOR SURFACE GLYCOPROTEIN G | HUMAN RESPIRATORY SYNCYTIAL VIRUS (SUBGROUP B/STRAI | 30–81 | | | | | | | |
| PVGLG_HRSVL | MAJOR SURFACE GLYCOPROTEIN G | HUMAN RESPIRATORY SYNCYTIAL VIRUS (STRAIN A2) | 30–67 | | | | | | | |
| PVGLG_HSVE4 | MAJOR SURFACE GLYCOPROTEIN G | HUMAN RESPIRATORY SYNCYTIAL VIRUS (SUBGROUP A/STRAI | 25–85 | | | | | | | |
| PVGLG_SIGMA | GLYCOPROTEIN G PRECURSOR | EQUINE HERPESVIRUS TYPE 4 (STRAIN 1942) | 271–305 | | | | | | | |
| PVGLG_SYNV | SPIKE GLYCOPROTEIN PRECURSOR | SIGMA VIRUS | 344–381 | 464–498 | | | | | | |
| PVGLG_VHSV0 | SPIKE GLYCOPROTEIN PRECURSOR | SONCHUS YELLOW NET VIRUS | 488–523 | | | | | | | |
| PVGLG_VSVIG | SPIKE GLYCOPROTEIN PRECURSOR | VIRAL HEMORRHAGIC SEPTICEMIA VIRUS (STRAIN 07-71) | 363–397 | | | | | | | |
| PVGLH_EBV | SPIKE GLYCOPROTEIN PRECURSOR | VESICULAR STOMATITIS VIRUS (SEROTYPE INDIANA/STRAIN G | 476–510 | | | | | | | |
| PVGLH_HCMVA | GLYCOPROTEIN GP85 PRECURSOR | EPSTEIN-BARR VIRUS (STRAIN B95-8) | 53–87 | 160–201 | 336–380 | 653–694 | | | | |
| PVGLH_HCMVT | GLYCOPROTEIN H PRECURSOR | HUMAN CYTOMEGALOVIRUS (STRAIN AD169) | 103–137 | 270–311 | 693–741 | | | | | |
| PVGLH_HSV11 | GLYCOPROTEIN H PRECURSOR | HUMAN CYTOMEGALOVIRUS (STRAIN TOWNE) | 102–136 | 692–740 | | | | | | |
| PVGLH_HSV1E | GLYCOPROTEIN H PRECURSOR | HERPES SIMPLEX VIRUS (TYPE 1/STRAIN 17) | 447–481 | | | | | | | |
| PVGLH_HSV6G | GLYCOPROTEIN H PRECURSOR | HERPES SIMPLEX VIRUS (TYPE 1/STRAIN HFEM) | 447–481 | | | | | | | |
| PVGLH_HSVBC | GLYCOPROTEIN H PRECURSOR | HERPES SIMPLEX VIRUS (TYPE 6/STRAIN GS) | 357–406 | | | | | | | |
| PVGLH_HSVE4 | GLYCOPROTEIN H PRECURSOR | BOVINE HERPESVIRUS TYPE 1 (STRAIN COOPER) | 364–416 | | | | | | | |
| PVGLH_HSVEB | GLYCOPROTEIN H PRECURSOR | EQUINE HERPESVIRUS TYPE 4 (STRAIN 1942) | 334–379 | 414–455 | | | | | | |
| PVGLH_HSVSA | GLYCOPROTEIN H PRECURSOR | EQUINE HERPESVIRUS TYPE 1 (STRAIN AB4P) AND (ISOLATE HV | 327–372 | 407–448 | | | | | | |
| PVGLH_MCMVS | GLYCOPROTEIN H PRECURSOR | HERPESVIRUS SAIMIRI (STRAIN 11) | 32–66 | 374–453 | 664–712 | | | | | |
| PVGLH_PRVKA | GLYCOPROTEIN H PRECURSOR | MURINE CYTOMEGALOVIRUS (STRAIN SMITH | 440–474 | | | | | | | |
| PVGLH_PRVN3 | GLYCOPROTEIN H PRECURSOR | PSEUDORABIES VIRUS (STRAIN KAPLAN) | 226–260 | | | | | | | |
| PVGLH_PRVRI | GLYCOPROTEIN H PRECURSOR | PSEUDORABIES VIRUS (STRAIN NIA-3) | 226–260 | | | | | | | |
| PVGLH_VZVD | GLYCOPROTEIN H PRECURSOR | PSEUDORABIES VIRUS (STRAIN RICE) | 226–260 | | | | | | | |
| PVGLI_HCMVA | PROBABLE GLYCOPROTEIN H PRECURSOR | VARICELLA-ZOSTER VIRUS (STRAIN DUMAS) | 455–506 | | | | | | | |
| PVGLM_BUNGE | IMMEDIATE EARLY GLYCOPROTEIN PRECURSOR | HUMAN CYTOMEGALOVIRUS (STRAIN AD169) | 47–111 | 323–359 | | | | | | |
| PVGLM_BUNL7 | M POLYPROTEIN PRECURSOR | BUNYAVIRUS GERMISTON | 512–567 | 685–737 | 1228–1262 | | | | | |
| PVGLM_BUNSH | M POLYPROTEIN PRECURSOR | BUNYAVIRUS LA CROSSE (ISOLATE L74) | 643–677 | 916–950 | | | | | | |
| PVGLM_BUNYW | M POLYPROTEIN PRECURSOR | BUNYAVIRUS SNOWSHOW HARE | 643–677 | | | | | | | |
| PVGLM_DUGBV | M POLYPROTEIN PRECURSOR | BUNYAMWERA VIRUS | 340–374 | 504–563 | 905–939 | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVGLM_HANTB | M POLYPROTEIN PRECURSOR | DUGBE VIRUS | 937–989 | 1239–1300 | | | | | | |
| PVGLM_HANTH | M POLYPROTEIN PRECURSOR | HANTAAN VIRUS (STRAIN B-1) | 693–727 | | | | | | | |
| PVGLM_HANTL | M POLYPROTEIN PRECURSOR | HANTAAN VIRUS (STRAIN HOJO) | 72–106 | | | | | | | |
| PVGLM_HANTV | M POLYPROTEIN PRECURSOR | HANTAAN VIRUS (STRAIN LEE) | 72–106 | | | | | | | |
| PVGLM_INSV | M POLYPROTEIN PRECURSOR | HANTAAN VIRUS (STRAIN 76-118) | 72–106 | | | | | | | |
| PVGLM_PHV | M POLYPROTEIN PRECURSOR | IMPATIENS NECROTIC SPOT VIRUS | 1067–1101 | | | | | | | |
| PVGLM_PTPV | M POLYPROTEIN PRECURSOR | PROSPECT HILL VIRUS | 73–111 | | | | | | | |
| PVGLM_SEOU8 | M POLYPROTEIN PRECURSOR | PUNTA TORO PHLEBOVIRUS | 149–251 | | | | | | | |
| PVGLM_SEOUR | M POLYPROTEIN PRECURSOR | SEOUL VIRUS (STRAIN 80-39) | 693–727 | | | | | | | |
| PVGLM_SEOUS | M POLYPROTEIN PRECURSOR | SEOUL VIRUS (STRAIN R22) | 694–728 | | | | | | | |
| PVGLN_BEFV | M POLYPROTEIN PRECURSOR | SEOUL VIRUS (STRAIN SR-11) | 693–730 | | | | | | | |
| PVGLP_BEV | NONSTRUCTURAL GLYCOPROTEIN GNS PRECURSOR | BOVINE EPHEMERAL FEVER VIRUS | 377–414 | 513–569 | | | | | | |
| PVGLX_PRVRI | PEPLOMER GLYCOPROTEIN PRECURSOR | BERNE VIRUS | 43–82 | 90–124 | 622–656 | 1128–1236 | | | | |
| PVGIY_JUNIN | SECRETED GLYCOPROTEIN GX | PSEUDORABIES VIRUS (STRAIN RICE) | 420–461 | | | | | | | |
| PVGIY_LASSG | GLYCOPROTEIN POLYPROTEIN PRECURSOR | JUNIN ARENAVIRUS | 301–349 | | | | | | | |
| PVGIY_LASSJ | GLYCOPROTEIN POLYPROTEIN PRECURSOR | LASSA VIRUS (STRAIN GA391) | 317–360 | 388–422 | | | | | | |
| PVGIY_LYCVA | GLYCOPROTEIN POLYPROTEIN PRECURSOR | LASSA VIRUS (STRAIN JOSIAH) | 318–361 | 389–423 | | | | | | |
| PVGIY_LYCVW | GLYCOPROTEIN POLYPROTEIN PRECURSOR | LYMPHOCYTIC CHORIOMENINGITIS VIRUS (STRAIN ARMSTRON | 333–367 | 395–432 | | | | | | |
| PVGIY_MOPEI | GLYCOPROTEIN POLYPROTEIN PRECURSOR | LYMPHOCYTIC CHORIOMENINGITIS VIRUS (STRAIN WE) | 124–158 | 333–367 | 395–432 | | | | | |
| PVGIY_PIARV | GLYCOPROTEIN POLYPROTEIN PRECURSOR | MOPEIA VIRUS | 316–359 | | | | | | | |
| PVGIY_TACV | GLYCOPROTEIN POLYPROTEIN PRECURSOR | PICHINDE ARENAVIRUS | 334–375 | | | | | | | |
| PVGIY_TACV5 | GLYCOPROTEIN POLYPROTEIN PRECURSOR | TACARIBE VIRUS | 315–363 | | | | | | | |
| PVGIY_TACV7 | GLYCOPROTEIN POLYPROTEIN PRECURSOR | TACARIBE VIRUS (STRAIN V5) | 303–351 | 382–416 | | | | | | |
| PVGIY_TACVT | GLYCOPROTEIN POLYPROTEIN PRECURSOR | TACARIBE VIRUS (STRAIN V7) | 302–350 | 381–415 | | | | | | |
| PVGNB_CPMV | GLYCOPROTEIN POLYPROTEIN PRECURSOR | TACARIBE VIRUS (STRAIN TRVL 11598) | 303–351 | 382–416 | | | | | | |
| PVGNM_CPMV | GENOME POLYPROTEIN B | COWPEA MOSAIC VIRUS | 835–869 | | | | | | | |
| PVGNM_CPSMV | GENOME POLYPROTEIN M | COWPEA MOSAIC VIRUS | 160–201 | | | | | | | |
| PVGNM_RCMV | GENOME POLYPROTEIN M | COWPEA SEVERE MOSAIC VIRUS (STRAIN DG) | 192–226 | 758–792 | 874–915 | | | | | |
| PVGP8_EBV | GENOME POLYPROTEIN M | RED CLOVER MOTTLE VIRUS | 837–871 | 912–946 | | | | | | |
| PVGP_EBOV | PROBABLE MEMBRANE ANTIGEN GP85 | EPSTEIN-BARR VIRUS (STRAIN B95-8) | 94–149 | | | | | | | |
| PVGP_MABVM | STRUCTURAL GLYCOPROTEIN PRECURSOR | EBOLA VIRUS | 280–321 | 334–368 | 469–503 | | | | | |
| PVGP_MABVP | STRUCTURAL GLYCOPROTEIN PRECURSOR | MARBURG VIRUS (STRAIN MUSOKE) | 562–596 | | | | | | | |
| PVH02_VACCC | STRUCTURAL GLYCOPROTEIN PRECURSOR | MARBURG VIRUS (STRAIN POPP) | 562–596 | | | | | | | |
| PVH02_VARV | LATE PROTEIN H2 | VACCINIA VIRUS (STRAIN COPENHAGEN) | 58–92 | | | | | | | |
| PVH05_VACCC | LATE PROTEIN H2 | VACCINIA VIRUS (STRAIN WR) | 58–94 | | | | | | | |
| PVH05_VACCV | LATE PROTEIN H2 | VARIOLA VIRUS | 58–92 | | | | | | | |
| PVH05_VARV | PROTEIN H5 | VACCINIA VIRUS (STRAIN COPENHAGEN) | 118–185 | | | | | | | |
| PVHEL_LSV | PROTEIN H5 | VACCINIA VIRUS (STRAIN WR) | 118–185 | | | | | | | |
| PVHRP_VACCC | PROTEIN H5 | VARIOLA VIRUS | 136–203 | | | | | | | |
| PVHRP_VACCV | PROBABLE HELICASE | LILY SYMPTOMLESS VIRUS | 126–160 | | | | | | | |
| | HOST RANGE PROTEIN | VACCINIA VIRUS (STRAIN COPENHAGEN) | 216–279 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVI03_VACCC | HOST RANGE PROTEIN | VACCINIA VIRUS (STRAIN WR) | 216–279 | | | | | | | |
| PVI03_VACCV | PROTEIN I3 | VACCINIA VIRUS (STRAIN COPENHAGEN) | 150–193 | 210–244 | | | | | | |
| PVI03_VARV | PROTEIN I3 | VACCINIA VIRUS (STRAIN WR) | 150–193 | 210–244 | | | | | | |
| PVI06_VACCV | PROTEIN I3 | VARIOLA VIRUS | 150–193 | 210–244 | | | | | | |
| PVI06_VARV | PROTEIN I6 | VACCINIA VIRUS (STRAIN WR) | 58–92 | | | | | | | |
| PVI07_VARV | PROTEIN I6 | VARIOLA VIRUS | 58–92 | | | | | | | |
| PVI08_VACCC | PROTEIN I7 | VARIOLA VIRUS | 373–407 | | | | | | | |
| PVI08_VACCV | PUTATIVE RNA HELICASE I8 | VACCINIA VIRUS (STRAIN COPENHAGEN) | 548–589 | | | | | | | |
| PVI08_VARV | PUTATIVE RNA HELICASE I8 | VACCINIA VIRUS (STRAIN WR) | 548–589 | | | | | | | |
| PVIE1_HCMVA | PUTATIVE RNA HELICASE I8 | VARIOLA VIRUS | 548–589 | | | | | | | |
| PVIE1_HCMVT | 55 KD IMMEDIATE-EARLY PROTEIN 1 | HUMAN CYTOMEGALOVIRUS (STRAIN AD169) | 78–112 | 171–205 | 368–402 | 416–450 | | | | |
| PVIE1_MCMVS | 55 KD IMMEDIATE-EARLY PROTEIN 1 | HUMAN CYTOMEGALOVIRUS (STRAIN TOWNE) | 78–112 | 171–205 | 368–402 | 416–450 | | | | |
| PVIE2_NPVOP | IMMEDIATE-EARLY PROTEIN 1 | MURINE CYTOMEGALOVIRUS (STRAIN SMITH) | 244–297 | | | | | | | |
| PVIEN_NPVAC | IMMEDIATE-EARLY PROTEIN IE-2 | ORGYIA PSEUDOTSUGATA MULTICAPSID POLYHEDROSIS VIRUS | 94–128 | 305–395 | | | | | | |
| PVIF_CAEVC | IMMEDIATE-EARLY REGULATORY PROTEIN IE-N | AUTOGRAPHA CALIFORNICA NUCLEAR POLYHEDROSIS VIRUS | 277–407 | | | | | | | |
| PVIF_FIVPE | VIRION INFECTIVITY FACTOR | CAPRINE ARTHRITIS ENCEPHALITIS VIRUS (STRAIN CORK) | 23–92 | | | | | | | |
| PVIF_FIVSD | VIRION INFECTIVITY FACTOR | FELINE IMMUNODEFICIENCY VIRUS (ISOLATE PETALUMA) | 53–94 | | | | | | | |
| PVIF_HC1A2 | VIRION INFECTIVITY FACTOR | FELINE IMMUNODEFICIENCY VIRUS (ISOLATE SAN DIEGO) | 32–80 | | | | | | | |
| PVIF_HV1B1 | VIRION INFECTIVITY FACTOR | HUMAN IMMUNODEFICIENCY VIRUS TYPE 1 (ARV2/SF2 ISOLATE | 1–42 | 62–96 | | | | | | |
| PVIF_HC1B5 | VIRION INFECTIVITY FACTOR | HUMAN IMMUNODEFICIENCY VIRUS TYPE 1 (BH10, BRU, HXB2, PV | 1–42 | 62–96 | | | | | | |
| PVIF_HV1EL | VIRION INFECTIVITY FACTOR | HUMAN IMMUNODEFICIENCY VIRUS TYPE 1 (BH5 ISOLATE) | 1–42 | 62–96 | | | | | | |
| PVIF_HV1JR | VIRION INFECTIVITY FACTOR | HUMAN IMMUNODEFICIENCY VIRUS TYPE 1 (ELI ISOLATE) | 1–42 | 62–96 | | | | | | |
| PVIF_HV1MA | VIRION INFECTIVITY FACTOR | HUMAN IMMUNODEFICIENCY VIRUS TYPE 1 (JRCSF ISOLATE) | 1–42 | 62–96 | | | | | | |
| PVIF_HV1MN | VIRION INFECTIVITY FACTOR | HUMAN IMMUNODEFICIENCY VIRUS TYPE 1 (MAL ISOLATE) | 2–36 | | | | | | | |
| PVIF_HV1N5 | VIRION INFECTIVITY FACTOR | HUMAN IMMUNODEFICIENCY VIRUS TYPE 1 (MN ISOLATE) | 1–42 | 62–96 | | | | | | |
| PVIF_HV1NA | VIRION INFECTIVITY FACTOR | HUMAN IMMUNODEFICIENCY VIRUS TYPE 1 (NEW YORK-5 ISOL | 1–42 | 62–96 | | | | | | |
| PVIF_HVIND | VIRION INFECTIVITY FACTOR | HUMAN IMMUNODEFICIENCY VIRUS TYPE 1 (ISOLATE NIT-A) | 1–42 | 62–96 | | | | | | |
| PVIF_HV1OY | VIRION INFECTIVITY FACTOR | HUMAN IMMUNODEFICIENCY VIRUS TYPE 1 (NDK ISOLATE) | 1–42 | 62–96 | | | | | | |
| PVIF_HV1RH | VIRION INFECTIVITY FACTOR | HUMAN IMMUNODEFICIENCY VIRUS TYPE 1 (OYI ISOLATE) | 1–42 | 62–96 | | | | | | |
| PVIF_HV1U4 | VIRION INFECTIVITY FACTOR | HUMAN IMMUNODEFICIENCY VIRUS TYPE 1 (RF/HAT ISOLATE) | 1–42 | 62–96 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVIF_HV1Z2 | VIRION INFECTIVITY FACTOR | HUMAN IMMUNODEFICIENCY VIRUS TYPE 1 (STRAIN UGANDAN | 1–42 | | | | | | | |
| PVIF_HV1Z6 | VIRION INFECTIVITY FACTOR | HUMAN IMMUNODEFICIENCY VIRUS TYPE 1 (Z2/CDC-Z34 ISOLAT | 1–42 | 62–96 | | | | | | |
| PVIF_HV2D2 | VIRION INFECTIVITY FACTOR | HUMAN IMMUNODEFICIENCY VIRUS TYPE 1 (ZAIRE 6 ISOLATE) | 1–42 | 62–96 | | | | | | |
| PVIF_HV2NZ | VIRION INFECTIVITY FACTOR | HUMAN IMMUNODEFICIENCY VIRUS TYPE 2 (ISOLATE D205,7) | 147–195 | | | | | | | |
| PVIF_HV2RO | VIRION INFECTIVITY FACTOR | HUMAN IMMUNODEFICIENCY VIRUS TYPE 2 (ISOLATE NIH-Z) | 152–193 | | | | | | | |
| PVIF_OMVVS | VIRION INFECTIVITY FACTOR | HUMAN IMMUNODEFICIENCY VIRUS TYPE 2 (ISOLATE ROD) | 163–197 | | | | | | | |
| PVIF_SIVAI | VIRION INFECTIVITY FACTOR | OVINE LENTIVIRUS (STRAIN SA-OMVV) | 44–114 | | | | | | | |
| PVIF_SIVAG | VIRION INFECTIVITY FACTOR | SIMIAN IMMUNODEFICIENCY VIRUS (AGM155 ISOLATE) | 2–58 | 150–202 | | | | | | |
| PVIF_SIVA1 | VIRION INFECTIVITY FACTOR | SIMIAN IMMUNODEFICIENCY VIRUS (AGM3 ISOLATE) | 17–58 | | | | | | | |
| PVIF_SIVAT | VIRION INFECTIVITY FACTOR | SIMIAN IMMUNODEFICIENCY VIRUS (ISOLATE AGM/CLONE GR1 | 2–36 | 143–187 | | | | | | |
| PVIF_SIVCZ | VIRION INFECTIVITY FACTOR | SIMIAN IMMUNODEFICIENCY VIRUS (TYO-1 ISOLATE) | 20–58 | 150–195 | | | | | | |
| PVIF_SIVGB | VIRION INFECTIVITY FACTOR | CHIMPANZEE IMMUNODEFICIENCY VIRUS | 1–42 | | | | | | | |
| PVIMP_HSV11 | VIRION INFECTIVITY FACTOR | SIMIAN IMMUNODEFICIENCY VIRUS (ISOLATE GB1) | 1–39 | | | | | | | |
| PVIMP_HSVEB | PROBABLE INTEGRAL MEMBRANE PROTEIN | HERPES SIMPLEX VIRUS (TYPE 1/STRAIN 17) | 85–134 | | | | | | | |
| PVIMP_HSVSA | PROBABLE INTEGRAL MEMBRANE PROTEIN | EQUINE HERPESVIRUS TYPE 1 (STRAIN AB4P) | 148–182 | 335–369 | | | | | | |
| PVIMP_VZVD | INTEGRAL MEMBRANE PROTEIN | HERPESVIRUS SAIMIRI (STRAIN 11) | 80–129 | | | | | | | |
| PVINT_SSV1 | PROBABLE INTEGRAL MEMBRANE PROTEIN | VARICELLA-ZOSTER VIRUS (STRAIN DUMAS) | 107–151 | 155–189 | 267–301 | | | | | |
| PVJ01_VACCC | PROBABLE INTEGRASE | SULFOLOBUS VIRUS-LIKE PARTICLE SSV1 | 85–130 | 138–172 | | | | | | |
| PVJ01_VACCV | PROTEIN J1 | VACCINIA VIRUS (STRAIN COPENHAGEN) | 22–56 | | | | | | | |
| PVJ01_VARV | PROTEIN J1 | VACCINIA VIRUS (STRAIN WR) | 22–56 | | | | | | | |
| PVK03_VACCC | PROTEIN J1 | VARIOLA VIRUS | 22–56 | | | | | | | |
| PVK03_VACCV | PROTEIN K3 | VACCINIA VIRUS (STRAIN COPENHAGEN) | 38–82 | | | | | | | |
| PVK07_VACCV | PROTEIN K3 | VACCINIA VIRUS (STRAIN WR) | 38–82 | | | | | | | |
| PVL02_VACCC | PROTEIN K7 | VACCINIA VIRUS (STRAIN WR), AND (STRAIN COPENHAGEN) | 115–149 | | | | | | | |
| PVL02_VACCV | PROTEIN L2 | VACCINIA VIRUS (STRAIN COPENHAGEN) | 47–81 | | | | | | | |
| PVL02_VARV | PROTEIN L2 | VACCINIA VIRUS (STRAIN WR) | 47–92 | | | | | | | |
| PVL1_CRPVK | PROTEIN L2 | VARIOLA VIRUS | 47–81 | | | | | | | |
| PVL1_FPVL | PROBABLE L1 PROTEIN | COTTONTAIL RABBIT (SHOPE) PAPILLOMAVIRUS (STRAIN KANS | 261–295 | 331–383 | | | | | | |
| PVL1_HPV05 | PROBABLE L1 PROTEIN | AVIAN PAPILLOMAVIRUS FPV-L | 38–90 | | | | | | | |
| PVL1_HPV08 | PROBABLE L1 PROTEIN | HUMAN PAPILLOMAVIRUS TYPE 5 | 355–393 | | | | | | | |
| PVL1_HPV1A | PROBABLE L1 PROTEIN | HUMAN PAPILLOMAVIRUS TYPE 8 | 354–392 | | | | | | | |
| PVL1_HPV47 | PROBABLE L1 PROTEIN | HUMAN PAPILLOMAVIRUS TYPE 1A | 345–379 | | | | | | | |
| PVL1_PAPVD | PROBABLE L1 PROTEIN | HUMAN PAPILLOMAVIRUS TYPE 47 | 353–391 | | | | | | | |
| PVL1_REOVD | PROBABLE L1 PROTEIN | DEER PAPILLOMAVIRUS | 23–57 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVL2_HPV05 | MAJOR CORE PROTEIN LAMBDA 1 | REOVIRUS (TYPE 3/STRAIN DEARING) | 94–142 | 437–471 | | | | | | |
| PVL2_HPV08 | PROBABLE L2 PROTEIN | HUMAN PAPILLOMAVIRUS TYPE | 341–375 | | | | | | | |
| PVL2_HPV16 | PROBABLE L2 PROTEIN | HUMAN PAPILLOMAVIRUS TYPE 8 | 354–392 | | | | | | | |
| PVL2_HPV1A | PROBABLE L2 PROTEIN | HUMAN PAPILLOMAVIRUS TYPE 16 | 295–333 | | | | | | | |
| PVL2_HPV31 | PROBABLE L1 PROTEIN | HUMAN PAPILLOMAVIRUS TYPE 1A | 345–379 | | | | | | | |
| PVL2_HPV35 | PROBABLE L2 PROTEIN | HUMAN PAPILLOMAVIRUS TYPE 31 | 288–326 | | | | | | | |
| PVL2_HPV47 | PROBABLE L1 PROTEIN | HUMAN PAPILLOMAVIRUS TYPE 35 | 292–333 | | | | | | | |
| PVL2_HPV58 | PROBABLE L2 PROTEIN | HUMAN PAPILLOMAVIRUS TYPE 47 | 341–375 | | | | | | | |
| PVL2_HPV5B | PROBABLE L2 PROTEIN | HUMAN PAPILLOMAVIRUS TYPE 58 | 293–327 | | | | | | | |
| PVL3_REOVD | PROBABLE L2 PROTEIN | HUMAN PAPILLOMAVIRUS TYPE 5B | 341–375 | | | | | | | |
| PVL3_REOVJ | MINOR CORE PROTEIN LAMBDA 3 | REOVIRUS (TYPE 3/STRAIN DEARING) | 107–148 | 1112–1178 | | | | | | |
| PVL3_REOVL | MINOR CORE PROTEIN LAMBDA 3 | REOVIRUS (TYPE 2/STRAIN D5/JONES) | 1112–1178 | | | | | | | |
| PVL96_IRV1 | MINOR CORE PROTEIN LAMBDA 3 | REOVIRUS (TYPE 1/STRAIN LANG) | 107–148 | 331–365 | 1112–1178 | | | | | |
| PVM01_VACCC | L96 PROTEIN | TIPULA IRIDESCENT VIRUS | 146–180 | 198–236 | | | | | | |
| PVM1_REOVL | PROTEIN M1 | VACCINIA VIRUS (STRAIN COPENHAGEN) | 5–56 | | | | | | | |
| PVM21_REOVD | MINOR VIRION STRUCTURAL PROTEIN MU-2 | REOVIRUS (TYPE 1/STRAIN LANG) | 287–321 | | | | | | | |
| PVM22_REOVD | MAJOR VIRION STRUCTURAL PROTEIN MU-1/MU-1C | REOVIRUS (TYPE 3/STRAIN DEARING) | 416–450 | 619–663 | | | | | | |
| PVM2_REOVJ | MAJOR VIRION STRUCTURAL PROTEIN MU-1/MU-1C | REOVIRUS (TYPE 3/STRAIN DEARING) | 416–450 | 618–662 | | | | | | |
| PVM2_REOVL | MAJOR VIRION STRUCTURAL PROTEIN MU-1/MU-1C | REOVIRUS (TYPE 2/STRAIN D5/JONES) | 416–450 | 618–662 | | | | | | |
| PVM3_REOVD | MAJOR VIRION STRUCTURAL PROTEIN MU-1/MU-1C | REOVIRUS (TYPE 1/STRAIN LANG) | 416–450 | 618–662 | | | | | | |
| PVMA2_BRSVA | MAJOR NONSTRUCTURAL PROTEIN MU-NS | REOVIRUS (TYPE 3/STRAIN DEARING) | 135–190 | 337–371 | 523–558 | 618–690 | | | | |
| PVMA2_HRSVA | MATRIX GLYCOPROTEIN M2 | BOVINE RESPIRATORY SYNCYTIAL VIRUS (STRAIN A51908) | 42–90 | | | | | | | |
| PVMA2_TRTV | MATRIX GLYCOPROTEIN M2 | HUMAN RESPIRATORY SYNCYTIAL VIRUS (STRAIN A2) | 42–90 | | | | | | | |
| PVMAT_CDVO | MATRIX GLYCOPROTEIN M2 | TURKEY RHINOTRACHEITIS VIRUS | 36–70 | | | | | | | |
| PVMAT_INCJ | MATRIX PROTEIN | CANINE DISTEMPER VIRUS (STRAIN ONDERSTEPOORT) | 193–234 | | | | | | | |
| PVMAT_NDVA | MATRIX (M) PROTEIN | INFLUENZA C VIRUS (STRAIN C/JJ/50) | 73–114 | 151–208 | | | | | | |
| PVMAT_NDVB | MATRIX PROTEIN | NEWCASTLE DISEASE VIRUS (STRAIN AUSTRALIA-VICTORIA/32) | 310–358 | | | | | | | |
| PVMAT_PI3B | MATRIX PROTEIN | NEWCASTLE DISEASE VIRUS (STRAIN BEAUDETTE C/45) | 324–358 | | | | | | | |
| PVMAT_PI3H4 | MATRIX PROTEIN | BOVINE PARAINFLUENZA 3 VIRUS | 99–133 | 204–252 | | | | | | |
| PVMAT_RABVA | MATRIX PROTEIN | HUMAN PARAINFLUENZA 3 VIRUS (STRAIN NIH 47885) | 99–133 | 204–252 | | | | | | |
| PVMAT_RABVC | MATRIX PROTEIN | RABIES VIRUS (STRAIN AVO1) | 69–103 | | | | | | | |
| PVMAT_RABVE | MATRIX PROTEIN | RABIES VIRUS (STRAIN CVS-11) | 69–103 | | | | | | | |
| PVMAT_RABVN | MATRIX PROTEIN | RABIES VIRUS (STRAIN ERA) | 69–103 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVMAT_RABVP | MATRIX PROTEIN | RABIES VIRUS (STRAIN NISHIGAHARA RCEH) | 69–103 | | | | | | | |
| PVMAT_RABVS | MATRIX PROTEIN | RABIES VIRUS (STRAIN PV) | 69–103 | | | | | | | |
| PVMAT_SYNV | MATRIX PROTEIN | RABIES VIRUS (STRAIN SAD B19) | 69–103 | | | | | | | |
| PVMAT_VSVIG | MATRIX PROTEIN | SONCHUS YELLOW NET VIRUS | 246–280 | | | | | | | |
| PVME1_CVBM | MATRIX PROTEIN | VESICULAR STOMATITIS VIRUS (SEROTYPE INDIANA/STRAIN G) | 198–232 | | | | | | | |
| PVME1_CVPFS | E1 GLYCOPROTEIN | BOVINE CORONAVIRUS (STRAIN MEBUS) | 175–209 | | | | | | | |
| PVME1_CVPPU | E1 GLYCOPROTEIN PRECURSOR | PORCINE TRANSMISSIBLE GASTROENTERITIS CORONAVIRUS (S | 98–146 | 212–257 | | | | | | |
| PVME1_CVPRM | E1 GLYCOPROTEIN PRECURSOR | PORCINE TRANSMISSIBLE GASTROENTERITIS CORONAVIRUS (S | 212–257 | | | | | | | |
| PVME1_CVTKE | E1 GLYCOPROTEIN PRECURSOR | PORCINE RESPIRATORY CORONAVIRUS (STRAIN RM4) | 212–257 | | | | | | | |
| PVME1_FIPV | E1 GLYCOPROTEIN | TURKEY ENTERIC CORONAVIRUS | 28–62 | 175–209 | | | | | | |
| PVME1_IBV6 | E1 GLYCOPROTEIN PRECURSOR | FELINE INFECTIOUS PERITONITIS VIRUS (STRAIN 79-1146) | 212–257 | | | | | | | |
| PVME1_IBVB | E1 GLYCOPROTEIN | AVIAN INFECTIOUS BRONCHITIS VIRUS (STRAIN 6/82) | 21–55 | 177–218 | | | | | | |
| PVME1_IBVB2 | E1 GLYCOPROTEIN | AVIAN INFECTIOUS BRONCHITIS VIRUS (STRAIN BEAUDETTE) | 21–55 | 177–218 | | | | | | |
| PVME1_IBVK | E1 GLYCOPROTEIN | AVIAN INFECTIOUS BRONCHITIS VIRUS (STRAIN BEAUDETTE M4) | 21–55 | 177–218 | | | | | | |
| PVMEM_EBV | E1 GLYCOPROTEIN | AVIAN INFECTIOUS BRONCHITIS VIRUS (STRAIN KB8523) | 177–218 | | | | | | | |
| PVMP_CAMVC | PROBABLE MEMBRANE PROTEIN | EPSTEIN-BARR VIRUS (STRAIN B95-8) | 36–94 | | | | | | | |
| PVMP_CAMVD | MOVEMENT PROTEIN | CAULIFLOWER MOSAIC VIRUS (STRAIN CM-1841) | 187–254 | 270–324 | | | | | | |
| PVMP_CAMVE | MOVEMENT PROTEIN | CAULIFLOWER MOSAIC VIRUS (STRAIN D/H) | 187–254 | 270–324 | | | | | | |
| PVMP_CAMVN | MOVEMENT PROTEIN | CAULIFLOWER MOSAIC VIRUS (STRAIN BBC) | 187–254 | 270–324 | | | | | | |
| PVMP_CAMVS | MOVEMENT PROTEIN | CAULIFLOWER MOSAIC VIRUS (STRAIN NY8153) | 187–254 | 270–324 | | | | | | |
| PVMP_CAMVW | MOVEMENT PROTEIN | CAULIFLOWER MOSAIC VIRUS (STRAIN STRASBOURG) | 187–254 | 270–324 | | | | | | |
| PVMP_CERV | MOVEMENT PROTEIN | CAULIFLOWER MOSAIC VIRUS (STRAIN W260) | 187–254 | 270–324 | | | | | | |
| PVMP_FMVD | MOVEMENT PROTEIN | CARNATION ETCHED RING VIRUS | 212–246 | | | | | | | |
| PVMP_SOCMV | MOVEMENT PROTEIN | FIGWORT MOSAIC VIRUS (STRAIN DXS) | 217–251 | | | | | | | |
| PVMSA_HPBDB | MAJOR SURFACE ANTIGEN PRECURSOR | SOYBEAN CHLOROTIC MOTTLE VIRUS | 76–118 | | | | | | | |
| PVMSA_HPBDC | MAJOR SURFACE ANTIGEN PRECURSOR | DUCK HEPATITIS B VIRUS (BROWN SHANGHAI DUCK ISOLATE S | 272–313 | 324–361 | | | | | | |
| PVMSA_HPBDU | MAJOR SURFACE ANTIGEN PRECURSOR | DUCK HEPATITIS B VIRUS (STRAIN CHINA) | 271–312 | 323–360 | | | | | | |
| PVMSA_HPBDW | MAJOR SURFACE ANTIGEN PRECURSOR | DUCK HEPATITIS B VIRUS | 234–275 | 289–323 | | | | | | |
| PVMSA_HPBGS | MAJOR SURFACE ANTIGEN PRECURSOR | DUCK HEPATITIS B VIRUS (WHITE SHANGHAI DUCK ISOLATE S3 | 272–313 | 324–361 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVMSA_HPBHE | MAJOR SURFACE ANTIGEN PRECURSOR | GROUND SQUIRREL HEPATITIS VIRUS | 210–244 | | | | | | | |
| PVMSA_WHV1 | MAJOR SURFACE ANTIGEN PRECURSOR | HERON HEPATITIS B VIRUS | 294–328 | | | | | | | |
| PVMSA_WHV59 | MAJOR SURFACE ANTIGEN PRECURSOR | WOODCHUCK HEPATITIS VIRUS 1 | 208–242 | | | | | | | |
| PVMSA_WHV7 | MAJOR SURFACE ANTIGEN PRECURSOR | WOODCHUCK HEPATITIS VIRUS 59 | 213–247 | | | | | | | |
| PVMSA_WHV81 | MAJOR SURFACE ANTIGEN PRECURSOR | WOODCHUCK HEPATITIS VIRUS 7 | 213–247 | | | | | | | |
| PVMT1_DHVI1 | PROBABLE MAJOR SURFACE ANTIGEN PRECURSOR | WOODCHUCK HEPATITIS VIRUS 8 (INFECTIOUS CLONE) | 213–247 | | | | | | | |
| PVMT1_IAANN | MATRIX PROTEIN 1 | DHORI VIRUS (STRAIN INDIAN/1313/61) | 201–235 | | | | | | | |
| PVMT1_IABAN | MATRIX (M1) PROTEIN | INFLUENZA A VIRUS (STRAIN A/ANN ARBOR/6/60) | 92–126 | 174–222 | | | | | | |
| PVMT1_IACAO | MATRIX (M1) PROTEIN | INFLUENZA A VIRUS (STRAIN A/BANGKOK/1/79) | 92–126 | 174–222 | | | | | | |
| PVMT1_IAFOW | MATRIX (M1) PROTEIN | INFLUENZA A VIRUS (STRAIN A/CAMEL/MONGOLIA/82) | 31–79 | | | | | | | |
| PVMT1_IAFPR | MATRIX (M1) PROTEIN | INFLUENZA A VIRUS (STRAIN A/FORT WARREN/1/50), AND (STR | 92–126 | 174–222 | | | | | | |
| PVMT1_IAFPW | MATRIX (M1) PROTEIN | INFLUENZA A VIRUS (STRAIN A/FOWL PLAGUE VIRUS/ROSTOCK | 92–126 | 174–222 | | | | | | |
| PVMT1_IALE1 | MATRIX (M1) PROTEIN | INFLUENZA A VIRUS (STRAIN A/FOWL PLAGUE VIRUS/WEYBRID | 92–126 | 174–222 | | | | | | |
| PVMT1_IALE2 | MATRIX (M1) PROTEIN | INFLUENZA A VIRUS (STRAIN A/LENINGRAD/134/57) | 92–126 | 174–222 | | | | | | |
| PVMT1_IAMAN | MATRIX (M1) PROTEIN | INFLUENZA A VIRUS (STRAIN A/LENINGRAD/134/17/57) | 92–126 | 174–222 | | | | | | |
| PVMT1_IAPOC | MATRIX (M1) PROTEIN | INFLUENZA A VIRUS (STRAIN A/MALLARD/NEW YORK/6750/78) | 92–126 | 174–222 | | | | | | |
| PVMT1_IAPUE | MATRIX (M1) PROTEIN | INFLUENZA A VIRUS (STRAIN A/PORT CHALMERS/1/73) | 92–126 | 174–222 | | | | | | |
| PVMT1_IAUDO | MATRIX (M1) PROTEIN | INFLUENZA A VIRUS (STRAIN A/PUERTO RICO/8/34) | 92–126 | 174–222 | | | | | | |
| PVMT1_IAW1L | MATRIX (M1) PROTEIN | INFLUENZA A VIRUS (STRAIN A/UDORN/307/72) | 92–126 | 174–222 | | | | | | |
| PVMT1_IAZI1 | MATRIX (M1) PROTEIN | INFLUENZA A VIRUS (STRAIN A/WILSON-SMITH/33) | 92–126 | 174–222 | | | | | | |
| PVMT1_INBAC | MATRIX (M1) PROTEIN | INFLUENZA A VIRUS (STRAIN A/SWINE/IOWA/15/30) | 175–209 | | | | | | | |
| PVMT1_INBAD | MATRIX (M1) PROTEIN | INFLUENZA B VIRUS (STRAIN B/ANN ARBOR/1/66 [COLD-ADAPTE | 175–209 | | | | | | | |
| PVMT1_INBLE | MATRIX (M1) PROTEIN | INFLUENZA B VIRUS (STRAIN B/ANN ARBOR/1/66 [WILD-TYPE]) | 175–209 | | | | | | | |
| PVMT1_INBSI | MATRIX (M1) PROTEIN | INFLUENZA B VIRUS (STRAIN B/LEE/40) | 175–209 | | | | | | | |
| PVMT2_INBAC | MATRIX (M1) PROTEIN | INFLUENZA B VIRUS (STRAIN B/SINGAPORE/222/79) | 175–209 | | | | | | | |
| PVMT2_INBAD | PROBABLE MATRIX (M2) PROTEIN | INFLUENZA B VIRUS (STRAIN B/ANN ARBOR/1/66 [COLD-ADAPTE | 132–184 | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVMT2_INBLE | PROBABLE MATRIX (M2) PROTEIN | INFLUENZA B VIRUS (STRAIN B/ANN ARBOR/1/66 [WILD-TYPE]) | 132–184 | | | | | | | |
| PVMT2_INBSI | PROBABLE MATRIX (M2) PROTEIN | INFLUENZA B VIRUS (STRAIN B/LEE/40) | 132–184 | | | | | | | |
| PVMT8_MYXVL | PROBABLE MATRIX (M2) PROTEIN | INFLUENZA B VIRUS (STRAIN B/SINGAPORE/222/79) | 132–184 | | | | | | | |
| PVN01_VACCC | M-T8 PROTEIN | MYXOMA VIRUS (STRAIN LAUSANNE) | 46–80 | 145–197 | | | | | | |
| PVN01_VACCV | PROTEIN N1 | VACCINIA VIRUS (STRAIN COPENHAGEN) | 64–112 | | | | | | | |
| PVN34_ROTBS | PROTEIN N1 | VACCINIA VIRUS (STRAIN WR) | 64–112 | | | | | | | |
| PVN34_ROTPC | NONSTRUCTURAL PROTEIN NS34 | BOVINE ROTAVIRUS (GROUP C/STRAIN SHINTOKU) | 64–169 | | | | | | | |
| PVNCA_AAV2 | NONSTRUCTURAL PROTEIN NS34 | PORCINE ROTAVIRUS (GROUP C/STRAIN COWDEN) | 64–117 | 121–169 | | | | | | |
| PVNCA_RSV | DNA REPLICATION PROTEIN | ADENO-ASSOCIATED VIRUS 2 | 91–125 | 217–251 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVNS1_IACKJ | NONSTRUCTURAL PROTEIN NS1 | INFLUENZA A VIRUS (STRAIN A/CHICKEN/GERMANY/N/49) | 49–83 | | | | | | | |
| PVNS1_IADA2 | NONSTRUCTURAL PROTEIN NS1 | INFLUENZA A VIRUS (STRAIN A/CHICKEN/JAPAN/24) | 46–80 | | | | | | | |
| PVNS1_IADE1 | NONSTRUCTURAL PROTEIN NS1 | INFLUENZA A VIRUS (STRAIN A/DUCK/ALBERTA/60/76) | 49–83 | | | | | | | |
| PVNS1_IADU3 | NONSTRUCTURAL PROTEIN NS1 | INFLUENZA A VIRUS (STRAIN A/DUCK/ENGLAND/1/56) | 46–80 | | | | | | | |
| PVNS1_IAFOM | NONSTRUCTURAL PROTEIN NS1 | INFLUENZA A VIRUS (STRAIN A/DUCK/UKRAINE/1/63) | 46–80 | | | | | | | |
| PVNS1_IAFOW | NONSTRUCTURAL PROTEIN NS1 | INFLUENZA A VIRUS (STRAIN A/FORT MONMOUTH/1/47) | 49–83 | | | | | | | |
| PVNS1_IAFPR | NONSTRUCTURAL PROTEIN NS1 | INFLUENZA A VIRUS (STRAIN A/FORT WARREN/1/50, AND (STRA | 49–83 | | | | | | | |
| PVNS1_IALE1 | NONSTRUCTURAL PROTEIN NS1 | INFLUENZA A VIRUS (STRAIN A/FOWL PLAGUE VIRUS/ROSTOCK | 49–83 | | | | | | | |
| PVNS1_IALEN | NONSTRUCTURAL PROTEIN NS1 | INFLUENZA A VIRUS (STRAIN A/LENINGRAD/134/57) | 49–83 | | | | | | | |
| PVNS1_IAMA6 | NONSTRUCTURAL PROTEIN NS1 | INFLUENZA A VIRUS (STRAIN A/LENINGRAD/54/1) | 49–83 | | | | | | | |
| PVNS1_IAMAN | NONSTRUCTURAL PROTEIN NS1 | INFLUENZA A VIRUS (STRAIN A/MALLARD/ALBERTA/88/76 | 49–83 | | | | | | | |
| PVNS1_IAMAO | NONSTRUCTURAL PROTEIN NS1 | INFLUENZA A VIRUS (STRAIN A/MALLARD/NEW YORK/6750/78) | 49–83 | | | | | | | |
| PVNS1_IAMYN | NONSTRUCTURAL PROTEIN NS1 | INFLUENZA A VIRUS (STRAIN A/MALLARD/NEW YORK/6874/78 | 49–83 | | | | | | | |
| PVNS1_IAPI0 | NONSTRUCTURAL PROTEIN NS1 | INFLUENZA A VIRUS (STRAIN A/MYNAH/HANEDA-THAI/76) | 46–80 | | | | | | | |
| PVNS1_IAPI1 | NONSTRUCTURAL PROTEIN NS1 | INFLUENZA A VIRUS (STRAIN A/PINTAIL/ALBERTA/119/79 | 49–83 | | | | | | | |
| PVNS1_IAPI2 | NONSTRUCTURAL PROTEIN NS1 | INFLUENZA A VIRUS (STRAIN A/PINTAIL/ALBERTA/121/79) | 49–83 | | | | | | | |
| PVNS1_IAPI3 | NONSTRUCTURAL PROTEIN NS1 | INFLUENZA A VIRUS (STRAIN A/PINTAIL/ALBERTA/268/78 | 49–83 | | | | | | | |
| PVNS1_IAPUE | NONSTRUCTURAL PROTEIN NS1 | INFLUENZA A VIRUS (STRAIN A/PINTAIL/ALBERTA/358/79) | 49–83 | | | | | | | |
| PVNS1_IATKB | NONSTRUCTURAL PROTEIN NS1 | INFLUENZA A VIRUS (STRAIN A/PUERTO RICO/8/34) | 49–83 | | | | | | | |
| PVNS1_IATKC | NONSTRUCTURAL PROTEIN NS1 | INFLUENZA A VIRUS (STRAIN A/TURKEY/BETHLEHEM-GLILIT/14 | 49–83 | | | | | | | |
| PVNS1_IATKR | NONSTRUCTURAL PROTEIN NS1 | INFLUENZA A VIRUS (STRAIN A/TURKEY/CANADA/63) | 49–83 | | | | | | | |
| PVNS1_IATRS | NONSTRUCTURAL PROTEIN NS1 | INFLUENZA A VIRUS (STRAIN A/TURKEY/OREGON/71) | 49–83 | | | | | | | |
| PVNS1_IATRT | NONSTRUCTURAL PROTEIN NS1 | INFLUENZA A VIRUS (STRAIN A/TERN/SOUTH AFRICA/61 | 46–80 | | | | | | | |

TABLE V-continued

| ALLMOTI5 SEARCH RESULTS SUMMARY FOR ALL VIRAL (NON-BACTERIOPHAGE) PROTEINS | | | | | | | | | | |
|---|---|---|---|---|---|---|---|---|---|---|
| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
| PVNS1__IAZI1 | NONSTRUCTURAL PROTEIN NS1 | INFLUENZA A VIRUS (STRAIN A/TERN/TURKMENIA/18/72) | 49–83 | | | | | | | |
| PVNS1__INBAC | NONSTRUCTURAL PROTEIN NS1 | INFLUENZA A VIRUS (STRAIN A/SWINE/IOWA/15/30) | 49–83 | | | | | | | |
| PVNS1__INBGA | NONSTRUCTURAL PROTEIN NS1 | INFLUENZA B VIRUS (STRAIN B/ANN ARBOR/1/66[COLD-ADAPTE | 143–177 | | | | | | | |
| PVNS1__INBHK | NONSTRUCTURAL PROTEIN NS1 | INFLUENZA B VIRUS (STRAIN B/GA/86) | 143–177 | | | | | | | |
| PVNS1__INBHT | NONSTRUCTURAL PROTEIN NS1 | INFLUENZA B VIRUS (STRAIN B/HONG KONG/8/73), AND (STRAIN | 143–177 | | | | | | | |
| PVNS1__INBID | NONSTRUCTURAL PROTEIN NS1 | INFLUENZA B VIRUS (STRAIN B/HT/84) | 143–177 | | | | | | | |
| PVNS1__INBLE | NONSTRUCTURAL PROTEIN NS1 | INFLUENZA B VIRUS (STRAIN B/ID/86) | 143–177 | | | | | | | |
| PVNS1__INBMD | NONSTRUCTURAL PROTEIN NS1 | INFLUENZA B VIRUS (STRAIN B/LEE/40) | 143–177 | | | | | | | |
| PVNS1__INBPA | NONSTRUCTURAL PROTEIN NS1 | INFLUENZA B VIRUS (STRAIN B/MARYLAND/59) | 143–177 | | | | | | | |
| PVNS1__INBRU | NONSTRUCTURAL PROTEIN NS1 | INFLUENZA B VIRUS (STRAIN B/PA/79) | 143–177 | 277–337 | | | | | | |
| PVNS1__INBSI | NONSTRUCTURAL PROTEIN NS1 | INFLUENZA B VIRUS (STRAIN B/RU/69) | 139–173 | | | | | | | |
| PVNS1__INBSJ | NONSTRUCTURAL PROTEIN NS1 | INFLUENZA B VIRUS (STRAIN B/SINGAPORE/222/79) | 143–177 | | | | | | | |
| PVNS1__INBVJ | NONSTRUCTURAL PROTEIN NS1 | INFLUENZA B VIRUS (STRAIN B/SINGAPORE/64) | 143–177 | | | | | | | |
| PVNS1__INBYA | NONSTRUCTURAL PROTEIN NS1 | INFLUENZA B VIRUS (STRAIN B/VICTORIA/87) | 143–177 | | | | | | | |
| PVNS2__AHSV9 | NONSTRUCTURAL PROTEIN NS1 | INFLUENZA B VIRUS (STRAIN B/YAMAGATA/1/73) | 143–177 | | | | | | | |
| PVNS2__BTV17 | NONSTRUCTURAL PROTEIN NS2 | AFRICAN HORSE SICKNESS VIRUS (SEROTYPE 9) | 67–101 | | | | | | | |
| PVNS2__BTV1X | NONSTRUCTURAL PROTEIN NS2 | BLUETONGUE VIRUS (SEROTYPE 17/ISOLATE USA) | 203–237 | | | | | | | |
| PVNS2__CVMJH | NONSTRUCTURAL PROTEIN NS2 | BLUETONGUE VIRUS (SEROTYPE 10) | 203–237 | | | | | | | |
| PVNS2__EHDV2 | NONSTRUCTURAL PROTEIN NS2 | MURINE CORONAVIRUS MHV (STRAIN JHM) | 71–105 | | | | | | | |
| PVNS2__IAALA | NONSTRUCTURAL PROTEIN NS2 | EPIZOOTIC HEMORRHAGIC DISEASE VIRUS (SEROTYPE 2/STRAI | 206–272 | 276–311 | | | | | | |
| PVNS2__IAANA | NONSTRUCTURAL PROTEIN NS2 | INFLUENZA A VIRUS (STRAIN A/ALASKA/6/77), AND (STRAIN A/U | 14–93 | | | | | | | |
| PVNS2__IAANN | NONSTRUCTURAL PROTEIN NS2 | INFLUENZA A VIRUS (STRAIN A/ANAS ACUTA/PRIMORJE/695/76) | 14–93 | | | | | | | |
| PVNS2__IACHI | NONSTRUCTURAL PROTEIN NS2 | INFLUENZA A VIRUS (STRAIN A/ANN ARBOR/6/60), AND (STRAIN | 14–93 | | | | | | | |
| PVNS2__IACKG | NONSTRUCTURAL PROTEIN NS2 | INFLUENZA A VIRUS (STRAIN A/CHILE/1/83) | 14–93 | | | | | | | |

TABLE V-continued

ALLMOT15 SEARCH RESULTS SUMMARY FOR ALL VIRAL (NON-BACTERIOPHAGE) PROTEINS

| PCGENE FILE NAME | ALLMOT15 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVNS2_IACKJ | NONSTRUCTURAL PROTEIN NS2 | INFLUENZA A VIRUS (STRAIN A/CHICKEN/GERMANY/N/49) | 14–79 | | | | | | | |
| PVNS2_IADA2 | NONSTRUCTURAL PROTEIN NS2 | INFLUENZA A VIRUS (STRAIN A/CHICKEN/JAPAN/24) | 11–90 | | | | | | | |
| PVNS2_IADE1 | NONSTRUCTURAL PROTEIN NS2 | INFLUENZA A VIRUS (STRAIN A/DUCK/ALBERTA/60/76) | 14–79 | | | | | | | |
| PVNS2_IADU3 | NONSTRUCTURAL PROTEIN NS2 | INFLUENZA A VIRUS (STRAIN A/DUCK/ENGLAND/1/56) | 11–90 | | | | | | | |
| PVNS2_IAFOM | NONSTRUCTURAL PROTEIN NS2 | INFLUENZA A VIRUS (STRAIN A/DUCK/UKRAINE/1/63) | 11–90 | | | | | | | |
| PVNS2_IAFOW | NONSTRUCTURAL PROTEIN NS2 | INFLUENZA A VIRUS (STRAIN A/FORT MONMOUTH/1/47) | 14–93 | | | | | | | |
| PVNS2_IAFPR | NONSTRUCTURAL PROTEIN NS2 | INFLUENZA A VIRUS (STRAIN A/FORT WARREN/1/50) | 14–93 | | | | | | | |
| PVNS2_IALE2 | NONSTRUCTURAL PROTEIN NS2 | INFLUENZA A VIRUS (STRAIN A/FOWL PLAGUE VIRUS/ROSTOCK | 14–93 | | | | | | | |
| PVNS2_IALEN | NONSTRUCTURAL PROTEIN NS2 | INFLUENZA A VIRUS (STRAIN A/LENINGRAD/134/17/57) | 14–93 | | | | | | | |
| PVNS2_IAMA6 | NONSTRUCTURAL PROTEIN NS2 | INFLUENZA A VIRUS (STRAIN A/LENINGRAD/54/1) | 14–93 | | | | | | | |
| PVNS2_IAMA8 | NONSTRUCTURAL PROTEIN NS2 | INFLUENZA A VIRUS (STRAIN A/MALLARD/ALBERTA/88/76) | 14–79 | | | | | | | |
| PVNS2_IAMAN | NONSTRUCTURAL PROTEIN NS2 | INFLUENZA A VIRUS (STRAIN A/MALLARD/ALBERTA/827/78) | 14–79 | | | | | | | |
| PVNS2_IAMAO | NONSTRUCTURAL PROTEIN NS2 | INFLUENZA A VIRUS (STRAIN A/MALLARD/NEW YORK/6750/78) | 14–93 | | | | | | | |
| PVNS2_IAMYN | NONSTRUCTURAL PROTEIN NS2 | INFLUENZA A VIRUS (STRAIN A/MALLARD/NEW YORK/6874/78) | 14–93 | | | | | | | |
| PVNS2_IAPI0 | NONSTRUCTURAL PROTEIN NS2 | INFLUENZA A VIRUS (STRAIN A/MYNAH/HANEDA-THAI/76) | 11–90 | | | | | | | |
| PVNS2_IAPI1 | NONSTRUCTURAL PROTEIN NS2 | INFLUENZA A VIRUS (STRAIN A/PINTAIL/ALBERTA/119/79) | 14–93 | | | | | | | |
| PVNS2_IAPI2 | NONSTRUCTURAL PROTEIN NS2 | INFLUENZA A VIRUS (STRAIN A/PINTAIL/ALBERTA/121/79) | 14–79 | | | | | | | |
| PVNS2_IAPUE | NONSTRUCTURAL PROTEIN NS2 | INFLUENZA A VIRUS (STRAIN A/PINTAIL/ALBERTA/268/78) | 14–93 | | | | | | | |
| PVNS2_IATKB | NONSTRUCTURAL PROTEIN NS2 | INFLUENZA A VIRUS (STRAIN A/PUERTO RICO/8/34) | 14–93 | | | | | | | |
| PVNS2_IATKR | NONSTRUCTURAL PROTEIN NS2 | INFLUENZA A VIRUS (STRAIN A/TURKEY/BETHLEHEM-GLILIT/14 | 14–79 | | | | | | | |
| PVNS2_IATRS | NONSTRUCTURAL PROTEIN NS2 | INFLUENZA A VIRUS (STRAIN A/TURKEY/OREGON/71 | 14–79 | | | | | | | |
| PVNS2_IAUSS | NONSTRUCTURAL PROTEIN NS2 | INFLUENZA A VIRUS (STRAIN A/TERN/SOUTH AFRICA/61) | 11–52 | | | | | | | |
| PVNS2_INBLE | NONSTRUCTURAL PROTEIN NS2 | INFLUENZA A VIRUS (STRAIN A/USSR/90/77) | 14–93 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVNS2_INBYA | NONSTRUCTURAL PROTEIN NS2 | INFLUENZA B VIRUS (STRAIN B/LEE/40 | 2–43 | 59–119 | | | | | | |
| PVNS2_INCJJ | NONSTRUCTURAL PROTEIN NS2 | INFLUENZA B VIRUS (STRAIN B/YAMAGATA/1/73) | 2–43 | 59–119 | | | | | | |
| PVNS2_PVM | NONSTRUCTURAL PROTEIN NS2 | INFLUENZA C VIRUS (STRAIN C/JJ/50) | 57–98 | | | | | | | |
| PVNS3_AHSV3 | NONSTRUCTURAL PROTEIN 2 | PNEUMONIA VIRUS OF MICE | 70–104 | | | | | | | |
| PVNS3_AHSV9 | NONSTRUCTURAL PROTEIN NS3 | AFRICAN HORSE SICKNESS VIRUS (SEROTYPE 3) | 44–78 | 166–215 | | | | | | |
| PVNS3_BRD | NONSTRUCTURAL PROTEIN NS3 | AFRICAN HORSE SICKNESS VIRUS (SEROTYPE 9) | 37–78 | 88–122 | 166–215 | | | | | |
| PVNS3_CVPFS | NONSTRUCTURAL PROTEIN NS3 | BROADHAVEN VIRUS | 26–98 | 102–147 | | | | | | |
| PVNS4_CVH22 | NONSTRUCTURAL PROTEIN 3-1 | PORCINE TRANSMISSIBLE GASTROENTERITIS CORONAVIRUS (S | 13–51 | | | | | | | |
| PVNS4_RSV | NONSTRUCTURAL PROTEIN 4 | HUMAN CORONAVIRUS (STRAIN 229E) | 11–52 | | | | | | | |
| PVNS7_CVCAE | NONSTRUCTURAL PROTEIN NS4 | RICE STRIPE VIRUS | 2–40 | | | | | | | |
| PVNS7_CVFE3 | NONSTRUCTURAL PROTEIN 7 | CANINE ENTERIC CORONAVIRUS (STRAIN K378) | 11–47 | | | | | | | |
| PVNS7_FIPV | NONSTRUCTURAL PROTEIN 7 | FELINE ENTERIC CORONAVIRUS (STRAIN 79-1683) | 1–42 | | | | | | | |
| PVNSC_CDVO | NONSTRUCTURAL PROTEIN 7 | FELINE INFECTIOUS PERITONITIS VIRUS (STRAIN 79-1146) | 1–42 | | | | | | | |
| PVNSC_MEASE | NONSTRUCTURAL PROTEIN C | CANINE DISTEMPER VIRUS (STRAIN ONDERSTEPOORT) | 50–84 | 95–152 | | | | | | |
| PVNSC_MEASI | NONSTRUCTURAL PROTEIN C | MEASLES VIRUS (STRAIN EDMONSTON) | 43–84 | | | | | | | |
| PVNSC_MEASY | NONSTRUCTURAL PROTEIN C | MEASLES VIRUS (STRAIN IP-3-CA) | 43–84 | | | | | | | |
| PVNSC_PI1HB | NONSTRUCTURAL PROTEIN C | MEASLES VIRUS (STRAIN YAMAGATA-1) | 43–84 | | | | | | | |
| PVNSC_PI1HC | NONSTRUCTURAL PROTEIN C | HUMAN PARAINFLUENZA 1 VIRUS (STRAIN C35) | 133–167 | | | | | | | |
| PVNSC_PI1HD | NONSTRUCTURAL PROTEIN C | HUMAN PARAINFLUENZA 1 VIRUS (STRAIN C39) | 133–167 | | | | | | | |
| PVNSC_PI1HE | NONSTRUCTURAL PROTEIN C | HUMAN PARAINFLUENZA 1 VIRUS (STRAIN C1-5/73) | 133–167 | | | | | | | |
| PVNSC_PI3H4 | NONSTRUCTURAL PROTEIN C | HUMAN PARAINFLUENZA 1 VIRUS (STRAIN C1-14/83) | 40–75 | 133–167 | | | | | | |
| PVNSC_SEND6 | NONSTRUCTURAL PROTEIN C | HUMAN PARAINFLUENZA 3 VIRUS (STRAIN NIH 47885) | 58–133 | 161–199 | | | | | | |
| PVNSC_SENDH | NONSTRUCTURAL PROTEIN C | SENDAI VIRUS (STRAIN 6/94) | 133–167 | | | | | | | |
| PVNSC_SENDZ | NONSTRUCTURAL PROTEIN C | SENDAI VIRUS (STRAIN HARRIS) | 133–167 | | | | | | | |
| PVNSM_INSV | NONSTRUCTURAL PROTEIN C | SENDAI VIRUS (STRAIN Z) | 133–167 | | | | | | | |
| PVNST_BUNGE | NONSTRUCTURAL PROTEIN NS-M | IMPATIENS NECROTIC SPOT VIRUS (INSV) | 44–102 | 262–296 | | | | | | |
| PVNST_BUNL7 | NONSTRUCTURAL PROTEIN NS-S | BUNYAVIRUS GERMISTON | 34–75 | | | | | | | |
| PVNST_BUNLC | NONSTRUCTURAL PROTEIN NS-S | BUNYAVIRUS LA CROSSE (ISOLATE L74) | 5–39 | | | | | | | |
| PVNST_MAGV | NONSTRUCTURAL PROTEIN NS-S | BUNYAVIRUS LA CROSSE | 5–39 | | | | | | | |
| PVNST_TOSV | NONSTRUCTURAL PROTEIN NS-S | MAGUARI VIRUS | 35–69 | | | | | | | |
| PVNST_UUK | NONSTRUCTURAL PROTEIN NS-S | TOSCANA VIRUS (TOS) | 144–183 | | | | | | | |
| PVNUA_PRVKA | NONSTRUCTURAL PROTEIN NS-S | UUKUNIEMI VIRUS (UUK) | 139–173 | | | | | | | |
| PVNUC_DHVI 1 | PROBABLE NUCLEAR ANTIGEN | PSEUDORABIES VIRUS (STRAIN KAPLAN) (PRV) | 1134–1175 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVNUC__EBOV | NUCLEOPROTEIN | DHORI VIRUS (STRAIN INDIAN/1313/61) (DHO) | 209–243 | | | | | | | |
| PVNUC__IAANA | NUCLEOPROTEIN | EBOLA VIRUS | 191–225 | 227–261 | 329–369 | | | | | |
| PVNUC__IAANN | NUCLEOPROTEIN | INFLUENZA A VIRUS (STRAIN A/ANAS ACUTA/PRIMORJE/695/76) | 1–42 | 96–154 | 357–408 | | | | | |
| PVNUC__IABRA | NUCLEOPROTEIN | INFLUENZA A VIRUS (STRAIN A/ANN ARBOR/6/60) | 1–42 | 357–408 | | | | | | |
| PVNUC__IABUD | NUCLEOPROTEIN | INFLUENZA A VIRUS (STRAIN A/BRAZIL/11/78) | 1–42 | 357–408 | | | | | | |
| PVNUC__IACAL | NUCLEOPROTEIN | INFLUENZA A VIRUS (STRAIN A/BUDGERIGAR/HOKKAIDO/1/77) | 1–42 | 96–154 | 357–408 | | | | | |
| PVNUC__IACKG | NUCLEOPROTEIN | INFLUENZA A VIRUS (STRAIN A/CALIFORNIA/10/78) | 1–42 | 357–409 | | | | | | |
| PVNUC__IACKP | NUCLEOPROTEIN | INFLUENZA A VIRUS (STRAIN A/CHICKEN/GERMANY/N/49) | 1–42 | 96–154 | 357–408 | | | | | |
| PVNUC__IADAU | NUCLEOPROTEIN | INFLUENZA A VIRUS (STRAIN A/CHICKEN/PENNSYLVANIA/1/83) | 1–42 | 96–154 | 357–408 | | | | | |
| PVNUC__IADBE | NUCLEOPROTEIN | INFLUENZA A VIRUS (STRAIN A/DUCK/AUSTRALIA/749/80) | 1–42 | 96–154 | 357–408 | | | | | |
| PVNUC__IADCZ | NUCLEOPROTEIN | INFLUENZA A VIRUS (STRAIN A/DUCK/BEIJING/1/78) | 1–42 | 96–154 | 357–408 | | | | | |
| PVNUC__IADE1 | NUCLEOPROTEIN | INFLUENZA A VIRUS (STRAIN A/DUCK/CZECHOSLOVAKIA/56) | 1–42 | 96–154 | 360–408 | | | | | |
| PVNUC__IADE2 | NUCLEOPROTEIN | INFLUENZA A VIRUS (STRAIN A/DUCK/ENGLAND/1/56) | 1–42 | 96–154 | 357–408 | | | | | |
| PVNUC__IADHK | NUCLEOPROTEIN | INFLUENZA A VIRUS (STRAIN A/DUCK/ENGLAND/1/62) | 1–42 | 96–154 | 357–408 | | | | | |
| PVNUC__IADM2 | NUCLEOPROTEIN | INFLUENZA A VIRUS (STRAIN A/DUCK/HONG KONG/7/75) | 1–42 | 96–154 | 357–408 | | | | | |
| PVNUC__IADMA | NUCLEOPROTEIN | INFLUENZA A VIRUS (STRAIN A/DUCK/MEMPHIS/928/74 | 1–42 | 96–154 | 357–408 | | | | | |
| PVNUC__IADNZ | NUCLEOPROTEIN | INFLUENZA A VIRUS (STRAIN A/DUCK/MANITOBA/1/53) | 1–42 | 96–154 | 357–408 | | | | | |
| PVNUC__IADU2 | NUCLEOPROTEIN | INFLUENZA A VIRUS (STRAIN A/DUCK/NEW ZEALAND/31/76) | 1–42 | 96–154 | 357–408 | | | | | |
| PVNUC__IAEN5 | NUCLEOPROTEIN | INFLUENZA A VIRUS (STRAIN A/DUCK/UKRAINE/2/60) | 96–154 | 357–408 | | | | | | |
| PVNUC__IAFOM | NUCLEOPROTEIN | INFLUENZA A VIRUS (STRAIN A/ENGLAND/19/55) | 1–42 | 357–409 | | | | | | |
| PVNUC__IAFOW | NUCLEOPROTEIN | INFLUENZA A VIRUS (STRAIN A/FORT MONMOUTH/1/47) | 1–42 | 357–409 | | | | | | |
| PVNUC__IAFPD | NUCLEOPROTEIN | INFLUENZA A VIRUS (STRAIN A/FORT WARREN/1/50) | 357–408 | | | | | | | |
| PVNUC__IAFPR | NUCLEOPROTEIN | INFLUENZA A VIRUS (STRAIN A/FOWL PLAGUE VIRUS/DOBSONA | 1–42 | 96–154 | 357–408 | | | | | |
| PVNUC__IAGRE | NUCLEOPROTEIN | INFLUENZA A VIRUS (STRAIN A/FOWL PLAGUE VIRUS/ROSTOCK | 1–42 | 96–154 | 360–408 | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVNUC_IAGU1 | NUCLEOPROTEIN | INFLUENZA A VIRUS (STRAIN A/GREY TEAL/AUSTRALIA/2/79) | 1-42 | 113-154 | 357-408 | | | | | |
| PVNUC_IAGU2 | NUCLEOPROTEIN | INFLUENZA A VIRUS (STRAIN A/GULL/MARYLAND/5/77) | 1-42 | 357-408 | | | | | | |
| PVNUC_IAGU3 | NUCLEOPROTEIN | INFLUENZA A VIRUS (STRAIN A/GULL/MARYLAND/704/77) | 96-154 | 357-409 | | | | | | |
| PVNUC_IAGU4 | NUCLEOPROTEIN | INFLUENZA A VIRUS (STRAIN A/GULL/MARYLAND/1824/78) | 1-42 | 96-154 | 357-409 | | | | | |
| PVNUC_IAGUA | NUCLEOPROTEIN | INFLUENZA A VIRUS (STRAIN A/GULL/MARYLAND/1815/79) | 1-42 | 96-154 | 357-409 | | | | | |
| PVNUC_IAGUM | NUCLEOPROTEIN | INFLUENZA A VIRUS (STRAIN A/GULL/ASTRAKHAN/227/84) | 1-42 | 96-154 | 357-409 | | | | | |
| PVNUC_IAGUN | NUCLEOPROTEIN | INFLUENZA A VIRUS (STRAIN A/GULL/MASSACHUSETTS/26/80) | 1-42 | 96-154 | 357-409 | | | | | |
| PVNUC_IAHIC | NUCLEOPROTEIN | INFLUENZA A VIRUS (STRAIN A/GULL/MINNESOTA/945/80) | 1-42 | 357-409 | | | | | | |
| PVNUC_IAHJI | NUCLEOPROTEIN | INFLUENZA A VIRUS (STRAIN A/HICKOX/40) | 1-42 | 96-154 | 357-408 | | | | | |
| PVNUC_IAHLO | NUCLEOPROTEIN | INFLUENZA A VIRUS (STRAIN A/EQUINE/JILLIN/1/89) | 1-42 | 96-154 | 357-409 | | | | | |
| PVNUC_IAHMI | NUCLEOPROTEIN | INFLUENZA A VIRUS (STRAIN A/EQUINE/LONDON/1416/73) | 1-42 | 96-154 | | | | | | |
| PVNUC_IAHO1 | NUCLEOPROTEIN | INFLUENZA A VIRUS (STRAIN A/EQUINE/MIAMI/1/63) | 1-42 | 357-409 | | | | | | |
| PVNUC_IAHO2 | NUCLEOPROTEIN | INFLUENZA A VIRUS (STRAIN A/HONG KONG/1/68) | 1-42 | 357-409 | | | | | | |
| PVNUC_IAHPR | NUCLEOPROTEIN | INFLUENZA A VIRUS (STRAIN A/HONG KONG/5/83) | 96-154 | 357-408 | | | | | | |
| PVNUC_IAHTE | NUCLEOPROTEIN | INFLUENZA A VIRUS (STRAIN A/EQUINE/PRAGUE/1/56) | 1-42 | 96-154 | 357-408 | | | | | |
| PVNUC_IAKIE | NUCLEOPROTEIN | INFLUENZA A VIRUS (STRAIN A/KIEV/59/79) | 1-42 | 357-409 | | | | | | |
| PVNUC_IALEN | NUCLEOPROTEIN | INFLUENZA A VIRUS (STRAIN A/LENINGRAD/54/1) | 1-42 | 357-409 | | | | | | |
| PVNUC_IAMAA | NUCLEOPROTEIN | INFLUENZA A VIRUS (STRAIN A/MALLARD/NEW YORK/6750/78) | 1-42 | 96-154 | 357-408 | | | | | |
| PVNUC_IAMAN | NUCLEOPROTEIN | INFLUENZA A VIRUS (STRAIN A/MINK/SWEDEN/84) | 1-42 | 96-154 | 357-408 | | | | | |
| PVNUC_IAMIN | NUCLEOPROTEIN | INFLUENZA A VIRUS (STRAIN A/NEW JERSEY/8/76) | 1-42 | 96-154 | 357-408 | | | | | |
| PVNUC_IANEJ | NUCLEOPROTEIN | INFLUENZA A VIRUS (STRAIN A/NT/60/68) | 1-42 | 96-154 | 357-408 | | | | | |
| PVNUC_IANT6 | NUCLEOPROTEIN | INFLUENZA A VIRUS (STRAIN A/OHIO/4/83) | 1-42 | 357-409 | | | | | | |
| PVNUC_IAOHI | NUCLEOPROTEIN | | 1-42 | 357-409 | | | | | | |
| PVNUC_IAPAR | NUCLEOPROTEIN | | | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVNUC_IAPUE | NUCLEOPROTEIN | INFLUENZA A VIRUS (STRAIN A/PARROT/ULSTER/73) | 1–42 | 96–154 | 357–408 | | | | | |
| PVNUC_IARUD | NUCLEOPROTEIN | INFLUENZA A VIRUS (STRAIN A/PUERTO RICO/8/34) | 1–42 | 357–409 | | | | | | |
| PVNUC_IASE0 | NUCLEOPROTEIN | INFLUENZA A VIRUS (STRAIN A/RUDDY TURNSTONE/NEW JERSE | 1–42 | 96–154 | 357–408 | | | | | |
| PVNUC_IASH2 | NUCLEOPROTEIN | INFLUENZA A VIRUS (STRAIN A/SEAL/MASSACHUSETTS/1/80) | 1–42 | 96–154 | 357–408 | | | | | |
| PVNUC_IASIN | NUCLEOPROTEIN | INFLUENZA A VIRUS (STRAIN A/SHEARWATER/AUSTRALIA/72) | 1–42 | 357–408 | | | | | | |
| PVNUC_IATEI | NUCLEOPROTEIN | INFLUENZA A VIRUS (STRAIN A/SINGAPORE/1/57) | 1–42 | 357–409 | | | | | | |
| PVNUC_IATKN | NUCLEOPROTEIN | INFLUENZA A VIRUS (STRAIN A/TEAL/ICELAND/29/80) | 1–42 | 96–154 | 357–408 | | | | | |
| PVNUC_IATKO | NUCLEOPROTEIN | INFLUENZA A VIRUS (STRAIN A/TURKEY/MINNESOTA/1661/81) | 1–42 | 96–154 | 357–408 | | | | | |
| PVNUC_IATRS | NUCLEOPROTEIN | INFLUENZA A VIRUS (STRAIN A/TURKEY/ONTARIO/7732/66) | 1–42 | 96–154 | 357–408 | | | | | |
| PVNUC_IATRT | NUCLEOPROTEIN | INFLUENZA A VIRUS (STRAIN A/TERN/SOUTH AFRICA/61) | 1–42 | 96–154 | 360–408 | | | | | |
| PVNUC_IATX7 | NUCLEOPROTEIN | INFLUENZA A VIRUS (STRAIN A/TERN/TURKMENIA/18/72) | 1–42 | 96–154 | 357–405 | | | | | |
| PVNUC_IAUDO | NUCLEOPROTEIN | INFLUENZA A VIRUS (STRAIN A/TEXAS/1/77) | 1–42 | 357–409 | | | | | | |
| PVNUC_IAUSS | NUCLEOPROTEIN | INFLUENZA A VIRUS (STRAIN A/UDORN/307/72) | 1–42 | 357–409 | | | | | | |
| PVNUC_IAV16 | NUCLEOPROTEIN | INFLUENZA A VIRUS (STRAIN A/USSR/90/77) | 1–42 | 357–408 | | | | | | |
| PVNUC_IAWHN | NUCLEOPROTEIN | INFLUENZA A VIRUS (STRAIN A/VICTORIA/5/68) | 357–408 | | | | | | | |
| PVNUC_IAWHP | NUCLEOPROTEIN | INFLUENZA A VIRUS (STRAIN A/WHALE/MAINE/328/84) | 1–42 | 96–154 | 357–409 | | | | | |
| PVNUC_IAWIL | NUCLEOPROTEIN | INFLUENZA A VIRUS (STRAIN A/WHALE/PACIFIC OCEAN/19/76) | 1–42 | 96–154 | 357–408 | | | | | |
| PVNUC_IAWIS | NUCLEOPROTEIN | INFLUENZA A VIRUS (STRAIN A/WILSON-SMITH/33) | 1–42 | 357–409 | | | | | | |
| PVNUC_IAZ29 | NUCLEOPROTEIN | INFLUENZA A VIRUS (STRAIN A/WISCONSIN/3523/88) | 1–42 | 96–154 | 357–408 | | | | | |
| PVNUC_IAZ41 | NUCLEOPROTEIN | INFLUENZA A VIRUS (STRAIN A/SWINE/29/37) | 1–42 | 96–154 | 357–408 | | | | | |
| PVNUC_IAZCA | NUCLEOPROTEIN | INFLUENZA A VIRUS (STRAIN A/SWINE/41/49) | 1–42 | 96–154 | 357–408 | | | | | |
| PVNUC_IAZDA | NUCLEOPROTEIN | INFLUENZA A VIRUS (STRAIN A/SWINE/CAMBRIDGE/1/35) | 1–42 | 357–409 | | | | | | |
| PVNUC_IAZGE | NUCLEOPROTEIN | INFLUENZA A VIRUS (STRAIN A/SWINE/DANDONG/9/83) | 1–42 | 357–409 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVNUC_IAZH1 | NUCLEOPROTEIN | INFLUENZA A VIRUS (STRAIN A/SWINE/GERMANY/2/81) | 1–42 | 96–154 | 357–408 | | | | | |
| PVNUC_IAZH3 | NUCLEOPROTEIN | INFLUENZA A VIRUS (STRAIN A/SWINE/HONG KONG/6/76) | 1–42 | 357–409 | | | | | | |
| PVNUC_IAZH4 | NUCLEOPROTEIN | INFLUENZA A VIRUS (STRAIN A/SWINE/HONG KONG/126/82) | 1–42 | 96–154 | 357–408 | | | | | |
| PVNUC_IAZI1 | NUCLEOPROTEIN | INFLUENZA A VIRUS (STRAIN A/SWINE/HONG KONG/127/82) | 1–42 | 96–154 | 357–408 | | | | | |
| PVNUC_IAZI2 | NUCLEOPROTEIN | INFLUENZA A VIRUS (STRAIN A/SWINE/IOWA/15/30) | 1–42 | 96–154 | 357–408 | | | | | |
| PVNUC_IAZI3 | NUCLEOPROTEIN | INFLUENZA A VIRUS (STRAIN A/SWINE/IOWA/1976/31) | 1–42 | 96–154 | 357–408 | | | | | |
| PVNUC_IAZJ1 | NUCLEOPROTEIN | INFLUENZA A VIRUS (STRAIN A/SWINE/IOWA/46) | 1–42 | 96–154 | 357–408 | | | | | |
| PVNUC_IAZJ2 | NUCLEOPROTEIN | INFLUENZA A VIRUS (STRAIN A/SWINE/ITALY/437/76) | 1–42 | 96–154 | 357–408 | | | | | |
| PVNUC_IAZJ3 | NUCLEOPROTEIN | INFLUENZA A VIRUS (STRAIN A/SWINE/ITALY/2/79) | 1–42 | 96–154 | 357–408 | | | | | |
| PVNUC_IAZJ4 | NUCLEOPROTEIN | INFLUENZA A VIRUS (STRAIN A/SWINE/ITALY/141/81) | 1–42 | 96–154 | 357–408 | | | | | |
| PVNUC_IAZJA | NUCLEOPROTEIN | INFLUENZA A VIRUS (STRAIN A/SWINE/ITALY/839/89) | 1–42 | 96–154 | 357–408 | | | | | |
| PVNUC_IAZMA | NUCLEOPROTEIN | INFLUENZA A VIRUS (STRAIN A/SWINE/JAMESBURG/42) | 1–42 | 96–154 | 357–408 | | | | | |
| PVNUC_IAZNE | NUCLEOPROTEIN | INFLUENZA A VIRUS (STRAIN A/SWINE/MAY/54) | 1–42 | 96–154 | 357–408 | | | | | |
| PVNUC_IAZOH | NUCLEOPROTEIN | INFLUENZA A VIRUS (STRAIN A/SWINE/NETHERLANDS/12/85) | 1–42 | 96–154 | 357–408 | | | | | |
| PVNUC_IAZON | NUCLEOPROTEIN | INFLUENZA A VIRUS (STRAIN A/SWINE/OHIO/23/35) | 1–42 | 96–154 | 357–408 | | | | | |
| PVNUC_IAZTE | NUCLEOPROTEIN | INFLUENZA A VIRUS (STRAIN A/SWINE/ONTARIO/2/81) | 1–42 | 96–154 | 357–408 | | | | | |
| PVNUC_IAZW1 | NUCLEOPROTEIN | INFLUENZA A VIRUS (STRAIN A/SWINE/TENNESSEE/24/77) | 1–42 | 96–154 | 357–408 | | | | | |
| PVNUC_IAZW2 | NUCLEOPROTEIN | INFLUENZA A VIRUS (STRAIN A/SWINE/WISCONSIN/1/57) | 1–42 | 96–154 | 357–408 | | | | | |
| PVNUC_INBAA | NUCLEOPROTEIN | INFLUENZA A VIRUS (STRAIN A/SWINE/WISCONSIN/1/61) | 1–42 | 96–154 | 357–408 | | | | | |
| PVNUC_INBAC | NUCLEOPROTEIN | INFLUENZA B VIRUS (STRAIN B/ANN ARBOR/1/86) | 75–142 | 480–514 | | | | | | |
| PVNUC_INBAD | NUCLEOPROTEIN | INFLUENZA B VIRUS (STRAIN B/ANN ARBOR/1/66 [COLD-ADAPTE | 75–142 | 480–514 | | | | | | |
| PVNUC_INBLE | NUCLEOPROTEIN | INFLUENZA B VIRUS (STRAIN B/ANN ARBOR/1/66 [WILD-TYPE]) | 75–145 | 480–514 | | | | | | |
| PVNUC_INBSI | NUCLEOPROTEIN | INFLUENZA B VIRUS (STRAIN B/LEE/40) | 75–146 | 480–514 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVNUC_INCCA | NUCLEOPROTEIN | INFLUENZA B VIRUS (STRAIN B/SINGAPORE/222/79) | 75–142 | 480–514 | | | | | | |
| PVNUC_MABVM | NUCLEOPROTEIN | INFLUENZA C VIRUS (STRAIN C/CALIFORNIA/78) | 92–203 | 406–447 | | | | | | |
| PVNUC_MABVP | NUCLEOPROTEIN | MARBURG VIRUS (STRAIN MUSOKE) | 173–207 | 322–407 | | | | | | |
| PVO01_VACCC | NUCLEOPROTEIN | MARBURG VIRUS (STRAIN POPP) | 173–207 | 322–407 | | | | | | |
| PVO01_VARV | PROTEIN O1 | VACCINIA VIRUS (STRAIN COPENHAGEN) | 102–145 | 245–279 | 341–382 | 581–615 | | | | |
| PVOR1_FXMV | PROTEIN O1 | VARIOLA VIRUS | 102–145 | 245–279 | 341–382 | 581–615 | | | | |
| PVOR1_NMV | 152 KD PROTEIN | FOXTAIL MOSAIC VIRUS | 293–327 | | | | | | | |
| PVOR1_PMV | 186 KD PROTEIN | NARCISSUS MOSAIC VIRUS (NMV) | 1519–1575 | | | | | | | |
| PVOR1_PVMR | 176 KD PROTEIN | PAPAYA MOSAIC POTEXVIRUS (PMV) | 1–39 | 299–337 | 1474–1532 | | | | | |
| PVOR1_PVX | 223 KD PROTEIN | POTATO VIRUS M (STRAIN RUSSIAN) (PVM) | 597–638 | 682–759 | | | | | | |
| PVOR1_PVXCP | 165 KD PROTEIN | POTATO VIRUS X (PVX) | 516–550 | | | | | | | |
| PVOR1_SMYEA | 165 KD PROTEIN | POTATO VIRUS X (STRAIN CP) (PVX) | 510–547 | | | | | | | |
| PVOR1_WCMVM | 150 KD PROTEIN | STRAWBERRY MILD YELLOW EDGE-ASSOCIATED VIRUS (SMYE | 308–342 | 931–965 | | | | | | |
| PVOR1_WCMVO | 147 KD PROTEIN | WHITE CLOVER MOSAIC VIRUS (STRAIN M) (WCMV) | 1240–1289 | | | | | | | |
| PVP10_NPVAC | 147 KD PROTEIN | WHITE CLOVER MOSAIC VIRUS (STRAIN O) (WCMV) | 1240–1289 | | | | | | | |
| PVP10_NPVOP | P10 PROTEIN | AUTOGRAPHA CALIFORNICA NUCLEAR POLYHEDROSIS VIRUS ( | 7–41 | | | | | | | |
| PVP10_RBSDV | P10 PROTEIN | ORGYIA PSEUDOTSUGATA MULTICAPSID POLYHEDROSIS VIRUS | 7–50 | | | | | | | |
| PVP10_RGDV | PROTEIN S10 | RICE BLACK STREAKED DWARF VIRUS (RBSDV) | 339–382 | 395–429 | 506–556 | | | | | |
| PVP10_WTV | NONSTRUCTURAL PROTEIN PNS10 | RICE GALL DWARF VIRUS (RGDV) | 186–273 | | | | | | | |
| PVP11_RDV | NONSTRUCTURAL PROTEIN PNS10 | WOUND TUMOR VIRUS (WTV) | 220–254 | | | | | | | |
| PVP11_WTV | NONSTRUCTURAL PROTEIN PNS11 | RICE DWARF VIRUS (RDV) | 25–80 | 273–314 | | | | | | |
| PVP12_RDV | NONSTRUCTURAL PROTEIN PNS11 | WOUND TUMOR VIRUS (WTV) | 16–74 | | | | | | | |
| PVP12_WTV | NONSTRUCTURAL PROTEIN P11 | RICE DWARF VIRUS (RDV)) | 140–181 | | | | | | | |
| PVP18_WTVNJ | NONSTRUCTURAL PROTEIN PNS12 | WOUND TUMOR VIRUS (WTV) | 68–108 | | | | | | | |
| PVP19_HSVEB | NONSTRUCTURAL PROTEIN PNS12 | WOUND TUMOR VIRUS (STRAIN NJ) (WTV) | 68–108 | | | | | | | |
| PVP23_HCMVA | CAPSID ASSEMBLY AND DNA MATURATION PROTE | EQUINE HERPESVIRUS TYPE 1 (STRAIN AB4P) (EHV-1) | 189–231 | | | | | | | |
| PVP23_HSV6U | PROBABLE CAPSID PROTEIN VP23 | HUMAN CYTOMEGALOVIRUS (STRAIN AD169) | 41–82 | 146–180 | | | | | | |
| PVP24_EBOV | PROBABLE CAPSID PROTEIN VP23 | HERPES SIMPLEX VIRUS (TYPE 6/STRAIN UGANDA-1102) | 47–81 | | | | | | | |
| PVP26_HSVEB | MEMBRANE-ASSOCIATED STRUCTURAL PROTEIN V | EBOLA VIRUS | 166–200 | | | | | | | |
| PVP26_HSVSA | CAPSID PROTEIN VP26 | EQUINE HERPESVIRUS TYPE 1 (STRAIN AB4P) (EHV-1) | 36–77 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVP26_NPVOP | CAPSID PROTEIN VP26 | HERPESVIRUS SAIMIRI (STRAIN 11) | 41–78 | | | | | | | |
| PVP26_VZVD | P26 PROTEIN | ORGYIA PSEUDOTSUGATA MULTICAPSID POLYHEDROSIS VIRUS | 118–159 | | | | | | | |
| PVP2_AHSV4 | CAPSID PROTEIN VP26 | VARICELLA-ZOSTER VIRUS (STRAIN DUMAS) (VZV) | 47–81 | | | | | | | |
| PVP2_BTV10 | OUTER CAPSID PROTEIN VP2 | AFRICAN HORSE SICKNESS VIRUS (SEROTYPE 4/STRAIN VACCI | 136–188 | 270–304 | 410–465 | 614–662 | 684–720 | 976–1056 | | |
| PVP2_BTV11 | OUTER CAPSID PROTEIN VP2 | BLUETONGUE VIRUS (SEROTYPE 10/ISOLATE USA) | 168–225 | | | | | | | |
| PVP2_BTV17 | OUTER CAPSID PROTEIN VP2 | BLUETONGUE VIRUS (SEROTYPE 11/ISOLATE USA) | 77–111 | 559–593 | | | | | | |
| PVP2_BTV1S | OUTER CAPSID PROTEIN VP2 | BLUETONGUE VIRUS (SEROTYPE 17/ISOLATE USA) | 77–111 | 168–209 | | | | | | |
| PVP2_EHDV1 | OUTER CAPSID PROTEIN VP2 | BLUETONGUE VIRUS (SEROTYPE 1/ISOLATE SOUTH AFRICA) | 119–153 | 576–610 | 668–702 | | | | | |
| PVP2_ROTBR | OUTER CAPSID PROTEIN VP2 | EPIZOOTIC HEMORRHAGIC DISEASE VIRUS (SEROTYPE 1) (EHDV | 72–106 | 247–301 | 405–453 | 461–495 | 895–929 | | | |
| PVP2_ROTBU | RNA-BINDING PROTEIN VP2 | BOVINE ROTAVIRUS (STRAIN RF) | 2–94 | 482–516 | 523–557 | 607–655 | 675–754 | | | |
| PVP2_ROTHW | RNA-BINDING PROTEIN VP2 | BOVINE ROTAVIRUS (STRAIN UK) | 2–94 | 483–517 | 524–558 | 608–656 | 676–755 | | | |
| PVP2_ROTPC | RNA-BINDING PROTEIN VP2 | HUMAN ROTAVIRUS (SEROTYPE 1/STRAIN WA) | 17–97 | 492–526 | 533–567 | 617–658 | 685–764 | | | |
| PVP2_ROTS1 | RNA-BINDING PROTEIN VP2 | PORCINE ROTAVIRUS (GROUP C/STRAIN COWDEN) | 1–50 | 52–99 | 194–228 | 515–551 | 599–643 | 705–746 | | |
| PVP30_ASFE7 | RNA-BINDING PROTEIN VP2 | SIMIAN 11 ROTAVIRUS (STRAIN SA11) | 36–96 | 483–517 | 608–656 | 680–755 | | | | |
| PVP31_FRG3V | PHOSPHOPROTEIN P30 | AFRICAN SWINE FEVER VIRUS (STRAIN E-75) (ASFV) | 29–89 | | | | | | | |
| PVP32_ASFB7 | EARLY 31 KD PROTEIN | FROG VIRUS 3 (FV3) | 227–261 | | | | | | | |
| PVP35_EBOV | PHOSPHOPROTEIN P32 | AFRICAN SWINE FEVER VIRUS (STRAIN BA71V) (ASFV) | 29–89 | | | | | | | |
| PVP35_NPVAC | POLYMERASE COMPLEX PROTEIN VP35 | EBOLA VIRUS | 80–119 | | | | | | | |
| PVP35_NPVBM | EARLY 35 KD PROTEIN | AUTOGRAPHA CALIFORNICA NUCLEAR POLYHEDROSIS VIRUS | 54–102 | | | | | | | |
| PVP35_VACCC | EARLY 35 KD PROTEIN | BOMBYX MORI NUCLEAR POLYHEDROSIS VIRUS (BMNPV) | 54–102 | 224–258 | | | | | | |
| PVP35_VACCP | IMMUNODOMINANT ENVELOPE PROTEIN P35 | VACCINIA VIRUS (STRAIN COPENHAGEN) | 140–181 | | | | | | | |
| PVP35_VACCV | IMMUNODOMINANT ENVELOPE PROTEIN P35 | VACCINIA VIRUS (STRAIN L-IVP) | 17–51 | | | | | | | |
| PVP35_VARV | IMMUNODOMINANT ENVELOPE PROTEIN P35 | VACCINIA VIRUS (STRAIN WR) | 140–181 | | | | | | | |
| PVP3_AHSV4 | IMMUNODOMINANT ENVELOPE PROTEIN P35 | VARIOLA VIRUS | 141–182 | | | | | | | |
| PVP3_BTV10 | VP3 CORE PROTEIN | AFRICAN HORSE SICKNESS VIRUS (SEROTYPE 4/STRAIN VACCI | 173–214 | 240–274 | 667–704 | | | | | |
| PVP3_BTV17 | VP3 CORE PROTEIN | BLUETONGUE VIRUS (SEROTYPE 10/ISOLATE USA) | 214–255 | 853–894 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVP3_BTV1A | VP3 CORE PROTEIN | BLUETONGUE VIRUS (SEROTYPE 17/ISOLATE USA) | 214–255 | 853–894 | | | | | | |
| PVP3_EHDV1 | VP3 CORE PROTEIN | BLUETONGUE VIRUS (SEROTYPE 1/ISOLATE AUSTRALIA) | 214–255 | 853–894 | | | | | | |
| PVP3_EHDVA | VP3 CORE PROTEIN | EPIZOOTIC HEMORRHAGIC DISEASE VIRUS (SEROTYPE 1) (EHDV) | 208–246 | 798–832 | 851–892 | | | | | |
| PVP3_GFLV | VP3 CORE PROTEIN | EPIZOOTIC HEMORRHAGIC DISEASE VIRUS | 208–246 | 735–770 | 798–832 | 851–892 | | | | |
| PVP3_RDV | P3 PROTEIN | GRAPEVINE FANLEAF VIRUS (GFLV) | 96–133 | | | | | | | |
| PVP3_ROTPC | MAJOR 114 KD STRUCTURAL PROTEIN | RICE DWARF VIRUS (RDV) | 299–337 | 817–872 | | | | | | |
| PVP3_ROTS1 | INNER CORE PROTEIN VP3 | PORCINE ROTAVIRUS (GROUP C/STRAIN COWDEN) | 24–58 | 229–263 | 329–395 | 406–446 | 640–688 | | | |
| PVP40_EBV | INNER CORE PROTEIN VP3 | SIMIAN 11 ROTAVIRUS (STRAIN SA11) | 26–76 | 244–278 | 331–365 | 415–492 | 662–696 | | | |
| PVP40_HSV11 | CAPSID PROTEIN P40 | EPSTEIN-BARR VIRUS (STRAIN B95-8) (HUMAN HERPESVIRUS 4) | 433–467 | | | | | | | |
| PVP40_HSVEB | CAPSID PROTEIN P40 | HERPES SIMPLEX VIRUS (TYPE 1/STRAIN 17) | 206–257 | 599–633 | | | | | | |
| PVP40_ILTVT | CAPSID PROTEIN P40 | EQUINE HERPESVIRUS TYPE 1 (STRAIN AB4P) (EHV-1) | 180–245 | | | | | | | |
| PVP40_SCMVC | CAPSID PROTEIN P40 | INFECTIOUS LARYNGOTRACHEITIS VIRUS (STRAIN THORNE V88 | 1–35 | 509–557 | | | | | | |
| PVP40_VZVD | CAPSID PROTEIN P40 | SIMIAN CYTOMEGALOVIRUS (STRAIN COLBURN) | 457–498 | | | | | | | |
| PVP41_NPVAC | STRUCTURAL GLYCOPROTEIN GP41 | VARICELLA-ZOSTER VIRUS (STRAIN DUMAS) (VZV) | 167–246 | 486–522 | | | | | | |
| PVP42_ROTS1 | OUTER CAPSID PROTEIN VP4 | AUTOGRAPHA CALIFORNICA NUCLEAR POLYHEDROSIS VIRUS ( | 132–166 | | | | | | | |
| PVP4A_VACCC | OUTER CAPSID PROTEIN VP4 | SIMIAN 11 ROTAVIRUS (STRAIN SA11) | 1–35 | 484–518 | 528–630 | | | | | |
| PVP4A_VARV | MAJOR CORE PROTEIN P4A PRECURSOR | SIMIAN 11 ROTAVIRUS (STRAIN SA11) | 1–35 | 237–518 | 531–646 | | | | | |
| PVP4B_FOWPV | MAJOR CORE PROTEIN P4A PRECURSOR | VACCINIA VIRUS (STRAIN COPENHAGEN) | 355–359 | 718–763 | 794–828 | 857–891 | | | | |
| PVP4B_VACCC | MAJOR CORE PROTEIN P4A PRECURSOR | VACCINIA VIRUS (STRAIN WR) | 262–296 | 355–359 | 718–763 | 794–828 | 857–891 | | | |
| PVP4B_VACCV | MAJOR CORE PROTEIN P4B PRECURSOR | VARIOLA VIRUS | 355–389 | 719–764 | 795–829 | 858–892 | | | | |
| PVP4B_VARV | MAJOR CORE PROTEIN P4B PRECURSOR | FOWLPOX VIRUS | 131–172 | 296–330 | | | | | | |
| PVP4_BTV10 | MAJOR CORE PROTEIN P4B PRECURSOR | VACCINIA VIRUS (STRAIN COPENHAGEN) | 3–37 | 125–163 | 249–283 | | | | | |
| PVP4_BTV11 | MAJOR CORE PROTEIN P4B PRECURSOR | VACCINIA VIRUS (STRAIN WR) | 3–37 | 125–163 | 249–283 | | | | | |
| | VP4 CORE PROTEIN | VARIOLA VIRUS | 3–37 | 125–163 | 249–283 | | | | | |
| | | BLUETONGUE VIRUS (SEROTYPE 10/ISOLATE USA) | 579–617 | 619–653 | | | | | | |
| PVP4_BTV13 | VP4 CORE PROTEIN | BLUETONGUE VIRUS (SEROTYPE 11/ISOLATE USA) | 569–607 | 609–643 | | | | | | |
| PVP4_BTV2A | VP4 CORE PROTEIN | BLUETONGUE VIRUS (SEROTYPE 13/ISOLATE USA) | 569–607 | 609–643 | | | | | | |
| PVP4_NCDV | VP4 CORE PROTEIN | BLUETONGUE VIRUS (SEROTYPE 2/ISOLATE USA) | 569–607 | 609–643 | | | | | | |
| PVP4_RDV | OUTER CAPSID PROTEIN VP4 | NEBRASKA CALF DIARRHEA VIRUS (STRAIN NCDV-LINCOLN) | 484–518 | 528–630 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVP4_ROTB4 | NONSTRUCTURAL PROTEIN PNS4 | RICE DWARF VIRUS (RDV) | 388–437 | 444–478 | 627–679 | | | | | |
| PVP4_ROTBC | OUTER CAPSID PROTEIN VP4 | BOVINE ROTAVIRUS (SEROTYPE 6/STRAIN B641) | 1–35 | 112–146 | 338–379 | 484–518 | 528–653 | | | |
| PVP4_ROTBU | OUTER CAPSID PROTEIN VP4 | BOVINE ROTAVIRUS (STRAIN C486) | 1–35 | 484–518 | 528–630 | | | | | |
| PVP4_ROTEH | OUTER CAPSID PROTEIN VP4 | BOVINE ROTAVIRUS (STRAIN UK) | 1–35 | 112–146 | 338–379 | 484–518 | 528–653 | | | |
| PVP4_ROTG1 | OUTER CAPSID PROTEIN VP4 | EQUINE ROTAVIRUS (STRAIN H-2) | 1–35 | 112–146 | 227–274 | 345–379 | 484–518 | 528–653 | | |
| PVP4_ROTH1 | OUTER CAPSID PROTEIN VP4 | ROTAVIRUS (GROUP B/STRAIN IDIR) | 117–151 | 476–519 | | | | | | |
| PVP4_ROTH5 | OUTER CAPSID PROTEIN VP4 | HUMAN ROTAVIRUS (SEROTYPE 1/STRAIN 1076) | 1–35 | 236–273 | 337–378 | 483–517 | 530–645 | | | |
| PVP4_ROTH6 | OUTER CAPSID PROTEIN VP4 | HUMAN ROTAVIRUS (SEROTYPE 2/STRAIN RV-5) | 1–35 | 236–273 | 337–378 | 483–517 | 527–652 | | | |
| PVP4_ROTHD | OUTER CAPSID PROTEIN VP4 | HUMAN ROTAVIRUS (SEROTYPE 1/STRAIN 69M) | 1–35 | 112–146 | 237–274 | 338–379 | 484–518 | 531–646 | | |
| PVP4_ROTHJ | OUTER CAPSID PROTEIN VP4 | HUMAN ROTAVIRUS (SEROTYPE 2/STRAIN DS1) | 1–35 | 236–273 | 337–378 | 483–517 | 527–652 | | | |
| PVP4_ROTHK | OUTER CAPSID PROTEIN VP4 | HUMAN ROTAVIRUS (STRAIN K8) | 1–35 | 237–274 | 345–379 | 484–518 | 528–588 | | | |
| PVP4_ROTHL | OUTER CAPSID PROTEIN VP4 | HUMAN ROTAVIRUS (STRAIN KU) | 1–35 | 337–378 | 483–517 | 527–652 | | | | |
| PVP4_ROTHM | OUTER CAPSID PROTEIN VP4 | HUMAN ROTAVIRUS (STRAIN L26) | 1–35 | 236–273 | 337–378 | 483–517 | 527–652 | | | |
| PVP4_ROTHN | OUTER CAPSID PROTEIN VP4 | HUMAN ROTAVIRUS (SEROTYPE 1/STRAIN M37) | 1–35 | 337–378 | 483–517 | 530–645 | | | | |
| PVP4_ROTHP | OUTER CAPSID PROTEIN VP4 | HUMAN ROTAVIRUS (SEROTYPE 3/STRAIN MCN13) | 1–35 | 237–274 | 338–379 | 484–518 | 531–645 | | | |
| PVP4_ROTHR | OUTER CAPSID PROTEIN VP4 | HUMAN ROTAVIRUS (SEROTYPE 3/STRAIN P) | 1–35 | 236–273 | 337–378 | 483–517 | 527–652 | | | |
| PVP4_ROTHT | OUTER CAPSID PROTEIN VP4 | HUMAN ROTAVIRUS (SEROTYPE 3/STRAIN RRV) | 1–38 | 91–146 | 227–274 | | | | | |
| PVP4_ROTHV | OUTER CAPSID PROTEIN VP4 | HUMAN ROTAVIRUS (SEROTYPE 4/STRAIN ST. THOMAS 3) | 1–35 | 236–273 | 337–378 | 483–517 | 530–644 | | | |
| PVP4_ROTHW | OUTER CAPSID PROTEIN VP4 | HUMAN ROTAVIRUS (SEROTYPE 4/STRAIN VA70) | 1–35 | 237–273 | 344–378 | 483–517 | 527–652 | | | |
| PVP4_ROTP5 | OUTER CAPSID PROTEIN VP4 | HUMAN ROTAVIRUS (SEROTYPE 1/STRAIN WA) | 1–35 | 237–273 | 344–378 | 483–517 | 527–652 | | | |
| PVP4_ROTPC | OUTER CAPSID PROTEIN VP4 | PORCINE ROTAVIRUS (SEROTYPE 5/STRAIN OSU) | 112–146 | 484–518 | 528–629 | | | | | |
| PVP4_ROTPG | OUTER CAPSID PROTEIN VP4 | PORCINE ROTAVIRUS (GROUP C/STRAIN COWDEN) | 6–40 | 127–161 | 241–278 | 293–334 | 580–614 | | | |
| PVP4_ROTPY | OUTER CAPSID PROTEIN VP4 | PORCINE ROTAVIRUS (STRAIN GOTTFRIED) | 1–35 | 236–273 | 337–378 | 483–517 | 530–564 | 569–638 | | |
| PVP4_ROTRH | OUTER CAPSID PROTEIN VP4 | PORCINE ROTAVIRUS (STRAIN YM) | 1–35 | 112–146 | 237–274 | 484–518 | 528–629 | | | |
| PVP4_RPTSF | OUTER CAPSID PROTEIN VP4 | RHESUS ROTAVIRUS | 1–38 | 112–146 | 237–274 | 338–379 | 484–522 | 531–646 | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVP4_ROTSS | OUTER CAPSID PROTEIN VP4 | SIMIAN 11 ROTAVIRUS (STRAIN SA11-FEM) | 1–35 | 484–518 | 528–630 | | | | | |
| PVP4_WTV | DE OUTER CAPSID PROTEIN VP4 | SIMIAN 11 ROTAVIRUS (STRAIN SA11-SEM) | 1–35 | 237–274 | 345–379 | 484–518 | 531–646 | | | |
| PVP5_AHSV4 | NONSTRUCTURAL PROTEIN PNS4 | WOUND TUMOR VIRUS (WTV) | 28–62 | 565–621 | | | | | | |
| PVP5_BRD | OUTER CAPSID PROTEIN VP5 | AFRICAN HORSE SICKNESS VIRUS (SEROTYPE 4/STRAIN VACCI | 7–58 | 113–229 | | | | | | |
| PVP5_BTV10 | OUTER CAPSID PROTEIN VP5 | BROADHAVEN VIRUS (BRD) | 45–86 | 98–226 | | | | | | |
| PVP5_BTV11 | OUTER CAPSID PROTEIN VP5 | BLUETONGUE VIRUS (SEROTYPE 10/ISOLATE USA) | 14–58 | 92–150 | 154–222 | 404–438 | | | | |
| PVP5_BTV13 | OUTER CAPSID PROTEIN VP5 | BLUETONGUE VIRUS (SEROTYPE 11/ISOLATE USA) | 14–58 | 92–150 | 154–222 | 404–445 | | | | |
| PVP5_BTV1A | OUTER CAPSID PROTEIN VP5 | BLUETONGUE VIRUS (SEROTYPE 13/ISOLATE USA) | 14–58 | 154–222 | 404–438 | | | | | |
| PVP5_BTV1S | OUTER CAPSID PROTEIN VP5 | BLUETONGUE VIRUS (SEROTYPE 1/ISOLATE AUSTRALIA) | 14–58 | 92–143 | 148–222 | 404–438 | | | | |
| PVP5_BTV2A | OUTER CAPSID PROTEIN VP5 | BLUETONGUE VIRUS (SEROTYPE 1/ISOLATE SOUTH AFRICA) | 14–58 | 92–143 | 148–222 | 404–438 | | | | |
| PVP5_EHDV1 | OUTER CAPSID PROTEIN VP5 | BLUETONGUE VIRUS (SEROTYPE 2/ISOLATE USA) | 14–58 | 92–222 | 404–438 | | | | | |
| PVP5_RDV | OUTER CAPSID PROTEIN VP5 | EPIZOOTIC HEMORRHAGIC DISEASE VIRUS (SEROTYPE 1) (EHDV | 24–58 | 92–126 | 163–233 | 291–325 | 399–433 | | | |
| PVP5_WTV | OUTER COAT PROTEIN P5 | RICE DWARF VIRUS (RDV) | 38–86 | 95–136 | 505–594 | | | | | |
| PVP61_BTV10 | OUTER COAT PROTEIN P5 | WOUND TUMOR VIRUS (WTV) | 434–503 | 547–581 | 751–798 | | | | | |
| PVP61_MRDV | VP6 PROTEIN | BLUETONGUE VIRUS (SEROTYPE 10/ISOLATE USA) | 163–215 | | | | | | | |
| PVP61_NPVAC | PROBABLE NONSTRUCTURAL 41.0 KD PROTEIN | MAIZE ROUGH DWARF VIRUS (MRDV) | 128–202 | | | | | | | |
| PVP62_BTV10 | 61 KD PROTEIN | AUTOGRAPHA CALIFORNICA NUCLEAR POLYHEDROSIS VIRUS ( | 29–96 | 351–386 | | | | | | |
| PVP64_NPVOP | VP6 PROTEIN | BLUETONGUE VIRUS (SEROTYPE 10/ISOLATE USA) | 47–88 | 159–207 | 214–251 | | | | | |
| PVP67_NPVAC | MAJOR ENVELOPE GLYCOPROTEIN PRECURSOR | ORGYIA PSEUDOTSUGATA MULTICAPSID POLYHEDROSIS VIRUS | 296–361 | 431–479 | | | | | | |
| PVP67_NPVGM | MAJOR ENVELOPE GLYCOPROTEIN PRECURSOR | AUTOGRAPHA CALIFORNICA NUCLEAR POLYHEDROSIS VIRUS ( | 44–78 | 289–364 | 443–477 | | | | | |
| PVP6_BTV11 | MAJOR ENVELOPE GLYCOPROTEIN | GALLERIA MELLONELLA NUCLEAR POLYHEDROSIS VIRUS (GMN | 206–281 | | | | | | | |
| PVP6_BTV13 | VP6 PROTEIN | BLUETONGUE VIRUS (SEROTYPE 11/ISOLATE USA) | 159–211 | | | | | | | |
| PVP6_BTV17 | VP6 PROTEIN | BLUETONGUE VIRUS (SEROTYPE 13/ISOLATE USA) | 159–211 | | | | | | | |
| PVP6_BTV1S | VP6 PROTEIN | BLUETONGUE VIRUS (SEROTYPE 17/ISOLATE USA) | 68–102 | 159–211 | | | | | | |
| PVP6_BTV2A | VP6 PROTEIN | BLUETONGUE VIRUS (SEROTYPE 1/ISOLATE SOUTH AFRICA) | 12–78 | 163–211 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVP6_RDV | VP6 PROTEIN | BLUETONGUE VIRUS (SEROTYPE 2/ISOLATE USA) | 44–78 | 135–187 | | | | | | |
| PVP6_WTV | STRUCTURAL PROTEIN P6 | RICE DWARF VIRUS (RDV) | 150–191 | 296–344 | 360–401 | | | | | |
| PVP6_WTVNJ | STRUCTURAL PROTEIN P6 | WOUND TUMOR VIRUS (WTV) | 144–178 | 286–334 | 400–434 | | | | | |
| PVP74_NPVAC | STRUCTURAL PROTEIN P6 | WOUND TUMOR VIRUS (STRAIN NJ) (WTV) | 144–178 | 286–334 | | | | | | |
| PVP74_NPVCF | P74 PROTEIN | AUTOGRAPHA CALIFORNICA NUCLEAR POLYHEDROSIS VIRUS ( | 387–456 | | | | | | | |
| PVP75_HSVSA | P74 PROTEIN | CHORISTONEURA FUMIFERANA NUCLEAR POLYHEDROSIS VIRU | 385–453 | | | | | | | |
| PVP79_NPVAC | PROBABLE MEMBRANE ANTIGEN 75 | HERPESVIRUS SAIMIRI (STRAIN 11) | 50–99 | 163–211 | 931–984 | | | | | |
| PVP7_BTV10 | 79 KD PROTEIN | AUTOGRAPHA CALIFORNICA NUCLEAR POLYHEDROSIS VIRUS ( | 44–78 | 363–397 | 406–440 | | | | | |
| PVP7_BTV13 | VP7 CORE PROTEIN | BLUETONGUE VIRUS (SEROTYPE 10/ISOLATE USA), (SEROTYPE | 184–228 | | | | | | | |
| PVP7_BTV17 | VP7 CORE PROTEIN | BLUETONGUE VIRUS (SEROTYPE 13/ISOLATE USA) | 201–235 | | | | | | | |
| PVP7_BTV1A | VP7 CORE PROTEIN | BLUETONGUE VIRUS (SEROTYPE 17/ISOLATE USA) | 184–228 | | | | | | | |
| PVP7_BTV1S | VP7 CORE PROTEIN | BLUETONGUE VIRUS (SEROTYPE 1/ISOLATE AUSTRALIA) | 184–235 | | | | | | | |
| PVP7_BTV2A | VP7 CORE PROTEIN | BLUETONGUE VIRUS (SEROTYPE 1/ISOLATE SOUTH AFRICA) | 184–228 | | | | | | | |
| PVP7_EHDV1 | VP7 CORE PROTEIN | BLUETONGUE VIRUS (SEROTYPE 2/ISOLATE USA) | 184–228 | | | | | | | |
| PVP7_RDV | VP7 CORE PROTEIN | EPIZOOTIC HEMORRHAGIC DISEASE VIRUS (SEROTYPE 1) (EHDV | 16–50 | 134–178 | | | | | | |
| PVP7_WTV | NONSTRUCTURAL PROTEIN PNS7 | RICE DWARF VIRUS (RDV) | 47–95 | 172–255 | | | | | | |
| PVP80_NPVAC | NONSTRUCTURAL PROTEIN PNS7 | WOUND TUMOR VIRUS (WTV) | 47–84 | 195–243 | 458–495 | | | | | |
| PVP87_NPVOP | CAPSID PROTEIN P80 | AUTOGRAPHA CALIFORNICA NUCLEAR POLYHEDROSIS VIRUS ( | 7–51 | 99–142 | 156–204 | 221–298 | | | | |
| PVP8_BTV10 | CAPSID PROTEIN P87 | ORGYIA PSEUDOTSUGATA MULTICAPSID POLYHEDROSIS VIRUS | 80–162 | 410–451 | | | | | | |
| PVP8_BTV11 | NONSTRUCTURAL PROTEIN P8 | BLUETONGUE VIRUS (SEROTYPE 10/ISOLATE USA) | 54–102 | 185–219 | | | | | | |
| PVP8_BTV13 | NONSTRUCTURAL PROTEIN P8 | BLUETONGUE VIRUS (SEROTYPE 11/ISOLATE USA) | 54–102 | 185–219 | | | | | | |
| PVP8_BTV17 | NONSTRUCTURAL PROTEIN P8 | BLUETONGUE VIRUS (SEROTYPE 13/ISOLATE USA) | 54–102 | 185–219 | | | | | | |
| PVP8_BTV1A | NONSTRUCTURAL PROTEIN P8 | BLUETONGUE VIRUS (SEROTYPE 17/ISOLATE USA) | 54–102 | 185–219 | | | | | | |
| PVP8_BTV1S | NONSTRUCTURAL PROTEIN P8 | BLUETONGUE VIRUS (SEROTYPE 1/ISOLATE AUSTRALIA) | 54–102 | 185–219 | | | | | | |
| PVP8_BTV2A | NONSTRUCTURAL PROTEIN P8 | BLUETONGUE VIRUS (SEROTYPE 1/ISOLATE SOUTH AFRICA) | 54–102 | 185–219 | | | | | | |
| PVP8_FOWPV | NONSTRUCTURAL PROTEIN P8 | BLUETONGUE VIRUS (SEROTYPE 2/ISOLATE USA) | 54–102 | 185–219 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVP9_RDV | STRUCTURAL PROTEIN VP8 PRECURSOR | FOWLPOX VIRUS | 193–245 | | | | | | | |
| PVP9_WTV | NONSTRUCTURAL PROTEIN PNS9 | RICE DWARF VIRUS (RDV) | 13–47 | 186–226 | | | | | | |
| PVP9_WTVNJ | STRUCTURAL PROTEIN P9 | WOUND TUMOR VIRUS (WTV) | 140–212 | | | | | | | |
| PVPG_BYDV1 | STRUCTURAL PROTEIN P9 | WOUND TUMOR VIRUS (STRAIN NJ) (WTV) | 140–212 | | | | | | | |
| PVPHE_NPVAC | PUTATIVE GENOME-LINKED PROTEIN PRECURSOR | BARLEY YELLOW DWARF VIRUS (ISOLATE MAV-PS1) (BYDV) | 25–59 | | | | | | | |
| PVPHE_NPVOP | 29 KD POLYHEDRAL ENVELOPE PROTEIN | AUTOGRAPHA CALIFORNICA NUCLEAR POLYHEDROSIS VIRUS ( | 146–223 | | | | | | | |
| PVPR_SIVML | 32 KD POLYHEDRAL ENVELOPE PROTEIN | ORGYIA PSEUDOTSUGATA MULTICAPSID POLYHEDROSIS VIRUS | 131–201 | 206–265 | | | | | | |
| PVPU_HV1A2 | VPR PROTEIN | SIMIAN IMMUNODEFICIENCY VIRUS (K78 ISOLATE) (SIV-MAC) | 78–115 | | | | | | | |
| PVPU_HV1B1 | VPU PROTEIN | HUMAN IMMUNODEFICIENCY VIRUS TYPE 1 (ARV2/SF2 ISOLATE | 1–38 | | | | | | | |
| PVPU_HV1B8 | VPU PROTEIN | HUMAN IMMUNODEFICIENCY VIRUS TYPE 1 (BH10 ISOLATE) (HI | 4–72 | | | | | | | |
| PVPU_HV1BN | VPU PROTEIN | HUMAN IMMUNODEFICIENCY VIRUS TYPE 1 (BH8 ISOLATE) (HIV | 5–72 | | | | | | | |
| PVPU_HV1BR | VPU PROTEIN | HUMAN IMMUNODEFICIENCY VIRUS TYPE 1 (BRAIN ISOLATE) (H | 4–59 | | | | | | | |
| PVPU_HV1C4 | VPU PROTEIN | HUMAN IMMUNODEFICIENCY VIRUS TYPE 1 (BRU ISOLATE) (HIV | 4–72 | | | | | | | |
| PVPU_HV1EL | VPU PROTEIN | HUMAN IMMUNODEFICIENCY VIRUS TYPE 1 (CDC-451 ISOLATE) | 3–40 | | | | | | | |
| PVPU_HV1H2 | VPU PROTEIN | HUMAN IMMUNODEFICIENCY VIRUS TYPE 1 (ELI ISOLATE) (HIV- | 6–40 | | | | | | | |
| PVPU_HV1J3 | VPU PROTEIN | HUMAN IMMUNODEFICIENCY VIRUS TYPE 1 (HXB2 ISOLATE) (HI | 5–72 | | | | | | | |
| PVPU_HV1JR | VPU PROTEIN | HUMAN IMMUNODEFICIENCY VIRUS TYPE 1 (JH3 ISOLATE) (HIV- | 2–50 | | | | | | | |
| PVPU_HV1MA | VPU PROTEIN | HUMAN IMMUNODEFICIENCY VIRUS TYPE 1 (JRCSF ISOLATE) (H | 4–59 | | | | | | | |
| PVPU_HV1ND | VPU PROTEIN | HUMAN IMMUNODEFICIENCY VIRUS TYPE 1 (MAL ISOLATE) (HI | 5–50 | | | | | | | |
| PVPU_HV1PV | VPU PROTEIN | HUMAN IMMUNODEFICIENCY VIRUS TYPE 1 (NDK ISOLATE) (HI | 4–40 | | | | | | | |
| PVPU_HV1RH | VPU PROTEIN | HUMAN IMMUNODEFICIENCY VIRUS TYPE 1 (PV22 ISOLATE) (HI | 4–72 | | | | | | | |
| PVPU_HV1S1 | VPU PROTEIN | HUMAN IMMUNODEFICIENCY VIRUS TYPE 1 (RF/HAT ISOLATE) ( | 1–39 | | | | | | | |
| PVPU_HV1Z2 | VPU PROTEIN | HUMAN IMMUNODEFICIENCY VIRUS TYPE 1 (SF162 ISOLATE) (HI | 4–59 | | | | | | | |
| PVPU_SIVCZ | VPU PROTEIN | HUMAN IMMUNODEFICIENCY VIRUS TYPE 1 (Z2/CDC-Z34 ISOLAT | 6–40 | | | | | | | |
| PVPX_HV2D2 | VPU PROTEIN | CHIMPANZEE IMMUNODEFICIENCY VIRUS (SIV(CPZ)) (CIV) | 21–78 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVRNA_BSMV | VPX PROTEIN | HUMAN IMMUNODEFICIENCY VIRUS TYPE 2 (ISOLATE D205,7) (H | 42–85 | | | | | | | |
| PVS05_ROTS1 | ALPHA-A PROTEIN | BARLEY STRIPE MOSAIC VIRUS (BSMV) | 40–74 | 857–898 | | | | | | |
| PVS06_ROTBS | NONSTRUCTURAL PROTEIN NCVP2 | SIMIAN 11 ROTAVIRUS (STRAIN SA11) | 248–287 | | | | | | | |
| PVS06_ROTGA | VP6 PROTEIN | BOVINE ROTAVIRUS (GROUP C/STRAIN SHINTOKU) | 6–44 | | | | | | | |
| PVS06_ROTGI | VP6 PROTEIN | ROTAVIRUS (GROUP B/STRAIN ADRV) (ADULT DIARRHEA ROTA | 69–144 | | | | | | | |
| PVS06_ROTHC | VP6 PROTEIN | ROTAVIRUS (GROUP B/STRAIN IDIR) | 24–58 | 64–103 | | | | | | |
| PVS06_ROTPC | VP6 PROTEIN | HUMAN ROTAVIRUS (GROUP C/STRAIN BRISTOL) | 9–43 | | | | | | | |
| PVS07_ROTBJ | VP6 PROTEIN | PORCINE ROTAVIRUS (GROUP C/STRAIN COWDEN) | 9–43 | | | | | | | |
| PVS07_ROTBU | GLYCOPROTEIN VP7 | BOVINE ROTAVIRUS (STRAIN KN-4) | 2–36 | 282–320 | | | | | | |
| PVS07_ROTP5 | NONSTRUCTURAL PROTEIN NCVP3 | BOVINE ROTAVIRUS (STRAIN UK) | 88–153 | 199–236 | | | | | | |
| PVS07_ROTS1 | NONSTRUCTURAL PROTEIN NCVP3 | PORCINE ROTAVIRUS (SEROTYPE 5/STRAIN OSU) | 88–162 | 202–236 | | | | | | |
| PVS08_ROTBU | NONSTRUCTURAL PROTEIN NCVP3 | SIMIAN 11 ROTAVIRUS (STRAIN SA11) | 88–153 | 199–236 | | | | | | |
| PVS08_ROTS1 | NONSTRUCTURAL PROTEIN NS2/VP9 | BOVINE ROTAVIRUS (STRAIN UK) | 2–70 | 75–119 | 160–226 | | | | | |
| PVS09_ROTB4 | NONSTRUCTURAL PROTEIN NCVP4 | SIMIAN 11 ROTAVIRUS (STRAIN SA11) | 2–46 | 144–212 | 217–255 | | | | | |
| PVS09_ROTB5 | GLYCOPROTEIN VP7 | BOVINE ROTAVIRUS (SEROTYPE 6/STRAIN B641) | 2–54 | 282–320 | | | | | | |
| PVS09_ROTB6 | GLYCOPROTEIN VP7 | BOVINE ROTAVIRUS (STRAIN A5) | 2–43 | 282–320 | | | | | | |
| PVS09_ROTBA | GLYCOPROTEIN VP7 | BOVINE ROTAVIRUS (SEROTYPE 6/STRAIN 61A) | 2–54 | 282–320 | | | | | | |
| PVS09_ROTBB | GLYCOPROTEIN VP7 | BOVINE ROTAVIRUS (STRAIN A44) | 2–54 | 282–320 | | | | | | |
| PVS09_ROTBK | GLYCOPROTEIN VP7 | BOVINE ROTAVIRUS (SEROTYPE 10/STRAIN B223) | 2–54 | 282–320 | | | | | | |
| PVS09_ROTBN | GLYCOPROTEIN VP7 | BOVINE ROTAVIRUS (STRAIN KK3) | 2–54 | 282–320 | | | | | | |
| PVS09_ROTBT | GLYCOPROTEIN VP7 | BOVINE ROTAVIRUS (STRAIN NCDV) | 2–54 | 282–320 | | | | | | |
| PVS09_ROTBU | GLYCOPROTEIN VP7 | BOVINE ROTAVIRUS (SEROTYPE 1/STRAIN T449) | 2–43 | 282–320 | | | | | | |
| PVS09_ROTC7 | GLYCOPROTEIN VP7 | BOVINE ROTAVIRUS (STRAIN UK) | 2–54 | 282–320 | | | | | | |
| PVS09_ROTEL | GLYCOPROTEIN VP7 | CHICKEN ROTAVIRUS A (SEROTYPE 7/STRAIN CH2) | 285–326 | | | | | | | |
| PVS09_ROTGA | GLYCOPROTEIN VP7 | EQUINE ROTAVIRUS (STRAIN L338) | 282–320 | | | | | | | |
| PVS09_ROTGI | GLYCOPROTEIN VP7 PRECURSOR | ROTAVIRUS (GROUP B/STRAIN ADRV) (ADULT DIARRHEA ROTA | 43–77 | | | | | | | |
| PVS09_ROTH4 | GLYCOPROTEIN VP7 PRECURSOR | ROTAVIRUS (GROUP B/STRAIN IDIR) | 45–79 | | | | | | | |
| PVS09_ROTH9 | GLYCOPROTEIN VP7 | HUMAN ROTAVIRUS (SEROTYPE 4/STRAIN RV-4) | 2–43 | 282–320 | | | | | | |
| PVS09_ROTHA | GLYCOPROTEIN VP7 | HUMAN ROTAVIRUS (SEROTYPE G/STRAIN RK9) | 282–320 | | | | | | | |
| PVS09_ROTHB | GLYCOPROTEIN VP7 | HUMAN ROTAVIRUS (SEROTYPE 2/STRAIN HU5) | 282–320 | | | | | | | |
| PVS09_ROTHD | GLYCOPROTEIN VP7 | HUMAN ROTAVIRUS (SEROTYPE G/STRAIN B37) | 2–43 | 282–320 | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVS09_ROTHH | GLYCOPROTEIN VP7 | HUMAN ROTAVIRUS (SEROTYPE 2/STRAIN DS1) | 282–320 | | | | | | | |
| PVS09_ROTHL | GLYCOPROTEIN VP7 | HUMAN ROTAVIRUS (SEROTYPE 2/STRAIN HN126) | 282–320 | | | | | | | |
| PVS09_ROTHM | GLYCOPROTEIN VP7 | HUMAN ROTAVIRUS (STRAIN L26) | 1–35 | 282–320 | | | | | | |
| PVS09_ROTHO | GLYCOPROTEIN VP7 | HUMAN ROTAVIRUS (SEROTYPE 1/STRAIN M37) | 2–43 | 282–320 | | | | | | |
| PVS09_ROTHP | GLYCOPROTEIN VP7 | HUMAN ROTAVIRUS (SEROTYPE 1/STRAIN MO AND STRAIN D) | 2–43 | 282–320 | | | | | | |
| PVS09_ROTHR | GLYCOPROTEIN VP7 | HUMAN ROTAVIRUS (SEROTYPE 3/STRAIN P) | 282–320 | | | | | | | |
| PVS09_ROTHS | GLYCOPROTEIN VP7 | HUMAN ROTAVIRUS (SEROTYPE 3/STRAIN RRV) | 282–320 | | | | | | | |
| PVS09_ROTHT | GLYCOPROTEIN VP7 | HUMAN ROTAVIRUS (SEROTYPE 2/STRAIN S2) | 282–320 | | | | | | | |
| PVS09_ROTHV | GLYCOPROTEIN VP7 | HUMAN ROTAVIRUS (SEROTYPE 4/STRAIN ST. THOMAS 3) | 18–56 | 208–242 | 282–320 | | | | | |
| PVS09_ROTHW | GLYCOPROTEIN VP7 | HUMAN ROTAVIRUS (SEROTYPE 4/STRAIN VA70) | 18–56 | 208–242 | 282–320 | | | | | |
| PVS09_ROTP2 | GLYCOPROTEIN VP7 | HUMAN ROTAVIRUS (SEROTYPE 1/STRAIN WA) | 2–43 | 282–320 | | | | | | |
| PVS09_ROTP3 | GLYCOPROTEIN VP7 | PORCINE ROTAVIRUS (SEROTYPE 3/STRAIN AI/76) | 282–320 | | | | | | | |
| PVS09_ROTP4 | GLYCOPROTEIN VP7 | PORCINE ROTAVIRUS (SEROTYPE 3/STRAIN CRW-8) | 282–320 | | | | | | | |
| PVS09_ROTP5 | GLYCOPROTEIN VP7 | PORCINE ROTAVIRUS (SEROTYPE 4/STRAIN OSU) | 2–56 | 208–242 | 282–320 | | | | | |
| PVS09_ROTP6 | GLYCOPROTEIN VP7 | PORCINE ROTAVIRUS (SEROTYPE 5/STRAIN OSU) | 282–320 | | | | | | | |
| PVS09_ROTPB | GLYCOPROTEIN VP7 | PORCINE ROTAVIRUS (SEROTYPE 5/STRAIN TFR-41) | 282–320 | | | | | | | |
| PVS09_ROTPK | GLYCOPROTEIN VP7 | PORCINE ROTAVIRUS (SEROTYPE 4/STRAIN BEN-144) | 18–56 | 208–242 | 282–320 | | | | | |
| PVS09_ROTPM | GLYCOPROTEIN VP7 | PORCINE ROTAVIRUS (STRAIN K) | 18–56 | 282–320 | | | | | | |
| PVS09_ROTPY | GLYCOPROTEIN VP7 | PORCINE ROTAVIRUS (SEROTYPE 4/STRAIN BMI-1) | 18–56 | 208–242 | | | | | | |
| PVS09_ROTRH | GLYCOPROTEIN VP7 | PORCINE ROTAVIRUS (STRAIN YM) | 1–35 | 282–320 | | | | | | |
| PVS09_ROTS1 | GLYCOPROTEIN VP7 | RHESUS ROTAVIRUS | 282–320 | | | | | | | |
| PVS10_ROTBN | GLYCOPROTEIN VP7 | SIMIAN 11 ROTAVIRUS (STRAIN SA11) | 282–320 | | | | | | | |
| PVS10_ROTBS | NONSTRUCTURAL GLYCOPROTEIN NCVP5 | BOVINE ROTAVIRUS (STRAIN NCDV) | 73–161 | | | | | | | |
| PVS10_ROTBU | MINOR OUTER CAPSID PROTEIN | BOVINE ROTAVIRUS (GROUP C/STRAIN SHINTOKU) | 17–58 | | | | | | | |
| PVS10_ROTH2 | NONSTRUCTURAL GLYCOPROTEIN NCVP5 | BOVINE ROTAVIRUS (STRAIN UK) | 73–161 | | | | | | | |
| PVS10_ROTH7 | NONSTRUCTURAL GLYCOPROTEIN NCVP5 | HUMAN ROTAVIRUS (STRAIN A28) | 73–162 | | | | | | | |
| PVS10_ROTH8 | NONSTRUCTURAL GLYCOPROTEIN NCVP5 | HUMAN ROTAVIRUS (STRAIN A64/CLONE 2) | 73–162 | | | | | | | |
| PVS10_ROTHC | NONSTRUCTURAL GLYCOPROTEIN NCVP5 | HUMAN ROTAVIRUS (STRAIN A64/CLONE 6) | 73–162 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVS10_ROTHW | MINOR OUTER CAPSID PROTEIN | HUMAN ROTAVIRUS (GROUP C/STRAIN BRISTOL) | 121-158 | | | | | | | |
| PVS10_ROTS1 | NONSTRUCTURAL GLYCOPROTEIN NCVP5 | HUMAN ROTAVIRUS (SEROTYPE 1/STRAIN WA) | 73-136 | | | | | | | |
| PVS11_ROTGA | NONSTRUCTURAL GLYCOPROTEIN NCVP5 | SIMIAN 11 ROTAVIRUS (STRAIN SA11) | 73-162 | 96-130 | | | | | | |
| PVS11_ROTGI | NONSTRUCTURAL PROTEIN | ROTAVIRUS (GROUP B/STRAIN ADRV) (ADULT DIARRHEA ROTA | 24-65 | | | | | | | |
| PVS11_ROTH5 | NONSTRUCTURAL PROTEIN | ROTAVIRUS (GROUP B/STRAIN IDIR) | 9-68 | | | | | | | |
| PVS11_ROTH6 | MINOR OUTER CAPSID PROTEIN | HUMAN ROTAVIRUS (SEROTYPE 2/STRAIN RV-5) | 100-145 | | | | | | | |
| PVS11_ROTHB | MINOR OUTER CAPSID PROTEIN | HUMAN ROTAVIRUS (SEROTYPE 1/STRAIN 69M) | 107-144 | | | | | | | |
| PVS11_ROTHD | MINOR OUTER CAPSID PROTEIN | HUMAN ROTAVIRUS (SEROTYPE G/STRAIN B37) | 107-144 | | | | | | | |
| PVS11_ROTHW | MINOR OUTER CAPSID PROTEIN | HUMAN ROTAVIRUS (SEROTYPE 2/STRAIN DS1) | 111-145 | | | | | | | |
| PVS11_ROTS1 | MINOR OUTER CAPSID PROTEIN | HUMAN ROTAVIRUS (SEROTYPE 1/STRAIN WA) | 111-145 | | | | | | | |
| PVS48_TBRVC | MINOR OUTER CAPSID PROTEIN | SIMIAN 11 ROTAVIRUS (STRAIN SA11) | 111-145 | | | | | | | |
| PVSH_MUMP1 | SATELLITE RNA 48 KD PROTEIN | TOMATO BLACK RING VIRUS (STRAIN C) (TBRV) | 217-265 | | | | | | | |
| PVSH_MUMP2 | SMALL HYDROPHOBIC PROTEIN | MUMPS VIRUS (STRAIN SBL-1), AND MUMPS VIRUS (STRAIN SBL) | 9-46 | | | | | | | |
| PVSH_MUMP4 | SMALL HYDROPHOBIC PROTEIN | MUMPS VIRUS (STRAIN EDINGBURGH 2), AND (STRAIN EDINGB | 13-47 | | | | | | | |
| PVSH_MUMPA | SMALL HYDROPHOBIC PROTEIN | MUMPS VIRUS (STRAIN EDINGBURGH 4) | 13-47 | | | | | | | |
| PVSH_MUMPB | SMALL HYDROPHOBIC PROTEIN | MUMPS VIRUS (STRAIN MATSUYAMA) | 13-51 | | | | | | | |
| PVSH_MUMPE | SMALL HYDROPHOBIC PROTEIN | MUMPS VIRUS (STRAIN BELFAST) | 13-52 | | | | | | | |
| PVSH_MUMPJ | SMALL HYDROPHOBIC PROTEIN | MUMPS VIRUS (STRAIN ENDERS) | 9-46 | | | | | | | |
| PVSH_MUMPK | SMALL HYDROPHOBIC PROTEIN | MUMPS VIRUS (STRAIN JERYL-LYNN) | 9-51 | | | | | | | |
| PVSH_MUMPL | SMALL HYDROPHOBIC PROTEIN | MUMPS VIRUS (STRAIN KILHAM) | 13-55 | | | | | | | |
| PVSH_MUMPM | SMALL HYDROPHOBIC PROTEIN | MUMPS VIRUS (STRAIN BRISTOL 1) | 17-51 | | | | | | | |
| PVSH_MUMPT | SMALL HYDROPHOBIC PROTEIN | MUMPS VIRUS (STRAIN MIYAHARA VACCINE) | 13-47 | | | | | | | |
| PVSH_MUMPU | SMALL HYDROPHOBIC PROTEIN | MUMPS VIRUS (STRAIN TAKAHASHI) | 13-47 | | | | | | | |
| PVSI1_REOVD | SMALL HYDROPHOBIC PROTEIN | MUMPS VIRUS (STRAIN URABE VACCINE AM9) | 13-47 | | | | | | | |
| PVSI1_REOVJ | SIGMA 1 PROTEIN PRECURSOR | REOVIRUS (TYPE 3/STRAIN DEARING) | 8-122 | 127-175 | 222-259 | | | | | |
| PVSI1_REOVL | SIGMA 1 PROTEIN PRECURSOR | REOVIRUS (TYPE 2/STRAIN D5/JONES) | 1-178 | | | | | | | |
| PVSI2_REOVL | SIGMA 1 PROTEIN PRECURSOR | REOVIRUS (TYPE 1/STRAIN LANG) | 3-107 | 112-198 | | | | | | |
| PVSI2_REOVD | SIGMA 2 PROTEIN | REOVIRUS (TYPE 3/STRAIN DEARING) | 350-384 | | | | | | | |
| PVSI2_REOVL | SIGMA 2 PROTEIN | REOVIRUS (TYPE 1/STRAIN LANG) | 350-384 | | | | | | | |
| PVSIS_REOVD | SIGMA 1-S PROTEIN | REOVIRUS (TYPE 3/STRAIN DEARING) | 85-119 | | | | | | | |
| PVSIS_REOVJ | SIGMA 1-S PROTEIN | REOVIRUS (TYPE 2/STRAIN D5/JONES) | 7-45 | | | | | | | |
| PVST2_HEVBU | STRUCTURAL PROTEIN 2 PRECURSOR | HEPATITIS E VIRUS (STRAIN BURMA) (HEV) | 318-352 | | | | | | | |
| PVST2_HEVME | STRUCTURAL PROTEIN 2 PRECURSOR | HEPATITIS E VIRUS (STRAIN MEXICO) (HEV) | 317-351 | | | | | | | |
| PVST2_HEVMY | STRUCTURAL PROTEIN 2 PRECURSOR | HEPATITIS E VIRUS (STRAIN MYANMAR) (HEV) | 318-352 | | | | | | | |
| PVST2_HEVPA | STRUCTURAL PROTEIN 2 PRECURSOR | HEPATITIS E VIRUS (STRAIN PAKISTAN) (HEV) | 318-352 | | | | | | | |
| PVST2_HEVRH | STRUCTURAL PROTEIN 2 PRECURSOR | | 318-352 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PVT3A_CAPVI | STRUCTURAL PROTEIN 2 | HEPATITIS E VIRUS (ISOLATE RHESUS) (HEV) | 186–220 | | | | | | | |
| PVT4_CAPVI | PROTEIN T3A | CAPRIPOXVIRUS (STRAIN INS-1) | 120–158 | | | | | | | |
| PVT4_CAPVK | T4 PROTEIN | CAPRIPOXVIRUS (STRAIN INS-1) | 86–120 | | | | | | | |
| PVTER_EBV | T4 PROTEIN | CAPRIPOXVIRUS (STRAIN KS-1) | 86–120 | | | | | | | |
| PVTER_HCMVA | PROBABLE DNA PACKAGING PROTEIN | EPSTEIN-BARR VIRUS (STRAIN B95-8) (HUMAN HERPESVIRUS 4) | 235–290 | 595–629 | | | | | | |
| PVTER_HSV6U | PROBABLE DNA PACKAGING PROTEIN | HUMAN CYTOMEGALOVIRUS (STRAIN AD169) | 417–451 | 617–658 | | | | | | |
| PVTER_HSVEB | PROBABLE DNA PACKAGING PROTEIN | HERPES SIMPLEX VIRUS (TYPE 6/STRAIN UGANDA-1102) | 468–502 | | | | | | | |
| PVTER_HSVI1 | PROBABLE DNA PACKAGING PROTEIN | EQUINE HERPESVIRUS TYPE 1 (STRAIN AB4P) (EHV-1) | 11–45 | | | | | | | |
| PVTER_HSVSA | PROBABLE DNA PACKAGING PROTEIN | ICTALURID HERPESVIRUS 1 (CHANNEL CATFISH VIRUS) (CCV) | 98–136 | 698–744 | | | | | | |
| PVTER_VZVD | PROBABLE DNA PACKAGING PROTEIN | HERPESVIRUS SAIMIRI (STRAIN 11) | 226–267 | | | | | | | |
| PVV_PI4HA | PROBABLE DNA PACKAGING PROTEIN | VARICELLA-ZOSTER VIRUS (STRAIN DUMAS) (VZV) | 588–622 | | | | | | | |
| PVY1_SEND6 | V PROTEIN | HUMAN PARAINFLUENZA 4A VIRUS (STRAIN TOSHIBA) (PIV-4A) | 4–38 | | | | | | | |
| PY101_SSV1 | Y1 PROTEIN | SENDAI VIRUS (STRAIN 6/94) | 104–138 | | | | | | | |
| PY108_SSV1 | HYPOTHETICAL 10.1 KD PROTEIN | SULFOLOBUS VIRUS-LIKE PARITCLE SSV1 | 16–80 | | | | | | | |
| PY110_SSV1 | HYPOTHETICAL 10.8 KD PROTEIN | SULFOLOBUS VIRUS-LIKE PARITCLE SSV1 | 4–65 | | | | | | | |
| PY119_SSV1 | HYPOTHETICAL 11.0 KD PROTEIN | SULFOLOBUS VIRUS-LIKE PARITCLE SSV1 | 55–59 | | | | | | | |
| PY11K_TYDVA | HYPOTHETICAL 11.9 KD PROTEIN | SULFOLOBUS VIRUS-LIKE PARITCLE SSV1 | 30–96 | | | | | | | |
| PY12K_FCVC6 | HYPOTHETICAL 11.2 KD PROTEIN | TOBACCO YELLOW DWARF VIRUS (STRAIN AUSTRALIA) (TYDV) | 63–87 | | | | | | | |
| PY12K_FCVF9 | HYPOTHETICAL 12.2 KD PROTEIN IN COAT PROTEIN | FELINE CALICIVIRUS (STRAIN CF1/68 FIV) (FCV) | 4–38 | | | | | | | |
| PY12K_RHDV | HYPOTHETICAL 12.1 KD PROTEIN IN COAT PROTEIN | FELINE CALICIVIRUS (STRAIN F9) (FCV) | 4–38 | | | | | | | |
| PY12K_RHDV3 | HYPOTHETICAL 12.7 KD PROTEIN IN COAT PROTEI | RABBIT HEMORRHAGIC DISEASE VIRUS (RHDV) | 13–50 | | | | | | | |
| PY13K_CLVK | HYPOTHETICAL 12.7 KD PROTEIN IN COAT PROTEIN | RABBIT HEMORRHAGIC DISEASE VIRUS (STRAIN V-351) (RHDV) | 13–50 | | | | | | | |
| PY13K_CLVN | HYPOTHETICAL 13.1 KD PROTEIN | CASSAVA LATENT VIRUS (STRAIN WEST KENYAN 844) | 40–77 | | | | | | | |
| PY13K_NPVOP | HYPOTHETICAL 13.1 KD PROTEIN | CASSAVA LATENT VIRUS (STRAIN NIGERIAN) | 43–77 | | | | | | | |
| PY13K_SSV1 | HYPOTHETICAL 14.5 KD PROTEIN IN 39 KD PROTEIN | ORGYIA PSEUDOTSUGATA MULTICAPSID POLYHEDROSIS VIRUS | 16–67 | | | | | | | |
| PY14K_SSV1 | HYPOTHETICAL 13.2 KD PROTEIN | SULFOLOBUS VIRUS-LIKE PARTICLE SSV1 | 2–36 | 62–96 | | | | | | |
| PY168_ADE02 | HYPOTHETICAL 13.7 KD PROTEIN | SULFOLOBUS VIRUS-LIKE PARTICLE SSV1 | 5–39 | | | | | | | |
| PY16K_SSV1 | HYPOTHETICAL PROTEIN C-168 | HUMAN ADENOVIRUS TYPE 2 | 119–166 | | | | | | | |
| PY17K_SSV1 | HYPOTHETICAL 15.6 KD PROTEIN | SULFOLOBUS VIRUS-LIKE PARTICLE SSV1 | 1–35 | 77–111 | | | | | | |
| PY18K_SSV1 | HYPOTHETICAL 17.8 KD PROTEIN | SULFOLOBUS VIRUS-LIKE PARTICLE SSV1 | 1–45 | 119–153 | | | | | | |
| PY20K_SSV1 | HYPOTHETICAL 18.0 KD PROTEIN | SULFOLOBUS VIRUS-LIKE PARTICLE SSV1 | 102–136 | | | | | | | |
| PY28K_SSV1 | HYPOTHETICAL 20.4 KD PROTEIN | SULFOLOBUS VIRUS-LIKE PARTICLE SSV1 | 73–107 | | | | | | | |
| PY2_SOCMV | HYPOTHETICAL 28.5 KD PROTEIN | SULFOLOBUS VIRUS-LIKE PARTICLE SSV1 | 127–180 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PY31K_SSV1 | HYPOTHETICAL PROTEIN 2 | SOYBEAN CHLOROTIC MOTTLE VIRUS | 117–154 | | | | | | | |
| PY32K_SSV1 | HYPOTHETICAL 31.5 KD PROTEIN | SULFOLOBUS VIRUS-LIKE PARTICLE SSV1 | 7–97 | 100–141 | | | | | | |
| PY38K_NPVAC | HYPOTHETICAL 31.7 KD PROTEIN | SULFOLOBUS VIRUS-LIKE PARTICLE SSV1 | 230–278 | | | | | | | |
| PY3_SOCMV | HYPOTHETICAL 37.7 KD PROTEIN | AUTOGRAPHA CALIFORNICA NUCLEAR POLYHEDROSIS VIRUS ( | 133–241 | | | | | | | |
| PY5K9_SSV1 | HYPOTHETICAL PROTEIN 3 | SOYBEAN CHLOROTIC MOTTLE VIRUS | 115–149 | | | | | | | |
| PY7_SOCMV | HYPOTHETICAL 5.9 KD PROTEIN | SULFOLOBUS VIRUS-LIKE PARTICLE SSV1 | 1–51 | | | | | | | |
| PY85K_SSV1 | HYPOTHETICAL PROTEIN 7 | SOYBEAN CHLOROTIC MOTTLE VIRUS | 56–94 | | | | | | | |
| PY8_SOCMV | HYPOTHETICAL 85.7 KD PROTEIN | SULFOLOBUS VIRUS-LIKE PARTICLE SSV1 | 81–125 | 503–537 | 546–587 | 658–700 | | | | |
| PYB01_FOWPM | HYPOTHETICAL PROTEIN 8 | SOYBEAN CHLOROTIC MOTTLE VIRUS | 46–83 | | | | | | | |
| PYB04_FOWPM | HYPOTHETICAL BAMHI-ORF1 PROTEIN | FOWLPOX VIRUS (ISOLATE HP-438 [MUNICH] | 74–115 | 184–221 | | | | | | |
| PYB05_FOWPM | HYPOTHETICAL BAMHI-ORF4 PROTEIN | FOWLPOX VIRUS (ISOLATE HP-438 [MUNICH] | 29–70 | | | | | | | |
| PYB06_FOWPM | HYPOTHETICAL BAMHI-ORF5 PROTEIN | FOWLPOX VIRUS (ISOLATE HP-438 [MUNICH] | 3–37 | 61–95 | | | | | | |
| PYB07_FOWPM | HYPOTHETICAL BAMHI-ORF6 PROTEIN | FOWLPOX VIRUS (ISOLATE HP-438 [MUNICH] | 115–149 | | | | | | | |
| PYB10_FOWPM | HYPOTHETICAL BAMHI-ORF7 PROTEIN | FOWLPOX VIRUS (ISOLATE HP-438 [MUNICH] | 344–378 | | | | | | | |
| PYB12_FOWPM | HYPOTHETICAL BAMHI-ORF10 PROTEIN | FOWLPOX VIRUS (ISOLATE HP-438 [MUNICH] | 162–253 | | | | | | | |
| PYB13_FOWPM | HYPOTHETICAL BAMHI-ORF12 PROTEIN | FOWLPOX VIRUS (ISOLATE HP-438 [MUNICH] | 4–47 | 117–153 | | | | | | |
| PYBL2_EBV | HYPOTHETICAL BAMHI-ORF13 PROTEIN | FOWLPOX VIRUS (ISOLATE HP-438 [MUNICH] | 122–163 | | | | | | | |
| PYDH1_HSVS7 | HYPOTHETICAL BBLF2 PROTEIN | EPSTEIN-BARR VIRUS (STRAIN B95-8) | 458–506 | | | | | | | |
| PYF30_FOWP1 | HYPOTHETICAL 24.1 KD PROTEIN IN DHFR 3'REGION | HERPESVIRUS SAIMIRI (STRAIN 484-77) (HUMAN HERPESVIRUS 4) | 147–188 | | | | | | | |
| PYGA1_HSVMB | HYPOTHETICAL 30.9 KD PROTEIN | FOWLPOX VIRUS (STRAIN FP-1) | 160–204 | | | | | | | |
| PYGA1_HSVMM | HYPOTHETICAL 23.6 KD PROTEIN IN GLYCOPROTEI | MAREK'S DISEASE HERPESVIRUS (STRAIN BC-1) (MDHV) | 176–211 | | | | | | | |
| PYH22_VACCV | HYPOTHETICAL 23.6 KD PROTEIN IN GLYCOPROTEI | MAREK'S DISEASE HERPESVIRUS (STRAIN MD5) (MDHV) | 176–211 | | | | | | | |
| PYHR3_VACCV | HYPOTHETICAL 21.7 KD HINDIII-C PROTEIN | VACCINIA VIRUS (STRAIN WR) | 34–78 | 95–139 | | | | | | |
| PYKR4_EBV | HYPOTHETICAL HOST RANGE 27.4 KD PROTEIN | VACCINIA VIRUS (STRAIN WR) | 24–58 | 181–222 | | | | | | |
| PYL15_ADE41 | HYPOTHETICAL BKRF4 PROTEIN | EPSTEIN-BARR VIRUS (STRAIN B95-8) (HUMAN HERPESVIRUS 4) | 16–58 | | | | | | | |
| PYLR2_EBV | HYPOTHETICAL 12.4 KD PROTEIN IN 33 KD PROTEIN | HUMAN ADENOVIRUS TYPE 41 | 39–81 | | | | | | | |
| PYOR1_COYMV | HYPOTHETICAL BLRF2 PROTEIN | EPSTEIN-BARR VIRUS (STRAIN B95-8) (HUMAN HERPESVIRUS 4) | 64–125 | | | | | | | |
| PYOR2_COYMV | HYPOTHETICAL 23 KD PROTEIN | COMMELINA YELLOW MOTTLE VIRUS (COYMV) | 94–147 | | | | | | | |
| PYOR2_LELV | HYPOTHETICAL 15 KD PROTEIN | COMMELINA YELLOW MOTTLE VIRUS (COYMV) | 33–77 | | | | | | | |
| PYOR3_TTV1 | HYPOTHETICAL 28.4 KD PROTEIN | LELYSTAD VIRUS (LV) | 100–134 | | | | | | | |
| PYOR5_ADEG1 | HYPOTHETICAL 6.9 KD PROTEIN | THERMOPROTEUS TENAX VIRUS 1 (STRAIN KRA1) (TTV1) | 14–54 | | | | | | | |
| PYORA_TTV1 | HYPOTHETICAL 31.5 KD PROTEIN | AVIAN ADENOVIRUS GAL1 (STRAIN PHELPS) (FOWL ADENOVIRU | 70–127 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PYORD_TTV1 | HYPOTHETICAL 8.1 KD PROTEIN | THERMOPROTEUS TENAX VIRUS 1 (STRAIN KRA1) (TTV1) | 21–67 | | | | | | | |
| PYORE_TTV1 | HYPOTHETICAL 15.4 KD PROTEIN | THERMOPROTEUS TENAX VIRUS 1 (STRAIN KRA1) (TTV1) | 6–51 | 89–130 | | | | | | |
| PYORL_TTV1 | HYPOTHETICAL 15.3 KD PROTEIN | THERMOPROTEUS TENAX VIRUS 1 (STRAIN KRA1) (TTV1) | 78–122 | | | | | | | |
| PYORQ_TTV1 | HYPOTHETICAL 26.8 KD PROTEIN | THERMOPROTEUS TENAX VIRUS 1 (STRAIN KRA1) (TTV1) | 1–45 | | | | | | | |
| PYORT_TTV1 | HYPOTHETICAL 7.3 KD PROTEIN | THERMOPROTEUS TENAX VIRUS 1 (STRAIN KRA1) (TTV1) | 1–43 | | | | | | | |
| PYORW_TTV1 | HYPOTHETICAL 38.7 KD PROTEIN | THERMOPROTEUS TENAX VIRUS 1 (STRAIN KRA1) (TTV1) | 4–38 | 281–315 | | | | | | |
| PYP12_RTBV | HYPOTHETICAL 12.1 KD PROTEIN | THERMOPROTEUS TENAX VIRUS 1 (STRAIN KRA1) (TTV1) | 4–89 | | | | | | | |
| PYP12_RTBVP | HYPOTHETICAL P12 PROTEIN | RICE TUNGRO BACILLIFORM VIRUS (RTBV) | 33–72 | | | | | | | |
| PYP24_RTBV | HYPOTHETICAL P12 PROTEIN | RICE TUNGRO BACILLIFORM VIRUS (ISOLATE PHILIPPINES) (RTE | 33–72 | | | | | | | |
| PYP24_RTBVP | HYPOTHETICAL P24 PROTEIN | RICE TUNGRO BACILLIFORM VIRUS (RTBV) | 51–101 | 106–157 | | | | | | |
| PYP46_RTBV | HYPOTHETICAL P24 PROTEIN | RICE TUNGRO BACILLIFORM VIRUS (ISOLATE PHILIPPINES) (RT | 51–101 | 106–157 | | | | | | |
| PYP46_RTBVP | HYPOTHETICAL P46 PROTEIN | RICE TUNGRO BACILLIFORM VIRUS (RTBV) | 49–111 | 197–231 | | | | | | |
| PYP63_NPVAC | HYPOTHETICAL P46 PROTEIN | RICE TUNGRO BACILLIFORM VIRUS (ISOLATE PHILIPPINES) (RT | 49–111 | 197–231 | | | | | | |
| PYP7A_TNVA | HYPOTHETICAL PROTEIN IN P6.5 5'REGION | AUTOGRAPHA CALIFORNICA NUCLEAR POLYHEDROSIS VIRUS ( | 32–73 | | | | | | | |
| PYPOH_NPVAC | HYPOTHETICAL P7A PROTEIN | TOBACCO NECROSIS VIRUS (STRAIN A) (TNV) | 1–65 | | | | | | | |
| PYPOL_IPNVJ | HYPOTHETICAL 23.6 KD PROTEIN IN POLYHEDRIN 5 | AUTOGRAPHA CALIFORNICA NUCLEAR POLYHEDROSIS VIRUS ( | 116–153 | | | | | | | |
| PYQ1_AMEPV | HYPOTHETICAL 17.3 KD PROTEIN | INFECTIOUS PANCREATIC NECROSIS VIRUS (SEROTYPE JASPER) | 25–66 | | | | | | | |
| PYQ3_AMEPV | HYPOTHETICAL 7.6 KD PROTEIN IN TK 5'REGION | AMSACTA MOOREI ENTOMOPOXVIRUS (AMEPV) | 9–61 | | | | | | | |
| PYRF2_HSV6G | HYPOTHETICAL PROTEIN IN TK 3'REGION | AMSACTA MOOREI ENTOMOPOXVIRUS (AMEPV) | 1–57 | 62–96 | 149–183 | | | | | |
| PYRF3_HSV6G | HYPOTHETICAL PROTEIN RF2 | HERPES SIMPLEX VIRUS (TYPE 6/STRAIN GS) | 193–264 | | | | | | | |
| PYRF4_HSV6G | HYPOTHETICAL PROTEIN RF3 | HERPES SIMPLEX VIRUS (TYPE 6/STRAIN GS) | 134–175 | | | | | | | |
| PYRP2_IRV6 | HYPOTHETICAL PROTEIN RF4 | HERPES SIMPLEX VIRUS (TYPE 6/STRAIN GS) | 252–286 | 404–442 | | | | | | |
| PYRR1_EBV | REPETITIVE PROTEIN ORF2 | CHILO IRIDESCENT VIRUS (CIV) (INSECT IRIDESCENT VIRUS TYP | 1–45 | | | | | | | |
| PYSR1_EBV | HYPOTHETICAL BRRF1 PROTEIN | EPSTEIN-BARR VIRUS (STRAIN B95-8) (HUMAN HERPESVIRUS 4) | 96–130 | | | | | | | |
| PYTR1_EBV | HYPOTHETICAL BSRF1 PROTEIN | EPSTEIN-BARR VIRUS (STRAIN B95-8) (HUMAN HERPESVIRUS 4) | 98–177 | | | | | | | |
| PYUB2_NPVOP | HYPOTHETICAL BTRF1 PROTEIN | EPSTEIN-BARR VIRUS (STRAIN B95-8) (HUMAN HERPESVIRUS 4) | 390–424 | | | | | | | |
| PYVAC_VACCC | HYPOTHETICAL 24.0 KD PROTEIN IN UBIQUITIN 3'RE | ORGYIA PSEUDOTSUGATA MULTICAPSID POLYHEDROSIS VIRUS | 25–69 | 170–204 | | | | | | |
| PYVAG_VACCC | HYPOTHETICAL 14.4 KD PROTEIN | VACCINIA VIRUS (STRAIN COPENHAGEN) | 29–63 | | | | | | | |

TABLE V-continued

ALLMOTI5 SEARCH RESULTS SUMMARY FOR ALL VIRAL (NON-BACTERIOPHAGE) PROTEINS

| PCGENE FILE NAME | ALLMOTI5 PROTEIN | All Viruses (no bacteriophages) VIRUS | AREA 1 | AREA 2 | AREA 3 | AREA 4 | AREA 5 | AREA 6 | AREA 7 | AREA 8 |
|---|---|---|---|---|---|---|---|---|---|---|
| PYVAH_VACCC | HYPOTHETICAL 9.3 KD PROTEIN | VACCINIA VIRUS (STRAIN COPENHAGEN) | 3–37 | | | | | | | |
| PYVAN_VACCC | HYPOTHETICAL 14.5 KD PROTEIN | VACCINIA VIRUS (STRAIN COPENHAGEN) | 78–112 | | | | | | | |
| PYVBH_VACCC | HYPOTHETICAL 7.9 KD PROTEIN | VACCINIA VIRUS (STRAIN COPENHAGEN) | 23–57 | | | | | | | |
| PYVCC_VACCC | HYPOTHETICAL 7.4 KD PROTEIN | VACCINIA VIRUS (STRAIN COPENHAGEN) | 5–39 | | | | | | | |
| PYVDB_VACCC | HYPOTHETICAL 9.2 KD PROTEIN | VACCINIA VIRUS (STRAIN COPENHAGEN) | 11–48 | | | | | | | |
| PYVDB_VACCV | HYPOTHETICAL 8.5 KD PROTEIN | VACCINIA VIRUS (STRAIN COPENHAGEN) | 29–80 | | | | | | | |
| PYVDC_VACCV | HYPOTHETICAL 8.5 KD PROTEIN | VACCINIA VIRUS (STRAIN WR) | 46–80 | | | | | | | |
| PYVGB_VACCC | HYPOTHETICAL 7.3 KD PROTEIN | VACCINIA VIRUS (STRAIN WR) | 7–41 | | | | | | | |
| PYVHA_VACCC | HYPOTHETICAL 8.4 KD PROTEIN | VACCINIA VIRUS (STRAIN COPENHAGEN) | 10–51 | | | | | | | |
| | HYPOTHETICAL 8.1 KD PROTEIN | VACCINIA VIRUS (STRAIN COPENHAGEN) | 9–53 | | | | | | | |

TABLE VI

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| P194K_TRVSY | POT 194 KD PRO | TOBACCO RATTLE VIRUS (STRAIN SYM) | 387–414 | 1087–1114 | 1142–1169 | | | | | | |
| PAANT_HDVAM | DELTA ANTIGEN | HEPATITIS DELTA VIRUS (ISOLATE AMERICAN) | 106–133 | | | | | | | | |
| PAANT_HDVD3 | DELTA ANTIGEN | HEPATITIS DELTA VIRUS (ISOLATE AMERICAN) | 106–133 | | | | | | | | |
| PAANT_HDVIT | DELTA ANTIGEN | HEPATITIS DELTA VIRUS (ISOLATE AMERICAN) | 106–133 | | | | | | | | |
| PAANT_HDVM2 | DELTA ANTIGEN | HEPATITIS DELTA VIRUS (ISOLATE AMERICAN) | 106–133 | | | | | | | | |
| PAANT_HDVS1 | DELTA ANTIGEN | HEPATITIS DELTA VIRUS (ISOLATE AMERICAN) | 16–43 | 106–133 | | | | | | | |
| PAANT_HDVS2 | DELTA ANTIGEN | HEPATITIS DELTA VIRUS (ISOLATE AMERICAN) | 16–43 | 106–133 | | | | | | | |
| PAANT_HDVWO | DELTA ANTIGEN | HEPATITIS DELTA VIRUS (ISOLATE AMERICAN) | 106–133 | | | | | | | | |
| PAT3H_FOWPM | ANTITHROMBIN-III HOMOLOG | FOWLPOX VIRUS (ISOLATE HP-438 [MUNICH]) | 72–106 | | | | | | | | |
| PATI1_VACCV | 94 KD A-TYPE INCLUSION PRO | VACCINIA VIRUS (STRAIN WR) | 14–56 | 67–94 | 424–472 | 570–625 | | | | | |
| PATI1_VARV | 81 KD A-TYPE INCLUSION PRO | VARIOLA VIRUS | 67–94 | 425–504 | 571–605 | | | | | | |
| PATI2_HSVI1 | ALPHA TRANS-IND FACTOR 78 KD PRO | HERPES SIMPLEX VIRUS (TYPE 1/STRAIN 17) | 308–335 | | | | | | | | |
| PATI2_HSVIF | ALPHA TRANS-IND FACTOR 77 KD PRO | HERPES SIMPLEX VIRUS (TYPE 1/STRAIN F) | 308–335 | | | | | | | | |
| PATI2_HSVEB | ALPHA TRANS-IND FACTOR 82 KD PRO | EQUINE HERPESVIRUS TYPE 1 (STRAIN AB4P) | 294–321 | | | | | | | | |
| PATIN_HSVEB | ALPHA TRANS-IND PROTEIN | EQUINE HERPESVIRUS TYPE 1 (STRAIN AB4P) | 255–289 | | | | | | | | |
| PATI_COWPX | A-TYPE INCLUSION PROTEIN | COWPOX VIRUS | 14–56 | 67–94 | 426–498 | 572–620 | 837–841 | 934–990 | 1234–1261 | | |
| PBZLF_EBV | BZLF1 TRANS-ACTIVATOR PROTEIN | EPSTEIN-BARR VIRUS (STRAIN B95-8) | 193–220 | | | | | | | | |
| PCAHH_VACCC | CELL SURFACE-BINDING PROTEIN | VACCINIA VIRUS (STRAIN COPENHAGEN) | 84–111 | 117–144 | | | | | | | |
| PCAHH_VACCV | CELL SURFACE-BINDING PROTEIN | VACCINIA VIRUS (STRAIN WR) | 84–111 | 117–144 | | | | | | | |
| PCAHH_VARV | CELL SURFACE-BINDING PROTEIN | VARIOLA VIRUS | 84–111 | 117–144 | | | | | | | |
| PCELF_HSVEB | CELL FUSION PROTEIN PRECURSOR | EQUINE HERPESVIRUS TYPE 1 (STRAINS AB4P and Ky A) | 312–339 | | | | | | | | |
| PCGH2_HSVSA | CYCLIN HOMOLOG | HERPESVIRUS SAIMIRI (STRAIN 11) | 127–154 | | | | | | | | |
| PCOA1_POVHA | COAT PROTEIN VP1 | HAMSTER POLYOMAVIRUS | 159–186 | | | | | | | | |
| PCOA2_BFDV | COAT PROTEIN VP2 | BUDGERIGAR FLEDGLING DISEASE VIRUS | 160–187 | | | | | | | | |
| PCOA2_POVBO | COAT PROTEIN VP2 | BOVINE POLYOMAVIRUS | 49–76 | | | | | | | | |
| PCOA2_POVJC | COAT PROTEIN VP2 | POLYOMAVIRUS JC | 37–64 | | | | | | | | |
| PCOA2_POVLY | COAT PROTEIN VP2 | LYMPHOTROPIC POLYOMAVIRUS | 170–204 | | | | | | | | |
| PCOA2_POVMK | COAT PROTEIN VP2 | MOUSE POLYOMAVIRUS (STRAIN KILHAM) | 22–49 | | | | | | | | |
| PCOA2_SV40 | COAT PROTEIN VP2 | SIMIAN VIRUS 40 | 178–205 | | | | | | | | |
| PCOA3_AAV2 | PROBABLE COAT PROTEIN 3 | ADENO-ASSOCIATED VIRUS 2 | 120–147 | | | | | | | | |
| PCOA3_TTV1 | COAT PROTEIN TP3 | THERMOPROTEUS TENAX VIRUS 1 (STRAIN KRA1) | 3–30 | | | | | | | | |
| PCOAT_ADVG | COAT PROTEIN VP1 | ALEUTIAN MINK DISEASE PARVOVIRUS (STRAIN G) | 194–221 | | | | | | | | |
| PCOAT_BLRV | COAT PROTEIN | BEAN LEAFROLL VIRUS | 96–123 | | | | | | | | |
| PCOAT_CAMVC | COAT PROTEIN | CAULIFLOWER MOSAIC VIRUS (STRAIN CM-184) | 63–90 | 193–220 | 461–488 | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PCOAT_CAMVD | COAT PROTEIN | CAULIFLOWER MOSAIC VIRUS (STRAIN D/H) | 64–91 | 194–221 | | | | | | | |
| PCOAT_CAMVE | COAT PROTEIN | CAULIFLOWER MOSAIC VIRUS (STRAIN BBC) | 63–90 | 193–220 | | | | | | | |
| PCOAT_CAMVN | COAT PROTEIN | CAULIFLOWER MOSAIC VIRUS (STRAIN NY8153) | 63–90 | 192–219 | 461–488 | | | | | | |
| PCOAT_CAMVS | COAT PROTEIN | CAULIFLOWER MOSAIC VIRUS (STRAIN STRASBOURG) | 64–91 | 194–221 | | | | | | | |
| PCOAT_CARMV | COAT PROTEIN | CARNATION MOTTLE VIRUS | 16–43 | | | | | | | | |
| PCOAT_CHVP1 | MAJOR CAPSID PROTEIN | PARAMECIUM BURSARIA CHLORELLA VIRUS 1 | 41–86 | | | | | | | | |
| PCOAT_CNV | COAT PROTEIN | CUCUMBER NECROSIS VIRUS | 328–362 | | | | | | | | |
| PCOAT_CSMV | COAT PROTEIN | CHLORIS STRIATE MOSAIC VIRUS | 62–89 | | | | | | | | |
| PCOAT_CYMV | COAT PROTEIN | CLOVER YELLOW MOSAIC VIRUS | 170–200 | | | | | | | | |
| PCOAT_FCVC6 | COAT PROTEIN | FELINE CALICIVIRUS (STRAIN CFI/68 FIV) | 566–600 | | | | | | | | |
| PCOAT_FCVF4 | COAT PROTEIN | FELINE CALICIVIRUS (STRAIN JAPANESE F4) | 516–543 | 566–600 | | | | | | | |
| PCOAT_FCVF9 | COAT PROTEIN | FELINE CALICIVIRUS (STRAIN F9) | 519–546 | 569–603 | | | | | | | |
| PCOAT_FMVD | PROBABLE COAT PROTEIN | FIGWORT MOSAIC VIRUS (STRAIN DXS) | 220–247 | 358–385 | | | | | | | |
| PCOAT_LSV | COAT PROTEIN | LILY SYMPTOMLESS VIRUS | 32–700 | 246–273 | | | | | | | |
| PCOAT_MISV | COAT PROTEIN | MISCANTHUS STREAK VIRUS | 139–166 | | | | | | | | |
| PCOAT_ORSV | COAT PROTEIN | ODONTOGLOSSUM RINGSPOT VIRUS | 106–133 | | | | | | | | |
| PCOAT_PAVHB | PROBABLE COAT PROTEIN VP1 | HUMAN PARVOVIRUS B19 | 524–551 | 569–596 | | | | | | | |
| PCOAT_POPMV | COAT PROTEIN | POPLAR MOSAIC VIRUS (ISOLATE ATCC PV275) | 46–73 | | | | | | | | |
| PCOAT_SOCMV | COAT PROTEIN | SOYBEAN CHLOROTIC MOTTLE VIRUS | 128–162 | | | | | | | | |
| PCOAT_TAMV | GENOME POLYPROTEIN | TAMARILLO MOSAIC VIRUS | 21–48 | | | | | | | | |
| PCOAT_TAV | COAT PROTEIN | TOMATO ASPERMY VIRUS | 23–50 | | | | | | | | |
| PCOAT_TBSVB | COAT PROTEIN | TOMATO BUSHY STUNT VIRUS (STRAIN BS-3) | 3–30 | 41–68 | | | | | | | |
| PCOAT_TBSVC | COAT PROTEIN | TOMATO BUSHY STUNT VIRUS (STRAIN CHERRY) | 97–134 | | | | | | | | |
| PCOAT_TCV | COAT PROTEIN | TURNIP CRINKLE VIRUS | 232–259 | | | | | | | | |
| PCOAT_TMGMV | COAT PROTEIN | TOBACCO MILD GREEN MOSAIC VIRUS | 104–131 | | | | | | | | |
| PCOAT_TMV | COAT PROTEIN | TOBACCO MOSAIC VIRUS (VULGARE) | 104–131 | | | | | | | | |
| PCOAT_TMVCO | COAT PROTEIN | TOBACCO MOSAIC VIRUS (STRAIN COWPEA) | 78–132 | | | | | | | | |
| PCOAT_TMVDA | COAT PROTEIN | TOBACCO MOSAIC VIRUS (STRAIN DAHLEMENSE) | 104–131 | | | | | | | | |
| PCOAT_TMVER | COAT PROTEIN | TOBACCO MOSAIC VIRUS (STRAIN ER) | 104–131 | | | | | | | | |
| PCOAT_TMVO | COAT PROTEIN | TOBACCO MOSAIC VIRUS (STRAIN O AND KOKUBU) | 104–131 | | | | | | | | |
| PCOAT_TMVOM | COAT PROTEIN | TOBACCO MOSAIC VIRUS (STRAIN OM) | 104–131 | | | | | | | | |
| PCOAT_TMVTO | COAT PROTEIN | TOBACCO MOSAIC VIRUS (STRAIN TOMATO/L) | 104–131 | | | | | | | | |
| PCOAT_TNVA | COAT PROTEIN | TOBACCO NECROSIS VIRUS (STRAIN A) | 90–117 | | | | | | | | |
| PCOAT_TRVPS | COAT PROTEIN | TOBACCO RATTLE VIRUS (STRAINS PSG and PLB) | 118–145 | | | | | | | | |
| PCOAT_TYDVA | COAT PROTEIN | TOBACCO YELLOW DWARF VIRUS (STRAIN AUSTRALIA) | 10–37 | | | | | | | | |
| PCOAT_TYMV | COAT PROTEIN | TURNIP YELLOW MOSAIC VIRUS | 41–68 | | | | | | | | |
| PCOAT_TYMVA | COAT PROTEIN | TURNIP YELLOW MOSAIC VIRUS (AUSTRALIAN ISOLATE) | 41–68 | | | | | | | | |
| PDNB2_ADE07 | EARLY E2A DNA-BINDING PROTEIN | HUMAN ADENOVIRUS TYPE 7 | 46–73 | | | | | | | | |
| PDNB1_EBV | MAJOR DNA-BINDING PROTEIN | EPSTEIN-BARR VIRUS (STRAIN B95-8) | 977–1004 | 1041–1068 | | | | | | | |
| PDNB1_HCMVA | MAJOR DNA-BINDING PROTEIN | HUMAN CYTOMEGALOVIRUS (STRAIN AD169) | 437–464 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDNB1_HSVSA | MAJOR DNA-BINDING PROTEIN | HERPESVIRUS SAIMIRI (STRAIN 11) | 333–368 | 512–539 | | | | | | | |
| PDNB1_MCMVS | MAJOR DNA-BINDING PROTEIN | MURINE CYTOMEGALOVIRUS (STRAIN SMITH) | 584–618 | | | | | | | | |
| PDNB1_POV1C | DNA-BINDING PROTEIN | POLYOMAVIRUS JC | 2–29 | | | | | | | | |
| PDNB1_SCMVC | MAJOR DNA-BINDING PROTEIN | SIMIAN CYTOMEGALOVIRUS (STRAIN COLBURN) | 435–462 | 532–559 | | | | | | | |
| PDNL1_VACCC | DNA LIGASE | VACCINIA VIRUS (STRAIN COPENHAGEN) | 104–131 | 172–199 | 358–385 | | | | | | |
| PDNL1_VACCV | DNA LIGASE | VACCINIA VIRUS (STRAIN WR) | 104–131 | 172–199 | 358–385 | | | | | | |
| PDNL1_VARV | DNA LIGASE | VARIOLA VIRUS | 104–131 | 172–199 | 358–385 | | | | | | |
| PDPOL_ADE12 | DNA POLYMERASE | HUMAN ADENOVIRUS TYPE 12 | 403–431 | | | | | | | | |
| PDPOL_CBEPV | DNA POLYMERASE | CHORISTONEURA BIENNIS ENTOMOPOXVIRUS | 23–64 | 202–240 | | | | | | | |
| PDPOL_CHVN2 | DNA POLYMERASE | CHLORELLA VIRUS NY-2A | 338–365 | | | | | | | | |
| PDPOL_CHVP1 | DNA POLYMERASE | PARAMECIUM BURSARIA CHLORELLA VIRUS 1 | 338–365 | | | | | | | | |
| PDPOL_FOWPV | DNA POLYMERASE | FOWLPOX VIRUS | 17–51 | 370–416 | 621–655 | 772–799 | | | | | |
| PDPOL_HCMVA | DNA POLYMERASE | HUMAN CYTOMEGALOVIRUS (STRAIN AD169) | 753–780 | | | | | | | | |
| PDPOL_HPBDB | DNA POLYMERASE | DUCK HEPATITIS B VIRUS (BROWN SHANGHAI DUCK ISOLATE S5) | 5–39 | | | | | | | | |
| PDPOL_HPBDC | DNA POLYMERASE | DUCK HEPATITIS B VIRUS (STRAIN CHINA) | 5–39 | | | | | | | | |
| PDPOL_HPBDW | DNA POLYMERASE | DUCK HEPATITIS B VIRUS (WHITE SHANGHAI DUCK ISOLATE S31) | 5–39 | 304–331 | | | | | | | |
| PDPOL_HPBGS | DNA POLYMERASE | GROUND SQUIRREL HEPATITIS VIRUS | 271–325 | | | | | | | | |
| PDPOL_HPBHE | DNA POLYMERASE | HERON HEPATITIS B VIRUS | 5–39 | | | | | | | | |
| PDPOL_HPBVP | DNA POLYMERASE | HEPATITIS B VIRUS (SUBTYPE ADW/STRAIN PHILIPPINO/PFDW294) | 456–483 | | | | | | | | |
| PDPOL_HPBVZ | DNA POLYMERASE | HEPATITIS B VIRUS (SUBTYPE ADYW) | 443–470 | | | | | | | | |
| PDPOL_HSVI1 | DNA POLYMERASE | ICTALURID HERPESVIRUS 1 | 328–366 | 710–737 | | | | | | | |
| PDPOL_HSVSA | DNA POLYMERASE | HERPESVIRUS SAIMIRI (STRAIN 11) | 625–652 | | | | | | | | |
| PDPOL_NPVAC | DNA POLYMERASE | AUTOGRAPHA CALIFORNICA NUCLEAR POLYHEDROSIS VIRUS | 598–643 | | | | | | | | |
| PDPOL_NPVLD | DNA POLYMERASE | LYMANTRIA DISPAR MULTICAPSID NUCLEAR POLYHEDROSIS VIRUS | 357–384 | | | | | | | | |
| PDPOL_VACCC | DNA POLYMERASE | VACCINIA VIRUS (STRAIN COPENHAGEN) | 770–797 | | | | | | | | |
| PDPOL_VACCV | DNA POLYMERASE | VACCINIA VIRUS (STRAIN WR) | 770–797 | | | | | | | | |
| PDPOL_VARV | DNA POLYMERASE | VARIOLA VIRUS | 769–796 | | | | | | | | |
| PDPOL_WHV1 | DNA POLYMERASE | WOODCHUCK HEPATITIS VIRUS 1 | 285–326 | | | | | | | | |
| PDPOL_WHV59 | DNA POLYMERASE | WOODCHUCK HEPATITIS VIRUS 59 | 290–331 | | | | | | | | |
| PDPOL_WHV7 | DNA POLYMERASE | WOODCHUCK HEPATITIS VIRUS 7 | 212–242 | 290–331 | | | | | | | |
| PDPOL_WHV8 | DNA POLYMERASE | WOODCHUCK HEPATITIS VIRUS 8 | 211–241 | 289–330 | | | | | | | |
| PDPOL_WHV81 | DNA POLYMERASE | WOODCHUCK HEPATITIS VIRUS 8 | 212–242 | 290–331 | | | | | | | |
| PDTXH_CORBE | DIPHTH TOXIN HOMOLOG CRM228 PREC | CORYNEPHAGE BETA | 516–533 | | | | | | | | |
| PDTX_CORBE | DIPHTHERIA TOXIN PRECURSOR | CORYNEPHAGE BETA | 523–560 | | | | | | | | |
| PDTX_COROM | DIPHTHERIA TOXIN PRECURSOR | CORYNEPHAGE OMEGA | 516–533 | | | | | | | | |
| PDUT_HSVE4 | DEOXYU 5'-TRIPHOSPH NUCHYDROLASE | EQUINE HERPESVIRUS TYPE 4 (STRAIN 1942) | 90–117 | | | | | | | | |
| PDUT_HSVSA | DEOXYU 5'-TRIPHOSPH NUCHYDROLASE | HERPESVIRUS SAIMIRI (STRAIN 11) | 179–213 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PE1BL_ADE07 | E1B PROTEIN, LARGE T-ANTIGEN | HUMAN ADENOVIRUS TYPE 7 | 126–153 | | | | | | | | |
| PE1BL_ADE40 | E1B PROTEIN, LARGE T-ANTIGEN | HUMAN ADENOVIRUS TYPE 40 | 136–163 | | | | | | | | |
| PE1BS_ADE12 | E1B PROTEIN, SMALL T-ANTIGEN | HUMAN ADENOVIRUS TYPE 12 | 3–30 | | | | | | | | |
| PE1BS_ADEM1 | E1B PROTEIN, SMALL T-ANTIGEN | MOUSE ADENOVIRUS TYPE 1 | 122–173 | | | | | | | | |
| PE314_ADE02 | EARLY E3B 14 KD PROTEIN | HUMAN ADENOVIRUS TYPE 2 | 2–29 | | | | | | | | |
| PE314_ADE07 | EARYL E3 15.3 KD PROTEIN | HUMAN ADENOVIRUS TYPE 7 | 21–48 | | | | | | | | |
| PE320_ADE03 | EARLY E3 20.1 KD GLYCOPROTEIN | HUMAN ADENOVIRUS TYPE 3 | 5–32 | 70–100 | | | | | | | |
| PE320_ADE35 | EARLY E3 20.3 KD GLYCOPROTEIN | HUMAN ADENOVIRUS TYPE 35 | 70–107 | | | | | | | | |
| PE321_ADE35 | EARLY E3 20.6 KD GLYCOPROTEIN | HUMAN ADENOVIRUS TYPE 35 | 125–161 | | | | | | | | |
| PE3GL_ADEM1 | EARLY E3 17.7 KD GLYCOPROTEIN | MOUSE ADENOVIRUS TYPE 1 | 38–66 | | | | | | | | |
| PEAR_EBV | EARLY ANTIGEN PROTEIN R | EPSTEIN-BARR VIRUS (STRAIN B95-8) | 55–82 | | | | | | | | |
| PEFT1_VARV | EARLY TRANS FACTOR 70 KD SUBUNIT | VARIOLA VIRUS | 307–341 | 470–497 | | | | | | | |
| PENV_AVIRE | ENV POLYPROTEIN | AVIAN RETICULOENDOTHELIOSIS VIRUS | 420–468 | | | | | | | | |
| PENV_AVISN | ENV POLYPROTEIN | AVIAN SPLEEN NECROSIS VIRUS | 6–33 | | | | | | | | |
| PENV_BAEVM | ENV POLYPROTEIN | BABOON ENDOGENOUS VIRUS (STRAIN M7) | 395–452 | 426–474 | | | | | | | |
| PENV_BIV06 | ENV POLYPROTEIN | BOVINE IMMUNODEFICIENCY VIRUS (ISOLATE 106) | 17–44 | 544–603 | 631–695 | | | | | | |
| PENV_BIV27 | ENV POLYPROTEIN | BOVINE IMMUNODEFICIENCY VIRUS (ISOLATE 127) | 17–44 | 573–632 | 660–724 | | | | | | |
| PENV_BLVAF | ENV POLYPROTEIN | BOVINE LEUKEMIA VIRUS (AMERICAN ISOLATE FLK) | 304–377 | | | | | | | | |
| PENV_BLVAU | ENV POLYPROTEIN | BOVINE LEUKEMIA VIRUS (AUSTRALIAN ISOLATE) | 304–377 | | | | | | | | |
| PENV_BLVAV | ENV POLYPROTEIN | BOVINE LEUKEMIA VIRUS (AMERICAN ISOLATE VDM) | 304–377 | | | | | | | | |
| PENV_BLVB2 | ENV POLYPROTEIN | BOVINE LEUKEMIA VIRUS (BELGIUM ISOLATE LB285) | 311–377 | | | | | | | | |
| PENV_BLVB5 | ENV POLYPROTEIN | BOVINE LEUKEMIA VIRUS (BELGIUM ISOLATE LB59) | 304–377 | | | | | | | | |
| PENV_BLVJ | ENV POLYPROTEIN | BOVINE LEUKEMIA VIRUS (JAPANESE ISOLATE BLV-1) | 304–377 | | | | | | | | |
| PENV_CAEVG | ENV POLYPROTEIN | CAPRINE ARTHRITIS ENCEPHALITIS VIRUS (STRAIN G63) | 165–192 | | | | | | | | |
| PENV_EIAV1 | ENV POLYPROTEIN | EQUINE INFECTIOUS ANEMIA VIRUS (CLONE P3.2-1) | 668–712 | | | | | | | | |
| PENV_EIAV2 | ENV POLYPROTEIN | EQUINE INFECTIOUS ANEMIA VIRUS (CLONE P3.2-2) | 668–695 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PENV_EIAV3 | ENV POLYPROTEIN | EQUINE TABLE VI-continued 107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PENV_HV1C4 | ENV POLYPROTEIN | HUMAN IMMUNODEFICIENCY VIRUS TYPE 1 (CDC-451 ISOLATE) | 397–424 | 557–606 | 643–695 | 803–835 | | | | | |
| PENV_HV1EL | ENV POLYPROTEIN | HUMAN IMMUNODEFICIENCY VIRUS TYPE 1 (ELI ISOLATE) | 255–296 | 386–413 | 543–591 | 628–680 | | | | | |
| PENV_HV1H2 | ENV POLYPROTEIN | HUMAN IMMUNODEFICIENCY VIRUS TYPE 1 (HXB2 ISOLATE) | 545–594 | 631–683 | 791–818 | | | | | | |
| PENV_HV1H3 | ENV POLYPROTEIN | HUMAN IMMUNODEFICIENCY VIRUS TYPE 1 (HXB3 ISOLATE) | 545–594 | 631–683 | 791–818 | | | | | | |
| PENV_HV1J3 | ENV POLYPROTEIN | HUMAN IMMUNODEFICIENCY VIRUS TYPE 1 (JH3 ISOLATE) | 350–377 | 556–605 | 642–694 | 802–829 | | | | | |
| PENV_HV1JR | ENV POLYPROTEIN | HUMAN IMMUNODEFICIENCY VIRUS TYPE 1 (JRCSF ISOLATE) | 336–363 | 622–675 | 783–811 | | | | | | |
| PENV_HV1KB | ENV POLYPROTEIN | HUMAN IMMUNODEFICIENCY VIRUS TYPE 1 (STRAIN KB-1-GP32) | 274–301 | 555–596 | 637–677 | 776–824 | | | | | |
| PENV_HV1MA | ENV POLYPROTEIN | HUMAN IMMUNODEFICIENCY VIRUS TYPE 1 (MAL ISOLATE) | 547–595 | 633–707 | 794–826 | | | | | | |
| PENV_HV1MF | ENV POLYPROTEIN | HUMAN IMMUNODEFICIENCY VIRUS TYPE 1 (MFA ISOLATE) | 543–592 | 629–681 | 789–816 | | | | | | |
| PENV_HV1MN | ENV POLYPROTEIN | HUMAN IMMUNODEFICIENCY VIRUS TYPE 1 (MN ISOLATE) | 343–370 | 567–595 | 632–684 | 791–819 | | | | | |
| PENV_HV1N5 | ENV POLYPROTEIN | HUMAN IMMUNODEFICIENCY VIRUS TYPE 1 (NEW YORK-5 ISOLATE) | 326–360 | | | | | | | | |
| PENV_HV1ND | ENV POLYPROTEIN | HUMAN IMMUNODEFICIENCY VIRUS TYPE 1 (NDK ISOLATE) | 249–290 | 536–583 | 621–673 | 783–813 | | | | | |
| PENV_HV1OY | ENV POLYPROTEIN | HUMAN IMMUNODEFICIENCY VIRUS TYPE 1 (OYI ISOLATE) | 544–593 | 630–704 | 789–820 | | | | | | |
| PENV_HV1PV | ENV POLYPROTEIN | HUMAN IMMUNODEFICIENCY VIRUS TYPE 1 (PV22 ISOLATE) | 545–594 | 631–683 | 791–818 | | | | | | |
| PENV_HV1RH | ENV POLYPROTEIN | HUMAN IMMUNODEFICIENCY VIRUS TYPE 1 (RF/HAT ISOLATE) | 280–307 | 351–378 | 554–602 | 640–692 | 800–832 | | | | |
| PENV_HV1S1 | ENV POLYPROTEIN | HUMAN IMMUNODEFICIENCY VIRUS TYPE 1 (SF162 ISOLATE) | 333–363 | 536–585 | 622–674 | 782–809 | | | | | |
| PENV_HV1S3 | ENV POLYPROTEIN | HUMAN IMMUNODEFICIENCY VIRUS TYPE 1 (SF33 ISOLATE) | 541–589 | 627–679 | 787–815 | | | | | | |
| PENV_HV1SC | ENV POLYPROTEIN | HUMAN IMMUNODEFICIENCY VIRUS TYPE 1 (SC ISOLATE) | 338–365 | 545–593 | 631–683 | | | | | | |
| PENV_HV1W1 | ENV POLYPROTEIN | HUMAN IMMUNODEFICIENCY VIRUS TYPE 1 (WMJ1 ISOLATE) | 338–365 | 545–593 | 631–683 | 791–818 | | | | | |
| PENV_HV1W2 | ENV POLYPROTEIN | HUMAN IMMUNODEFICIENCY VIRUS TYPE 1 (WMJ2 ISOLATE) | 334–361 | 536–584 | 622–674 | 782–809 | | | | | |
| PENV_HV1Z2 | ENV POLYPROTEIN | HUMAN IMMUNODEFICIENCY VIRUS TYPE 1 (Z2/CDC-Z34 ISOLATE) | 255–296 | 542–591 | 628–680 | 790–820 | | | | | |
| PENV_HV1Z3 | ENV POLYPROTEIN | HUMAN IMMUNODEFICIENCY VIRUS TYPE 1 (ZAIRE 3 ISOLATE) | 251–292 | | | | | | | | |
| PENV_HV1Z6 | ENV POLYPROTEIN | HUMAN IMMUNODEFICIENCY VIRUS TYPE 1 (ZAIRE 6 ISOLATE) | 256–297 | 545–593 | 630–682 | 792–822 | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PENV_HV1Z8 | ENV POLYPROTEIN | HUMAN IMMUNODEFICIENCY VIRUS TYPE 1 (Z-84 ISOLATE) | 266–307 | 573–601 | 634–678 | 797–828 | | | | | |
| PENV_HV1ZH | ENV POLYPROTEIN | HUMAN IMMUNODEFICIENCY VIRUS TYPE 1 (ZAIRE HZ321 ISOLATE) | 545–594 | 627–666 | 791–823 | | | | | | |
| PENV_HV2BE | ENV POLYPROTEIN | HUMAN IMMUNODEFICIENCY VIRUS TYPE 2 (ISOLATE BEN) | 61–88 | 532–591 | 621–648 | 653–697 | | | | | |
| PENV_HV2CA | ENV POLYPROTEIN | HUMAN IMMUNODEFICIENCY VIRUS TYPE 2 (ISOLATE CAM2) | 534–593 | 623–650 | 655–699 | | | | | | |
| PENV_HV2D1 | ENV POLYPROTEIN | HUMAN IMMUNODEFICIENCY VIRUS TYPE 2 (ISOLATE D194) | 61–88 | 523–550 | 555–582 | 644–688 | | | | | |
| PENV_HV2G1 | ENV POLYPROTEIN | HUMAN IMMUNODEFICIENCY VIRUS TYPE 2 (ISOLATE GHANA-1) | 60–87 | 524–551 | 556–583 | 613–640 | 645–693 | | | | |
| PENV_HV2NZ | ENV POLYPROTEIN | HUMAN IMMUNODEFICIENCY VIRUS TYPE 2 (ISOLATE NIH-Z) | 61–88 | 524–551 | 556–583 | 613–640 | 662–689 | | | | |
| PENV_HV2RO | ENV POLYPROTEIN | HUMAN IMMUNODEFICIENCY VIRUS TYPE 2 (ISOLATE ROD) | 58–85 | 533–592 | 622–698 | | | | | | |
| PENV_HV2S2 | ENV POLYPROTEIN | HUMAN IMMUNODEFICIENCY VIRUS TYPE 2 (ISOLATE ST/24 IC#2) | 442–476 | 527–554 | 559–586 | 648–682 | | | | | |
| PENV_HV2SB | ENV POLYPROTEIN | HUMAN IMMUNODEFICIENCY VIRUS TYPE 2 (ISOLATE SBL1SY) | 557–584 | 614–673 | | | | | | | |
| PENV_HV2ST | ENV POLYPROTEIN | HUMAN IMMUNODEFICIENCY VIRUS TYPE 2 (ISOLATE ST) | 442–476 | 527–554 | 559–586 | 648–692 | | | | | |
| PENV_MCFF | ENV POLYPROTEIN | MINK CELL FOCUS-FORMING MURINE LEUKEMIA VIRUS | 473–512 | | | | | | | | |
| PENV_MCFF3 | ENV POLYPROTEIN | MINK CELL FOCUS-FORMING MURINE LEUKEMIA VIRUS (ISOLATE C1-3) | 488–515 | | | | | | | | |
| PENV_MLVAV | ENV POLYPROTEIN | AKV MURINE LEUKEMIA VIRUS | 517–544 | | | | | | | | |
| PENV_MLVCB | ENV POLYPROTEIN | CAS-BR-E MURINE LEUKEMIA VIRUS | 510–539 | | | | | | | | |
| PENV_MLVF5 | ENV POLYPROTEIN | FRIEND MURINE LEUKEMIA VIRUS (ISOLATE 57) | 523–553 | | | | | | | | |
| PENV_MLVFF | ENV POLYPROTEIN | FRIEND MURINE LEUKEMIA VIRUS (ISOLATE FB29) | 523–553 | | | | | | | | |
| PENV_MLVFP | ENV POLYPROTEIN | FRIEND MURINE LEUKEMIA VIRUS (ISOLATE PVC-211) | 523–553 | | | | | | | | |
| PENV_MLVHO | ENV POLYPROTEIN | HOMULV MURINE LEUKEMIA VIRUS | 510–540 | | | | | | | | |
| PENV_MLVK1 | ENV POLYPROTEIN | KIRSTEN MURINE LEUKEMIA VIRUS | 40–81 | | | | | | | | |
| PENV_MLVMO | ENV POLYPROTEIN | MOLONEY MURINE LEUKEMIA VIRUS | 502–543 | | | | | | | | |
| PENV_MLVRD | ENV POLYPROTEIN | RADIATION MURINE LEUKEMIA VIRUS | 497–538 | | | | | | | | |
| PENV_MLVRK | ENV POLYPROTEIN | RADIATION MURINE LEUKEMIA VIRUS (STRAIN KAPLAN) | 497–538 | | | | | | | | |
| PENV_MMTVB | ENV POLYPROTEIN | MOUSE MAMMARY TUMOR VIRUS (STRAIN BR6) | 458–485 | 562–589 | | | | | | | |
| PENV_MMTVG | ENV POLYPROTEIN | MOUSE MAMMARY TUMOR VIRUS (STRAIN GR) | 458–485 | 562–589 | | | | | | | |
| PENV_MPMV | ENV POLYPROTEIN | SIMIAN MASON-PFIZER VIRUS | 422–470 | | | | | | | | |
| PENV_MSVFB | ENV POLYPROTEIN | FBJ MURINE OSTEOSARCOMA VIRUS | 57–84 | | | | | | | | |
| PENV_OMVVS | ENV POLYPROTEIN | OVINE LENTIVIRUS (STRAIN SA-OMVV) | 42–69 | 196–223 | 780–807 | | | | | | |
| PENV_RMCFV | ENV POLYPROTEIN | RAUSCHER MINK CELL FOCUS-INDUCING VIRUS | 487–517 | | | | | | | | |
| PENV_SFV1 | ENV POLYPROTEIN | SIMIAN FOAMY VIRUS (TYPE 1) | 14–41 | 866–901 | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PENV_SFV3L | ENV POLYPROTEIN | SIMIAN FOAMY VIRUS (TYPE 3/STRAIN LK3) | 18–45 | 319–357 | 673–700 | 863–898 | | | | | |
| PENV_SIVA1 | ENV POLYPROTEIN | SIMIAN IMMUNODEFICIENCY VIRUS (AGM155 ISOLATE) | 269–310 | 561–588 | 592–619 | 652–679 | 697–724 | | | | |
| PENV_SIVAG | ENV POLYPROTEIN | SIMIAN IMMUNODEFICIENCY VIRUS (AGM3 ISOLATE) | 270–301 | 566–593 | 597–624 | 658–685 | 703–730 | | | | |
| PENV_SIVA1 | ENV POLYPROTEIN | SIMIAN IMMUNODEFICIENCY VIRUS (ISOLATE AGM/CLONE GR1-1) | 257–291 | 336–372 | 548–603 | 634–708 | | | | | |
| PENV_SIVAT | ENV POLYPROTEIN | SIMIAN IMMUNODEFICIENCY VIRUS (TYO-1 ISOLATE) | 3–30 | 268–298 | 590–617 | 651–678 | | | | | |
| PENV_SIVCZ | ENV POLYPROTEIN | CHIMPANZEE IMMUNODEFICIENCY VIRUS | 160–187 | 253–289 | 336–366 | 526–584 | 627–654 | | | | |
| PENV_SIVGB | ENV POLYPROTEIN | SIMIAN IMMUNODEFICIENCY VIRUS (ISOLATE GB1) | 8–35 | 158–185 | 589–650 | 784–816 | | | | | |
| PENV_SIVM1 | ENV POLYPROTEIN | SIMIAN IMMUNODEFICIENCY VIRUS (MM142-83 ISOLATE) | 120–150 | 550–609 | 671–715 | | | | | | |
| PENV_SIVM2 | ENV POLYPROTEIN | SIMIAN IMMUNODEFICIENCY VIRUS (MM251 ISOLATE) | 156–215 | 277–289 | | | | | | | |
| PENV_SIVMK | ENV POLYPROTEIN | SIMIAN IMMUNODEFICIENCY VIRUS (K6W ISOLATE) | 553–608 | | | | | | | | |
| PENV_SIVML | ENV POLYPROTEIN | SIMIAN IMMUNODEFICIENCY VIRUS (K78 ISOLATE) | 549–608 | | | | | | | | |
| PENV_SIVS4 | ENV POLYPROTEIN | SIMIAN IMMUNODEFICIENCY VIRUS (F236/SMH4 ISOLATE) | 281–308 | 553–612 | 642–669 | 691–718 | | | | | |
| PENV_SIVSP | ENV POLYPROTEIN | SIMIAN IMMUNODEFICIENCY VIRUS (PBJ/BC13 ISOLATE) | 286–313 | 554–595 | 646–722 | | | | | | |
| PENV_SMRVH | ENV POLYPROTEIN | SQUIRREL MONKEY RETROVIRUS (SMRV-H) | 400–462 | | | | | | | | |
| PENV_SRV1 | ENV POLYPROTEIN | SIMIAN RETROVIRUS SRV-1 | 409–471 | | | | | | | | |
| PENV_VILV | ENV POLYPROTEIN | VISNA LENTIVIRUS (STRAIN 1514) | 22–62 | 773–800 | | | | | | | |
| PENV_VILV1 | ENV POLYPROTEIN | VISNA LENTIVIRUS (STRAIN 1514/CLONE LV1-1KS1) | 22–62 | 780–807 | | | | | | | |
| PENV_VILV2 | ENV POLYPROTEIN | VISNA LENTIVIRUS (STRAIN 1514/CLONE LV1-1KS2) | 22–62 | 782–809 | | | | | | | |
| PETF1_FOWP1 | EARLY TRANS FACTOR 70 KD SUBUNIT | FOWLPOX VIRUS (STRAIN FP-1) | 190–224 | | | | | | | | |
| PETF1_SFVKA | EARLY TRANS FACTOR 70 KD SUBUNIT | SHOPE FIBROMA VIRUS (STRAIN KASZA) | 306–340 | 469–496 | 550–587 | | | | | | |
| PETF1_VACCC | EARLY TRANS FACTOR 70 KD SUBUNIT | VACCINIA VIRUS (STRAIN COPENHAGEN) | 307–341 | 470–497 | | | | | | | |
| PETF1_VACCV | EARLY TRANS FACTOR 70 KD SUBUNIT | VACCINIA VIRUS (STRAIN WR) | 307–341 | 470–497 | | | | | | | |
| PETF2_VACCC | EARLY TRANSCRIPTION FACTOR 82 | VACCINIA VIRUS (STRAIN COPENHAGEN) | 66–97 | 174–210 | 302–331 | | | | | | |
| PETF2_VARV | EARLY TRANSCRIPTION FACTOR 82 | VARIOLA VIRUS | 66–97 | 174–210 | 302–332 | | | | | | |
| PEXON_VZVD | ALKALINE EXONUCLEASE | VARICELLA-ZOSTER VIRUS (STRAIN DUMAS) | 109–139 | | | | | | | | |
| PFIB2_ADE40 | 41.4 KD FIBER PROTEIN | HUMAN ADENOVIRUS TYPE 40 | 179–237 | | | | | | | | |
| PFIB2_ADE41 | 41.4 KD FIBER PROTEIN | HUMAN ADENOVIRUS TYPE 41 | 178–216 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PFIBP_ADE02 | FIBER PROTEIN | HUMAN ADENOVIRUS TYPE 2 | 308–335 | | | | | | | | |
| PFIBP_ADE40 | FIBER PROTEIN | HUMAN ADENOVIRUS TYPE 40 | 324–351 | 446–473 | | | | | | | |
| PFIBP_ADE41 | FIBER PROTEIN | HUMAN ADENOVIRUS TYPE 41 | 339–366 | 461–488 | | | | | | | |
| PFIBP_ADEB3 | FIBER PROTEIN | BOVINE ADENOVIRUS TYPE 3 | 118–145 | 164–191 | | | | | | | |
| PFIBP_ADEM1 | FIBER PROTEIN | MOUSE ADENOVIRUS TYPE 1 | 275–305 | 325–352 | | | | | | | |
| PFOSX_MSVFR | V-FOS/FOX TRANSFORMING PROTEIN | FBR MURINE OSTEOSARCOMA VIRUS | 138–169 | | | | | | | | |
| PFOS_AVINK | P55-V-FOS TRANSFORMING PROTEIN | AVIAN RETROVIRUS NK24 | 116–147 | | | | | | | | |
| PFOS_MSVFB | P55-V-FOS TRANSFORMING PROTEIN | FBJ MURINE OSTEOSARCOMA VIRUS | 162–193 | | | | | | | | |
| PGAG_AVISN | GAG POLYPROTEIN | AVIAN SPLEEN NECROSIS VIRUS | 270–297 | | | | | | | | |
| PGAG_EIAVY | GAG POLYPROTEIN | EQUINE INFECTIOUS ANEMIA VIRUS (ISOLATE WYOMING) | 144–171 | | | | | | | | |
| PGAG_FOAMV | GAG POLYPROTEIN | HUMAN SPUMARETROVIRUS | 621–648 | | | | | | | | |
| PGAG_GALV | GAG POLYPROTEIN | GIBBON APE LEUKEMIA VIRUS | 396–442 | 447–474 | | | | | | | |
| PGAG_HV1A2 | GAG POLYPROTEIN | HUMAN IMMUNODEFICIENCY VIRUS TYPE 1 (ARV2/SF2 ISOLATE) | 91–118 | | | | | | | | |
| PGAG_HV1J3 | GAG POLYPROTEIN | HUMAN IMMUNODEFICIENCY VIRUS TYPE 1 (JH3 ISOLATE) | 91–118 | | | | | | | | |
| PGAG_HV1MN | GAG POLYPROTEIN | HUMAN IMMUNODEFICIENCY VIRUS TYPE 1 (MN ISOLATE) | 87–118 | | | | | | | | |
| PGAG_HV2BE | GAG POLYPROTEIN | HUMAN IMMUNODEFICIENCY VIRUS TYPE 2 (ISOLATE BEN) | 88–115 | | | | | | | | |
| PGAG_HV2D1 | GAG POLYPROTEIN | HUMAN IMMUNODEFICIENCY VIRUS TYPE 2 (ISOLATE D194) | 88–115 | | | | | | | | |
| PGAG_HV2NZ | GAG POLYPROTEIN | HUMAN IMMUNODEFICIENCY VIRUS TYPE 1 (ISOLATE NIH-Z) | 88–115 | | | | | | | | |
| PGAG_HV2ST | GAG POLYPROTEIN | HUMAN IMMUNODEFICIENCY VIRUS TYPE 1 (ISOLATE ST) | 88–115 | | | | | | | | |
| PGAG_IPHA | RETROVIRUS-RELATED GAG POLYPROTEI | HAMSTER INTRACISTERNAL A-PARTICLE | 270–297 | | | | | | | | |
| PGAG_IPMA | RETROVIRUS-RELATED GAG POLYPROTEI | MOUSE INTRACISTERNAL A-PARTICLE | 33–60 | 69–103 | 232–259 | | | | | | |
| PGAG_IPMAE | RETROVIRUS-RELATED GAG POLYPROTEI | MOUSE INTRACISTERNAL A-PARTICLE | 96–130 | | | | | | | | |
| PGAG_MMTVB | GAG POLYPROTEIN | MOUSE MAMMARY TUMOR VIRUS (STRAIN BR6) | 84–151 | 156–187 | | | | | | | |
| PGAG_MMTVC | GAG POLYPROTEIN | MOUSE MAMMARY TUMOR VIRUS (STRAIN C3H) | 84–116 | | | | | | | | |
| PGAG_MMTVG | GAG POLYPROTEIN | MOUSE MAMMARY TUMOR VIRUS (STRAIN GR) | 84–151 | 156–187 | | | | | | | |
| PGAG_MPMV | GAG POLYPROTEIN | SIMIAN MASON-PFIZER VIRUS (MPMV) | 222–260 | | | | | | | | |
| PGAG_SCVLA | MAJOR COAT PROTEIN | SACCHAROMYCES CEREVISIAE VIRUS L-A | 497–531 | 624–651 | | | | | | | |
| PGAG_SIVAI | GAG POLYPROTEIN | SIMIAN IMMUNODEFICIENCY VIRUS (ISOLATE AGM/CLONE GRI-1) | 473–507 | | | | | | | | |
| PGAG_SIVMK | GAG POLYPROTEIN | SIMIAN IMMUNODEFICIENCY VIRUS (K6W ISOLATE) | 88–115 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PGAG_SIVMS | GAG POLYPROTEIN | SIMIAN IMMUNODEFICIENCY VIRUS (STM ISOLATE) | 88–115 | | | | | | | | |
| PGAG_SIVS4 | GAG POLYPROTEIN | SIMIAN IMMUNODEFICIENCY VIRUS (F236/SMH4 ISOLATE) | 88–115 | | | | | | | | |
| PGAG_SIVSP | GAG POLYPROTEIN | SIMIAN IMMUNODEFICIENCY VIRUS (PBJ/BC13 ISOLATE) | 88–115 | | | | | | | | |
| PGAG_SMSAV | GAG POLYPROTEIN | SIMIAN SARCOMA VIRUS | 397–443 | | | | | | | | |
| PGAG_SRV1 | GAG POLYPROTEIN | SIMIAN RETROVIRUS SRV-1 | 223–261 | | | | | | | | |
| PHEL1_HSVEB | PROBABLE HELICASE | EQUINE HERPESVIRUS TYPE 1 (STRAIN AB4P) | 184–211 | 321–348 | | | | | | | |
| PHEL1_HSVSA | PROBABLE HELICASE | HERPESVIRUS SAIMIRI (STRAIN 11) | 418–449 | | | | | | | | |
| PHEL1_VZVD | PROBABLE HELICASE | VARICELLA-ZOSTER VIRUS (STRAIN DUMAS) | 490–517 | 701–728 | | | | | | | |
| PHEMA_CVBF | HEMAGGLUTININ-ESTERASE PRECURSOR | BOVINE CORONAVIRUS (STRAIN F15) | 208–242 | | | | | | | | |
| PHEMA_CVBLY | HEMAGGLUTININ-ESTERASE PRECURSOR | BOVINE CORONAVIRUS (STRAIN LY-138) | 208–242 | | | | | | | | |
| PHEMA_CVBM | HEMAGGLUTININ-ESTERASE PRECURSOR | BOVINE CORONAVIRUS (STRAIN MEBUS) | 208–242 | | | | | | | | |
| PHEMA_CVBQ | HEMAGGLUTININ-ESTERASE PRECURSOR | BOVINE CORONAVIRUS (STRAIN QUEBEC) | 208–242 | | | | | | | | |
| PHEMA_CVHOC | HEMAGGLUTININ-ESTERASE PRECURSOR | HUMAN CORONAVIRUS (STRAIN OC43) | 208–242 | | | | | | | | |
| PHEMA_IAA1C | HEMAGGLUTININ PRECURSOR | INFLUENZA A VIRUS (STRAIN A/A1CH1/2/68) | 387–453 | | | | | | | | |
| PHEMA_IABAN | HEMAGGLUTININ PRECURSOR | INFLUENZA A VIRUS (STRAIN A/BANGKOK/1/79) | 24–51 | 371–437 | | | | | | | |
| PHEMA_IABUD | HEMAGGLUTININ PRECURSOR | INFLUENZA A VIRUS (STRAIN A/BUDGERIGAR/HOKKAIDO/1/77) | 381–451 | | | | | | | | |
| PHEMA_IACAO | HEMAGGLUTININ | INFLUENZA A VIRUS (STRAIN A/CAMEL/MONGOLIA/82) | 9–36 | | | | | | | | |
| PHEMA_IACKA | HEMAGGLUTININ PRECURSOR | INFLUENZA A VIRUS (STRAIN A/CHICKEN/ALABAMA/1/75) | 381–451 | | | | | | | | |
| PHEMA_IACKG | HEMAGGLUTININ PRECURSOR | INFLUENZA A VIRUS (STRAIN A/CHICKEN/GERMANY/N/49) | 31–58 | 382–441 | 494–528 | | | | | | |
| PHEMA_IACKP | HEMAGGLUTININ PRECURSOR | INFLUENZA A VIRUS (STRAIN A/CHICKEN/PENNSYLVANIA/1/83) | 396–426 | | | | | | | | |
| PHEMA_IACKQ | HEMAGGLUTININ PRECURSOR | INFLUENZA A VIRUS (STRAIN A/CHICKEN/PENNSYLVANIA/1370/83) | 396–426 | | | | | | | | |
| PHEMA_IACKV | HEMAGGLUTININ PRECURSOR | INFLUENZA A VIRUS (STRAIN A/CHICKEN/VICTORIA/1/85) | 119–146 | 384–443 | | | | | | | |
| PHEMA_IADA1 | HEMAGGLUTININ PRECURSOR | INFLUENZA A VIRUS (STRAIN A/DUCK/ALBERTA/28/76) | 381–451 | | | | | | | | |
| PHEMA_IADA2 | HEMAGGLUTININ PRECURSOR | INFLUENZA A VIRUS (STRAIN A/DUCK/ALBERTA/60/76) | 423–453 | 499–543 | | | | | | | |
| PHEMA_IADA3 | HEMAGGLUTININ PRECURSOR | INFLUENZA A VIRUS (STRAIN A/DUCK/ALBERTA/78/76) | 387–453 | | | | | | | | |
| PHEMA_IADA4 | HEMAGGLUTININ PRECURSOR | INFLUENZA A VIRUS (STRAIN A/DUCK/ALBERTA/35/76) | 29–56 | 418–478 | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IADCZ | HEMAGGLUTININ PRECURSOR | INFLUENZA A VIRUS (STRAIN A/DUCK/CZECHOSLOVAKIA/56) | 381–451 | | | | | | | | |
| PHEMA_IADE1 | HEMAGGLUTININ PRECURSOR | INFLUENZA A VIRUS (STRAIN A/DUCK/ENGLAND/1/56) | 21–55 | 402–453 | 506–533 | | | | | | |
| PHEMA_IADH1 | HEMAGGLUTININ PRECURSOR | INFLUENZA A VIRUS (STRAIN A/DUCK/HOKKAIDO/5/77) | 371–437 | | | | | | | | |
| PHEMA_IADH2 | HEMAGGLUTININ PRECURSOR | INFLUENZA A VIRUS (STRAIN A/DUCK/HOKKAIDO/8/80) | 371–437 | | | | | | | | |
| PHEMA_IADH3 | HEMAGGLUTININ PRECURSOR | INFLUENZA A VIRUS (STRAIN A/DUCK/HOKKAIDO/33/80) | 371–437 | | | | | | | | |
| PHEMA_IADH4 | HEMAGGLUTININ PRECURSOR | INFLUENZA A VIRUS (STRAIN A/DUCK/HOKKAIDO/7/82) | 371–437 | | | | | | | | |
| PHEMA_IADH5 | HEMAGGLUTININ PRECURSOR | INFLUENZA A VIRUS (STRAIN A/DUCK/HOKKAIDO/21/82) | 371–437 | | | | | | | | |
| PHEMA_IADH6 | HEMAGGLUTININ PRECURSOR | INFLUENZA A VIRUS (STRAIN A/DUCK/HOKKAIDO/9/85) | 371–437 | | | | | | | | |
| PHEMA_IADH7 | HEMAGGLUTININ PRECURSOR | INFLUENZA A VIRUS (STRAIN A/DUCK/HOKKAIDO/10/85) | 371–437 | | | | | | | | |
| PHEMA_IADIR | HEMAGGLUTININ PRECURSOR | INFLUENZA A VIRUS (STRAIN A/DUCK/IRELAND/113/83) | 415–445 | | | | | | | | |
| PHEMA_IADM2 | HEMAGGLUTININ PRECURSOR | INFLUENZA A VIRUS (STRAIN A/DUCK/MEMPHIS/546/76) | 21–56 | | | | | | | | |
| PHEMA_IADM2 | HEMAGGLUTININ PRECURSOR | INFLUENZA A VIRUS (STRAIN A/DUCK/MEMPHIS/928/74) | 387–453 | | | | | | | | |
| PHEMA_IADMA | HEMAGGLUTININ PRECURSOR | INFLUENZA A VIRUS (STRAIN A/DUCK/MANITOBA/1/53) | 31–58 | | | | | | | | |
| PHEMA_IADNY | HEMAGGLUTININ PRECURSOR | INFLUENZA A VIRUS (STRAIN A/DUCK/NEW YORK/12/78) | 21–55 | | | | | | | | |
| PHEMA_IADNZ | HEMAGGLUTININ PRECURSOR | INFLUENZA A VIRUS (STRAIN A/DUCK/NEW ZEALAND/31/76) | 381–451 | | | | | | | | |
| PHEMA_IADU1 | HEMAGGLUTININ PRECURSOR | INFLUENZA A VIRUS (STRAIN A/DUCK/UKRAINE/1/60) | 21–55 | | | | | | | | |
| PHEMA_IADU3 | HEMAGGLUTININ PRECURSOR | INFLUENZA A VIRUS (STRAIN A/DUCK/UKRAINE/1/63) | 387–453 | | | | | | | | |
| PHEMA_IAEN6 | HEMAGGLUTININ PRECURSOR | INFLUENZA A VIRUS (STRAIN A/ENGLAND/878/69) | 24–51 | | | | | | | | |
| PHEMA_IAEN7 | HEMAGGLUTININ PRECURSOR | INFLUENZA A VIRUS (STRAIN A/ENGLAND/321/77) | 40–67 | 387–453 | | | | | | | |
| PHEMA_IAFPR | HEMAGGLUTININ PRECURSOR | INFLUENZA A VIRUS (STRAIN A/FOWL PLAGUE VIRUS/ROSTOCK/34) | 177–221 | 384–442 | | | | | | | |
| PHEMA_IAGRE | HEMAGGLUTININ PRECURSOR | INFLUENZA A VIRUS (STRAIN A/GREY TEAL/AUSTRALIA/2/79) | 381–451 | | | | | | | | |
| PHEMA_IAGU2 | HEMAGGLUTININ PRECURSOR | INFLUENZA A VIRUS (STRAIN A/GULL/MARYLAND/704/77) | 505–532 | | | | | | | | |
| PHEMA_IAGUA | HEMAGGLUTININ PRECURSOR | INFLUENZA A VIRUS (STRAIN A/GULL/ASTRAKHAN/227/84) | 504–531 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IAHAL | HEMAGGLUTININ PRECURSOR | INFLUENZA A VIRUS (STRAIN A/EQUINE/ALGIERS/72) | 386–452 | | | | | | | | |
| PHEMA_IAHAR | HEMAGGLUTININ PRECURSOR | INFLUENZA A VIRUS (STRAIN A/HARBIN/1/88) | 29–56 | | | | | | | | |
| PHEMA_IAHC6 | HEMAGGLUTININ PRECURSOR | INFLUENZA A VIRUS (STRAIN A/EQUINE/CAMBRIDGE/1/63) | 29–56 | 194–221 | 388–457 | | | | | | |
| PHEMA_IAHC7 | HEMAGGLUTININ PRECURSOR | INFLUENZA A VIRUS (STRAIN A/EQUINE/CAMBRIDGE/1/73) | 29–56 | 194–221 | 388–457 | | | | | | |
| PHEMA_IAHCD | HEMAGGLUTININ PRECURSOR | INFLUENZA A VIRUS (STRAIN A/EQUINE/C.DETROIT/1/64) | 29–56 | 194–221 | 388–457 | | | | | | |
| PHEMA_IAHDE | HEMAGGLUTININ PRECURSOR | INFLUENZA A VIRUS (STRAIN A/EQUINE/DETROIT/1/64) | 29–56 | 194–221 | 388–457 | | | | | | |
| PHEMA_IAHFO | HEMAGGLUTININ PRECURSOR | INFLUENZA A VIRUS (STRAIN A/EQUINE/FONTAINEBLEAU/76) | 386–452 | | | | | | | | |
| PHEMA_IAHK6 | HEMAGGLUTININ PRECURSOR | INFLUENZA A VIRUS (STRAIN A/EQUINE/KENTUCKY/2/86) | 386–452 | | | | | | | | |
| PHEMA_IAHK7 | HEMAGGLUTININ PRECURSOR | INFLUENZA A VIRUS (STRAIN A/EQUINE/KENTUCKY/1/87) | 386–452 | | | | | | | | |
| PHEMA_IAHLE | HEMAGGLUTININ PRECURSOR | INFLUENZA A VIRUS (STRAIN A/EQUINE/LEXINGTON/1/66) | 29–56 | 194–221 | 388–457 | | | | | | |
| PHEMA_IAHLO | HEMAGGLUTININ PRECURSOR | INFLUENZA A VIRUS (STRAIN A/EQUINE/LONDON/1416/73) | 29–56 | 194–221 | 388–457 | | | | | | |
| PHEMA_IAHMI | HEMAGGLUTININ PRECURSOR | INFLUENZA A VIRUS (STRAIN A/EQUINE/MIAMI/1/63) | 386–452 | | | | | | | | |
| PHEMA_IAHNM | HEMAGGLUTININ PRECURSOR | INFLUENZA A VIRUS (STRAIN A/EQUINE/NEW MARKET/76) | 386–452 | | | | | | | | |
| PHEMA_IAHNN | HEMAGGLUTININ PRECURSOR | INFLUENZA A VIRUS (STRAIN A/EQUINE/NEW MARKET/1/77) | 29–56 | 194–221 | 388–457 | | | | | | |
| PHEMA_IAHPR | HEMAGGLUTININ PRECURSOR | INFLUENZA A VIRUS (STRAIN A/EQUINE/PRAGUE/1/56) | 29–56 | 194–221 | 388–457 | | | | | | |
| PHEMA_IAHRO | HEMAGGLUTININ PRECURSOR | INFLUENZA A VIRUS (STRAIN A/EQUINE/ROMANIA/80) | 386–452 | | | | | | | | |
| PHEMA_IAHSA | HEMAGGLUTININ PRECURSOR | INFLUENZA A VIRUS (STRAIN A/EQUINE/SANTIAGO/1/85) | 386–452 | | | | | | | | |
| PHEMA_IAHSP | HEMAGGLUTININ PRECURSOR | INFLUENZA A VIRUS (STRAIN A/EQUINE/SAO PAULO/1/76) | 29–56 | 194–221 | 388–457 | | | | | | |
| PHEMA_IAHSW | HEMAGGLUTININ PRECURSOR | INFLUENZA A VIRUS (STRAIN) A/EQUINE/SWITZERLAND/137/72 | 29–56 | 194–221 | 388–457 | | | | | | |
| PHEMA_IAHTE | HEMAGGLUTININ PRECURSOR | INFLUENZA A VIRUS (STRAIN A/EQUINE/TENNESSEE/5/86) | 386–452 | | | | | | | | |
| PHEMA_IAHTO | HEMAGGLUTININ PRECURSOR | INFLUENZA A VIRUS (STRAIN A/EQUINE/TOKYO/71) | 386–455 | | | | | | | | |
| PHEMA_IAHUR | HEMAGGLUTININ PRECURSOR | INFLUENZA A VIRUS (STRAIN A/EQUINE/URUGUAY/1/63) | 386–452 | | | | | | | | |
| PHEMA_IAJAP | HEMAGGLUTININ PRECURSOR | INFLUENZA A VIRUS (STRAIN A/JAPAN/305/57) | 196–223 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IAKIE | HEMAGGLUTININ PRECURSOR | INFLUENZA A VIRUS (STRAIN A/KIEV/59/79) | 29–56 | 425–478 | | | | | | | |
| PHEMA_IALEN | HEMAGGLUTININ PRECURSOR | INFLUENZA A VIRUS (STRAIN A/LENINGRAD/54/1) | 29–56 | 425–478 | | | | | | | |
| PHEMA_IAMAA | HEMAGGLUTININ PRECURSOR | INFLUENZA A VIRUS (STRAIN A/MALLARD/ASTRAKHAN/244/82) | 380–450 | | | | | | | | |
| PHEMA_IAMAB | HEMAGGLUTININ PRECURSOR | INFLUENZA A VIRUS (STRAIN A/MALLARD/ASTRAKHAN/263/82) | 385–455 | | | | | | | | |
| PHEMA_IAMAO | HEMAGGLUTININ PRECURSOR | INFLUENZA A VIRUS (STRAIN A/MALLARD/NEW YORK/6874/78) | 387–453 | | | | | | | | |
| PHEMA_IAME1 | HEMAGGLUTININ PRECURSOR | INFLUENZA A VIRUS (STRAIN A/MEMPHIS/1/71) | 40–67 | 387–453 | | | | | | | |
| PHEMA_IAME2 | HEMAGGLUTININ PRECURSOR | INFLUENZA A VIRUS (STRAIN A/MEMPHIS/102/72) | 40–67 | 387–453 | | | | | | | |
| PHEMA_IAME6 | HEMAGGLUTININ PRECURSOR | INFLUENZA A VIRUS (STRAIN A/MEMPHIS/6/86) | 24–51 | 371–437 | | | | | | | |
| PHEMA_IAMIN | HEMAGGLUTININ PRECURSOR | INFLUENZA A VIRUS (STRAIN A/MINK/SWEDEN/84) | 31–58 | 382–441 | | | | | | | |
| PHEMA_IANT6 | HEMAGGLUTININ PRECURSOR | INFLUENZA A VIRUS (STRAIN A/NT/60/68) | 387–453 | | | | | | | | |
| PHEMA_IAP1L | HEMAGGLUTININ PRECURSOR | INFLUENZA A VIRUS (STRAIN A/PILOT WHALE/MAINE/328/84) | 505–534 | | | | | | | | |
| PHEMA_IAPUE | HEMAGGLUTININ PRECURSOR | INFLUENZA A VIRUS (STRAIN A/PUETRO RICO/8/34) | 29–56 | 425–478 | | | | | | | |
| PHEMA_IAQU7 | HEMAGGLUTININ PRECURSOR | INFLUENZA A VIRUS (STRAIN A/QU/7/70) | 24–51 | | | | | | | | |
| PHEMA_IARUD | HEMAGGLUTININ PRECURSOR | INFLUENZA A VIRUS (STRAIN A/RUDDY TURNSTONE/NEW JERSEY/47/85) | 381–451 | | | | | | | | |
| PHEMA_IASE2 | HEMAGGLUTININ PRECURSOR | INFLUENZA A VIRUS (STRAIN A/SEAL/MASSACHUSETTS/133/82) | 381–451 | | | | | | | | |
| PHEMA_IASH2 | HEMAGGLUTININ PRECURSOR | INFLUENZA A VIRUS (STRAIN A/SHEARWATER/AUSTRALIA/72) | 28–56 | 160–187 | 506–547 | | | | | | |
| PHEMA_IASTA | HEMAGGLUTININ PRECURSOR | INFLUENZA A VIRUS (STRAIN A/STARLING/VICTORIA/5156/85) | 119–146 | 384–443 | | | | | | | |
| PHEMA_IATA1 | HEMAGGLUTININ PRECURSOR | INFLUENZA A VIRUS (STRAIN A/TAIWAN/1/86) | 29–56 | | | | | | | | |
| PHEMA_IATK1 | HEMAGGLUTININ PRECURSOR | INFLUENZA A VIRUS (STRAIN A/TURKEY/IRELAND/1378/83) | 415–445 | | | | | | | | |
| PHEMA_IATKM | HEMAGGLUTININ PRECURSOR | INFLUENZA A VIRUS (STRAIN A/TURKEY/MINNESOTA/833/80) | 381–451 | | | | | | | | |
| PHEMA_IATKO | HEMAGGLUTININ PRECURSOR | INFLUENZA A VIRUS (STRAIN A/TURKEY/ONTARIO/7732/66) | 507–534 | | | | | | | | |
| PHEMA_IATKP | HEMAGGLUTININ PRECURSOR | INFLUENZA A VIRUS (STRAIN A/TURKEY/ONTARIO/6118/68) | 424–454 | 493–539 | | | | | | | |
| PHEMA_IATKR | HEMAGGLUTININ PRECURSOR | INFLUENZA A VIRUS (STRAIN A/TURKEY/OREGON/71) | 32–62 | 194–221 | 381–422 | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IATKW | HEMAGGLUTININ PRECURSOR | INFLUENZA A VIRUS (STRAIN A/TURKEY/WISCONSIN/1/66) | 419–449 | 500–536 | | | | | | | |
| PHEMA_IATRA | HEMAGGLUTININ PRECURSOR | INFLUENZA A VIRUS (STRAIN A/TERN/AUSTRALIA/G70C/75) | 21–55 | | | | | | | | |
| PHEMA_IAUDO | HEMAGGLUTININ PRECURSOR | INFLUENZA A VIRUS (STRAIN A/UDORN/307/72) | 40–67 | 387–453 | | | | | | | |
| PHEMA_IAUSS | HEMAGGLUTININ PRECURSOR | INFLUENZA A VIRUS (STRAIN A/USSR/90/77) | 29–56 | 425–478 | | | | | | | |
| PHEMA_IAV7 | HEMAGGLUTININ PRECURSOR | INFLUENZA A VIRUS (STRAIN A/VICTORIA/3/75) | 41–68 | 388–454 | | | | | | | |
| PHEMA_IAWIL | HEMAGGLUTININ PRECURSOR | INFLUENZA A VIRUS (STRAIN A/WILSON-SMITH/33) | 424–477 | | | | | | | | |
| PHEMA_IAXIA | HEMAGGLUTININ PRECURSOR | INFLUENZA A VIRUS (STRAIN A/XIANFENG/3/89) | 29–56 | | | | | | | | |
| PHEMA

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA TABLE VI-continued 107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_PI1HW | HEMAGGLUTININ-NEURAMINIDASE | HUMAN PARAINFLUENZA 1 VIRUS (STRAIN WASHINGTON/1957) | 79–110 | 366–393 | | | | | | | |
| PHEMA_PI3B | HEMAGGLUTININ-NEURAMINIDASE | BOVINE PARAINFLUENZA 3 VIRUS | 66–93 | | | | | | | | |
| PHEMA_PI3H4 | HEMAGGLUTININ-NEURAMINIDASE | HUMAN PARAINFLUENZA 3 VIRUS (STRAIN NIH 47885) | 27–61 | | | | | | | | |
| PHEMA_PI3HA | HEMAGGLUTININ-NEURAMINIDASE | HUMAN PARAINFLUENZA 3 VIRUS (STRAIN AUS/124854/74) | 27–61 | | | | | | | | |
| PHEMA_PI3HT | HEMAGGLUTININ-NEURAMINIDASE | HUMAN PARAINFLUENZA 3 VIRUS (STRAIN TEX/545/80) | 27–76 | | | | | | | | |
| PHEMA_PI3HU | HEMAGGLUTININ-NEURAMINIDASE | HUMAN PARAINFLUENZA 3 VIRUS (STRAIN TEX/9305/82) | 23–70 | | | | | | | | |
| PHEMA_PI3HV | HEMAGGLUTININ-NEURAMINIDASE | HUMAN PARAINFLUENZA 3 VIRUS (STRAIN TEX/12677/83) | 27–61 | | | | | | | | |
| PHEMA_PI3HW | HEMAGGLUTININ-NEURAMINIDASE | HUMAN PARAINFLUENZA 3 VIRUS (STRAIN WASH/641/79) | 27–61 | | | | | | | | |
| PHEMA_PI3HX | HEMAGGLUTININ-NEURAMINIDASE | HUMAN PARAINFLUENZA 3 VIRUS (STRAIN WASH/1511/73) | 27–61 | | | | | | | | |
| PHEMA_RACVI | HEMAGGLUTININ PRECURSOR | RACCOON POXVIRUS | 166–214 | 256–283 | | | | | | | |
| PHEMA_SEND5 | HEMAGGLUTININ-NEURAMINIDASE | SENDAI VIRUS (STRAIN Z/HOST MUTANTS) | 79–106 | | | | | | | | |
| PHEMA_SENDF | HEMAGGLUTININ-NEURAMINIDASE | SENDAI VIRUS (STRAIN FUSHIMI) | 79–106 | | | | | | | | |
| PHEMA_SENDH | HEMAGGLUTININ-NEURAMINIDASE | SENDAI VIRUS (STRAIN HARRIS) | 79–106 | | | | | | | | |
| PHEMA_SENDJ | HEMAGGLUTININ-NEURAMINIDASE | SENDAI VIRUS (STRAIN HVJ) | 79–106 | | | | | | | | |
| PHEMA_SENDZ | HEMAGGLUTININ-NEURAMINIDASE | SENDAI VIRUS (STRAIN Z) | 79–106 | | | | | | | | |
| PHEMA_SV41 | HEMAGGLUTININ-NEURAMINIDASE | SIMIAN VIRUS 41 | 22–52 | 394–421 | | | | | | | |
| PHEMA_VACCC | HEMAGGLUTININ PRECURSOR | VACCINIA VIRUS (STRAIN COPENHAGEN) | 119–146 | 175–202 | 216–243 | | | | | | |
| PHEMA_VACCI | HEMAGGLUTININ PRECURSOR | VACCINIA VIRUS (STRAIN IHD-J) | 109–146 | 175–202 | 216–243 | | | | | | |
| PHEMA_VACCT | HEMAGGLUTININ PRECURSOR | VACCINIA VIRUS (STRAIN TIAN TAN) | 119–146 | 175–202 | 216–243 | | | | | | |
| PHEMA_VACCV | HEMAGGLUTININ PRECURSOR | VACCINIA VIRUS (STRAIN WR) | 109–146 | 175–202 | 215–242 | | | | | | |
| PHEMA_VARV | HEMAGGLUTININ PRECURSOR | VARIOLA VIRUS | 111–148 | 177–211 | 214–244 | | | | | | |
| PHEX9_ADE02 | HEXON-ASSOCIATED PROTEIN | HUMAN ADENOVIRUS TYPE 2 | 100–134 | | | | | | | | |
| PHEX9_ADE05 | HEXON-ASSOCIATED PROTEIN | HUMAN ADENOVIRUS TYPE 5 | 100–134 | | | | | | | | |
| PHEX9_ADE07 | HEXON-ASSOCIATED PROTEIN | HUMAN ADENOVIRUS TYPES 3 and 7 | 97–127 | | | | | | | | |
| PHEX_ADE02 | HEXON PROTEIN | HUMAN ADENOVIRUS TYPE 2 | 146–173 | 359–386 | 433–460 | | | | | | |
| PHEX_ADE05 | HEXON PROTEIN | HUMAN ADENOVIRUS TYPE 5 | 348–375 | | | | | | | | |
| PHEX_ADE40 | HEXON PROTEIN | HUMAN ADENOVIRUS TYPE 40 | 396–423 | | | | | | | | |
| PHEX_ADEB3 | HEXON PROTEIN | BOVINE ADENOVIRUS TYPE 3 | 305–338 | | | | | | | | |
| PHI38_COWPX | HEMORRHAGE-INDUCING 38 KD PROTEIN | COWPOX VIRUS | 28–55 | | | | | | | | |
| PHRG_COWPX | HOST RANGE PROTEIN | COWPOX VIRUS | 462–489 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PI196_ASFB7 | LATE PROTEIN I196L | AFRICAN SWINE FEVER VIRUS (STRAIN BA71V) | 12–43 | | | | | | | | |
| PI226_ASFB7 | LATE PROTEIN I226R | AFRICAN SWINE FEVER VIRUS (STRAIN BA71V) | 113–147 | | | | | | | | |
| PIBMP_CAMV4 | INCLUSION BODY MATRIX PROTEIN | CAULIFLOWER MOSAIC VIRUS (STRAIN D4) | 17–44 | | | | | | | | |
| PIBMP_CAMVD | INCLUSION BODY MATRIX PROTEIN | CAULIFLOWER MOSAIC VIRUS (STRAIN D/H) | 17–44 | | | | | | | | |
| PIBMP_CAMVP | INCLUSION BODY MATRIX PROTEIN | CAULIFLOWER MOSAIC VIRUS (STRAIN PV147) | 383–410 | | | | | | | | |
| PIBMP_CERV | INCLUSION BODY MATRIX PROTEIN | CARNATION ETCHED RING VIRUS | 6–33 | | | | | | | | |
| PIBMP_FMVD | INCLUSION BODY MATRIX PROTEIN | FIGWORT MOSAIC VIRUS (STRAIN DXS) | 372–407 | | | | | | | | |
| PIBMP_SOCMV | INCLUSION BODY MATRIX PROTEIN | SOYBEAN CHLOROTIC MOTTLE VIRUS | 3–48 | 331–358 | | | | | | | |
| PIC18_HCMVA | PROB PROC & TRANSPORT PRO UL56 | HUMAN CYTOMEGALOVIRUS (STRAIN AD169) | 294–324 | | | | | | | | |
| PIC18_HSVSA | PROBABLE PROC & TRANSPORT PRO | HERPESVIRUS SAIMIRI (STRAIN 11) | 58–85 | 482–522 | | | | | | | |
| PIC18_MCMVS | PROB PROC & TRANSPORT PRO | MURINE CYTOMEGALOVIRUS (STRAIN SMITH) | 661–691 | | | | | | | | |
| PIE63_HSV11 | TRANSCRIPTIONAL REGULATOR IE63 | HERPES SIMPLEX VIRUS (TYPE 1/STRAIN 17) | 248–275 | | | | | | | | |
| PIE68_HSV11 | IMMEDIATE-EARLY PROTEIN IE68 | HERPES SIMPLEX VIRUS (TYPE 1/STRAIN 17) | 40–67 | | | | | | | | |
| PIE68_HSVSA | IMMEDIATE-EARLY PROTEIN | HERPESVIRUS SAIMIRI (STRAIN 11) | 48–78 | | | | | | | | |
| PIR05_HCMVA | HYPOTHETICAL PROTEIN IRL5 | HUMAN CYTOMEGALOVIRUS (STRAIN AD169) | 22–49 | | | | | | | | |
| PIR12_HCMVA | HYPOTHETICAL PROTEIN IRL12 | HUMAN CYTOMEGALOVIRUS (STRAIN AD169) | 74–162 | | | | | | | | |
| PIR13_HCMVA | HYPOTHETICAL PROTEIN IRL13 | HUMAN CYTOMEGALOVIRUS (STRAIN AD169) | 31–62 | | | | | | | | |
| PKFES_FSVGA | TYROSINE KINASE TRANSF PROTEIN FES | FELINE SARCOMA VIRUS (STRAIN GARDNER-ARNSTEIN) | 106–150 | | | | | | | | |
| PKFGR_FSVGR | TYROSINE KINASE TRANSF PROTEIN FGR | FELINE SARCOMA VIRUS (STRAIN GARDNER-RASHEED) | 218–252 | | | | | | | | |
| PKFMS_FSVMD | FMS TYROSINE KINASE TRANSF PROTEIN | FELINE SARCOMA VIRUS (STRAIN MCDONOUGH) | 327–362 | | | | | | | | |
| PKFPS_FUJSV | TYROSINE KINASE TRANSF PROTEIN FPS | FUJINAMI SARCOMA VIRUS | 155–243 | 349–397 | | | | | | | |
| PKITH_AMEPV | THYMIDINE KINASE | AMSACTA MOOREI ENTOMOPOXVIRUS | 47–84 | | | | | | | | |
| PKITH_CAPVK | THYMIDINE KINASE | CAPRIPOXVIRUS (STRAIN KS-1) | 41–68 | | | | | | | | |
| PKITH_HSVSA | THYMIDINE KINASE | HERPESVIRUS SAIMIRI (STRAIN 11) | 340–386 | | | | | | | | |
| PKITH_ILTVT | THYMIDINE KINASE | INFECTIOUS LARYNGOTRACHEITIS VIRUS (STRAIN THORNE V882) | 334–361 | | | | | | | | |
| PKR74_HSVI1 | GENE 74 PROTEIN KINASE | ICTALURID HERPESVIRUS 1 | 491–518 | | | | | | | | |
| PKRB1_VACCC | 30 KD PROTEIN KINASE HOMOLOG | VACCINIA VIRUS (STRAIN COPENHAGEN) | 141–168 | | | | | | | | |
| PKRB1_VACCV | 30 KD PROTEIN KINASE HOMOLOG | VACCINIA VIRUS (STRAIN WR) | 141–168 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PKRB2_VACCC | POSSIBLE PROTEIN KINASE B12 | VACCINIA VIRUS (STRAIN COPENHAGEN) | 147–174 | | | | | | | | |
| PKRB2_VACCV | POSSIBLE PROTEIN KINASE B12 | VACCINIA VIRUS (STRAIN WR) | 147–174 | | | | | | | | |
| PKRF1_VACCC | POSSIBLE PROTEIN KINASE F10 | VACCINIA VIRUS (STRAIN COPENHAGEN) | 47–74 | | | | | | | | |
| PKRF1_VARV | POSSIBLE PROTEIN KINASE F10 | VARIOLA VIRUS | 47–74 | | | | | | | | |
|

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PNCAP_BUNLC | NUCLEOCAPSID PROTEIN | BUNYAVIRUS LA CROSSE | 85–112 | | | | | | | | |
| PNCAP_BUNSH | NUCLEOCAPSID PROTEIN | BUNYAVIRUS SNOWSHOE HARE | 96–123 | | | | | | | | |
| PNCAP_BUNYW | NUCLEOCAPSID PROTEIN | BUNYAMWERA VIRUS | 48–75 | 189–220 | | | | | | | |
| PNCAP_CCHFV | NUCLEOCAPSID PROTEIN | CRIMEAN-CONGO HEMORRHAGIC FEVER VIRUS (ISOLATE C68031) | 223–271 | | | | | | | | |
| PNCAP_CDVO | NUCLEOCAPSID PROTEIN | CANINE DISTEMPER VIRUS (STRAIN ONDERSTEPOORT) | 140–174 | | | | | | | | |
| PNCAP_CHAV | NUCLEOCAPSID PROTEIN | CHANDIPURA VIRUS (STRAIN 1653514) | 40–74 | | | | | | | | |
| PNCAP_CVCAE | NUCLEOCAPSID PROTEIN | CANINE ENTERIC CORONAVIRUS (STRAIN K378) | 191–227 | | | | | | | | |
| PNCAP_CVPPU | NUCLEOCAPSID PROTEIN | PORCINE TRANSMISSIBLE GASTROENTERITIS CORONAVIRUS (STRAIN PURD) | 191–227 | | | | | | | | |
| PNCAP_CVPR8 | NUCLEOCAPSID PROTEIN | PORCINE RESPIRATORY CORONAVIRUS (STRAIN 86/137004/BRITISH ISOLAT | 191–227 | | | | | | | | |
| PNCAP_CVPRM | NUCLEOCAPSID PROTEIN | PORCINE RESPIRATORY CORONAVIRUS (STRAIN RM4) | 191–227 | | | | | | | | |
| PNCAP_DUGBV | NUCLEOCAPSID PROTEIN | DUGBE VIRUS | 238–265 | | | | | | | | |
| PNCAP_FIPV | NUCLEOCAPSID PROTEIN | FELINE INFECTIOUS PERITONITIS VIRUS (STRAIN 79–1146) | 182–209 | | | | | | | | |
| PNCAP_HAZVJ | NUCLEOCAPSID PROTEIN | HAZARA VIRUS (ISOLATE JC280) | 6–33 | 256–283 | | | | | | | |
| PNCAP_HRSV1 | NUCLEOCAPSID PROTEIN | HUMAN RESPIRATORY SYNCYTIAL VIRUS (SUBGROUP B/STRAIN 18537) | 4–31 | 74–108 | 112–141 | | | | | | |
| PNCAP_HRSVA | NUCLEOCAPSID PROTEIN | HUMAN RESPIRATORY SYNCYTIAL VIRUS (STRAIN A2) | 4–31 | | | | | | | | |
| PNCAP_LASSG | NUCLEOCAPSID PROTEIN | LASSA VIRUS (STRAIN GA391) | 64–99 | 147–174 | | | | | | | |
| PNCAP_LASSI | NUCLEOCAPSID PROTEIN | LASSA VIRUS (STRAIN JOSIAH) | 64–99 | 467–504 | | | | | | | |
| PNCAP_LYCVA | NUCLEOCAPSID PROTEIN | LYMPHOCYTIC CHORIOMENINGITIS VIRUS (STRAIN ARMSTRONG) | 64–97 | | | | | | | | |
| PNCAP_MAGV | NUCLEOCAPSID PROTEIN | MAGUARI VIRUS | 41–68 | 192–219 | | | | | | | |
| PNCAP_MOPEI | NUCLEOCAPSID PROTEIN | MOPEIA VIRUS | 64–99 | | | | | | | | |
| PNCAP_PI1HC | NUCLEOCAPSID PROTEIN | HUMAN PARAINFLUENZA 1 VIRUS (STRAIN C39) | 377–404 | 455–482 | | | | | | | |
| PNCAP_PI1HW | NUCLEOCAPSID PROTEIN | HUMAN PARAINFLUENZA 1 VIRUS (STRAIN WASHINGTON/1957) | 377–404 | 444–488 | | | | | | | |
| PNCAP_PI3H4 | NUCLEOCAPSID PROTEIN | HUMAN PARAINFLUENZA 3 VIRUS (STRAIN NIH) 47885 | 376–403 | | | | | | | | |
| PNCAP_PTTV | NUCLEOCAPSID PROTEIN | PUNTA TORO PHLEBOVIRUS | 3–30 | | | | | | | | |
| PNCAP_PUUMH | NUCLEOCAPSID PROTEIN | PUUMALA VIRUS (STRAIN HALLNAS B1) | 2–29 | | | | | | | | |
| PNCAP_PUUMS | NUCLEOCAPSID PROTEIN | PUUMALA VIRUS (STRAIN SOTKAMO) | 2–29 | | | | | | | | |
| PNCAP_PVM | NUCLEOCAPSID PROTEIN | PNEUMONIA VIRUS OF MICE | 93–120 | | | | | | | | |
| PNCAP_RABVA | NUCLEOCAPSID PROTEIN | RABIES VIRUS (STRAIN AVO1) | 133–167 | | | | | | | | |
| PNCAP_RABVP | NUCLEOCAPSID PROTEIN | RABIES VIRUS (STRAIN PV) | 133–167 | | | | | | | | |
| PNCAP_RABVS | NUCLEOCAPSID PROTEIN | RABIES VIRUS (STRAIN SAD B19) | 133–167 | | | | | | | | |
| PNCAP_SEND5 | NUCLEOCAPSID PROTEIN | SENDAI VIRUS (STRAIN Z/HOST MUTANTS) | 363–404 | | | | | | | | |
| PNCAP_SENDE | NUCLEOCAPSID PROTEIN | SENDAI VIRUS (STRAIN ENDERS) | 363–404 | | | | | | | | |
| PNCAP_SENDZ | NUCLEOCAPSID PROTEIN | SENDAI VIRUS (STRAIN Z) | 363–404 | | | | | | | | |
| PNCAP_SFSV | NUCLEOCAPSID PROTEIN | SANDFLY FEVER SICILIAN VIRUS | 4–31 | | | | | | | | |
| PNCAP_SV41 | NUCLEOCAPSID PROTEIN | SIMIAN VIRUS 41 | 507–534 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PNCAP_TACV | NUCLEOCAPSID PROTEIN | TACARIBE VIRUS | 50–77 | | | | | | | | |
| PNCAP_TOSV | NUCLEOCAPSID PROTEIN | TOSCANA VIRUS | 6–33 | | | | | | | | |
| PNCAP_UUK | NUCLEOCAPSID PROTEIN | UUKUNIEMI VIRUS | 68–102 | | | | | | | | |
| PNCAP_VHSV0 | NUCLEOCAPSID PROTEIN |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PNRAM_IARUE | NEURAMINIDASE | INFLUENZA A VIRUS (STRAIN A/RUDDY TURNSTONE/NEW JERSEY/60/85) | 49–88 | | | | | | | | |
| PNRAM_IATRA | NEURAMINIDASE | INFLUENZA A VIRUS (STRAIN A/TERN/AUSTRALIA/G70C/75) | 49–82 | | | | | | | | |
| PNRAM_IAUSS | NEURAMINIDASE | INFLUENZA A VIRUS (STRAIN A/USSR/90/77) | 50–81 | | | | | | | | |
| PNRAM_IAWHM | NEURAMINIDASE | INFLUENZA A VIRUS (STRAIN A/WHALE/MAINE/1/84) | 49–88 | | | | | | | | |
| PNRAM_IAWIL | NEURAMINIDASE | INFLUENZA A VIRUS (STRAIN A/WILSON-SMITH/33) | 16–43 | | | | | | | | |
| PNRAM_INBLE | NEURAMINIDASE | INFLUENZA B VIRUS (STRAIN B/LEE/40) | 4–35 | | | | | | | | |
| PNS1_SIDEV | PROB NONSTRUC PRO PRECURSOR | BOMBYX DENSONUCLEOSIS VIRUS | 283–310 | | | | | | | | |
| PNS2_SIDEV | PROB NONSTRUC PRO PRECURSOR | BOMBYX DENSONUCLEOSIS VIRUS | 42–69 | | | | | | | | |
| PNSS_INSVN | NON-STRUCTURAL PROTEIN | IMPATIENS NECROTIC SPOT VIRUS (STRAIN NL-07) | 95–122 | | | | | | | | |
| PNSS_TSWVB | NON-STRUCTURAL PROTEIN | TOMATO SPOTTED WILT VIRUS (BRAZILIAN ISOLATE CPNH1/BR-01) | 5–32 | 432–462 | | | | | | | |
| PNSS_TSWVL | NON-STRUCTURAL PROTEIN | TOMATO SPOTTED WILT VIRUS (STRAIN L3) | 5–32 | | | | | | | | |
| PNTP1_AMEPV | NUCLEOSIDE TRIPHOS-PHATASE I | AMSACTA MOOREI ENTOMOPOXVIRUS | 28–69 | | | | | | | | |
| PNTP1_CBEPV | NUCLEOSIDE TRIPHOS-PHATASE I | CHORISTONEURA BIENNIS ENTOMOPOXVIRUS | 122–166 | 347–374 | 524–551 | | | | | | |
| PNTP1_VACCC | NUCLEOSIDE TRIPHOS-PHATASE I | VACCINIA VIRUS (STRAIN COPENHAGEN) | 65–92 | 394–421 | 514–587 | | | | | | |
| PNTP1_VACCV | NUCLEOSIDE TRIPHOS-PHATASE I | VACCINIA VIRUS (STRAIN WR) | 65–92 | 394–421 | 514–587 | | | | | | |
| PNTP1_VARV | NUCLEOSIDE TRIPHOS-PHATASE I | VARIOLA VIRUS | 300–327 | 420–447 | 455–493 | | | | | | |
| PP100_HSV6U | MAJOR ANTIGENIC STRUCTL PROTEIN | HERPES SIMPLEX VIRUS (TYPE 6/STRAIN UGANDA-1102) | 81–108 | 189–216 | 688–715 | 785–812 | | | | | |
| PPAP1_VACCC | POLY(A) POL CATALYTIC SUBUNIT | VACCINIA VIRUS (STRAIN COPENHAGEN) | 88–115 | | | | | | | | |
| PPAP1_VACCV | POLY(A) POL CATALYTIC SUBUNIT | VACCINIA VIRUS (STRAIN WR) | 88–115 | | | | | | | | |
| PPAP1_VARV | POLY(A) POL CATALYTIC SUBUNIT | VARIOLA VIRUS | 88–115 | | | | | | | | |
| PPAP2_CAPVK | POLY(A) POL REG SUBUNIT | CAPRIPOXVIRUS (STRAIN KS-1) | 118–145 | | | | | | | | |
| PPAP2_FOWPV | POLY(A) POL REG SUBUNIT | FOWLPOX VIRUS | 27–54 | | | | | | | | |
| PPE12_NPVAC | 12.1 KD PROTEIN IN PE 5REGION | AUTOGRAPHA CALIFORNICA NUCLEAR POLYHEDROSIS VIRUS | 61–105 | | | | | | | | |
| PPE12_NPVOP | 11.5 KD PROTEIN IN P26 5REGION | ORGYIA PSEUDOTSUGATA MULTICAPSID POLYHEDROSIS VIRUS | 61–95 | | | | | | | | |
| PPE38_NPVAC | MAJOR IMMEDIATE EARLY PROTEIN | AUTOGRAPHA CALIFORNICA NUCLEAR POLYHEDROSIS VIRUS | 204–248 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPE48_NPVAC | 48.3 KD IN PE-P26 INTERGENIC REGION | AUTOGRAPHA CALIFORNICA NUCLEAR POLYHEDROSIS VIRUS | 4–38 | 51–78 | | | | | | | |
| PPEN3_ADEGX | PENTON PROTEIN | AVIAN ADENOVIRUS GAL10 (STRAIN SA2) | 96–123 | | | | | | | | |
| PPOL1_BAYMG | GENOME POLYPROTEIN 1 | BARLEY YELLOW MOSAIC VIRUS (GERMAN ISOLATE) | 1272–1299 | 1775–1802 | 2236–2263 | | | | | | |
| PPOL1_BAYMJ | GENOME POLYPROTEIN 1 | BARLEY YELLOW MOSAIC VIRUS (JAPANESE STRAIN II-1) | 1774–1801 | 2234–2261 | | | | | | | |
| PPOL1_GCMV | RNA1 POLYPROTEIN | HUNGARIAN GRAPEVINE CHROME MOSAIC VIRUS | 481–508 | 1909–1941 | | | | | | | |
| PPOL1_GFLV | RNA1 POLYPROTEIN | GRAPEVINE FANLEAF VIRUS | 170–197 | 636–677 | 958–985 | 1161–1195 | | | | | |
| PPOL1_TBRVS | RNA1 POLYPROTEIN | TOMATO BLACK RING VIRUS (STRAIN S) | 1096–1123 | | | | | | | | |
| PPOL2_BAYMG | GENOME POLYPROTEIN 2 | BARLEY YELLOW MOSAIC VIRUS (GERMAN ISOLATE) | 240–281 | 801–828 | | | | | | | |
| PPOL2_BAYMJ | GENOME POLYPROTEIN 2 | BARLEY YELLOW MOSAIC VIRUS (JAPANESE STRAIN II-1) | 240–267 | 801–828 | | | | | | | |
| PPOL2_GCMV | RNA2 POLYPROTEIN | HUNGARIAN GRAPEVINE CHROME MOSAIC VIRUS | 11–38 | | | | | | | | |
| PPOL2_GFLV | RNA2 POLYPROTEIN | GRAPEVINE FANLEAF VIRUS | 549–576 | | | | | | | | |
| PPOL2_TRSVR | RNA2 POLYPROTEIN | TOMATO RINGSPOT VIRUS (ISOLATE RASPBERRY) | 982–1009 | | | | | | | | |
| PPOLG_BOVEV | GENOME POLYPROTEIN | BOVINE ENTEROVIRUS (STRAIN VG-5-27) | 17–44 | 1030–1057 | 1145–1172 | | | | | | |
| PPOLG_BVDVN | GENOME POLYPROTEIN | BOVINE VIRAL DIARRHEA VIRUS (ISOLATE NADL) | 629–660 | 1082–1112 | 1303–1330 | 2233–2261 | 2476–2503 | 2609–2636 | 3613–3642 | | |
| PPOLG_BVDVS | GENOME POLYPROTEIN | BOVINE VIRAL DIARRHEA VIRUS (STRAIN SD-1) | 1303–1333 | 2143–2171 | 2519–2546 | 2802–2829 | 3523–3550 | | | | |
| PPOLG_BYMV | GENOME POLYPROTEIN | BEAN YELLOW MOSAIC VIRUS | 96–123 | | | | | | | | |
| PPOLG_COXA2 | GENOME POLYPROTEIN | COXSACKIEVIRUS A21 (STRAIN COE) | 7–43 | 664–694 | 1062–1099 | 1900–1930 | | | | | |
| PPOLG_COXA9 | GENOME POLYPROTEIN | COXSACKIEVIRUS A9 (STRAIN GRIGGS) | 1040–1076 | | | | | | | | |
| PPOLG_COXB1 | GENOME POLYPROTEIN | COXSACKIEVIRUS B1 | 645–672 | 841–868 | 1021–1057 | | | | | | |
| PPOLG_COXB3 | GENOME POLYPROTEIN | COXSACKIEVIRUS B3 | 1024–1060 | 1881–1908 | | | | | | | |
| PPOLG_COXB4 | GENOME POLYPROTEIN | COXSACKIEVIRUS B4 | 644–673 | 1022–1058 | | | | | | | |
| PPOLG_COXB5 | GENOME POLYPROTEIN | COXSACKIEVIRUS B5 | 1024–1060 | | | | | | | | |
| PPOLG_CYVV | GENOME POLYPROTEIN | CLOVER YELLOW VEIN VIRUS | 120–154 | | | | | | | | |
| PPOLG_DEN1S | GENOME POLYPROTEIN | DENGUE VIRUS TYPE 1 (STRAIN SINGAPORE S275/90) | 1858–1885 | 2890–2935 | 2989–3016 | | | | | | |
| PPOLG_DEN26 | GENOME POLYPROTEIN | DENGUE VIRUS TYPE 2 (STRAIN 16681) | 1544–1571 | 1858–1885 | 2908–2935 | 2982–3016 | 3117–3147 | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLG_DEN27 | GENOME POLYPROTEIN | DENGUE VIRUS TYPE 2 (STRAIN 16681-PDK53) | 1544–1571 | 1858–1885 | 2485–2519 | 2908–2935 | 2982–3016 | 3117–3147 | | | |
| PPOLG_DEN2J | GENOME POLYPROTEIN | DENGUE VIRUS TYPE 2 (STRAIN JAMAICA) | 1544–1571 | 1858–1885 | 2908–2935 | 3117–3147 | 3346–3373 | | | | |
| PPOLG_DEN2P | GENOME POLYPROTEIN | DENGUE VIRUS TYPE 2 (STRAIN PR159/S1) | 1544–1571 | 2905–1885 | 2979–2932 | 3114–3013 | 3343–3144 | 3370 | | | |
| PPOLG_DEN2T | GENOME POLYPROTEIN | DENGUE VIRUS TYPE 2 (STRAIN TONGA 1974) | 1134–1161 | 1448–1475 | | | | | | | |
| PPOLG_DEN3 | GENOME POLYPROTEIN | DENGUE VIRUS TYPE 3 | 837–864 | 1542–1569 | 1857–1884 | 2494–2521 | 2980–3014 | 3345–3372 | | | |
| PPOLG_DEN4 | GENOME POLYPROTEIN | DENGUE VIRUS TYPE 4 | 2885–2930 | 2977–3011 | 3342–3369 | | | | | | |
| PPOLG_EC11G | GENOME POLYPROTEIN | ECHOVIRUS 11 (STRAIN GREGORY) | 213–249 | | | | | | | | |
| PPOLG_EMCV | GENOME POLYPROTEIN | ENCEPHALOMYOCARDITIS VIRUS | 70–108 | 1484–1518 | 1522–1563 | | | | | | |
| PPOLG_EMCVB | GENOME POLYPROTEIN | ENCEPHALOMYOCARDITIS VIRUS (STRAIN EMC-B NONDIABETOGENIC) | 70–97 | 1486–1520 | 1524–1565 | | | | | | |
| PPOLG_EMCVD | GENOME POLYPROTEIN | ENCEPHALOMYOCARDITIS VIRUS (STRAIN EMC-D DIABETOGENIC) | 70–97 | 1486–1520 | 1524–1565 | | | | | | |
| PPOLG_ENMG3 | GENOME POLYPROTEIN | MENGO ENCEPHALOMYOCARDITIS VIRUS (STRAIN 37A) | 70–108 | | | | | | | | |
| PPOLG_ENMGO | GENOME POLYPROTEIN | MENGO ENCEPHALOMYOCARDITIS VIRUS | 3–41 | | | | | | | | |
| PPOLG_FMDV1 | GENOME POLYPROTEIN | FOOT-AND-MOUTH DISEASE VIRUS (STRAIN A10–61) | 302–329 | 1119–1146 | | | | | | | |
| PPOLG_FMDVA | GENOME POLYPROTEIN | FOOT-AND-MOUTH DISEASE VIRUS (STRAIN A12) | 301–328 | 1119–1146 | | | | | | | |
| PPOLG_FMDVO | GENOME POLYPROTEIN | FOOT-AND-MOUTH DISEASE VIRUS (STRAINS O1K AND O1BFS) | 1119–1146 | | | | | | | | |
| PPOLG_FMDVS | GENOME POLYPROTEIN | FOOT-AND-MOUTH DISEASE VIRUS (STRAIN C1-SANTA PAU [C-58]) | 101–128 | | | | | | | | |
| PPOLG_HCV1 | GENOME POLYPROTEIN | HEPATITIS C VIRUS (ISOLATE 1) | 702–729 | | | | | | | | |
| PPOLG_HCVA | GENOME POLYPROTEIN | HOG CHOLERA VIRUS (STRAIN ALFORT) | 699–726 | 1195–1232 | 1303–1333 | 1434–1461 | 3068–3095 | 3406–3440 | | | |
| PPOLG_HCVB | GENOME POLYPROTEIN | HOG CHOLERA VIRUS (STRAIN BRESCIA) | 699–726 | 1195–1232 | 3068–3095 | 3406–3440 | 3532–3559 | | | | |
| PPOLG_HCVBK | GENOME POLYPROTEIN | HEPATITIS C VIRUS (ISOLATE BK) | 702–729 | 1045–1072 | | | | | | | |
| PPOLG_HCVH | GENOME POLYPROTEIN | HEPATITIS C VIRUS (ISOLATE H) | 702–729 | 1045–1072 | | | | | | | |
| PPOLG_HCVJ6 | GENOME POLYPROTEIN | HEPATITIS C VIRUS (ISOLATE HC-J6) | 374–401 | 2089–2116 | | | | | | | |
| PPOLG_HCVJ8 | GENOME POLYPROTEIN | HEPATITIS C VIRUS (ISOLATE HC-J8) | 1049–1076 | 2089–2116 | | | | | | | |
| PPOLG_HCVJA | GENOME POLYPROTEIN | HEPATITIS C VIRUS (ISOLATE JAPANESE) | 378–405 | 702–729 | 1045–1072 | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLG_HCVJT | GENOME POLYPROTEIN | HEPATITIS C VIRUS (ISOLATE HC-JT) | 702–729 | 1045–1072 | | | | | | | |
| PPOLG_HCVTW | GENOME POLYPROTEIN | HEPATITIS C VIRUS (ISOLATE TAIWAN) | 702–729 | 1045–1072 | | | | | | | |
| PPOLG_HPAV2 | GENOME POLYPROTEIN | HEPATITIS A VIRUS (STRAIN 24A) | 203–237 | 1021–1048 | 1117–1149 | 1454–1481 | | | | | |
| PPOLG_HPAV4 | GENOME POLYPROTEIN | HEPATITIS A VIRUS (STRAIN 43C) | 203–237 | 1021–1048 | 1117–1149 | 1454–1481 | | | | | |
| PPOLG_HPAV8 | GENOME POLYPROTEIN | HEPATITIS A VIRUS (STRAIN 18F) | 203–237 | 1021–1048 | 1117–1149 | 1454–1481 | | | | | |
| PPOLG_HPAVC | GENOME POLYPROTEIN | HEPATITIS A VIRUS (STRAIN CR326) | 203–237 | | | | | | | | |
| PPOLG_HPAVG | GENOME POLYPROTEIN | HEPATITIS A VIRUS (STRAIN GA76) | 182–216 | | | | | | | | |
| PPOLG_HPAVH | GENOME POLYPROTEIN | HEPATITIS A VIRUS (STRAIN HM-175) | 203–237 | 1021–1048 | 1103–1149 | | | | | | |
| PPOLG_HPAVL | GENOME POLYPROTEIN | HEPATITIS A VIRUS (STRAIN LA) | 203–237 | 1021–1048 | 1103–1149 | | | | | | |
| PPOLG_HPAVM | GENOME POLYPROTEIN | HEPATITIS A VIRUS (STRAIN MBB) | 203–237 | 1021–1048 | 1103–1149 | | | | | | |
| PPOLG_HPAVS | GENOME POLYPROTEIN | SIMIAN HEPATITIS A VIRUS (STRAIN AGM-27) | 207–241 | 1025–1052 | 1115–1192 | | | | | | |
| PPOLG_HPAVT | GENOME POLYPROTEIN | SIMIAN HEPATITIS A VIRUS (STRAIN CY-145) | 203–237 | | | | | | | | |
| PPOLG_HRV14 | GENOME POLYPROTEIN | HUMAN RHINOVIRUS 14 | 17–44 | 559–586 | 652–679 | 1877–1904 | | | | | |
| PPOLG_HRV1B | GENOME POLYPROTEIN | HUMAN RHINOVIRUS 1B | 1132–1159 | 1855–1882 | | | | | | | |
| PPOLG_HRV2 | GENOME POLYPROTEIN | HUMAN RHINOVIRUS 2 | 1125–1152 | 1552–1593 | | | | | | | |
| PPOLG_HRV89 | GENOME POLYPROTEIN | HUMAN RHINOVIRUS 89 | 883–910 | 1141–1168 | 1566–1607 | 1862–1889 | | | | | |
| PPOLG_HUEV7 | GENOME POLYPROTEIN | HUMAN ENTEROVIRUS 70 (STRAIN J670/71) | 876–910 | | | | | | | | |
| PPOLG_IBDVO | STRUCTURAL POLYPROTEIN | AVIAN INFECTIOUS BURSAL DISEASE VIRUS (STRAIN OH) | 231–277 | | | | | | | | |
| PPOLG_JAEV1 | GENOME POLYPROTEIN | JAPANESE ENCEPHALITIS VIRUS (STRAIN SA-14) | 214–248 | 983–1010 | 2796–2823 | | | | | | |
| PPOLG_JAEV5 | GENOME POLYPROTEIN | JAPANESE ENCEPHALITIS VIRUS (STRAIN SA(V)) | 214–248 | 983–1010 | 2796–2823 | | | | | | |
| PPOLG_JAEVJ | GENOME POLYPROTEIN | JAPANESE ENCEPHALITIS VIRUS (STRAIN JAOARS982) | 214–248 | 983–1010 | 2796–2823 | | | | | | |
| PPOLG_JAEVN | GENOME POLYPROTEIN | JAPANESE ENCEPHALAITS VIRUS (STRAIN NAKAYAMA) | 141–175 | 911–938 | | | | | | | |
| PPOLG_KUNJM | GENOME POLYPROTEIN | KUNJIN VIRUS (STRAIN MRM61C) | 980–1007 | | | | | | | | |
| PPOLG_LANVT | GENOME POLYPROTEIN | LANGAT VIRUS (STRAIN TP21) | 431–465 | 1634–1661 | | | | | | | |
| PPOLG_LANVY | GENOME POLYPROTEIN | LANGAT VIRUS (STRAIN YELANTSEV) | 431–465 | | | | | | | | |
| PPOLG_LIV | GENOME POLYPROTEIN | LOUPING ILL VIRUS | 431–465 | | | | | | | | |
| PPOLG_LIVSB | GENOME POLYPROTEIN | LOUPING ILL VIRUS (STRAIN SB 526) | 151–185 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLG_MCFA | GENOME POLYPROTEIN | MOSQUITO CELL FUSING AGENT | 671–698 | 3056–3083 | 3303–3330 | | | | | | |
| PPOLG_MDMV | GENOME POLYPROTEIN | MAIZE DWARF MOSAIC VIRUS | 10–37 | | | | | | | | |
| PPOLG_MVEV | GENOME POLYPROTEIN | MURRAY VALLEY ENCEPHALITIS VIRUS | 212–256 | | | | | | | | |
| PPOLG_OMV | GENOME POLYPROTEIN | ORNITHOGALUM MOSAIC VIRUS | 24–51 | 946–973 | | | | | | | |
| PPOLG_PEMVC | GENOME POLYPROTEIN | PEPPER MOTTLE VIRUS (CALIFORNIA ISOLATE) | 377–404 | 704–738 | 831–858 | 900–927 | 1167–1201 | | | | |
| PPOLG_POL1M | GENOME POLYPROTEIN | POLIOVIRUS TYPE 1 (STRAIN MAHONEY) | 1060–1100 | 1901–1931 | | | | | | | |
| PPOLG_POL1S | GENOME POLYPROTEIN | POLIOVIRUS TYPE 1 (STRAIN SABIN) | 670–697 | 1063–1101 | 1903–1933 | | | | | | |
| PPOLG_POL2L | GENOME POLYPROTEIN | POLIOVIRUS TYPE 2 (STRAIN LANSING) | 1061–1099 | 1901–1931 | | | | | | | |
| PPOLG_POL2W | GENOME POLYPROTEIN | POLIOVIRUS TYPE 2 (STRAIN W-2) | 1061–1099 | 1901–1931 | | | | | | | |
| PPOLG_POL32 | GENOME POLYPROTEIN | POLIOVIRUS TYPE 3 (STRAIN 23127) | 1060–1098 | 1900–1930 | | | | | | | |
| PPOLG_POL3L | GENOME POLYPROTEIN | POLIOVIRUS TYPE 3 (STRAINS P3/LEON/37 AND P3/LEON 12A[1]B) | 1060–1098 | 1900–1930 | | | | | | | |
| PPOLG_PVD | GENOME POLYPROTEIN | PLUM POX POTYVIRUS (STRAIN D) | 921–948 | 1498–1525 | 2771–2798 | | | | | | |
| PPOLG_PPVEA | GENOME POLYPROTEIN | PLUM POX POTYVIRUS (STRAIN EL AMAR) | 1146–1187 | | | | | | | | |
| PPOLG_PPVNA | GENOME POLYPROTEIN | PLUM POX POTYVIRUS (ISOLATE NAT) | 920–947 | 1497–1524 | 2770–2800 | | | | | | |
| PPOLG_PPVRA | GENOME POLYPROTEIN | PLUM POX POTYVIRUS (STRAIN RANKOVIC) | 920–947 | 1497–1524 | 2770–2797 | | | | | | |
| PPOLG_PRSVH | GENOME POLYPROTEIN | PAPAYA RINGSPOT VIRUS (STRAIN P/MUTANT HA) | 500–527 | | | | | | | | |
| PPOLG_PRSVP | GENOME POLYPROTEIN | PAPAYA RINGSPOT VIRUS (STRAIN P/MUTANT HA 5-1) | 391–418 | | | | | | | | |
| PPOLG_PRSVW | GENOME POLYPROTEIN | PAPAYA RINGSPOT VIRUS (STRAIN W) | 489–516 | | | | | | | | |
| PPOLG_PSBMV | GENOME POLYPROTEIN | PEA SEED-BORNE MOSAIC VIRUS (STRAIN DPD1) | 271–315 | 1132–1177 | 1510–1537 | | | | | | |
| PPOLG_PVYC | GENOME POLYPROTEIN | POTATO VIRUS Y (STRAIN C) (PVY) | 433–460 | 701–735 | | | | | | | |
| PPOLG_PVYHU | GENOME POLYPROTEIN | POTATO VIRUS Y (STRAIN HUNGARIAN) | 218–245 | 433–460 | 701–735 | 1486–1513 | 1777–1811 | | | | |
| PPOLG_PVYN | GENOME POLYPROTEIN | POTATA VIRUS Y (STRAIN N) | 433–460 | 701–735 | 1486–1513 | 1777–1811 | | | | | |
| PPOLG_PVYO | GENOME POLYPROTEIN | POTATO VIRUS Y (STRAIN O) | 433–460 | 701–735 | | | | | | | |
| PPOLG_PYFV1 | GENOME POLYPROTEIN | PARSNIP YELLOW FLECK VIRUS (ISOLATE P-121) | 1124–1151 | 2707–2734 | | | | 1485–1512 | 1787–1814 | 2433–2464 | |
| PPOLG_SUMVS | GENOME POLYPROTEIN | SUGARCANE MOSAIC VIRUS (STRAIN SC) | 10–37 | | | | | | | | |
| PPOLG_SVDVH | GENOME POLYPROTEIN | SWINE VESICULAR DISEASE VIRUS (STRAIN H/3 '76) | 1024–1060 | | | | | | | | |
| PPOLG_SVDVU | GENOME POLYPROTEIN | 1024–1060 | 1024–1060 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLG_TBEVS | GENOME POLYPROTEIN | TICK-BORNE ENCEPHALITIS VIRUS (STRAIN SOFJIN) | 87–121 | 234–272 | 1632–1661 | 2265–2292 | 2909–2936 | | | | |
| PPOLG_TBEVW | GENOME POLYPROTEIN | BORNE ENCEPHALATIS VIRUS (WESTERN SUBTYPE) | 1632–1659 | | | | | | | | |
| PPOLG_TEV | GENOME POLYPROTEIN | TOBACCO ETCH VIRUS | 845–872 | 1148–1175 | 1416–1443 | 1773–1800 | | | | | |
| PPOLG_TMEVB | GENOME POLYPROTEIN | THEILER'S MURINE ENCEPHALOMYELITIS VIRUS (STRAIN BEAN 8386) | 79–117 | 200–227 | | | | | | | |
| PPOLG_TMEVD | GENOME POLYPROTEIN | THEILER'S MURINE ENCEPHALOMYELITIS VIRUS (STRAIN DA) | 90–117 | 200–227 | | | | | | | |
| PPOLG_TMEVG | GENOME POLYPROTEIN | THEILER'S MURINE ENCEPHALOMYELITIS VIRUS (STRAIN GDVII) | 90–117 | 200–227 | | | | | | | |
| PPOLG_TUMV | GENOME POLYPROTEIN | TURNIP MOSAIC VIRUS | 232–262 | 773–800 | | | | | | | |
| PPOLG_TVMV | GENOME POLYPROTEIN | TOBACCO VEIN MOTTLING VIRUS | 406–433 | 670–704 | 2708–2742 | | | | | | |
| PPOLG_WMV2 | GENOME POLYPROTEIN | WATERMELON MOSAIC VIRUS II | 202–229 | | | | | | | | |
| PPOLG_WNV | GENOME POLYPROTEIN | WEST NILE VIRUS | 210–254 | 3385–3412 | | | | | | | |
| PPOLG_YEFV1 | GENOME POLYPROTEIN | YELLOW FEVER VIRUS (STRAIN 17D) | 436–463 | | | | | | | | |
| PPOLG_YEFV2 | GENOME POLYPROTEIN | YELLOW FEVER VIRUS (STRAIN PASTEUR 17D-204) | 436–463 | | | | | | | | |
| PPOLG_ZYMV | GENOME POLYPROTEIN | ZUCCHINI YELLOW MOSAIC VIRUS | 69–96 | | | | | | | | |
| PPOLH_POL1M | GENOME POLYPROTEIN | POLIOVIRUS TYPE 1 (STRAIN MAHONEY) | 1063–1101 | 1903–1933 | | | | | | | |
| PPOLN_EEVVT | NONSTRUCTURAL POLYPROTEIN | VENEZUELAN EQUINE ENCEPHALITIS VIRUS (STRAIN TRINIDAD DONKEY) | 1402–1467 | 1894–1921 | | | | | | | |
| PPOLN_FCVC6 | NON-STRUCTURAL POLYPROTEIN | FELINE CALICIVIRUS (STRAIN CFI/68 FIV) | 445–472 | | | | | | | | |
| PPOLN_FCVF9 | NON-STRUCTURAL POLYPROTEIN | FELINE CALICIVIRUS (STRAIN F9) | 1034–1061 | | | | | | | | |
| PPOLN_HEVBU | NON-STRUCTURAL POLYPROTEIN | HEPATITIS E VIRUS (STRAIN BURMA) | 219–246 | 349–376 | | | | | | | |
| PPOLN_HEVME | NON-STRUCTURAL POLYPROTEIN | HEPATITIS E VIRUS (STRAIN MEXICO) | 219–246 | 349–376 | | | | | | | |
| PPOLN_HEVMY | N-STRUCTURAL POLYPROTEIN | HEPATITIS E VIRUS (STRAIN MYANMAR) | 219–246 | 349–376 | | | | | | | |
| PPOLN_HEVPA | NON-STRUCTURAL POLYPROTEIN | HEPATITIS E VIRUS (STRAIN PAKISTAN) | 218–245 | 348–375 | | | | | | | |
| PPOLN_MIDDV | NONSTRUCTURAL POLYPROTEIN | MIDDELBURG VIRUS | 955–982 | | | | | | | | |
| PPOLN_ONNVG | NONSTRUCTURAL POLYPROTEIN | O'NYONG-NYONG VIRUS (STRAIN GULU) | 2453–2480 | | | | | | | | |
| PPOLN_RHDV | NON-STRUCTURAL POLYPROTEIN | RABBIT HEMORRHAGIC DISEASE VIRUS | 313–347 | 1657–1684 | | | | | | | |
| PPOLN_RRVN | NONSTRUCTURAL POLYPROTEIN | ROSS RIVER VIRUS (STRAIN NB5092) | 1057–1084 | 1477–1504 | 2418–2445 | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLN_RRVT | NONSTRUCTURAL POLYPROTEIN | ROSS RIVER VIRUS (STRAIN T48) | 146–173 | 1087–1114 | | | | | | | |
| PPOLN_RUBVT | NONSTRUCTURAL POLYPROTEIN | RUBELLA VIRUS (STRAIN THERIEN) | 2060–2087 | | | | | | | | |
| PPOLN_SFV | NONSTRUCTURAL POLYPROTEIN | SEMLIKI FOREST VIRUS | 1154–1181 | | | | | | | | |
| PPOLN_SINDO | NONSTRUCTURAL POLYPROTEIN | SINDBIS VIRUS (SUBTYPE OCKELBO/STRAIN EDSBYN 82-5) | 936–970 | | | | | | | | |
| PPOLN_WEEV | NONSTRUCTURAL POLYPROTEIN | WESTERN EQUINE ENCEPHALITIS VIRUS | 4–31 | | | | | | | | |
| PPOLS_IBDV5 | STRUCTURAL POLYPROTEIN | AVIAN INFECTIOUS BURSAL DISEASE VIRUS (STRAIN 52/70) | 231–258 | | | | | | | | |
| PPOLS_IBDVA | STRUCTURAL POLYPROTEIN | AVIAN INFECTIOUS BURSAL DISEASE VIRUS (STRAIN AUSTRALIAN 002-73) | 231–258 | | | | | | | | |
| PPOLS_IBDVC | STRUCTURAL POLYPROTEIN | AVIAN INFECTIOUS BURSAL DISEASE VIRUS (STRAIN CU-1) | 231–258 | | | | | | | | |
| PPOLS_IBDVE | STRUCTURAL POLYPROTEIN | AVIAN INFECTIOUS BURSAL DISEASE VIRUS (STRAIN E) | 231–258 | | | | | | | | |
| PPOLS_IBDVP | STRUCTURAL POLYPROTEIN | AVIAN INFECTIOUS BURSAL DISEASE VIRUS (STRAIN PBG-98) | 212–239 | | | | | | | | |
| PPOLS_IBDVS | STRUCTURAL POLYPROTEIN | AVIAN INFECTIOUS BURSAL DISEASE VIRUS (STRAIN STC) | 231–258 | | | | | | | | |
| PPOLS_ONNVG | STRUCTURAL POLYPROTEIN | O'NYONG-NYONG VIRUS (STRAIN GULU) | 356–383 | | | | | | | | |
| PPOLS_RRVN | STRUCTURAL POLYPROTEIN | ROSS RIVER VIRUS (STRAIN NB5092) | 939–973 | | | | | | | | |
| PPOLS_RRVT | STRUCTURAL POLYPROTEIN | ROSS RIVER VIRUS (STRAIN T48) | 939–973 | | | | | | | | |
| PPOLS_SINDO | STRUCTURAL POLYPROTEIN | SINDBIS VIRUS (SUBTYPE OCKELBO/STRAIN EDSBYN 82-5) | 1138–1165 | | | | | | | | |
| PPOLS_SINDV | STRUCTURAL POLYPROTEIN | SINDBIS VIRUS (STRAINS HRSP AND HRLP) | 1138–1165 | | | | | | | | |
| PPOLS_WEEV | STRUCTURAL POLYPROTEIN | WESTERN EQUINE ENCEPHALITIS VIRUS | 920–947 | | | | | | | | |
| PPOL_BAEVM | POL POLYPROTEIN | BABOON ENDOGENOUS VIRUS (STRAIN M7) | 675–706 | 715–742 | | | | | | | |
| PPOL_CAEVC | POL POLYPROTEIN | CAPRINE ARTHRITIS ENCEPHALITIS VIRUS (STRAIN CORK) | 886–924 | | | | | | | | |
| PPOL_COYMV | PUTATIVE POLYPROTEIN | COMMELINA YELLOW MOTTLE VIRUS | 333–360 | 838–865 | 1075–1102 | 1178–1205 | 1313–1347 | | | | |
| PPOL_EIAV9 | POL POLYPROTEIN | EQUINE INFECTIOUS ANEMIA VIRUS (CLONE 1369) | 472–505 | 826–853 | | | | | | | |
| PPOL_EIAVC | POL POLYPROTEIN | EQUINE INFECTIOUS ANEMIA VIRUS (CLONE CL22) | 472–505 | 826–853 | | | | | | | |
| PPOL_EIAVY | POL POLYPROTEIN | EQUINE INFECTIOUS ANEMIA VIRUS (ISOLATE WYOMING) | 471–504 | 825–852 | | | | | | | |
| PPOL_FENV1 | POL POLYPROTEIN | FELINE ENDOGENOUS VIRUS ECE1 | 532–599 | 627–654 | | | | | | | |
| PPOL_FIVPE | POL POLYPROTEIN | FELINE IMMUNODEFICIENCY VIRUS (ISOLATE PETALUMA) | 442–473 | | | | | | | | |
| PPOL_FMVD | ENZYMATIC POLYPROTEIN | FIGWORT MOSAIC VIRUS (STRAIN DXS) | 403–430 | | | | | | | | |
| PPOL_GALV | POL POLYPROTEIN | GIBBON APE LEUKEMIA VIRUS | 535–562 | 676–703 | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOL_HTL1A | POL POLYPROTEIN | HUMAN T-CELL LEUKEMIA VIRUS TYPE 1 (STRAIN ATK) | 674–712 | | | | | | | | |
| PPOL_HTL1C | POL POLYPROTEIN | HUMAN T-CELL LEUKEMIA VIRUS TYPE 1 (CARIBBEAN ISOLATE) | 674–712 | | | | | | | | |
| PPOL_HV1A2 | POL POLYPROTEIN | HUMAN IMMUNODEFICIENCY VIRUS TYPE 1 (ARV2/SF2 ISOLATE) | 218–245 | 620–661 | | | | | | | |
| PPOL_HV1B1 | POL POLYPROTEIN | HUMAN IMMUNODEFICIENCY VIRUS TYPE 1 (BH10 ISOLATE) | 230–257 | 637–673 | | | | | | | |
| PPOL_HV1B5 | POL POLYPROTEIN | HUMAN IMMUNODEFICIENCY VIRUS TYPE 1 (BH5 ISOLATE) | 230–257 | 632–673 | | | | | | | |
| PPOL_HV1BR | POL POLYPROTEIN | HUMAN IMMUNODEFICIENCY VIRUS TYPE 1 (BRU ISOLATE) | 230–257 | 632–673 | | | | | | | |
| PPOL_HV1EL | POL POLYPROTEIN | HUMAN IMMUNODEFICIENCY VIRUS TYPE 1 (ELI ISOLATE) | 217–244 | 624–660 | | | | | | | |
| PPOL_HV1H2 | POL POLYPROTEIN | HUMAN IMMUNODEFICIENCY VIRUS TYPE 1 (HXB2 ISOLATE) | 218–245 | 620–661 | 921–951 | | | | | | |
| PPOL_HV1JR | POL POLYPROTEIN | HUMAN IMMUNODEFICIENCY VIRUS TYPE 1 (JRCSF ISOLATE) | 222–249 | 624–665 | | | | | | | |
| PPOL_HV1MA | POL POLYPROTEIN | HUMAN IMMUNODEFICIENCY VIRUS TYPE 1 (MAL ISOLATE) | 217–244 | 476–510 | 619–660 | | | | | | |
| PPOL_HV1MN | POL POLYPROTEIN | HUMAN IMMUNODEFICIENCY VIRUS TYPE 1 (MN ISOLATE) | 221–248 | 623–664 | | | | | | | |
| PPOL_HV1N5 | POL POLYPROTEIN | HUMAN IMMUNODEFICIENCY VIRUS TYPE 1 (NEW YORK-5 ISOLATE) | 218–245 | 625–661 | | | | | | | |
| PPOL_HV1ND | POL POLYPROTEIN | HUMAN IMMUNODEFICIENCY VIRUS TYPE 1 (NDK ISOLATE) | 217–244 | 624–660 | | | | | | | |
| PPOL_HV1OY | POL POLYPROTEIN | HUMAN IMMUNODEFICIENCY VIRUS TYPE 1 (OYI ISOLATE) | 218–245 | 620–661 | | | | | | | |
| PPOL_HV1PV | POL POLYPROTEIN | HUMAN IMMUNODEFICIENCY VIRUS TYPE 1 (PV22 ISOLATE) | 230–257 | 637–673 | | | | | | | |
| PPOL_HV1RH | POL POLYPROTEIN | HUMAN IMMUNODEFICIENCY VIRUS TYPE 1 (RF/HAT ISOLATE) | 217–244 | 619–660 | | | | | | | |
| PPOL_HV1U4 | POL POLYPROTEIN | HUMAN IMMUNODEFICIENCY VIRUS TYPE 1 (STRAIN UGANDAN/IOSLATE U | 217–244 | 613–540 | 619–660 | | | | | | |
| PPOL_HV1Z2 | POL POLYPROTEIN | HUMAN IMMUNODEFICIENCY VIRUS TYPE 1 (Z2/CDC-Z34 ISOLATE) | 217–244 | 619–660 | | | | | | | |
| PPOL_HV2BE | POL POLYPROTEIN | HUMAN IMMUNODEFICIENCY VIRUS TYPE 2 (ISOLATE BEN) | 491–582 | | | | | | | | |
| PPOL_HV2CA | POL POLYPROTEIN | HUMAN IMMUNODEFICIENCY VIRUS TYPE 2 (ISOLATE CAM2) | 471–562 | | | | | | | | |
| PPOL_HV2D1 | POL POLYPROTEIN | HUMAN IMMUNODEFICIENCY VIRUS TYPE 2 (ISOLATE D194) | 509–600 | | | | | | | | |
| PPOL_HV2D2 | POL POLYPROTEIN | HUMAN IMMUNODEFICIENCY VIRUS TYPE 2 (ISOLATE D205,7) | 491–568 | | | | | | | | |
| PPOL_HV2G1 | POL POLYPROTEIN | HUMAN IMMUNODEFICIENCY VIRUS TYPE 2 (ISOLATE GHANA-1) | 471–562 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOL_HV2NZ | POL POLYPROTEIN | HUMAN IMMUNODEFICIENCY VIRUS TYPE 2 (ISOLATE NIH-Z) | 471–529 | | | | | | | | |
| PPOL_HV2RO | POL POLYPROTEIN | HUMAN IMMUNODEFICIENCY VIRUS TYPE 2 (ISOLATE ROD) | 472–563 | | | | | | | | |
| PPOL_HV2SB | POL POLYPROTEIN | HUMAN IMMUNODEFICIENCY VIRUS TYPE 2 (ISOLATE SBL/SY) | 473–562 | | | | | | | | |
| PPOL_HV2ST | POL POLYPROTEIN | HUMAN IMMUNODEFICIENCY VIRUS TYPE 2 (ISOLATE ST) | 491–582 | | | | | | | | |
| PPOL_IPHA | PUTATIVE POL POLYPROTEIN | HAMSTER INTRACISTERNAL A-PARTICLE | 200–227 | 354–381 | 461–499 | | | | | | |
| PPOL_IPMA | PUTATIVE POL POLYPROTEIN | MOUSE INTRACISTERNAL A-PARTICLE | 211–238 | 302–329 | 400–427 | | | | | | |
| PPOL_IPMAI | PROBABLE POL POLYPROTEIN | MOUSE INTRACISTERNAL A-PARTICLE | 130–157 | 221–248 | | | | | | | |
| PPOL_JSRV | POL POLYPROTEIN | SHEEP PULMONARY ADENOMATOSIS VIRUS | 204–231 | | | | | | | | |
| PPOL_MLVAK | POL POLYPROTEIN | AKR MURINE LEUKEMIA VIRUS | 453–480 | | | | | | | | |
| PPOL_MLVAV | POL POLYPROTEIN | AKV MURINE LEUKEMIA VIRUS | 805–832 | | | | | | | | |
| PPOL_MLVRD | POL POLYPROTEIN | RADIATION MURINE LEUKEMIA VIRUS | 716–743 | 805–832 | | | | | | | |
| PPOL_MLVRK | POL POLYPROTEIN | RADIATION MURINE LEUKEMIA VIRUS (STRAIN KAPLAN) | 101–128 | 190–217 | | | | | | | |
| PPOL_MPMV | POL POLYPROTEIN | SIMIAN MASON-PFIZER VIRUS | 574–612 | 670–697 | | | | | | | |
| PPOL_OMVVS | POL POLYPROTEIN | OVINE LENTIVIRUS (STRAIN SA-OMVV) | 67–94 | 471–505 | 873–900 | | | | | | |
| PPOL_RSVP | POL POLYPROTEIN | ROUS SARCOMA VIRUS (STRAIN PRAGUE C) | 797–824 | | | | | | | | |
| PPOL_RTBV | POLYPROTEIN | RICE TUNGRO BACILLIFORM VIRUS | 7–44 | 59–93 | 176–203 | 202–229 | 410–437 | 447–476 | 1022–1049 | | |
| PPOL_RTBVP | POLYPROTEIN | RICE TUNGRO BACILLIFORM VIRUS (ISOLATE PHILIPPINES) | 7–44 | 59–93 | 176–203 | 202–229 | 410–437 | 447–476 | 1022–1049 | | |
| PPOL_SFV1 | POL POLYPROTEIN | SIMIAN FOAMY VIRUS (TYPE 1) | 427–454 | | | | | | | | |
| PPOL_SIVA1 | POL POLYPROTEIN | SIMIAN IMMUNODEFICIENCY VIRUS (AGM155 ISOLATE) | 431–458 | 547–574 | 637–671 | | | | | | |
| PPOL_SIVA2 | POL POLYPROTEIN | SIMIAN IMMUNODEFICIENCY VIRUS (AGM266 ISOLATE) | 45–72 | | | | | | | | |
| PPOL_SIVA3 | POL POLYPROTEIN | SIMIAN IMMUNODEFICIENCY VIRUS (AGM385 ISOLATE) | 71–98 | | | | | | | | |
| PPOL_SIVAG | POL POLYPROTEIN | SIMIAN IMMUNODEFICIENCY VIRUS (AGM3 ISOLATE) | 436–463 | 482–516 | 642–669 | | | | | | |
| PPOL_SIVAI | POL POLYPROTEIN | SIMIAN IMMUNODEFICIENCY VIRUS (ISOLATE AGM/CLONE GR1-1) | 478–515 | | | | | | | | |
| PPOL_SIVAT | POL POLYPROTEIN | SIMIAN IMMUNODEFICIENCY VIRUS (TYO-1 ISOLATE) | 657–691 | | | | | | | | |
| PPOL_SIVCZ | POL POLYPROTEIN | CHIMPANZEE IMMUNODEFICIENCY VIRUS (SIV(CPZ) | 242–269 | 626–685 | | | | | | | |
| PPOL_SIVGB | POL POLYPROTEIN | SIMIAN IMMUNODEFICIENCY VIRUS (ISOLATE GB1) | 227–254 | 636–670 | | | | | | | |
| PPOL_SIVM1 | POL POLYPROTEIN | SIMIAN IMMUNODEFICIENCY VIRUS (MM142-83 ISOLATE) | 533–560 | | | | | | | | |
| PPOL_SIVMK | POL POLYPROTEIN | SIMIAN IMMUNODEFICIENCY VIRUS (K6W ISOLATE) | 533–560 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOL_SIVS4 | POL POLYPROTEIN | SIMIAN IMMUNODEFICIENCY VIRUS (F236/SMH4 ISOLATE) | 496–523 | | | | | | | | |
| PPOL_SIVSP | POL POLYPROTEIN | SIMIAN IMMUNODEFICIENCY VIRUS (PBJ/BC13 ISOLATE) | 499–526 | | | | | | | | |
| PPOL_SMRVH | POL POLYPROTEIN | SQUIRREL MONKEY RETROVIRUS (SMRV-H) | 601–628 | | | | | | | | |
| PPOL_SOCMV | ENZYMATIC POLYPROTEIN | SOYBEAN CHLOROTIC MOTTLE VIRUS | 268–295 | 348–419 | | | | | | | |
| PPOL_SRV1 | POL POLYPROTEIN | SIMIAN RETROVIRUS SRV-1 | 578–612 | 670–697 | | | | | | | |
| PPOL_VILV | POL POLYPROTEIN | VISNA LENTIVIRUS (STRAIN 1514) | 490–524 | 881–919 | | | | | | | |
| PPOL_VILV1 | POL POLYPROTEIN | VISNA LENTIVIRUS (STRAIN 1514/CLONE LV1-1KS1) | 89–116 | 490–524 | | | | | | | |
| PPOL_VILV2 | POL POLYPROTEIN | VISNA LENTIVIRUS (STRAIN 1514/CLONE LV1-1KS2) | 490–524 | 881–919 | | | | | | | |
| PPR73_MMTVB | PROTEIN PR73 | MOUSE MAMMARY TUMOR VIRUS (STRAIN BR6) | 288–315 | | | | | | | | |
| PPR73_MMTVC | PROTEIN PR73 | MOUSE MAMMARY TUMOR VIRUS (STRAIN C3H) | 45–79 | | | | | | | | |
| PPR73_MMTVG | PROTEIN PR73 | MOUSE MAMMARY TUMOR VIRUS (STRAIN GR) | 167–201 | | | | | | | | |
| PPYHD_CPVBM | POLYHEDRIN PRECURSOR | BOMBYX MORI CYTOPLASMIC POLYHEDROSIS VIRUS | 37–71 | | | | | | | | |
| PPYHD_NPVAC | POLYHEDRIN | AUTOGRAPHA CALIFORNICA NUCLEAR POLYHEDROSIS VIRUS | 13–47 | | | | | | | | |
| PPYHD_NPVAS | POLYHEDRIN | AGROTIS SEGETUM NUCLEAR POLYHEDROSIS VIRUS | 14–48 | 201–228 | | | | | | | |
| PPYHD_NPVBM | POLYHEDRIN | BOMBYX MORI NUCLEAR POLYDEDROSIS VIRUS | 12–46 | | | | | | | | |
| PPYHD_NPVBS | POLYHEDRIN | BUZURA SUPPRESSARIA NUCLEAR POLYHEDROSIS VIRUS | 14–48 | | | | | | | | |
| PPYHD_NPVHC | POLYHEDRIN | HYPHANTRIA CUNEA NUCLEAR POLYHEDROSIS VIRUS | 13–40 | | | | | | | | |
| PPYHD_NPVLD | POLYHEDRIN | LYMANTRIA DISPAR MULTICAPSID NUCLEAR POLYHEDROSIS VIRUS | 14–48 | | | | | | | | |
| PPYHD_NPVMB | POLYHEDRIN | MAMESTRA BRASSICAE NUCLEAR POLYHEDROSIS VIRUS | 14–48 | | | | | | | | |
| PPYHD_NPVOP | POLYHEDRIN | ORGYIA PSEUDOTSUGATA MULTICAPSID POLYHEDROSIS VIRUS | 13–47 | | | | | | | | |
| PPYHD_NPVOS | POLYHEDRIN | ORGYIA PSEUDOTSUGATA SINGLE CAPSID NUCLEAR POLYHEDROSIS VIRUS | 14–48 | | | | | | | | |
| PPYHD_NPVPF | POLYHEDRIN | PANOLIS FLAMMEA MULTIPLE NUCLEOCAPSID POLYHEDROSIS VIRUS | 14–48 | | | | | | | | |
| PPYHD_NPVSE | POLYHEDRIN | SPODOPTERA EXIGUA NUCLEAR POLYHEDROSIS VIRUS (STRAIN US) | 14–48 | | | | | | | | |
| PPYHD_NPVSF | POLYHEDRIN | SPODOPTERA FRUGIPERDA NUCLEAR POLYHEDROSIS VIRUS | 14–48 | | | | | | | | |
| PREV_SIVAT | REV PROTEIN | SIMIAN IMMUNODEFICIENCY VIRUS (TYO-1 ISOLATE) | 41–68 | | | | | | | | |
| PREV_VILV | REV PROTEIN | VISNA LENTIVIRUS (STRAIN 1514) | 22–62 | | | | | | | | |
| PRIR1_ASFM2 | RIBONUC-DIPHOSPH REDUCT LARGE CHA | AFRICAN SWINE FEVER VIRUS (ISOLATE MALAWI LIL 20/1) | 7–41 | 88–119 | 363–390 | | | | | | |
| PRIR1_HCMVA | RIBONUC-DIPHOSPH REDUCT LARGE CHA | HUMAN CYTOMEGALOVIRUS (STRAIN AD169) | 622–649 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRIR1_HSVEB | RIBONUC-DIPHOSPH REDUCT LARGE CHA | EQUINE HERPESVIRUS TYPE 1 (STRAIN AB4P) | 75–102 | | | | | | | | |
| PRIR1_HSVSA | RIBONUC-DIPHOSPH REDUCT LARGE CHA | HERPESVIRUS SAIMIRI (STRAIN 11) | 324–351 | | | | | | | | |
| PRIR1_VACCC | RIBONUC-DIPHOSPH REDUCT LARGE CHA | VACCINIA VIRUS (STRAIN COPENHAGEN) | 367–401 | | | | | | | | |
| PRIR1_VACCV | RIBONUC-DIPHOSPH REDUCT LARGE CHA | VACCINIA VIRUS (STRAIN WR) | 367–401 | | | | | | | | |
| PRIR1_VARV | RIBONUC-DIPHOSPH REDUCT LARGE CHA | VARIOLA VIRUS | 367–401 | | | | | | | | |
| PRIR1_VZVD | RIBONUC-DIPHOSPH REDUCT LARGE CHA | VARICELLA-ZOSTER VIRUS (STRAIN DUMAS) | 119–146 | | | | | | | | |
| PRIR2_HSVB3 | RIBONUC-DIPHOSPH REDUCT SMALL CHA | BOVINE HERPESVIRUS TYPE 1 (STRAIN 34) | 90–117 | | | | | | | | |
| PRP94_VACCV | RNA-POL-ASSOC TRANS SPEC FACTOR | VACCINIA VIRUS (STRAIN WR) | 41–68 | 513–540 | | | | | | | |
| PRP94_VARV | RNA-POL-ASSOC TRANS SPEC FACTOR | VARIOLA VIRUS | 41–75 | 77–104 | 513–540 | | | | | | |
| PRPO1_VACCC | DNA-DIRECTED RNA POL 147 KD | VACCINIA VIRUS (STRAIN COPENHAGEN) | 237–264 | 587–616 | 810–837 | 961–992 | | | | | |
| PRPO1_VACCV | DNA-DIRECTED RNA POL 147 KD | VACCINIA VIRUS (STRAIN WR) | 237–264 | 587–616 | 810–837 | 961–992 | 1011–1038 | | | | |
| PRPO1_VARV | DNA-DIRECTED RNA POL 147 KD | VARIOLA VIRUS | 237–264 | 587–616 | 810–837 | 961–992 | | | | | |
| PRPO2_CAPVK | DNA-DIRECTED RNA POL 132 KD | CAPRIPOXVIRUS (STRAIN KS-1) | 19–65 | 114–155 | | | | | | | |
| PRPO2_COWPX | DNA-DIRECTED RNA POL 132 KD | COWPOX VIRUS | 211–241 | 481–509 | | | | | | | |
| PRPO2_VACCV | DNA-DIRECTED RNA POL 132 KD | VACCINIA VIRUS (STRAIN WR) | 211–241 | 481–509 | | | | | | | |
| PRPO2_VARV | DNA-DIRECTED RNA POL 132 KD | VARIOLA VIRUS | 211–241 | 481–509 | | | | | | | |
| PRPO4_CAPVK | DNA-DIRECTED RNA POL 35 KD | CAPRIPOXVIRUS (STRAIN KS-1) | 36–63 | | | | | | | | |
| PRPO7_VACCV | DNA-DIRECTED RNA POL 19 KD | VACCINIA VIRUS (STRAIN WR) | 8–35 | 43–70 | | | | | | | |
| PRPO7_VARV | DNA-DIRECTED RNA POL 19 KD | VARIOLA VIRUS | 43–70 | | | | | | | | |
| PRPOA_LELV | RNA-DIRECTED RNA POLYMERASE | LELYSTAD VIRUS | 1533–1560 | | | | | | | | |
| PRPOL_EAV | RNA-DIRECTED RNA POLYMERASE | EQUINE ARTERITIS VIRUS | 888–915 | 1639–1673 | | | | | | | |
| PRRP1_IAKOR | RNA-DIRECTED RNA POL SUB P1 | INFLUENZA A VIRUS (STRAIN A/KOREA/426/68) | 575–602 | | | | | | | | |
| PRRP2_IAANN | RNA-DIRECTED RNA POL SUB P2 | INFLUENZA A VIRUS (STRAIN A/ANN ARBOR/6/60) | 119–146 | | | | | | | | |
| PRRP2_IADH2 | RNA-DIRECTED RNA POL SUB P2 | INFLUENZA A VIRUS (STRAIN A/DUCK/HOKKAIDO/8/80) | 119–146 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRP2_IAFPR | RNA-DIRECTED RNA POL SUB P2 | INFLUENZA A VIRUS (STRAIN A/FOWL PLAGUE VIRUS/ROSTOCK/34) | 119–146 | | | | | | | | |
| PRRP2_IAGU2 | RNA-DIRECTED RNA POL SUB P2 | INFLUENZA A VIRUS (STRAIN A/GULL/MARYLAND/704/77) | 119–146 | | | | | | | | |
| PRRP2_IAHLO | RNA-DIRECTED RNA POL SUB P2 | INFLUENZA A VIRUS (STRAIN A/EQUINE/LONDON/1416/73) | 119–146 | | | | | | | | |
| PRRP2_IAHTE | RNA-DIRECTED RNA POL SUB P2 | INFLUENZA A VIRUS (STRAIN A/EQUINE/TENNESSEE/5/86) | 119–146 | | | | | | | | |
| PRRP2_IAKOR | RNA-DIRECTED RNA POL SUB P2 | INFLUENZA A VIRUS (STRAIN A/KOREA/426/68) | 119–146 | | | | | | | | |
| PRRP2_IALE1 | RNA-DIRECTED RNA POL SUB P2 | INFLUENZA A VIRUS (STRAIN A/LENINGRAD/134/57) | 119–146 | | | | | | | | |
| PRRP2_IALE2 | RNA-DIRECTED RNA POL SUB P2 | INFLUENZA A VIRUS (STRAIN A/LENINGRAD/134/17/57) | 119–146 | | | | | | | | |
| PRRP2_IAMAN | RNA-DIRECTED RNA POL SUB P2 | INFLUENZA A VIRUS (STRAIN A/MALLARD/NEW YORK/6750/78) | 119–146 | | | | | | | | |
| PRRP2_IANT6 | RNA-DIRECTED RNA POL SUB P2 | INFLUENZA A VIRUS (STRAIN A/NT/60/68) | 119–146 | | | | | | | | |
| PRRP2_IAP10 | RNA-DIRECTED RNA POL SUB P2 | INFLUENZA A VIRUS (STRAIN A/PINTAIL/ALBERTA/119/79) | 119–146 | | | | | | | | |
| PRRP2_IAPUE | RNA-DIRECTED RNA POL SUB P2 | INFLUENZA A VIRUS (STRAIN A/PUERTO RICO/8/34) | 119–146 | | | | | | | | |
| PRRP2_IARUD | RNA-DIRECTED RNA POL SUB P2 | INFLUENZA A VIRUS (STRAIN A/RUDDY TURNSTONE/NEW JERSEY/47/85) | 119–146 | | | | | | | | |
| PRRP2_IASIN | RNA-DIRECTED RNA POL SUB P2 | INFLUENZA A VIRUS (STRAIN A/SINGAPORE/1/57) | 119–146 | | | | | | | | |
| PRRP2_IATKM | RNA-DIRECTED RNA POL SUB P2 | INFLUENZA A VIRUS (STRAIN A/TURKEY/MINNESOTA/833/80) | 119–146 | | | | | | | | |
| PRRP2_IAVI7 | RNA-DIRECTED RNA POL SUB P2 | INFLUENZA A VIRUS (STRAIN A/VICTORIA/3/75) | 119–146 | 327–354 | | | | | | | |
| PRRP2_IAWIL | RNA-DIRECTED RNA POL SUB P2 | INFLUENZA A VIRUS (STRAIN A/WILSON-SMITH/33) | 119–146 | | | | | | | | |
| PRRP2_IAZH2 | RNA-DIRECTED RNA POL SUB P2 | INFLUENZA A VIRUS (STRAIN A/SWINE/HONG KONG/81/78) | 119–146 | | | | | | | | |
| PRRP2_IAZH3 | RNA-DIRECTED RNA POL SUB P2 | INFLUENZA A VIRUS (STRAIN A/SWINE/HONG KONG/126/82) | 119–146 | | | | | | | | |
| PRRP2_IAZI1 | RNA-DIRECTED RNA POL SUB P2 | INFLUENZA A VIRUS (STRAIN A/SWINE/IOWA/15/30) | 119–146 | | | | | | | | |
| PRRP2_IAZTF | RNA-DIRECTED RNA POL SUB P2 | INFLUENZA A VIRUS (STRAIN A/SWINE/TENNESSEE/26/77) | 119–146 | | | | | | | | |
| PRRP2_INBAC | RNA-DIRECTED RNA POL SUB P2 | INFLUENZA B VIRUS (STRAIN B/ANN ARBOR/1/66 [COLD-ADAPTED]) | 157–194 | | | | | | | | |
| PRRP2_INBAD | RNA-DIRECTED RNA POL SUB P2 | INFLUENZA B VIRUS (STRAIN B/ANN ARBOR/1/66 [WILD-TYPE) | 164–194 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRP2_INBS1 | RNA-DIRECTED RNA POL SUB P2 | INFLUENZA B VIRUS (STRAIN B/SINGAPORE/222/79) | 157–194 | | | | | | | | |
| PRRP3_IABUD | RNA-DIRECTED RNA POL SUB P3 | INFLUENZA A VIRUS (STRAIN A/BUDGERIGAR/HOKKAIDO/1/77) | 537–567 | | | | | | | | |
| PRRP3_IACH1 | RNA-DIRECTED RNA POL SUB P3 | INFLUENZA A VIRUS (STRAIN A/CHILE/1/83) | 331–358 | | | | | | | | |
| PRRP3_IAHPR | RNA-DIRECTED RNA POL SUB P3 | INFLUENZA A VIRUS (STRAIN A/EQUINE/PRAGUE/1/56) | 331–361 | 480–507 | | | | | | | |
| PRRP3_IAZTE | RNA-DIRECTED RNA POL SUB P3 | INFLUENZA A VIRUS (STRAIN A/SWINE/TENNESSEE/24/77) | 487–514 | | | | | | | | |
| PRRP3_INBAC | RNA-DIRECTED RNA POL SUB P3 | INFLUENZA B VIRUS (STRAIN B/ANN ARBOR/1/66 [COLD-ADAPTED]) | 2–33 | 472–509 | | | | | | | |
| PRRP3_INBAD | RNA-DIRECTED RNA POL SUB P3 | INFLUENZA B VIRUS (STRAIN B/ANN ARBOR/1/66 [WILD-TYPE]) | 2–33 | 472–509 | | | | | | | |
| PRRP3_INCBE | RNA-DIRECTED RNA POL SUB P3 | INFLUENZA C VIRUS (STRAIN C/BERLIN/1/85) | 509–536 | | | | | | | | |
| PRRP3_INCJJ | RNA-DIRECTED RNA POL SUB P3 | INFLUENZA C VIRUS (STRAIN C/JJ/50) | 509–536 | | | | | | | | |
| PRRP3_THOGV | RNA-DIRECTED RNA POL SUB P3 | THOGOTO VIRUS | 149–176 | 358–385 | | | | | | | |
| PRRPA_CVH22 | RNA-DIRECTED RNA POLYMERASE | HUMAN CORONAVIRUS (STRAIN 229E) | 516–543 | 724–751 | 1971–2008 | 3781–3811 | | | | | |
| PRRPA_CVMJH | RNA-DIRECTED RNA POLYMERASE | MURINE CORONAVIRUS MHV (STRAIN JHM) | 624–651 | 4326–4353 | | | | | | | |
| PRRPB_BEV | RNA-DIRECTED RNA POLYMERASE | BERNE VIRUS | 27–54 | 557–584 | 943–984 | | | | | | |
| PRRPB_CVMA5 | RNA-DIRECTED RNA POLYMERASE | MURINE CORONAVIRUS MHV (STRAIN A59) | 885–915 | 1129–1170 | | | | | | | |
| PRRPB_CVMJH | RNA-DIRECTED RNA POLYMERASE | MURINE CORONAVIRUS MHV (STRAIN JHM) | 885–915 | 1129–1170 | | | | | | | |
| PRRPB_CVPFS | RNA-DIRECTED RNA POLYMERASE | PORCINE TRANSMISSIBLE GASTROENTERITIS CORONAVIRUS (STRAIN FS722) | 20–47 | 353–380 | 385–412 | | | | | | |
| PRRPB_IBVB | RNA-DIRECTED RNA POLYMERASE | AVIAN INFECTIOUS BRONCHITIS VIRUS (STRAIN BEAUDETTE) | 1510–1547 | 2296–2331 | 2547–2574 | | | | | | |
| PRRPB_IBVK | RNA-DIRECTED RNA POLYMERASE | AVIAN INFECTIOUS BRONCHITIS VIRUS (STRAIN KB8523) | 165–200 | 416–443 | | | | | | | |
| PRRPL_BTV10 | RNA-DIRECTED RNA POLYMERASE | BLUETONGUE VIRUS (SEROTYPE 10/ISOLATE USA) | 1032–1059 | | | | | | | | |
| PRRPL_BUNYW | RNA POLYMERASE | BUNYAMWERA VIRUS | 80–114 | 317–350 | 1802–1861 | 1892–1919 | | | | | |
| PRRPL_CDVO | RNA POLYMERASE BETA SUBUNIT | CANINE DISTEMPER VIRUS (STRAIN ONDERSTEPOORT) | 24–51 | | | | | | | | |
| PRRPL_HANTV | RNA POLYMERASE | HANTAAN VIRUS (STRAIN 76–118) | 404–433 | 461–510 | 564–591 | 738–765 | 905–946 | 1993–2020 | 1453–1480 | 1776–1803 | |
| PRRPL_HRSVA | RNA POLYMERASE BETA SUBUNIT | HUMAN RESPIRATORY SYNCYTIAL VIRUS (STRAIN A2) | 103–192 | 210–237 | 667–694 | 788–815 | 1007–1034 | 1138–1165 | | | 2062–2089 |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRPL_MABVM | RNA-DIRECTED RNA POLYMERASE | MARBURG VIRUS (STRAIN MUSOKE) | 991–1018 | 1143–1170 | 1490–1524 | 1811–1838 | 2029–2067 | 2216–2266 | | | |
| PRRPL_MABVP | RNA-DIRECTED RNA POLYMERASE | MARBURG VIRUS (STRAIN POPP) | 991–1018 | 1490–1524 | 2239–2267 | | | | | | |
| PRRPL_MEASE | RNA POLYMERASE BETA SUBUNIT | MEASLES VIRUS (STRAIN EDMONSTON) | 95–122 | 196–223 | 2121–2148 | | | | | | |
| PRRPL_MUMPM | RNA POLYMERASE BETA SUBUNIT | MUMPS VIRUS (STRAIN MIYAHARA VACCINE) | 111–142 | 780–807 | 1602–1632 | | | | | | |
| PRRPL_NDVB | RNA POLYMERASE BETA SUBUNIT | NEWCASTLE DISEASE VIRUS (STRAIN BEAUDETTE C/45) | 250–284 | 477–504 | 1979–2013 | | | | | | |
| PRRPL_PI2HT | RNA POLYMERASE BETA SUBUNIT | HUMAN PARAINFLUENZA 2 VIRUS (STRAIN TOSHIBA) | 322–349 | 1564–1598 | 1687–1721 | 1901–1946 | | | | | |
| PRRPL_PI3H4 | RNA POLYMERASE BETA SUBUNIT | HUMAN PARAINFLUENZA 3 VIRUS (STRAIN NIH 47885) | 52–86 | 136–163 | 608–638 | 1081–1123 | 1994–2036 | 2115–2142 | | | |
| PRRPL_PUUMH | RNA-DIRECTED RNA POLYMERASE | PUUMALA VIRUS (STRAIN HALLNAS B1) | 388–415 | 557–591 | 731–758 | 864–891 | 926–953 | 1940–1971 | 1998–2025 | | |
| PRRPL_RABVP | RNA POLYMERASE BETA SUBUNIT | RABIES VIRUS (STRAIN PV) | 204–231 | 605–632 | 2068–2123 | | | | | | |
| PRRPL_RABVS | RNA POLYMERASE BETA SUBUNIT | RABIES VIRUS (STRAIN SAD B19) | 204–231 | 605–632 | 2068–2123 | | | | | | |
| PRRPL_RDV | RNA-DIRECTED RNA POLYMERASE | RICE DWARF VIRUS | 855–882 | | | | | | | | |
| PRRPL_RVFVZ | RNA-DIRECTED RNA POLYMERASE | RIFT VALLEY FEVER VIRUS (STRAIN ZH-548 M12) | 1536–1563 | 1653–1687 | | | | | | | |
| PRRPL_SEND5 | RNA POLYMERASE BETA SUBUNIT | SENDAI VIRUS (STRAIN Z/HOST MUTANTS) | 629–656 | 1082–1116 | 1729–1756 | 2145–2180 | | | | | |
| PRRPL_SENDE | RNA POLYMERASE BETA SUBUNIT | SENDAI VIRUS (STRAIN ENDERS) | 449–476 | 902–936 | 1549–1576 | 1965–2000 | | | | | |
| PRRPL_SENDZ | RNA POLYMERASE BETA SUBUNIT | SENDAI VIRUS (STRAIN 2) | 629–656 | 1082–1116 | 1729–1756 | 2145–2180 | | | | | |
| PRRPL_SEOU8 | RNA-DIRECTED RNA POLYMERASE | SEOUL VIRUS (STRAIN 80-39) | 461–488 | 564–591 | 731–758 | 905–932 | | | | | |
| PRRPL_SV5WR | RNA POLYMERASE BETA SUBUNIT | SIMIAN VIRUS 5 (STRAIN 21004-WR) | 1096–1123 | 1250–1277 | 1680–1710 | 2120–2147 | | | | | |
| PRRPL_SYNV | RNA POLYMERASE BETA SUBUNIT | SONCHUS YELLOW NET VIRUS | 825–859 | 1092–1119 | 1490–1520 | 1973–2000 | 2080–2107 | | | | |
| PRRPL_TSWVB | RNA-DIRECTEED RNA POLYMERASE | TOMATO SPOTTED WILT VIRUS (BRAZILIAN ISOLATE CPNH1/BR-01) | 477–504 | 542–573 | 1119–1150 | 1195–1229 | 1330–1357 | 1415–1442 | 1671–1698 | 1857–1884 | 2083–2110 |
| PRRPL_UUK | RNA POLYMERASE | UUKUNIEMI VIRUS | 2166–2193 | 2324–2368 | 2771–2798 | | | | | | |
| PRRPL_VSVIH | RNA POLYMERASE BETA SUBUNIT | VESICULAR STOMATITIS VIRUS (SEROTYPE NEW JERSEY/STRAIN HAZELHU | 142–187 | 1037–1071 | 1304–1331 | | | | | | |
| | | VESICULAR STOMATITIS VIRUS (SEROTYPE NEW JERSEY/STRAIN HAZELHU | 1530–1557 | 1809–1836 | | | | | | | |
| PRRPL_VSVIO | RNA POLYMERASE BETA SUBUNIT | VESICULAR STOMATITIS VIRUS (SEROTYPE NEW JERSEY/STRAIN OGDEN) | 1205–1232 | 1809–1836 | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRPL_VSVSJ | RNA POLYMERASE BETA SUBUNIT | VESICULAR STOMATITIS VIRUS (STRAIN SAN JUAN) | 1540–1567 | 1768–1798 | | | | | | | |
| PRRPO_ACLSV | RNA-DIRECTED RNA POLYMERASE | APPLE CHLOROTIC LEAF SPOT VIRUS | 228–264 | 564–591 | | | | | | | |
| PRRPO_BWYVF | PUTATIVE RNA-DIR RNA POL | BEET WESTERN YELLOWS VIRUS (ISOLATE FL-1) | 356–383 | | | | | | | | |
| PRRPO_BYDV1 | PUTATIVE RNA-DIR RNA POL | BARLEY YELLOW DWARF VIRUS (ISOLATE MAV-PS1) | 772–799 | | | | | | | | |
| PRRPO_BYDVP | PUTATIVE RNA-DIR RNA POL | BARLEY YELLOW DWARF VIRUS (ISOLATE PAV) | 772–799 | | | | | | | | |
| PRRPO_BYDVR | PUTATIVE RNA-DIR RNA POL | BARLEY YELLOW DWARF VIRUS (ISOLATE P-PAV) | 772–799 | | | | | | | | |
| PRRPO_CARMV | PUTATIVE RNA-DIR RNA POL | CARNATION MOTTLE VIRUS | 93–127 | 277–304 | 667–694 | | | | | | |
| PRRPO_CGMVS | PUTATIVE RNA-DIR RNA POL | CUCUMBER GREEN MOTTLE MOSAIC VIRUS (WATERMELON STRAIN SH) | 387–414 | 1040–1067 | | | | | | | |
| PRRPO_IBDV5 | PUTATIVE RNA-DIR RNA POL | AVIAN INFECTIOUS BURSAL DISEASE VIRUS (STRAIN 52/70) | 336–363 | 392–419 | | | | | | | |
| PRRPO_IBDVA | PUTATIVE RNA-DIR RNA POL | AVIAN INFECTIOUS BURSAL DISEASE VIRUS (STRAIN AUSTRALIAN 002-73) | 661–688 | 717–744 | | | | | | | |
| PRRPO_IPNVJ | PUTATIVE RNA-DIR RNA POL | INFECTIOUS PANCREATIC NECROSIS VIRUS (SEROTYPE JASPER) | 773–800 | | | | | | | | |
| PRRPO_IPNVS | PUTATIVE RNA-DIR RNA POL | INFECTIOUS PANCREATIC NECROSIS VIRUS (SEROTYPE SP) | 773–800 | | | | | | | | |
| PRRPO_LYCVA | RNA POLYMERASE | LYMPHOCYTIC CHORIOMENINGITIS VIRUS (STRAIN ARMSTRONG) | 834–886 | 1052–1079 | | | | | | | |
| PRRPO_PPMVS | PUTATIVE RNA-DIR RNA POL | PEPPER MILD MOTTLE VIRUS (STRAIN SPAIN) | 402–429 | 709–736 | 1072–1099 | | | | | | |
| PRRPO_REOVD | RNA-DIRECTED RNA POLYMERASE | REOVIRUS (TYPE 3/STRAIN DEARING) | 61–88 | | | | | | | | |
| PRRPO_REOVL | RNA-DIRECTED RNA POLYMERASE | REOVIRUS (TYPE 1/STRAIN LANG) | 61–88 | | | | | | | | |
| PRRPO_ROTBR | RNA-DIR RNA POL SUBUNIT VP1 | BOVINE ROTAVIRUS (STRAIN RF) | 68–95 | 218–245 | 791–818 | | | | | | |
| PRRPO_ROTBU | RNA-DIR RNA POL SUBUNIT VP1 | BOVINE ROTAVIRUS (STRAIN UK) | 65–95 | 218–245 | 791–841 | 975–1002 | | | | | |
| PRRPO_ROTPC | RNA-DIR RNA POL SUBUNIT VP1 | PORCINE ROTAVIRUS (GROUP C/STRAIN COWDEN) | 3–44 | 75–102 | 363–390 | 543–585 | | | | | |
| PRRPO_ROTPG | RNA-DIR RNA POL SUBUNIT VP1 | PORCINE ROTAVIRUS (STRAIN GOTTFRIED | 65–95 | 102–129 | 791–839 | 973–1002 | | | | | |
| PRRPO_ROTS1 | RNA-DIR RNA POL SUBUNIT VP1 | SIMIAN 11 ROTAVIRUS (STRAIN SA11) | 65–95 | 791–839 | 975–1002 | | | | | | |
| PRRPO_SCVLA | RNA-DIRECTED RNA POLYMERASE | SACCHAROMYCES CEREVISIAE VIRUS L-A | 147–188 | | | | | | | | |
| PRRPO_TACV | RNA POLYMERASE | TACARIBE VIRUS | 163–204 | 241–271 | 1107–1134 | 1978–2008 | | | | | |
| PRRPO_TMGMV | PUTATIVE RNA-DIR RNA POL | TOBACCO MILD GREEN MOSAIC VIRUS (TMV STRAIN U2) | 230–257 | 1316–1343 | 1397–1424 | | | | | | |
| PRRPP_BRSVA | RNA POLYMERASE ALPHA SUBUNIT | BOVINE RESPIRATORY SYNCYTIAL VIRUS (STRAIN A51908) | 99–133 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRPP_CDVO | RNA POLYMERASE ALPHA SUBUNIT | CANINE DISTEMPER VIRUS (STRAIN ONDERSTEPOORT) | 315–370 | | | | | | | | |
| PRRPP_HRSV | RNA POLYMERASE ALPHA SUBUNIT | HUMAN RESPIRATORY SYNCYTIAL VIRUS | 99–141 | | | | | | | | |
| PRRPP_HRSV1 | RNA POLYMERASE ALPHA SUBUNIT | HUMAN RESPIRATORY SYNCYTIAL VIRUS (SUBGROUP B/STRAIN 18537) | 99–141 | | | | | | | | |
| PRRPP_HRSVA | RNA POLYMERASE ALPHA SUBUNIT | HUMAN RESPIRATORY SYNCYTIAL VIRUS (STRAIN A2) | 99–141 | | | | | | | | |
| PRRPP_HRSVL | RNA POLYMERASE ALPHA SUBUNIT | HUMAN RESPIRATORY SYNCYTIAL VIRUS (SUBGROUP A/STRAIN LONG) | 99–141 | | | | | | | | |
| PRRPP_MEASE | RNA POLYMERASE ALPHA SUBUNIT | MEASLES VIRUS (STRAIN EDMONSTON) | 315–370 | | | | | | | | |
| PRRPP_MEASI | RNA POLYMERASE ALPHA SUBUNIT | MEASLES VIRUS (STRAIN IP-3-CA) | 315–370 | | | | | | | | |
| PRRPP_MEASY | RNA POLYMERASE ALPHA SUBUNIT | MEASELS VIRUS (STRAIN YAMAGATA-1) | 315–370 | | | | | | | | |
| PRRPP_PI1HB | RNA POLYMERASE ALPHA SUBUNIT | HUMAN PARAINFLUENZA 1 VIRUS (STRAIN C35) | 84–111 | 234–261 | 375–416 | | | | | | |
| PRRPP_PI1HC | RNA POLYMERASE ALPHA SUBUNIT | HUMAN PARAINFLUENZA 1 VIRUS (STRAIN C39) | 84–111 | 234–261 | 375–416 | | | | | | |
| PRRPP_PI1HD | RNA POLYMERASE ALPHA SUBUNIT | HUMAN PARAINFLUENZA 1 VIRUS (STRAIN C1-5/73) | 84–111 | 232–262 | 375–416 | | | | | | |
| PRRPP_PI1HE | RNA POLYMERASE ALPHA SUBUNIT | HUMAN PARAINFLUENZA 1 VIRUS (STRAIN C1-14/83) | 84–111 | 244–271 | 375–416 | | | | | | |
| PRRPP_PI2H | RNA POLYMERASE ALPHA SUBUNIT | HUMAN PARAINFLUENZA 2 VIRUS | 167–194 | 222–256 | | | | | | | |
| PRRPP_PI2HT | RNA POLYMERASE ALPHA SUBUNIT | HUMAN PARAINFLUENZA 2 VIRUS (STRAIN TOSHIBA) | 167–194 | 222–256 | | | | | | | |
| PRRPP_PI3B | RNA POLYMERASE ALPHA SUBUNIT | BOVINE PARAINFLUENZA 3 VIRUS | 34–91 | 255–282 | 285–314 | | | | | | |
| PRRPP_PI3H4 | RNA POLYMERASE ALPHA SUBUNIT | HUMAN PARAINFLUENZA 3 VIRUS (STRAIN NIH 47885) | 114–144 | 269–299 | | | | | | | |
| PRRPP_PI4HA | RNA POLYMERASE ALPHA SUBUNIT | HUMAN PARAINFLUENZA 4A VIRUS (STRAIN TOSHIBA) | 4–38 | | | | | | | | |
| PRRPP_RABVP | RNA POLYMERASE ALPHA SUBUNIT | RABIES VIRUS (STRAIN PV) | 93–127 | | | | | | | | |
| PRRPP_SEND5 | RNA POLYMERASE ALPHA SUBUNIT | SENDAI VIRUS (STRAIN Z/HOST MUTANTS) | 330–357 | 379–420 | | | | | | | |
| PRRPP_SEND6 | RNA POLYMERASE ALPHA SUBUNIT | SENDAI VIRUS (STRAIN 6/94) | 330–357 | 379–420 | | | | | | | |
| PRRPP_SENDF | RNA POLYMERASE ALPHA SUBUNIT | SENDAI VIRUS (STRAIN FUSHIMI) | 330–357 | 379–420 | | | | | | | |
| PRRPP_SENDH | RNA POLYMERASE ALPHA SUBUNIT | SENDAI VIRUS (STRAIN HARRIS) | 330–357 | 379–420 | | | | | | | |
| PRRPP_SENDZ | RNA POLYMERASE ALPHA SUBUNIT | SENDAI VIRUS (STRAIN Z) | 330–357 | 379–420 | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRPP_SV5 | RNA POLYMERASE ALPHA SUBUNIT | SIMIAN VIRUS 5 (STRAIN W3) | 205–232 | 236–263 | | | | | | | |
| PSODC_VACCV | SUPEROXIDE DISMUTASE LIKE PROTEIN | VACCINIA VIRUS (STRAIN WR) | 72–99 | | | | | | | | |
| PSODC_VARV | SUPEROXIDE DISMUTASE LIKE PROTEIN | VARIOLA VIRUS | 72–99 | | | | | | | | |
| PSPHR_AMEPV | SPHEROIDIN | AMSACTA MOOREI ENTOMOPOXVIRUS | 91–118 | 140–167 | 227–261 | 361–390 | | | | | |
| PSPI1_MYXVL | SERPIN 1 | MYXOMA VIRUS (STRAIN LAUSANNE) | 286–313 | | | | | | | | |
| PSPI2_VACCV | SERINE PROTEINASE INHIBITOR 2 | VACCINIA VIRUS (STRAIN WR) | 59–86 | | | | | | | | |
| PSPIA_VACCC | SERINE PROTEASE INH 2 HOMOLOG | VACCINIA VIRUS (STRAIN COPENHAGEN) | 18–65 | | | | | | | | |
| PT2C2_CHVP1 | TYPE II RESTRICTION ENZYME CVIAII | PARAMECIUM BURSARIA CHLORELLA VIRUS 1 | 16–43 | | | | | | | | |
| PTAA2_VACCV | TRANS-ACTIVATOR PROTEIN A2 | VACCINIA VIRUS | 95–133 | | | | | | | | |
| PTAG8_FOWPV | TRANS-ACTIVATOR PROTEIN FP0 | FOWLPOX VIRUS | 3–51 | | | | | | | | |
| PTAG8_VACCV | TRANS-ACTIVATOR PROTEIN GK1 | VACCINIA VIRUS | 3–30 | | | | | | | | |
| PTAG8_VARV | TRANS-ACTIVATOR PROTEIN GK1 | VARIOLA VIRUS | 3–30 | | | | | | | | |
| PTIALA_BFDV | LARGE T ANTIGEN | BUDGERIGAR FLEDGLING DISEASE VIRUS | 291–318 | | | | | | | | |
| PTIALA_POVBO | LARGE T ANTIGEN | BOVINE POLYOMAVIRUS | 502–537 | | | | | | | | |
| PTIALA_POVHA | LARGE T ANTIGEN | HAMSTER POLYOMAVIRUS | 587–621 | | | | | | | | |
| PTIALA_POVLY | LARGE T ANTIGEN | LYMPHOTROPIC POLYOMAVIRUS | 224–258 | 616–684 | | | | | | | |
| PTIALA_POVM3 | LARGE T ANTIGEN | MOUSE POLYOMA VIRUS (STRAIN 3) | 513–540 | | | | | | | | |
| PTIALA_POVMA | LARGE T ANTIGEN | MOUSE POLYOMA VIRUS (STRAIN A2) | 511–538 | | | | | | | | |
| PTIALA_POVMC | LARGE T ANTIGEN | MOUSE POLYOMA VIRUS (STRAIN CRAWFORD SMALL-PLAQUE) | 508–535 | | | | | | | | |
| PTATR_NPVAC | TRANS-ACT TRANS REG PROTEIN | AUTOGRAPHA CALIFORNICA NUCLEAR POLYHEDROSIS VIRUS | 407–434 | 489–523 | 532–559 | | | | | | |
| PTATR_NPVBM | TRANS-ACT TRANS REG PROTEIN | BOMBYX MORI NUCLEAR POLYHEDROSIS VIRUS | 412–439 | 494–528 | 537–564 | | | | | | |
| PTATR_NPVOP | TRANS-ACT TRANS REG PROTEIN | ORGYIA PSEUDOTSUGATA MULTICAPSID POLYHEDROSIS VIRUS | 512–554 | | | | | | | | |
| PTEGU_EBV | LARGE TEGUMENT PROTEIN | EPSTEIN-BARR VIRUS (STRAIN B95-8) | 145–172 | 1215–1242 | 1344–1371 | 1876–1903 | | | | | |
| PTEGU_HCMVA | PROBABLE LARGE TEGUMENT PROTEIN | HUMAN CYTOMEGALOVIRUS (STRAIN AD169) | 1251–1281 | 2202–2229 | | | | | | | |
| PTEGU_HSV11 | LARGE TEGUMENT PROTEIN | HERPES SIMPLEX VIRUS (TYPE 1/STRAIN 17) | 667–694 | 1673–1710 | | | | | | | |
| PTEGU_HSV6G | LARGE TEGUMENT PROTEIN | HERPES SIMPLEX VIRUS (TYPE 6/STRAIN GS) | 102–129 | 228–262 | 567–611 | 962–993 | 1098–1181 | 1661–1688 | 1884–1911 | | |
| PTEGU_HSVEB | LARGE TEGUMENT PROTEIN | EQUINE HERPESVIRUS TYPE 1 (STRAIN AB4P) | 229–256 | 566–593 | 1205–1232 | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTEGU_HSVSA | PROBABLE LARGE TEGUMENT PROTEIN | HERPESVIRUS SAIMIRI (STRAIN 11) | 524–607 | 672–700 | 777–814 | 846–898 | 949–986 | 990–1017 | 1467–1497 | 2102–2135 | |
| PTEGU_VZVD | LARGE TEGUMENT PROTEIN | VARICELLA-ZOSTER VIRUS (STRAIN DUMAS) | 1121–1158 | 1579–1609 | | | | | | | |
| PTERM_ADE07 | DNA TERMINAL PROTEIN | HUMAN ADENOVIRUS TYPE 7 | 375–413 | | | | | | | | |
| PTMAF_AVIS4 | TRANSFORMING PROTEIN MAF | AVIAN MUSCULOAPONEUROTIC FIBROSARCOMA VIRUS AS42 | 302–336 | | | | | | | | |
| PTOP1_SFVKA | DNA TOPOISOMERASE I | SHOPE FIBROMA VIRUS (STRAIN KASZA) | 38–65 | 132–176 | | | | | | | |
| PTOP1_VACCV | DNA TOPOISOMERASE I | VACCINIA VIRUS | 38–65 | | | | | | | | |
| PTOP1_VARV | DNA TOPOISOMERASE I | VARIOLA VIRUS | 38–65 | | | | | | | | |
| PTOP2_ASFM2 | DNA TOPOISOMERASE II | AFRICAN SWINE FEVER VIRUS (ISOLATE MALAWI LIL 20/1) | 902–936 | | | | | | | | |
| PTYSY_HSVAT | THYMIDYLATE SYNTHASE | HERPESVIRUS ATELES | 116–143 | | | | | | | | |
| PTYSY_HSVSA | THYMIDYLATE SYNTHASE | HERPESVIRUS SAIMIRI (STRAIN 11) | 120–147 | | | | | | | | |
| PUL6_EBV | VIRION PROTEIN BBRF1 | EPSTEIN-BARR VIRUS (STRAIN B95-8) | 115–142 | 313–340 | 542–569 | | | | | | |
| PUL6_HSV11 | VIRION PROTEIN UL6 | HERPES SIMPLEX VIRUS (TYPE 1/STRAIN 17) | 586–613 | | | | | | | | |
| PUL6_HSVEB | VIRION GENE 56 PROTEIN | EQUINE HERPESVIRUS TYPE 1 (STRAIN AB4P) | 640–667 | | | | | | | | |
| PUL6_HSVSA | VIRION GENE 43 PROTEIN | HERPESVIRUS SAIMIRI (STRAIN 11) | 15–42 | 302–358 | 368–402 | | | | | | |
| PUL8_HCMVA | HYPOTHETICAL PROTEIN UL8 | HUMAN CYTOMEGALOVIRUS (STRAIN AD169) | 6–47 | | | | | | | | |
| PUL11_EBV | HYPOTHETICAL PROTEIN BBLF1 | EPSTEIN-BARR VIRUS (STRAIN B95-8) | 15–42 | | | | | | | | |
| PUL13_HCMVA | HYPOTHETICAL PROTEIN UL13 | HUMAN CYTOMEGALOVIRUS (STRAIN AD169) | 347–374 | | | | | | | | |
| PUL14_HSVEB | HYPOTHETICAL GENE 48 PROTEIN | EQUINE HERPESVIRUS TYPE 1 (STRAIN AB4P) | 247–286 | | | | | | | | |
| PUL14_VZVD | HYPOTHETICAL GENE 46 PROTEIN | VARICELLA-ZOSTER VIRUS (STRAIN DUMAS) | 64–101 | | | | | | | | |
| PUL16_HCMVA | HYPOTHETICAL PROTEIN UL16 | HUMAN CYTOMEGALOVIRUS (STRAIN AD169) | 81–112 | | | | | | | | |
| PUL20_HCMVA | HYPOTH PRO UL20 PRECURSOR | HUMAN CYTOMEGALOVIRUS (STRAIN AD169) | 34–61 | | | | | | | | |
| PUL21_HSVEB | HYPOTHETICAL PROTEIN UL21 | EQUINE HERPESVIRUS TYPE 1 (STRAIN AB4P) | 44–71 | | | | | | | | |
| PUL21_VZVD | GENE 40 PROTEIN | VARICELLA-ZOSTER VIRUS (STRAIN DUMAS) | 380–407 | | | | | | | | |
| PUL25_HSVSA | GENE 38 PROTEIN | HERPESVIRUS SAIMIRI (STRAIN 11) | 34–61 | 204–231 | 362–389 | | | | | | |
| PUL31_HCMVA | VIRION GENE 19 PROTEIN | HUMAN CYTOMEGALOVIRUS (STRAIN AD169) | 167–194 | 254–284 | | | | | | | |
| PUL32_HSVEB | HYPOTHETICAL PROTEIN UL31 | EQUINE HERPESVIRUS TYPE 1 | 345–375 | | | | | | | | |
| PUL34_HSV11 | MAJOR ENVELOPE GLYCOPROTEIN 300 | HERPES SIMPLEX VIRUS (TYPE 1/STRAIN 17) | 116–143 | | | | | | | | |
| PUL34_HSVSA | VIRION PROTEIN UL34 | HERPESVIRUS SAIMIRI (STRAIN 11) | 208–235 | | | | | | | | |
| PUL34_VZVD | GENE 67 PROTEIN | VARICELLA-ZOSTER VIRUS (STRAIN DUMAS) | 112–139 | | | | | | | | |
| PUL35_HCMVA | VIRION GENE 34 PROTEIN | HUMAN CYTOMEGALOVIRUS (STRAIN AD169) | 535–562 | | | | | | | | |
| PUL37_HSV11 | HYPOTHETICAL PROTEIN UL35 | HERPES SIMPLEX VIRUS (TYPE 1/STRAIN 17) | 470–497 | 853–884 | | | | | | | |
| PUL37_HSVEB | PROTEIN UL37 | EQUINE HERPESVIRUS TYPE 1 (STRAIN AB4P) | 715–749 | 987–1014 | | | | | | | |
| PUL37_HSVSA | GENE 23 PROTEIN | HERPESVIRUS SAIMIRI (STRAIN 11) | 31–65 | 685–737 | | | | | | | |
| PUL37_VZVD | GENE 63 PROTEIN | VARICELLA-ZOSTER VIRUS (STRAIN DUMAS) | 107–134 | 485–512 | 719–746 | 976–1003 | | | | | |
| PUL41_VZVD | GENE 21 PROTEIN | VARICELLA-ZOSTER VIRUS (STRAIN DUMAS) | 330–364 | | | | | | | | |
| PUL42_HSV11 | HOST SHUTOFF VIRION PROTEIN | HERPES SIMPLEX VIRUS (TYPE 1/STRAIN 17) | 231–258 | | | | | | | | |
| PUL43_VZVD | DNA-BINDING PROTEIN UL42 | VARICELLA-ZOSTER VIRUS (STRAIN DUMAS) | 129–156 | 312–349 | 763–790 | 802–853 | | | | | |
| PUL47_HCMVA | GENE 15 MEMBRANE PROTEIN | HUMAN CYTOMEGALOVIRUS (STRAIN AD169) | 114–148 | 448–485 | | | | | | | |
| | PROTEIN UL47 | | | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUL47_HSV11 | VIRION PROTEIN UL47 | HERPES SIMPLEX VIRUS (TYPE 1/STRAIN 17) | 448–515 | | | | | | | | |
| PUL47_HSV1F | VIRION PROTEIN UL47 | HERPES SIMPLEX VIRUS (TYPE 1/STRAIN F) | 488–515 | | | | | | | | |
| PUL47_HSVE4 | 97 KD ALPHA TRANS-INDUCING PROTEIN | EQUINE HERPESVIRUS TYPE 4 | 190–217 | | | | | | | | |
| PUL50_HCMVA | PROTEIN UL50 | HUMAN CYTOMEGALOVIRUS (STRAIN AD169) | 159–186 | | | | | | | | |
| PUL52_EBV | PROB DNA REPLICATION PROTEIN B SLF1 | EPSTEIN-BARR VIRUS (STRAIN B95-8) | 185–212 | 787–814 | | | | | | | |
| PUL52_HSVEB | DNA REPLICATION PROTEIN UL52 | EQUINE HERPESVIRUS TYPE 1 (STRAIN AB4') | 193–220 | 943–970 | | | | | | | |
| PUL52_HSVSA | PROB DNA REP GENE 56 PROTEIN | HERPESVIRUS SAIMIRI (STRAIN 11) | 130–157 | | | | | | | | |
| PUL52_VZVD | PROB DNA REP GENE 6 PROTEIN | VARICELLA-ZOSTER VIRUS (STRAIN DUMAS) | 301–337 | | | | | | | | |
| PUL59_HCMVA | HYPOTHETICAL PROTEIN UL59 | HUMAN CYTOMEGALOVIRUS (STRAIN AD169) | 74–101 | | | | | | | | |
| PUL70_HCMVA | PROB DNA REP PROTEIN UL70 | HUMAN CYTOMEGALOVIRUS (STRAIN AD169) | 65–92 | | | | | | | | |
| PUL73_HCMVA | UL73 GLYCOPROTEIN PRECURSOR | HUMAN CYTOMEGALOVIRUS (STRAIN AD169) | 5–73 | | | | | | | | |
| PUL73_HSVSA | HYPOTHETICAL GENE 53 PROTEIN | HERPESVIRUS SAIMIRI (STRAIN 11) | 9–36 | | | | | | | | |
| PUL74_HCMVA | HYPOTHETICAL PROTEIN UL74 | HUMAN CYTOMEGALOVIRUS (STRAIN AD169) | 45–79 | | | | | | | | |
| PUL87_EBV | HYPOTHETICAL PROTEIN B(C)RF1 | EPSTEIN-BARR VIRUS (STRAIN B95-8) | 409–436 | | | | | | | | |
| PUL87_HSV6U | HYPOTHETICAL PROTEIN 5R | HERPES SIMPLEX VIRUS (TYPE 6/STRAIN UGANDA-1102) | 536–563 | 729–768 | | | | | | | |
| PUL87_HSVSA | HYPOTHETICAL GENE 24 PROTEIN | HERPESVIRUS SAIMIRI (STRAIN 11) | 582–609 | | | | | | | | |
| PUL92_EBV | HYPOTHETICAL PROTEIN BDLF4 | EPSTEIN-BARR VIRUS (STRAIN B95-8) | 107–144 | 168–196 | | | | | | | |
| PUL92_HSVSA | HYPOTHETICAL GENE 31 PROTEIN | HERPESVIRUS SAIMIRI (STRAIN 11) | 92–122 | | | | | | | | |
| PUL93_HCMVA | PROTEIN UL93 | HUMAN CYTOMEGALOVIRUS (STRAIN AD169) | 26–53 | 314–381 | | | | | | | |
| PUL95_HCMVA | HYPOTHETICAL PROTEIN UL95 | HUMAN CYTOMEGALOVIRUS (STRAIN AD169) | 37–71 | 105–134 | | | | | | | |
| PUL95_HSV6U | HYPOTHETICAL PROTEIN 13R | HERPES SIMPLEX VIRUS (TYPE 6/STRAIN UGANDA-1102) | 73–100 | | | | | | | | |
| PULA4_HCMVA | VIRION PROTEIN UL104 | HUMAN CYTOMEGALOVIRUS (STRAIN AD169) | 4–31 | 443–477 | | | | | | | |
| PULB9_HCMVA | HYPOTHETICAL PROTEIN UL119 | HUMAN CYTOMEGALOVIRUS (STRAIN AD169) | 33–78 | | | | | | | | |
| PULD0_HCMVA | HYPOTHETICAL PROTEIN UL130 | HUMAN CYTOMEGALOVIRUS (STRAIN AD169) | 90–124 | | | | | | | | |
| PUNG_HSVSA | URACIL-DNA GLYCOSYLASE | HERPESVIRUS SAIMIRI (STRAIN 11) | 135–176 | | | | | | | | |
| PUNG_SFVKA | URACIL-DNA GLYCOSYLASE | SHOPE FIBROMA VIRUS (STRAIN KASZA) | 81–115 | | | | | | | | |
| PUNG_VACCC | URACIL-DNA GLYCOSYLASE | VACCINIA VIRUS (STRAIN COPENHAGEN) | 85–116 | 129–156 | | | | | | | |
| PUNG_VACCV | URACIL-DNA GLYCOSYLASE | VACCINIA VIRUS (STRAIN WR) | 85–116 | 129–156 | | | | | | | |
| PUNG_VARV | URACIL-DNA GLYCOSYLASE | VARIOLA VIRUS | 85–116 | | | | | | | | |
| PUS09_HCMVA | HYPOTHETICAL PROTEIN HXLF3 | HUMAN CYTOMEGALOVIRUS (STRAIN AD169) | 20–47 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUS14_HCMVA | HYPOTHETICAL PROTEIN HVLF4 | HUMAN CYTOMEGALOVIRUS (STRAIN AD169) | 277–308 | | | | | | | | |
| PUS18_HCMVA | MEMBRANE PROTEIN HWLF5 | HUMAN CYTOMEGALOVIRUS (STRAIN AD169) | 191–218 | | | | | | | | |
| PV121_ASFL5 | LIS 121-1 PROTEIN | AFRICAN SWINE FEVER VIRUS (STRAIN LIS57) | 2–29 | | | | | | | | |
| PV125_AMVLE | 125 KD PROTEIN | ALFALFA MOSAIC VIRUS (STRAIN 425/ISOLATE LEIDEN) | 702–729 | | | | | | | | |
| PV137_ASFL5 | LIS 137 PROTEIN | AFRICAN SWINE FEVER VIRUS (STRAIN LIS57) | 2–29 | | | | | | | | |
| PV13K_TRVPL | 16 KD PROTEIN | TOBACCO RATTLE VIRUS (STRAIN PLB) | 59–86 | | | | | | | | |
| PV143_NPVAC | HELICASE | AUTOGRAPHA CALIFORNICA NUCLEAR POLYHEDROSIS VIRUS | 496–560 | 945–972 | | | | | | | |
| PV16K_TRVPS | 16 KD PROTEIN | TOBACCO RATTLE VIRUS (STRAIN PSG) | 79–113 | | | | | | | | |
| PV1A_BBMV | 1A PROTEIN | BROAD BEAN MOTTLE VIRUS | 23–54 | 710–737 | 840–868 | | | | | | |
| PV1A_BMV | 1A PROTEIN | BROME MOSAIC VIRUS | 22–58 | 384–411 | 836–863 | 892–919 | | | | | |
| PV1A_CCMV | 1A PROTEIN | COWPEA CHLOROTIC MOTTLE VIRUS | 249–276 | | | | | | | | |
| PV1A_CMVFN | 1A PROTEIN | CUCUMBER MOSAIC VIRUS (STRAIN FNY) | 11–38 | | | | | | | | |
| PV1A_CMVO | 1A PROTEIN | CUCUMBER MOSAIC VIRUS (STRAIN O) | 11–38 | 864–902 | | | | | | | |
| PV1A_CMVQ | 1A PROTEIN | CUCUMBER MOSAIC VIRUS (STRAIN Q) | 11–38 | | | | | | | | |
| PV1A_PSVJ | 1A PROTEIN | PEANUT STUNT VIRUS (STRAIN J) | 4–38 | 372–399 | | | | | | | |
| PV1A_TAV | 1A PROTEIN | TOMATO ASPERMY VIRUS | 11–38 | 271–298 | 376–403 | 857–884 | | | | | |
| PV25K_NPVAC | 25 KD PROTEIN | AUTOGRAPHA CALIFORNICA NUCLEAR POLYHEDROSIS VIRUS | 4–31 | | | | | | | | |
| PV29K_PEBV | 29.6 KD PROTEIN | PEA EARLY BROWNING VIRUS | 140–170 | | | | | | | | |
| PV29K_TRVSY | 29 KD PROTEIN | TOBACCO RATTLE VIRUS | 170–197 | | | | | | | | |
| PV29K_TRVTC | 29 KD PROTEIN | TOBACCO RATTLE VIRUS (STRAIN TCM) | 48–75 | | | | | | | | |
| PV2A_BBMV | 2A PROTEIN | BROAD BEAN MOTTLE VIRUS | 301–328 | | | | | | | | |
| PV2A_CCMV | 2A PROTEIN | COWPEA CHLOROTIC MOTTLE VIRUS | 178–205 | | | | | | | | |
| PV2A_CMVFN | 2A PROTEIN | CUCUMBER MOSAIC VIRUS (STRAIN FNY) | 792–819 | | | | | | | | |
| PV2A_PSVJ | 2A PROTEIN | PEANUT STUNT VIRUS (STRAIN J) | 325–352 | 717–751 | | | | | | | |
| PV2A_TAV | 2A PROTEIN | TOMATO ASPERMY VIRUS | 313–340 | 722–756 | | | | | | | |
| PV30K_HCMVE | 30 KD MAJOR EARLY PROTEIN | HUMAN CYTOMEGALOVIRUS (STRAIN EISENHARDT) | 194–221 | | | | | | | | |
| PV30K_TRVTC | 29.1 KD PROTEIN | TOBACCO RATTLE VIRUS (STRAIN TCM) | 130–160 | | | | | | | | |
| PV33P_ADE41 | 33 KD PHOSPHOPROTEIN | HUMAN ADENOVIRUS TYPE 41 | 15–42 | | | | | | | | |
| PV362_ASFB7 | K362 PROTEIN | AFRICAN SWINE FEVER VIRUS (STRAIN BA71V) | 75–102 | 172–199 | | | | | | | |
| PV363_ASFB7 | D363 PROTEIN | AFRICAN SWINE FEVER VIRUS (STRAIN BA71V) | 3–30 | | | | | | | | |
| PV3A_BMV | 3A PROTEIN | BROME MOSAIC VIRUS | 11–38 | | | | | | | | |
| PV3A_CMVFN | 3A PROTEIN | CUCUMBER MOSAIC VIRUS (STRAIN FNY) | 222–252 | | | | | | | | |
| PV3A_CMVM | 3A PROTEIN | CUCUMBER MOSAIC VIRUS (STRAIN M) | 217–252 | | | | | | | | |
| PV3A_CMVO | 3A PROTEIN | CUCUMBER MOSAIC VIRUS (STRAIN O) | 222–253 | | | | | | | | |
| PV3A_CMVY | 3A PROTEIN | CUCUMBER MOSAIC VIRUS (STRAIN Y) | 222–253 | | | | | | | | |
| PV3A_IBVB | 3A PROTEIN | AVIAN INFECTIOUS BRONCHITIS VIRUS (STRAIN BEAUDETTE) | 25–57 | | | | | | | | |
| PV3A_IBVU5 | 3A PROTEIN | AVIAN INFECTIOUS BRONCHITIS VIRUS (STRAIN UK/183/66) | 29–56 | | | | | | | | |
| PV3B_IBVB | 3B PROTEIN | AVIAN INFECTIOUS BRONCHITIS VIRUS (STRAIN BEAUDETTE) | 6–33 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PV50K_BYDVP | 50 KD PROTEIN | BARLEY YELLOW DWARF VIRUS (ISOLATE PAV) | 119–146 | | | | | | | | |
| PV51K_BWYVF | 51 KD PROTEIN | BEET WESTERN YELLOWS VIRUS (ISOLATE FL-1) | 113–147 | 424–451 | | | | | | | |
| PV51K_BWYVG | 51 KD PROTEIN | BEET WESTERN YELLOWS VIRUS (ISOLATE GB1) | 113–147 | 424–451 | | | | | | | |
| PV56K_PLRV1 | 56 KD PROTEIN | POTATO LEAFROLL VIRUS (STRAIN 1) | 124–151 | 438–472 | | | | | | | |
| PV56K_PLRVW | 56 KD PROTEIN | POTATO LEAFROLL VIRUS (STRAIN WAGENINGEN) | 124–151 | 438–472 | | | | | | | |
| PV58K_BSMV | 58 KD PROTEIN | BARLEY STRIPE MOSAIC VIRUS | 128–155 | | | | | | | | |
| PV70K_PLRV1 | 69.7 KD PROTEIN | POTATO LEAFROLL VIRUS (STRAIN 1) | 110–140 | | | | | | | | |
| PV70K_PLRVW | 69.7 KD PROTEIN | POTATO LEAFROLL VIRUS (STRAIN WAGENINGEN) | 110–140 | | | | | | | | |
| PV90K_AMVLE | 90 KD PROTEIN | ALFALFA MOSAIC VIRUS (STRAIN 425/ ISOLATE LEIDEN) | 107–134 | | | | | | | | |
| PVA06_VACCC | PROTEIN A6 | VACCINIA VIRUS (STRAIN COPENHAGEN) | 157–216 | 250–277 | 283–310 | 314–355 | | | | | |
| PVA06_VACCV | PROTEIN A6 | VACCINIA VIRUS (STRAIN WR) | 156–215 | 249–276 | 282–309 | 313–354 | | | | | |
| PVA06_VARV | PROTEIN A6 | VARIOLA VIRUS | 157–216 | 250–277 | 283–310 | 314–355 | | | | | |
| PVA08_VACCC | PROTEIN A8 | VACCINIA VIRUS (STRAIN COPENHAGEN) | 176–206 | | | | | | | | |
| PVA08_VARV | PROTEIN A8 | VARIOLA VIRUS | 176–206 | | | | | | | | |
| PVA09_VARV | PROTEIN A9 | VARIOLA VIRUS | 60–95 | | | | | | | | |
| PVA11_VACCC | PROTEIN A11 | VACCINIA VIRUS (STRAIN COPENHAGEN) | 219–283 | | | | | | | | |
| PVA11_VARV | PROTEIN A11 | VARIOLA VIRUS | 220–284 | | | | | | | | |
| PVA18_VARV | 56 KD ABORTIVE LATE PROTEIN | VARIOLA VIRUS | 440–467 | | | | | | | | |
| PVA20_VACCC | PROTEIN A20 | VACCINIA VIRUS (STRAIN COPENHAGEN) | 8–67 | 330–357 | | | | | | | |
| PVA20_VARV | PROTEIN A20 | VARIOLA VIRUS | 8–67 | 330–357 | | | | | | | |
| PVA22_VACCC | PROTEIN A22 | VACCINIA VIRUS (STRAIN COPENHAGEN) | 45–72 | | | | | | | | |
| PVA22_VARV | PROTEIN A22 | VARIOLA VIRUS | 56–83 | | | | | | | | |
| PVA23_VACCC | PROTEIN A23 | VACCINIA VIRUS (STRAIN COPENHAGEN) | 95–144 | | | | | | | | |
| PVA23_VARV | PROTEIN A23 | VARIOLA VIRUS | 95–144 | | | | | | | | |
| PVA28_VACCV | PROTEIN A28 | VACCINIA VIRUS (STRAIN WR) | 22–49 | | | | | | | | |
| PVA28_VARV | PROTEIN A28 | VARIOLA VIRUS | 22–49 | | | | | | | | |
| PVA30_VACCC | PROTEIN A30 | VACCINIA VIRUS (STRAIN COPENHAGEN) | 12–55 | | | | | | | | |
| PVA31_VACCC | PROTEIN A31 | VACCINIA VIRUS (STRAIN COPENHAGEN) | 88–115 | | | | | | | | |
| PVA31_VARV | PROTEIN A31 | VARIOLA VIRUS | 88–122 | | | | | | | | |
| PVA34_VACCC | PROTEIN A34 | VACCINIA VIRUS (STRAIN COPENHAGEN) | 87–114 | | | | | | | | |
| PVA34_VACCV | PROTEIN A34 | VACCINIA VIRUS (STRAIN WR) | 87–114 | | | | | | | | |
| PVA34_VARV | PROTEIN A34 | VARIOLA VIRUS | 87–114 | | | | | | | | |
| PVA36_VACCV | PROTEIN A36 PRECURSOR | VACCINIA VIRUS (STRAIN WR) | 120–155 | | | | | | | | |
| PVA36_VARV | PROTEIN A36 PRECURSOR | VARIOLA VIRUS | 127–154 | | | | | | | | |
| PVA38_VACCC | PROTEIN A38 | VACCINIA VIRUS (STRAIN COPENHAGEN) | 44–81 | | | | | | | | |
| PVA38_VACCV | PROTEIN A38 | VACCINIA VIRUS (STRAIN WR) | 44–81 | | | | | | | | |
| PVA38_VARV | PROTEIN A38 | VARIOLA VIRUS | 44–91 | | | | | | | | |
| PVA39_VACCC | PROTEIN A39 | VACCINIA VIRUS (STRAIN COPENHAGEN) | 37–71 | 155–182 | | | | | | | |
| PVA39_VACCV | PROTEIN A39 | VACCINIA VIRUS (STRAIN WR) | 75–109 | 193–220 | | | | | | | |
| PVA43_VACCC | PROTEIN A43 | VACCINIA VIRUS (STRAIN COPENHAGEN) | 145–172 | | | | | | | | |
| PVA43_VACCV | PROTEIN A43 | VACCINIA VIRUS (STRAIN WR) | 145–172 | | | | | | | | |
| PVA43_VARV | PROTEIN A43 | VARIOLA VIRUS | 146–173 | | | | | | | | |
| PVA47_VACCC | PROTEIN A47 | VACCINIA VIRUS (STRAIN COPENHAGEN) | 143–184 | | | | | | | | |
| PVA47_VACCV | PROTEIN A47 | VACCINIA VIRUS (STRAIN WR) | 143–184 | | | | | | | | |
| PVA47_VARV | PROTEIN A47 | VARIOLA VIRUS | 142–184 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVA49_VACCC | PROTEIN A49 | VACCINIA VIRUS (STRAIN COPENHAGEN) | 61–91 | | | | | | | | |
| PVA49_VACCV | PROTEIN A49 | VACCINIA VIRUS (STRAIN WR) | 61–91 | | | | | | | | |
| PVA49_VARV | PROTEIN A49 | VARIOLA VIRUS | 61–91 | | | | | | | | |
| PVA55_VACCC | PROTEIN A55 | VACCINIA VIRUS (STRAIN COPENHAGEN) | 55–82 | 126–156 | 435–462 | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVB19_VACCD | SURFACE ANTIGEN S PRECURSOR | VACCINIA VIRUS (STRAIN DAIREN I) | 180–210 | | | | | | | | |
| PVB19_VACCV | SURFACE ANTIGEN S PRECURSOR | VACCINIA VIRUS (STRAIN WR) | 180–210 | | | | | | | | |
| PVB19_VARV | SURFACE ANTIGEN S PRECURSOR | VARIOLA VIRUS | 180–210 | | | | | | | | |
| PVB20_VACCC | PROTEIN B20 | VACCINIA VIRUS (STRAIN COPENHAGEN) | 48–82 | | | | | | | | |
| PVB21_VACCV | PROTEIN B21 | VACCINIA VIRUS (STRAIN WR) | 64–91 | | | | | | | | |
| PVBL1_BGMV | BL1 PROTEIN | BEAN GOLDEN MOSAIC VIRUS | 120–147 | 248–275 | | | | | | | |
| PVBL1_CLVK | BL1 PROTEIN | CASSAVA LATENT VIRUS (STRAIN WEST KENYAN 844) | 118–145 | | | | | | | | |
| PVBL1_CLVN | BL1 PROTEIN | CASSAVA LATENT VIRUS (STRAIN NIGERIAN) | 118–145 | | | | | | | | |
| PVBL1_PYMVV | BL1 PROTEIN | POTATO YELLOW MOSIAC VIRUS (ISOLATE VENEZUELA) | 120–147 | | | | | | | | |
| PVC02_VACCC | PROTEIN C2 | VACCINIA VIRUS (STRAIN COPENHAGEN) | 405–432 | | | | | | | | |
| PVC02_VACCV | PROTEIN C2 | VACCINIA VIRUS (STRAIN WR) | 41–71 | 405–432 | | | | | | | |
| PVC04_SFVKA | PROTEIN C4 | SHOPE FIBROMA VIRUS (STRAIN KASZA) | 209–236 | 484–515 | | | | | | | |
| PVC04_VACCC | PROTEIN C4 | VACCINIA VIRUS (STRAIN COPENHAGEN) | 12–46 | | | | | | | | |
| PVC04_VACCV | PROTEIN C4 | VACCINIA VIRUS (STRAIN WR) | 12–16 | | | | | | | | |
| PVC04_VARV | PROTEIN C4 | VARIOLA VIRUS | 12–46 | | | | | | | | |
| PVC05_SFVKA | HYPOTHETICAL PROTEIN C5 | SHOPE FIBROMA VIRUS (STRAIN KASZA) | 85–125 | 152–179 | | | | | | | |
| PVC05_VACCC | PROTEIN C5 | VACCINIA VIRUS (STRAIN COPENHAGEN) | 38–65 | | | | | | | | |
| PVC05_VACCV | PROTEIN C5 | VACCINIA VIRUS (STRAIN WR) | 38–65 | | | | | | | | |
| PVC05_VARV | PROTEIN C5 | VARIOLA VIRUS | 36–66 | | | | | | | | |
| PVC07_VACCV | PROTEIN C7 | VACCINIA VIRUS (STRAIN WR) | 80–111 | | | | | | | | |
| PVC07_VARV | PROTEIN C7 | VARIOLA VIRUS | 80–111 | | | | | | | | |
| PVC09_VACCC | PROTEIN C9 | VACCINIA VIRUS (STRAIN COPENHAGEN) | 42–69 | 82–116 | 178–205 | 252–279 | 289–325 | 575–605 | | | |
| PVC09_VACCV | PROTEIN C9 | VACCINIA VIRUS (STRAIN WR) | 42–69 | 82–116 | 178–205 | 252–279 | 289–325 | 575–605 | | | |
| PVC10_VACCC | PROTEIN C10 | VACCINIA VIRUS (STRAIN COPENHAGEN) | 136–180 | | | | | | | | |
| PVC10_VACCV | PROTEIN C10 | VACCINIA VIRUS (STRAIN WR) | 136–163 | | | | | | | | |
| PVC10_VARV | PROTEIN C10 | VARIOLA VIRUS | 136–163 | | | | | | | | |
| PVC13_SFVKA | PROTEIN C13 | SHOPE FIBROMA VIRUS (STRAIN KASZA) | 3–30 | 39–66 | 137–182 | 206–240 | | | | | |
| PVC17_VACCC | PROTEIN C17/B23 | VACCINIA VIRUS (STRAIN COPENHAGEN) | 111–152 | | | | | | | | |
| PVC18_VACCC | PROTEIN C18/B24 | VACCINIA VIRUS (STRAIN COPENHAGEN) | 40–74 | | | | | | | | |
| PVC19_SFVKA | PROTEIN C19 | SHOPE FIBROMA VIRUS (STRAIN KASZA) | 56–97 | | | | | | | | |
| PVC20_VACCC | PROTEIN C20/B26 | VACCINIA VIRUS (STRAIN COPENHAGEN) | 72–99 | | | | | | | | |
| PVC22_VARV | PROTEIN C22/B28 HOMOLOG | VARIOLA VIRUS | 299–326 | | | | | | | | |
| PVCAP_EBV | MAJOR CAPSID PROTEIN | EPSTEIN-BARR VIRUS (STRAIN B95-8) | 847–874 | | | | | | | | |
| PVCAP_HSV6U | MAJOR CAPSID PROTEIN | HERPES SIMPLEX VIRUS (TYPE 6/STRAIN UGANDA-1102) | 136–170 | 355–382 | | | | | | | |
| PVCAP_HSVSA | MAJOR CAPSID PROTEIN | HERPESVIRUS SAIMIRI (STRAIN 11) | 769–799 | | | | | | | | |
| PVCG3_NPVAC | DNA-BINDING PROTEIN | AUTOGRAPHA CALIFORNICA NUCLEAR POLYHEDROSIS VIRUS | 133–165 | 199–248 | | | | | | | |
| PVCOM_ADE02 | MINOR CORE PROTEIN | HUMAN ADENOVIRUS TYPE 2 | 88–115 | | | | | | | | |
| PVCOM_ADE05 | MINOR CORE PROTEIN | HUMAN ADENOVIRUS TYPE 5 | 87–114 | | | | | | | | |
| PVD05_FOWP1 | 92.6 KD PROTEIN | FOWLPOX VIRUS (STRAIN FP-1) | 6–33 | 184–211 | 321–348 | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVD05_VACCC | PROTEIN D5 | VACCINIA VIRUS (STRAIN COPENHAGEN) | 240–267 | 333–360 | | | | | | | |
| PVD05_VACCV | PROTEIN D5 | VACCINIA VIRUS (STRAIN WR) | 240–267 | | | | | | | | |
| PVD05_VARV | PROTEIN D5 | VARIOLA VIRUS | 240–267 | | | | | | | | |
| PVD09_VACCC | PROTEIN D9 | VACCINIA VIRUS (STRAIN COPENHAGEN) | 123–150 | | | | | | | | |
| PVD09_VACCV | PROTEIN D9 | VACCINIA VIRUS (STRAIN WR) | 123–150 | | | | | | | | |
| PVD09_VARV | PROTEIN D9 | VARIOLA VIRUS | 123–160 | | | | | | | | |
| PVD10_SFVKA | PROTEIN D10 | SHOPE FIBROMA VIRUS (STRAIN KASZA) | 18–52 | | | | | | | | |
| PVDBP_CERV | DNA-BINDING PROTEIN | CARNATION ETCHED RING VIRUS | 2–35 | | | | | | | | |
| PVE02_VARV | PROTEIN E2 | VARIOLA VIRUS | 282–322 | | | | | | | | |
| PVE06_VACCC | PROTEIN E6 | VACCINIA VIRUS (STRAIN COPENHAGEN) | 89–116 | 437–464 | | | | | | | |
| PVE06_VACCV | PROTEIN E6 | VACCINIA VIRUS (STRAIN WR) | 89–116 | 437–464 | | | | | | | |
| PVE06_VARV | PROTEIN E6 | VARIOLA VIRUS | 89–116 | 367–394 | 437–464 | | | | | | |
| PVE1_HPV18 | E1 PROTEIN | HUMAN PAPILLOMAVIRUS TYPE 18 | 60–87 | | | | | | | | |
| PVE1_HPV2A | E1 PROTEIN | HUMAN PAPILLOMAVIRUS TYPE 2A | 21–48 | | | | | | | | |
| PVE1_HPV33 | E1 PROTEIN | HUMAN PAPILLOMAVIRUS TYPE 33 | 180–207 | | | | | | | | |
| PVE1_HPV39 | E1 PROTEIN | HUMAN PAPILLOMAVIRUS TYPE 39 | 103–130 | | | | | | | | |
| PVE1_HPV41 | E1 PROTEIN | HUMAN PAPILLOMAVIRUS TYPE 41 | 55–89 | | | | | | | | |
| PVE1_HPV42 | E1 PROTEIN | HUMAN PAPILLOMAVIRUS TYPE 42 | 25–59 | | | | | | | | |
| PVE1_HPV47 | E1 PROTEIN | HUMAN PAPILLOMAVIRUS TYPE 47 | 146–173 | | | | | | | | |
| PVE1_HPV57 | E1 PROTEIN | HUMAN PAPILLOMAVIRUS TYPE 57 | 21–48 | | | | | | | | |
| PVE26_NPVAC | EARLY 25.9 KD PROTEIN | AUTOGRAPHA CALIFORNICA NUCLEAR POLYHEDROSIS VIRUS | 72–113 | | | | | | | | |
| PVE2_CRPVK | PROBABLE E2 PROTEIN | COTTONTAIL RABBIT (SHOPE) PAPILLOMAVIRUS (STRAIN KANSAS) | 5–34 | | | | | | | | |
| PVE2_HPV05 | E2 PROTEIN | HUMAN PAPILLOMAVIRUS TYPE 5 | 17–51 | | | | | | | | |
| PVE2_HPV13 | E2 PROTEIN | HUMAN PAPILLOMAVIRUS TYPE 13 | 157–184 | 334–361 | | | | | | | |
| PVE2_HPV16 | E2 PROTEIN | HUMAN PAPILLOMAVIRUS TYPE 16 | 61–105 | 312–342 | | | | | | | |
| PVE2_HPV18 | E2 PROTEIN | HUMAN PAPILLOMAVIRUS TYPE 18 | 313–340 | | | | | | | | |
| PVE2_HPV1A | E2 PROTEIN | HUMAN PAPILLOMAVIRUS TYPE 1A | 159–186 | | | | | | | | |
| PVE2_HPV2A | E2 PROTEIN | HUMAN PAPILLOMAVIRUS TYPE 2A | 159–193 | | | | | | | | |
| PVE2_HPV33 | E2 PROTEIN | HUMAN PAPILLOMAVIRUS TYPE 33 | 304–331 | 327–354 | | | | | | | |
| PVE2_HPV35 | E2 PROTEIN | HUMAN PAPILLOMAVIRUS TYPE 35 | 158–192 | 323–357 | | | | | | | |
| PVE2_HPV39 | E2 PROTEIN | HUMAN PAPILLOMAVIRUS TYPE 39 | 7–34 | 148–175 | 276–303 | | | | | | |
| PVE2_HPV47 | E2 PROTEIN | HUMAN PAPILLOMAVIRUS TYPE 47 | 17–51 | | | | | | | | |
| PVE2_HPV51 | E2 PROTEIN | HUMAN PAPILLOMAVIRUS TYPE 51 | 137–184 | | | | | | | | |
| PVE2_HPV57 | E2 PROTEIN | HUMAN PAPILLOMAVIRUS TYPE 57 | 166–193 | | | | | | | | |
| PVE2_HPV58 | E2 PROTEIN | HUMAN PAPILLOMAVIRUS TYPE 58 | 2–36 | 309–336 | | | | | | | |
| PVE2_HPV5B | PROBABLE E2 PROTEIN | HUMAN PAPILLOMAVIRUS TYPE 5B | 17–51 | | | | | | | | |
| PVE2_PAPVE | PROBABLE E2 PROTEIN | EUROPEAN ELK PAPILLOMAVIRUS | 120–150 | | | | | | | | |
| PVE2_PCPV1 | E2 PROTEIN | PYGMY CHIMPANZEE PAPILLOMAVIRUS TYPE 1 | 267–294 | 327–361 | | | | | | | |
| PVE4_HPV05 | PROBABLE E4 PROTEIN | HUMAN PAPILLOMAVIRUS TYPE 5 | 202–229 | | | | | | | | |
| PVE4_HPV11 | PROBABLE E4 PROTEIN | HUMAN PAPILLOMAVIRUS TYPE 11 | 81–108 | | | | | | | | |
| PVE4_HPV16 | PROBABLE E4 PROTEIN | HUMAN PAPILLOMAVIRUS TYPE 16 | 66–93 | | | | | | | | |
| PVE4_HPV18 | PROBABLE E4 PROTEIN | HUMAN PAPILLOMAVIRUS TYPE 18 | 59–86 | | | | | | | | |
| PVE4_HPV31 | PROBABLE E4 PROTEIN | HUMAN PAPILLOMAVIRUS TYPE 31 | 75–102 | | | | | | | | |
| PVE4_HPV41 | PROBABLE E4 PROTEIN | HUMAN PAPILLOMAVIRUS TYPE 41 | 63–97 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVE4_HPV5B | PROBABLE E4 PROTEIN | HUMAN PAPILLOMAVIRUS TYPE 5B | 202–229 | | | | | | | | |
| PVE5A_HPV11 | PROBABLE E5A PROTEIN | HUMAN PAPILLOMAVIRUS TYPE 11 | 30–60 | | | | | | | | |
| PVE5A_HPV6B | PROBABLE E5A PROTEIN | HUMAN PAPILLOMAVIRUS TYPE 6B | 30–60 | | | | | | | | |
| PVE5A_HPV6C | PROBABLE E5A PROTEIN | HUMAN PAPILLOMAVIRUS TYPE 6C | 30–60 | | | | | | | | |
| PVE5_HPV35 | PROBABLE E5 PROTEIN | HUMAN PAPILLOMAVIRUS TYPE 35 | 27–54 | | | | | | | | |
| PVE5_HPV5B | PROBABLE E5 PROTEIN | HUMAN PAPILLOMAVIRUS TYPE 5B | 11–41 | | | | | | | | |
| PVE5_PCPV1 | PROBABLE E5 PROTEIN | PYGMY CHIMPANZEE PAPILLOMAVIRUS TYPE 1 | 35–62 | | | | | | | | |
| PVE6_HPV18 | E6 PROTEIN | HUMAN PAPILLOMAVIRUS TYPE 18 | 75–102 | | | | | | | | |
| PVE6_HPV31 | E6 PROTEIN | HUMAN PAPILLOMAVIRUS TYPE 31 | 69–96 | | | | | | | | |
| PVE6_HPV39 | E6 PROTEIN | HUMAN PAPILLOMAVIRUS TYPE 39 | 71–102 | | | | | | | | |
| PVE6_HPV41 | E6 PROTEIN | HUMAN PAPILLOMAVIRUS TYPE 41 | 119–146 | | | | | | | | |
| PVE6_HPV45 | E6 PROTEIN | HUMAN PAPILLOMAVIRUS TYPE 45 | 75–102 | | | | | | | | |
| PVE6_HPV51 | E6 PROTEIN | HUMAN PAPILLOMAVIRUS TYPE 51 | 72–99 | | | | | | | | |
| PVE6_HPVME | E6 PROTEIN | HUMAN PAPILLOMAVIRUS TYPE ME180 | 71–102 | | | | | | | | |
| PVE94_NPVAC | EARLY 94 KD PROTEIN | AUTOGRAPHA CALIFORNICA NUCLEAR POLYHEDROSIS VIRUS | 620–647 | | | | | | | | |
| PVEF_GVTN | VIRAL ENHANCING FACTOR | TRICHOPLUSIA NI GRANULOSIS VIRUS | 411–438 | | | | | | | | |
| PVENV_DHV11 | ENVELOPE GLYCOPROTEIN PRECURSOR | DHORI VIRUS (STRAIN INDIAN/1313/61) | 318–366 | | | | | | | | |
| PVENV_EAV | PROBABLE ENVELOPE PROTEIN | EQUINE ARTERITIS VIRUS | 120–147 | | | | | | | | |
| PVENV_THOGV | ENVELOPE GLYCOPROTEIN PRECURSOR | THOGOTO VIRUS | 313–347 | | | | | | | | |
| PVF03_VACCC | PROTEIN F3 | VACCINIA VIRUS (STRAIN COPENHAGEN) | 71–110 | 185–212 | | | | | | | |
| PVF03_VACCV | PROTEIN F3 | VACCINIA VIRUS (STRAIN WR) | 71–110 | 185–212 | | | | | | | |
| PVF05_VACCP | 36 KD MAJOR MEMBRANE PRO PRECURSO | VACCINIA VIRUS (STRAIN L-IVP) | 33–60 | | | | | | | | |
| PVF05_VACCV | 36 KD MAJOR MEMBRANE PRO PRECURSO | VACCINIA VIRUS (STRAIN WR) | 33–60 | | | | | | | | |
| PVF06_VARV | PROTEIN F6 | VARIOLA VIRUS | 10–44 | | | | | | | | |
| PVF11_VACCC | PROTEIN F11 | VACCINIA VIRUS (STRAIN COPENHAGEN) | 274–321 | | | | | | | | |
| PVF11_VACCP | PROTEIN F11 | VACCINIA VIRUS (STRAIN L-IVP) | 270–317 | | | | | | | | |
| PVF11_VARV | PROTEIN F11 | VARIOLA VIRUS | 274–321 | | | | | | | | |
| PVF12_VACCC | PROTEIN F12 | VACCINIA VIRUS (STRAIN COPENHAGEN) | 10–37 | 113–140 | 554–581 | | | | | | |
| PVF12_VACCP | PROTEIN F12 | VACCINIA VIRUS (STRAIN L-IVP) | 10–37 | 113–140 | 554–581 | | | | | | |
| PVF12_VARV | PROTEIN F12 | VARIOLA VIRUS | 10–37 | 202–236 | 554–581 | | | | | | |
| PVF16_VACCC | PROTEIN F16 | VACCINIA VIRUS (STRAIN COPENHAGEN) | 35–62 | 152–179 | | | | | | | |
| PVF16_VACCP | PROTEIN F16 | VACCINIA VIRUS (STRAIN L-IVP) | 35–62 | 152–179 | | | | | | | |
| PVF16_VARV | PROTEIN F16 | VARIOLA VIRUS | 146–173 | 149–179 | | | | | | | |
| PVFP4_FOWPV | PROTEIN FP4 | FOWLPOX VIRUS | 59–86 | | | | | | | | |
| PVFUS_ORNFNZ | 10 KD FUSION PROTEIN | ORF VIRUS (STRAIN NZ2) | 37–64 | | | | | | | | |
| PVFUS_VACCC | 14 KD FUSION PROTEIN | VACCINIA VIRUS (STRAIN COPENHAGEN) | 37–64 | | | | | | | | |
| PVFUS_VACCV | KD FUSION PROTEIN | VACCINIA VIRUS (STRAIN WR) | 225–252 | 301–335 | | | | | | | |
| PVG01_VACCC | PROTEIN G1 | VACCINIA VIRUS (STRAIN COPENHAGEN) | 164–191 | 240–274 | | | | | | | |
| PVG01_VACCV | PROTEIN G1 | VACCINIA VIRUS (STRAIN WR) | 225–252 | 301–335 | | | | | | | |
| PVG01_VARV | PROTEIN G1 | VARIOLA VIRUS | 96–123 | | | | | | | | |
| PVG02_VACCV | ISATIN-B-TSC DEP PROTEIN | VACCINIA VIRUS (STRAIN WR) | | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVG02_VARV | ISATIN-B-TSC DEP PROTEIN | VARIOLA VIRUS | 96–123 | | | | | | | | |
| PVG03_HSVEB | GENE 3 PROTEIN | EQUINE HERPESVIRUS TYPE 1 (STRAIN AB4P) | 146–176 | | | | | | | | |
| PVG03_HSVEK | GENE 3 PROTEIN | EQUINE HERPESVIRUS TYPE 1 (STRAIN KENTUCKY A) | 146–176 | | | | | | | | |
| PVG05_VACCC | PROTEIN G5 | VACCINIA VIRUS (STRAIN COPENHAGEN) | 48–75 | 131–161 | 225–289 | 355–389 | | | | | |
| PVG05_VARV | PROTEIN G5 | VARIOLA VIRUS | 48–75 | 124–161 | 255–289 | 355–389 | | | | | |
| PVG07_HSVI1 | HYPOTH GENE 7 MEMB PRO | ICTALURID HERPESVIRUS 1 | 71–98 | | | | | | | | |
| PVG09_VACCC | PROTEIN F1 | VACCINIA VIRUS (STRAIN COPENHAGEN) | 308–338 | | | | | | | | |
| PVG09_VACCV | PROTEIN F1 | VACCINIA VIRUS (STRAIN WR) | 271–301 | | | | | | | | |
| PVG09_VARV | PROTEIN F1 | VARIOLA VIRUS | 308–338 | | | | | | | | |
| PVG12_SPVIR | GENE 12 PROTEIN | SPIROPLASMA VIRUS SPV1-R8A2 B | 11–45 | | | | | | | | |
| PVG17_HSVI1 | HYPOTHETICAL GENE 17 PROTEIN | ICTALURID HERPESVIRUS 1 | 177–204 | | | | | | | | |
| PVG18_HSVI1 | HYPOTHETICAL GENE 18 PROTEIN | ICTALURID HERPESVIRUS 1 | 174–208 | | | | | | | | |
| PVG1_SPVIR | CAPSID PROTEIN | SPIROPLASMA VIRUS SPV1-R8A2 B | 260–287 | | | | | | | | |
| PVG1_SPV4 | CAPSID PROTEIN | SPIROPLASMA VIRUS 4 | 287–314 | 383–410 | | | | | | | |
| PVG22_HSVI1 | HYPOTHETICAL GENE 22 PROTEIN | ICTALURID HERPESVIRUS 1 | 373–400 | 581–622 | 668–705 | 766–824 | | | | | |
| PVG24_HSVI1 | HYPOTHETICAL GENE 24 PROTEIN | ICTALURID HERPESVIRUS 1 | 31–58 | | | | | | | | |
| PVG28_HSVI1 | HYPOTHETICAL GENE 28 PROTEIN | ICTALURID HERPESVIRUS 1 | 253–290 | 497–528 | | | | | | | |
| PVG2R_AMEPV | HYPOTHETICAL G2R PROTEIN | AMSACTA MOOREI ENTOMOPOXVIRUS | 33–64 | 91–118 | | | | | | | |
| PVG2_SPVIR | GENE 2 PROTEIN | SPIROPLASMA VIRUS SPV1-R8A2 B | 285–326 | | | | | | | | |
| PVG2_SPV4 | GENE 2 PROTEIN | SPIROPLASMA VIRUS 4 | 146–173 | 175–205 | 262–310 | | | | | | |
| PVG34_HSVI1 | HYPOTHETICAL GENE 34 PROTEIN | ICTALURID HERPESVIRUS 1 | 95–122 | | | | | | | | |
| PVG37_HSVI1 | HYPOTHETICAL GENE 37 PROTEIN | ICTALURID HERPESVIRUS 1 | 442–469 | | | | | | | | |
| PVG39_HSVI1 | HYPOTHETICAL GENE 39 PROTEIN | ICTALURID HERPESVIRUS 1 | 651–678 | 1088–1115 | | | | | | | |
| PVG3L_AMEPV | HYPOTHETICAL G3L PROTEIN | AMSACTA MOOREI ENTOMOPOXVIRUS | 2–29 | | | | | | | | |
| PVG3_SPVIR | GENE 3 PROTEIN | SPIROPLASMA VIRUS SPV1-R8A2 B | 15–49 | | | | | | | | |
| PVG3_SPV4 | GENE 3 PROTEIN | SPIROPLASMA VIRUS 4 | 18–52 | 87–148 | | | | | | | |
| PVG45_HSVSA | HYPOTHETICAL GENE 45 PROTEIN | HERPESVIRUS SAIMIRI (STRAIN 11) | 138–165 | | | | | | | | |
| PVG46_HSVI1 | PROBABLE MAJOR GLYCOPROTEIN | ICTALURID HERPESVIRUS 1 | 142–169 | 346–373 | 897–924 | 973–1007 | | | | | |
| PVG48_HSVSA | HYPOTHETICAL GENE 48 PROTEIN | HERPESVIRUS SAIMIRI (STRAIN 11) | 360–394 | | | | | | | | |
| PVG4R_AMEPV | G4R PROTEIN | AMSACTA MOOREI ENTOMOPOXVIRUS | 4–31 | | | | | | | | |
| PVG4_SPVIR | GENE 4 PROTEIN | SPIROPLASMA VIRUS SPV1-R8A2 B | 116–146 | | | | | | | | |
| PVG51_HSVI1 | HYPOTH GENE 51 MEMBRANE PROTEIN | ICTALURID HERPESVIRUS 1 | 34–61 | 87–114 | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVG52_HSVSA | HYPOTHETICAL GENE 52 PROTEIN | HERPESVIRUS SAIMIRI (STRAIN 11) | 47–74 | | | | | | | | |
| PVG56_HSVI1 | HYPOTHETICAL GENE 56 PROTEIN | ICTALURID HERPESVIRUS 1 | 582–609 | | | | | | | | |
| PVG5_SPV1R | GENE 5 PROTEIN | SPIROPLASMA VIRUS SPV1-R8A2 B | 65–92 | | | | | | | | |
| PVG5_SPV4 | GENE 5 PROTEIN | SPIROPLASMA VIRUS 4 | 56–83 | | | | | | | | |
| PVG63_HSVI1 | HYPOTHETICAL GENE 63 PROTEIN | ICTALURID HERPESVIRUS 1 | 550–584 | | | | | | | | |
| PVG64_HSVI1 | HYPOTHETICAL GENE 64 PROTEIN | ICTALURID HERPESVIRUS 1 | 447–504 | | | | | | | | |
| PVG65_HSVI1 | HYPOTHETICAL GENE 65 PROTEIN | ICTALURID HERPESVIRUS 1 | 1213–1254 | | | | | | | | |
| PVG66_HSVI1 | HYPOTHETICAL GENE 66 PROTEIN | ICTALURID HERPESVIRUS 1 | 362–406 | | | | | | | | |
| PVG67_HSVI1 | HYPOTHETICAL GENE 67 PROTEIN | ICTALURID HERPESVIRUS 1 | 1342–1369 | | | | | | | | |
| PVG68_HSVI1 | HYPOTHETICAL GENE 68 PROTEIN | ICTALURID HERPESVIRUS 1 | 261–288 | | | | | | | | |
| PVG72_HSVI1 | HYPOTHETICAL GENE 72 PROTEIN | ICTALURID HERPESVIRUS 1 | 447–481 | | | | | | | | |
| PVG75_HSVI1 | HYPOTHETICAL GENE 75 PROTEIN | ICTALURID HERPESVIRUS 1 | 388–422 | | | | | | | | |
| PVG76_HSVI1 | HYPOTHETICAL GENE 76 PROTEIN | ICTALURID HERPESVIRUS 1 | 200–227 | | | | | | | | |
| PVG7_SPV4 | GENE 7 PROTEIN | SPIROPLASMA VIRUS 4 | 14–44 | | | | | | | | |
| PVGF1_IBVB | F1 PROTEIN | AVIAN INFECTIOUS BRONCHITIS VIRUS | 1230–1260 | 2408–2435 | | | | | | | |
| PVGL2_CVBF | E2 GLYCOPROTEIN PRECURSOR | BOVINE CORONAVIRUS (STRAIN F15) | 399–426 | 642–676 | 1022–1084 | 1278–1305 | | | | | |
| PVGL2_CVBL9 | E2 GLYCOPROTEIN PRECURSOR | BOVINE CORONAVIRUS (STRAIN L9) | 399–426 | | 1022–1084 | 1278–1305 | | | | | |
| PVGL2_CVBLY | E2 GLYCOPROTEIN PRECURSOR | BOVINE CORONAVIRUS (STRAIN LY-138) | 399–426 | 642–676 | 1022–1084 | 1278–1305 | | | | | |
| PVGL2_CVBM | E2 GLYCOPROTEIN PRECURSOR | BOVINE CORONAVIRUS (STRAIN MEBUS) | 399–426 | 642–676 | 1022–1084 | 1278–1305 | | | | | |
| PVGL2_CVBQ | E2 GLYCOPROTEIN PRECURSOR | BOVINE CORONAVIRUS (STRAIN QUEBEC) | 399–426 | 642–676 | 1022–1084 | 1278–1305 | | | | | |
| PVGL2_CVBV | E2 GLYCOPROTEIN PRECURSOR | BOVINE CORONAVIRUS (STRAIN VACCINE) | 399–426 | 642–676 | 1022–1084 | 1278–1305 | | | | | |
| PVGL2_CVH22 | E2 GLYCOPROTEIN PRECURSOR | HUMAN CORONAVIRUS (STRAIN 229E) | 770–797 | 809–875 | 1056–1112 | | | | | | |
| PVGL2_CVM4 | E2 GLYCOPROTEIN PRECURSOR | MURINE CORONAVIRUS MHV (STRAIN WILD TYPE 4) | 643–684 | 1030–1092 | | | | | | | |
| PVGL2_CVMA5 | E2 GLYCOPROTEIN PRECURSOR | MURINE CORONAVIRUS MHV (STRAIN A59) | 36–63 | 591–632 | 978–1040 | | | | | | |
| PVGL2_CVMJC | E2 GLYCOPROTEIN PRECURSOR | MURINE CORONAVIRUS MHV (STRAIN JHMV/VARIANT CL-2) | 643–684 | 1030–1092 | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGL2_CVMJH | E2 GLYCOPROTEIN PRECURSOR | MURINE CORONAVIRUS MHV (STRAIN JHM) | 502–543 | 889–951 | | | | | | | |
| PVGL2_CVPFS | E2 GLYCOPROTEIN PRECURSOR | PORCINE TRANSMISSIBLE GASTROENTERITIS CORONAVIRUS (STRAIN FS722 | 69–110 | 692–733 | 1072–1145 | 1353–1389 | | | | | |
| PVGL2_CVPM1 | E2 GLYCOPROTEIN PRECURSOR | PORCINE TRANSMISSIBLE GASTROENTERITIS CORONAVIRUS (STRAIN MILLE | 69–110 | 692–733 | 1069–1145 | 1353–1389 | | | | | |
| PVGL2_CVPPR | E2 GLYCOPROTEIN PRECURSOR | PORCINE TRANSMISSIBLE GASTROENTERITIS CORONAVIRUS (STRAIN PUR46 | 73–107 | 690–731 | 1067–1143 | 1351–1387 | | | | | |
| PVGL2_CVPPU | E2 GLYCOPROTEIN PRECURSOR | PORCINE TRANSMISSIBLE GASTROENTERITIS CORONAVIRUS (STRAIN PURD | 69–107 | 690–731 | 1067–1143 | 1351–1387 | | | | | |
| PVGL2_CVPR8 | E2 GLYCOPROTEIN PRECURSOR | PORCINE RESPIRATORY CORONAVIRUS (STRAIN 86/137004/BRITISH ISOLAT | 468–509 | 845–921 | 1129–1165 | | | | | | |
| PVGL2_CVPRM | E2 GLYCOPROTEIN PRECURSOR | PORCINE RESPIRATORY CORONAVIRUS (STRAIN RM4) | 468–509 | 845–921 | 1129–1165 | | | | | | |
| PVGL2_CVPRT | E2 GLYCOPROTEIN PRECURSOR | PORCINE TRANSMISSIBLE GASTROENTERITIS CORONAVIRUS (STRAIN NEB72 | 69–107 | 690–731 | 1067–1143 | 1353–1387 | | | | | |
| PVGL2_EBV | PROBABLE MEMBRANE GLYCOPROTEIN | EPSTEIN-BARR VIRUS (STRAIN B95-8) | 68–102 | | | | | | | | |
| PVGL2_FIPV | E2 GLYCOPROTEIN PRECURSOR | FELINE INFECTIOUS PERITONITIS VIRUS (STRAIN 79-1146) | 189–233 | 454–481 | 709–736 | 1072–1148 | 1356–1392 | | | | |
| PVGL2_IBV6 | E2 GLYCOPROTEIN PRECURSOR | AVIAN INFECTIOUS BRONCHITIS VIRUS (STRAIN 6/82) | 809–836 | 876–903 | 1057–1091 | | | | | | |
| PVGL2_IBVB | E2 GLYCOPROTEIN PRECURSOR | AVIAN INFECTIOUS BRONCHITIS VIRUS (STRAIN BEAUDETTE) | 808–835 | 875–902 | 1056–1090 | | | | | | |
| PVGL2_IBVD2 | E2 GLYCOPROTEIN PRECURSOR | AVIAN INFECTIOUS BRONCHITIS VIRUS (STRAIN D274) | 809–836 | 876–903 | 1057–1091 | | | | | | |
| PVGL2_IBVK | E2 GLYCOPROTEIN PRECURSOR | AVIAN INFECTIOUS BRONCHITIS VIRUS (STRAIN KB8523) | 808–835 | 875–902 | 1056–1090 | | | | | | |
| PVGL2_IBVM | E2 GLYCOPROTEIN PRECURSOR | AVIAN INFECTIOUS BRONCHITIS VIRUS (STRAIN M41) | 808–835 | 875–902 | 1056–1090 | | | | | | |
| PVGLB_EBV | GLYCOPROTEIN GP110 PRECURSOR | EPSTEIN-BARR VIRUS (STRAIN B95-8) | 95–122 | 631–658 | | | | | | | |
| PVGLB_HCMVA | GLYCOPROTEIN B PRECURSOR | HUMAN CYTOMEGALOVIRUS (STRAIN AD169) | 25–88 | 397–424 | 440–467 | 851–878 | | | | | |
| PVGLB_HCMVT | GLYCOPROTEIN B PRECURSOR | HUMAN CYTOMEGALOVIRUS (STRAIN TOWNE) | 50–88 | 397–424 | 435–462 | 852–879 | | | | | |
| PVGLB_HSVB1 | GLYCOPROTEIN 1 PRECURSOR | BOVINE HERPESVIRUS TYPE 1 | 427–454 | | | | | | | | |
| PVGLB_HSVB2 | GLYCOPROTEIN B-1 PRECURSOR | BOVINE HERPESVIRUS TYPE 2 (STRAIN BMV) | 447–474 | | | | | | | | |
| PVGLB_HSVE1 | GLYCOPROTEIN B PRECURSOR | EQUINE HERPESVIRUS TYPE 1 (ISOLATE HVS25A) | 443–470 | 934–961 | | | | | | | |
| PVGLB_HSVE4 | GLYCOPROTEIN B PRECURSOR | EQUINE HERPESVIRUS TYPE 4 | 486–513 | 616–643 | | | | | | | |
| PVGLB_HSVEA | GLYCOPROTEIN B PRECURSOR | EQUINE HERPESVIRUS TYPE 1 (STRAIN AB1) | 443–470 | 934–961 | | | | | | | |
| PVGLB_HSVEB | GLYCOPROTEIN B PRECURSOR | EQUINE HERPESVIRUS TYPE 1 (STRAIN AB4P) | 443–470 | 934–961 | | | | | | | |
| PVGLB_HSVEL | GLYCOPROTEIN B PRECURSOR | EQUINE HERPESVIRUS TYPE 1 (STRAIN KENTUCKY D) | 443–470 | 933–960 | | | | | | | |
| PVGLB_HSVMD | GLYCOPROTEIN B PRECURSOR | MAREK'S DISEASE HERPESVIRUS (STRAIN RB-1B) | 93–120 | 352–379 | | | | | | | |
| PVGLB_MCMVS | GLYCOPROTEIN B PRECURSOR | MURINE CYTOMEGALOVIRUS (STRAIN SMITH) | 381–408 | 441–475 | | | | | | | |
| PVGLC_HSV11 | GLYCOPROTEIN C PRECURSOR | HERPES SIMPLEX VIRUS (TYPE 1/STRAIN 17) | 469–510 | | | | | | | | |
| PVGLC_HSV1K | GLYCOPROTEIN C PRECURSOR | HERPES SIMPLEX VIRUS (TYPE 1/STRAIN KOS) | 469–510 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLC_HSVEB | GLYCOPROTEIN C PRECURSOR | EQUINE HERPESVIRUS TYPE 1 | 124–151 | | | | | | | | |
| PVGLC_VZVD | GLYCOPROTEIN GPV | VARICELLA-ZOSTER VIRUS (STRAIN DUMAS) | 295–322 | | | | | | | | |
| PVGLC_VZVS | GLYCOPROTEIN GPV | VARICELLA-ZOSTER VIRUS (STRAIN SCOTT) | 295–322 | | | | | | | | |
| PVGLE_HSV2 | GLYCOPROTEIN E PRECURSOR | HERPES SIMPLEX VIRUS (TYPE 2) | 111–148 | | | | | | | | |
| PVGLF_BRSVA | FUSION GLYCOPROTEIN PRECURSOR | BOVINE RESPIRATORY SYNCYTIAL VIRUS (STRAIN A51908) | 38–65 | 154–202 | 216–243 | 442–469 | 486–531 | | | | |
| PVGLF_BRSVC | FUSION GLYCOPROTEIN PRECURSOR | BOVINE RESPIRATORY SYNCYTIAL VIRUS (STRAIN COPENHAGEN) | 38–65 | 154–202 | 216–243 | 444–471 | 488–533 | | | | |
| PVGLF_BRSVR | FUSION GLYCOPROTEIN PRECURSOR | BOVINE RESPIRATORY SYNCYTIAL VIRUS (STRAIN RB94) | 38–65 | 154–202 | 216–243 | 444–471 | 488–533 | | | | |
| PVGLF_CDVO | FUSION GLYCOPROTEIN PRECURSOR | CANINE DISTEMPER VIRUS (STRAIN ONDERSTEPOORT) | 252–293 | 340–367 | | | | | | | |
| PVGLF_HRSV1 | FUSION GLYCOPROTEIN PRECURSOR | HUMAN RESPIRATORY SYNCYTIAL VIRUS (SUBGROUP B/STRAIN 18537) | 38–65 | 154–203 | 442–471 | 488–515 | | | | | |
| PVGLF_HRSVA | FUSION GLYCOPROTEIN PRECURSOR | HUMAN RESPIRATORY SYNCYTIAL VIRUS (STRAIN A2) | 38–65 | 154–202 | 213–243 | 488–518 | | | | | |
| PVGLF_HRSVL | FUSION GLYCOPROTEIN PRECURSOR | HUMAN RESPIRATORY SYNCYTIAL VIRUS (SUBGROUP A/STRAIN LONG) | 38–65 | 154–202 | 216–243 | 444–471 | 488–515 | | | | |
| PVGLF_HRSVR | FUSION GLYCOPROTEIN PRECURSOR | HUMAN RESPIRATORY SYNCYTIAL VIRUS (STRAIN RSS-2) | 38–65 | 154–202 | 213–243 | 442–471 | 488–518 | | | | |
| PVGLF_MEASE | FUSION GLYCOPROTEIN PRECURSOR | MEASLES VIRUS (STRAINS EDMONSTON AND HALLE) | 228–262 | | | | | | | | |
| PVGLF_MEASI | FUSION GLYCOPROTEIN PRECURSOR | MEASLES VIRUS (STRAIN IP-3-CA) | 231–265 | | | | | | | | |
| PVGLF_MEASY | FUSION GLYCOPROTEIN PRECURSOR | MEASLES VIRUS (STRAIN YAMAGATA-1) | 228–262 | | | | | | | | |
| PVGLF_MUMP1 | FUSION GLYCOPROTEIN PRECURSOR | MUMPS VIRUS (STRAIN SBL-1) | 20–54 | 447–486 | | | | | | | |
| PVGLF_MUMPM | FUSION GLYCOPROTEIN PRECURSOR | MUMPS VIRUS (STRAIN MIYAHARA VACCINE) | 20–54 | 447–486 | | | | | | | |
| PVGLF_MUMPR | FUSION GLYCOPROTEIN PRECURSOR | MUMPS VIRUS (STRAIN RW) | 20–54 | 447–486 | | | | | | | |
| PVGLF_MUMPS | FUSION GLYCOPROTEIN PRECURSOR | MUMPS VIRUS (STRAIN SBL) | 151–178 | 426–511 | | | | | | | |
| PVGLF_NDVA | FUSION GLYCOPROTEIN PRECURSOR | NEWCASTLE DISEASE VIRUS (STRAIN AUSTRALIA-VICTORIA/32) | 151–178 | 426–512 | | | | | | | |
| PVGLF_NDVB | FUSION GLYCOPROTEIN PRECURSOR | NEWCASTLE DISEASE VIRUS (STRAIN BEAUDETTE C/45) | 151–178 | 426–512 | | | | | | | |
| PVGLF_NDVH3 | FUSION GLYCOPROTEIN PRECURSOR | NEWCASTLE DISEASE VIRUS (STRAIN HER/33) | 151–178 | 426–512 | | | | | | | |
| PVGLF_NDVH4 | FUSION GLYCOPROTEIN PRECURSOR | NEWCASTLE DISEASE VIRUS (STRAIN B1-HITCHNER/47) | 151–178 | 426–512 | | | | | | | |
| PVGLF_NDVI | FUSION GLYCOPROTEIN PRECURSOR | NEWCASTLE DISEASE VIRUS (STRAIN ITALIEN/45) | 151–178 | 426–512 | | | | | | | |
| PVGLF_NDVL | FUSION GLYCOPROTEIN PRECURSOR | NEWCASTLE DISEASE VIRUS (STRAIN LAS/46) | 151–178 | 192–219

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLF_NDVM | FUSION GLYCOPROTEIN PRECURSOR | NEWCASTLE DISEASE VIRUS (STRAIN MIYADERA/51) | 151–178 | 437–512 | | | | | | | |
| PVGLF_NDVQ | FUSION GLYCOPROTEIN PRECURSOR | NEWCASTLE DISEASE VIRUS (STRAIN QUEENSLAND/66) | 151–178 | 433–512 | | | | | | | |
| PVGLF_NDVT | FUSION GLYCOPROTEIN PRECURSOR | NEWCASTLE DISEASE VIRUS (STRAIN TEXAS) | 151–178 | 426–512 | | | | | | | |
| PVGLF_NDVTG | FUSION GLYCOPROTEIN PRECURSOR | NEWCASTLE DISEASE VIRUS (STRAIN TEXAS G.B./48) | 151–178 | 426–512 | | | | | | | |
| PVGLF_NDVU | FUSION GLYCOPROTEIN PRECURSOR | NEWCASTLE DISEASE VIRUS (STRAIN ULSTER/67) | 151–178 | 426–512 | | | | | | | |
| PVGLF_PHODV | FUSION GLYCOPROTEIN PRECURSOR | PHOCINE DISTEMPER VIRUS | 36–63 | 221–262 | 309–336 | | | | | | |
| PVGLF_PI1HC | FUSION GLYCOPROTEIN PRECURSOR | HUMAN PARAINFLUENZA 1 VIRUS (STRAIN C39) | 147–174 | 210–266 | | | | | | | |
| PVGLF_PI2H | FUSION GLYCOPROTEIN PRECURSOR | HUMAN PARAINFLUENZA 2 VIRUS | 90–117 | 141–175 | 238–266 | 483–528 | | | | | |
| PVGLF_PI2HG | FUSION GLYCOPROTEIN PRECURSOR | HUMAN PARAINFLUENZA 2 VIRUS (STRAIN GREER) | 90–117 | 141–175 | 238–266 | 483–528 | | | | | |
| PVGLF_PI2HT | FUSION GLYCOPROTEIN PRECURSOR | HUMAN PARAINFLUENZA 2 VIRUS (STRAIN TOSHIBA) | 90–117 | 141–175 | 238–266 | 483–528 | | | | | |
| PVGLF_PI3B | FUSION GLYCOPROTEIN PRECURSOR | BOVINE PARAINFLUENZA 3 VIRUS | 115–182 | 207–241 | 459–497 | | | | | | |
| PVGLF_PI3H4 | FUSION GLYCOPROTEIN PRECURSOR | HUMAN PARAINFLUENZA 3 VIRUS (STRAIN N1H 47885) | 115–182 | 207–241 | 459–497 | | | | | | |
| PVGLF_RINDK | FUSION GLYCOPROTEIN PRECURSOR | RINDERPEST VIRUS (STRAIN KABETE O) | 224–265 | 458–485 | | | | | | | |
| PVGLF_RINDL | FUSION GLYCOPROTEIN PRECURSOR | RINDERPEST VIRUS (STRAIN L) | 224–265 | 458–506 | | | | | | | |
| PVGLF_SEND5 | FUSION GLYCOPROTEIN PRECURSOR | SENDAI VIRUS (STRAIN Z/HOST MUTANTS) | 122–149 | 211–245 | 480–507 | | | | | | |
| PVGLF_SENDF | FUSION GLYCOPROTEIN PRECURSOR | SENDAI VIRUS (STRAIN FUSHIMI) | 122–149 | 211–245 | 480–507 | | | | | | |
| PVGLF_SENDH | FUSION GLYCOPROTEIN PRECURSOR | SENDAI VIRUS (STRAIN HARRIS) | 122–149 | 211–245 | 480–507 | | | | | | |
| PVGLF_SENDJ | FUSION GLYCOPROTEIN PRECURSOR | SENDAI VIRUS (STRAIN HVJ) | 122–149 | 211–245 | 480–507 | | | | | | |
| PVGLF_SENDZ | FUSION GLYCOPROTEIN PRECURSOR | SENDAI VIRUS (STRAIN Z) | 122–149 | 211–245 | 480–507 | | | | | | |
| PVGLF_SV41 | FUSION GLYCOPROTEIN PRECURSOR | SIMIAN VIRUS 41 | 144–185 | 241–269 | 459–496 | | | | | | |
| PVGLF_SV5 | FUSION GLYCOPROTEIN PRECURSOR | SIMIAN VIRUS 5 (STRAIN W3) | 137–171 | 417–444 | | | | | | | |
| PVGLF_TRTV | FUSION GLYCOPROTEIN PRECURSOR | TURKEY RHINOTRACHEITIS VIRUS | 124–161 | 193–200 | 457–484 | | | | | | |
| PVGLG_BEFV | SPIKE GLYCOPROTEIN PRECURSOR | BOVINE EPHEMERAL FEVER VIRUS | 523–557 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLG_BRSVC | MAJOR SURFACE GLYCOPROTEIN G | BOVINE RESPIRATORY SYNCYTIAL VIRUS (STRAIN COPENHAGEN) | 92–123 | | | | | | | | |
| PVGLG_HRSV1 | MAJOR SURFACE GLYCOPROTEIN G | HUMAN RESPIRATORY SYNCYTIAL VIRUS (SUBGROUP B/STRAIN 18537) | 63–93 | | | | | | | | |
| PVGLG_HRSV4 | MAJOR SURFACE GLYCOPROTEIN G | HUMAN RESPIRATORY SYNCYTIAL VIRUS (STRAIN RSB5857) | 66–107 | | | | | | | | |
| PVGLG_HRSV5 | MAJOR SURFACE GLYCOPROTEIN G | HUMAN RESPIRATORY SYNCYTIAL VIRUS (STRAIN RSB6190) | 243–273 | | | | | | | | |
| PVGLG_HRSV8 | MAJOR SURFACE GLYCOPROTEIN G | HUMAN RESPIRATORY SYNCYTIAL VIRUS (SUBGROUP B/STRAIN 8/60) | 66–93 | | | | | | | | |
| PVGLG_HSVE4 | GLYCOPROTEIN G PRECURSOR | EQUINE HERPESVIRUS TYPE 4 | 271–298 | | | | | | | | |
| PVGLG_HSVEB | GLYCOPROTEIN G PRECURSOR | EQUINE HERPESVIRUS TYPE 1 (STRAIN AB4P) | 383–410 | | | | | | | | |
| PVGLG_RABVT | SPIKE GLYCOPROTEIN PRECURSOR | RABIES VIRUS (STRAIN STREET) | 489–519 | | | | | | | | |
| PVGLG_VSVIG | SPIKE GLYCOPROTEIN PRECURSOR | VESICULAR STOMATITIS VIRUS (SEROTYPE INDIANA/STRAIN GLASGOW) | 472–499 | | | | | | | | |
| PVGLH_EBV | GLYCOPROTEIN GP85 PRECURSOR | EPSTEIN-BARR VIRUS (STRAIN B95-8) | 549–576 | 619–648 | | | | | | | |
| PVGLH_HCMVA | GLYCOPROTEIN H PRECURSOR | HUMAN CYTOMEGALOVIRUS (STRAIN AD169) | 107–136 | 270–297 | | | | | | | |
| PVGLH_HCMVT | GLYCOPROTEIN H PRECURSOR | HUMAN CYTOMEGALOVIRUS (STRAIN TOWNE) | 106–135 | | | | | | | | |
| PVGLH_HSV6G | GLYCOPROTEIN H PRECURSOR | HERPES SIMPLEX VIRUS (TYPE 6/STRAIN GS) | 62–89 | 360–403 | | | | | | | |
| PVGLH_HSVSA | GLYCOPROTEIN H PRECURSOR | HERPESVIRUS SAIMIRI (STRAIN 11) | 388–415 | | | | | | | | |
| PVGLL_HCMVA | IE GLYCOPROTEIN PRECURSOR | HUMAN CYTOMEGALOVIRUS (STRAIN AD169) | 47–111 | | | | | | | | |
| PVGLM_BUNGE | M POLYPROTEIN PRECURSOR | BUNYAVIRUS GERMISTON | 512–546 | 914–941 | 1128–1255 | | | | | | |
| PVGLM_BUNL7 | M POLYPROTEIN PRECURSOR | BUNYAVIRUS LA CROSSE (ISOLATE L74) | 913–950 | | | | | | | | |
| PVGLM_BUNYW | M POLYPROTEIN PRECURSOR | BUNYAMWERA VIRUS | 340–374 | 504–535 | 682–709 | | | | | | |
| PVGLM_DUGBV | M POLYPROTEIN PRECURSOR | DUGBE VIRUS | 945–972 | | | | | | | | |
| PVGLM_HANTB | M POLYPROTEIN PRECURSOR | HANTAAN VIRUS (STRAIN B-1) | 73–100 | 693–720 | | | | | | | |
| PVGLM_HANTH | M POLYPROTEIN PRECURSOR | HANTAAN VIRUS (STRAIN HOJO) | 75–102 | | | | | | | | |
| PVGLM_HANTL | M POLYPROTEIN PRECURSOR | HANTAAN VIRUS (STRAIN LEE) | 75–102 | | | | | | | | |
| PVGLM_HANTV | M POLYPROTEIN PRECURSOR | HANTAAN VIRUS (STRAIN 76-118) | 75–102 | | | | | | | | |
| PVGLM_INSV | M POLYPROTEIN PRECURSOR | IMPATIENS NECROTIC SPOT VIRUS | 628–655 | 1069–1101 | | | | | | | |
| PVGLM_PHV | M POLYPROTEIN PRECURSOR | PROSPECT HILL VIRUS | 69–96 | | | | | | | | |
| PVGLM_PUUMH | M POLYPROTEIN PRECURSOR | PUUMALA VIRUS (STRAIN HALLNAS B1) | 72–110 | | | | | | | | |
| PVGLM_PUUMS | M POLYPROTEIN PRECURSOR | PUUMALA VIRUS (STRAIN SOTKAMO) | 72–110 | | | | | | | | |
| PVGLM_SEOU8 | M POLYPROTEIN PRECURSOR | SEOUL VIRUS (STRAIN 80-39) | 513–540 | 693–720 | | | | | | | |
| PVGLM_SEOUR | M POLYPROTEIN PRECURSOR | SEOUL VIRUS (STRAIN R22) | 73–100 | 513–540 | 694–721 | | | | | | |
| PVGLM_SEOUS | M POLYPROTEIN PRECURSOR | SEOUL VIRUS (STRAIN SR-11) | 73–100 | 513–540 | 694–721 | | | | | | |
| PVGLN_BEFV | NONSTRUCT GLYCOPRO GNS PRECURSOR | BOVINE EPHEMERAL FEVER VIRUS | 523–564 | | | | | | | | |
| PVGLP_BEV | PEPLOMER GLYCOPROTEIN PRECURSOR | BERNE VIRUS | 48–82 | 1145–1179 | 1184–1211 | 1505–1532 | | | | | |
| PVGLY_JUNIN | GLYCOPROTEIN POLYPROTEIN PRECURSO | JUNIN ARENAVIRUS | 14–41 | | | | | | | | |

TABLE VI-continued

107 × 178 × 4 SEARCH MOTIF RESULTS SUMMARY
FOR ALL VIRAL (NON-BACTERIOPHAGE) PROTEINS

| PCGENE FILE NAME | 107×178×4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLY_LASSG | GLYCOPROTEIN POLYPROTEIN PRECURSO | LASSA VIRUS (STRAIN GA391) | 86–113 | | | | | | | | |
| PVGLY_MOPEI | GLYCOPROTEIN POLYPROTEIN PRECURSO | MOPEIA VIRUS | 86–113 | 316–346 | | | | | | | |
| PVGLY_PIARV | GLYCOPROTEIN POLYPROTEIN PRECURSO | PICHINDE ARENAVIRUS | 334–375 | | | | | | | | |
| PVGLY_TACV | GLYCOPROTEIN POLYPROTEIN PRECURSO | TACARIBE VIRUS | 109–136 | 315–350 | | | | | | | |
| PVGLY_TACV5 | GLYCOPROTEIN POLYPROTEIN PRECURSO | TACARIBE VIRUS (STRAIN V5) | 303–338 | | | | | | | | |
| PVGLY_TACV7 | GLYCOPROTEIN POLYPROTEIN PRECURSO | TACARIBE VIRUS (STRAIN V7) | 302–337 | | | | | | | | |
| PVGLY_TACVT | GLYCOPROTEIN POLYPROTEIN PRECURSO | TACARIBE VIRUS (STRAIN TRVL 11598) | 303–338 | | | | | | | | |
| PVGNM_CPSMV | GENOME POLYPROTEIN M | COWPEA SEVERE MOSAIC VIRUS (STRAIN DG) | 192–221 | | | | | | | | |
| PVGP8_EBV | PROBABLE MEMBRANE ANTIGEN GP85 | EPSTEIN-BARR VIRUS (STRAIN B95-8) | 104–149 | | | | | | | | |
| PVGP_EBOV | STRUCTURAL GLYCOPROTEIN PRECURSO | EBOLA VIRUS | 280–314 | | | | | | | | |
| PVGP_MABVM | STRUCTURAL GLYCOPROTEIN PRECURSO | MARBURG VIRUS (STRAIN MUSOKE) | 559–589 | 619–646 | | | | | | | |
| PVGP_MABVP | STRUCTURAL GLYCOPROTEIN PRECURSO | MARBURG VIRUS (STRAIN POPP) | 559–589 | 619–646 | | | | | | | |
| PVH05_VACCC | PROTEIN H5 | VACCINIA VIRUS (STRAIN COPENHAGEN) | 132–166 | | | | | | | | |
| PVH05_VACCV | PROTEIN H5 | VACCINIA VIRUS (STRAIN WR) | 132–166 | | | | | | | | |
| PVH05_VARV | PROTEIN H5 | VARIOLA VIRUS | 64–91 | 150–184 | | | | | | | |
| PVHEL_LSV | PROBABLE HELICASE | LILY SYMPTOMLESS VIRUS | 130–160 | | | | | | | | |
| PVHRP_VACCC | HOST RANGE PROTEIN | VACCINIA VIRUS (STRAIN COPENHAGEN) | 241–275 | | | | | | | | |
| PVHRP_VACCV | HOST RANGE PROTEIN | VACCINIA VIRUS (STRAIN WR) | 241–275 | | | | | | | | |
| PV101_VACCC | PROTEIN I1 | VACCINIA VIRUS (STRAIN COPENHAGEN) | 90–117 | 153–180 | | | | | | | |
| V101_VARV | PROTEIN I1 | VARIOLA VIRUS | 90–117 | 153–180 | | | | | | | |
| V103_VACCC | PROTEIN I3 | VACCINIA VIRUS (STRAIN COPENHAGEN) | 160–190 | | | | | | | | |
| V103_VACCV | PROTEIN I3 | VACCINIA VIRUS (STRAIN WR) | 160–190 | | | | | | | | |
| V103_VARV | PROTEIN I3 | VARIOLA VIRUS | 160–190 | | | | | | | | |
| V108_VACCC | PUTATIVE RNA HELICASE I8 | VACCINIA VIRUS (STRAIN COPENHAGEN) | 290–317 | 548–575 | 593–632 | | | | | | |
| V108_VACCV | PUTATIVE RNA HELICASE I8 | VACCINIA VIRUS (STRAIN WR) | 290–317 | 548–575 | 593–632 | | | | | | |
| V108_VARV | PUTATIVE RNA HELICASE I8 | VARIOLA VIRUS | 290–317 | 548–575 | 593–632 | | | | | | |
| VIE1_MCMVS | IMMEDIATE-EARLY PROTEIN 1 | MURINE CYTOMEGALOVIRUS (STRAIN SMITH) | 261–288 | | | | | | | | |
| VIE2_NPVOP | IMMEDIATE-EARLY PROTEIN IE-2 | ORGYIA PSEUDOTSUGATA MULTICAPSID POLYHEDROSIS VIRUS | 355–385 | | | | | | | | |
| VIEN_NPVAC | IE-REG PROTEIN IE-N | AUTOGRAPHA CALIFORNICA NUCLEAR POLYHEDROSIS VIRUS | 217–325 | 343–400 | | | | | | | |
| VIF_HV1RH | VIRION INFECTIVITY FACTOR | HUMAN IMMUNODEFICIENCY VIRUS TYPE 1 (RF/HAT ISOLATE) | 62–89 | | | | | | | | |
| VIF_SIVAI | VIRION INFECTIVITY FACTOR | SIMIAN IMMUNODEFICIENCY VIRUS (ISOLATE AGM/CLONE GRI-1) | 2–36 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| VIMP_HSVEB | PROB INTEGRAL MEMBRANE PROTEIN | EQUINE HERPESVIRUS TYPE 1 (STRAIN AB4P) | 147–174 | | | | | | | | |
| VIMP_HSVSA | INTEGRAL MEMBRANE PROTEIN | HERPESVIRUS SAIMIRI (STRAIN 11) | 80–107 | | | | | | | | |
| VINT_SSV1 | PROBABLE INTEGRASE | SULFOLOBUS VIRUS-LIKE PARTICLE SSV1 | 73–100 | | | | | | | | |
| VJ01_VACCC | PROTEIN J1 | VACCINIA VIRUS (STRAIN COPENHAGEN) | 22–56 | | | | | | | | |
| VJ01_VACCV | PROTEIN J1 | VACCINIA VIRUS (STRAIN WR) | 22–56 | | | | | | | | |
| VJ01_VARV | PROTEIN J1 | VARIOLA VIRUS | 22–56 | | | | | | | | |
| VL1_CRPVK | PROBABLE L1 PROTEIN | COTTONTAIL RABBIT (SHOPE) PAPILLOMAVIRUS (STRAIN KANSAS) | 331–383 | | | | | | | | |
| VL1_FPVL | PROBABLE L1 PROTEIN | AVIAN PAPILLOMAVIRUS FPV-L | 38–65 | | | | | | | | |
| VL1_HPV08 | PROBABLE L1 PROTEIN | HUMAN PAPILLOMAVIRUS TYPE 8 | 354–392 | | | | | | | | |
| VL1_HPV18 | PROBABLE L1 PROTEIN | HUMAN PAPILLOMAVIRUS TYPE 18 | 183–210 | | | | | | | | |
| VL1_HPV33 | PROBABLE L1 PROTEIN | HUMAN PAPILLOMAVIRUS TYPE 33 | 19–46 | | | | | | | | |
| VL1_HPV41 | PROBABLE L1 PROTEIN | HUMAN PAPILLOMAVIRUS TYPE 41 | 345–372 | | | | | | | | |
| VL1_HPV51 | PROBABLE L1 PROTEIN | HUMAN PAPILLOMAVIRUS TYPE 51 | 19–46 | | | | | | | | |
| VL1_HPV58 | PROBABLE L1 PROTEIN | HUMAN PAPILLOMAVIRUS TYPE 58 | 45–72 | | | | | | | | |
| VL2_HPV1A | PROBABLE L2 PROTEIN | HUMAN PAPILLOMAVIRUS TYPE 1A | 407–445 | | | | | | | | |
| VL2_HPV41 | PROBABLE L2 PROTEIN | HUMAN PAPILLOMAVIRUS TYPE 41 | 415–442 | | | | | | | | |
| VL3_REOVD | MINOR CORE PROTEIN LAMBDA 3 | REOVIRUS (TYPE 3/STRAIN DEARING) | 330–357 | | | | | | | | |
| VL3_REOVL | MINOR CORE PROTEIN LAMBDA 3 | REOVIRUS (TYPE 1/STRAIN LANG) | 330–357 | | | | | | | | |
| VL96_IRV1 | L96 PROTEIN | TIPULA IRIDESCENT VIRUS | 146–180 | 625–652 | | | | | | | |
| PVM1_REOVL | MINOR VIRION STRUCTURAL PROTEIN MU | REOVIRUS (TYPE 1/STRAIN LANG) | 290–317 | | | | | | | | |
| PVM21_REOVD | MAJOR VIRION STRUC PROTEIN MU-1/MU- | REOVIRUS (TYPE 3/STRAIN DEARING) | 625–662 | | | | | | | | |
| PVM22_REOVD | MAJOR VIRION STRUC PROTEIN MU-1/MU- | REOVIRUS (TYPE 3/STRAIN DEARING) | 624–661 | | | | | | | | |
| PVM2_REOVJ | MAJOR VIRION STRUC PROTEIN MU-1/MU- | REOVIRUS (TYPE 2/STRAIN D5/JONES) | 624–661 | | | | | | | | |
| PVM3_REOVD | MAJOR NONSTRUCTURAL PROTEIN MU-N | REOVIRUS (TYPE 3/STRAIN DEARING) | 159–186 | 343–370 | 456–483 | 631–690 | | | | | |
| PVMA2_BRSVA | MATRIX GLYCOPROTEIN M2 | BOVINE RESPIRATORY SYNCYTIAL VIRUS (STRAIN A51908) | 124–152 | | | | | | | | |
| PVMA2_HRSVA | MATRIX GLYCOPROTEIN M2 | HUMAN RESPIRATORY SYNCYTIAL VIRUS (STRAIN A2) | 124–151 | | | | | | | | |
| PVMAT_BRSVA | MATRIX PROTEIN | BOVINE RESPIRATORY SYNCYTIAL VIRUS (STRAIN A51908) | 219–246 | | | | | | | | |
| PVMAT_HRSVA | MATRIX PROTEIN | HUMAN RESPIRATORY SYNCYTIAL VIRUS (STRAIN A2) | 219–246 | | | | | | | | |
| PVMAT_INCJJ | MATRIX (M) PROTEIN | INFLUENZA C VIRUS (STRAIN C/JJ/50) | 151–185 | | | | | | | | |
| PVMAT_NDVA | MATRIX PROTEIN | NEWCASTLE DISEASE VIRUS (STRAIN AUSTRALIA-VICTORIA/32) | 247–274 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVMAT_PI2HT | MATRIX PROTEIN | HUMAN PARAINFLUENZA 2 VIRUS (STRAIN TOSHIBA) | 96–123 | | | | | | | | |
| PVMAT_P13B | MATRIX PROTEIN | BOVINE PARAINFLUENZA 3 VIRUS | 201–231 | | | | | | | | |
| PVMAT_PI3H4 | MATRIX PROTEIN | HUMAN PARAINFLUENZA 3 VIRUS (STRAIN NIH 47885) | 201–231 | | | | | | | | |
| PVMAT_SV41 | MATRIX PROTEIN | SIMIAN VIRUS 41 | 323–353 | | | | | | | | |
| PVME1_CVBM | E1 GLYCOPROTEIN | BOVINE CORONAVIRUS (STRAIN MEBUS) | 175–209 | | | | | | | | |
| PVME1_CVTKE | E1 GLYCOPROTEIN | TURKEY ENTERIC CORONAVIRUS | 175–209 | | | | | | | | |
| PVME1_IBV6 | E1 GLYCOPROTEIN | AVIAN INFECTIOUS BRONCHITIS VIRUS (STRAIN 6/82) | 21–48 | 184–218 | | | | | | | |
| PVME1_IBVB | E1 GLYCOPROTEIN | AVIAN INFECTIOUS BRONCHITIS VIRUS (STRAIN BEAUDETTE) | 21–48 | 184–218 | | | | | | | |
| PVME1_IBVB2 | E1 GLYCOPROTEIN | AVIAN INFECTIOUS BRONCHITIS VIRUS (STRAIN BEAUDETTE M42) | 21–48 | 184–218 | | | | | | | |
| PVME1_IBVK | E1 GLYCOPROTEIN | AVIAN INFECTIOUS BRONCHITIS VIRUS (STRAIN KB8523) | 184–218 | | | | | | | | |
| PVMP_CAMVC | MOVEMENT PROTEIN | CAULIFLOWER MOSAIC VIRUS (STRAIN CM-1841) | 220–254 | 273–324 | | | | | | | |
| PVMP_CAMVD | MOVEMENT PROTEIN | CAULIFLOWER MOSAIC VIRUS (STRAIN D/H) | 29–56 | 220–254 | 273–324 | | | | | | |
| PVMP_CAMVE | MOVEMENT PROTEIN | CAULIFLOWER MOSAIC VIRUS (STRAIN BBC) | 227–254 | 273–324 | | | | | | | |
| PVMP_CAMVN | MOVEMENT PROTEIN | CAULIFLOWER MOSAIC VIRUS (STRAIN NY8153) | 220–254 | 273–324 | | | | | | | |
| PVMP_CAMVS | MOVEMENT PROTEIN | CAULIFLOWER MOSAIC VIRUS (STRAIN STRASBOURG) | 220–254 | 273–324 | | | | | | | |
| PVMP_CAMVW | MOVEMENT PROTEIN | CAULIFLOWER MOSAIC VIRUS (STRAIN W260) | 220–254 | 273–324 | | | | | | | |
| PVMP_CERV | MOVEMENT PROTEIN | CARNATION ETCHED RING VIRUS | 26–53 | 100–127 | | | | | | | |
| PVMP_SOCMV | MOVEMENT PROTEIN | SOYBEAN CHLOROTIC MOTTLE VIRUS | 4–31 | 78–118 | | | | | | | |
| PVMSA_HPBHE | MAJOR SURFACE ANTIGEN PRECURSOR | HERON HEPATITIS B VIRUS | 294–328 | | | | | | | | |
| PVMT1_DHVI1 | MATRIX PROTEIN 1 | DHORI VIRUS (STRAIN INDIAN/1313/61) | 38–65 | 237–264 | | | | | | | |
| PVMT8_MYXVL | M-T8 PROTEIN | MYXOMA VIRUS (STRAIN LAUSANNE) | 163–190 | | | | | | | | |
| PVMT9_MYXVL | MT-9 PROTEIN | MYXOMA VIRUS (STRAIN LAUSANNE) | 465–492 | | | | | | | | |
| PVN34_ROTPC | NONSTRUCTURAL PROTEIN NS34 | PROCINE ROTAVIRUS (GROUP C/STRAIN COWDEN) | 83–113 | | | | | | | | |
| PVNCN_PAVBO | PROBABLE NONCAPSID PROTEIN NP1 | BOVINE PARVOVIRUS | 149–176 | | | | | | | | |
| PVNCS_ADVG | NONCAPSID PROTEIN NS-1 | ALEUTIAN MINK DISEASE PARVOVIRUS (STRAIN G) | 86–148 | | | | | | | | |
| PVNCS_AEDEV | NONCAPSID PROTEIN NS-1 | AEDES DENSONUCLEOSIS VIRUS (STRAIN GK V 002 002) | 14–41 | 279–339 | 487–517 | 585–612 | 780–817 | 821–848 | | | |
| PVNCS_MUMIM | NONCAPSID PROTEIN NS-1 | MURINE MINUTE VIRUS (STRAIN MVMI) | 35–62 | 262–289 | | | | | | | |
| PVNCS_MUMIV | NONCAPSID PROTEIN NS-1 | MURINE MINUTE VIRUS | 35–62 | 262–289 | | | | | | | |
| PVNCS_PAVHB | NONCAPSID PROTEIN NS-1 | HUMAN PARVOVIRUS B19 | 236–270 | | | | | | | | |
| PVNCS_PAVHH | NONCAPSID PROTEIN NS-1 | HAMSTER PARVOVIRUS H1 | 35–62 | | | | | | | | |
| PVNCS_PAVPN | NONCAPSID PROTEIN NS-1 | PORCINE PARVOVIRUS (STRAIN NADL-2) | 24–55 | 169–196 | 316–346 | | | | | | |
| PVNS1_EHDV2 | NONSTRUCTURAL PROTEIN NS1 | EPIZOOTIC HEMORRHAGIC DISEASE VIRUS (SEROTYPE 2/STRAIN ALBERTA) | 411–438 | | | | | | | | |
| PVNS1_IAALA | NONSTRUCTURAL PROTEIN NS1 | INFLUENZA A VIRUS (STRAIN A/ALASKA/6/77) | 171–198 | | | | | | | | |
| PVNS1_IAANN | NONSTRUCTURAL PROTEIN NS1 | INFLUENZA A VIRUS (STRAIN A/ANN ARBOR/6/60) | 171–198 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNS1_IACHI | NONSTRUCTURAL PROTEIN NS1 | INFLUENZA A VIRUS (STRAIN A/CHILE/1/83) | 171–198 | | | | | | | | |
| PVNS1_IACKG | NONSTRUCTURAL PROTEIN NS1 | INFLUENZA A VIRUS (STRAIN A/CHICKEN/GERMANY/N/49) | 171–198 | | | | | | | | |
| PVNS1_IACKJ | NONSTRUCTURAL PROTEIN NS1 | INFLUENZA A VIRUS (STRAIN A/CHICKEN/JAPAN/24) | 168–195 | | | | | | | | |
| PVNS1_IADA2 | NONSTRUCTURAL PROTEIN NS1 | INFLUENZA A VIRUS (STRAIN A/DUCK/ALBERTA/60/76) | 171–198 | | | | | | | | |
| PVNS1_IAFOM | NONSTRUCTURAL PROTEIN NS1 | INFLUENZA A VIRUS (STRAIN A/FORT MONMOUTH/1/47) | 171–198 | | | | | | | | |
| PVNS1_IAFOW | NONSTRUCTURAL PROTEIN NS1 | INFLUENZA A VIRUS (STRAIN A/FORT WARREN/1/50) | 171–198 | | | | | | | | |
| PVNS1_IALE1 | NONSTRUCTURAL PROTEIN NS1 | INFLUENZA A VIRUS (STRAIN A/LENINGRAD/134/57) | 171–198 | | | | | | | | |
| PVNS1_IAMA6 | NONSTRUCTURAL PROTEIN NS1 | INFLUENZA A VIRUS (STRAIN A/MALLARD/ALBERTA/88/76) | 171–198 | | | | | | | | |
| PVNS1_IAPII | NONSTRUCTURAL PROTEIN NS1 | INFLUENZA A VIRUS (STRAIN A/PINTAIL/ALBERTA/121/79) | 171–198 | | | | | | | | |
| PVNS1_IAPI3 | NONSTRUCTURAL PROTEIN NS1 | INFLUENZA A VIRUS (STRAIN A/PINTAIL/ALBERTA/358/79) | 171–198 | | | | | | | | |
| PVNS1_IATKB | NONSTRUCTURAL PROTEIN NS1 | INFLUENZA A VIRUS (STRAIN A/TURKEY/BETHLEHEM-GLILIT/1492-B/82) | 171–198 | | | | | | | | |
| PVNS1_IATKC | NONSTRUCTURAL PROTEIN NS1 | INFLUENZA A VIRUS (STRAIN A/TURKEY/CANADA/63) | 171–198 | | | | | | | | |
| PVNS1_IATRT | NONSTRUCTURAL PROTEIN NS1 | INFLUENZA A VIRUS (STRAIN A/TERN/TURKMENIA/18/72) | 171–198 | | | | | | | | |
| PVNS1_IAUDO | NONSTRUCTURAL PROTEIN NS1 | INFLUENZA A VIRUS (STRAIN A/UDORN/307/72) | 171–198 | | | | | | | | |
| PVNS1_IAUSS | NONSTRUCTURAL PROTEIN NS1 | INFLUENZA A VIRUS (STRAIN A/USSR/90/77) | 171–198 | | | | | | | | |
| PVNS1_INBPA | NONSTRUCTURAL PROTEIN NS1 | INFLUENZA A VIRUS (STRAIN B/PA/79) | 171–198 | | | | | | | | |
| PVNS2_IATKR | NONSTRUCTURAL PROTEIN NS2 | INFLUENZA A VIRUS (STRAIN A/TURKEY/OREGON/71) | 87–114 | | | | | | | | |
| PVNS2_INBLE | NONSTRUCTURAL PROTEIN NS2 | INFLUENZA B VIRUS (STRAIN B/LEE/40) | 51–78 | | | | | | | | |
| PVNS2_INBYA | NONSTRUCTURAL PROTEIN NS2 | INFLUENZA B VIRUS (STRAIN B/YAMAGATA/1/73) | 51–78 | | | | | | | | |
| PVNS2_INCJJ | NONSTRUCTURAL PROTEIN NS2 | INFLUENZA C VIRUS (STRAIN C/JJ/50) | 71–98 | | | | | | | | |
| PVNS3_CVPFS | NONSTRUCTURAL PROTEIN 3-1 | PORCINE TRANSMISSIBLE GASTROENTERITIS CORONAVIRUS (STRAIN FS772) | 9–36 | | | | | | | | |
| PVNS4_CVH22 | NONSTRUCTURAL PROTEIN 4 | HUMAN CORONAVIRUS (STRAIN 229E) | 9–36 | | | | | | | | |
| PVNS4_RSV | NONSTRUCTURAL PROTEIN NS4 | RICE STRIPE VIRUS | 6–40 | | | | | | | | |
| PVNS7_CVCAE | NONSTRUCTURAL PROTEIN 7 | CANINE ENTERIC CORONAVIRUS (STRAIN K378) | 11–45 | | | | | | | | |
| PVNS7_CVFE3 | NONSTRUCTURAL PROTEIN 7 | FELINE ENTERIC CORONAVIRUS (STRAIN 79-1683) | 8–42 | | | | | | | | |
| PVNS7_CVPFS | NONSTRUCTURAL PROTEIN 7 | PORCINE TRANSMISSIBLE GASTROENTERITIS CORONAVIRUS (STRAIN FS772) | 34–61 | | | | | | | | |
| PVNS7_CVPPU | NONSTRUCTURAL PROTEIN 7 | PORCINE TRANSMISSIBLE GASTROENTERITIS CORONAVIRUS (STRAIN PURD) | 34–61 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNS7_CVPRM | NONSTRUCTURAL PROTEIN 7 | PORCINE RESPIRATORY CORONAVIRUS | 34–61 | | | | | | | | |
| PVNS7_FIPV | NONSTRUCTURAL PROTEIN 7 | FELINE INFECTIOUS PERITONITS VIRUS (STRAIN 79-1146) | 8–42 | | | | | | | | |
| PVNSC_PI1HE | NONSTRUCTURAL PROTEIN C | HUMAN PARAINFLUENZA 1 VIRUS (STRAIN CI-14/83) | 41–75 | | | | | | | | |
| PVNSC_PI3H4 | NONSTRUCTURAL PROTEIN C | HUMAN PARAINFLUENZA 3 VIRUS (STRAIN NIH 47885) | 58–99 | | | | | | | | |
| PVNSM_INSV | NONSTRUCTURAL PROTEIN NS-M | IMPATIENS NECROTIC SPOT VIRUS | 262–296 | | | | | | | | |
| PVNST_BUNLC | NONSTRUCTURAL PROTEIN NS-S | BUNYAVIRUS LA CROSSE | 57–84 | | | | | | | | |
| PVNST_TOSV | NONSTRUCTURAL PROTEIN NS-S | TOSCANA VIRUS | 146–180 | | | | | | | | |
| PVNUC_EBOV | NUCLEOPROTEIN | EBOLA VIRUS | 331–369 | | | | | | | | |
| PVNUC_IAANA | NUCLEOPROTEIN | INFLUENZA A VIRUS (STRAIN A/ANAS ACUTA/PRIMORJE/695/76) | 378–405 | | | | | | | | |
| PVNUC_IAANN | NUCLEOPROTEIN | INFLUENZA A VIRUS (STRAIN A/ANN ARBOR/6/60) | 378–405 | | | | | | | | |
| PVNUC_IABRA | NUCLEOPROTEIN | INFLUENZA A VIRUS (STRAIN A/BRAZIL/11/78) | 378–405 | | | | | | | | |
| PVNUC_IABUD | NUCLEOPROTEIN | INFLUENZA A VIRUS (STRAIN A/BUDGERIGAR/HOKKAIDO/1/77) | 378–405 | | | | | | | | |
| PVNUC_IACAL | NUCLEOPROTEIN | INFLUENZA A VIRUS (STRAIN A/CALIFORNIA/10/78) | 378–405 | | | | | | | | |
| PVNUC_IACKG | NUCLEOPROTEIN | INFLUENZA A VIRUS (STRAIN A/CHICKEN/GERMANY/N/49) | 378–405 | | | | | | | | |
| PVNUC_IACKP | NUCLEOPROTEIN | INFLUENZA A VIRUS (STRAIN A/CHICKEN/PENNSYLVANIA/1/83) | 378–405 | | | | | | | | |
| PVNUC_IADAU | NUCLEOPROTEIN | INFLUENZA A VIRUS (STRAIN A/DUCK/AUSTRALIA/749/80) | 378–405 | | | | | | | | |
| PVNUC_IADBE | NUCLEOPROTEIN | INFLUENZA A VIRUS (STRAIN A/DUCK/BEIJING/1/78) | 378–405 | | | | | | | | |
| PVNUC_IADCZ | NUCLEOPROTEIN | INFLUENZA A VIRUS (STRAIN A/DUCK/CZECHOSLOVAKIA/56) | 378–405 | | | | | | | | |
| PVNUC_IADE1 | NUCLEOPROTEIN | INFLUENZA A VIRUS (STRAIN A/DUCK/ENGLAND/1/) | 378–405 | | | | | | | | |
| PVNUC_IADE2 | NUCLEOPROTEIN | INFLUENZA A VIRUS (STRAIN A/DUCK/ENGLAND/1/62) | 378–405 | | | | | | | | |
| PVNUC_IADHK | NUCLEOPROTEIN | INFLUENZA A VIRUS (STRAIN A/DUCK/HONG KONG/7/75) | 378–405 | | | | | | | | |
| PVNUC_IADM2 | NUCLEOPROTEIN | INFLUENZA A VIRUS (STRAIN A/DUCK/MEMPHIS/928/74) | 378–405 | | | | | | | | |
| PVNUC_IADMA | NUCLEOPROTEIN | INFLUENZA A VIRUS (STRAIN A/DUCK/MANITOBA/1/53) | 378–405 | | | | | | | | |
| PVNUC_IADNZ | NUCLEOPROTEIN | INFLUENZA A VIRUS (STRAIN A/DUCK/NEW ZEALAND/31/76) | 378–405 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNUC_IADU2 | NUCLEOPROTEIN | INFLUENZA A VIRUS (STRAIN A/DUCK/UKRAINE/2/60) | 378

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNUC_IAMAN | NUCLEOPROTEIN | INFLUENZA A VIRUS (STRAIN A/MALLARD/NEW YORK/6750/78) | 378–405 | | | | | | | | |
| PVNUC_IAMIN | NUCLEOPROTEIN | INFLUENZA A VIRUS (STRAIN A/MINK/SWEDEN/84) | 378–405 | | | | | | | | |
| PVNUC_IANEJ | NUCLEOPROTEIN | INFLUENZA A VIRUS (STRAIN A/NEW JERSEY/8/76) | 378–405 | | | | | | | | |
| PVNUC_IANT6 | NUCLEOPROTEIN | INFLUENZA A VIRUS (STRAIN A/NT/60/68) | 378–405 | | | | | | | | |
| PVNUC_IAOHI | NUCLEOPROTEIN | INFLUENZA A VIRUS (STRAIN A/OHIO/4/83) | 378–405 | | | | | | | | |
| PVNUC_IAPAR | NUCLEOPROTEIN | INFLUENZA A VIRUS (STRAIN A/PARROT/ULSTER/73) | 378–405 | | | | | | | | |
| PVNUC_IAUPE | NUCLEOPROTEIN | INFLUENZA A VIRUS (STRAIN A/PUERTO RICO/8/34) | 378–405 | | | | | | | | |
| PVNUC_IARUD | NUCLEOPROTEIN | INFLUENZA A VIRUS (STRAIN A/RUDDY TURNSTONE/NEW JERSEY/47/85) | 378–405 | | | | | | | | |
| PVNUC_IASE0 | NUCLEOPROTEIN | INFLUENZA A VIRUS (STRAIN A/SEAL/MASSACHUSETTS/1/80) | 378–405 | | | | | | | | |
| PVNUC_IASH2 | NUCLEOPROTEIN | INFLUENZA A VIRUS (STRAIN A/SHEARWATER/AUSTRALIA/72) | 378–405 | | | | | | | | |
| PVNUC_IAS1N | NUCLEOPROTEIN | INFLUENZA A VIRUS (STRAIN A/SINGAPORE/1/57) | 378–405 | | | | | | | | |
| PVNUC_IATE1 | NUCLEOPROTEIN | INFLUENZA A VIRUS (STRAIN A/TEAL/ICELAND/29/80) | 378–405 | | | | | | | | |
| PVNUC_IATKN | NUCLEOPROTEIN | INFLUENZA A VIRUS (STRAIN A/TURKEY/MINNESOTA/1661/81) | 378–405 | | | | | | | | |
| PVNUC_IATKO | NUCLEOPROTEIN | INFLUENZA A VIRUS (STRAIN A/TURKEY/ONTARIO/7732/66) | 378–405 | | | | | | | | |
| PVNUC_IATRS | NUCLEOPROTEIN | INFLUENZA A VIRUS (STRAIN A/TERN/SOUTH AFRICA/61) | 378–405 | | | | | | | | |
| PVNUC_IATRT | NUCLEOPROTEIN | INFLUENZA A VIRUS (STRAIN A/TERN/TURKMENIA/18/72) | 378–405 | | | | | | | | |
| PVNUC_IATX7 | NUCLEOPROTEIN | INFLUENZA A VIRUS (STRAIN A/TEXAS/1/77) | 378–405 | | | | | | | | |
| PVNUC_IAUDO | NUCLEOPROTEIN | INFLUENZA A VIRUS (STRAIN A/UDORN/307/72) | 378–405 | | | | | | | | |
| PVNUC_IAUSS | NUCLEOPROTEIN | INFLUENZA A VIRUS (STRAIN A/USSR/90/77) | 378–405 | | | | | | | | |
| PVNUC_IAVI6 | NUCLEOPROTEIN | INFLUENZA A VIRUS (STRAIN A/VICTORIA/5/68) | 378–405 | | | | | | | | |
| PVNUC_IAWHN | NUCLEOPROTEIN | INFLUENZA A VIRUS (STRAIN A/WHALE/MAINE/328/84) | 378–405 | | | | | | | | |
| PVNUC_IAWHP | NUCLEOPROTEIN | INFLUENZA A VIRUS (STRAIN A/WHALE/PACIFIC OCEAN/19/76) | 378–405 | | | | | | | | |
| PVNUC_IAWIL | NUCLEOPROTEIN | INFLUENZA A VIRUS (STRAIN A/WILSON-SMITH/33) | 378–405 | | | | | | | | |
| PVNUC_IAWIS | NUCLEOPROTEIN | INFLUENZA A VIRUS (STRAIN A/WISCONSIN/3523/88) | 378–405 | | | | | | | | |
| PVNUC_IAZ29 | NUCLEOPROTEIN | INFLUENZA A VIRUS (STRAIN A/SWINE/29/37) | 378–405 | | | | | | | | |
| PVNUC_IAZ41 | NUCLEOPROTEIN | INFLUENZA A VIRUS (STRAIN A/SWINE/41/49) | 378–405 | | | | | | | | |
| PVNUC_IAZCA | NUCLEOPROTEIN | INFLUENZA A VIRUS (STRAIN A/SWINE/CAMBRIDGE/1/35) | 378–405 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNUC_IAZDA | NUCLEOPROTEIN | INFLUENZA A VIRUS (STRAIN A/SWINE/DANDONG/9/83) | 378–405 | | | | | | | | |
| PVNUC_IAZGE | NUCLEOPROTEIN | INFLUENZA A VIRUS (STRAIN A/SWINE/GERMANY/2/81) | 378–405 | | | | | | | | |
| PVNUC_IAZH1 | NUCLEOPROTEIN | INFLUENZA A VIRUS (STRAIN A/SWINE/HONG KONG/6/76) | 378–405 | | | | | | | | |
| PVNUC_IAZH3 | NUCLEOPROTEIN | INFLUENZA A VIRUS (STRAIN A/SWINE/HONG KONG/126/82) | 378–405 | | | | | | | | |
| PVNUC_IAZH4 | NUCLEOPROTEIN | INFLUENZA A VIRUS (STRAIN A/SWINE/HONG KONG/127/82) | 378–405 | | | | | | | | |
| PVNUC_IAZII | NUCLEOPROTEIN | INFLUENZA A VIRUS (STRAIN A/SWINE/IOWA/15/30) | 378–405 | | | | | | | | |
| PVNUC_IAZI2 | NUCLEOPROTEIN | INFLUENZA A VIRUS (STRAIN A/SWINE/IOWA/1976/31) | 378–405 | | | | | | | | |
| PVNUC_IAZI3 | NUCLEOPROTEIN | INFLUENZA A VIRUS (STRAIN A/SWINE/IOWA/46) | 378–405 | | | | | | | | |
| PVNUC_IAZI1 | NUCLEOPROTEIN | INFLUENZA A VIRUS (STRAIN A/SWINE/ITALY/437/76) | 378–405 | | | | | | | | |
| PVNUC_IAZJ2 | NUCLEOPROTEIN | INFLUENZA A VIRUS (STRAIN A/SWINE/ITALY/2/79) | 378–405 | | | | | | | | |
| PVNUC_IAZJ3 | NUCLEOPROTEIN | INFLUENZA A VIRUS (STRAIN A/SWINE/ITALY/141/81) | 378–405 | | | | | | | | |
| PVNUC_IAZJ4 | NUCLEOPROTEIN | INFLUENZA A VIRUS (STRAIN A/SWINE/ITALY/839/89) | 378–405 | | | | | | | | |
| PVNUC_IAZIA | NUCLEOPROTEIN | INFLUENZA A VIRUS (STRAIN A/SWINE/JAMESBURG/42) | 378–405 | | | | | | | | |
| PVNUC_IAZMA | NUCLEOPROTEIN | INFLUENZA A VIRUS (STRAIN A/SWINE/MAY/54) | 378–405 | | | | | | | | |
| PVNUC_IAZNE | NUCLEOPROTEIN | INFLUENZA A VIRUS (STRAIN A/SWINE/NETHERLANDS/12/85) | 378–405 | | | | | | | | |
| PVNUC_IAZOH | NUCLEOPROTEIN | INFLUENZA A VIRUS (STRAIN A/SWINE/OHIO/23/35) | 378–405 | | | | | | | | |
| PVNUC_IAZON | NUCLEOPROTEIN | INFLUENZA A VIRUS (STRAIN A/SWINE/ONTARIO/2/81) | 378–405 | | | | | | | | |
| PVNUC_IAZTE | NUCLEOPROTEIN | INFLUENZA A VIRUS (STRAIN A/SWINE/TENNESSEE/24/77) | 378–405 | | | | | | | | |
| PVNUC_IAZW1 | NUCLEOPROTEIN | INFLUENZA A VIRUS (STRAIN A/SWINE/WISCONSIN/1/57) | 378–405 | | | | | | | | |
| PVNUC_IAZW2 | NUCLEOPROTEIN | INFLUENZA A VIRUS (STRAIN A/SWINE/WISCONSIN/1/61) | 378–405 | | | | | | | | |
| PVNUC_INCCA | NUCLEOPROTEIN | INFLUENZA C VIRUS (STRAIN C/CALIFORNIA/78) | 99–126 | 416–443 | 451–478 | | | | | | |
| PVNUC_MABVM | NUCLEOPROTEIN | MARBURG VIRUS (STRAIN MUSOKE) | 366–407 | | | | | | | | |
| PVNUC_MABVP | NUCLEOPROTEIN | MARBURG VIRUS (STRAIN POPP) | 366–407 | | | | | | | | |
| PV001_VACCC | PROTEIN O1 | VACCINIA VIRUS (STRAIN COPENHAGEN) | 7–37 | 109–138 | 581–608 | | | | | | |
| PV001_VARV | PROTEIN O1 | VARIOLA VIRUS | 7–37 | 109–138 | 581–608 | | | | | | |
| PVOR1_FXMV | 152 KD PROTEIN | FOXTAIL MOSAIC VIRUS | 1023–1050 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVOR1_NMV | 186 KD PROTEIN | NARCISSUS MOSAIC VIRUS | 996–1023 | 1527–1561 | | | | | | | |
| PVOR1_PMV | 176 KD PROTEIN | PAPAYA MOSAIC POTEXVIRUS | 948–978 | 1481–1532 | | | | | | | |
| PVOR1_PVMR | 223 KD PROTEIN | POTATO VIRUS M (STRAIN RUSSIAN) | 597–627 | | | | | | | | |
| PVOR1_PVX | 165 KD PROTEIN | POTATO VIRUS X | 698–725 | 1017–1044 | | | | | | | |
| PVOR1_PVXX3 | 165 KD PROTEIN | POTATO VIRUS X (STRAIN X3) | 698–725 | 1017–1044 | | | | | | | |
| PVOR1_SMYEA | 150 KD PROTEIN | STRAWBERRY MILD YELLOW EDGE-ASSOCIATED VIRUS | 312–342 | 691–721 | | | | | | | |
| PVP10_NPVAC | P10 PROTEIN | AUTOGRAPHA CALIFORNICA NUCLEAR POLYHEDROSIS VIRUS | 7–41 | | | | | | | | |
| PVP10_NPVOP | P10 PROTEIN | ORGYIA PSEUDOTSUGATA MULTICAPSID POLYHEDROSIS VIRUS | 7–48 | | | | | | | | |
| PVP10_NPVSE | P10 PROTEIN | SPODOPTERA EXIGUA NUCLEAR POLYHEDROSIS VIRUS (STRAIN US) | 6–33 | 37–64 | | | | | | | |
| PVP10_RGDV | NONSTRUCTURAL PROTEIN PNS10 | RICE GALL DWARF VIRUS | 205–242 | | | | | | | | |
| PVP10_WTV | NONSTRUCTURAL PROTEIN PNS10 | WOUND TUMOR VIRUS | 151–181 | 227–254 | | | | | | | |
| PVP11_RDV | NONSTRUCTURAL PROTEIN PNS11 | RICE DWARF VIRUS | 53–80 | | | | | | | | |
| PVP12_WTV | NONSTRUCTURAL PROTEIN PNS12 | WOUND TUMOR VIRUS | 81–108 | | | | | | | | |
| PVP18_WTVNJ | NONSTRUCTURAL PROTEIN PNS12 | WOUND TUMOR VIRUS (STRAIN NJ) | 81–108 | | | | | | | | |
| PVP19_AMCV | CORE PROTEIN P19 | ARTICHOKE MOTTLED CRINKLE VIRUS | 73–100 | | | | | | | | |
| PVP19_TBSVC | CORE PROTEIN P19 | TOMATO BUSHY STUNT VIRUS (STRAIN CHERRY) | 73–100 | | | | | | | | |
| PVP23_HSVSA | PROBABLE CAPSID PROTEIN VP23 | HERPESVIRUS SAIMIRI (STRAIN 11) | 2–29 | | | | | | | | |
| PVP26_HSVEB | CAPSID PROTEIN VP26 | EQUINE HERPESVIRUS TYPE 1 (STRAIN AB4P) | 36–63 | | | | | | | | |
| PVP26_HSVSA | CAPSID PROTEIN VP26 | HERPESVIRUS SAIMIRI (STRAIN 11) | 48–75 | | | | | | | | |
| PVP2_AHSV4 | OUTER CAPSID PROTEIN VP2 | AFRICAN HORSE SICKNESS VIRUS (SEROTYPE 4/STRAIN VACCINE) | 277–304 | 410–437 | 632–662 | 907–934 | | | | | |
| PVP2_BTV13 | OUTER CAPSID PROTEIN VP2 | BLUETONGUE VIRUS (SEROTYPE 13/ISOLATE USA) | 815–846 | | | | | | | | |
| PVP2_BTV1A | OUTER CAPSID PROTEIN VP2 | BLUETONGUE VIRUS (SEROTYPE 1/ISOLATE AUSTRALIA) | 898–925 | | | | | | | | |
| PVP2_BTV1S | OUTER CAPSID PROTEIN VP2 | BLUETONGUE VIRUS (SEROTYPE 1/ISOLATE SOUTH AFRICA) | 119–146 | | | | | | | | |
| PVP2_EHDV1 | OUTER CAPSID PROTEIN VP2 | EPIZOOTIC HEMORRHAGIC DISEASE VIRUS (SEROTYPE 1) | 72–103 | 415–453 | | | | | | | |
| PVP2_ROTBR | RNA-BINDING PROTEIN VP2 | BOVINE ROTAVIRUS (STRAIN RF) | 39–94 | 523–553 | | | | | | | |
| PVP2_ROTBU | RNA-BINDING PROTEIN VP2 | BOVINE ROTAVIRUS (STRAIN UK) | 39–94 | 524–554 | | | | | | | |
| PVP2_ROTHW | RNA-BINDING PROTEIN VP2 | HUMAN ROTAVIRUS (SEROTYPE 1/STRAIN WA) | 70–101 | 533–567 | | | | | | | |
| PVP2_ROTPC | RNA-BINDING PROTEIN VP2 | PORCINE ROTAVIRUS (GROUP C/STRAIN COWDEN) | 52–99 | 128–156 | 518–545 | 705–746 | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVP2_ROTS1 | RNA-BINDING PROTEIN VP2 | SIMIAN 11 ROTOVIRUS (STRAIN SA11) | 36–96 | | | | | | | | |
| PVP30_ASFE7 | PHOSPHOPROTEIN P30 | AFRICAN SWINE FEVER VIRUS (STRAIN E-75) | 39–75 | | | | | | | | |
| PVP32_ASFB7 | PHOSPHOPROTEIN P32 | AFRICAN SWINE FEVER VIRUS (STRAIN BA71V) | 39–75 | | | | | | | | |
| PVP35_EBOV | POLYMERASE COMPLEX PROTEIN VP35 | EBOLA VIRUS | 83–119 | | | | | | | | |
| PVP35_MABVM | POLYMERASE COMPLEX PROTEIN VP35 | MARBURG VIRUS (STRAIN MUSOKE) | 80–107 | 231–258 | | | | | | | |
| PVP35_MABVP | POLYMERASE COMPLEX PROTEIN VP35 | MARBURG VIRUS (STRAIN POPP) | 80–107 | 231–258 | | | | | | | |
| PVP35_NPVAC | EARLY 35 KD PROTEIN | AUTOGRAPHA CALIFORNICA NUCLEAR POLYHEDROSIS VIRUS | 270–297 | | | | | | | | |
| PVP35_NPVBM | EARLY 35 KD PROTEIN | BOMBYX MORI NUCLEAR POLYHEDROSIS VIRUS | 68–102 | | | | | | | | |
| PVP35_VACCV | IMMUNODOM ENV PRO P35 | VACCINIA VIRUS (STRAIN WR) | 178–205 | | | | | | | | |
| PVP39_NPVAC | MAJOR CAPSID PROTEIN | AUTOGRAPHA CALIFORNICA NUCLEAR POLYHEDROSIS VIRUS | 134–161 | 264–291 | | | | | | | |
| PVP39_NPVOP | MAJOR CAPSID PROTEIN | ORGYIA PSEUDOTSUGATA MULITCAPSID POLYHEDROSIS VIRUS | 263–290 | | | | | | | | |
| PVP3_AHSV4 | VP3 CORE PROTEIN | AFRICAN HORSE SICKNESS VIRUS (SEROTYPE 4/STRAIN VACCINE) | 132–159 | | | | | | | | |
| PVP3_BTV10 | VP3 CORE PROTEIN | BLUETONGUE VIRUS (SEROTYPE 10/ISOLATE USA) | 214–252 | | | | | | | | |
| PVP3_BTV17 | VP3 CORE PROTEIN | BLUETONGUE VIRUS (SEROTYPE 17/ISOLATE USA) | 214–252 | | | | | | | | |
| PVP3_BTV1A | VP3 CORE PROTEIN | BLUETONGUE VIRUS (SEROTYPE 1/ISOLATE AUSTRALIA) | 214–252 | | | | | | | | |
| PVP3_EHDV1 | VP3 CORE PROTEIN | EPIZOOTIC HEMORRHAGIC DISEASE VIRUS (SEROTYPE 1) | 209–243 | 798–832 | | | | | | | |
| PVP3_EHDVA | VP3 CORE PROTEIN | EPIZOOTIC HEMORRHAGIC DISEASE VIRUS (SEROTYPE 2/STRAIN AUSTRAL | 798–832 | | | | | | | | |
| PVP3_GFLV | P3 PROTEIN | GRAPEVINE FANLEAF VIRUS | 99–133 | | | | | | | | |
| PVP3_ROTPC | INNER CORE PROTEIN VP3 | PORCINE ROTAVIRUS (GROUP C/STRAIN COWDEN) | 39–66 | 329–384 | | | | | | | |
| PVP3_ROTS1 | INNER CORE PROTEIN VP3 | SIMIAN 11 ROTAVIRUS (STRAIN SA11) | 26–67 | 350–377 | 451–497 | 619–692 | | | | | |
| PVP40_EBV | CAPSID PROTEIN P40 | EPSTEIN-BARR VIRUS (STRAIN B95-8) | 440–470 | | | | | | | | |
| PVP40_HSVSA | CAPSID PROTEIN P40 | HERPESVIRUS SAIMIRI (STRAIN 11) | 205–232 | 344–372 | | | | | | | |
| PVP40_ILTVI | CAPSID PROTEIN P40 | INFECTIOUS LARYNGOTRACHEITIS VIRUS (STRAIN THORNE V882) | 515–549 | | | | | | | | |
| PVP40_VZVD | CAPSID PROTEIN P40 | VARICELLA-ZOSTER VIRUS (STRAIN DUMAS) | 174–208 | 495–522 | | | | | | | |
| PVP41_ROTS1 | OUTER CAPSID PROTEIN VP4 | SIMIAN 11 ROTAVIRUS (STRAIN SA11) | 8–35 | 589–619 | | | | | | | |
| PVP42_ROTS1 | OUTER CAPSID PROTEIN VP4 | SIMIAN 11 ROTAVIRUS (STRAIN SA11) | 8–35 | 584–622 | | | | | | | |
| PVP4A_VACCC | MAJOR CORE PROTEIN P4A PRECURSOR | VACCINIA VIRUS (STRAIN COPENHAGEN) | 48–75 | | | | | | | | |
| PVP4A_VACCV | MAJOR CORE PROTEIN P4A PRECURSOR | VACCINIA VIRUS (STRAIN WR) | 48–75 | | | | | | | | |
| PVP4A_VARV | MAJOR CORE PROTEIN P4A PRECURSOR | VARIOLA VIRUS | 48–75 | | | | | | | | |
| PVP4B_FOWPV | MAJOR CORE PROTEIN P4B PRECURSOR | FOWLPOX VIRUS | 80–110 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVP4B_VACCC | MAJOR CORE PROTEIN P4B PRECURSOR | VACCINIA VIRUS (STRAIN COPENHAGEN) | 7–37 | | | | | | | | |
| PVP4B_VACCV | MAJOR CORE PROTEIN P4B PRECURSOR | VACCINIA VIRUS (STRAIN WR) | 7–37 | | | | | | | | |
| PVP4B_VARV | MAJOR CORE PROTEIN P4B PRECURSOR | VARIOLA VIRUS | 7–37 | | | | | | | | |
| PVP4_BTV10 | VP4 CORE PROTEIN | BLUETONGUE VIRUS (SEROTYPE 10/ISOLATE USA) | 34–61 | 576–603 | | | | | | | |
| PVP4_BTV11 | VP4 CORE PROTEIN | BLUETONGUE VIRUS (SEROTYPE 13/ISOLATE USA) | 34–61 | 576–603 | | | | | | | |
| PVP4_BTV13 | VP4 CORE PROTEIN | BLUETONGUE VIRUS (SEROTYPE 2/ISOLATE USA) | 34–61 | 576–603 | | | | | | | |
| PVP4_BTV2A | OUTER CAPSID PROTEIN VP4 | NEBRASKA CALF DIARRHEA VIRUS (STRAIN NCDV-LINCOLN) | 552–622 | | | | | | | | |
| PVP4_NCDV | OUTER CAPSID PROTEIN VP4 | BOVINE ROTAVIRUS (SEROTYPE 6/STRAIN B641) | 595–629 | | | | | | | | |
| PVP4_ROTB4 | OUTER CAPSID PROTEIN VP4 | BOVINE ROTAVIRUS (STRAIN C486) | 8–35 | 584–622 | | | | | | | |
| PVP4_ROTBC | OUTER CAPSID PROTEIN VP4 | BOVINE ROTAVIRUS (STRAIN UK) | 595–629 | | | | | | | | |
| PVP4_ROTBU | OUTER CAPSID PROTEIN VP4 | EQUINE ROTAVIRUS (STRAIN H-2) | 112–146 | 235–269 | 552–629 | | | | | | |
| PVP4_ROTEH | OUTER CAPSID PROTEIN VP4 | ROTAVIRUS (GROUP B/STRAIN IDIR) | 5–32 | | | | | | | | |
| PVP4_ROTG1 | OUTER CAPSID PROTEIN VP4 | HUMAN ROTAVIRUS (SEROTYPE 1/STRAIN 1076) | 8–35 | 572–628 | 565–621 | | | | | | |
| PVP4_ROTH1 | OUTER CAPSID PROTEIN VP4 | HUMAN ROTAVIRUS (SEROTYPE 2/STRAIN RV-5) | 8–35 | 279–306 | 584–629 | | | | | | |
| PVP4_ROTH5 | OUTER CAPSID PROTEIN VP4 | HUMAN ROTAVIRUS (SEROTYPE 1/STRAIN 69M) | 8–35 | 112–139 | 565–621 | | | | | | |
| PVP4_ROTH6 | OUTER CAPSID PROTEIN VP4 | HUMAN ROTAVIRUS (SEROTYPE 1/STRAIN 69M) | 8–35 | 279–306 | 565–621 | | | | | | |
| PVP4_ROTHD | OUTER CAPSID PROTEIN VP4 | HUMAN ROTAVIRUS (SEROTYPE 2/STRAIN DS1) | 8–35 | 279–306 | | | | | | | |
| PVP4_ROTHJ | OUTER CAPSID PROTEIN VP4 | HUMAN ROTAVIRUS (STRAIN K8) | 8–35 | 111–138 | | | | | | | |
| PVP4_ROTHK | OUTER CAPSID PROTEIN VP4 | HUMAN ROTAVIRUS (STRAIN KU) | 8–35 | 77–104 | 279–306 | 577–621 | | | | | |
| PVP4_ROTHL | OUTER CAPSID PROTEIN VP4 | HUMAN ROTAVIRUS (STRAIN L26) | 8–35 | 279–306 | 565–621 | | | | | | |
| PVP4_ROTHM | OUTER CAPSID PROTEIN VP4 | HUMAN ROTAVIRUS (SEROTYPE 1/STRAIN M37) | 8–35 | 572–610 | | | | | | | |
| PVP4_ROTHN | OUTER CAPSID PROTEIN VP4 | HUMAN ROTAVIRUS (SEROTYPE 3/STRAIN MCN13 ST. THOMAS 3) | 8–35 | 573–628 | | | | | | | |
| PVP4_ROTHP | OUTER CAPSID PROTEIN VP4 | HUMAN ROTAVIRUS (SEROTYPE 3/STRAIN P) | 8–35 | 577–621 | | | | | | | |
| PVP4_ROTHR | OUTER CAPSID PROTEIN VP4 | HUMAN ROTAVIRUS (SEROTYPE 3/STRAIN RRV) | 8–38 | 105–135 | 235–262 | | | | | | |
| PVP4_ROTHT | OUTER CAPSID PROTEIN VP4 | HUMAN ROTAVIRUS (SEROTYPE 4/STRAIN | 8–35 | 572–627 | | | | | | | |
| PVP4_ROTHV | OUTER CAPSID PROTEIN VP4 | HUMAN ROTAVIRUS (SEROTYPE 4/STRAIN VA70) | 8–35 | 279–306 | 590–617 | | | | | | |
| PVP4_ROTHW | OUTER CAPSID PROTEIN VP4 | HUMAN ROTAVIRUS (SEROTYPE 1/STRAIN WA) | 8–35 | 577–621 | | | | | | | |
| PVP4_ROTP5 | OUTER CAPSID PROTEIN VP4 | PORCINE ROTAVIRUS (SEROTYPE 5/STRAIN OSU) | 112–146 | 584–625 | | | | | | | |
| PVP4_ROTPC | OUTER CAPSID PROTEIN VP4 | PORCINE ROTAVIRUS (GROUP C/STRAIN COWDEN) | 5–33 | 115–161 | 293–320 | | | | | | |
| PVP4_ROTPG | OUTER CAPSID PROTEIN VP4 | PORCINE ROTAVIRUS (STRAIN GOTTFRIED) | 8–35 | 572–628 | | | | | | | |
| PVP4_ROTPY | OUTER CAPSID PROTEIN VP4 | PORCINE ROTAVIRUS (STRAIN YM) | 8–35 | 112–146 | 584–625 | | | | | | |
| PVP4_ROTRH | OUTER CAPSID PROTEIN VP4 | RHESUS ROTARVIRUS | 8–38 | 584–622 | | | | | | | |
| PVP4_ROTSF | OUTER CAPSID PROTEIN VP4 | SIMIAN 11 ROTAVIRUS (STRAIN SA11-FEM) | 8–35 | 589–619 | | | | | | | |
| PVP4_ROTSS | OUTER CAPSID PROTEIN VP4 | SIMIAN 11 ROTAVIRUS (STRAIN SA11-SEM) | 8–35 | 130–157 | 584–622 | | | | | | |
| PVP4_WTV | NONSTRUCTURAL PROTEIN PNS4 | WOUND TUMOR VIRUS | 28–62 | | | | | | | | |
| PVP5_AHSV4 | OUTER CAPSID PROTEIN VP5 | AFRICAN HORSES SICKNESS VIRUS (SEROTYPE 4/STRAIN VACCINE) | 113–183 | 191–218 | | | | | | | |
| PVP5_BTV10 | OUTER CAPSID PROTEIN VP5 | BLUETONGUE VIRUS (SEROTYPE 10/ISOLATE USA) | 53–80 | 99–126 | | | | | | | |
| PVP5_BTV11 | OUTER CAPSID PROTEIN VP5 | BLUETONGUE VIRUS (SEROTYPE 11/ISOLATE USA) | 53–80 | 92–126 | | | | | | | |
| PVP5_BTV13 | OUTER CAPSID PROTEIN VP5 | BLUETONGUE VIRUS (SEROTYPE 13/ISOLATE USA) | 53–80 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVP5_BTV1A | OUTER CAPSID PROTEIN VP5 | BLUETONGUE VIRUS (SEROTYPE 1/ISOLATE AUSTRALIA) | 53–80 | 89–126 | | | | | | | |
| PVP5_BTV1S | OUTER CAPSID PROTEIN VP5 | BLUETONGUE VIRUS (SEROTYPE 1/ISOLATE SOUTH AFRICA) | 53–80 | 92–126 | 148–182 | | | | | | |
| PVP5_BTV2A | OUTER CAPSID PROTEIN VP5 | BLUETONGUE VIRUS (SEROTYPE 2/ISOLATE USA) | 53–80 | 89–126 | | | | | | | |
| PVP5_EHDV1 | OUTER CAPSID PROTEIN VP5 | EPIZOOTIC HEMORRHAGIC DISEASE VIRUS (SEROTYPE 1) | 31–80 | 191–218 | 399–426 | | | | | | |
| PVP5_WTV | OUTER COAT PROTEIN P5 | WOUND TUMOR VIRUS | 648–675 | | | | | | | | |
| PVP61_BTV10 | VP6 PROTEIN | BLUETONGUE VIRUS (SEROTYPE 10/ISOLATE USA) | 161–193 | | | | | | | | |
| PVP61_MRDV | PROB NONSTRUCT 41.0 KD PRO | MAIZE ROUGH DWARF VIRUS | 153–202 | | | | | | | | |
| PVP61_NPVAC | 61 KD PROTEIN | AUTOGRAPHA CALIFORNICA NUCLEAR POLYHEDROSIS VIRUS | 36–63 | | | | | | | | |
| PVP62_BTV10 | VP6 PROTEIN | BLUETONGUE VIRUS (SEROTYPE 10/ISOLATE USA) | 157–189 | | | | | | | | |
| PVP64_NPVOP | MAJOR ENV GLYCOPRO PRECURSOR | ORGYIA PSEUDOTSUGATA MULITCAPSID POLYHEDROSIS VIRUS | 45–72 | | | | | | | | |
| PVP67_NPVAC | MAJOR ENV GLYCOPRO PRECURSOR | AUTOGRAPHA CALIFORNICA NUCLEAR POLYHEDROSIS VIRUS | 44–81 | | | | | | | | |
| PVP6_BTV11 | VP6 PROTEIN | BLUETONGUE VIRUS (SEROTYPE 11/ISOLATE USA) | 157–189 | | | | | | | | |
| PVP6_BTV13 | VP6 PROTEIN | BLUETONGUE VIRUS (SEROTYPE 13/ISOLATE USA) | 157–189 | | | | | | | | |
| PVP6_BTV17 | VP6 PROTEIN | BLUETONGUE VIRUS (SEROTYPE 17/ISOLATE USA) | 157–189 | | | | | | | | |
| PVP6_BTV1S | VP6 PROTEIN | BLUETONGUE VIRUS (SEROTYPE 1/ISOLATE SOUTH AFRICA) | 161–193 | | | | | | | | |
| PVP6_BTV2A | VP6 PROTEIN | BLUETONGUE VIRUS (SEROTYPE 2/ISOLATE USA) | 133–172 | | | | | | | | |
| PVP6_RDV | STRUCTURAL PROTEIN P6 | RICE DWARF VIRUS | 10–37 | 354–381 | | | | | | | |
| PVP74_NPVAC | P74 PROTEIN | AUTOGRAPHA CALIFORNICA NUCLEAR POLYHEDROSIS VIRUS | 413–440 | | | | | | | | |
| PVP75_HSVSA | PROBABLE MEMBRANE ANTIGEN 75 | HERPESVIRUS SAIMIRI (STRAIN 11) | 181–208 | 929–977 | | | | | | | |
| PVP79_NPVAC | 79 KD PROTEIN | AUTOGRAPHA CALIFORNICA NUCLEAR POLYHEDROSIS VIRUS | 44–78 | 370–397 | | | | | | | |
| PVP7_EHDV1 | VP7 CORE PROTEIN | EPIZOOTIC HEMORRHAGIC DISEASE VIRUS (SEROTYPE 1) | 16–43 | | | | | | | | |
| PVP7_WTV | NONSTRUCTURAL PROTEIN PNS7 | WOUND TUMOR VIRUS | 458–485 | | | | | | | | |
| PVP80_NPVAC | CAPSID PROTEIN P80 | AUTOGRAPHA CALIFORNICA NUCLEAR POLYHEDROSIS VIRUS | 101–142 | 240–298 | | | | | | | |
| PVP87_NPVOP | CAPSID PROTEIN P87 | ORGYIA PSEUDOTSUGATA MULITCAPSID POLYHEDROSIS VIRUS | 132–159 | | | | | | | | |
| PVP8_BTV10 | NONSTRUCTURAL PROTEIN P8 | BLUETONGUE VIRUS (SEROTYPE 10/ISOLATE USA) | 105–132 | | | | | | | | |
| PVP8_FOWPV | STRUCTURAL PROTEIN VP8 PRECURSOR | FOWLPOX VIRUS | 211–238 | | | | | | | | |
| PVP8_WTV | OUTER CAPSID PROTEIN P8 | WOUND TUMOR VIRUS | 29–56 | 112–143 | | | | | | | |
| PVP9_RDV | NONSTRUCTURAL PROTEIN PNS9 | RICE DWARF VIRUS | 197–224 | | | | | | | | |
| PVP9_WTV | STRUCTURAL PROTEIN P9 | WOUND TUMOR VIRUS | 22–49 | | | | | | | | |
| PVP9_WTNVJ | STRUCTURAL PROTEIN P9 | WOUND TUMOR VIRUS (STRAIN NJ) | 22–49 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVPHE_NPVAC | 29 KD POLYHEDRAL ENVELOPE PROTEIN | AUTOGRAPHA CALIFORNICA NUCLEAR POLYHEDROSIS VIRUS | 196–223 | | | | | | | | |
| PVPHE_NPVOP | 32 KD POLYHEDRAL ENVELOPE PROTEIN | ORGYIA PSEUDOTSUGATA MULTICAPSID POLYHEDROSIS VIRUS | 127–186 | 238–265 | | | | | | | |
| PVPRT_ADEM1 | ENDOPROTEASE | MOUSE ADENOVIRUS TYPE 1 | 167–194 | | | | | | | | |
| PVPU_HV1A2 | VPU PROTEIN | HUMAN IMMUNODEFICIENCY VIRUS TYPE 1 (ARV2/SF2 ISOLATE) | 3–31 | | | | | | | | |
| PVPU_HV1B1 | VPU PROTEIN | HUMAN IMMUNODEFICIENCY VIRUS TYPE 1 (BH10 AND HXB3 ISOLATES) | 5–48 | | | | | | | | |
| PVPU_HV1B8 | VPU PROTEIN | HUMAN IMMUNODEFICIENCY VIRUS TYPE 1 (BH8 ISOLATE) | 21–48 | | | | | | | | |
| PVPU_HV1BN | VPU PROTEIN | HUMAN IMMUNODEFICIENCY VIRUS TYPE 1 (BRAIN ISOLATE) | 22–49 | | | | | | | | |
| PVPU_HV1BR | VPU PROTEIN | HUMAN IMMUNODEFICIENCY VIRUS TYPE 1 (BRU ISOLATE) | 5–48 | | | | | | | | |
| PVPU_HV1C4 | VPU PROTEIN | HUMAN IMMUNODEFICIENCY VIRUS TYPE 1 (CDC-451 ISOLATE) | 3–30 | | | | | | | | |
| PVPU_HV1EL | VPU PROTEIN | HUMAN IMMUNODEFICIENCY VIRUS TYPE 1 (ELI ISOLATE) | 6–33 | | | | | | | | |
| PVPU_HV1H2 | VPU PROTEIN | HUMAN IMMUNODEFICIENCY VIRUS TYPE 1 (HXB2 ISOLATE) | 5–48 | | | | | | | | |
| PVPU_HV1J3 | VPU PROTEIN | HUMAN IMMUNODEFICIENCY VIRUS TYPE 1 (JH3 ISOLATE) | 2–29 | | | | | | | | |
| PVPU_HV1JR | VPU PROTEIN | HUMAN IMMUNODEFICIENCY VIRUS TYPE 1 (JRCSF ISOLATE) | 22–49 | | | | | | | | |
| PVPU_HV1MA | VPU PROTEIN | HUMAN IMMUNODEFICIENCY VIRUS TYPE 1 (MAL ISOLATE) | 5–32 | | | | | | | | |
| PVPU_HV1ND | VPU PROTEIN | HUMAN IMMUNODEFICIENCY VIRUS TYPE 1 (NDK ISOLATE) | 6–33 | | | | | | | | |
| PVPU_HV1PV | VPU PROTEIN | HUMAN IMMUNODEFICIENCY VIRUS TYPE 1 (PV22 ISOLATE) | 5–48 | | | | | | | | |
| PVPU_HV1S1 | VPU PROTEIN | HUMAN IMMUNODEFICIENCY VIRUS TYPE 1 (SF162 ISOLATE) | 22–49 | | | | | | | | |
| PVPU_SIVCZ | VPU PROTEIN | CHIMPANZEE IMMUNODEFICIENCY VIRUS | 51–78 | | | | | | | | |
| PVPX_LDV | VPX PROTEIN | LACTATE DEHYDROGENASE-ELEVATING VIRUS | 64–94 | | | | | | | | |
| PVRNA_BSMV | ALPHA-A PROTEIN | BARLEY STRIPE MOSAIC VIRUS | 1051–1078 | | | | | | | | |
| PVS06_ROTBS | VP6 PROTEIN | BOVINE ROTAVIRUS (GROUP C/STRAIN SHINTOKU) | 6–43 | | | | | | | | |
| PVS06_ROTGA | VP6 PROTEIN | ROTAVIRUS (GROUP B/STRAIN ADRV) | 114–144 | | | | | | | | |
| PVS06_ROTGI | VP6 PROTEIN | ROTAVIRUS (GROUP B/STRAIN IDIR) | 28–55 | | | | | | | | |
| PVS06_ROTHC | VP6 PROTEIN | HUMAN ROTAVIRUS | 9–44 | | | | | | | | |
| PVS06_ROTPC | VP6 PROTEIN | PORCINE ROTAVIRUS (GROUP C/STRAIN COWDEN) | 9–44 | | | | | | | | |
| PVS07_ROTBJ | GLYCOPROTEIN VP7 | BOVINE ROTAVIRUS (STRAIN KN-4) | 2–29 | | | | | | | | |
| PVS07_ROTBU | NONSTRUCTURAL PROTEIN NCVP3 | BOVINE ROTAVIRUS (STRAIN UK) | 91–146 | 199–236 | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVS07_ROTP5 | NONSTRUCTURAL PROTEIN NCVP3 | PORCINE ROTAVIRUS (SEROTYPE 5/STRAIN OSU) | 91–146 | 202–236 | | | | | | | |
| PVS07_ROTS1 | NONSTRUCTURAL PROTEIN NCVP3 | SIMIAN 11 ROTAVIRUS (STRAIN SA11) | 91–146 | 199–236 | | | | | | | |
| PVS08_ROTBU | NONSTRUCTURAL PROTEIN NS2/VP9 | BOVINE ROTAVIRUS (STRAIN UK) | 164–201 | | | | | | | | |
| PVS08_ROTS1 | NONSTRUCTURAL PROTEIN NCVP4 | SIMIAN 11 ROTAVIRUS (STRAIN SA11) | 164–201 | 217–251 | | | | | | | |
| PVS09_ROTB4 | GLYCOPROTEIN VP7 | BOVINE ROTAVIRUS (SEROTYPE 6/STRAIN B641) | 2–29 | | | | | | | | |
| PVS09_ROTB5 | GLYCOPROTEIN VP7 | BOVINE ROTAVIRUS (STRAIN A5) | 2–29 | | | | | | | | |
| PVS09_ROTBU | GLYCOPROTEIN VP7 | BOVINE ROTAVIRUS (STRAIN UK) | 2–29 | | | | | | | | |
| PVS09_ROTGA | GLYCOPROTEIN VP7 PRECURSOR | ROTAVIRUS (GROUP B/STRAIN ADRV) | 210–237 | | | | | | | | |
| PVS09_ROTH4 | GLYCOPROTEIN VP7 | HUMAN ROTAVIRUS (SEROTYPE 4/STRAIN RV-4) | 2–29 | | | | | | | | |
| PVS09_ROTHA | GLYCOPROTEIN VP7 | HUMAN ROTAVIRUS (SEROTYPE 2/STRAIN HU5) | 2–29 | | | | | | | | |
| PVS09_ROTHB | GLYCOPROTEIN VP7 | HUMAN ROTAVIRUS (SEROTYPE G/STRAIN B37) | 2–29 | | | | | | | | |
| PVS09_ROTHD | GLYCOPROTEIN VP7 | HUMAN ROTAVIRUS (SEROTYPE 2/STRAIN DS1) | 2–29 | | | | | | | | |
| PVS09_ROTHH | GLYCOPROTEIN VP7 | HUMAN ROTAVIRUS (SEROTYPE 2/STRAIN HN126) | 2–29 | | | | | | | | |
| PVS09_ROTHM | GLYCOPROTEIN VP7 | HUMAN ROTAVIRUS (SEROTYPE 1/STRAIN M37) | 2–29 | | | | | | | | |
| PVS09_ROTHO | GLYCOPROTEIN VP7 | HUMAN ROTAVIRUS (SEROTYPE 1/STRAIN MO AND STRAIN D) | 2–29 | | | | | | | | |
| PVS09_ROTHP | GLYCOPROTEIN VP7 | HUMAN ROTAVIRUS (SEROTYPE 3/STRAIN P) | 2–29 | | | | | | | | |
| PVS09_ROTHS | GLYCOPROTEIN VP7 | HUMAN ROTAVIRUS (SEROTYPE 2/STRAIN S2) | 2–29 | | | | | | | | |
| PVS09_ROTHW | GLYCOPROTEIN VP7 | HUMAN ROTAVIRUS (SEROTYPE 1/STRAIN WA) | 2–29 | | | | | | | | |
| PVS09_ROTP2 | GLYCOPROTEIN VP7 | PORCINE ROTAVIRUS (SEROTYPE 3/STRAIN AT/76) | 2–29 | | | | | | | | |
| PVS09_ROTP3 | GLYCOPROTEIN VP7 | PORCINE ROTAVIRUS (SEROTYPE 3/STRAIN CRW-8) | 2–29 | | | | | | | | |
| PVS09_ROTS1 | GLYCOPROTEIN VP7 | SIMIAN 11 ROTAVIRUS (STRAIN SA11) | 2–29 | | | | | | | | |
| PVS10_ROTBS | MINOR OUTER CAPSID PROTEIN | BOVINE ROTAVIRUS (GROUP C/STRAIN SHINTOKU) | 125–152 | | | | | | | | |
| PVS10_ROTS1 | NONSTRUCTURAL GLYCO-PROTEIN NCVP5 | SIMIAN 11 ROTAVIRUS (STRAIN SA11) | 113–140 | | | | | | | | |
| PVS11_ROTBU | MINOR OUTER CAPSID PROTEIN | BOVINE ROTAVIRUS (STRAIN UK) | 13–40 | 114–145 | | | | | | | |
| PVS11_ROTBV | MINOR OUTER CAPSID PROTEIN | BOVINE ROTAVIRUS (STRAIN VMRI) | 13–40 | 114–145 | | | | | | | |
| PVS11_ROTGA | NONSTRUCTURAL PROTEIN | ROTAVIRUS (GROUP B/STRAIN ADRV) (ADULT DIARRHEA ROTAVIRUS) | 31–60 | | | | | | | | |
| PVS11_ROTH5 | MINOR OUTER CAPSID PROTEIN | HUMAN ROTAVIRUS (SEROTYPE 2/STRAIN RV-5) | 13–40 | 111–145 | | | | | | | |
| PVS11_ROTHD | MINOR OUTER CAPSID PROTEIN | HUMAN ROTAVIRUS (SEROTYPE 2/STRAIN DS1) | 13–40 | 111–145 | | | | | | | |
| PVS11_ROTHW | MINOR OUTER CAPSID PROTEIN | HUMAN ROTAVIRUS (SEROTYPE 1/STRAIN WA) | 111–145 | | | | | | | | |
| PVS11_ROTRA | MINOR OUTER CAPSID PROTEIN | RABBIT ROTAVIRUS (STRAIN ALABAMA) | 118–145 | | | | | | | | |
| PVS11_ROTS1 | MINOR OUTER CAPSID PROTEIN | SIMIAN 11 ROTAVIRUS (STRAIN SA11) | 111–146 | | | | | | | | |
| PVSH_MUMP1 | SMALL HYDROPHOBIC PROTEIN | MUMPS VIRUS | 9–46 | | | | | | | | |
| PVSH_MUMPA | SMALL HYDROPHOBIC PROTEIN | MUMPS VIRUS (STRAIN MATSUYAMA) | 12–41 | | | | | | | | |
| PVSH_MUMPB | SMALL HYDROPHOBIC PROTEIN | MUMPS VIRUS (STRAIN BELFAST) | 9–41 | | | | | | | | |
| PVSH_MUMPE | SMALL HYDROPHOBIC PROTEIN | MUMPS VIRUS (STRAIN ENDERS) | 9–46 | | | | | | | | |
| PVSH_MUMPJ | SMALL HYDROPHOBIC PROTEIN | MUMPS VIRUS (STRAIN JERYL-LYNN) | 9–46 | | | | | | | | |
| PVSH_MUMPK | SMALL HYDROPHOBIC PROTEIN | MUMPS VIRUS (STRAIN KILHAM) | 9–46 | | | | | | | | |
| PVSH_MUMPL | SMALL HYDROPHOBIC PROTEIN | MUMPS VIRUS (STRAIN BRISTOL 1) | 9–46 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVSH_MUMPM | SMALL HYDROPHOBIC PROTEIN | MUMPS VIRUS (STRAIN MIYAHARA VACCINE) | 12–41 | | | | | | | | |
| PVSH_MUMPR | SMALL HYDROPHOBIC PROTEIN | MUMPS VIRUS (STRAIN RW) | 9–41 | | | | | | | | |
| PVSH_MUMPU | SMALL HYDROPHOBIC PROTEIN | MUMPS VIRUS (STRAIN URABE VACCINE AM9) | 12–41 | | | | | | | | |
| PVSI1_REOVD | SIGMA 1 PROTEIN PRECURSOR | REOVIRUS (TYPE 3/STRAIN DEARING) | 26–63 | 71–122 | 127–168 | 222–259 | | | | | |
| PVSI1_REOVJ | SIGMA 1 PROTEIN PRECURSOR | REOVIRUS (TYPE 2/STRAIN D5/JONES) | 4–104 | 130–193 | | | | | | | |
| PVSI1_REOVL | SIGMA 1 PROTEIN PRECURSOR | REOVIRUS (TYPE 1/STRAIN LANG) | 4–52 | 75–104 | 112–160 | | | | | | |
| PVSI2_REOVD | SIGMA 2 PROTEIN | REOVIRUS (TYPE 3/STRAIN DEARING) | 350–384 | | | | | | | | |
| PVSI3_REOVJ | SIGMA 3 PROTEIN | REOVIRUS (TYPE 2/STRAIN D5/JONES) | 289–316 | | | | | | | | |
| PVSIS_REOVD | SIGMA 1-S PROTEIN | REOVIRUS (TYPE 3/STRAIN DEARING) | 90–117 | | | | | | | | |
| PVSIS_REOVL | SIGMA 1-S PROTEIN | REOVIRUS (TYPE 1/STRAIN LANG) | 50–77 | | | | | | | | |
| PVT3A_CAPVI | PROTEIN T3A | CAPRIPOXVIRUS (STRAIN INS-1) | 124–158 | | | | | | | | |
| PVT5_SFVKA | PROTEIN T5 | SHOPE FIBROMA VIRUS (STRAIN KASZA) | 250–277 | | | | | | | | |
| PVTER_EBV | PROBABLE DNA PACKAGING PROTEIN | EPSTEIN-BARR VIRUS (STRAIN B95-8) | 234–290 | | | | | | | | |
| PVTER_HCMVA | PROBABLE DNA PACKAGING PROTEIN | HUMAN CYTOMEGALOVIRUS (STRAIN AD169) | 417–451 | | | | | | | | |
| PVTER_HSV6U | PROBABLE DNA PACKAGING PROTEIN | HERPES SIMPLEX VIRUS (TYPE 6/STRAIN UGANDA-1102) | 176–203 | | | | | | | | |
| PVTER_HSVI1 | PROBABLE DNA PACKAGING PROTEIN | ICTALURID HERPESVIRUS 1 | 710–737 | | | | | | | | |
| PVTER_VZVD | PROBABLE DNA PACKAGING PROTEIN | VARICELLA-ZOSTER VIRUS (STRAIN DUMAS) | 394–421 | | | | | | | | |
| PVTP3_TTV1V | VIRAL PROTEIN TPX | THERMOPROTEUS TENAX VIRUS 1 (STRAIN VT3) | 169–196 | | | | | | | | |
| PVTPX_TTV1 | VIRAL PROTEIN TPX | THERMOPROTEUS TENAX VIRUS 1 (STRAIN KRA1) | 169–196 | | | | | | | | |
| PVV_PI4HA | V PROTEIN | HUMAN PARAINFLUENZA 4A VIRUS (STRAIN TOSHIBA) | 4–38 | | | | | | | | |
| PY101_SSV1 | HYPOTHETICAL 10.1 KD PROTEIN | SULFOLOBUS VIRUS-LIKE PARTICLE SSV1 | 25–65 | | | | | | | | |
| PY108_SSV1 | HYPOTHETICAL 10.8 KD PROTEIN | SULFOLOBUS VIRUS-LIKE PARTICLE SSV1 | 4–61 | | | | | | | | |
| PY119_SSV1 | HYPOTHETICAL 11.9 KD PROTEIN | SULFOLOBUS VIRUS-LIKE PARTICLE SSV1 | 30–78 | | | | | | | | |
| PY11K_TYDVA | HYPOTHETICAL 11.2 KD PROTEIN | TOBACCO YELLOW DWARF VIRUS (STRAIN AUSTRALIA) | 53–87 | | | | | | | | |
| PY13K_NPVAC | HYPOTH 13.1 KD IN 39 KD 5REGION | AUTOGRAPHA CALIFORNICA NUCLEAR POLYHEDROSIS VIRUS | 85–112 | | | | | | | | |
| PY13K_SSV1 | HYPOTHETICAL 13.2 KD PROTEIN | SULFOLOBUS VIRUS-LIKE PARTICLE SSV1 | 59–86 | | | | | | | | |
| PY14K_SSV1 | HYPOTHETICAL 13.7 KD PROTEIN | SULFOLOBUS VIRUS-LIKE PARTICLE SSV1 | 5–39 | | | | | | | | |
| PY16K_NPVAC | HYPOTH IN 39 KD PROTEIN 5REGION | AUTOGRAPHA CALIFORNICA NUCLEAR POLYHEDROSIS VIRUS | 80–107 | | | | | | | | |
| PY16K_SSV1 | HYPOTHETICAL 15.6 KD PROTEIN | SULFOLOBUS VIRUS-LIKE PARTICLE SSV1 | 77–111 | | | | | | | | |
| PY17K_SSV1 | HYPOTHETICAL 17.8 KD PROTEIN | SULFOLOBUS VIRUS-LIKE PARTICLE SSV1 | 9–36 | 119–153 | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PY18K_MSVN | HYPOTHETICAL 17.7 KD PROTEIN | MAIZE STREAK VIRUS (NIGERIAN ISOLATE) | 34–61 | | | | | | | | |
| PY18K_MSVS | HYPOTHETICAL 17.2 KD PROTEIN | MAIZE STREAK VIRUS (SOUTH-AFRICAN ISOLATE) | 34–61 | | | | | | | | |
| PY20K_SSV1 | HYPOTHETICAL 20.4 KD PROTEIN | SULFOLOBUS VIRUS-LIKE PARTICLE SSV1 | 76–103 | | | | | | | | |
| PY28K_SSV1 | HYPOTHETICAL 28.5 KD PROTEIN | SULFOLOBUS VIRUS-LIKE PARTICLE SSV1 | 93–164 | | | | | | | | |
| PY2_SOCMV | HYPOTHETICAL PROTEIN 2 | SOYBEAN CHLOROTIC MOTTLE VIRUS | 118–148 | | | | | | | | |
| PY31K_SSV1 | HYPOTHETICAL 31.5 KD PROTEIN | SULFOLOBUS VIRUS-LIKE PARTICLE SSV1 | 24–97 | | | | | | | | |
| PY32K_SSV1 | HYPOTHETICAL 31.7 KD PROTEIN | SULFOLOBUS VIRUS-LIKE PARTICLE SSV1 | 233–267 | | | | | | | | |
| PY38K_NPVAC | HYPOTHETICAL 37.7 KD PROTEIN | AUTOGRAPHA CALIFORNICA NUCLEAR POLYHEDROSIS VIRUS | 133–184 | | | | | | | | |
| PY3_SOCMV | HYPOTHETICAL PROTEIN 3 | SOYBEAN CHLOROTIC MOTTLE VIRUS | 122–149 | | | | | | | | |
| PY7_SOCMV | HYPOTHETICAL PROTEIN 7 | SOYBEAN CHLOROTIC MOTTLE VIRUS | 56–94 | | | | | | | | |
| PY85K_SSV1 | HYPOTHETICAL 85.7 KD PROTEIN | SULFOLOBUS VIRUS-LIKE PARTICLE SSV1 | 81–121 | 546–573 | 658–700 | | | | | | |
| PY8_SOCMV | HYPOTHETICAL PROTEIN 8 | SOYBEAN CHLOROTIC MOTTLE VIRUS | 13–40 | | | | | | | | |
| PYB01_FOWPM | HYPOTHETICAL BAMHI-ORF1 PROTEIN | FOWLPOX VIRUS (ISOLATE HP-438[MUNICH]) | 74–108 | 152–179 | 184–218 | | | | | | |
| PYB05_FOWPM | HYPOTHETICAL BAMHI-ORF5 PROTEIN | FOWLPOX VIRUS (ISOLATE HP-438[MUNICH]) | 62–89 | | | | | | | | |
| PYB10_FOWPM | HYPOTHETICAL BAMHI-ORF10 PROTEIN | FOWLPOX VIRUS (ISOLATE HP-438[MUNICH]) | 162–197 | 214–241 | | | | | | | |
| PYB12_FOWPM | HYPOTHETICAL BAMHI-ORF12 PROTEIN | FOWLPOX VIRUS (ISOLATE HP-438[MUNICH]) | 11–38 | | | | | | | | |
| PYB13_FOWPM | HYPOTHETICAL BAMHI-ORF13 PROTEIN | FOWLPOX VIRUS (ISOLATE HP-438[MUNICH]) | 128–167 | | | | | | | | |
| PYBL3_FOAMV | BEL-3 PROTEIN | HUMAN SPUMARETROVIRUS | 87–116 | | | | | | | | |
| PYDH1_HSVS7 | HYPOTH 24.1 KD IN DHFR 3REGION | HERPESVIRUS SAIMIRI (STRAIN 484-77) | 161–188 | | | | | | | | |
| PYDH3_HSVSC | HYPOTH 28.7 KD IN DHFR 3REGION | HERPESVIRUS SAIMIRI (SUBGROUP C/STRAIN 488) | 52–82 | | | | | | | | |
| PYDH4_HSVSC | HYPOTH 9.9 KD IN DHFR 3REGION | HERPESVIRUS SAIMIRI (SUBGROUP C/STRAIN 488) | 53–83 | | | | | | | | |
| PYF26_FOWP1 | HYPOTHETICAL 25.9 KD PROTEIN | FOWLPOX VIRUS (STRAIN FP-1) | 8–35 | | | | | | | | |
| PYF30_FOWP1 | HYPOTHETICAL 30.9 KD PROTEIN | FOWLPOX VIRUS (STRAIN FP-1) | 170–204 | | | | | | | | |
| PYH22_VACCV | HYPOTH 21.7 KD HINDIII-C PRO | VACCINIA VIRUS (STRAIN WR) | 37–64 | 95–126 | 144–171 | | | | | | |
| PYHR3_VACCV | HYPOTH HOST RANGE 27.4 KD PRO | VACCINIA VIRUS (STRAIN WR) | 31–58 | 179–206 | | | | | | | |
| PYKR2_EBV | HYPOTHETICAL BKRF2 PROTEIN | EPSTEIN-BARR VIRUS (STRAIN B95-8) | 90–121 | | | | | | | | |

TABLE VI-continued

107 X 178 X 4 SEARCH MOTIF RESULTS SUMMARY FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYKR4_EBV | HYPOTHETICAL BKRF4 PROTEIN | EPSTEIN-BARR VIRUS (STRAIN B95-8) | 19–53 | | | | | | | | |
| PYL15_ADE41 | HYPOTH 12.4 KD IN 33 KD REGION | HUMAN ADENOVIRUS TYPE 41 | 47–86 | | | | | | | | |
| PYLR3_EBV | HYPOTHETICAL BLRF3 PROTEIN | EPSTEIN-BARR VIRUS (STRAIN B95-8) | 27–54 | | | | | | | | |
| PYOR1_COYMV | HYPOTHETICAL 23 KD PROTEIN | COMMELINA YELLOW MOTTLE VIRUS | 94–143 | | | | | | | | |
| PYOR2_COYMV | HYPOTHETICAL 15 KD PROTEIN | COMMELINA YELLOW MOTTLE VIRUS | 35–76 | | | | | | | | |
| PYOR3_WCMVM | HYPOTHETICAL 13 KD PROTEIN | WHITE CLOVER MOSAIC VIRUS (STRAIN M) | 64–94 | | | | | | | | |
| PYOR3_WCMVO | HYPOTHETICAL 13 KD PROTEIN | WHITE CLOVER MOSAIC VIRUS (STRAIN O) | 65–95 | | | | | | | | |
| PYOR5_ADEG1 | HYPOTHETICAL 31.5 KD PROTEIN | AVIAN ADENOVIRUS GALI (STRAIN PHELPS) | 92–119 | | | | | | | | |
| PYORA_TTV1 | HYPOTHETICAL 8.1 KD PROTEIN | THERMOPROTEUS TENAX VIRUS 1 (STRAIN KRA1) | 23–57 | | | | | | | | |
| PYORL_TTV1 | HYPOTHETICAL 26.8 KD PROTEIN | THERMOPROTEUS TENAX VIRUS 1 (STRAIN KRA1) | 15–42 | | | | | | | | |
| PYORQ_TTV1 | HYPOTHETICAL 7.3 KD PROTEIN | THERMOPROTEUS TENAX VIRUS 1 (STRAIN KRA1) | 3–31 | | | | | | | | |
| PYORW_TTV1 | HYPOTHETICAL 12.1 KD PROTEIN | THERMOPROTEUS TENAX VIRUS 1 (STRAIN KRA1) | 4–40 | | | | | | | | |
| PYP12_RTBV | HYPOTHETICAL P12 PROTEIN | RICE TUNGRO BACILLIFORM VIRUS | 44–71 | | | | | | | | |
| PYP12_RTBVP | HYPOTHETICAL P12 PROTEIN | RICE TUNGRO BACILLIFORM VIRUS (ISOLATE PHILIPPINES) | 44–71 | | | | | | | | |
| PYP24_RTBV | HYPOTHETICAL P24 PROTEIN | RICE TUNGRO BACILLIFORM VIRUS | 59–101 | 106–157 | | | | | | | |
| PYP24_RTBVP | HYPOTHETICAL P24 PROTEIN | RICE TUNGRO BACILLIFORM VIRUS (ISOLATE PHILIPPINES) | 51–101 | 106–157 | | | | | | | |
| PYP46_RTBV | HYPOTHETICAL P46 PROTEIN | RICE TUNGRO BACILLIFORM VIRUS | 58–107 | 197–231 | | | | | | | |
| PYP46_RTBVP | HYPOTHETICAL P46 PROTEIN | RICE TUNGRO BACILLIFORM VIRUS (ISOLATE PHILIPPINES) | 58–107 | 197–231 | | | | | | | |
| PYP63_NPVAC | HYPOTH PRO P6.5 5'REGION | AUTOGRAPHA CALIFORNICA NUCLEAR POLYHEDROSIS VIRUS | 44–71 | | | | | | | | |
| PYP63_NPVOP | HYPOTH 40.0 KD IN P6.5 5'REGION | ORGYIA PSEUDOTSUGATA MULTICAPSID POLYHEDROSIS VIRUS | 325–352 | | | | | | | | |
| PYPOH_NPVAC | HYPOTH 23.6 KD IN POLYHEDRIN 5'REGION | AUTOGRAPHA CALIFORNICA NUCLEAR POLYHEDROSIS VIRUS | 116–153 | | | | | | | | |
| PYPOL_IPNVN | HYPOTHETICAL 17.0 KD PROTEIN | INFECTIOUS PANCREATIC NECROSIS VIRUS (STRAIN N1) | 5–32 | | | | | | | | |
| PYQ3_AMEPV | HYPOTHETICAL PROTEIN IN TK 3'REGION | AMSACTA MOOREI ENTOMOPOXVIRUS | 8–57 | 59–96 | 156–183 | | | | | | |
| PYRF1_HSV6G | HYPOTHETICAL PROTEIN RF1 | HERPES SIMPLEX VIRUS (TYPE 6/STRAIN GS) | 208–235 | | | | | | | | |
| PYRF2_HSV6G | HYPOTHETICAL PROTEIN RF2 | HERPES SIMPLEX VIRUS (TYPE 6/STRAIN GS) | 223–257 | 268–299 | | | | | | | |
| PYRF3_HSV6G | HYPOTHETICAL PROTEIN RF3 | HERPES SIMPLEX VIRUS (TYPE 6/STRAIN GS) | 141–168 | | | | | | | | |
| PYRF4_HSV6G | HYPOTHETICAL PROTEIN RF4 | HERPES SIMPLEX VIRUS (TYPE 6/STRAIN GS) | 404–441 | | | | | | | | |
| PYRP2_IRV6 | REPETITIVE PROTEIN ORF2 | CHILO IRIDESCENT VIRUS | 10–45 | | | | | | | | |
| PYVAG_VACCC | HYPOTHETICAL 9.3 KD PROTEIN | VACCINIA VIRUS (STRAIN COPENHAGEN) | 7–34 | | | | | | | | |
| PYVAH_VACCC | HYPOTHETICAL 14.5 KD PROTEIN | VACCINIA VIRUS (STRAIN COPENHAGEN) | 81–112 | | | | | | | | |
| PYVDB_VACCC | HYPOTHETICAL 8.5 KD PROTEIN | VACCINIA VIRUS (STRAIN COPENHAGEN) | 29–77 | | | | | | | | |
| PYVDB_VACCV | HYPOTHETICAL 8.5 KD PROTEIN | VACCINIA VIRUS (STRAIN WR) | 46–77 | | | | | | | | |

TABLE VI-continued

107 X 178 X 4 SEARCH MOTIF RESULTS SUMMARY
FOR ALL VIRAL (NON-BACTERIOPHAGE) PROTEINS

| PCGENE FILE NAME | 107x178x4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYVDH_VACCV | HYPOTHETICAL 7.2 KD PROTEIN | VACCINIA VIRUS (STRAIN WR) | 20–50 | | | | | | | | |
| PYVGB_VACCC | HYPOTHETICAL 8.4 KD PROTEIN | VACCINIA VIRUS (STRAIN COPENHAGEN) | 10–44 | | | | | | | | |
| PYZL2_EBV | HYPOTHETICAL BZLF2 PROTEIN | EPSTEIN-BARR VIRUS (STRAIN B95-8) | 152–179 | | | | | | | | |

TABLE VII

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| | | 107 × 178 × 4 SEARCH MOTIF RESULTS SUMMARY (PREFERRED VIRAL SEQUENCES) | | | | | | | | | |
| PPOL_MLVAK | POL POLYPROTEIN | AKR MURINE LEUKEMIA VIRUS | 453–480 | | | | | | | | |
| PENV_MLVAV | ENV POLYPROTEIN | AKV MURINE LEUKEMIA VIRUS | 517–544 | | | | | | | | |
| PPOL_MLVAV | POL POLYPROTEIN | AKV MURINE LEUKEMIA VIRUS | 805–832 | | | | | | | | |
| PMYC_AVIM2 | MYC TRANSFORMING PROTEIN | AVIAN MYELOCYTOMATOSIS VIRUS CMII | 232–266 | 375–402 | | | | | | | |
| PMYC_AVIMD | MYC TRANSFORMING PROTEIN | AVIAN MYELOCYTOMATOSIS VIRUS HBI | 233–267 | 376–403 | | | | | | | |
| PMYC_AVIMC | MYC TRANSFORMING PROTEIN | AVIAN MYELOCYTOMATOSIS VIRUS MC29 | 233–267 | 376–403 | | | | | | | |
| VL1_FPVL | PROBABLE L1 PROTEIN | AVIAN PAPILLOMA VIRUS FPV-L | 38–65 | | | | | | | | |
| PVGLB_HSVB1 | GLYCOPROTEIN I PRECURSOR | BOVINE HERPES VIRUS TYPE 1 | 427–454 | | | | | | | | |
| PRIR2_HSVB3 | RIBONUC-DIPHOSPH REDUCT SMALL CHA | BOVINE HERPES VIRUS TYPE 1 (STRAIN 34) | 90–117 | | | | | | | | |
| PVGLB_HSVB2 | GLYCOPROTEIN B-1 PRECURSOR | BOVINE HERPES VIRUS TYPE 2 (STRAIN BMV) | 447–474 | | | | | | | | |
| PENV_BIV06 | ENV POLYPROTEIN | BOVINE IMMUNODEFICIENCY VIRUS (ISOLATE 106) | 17–44 | 544–603 | 631–695 | | | | | | |
| PENV_BIV27 | ENV POLYPROTEIN | BOVINE IMMUNODEFICIENCY VIRUS (ISOLATE 127) | 17–44 | 573–632 | 660–724 | | | | | | |
| PENV_BLVAF | ENV POLYPROTEIN | BOVINE LEUKEMIA VIRUS (AMERICAN ISOLATE FLK) | 304–377 | | | | | | | | |
| PENV_BLVAV | ENV POLYPROTEIN | BOVINE LEUKEMIA VIRUS (AMERICAN ISOLATE VDM) | 304–377 | | | | | | | | |
| PENV_BLVAU | ENV POLYPROTEIN | BOVINE LEUKEMIA VIRUS (AUSTRALIAN ISOLATE) | 304–377 | | | | | | | | |
| PENV_BLVB2 | ENV POLYPROTEIN | BOVINE LEUKEMIA VIRUS (BELGIUM ISOLATE LB285) | 311–377 | | | | | | | | |
| PENV_BLVB5 | ENV POLYPROTEIN | BOVINE LEUKEMIA VIRUS (BELGIUM ISOLATE LB59) | 304–377 | | | | | | | | |
| PENV_BLVJ | ENV POLYPROTEIN | BOVINE LEUKEMIA VIRUS (JAPANESE ISOLATE BLV-1) | 304–377 | | | | | | | | |
| PHEMA_P13B | HEMAGGLUTININ-NEURAMINIDASE | BOVINE PARAINFLUENZA 3 VIRUS | 66–93 | | | | | | | | |
| PRRPP_P13B | RNA POLYMERASE ALPHA SUBUNIT | BOVINE PARAINFLUENZA 3 VIRUS | 34–91 | 255–282 | 285–314 | | | | | | |
| PVGLF_P13B | FUSION GLYCOPROTEIN PRECURSOR | BOVINE PARAINFLUENZA 3 VIRUS | 115–182 | 207–241 | 459–497 | | | | | | |
| PVMAT_P13B | MATRIX PROTEIN | BOVINE PARAINFLUENZA 3 VIRUS | 201–231 | | | | | | | | |
| PRRPP_BRSVA | RNA POLYMERASE ALPHA SUBUNIT | BOVINE RESPIRATORY SYNCYTIAL VIRUS (STRAIN A51908) | 99–133 | | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLF_BRSVA | FUSION GLYCOPROTEIN PRECURSOR | BOVINE RESPIRATORY SYNCYTIAL VIRUS (STRAIN A51908) | 38–65 | 154–202 | 216–243 | 442–469 | 486–531 | | | | |
| PVMA2_BRSVA | MATRIX GLYCOPROTEIN M2 | BOVINE RESPIRATORY SYNCYTIAL VIRUS (STRAIN A51908) | 124–152 | | | | | | | | |
| PVMAT_BRSVA | MATRIX PROTEIN | BOVINE RESPIRATORY SYNCYTIAL VIRUS (STRAIN A51908) | 219–246 | | | | | | | | |
| PVGLF_BRSVC | FUSION GLYCOPROTEIN PRECURSOR | BOVINE RESPIRATORY SYNCYTIAL VIRUS (STRAIN COPENHAGEN) | 38–65 | 154–202 | 216–243 | 444–471 | 488–533 | | | | |
| PVGLG_BRSVC | MAJOR SURFACE GLYCOPROTEIN G | BOVINE RESPIRATORY SYNCYTIAL VIRUS (STRAIN COPENHAGEN) | 92–123 | | | | | | | | |
| PVGLF_BRSVR | FUSION GLYCOPROTEIN PRECURSOR | BOVINE RESPIRATORY SYNCYTIAL VIRUS (STRAIN RB94) | 38–65 | 154–202 | 216–243 | 444–471 | 488–533 | | | | |
| PENV_MLVCB | ENV POLYPROTEIN | CAS-BR-E MURINE LEUKEMIA VIRUS | 510–539 | | | | | | | | |
| PENV_SIVCZ | ENV POLYPROTEIN | CHIMPANZEE IMMUNO-DEFICIENCY VIRUS | 160–187 | 253

TABLE VII-continued 107 x 178 x 4 SEARCH MOTIF RESULTS SUMMARY
(PREFERRED VIRAL SEQUENCES)

| PCGENE FILE NAME | 107 x 178 x 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDPOL_HPBDB | DNA POLYMERASE | DUCK HEPATITIS B VIRUS SHANGHAI DUCK ISOLATE S5) | 5–39 | | | | | | | | |
| PDPOL_HPBDC | DNA POLYMERASE | DUCK HEPATITIS B VIRUS (STRAIN CHINA) | 5–39 | | | | | | | | |
| PDPOL_HPBDW | DNA POLYMERASE | DUCK HEPATITIS B VIRUS (WHITE SHANGHAI DUCK ISOLATE S31) | 5–39 | 304–331 | | | | | | | |
| PTEGU_EBV | LARGE TEGUMENT PROTEIN | EPSTEIN-BARR VIRUS (STRAIN B95-8) | 145–172 | 1215–1242 | 1344–1371 | 1876–1903 | | | | | |
| PUL06_EBV | VIRION PROTEIN BBRF1 | EPSTEIN-BARR VIRUS (STRAIN B95-8) | 115–142 | 313–340 | 542–569 | | | | | | |
| PUL11_EBV | HYPOTHETICAL PROTEIN BBLF1 | EPSTEIN-BARR VIRUS (STRAIN B95-8) | 15–42 | | | | | | | | |
| PUL52_EB | PROB DNA REPLICATION PROTEIN BSLF1 | EPSTEIN-BARR VIRUS (STRAIN B95-8) | 185–212 | 787–814 | | | | | | | |
| PUL87_EBV | HYPOTHETICAL PROTEIN B(C)RF1 | EPSTEIN-BARR VIRUS (STRAIN B95-8) | 409–436 | | | | | | | | |
| PUL92_EBV | HYPOTHETICAL PROTEIN BDLF4 | EPSTEIN-BARR VIRUS (STRAIN B95-8) | 107–144 | 168–196 | | | | | | | |
| PVCAP_EBV | MAJOR CAPSID PROTEIN | EPSTEIN-BARR VIRUS (STRAIN B95-8) | 847–874 | | | | | | | | |
| PVGL2_EBV | PROBABLE MEMBRANE GLYCOPROTEIN | EPSTEIN-BARR VIRUS (STRAIN B95-8) | 68–102 | | | | | | | | |
| PVGLB_EBV | GLYCOPROTEIN GP110 PRECURSOR | EPSTEIN-BARR VIRUS (STRAIN B95-8) | 95–122 | 631–658 | | | | | | | |
| PVGLH_EBV | GLYCOPROTEIN GP85 PRECURSOR | EPSTEIN-BARR VIRUS (STRAIN B95-8) | 549–576 | 619–648 | | | | | | | |
| PVGP8_EBV | PROBABLE MEMBRANE ANTIGEN GP85 | EPSTEIN-BARR VIRUS (STRAIN B95-8) | 104–149 | | | | | | | | |
| PVP40_EBV | CAPSID PROTEIN P40 | EPSTEIN-BARR VIRUS (STRAIN B95-8) | 440–470 | | | | | | | | |
| PVTER_EBV | PROBABLE DNA PACKAGING PROTEIN | EPSTEIN-BARR VIRUS (STRAIN B95-8) | 234–290 | | | | | | | | |
| PYKR2_EBV | HYPOTHETICAL BKRF2 PROTEIN | EPSTEIN-BARR VIRUS (STRAIN B95-8) | 90–21 | | | | | | | | |
| PYKR4_EBV | HYPOTHETICAL BKRF4 PROTEIN | EPSTEIN-BARR VIRUS (STRAIN B95-8) | 19–53 | | | | | | | | |
| PYLR3_EBV | HYPOTHETICAL BLRF3 PROTEIN | EPSTEIN-BARR VIRUS (STRAIN B95-8) | 27–54 | | | | | | | | |
| PYZL2_EBV | HYPOTHETICAL BZLF2 PROTEIN | EPSTEIN-BARR VIRUS (STRAIN B95-8) | 152–179 | | | | | | | | |
| PBZLF_EBV | BZLF1 TRANS-ACTIVATOR PROTEIN | EPSTEIN-BARR VIRUS (STRAIN B95-8) | 193–220 | | | | | | | | |
| PDNB1_EBV | MAJOR DNA-BINDING PROTEIN | EPSTEIN-BARR VIRUS (STRAIN B95-8) | 977–1004 | 1041–1068 | | | | | | | |

TABLE VII-continued 107 x 178 x 4 SEARCH MOTIF RESULTS SUMMARY
(PREFERRED VIRAL SEQUENCES)

| PCGENE FILE NAME | 107 x 178 x 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PEAR_EBV | EARLY ANTIGEN PROTEIN R | EPSTEIN-BARR VIRUS (STRAIN B95-8) | 55–82 | | | | | | | | |
| PLMP1_EBV | LATENT MEMBRANE PROTEIN 1 | EPSTEIN-BARR VIRUS (STRAIN B95-8) | 148–175 | | | | | | | | |
| PLMP2_EBV | GENE TERMINAL PROTEIN | EPSTEIN-BARR VIRUS (STRAIN B95-8) | 294–321 | | | | | | | | |
| PLMP1_EBVC | LATENT MEMBRANE PROTEIN 1 | EPSTEIN-BARR VIRUS (STRAIN CAO) | 148–175 | | | | | | | | |
| PLMP1_EBVR | LATENT MEMBRANE PROTEIN 1 | EPSTEIN-BARR VIRUS (STRAIN RAJI) | 148–175 | | | | | | | | |
| PUL32_HSVEB | MAJOR ENVELOPE GLYCOPROTEIN 300 | EQUINE HERPES VIRUS TYPE 1 | 345–375 | | | | | | | | |
| PVG1C_HSVEB | GLYCOPROTEIN C PRECURSOR | EQUINE HERPES VIRUS TYPE 1 | 124–151 | | | | | | | | |
| PVGLB_HSVE1 | GLYCOPROTEIN B PRECURSOR | EQUINE HERPES VIRUS TYPE 1 (ISOLATE HVS25A) | 443–470 | 934–961 | | | | | | | |
| PVGLB_HSVEA | GLYCOPROTEIN B PRECURSOR | EQUINE HERPES VIRUS TYPE 1 (STRAIN AB1) | 443–470 | 934–961 | | | | | | | |
| PAIT2_HSVEB | ALPHA TRANS-IND FACTOR 82 KD PRO | EQUINE HERPES VIRUS TYPE 1 (STRAIN AB4P) | 294–321 | | | | | | | | |
| PATIN_HSVEB | ALPHA TRANS-IND PROTEIN | EQUINE HERPES VIRUS TYPE 1 (STRAIN AB4P) | 255–289 | | | | | | | | |
| PHEL1_HSVEB | PROBABLE HELICASE | EQUINE HERPES VIRUS TYPE 1 (STRAIN AB4P) | 184–211 | 321–348 | | | | | | | |
| PRIR1_HSVEB | RIBONUC-DIPHOSPH REDUCT LARGE CHAS | EQUINE HERPES VIRUS TYPE 1 (STRAIN AB4P) | 75–102 | | | | | | | | |
| PTEGU_HSVEB | LARGE TEGUMENT PROTEIN | EQUINE HERPES VIRUS TYPE 1 (STRAIN AB4P) | 229–256 | 566–593 | 1205–1232 | | | | | | |
| PUL06_HSVEB | VIRION GENE 56 PROTEIN | EQUINE HERPES VIRUS TYPE 1 (STRAIN AB4P) | 640–667 | | | | | | | | |
| PUL14_HSVEB | HYPOTHETICAL GENE 48 PROTEIN | EQUINE HERPES VIRUS TYPE 1 (STRAIN AB4P) | 247–286 | | | | | | | | |
| PUL21_HSVEB | GENE 40 PROTEIN | EQUINE HERPES VIRUS TYPE 1 (STRAIN AB4P) | 44–71 | | | | | | | | |
| PUL37_HSVEB | GENE 23 PROTEIN | EQUINE HERPES VIRUS TYPE 1 (STRAIN AB4P) | 715–749 | 987–1014 | | | | | | | |
| PUL52_HSVEB | DNA REPLICATION PROTEIN UL52 | EQUINE HERPES VIRUS TYPE 1 (STRAIN AB4P) | 193–220 | 943–970 | | | | | | | |
| PVG03_HSVEB | GENE 3 PROTEIN | EQUINE HERPES VIRUS TYPE 1 (STRAIN AB4P) | 146–176 | | | | | | | | |
| PVGLB_HSVEB | GLYCOPROTEIN B PRECURSOR | EQUINE HERPES VIRUS TYPE 1 (STRAIN AB4P) | 443–470 | 934–961 | | | | | | | |
| PVGLG_HSVEB | GLYCOPROTEIN G PRECURSOR | EQUINE HERPES VIRUS TYPE 1 (STRAIN AB4P) | 383–410 | | | | | | | | |
| VIMP_HSVEB | PROB INTEGRAL MEMBRANE PROTEIN | EQUINE HERPES VIRUS TYPE 1 (STRAIN AB4P) | 147–174 | | | | | | | | |

TABLE VII-continued

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| | | 107 × 178 × 4 SEARCH MOTIF RESULTS SUMMARY (PREFERRED VIRAL SEQUENCES) | | | | | | | | | |
| PVP26_HSVEB | CAPSID PROTEIN VP26 | EQUINE HERPES VIRUS TYPE 1 (STRAIN AB4P) | 36–63 | | | | | | | | |
| PVG03_HSVEK | GENE 3 PROTEIN | EQUINE HERPES VIRUS TYPE 1 (STRAIN KENTUCKY A) | 146–176 | | | | | | | | |
| PVGLB_HSVEL | GLYCOPROTEIN B PRECURSOR | EQUINE HERPES VIRUS TYPE 1 (STRAIN KENTUCKY D) | 443–470 | 933–960 | | | | | | | |
| PCELF_HSVEB | CELL FUSION PROTEIN PRECURSOR | EQUINE HERPES VIRUS TYPE 1 (STRAINS AB4P and Ky A) | 312–339 | | | | | | | | |
| PUL47_HSVE4 | 97 KD ALPHA TRANS-INDUCING | EQUINE HERPES VIRUS TYPE 4 | 190–217 | | | | | | | | |
| PVGLB_HSVE4 | GLYCOPROTEIN B PRECURSOR | EQUINE HERPES VIRUS TYPE 4 | 486–513 | 616–643 | | | | | | | |
| PVGLG_HSVE4 | GLYCOPROTEIN G PRECURSOR | EQUINE HERPES VIRUS TYPE 4 | 271–298 | | | | | | | | |
| PDUT_HSVE4 | DEOXYU 5'-TRIPHOSPH NUCHYDROLASE | EQUINE HERPES VIRUS TYPE 4 (STRAIN 1942) | 90–117 | | | | | | | | |
| PVE2_PAPVE | PROBABLE E2 PROTEIN | EUROPEAN ELK PAPILLOMA-VIRUS | 120–150 | | | | | | | | |
| PENV_FIVPE | ENV POLYPROTEIN | FELINE IMMUNODEFICIENCY VIRUS (ISOLATE PETALUMA) | 650–680 | 722–749 | | | | | | | |
| PPOL_FIVPE | POL POLYPROTEIN | FELINE IMMUNODEFICIENCY VIRUS (ISOLATE PETALUMA) | 442–473 | | | | | | | | |
| PENV_FIVSD | ENV POLYPROTEIN | FELINE IMMUNODEFICIENCY VIRUS (ISOLATE SAN DIEGO) | 639–668 | 720–747 | | | | | | | |
| PENV_FIVT2 | ENV POLYPROTEIN | FELINE IMMUNODEFICIENCY VIRUS (ISOLATE TM2) | 640–679 | 721–748 | | | | | | | |
| PENV_FLVC6 | ENV POLYPROTEIN | FELINE LEUKEMIA PROVIRUS (CLONE CFE-6) | 509–538 | | | | | | | | |
| PMYC_FLVTT | MYC TRANSFORMING PROTEIN | FELINE LEUKEMIA PROVIRUS FTT | 393–420 | | | | | | | | |
| PMYC_FLV | MYC TRANSFORMING PROTEIN | FELINE LEUKEMIA VIRUS | 393–420 | | | | | | | | |
| PENV_FLVGL | ENV POLYPROTEIN | FELINE LEUKEMIA VIRUS (STRAIN A/GLASGOW-1) | 490–519 | | | | | | | | |
| PENV_FLVLB | ENV POLYPROTEIN | FELINE LEUKEMIA VIRUS (STRAIN LAMBDA-B1) | 510–539 | | | | | | | | |
| PENV_FLVSA | ENV POLYPROTEIN | FELINE LEUKEMIA VIRUS (STRAIN SARMA) | 487–516 | | | | | | | | |
| PENV_MLVF5 | ENV POLYPROTEIN | FRIEND MURINE LEUKEMIA VIRUS (ISOLATE 57) | 523–553 | | | | | | | | |
| PENV_MLVTF | ENV POLYPROTEIN | FRIEND MURINE LEUKEMIA VIRUS (ISOLATE FB29) | 523–553 | | | | | | | | |
| PENV_MLVFP | ENV POLYPROTEIN | FRIEND MURINE LEUKEMIA VIRUS (ISOLATE PVC-211) | 523–553 | | | | | | | | |
| PENV_GALV | ENV POLYPROTEIN | GIBBON APE LEUKEMIA VIRUS | 176–203 | 523–564 | | | | | | | |
| PGAG_GALV | GAG POLYPROTEIN | GIBBON APE LEUKEMIA VIRUS | 396–442 | 447–474 | | | | | | | |
| PPOL_GALV | POL POLYPROTEIN | GIBBON APE LEUKEMIA VIRUS | 535–562 | 676–703 | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDPOL_HPBGS | DNA POLYMERASE | GROUND SQUIRREL HEPATITIS VIRUS | 271–325 | | | | | | | | |
| PPOLG_HPAV8 | GENOME POLYPROTEIN | HEPATITIS A VIRUS (STRAIN 18F) | 203–237 | 1021–1048 | 1117–1149 | 1454–1481 | | | | | |
| PPOLG_HPAV2 | GENOME POLYPROTEIN | HEPATITIS A VIRUS (STRAIN 24A) | 203–237 | 1021–1048 | 1117–1149 | 1454–1481 | | | | | |
| PPOLG_HPAV4 | GENOME POLYPROTEIN | HEPATITIS A VIRUS (STRAIN 43C) | 203–237 | 1021–1048 | 1117–1149 | 1454–1481 | | | | | |
| PPOLG_HPAVC | GENOME POLYPROTEIN | HEPATITIS A VIRUS (STRAIN CR326) | 203–237 | | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PAANT_HDVWO | DELTA ANTIGEN | HEPATITIS DELTA VIRUS (ISOLATE AMERICAN) | 106–133 | | | | | | | | |
| PAANT_HDVIT | DELTA ANTIGEN | HEPATITIS DELTA VIRUS (ISOLATE AMERICAN) | 106–133 | | | | | | | | |
| PAANT_HDVM2 | DELTA ANTIGEN | HEPATITIS DELTA VIRUS (ISOLATE AMERICAN) | 106–133 | | | | | | | | |
| PPOLN_HEVBU | NON-STRUCTURAL POLY-PROTEIN | HEPATITIS E VIRUS (STRAIN BURMA) | 219–246 | 349–376 | | | | | | | |
| PPOLN_HEVME | NON-STRUCTURAL POLY-PROTEIN | HEPATITIS E VIRUS (STRAIN MEXICO) | 219–246 | 349–376 | | | | | | | |
| PPOLN_HEVMY | N-STRUCTURAL POLY-PROTEIN | HEPATITIS E VIRUS (STRAIN MYANMAR) | 219–246 | 349–376 | | | | | | | |
| PPOLN_HEVPA | NON-STRUCTURAL POLY-PROTEIN | HEPATITIS E VIRUS (STRAIN PAKISTAN) | 218–245 | 348–375 | | | | | | | |
| PDPOL_HPBHE | DNA POLYMERASE | HERON HEPATITIS B VIRUS | 5–39 | | | | | | | | |
| PVMSA_HPBHE | MAJOR SURFACE ANTIGEN PRECURSOR | HERON HEPATITIS B VIRUS | 294–328 | | | | | | | | |
| PIE63_HSV11 | TRANSCRIPTIONAL REGULATOR | HERPES SIMPLEX VIRUS (TYPE 1/STRAIN 17) | 248–275 | | | | | | | | |
| PIE68_HSV11 | IMMEDIATE-EARLY PROTEIN IE68 | HERPES SIMPLEX VIRUS (TYPE 1/STRAIN 17) | 40–67 | | | | | | | | |
| PTEGU_HSV11 | LARGE TEGUMENT PROTEIN | HERPES SIMPLEX VIRUS (TYPE 1/STRAIN 17) | 667–694 | 1673–1710 | | | | | | | |
| PUL06_HSV11 | VIRION PROTEIN UL6 | HERPES SIMPLEX VIRUS (TYPE 1/STRAIN 17) | 586–613 | | | | | | | | |
| PUL34_HSV11 | VIRION PROTEIN UL34 | HERPES SIMPLEX VIRUS (TYPE 1/STRAIN 17) | 116–143 | | | | | | | | |
| PUL37_HSV11 | PROTEIN UL37 | HERPES SIMPLEX VIRUS (TYPE 1/STRAIN 17) | 470–497 | 853–884 | | | | | | | |
| PUL42_HSV11 | DNA-BINDING PROTEIN UL42 | HERPES SIMPLEX VIRUS (TYPE 1/STRAIN 17) | 231–258 | | | | | | | | |
| PUL47_HSV11 | VIRION PROTEIN UL47 | HERPES SIMPLEX VIRUS (TYPE 1/STRAIN 17) | 488–515 | | | | | | | | |
| PVGLC_HSV11 | GLYCOPROTEIN C PRECURSOR | HERPES SIMPLEX VIRUS (TYPE 1/STRAIN 17) | 469–510 | | | | | | | | |
| PAT12_HSV11 | ALPHA TRANS-IND FACTOR 78 KD PRO | HERPES SIMPLEX VIRUS (TYPE 1/STRAIN 17) | 308–335 | | | | | | | | |
| PUL47_HSV1F | VIRION PROTEIN UL47 | HERPES SIMPLEX VIRUS (TYPE 1/STRAIN F) | 488–515 | | | | | | | | |
| PAT12_HSV1F | ALPHA TRANS-IND FACTOR 77 KD PRO | HERPES SIMPLEX VIRUS (TYPE 1/STRAIN F) | 308–335 | | | | | | | | |
| PVGLC_HSV1K | GLYCOPROTEIN C PRECURSOR | HERPES SIMPLEX VIRUS (TYPE 1/STRAIN KOS) | 469–510 | | | | | | | | |
| PVGLE_HSV2 | GLYCOPROTEIN E PRECURSOR | HERPES SIMPLEX VIRUS (TYPE 2) | 111–148 | | | | | | | | |

TABLE VII-continued 107 x 178 x 4 SEARCH MOTIF RESULTS SUMMARY
(PREFERRED VIRAL SEQUENCES)

| PCGENE FILE NAME | 107 x 178 x 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTEGU_HSV6G | LARGE TEGUMENT PROTEIN | HERPES SIMPLEX VIRUS (TYPE 6/STRAIN GS) | 102–129 | 228–262 | 567–611 | 962–993 | 1098–1181 | 1661–1688 | 1884–1911 | | |
| PVG1H_HSV6G | GLYCOPROTEIN H PRECURSOR | HERPES SIMPLEX VIRUS (TYPE 6/STRAIN GS) | 62–89 | 360–403 | | | | | | | |
| PYRF1_HSV6G | HYPOTHETICAL PROTEIN RF1 | HERPES SIMPLEX VIRUS (TYPE 6/STRAIN GS) | 208–235 | | | | | | | | |
| PYRF2_HSV6G | HYPOTHETICAL PROTEIN RF2 | HERPES SIMPLEX VIRUS (TYPE 6/STRAIN GS) | 223–257 | 268–299 | | | | | | | |
| PYRF3_HSV6G | HYPOTHETICAL PROTEIN RF3 | HERPES SIMPLEX VIRUS (TYPE 6/STRAIN GS) | 141–168 | | | | | | | | |
| PYRF4_HSV6G | HYPOTHETICAL PROTEIN RF4 | HERPES SIMPLEX VIRUS (TYPE 6/STRAIN GS) | 404–441 | | | | | | | | |
| PP100_HSV6J | MAJOR ANTIGENIC STRUCTL PROTEIN | HERPES SIMPLEX VIRUS (TYPE 6/STRAIN UGANDA-1102) | 81–108 | 189–216 | 688–715 | 785–812 | | | | | |
| PUL87_HSV6U | HYPOTHETICAL PROTEIN 5R | HERPES SIMPLEX VIRUS (TYPE 6/STRAIN UGANDA-1102) | 536–563 | 729–768 | | | | | | | |
| PUL95_HSV6U | HYPOTHETICAL PROTEIN 13R | HERPES SIMPLEX VIRUS (TYPE 6/STRAIN UGANDA-1102) | 73–100 | 105–134 | | | | | | | |
| PVCAP_HSV6U | MAJOR CAPSID PROTEIN | HERPES SIMPLEX VIRUS (TYPE 6/STRAIN UGANDA-1102) | 136–170 | 355–382 | | | | | | | |
| PVTER_HSV6U | PROBABLE DNA PACKAGING PROTEIN | HERPES SIMPLEX VIRUS (TYPE 6/STRAIN UGANDA-1102) | 176–203 | | | | | | | | |
| PTYSY_HSVAT | THYMIDYLATE SYNTHASE | HERPES VIRUS ATELES | 116–143 | | | | | | | | |
| PDPOL_HSVSA | DNA POLYMERASE | HERPES VIRUS SAIMIRI (STRAIN 11) | 625–652 | | | | | | | | |
| PDUT_HSVSA | DEOXYU 5'-TRIPHOSPH NUCHYDROLASE | HERPES VIRUS SAIMIRI (STRAIN 11) | 179–213 | | | | | | | | |
| PHEL1_HSVSA | PROBABLE HELICASE | HERPES VIRUS SAIMIRI (STRAIN 11) | 418–449 | | | | | | | | |
| PIC18_HSVSA | PROBABLE PROC & TRANSPORT PRO | HERPES VIRUS SAIMIRI (STRAIN 11) | 58–85 | 482–522 | | | | | | | |
| PIE68_HSVSA | IMMEDIATE-EARLY PROTEIN | HERPES VIRUS SAIMIRI (STRAIN 11) | 48–78 | | | | | | | | |
| PKITH_HSVSA | THYMIDINE KINASE | HERPES VIRUS SAIMIRI (STRAIN 11) | 340–386 | | | | | | | | |
| PRIR1_HSVSA | RIBONUC-DIPHOSPH REDUCT LARGE CHA | HERPES VIRUS SAIMIRI (STRAIN 11) | 324–351 | | | | | | | | |
| PTEGU_HSVSA | PROBABLE LARGE TEGUMENT PROTEIN | HERPES VIRUS SAIMIRI (STRAIN 11) | 524–607 | 672–700 | 777–814 | 846–898 | 949–986 | 990–1017 | 1467–1497 | 2102–2135 | |
| PTYSY_HSVSA | THYMIDYLATE SYNTHASE | HERPES VIRUS SAIMIRI (STRAIN 11) | 120–147 | | | | | | | | |
| PUL06_HSVSA | VIRION GENE 43 PROTEIN | HERPES VIRUS SAIMIRI (STRAIN 11) | 15–42 | 302–358 | 368–402 | | | | | | |
| PUL25_HSVSA | VIRION GENE 19 PROTEIN | HERPES VIRUS SAIMIRI (STRAIN 11) | 34–61 | 204–231 | 362–389 | | | | | | |

TABLE VII-continued

107 × 178 × 4 SEARCH MOTIF RESULTS SUMMARY (PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUL34_HSVSA | GENE 67 PROTEIN | HERPES VIRUS SAIMIRI (STRAIN 11) | 208–235 | | | | | | | | |
| PUL37_HSVSA | GENE 63 PROTEIN | HERPES VIRUS SAIMIRI (STRAIN 11) | 31–65 | 685–737 | | | | | | | |
| PUL52_HSVSA | PROB DNA REP GENE 56 PROTEIN | HERPES VIRUS SAIMIRI (STRAIN 11) | 130–157 | | | | | | | | |
| PUL73_HSVSA | HYPOTHETICAL GENE 53 PROTEIN | HERPES VIRUS SAIMIRI (STRAIN 11) | 9–36 | | | | | | | | |
| PUL87_HSVSA | HYPOTHETICAL GENE 24 PROTEIN | HERPES VIRUS SAIMIRI (STRAIN 11) | 582–609 | | | | | | | | |
| PUL92_HSVSA | HYPOTHETICAL GENE 31 PROTEIN | HERPES VIRUS SAIMIRI (STRAIN 11) | 92–122 | | | | | | | | |
| PUNG_HSVSA | URACIL-DNA GLYCOSYLASE | HERPES VIRUS SAIMIRI (STRAIN 11) | 135–176 | | | | | | | | |
| PVCAP_HSVSA | MAJOR CAPSID PROTEIN | HERPES VIRUS SAIMIRI (STRAIN 11) | 769–799 | | | | | | | | |
| PVG45_HSVSA | HYPOTHETICAL GENE 45 PROTEIN | HERPES VIRUS SAIMIRI (STRAIN 11) | 138–165 | | | | | | | | |
| PVG48_HSVSA | HYPOTHETICAL GENE 48 PROTEIN | HERPES VIRUS SAIMIRI (STRAIN 11) | 360–394 | | | | | | | | |
| PVG52_HSVSA | HYPOTHETICAL GENE 52 PROTEIN | HERPES VIRUS SAIMIRI (STRAIN 11) | 47–74 | | | | | | | | |
| PVGLH_HSVSA | GLYCOPROTEIN H PRECURSOR | HERPES VIRUS SAIMIRI (STRAIN 11) | 388–415 | | | | | | | | |
| VIMP_HSVSA | INTEGRAL MEMBRANE PROTEIN | HERPES VIRUS SAIMIRI (STRAIN 11) | 80–107 | | | | | | | | |
| PVP23_HSVSA | PROBABLE CAPSID PROTEIN VP23 | HERPES VIRUS SAIMIRI (STRAIN 11) | 2–29 | | | | | | | | |
| PVP26_HSVSA | CAPSID PROTEIN VP26 | HERPES VIRUS SAIMIRI (STRAIN 11) | 48–75 | | | | | | | | |
| PVP40_HSVSA | CAPSID PROTEIN P40 | HERPES VIRUS SAIMIRI (STRAIN 11) | 205–232 | 344–372 | | | | | | | |
| PVP75_HSVSA | PROBABLE MEMBRANE ANTIGEN 75 | HERPES VIRUS SAIMIRI (STRAIN 11) | 181–208 | 929–977 | | | | | | | |
| PDNBI_HSVSA | MAJOR DNA-BINDING PROTEIN | HERPES VIRUS SAIMIRI (STRAIN 11) | 333–368 | 512–539 | | | | | | | |
| PCGH2_HSVSA | CYCLIN HOMOLOG | HERPES VIRUS SAIMIRI (STRAIN 11) | 127–154 | | | | | | | | |
| PYDH1_HSVS7 | HYPOTH 24.1 KD IN DHFR 3'REGION | HERPES VIRUS SAIMIRI (STRAIN 484-77) | 161–188 | | | | | | | | |
| PYDH1_HSVSC | HYPOTH 28.7 KD IN DHFR 3'REGION | HERPES VIRUS SAIMIRI (SUBGROUP C/STRAIN 488) | 52–82 | | | | | | | | |
| PYDH4_HSVSC | HYPOTH 9.9 KD IN DHFR 3'REGION | HERPES VIRUS SAIMIRI (SUBGROUP C/STRAIN 488) | 53–83 | | | | | | | | |
| PENV_MLVHO | ENV POLYPROTEIN | HOMULV MURINE LEUKEMIA VIRUS | 510–540 | | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDPOL_HCMVA | DNA POLYMERASE | HUMAN CYTOMEGALO VIRUS (STRAIN AD169) | 753–780 | | | | | | | | |
| PIC18_HCMVA | PROB PROC 7 TRANSPORT PRO UL56 | HUMAN CYTOMEGALO VIRUS (STRAIN AD169) | 294–324 | | | | | | | | |
| PIR05_HCMVA | HYPOTHETICAL PROTEIN IRL5 | HUMAN CYTOMEGALO VIRUS (STRAIN AD169) | 22–49 | | | | | | | | |
| PIR12_HCMVA | HYPOTHETICAL PROTEIN IRL12 | HUMAN CYTOMEGALO VIRUS (STRAIN AD169) | 74–162 | | | | | | | | |
| PIR13_HCMVA | HYPOTHETICAL PROTEIN IRL13 | HUMAN CYTOMEGALO VIRUS (STRAIN AD169) | 31–62 | | | | | | | | |
| PRIR1_HCMVA | RIBONUC-DIPHOSPH REDUCT LARGE CHA | HUMAN CYTOMEGALO VIRUS (STRAIN AD169) | 622–649 | | | | | | | | |
| PTEGU_HCMVA | PROBABLE LARGE TEGUMENT PROTEIN | HUMAN CYTOMEGALO VIRUS (STRAIN AD169) | 1251–1281 | 2202–2229 | | | | | | | |
| PUL08_HCMVA | HYPOTHETICAL PROTEIN UL8 | HUMAN CYTOMEGALO VIRUS (STRAIN AD169) | 6–47 | | | | | | | | |
| PUL13_HCMVA | HYPOTHETICAL PROTEIN UL13 | HUMAN CYTOMEGALO VIRUS (STRAIN AD169) | 347–374 | | | | | | | | |
| PUL16_HCMVA | HYPOTHETICAL PROTEIN UL16 | HUMAN CYTOMEGALO VIRUS (STRAIN AD169) | 81–112 | | | | | | | | |
| PUL20_HCMVA | HYPOTH PRO UL20 PRECURSOR | HUMAN CYTOMEGALO VIRUS (STRAIN AD169) | 34–61 | | | | | | | | |
| PUL31_HCMVA | HYPOTHETICAL PROTEIN UL31 | HUMAN CYTOMEGALO VIRUS (STRAIN AD169) | 167–194 | 254–284 | | | | | | | |
| PUL35_HCMVA | HYPOTHETICAL PROTEIN UL35 | HUMAN CYTOMEGALO VIRUS (STRAIN AD169) | 533–562 | | | | | | | | |
| PUL47_HCMVA | PROTEIN UL47 | HUMAN CYTOMEGALO VIRUS (STRAIN AD169) | 114–148 | 448–485 | 763–790 | 802–853 | | | | | |
| PUL50_HCMVA | PROTEIN UL50 | HUMAN CYTOMEGALO VIRUS (STRAIN AD169) | 159–186 | | | | | | | | |
| PUL59_HCMVA | HYPOTHETICAL PROTEIN UL59 | HUMAN CYTOMEGALO VIRUS (STRAIN AD169) | 74–101 | | | | | | | | |
| PUL70_HCMVA | PROB DNA REP PROTEIN UL70 | HUMAN CYTOMEGALO VIRUS (STRAIN AD169) | 65–92 | | | | | | | | |
| PUL73_HCMVA | UL73 GLYCOPROTEIN PRECURSOR | HUMAN CYTOMEGALO VIRUS (STRAIN AD169) | 5–73 | | | | | | | | |
| PUL74_HCMVA | HYPOTHETICAL PROTEIN UL74 | HUMAN CYTOMEGALO VIRUS (STRAIN AD169) | 45–79 | | | | | | | | |
| PUL93_HCMVA | PROTEIN UL93 | HUMAN CYTOMEGALO VIRUS (STRAIN AD169) | 26–53 | 314–381 | | | | | | | |
| PUL95_HCMVA | HYPOTHETICAL PROTEIN UL95 | HUMAN CYTOMEGALO VIRUS (STRAIN AD169) | 37–71 | | | | | | | | |
| PULA4_HCMVA | VIRION PROTEIN UL104 | HUMAN CYTOMEGALO VIRUS (STRAIN AD169) | 4–31 | 443–477 | | | | | | | |
| PULB9_HCMVA | HYPOTHETICAL PROTEIN UL119 | HUMAN CYTOMEGALO VIRUS (STRAIN AD169) | 33–78 | | | | | | | | |

TABLE VII-continued 107 x 178 x 4 SEARCH MOTIF RESULTS SUMMARY (PREFERRED VIRAL SEQUENCES)

| PCGENE FILE NAME | 107 x 178 x 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PULD0_HCMVA | HYPOTHETICAL PROTEIN UL130 | HUMAN CYTOMEGALO VIRUS (STRAIN AD169) | 90–124 | | | | | | | | |
| PUS09_HCMVA | HYPOTHETICAL PROTEIN HXLF3 | HUMAN CYTOMEGALO VIRUS (STRAIN AD169) | 20–47 | | | | | | | | |
| PUS14_HCMVA | HYPOTHETICAL PROTEIN HVLF4 | HUMAN CYTOMEGALO VIRUS (STRAIN AD169) | 277–308 | | | | | | | | |
| PUS18_HCMVA | MEMBRANE PROTEIN HWLF5 | HUMAN CYTOMEGALO VIRUS (STRAIN AD169) | 191–218 | | | | | | | | |
| PVGLB_HCMVA | GLYCOPROTEIN B PRECURSOR | HUMAN CYTOMEGALO VIRUS (STRAIN AD169) | 25–88 | 397–424 | 440–467 | 851–878 | | | | | |
| PVG1H_HCMVA | GLYCOPROTEIN H PRECURSOR | HUMAN CYTOMEGALO VIRUS (STRAIN AD169) | 107–136 | 270–297 | | | | | | | |
| PVGLI_HCMVA | IE GLYCOPROTEIN PRECURSOR | HUMAN CYTOMEGALO VIRUS (STRAIN AD169) | 47–111 | | | | | | | | |
| PVTER_HCMVA | PROBABLE DNA PACKAGING PROTEIN | HUMAN CYTOMEGALO VIRUS (STRAIN AD169) | 417–451 | | | | | | | | |
| PDNBI_HCMVA | MAJOR DNA-BINDING PROTEIN | HUMAN CYTOMEGALO VIRUS (STRAIN AD169) | 437–464 | | | | | | | | |
| PV30K_HCMVE | 30 KD MAJOR EARLY PROTEIN | HUMAN CYTOMEGALO VIRUS (STRAIN EISENHARDT) | 194–221 | | | | | | | | |
| PVGLB_HCMVT | GLYCOPROTEIN B PRECURSOR | HUMAN CYTOMEGALO VIRUS (STRAIN TOWNE) | 50–88 | 397–424 | 435–462 | 852–879 | | | | | |
| PVGLH_HCMVT | GLYCOPROTEIN H PRECURSOR | HUMAN CYTOMEGALO VIRUS (STRAIN TOWNE) | 106–135 | | | | | | | | |
| PENV_HV1A2 | ENV POLYPROTEIN | HUMAN IMMUNODEFICIENCY VIRUS TYPE 1 (ARV2/SF2 ISOLATE) | 544–592 | 630–682 | 790–825 | | | | | | |
| PGAG_HV1A2 | GAG POLYPROTEIN | HUMAN IMMUNODEFICIENCY VIRUS TYPE 1 (ARV2/SF2 ISOLATE) | 91–118 | | | | | | | | |
| PPOL_HV1A2 | POL POLYPROTEIN | HUMAN IMMUNODEFICIENCY VIRUS TYPE 1 (ARV2/SF2 ISOLATE) | 219–245 | 620–661 | | | | | | | |
| PVPU_HV1A2 | VPU PROTEIN | HUMAN IMMUNODEFICIENCY VIRUS TYPE 1 (ARV2/SF2 ISOLATE) | 3–31 | | | | | | | | |
| PVPU_HV1B1 | VPU PROTEIN | HUMAN IMMUNODEFICIENCY VIRUS TYPE 1 (BH10 AND HXB3 ISOLATES) | 5–48 | | | | | | | | |
| PENV_HV1B1 | ENV POLYPROTEIN | HUMAN IMMUNODEFICIENCY VIRUS TYPE 1 (BH10 ISOLATE) | 545–594 | 631–683 | 791–818 | | | | | | |
| PPOL_HV1B1 | POL POLYPROTEIN | HUMAN IMMUNODEFICIENCY VIRUS TYPE 1 (BH10 ISOLATE) | 230–257 | 637–673 | | | | | | | |
| PPOL_HV1B5 | POL POLYPROTEIN | HUMAN IMMUNODEFICIENCY VIRUS TYPE 1 (BH5 ISOLATE) | 230–257 | 632–673 | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PENV_HV1B8 | ENV POLYPROTEIN | HUMAN IMMUNODEFICIENCY VIRUS TYPE 1 (BH8 ISOLATE) | 540–589 | 626–678 | 786–813 | | | | | | |
| PVPU_HV1B8 | VPU PROTEIN | HUMAN IMMUNODEFICIENCY VIRUS TYPE 1 (BH8 ISOLATE) | 21–48 | | | | | | | | |
| PENV_HV1BN | ENV POLYPROTEIN | HUMAN IMMUNODEFICIENCY VIRUS TYPE 1 (BRAIN ISOLATE) | 267–294 | 338–365 | 562–590 | 628–679 | 787–815 | | | | |
| PVPU_HV1BN | VPU PROTEIN | HUMAN IMMUNODEFICIENCY VIRUS TYPE 1 (BRAIN ISOLATE) | 22–49 | | | | | | | | |
| PENV_HV1BR | ENV POLYPROTEIN | HUMAN IMMUNODEFICIENCY VIRUS TYPE 1 (BRU ISOLATE) | 550–599 | 636–688 | 796–823 | | | | | | |
| PPOL_HV1BR | POL POLYPROTEIN | HUMAN IMMUNODEFICIENCY VIRUS TYPE 1 (BRU ISOLATE) | 230–257 | 632–673 | | | | | | | |
| PVPU_HV1BR | VPU PROTEIN | HUMAN IMMUNODEFICIENCY VIRUS TYPE 1 (BRU ISOLATE) | 5–48 | | | | | | | | |
| PENV_HV1C4 | ENV POLYPROTEIN | HUMAN IMMUNODEFICIENCY VIRUS TYPE 1 (CDC-451 ISOLATE) | 397–424 | 557–606 | 643–695 | 803–835 | | | | | |
| PVPU_HV1C4 | VPU PROTEIN | HUMAN IMMUNODEFICIENCY VIRUS TYPE 1 (CDC-451 ISOLATE) | 3–30 | | | | | | | | |
| PENV_HV1EL | ENV POLYPROTEIN | HUMAN IMMUNODEFICIENCY VIRUS TYPE 1 (ELI ISOLATE) | 255–296 | 386–413 | 543–591 | 628–680 | | | | | |
| PNEV_HV1EL | NEGATIVE FACTOR | HUMAN IMMUNODEFICIENCY VIRUS TYPE 1 (ELI ISOLATE) | 81–119 | | | | | | | | |
| PPOL_HV1EL | POL POLYPROTEIN | HUMAN IMMUNODEFICIENCY VIRUS TYPE 1 (ELI ISOLATE) | 217–244 | 624–660 | | | | | | | |
| PVPU_HV1EL | VPU PROTEIN | HUMAN IMMUNODEFICIENCY VIRUS TYPE 1 (ELI ISOLATE) | 6–33 | | | | | | | | |
| PENV_HV1H2 | ENV POLYPROTEIN | HUMAN IMMUNODEFICIENCY VIRUS TYPE 1 (HXB2 ISOLATE) | 545–594 | 631–683 | 791–818 | | | | | | |
| PPOL_HV1H2 | POL POLYPROTEIN | HUMAN IMMUNODEFICIENCY VIRUS TYPE 1 (HXB2 ISOLATE) | 218–245 | 620–661 | 921–951 | | | | | | |
| PVPU_HV1H2 | VPU PROTEIN | HUMAN IMMUNODEFICIENCY VIRUS TYPE 1 (HSB2 ISOLATE) | 5–48 | | | | | | | | |
| PENV_HV1H3 | ENV POLYPROTEIN | HUMAN IMMUNODEFICIENCY VIRUS TYPE 1 (HSB3 ISOLATE) | 545–594 | 631–683 | 791–818 | 802–829 | | | | | |
| PENV_HV1J3 | ENV POLYPROTEIN | HUMAN IMMUNODEFICIENCY VIRUS TYPE 1 (JH3 ISOLATE) | 350–377 | 556–605 | 642–694 | | | | | | |
| PGAG_HV1J3 | GAG POLYPROTEIN | HUMAN IMMUNODEFICIENCY VIRUS TYPE 1 (JH3 ISOLATE) | 91–118 | | | | | | | | |
| PVPU_HV1J3 | VPU PROTEIN | HUMAN IMMUNODEFICIENCY VIRUS TYPE 1 (JH3 ISOLATE) | 2–29 | | | | | | | | |
| PENV_HV1JR | ENV POLYPROTEIN | HUMAN IMMUNODEFICIENCY VIRUS TYPE 1 (JRCSF ISOLATE) | 336–363 | 622–675 | 783–811 | | | | | | |
| PPOL_HV1JR | POL POLYPROTEIN | HUMAN IMMUNODEFICIENCY VIRUS TYPE 1 (JRCSF ISOLATE) | 222–249 | 624–665 | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVPU_HV1JR | VPU PROTEIN | HUMAN IMMUNODEFICIENCY VIRUS TYPE 1 (JRCSF ISOLATE) | 22–49 | | | | | | | | |
| PENV_HV1MA | ENV POLYPROTEIN | HUMAN IMMUNODEFICIENCY VIRUS TYPE 1 (MAL ISOLATE) | 547–595 | 633–707 | 794–826 | | | | | | |
| PPOL_HV1MA | POL POLYPROTEIN | HUMAN IMMUNODEFICIENCY VIRUS TYPE 1 (MAL ISOLATE) | 217–244 | 476–510 | 619–660 | | | | | | |
| PVPU_HV1MA | VPU PROTEIN | HUMAN IMMUNODEFICIENCY VIRUS TYPE 1 (MAL ISOLATE) | 5–32 | | | | | | | | |
| PENV_HV1MF | ENV POLYPROTEIN | HUMAN IMMUNODEFICIENCY VIRUS TYPE 1 (MFA ISOLATE) | 543–592 | 629–681 | 789–816 | | | | | | |
| PENV_HV1MN | ENV POLYPROTEIN | HUMAN IMMUNODEFICIENCY VIRUS TYPE 1 (MN ISOLATE) | 343–370 | 567–595 | 632–684 | 791–819 | | | | | |
| PGAG_HV1MN | GAG POLYPROTEIN | HUMAN IMMUNODEFICIENCY VIRUS TYPE 1 (MN ISOLATE) | 87–118 | | | | | | | | |
| PPOL_HV1MN | POL POLYPROTEIN | HUMAN IMMUNODEFICIENCY VIRUS TYPE 1 (MN ISOLATE) | 221–248 | 623–664 | | | | | | | |
| PENV_HV1ND | ENV POLYPROTEIN | HUMAN IMMUNODEFICIENCY VIRUS TYPE 1 (NDK ISOLATE) | 249–290 | 536–583 | 621–673 | 783–813 | | | | | |
| PNEF_HV1ND | NEGATIVE FACTOR | HUMAN IMMUNODEFICIENCY VIRUS TYPE 1 (NDK ISOLATE) | 81–119 | | | | | | | | |
| PPOL_HV1ND | POL POLYPROTEIN | HUMAN IMMUNODEFICIENCY VIRUS TYPE 1 (NDK ISOLATE) | 217–244 | 624–660 | | | | | | | |
| PVPU_HV1ND | VPU PROTEIN | HUMAN IMMUNODEFICIENCY VIRUS TYPE 1 (NDK ISOLATE) | 6–33 | | | | | | | | |
| PENV_HV1N5 | ENV POLYPROTEIN | HUMAN IMMUNODEFICIENCY VIRUS TYPE 1 (NEW YORK-5 ISOLATE) | 326–360 | | | | | | | | |
| PPOL_HV1N5 | POL POLYPROTEIN | HUMAN IMMUNODEFICIENCY VIRUS TYPE 1 (NEW YORK-5 ISOLATE) | 218–245 | 625–661 | | | | | | | |
| PENV_HV1OY | ENV POLYPROTEIN | HUMAN IMMUNODEFICIENCY VIRUS TYPE 1 (OY1 ISOLATE) | 544–591 | 630–704 | 789–820 | | | | | | |
| PPOL_HV1OY | POL POLYPROTEIN | HUMAN IMMUNODEFICIENCY VIRUS TYPE 1 (OY1 ISOLATE) | 218–245 | 620–661 | | | | | | | |
| PENV_HV1PV | ENV POLYPROTEIN | HUMAN IMMUNODEFICIENCY VIRUS TYPE 1 (PV22 ISOLATE) | 545–594 | 631–683 | 791–818 | | | | | | |
| PPOL_HV1PV | POL POLYPROTEIN | HUMAN IMMUNODEFICIENCY VIRUS TYPE 1 (PV22 ISOLATE) | 230–257 | 637–673 | | | | | | | |
| PVPU_HV1PV | VPU PROTEIN | HUMAN IMMUNODEFICIENCY VIRUS TYPE 1 (PV22 ISOLATE) | 5–48 | | | | | | | | |
| PENV_HV1RH | ENV POLYPROTEIN | HUMAN IMMUNODEFICIENCY VIRUS TYPE 1 (RF/HAT ISOLATE) | 280–307 | 351–378 | 554–602 | 640–692 | 800–832 | | | | |
| PPOL_HV1RH | POL POLYPROTEIN | HUMAN IMMUNODEFICIENCY VIRUS TYPE 1 (RF/HAT ISOLATE) | 217–244 | 619–660 | | | | | | | |

TABLE VII-continued

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| | | 107 × 178 × 4 SEARCH MOTIF RESULTS SUMMARY (PREFERRED VIRAL SEQUENCES) | | | | | | | | | |
| VIF_HV1RH | VIRION INFECTIVITY FACTOR | HUMAN IMMUNODEFICIENCY VIRUS TYPE 1 (RF/HAT ISOLATE) | 62–89 | | | | | | | | |
| PENV_HV1SC | ENV POLYPROTEIN | HUMAN IMMUNODEFICIENCY VIRUS TYPE 1 (SC ISOLATE) | 338–365 | 545–593 | 631–683 | | | | | | |
| PENV_HV1S1 | ENV POLYPROTEIN | HUMAN IMMUNODEFICIENCY VIRUS TYPE 1 (SF162 ISOLATE) | 333–363 | 536–585 | 622–674 | 782–809 | | | | | |
| PVPU_HV1S1 | VPU PROTEIN | HUMAN IMMUNODEFICIENCY VIRUS TYPE 1 (SF162 ISOLATE) | 22–49 | | | | | | | | |
| PENV_HV1S3 | ENV POLYPROTEIN | HUMAN IMMUNODEFICIENCY VIRUS TYPE 1 (SF33 ISOLATE) | 541–589 | 627–679 | 787–815 | | | | | | |
| PENV_HV1KB | ENV POLYPROTEIN | HUMAN IMMUNODEFICIENCY VIRUS TYPE 1 (STRAIN KB-1-GP32) | 274–301 | 555–596 | 637–677 | 776–824 | | | | | |
| PPOL_HVIU4 | POL POLYPROTEIN | HUMAN IMMUNODEFICIENCY VIRUS TYPE 1 (STRAIN UGANDAN/ISOLATE U) | 217–244 | 513–540 | 619–660 | | | | | | |
| PENV_HV1W1 | ENV POLYPROTEIN | HUMAN IMMUNODEFICIENCY VIRUS TYPE 1 (WMJ1 ISOLATE) | 338–365 | 545–593 | 631–683 | 791–818 | | | | | |
| PENV_HV1W2 | ENV POLYPROTEIN | HUMAN IMMUNODEFICIENCY VIRUS TYPE 1 (WMJ2 ISOLATE) | 334–361 | 536–584 | 622–674 | 782–809 | | | | | |
| PENV_HV1Z8 | ENV POLYPROTEIN | HUMAN IMMUNODEFICIENCY VIRUS TYPE 1 (Z-84 ISOLATE) | 266–307 | 573–601 | 634–678 | 797–828 | | | | | |
| PENV_HV1Z2 | ENV POLYPROTEIN | HUMAN IMMUNODEFICIENCY VIRUS TYPE 1 (Z2/CDC-Z34 ISOLATE) | 255–296 | 542–591 | 628–680 | 790–820 | | | | | |
| PPOL_HV1Z2 | POL POLYPROTEIN | HUMAN IMMUNODEFICIENCY VIRUS TYPE 1 (Z2/CDC-Z34 ISOLATE) | 217–244 | 619–660 | | | | | | | |
| PENV_HV1Z3 | ENV POLYPROTEIN | HUMAN IMMUNODEFICIENCY VIRUS TYPE 1 (ZAIRE 3 ISOLATE) | 251–292 | | | | | | | | |
| PENV_HV1Z6 | ENV POLYPROTEIN | HUMAN IMMUNODEFICIENCY VIRUS TYPE 1 (ZAIRE 6 ISOLATE) | 256–297 | 545–593 | 630–682 | 792–822 | | | | | |
| PNEF_HV1Z6 | NEGATIVE FACTOR | HUMAN IMMUNODEFICIENCY VIRUS TYPE 1 (ZAIRE 6 ISOLATE) | 86–124 | | | | | | | | |
| PENV_HZ1ZH | ENV POLYPROTEIN | HUMAN IMMUNODEFICIENCY VIRUS TYPE 1 (ZAIRE HZ321 ISOLATE) | 545–594 | 627–666 | 791–823 | | | | | | |
| PENV_HV2BE | ENV POLYPROTEIN | HUMAN IMMUNODEFICIENCY VIRUS TYPE 2 (ISOLATE BEN) | 61–88 | 532–591 | 621–648 | 653–697 | | | | | |
| PGAG_HV2BE | GAG POLYPROTEIN | HUMAN IMMUNODEFICIENCY VIRUS TYPE 2 (ISOLATE BEN) | 88–115 | | | | | | | | |

TABLE VII-continued

107 × 178 × 4 SEARCH MOTIF RESULTS SUMMARY (PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOL_HV2BE | POL POLYPROTEIN | HUMAN IMMUNODEFICIENCY VIRUS TYPE 2 (ISOLATE BEN) | 491–582 | | | | | | | | |
| PENV_HV2CA | ENV POLYPROTEIN | HUMAN IMMUNODEFICIENCY VIRUS TYPE 2 (ISOLATE CAM2) | 534–593 | 623–650 | 655–699 | | | | | | |
| PPOL_HV2CA | POL POLYPROTEIN | HUMAN IMMUNODEFICIENCY VIRUS TYPE 2 (ISOLATE CAM2) | 471–562 | | | | | | | | |
| PENV_HV2D1 | ENV POLYPROTEIN | HUMAN IMMUNODEFICIENCY VIRUS TYPE 2 (ISOLATE D194) | 61–88 | 523–550 | 555–582 | 644–688 | | | | | |
| PGAG_HV2D1 | GAG POLYPROTEIN | HUMAN IMMUNODEFICIENCY VIRUS TYPE 2 (ISOLATE D194) | 88–115 | | | | | | | | |
| PPOL_HV2D1 | POL POLYPROTEIN | HUMAN IMMUNODEFICIENCY VIRUS TYPE 2 (ISOLATE D194) | 509–600 | | | | | | | | |
| PPOL_HV2D2 | POL POLYPROTEIN | HUMAN IMMUNODEFICIENCY VIRUS TYPE 2 (ISOLATE D194) | 491–568 | | | | | | | | |
| PENV_HV2G1 | ENV POLYPROTEIN | HUMAN IMMUNODEFICIENCY VIRUS TYPE 2 (ISOLATE D205,7) | 60–87 | 524–551 | 556–583 | 613–640 | 645–693 | | | | |
| PPOL_HV2G1 | POL POLYPROTEIN | HUMAN IMMUNODEFICIENCY VIRUS TYPE 2 (ISOLATE GHANA-1) | 471–562 | | | | | | | | |
| PENV_HV2NZ | ENV POLYPROTEIN | HUMAN IMMUNODEFICIENCY VIRUS TYPE 2 (ISOLATE NIH-Z) | 61–88 | 524–551 | 556–583 | 613–640 | 662–689 | | | | |
| PGAG_HV2NZ | GAG POLYPROTEIN | HUMAN IMMUNODEFICIENCY VIRUS TYPE 2 (ISOLATE NIH-Z) | 88–115 | | | | | | | | |
| PPOL_HV2NZ | POL POLYPROTEIN | HUMAN IMMUNODEFICIENCY VIRUS TYPE 2 (ISOLATE NIH-Z) | 471–529 | | | | | | | | |
| PENV_HV2RO | ENV POLYPROTEIN | HUMAN IMMUNODEFICIENCY VIRUS TYPE 2 (ISOLATE ROD) | 58–85 | 533–592 | 622–698 | | | | | | |
| PPOL_HV2RO | POL POLYPROTEIN | HUMAN IMMUNODEFICIENCY VIRUS TYPE 2 (ISOLATE ROD) | 472–563 | | | | | | | | |
| PENV_HV2SB | ENV POLYPROTEIN | HUMAN IMMUNODEFICIENCY VIRUS TYPE 2 (ISOLATE SBL/ISY) | 557–584 | 614–673 | | | | | | | |
| PPOL_HV2SB | POL POLYPROTEIN | HUMAN IMMUNODEFICIENCY VIRUS TYPE 2 (ISOLATE SBL/ISY) | 473–562 | | | | | | | | |
| PENV_HV2ST | ENV POLYPROTEIN | HUMAN IMMUNODEFICIENCY VIRUS TYPE 2 (ISOLATE ST) | 442–476 | 527–554 | 559–586 | 648–692 | | | | | |
| PGAG_HV2ST | GAG POLYPROTEIN | HUMAN IMMUNODEFICIENCY VIRUS TYPE 2 (ISOLATE ST) | 88–115 | | | | | | | | |
| PPOL_HV2ST | POL POLYPROTEIN | HUMAN IMMUNODEFICIENCY VIRUS TYPE 2 (ISOLATE ST) | 491–582 | | | | | | | | |
| PENV_HV2S2 | ENV POLYPROTEIN | HUMAN IMMUNODEFICIENCY VIRUS TYPE 2 (ISOLATE ST/24 1C#2) | 442–476 | 527–554 | 559–586 | 648–682 | | | | | |
| PVE4_HPV11 | PROBABLE E4 PROTEIN | HUMAN PAPILLOMA VIRUS TYPE 11 | 81–108 | | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVE5A_HPV11 | PROBABLE E5A PROTEIN | HUMAN PAPILLOMA VIRUS TYPE 11 | 30–60 | | | | | | | | |
| PVE2_HPV13 | E2 PROTEIN | HUMAN PAPILLOMA VIRUS TYPE 13 | 157–184 | 334–361 | | | | | | | |
| PVE2_HPV16 | E2 PROTEIN | HUMAN PAPILLOMA VIRUS TYPE 16 | 61–105 | 312–342 | | | | | | | |
| PVE4_PPV16 | PROBABLE E4 PROTEIN | HUMAN PAPILLOMA VIRUS TYPE 16 | 66–93 | | | | | | | | |
| PVE1_HPV18 | E1 PROTEIN | HUMAN PAPILLOMA VIRUS TYPE 18 | 60–87 | | | | | | | | |
| PVE2_HPV18 | E2 PROTEIN | HUMAN PAPILLOMA VIRUS TYPE 18 | 313–340 | | | | | | | | |
| PVE4_HPV18 | PROBABLE E4 PROTEIN | HUMAN PAPILLOMA VIRUS TYPE 18 | 59–86 | | | | | | | | |
| PVE6_HPV18 | E6 PROTEIN | HUMAN PAPILLOMA VIRUS TYPE 18 | 75–102 | | | | | | | | |
| VL1_HPV18 | PROBABLE L1 PROTEIN | HUMAN PAPILLOMA VIRUS TYPE 18 | 183–210 | | | | | | | | |
| PVE2_HPV1A | E2 PROTEIN | HUMAN PAPILLOMA VIRUS TYPE 1A | 159–186 | | | | | | | | |
| VL2_HPV1A | PROBABLE L2 PROTEIN | HUMAN PAPILLOMA VIRUS TYPE 1A | 407–445 | | | | | | | | |
| PVE1_HPV2A | E1 PROTEIN | HUMAN PAPILLOMA VIRUS TYPE 2A | 21–48 | | | | | | | | |
| PVE2_HPV2A | E2 PROTEIN | HUMAN PAPILLOMA VIRUS TYPE 2A | 159–193 | | | | | | | | |
| PVE4_HPV31 | PROBABLE E4 PROTEIN | HUMAN PAPILLOMA VIRUS TYPE 31 | 75–102 | | | | | | | | |
| PVE6_HPV31 | E6 PROTEIN | HUMAN PAPILLOMA VIRUS TYPE 31 | 69–96 | | | | | | | | |
| PVE1_HPV33 | E1 PROTEIN | HUMAN PAPILLOMA VIRUS TYPE 33 | 180–207 | | | | | | | | |
| PVE2_HPV33 | E2 PROTEIN | HUMAN PAPILLOMA VIRUS TYPE 33 | 304–331 | | | | | | | | |
| VL1_HPV33 | PROBABLE L1 PROTEIN | HUMAN PAPILLOMA VIRUS TYPE 33 | 19–46 | | | | | | | | |
| PVE2_HPV35 | E2 PROTEIN | HUMAN PAPILLOMA VIRUS TYPE 35 | 158–192 | 327–354 | | | | | | | |
| PVE5_HPV35 | PROBABLE E5 PROTEIN | HUMAN PAPILLOMA VIRUS TYPE 35 | 27–54 | | | | | | | | |
| PVE1_HPV39 | E1 PROTEIN | HUMAN PAPILLOMA VIRUS TYPE 39 | 103–130 | | | | | | | | |
| PVE2_HPV39 | E2 PROTEIN | HUMAN PAPILLOMA VIRUS TYPE 39 | 7–34 | 323–357 | | | | | | | |
| PVE6_HPV39 | E6 PROTEIN | HUMAN PAPILLOMA VIRUS TYPE 39 | 71–102 | | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVE1_HPV41 | E1 PROTEIN | HUMAN PAPILLOMA VIRUS TYPE 41 | 55–89 | | | | | | | | |
| PVE4_HPV41 | PROBABLE E4 PROTEIN | HUMAN PAPILLOMA VIRUS TYPE 41 | 63–97 | | | | | | | | |
| PVE6_HPV41 | E6 PROTEIN | HUMAN PAPILLOMA VIRUS TYPE 41 | 119–146 | | | | | | | | |
| VL1_HPV41 | PROBABLE L1 PROTEIN | HUMAN PAPILLOMA VIRUS TYPE 41 | 345–372 | | | | | | | | |
| VL2_HPV41 | PROBABLE L2 PROTEIN | HUMAN PAPILLOMA VIRUS TYPE 41 | 415–442 | | | | | | | | |
| PVE1_HPV42 | E1 PROTEIN | HUMAN PAPILLOMA VIRUS TYPE 42 | 25–59 | | | | | | | | |
| PVE6_HPV45 | E6 PROTEIN | HUMAN PAPILLOMA VIRUS TYPE 45 | 75–102 | | | | | | | | |
| PVE1_HPV47 | E1 PROTEIN | HUMAN PAPILLOMA VIRUS TYPE 47 | 146–173 | | | | | | | | |
| PVE2_HPV47 | E2 PROTEIN | HUMAN PAPILLOMA VIRUS TYPE 47 | 17–51 | 148–175 | 276–303 | | | | | | |
| PVE2_HPV05 | PROBABLE E2 PROTEIN | HUMAN PAPILLOMA VIRUS TYPE 5 | 17–51 | | | | | | | | |
| PVE4_HPV05 | PROBABLE E4 PROTEIN | HUMAN PAPILLOMA VIRUS TYPE 5 | 202–229 | | | | | | | | |
| PVE2_HPV51 | E2 PROTEIN | HUMAN PAPILLOMA VIRUS TYPE 51 | 137–284 | | | | | | | | |
| PVE6_HPV51 | E6 PROTEIN | HUMAN PAPILLOMA VIRUS TYPE 51 | 72–99 | | | | | | | | |
| VL1_HPV51 | PROBABLE L1 PROTEIN | HUMAN PAPILLOMA VIRUS TYPE 51 | 19–46 | | | | | | | | |
| PVE1_HPV57 | E1 PROTEIN | HUMAN PAPILLOMA VIRUS TYPE 57 | 21–48 | | | | | | | | |
| PVE2_HPV57 | E2 PROTEIN | HUMAN PAPILLOMA VIRUS TYPE 57 | 166–193 | | | | | | | | |
| PVE2_HPV58 | E2 PROTEIN | HUMAN PAPILLOMA VIRUS TYPE 58 | 2–36 | 309–336 | | | | | | | |
| VL1_HPV58 | PROBABLE L1 PROTEIN | HUMAN PAPILLOMA VIRUS TYPE 58 | 45–72 | | | | | | | | |
| PVE2_HPV5B | PROBABLE E2 PROTEIN | HUMAN PAPILLOMA VIRUS TYPE 5B | 17–51 | | | | | | | | |
| PVE4_HPV5B | PROBABLE E4 PROTEIN | HUMAN PAPILLOMA VIRUS TYPE 5B | 202–229 | | | | | | | | |
| PVE5_HPV5B | PROBABLE E5 PROTEIN | HUMAN PAPILLOMA VIRUS TYPE 5B | 11–41 | | | | | | | | |
| PVE5A_HPV6B | PROBABLE E5A PROTEIN | HUMAN PAPILLOMA VIRUS TYPE 6B | 30–60 | | | | | | | | |
| PVE5A_HPV6C | PROBABLE E5A PROTEIN | HUMAN PAPILLOMA VIRUS TYPE 6C | 30–60 | | | | | | | | |

TABLE VII-continued 107 x 178 x 4 SEARCH MOTIF RESULTS SUMMARY
(PREFERRED VIRAL SEQUENCES)

| PCGENE FILE NAME | 107 x 178 x 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| VL1_HPV08 | PROBABLE L1 PROTEIN | HUMAN PAPILLOMA VIRUS TYPE 8 | 354–392 | | | | | | | | |
| PVE6_HPVME | E6 PROTEIN | HUMAN PAPILLOMA VIRUS TYPE ME180 | 71–102 | | | | | | | | |
| PRRPP_PI1HB | RNA POLYMERASE ALPHA SUBUNIT | HUMAN PARAINFLUENZA 1 VIRUS (STRAIN C35) | 84–111 | 234–261 | 375–416 | | | | | | |
| PNCAP_PI1HC | NUCLEOCAPSID PROTEIN | HUMAN PARAINFLUENZA 1 VIRUS (STRAIN C39) | 377–404 | 455–482 | | | | | | | |
| PRRPP_PI1HC | RNA POLYMERASE ALPHA SUBUNIT | HUMAN PARAINFLUENZA 1 VIRUS (STRAIN C39) | 84–111 | 234–261 | 375–416 | | | | | | |
| PVGLF_PI1HC | FUSION GLYCOPROTEIN PRECURSOR | HUMAN PARAINFLUENZA 1 VIRUS (STRAIN C39) | 147–174 | 210–266 | | | | | | | |
| PRRPP_PI1HE | RNA POLYMERASE ALPHA SUBUNIT | HUMAN PARAINFLUENZA 1 VIRUS (STRAIN CI-14/83) | 84–111 | 244–271 | 375–416 | | | | | | |
| PVNSC_PI1HE | NONSTRUCTURAL PROTEIN C | HUMAN PARAINFLUENZA 1 VIRUS (STRAIN CI-14/83) | 41–75 | | | | | | | | |
| PRRPP_PI1HD | RNA POLYMERASE ALPHA SUBUNIT | HUMAN PARAINFLUENZA 1 VIRUS (STRAIN CI-5/73) | 84–111 | 232–262 | 375–416 | | | | | | |
| PHEMA_PI1HW | HEMAGGLUTININ-NEURAMINIDASE | HUMAN PARAINFLUENZA 1 VIRUS (STRAIN WASHINGTON/1957) | 79–110 | 366–393 | | | | | | | |
| PNCAP_PI1HW | NUCLEOCAPSID PROTEIN | HUMAN PARAINFLUENZA 1 VIRUS (STRAIN WASHINGTON/1957) | 377–404 | 444–488 | | | | | | | |
| PRRPP_PI2H | RNA POLYMERASE ALPHA SUBUNIT | HUMAN PARAINFLUENZA 2 VIRUS | 167–194 | 222–256 | | | | | | | |
| PVGLF_PI2H | FUSION GLYCOPROTEIN PRECURSOR | HUMAN PARAINFLUENZA 2 VIRUS | 90–117 | 141–175 | 238–266 | 483–528 | | | | | |
| PVGLF_PI2HG | FUSION GLYCOPROTEIN PRECURSOR | HUMAN PARAINFLUENZA 2 VIRUS (STRAIN GREER) | 90–117 | 114–175 | 238–266 | 483–528 | | | | | |
| PRRPL_PI2HT | RNA POLYMERASE BETA SUBUNIT | HUMAN PARAINFLUENZA 2 VIRUS (STRAIN TOSHIBA) | 322–349 | 1564–1598 | 1687–1721 | 1901–1946 | | | | | |
| PRRPP_PI2HT | RNA POLYMERASE ALPHA SUBUNIT | HUMAN PARAINFLUENZA 2 VIRUS (STRAIN TOSHIBA) | 167–194 | 222–256 | | | | | | | |
| PVGLF_PI2HT | FUSION GLYCOPROTEIN PRECURSOR | HUMAN PARAINFLUENZA 2 VIRUS (STRAIN TOSHIBA) | 90–117 | 141–175 | 238–266 | 483–528 | | | | | |
| PVMAT_PI2HT | MATRIX PROTEIN | HUMAN PARAINFLUENZA 2 VIRUS (STRAIN TOSHIBA) | 96–123 | | | | | | | | |
| PHEMA_PI3HA | HEMAGGLUTININ-NEURAMINIDASE | HUMAN PARAINFLUENZA 3 VIRUS (STRAIN AUS/124854/74 | 27–61 | | | | | | | | |
| PNCAP_PI3H4 | NUCLEOCAPSID PROTEIN | HUMAN PARAINFLUENZA 3 VIRUS (STRAIN NIH 47885) | 376–403 | | | | | | | | |
| PHEMA_PI3H4 | HEMAGGLUTININ-NEURAMINIDASE | HUMAN PARAINFLUENZA 3 VIRUS (STRAIN NIH 47885) | 27–61 | | | | | | | | |
| PRRPL_PI3H4 | RNA POLYMERASE BETA SUBUNIT | HUMAN PARAINFLUENZA 3 VIRUS (STRAIN NIH 47885) | 52–86 | 136–163 | 608–638 | 1081–1123 | 1994–2036 | 2115–2142 | | | |

TABLE VII-continued

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| | | 107 × 178 × 4 SEARCH MOTIF RESULTS SUMMARY (PREFERRED VIRAL SEQUENCES) | | | | | | | | | |
| PRRRP_PI3H4 | RNA POLYMERASE ALPHA SUBUNIT | HUMAN PARAINFLUENZA 3 VIRUS (STRAIN NIH 47885) | 114–144 | 269–299 | | | | | | | |
| PVGLF_PI3H4 | FUSION GLYCOPROTEIN PRECURSOR | HUMAN PARAINFLUENZA 3 VIRUS (STRAIN NIH 47885) | 115–182 | 207–241 | 457–497 | | | | | | |
| PVMAT_PI3H4 | MATRIX PROTEIN | HUMAN PARAINFLUENZA 3 VIRUS (STRAIN NIH 47885) | 201–231 | | | | | | | | |
| PVNSC_PI3H4 | NONSTRUCTURAL PROTEIN C | HUMAN PARAINFLUENZA 3 VIRUS (STRAIN NIH 47885) | 58–99 | | | | | | | | |
| PHEMA_PI3HV | HEMAGGLUTININ-NEURAMINIDASE | HUMAN PARAINFLUENZA 3 VIRUS (STRAIN TEX/12677/83) | 27–61 | | | | | | | | |
| PHEMA_PI3HT | HEMAGGLUTININ-NEURAMINIDASE | HUMAN PARAINFLUENZA 3 VIRUS (STRAIN TEX/545/80) | 27–76 | | | | | | | | |
| PHEMA_PI3HU | HEMAGGLUTININ-NEURAMINIDASE | HUMAN PARAINFLUENZA 3 VIRUS (STRAIN TEX/9305/82) | 23–70 | | | | | | | | |
| PHEMA_PI3HX | HEMAGGLUTININ-NEURAMINIDASE | HUMAN PARAINFLUENZA 3 VIRUS (STRAIN WASH/1511/73) | 27–61 | | | | | | | | |
| PHEMA_PI3HW | HEMAGGLUTININ-NEURAMINIDASE | HUMAN PARAINFLUENZA 3 VIRUS (STRAIN WASH/641/79) | 27–61 | | | | | | | | |
| PRRPP_PI4HA | RNA POLYMERASE ALPHA SUBUNIT | HUMAN PARAINFLUENZA 4A VIRUS (STRAIN TOSHIBA) | 4–38 | | | | | | | | |
| PVV_PI4HA | V PROTEIN | HUMAN PARAINFLUENZA 4A VIRUS (STRAIN TOSHIBA) | 4–38 | | | | | | | | |
| PRRPP_HRSV | RNA POLYMERASE ALPHA SUBUNIT | HUMAN RESPIRATORY SYNCYTIAL VIRUS | 99–141 | | | | | | | | |
| PNCAP_HRSVA | NUCLEOCAPSID PROTEIN | HUMAN RESPIRATORY SYNCYTIAL VIRUS (STRAIN A2) | 4–31 | | | | | | | | |
| PRRPL_HRSVA | RNA POLYMERASE BETA SUBUNIT | HUMAN RESPIRATORY SYNCYTIAL VIRUS 9STRAIN A2) | 103–192 | 210–237 | 667–694 | 788–815 | 1007–1034 | 1138–1165 | 1453–1480 | 1776–1803 | 2062–2089 |
| PRRPP_HRSVA | RNA POLYMERASE ALPHA SUBUNIT | HUMAN RESPIRATORY SYNCYTIAL VIRUS (STRAIN A2) | 99–141 | | | | | | | | |
| PVGLF_HRSVA | FUSION GLYCOPROTEIN PRECURSOR | HUMAN RESPIRATORY SYNCYTIAL VIRUS (STRAIN A2) | 38–65 | 154–202 | 213–243 | 488–518 | | | | | |
| PVMA2_HRSVA | MATRIX GLYCOPROTEIN M2 | HUMAN RESPIRATORY SYNCYTIAL VIRUS (STRAIN A2) | 124–151 | | | | | | | | |
| PVMAT_HRSVA | MATRIX PROTEIN | HUMAN RESPIRATORY SYNCYTIAL VIRUS (STRAIN A2) | 219–246 | | | | | | | | |
| PVGLG_HRSV4 | MAJOR SURFACE GLYCOPROTEIN G | HUMAN RESPIRATORY SYNCYTIAL VIRUS (STRAIN RSB5857) | 66–107 | | | | | | | | |
| PVGLG_HRSV5 | MAJOR SURFACE GLYCOPROTEIN G | HUMAN RESPIRATORY SYNCYTIAL VIRUS (STRAIN RSB6190) | 243–273 | | | | | | | | |
| PVGLF_HRSVR | FUSION GLYCOPROTEIN PRECURSOR | HUMAN RESPIRATORY VIRUS (STRAIN RSS-2) | 38–65 | 154–202 | 213–243 | 442–471 | 488–518 | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRPP_HRSVL | RNA POLYMERASE ALPHA SUBUNIT | HUMAN RESPIRATORY SYNCYTIAL VIRUS (SUBGROUP A/STRAIN LONG) | 99–141 | | | | | | | | |
| PVGLF_HRSVL | FUSION GLYCOPROTEIN PRECURSOR | HUMAN RESPIRATORY SYNYTIAL VIRUS (SUBGROUP A/STRAIN LONG) | 38–65 | 154–202 | 216–243 | 444–471 | 488–515 | | | | |
| PNCAP_HRSV1 | NUCLEOCAPSID PROTEIN | HUMAN RESPIRATORY SYNCYTIAL VIRUS (SUBGROUP B/STRAIN 18537) | 4–31 | 74–108 | 112–141 | | | | | | |
| PRRPP_HRSV1 | RNA POLYMERASE ALPHA SUBUNIT | HUMAN RESPIRATORY SYNCYTIAL VIRUS (SUBGROUP B/STRAIN 18537) | 99–141 | | | | | | | | |
| PVGLF_HRSV1 | FUSION GLYCOPROTEIN PRECURSOR | HUMAN RESPIRATORY SYNCYTIAL VIRUS (SUBGROUP B/STRAIN 18537) | 38–65 | 154–203 | 442–471 | 488–515 | | | | | |
| PVGLG_HRSV1 | MAJOR SURFACE GLYCOPROTEIN G | HUMAN RESPIRATORY SYNCYTIAL VIRUS (SUBGROUP B/STRAIN 18537) | 63–93 | | | | | | | | |
| PVGLG_HRSV8 | MAJOR SURFACE GLYCOPROTEIN G | HUMAN RESPIRATORY SYNCYTIAL VIRUS (SUBGROUP 8/60) | 66–93 | | | | | | | | |
| PENV_HTL1C | ENV POLYPROTEIN | HUMAN T-CELL LEUKEMIA VIRUS TYPE 1 (CARIBBEAN ISOLATE) | 342–376 | | | | | | | | |
| PPOL_HTL1C | POL POLYPROTEIN | HUMAN T-CELL LEUKEMIA VIRUS TYPE I (CARIBBEAN ISOLATE) | 674–712 | | | | | | | | |
| PENV_HTL1M | ENV POLYPROTEIN | HUMAN T-CELL LEUKEMIA VIRUS TYPE 1 (ISOLATE MT-2) | 342–376 | | | | | | | | |
| PENV_HTL1A | ENV POLYPROTEIN | HUMAN T-CELL LEUKEMIA VIRUS TYPE 1 (STRAIN ATK) | 342–376 | | | | | | | | |
| PPOL_HTL1A | POL POLYPROTEIN | HUMAN T-CELL LEUKEMIA VIRUS TYPE 1 (STRAIN ATK) | 674–712 | | | | | | | | |
| PENV_HTLV2 | ENV POLYPROTEIN | HUMAN T-CELL LEUKEMIA VIRUS TYPE II | 336–370 | | | | | | | | |
| PDPOL_HSVI1 | DNA POLYMERASE | ICTALURID HERPES VIRUS 1 | 328–366 | 710–737 | | | | | | | |
| PKR74_HSVI1 | GENE 74 PROTEIN KINASE | ICTALURID HERPES VIRUS 1 | 491–518 | | | | | | | | |
| PVG07_HSVI1 | HYPOTH GENE 7 MEMB PRO | ICTALURID HERPES VIRUS 1 | 71–98 | | | | | | | | |
| PVG17_HSVI1 | HYPOTHETICAL GENE 17 PROTEIN | ICTALURID HERPES VIRUS 1 | 177–204 | | | | | | | | |
| PVG18_HSVI1 | HYPOTHETICAL GENE 18 PROTEIN | ICTALURID HERPES VIRUS 1 | 174–208 | | | | | | | | |
| PVG22_HSVI1 | HYPOTHETICAL GENE 22 PROTEIN | ICTALURID HERPES VIRUS 1 | 373–400 | 581–622 | 668–705 | 766–824 | | | | | |
| PVG24_HSVI1 | HYPOTHETICAL GENE 24 PROTEIN | ICTALURID HERPES VIRUS 1 | 31–58 | | | | | | | | |

TABLE VII-continued

| | | 107 × 178 × 4 SEARCH MOTIF RESULTS SUMMARY (PREFERRED VIRAL SEQUENCES) | | | | | | | | | | |
|---|---|---|---|---|---|---|---|---|---|---|---|---|
| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
| PVG28_HSVI1 | HYPOTHETICAL GENE 28 PROTEIN | ICTALURID HERPES VIRUS 1 | 253–290 | 497–528 | | | | | | | |
| PVG34_HSVI1 | HYPOTHETICAL GENE 34 PROTEIN | ICTALURID HERPES VIRUS 1 | 95–122 | | | | | | | | |
| PVG37_HSVI1 | HYPOTHETICAL GENE 37 PROTEIN | ICTALURID HERPES VIRUS 1 | 442–469 | | | | | | | | |
| PVG39_HSVI1 | HYPOTHETICAL GENE 39 PROTEIN | ICTALURID HERPES VIRUS 1 | 651–678 | 1088–1115 | | | | | | | |
| PVG46_HSVI1 | PROBABLE MAJOR GLYCOPROTEIN | ICTALURID HERPES VIRUS 1 | 142–169 | 346–373 | 897–924 | 973–1007 | | | | | |
| PVG51_HSVI1 | HYPOTH GENE 51 MEMBRANE PROTEIN | ICTALURID HERPES VIRUS 1 | 34–61 | 87–114 | | | | | | | |
| PVG56_HSVI1 | HYPOTHETICAL GENE 56 PROTEIN | ICTALURID HERPES VIRUS 1 | 582–609 | | | | | | | | |
| PVG63_HSVI1 | HYPOTHETICAL GENE 63 PROTEIN | ICTALURID HERPES VIRUS 1 | 550–584 | | | | | | | | |
| PVG64_HSVI1 | HYPOTHETICAL GENE 64 PROTEIN | ICTALURID HERPES VIRUS 1 | 477–504 | | | | | | | | |
| PVG65_HSVI1 | HYPOTHETICAL GENE 65 PROTEIN | ICTALURID HERPES VIRUS 1 | 1213–1254 | | | | | | | | |
| PVG66_HSVI1 | HYPOTHETICAL GENE 66 PROTEIN | ICTALURID HERPES VIRUS 1 | 362–406 | | | | | | | | |
| PVG67_HSVI1 | HYPOTHETICAL GENE 67 PROTEIN | ICTALURID HERPES VIRUS 1 | 1342–1369 | | | | | | | | |
| PVG68_HSVI1 | HYPOTHETICAL GENE 68 PROTEIN | ICTALURID HERPES VIRUS 1 | 261–288 | | | | | | | | |
| PVG72_HSVI1 | HYPOTHETICAL GENE 72 PROTEIN | ICTALURID HERPES VIRUS 1 | 447–481 | | | | | | | | |
| PVG75_HSVI1 | HYPOTHETICAL GENE 75 PROTEIN | ICTALURID HERPES VIRUS 1 | 388–422 | | | | | | | | |
| PVG76_HSVI1 | HYPOTHETICAL GENE 76 PROTEIN | ICTALURID HERPES VIRUS 1 | 200–227 | | | | | | | | |
| PVTER_HSVI1 | PROBABLE DNA PACKAGING PROTEIN | ICTALURID HERPES VIRUS 1 | 710–737 | | | | | | | | |
| PHEMA_IAHSW | HEMAGGLUTININ PRECURSOR | INFLUENZA A VIRUS (STRAIN A/ EQUINE/SWITZERLAND/137/72 | 29–56 | 194–221 | 388–457 | | | | | | |
| PHEMA_IAAIC | HEMAGGLUTININ PRECURSOR | INFLUENZA A VIRUS (STRAIN A/ AICHI/2/68) | 387–453 | | | | | | | | |
| PVNS1_IAALA | NONSTRUCTURAL PROTEIN NS1 | INFLUENZA A VIRUS (STRAIN A/ ALASKA/6/7) | 171–198 | | | | | | | | |
| PVNUC_IAANA | NUCLEOPROTEIN | INFLUENZA A VIRUS (STRAIN A/ ANAS ACUTA/PRIMORJE/695/76) | 378–405 | | | | | | | | |
| PRRP2_IAANN | RNA-DIRECTED RNA POL SUB P2 | INFLUENZA A VIRUS (STRAIN A/ ANN ARBOR/6/60) | 119–146 | | | | | | | | |
| PVNS1_IAANN | NONSTRUCTURAL PROTEIN NS1 | INFLUENZA A VIRUS (STRAIN A/ ANN ARBOR/6/60) | 171–198 | | | | | | | | |

TABLE VII-continued 107 x 178 x 4 SEARCH MOTIF RESULTS SUMMARY
(PREFERRED VIRAL SEQUENCES)

| PCGENE FILE NAME | 107 x 178 x 4 PROTEIN | All Viruses (no bacteriophages) VIRUS | AREA TABLE VII-continued

| PCGENE FILE NAME | 107 × 178 × 4 PROTEIN | 107 × 178 × 4 SEARCH MOTIF RESULTS SUMMARY (PREFERRED VIRAL SEQUENCES) All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IADA1 | HEMAGGLUTININ PRECURSOR | INFLUENZA A VIRUS (STRAIN A/ DUCK/ALBERTA/28/76) | 381–451 | | | | | | | | |
| PNRAM_IADA1 | NEURAMINIDASE | INFLUENZA A VIRUS (STRAIN A/ DUCK/ALBERTA/28/76) | 51–81 | | | | | | | | |
| PHEMA_IADA4 | HEMAGGLUTININ PRECURSOR | INFLUENZA A VIRUS (STRAIN A/ DUCK/ALBERTA/35/76) | 29–56 | 418–478 | | | | | | | |
| PHEMA_IADA2 | HEMAGGLUTININ PRECURSOR | INFLUENZA A VIRUS (STRAIN A/ DUCK/ALBERTA/60/76) | 423–453 | 499–543 | | | | | | | |
| PVNS1_IADA2 | NONSTRUCTURAL PROTEIN NS1 | INFLUENZA A VIRUS (STRAIN A/ DUCK/ALBERTA/60/76) | 171–198 | | | | | | | | |
| PHEMA_IADA3 | HEMAGGLUTININ PRECURSOR | INFLUENZA A VIRUS (STRAIN A/ DUCK/ALBERTA/78/76) | 387–453 | | | | | | | | |
| PVNUC_IADAU | NUCLEOPROTEIN | INFLUENZA A VIRUS (STRAIN A/ DUCK/AUSTRALIA/749/80) | 378–405 | | | | | | | | |
| PVNUC_IADBE | NUCLEOPROTEIN | INFLUENZA A VIRUS (STRAIN A/ DUCK/BEIJING/1/78) | 378–405 | | | | | | | | |
| PHEMA_IADCZ | HEMAGGLUTININ PRECURSOR | INFLUENZA A VIRUS (STRAIN A/ DUCK/CZECHOSLOVAKIA/56) | 381–451 | | | | | | | | |
| PVNUC_IADCZ | NUCLEOPROTEIN | INFLUENZA A VIRUS (STRAIN A/ DUCK/CZECHOSLOVAKIA/56) | 378–405 | | | | | | | | |
| PVNUC_IADE1 | NUCLEOPROTEIN | INFLUENZA A VIRUS (STRAIN A/ DUCK/ENGLAND/1/) | 378–405 | | | | | | | | |
| PHEMA_IADE1 | HEMAGGLUTININ PRECURSOR | INFLUENZA A VIRUS (STRAIN A/ DUCK/ENGLAND/1/56) | 21–55 | 402–453 | 506–533 | | | | | | |
| PVNUC_IADE2 | NUCLEOPROTEIN | INFLUENZA A VIRUS (STRAIN A/ DUCK/ENGLAND/1/62) | 378–405 | | | | | | | | |
| PNRAM_IADGE | NEURAMINIDASE | INFLUENZA A VIRUS (STRAIN A/ DUCK/GERMANY/49) | 21–48 | | | | | | | | |
| PHEMA_IADH7 | HEMAGGLUTININ PRECURSOR | INFLUENZA A VIRUS (STRAIN A/ DUCK/HOKKAIDO/10/85) | 371–437 | | | | | | | | |
| PHEMA_IADH5 | HEMAGGLUTININ PRECURSOR | INFLUENZA A VIRUS (STRAIN A/ DUCK/HOKKAIDO/21/82) | 371–437 | | | | | | | | |
| PHEMA_IADH3 | HEMAGGLUTININ PRECURSOR | INFLUENZA A VIRUS (STRAIN A/ DUCK/HOKKAIDO/33/80) | 371–437 | | | | | | | | |
| PHEMA_IADH1 | HEMAGGLUTININ PRECURSOR | INFLUENZA A VIRUS (STRAIN A/ DUCK/HOKKAIDO/5/77) | 371–437 | | | | | | | | |
| PHEMA_IADH4 | HEMAGGLUTININ PRECURSOR | INFLUENZA A VIRUS (STRAIN A/ DUCK/HOKKAIDO/7/82) | 371–437 | | | | | | | | |
| PHEMA_IADH2 | HEMAGGLUTININ PRECURSOR | INFLUENZA A VIRUS (STRAIN A/ DUCK/HOKKAIDO/8/80) | 371–437 | | | | | | | | |
| PRRP2_IADH2 | RNA-DIRECTED RNA POL SUB P2 | INFLUENZA A VIRUS (STRAIN A/ DUCK/HOKKAIDO/8/80) | 119–146 | | | | | | | | |
| PHEMA_IADH6 | HEMAGGLUTININ PRECURSOR | INFLUENZA A VIRUS (STRAIN A/ DUCK/HOKKAIDO/9/85) | 371–437 | | | | | | | | |
| PVNUC_IADHK | NUCLEOPROTEIN | INFLUENZA A VIRUS (STRAIN A/ DUCK/HONG KONG/7/75) | 378–405 | | | | | | | | |

TABLE VII-continued

| PCGENE FILE NAME | 107 × 178 × 4 PROTEIN | 107 × 178 × 4 SEARCH MOTIF RESULTS SUMMARY (PREFERRED VIRAL SEQUENCES) All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IADIR | HEMAGGLUTININ PRECURSOR | INFLUENZA A VIRUS (STRAIN A/ DUCK/IRELAND/113/83) | 415–445 | | | | | | | | |
| PHEMA_IADMA | HEMAGGLUTININ PRECURSOR | INFLUENZA A VIRUS (STRAIN A/ DUCK/MANITOBA/1/53) | 31–58 | | | | | | | | |
| PVNUC_IADMA | NUCLEOPROTEIN | INFLUENZA A VIRUS (STRAIN A/ DUCK/MANITOBA/1/53) | 378–405 | | | | | | | | |
| PHEMA_IADM2 | HEMAGGLUTININ PRECURSOR | INFLUENZA A VIRUS (STRAIN A/ DUCK/MEMPHIS/546/76) | 21–56 | | | | | | | | |
| PHEMA/IADM2 | HEMAGGLUTININ PRECURSOR | INFLUENZA A VIRUS (STRAIN A/ DUCK/MEMPHIS/928/74) | 387–453 | | | | | | | | |
| PVNUC_IADM2 | NUCLEOPROTEIN | INFLUENZA A VIRUS (STRAIN A/ DUCK/MEMPHIS/928/74) | 378–405 | | | | | | | | |
| PHEMA_IADNY | HEMAGGLUTININ PRECURSOR | INFLUENZA A VIRUS (STRAIN A/ DUCK/NEW YORK/12/78) | 21–55 | | | | | | | | |
| PHEMA_IADNZ | HEMAGGLUTININ PRECURSOR | INFLUENZA A VIRUS (STRAIN A/ DUCK/NEW ZEALAND/31/76) | 381–453 | | | | | | | | |
| PVNUC_IADNZ | NUCLEOPROTEIN | INFLUENZA A VIRUS (STRAIN A/ DUCK/NEW ZEALAND/31/76) | 378–405 | | | | | | | | |
| PHEMA_IADU1 | HEMAGGLUTININ PRECURSOR | INFLUENZA A VIRUS (STRAIN A/ DUCK/UKRAINE/1/60) | 21–55 | | | | | | | | |
| PHEMA_IADU3 | HEMAGGLUTININ PRECURSOR | INFLUENZA A VIRUS (STRAIN A/ DUCK/UKRAINE/1/63) | 387–453 | | | | | | | | |
| PVNUC_IADU2 | NUCLEOPROTEIN | INFLUENZA A VIRUS (STRAIN A/ DUCK/UKRAINE/2/60) | 378–405 | | | | | | | | |
| PVNUC_IAEN5 | NUCLEOPROTEIN | INFLUENZA A VIRUS (STRAIN A/ ENGLAND/19/55) | 378–405 | | | | | | | | |
| PHEMA_IAEN7 | HEMAGGLUTININ PRECURSOR | INFLUENZA A VIRUS (STRAIN A/ ENGLAND/321/77) | 40–67 | 387–453 | | | | | | | |
| PHEMA_IAEN6 | HEMAGGLUTININ PRECURSOR | INFLUENZA A VIRUS (STRAIN A/ ENGLAND/878/69) | 24–51 | | | | | | | | |
| PHEMA_IAHAL | HEMAGGLUTININ PRECURSOR | INFLUENZA A VIRUS (STRAIN A/ EQUINE/ALGIERS/72) | 386–452 | | | | | | | | |
| PHEMA_IAHCD | HEMAGGLUTININ PRECURSOR | INFLUENZA A VIRUS (STRAIN A/ EQUINE/C.DETROIT/1/64) | 29–56 | 194–221 | 388–457 | | | | | | |
| PHEMA_IAHC6 | HEMAGGLUTININ PRECURSOR | INFLUENZA A VIRUS (STRAIN A/ EQUINE/CAMBRIDGE/1/63) | 29–56 | 194–221 | 388–457 | | | | | | |
| PHEMA_IAHC7 | HEMAGGLUTININ PRECURSOR | INFLUENZA A VIRUS (STRAIN A/ EQUINE/CAMBRIDGE/1/73) | 29–56 | 194–221 | 388–457 | | | | | | |
| PNRAM_IAHCO | NEURAMINIDASE | INFLUENZA A VIRUS (STRAIN A/ EQUINE/COR/16/74) | 197–224 | 386–413 | | | | | | | |
| PHEMA_IAHDE | HEMAGGLUTININ PRECURSOR | INFLUENZA A VIRUS (STRAIN A/ EQUINE/DETROIT/1/64) | 29–56 | 194–221 | 388–457 | | | | | | |
| PHEMA_IAHFO | HEMAGGLUTININ PRECURSOR | INFLUENZA A VIRUS (STRAIN A/ EQUINE/FONTAINEBLEAU/76) | 386–452 | | | | | | | | |
| PVNUC_IAHJI | NUCLEOPROTEIN | INFLUENZA A VIRUS (STRAIN A/ EQUINE/JILLIN/1/89) | 378–405 | | | | | | | | |

TABLE VII-continued 107 x 178 x 4 SEARCH MOTIF RESULTS SUMMARY
(PREFERRED VIRAL SEQUENCES)

| PCGENE FILE NAME | 107 x 178 x

TABLE VII-continued

| PCGENE FILE NAME | 107 × 178 × 4 PROTEIN | 107 × 178 × 4 SEARCH MOTIF RESULTS SUMMARY (PREFERRED VIRAL SEQUENCES) All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNUC_IAFOM | NUCLEOPROTEIN | INFLUENZA A VIRUS (STRAIN A/ FORT MONMOUTH/1/47) | 378–405 | | | | | | | | |
| PVNS1_IAFOW | NONSTRUCTURAL PROTEIN NS1 | INFLUENZA A VIRUS (STRAIN A/ FORT WARREN/1/50) | 171–198 | | | | | | | | |
| PVNUC_IAFOW | NUCLEOPROTEIN | INFLUENZA A VIRUS (STRAIN A/ FORT WARREN/1/50) | 378–405 | | | | | | | | |
| PVNUC_IAFPD | NUCLEOPROTEIN | INFLUENZA A VIRUS (STRAIN A/ FOWL PLAGUE VIRUS/DOBSON/ 'DUTCH'/27) | 378–405 | | | | | | | | |
| PHEMA_IAFPR | HEMAGGLUTININ PRECURSOR | INFLUENZA A VIRUS (STRAIN A/ FOWL PLAGUE VIRUS/ ROSTOCK/34) | 177–221 | 384–442 | | | | | | | |
| PRRP2_IAFPR | RNA-DIRECTED RNA POL SUB P2 | INFLUENZA A VIRUS (STRAIN A/ FOWL PLAGUE VIRUS/ ROSTOCK/34) | 119–146 | | | | | | | | |
| PVNUC_IAFPR | NUCLEOPROTEIN | INFLUENZA A VIRUS (STRAIN A/ FOWL PLAGUE VIRUS/ ROSTOCK/34) | 378–405 | | | | | | | | |
| PNRAM_IAFPW | NEURAMINIDASE | INFLUENZA A VIRUS (STRAIN A/ FOWL PLAGUE VIRUS/ WEYBRIDGE) | 10–48 | 52–80 | 197–224 | | | | | | |
| PHEMA_IAGRE | HEMAGGLUTININ PRECURSOR | INFLUENZA A VIRUS (STRAIN A/ GREY TEAL/AUSTRALIA/2/79) | 381–451 | | | | | | | | |
| PVNUC_IAURE | NUCLEOPROTEIN | INFLUENZA A VIRUS (STRAIN A/ GREY TEAL/AUSTRALIA/2/79) | 378–405 | | | | | | | | |
| PHEMA_IAGUA | HEMAGGLUTININ PRECURSOR | INFLUENZA A VIRUS (STRAIN A/ GULL/ASTRAKHAN/227/84) | 504–531 | | | | | | | | |
| PVNUC_IAGUA | NUCLEOPROTEIN | INFLUENZA A VIRUS (STRAIN A/ GULL/ASTRAKHAN/227/84) | 389–405 | | | | | | | | |
| PVNUC_IAGU4 | NUCLEOPROTEIN | INFLUENZA A VIRUS (STRAIN A/ GULL/MARYLAND/1815/79) | 378–405 | | | | | | | | |
| PVNUC_IAGU3 | NUCLEOPROTEIN | INFLUENZA A VIRUS (STRAIN A/ GULL/MARYLAND/1824/78) | 378–405 | | | | | | | | |
| PVNUC_IAGU1 | NUCLEOPROTEIN | INFLUENZA A VIRUS (STRAIN A/ GULL/MARYLAND/5/77) | 379–405 | | | | | | | | |
| PHEMA_IAGU2 | HEMAGGLUTININ PRECURSOR | INFLUENZA A VIRUS (STRAIN A/ GULL/MARYLAND/704/77) | 505–532 | | | | | | | | |
| PRRP2_IAGU2 | RNA-DIRECTED RNA POL SUB P2 | INFLUENZA A VIRUS (STRAIN A/ GULL/MARYLAND/704/77) | 119–146 | | | | | | | | |
| PVNUC_IAGU2 | NUCLEOPROTEIN | INFLUENZA A VIRUS (STRAIN A/ GULL/MARYLAND/704/77) | 378–405 | | | | | | | | |
| PVNUC_IAGUM | NUCLEOPROTEIN | INFLUENZA A VIRUS (STRAIN A/ GULL/MASSACHUSETTS/26/80) | 378–405 | | | | | | | | |
| PVNUC_IAGUN | NUCLEOPROTEIN | INFLUENZA A VIRUS (STRAIN A/ GULL/MINNESOTA/945/80) | 378–405 | | | | | | | | |

TABLE VII-continued

107 × 178 × 4 SEARCH MOTIF RESULTS SUMMARY (PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IAHAR | HEMAGGLUTININ PRECURSOR | INFLUENZA A VIRUS (STRAIN A/HARBIN/1/88) | 29–56 | | | | | | | | |
| PVNUC_IAHIC | NUCLEOPROTEIN | INFLUENZA A VIRUS (STRAIN A/HICKOX/40) | 378–405 | | | | | | | | |
| PVNUC_IAHO1 | NUCLEOPROTEIN | INFLUENZA A VIRUS (STRAIN A/HONG KONG/1/68) | 378–405 | | | | | | | | |
| PVNUC_IAHO2 | NUCLEOPROTEIN | INFLUENZA A VIRUS (STRAIN A/HONG KONG/5/83) | 378–405 | | | | | | | | |
| PHEMA_IAJAP | HEMAGGLUTININ PRECURSOR | INFLUENZA A VIRUS (STRAIN A/JAPAN/305/57) | 196–223 | | | | | | | | |
| PHEMA_IAKIE | HEMAGGLUTININ PRECURSOR | INFLUENZA A VIRUS (STRAIN A/KIEV/59/79) | 29–56 | | 425–478 | | | | | | |
| PNRAM_IAKIE | NEURAMINIDASE | INFLUENZA A VIRUS (STRAIN A/KIEV/59/79) | 50–81 | | | | | | | | |
| PVNUC_IAKIE | NUCLEOPROTEIN | INFLUENZA A VIRUS (STRAIN A/KIEV/59/79) | 378–405 | | | | | | | | |
| PRRP1_IAKOR | RNA-DIRECTED RNA POL SUB P1 | INFLUENZA A VIRUS (STRAIN A/KOREA/426/68) | 575–602 | | | | | | | | |
| PRRP2_IAKOR | RNA-DIRECTED RNA POL SUB P2 | INFLUENZA A VIRUS (STRAIN A/KOREA/426/68) | 119–146 | | | | | | | | |
| PRRP2_IALE2 | RNA-DIRECTED RNA POL SUB P2 | INFLUENZA A VIRUS (STRAIN A/LENINGRAD/134/17/57) | 119–146 | | | | | | | | |
| PRRP2_IALE1 | RNA-DIRECTED RNA POL SUB P2 | INFLUENZA A VIRUS (STRAIN A/LENINGRAD/134/57) | 119–146 | | | | | | | | |
| PVNS1_IALE1 | NONSTRUCTURAL PROTEIN NS1 | INFLUENZA A VIRUS (STRAIN A/LENINGRAD/134/57) | 171–198 | | | | | | | | |
| PHEMA_IALEN | HEMAGGLUTININ PRECURSOR | INFLUENZA A VIRUS (STRAIN A/LENINGRAD/54/1) | 29–56 | | 425–478 | | | | | | |
| PNRAM_IALEN | NEURAMINIDASE | INFLUENZA A VIRUS (STRAIN A/LENINGRAD/54/1) | 50–81 | | | | | | | | |
| PVNUC_IALEN | NUCLEOPROTEIN | INFLUENZA A VIRUS (STRAIN A/LENINGRAD/54/1) | 378–405 | | | | | | | | |
| PVNS1_IAMA6 | NONSTRUCTURAL PROTEIN NS1 | INFLUENZA A VIRUS (STRAIN A/MALLARD/ALBERTA/88/76) | 171–198 | | | | | | | | |
| PHEMA_IAMAA | HEMAGGLUTININ PRECURSOR | INFLUENZA A VIRUS (STRAIN A/MALLARD/ASTRAKHAN/244/82) | 380–450 | | | | | | | | |
| PVNUC_IAMAA | NUCLEOPROTEIN | INFLUENZA A VIRUS (STRAIN A/MALLARD/ASTRAKHAN/244/82) | 378–405 | | | | | | | | |
| PHEMA_IAMAB | HEMAGGLUTININ PRECURSOR | INFLUENZA A VIRUS (STRAIN A/MALLARD/ASTRAKHAN/263/82) | 385–455 | | | | | | | | |
| PRRP2_IAMAN | RNA-DIRECTED RNA POL SUB P2 | INFLUENZA A VIRUS (STRAIN A/MALLARD/NEW YORK/6750/78) | 119–146 | | | | | | | | |
| PVNUC_IAMAN | NUCLEOPROTEIN | INFLUENZA A VIRUS (STRAIN A/MALLARD/NEW YORK/6750/78) | 378–405 | | | | | | | | |
| PHEMA_IAMAO | HEMAGGLUTININ PRECURSOR | INFLUENZA A VIRUS (STRAIN A/MALLARD/NEW YORK/6874/78) | 387–453 | | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IAME1 | HEMAGGLUTININ PRECURSOR | INF TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IARUD | HEMAGGLUTININ PRECURSOR | INFLUENZA A VIRUS (STRAIN A/RUDDY TURNSTONE/NEW JERSEY/47/85) | 381–451 | | | | | | | | |
| PRRP2_IARUD | RNA-DIRECTED RNA POL SUB P2 | INFLUENZA A VIRUS (STRAIN A/RUDDY TURNSTONE/NEW JERSEY/47/85) | 119–146 | | | | | | | | |
| PVNUC_IARUD | NUCLEOPROTEIN | INFLUENZA A VIRUS (STRAIN A/RUDDY TURNSTONE/NEW JERSEY/47/85) | 378–405 | | | | | | | | |
| PNRAM_IARUE | NEURAMINIDASE | INFLUENZA A VIRUS (STRAIN A/RUDDY TURNSTONE/NEW JERSEY/60/85) | 49–88 | | | | | | | | |
| PVNUC_IASE0 | NUCLEOPROTEIN | INFLUENZA A VIRUS (STRAIN A/SEAL/MASSACHUSETTS/1/80) | 378–405 | | | | | | |

TABLE VII-continued

107 × 178 × 4 SEARCH MOTIF RESULTS SUMMARY (PREFERRED VIRAL SEQUENCES)

| PCGEN

TABLE VII-continued

107 × 178 × 4 SEARCH MOTIF RESULTS SUMMARY (PREFERRED VIRAL SEQUENCES)

| PCGEN

TABLE VII-continued

107 × 178 × 4 SEARCH MOTIF RESULTS SUMMARY
(PREFERRED VIRAL SEQUENCES)

|

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRP3_INBAD | RNA-DIRECTED RNA POL SUB P3 | INFLUENZA B VIRUS (STRAIN B/ANN ARBOR/1/66 [WILD-TYPE] | 2–33 | 472–509 | | | | | | | |
| PHEMA_INBBE | HEMAGGLUTININ PRECURSOR | INFLUENZA B VIRUS (STRAIN B/BEIJING/1/87) | 400–431 | 439–483 | | | | | | | |
| PHEMA_INBBO | HEMAGGLUTININ PRECURSOR | INFLUENZA B VIRUS (STRAIN B/BONN/43) | 390–421 | 429–473 | | | | | | | |
| PHEMA_INBEN | HEMAGGLUTININ PRECURSOR | INFLUENZA B VIRUS (STRAIN B/ENGLAND/222/82) | 398–429 | 437–481 | | | | | | | |
| PHEMA_INBHK | HEMAGGLUTININ PRECURSOR | INFLUENZA B VIRUS (STRAIN B/HONG KONG/8/73) | 391–418 | 429–473 | | | | | | | |
| PHEMA_INBLE | HEMAGGLUTININ PRECURSOR | INFLUENZA B VIRUS (STRAIN B/LEE/40) | 399–430 | 438–482 | | | | | | | |
| PNRAM_INBLE | NEURAMINIDASE | INFLUENZA B VIRUS (STRAIN B/LEE/40) | 4–35 | | | | | | | | |
| PVNS2_INBLE | NONSTRUCTURAL PROTEIN NS2 | INFLUENZA B VIRUS (STRAIN B/LEE/40) | 51–78 | | | | | | | | |
| PHEMA_INBMD | HEMAGGLUTININ PRECURSOR | INFLUENZA B VIRUS (STRAIN B/MARYLAND/59) | 389–420 | 428–472 | | | | | | | |
| PHEMA_INBME | HEMAGGLUTININ PRECURSOR | INFLUENZA B VIRUS (STRAIN B/MEMPHIS/6/86) | 393–424 | 432–476 | | | | | | | |
| PHGEMA_INBOR | HEMAGGLUTININ PRECURSOR | INFLUENZA B VIRUS (STRAIN B/OREGON/5/80) | 398–429 | 437–481 | | | | | | | |
| PVNS1_INBPA | NONSTRUCTURAL PROTEIN NS1 | INFLUENZA B VIRUS (STRAIN B/PA/79) | 171–198 | | | | | | | | |
| PHEMA_INBSI | HEMAGGLUTININ PRECURSOR | INFLUENZA B VIRUS (STRAIN B/SINGAPORE/222/79) | 398–429 | 437–481 | | | | | | | |
| PRRP2_INBSI | RNA-DIRECTED RNA POL SUB P2 | INFLUENZA B VIRUS (STRAIN B/SINGAPORE/222/79) | 157–194 | | | | | | | | |
| PHEMA_INBUS | HEMAGGLUTININ PRECURSOR | INFLUENZA B VIRUS (STRAIN B/USSR/100/83) | 391–422 | 430–474 | | | | | | | |
| PHEMA_INBVK | HEMAGGLUTININ PRECURSOR | INFLUENZA B VIRUS (STRAIN B/VICTORIA/2/87) | 400–431 | 439–483 | | | | | | | |
| PHEMA_INBVI | HEMAGGLUTININ PRECURSOR | INFLUENZA B VIRUS (STRAIN B/VICTORIA/3/85) | 393–4224 | 432–476 | | | | | | | |
| PVNS2_INBYA | NONSTRUCTURAL PROTEIN NS2 | INFLUENZA B VIRUS (STRAIN B/YAMAGATA/1/73) | 51–78 | | | | | | | | |
| PRRP3_INCBE | RNA-DIRECTED RNA POL SUB P3 | INFLUENZA C VIRUS (STRAIN C/BERLIN/1/85) | 509–536 | | | | | | | | |
| PHEMA_INCCA | HEMAGGLUTININ PRECURSOR | INFLUENZA C VIRUS (STRAIN C/CALIFORNIA/78) | 495–571 | | | | | | | | |
| PVNUC_INCAA | NUCLEOPROTEIN | INFLUENZA C VIRUS (STRAIN C/CALIFORNIA/78) | 99–126 | 416–443 | 451–478 | | | | | | |
| PHEMA_INCEN | HEMAGGLUTININ PRECURSOR | INFLUENZA C VIRUS (STRAIN C/ENGLAND/892/83) | 483–559 | | | | | | | | |
| PHEMA_INCGL | HEMAGGLUTININ PRECURSOR | INFLUENZA C VIRUS (STRAIN C/GREAT LAKES/1167/54) | 483–559 | | | | | | | | |

TABLE VII-continued

107 × 178 × 4 SEARCH MOTIF RESULTS SUMMARY
(PREFERRED VIRAL SEQUENCES)

| PCGENE FILE NAME | 107 × 178 × 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_INCHY | HEMAGGLUTININ PRECURSOR | INFLUENZA C VIRUS (STRAIN C/HYOGO/1/83) | 482–558 | | | | | | | | |
| PRRP_INCJJ | RNA-DIRECTED RNA POL SUB P3 | INFLUENZA C VIRUS (STRAIN C/JJ/50) | 509–536 | | | | | | | | |
| PVMAT_INCJJ | MATRIX (M) PROTEIN | INFLUENZA C VIRUS (STRAIN C/JJ/50) | 151–185 | | | | | | | | |
| PVNS2_INCJJ | NONSTRUCTURAL PROTEIN NS2 | INFLUENZA C VIRUS (STRAIN C/JJ/50) | 71–98 | | | | | | | | |
| PHEMA_INCJH | HEMAGGLUTININ PRECURSOR | INFLUENZA C VIRUS (STRAIN C/JOHANNESBURG/1/66) | 496–572 | | | | | | | | |
| PHEMA_INCKY | HEMAGGLUTININ PRECURSOR | INFLUENZA C VIRUS (STRAIN C/KYOTO/41/82) | 482–558 | | | | | | | | |
| PHEMA_INCMI | HEMAGGLUTININ PRECURSOR | INFLUENZA C VIRUS (STRAIN C/MISSISSIPPI/80) | 482–558 | | | | | | | | |
| PHEMA_INCNA | HEMAGGLUTININ PRECURSOR | INFLUENZA C VIRUS (STRAIN C/NARA/82) | 482–558 | | | | | | | | |
| PHEMA_INCP1 | HEMAGGLUTININ PRECURSOR | INFLUENZA C VIRUS (STRAIN C/PIG/BEIJING/10/81) | 483–559 | | | | | | | | |
| PHEMA_INCP2 | HEMAGGLUTININ PRECURSOR | INFLUENZA C VIRUS (STRAIN C/PIG/BEIJING/115/81) | 483–559 | | | | | | | | |
| PHEMA_INCP3 | HEMAGGLUTININ PRECURSOR | INFLUENZA C VIRUS (STRAIN C/PIG/BEIJING/439/82) | 483–559 | | | | | | | | |
| PHEMA_INCTA | HEMAGGLUTININ PRECURSOR | INFLUENZA C VIRUS (STRAIN C/TAYLOR/1233/47) | 483–559 | | | | | | | | |
| PHEMA_INCYA | HEMAGGLUTININ PRECURSOR | INFLUENZA C VIRUS (STRAIN C/YAMAGATA/10/81) | 483–559 | | | | | | | | |
| PENV_MLVKI | ENV POLYPROTEIN | KIRSTEN MURINE LEUKEMIA VIRUS | 40–81 | | | | | | | | |
| PVGLB_HSVMD | GLYCOPROTEIN B PRECURSOR | MAREK'S DISEASE HERPES VIRUS (STRAIN RB-1B) | 93–120 | 352–379 | | | | | | | |
| PENV_MCFF | ENV POLYPROTEIN | MINK CELL FOCUS-FORMING MURINE LEUKEMIA VIRUS | 473–512 | | | | | | | | |
| PENV_MCFF3 | ENV POLYPROTEIN | MINK CELL FOCUS-FORMING MURINE LEUKEMIA VIRUS (ISOLATE CI-3) | 488–515 | | | | | | | | |
| PENV_MLVMO | ENV POLYPROTEIN | MOLONEY MURINE LEUKEMIA VIRUS | 502–543 | | | | | | | | |
| PDNBI_MCMVS | MAJOR DNA-BINDING PROTEIN | MURINE CYTOMEGALO VIRUS (STRAIN SMITH) | 584–618 | | | | | | | | |
| PIC18_MCMVS | PROB PROC & TRANSPORT PRO | MURINE CYTOMEGALO VIRUS (STRAIN SMITH) | 661–691 | | | | | | | | |
| PVGLB_MCMVS | GLYCOPROTEIN B PRECURSOR | MURINE CYTOMEGALO VIRUS (STRAIN SMITH) | 381–408 | 441–475 | | | | | | | |
| PVE2_PCPV1 | E2 PROTEIN | PYGMY CHIMPANZEE PAPILLOMA VIRUS TYPE 1 | 267–294 | 327–361 | | | | | | | |

TABLE VII-continued 107 x 178 x 4 SEARCH MOTIF RESULTS SUMMARY
(PREFERRED VIRAL SEQUENCES)

| PCGENE FILE NAME | 107 x 178 x 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVE5_PCPV1 | PROBABLE E5 PROTEIN | PYGMY CHIMPANZEE PA

TABLE VII-continued

107 × 178 × 4 SEARCH MOTIF RESULTS SUMMARY (PREFERRED VIRAL SEQUENCES)

| PCGEN

TABLE VII-continued 107 x 178 x 4 SEARCH MOTIF RESULTS SUMMARY
(PREFERRED VIRAL SEQUENCES)

| PCGENE FILE NAME | 107 x 178 x 4 PROTEIN | All Viruses (no bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRIR1_VZVD | RIBONUC-DIPHOSPH REDUCT LARGE CHA | VARICELLA-ZOSTER VIRUS (STRAIN DUMAS) | 119–146 | | | | | | | | |
| PTEGU_VZVD | LARGE TEGUMENT PROTEIN | VARICELLA-ZOSTER VIRUS (STRAIN DUMAS) | 1121–1158 | 1579–1609 | | | | | | | |
| PUL14_VZVD | HYPOTHETICAL GENE 46 PROTEIN | VARICELLA-ZOSTER VIRUS (STRAIN DUMAS) | 64–101 | | | | | | | | |
| PUL21_VZVD | GENE 38 PROTEIN | VARICELLA-ZOSTER VIRUS (STRAIN DUMAS) | 380–407 | | | | | | | | |
| PUL34_VZVD | VIRION GENE 24 PROTEIN | VARICELLA-ZOSTER VIRUS (STRAIN DUMAS) | 112–139 | | | | | | | | |
| PUL37_VZVD | GENE 21 PROTEIN | VARICELLA-ZOSTER VIRUS (STRAIN DUMAS) | 107–134 | 485–512 | 719–746 | | | | | | |
| PUL41_VZVD | HOST SHUTOFF VIRION PROTEIN | VARICELLA-ZOSTER VIRUS (STRAIN DUMAS) | 330–364 | | | | | | | | |
| PUL43_VZVD | GENE 15 MEMBRANE PROTEIN | VARICELLA-ZOSTER VIRUS (STRAIN DUMAS) | 129–156 | 312–349 | | | | | | | |
| PUL52_VZVD | PROB DNA REP GENE 6 PROTEIN | VARICELLA-ZOSTER VIRUS (STRAIN DUMAS) | 301–337 | | | | | | | | |
| PVGLC_VZVD | GLYCOPROTEIN GPV | VARICELLA-ZOSTER VIRUS (STRAIN DUMAS) | 295–322 | | |

TABLE VIII

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| | | 107 × 178 × 4 SEARCH MOTIF RESULTS SUMMARY FOR ALL PROCARYOTIC PROTEINS | | | | | | | | | |
| P120K_RICRI | 120 KD SURFACE-EXPOSED PROTEIN | *RICKETTSIA RICKETTSII* | 83–110 | 240–298 | 355–382 | 638–672 | 746–838 | 1168–1202 | | | |
| P17K_RICTY | 17 KD ANTIGEN PRECURSOR | *RICKETTSIA TYPHI* | 67–94 | | | | | | | | |
| P190K_RICRI | 190 KD ANTIGEN PRECURSOR (CELL SURFACE) | *RICKETTSIA RICKETTSII* | 241–268<br>2065–2096 | 406–487<br>2131–2168 | 607–634 | 754–781 | 829–856 | 904–931 | 1220–1254 | 1544–1571 | 1723–1750 |
| P22KD_DESMO | 22.6 KD PROTEIN | *DESULFUROCOCCUS MOBILIS* | 25–52 | 59–89 | 120–147 | | | | | | |
| P40KD_VIBAN | 40 KD PROTEIN PRECURSOR | *VIBRIO ANGUILLARUM* | 153–196 | | | | | | | | |
| P60IM_ECOLI | 60 KD INNER-MEMBRANE PROTEIN | *ESCHERICHIA COLI* | 511–538 | | | | | | | | |
| P60IM_PROMI | 60 KD INNER-MEMBRANE PROTEIN | *PROTEUS MIRABILIS* | 14–41 | | | | | | | | |
| P65KD_ZYMMO | 65 KD PROTEIN | *ZYMOMONAS MOBILIS* | 95–122 | 444–524 | | | | | | | |
| P6PGD_BACSU | PROB 6-PHOSPHOGLUCONATE DEHYDROGENASE | *BACILLUS SUBTILIS* | 24–51 | 218–246 | | | | | | | |
| P6PGD_ECOLI | 6-PHOSPHOGLUCONATE DEHYDROGENASE | *ESCHERICHIA COLI* | 205–232 | | | | | | | | |
| P6PGD_SALTY | 6-PHOSPHOGLUCONATE DEHYDROGENASE | *SALMONELLA TYPHIMURIUM* | 205–232 | | | | | | | | |
| PAACA_STAAU | 6'-AMINOGLYCOSIDE N-ACETYLTRANSFERASE | *STAPHYLOCOCCUS AUREUS* | 450–477 | | | | | | | | |
| PAAT_BACSP | ASPARTATE AMINOTRANS-FERASE | BACILLUS SP | 146–173 | 185–212 | | | | | | | |
| PAAT_ECOLI | ASPARTATE AMINOTRANS-FERASE | *ESCHERICHIA COLI* | 351–378 | | | | | | | | |
| PABC_ECOLI | ABC PROTEIN | *ESCHERICHIA COLI* | 176–203 | | | | | | | | |
| PABIC_LACLA | ABORTIVE PHAGE RESIS-TANCE PROTEIN ABIC | *LACTOCOCCUS LACTIS* | 85–126 | 170–204 | 209–273 | | | | | | |
| PACCR_AGRTU | TRANSCRIPTIONAL REPRESSOR ACCR | *AGROBACTERIUM TUMEFACIENS* | 127–154 | | | | | | | | |
| PACEA_ECOLI | ISOCITRATE LYASE | *ESCHERICHIA COLI* | 398–432 | | | | | | | | |
| PACON_BACSU | ACONITATE HYDRATASE | *BACILLUS SUBTILIS* | 48–75 | | | | | | | | |
| PACON_ECOLI | ACONITATE HYDRATASE | *ESCHERICHIA COLI* | 41–68 | 613–640 | | | | | | | |
| PACOR_ALCEU | ACETOIN CATABOLISM REG PRO | *ALCALIGENES EUTROPHUS* | 85–112 | | | | | | | | |
| PACP_ECOLI | ACYL CARRIER PROTEIN | *ESCHERICHIA COLI* | 4–31 | | | | | | | | |
| PACRA_ECOLI | ACRIFLAVIN RESISTANCE PROTEIN A PRECURSOR | *ESCHERICHIA COLI* | 213–247 | | | | | | | | |
| PACRB_ECOLI | ACRIFLAVIN RESISTANCE PROTEIN B | *ESCHERICHIA COLI* | 520–551 | | | | | | | | |
| PACRF_ECOLI | ACRIFLAVIN RESISTANCE PROTEIN F | *ESCHERICHIA COLI* | 512–550 | 726–753 | | | | | | | |
| PACT3_STRCO | PUTATIVE KETOACYL REDUCTASE | *STREPTOMYCES COELICOLOR* | 157–184 | | | | | | | | |
| PACTA_LISMO | ACTIN-ASSEMBLY INDUCING PROTEIN PRECURSOR | *LISTERIA MONOCYTOGENES* | 237–264 | 576–603 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PACVS_NOCLA | ACV SYNTHETASE | NOCARDIA LACTAMDURANS | 3129–3163 | | | | | | | | |
| PADAA_BACSU | METPHOSTRIESTER-DNA ALKYLTRANSFERASE | BACILLUS SUBTILIS | 136–170 | | | | | | | | |
| PADDA_BACSU | ATP-DEPENDENT NUCLEASE SUBUNIT A | BACILLUS SUBTILIS | 398–425 | 454–481 | 522–556 | 1005–1032 | | | | | |
| PADDB_BACSU | ATP-DEPENDENT NUCLEASE SUBUNIT B | BACILLUS SUBTILIS | 257–284 | 870–903 | 943–977 | | | | | | |
| PADHI_CLOAB | NADPH-DEPENDENT BETANOL DEHYDROGENASE | CLOSTRIDIUM ACETOBUTYLICUM | 284–311 | | | | | | | | |
| PADHA_CLOAB | NADH-DEPENDENT BUTANOL DEHYDROGENASE A | CLOSTRIDIUM ACETOBUTYLICUM | 298–325 | | | | | | | | |
| PADHB_CLOAB | NADH-DEPENDENT BUTANOL DEHYDROGENASE B | CLOSTRIDIUM ACETOBUTYLICUM | 298–325 | | | | | | | | |
| PADHE_CLOAB | ALCOHOL DEHYDROGENASE | CLOSTRIDIUM ACETOBUTYLICUM | 653–680 | 779–806 | | | | | | | |
| PADHE_ECOLI | ALCOHOL DEHYDROGENASE | ESCHERICHIA COLI | 271–298 | | | | | | | | |
| PADIY_ECOLI | PUTATIVE REGULATORY PROTEIN ADIY | ESCHERICHIA COLI | 45–72 | | | | | | | | |
| PADP1_MYCGE | 140 KD ADHESION PRECURSOR | MYCOPLASMA GENITALIUM | 90–131 | 697–724 | 923–950 | 990–1017 | 1169–1199 | 1387–1414 | | | |
| PADP1_MYCPN | ADHESION P1 PRECURSOR | MYCOPLASMA PNEUMONIAE | 1557–1584 | | | | | | | | |
| PADT_RICPR | ADP, ATP CARRIER PROTEIN | RICKETTSIA PROWAZEKII | 276–307 | | | | | | | | |
| PAERA_AERHY | AEROLYSIN PRECURSOR | AEROMONAS HYDROPHILA | 278–305 | | | | | | | | |
| PAGAL_STRMU | ALPHA-GALACTOSIDASE | STREPTOCOCCUS MUTANS | 419–483 | 597–633 | | | | | | | |
| PAGAR_PSEAT | BETA-AGARASE PRECURSOR | PSEUDOMONAS ATLANTICA | 26–53 | | | | | | | | |
| PAGR_STAAU | ACCESSORY GENE REGULATOR PROTEIN | STAPHYLOCOCCUS AUREUS | 129–159 | 165–192 | | | | | | | |
| PAIL_YEREN | ATTACH INVAS LOCUS PROTEIN PRECURSOR | YERSINIA ENTEROCOLITICA | 19–46 | | | | | | | | |
| PAK1H_ECOLI | ASPARTOKINASE I | ESCHERICHIA COLI | 3–30 | 466–493 | 503–530 | | | | | | |
| PAK2H_ECOLI | ASPARTOKINASE II | ESCHERICHIA COLI | 51–78 | 608–635 | | | | | | | |
| PAK2_BACSU | ASPARTATE KINASE II ALPHA AND BETA SUBUNITS | BACILLUS SUBTILIS | 266–312 | | | | | | | | |
| PAKAB_CORGL | ASPARTATE KINASE ALPHA AND BETA SUBUNITS | CORYNEBACTERIUM GLUTMICUM | 5–32 | | | | | | | | |
| PALF_ECOLI | FRUCTOSE-BISPHOSPHATE ALDOLASE | ESCHERICHIA COLI | 286–316 | | | | | | | | |
| PALGB_PSEAE | ALGINATE BIOSYN TRANSL REG PROTEIN ALBG | PSEUDOMONAS AERUGINOSA | 160–194 | | | | | | | | |
| PALGE_PSEAE | ALGINATE PRODUCTION PROTEIN ALGE PRECURSOR | PSEUDOMONAS AERUGINOSA | 349–376 | | | | | | | | |
| PALGP_PSEAE | TRANSCRIPTIONAL REGULATORY PROTEIN ALGP | PSEUDOMONAS AERUGINOSA | 81–115 | | | | | | | | |
| PALKB_PSEOL | ALKANE-1 MONOOXYGENASE | PSEUDOMONAS OLEOVORANS | 115–142 | | | | | | | | |
| PALKT_PSEOL | RUBREDOXIN-NAD(+) REDUCTASE | PSEUDOMONAS OLEOVORANS | 138–172 | 338–365 | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PALR2_ECOLI | ALANINE RACEMASE, CATABOLIC PRECURSOR | ESCHERICHIA COLI | 9–36 | | | | | | | | |
| PALR_BACST | ALANINE RACEMASE | BACILLUS STEAROTHERMOPHILUS | 326–353 | | | | | | | | |
| PALSR_BACSU | ALS OPERON REGULATORY PROTEIN | BACILLUS SUBTILIS | 119–146 | | | | | | | | |
| PALYS_BACSP | AUTOLYSIN PRECURSOR | BACILLUS SP | 157–187 | | | | | | | | |
| PALYS_BACSU | AUTOLYSIN PRECURSOR | BACILLUS SUBTILIS | 147–191 | | | | | | | | |
| PALYS_STAAU | AUTOLYSIN | STRAPHYLOCOCCUS AUREUS | 244–271 | | | | | | | | |
| PAMIA_STRPN | AMIA PROTEIN PRECURSOR | STREPTOCOCCUS PNEUMONIAE | 223–264 | 297–338 | 446–473 | | | | | | |
| PAMID_PSECL | AMIDASE | PSEUDOMONAS CHLORORAPHIS | 72–99 | | | | | | | | |
| PAMIE_STRPN | OLIGOPEPTIDE TRANSPORT PROTEIN AMIE | STREPTOCOCCUS PNEUMONIAE | 187–214 | | | | | | | | |
| PAMPA_ECOLI | AMINOPEPTIDASE A/I | ESCHERICHIA COLI | 111–138 | 199–226 | | | | | | | |
| PAMPC_SERMA | BETA-LACTAMASE PRECURSOR | SERRATIA MERCESCENS | 231–258 | | | | | | | | |
| PAMPL_RICPR | CYTOSOL AMINOPEPTIDASE | RICKETTSIA PROWAZEKII | 3–47 | 72–99 | | | | | | | |
| PAMPN_ECOLI | AMINOPEPTIDASE N | ESCHERICHIA COLI | 655–682 | | | | | | | | |
| PAMPP_ECOLI | X-PRO AMINOPEPTIDASE | ESCHERICHIA COLI | 110–137 | | | | | | | | |
| PAMPT_THEAQ | AMINOPEPTIDASE T | THERMUS AQUATICUS | 281–308 | | | | | | | | |
| PAMY1_DICTH | ALPHA-AMYLASE 1 | DICTYOGLOMUS THERMOPHILUM | 507–534 | | | | | | | | |
| PAMY2_DICTH | ALPHA-AMYLASE 2 | DICTYOGLOMUS THERMOPHILUM | 151–178 | 507–534 | | | | | | | |
| PAMY2_SALTY | CYTOPLASMIC ALPHA-AMYLASE | SALMONELLA TYPHIMURIUM | 70–104 | | | | | | | | |
| PAMY3_DICTH | ALPHA-AMYLASE 3 | DICTYOGLOMUS THERMOPHILUM | 280–307 | | | | | | | | |
| PAMYB_BACCI | BETA-AMYLASE PRECURSOR | BACILLUS CIRCULANS | 61–88 | 266–293 | 1143–1184 | | | | | | |
| PAMYB_BACPO | BETA-AMYLASE | BACILLUS POLYMYXA | 60–87 | 378–405 | 459–486 | | | | | | |
| PAMYB_CLOTU | BETA-AMYLASE, THERMO-PHILIC PRECURSOR | CLOSTRIDIUM THERMO-SULFUROGENES | 269–296 | | | | | | | | |
| PAMYG_CLOSP | GLUCOAMYLASE PRECURSOR | CLOSTRIDIUM SP | 103–148 | 480–510 | | | | | | | |
| PAMYM_BACST | MALTOGENIC ALPHA-AMYLASE PRECURSOR | BACILLUS STEAROTHERMOPHILUS | 426–453 | | | | | | | | |
| PAMYR_BACS8 | RAW-STARCH-DIGESTING AMYLASE | BACILLUS SP | 210–237 | 435–465 | 615–642 | | | | | | |
| PAMY_AERHY | ALPHA-AMYLASE PRECURSOR | AEROMONAS HYDROPHILA | 415–453 | | | | | | | | |
| PAMY_ALTHA | ALPHA-AMYLASE PRECURSOR | ALTEROMONAS HALOPLANKTIS | 166–193 | | | | | | | | |
| PAMY_BACAM | ALPHA-AMYLASE PRECURSOR | BACILLUS AMYLOLIQUE-FACIENS | 102–136 | | | | | | | | |
| PAMY_BACCI | ALPHA-AMYLASE PRECURSOR | BACILLUS CIRCULANS | 212–239 | 437–474 | | | | | | | |
| PAMY_BACME | ALPHA-AMYLASE PRECURSOR | BACILLUS MEGATERIUM | 61–88 | 441–482 | | | | | | | |
| PAMY_BACSU | ALPHA-AMYLASE PRECURSOR | BACILLUS SUBTILIS | 165–205 | 281–308 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PAMY_BUTFI | ALPHA-AMYLASE PRECURSOR | BUTYRIVIBRIO FIBRISOLVENS | 377–418 | 546–573 | 579–606 | 795–822 | | | | | |
| PAMY_CLOAB | PUTATIVE ALPHA-AMYLASE | CLOSTRIDIUM ACETOBUTYLICUM | 283–310 | | | | | | | | |
| PAMY_CLOTU | ALPHA-AMYLASE PRECURSOR | CLOSTRIDIUM THERMO-SULFUROGENES | 431–468 | 612–642 | | | | | | | |
| PAMY_STRLM | ALPHA-AMYLASE PRECURSOR | STREPTOMYCES LIMOSUS | 173–200 | | | | | | | | |
| PANFA_AZOVI | NITROGEN FIXATION PROTEIN ANFA | AZOTOBACTER VINELANDII | 232–259 | | | | | | | | |
| PANFD_AZOVI | NITROGENASE IRON-IRON PROTEIN ALPHA CHAIN | AZOTOBACTER VINELANDII | 95–122 | | | | | | | | |
| PANFK_AZOVI | NITROGENASE IRON-IRON PROTEIN BETA CHAIN | AZOTOBACTER VINELANDII | 369–396 | | | | | | | | |
| PANGR_VIBAN | ANGR PROTEIN | VIBRIO ANGUILLARIUM | 93–120 | 169–203 | | | | | | | |
| PAPCE_FREDI | PHYCOBILISOME 120 KD LINKER POLYPEPTIDE | FREMYELLA DIPLOSIPHON | 51–78 | | | | | | | | |
| PAPCE_SYNP6 | PHYCOBILISOME LINKER POLYPEPTIDE | SYNECHOCOCCUS SP | 37–64 | 585–615 | | | | | | | |
| PAPCE_SYNY4 | PHYCOBILISOME 120 KD LINKER POLYPEPTIDE | SYNECHOCYSTIS SP | 52–79 | | | | | | | | |
| PAPHC_SALTY | ALKYL HYDROPEROXIDE REDUCTASE C22 PROTEIN | SALMONELLA TYPHIMURIUM | 62–89 | | | | | | | | |
| PAPI_ACHLY | PROTEASE I PRECURSOR | ACHROMOBACTER LYTICUS | 478–505 | | | | | | | | |
| PAPPC_ECOLI | PROBABLE CYTOCHROME OXIDASE SUBUNIT I | ESCHERICHIA COLI | 118–148 | | | | | | | | |
| PAPRD_PSEAE | ALKALINE PROTEASE SECRETION PROTEIN APRD | PSEUDOMONAS AERUGINOSA | 416–450 | | | | | | | | |
| PAPRE_PSEAE | ALKALINE PROTEASE SECRETION PROTEIN APRE | PSEUDOMONAS AERUGINOSA | 133–193 | 208–235 | 247–277 | | | | | | |
| PAPT_ECOLI | ADENINE PHOSPHORIBOSYL-TRANSFERASE | ESCHERICHIA COLI | 121–148 | | | | | | | | |
| PAPU_THEET | ALPHA-AMYLASE-PULLULANASE PRECURSOR | THERMOANAEROBACTER ETHANOLICUS | 276–303 | 347–374 | 936–982 | 987–1014 | 1210–1254 | 1381–1408 | | | |
| PARCA_MYCAR | ARGININE DEIMINASE | MYCOPLASMA ARGININI | 60–87 | 218–245 | | | | | | | |
| PARCB_ECOLI | AEROBIC RESPIRATION CONTROL PROTEIN ARCB | ESCHERICHIA COLI | 102–150 | 302–329 | 399–426 | | | | | | |
| PARCD_PSEAE | PROBABLE ARGININE/ORNITHINE ANTIPORTER | PSEUDOMONAS AERUGINOSA | 274–301 | 386–420 | | | | | | | |
| PARGA_ECOLI | AMINO-ACID ACETYL-TRANSFERASE | ESCHERICHIA COLI | 82–109 | | | | | | | | |
| PARGT_ECOLI | LYS-ARG-ORN-BINDING PROTEIN (LAO) PRECURSO | ESCHERICHIA COLI | 84–111 | | | | | | | | |
| PAROA_STAAU | PHOSPHOSHIKIMATE 1-CARBOXYVINYLTRANSFER | STAPHYLOCOCCUS AUREUS | 86–120 | | | | | | | | |
| PAROC_ECOLI | CHORISMATE SYNTHASE | ESCHERICHIA COLI | 68–95 | | | | | | | | |
| PAROC_SALTI | CHORISMATE SYNTHASE | SALMONELLA TYPHI | 68–95 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PAROD_BACSU | DEHYDROQUINATE DEHYDRATASE | BACILLUS SUBTILIS | 49–76 | | | | | | | | |
| PAROK_ECOLI | SHIKIMATE KINASE I | ESCHERICHIA COLI | 84–118 | | | | | | | | |
| PARP4_STRPY | IGA RECEPTOR PRECURSOR | STREPTOCOCCUS PYOGENES | 12–46 | 127–157 | 266–324 | | | | | | |
| PARP_ECOLI | ARP PROTEIN | ESCHERICHIA COLI | 255–282 | | | | | | | | |
| PARSA_ECOLI | ARSENICAL PUMP-DRIVING ATPASE | ESCHERICHIA COLI | 201–238 | | | | | | | | |
| PARSB_ECOLI | ARSENICAL PUMP MEMBRANE PROTEIN | ESCHERICHIA COLI | 291–318 | | | | | | | | |
| PARSB_STAAU | ARSENICAL PUMP MEMBRANE PROTEIN | STAPHYLOCOCCUS AUREUS | 27–71 | 295–322 | | | | | | | |
| PARSB_STAXY | ARSENICAL PUMP MEMBRANE PROTEIN | STAPHYLOCOCCUS XYLOSUS | 27–71 | 295–322 | | | | | | | |
| PARSR_STAAU | ARSENICAL RESIST OPERON REPRESSOR PROTEIN | STAPHYLOCOCCUS AUREUS | 56–93 | | | | | | | | |
| PARTA_ECOLI | ARTA PROTEIN | ESCHERICHIA COLI | 3–30 | | | | | | | | |
| PARTI_ECOLI | TRANSPORT SYSTEM PROTEIN ARTI | ESCHERICHIA COLI | 105–132 | 213–240 | | | | | | | |
| PARTP_ECOLI | TRANSPORT SYSTEM PROTEIN ARTP | ESCHERICHIA COLI | 176–206 | | | | | | | | |
| PASA1_ENTFA | AGGREGATION SUBSTANCE PRECURSOR | ENTEROCOCCUS FAECALIS | 195–254 | 478–505 | 799–826 | 859–896 | | | | | |
| PASNA_ECOLI | ASPARTATE-AMMONIA LIGASE | ESCHERICHIA COLI | 127–158 | | | | | | | | |
| PASNB_ECOLI | ASPARAGINE SYNTHETASE B | ESCHERICHIA COLI | 450–477 | | | | | | | | |
| PASNC_ECOLI | REGULATORY PROTEIN ASNC | ESCHERICHIA COLI | 116–143 | | | | | | | | |
| PASPA_BACSU | ASPARTATE AMMONIA-LYASE | BACILLUS SUBTILIS | 7–34 | | | | | | | | |
| PASPA_ECOLI | ASPARTATE AMMONIA-LYASE | ESCHERICHIA COLI | 204–236 | | | | | | | | |
| PASPA_SERMA | ASPARTATE AMMONIA-LYASE | SERRATIA MARCESCENS | 204–231 | | | | | | | | |
| PASPG_BACLI | L-ASPARAGINASE | BACILLUS LICHENIFORMIS | 252–288 | | | | | | | | |
| PASPG_ERWCH | L-ASPARAGINASE PRECURSOR | ERWINIA CHRYSANTHEMI | 188–218 | | | | | | | | |
| PASPQ_ACIGL | GLUTAMINASE-ASPARAGINASE | ACINETOBACTER GLUTAMINASIFICANS | 46–80 | | | | | | | | |
| PASSY_ECOLI | ARGININOSUCCINATE SYNTHASE | ESCHERICHIA COLI | 354–381 | | | | | | | | |
| PASSY_METBA | ARGININOSUCCINATE SYNTHASE | METHANOSARCINA BARKERI | 287–314 | | | | | | | | |
| PATBP_STAAU | POTENTIAL ATP-BINDING PROTEIN | STAPHYLOCOCCUS AUREUS | 41–68 | 201–245 | | | | | | | |
| PATKA_ENTFA | POTASSIUM/COPPER-TRANSPORTING ATPASE A | ENTEROCOCCUS FAECALIS | 41–80 | 347–374 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PATKB_ENTFA | POTASSIUM/COPPER-TRANSPORTING ATAPSE B | ENTEROCOCCUS FAECALIS | 280–310 | 450–477 | | | | | | | |
| PATMBD_SALTY | MG (2+) TRANSPORT ATPASE, P-TYPE | SALMONELLA TYPHIMURIUM | 503–530 | | | | | | | | |
| PATP6_SYNP6 | ATP SYNTHASE A CHAIN | SYNECHOCOCCUS SP | 233–260 | | | | | | | | |
| PATP6_VIBAL | ATP SYNTHASE A CHAIN | VIBRIO ALGINOLYTICUS | 11–38 | | | | | | | | |
| PATPA_ANASP | ATP SYNTHASE ALPHA CHAIN | ANABAENA SP | 9–36 | 96–130 | | | | | | | |
| PATPA_BACME | ATP SYNTHASE ALPHA CHAIN | BACILLUS MEGATERIUM | 4–36 | 453–480 | | | | | | | |
| PATPA_ECOLI | ATP SYNTHASE ALPHA CHAIN | ESCHERICHIA COLI | 486–513 | | | | | | | | |
| PATPA_ENTFA | ATP SYNTHASE ALPHA CHAIN | ENTEROCOCCUS FAECALIS | 4–36 | 484–518 | | | | | | | |
| PATPA_MYCGA | ATP SYNTHASE ALPHA CHAIN | MYCOPLASMA GALLISEPTICUM | 362–409 | | | | | | | | |
| PATPA_PROMO | ATP SYNTHASE ALPHA CHAIN | PROPIONIGENIUM MODESTUM | 6–36 | | | | | | | | |
| PATPA_RHORU | ATP SYNTHASE ALPHA CHAIN | RHODOSPIRILLUM RUBRUM | 165–200 | 459–486 | | | | | | | |
| PATPA_SULAC | ATPASE ALPHA CHAIN | SULFOLOBUS ACIDOCALDARIUS | 318–345 | 562–589 | | | | | | | |
| PATPA_SYNP1 | ATP SYNTHASE ALPHA CHAIN | SYNECHOCOCCUS SP | 7–44 | | | | | | | | |
| PATPA_SYNP6 | ATP SYNTHASE ALPHA CHAIN | SYNECHOCOCCUS SP | 8–45 | 362–389 | | | | | | | |
| PATPA_SYNY3 | ATP SYNTHASE ALPHA CHAIN | SYNECHOCYSTIS SP | 8–37 | 454–500 | | | | | | | |
| PATPA_THEP3 | ATP SYNTHASE ALPHA CHAIN | THERMOPHILIC BACTERIUM PS-3 | 9–36 | | | | | | | | |
| PATPA_VIBAL | ATP SYNTHASE ALPHA CHAIN | VIBRIO ALGINOLYTICUS | 464–513 | | | | | | | | |
| PATPB_ANASP | ATP SYNTHASE BETA CHAIN | ANABAENA SP | 280–307 | 370–397 | | | | | | | |
| PATPB_BACFI | ATP SYNTHASE BETA CHAIN | BACILLUS FIRMUS | 163–190 | 358–385 | | | | | | | |
| PATPB_MYCGA | ATP SYNTHASE BETA CHAIN | MYCOPLASMA GALLISEPTICUM | 375–402 | | | | | | | | |
| PATPB_RHORU | ATP SYNTHASE BETA CHAIN | RHODOSPIRILLUM RUBRUM | 359–386 | | | | | | | | |
| PATPB_SULAC | ATPASE BETA CHAIN | SULFOLOBUS ACIDOCALDARIUS | 164–191 | | | | | | | | |
| PATPB_SYNP1 | ATP SYNTHASE BETA CHAIN | SYNECHOCOCCUS SP | 381–408 | | | | | | | | |
| PATPB_SYNP6 | ATP SYNTHASE BETA CHAIN | SYNECHOCOCCUS SP | 291–318 | 381–408 | | | | | | | |
| PATPB_SYNY3 | ATP SYNTHASE BETA CHAIN | SYNECHOCYSTIS SP | 381–408 | | | | | | | | |
| PATPD_ANASP | ATP SYNTHASE DELTA CHAIN | ANABAENA SP | 109–139 | 143–170 | | | | | | | |
| PATPD_BACFI | ATP SYNTHASE DELTA CHAIN | BACILLUS FIRMUS | 63–90 | 133–160 | | | | | | | |
| PATPD_BACME | ATP SYNTHASE DELTA CHAIN | BACILLUS MEGATERIUM | 132–159 | | | | | | | | |
| PATPD_ENTFA | ATP SYNTHASE DELTA CHAIN | ENTEROCOCCUS FAECALIS | 14–41 | | | | | | | | |
| PATPD_PROMO | ATP SYNTHASE DELTA CHAIN | PROPIONIGENIUM MODESTUM | 79–116 | 118–149 | | | | | | | |
| PATPD_RHOBL | ATP SYNTHASE DELTA CHAIN | RHODOPSEUDOMONAS BLASTICA | 125–152 | | | | | | | | |
| PATPD_RHORU | ATP SYNTHASE DELTA CHAIN | RHODOSPIRILLUM RUBRUM | 119–146 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PATPD_SYNP1 | ATP SYNTHASE DELTA CHAIN | SYNECHOCOCCUS SP | 100–127 | | | | | | | | |
| PATPD_SYNY3 | ATP SYNTHASE DELTA CHAIN | SYNECHOCYSTIS SP | 113–147 | | | | | | | | |
| PATPD_VIBAL | ATP SYNTHASE DELTA CHAIN | VIBRIO ALGINOLYTICUS | 110–137 | | | | | | | | |
| PATPE_BACFI | ATP SYNTHASE EPSILON CHAIN | BACILLUS FIRMUS | 53–80 | | | | | | | | |
| PATPE_MYCGA | ATP SYNTHASE EPSILON CHAIN | MYCOPLASMA GALLISEPTICUM | 99–126 | | | | | | | | |
| PATPE_PROMO | ATP SYNTHASE EPSILON CHAIN | PROPIONIGENIUM MODESTUM | 100–127 | | | | | | | | |
| PATPE_SYNP1 | ATP SYNTHASE EPSILON CHAIN | SYNECHOCOCCUS SP | 72–106 | | | | | | | | |
| PATPF_ANASP | ATP SYNTHASE B CHAIN | ANABAENA SP | 17–44 | 51–78 | 137–164 | | | | | | |
| PATPF_BACFI | ATP SYNTHASE B CHAIN | BACILLUS FIRMUS | 110–151 | | | | | | | | |
| PATPF_BACME | ATP SYNTHASE B CHAIN | BACILLUS MEGATERIUM | 55–85 | 122–170 | | | | | | | |
| PATPF_MYCGA | ATP SYNTHASE B CHAIN | MYCOPLASMA GALLISEPTICUM | 82–135 | 170–197 | | | | | | | |
| PATPF_SYNP1 | ATP SYNTHASE B CHAIN | SYNECHOCOCCUS SP | 15–49 | 111–159 | | | | | | | |
| PATPF_SYNP6 | ATP SYNTHASE B CHAIN | SYNECHOCOCCUS SP | 12–39 | 128–155 | | | | | | | |
| PATPF_THEP3 | ATP SYNTHASE B CHAIN PRECURSOR | THERMOPHILIC BACTERIUM PS-3 | 50–77 | | | | | | | | |
| PATPG_ANASP | ATP SYNTHASE GAMMA CHAIN | ANABAENA SP | 276–310 | | | | | | | | |
| PATPG_ECOLI | ATP SYNTHASE GAMMA CHAIN | ESCHERICHIA COLI | 253–283 | | | | | | | | |
| PATPG_MYCGA | ATP SYNTHASE GAMMA CHAIN | MYCOPLASMA GALLISEPTICUM | 28–62 | 92–140 | | | | | | | |
| PATPG_RHORU | ATP SYNTHASE GAMMA CHAIN | RHODOSPIRILLUM RUBRUM | 270–297 | | | | | | | | |
| PATPG_SYNP1 | ATP SYNTHASE GAMMA CHAIN | SYNECHOCOCCUS SP | 280–307 | | | | | | | | |
| PATPG_SYNY3 | ATP SYNTHASE GAMMA CHAIN | SYNECHOCYSTIS SP | 96–126 | 280–307 | | | | | | | |
| PATP1_MYCGA | ATP SYNTHASE PROTEIN I | MYCOPLASMA GALLISEPTICUM | 133–167 | | | | | | | | |
| PATPX_ANASP | ATP SYNTHASE B' CHAIN | ANABAENA SP | 129–156 | | | | | | | | |
| PATPX_BACFI | ATP SYNTHASE B' CHAIN | BACILLUS FIRMUS | 162–189 | 356–383 | | | | | | | |
| PATPX_RHORU | ATP SYNTHASE BETA CHAIN | RHODOSPIRILLUM RUBRUM | 40–74 | | | | | | | | |
| PATPX_SYNP1 | ATP SYNTHASE B' CHAIN | SYNECHOCOCCUS SP | 57–110 | 128–155 | | | | | | | |
| PATPX_SYNP6 | ATP SYNTHASE B' CHAIN | SYNECHOCOCCUS SP | 70–100 | | | | | | | | |
| PATPX_SYNY3 | ATP SYNTHASE B' CHAIN | SYNECHOCYSTIS SP | 108–135 | | | | | | | | |
| PATPZ_BACME | ATP SYNTHASE PROTEIN I | BACILLUS MEGATERIUM | 14–62 | | | | | | | | |
| PATPZ_SYNP1 | ATP SYNTHASE PROTEIN I | SYNECHOCOCCUS SP | 90–131 | | | | | | | | |
| PAVRB_PSESG | AVIRULENCE B PROTEIN | PSEUDOMONAS SYRINGAE | 184–211 | 233–260 | | | | | | | |
| PBA71_EUBSP | 7-ALPHA-HYDROXYSTEROID DEHYDROGENASE | EUBACTERIUM SP | 26–53 | | | | | | | | |
| PBA72_EUBSP | 7-ALPHA-HYDROXYSTEROID DEHYDROGENASE | EUBACTERIUM SP | 26–53 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PBACH_HALHM | HALORHODOPSIN | HALOBACTERIUM HALOBIUM | 145–179 | | | | | | | | |
| PBACH_HALSG | HALORHODOPSIN PRECURSOR | HALOBACTERIUM SP | 180–214 | | | | | | | | |
| PBAES_ECOLI | SENSOR PROTEIN BAES | ESCHERICHIA COLI | 152–186 | | | | | | | | |
| PBAG_STRAG | IGA FC RECEPTOR PRECURSOR | STREPTOCOCCUS AGALACTIAE | 92–119 | 138–204 | 267–204 | 267–306 | 343–385 | 487–524 | 562–589 | 1014–1041 | |
| PBAHG_VITSP | BACTERIAL HEMOGLOBIN | VITREOSCILLA SP | 119–146 | | | | | | | | |
| PBAIC_EUBSP | BILE ACID-INDUCIBLE OPERON PROTEIN C | EUBACTERIUM SP | 423–450 | | | | | | | | |
| PBARA_ECOLI | SENSOR PROTEIN BARA | ESCHERICHIA COLI | 334–361 | 425–455 | | | | | | | |
| PBASS_ECOLI | SENSOR PROTEIN BASS | ESCHERICHIA COLI | 122–156 | | | | | | | | |
| PBAT_HALHA | PUTATIVE BACTERIO-OPSIN ACTIVATOR | HALOBACTERIUM HALOBIUM | 408–442 | | | | | | | | |
| PBAX_ECOLI | BAX PROTEIN | ESCHERICHIA COLI | 21–64 | | | | | | | | |
| PBCP_ECOLI | BIOTIN CARBOXYL CARRIER PROTEIN | ESCHERICHIA COLI | 6–35 | | | | | | | | |
| PBCHH_RHOCA | METHYLTRANSFERASE | RHODOBACTER CAPSULATUS | 1000–1032 | | | | | | | | |
| PBCHN_RHOCA | PROTOCHLOROPHYLLIDE REDUCTASE 46 KD CHAIN | RHODOBACTER CAPSULATUS | 249–276 | | | | | | | | |
| PBCN5_CLOPE | BACTERIOCIN BCN5 | CLOSTRIDIUM PERFRINGENS | 72–99 | 585–646 | | | | | | | |
| PBCPA_PROAE | BACTERIOCHLOROPHYLL A PROTEIN | PROSTHECOCHLORIS AESTUARII | 63–93 | | | | | | | | |
| PBCSC_ACEXY | CELLULOSE SYNTHASE OPERON C PROTEIN | ACETOBACTER XYLINUM | 131–158 | 1055–1082 | | | | | | | |
| PBCSD_ACEXY | CELLULOSE SYNTHASE OPERON D PROTEIN | ACETOBACTER XYLINUM | 10–37 | | | | | | | | |
| PBENA_ACICA | BENZOATE 1,2-DIOXYGENASE ALPHA SUBUNIT | ACINETOBACTER CALCOACETICUS | 190–217 | | | | | | | | |
| PBETT_ECOLI | HIGH AFFINITY CHOLINE TRANSPORT PROTEIN | ESCHERICHIA COLI | 243–270 | | | | | | | | |
| PBEXA_HAEIN | BEXA PROTEIN | HAEMOPHILUS INFLUENZAE | 23–50 | | | | | | | | |
| PBEXC_HAEIN | BEXC PROTEIN | HAEMOPHILUS INFLUENZAE | 157–184 | | | | | | | | |
| PBEXD_HAEIN | BEXD PROTEIN | HAEMOPHILUS INFLUENZAE | 205–239 | 226–253 | | | | | | | |
| PBFR_NITWI | BACTERIOFERRITIN | NITROBACTER WINOGRADSKYI | 8–35 | | | | | | | | |
| PBGA2_ECOLI | EVOLVED BETA-GALACTO-SIDASE ALPHA-SUBUNIT | ESCHERICHIA COLI | 955–985 | | | | | | | | |
| PBGAL_BACST | BETA-GALACTOSIDASE | BACILLUS STEAROTHERMOPHILUS | 599–633 | | | | | | | | |
| PBGAL_CLOAB | BETA-GALACTOSIDASE | CLOSTRIDIUM ACETOBUTYLICUM | 824–851 | | | | | | | | |
| PBGAL_CLOTU | BETA-GALACTOSIDASE | CLOSTRIDIUM THERMO-SULFUROGENES | 161–191 | | | | | | | | |
| PBGAL_KLEPN | BETA-GALACTOSIDASE | KLEBSIELLA PNEUMONIAE | 245–272 | | | | | | | | |
| PBGAL_LACDE | BETA-GALACTOSIDASE | LACTOBACILLUS DELBRUECKII | 305–332 | | | | | | | | |
| PBGAL_STRTR | BETA-GALACTOSIDASE | STREPTOCOCCUS THERMOPHILUS | 188–215 | | | | | | | | |
| PBGAL_SULSO | BETA-GALACTOSIDASE | SULFOLOBUS SOLFATARICUS | 59–86 | 179–206 | | | | | | | |
| PBGAM_LEULA | BETA-GALACTOSIDASE SMALL SUBUNIT | LEUCONOSTOC LACTIS | 129–156 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PBGAM_SULSO | BETA-GALACTOSIDASE | SULFOLOBUS SOLFATARICUS | 106–140 | | | | | | | | |
| PBGLA_CLOTM | BETA-GLUCOSIDASE A | CLOSTRIDIUM THERMOCELLUM | 353–380 | 418–445 | | | | | | | |
| PBGLB_CLOTM | THERMOSTABLE BETA-GLUCOSIDASE B | CLOSTRIDIUM THERMOCELLUM | 259–286 | 375–409 | 554–581 | 631–665 | | | | | |
| PBG1R_ECOLI | BETA-GLUCURONIDASE | ESCHERICHIA COLI | 464–494 | 536–563 | | | | | | | |
| PBGLS_AGRSP | BETA-GLUCOSIDASE | AGROBACTERIUM SP | 421–448 | | | | | | | | |
| PBGLS_BUTFI | BETA-GLUCOSIDASE A | BUTYRIVIBRIO FIBRISOLVENS | 85–112 | 435–462 | 692–719 | 738–765 | | | | | |
| PBIN3_STAAU | POTENTIAL DNA-INVERTASE BIN3 | STAPHYLOCOCCUS AUREUS | 60–87 | | | | | | | | |
| PBINL_STAAU | TRANSPOSON TN552 RESOLVASE | STAPHYLOCOCCUS AUREUS | 163–197 | | | | | | | | |
| PBINR_STAAU | DNA-INVERTASE BINR | STAPHYLOCOCCUS AUREUS | 163–190 | | | | | | | | |
| PGIOA_BACSH | AMINOTRANSFERASE | BACILLUS SPHAERICUS | 33–60 | | | | | | | | |
| PBIOB_BACSH | BIOTIN SYNTHETASE | BACILLUS SPHAERICUS | 145–172 | | | | | | | | |
| PBIOB_ECOLI | BIOTIN SYNTHETASE | ESCHERICHIA COLI | 130–157 | | | | | | | | |
| PBIOD_BACSH | DETHIOBIOTIN SYNTHASE | BACILLUS SPHAERICUS | 144–171 | | | | | | | | |
| PBLA1_BACCE | BETA-LACTAMASE PRECURSOR, TYPE I | BACILLUS CEREUS | 91–118 | 275–305 | | | | | | | |
| PBLA1_HAEIN | BETA-LACTAMASE ROB-1 PRECURSOR | HAEMOPHILUS INFLUENZAE | 152–179 | 204–231 | | | | | | | |
| PBLA2_BACCE | BETA-LACTAMASE PRECURSOR, TYPE II | BACILLUS CEREUS | 18–67 | 201–228 | | | | | | | |
| PBLA2_BACSP | BETA-LACTAMASE PRECURSOR, TYPE II | BACILLUS SP | 18–67 | | | | | | | | |
| PBLA3_BACCE | BETA-LACTAMASE PRECURSOR, TYPE II | BACILLUS CEREUS | 35–83 | 95–129 | | | | | | | |
| PBLA4_PSEAE | BETA-LACTAMASE PSE-4 PRECURSOR | PSEUDOMONAS AERUGINOSA | 19–50 | | | | | | | | |
| PBLAB_BACCE | BETA-LACTAMASE PRECURSOR, TYPE II | BACILLUS CEREUS | 20–66 | 200–227 | | | | | | | |
| PBLAB_BACFR | BETA-LACTAMASE PRECURSOR | BACTEROIDES FRAGILIS | 22–49 | | | | | | | | |
| PBLAC_BACCE | BETA-LACTAMASE PRECURSOR, TYPE II | BACILLUS CEREUS | 93–120 | 276–303 | | | | | | | |
| PBLAC_BACLI | BETA-LACTAMASE PRECURSOR, TYPE I | BACILLUS LICHENIFORMIS | 47–74 | 86–115 | | | | | | | |
| PBLAC_PROMI | BETA-LACTAMASE PRECURSOR | PROTEUS MIRABILIS | 191–221 | | | | | | | | |
| PBLAC_PROVU | BETA-LACTAMASE PRECURSOR | PROTEUS VULGARIS | 4–38 | 240–267 | | | | | | | |
| PBLAC_STRAL | BETA-LACTAMASE PRECURSOR | STREPTOMYCES ALBUS G | 43–70 | | | | | | | | |
| PBLAD_KLEPN | BETA-LACTAMASE PRECURSOR | KLEBSIELLA PNEUMONIAE | 121–148 | | | | | | | | |
| PBLAI_STAAU | PENICILLINASE REPRESSOR | STAPHYLOCOCCUS AUREUS | 19–74 | 99–126 | | | | | | | |
| PBLAO_ECOLI | BETA-LACTAMASE PRECURSOR | ESCHERICHIA COLI | 118–166 | 235–262 | | | | | | | |

TABLE VIII-continued

| PCGENE FILE NAME | 107 × 178 × 4 PROTEIN | Prokaryotic Sequences ORGANISM | 107 × 178 × 4 SEARCH MOTIF RESULTS SUMMARY FOR ALL PROCARYOTIC PROTEINS AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PBLAP_ECOLI | BETA-LACTAMASE PSE-2 PRECURSOR | *ESCHERICHIA COLI* | 155–196 | | | | | | | | |
| PBLAR_BACLI | REGULATORY PROTEIN BLAR1 | *BACILLUS LICHENIFORMIS* | 129–156 | 515–552 | | | | | | | |
| PBLAR_STAAU | REGULATORY PROTEIN BLAR1 | *STAPHYLOCOCCUS AUREUS* | 87–114 | 122–161 | 234–261 | 281–312 | 503–539 | | | | |
| PBMP_TREPA | BASIC MEMBRANE PROTEIN PRECURSOR | *TREPONEMA PALLIDUM* | 312–346 | | | | | | | | |
| PBMR_BACSU | MULTIDRUG RESISTANCE PROTEIN | *BACILLUS SUBTILIS* | 277–304 | | | | | | | | |
| PBNZA_PSEPU | BENZENE 1,2-DIOXYGENASE ALPHA SUBUNIT | *PSEUDOMONAS PUTIDA* | 36–63 | | | | | | | | |
| PBNZB_PSEPU | BENZENE 1,2-DIOXYGENASE BETA SUBUNIT | *PSEUDOMONAS PUTIDA* | 119–153 | | | | | | | | |
| PBNZD_PSEPU | P4 SUBUNIT | *PSEUDOMONAS PUTIDA* | 179–213 | | | | | | | | |
| PBPS2_DESAM | BPS2 PROTEIN | *DESULFUROLOBUS AMBIVALENS* | 157–237 | 242–290 | 311–355 | 391–425 | 543–573 | | | | |
| PBRAB_PSEAE | CARRIER PROTEIN | *PSEUDOMONAS AERUGINOSA* | 260–287 | 313–340 | | | | | | | |
| PBRAE_PSEAE | TRANSPORT PROTEIN BRAE | *PSEUDOMONAS AERUGINOSA* | 254–281 | | | | | | | | |
| PBRAG_PSEAE | BRAG PROTEIN | *PSEUDOMONAS AERUGINOSA* | 7–34 | | | | | | | | |
| PBTUB_ECOLI | VITAMIN B12 RECEPTOR PRECURSOR | *ESCHERICHIA COLI* | 439–466 | | | | | | | | |
| PBTUE_ECOLI | VITAMIN B12 TRANSPORT PERIPLASMIC PROTEIN | *ESCHERICHIA COLI* | 6–33 | | | | | | | | |
| PBVGA_BORPE | TRANSCRIPTION REGULATOR BVGA | *BORDETELLA PERTUSSIS* *BORDETELLA BRONCHISEPTICA* | 174–205 | | | | | | | | |
| PBVGB_BORPE | PERIPLASMIC PROTEIN BVGB PRECURSOR | *BORDETELLA PERTUSSIS* | 116–143 | | | | | | | | |
| PBVGC_BORPE | SENSOR PROTEIN BVGC | *BORDETELLA PERTUSSIS* | 39–66 | 202–229 | | | | | | | |
| PBVGS_BORBR | VIRULENCE BVGS PROTEIN PRECURSOR | *BORDETELLA BRONCHISEPTICA* | 113–143 | 341–368 | 501–531 | | | | | | |
| PBXA_CLOBO | BOTULINUM NEUROTOXIN TYPE A PRECURSOR | *CLOSTRIDIUM BOTULINUM* | 313–340 | 686–729 | 733–762 | 815–842 | 851–893 | 968–995 | 1159–1207 | | |
| PBXB_CLOBO | BOTULINUM NEUROTOXIN TYPE B PRECURSOR | *CLOSTRIDIUM BOTULINUM* | 666–693 | 720–762 | 802–832 | 853–890 | 1004–1031 | 1058–1089 | | | |
| PBXC1_CLOBO | BOTULINUM NEUROTOXIN TYPE C1 PRECURSOR | *CLOSTRIDIUM BOTULINUM* | 86–113 | 314–341 | 730–773 | 798–825 | 850–892 | | | | |
| PBXD_CLOBO | BOTULINUM NEUROTOXIN TYPE D PRECURSOR | *CLOSTRIDIUM BOTULINUM* | 473–500 | 526–576 | 727–770 | 804–831 | 847–892 | 906–963 | 1060–1087 | | |
| PBXE_CLOBO | BOTULINUM NEUROTOXIN TYPE E PRECURSOR | *CLOSTRIDIUM BOTULINUM* | 254–291 | 350–381 | 704–753 | 773–811 | 890–917 | 992–1019 | 1115–1149 | | |
| PBXE_CLOBU | BOTULINUM NEUROTOXIN TYPE E PRECURSOR | *CLOSTRIDIUM BOTULINUM* | 254–291 | 350–381 | 704–753 | 774–808 | 890–917 | 992–1019 | 1115–1149 | | |
| PBXF_CLOBO | BOTULINUM NEUROTOXIN TYPE F PRECURSOR | *CLOSTRIDIUM BOTULINUM* | 669–710 | 735–772 | 892–919 | 1013–1040 | 1095–1122 | 1183–1210 | | | |
| PC550_MICAE | CYTOCHROME C550 | *MICROCYSTIS AERUGINOSA* | 3–30 | | | | | | | | |

TABLE VIII-continued

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| | | 107 × 178 × 4 SEARCH MOTIF RESULTS SUMMARY FOR ALL PROCARYOTIC PROTEINS | | | | | | | | | |
| PCADA_BACFI | PROBABLE CADMIUM-TRANSPORTING ATPASE | *BACILLUS FIRMUS* | 30–57 | 100–131 | 165–192 | 276–306 | 533–567 | | | | |
| PCADA_STAAU | PROBABLE CADMIUM-TRANSPORTING ATPASE | *STAPHYLOCOCCUS AUREUS* | 282–309 | 536–570 | | | | | | | |
| PCADC_ECOLI | TRANSCRIPTIONAL ACTIVATOR CADC | *ESCHERICHIA COLI* | 54–85 | 412–443 | | | | | | | |
| PCAFA_YERPE | F1 CAPSULE ANCHORING PROTEIN PRECURSOR | *YERSINIA PESTIS* | 203–240 | 416–457 | 530–557 | 619–646 | | | | | |
| PCAPA_BACAN | CAPA PROTEIN | *BACILLUS ANTHRACIS* | 108–138 | | | | | | | | |
| PCAPB_BACAN | CAPB PROTEIN | *BACILLUS ANTHRACIS* | 36–70 | | | | | | | | |
| PCAPP_ANANI | PHOSPHOENOLPYRUVATE CARBOXYLASE | *ANACYSTIS NIDULANS* | 248–293 | | | | | | | | |
| PCAPP_ANASP | PHOSPHOENOLPYRUVATE CARBOXYLASE | ANABAENA SP | 98–125 | 157–184 | 687–728 | | | | | | |
| PCAPP_CORGL | PHOSPHOENOLPYRUVATE CARBOXYLASE | *CORYNEBACTERIUM GLUTMICUM* | 15–42 | | | | | | | | |
| PCAPP_ECOLI | PHOSPHOENOLPYRUVATE CARBOXYLASE | *ESCHERICHIA COLI* | 35–62 | | | | | | | | |
| PCARA_BACSU | CARBAMOYL-PHOSPHATE SYNTHASE | *BACILLUS SUBTILIS* | 274–319 | | | | | | | | |
| PCARB_BACSU | CARBAMOYL-PHOSPHATE SYNTHASE | *BACILLUS SUBTILIS* | 790–831 | | | | | | | | |
| PCARB_ECOLI | CARBAMOYL-PHOSPHATE SYNTHASE LARGE CHAI | *ESCHERICHIA COLI* | 454–481 | | | | | | | | |
| PCAT2_STAAU | CHLORAMPHENICOL ACETYLTRANSFERASE | *STAPHYLOCOCCUS AUREUS* | 7–34 | 87–114 | | | | | | | |
| PCAT3_STAAU | CHLORAMPHENICOL ACETYLTRANSFERASE | *STAPHYLOCOCCUS AUREUS* | 7–34 | 87–114 | | | | | | | |
| PCATA_ACICA | CATECHOL 1,2-DIOXYGENASE | *ACINETOBACTER CALCOACETICUS* | 31–65 | | | | | | | | |
| PCATA_BACST | PEROXIDASE/CATALASE | *BACILLUS STEAROTHERMOPHILUS* | 440–470 | | | | | | | | |
| PCATA_ECOLI | CATALASE HPI | *ESCHERICHIA COLI* | 579–606 | | | | | | | | |
| PCATA_MICLU | CATALASE | *MICROCOCCUS LUTEUS* | 453–480 | | | | | | | | |
| PCATA_SALTY | CATALASE HPI | *SALMONELLA TYPHIMURIUM* | 515–542 | 580–607 | | | | | | | |
| PCATE_ECOLI | CATALASE HPII | *ESCHERICHIA COLI* | 175–202 | | | | | | | | |
| PCAT_CAMCO | CHLORAMPHENICOL ACETYLTRANSFERASE | *CAMPYLOBACTER COLI* | 84–111 | | | | | | | | |
| PCAT_CLOBU | CHLORAMPHENICOL ACETYLTRANSFERASE | *CLOSTRIDIUM BUTYRICUM* | 88–115 | | | | | | | | |
| PCAT_ECOLI | CHLORAMPHENICOL ACETYLTRANSFERASE | *ESCHERICHIA COLI* | 92–119 | | | | | | | | |
| PCAT_PROMI | CHLORAMPHENICOL ACETYLTRANSFERASE | *PROTEUS MIRABILIS* | 92–119 | | | | | | | | |
| PCAT_STAIN | CHLORAMPHENICOL ACETYLTRANSFERASE | *STAPHYLOCOCCUS INTERMEDIUS* | 7–34 | 87–114 | | | | | | | |
| PCAT_STRAG | CHLORAMPHENICOL ACETYLTRANSFERASE | *STREPTOCOCCUS AGALACTIAE* | 7–34 | 87–114 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PCBHE_COXBU | CBHE PROTEIN | COXIELLA BURNETII | 209–236 | | | | | | | | |
| PCBPT_THEVU | CARBOXYPEPTIDASE T PRECURSOR | THERMOACTINOMYCES VULGARIS | 48–75 | | | | | | | | |
| PCCA_ECOLI | TRNA NUCLEOTIDYL-TRANSFERASE | ESCHERICHIA COLI | 376–403 | | | | | | | | |
| PCCMK_SYNP7 | CO2 CONC MECH PROTEIN CCMK | SYNECHOCOCCUS SP | 29–56 | | | | | | | | |
| PCCMM_SYNP7 | CO2 CONC MECH PROTEIN CCMM | SYNECHOCOCCUS SP | 212–256 | 331–372 | 445–486 | | | | | | |
| PCDAS_THEET | CYCLOMALTODEXTRINASE | THERMOANAEROBACTER ETHANOLICUS | 305–332 | | | | | | | | |
| PCDG1_BACMA | CYCLOMALTODEXT GLUCANOTRANS PRECURSOR | BACILLUS MACERANS | 439–466 | 616–643 | | | | | | | |
| PCDG2_BACMA | CYCLOMALTODEXT GLUCANOTRANS PRECURSOR | BACILLUS MACERANS | 210–251 | 436–466 | 615–642 | | | | | | |
| PCDGT_BACCI | CYCLOMALTODEXT GLUCANOTRANS PRECURSOR | BACILLUS CIRCULANS | 217–244 | 442–472 | 594–651 | | | | | | |
| PCDGT_BACLI | CYCLOMALTODEXT GLUCANOTRANS PRECURSOR | BACILLUS LICHENIFORMIS | 217–244 | 442–472 | 594–647 | | | | | | |
| PCDGT_BACOH | CYCLOMALTODEXT GLUCANOTRANS PRECURSOR | BACILLUS OHBENSIS | 430–471 | | | | | | | | |
| PCDGT_BACS0 | CYCLOMALTODEXT GLUCANOTRANS PRECURSOR | BACILLUS SP | 210–237 | 435–462 | 615–642 | | | | | | |
| PCDGT_BACS2 | CYCLOMALTODEXT GLUCANOTRANS PRECURSOR | BACILLUS SP | 409–471 | | | | | | | | |
| PCDGT_BACS3 | CYCLOMALTODEXT GLUCANOTRANS PRECURSOR | BACILLUS SP | 210–237 | 435–462 | 614–641 | | | | | | |
| PCDGT_BACSP | CYCLOMALTODEXT GLUCANOTRANS PRECURSOR | BACILLUS SP | 210–237 | 435–465 | 615–642 | | | | | | |
| PCDGT_BACSS | CYCLOMALTODEXT GLUCANOTRANS PRECURSOR | BACILLUS SP | 217–244 | 442–472 | 594–651 | | | | | | |
| PCDGT_BACST | CYCLOMALTODEXT GLUCANOTRANS PRECURSOR | BACILLUS STEAROTHERMOPHILUS | 586–646 | | | | | | | | |
| PCDGT_KLEPN | CYCLOMALTODEXT GLUCANOTRANS PRECURSOR | KLEBSIELLA PNEUMONIAE | 212–239 | | | | | | | | |
| PCEA1_ECOLI | COLICIN E1 PROTEIN | ESCHERICHIA COLI | 44–71 | 285–326 | | | | | | | |
| PCEA1_SHISO | COLICIN E1* PROTEIN | SHIGELLA SONNEI | 44–71 | 284–325 | | | | | | | |
| PCEA2_ECOLI | COLICIN E2 | ESCHERICHIA COLI | 334–368 | | | | | | | | |
| PCEA3_ECOLI | COLICIN E3 | ESCHERICHIA COLI | 334–368 | | | | | | | | |
| PCEA6_ECOLI | COLICIN E6 | ESCHERICHIA COLI | 334–368 | | | | | | | | |
| PCEAB_ECOLI | COLICIN B | ESCHERICHIA COLI | 283–341 | | | | | | | | |
| PCEAD_ECOLI | COLICIN D | ESCHERICHIA COLI | 284–311 | | | | | | | | |
| PCEAM_ECOLI | COLICIN M | ESCHERICHIA COLI | 178–227 | | | | | | | | |
| PCEAN_ECOLI | COLICIN N | ESCHERICHIA COLI | 119–146 | 173–200 | | | | | | | |
| PCEA_CITFR | COLICIN A | CITROBACTER FREUNDII | 228–258 | | | | | | | | |
| PCEFD_STRCL | ISOPENICILLIN N EPIMERASE | STREPTOMYCES CLAVULIGERUS | 370–397 | | 413–440 | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PCEIA_ECOLI | COLICIN IA PROTEIN | ESCHERICHIA COLI | 68–95 | 255–282 | 378–412 | 415–452 | | | | | |
| PCEIB_ECOLI | COLICIN IB PROTEIN | ESCHERICHIA COLI | 68–95 | 255–282 | 378–412 | 415–452 | | | | | |
| PCELA_ACEXY | UTP URIDYLYLTRANSFERASE | ACETOBACTER XYLINUM | 59–89 | | | | | | | | |
| PCELA_ECOLI | PROTEIN CELA | ESCHERICHIA COLI | 76–103 | | | | | | | | |
| PCFAA_ECOLI | CFA/1 FIMBRIAL SUBUNIT A PRECURSOR | ESCHERICHIA COLI | 27–58 | | | | | | | | |
| PCFAC_ECOLI | CFA/1 FIMBRIAL SUBUNIT C PRECURSOR | ESCHERICHIA COLI | 138–187 | 388–456 | 561–595 | | | | | | |
| PCFAD_ECOLI | CFA/1 FIMBRIAL SUBUNIT D | ESCHERICHIA COLI | 133–160 | | | | | | | | |
| PCFAE_ECOLI | CFA/1 FIMBRIAL SUBUNIT E | ESCHERICHIA COLI | 180–207 | 244–271 | | | | | | | |
| PCH10_ACYPS | 10 KD CHAPERONIN | ACYRTHOSIPHON PISUM SYMBIOTIC BACTERIU | 57–95 | | | | | | | | |
| PCH10_BACSU | 10 KD CHAPERONIN | BACILLUS SUBTILIS | 66–93 | | | | | | | | |
| PCH10_CHLTR | 10 KD CHAPERONIN | CHLAMYDIA TRACHOMATIS | 64–91 | | | | | | | | |
| PCH10_ECOLI | 10 KD CHAPERONIN | ESCHERICHIA COLI | 57–84 | | | | | | | | |
| PCH10_HAEDU | 10 KD CHAPERONIN | HAEMOPHILUS DUCREYI | 68–95 | | | | | | | | |
| PCH10_LEGMI | 10 KD CHAPERONIN | LEGIONELLA MICDADEI | 57–84 | | | | | | | | |
| PCH10_RICTS | 10 KD CHAPERONIN | RICKETTSIA TSUTSUGAMUSHI | 65–92 | | | | | | | | |
| PCH10_THEP3 | 10 KD CHAPERONIN | THERMOPHILIC BACTERIUM PS-3 | 66–93 | | | | | | | | |
| PCH60_ACYPS | 60 KD CHAPERONIN | ACYRTHOSIPHON PISUM SYMBIOTIC BACTERIU | 341–382 | | | | | | | | |
| PCH60_AGRTU | 60 KD CHAPERONIN | AGROBACTERIUM TUMEFACIENS | 117–163 | 339–370 | 425–466 | | | | | | |
| PCH60_AMOPS | 60 KD CHAPERONIN | AMOEBA PROTEUS SYMBIOTIC BACTERIUM | 299–333 | | | | | | | | |
| PCH60_BACSU | 60 KD CHAPERONIN | BACILLUS SUBTILIS | 298–332 | 337–364 | | | | | | | |
| PCH60_BORBU | 60 KD CHAPERONIN | BORRELIA BURGDORFERI | 125–163 | 299–368 | | | | | | | |
| PCH60_BRUAB | 60 KD CHAPERONIN | BRUCELLA ABORTUS | 117–144 | 339–366 | | | | | | | |
| PCH60_CHLPN | 60 KD CHAPERONIN | CHLAMYDIA PNEUMONIAE | 4–31 | | | | | | | | |
| PCH60_CHLTR | 60 KD CHAPERONIN | CHLAMYDIA TRACHOMATIS | 4–31 | | | | | | | | |
| PCH60_CHRVI | 60 KD CHAPERONIN | CHROMATIUM VINOSUM | 300–327 | | | | | | | | |
| PCH60_CLOAB | 60 KD CHAPERONIN | CLOSTRIDIUM ACETOBUTYLICUM | 238–332 | 337–364 | 455–482 | | | | | | |
| PCH60_CLOPE | 60 KD CHAPERONIN | CLOSTRIDIUM PERFRINGENS | 337–368 | 417–444 | | | | | | | |
| PCH60_COXBU | 60 KD CHAPERONIN | COXIELLA BURNETII | 300–327 | 348–382 | | | | | | | |
| PCH60_HAEDU | 60 KD CHAPERONIN | HAEMOPHILUS DUCREYI | 339–366 | 417–444 | | | | | | | |
| PCH60_LEGMI | 60 KD CHAPERONIN | LEGIONELLA MICDADEI | 299–333 | | | | | | | | |
| PCH60_LEGPN | 60 KD CHAPERONIN | LEGIONELLA PNEUMOPHILA | 298–332 | 452–479 | | | | | | | |
| PCH60_MYCLE | 60 KD CHAPERONIN | MYCOBACTERIUM LEPRAE | 125–152 | 236–263 | 337–364 | | | | | | |
| PCH60_MYCTU | 60 KD CHAPERONIN | MYCOBACTERIUM TUBERCULOSIS & BOVIS | 125–152 | 337–364 | | | | | | | |
| PCH60_PSEAE | 60 KD CHAPERONIN | PSEUDOMONAS AERUGINOSA | 339–366 | | | | | | | | |
| PCH60_RHILV | 60 KD CHAPERONIN | RHIZOBIUM LEGUMINOSARUM | 117–163 | 322–370 | 425–466 | | | | | | |
| PCH60_RICTS | 60 KD CHAPERONIN | RICKETTSIA TSUTSUGAMUSHI | 103–130 | 293–336 | 360–394 | | | | | | |
| PCH60_SYNP7 | 60 KD CHAPERONIN | SYNECHOCOCCUS SP | 308–335 | 337–380 | | | | | | | |
| PCH60_SYNY3 | 60 KD CHAPERONIN | SYNECHOCYSTIS SP | 338–365 | 455–489 | | | | | | | |
| PCH60_THEP3 | 60 KD CHAPERONIN | THERMOPHILIC BACTERIUM PS-3 | 337–364 | 337–364 | | | | | | | |
| PCH62_STRAL | 60 KD CHAPERONIN 2 | STREPTOMYCES ALBUS G | 116–148 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PCHB_VIBHA | N,N-DIACETYLCHITOBIASE PRECURSOR | VIBRIO HARVEYI | 21–48 | 772–799 | | | | | | | |
| PCHEA_BACSU | CHEMOTAXIS PROTEIN CHEA | BACILLUS SUBTILIS | 373–400 | | | | | | | | |
| PCHEA_ECOLI | CHEMOTAXIS PROTEIN CHEA | ESCHERICHIA COLI | 256–286 | 590–617 | | | | | | | |
| PCHEA_SALTY | CHEMOTAXIS PROTEIN CHEA | SALMONELLA TYPHIMURIUM | 162–197 | | | | | | | | |
| PCHER_BACSU | CHEMOTAXIS PROTEIN METHYLTRANSFERASE | BACILLUS SUBTILIS | 124–151 | | | | | | | | |
| PCHEW_ECOLI | PURINE-BINDING CHEMO-TAXIS PROTEIN | ESCHERICHIA COLI | 68–115 | | | | | | | | |
| PCHEW_SALTY | PURINE-BINDING CHEMO-TAXIS PROTEIN | SALMONELLA TYPHIMURIUM | 88–115 | | | | | | | | |
| PCHEY_ECOLI | CHEMOTAXIS PROTEIN CHEY | ESCHERICHIA COLI | 22–49 | | | | | | | | |
| PCHEY_SALTY | CHEMOTAXIS PROTEIN CHEY | SALMONELLA TYPHIMURIUM | 22–49 | | | | | | | | |
| PCHI1_BACCI | CHITINASE A1 PRECURSOR | BACILLUS CIRCULANS | 491–518 | 566–593 | | | | | | | |
| PCHIA_ALTSO | CHITINASE A PRECURSOR | ALTEROMONAS SP | 345–372 | | | | | | | | |
| PCHIA_SERMA | CHITINASE A PRECURSOR | SERRATIA MARCESCENS | 346–373 | | | | | | | | |
| PCHID_BACCI | CHITINASE D PRECURSOR | BACILLUS CIRCULANS | 102–161 | 189–216 | | | | | | | |
| PCHIT_SACER | CHITINASE | SACCHAROPOLYSPORA ERYTHRAEA | 92–119 | | | | | | | | |
| PCHIT_STRPL | CHITINASE 63 PRECURSOR | STREPTOMYCES PLICATUS | 250–284 | | | | | | | | |
| PCHMU_BACSU | CHORISMATE MUTASE | BACILLUS SUBTILIS | 3–37 | | | | | | | | |
| PCHOD_BREST | CHOLESTEROL OXIDASE PRECURSOR | BREVIBACTERIUM STEROLICUM | 263–290 | | | | | | | | |
| PCHTA_VIBCH | CHOLERA ENTEROTOXIN, A CHAIN PRECURSOR | VIBRIO CHOLERAE | 79–106 | | | | | | | | |
| PCHVA_AGRTU | BETA-(1->2)GLUCAN EXPORT PROTEIN | AGROBACTERIUM TUMEFACIENS | 4–31 | 181–208 | | | | | | | |
| PCHVE_AGRTU | RECEPTOR PROTEIN CHVE PRECURSOR | AGROBACTERIUM TUMEFACIENS | 100–127 | | | | | | | | |
| PCIRL_CITFR | CITROLYSIN PROTEIN I | CITROBACTER FREUNDII | 435–462 | | | | | | | | |
| PCIRA_ECOLI | COLICIN I RECEPTOR PRECURSOR | ESCHERICHIA COLI | 146–173 | | | | | | | | |
| PCISA_BACSU | PUTATIVE DNA RECOMBINASE | BACILLUS SUBTILIS | 378–405 | | | | | | | | |
| PCISY_ACIAN | CITRATE SYNTHASE | ACINETOBACTER ANITRATUM | 143–170 | | | | | | | | |
| PCISY_BACCO | CITRATE SYNTHASE | BACILLUS COAGULANS | 24–51 | | | | | | | | |
| PCITA_SALTY | CITRATE-PROTON SYMPORT | SALMONELLA TYPHIMURIUM | 154–181 | | | | | | | | |
| PCITN_KLEPN | CITRATE-SODIUM SYMPORT | KLEBSIELLA PNEUMONIAE | 194–221 | | | | | | | | |
| PCITN_SALDU | CITRATE-SODIUM SYMPORT | SALMONELLA DUBLIN | 194–221 | | | | | | | | |
| PCITN_SALPU | CITRATE-SODIUM SYMPORT | SALMONELLA PULLORUM | 194–221 | | | | | | | | |
| PCLCA_PSEPU | CHLOROCATECHOL 1,2-DIOXYGENASE | PSEUDOMONAS PUTIDA | 13–36 | | | | | | | | |
| PCLD1_ECOLI | CHAIN LENGTH DETER-MINANT PROTEIN | ESCHERICHIA COLI | 133–167 | | | | | | | | |
| PCLD2_ECOLI | CHAIN LENGTH DETER-MINANT PROTEIN | ESCHERICHIA COLI | 178–212 | 250–277 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PCLD_SALTY | CHAIN LENGTH DETERMINANT PROTEIN | SALMONELLA TYPHIMURIUM | 96–127 | 151–212 | | | | | | | |
| PCLOS_CLOHI | ALPHA-CLOSTRIPAIN PRECURSOR | CLOSTRIDIUM HISTOLYTICUM | 30–58 | 497–524 | | | | | | | |
| PCLPA_ECOLI | ATP-BINDING SUBUNIT CLPA | ESCHERICHIA COLI | 655–695 | | | | | | | | |
| PCLPA_RHOBL | CLPA HOMOLOG PROTEIN | RHODOPSEUDOMONAS BLASTICA | 439–466 | | | | | | | | |
| PCLPB_BACNO | CLPB HOMOLOG PROTEIN | BACTEROIDES NODOSUS | 116–157 | 442–476 | | | | | | | |
| PCLPB_ECOLI | CLPB PROTEIN | ESCHERICHIA COLI | 444–489 | 563–590 | | | | | | | |
| PCLPX_AZOVI | CLPX HOMOLOG PROTEIN | AZOTOBACTER VINELANDII | 215–242 | 332–359 | | | | | | | |
| PCLPX_ECOLI | ATP-BINDING SUBUNIT CLPX | ESCHERICHIA COLI | 255–282 | | | | | | | | |
| PCN16_ECOLI | 2′,3′-CYCLIC-NUC 2′-PHOSPHODIESTERASE PRECURS | ESCHERICHIA COLI | 50–77 | | 558–595 | | | | | | |
| PCODA_ECOLI | CYTOSINE DEAMINASE | ESCHERICHIA COLI | 102–129 | | | | | | | | |
| PCOM1_BACSU | A COMPETENCE PROTEIN 1 | BACILLUS SUBTILIS | 108–135 | 186–213 | | | | | | | |
| PCOMQ_BACSU | COMPETENCE REGULATORY PROTEIN | BACILLUS SUBTILIS | 154–239 | | | | | | | | |
| PCOP6_STAAU | COP-6 PROTEIN | STAPHYLOCOCCUS AUREUS | 7–53 | | | | | | | | |
| PCOPB_PSESM | COPPER RESISTANCE PROTEIN B PRECURSOR | PSEUDOMONAS SYRINGAE | 140–167 | | | | | | | | |
| PCORA_ECOLI | MAGNESIUM/COBALT TRANSPORT PROTEIN CORA | ESCHERICHIA COLI | 134–161 | | | | | | | | |
| PCORA_SALTY | MAGNESIUM/COBALT TRANSPORT PROTEIN CORA | SALMONELLA TYPHIMURIUM | 134–161 | | | | | | | | |
| PCOTE_BACSU | SPORE COAT PROTEIN E | BACILLUS SUBTILIS | 42–92 | | | | | | | | |
| PCOX1_BRAJA | CYTOCHROME C OXIDASE POLYPEPTIDE I | BRADYRHIZOBIUM JAPONICUM | 380–407 | | | | | | | | |
| PCOX1_PARDE | CYTOCHROME C OXIDASE POLYPEPTIDE I | PARACOCCUS DENITRIFICANS | 383–410 | | | | | | | | |
| PCOX1_RHOSH | CYTOCHROME C OXIDASE POLYPEPTIDE I | RHODOBACTER SPHAEROIDES | 396–423 | | | | | | | | |
| PCOXX_BACFI | OXIDASE ASSEMBLY FACTOR | BACILLUS FIRMUS | 36–63 | | | | | | | | |
| PCOXX_BACSU | OXIDASE ASSEMBLY FACTOR | BACILLUS SUBTILIS | 49–76 | | | | | | | | |
| PCPPB_NEIGO | CRYPTIC PLASMID PROTEIN B | NEISSERIA GONORRHOEAE | 72–99 | 165–209 | | | | | | | |
| PCPSB_ECOLI | MANNOSE-1-PHOSPHATE GUANYLYLTRANSFERASE | ESCHERICHIA COLI | 309–336 | | | | | | | | |
| PCPSB_SALTY | MANNOSE-1-PHOSPHATE GUANYLYLTRANSFERASE | SALMONELLA TYPHIMURIUM | 311–338 | | | | | | | | |
| PCPXA_ECOLI | SENSOR PROTEIN CPXA | ESCHERICHIA COLI | 254–281 | | | | | | | | |
| PCPXG_STRSQ | CYTOCHROME P450 105C1 | STREPTOMYCES SP | 157–184 | | | | | | | | |
| PCPXJ_SACER | 6-DEOXYERYTHRONOLIDE B (DEB) HYDROXYLASE | SACCHAROPOLYSPORA ERTHRAEA | 233–260 | | | | | | | | |
| PCPXM_BACSU | CYTOCHROME P450 109 | BACILLUS SUBTILIS | 240–283 | | | | | | | | |
| PCPXN_ANASP | PROBABLE CYTOCHROME P450 | ANABAENA SP | 98–125 | | | | | | | | |

TABLE VIII-continued

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| | | 107 × 178 × 4 SEARCH MOTIF RESULTS SUMMARY FOR ALL PROCARYOTIC PROTEINS | | | | | | | | | |
| PCR27_BACTI | 27 KD CRYSTAL PROTEIN | *BACILLUS THURINGIENSIS* | 153–187 | | | | | | | | |
| PCR27_BACTM | 27 KD CRYSTAL PROTEIN | *BACILLUS THURINGIENSIS* | 153–187 | | | | | | | | |
| PCR41_BACSH | 1.9 KD INSECTICIDAL TOXIN | *BACILLUS SPHAERICUS* | 276–308 | | | | | | | | |
| PCR42_BACSH | 1.9 KD INSECTICIDAL TOXIN | *BACILLUS SPHAERICUS* | 276–308 | | | | | | | | |
| PCR43_BACSH | 41.9 KD INSECTICIDAL TOXIN | *BACILLUS SPHAERICUS* | 276–308 | | | | | | | | |
| PCR70_BACTD | 70 KD CRYSTAL PROTEIN | *BACILLUS THURINGIENSIS* | 207–234 | 252–279 | 429–463 | | | | | | |
| PCR70_BACTO | 75 KD CRYSTAL PROTEIN | *BACILLUS THURINGIENSIS* | 57–84 | 125–159 | 427–464 | | | | | | |
| PCR70_BACTT | 70 KD CRYSTAL PROTEIN | *BACILLUS THURINGIENSIS* | 199–226 | 244–271 | 421–455 | | | | | | |
| PCR71_BACTK | 70 KD CRYSTAL PROTEIN | *BACILLUS THURINGIENSIS* | 93–133 | 191–218 | 552–615 | | | | | | |
| PCR72_BACTI | 72 KD CRYSTAL PROTEIN | *BACILLUS THURINGIENSIS* | 74–111 | 383–414 | | | | | | | |
| PCR72_BACTK | 70 KD CRYSTAL PROTEIN | *BACILLUS THURINGIENSIS* | 93–133 | 191–218 | 552–593 | | | | | | |
| PCR77_BACTI | 77 KD CRYSTAL PROTEIN | *BACILLUS THURINGIENSIS* | 308–335 | 502–529 | | | | | | | |
| PCREC_ECOLI | SENSOR PROTEIN CREC | *ESCHERICHIA COLI* | 103–130 | | | | | | | | |
| PCRED_ECOLI | INNER MEMBRANE PROTEIN CRED | *ESCHERICHIA COLI* | 94–121 | | | | | | | | |
| PCRP_ECOLI | CATABOLITE GENE ACTI-VATOR | *ESCHERICHIA COLI & SHIGELLA FLEXNERI* | 26–53 | 127–154 | | | | | | | |
| PCRP_SALTY | CATABOLITE GENE ACTI-VATOR | *SALMONELLA TYPHIMURIUM KLEBSIELLA AEROGENES* | 26–53 | 127–154 | | | | | | | |
| PCRTI_ERWHE | PHYTOENE DEHYDROGENASE | *ERWINIA HERBICOLA* | 231–258 | | | | | | | | |
| PCRTI_RHOCA | PHYTOENE DEHYDROGENASE | *RHODOBACTER CAPSULATUS* | 389–416 | | | | | | | | |
| PCRTJ_RHOCA | CRTJ PROTEIN | *RHODOBACTER CAPSULATUS* | 133–160 | 334–361 | 431–458 | | | | | | |
| PCRYS_BACTA | 132 KD CRYSTAL PROTEIN | *BACILLUS THURINGIENSIS* | 721–755 | 875–902 | | | | | | | |
| PCRYS_BACTB | 130 KD CRYSTAL PROTEIN | *BACILLUS THURINGIENSIS* | 730–771 | 865–892 | 1053–1080 | | | | | | |
| PCRYS_BACTE | 133 KD CRYSTAL PROTEIN | *BACILLUS THURINGIENSIS* | 736–770 | 890–917 | | | | | | | |
| PCRYS_BACTI | 130 KD CRYSTAL PROTEIN | *BACILLUS THURINGIENSIS* | 218–252 | 701–728 | 775–802 | | | | | | |
| PCRYS_BACTK | 130 KD CRYSTAL PROTEIN | *BACILLUS THURINGIENSIS* | 737–771 | 865–892 | 1053–1080 | | | | | | |
| PCRYS_BACTS | 130 KD CRYSTAL PROTEIN | *BACILLUS THURINGIENSIS* | 736–770 | 890–917 | | | | | | | |
| PCRYT_BACTA | 130 KD CRYSTAL PROTEIN | *BACILLUS THURINGIENSIS* | 730–771 | 865–892 | 1053–1080 | | | | | | |
| PCRYT_BACTE | 134 KD CRYSTAL PROTEIN | *BACILLUS THURINGIENSIS* | 745–779 | 899–926 | | | | | | | |
| PCRYT_BACTI | 130 KD CRYSTAL PROTEIN | *BACILLUS THURINGIENSIS* | 217–251 | 354–384 | 701–728 | 775–802 | | | | | |
| PCRYT_BACTK | 130 KD CRYSTAL PROTEIN | *BACILLUS THURINGIENSIS* | 737–771 | 865–892 | | | | | | | |
| PCRYU_BACTA | 135 KD CRYSTAL PROTEIN | *BACILLUS THURINGIENSIS* | 736–770 | 890–917 | | | | | | | |
| PCRYU_BACTI | 130 KD CRYSTAL PROTEIN | *BACILLUS THURINGIENSIS* | 217–251 | 700–727 | 774–801 | | | | | | |
| PCRYU_BACTK | 131 KD CRYSTAL PROTEIN | *BACILLUS THURINGIENSIS* | 738–772 | 866–893 | 1054–1081 | | | | | | |
| PCRYV_BACTA | 130 KD CRYSTAL PROTEIN | *BACILLUS THURINGIENSIS* | 737–771 | 865–892 | 1053–1080 | | | | | | |
| PCRYV_BACTI | 135 KD CRYSTAL PROTEIN | *BACILLUS THURINGIENSIS* | 110–151 | 745–772 | 819–846 | | | | | | |
| PCRYV_BACTK | 133 KD CRYSTAL PROTEIN | *BACILLUS THURINGIENSIS* | 736–770 | 890–917 | | | | | | | |
| PCRYW_BACTA | 130 KD CRYSTAL PROTEIN | *BACILLUS THURINGIENSIS* | 745–779 | | | | | | | | |
| PCRYW_BACTK | 133 KD CRYSTAL PROTEIN | *BACILLUS THURINGIENSIS* | 608–659 | 662–696 | 892–919 | | | | | | |
| PCRYX_BACTK | 139 KD CRYSTAL PROTEIN | *BACILLUS THURINGIENSIS* | 92–119 | 227–254 | 605–632 | 783–817 | 937–964 | | | | |
| PCS32_ECOLI | CS3 PILI SYNTHESIS 63 KD PROTEIN | *ESCHERICHIA COLI* | 42–69 | 226–253 | 290–317 | 344–378 | | | | | |
| PCS53_ECOLI | CS3 PILI SYNTHESIS 48 KD PROTEIN | *ESCHERICHIA COLI* | 90–117 | 154–181 | 208–242 | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PCS34_ECOLI | CS3 PILI SYNTHESIS 33 KD PROTEIN | ESCHERICHIA COLI | 20–47 | 74–108 | | | | | | | |
| PCSG_HALHA | CELL SURFACE GLYCOPROTEIN PRECURSOR | HALOBACTERIUM HALOBIUM | 256–283 | 584–611 | | | | | | | |
| PCSG_HALVO | CELL SURFACE GLYCOPROTEIN PRECURSOR | HALOBACTERIUM VOLCANII | 143–170 | 237–271 | | | | | | | |
| PCSG_METFE | CELL SURFACE GLYCOPROTEIN PRECURSOR | METHANOTHERMUS FERVIDUS | 59–107 | | | | | | | | |
| PCSG_METSC | CELL SURFACE GLYCOPROTEIN PRECURSOR | METHANOTHERMUS SOCIABILIS | 59–107 | | | | | | | | |
| PCSOB_ECOLI | CS1 FIMBRIAL SUBUNIT B PRECURSOR | ESCHERICHIA COLI | 25–56 | | | | | | | | |
| PCTFA_CLOAB | COA-TRANSFERASE SUBUNIT A | CLOSTRIDIUM ACETOBUTYLICUM | 118–145 | | | | | | | | |
| PCTFB_CLOAB | COA-TRANSFERASE SUBUNIT B | CLOSTRIDIUM ACETOBUTYLICUM | 174–208 | | | | | | | | |
| PCTRB_NEIME | INNER-MEMBRANE PROTEIN CTRB | NEISSERIA MENINGITIDIS | 152–193 | | | | | | | | |
| PCTX_PSEAE | CYTOTOXIN PRECURSOR | PSEUDOMONAS AERUGINOSA | 78–115 | 124–151 | 160–194 | | | | | | |
| PCVAA_ECOLI | COLICIN V SECRETION PROTEIN CVAA | ESCHERICHIA COLI | 104–138 | 163–219 | | 217–251 | | | | | |
| PCVAB_ECOLI | COLICIN V SECRETION PROTEIN CVAB | ESCHERICHIA COLI | 151–178 | | | | | | | | |
| PCWPM_BACBR | MIDDLE CELL WALL PROTEIN PRECURSOR | BACILLUS BREVIS | 197–224 | 411–438 | 1010–1044 | | | | | | |
| PCWPO_BACBR | OUTER CELL WALL PROTEIN PRECURSOR | BACILLUS BREVIS | 178–216 | 560–587 | 947–988 | | | | | | |
| PCYAA_BORPE | ADENYLATE CYCLASE PRECURSOR | BORDETELLA PERTUSSIS | 48–75 | 632–659 | 962–996 | | | | | | |
| PCYAA_YERIN | ADENYLATE CYCLASE | YERSINIA INTERMEDIA | 343–387 | 593–620 | | | | | | | |
| PCYAB_BORPE | CYAB PROTEIN | BORDETELLA PERTUSSIS | 541–568 | | | | | | | | |
| PCYAD_BORPE | CYAD PROTEIN | BORDETELLA PERTUSSIS | 178–212 | | | | | | | | |
| PCYAE_BORPE | CYAE PROTEIN | BORDETELLA PERTUSSIS | 313–340 | | | | | | | | |
| PCYB_RHOCA | CYTOCHROME B | RHODOBACTER CAPSULATUS | 38–65 | 382–409 | | | | | | | |
| PCYDD_ECOLI | TRANSPORT PROTEIN CYDD | ESCHERICHIA COLI | 3–30 | | | | | | | | |
| PCYF_NOSSP | APOCYTOCHROME F PRECURSOR | NOSTOC SP | 209–243 | | | | | | | | |
| PCYMO_ACISP | CYCLOHEXANONE MONOOXYGENASE | ACINETOBACTER SP | 439–473 | | | | | | | | |
| PCYNT_SYNP7 | CARBONIC ANHYDRASE | SYNECHOCOCCUS SP | 170–200 | | | | | | | | |
| PCYNX_ECOLI | CYNX PROTEIN | ESCHERICHIA COLI | 53–80 | | | | | | | | |
| PCYOB_ECOLI | CYTOCHROME O UBIQUINOL OXIDASE SUBUNIT 1 | ESCHERICHIA COLI | 31–58 | | | | | | | | |
| PCYPH_SYNP7 | PEPTIDYL-PROLYL CIS-TRANS ISOMERASE | SYNECHOCOCCUS SP | 107–141 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PCYSA_ECOLI | SULFATE PERMEASE A PROTEIN | ESCHERICHIA COLI | 164–191 | | | | | | | | |
| PCYSB_ECOLI | CYS REGULON TRANS-CRIPTIONAL ACTIVATOR | ESCHERICHIA COLI | 3–30 | | | | | | | | |
| PCYSB_SALTY | CYS REGULON TRANS-CRIPTIONAL ACTIVATOR | SALMONELLA TYPHIMURIUM | 3–30 | | | | | | | | |
| PCYSE_ECOLI | SERINE ACETYL-TRANSFERASE | ESCHERICHIA COLI | 164–191 | | | | | | | | |
| PCYSE_SALTY | SERINE ACETYL-TRANSFERASE | SALMONELLA TYPHIMURIUM | 164–191 | | | | | | | | |
| PCYSG_ECOLI | SIROHEM SYNTHASE | ESCHERICHIA COLI | 405–432 | | | | | | | | |
| PCYSG_SALTY | SIROHEM SYNTHASE | SALMONELLA TYPHIMURIUM | 405–432 | | | | | | | | |
| PCYSN_ECOLI | SULFATE ADENYLATE TRANSFERASE SUBUNIT 1 | ESCHERICHIA COLI | 64–91 | | | | | | | | |
| PCYSW_ECOLI | SULFATE PERMEASE W PROTEIN | ESCHERICHIA COLI | 201–228 | | | | | | | | |
| PCYSW_SYNP7 | SULFATE PERMEASE W PROTEIN | SYNECHOCOCCUS SP | 211–238 | | | | | | | | |
| PCZCB_ALCEU | CATION EFFLUX SYSTEM PROTEIN CZCB | ALCALIGENES EUTROPHUS | 241–268 | 283–320 | 364–391 | | | | | | |
| PCZCD_ALCEU | CATION EFFLUX SYSTEM PROTEIN CZCD | ALCALIGENES EUTROPHUS | 139–169 | | | | | | | | |
| PDACB_BACSU | PENICILLIN-BINDING PROTEIN 5° PRECURSOR | BACILLUS SUBTILIS | 80–107 | | | | | | | | |
| PDADA_ECOLI | D-AMINO ACID DEHYDRO-GENASE | ESCHERICHIA COLI | 127–154 | | | | | | | | |
| PDAGA_ALTHA | NA(+)-LINKED D-ALANINE GLYCINE PERMEASE | ALTEROMONAS HALOPLANKTIS | 332–373 | | | | | | | | |
| PDAMX_ECOLI | DAMX PROTEIN | ESCHERICHIA COLI | 68–95 | 349–380 | | | | | | | |
| PDAPA_ECOLI | DIHYDRODIPICOLINATE SYNTHASE | ESCHERICHIA COLI | 27–54 | 157–194 | | | | | | | |
| PDAT1_BACSU | DNA-PROTEIN-CYSTEINE METHYLTRANSFERASE | BACILLUS SUBTILIS | 13–47 | | | | | | | | |
| PDBHA_ECOLI | DNA-BINDING PROTEIN HU-ALPHA | ESCHERICHIA COLI | 12–39 | | | | | | | | |
| PDBH_CLOPA | DNA-BINDING PROTEIN HU | CLOSTRIDIUM PASTEURIANUM | 12–53 | | | | | | | | |
| PDCAM_ECOLI | DECARBOXYLASE ENZYME | ESCHERICHIA COLI | 146–173 | | | | | | | | |
| PDCDA_CORGL | DIAMINOPIMELATE DECARBOXYLASE | CORYNEBACTERIUM GLUTMICUM | 134–161 | | | | | | | | |
| PDCDA_PSEAE | DIAMINOPIMELATE DECARBOXYLASE | PSEUDOMONAS AERUGINOSA | 57–84 | | | | | | | | |
| PDCEB_ECOLI | GLUTAMATE DECARBOXY-LASE BETA | ESCHERICHIA COLI | 4–31 | | | | | | | | |
| PDCHS_ENTAE | HISTIDINE DECARBOXYLASE | ENTEROBACTER AEROGENES | 111–138 | | | | | | | | |
| PDCHS_KLEPL | HISTIDINE DECARBOXYLASE | KLEBSIELLA PLANTICOLA | 111–138 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDCHS_MORMO | HISTIDINE DECARBOXYLASE | MORGANELA MORGANII | 111–138 | | | | | | | | |
| PDCID_BACSU | DIPEPTIDE TRANSPORT PROTEIN DCIAD | BACILLUS SUBTILIS | 188–222 | | | | | | | | |
| PDCLY_HAFAL | LYSINE DECARBOXYLASE | HAFNIA ALVEI | 305–332 | | | | | | | | |
| PDCOA_KLEPN | OXALOACETATE DECARBOXYLASE ALPHA CHAIN | KLEBSIELLA PNEUMONIAE | 261–288 | 342–369 | | | | | | | |
| PDCOA_SALTY | OXALOACETATE DECARBOXYLASE ALPHA CHAIN | SALMONELLA TYPHIMURIUM | 261–288 | 342–369 | | | | | | | |
| PDCOB_SALTY | OXALOACETATE DECARBOXYLASE BETA CHAIN | SALMONELLA TYPHIMURIUM | 299–326 | | | | | | | | |
| PDCTB_RHILE | TRANSPORT SENSOR PROTEIN DCTB | RHIZOBIUM LEGUMINOSARUM | 377–411 | | | | | | | | |
| PDCTB_RHIME | TRANSPORT SENSOR PROTEIN DCTB | RHIZOBIUM MELILOTI | 511–538 | | | | | | | | |
| PDEAD_ECOLI | ATP-DEPENDENT RNA HELICASE DEAD | ESCHERICHIA COLI | 268–295 | 518–545 | | | | | | | |
| PDEAD_KLEPN | ATP-DEPENDENT RNA HELICASE DEAD | KLEBSIELLA PNEUMONIAE | 267–294 | 519–546 | | | | | | | |
| PDEDA_ECOLI | DEDA PROTEIN | ESCHERICHIA COLI | 106–133 | | | | | | | | |
| PDEGS_BACSU | SENSOR PROTEIN DEGS | BACILLUS SUBTILIS | 31–70 | 75–159 | | | | | | | |
| PDEH2_MORSP | HALOACETATE DEHALOGENASE H-2 | MORAXELLA SP | 144–141 | | | | | | | | |
| PDEOC_ECOLI | DEOXYRIBOSE-PHOSPHATE ALDOLASE | ESCHERICHIA COLI | 134–161 | | | | | | | | |
| PDHAL_PSEOL | ALDEHYDE DEHYDROGENASE | PSEUDOMONAS OLEOVORANS | 6–33 | | 292–327 | | | | | | |
| PDHAS_BACSU | ASPARTATE-SEMIALDEHYDE DEHYDROGENASE | BACILLUS SUBTILIS | 150–184 | | | | | | | | |
| PDHAS_CORGL | ASPARTATE-SEMIALDEHYDE DEHYDROGENASE | CORYNEBACTERIUM GLUTMICUM | 43–70 | 312–339 | | | | | | | |
| PDHAS_ECOLI | ASPARTATE-SEMIALDEHYDE DEHYDROGENASE | ESCHERICHIA COLI | 229–256 | | | | | | | | |
| PDHAS_VIBCH | ASPARTATE-SEMIALDEHYDE DEHYDROGENASE | VIBRIO CHOLERAE | 309–336 | | | | | | | | |
| PDHA_BACSH | ALANINE DEHYDROGENASE | BACILLUS SPHAERICUS | 149–176 | | | | | | | | |
| PDHA_BACST | ALANINE DEHYDROGENASE | BACILLUS STEAROTHERMOPHILUS | 94–121 | | | | | | | | |
| PDHE2_CLODI | NAD-SPECIFIC GLUTAMATE DEHYDROGENASE | CLOSTRIDIUM DIFFICILE | 116–143 | | | | | | | | |
| PDHE2_PEPAS | D-SPECIFIC GLUTAMATE DEHYDROGENASE | PEPTOSTREPTOCOCCUS ASACCHAROLYTICUS | 247–274 | 345–380 | | | | | | | |
| PDHE3_SULSO | GLUTAMATE DEHYDROGENASE | SULFOLOBUS SOLFATARICUS | 2–36 | | | | | | | | |
| PDHE4_CORGL | NADP-SPECIFIC GLUTAMATE DEHYDROGENASE | CORYNEBACTERIUM GLUTMICUM | 188–215 | 229–256 | | | | | | | |
| PDHGA_ACICA | GLUCOSE DEHYDROGENASE-A | ACINETOBACTER CALCOACETICUS | 10–59 | 190–217 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDHGB_BACME | GLUCOSE 1-DEHYDROGENASE B | BACILLUS MEGATERIUM | 27–57 | | | | | | | | |
| PDHG_ECOLI | GLUCOSE DEHYDROGENASE | ESCHERICHIA COLI | 436–463 | | | | | | | | |
| PDHK1_STRVN | KETOACYL REDUCASE 1 | STREPTOMYCES VIOLACEORUBER | 168–195 | | | | | | | | |
| PDHLE_BACST | LEUCINE DEHYDROGENASE | BACILLUS STEAROTHERMOPHILUS | 192–219 | | | | | | | | |
| PDHLO_AGRT4 | D-LYSOPINE DEHYDROGENASE | AGROBACTERIUM TUMEFACIENS | 317–344 | | | | | | | | |
| PDHM1_METEX | METHANOL DEHYDROGENASE SUBUNIT 1 PREC | METHYLOBACTERIUM EXTORQUENS | 153–187 | 190–224 | | | | | | | |
| PDHM1_METOR | METHANOL DEHYDROGENASE SUBUNIT 1 PREC | METHYLBACTERIUM ORGANOPHILUM | 153–187 | 190–224 | | | | | | | |
| PDHM1_PARDE | METHANOL DEHYDROGENASE SUBUNIT 1 PREC | PARACOCCUS DENITRIFICANS | 195–222 | | | | | | | | |
| PDHNA_BACSP | NADH DEHYDROGENASE | BACILLUS SP | 284–314 | | | | | | | | |
| PDHNA_ECOLI | NADH DEHYDROGENASE | ESCHERICHIA COLI | 180–214 | | | | | | | | |
| PDHOM_BACSU | HOMOSERINE DEHYDROGENASE | BACILLUS SUBTILIS | 73–107 | 406–433 | | | | | | | |
| PDHOM_CORGL | HOMOSERINE DEHYDROGENASE | CORYNEBACTERIUM GLUTMICUM | 105–132 | | | | | | | | |
| PDHPH_BACSH | PHENYLALANINE DEHYDROGENASE | BACILLUS SPHAERICUS | 212–239 | | | | | | | | |
| PDHSA_ECOLI | SUCC DEHYDROGENASE FLAVOPROTEIN SUBUNIT | ESCHERICHIA COLI | 482–512 | | | | | | | | |
| PDHSS_ANACY | SOLUBLE HYDROGENASE 42 KD SUBUNIT | ANABAENA CYLINDRICA | 86–113 | 130–168 | | | | | | | |
| PDHSS_SYNP1 | SOLUBLE HYDROGENASE, SMALL SUBUNIT | SYNECHOCOCCUS SP | 133–160 | | | | | | | | |
| PDHTM_METME | TRIMETHYLAMINE DEHYDROGENASE | METHYLOTROPHUS METHYLOPHILUS | 439–466 | | | | | | | | |
| PDING_ECOLI | PROBABLE ATP-DEPENDENT HELICASE DING | ESCHERICHIA COLI | 584–611 | | | | | | | | |
| PDIVB_BACSU | DIVISION INITIATION PROTEIN | BACILLUS SUBTILIS | 54–82 | 144–141 | | | | | | | |
| PDLD3_PSEPU | DIHYDROLIPOAMIDE DEHYDROGENASE | PSEUDOMONAS PUTIDA | 93–120 | | | | | | | | |
| PDLDH_AZOVI | LIPOAMIDE DEHYDROGENASE COMP (E3) | AZOTOBACTER VINELANDII | 18–45 | 224–276 | | | | | | | |
| PDLDH_BACST | LIPOAMIDE DEHYDROGENASE COMP (E3) | BACILLUS STEAROTHERMOPHILUS | 82–124 | | | | | | | | |
| PDLDH_BACSU | LIPOAMIDE DEHYDROGENASE COMP (E3) | BACILLUS SUBTILIS | 82–109 | | | | | | | | |
| PDLDH_ECOLI | DIHYDROLIPOAMIDE DEHYDROGENASE | ESCHERICHIA COLI | 108–135 | | | | | | | | |
| PDLDH_PSEFL | DIHYDROLIPOAMIDE DEHYDROGENASE | PSEUDOMONAS FLUORESCENS | 124–151 | 223–275 | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDMPN_PSEPU | PHENOL HYDROXYLASE PJ PROTEIN | PSEUDOMONAS PUTIDA | 63–90 | | | | | | | | |
| PDNA1_BACSU | DNAK PROTEIN | BACILLUS SUBTILIS | 497–524 | 548–581 | | | | | | | |
| PDNA2_BACSU | DNAK PROTEIN | BACILLUS SUBTILIS | 456–483 | | | | | | | | |
| PDNAA_BACSU | DNAA PROTEIN | BACILLUS SUBTILIS | 316–380 | | | | | | | | |
| PDNAA_BORBU | DNAA PROTEIN | BORRELIA BURGDORFERI | 182–216 | 248–275 | 341–387 | 436–463 | | | | | |
| PDNAA_BUCAP | DNAA PROTEIN | BUCHNERA APHIDICOLA | 73–100 | 111–138 | 353–380 | | | | | | |
| PDNAA_ECOLI | DNAA PROTEIN | ESCHERICHIA COLI | 366–400 | | | | | | | | |
| PDNAA_MICLU | DNAA PROTEIN | MICROCOCCUS LUTEUS | 385–415 | | | | | | | | |
| PDNAA_MYCCA | DNAA PROTEIN | MYCOPLASMA CAPRICOLUM | 8–56 | 75–112 | 274–310 | 350–389 | | | | | |
| PDNAA_PROMI | DNAA PROTEIN | PROTEUS MIRABILIS | 365–399 | | | | | | | | |
| PDNAA_PSEPU | DNAA PROTEIN | PSEUDOMONAS PUTIDA | 398–439 | | | | | | | | |
| PDNAA_SPICI | DNAA PROTEIN | SPIROPLASMA CITRI | 45–72 | 76–110 | 145–180 | | | | | | |
| PDNAB_CHLTR | DNAB-LIKE PROTEIN | CHLAMYDIA TRACHOMATIS | 312–353 | | | | | | | | |
| PDNAB_ECOLI | DNAB PROTEIN | ESCHERICHIA COLI | 82–109 | | | | | | | | |
| PDNAB_SALTY | DNAB PROTEIN | SALMONELLA TYPHIMURIUM | 82–109 | | | | | | | | |
| PDNAC_ECOLI | DNAC PROTEIN | ESCHERICHIA COLI | 146–190 | | | | | | | | |
| PDNAK_BACME | DNAK PROTEIN | BACILLUS MEGATERIUM | 497–524 | 548–581 | | | | | | | |
| PKNAK_BORBU | DNAK PROTEIN | BORRELIA BURGDORFERI | 512–594 | | | | | | | | |
| PDNAK_BRUOV | DNAK PROTEIN | BRUCELLA OVIS | 248–275 | 512–546 | | | | | | | |
| PDNAK_CAUCR | DNAK PROTEIN | CAULOBACTER CRESCENTUS | 561–588 | | | | | | | | |
| PDNAK_CLOAB | DNAK PROTEIN | CLOSTRIDIUM ACETOBUTYLICUM | 499–526 | | | | | | | | |
| PDNAK_CLOPE | DNAK PROTEIN | CLOSTRIDIUM PERFRINGENS | 496–527 | | | | | | | | |
| PDNAK_METMA | DNAK PROTEIN | METHANOSARCINA MAZEI | 523–550 | | | | | | | | |
| PDNAK_MYCTU | DNAK PROTEIN | MYCOBACTERIUM TUBERCULOSIS | 502–529 | | | | | | | | |
| PDNAK_STRCO | DNAK PROTEIN | STREPTOMYCES COELICOLOR | 45–72 | 533–572 | | | | | | | |
| PDNIR_ECOLI | REGULATORY PROTEIN DNIR | ESCHERICHIA COLI | 114–141 | | | | | | | | |
| PDNL1_ZYMMO | DNA LIGASE | ZYMOMONAS MOBILIS | 658–712 | | | | | | | | |
| PDNRJ_STRPE | TRANSDUCTION PROTEIN DNRJ | STREPTOMYCES PEUCETIUS | 24–51 | | | | | | | | |
| PDOCK_SULSO | PROBABLE SIGNAL RECOGNITION PARTICLE PROTE | SULFOLOBUS SOLFATARICUS | 104–172 | | | | | | | | |
| PDP3A_BACSU | DNA POLYMERASE III, ALPHA CHAIN | BACILLUS SUBTILIS | 58–85 | 417–444 | 1382–1416 | | | | | | |
| PDP3A_ECOLI | DNA POLYMERASE III, ALPHA CHAIN | ESCHERICHIA COLI | 77–104 | | | | | | | | |
| PDP3A_SACER | DNA POLYMERASE III, ALPHA CHAIN | SACCHAROPOLYSPORA ERTHRAEA | 230–257 | | | | | | | | |
| PDPJA_SALTY | DNA POLYMERASE III, ALPHA CHAIN | SALMONELLA TYPHIMURIUM | 77–104 | | | | | | | | |
| PDPJB_BACSU | DNA POLYMERASE III, BETA CHAIN | BACILLUS SUBTILIS | 212–239 | | | | | | | | |
| PDP3B_BORBU | DNA POLYMERASE III, BETA CHAIN | BORRELIA BURGDORFERI | 266–313 | | | | | | | | |
| PDP3B_BUCAP | DNA POLYMERASE III, BETA CHAIN | BUCHNERA APHIDICOLA | 31–62 | 308–359 | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDP3B_MICLU | DNA POLYMERASE III, BETA CHAIN | MICROCOCCUS LUTEUS | 191–218 | | | | | | | | |
| PDP3B_MYCCA | DNA POLYMERASE III, BETA CHAIN | MYCOPLASMA CAPRICOLUM | 36–70 | | | | | | | | |
| PDP3B_PSEPU | DNA POLYMERASE III, BETA CHAIN | PSEUDOMONAS PUTIDA | 30–60 | | | | | | | | |
| PDP3B_SPICI | DNA POLYMERASE III, BETA CHAIN | SPIROPLASMA CITRI | 78–112 | 129–177 | 273–310 | | | | | | |
| PDP3X_BACSU | DNA POLYMERASE III SUBUNITS AND GAMMA AND TAU | BACILLUS SUBTILIS | 231–272 | | | | | | | | |
| PDPC2_ECOLI | DNA PRIMASE TRAC-2 | ESCHERICHIA COLI | 691–743 | | | | | | | | |
| PDPC4_ECOLI | DNA PRIMASE TRAC-4 | ESCHERICHIA COLI | 401–448 | | | | | | | | |
| PDPND_STRPN | DPND PROTEIN | STREPTOCOCCUS PNEUMONIAE | 79–120 | | | | | | | | |
| PDPO1_BACCA | DNA POLYMERASE I | BACILLUS CALDOTENOX | 208–235 | | | | | | | | |
| PDPO1_STRPN | DNA POLYMERASE I | STREPTOCOCCUS PNEUMONIAE | 198–225 | 398–425 | 571–598 | 645–672 | | | | | |
| PDPO1_THEAQ | DNA POLYMERASE | THERMUS AQUATICUS | 196–223 | 602–629 | | | | | | | |
| PDPO1_THEFL | DNA POLYMERASE | THERMUS AQUATICUS | 597–628 | | | | | | | | |
| PDPO2_ECOLI | DNA POLYMERASE II | ESCHERICHIA COLI | 569–596 | | | | | | | | |
| PDPOL_PYRFU | DNA POLYMERASE | PYROCOCCUS FURIOSUS | 746–773 | | | | | | | | |
| PDPOL_SULSO | DNA POLYMERASE | SULFOLOBUS SOLFATARICUS | 379–406 | 436–463 | 625–659 | 747–774 | | | | | |
| PDPOL_THELI | DNA POLYMERASE | THERMOCOCCUS LITORALIS | 332–370 | 551–589 | 892–926 | 1004–1031 | 1153–1194 | | | | |
| PDPP_LACLA | DIPEPTIDYL PEPTIDASE IV | LACTOCOCCUS LACTIS | 716–753 | | | | | | | | |
| PDPP_LACLC | DIPEPTIDYL PEPTIDASE IV | LACTOCOCCUS LACTIS | 716–753 | | | | | | | | |
| PDPS_ECOLI | DNA PROTECTION DURING STARVATION PROTEIN | ESCHERICHIA COLI | 4–45 | | | | | | | | |
| PDRN1_STREQ | DEOXYRIBONUCLEASE PRECURSOR | STREPTOCOCCUS EQUISIMILIS | 33–60 | 291–318 | | | | | | | |
| PDRRA_STRPE | DAUNORUBICIN RESISTANCE ATP-BINDING PROTEI | STREPTOMYCES PEUCETIUS | 286–313 | | | | | | | | |
| PDYRA_STAAU | DIHYDROFOLATE REDUCTASE TYPE I | STAPHYLOCOCCUS AUREUS | 62–89 | | | | | | | | |
| PE13B_BACCI | GLUCAN ENDO-1,3-BETA-GLUCOSIDASE A1 PREC | BACILLUS CIRCULANS | 134–161 | 305–339 | 424–451 | | | | | | |
| PEAE_ECOLI | ATTACHING AND EFFACING PROTEIN | ESCHERICHIA COLI | 66–100 | 158–185 | 525–552 | 691–725 | 802–836 | 871–905 | | | |
| PEBGR_ECOLI | EBG OPERON REPRESSOR PROTEIN | ESCHERICHIA COLI | 151–178 | | | | | | | | |
| PEBR_STAAU | ETHIDIUM BROMIDE RESISTANCE PROTEIN | STAPHYLOCOCCUS AUREUS | 68–98 | | | | | | | | |
| PECHH_RHOCA | ENOYL-COA HYDRATASE HOMOLOG | RHODOBACTER CAPSULATUS | 222–249 | | | | | | | | |
| PECPD_ECOLI | CHAPERONE PROTEIN ECPD PRECURSOR | ESCHERICHIA COLI | 20–47 | | | | | | | | |
| PEDD_ZYMMO | PHOSPHOGLUCONATE DEHYDRATASE | ZYMOMONAS MOBILIS | 12–39 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PEDIN_STAAU | EPIDERMAL CELL DIF INH PRECURSOR | STAPHYLOCOCCUS AUREUS | 52–79 | 119–146 | | | | | | | |
| PEF2_DESMO | ELONGATION FACTOR 2 | DESULFUROCOCCUS MOBILIS | 427–461 | | | | | | | | |
| PEF2_HALHA | ELONGATION FACTOR 2 | HALOBACTERIUM HALOBIUM | 186–213 | | | | | | | | |
| PEF2_METVA | ELONGATION FACTOR 2 | METHANOCOCCUS VANNIELII | 409–436 | | | | | | | | |
| PEF2_SULAC | ELONGATION FACTOR 2 | SULFOLOBUS ACIDOCALDARIUS | 36–63 | 145–180 | | | | | | | |
| PEF2_THEAC | ELONGATION FACTOR 2 | THERMOPLASMA ACIDOPHILUM | 13–40 | 49–76 | 220–247 | | | | | | |
| PEFG_ANANI | ELONGATION FACTOR G | ANACYSTIS NIDULANS | 332–359 | | | | | | | | |
| PEFG_ECOLI | ELONGATION FACTOR G | ESCHERICHIA COLI | 234–261 | | | | | | | | |
| PEFG_MYCLE | ELONGATION FACTOR G | MYCOBACTERIUM LEPRAE | 211–259 | 330–357 | | | | | | | |
| PEFG_SALTY | ELONGATION FACTOR G | SALMONELLA TYPHIMURIUM | 234–261 | | | | | | | | |
| PEFG_SPIPL | ELONGATION FACTOR G | SPIRULINA PLATENSIS | 334–374 | 481–511 | | | | | | | |
| PEFG_SYNY3 | ELONGATION FACTOR G | SYNECHOCYSTIS SP | 14–41 | | | | | | | | |
| PEFT1_STRRA | ELONGATION FACTOR TU1 | STREPTOMYCES RAMOCISSIMUS | 221–258 | | | | | | | | |
| PEFT2_STRRA | ELONGATION FACTOR TU2 | STREPTOMYCES RAMOCISSIMUS | 221–258 | | | | | | | | |
| PEFT3_STRRA | ELONGATION FACTOR TU3 | STREPTOMYCES RAMOCISSIMUS | 228–255 | | | | | | | | |
| PEFTS_ECOLI | ELONGATION FACTOR EF-TS | ESCHERICHIA COLI | 101–135 | | | | | | | | |
| PEFTS_SPICI | ELONGATION FACTOR EF-TS | SPIROPLASMA CITRI | 27–54 | 134–161 | | | | | | | |
| PEFTU_BACFR | ELONGATION FACTOR TU | BACTEROIDES FRAGILIS | 18–45 | 229–256 | | | | | | | |
| PEFTU_BACSU | ELONGATION FACTOR TU | BACILLUS SUBTILIS | 11–45 | 230–257 | | | | | | | |
| PEFTU_BURCE | ELONGATION FACTOR TU | BURKHOLDERIA CEPACIA | 26–53 | | | | | | | | |
| PEFTU_CHLTR | ELONGATION FACTOR TU | CHLAMYDIA TRACHOMATIS | 218–245 | | | | | | | | |
| PEFTU_DEISP | ELONGATION FACTOR TU | DEINONEMA SP | 230–257 | | | | | | | | |
| PEFTU_FLESI | ELONGATION FACTOR TU | FLEXISTIPES SINUSARABICI | 221–248 | | | | | | | | |
| PEFTU_HALMA | ELONGATION FACTOR TU | HALOARCULA MARISMORTUI | 4–31 | | | | | | | | |
| PEFTU_MICLU | ELONGATION FACTOR TU | MICROCOCCUS LUTEUS | 221–248 | | | | | | | | |
| PEFTU_MYCHO | ELONGATION FACTOR TU | MYCOPLASMA HOMINIS | 222–249 | | | | | | | | |
| PEFTU_MYCLE | ELONGATION FACTOR TU | MYCOBACTERIUM LEPRAE | 220–257 | | | | | | | | |
| PEFTU_MYCTU | ELONGATION FACTOR TU | MYCOBACTERIUM TUBERCULOSIS | 220–247 | | | | | | | | |
| PEFTU_SHEPU | ELONGATION FACTOR TU | SHEWANELLA PUTREFACIENS | 26–53 | | | | | | | | |
| PEFTU_STROR | ELONGATION FACTOR TU | STREPTOCOCCUS ORALIS | 232–259 | | | | | | | | |
| PELAS_PSEAE | PSEUDOLYSIN PRECURSOR | PSEUDOMONAS AERUGINOSA | 141–168 | | | | | | | | |
| PELT1_ECOLI | T-LABILE ENTEROTOXIN A CHAIN PRECURSOR | ESCHERICHIA COLI | 78–105 | | | | | | | | |
| PELT3_ECOLI | T-LABILE ENTEROTOXIN A CHAIN PRECURSOR | ESCHERICHIA COLI | 79–106 | | | | | | | | |
| PELTB_CLOPE | T-LABILE ENTEROTOXIN B CHAIN PRECURSOR | CLOSTRIDIUM PERFRINGENS | 228–269 | | | | | | | | |
| PENTD_ECOLI | ENTEROBACTIN SYNTHETASE COMPONENT D | ESCHERICHIA COLI | 154–188 | | | | | | | | |
| PENVM_SALTY | ENVM PROTEIN | SALMONELLA TYPHIMURIUM | 34–61 | | | | | | | | |
| PEPIB_STAEP | 117 KD MEMBRANE ASSOCI-ATED PROTEIN | STAPHYLOCOCCUS EPIDERMIDIS | 51–80 | 125–229 | 290–325 | 387–421 | 857–889 | | | | |
| PEPIC_STAEP | EPIDERMIN BIOSYNTHESIS PROTEIN EPIC | STAPHYLOCOCCUS EPIDERMIDIS | 411–447 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PEPIP_STAEP | SERINE PROTEASE EPIP PRECURSOR | STAPHYLOCOCCUS EPIDERMIDIS | 7–68 | 297–324 | | | | | | | |
| PEPTY_STAEP | HYPOTHETICAL 16.7 KD PROTEIN IN EPIA 5' REGION | STAPHYLOCOCCUS EPIDERMIDIS | 70–101 | | | | | | | | |
| PEPIZ_STAEP | HYPOTHETICAL PROTEIN IN EPIA 5' REGION | STAPHYLOCOCCUS EPIDERMIDIS | 42–100 | | | | | | | | |
| PERA_ECOLI | GTP-BINDING ERA PROTEIN | ESCHERICHIA COLI | 18–45 | | | | | | | | |
| PERBS_SACER | SENSORY TRANSDUCTION PROTEIN ERYC1 | SACCHAROPOLYSPORA ERYTHRAEA | 209–243 | | | | | | | | |
| PEREA_ECOLI | ERYTHROMYCIN ESTERASE TYPE 1 | ESCHERICHIA COLI | 37–64 | 143–170 | | | | | | | |
| PERY3_SACER | ERYTHRONOLIDE SYNTHASE, MODULES 5 AND 6 | SACCHAROPOLYSPORA ERYTHRAEA | 9–36 | 967–994 | 1117–1144 | | | | | | |
| PESTA_STRSC | ESTERASE PRECURSOR | STREPTOMYCES SCABIES | 128–155 | | | | | | | | |
| PESTE_PSEFL | ARYLESTERASE | PSEUDOMONAS FLUORESCENS | 162–189 | | | | | | | | |
| PETC1_STAAU | ENTEROTOXIN TYPE C-1 PRECURSOR | STAPHYLOCOCCUS AUREUS | 76–117 | 155–206 | | | | | | | |
| PETC2_STAAU | ENTEROTOXIN TYPE C-2 PRECURSOR | STAPHYLOCOCCUS AUREUS | 76–117 | 155–206 | | | | | | | |
| PETC3_STAAU | ENTEROTOXIN TYPE C-3 PRECURSOR | STAPHYLOCOCCUS AUREUS | 76–117 | 155–206 | | | | | | | |
| PETXA_STAAU | ENTEROTOXIN TYPE A PRECURSOR | STAPHYLOCOCCUS AUREUS | 26–69 | 165–192 | | | | | | | |
| PETXB_CLOPE | EPSILON-TOXIN, TYPE B PRECURSOR | CLOSTRIDIUM PERFRINGENS | 209–236 | | | | | | | | |
| PETXB_STAAU | ENTEROTOXIN TYPE B PRECURSOR | STAPHYLOCOCCUS AUREUS | 64–101 | 173–207 | | | | | | | |
| PETXD_STAAU | ENTEROTOXIN TYPE D PRECURSOR | STAPHYLOCOCCUS AUREUS | 153–200 | | | | | | | | |
| PETXE_STAAU | ENTEROTOXIN TYPE E PRECURSOR | STAPHYLOCOCCUS AUREUS | 26–69 | 88–115 | | | | | | | |
| PEUTC_SALTY | ENTHANOLAMINE AMMONIA-LYASE LIGHT CHAIN | SALMONELLA TYPHIMURIUM | 116–150 | | | | | | | | |
| PEVGA_ECOLI | PUTATIVE TRANSCRIPTION REG EVGA | ESCHERICHIA COLI | 62–89 | | | | | | | | |
| PEVGS_ECOLI | PUTATIVE SENSOR PROTEIN EVGS | ESCHERICHIA COLI | 45–79 | 249–276 | 431–458 | 526–553 | 829–856 | | | | |
| PEX5B_ECOLI | EXODEOXYRIBONUCLEASE V | ESCHERICHIA COLI | 226–253 | | | | | | | | |
| PEXBB_ECOLI | BIOPOLYMER TRANSPORT EXBB PROTEIN | ESCHERICHIA COLI | 80–107 | | | | | | | | |
| PEXOA_RHIME | SUCCINOGLYCAN BIO-SYNTHESIS PROTEIN EXOA | RHIZOBIUM MELILOTI | 180–207 | | | | | | | | |
| PEXOA_STRPN | EXODEOXYRIBONUCLEASE | STREPTOCOCCUS PNEUMONIAE | 218–254 | | | | | | | | |
| PEXOF_RHIME | EXOF PROTEIN | RHIZOBIUM MELILOTI | 236–270 | | | | | | | | |
| PEXOH_RHIME | SUCCINOGLYCAN BIO-SYNTHESIS PROTEIN EXOH | RHIZOBIUM MELILOTI | 252–279 | 327–361 | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PEXOP_RHIME | SUCCINOGLYCAN BIO-SYNTHESIS PROTEIN EXOP | RHIZOBIUM MELILOTI | 211–242 | 272–299 | 350–391 | | | | | | |
| PFADB_ECOLI | FATTY OXIDATION COMPLEX ALPHA SUBUNIT | ESCHERICHIA COLI | 36–63 | 177–204 | | | | | | | |
| PFADL_ECOLI | FATTY ACID TRANSPORT PROTEIN PRECURSOR | ESCHERICHIA COLI | 220–247 | | | | | | | | |
| PFAED_ECOLI | OUTER MEMBRANE PROTEIN FAED PRECURSOR | ESCHERICHIA COLI | 223–257 | 421–453 | 507–541 | | | | | | |
| PFAEF_ECOLI | K88 MINOR FIMBRIAL SUB-UNIT PRECURSOR | ESCHERICHIA COLI | 18–48 | | | | | | | | |
| PFAND_ECOLI | FAND PROTEIN PRECURSOR | ESCHERICHIA COLI | 160–194 | 386–423 | 596–623 | 730–757 | | | | | |
| PFANE_ECOLI | CHAPERONE PROTEIN FANE PRECURSOR | ESCHERICHIA COLI | 22–58 | | | | | | | | |
| PFANG_ECOLI | FANG PROTEIN PRECURSOR | ESCHERICHIA COLI | 104–131 | | | | | | | | |
| PFANH_ECOLI | FANH PROTEIN PRECURSOR | ESCHERICHIA COLI | 83–141 | | | | | | | | |
| PFAOB_PSERF | FATTY OXIDATION COMPLEX ALPHA SUBUNIT | PSEUDOMONAS FRAGI | 8–42 | 295–322 | | | | | | | |
| PFDHD_WOLSU | FDHD PROTEIN | WOLINELLA SUCCINOGENES | 64–98 | | | | | | | | |
| PFDHF_ECOLI | FORMATE DEHYDROGENASE | ESCHERICHIA COLI | 613–640 | | | | | | | | |
| PFDH_PSESR | FORMATE DEHYDROGENASE | PSEUDOMONAS SP | 49–76 | 366–393 | | | | | | | |
| PFDNG_ECOLI | FORMATE DEHYDROGENASE | ESCHERICHIA COLI | 288–315 | 323–350 | 696–730 | | | | | | |
| PFECA_ECOLI | TRANSPORT PROTEIN FECA PRECURSOR | ESCHERICHIA COLI | 531–561 | | | | | | | | |
| PFECC_ECOLI | TRANSPORT PROTEIN 1, CYTOSOLIC | ESCHERICHIA COLI | 210–237 | | | | | | | | |
| PFECL_ECOLI | FECI PROTEIN | ESCHERICHIA COLI | 131–158 | | | | | | | | |
| PFEMB_STAAU | POSSIBLE PROTEIN FEMB | STAPHYLOCOCCUS AUREUS | 22–56 | | | | | | | | |
| PFENR_SYNP2 | FERREDOXIN-NADP REDUCTASE | SYNECHOCOCCUS SP | 4–31 | | | | | | | | |
| PFEPC_ECOLI | FERRIC ENTEROBACTIN TRANSPORT PROTEIN FEPC | ESCHERICHIA COLI | 176–203 | | | | | | | | |
| PFEPE_ECOLI | FERRIC ENTEROBACTIN TRANSPORT PROTEIN FEPE | ESCHERICHIA COLI | 182–234 | 281–308 | | | | | | | |
| PFEPG_ECOLI | FERRIC ENTEROBACTIN TRANSPORT PROTEIN FEPG | ESCHERICHIA COLI | 128–155 | | | | | | | | |
| PFERH_ANASP | FERREDOXIN, HETEROCYST | ANABAENA SP | 2–29 | | | | | | | | |
| PFERX_ANASP | FERRODOXIN-LIKE PROTEIN IN NIF REGION | ANABAENA SP | 67–94 | | | | | | | | |
| PFHAB_BORPE | FILAMENTOUS HEMAG-GLUTININ | BORDETELLA PERTUSSIS | 1128–1158 | 1359–1386 | 2063–2114 | 2841–2868 | 3051–3085 | 3167–3194 | | | |
| PFHAC_BORPE | HAEMOLYSIN-LIKE PROTEIN FHAC PRECURSOR | BORDETELLA PERTUSSIS | 342–369 | | | | | | | | |
| PFHLA_ECOLI | FORMATE HYDROGENLYASE TRANSACTIVATOR | ESCHERICHIA COLI | 36–63 | 350–384 | 401–428 | | | | | | |
| PFHUA_ECOLI | FERRICHROME-IRON RECEPTOR PRECURSOR | ESCHERICHIA COLI | 458–485 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PFHUB_ECOLI | PROTEIN FHUB PRECURSOR | ESCHERICHIA COLI | 227–254 | | | | | | | | |
| PFHUE_ECOLI | OUTER-MEMBRANE RECEPTOR | ESCHERICHIA COLI | 587–614 | | | | | | | | |
| PFIB_SPICI | FIBRIL PROTEIN | SPIROPLASMA CITRI | 161–195 | 326–367 | | | | | | | |
| PFIC_ECOLI | CELL FILAMENTATION PROTEIN FIC | ESCHERICHIA COLI | 151–178 | | | | | | | | |
| PFIC_SAITY | CELL FILAMENTATION PROTEIN FIC | SALMONELLA TYPHIMURIUM | 151–178 | | | | | | | | |
| PFIMC_BORPE | OUTER MEMBRANE PROTEIN FIMC PRECURSOR | BORDETELLA PERTUSSIS | 208–235 | 540–567 | 618–645 | | | | | | |
| PFIMC_ECOLI | CHAPERONE PROTEIN FIMC PRECURSOR | ESCHERICHIA COLI | 51–78 | | | | | | | | |
| PFIMD_ECOLI | FIMD PROTEIN PRECURSOR | ESCHERICHIA COLI | 222–253 | 458–485 | 534–561 | 563–590 | | | | | |
| PFIME_ECOLI | TYPE 1 FIMBRIAE REGULATORY PROTEIN FIME | ESCHERICHIA COLI | 165–192 | | | | | | | | |
| PFIMY_SAITY | FIMBRIAE Y PROTEIN | SALMONELLA TYPHIMURIUM | 49–76 | | | | | | | | |
| PFIMZ_ECOLI | FIMBRIAE Z PROTEIN | ESCHERICHIA COLI | 42–69 | 162–192 | 196–230 | | | | | | |
| PFIMZ_SAITY | FIMBRIAE Z PROTEIN | SALMONELLA TYPHIMURIUM | 175–209 | | | | | | | | |
| PFINQ_ECOLI | FINQ PROTEIN | ESCHERICHIA COLI | 145–172 | | | | | | | | |
| PFIRA_RICRI | FIRA PROTEIN | RICKETTSIA RICKETTSII | 162–189 | | | | | | | | |
| PFIXC_AZOCA | FIXC PROTEIN | AZORHIZOBIUM CAULINODANS | 129–156 | | | | | | | | |
| PFIXL_AZOCA | SENSOR PROTEIN FIXL | AZORHIZOBIUM CAULINODANS | 247–274 | 253–280 | | | | | | | |
| PFIXL_BRAJA | SENSOR PROTEIN FIXL | BRADYRHIZOBIUM JAPONICUM | 27–54 | 271–298 | | | | | | | |
| PFLA1_BORBU | FLAGELLAR FILAMENT 41 KD CORE PROTEIN | BORRELIA BURGDORFERI | 8–35 | | | | | | | | |
| PFLA1_HALHA | FLAGELLIN A1 PRECURSOR | HALOBACTERIUM HALOBIUM | 63–92 | 157–184 | | | | | | | |
| PFLA1_METVO | FLAGELLIN B1 PRECURSOR | METHANOCOCCUS VOLTAE | 28–73 | 133–160 | | | | | | | |
| PFLA2_METVO | FLAGELLIN B2 PRECURSOR | METHANOCOCCUS VOLTAE | 28–66 | | | | | | | | |
| PFLA3_HALHA | FLAGELLIN B1 PRECURSOR | HALOBACTERIUM HALOBIUM | 36–63 | | | | | | | | |
| PFLA3_METVO | FLAGELLIN B3 PRECURSOR | METHANOCOCCUS VOLTAE | 35–76 | | | | | | | | |
| PFLA4_HALHA | FLAGELLIN B2 PRECURSOR | HALOBACTERIUM HALOBIUM | 36–90 | 157–184 | | | | | | | |
| PFLA5_HALHA | FLAGELLIN B3 PRECURSOR | HALOBACTERIUM HALOBIUM | 36–63 | 154–181 | | | | | | | |
| PFLA6_BACSU | FLAA LOCUS 22.9 KD PRECURSOR | BACILLUS SUBTILIS | 73–149 | 155–186 | | | | | | | |
| PFLAA_COMCO | FLAGELLIN A | CAMPYLOBACTER COLI | 15–42 | 144–191 | 497–535 | | | | | | |
| PFLAA_CAMJE | FLAGELLIN A | CAMPYLOBACTER JEJUNI | 220–266 | 310–337 | 500–538 | | | | | | |
| PFLAA_METVO | FLAGELLIN A PRECURSOR | METHANOCOCCUS VOLTAE | 28–62 | | | | | | | | |
| PFLAA_PSEAE | FLAGELLIN | PSEUDOMONAS AERUGINOSA | 3–41 | 51–88 | 97–124 | | | | | | |
| PFLAA_RHIME | FLAGELLIN | RHIZOBIUM MELILOTI | 181–219 | 228–265 | 360–391 | | | | | | |
| PFLAA_SPIAU | FLAGELLAR FILAMENT PROTEIN PRECURSOR | SPIROCHAETA AURANTIA | 162–189 | | | | | | | | |
| PFLAA_TREHY | FLAGELLAR FILAMENT PROTEIN PRECURSOR | TREPONEMA HYODYSENTERIAE | 55–89 | 219–285 | | | | | | | |
| PFLAA_TREPA | FLAGELLAR FILAMENT OUTER LAYER PROTEIN | TREPONEMA PALLIDUM | 243–270 | | | | | | | | |
| PFLAB_CAMCO | FLAGELLIN B | CAMPYLOBACTER COLI | 144–191 | 497–535 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PFLAB_CAMJE | FLAGELLIN B | CAMPYLOBACTER JEJUNI | 220–266 | 310–337 | 500–538 | | | | | | |
| PFLAB_RHIME | FLAGELLIN | RHIZOBIUM MELILOTI | 86–113 | 177–219 | 228–255 | 360–391 | | | | | |
| PFLAV_CLOMP | FLAVODOXIN | CLOSTRIDIUM MP | 18–52 | | | | | | | | |
| PFLAY_CAUCR | REGULATORY PROTEIN FLAY | CAULOBACTER CRESCENTUS | 291–318 | 551–578 | | | | | | | |
| PFLA_BACSU | FLAGELLIN | BACILLUS SUBTILIS | 102–129 | 228–255 | | | | | | | |
| PFLGG_BACSU | FLAGELLAR BASAL-BODY ROD PROTEIN FLGG | BACILLUS SUBTILIS | 62–89 | | | | | | | | |
| PFLGK_SALTY | FLAGELLAR HOOK-ASSOCIATED PROTEIN 1 | SALMONELLA TYPHIMURIUM | 12–50 | 333–360 | 456–540 | | | | | | |
| PFLGL_ECOLI | FLAGELLAR HOOK-ASSOCIATED PROTEIN 3 | ESCHERICHIA COLI | 61–105 | 229–266 | | | | | | | |
| PFLGL_SALTY | FLAGELLAR HOOK-ASSOCIATED PROTEIN 3 | SALMONELLA TYPHIMURIUM | 61–105 | 229–266 | | | | | | | |
| PFLHD_ECOLI | FLAGELLAR TRANSCRIPTIONAL ACTIVATOR FLHD | ESCHERICHIA COLI | 6–33 | | | | | | | | |
| PFLIA_PSEAE | FLAGELLAR OPERON RNA POL SIGMA FACTOR | PSEUDOMONAS AERUGINOSA | 198–232 | | | | | | | | |
| PFLIC_ECOLI | FLAGELLIN | ESCHERICHIA COLI | 3–41 | 186–213 | 295–329 | 431–466 | | | | | |
| PFLIC_SALCH | FLAGELLIN | SALMONELLA CHOLERAE-SUIS | 5–41 | 54–125 | 136–198 | | | | | | |
| PFLIC_SALMU | FLAGELLIN | SALMONELLA MUENCHEN | 5–41 | 54–88 | 136–177 | 232–259 | 272–299 | 376–403 | | | |
| PFLIC_SALPA | FLAGELLIN | SALMONELLA PARATYPHI-A | 5–41 | 54–125 | 136–184 | | | | | | |
| PFLIC_SALRU | FLAGELLIN | SALMONELLA RUBISLAW | 5–41 | 54–125 | 136–196 | | | | | | |
| PFLIC_SALTY | FLAGELLIN | SALMONELLA TYPHIMURIUM | 5–41 | 54–125 | 136–200 | 103–130 | 137–164 | 275–321 | | | |
| PFLIC_SERMA | FLAGELLIN | SERRATIA MARCESCENS | | 15–42 | 55–89 | 216–298 | 386–445 | | | | |
| PFLID_ECOLI | FLAGELLAR HOOK-ASSOCIATED PROTEIN 2 | ESCHERICHIA COLI | 32–66 | 106–133 | 160–187 | | | | | | |
| PFLID_SALTY | FLAGELLAR HOOK-ASSOCIATED PROTEIN 2 | SALMONELLA TYPHIMURIUM | 32–66 | 106–133 | 255–299 | 407–438 | | | | | |
| PFLIE_BACSU | FLAG HOOK-BASAL BODY PROTEIN FLIE | BACILLUS SUBTILIS | 8–35 | | | | | | | | |
| PFLIF_BACSU | FLAGELLAR M-RING PROTEIN | BACILLUS SUBTILIS | 327–361 | 391–418 | | | | | | | |
| PFLIF_CAUCR | FLAGELLAR M-RING PROTEIN | CAULOBACTER CRESCENTUS | 24–51 | 297–324 | 361–388 | | | | | | |
| PFLIF_SALTY | FLAGELLAR M-RING PROTEIN | SALMONELLA TYPHIMURIUM | 484–529 | | | | | | | | |
| PFLIG_BACSU | FLAGELLAR SWITCH PROTEIN FLIG | BACILLUS SUBTILIS | 35–62 | | | | | | | | |
| PFLIG_ECOLI | FLAGELLAR SWITCH PROTEIN FLIG | ESCHERICHIA COLI | 44–71 | | | | | | | | |
| PFLIH_BACSU | PROBABLE FLIH PROTEIN | BACILLUS SUBTILIS | 19–46 | 105–132 | | | | | | | |
| PFLIJ_BACSU | FLAGELLAR FLIJ PROTEIN | BACILLUS SUBTILIS | 7–37 | | | | | | | | |
| PFLIJ_SALTY | FLAGELLAR FLIJ PROTEIN | SALMONELLA TYPHIMURIUM | 75–118 | | | | | | | | |
| PFLIK_BACSU | PROBABLE FLIK PROTEIN | BACILLUS SUBTILIS | 77–104 | 117–144 | | | | | | | |
| PFLII_BACSU | FLII PROTEIN | BACILLUS SUBTILIS | 30–71 | 78–105 | 109–136 | | | | | | |
| PFLII_ECOLI | FLII PROTEIN | ESCHERICHIA COLI | 105–132 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PFLIL_SALTY | FLIL PROTEIN | SALMONELLA TYPHIMURIUM | 103–133 | | | | | | | | |
| PFLIM_BACSU | FLIM PROTEIN | BACILLUS SUBTILIS | 148–175 | | | | | | | | |
| PFLIM_ECOLI | FLIM PROTEIN | ESCHERICHIA COLI | 251–278 | | | | | | | | |
| PFLIN_CAUCR | FLAGELLAR MOTOR SWITCH PROTEIN | CAULOBACTER CRESCENTUS | 56–83 | | | | | | | | |
| PFLIS_ECOLI | FLAGELLAR PROTEIN FLIS | ESCHERICHIA COLI | 59–86 | | | | | | | | |
| PFLIT_SALTY | FLAGELLAR PROTEIN FLIT | SALMONELLA TYPHIMURIUM | 9–46 | 67–106 | | | | | | | |
| PFM12_PSEAE | FIMBRIAL PROTEIN PRECURSOR | PSEUDOMONAS AERUGINOSA | 30–67 | 80–114 | | | | | | | |
| PFM1A_ECOLI | TYPE-1 FIMBRIAL PROTEIN, A CHAIN PRECURSOR | ESCHERICHIA COLI | 5–32 | | | | | | | | |
| PFM1C_ECOLI | TYPE-1 FIMBRIAL PROTEIN, C CHAIN PRECURSOR | ESCHERICHIA COLI | 11–38 | | | | | | | | |
| PFM1_ACTVI | FIMBRIAL SUBUNIT TYPE 1 PRECURSOR | ACTINOMYCES VISCOSUS | 248–282 | 352–379 | 417–444 | | | | | | |
| PFM98_ECOLI | FIMBRIAL PROTEIN 987P PRECURSOR | ESCHERICHIA COLI | 114–141 | | | | | | | | |
| PFMA0_BACNO | FIMBRIAL PROTEIN PRECURSOR | BACTEROIDES NODOSUS | 110–137 | | | | | | | | |
| PFMA1_BACNO | FIMBRIAL PROTEIN PRECURSOR | BACTEROIDES NODOSUS | 107–134 | | | | | | | | |
| PFMA2_BACNO | FIMBRIAL PROTEIN PRECURSOR | BACTEROIDES NODOSUS | 107–134 | | | | | | | | |
| PFMA7_BACNO | FIMBRIAL PROTEIN PRECURSOR | BACTEROIDES NODOSUS | 110–137 | | | | | | | | |
| PFMAA_BACNO | FIMBRIAL PROTEIN PRECURSOR | BACTEROIDES NODOSUS | 123–150 | | | | | | | | |
| PFMAF_BACNO | FIMBRIAL PROTEIN PRECURSOR | BACTEROIDES NODOSUS | 107–141 | | | | | | | | |
| PFMAH_BACNO | FIMBRIAL PROTEIN PRECURSOR | BACTEROIDES NODOSUS | 95–122 | | | | | | | | |
| PFMAI_BACNO | FIMBRIAL PROTEIN PRECURSOR | BACTEROIDES NODOSUS | 111–145 | | | | | | | | |
| PFMAJ_BACNO | FIMBRIAL PROTEIN PRECURSOR | BACTEROIDES NODOSUS | 96–123 | | | | | | | | |
| PFMCD_PSEAE | FIMBRIAL PROTEIN PRECURSOR | PSEUDOMONAS AERUGINOSA | 70–97 | | | | | | | | |
| PFMDD_BACNO | POSSIBLE FIMBRIAL ASSEMBLY PROTEIN FIMD | BACTEROIDES NODOSUS | 106–144 | 355–382 | | | | | | | |
| PFMDH_BACNO | POSSIBLE FIMBRIAL ASSEMBLY PROTEIN FIMD | BACTEROIDES NODOSUS | 106–144 | 355–382 | | | | | | | |
| PFMF3_ECOLI | F17 FIMBRIAL PROTEIN PRECURSOR | ESCHERICHIA COLI | 97–124 | | | | | | | | |
| PFMM1_NEIME | FIMBRIAL PROTEIN PRECURSOR | NEISSERIA MENINGITIDIS | 70–97 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PFMM2_NEIGO | FIMBRIAL PROTEIN PRECURSOR | NEISSERIA GONORRHOEAE | 66–97 | | | | | | | | |
| PFMM_MORNO | FIMBRIAL PROTEIN PRECURSOR | MORAXELLA NONLIQUEFACIENS | 108–146 | | | | | | | | |
| PFMP1_PSEAE | FIMBRIAL PROTEIN PRECURSOR | PSEUDOMONAS AERUGINOSA | 30–67 | 80–114 | | | | | | | |
| PFMP3_PSEAE | FIMBRIAL PROTEIN PRECURSOR | PSEUDOMONAS AERUGINOSA | 70–97 | | | | | | | | |
| PFMS1_ECOLI | CS1 FIMBRIAL SUBUNIT A PRECURSOR | ESCHERICHIA COLI | 60–87 | 112–139 | | | | | | | |
| PFMS3_ECOLI | CS3 FIMBRIAL SUBUNIT A PRECURSOR | ESCHERICHIA COLI | 49–98 | | | | | | | | |
| PFM_HAEIN | MAJOR FIMBRIAL SUBUNIT PRECURSOR | HAEMOPHILUS INFLUENZAE | 102–129 | | | | | | | | |
| PFNBA_STAAU | FIBRONECTIN-BINDING PROTEIN PRECURSOR | STAPHYLOCOCCUS AUREUS | 41–83 | 188–215 | 311–365 | 431–458 | 517–555 | 652–686 | 722–756 | | |
| PFOLC_ECOLI | FOLYPOLYGLUTAMATE SYNTHASE | ESCHERICHIA COLI | 125–159 | | | | | | | | |
| PFOLC_LACCA | FOLYPOLYGLUTAMATE SYNTHASE | LACTOBACILLUS CASEI | 129–156 | | | | | | | | |
| PPPG_BACFI | FORMAMIDOPYRIMIDINE-DNA GLYCOSYLASE | BACILLUS FIRMUS | 153–180 | | | | | | | | |
| PFRDA_ECOLI | FUMARATE REDUCTASE FLAVOPROTEIN SUBUNIT | ESCHERICHIA COLI | 395–422 | | | | | | | | |
| PFRDA_WOLSU | FUMARATE REDUCTASE FLAVOPROTEIN SUBUNIT | WOLINELLA SUCCINOGENES | 8–35 | 487–514 | | | | | | | |
| PFRZE_MYXXA | GLIDING MOTILITY REGULATORY PROTEIN | MYXOCOCCUS XANTHUS | 15–42 | 478–505 | | | | | | | |
| PFTHS_CLOTH | FORMATE–TETRAHYDROFOLATE LIGASE | CLOSTRIDIUM THERMOACETUM | 163–190 | | | | | | | | |
| PFTR_METTH | FORMYLTRANSFERASE | METHANOBACTERIUM THERMOAUTOTROPHICU | 9–43 | | | | | | | | |
| PFTSA_BACSU | CELL DIVISION PROTEIN FTSA | BACILLUS SUBTILIS | 76–110 | | | | | | | | |
| PFTSA_ECOLI | CELL DIVISION PROTEIN FTSA | ESCHERICHIA COLI | 301–338 | 375–418 | | | | | | | |
| PFTSJ_ECOLI | CELL DIVISION PROTEIN FTSJ | ESCHERICHIA COLI | 4–31 | | | | | | | | |
| PFTSL_ECOLI | CELL DIVISION PROTEIN FTSL | ESCHERICHIA COLI | 63–90 | | | | | | | | |
| PFTSN_ECOLI | CELL DIVISION PROTEIN FTSN | ESCHERICHIA COLI | 151–188 | | | | | | | | |
| PFTSX_ECOLI | CELL DIVISION PROTEIN FTSX | ESCHERICHIA COLI | 278–305 | | | | | | | | |
| PFTSY_ECOLI | CELL DIVISION PROTEIN FTSY | ESCHERICHIA COLI | 230–260 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PFUCR_ECOLI | L-FUCOSE OPERON ACTIVATOR | ESCHERICHIA COLI | 7–45 | | | | | | | | |
| PFUMA_BACST | FUMARATE HYDRATASE CLASS I, AEROBIC | BACILLUS STEAROTHERMOPHILUS | 290–317 | | | | | | | | |
| PFUMH_BACSU | FUMARATE HYDRATASE | BACILLUS SUBTILIS | 414–445 | | | | | | | | |
| PFUR_YERPE | FERRIC UPTAKE REGULATION PROTEIN | YERSINIA PESTIS | 99–130 | | | | | | | | |
| PG3P1_ECOLI | GLYC 3-PHOS DEHYDROGENASE A | ESCHERICHIA COLI | 302–329 | | | | | | | | |
| PG3P2_ANAVA | GLYC 3-PHOS DEHYDROGENASE 2 | ANABAENA VARIABILIS | 87–114 | | | | | | | | |
| PG3P3_ANAVA | GLYC 3-PHOS DEHYDROGENASE 3 | ANABAENA VARIABILIS | 162–189 | | | | | | | | |
| PG3P3_ECOLI | GLYC 3-PHOS DEHYDROGENASE C | ESCHERICHIA COLI | 236–324 | | | | | | | | |
| PG3P_BACME | GLYC 3-PHOS DEHYDROGENASE | BACILLUS MEGATERIUM | 49–76 | 237–271 | | | | | | | |
| PG3P_BACSU | GLYC 3-PHOS DEHYDROGENASE | BACILLUS SUBTILIS | 49–76 | | | | | | | | |
| PG3P_PYRWO | GLYC 3-PHOS DEHYDROGENASE | PYROCOCCUS WOESEI | 259–286 | | | | | | | | |
| PG3P_THEMA | GLYC 3-PHOS DEHYDROGENASE | THERMOTOGA MARITIMA | 290–328 | | | | | | | | |
| PG6PB_BACST | GLUCOSE-6-PHOSPHATE ISOMERASE B | BACILLUS STEAROTHERMOPHILUS | 103–143 | 241–268 | | | | | | | |
| PG6PD_ECOLI | GLUCOSE-6-PHOSPHATE 1-DEHYDROGENASE | ESCHERICHIA COLI | 301–328 | | | | | | | | |
| PG6PD_ZYMMO | GLUCOSE-6-PHOSPHATE 1-DEHYDROGENASE | ZYMOMONAS MOBILIS | 165–192 | | | | | | | | |
| PGACA_PSEFL | CYANIDE CONTROL PROTEIN | PSEUDOMONAS FLUORESCENS | 178–205 | | | | | | | | |
| PGAL1_SALTY | GALACTOKINASE | SALMONELLA TYPHIMURIUM | 86–113 | | | | | | | | |
| PGAL7_HAEIN | GAL-1-PHOS URIDYLYL-TRANSFERASE | HAEMOPHILUS INFLUENZAE | 124–158 | 239–269 | | | | | | | |
| PGAL7_LACHE | GAL-1-PHOS URIDYLYL-TRANSFERASE | LACTOBACILLUS HELVETICUS | 304–338 | | | | | | | | |
| PGALF_SALTY | GALACTOSE OPERON REPRESSOR | SALMONELLA TYPHIMURIUM | 53–91 | | | | | | | | |
| PGALR_HAEIN | GALACTOSE OPERON REPRESSOR | HAEMOPHILUS INFLUENZAE | 182–209 | | | | | | | | |
| PGAL_PSEFL | DE D-GALACTOSE 1-DEHYDROGENASE | PSEUDOMONAS FLUORESCENS | 251–278 | | | | | | | | |
| PGCH2_ECOLI | GTP CYCLOHYDROLASE II | ESCHERICHIA COLI | 78–105 | | | | | | | | |
| PGCH2_PHOLE | GTP CYCLOHYDROLASE II | PHOTOBACTERIUM LEIOGNATHI | 197–227 | 246–273 | | | | | | | |
| PGCSH_ECOLI | GLYCINE CLEAVAGE SYSTEM H PROTEIN | ESCHERICHIA COLI | 10–37 | | | | | | | | |
| PGCSP_ECOLI | GLYCINE DEHYDROGENASE | ESCHERICHIA COLI | 216–246 | | | | | | | | |

TABLE VIII-continued

| PCGENE FILE NAME | 107 x 178 x 4 PROTEIN | Prokaryotic Sequences ORGANISM | 107 x 178 x 4 SEARCH MOTIF RESULTS SUMMARY FOR ALL PROCARYOTIC PROTEINS | | | | | | | | |
|---|---|---|---|---|---|---|---|---|---|---|---|
| | | | AREA 1 | AREA 2 | AREA 3 | AREA 4 | AREA 5 | AREA 6 | AREA 7 | AREA 8 | AREA 9 |
| PGCVA_ECOLI | GLYCINE CLEAVAGE SYSTEM TRANSACTIVATOR | ESCHERICHIA COLI | 61–94 | | | | | | | | |
| PGENK_ECOLI | PROTEIN K | ESCHERICHIA COLI | 24–51 | | | | | | | | |
| PGER1_BACSU | SPORE GERMINATION PROTEIN I | BACILLUS SUBTILIS | 49–83 | 182–216 | 350–384 | | | | | | |
| PGER3_BACSU | SPORE GERMINATION PROTEIN III PRECURSOR | BACILLUS SUBTILIS | 293–323 | | | | | | | | |
| PGERE_BACSU | GERMINATION PROTEIN GERE | BACILLUS SUBTILIS | 13–40 | | | | | | | | |
| PGGI2_STAHA | ANTIBACTERIAL PROTEIN 2 | STAPHYLOCOCCUS HAEMOLYTICUS | 6–33 | | | | | | | | |
| PGGI3_STAHA | ANTIBACTERIAL PROTEIN 3 | STAPHYLOCOCCUS HAEMOLYTICUS | 6–33 | | | | | | | | |
| PGIDA_BACSU | GLUCOSE INHIBITED DIVISION PROTEIN A | BACILLUS SUBTILIS | 396–423 | | | | | | | | |
| PGIDA_ECOLI | GLUCOSE INHIBITED DIVISION PROTEIN A | ESCHERICHIA COLI | 533–568 | | | | | | | | |
| PGIDA_PSEPU | GLUCOSE INHIBITED DIVISION PROTEIN A | PSEUDOMONAS PUTIDA | 539–566 | | | | | | | | |
| PGIDB_BACSU | GLUCOSE INHIBITED DIVISION PROTEIN B | BACILLUS SUBTILIS | 34–61 | | | | | | | | |
| PGIDB_PSEPU | GLUCOSE INHIBITED DIVISION PROTEIN B | PSEUDOMONAS PUTIDA | 25–52 | | | | | | | | |
| PGLCP_SYNY3 | GLUCOSE TRANSPORT PROTEIN | SYNECHOCYSTIS SP | 288–322 | | | | | | | | |
| PGLDA_BACST | GLYCEROL DEHYDROGENASE | BACILLUS STEAROTHERMOPHILUS | 20–79 | | | | | | | | |
| PGLGA_ECOLI | GLYCOGEN SYNTHASE | ESCHERICHIA COLI | 256–283 | | | | | | | | |
| PGLGC_ECOLI | GLUCOSE-1-PHOSPHATE ADENYLYLTRANSFERASE | ESCHERICHIA COLI | 114–141 | | | | | | | | |
| PGLGC_SALTY | GLUCOSE-1-PHOSPHATE ADENYLYLTRANSFERASE | SALMONELLA TYPHIMURIUM | 114–141 | | | | | | | | |
| PGLMS_ECOLI | GLUC–FRUC-6-PHOSAMINO-TRANSFERASE | ESCHERICHIA COLI | 209–243 | | | | | | | | |
| PGLN1_METTL | GLNB-LIKE PROTEIN 1 | METHANOCOCCUS THERMOLITHOTROPHICUS | 58–85 | | | | | | | | |
| PGLNA_ANASP | GLUTAMINE SYNTHETASE | ANABAENA SP | 8–42 | | | | | | | | |
| PGLNA_BACSU | GLUTAMINE SYNTHETASE | BACILLUS SUBTILIS | 4–31 | | | | | | | | |
| PGLNA_CLOAB | GLUTAMINE SYNTHETASE | CLOSTRIDIUM ACETOBUTYLICUM | 413–440 | | | | | | | | |
| PGLNA_ECOLI | GLUTAMINE SYNTHETASE | ESCHERICHIA COLI | 144–171 | | | | | | | | |
| PGLNA_METVO | GLUTAMINE SYNTHETASE | METHANOCOCCUS VOLTAE | 203–230 | | | | | | | | |
| PGLNA_PROVU | GLUTAMINE SYNTHETASE | PROTEUS VOLGARIS | 142–169 | | | | | | | | |
| PGLNA_PYRFU | GLUTAMINE SYNTHETASE | PYROCOCCUS FURIOSUS | 391–421 | | | | | | | | |
| PGLNA_SALTY | GLUTAMINE SYNTHETASE | SALMONELLA TYPHIMURIUM | 144–171 | | | | | | | | |
| PGLNA_STRCO | GLUTAMINE SYNTHETASE | STREPTOMYCES COELICOLOR | 186–213 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PGLNB_AZOBR | NITROGEN REGULATORY PROTEIN P-II | AZOSPIRILLUM BRASILENSE | 15–49 | | | | | | | | |
| PGLNB_RHOCA | NITROGEN REGULATORY PROTEIN P-II | RHODOBACTER CAPSULATUS | 15–49 | | | | | | | | |
| PGLNB_SYNP6 | NITROGEN REGULATORY PROTEIN P-II | SYNECHOCOCCUS SP | 52–79 | | | | | | | | |
| PGLND_ECOLI | UDP URIDYLYLTRANSFERASE | ESCHERICHIA COLI | 120–147 | | | | | | | | |
| PGLND_SALTY | UDP URIDYLYLTRANSFERASE | SALMONELLA TYPHIMURIUM | 151–178 | 151–178 | | | | | | | |
| PGLNE_ECOLI | ADENYLYLTRANSFERASE | ESCHERICHIA COLI | 103–130 | 433–460 | | | | | | | |
| PGLNH_ECOLI | GLUTAMINE-BINDING PROTEIN PRECURSOR | ESCHERICHIA COLI | 126–153 | | | | | | | | |
| PGLNQ_BACST | GLUTAMINE PERMEASE OPERON PROTEIN GLNQ | BACILLUS STEAROTHERMOPHILUS | 7–34 | | | | | | | | |
| PGLPD_BACSU | AEROBIC GLYC-3-PHOS DEHYDROGENASE | BACILLUS SUBTILIS | 194–230 | | | | | | | | |
| PGLPD_ECOLI | AEROBIC GLYC-3-PHOS DEHYDROGENASE | ESCHERICHIA COLI | 410–437 | | | | | | | | |
| PGLPF_BACSU | GLYCEROL UPTAKE FACILITATOR PROTEIN | BACILLUS SUBTILIS | 235–274 | | | | | | | | |
| PGLPK_BACSU | GLYCEROL KINASE | BACILLUS SUBTILIS | 44–93 | | | | | | | | |
| PGLPK_ECOLI | GLYCEROL KINASE | ESCHERICHIA COLI | 56–90 | | | | | | | | |
| PGLPR_ECOLI | GLYCEROL-3-PHOSPHATE REGULON REPRESSOR | ESCHERICHIA COLI | 5–32 | | | | | | | | |
| PGLPX_ECOLI | GLPX PROTEIN | ESCHERICHIA COLI | 297–324 | | | | | | | | |
| PGLPX_SHIFL | GLPX PROTEIN | SHIGELLA FLEXNERI | 297–324 | | | | | | | | |
| PGLRX_ECOLI | GLUTAREDOXIN | ESCHERICHIA COLI | 24–51 | | | | | | | | |
| PGLTB_ECOLI | GLUTAMATE SYNTHASE | ESCHERICHIA COLI | 482–509 | | | | | | | | |
| PGLTP_ECOLI | PROTON GLUTAMATE SYMPORT PROTEIN | ESCHERICHIA COLI | 319–346 | | | | | | | | |
| PGLVB_ECOLI | PHOSPHOTRANSFERASE ENZYME TYPE-IIB | ESCHERICHIA COLI | 130–157 | | | | | | | | |
| PGLYA_BRAJA | SERINE HYDROXYMETHYLTRANSFERASE | BRADYRHIZOBIUM JAPONICUM | 29–60 | | | | | | | | |
| PGLYA_CAMJE | SERINE HYDROXYMETHYLTRANSFERASE | CAMPYLOBACTER JEJUNI | 376–403 | | | | | | | | |
| PGLYA_HYPME | SERINE HYDROXYMETHYLTRANSFERASE | HYPHOMICROBIUM METHYLOVORUM | 28–55 | | | | | | | | |
| PGMG7_BACSU | COMG OPERON PROTEIN 7 | BACILLUS SUBTILIS | 37–67 | | | | | | | | |
| PGNTK_BACSU | GLUCONOKINASE | BACILLUS SUBTILIS | 238–271 | 88–122 | | | | | | | |
| PGP1D_CHLTR | VIRULENCE PROTEIN PGP1-D | CHLAMYDIA TRACHOMATIS | 312–353 | | | | | | | | |
| PGP2D_CHLTR | VIRULENCE PROTEIN PGP2-D | CHLAMYDIA TRACHOMATIS | 97–131 | | | | | | | | |
| PGP5D_CHLTR | VIRULENCE PROTEIN PGP5-D | CHLAMYDIA TRACHOMATIS | 25–52 | | | | | | | | |
| PGP6D_CHLTR | VIRULENCE PROTEIN PGP6-D | CHLAMYDIA TRACHOMATIS | 63–106 | 193–220 | | | | | | | |
| PGP7D_CHLTR | VIRULENCE PROTEIN PGP7-D | CHLAMYDIA TRACHOMATIS | 12–60 | | | | | | | | |
| PGP8D_CHLTR | VIRULENCE PROTEIN PGP8-D | CHLAMYDIA TRACHOMATIS | 94–121 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PGREA_RICPR | TRANSCRIPTION ELONGATION FACTOR GREA | RICKETTSIA PROWAZEKII | 15–49 | | | | | | | | |
| PGRPE_BACSU | GRPE-LIKE PROTEIN | BACILLUS SUBTILIS | 27–73 | | | | | | | | |
| PGRPE_BORBU | GRPE-LIKE PROTEIN | BORRELIA BURGDORFERI | 2–79 | | | | | | | | |
| PGRPE_CLOAB | GRPE-LIKE PROTEIN | CLOSTRIDIUM ACETOBUTYLICUM | 12–83 | | | | | | | | |
| PGRSA_BACBR | GRAMICIDIN S SYNTHETASE | BACILLUS BREVIS | 545–572 | 799–826 | 840–882 | 1035–1062 | 1213–1240 | 2162–2189 | 2559–2586 | 2819–2846 | 3606–3633 |
| PGRSB_BACBR | GRAMICIDIN S SYNTHETASE II | BACILLUS BREVIS | 48–75 | 94–121 | 241–282 | 1126–1153 | | | | | |
| PGSH1_ECOLI | GLUTAMATE-CYSTEINE LIGASE | ESCHERICHIA COLI | 239–266 | 274–301 | | | | | | | |
| PGSHR_ECOLI | GLUTATHIONE REDUCTASE | ESCHERICHIA COLI | 100–134 | 270–311 | | | | | | | |
| PGSHR_PSEAE | GLUTATHIONE REDUCTASE | PSEUDOMONAS AERUGINOSA | 80–114 | 265–296 | | | | | | | |
| PGSIA_BACSU | STARVATION-INDUCIBLE PROTEIN A | BACILLUS SUBTILIS | 74–101 | | | | | | | | |
| PGSPD_ERWCA | PROTEIN D PRECURSOR | ERWINIA CAROTOVORA | 258–285 | 516–543 | 589–619 | | | | | | |
| PGSPD_ERWCH | PROTEIN D PRECURSOR | ERWINIA CHRYSANTHEMI | 259–302 | 307–338 | 551–578 | | | | | | |
| PGSPD_KLEPN | PROTEIN D PRECURSOR | KLEBSIELLA PNEUMONIAE | 259–286 | | | | | | | | |
| PGSPE_ERWCA | PROTEIN E | ERWINIA CAROTOVORA | 329–367 | | | | | | | | |
| PGSPE_ERWCH | PROTEIN E | ERWINIA CHRYSANTHEMI | 323–361 | | | | | | | | |
| PGSPE_KLEPN | PROTEIN E | KLEBSIELLA PNEUMONIAE | 122–149 | 331–369 | | | | | | | |
| PGSPE_PSEAE | PROTEIN E | PSEUDOMONAS AERUGINOSA | 230–257 | | | | | | | | |
| PGSPF_XANCP | PROTEIN F | XANTHOMONAS CAMPESTRIS | 18–59 | | | | | | | | |
| PGSPH_PSEAE | PROTEIN H PRECURSOR | PSEUDOMONAS AERUGINOSA | 27–61 | | | 659–686 | | | | | |
| PGSPI_AERHY | PROTEIN I PRECURSOR | AEROMONAS HYDROPHILA | 35–62 | | | | | | | | |
| PGSPI_ERWCA | PROTEIN I PRECURSOR | ERWINIA CAROTOVORA | 140–167 | | | | | | | | |
| PGSPJ_KLEPN | PROTEIN J PRECURSOR | KLEBSIELLA PNEUMONIAE | 28–55 | | | | | | | | |
| PGSPK_ERWCA | PROTEIN K | ERWINIA CAROTOVORA | 28–55 | | | | | | | | |
| PGSPK_ERWCH | PROTEIN K | ERWINIA CHRYSANTHEMI | 72–99 | | | | | | | | |
| PGSPK_KLEPN | PROTEIN K | KLEBSIELLA PNEUMONIAE | 262–289 | | | | | | | | |
| PGSPK_PSEAE | PROTEIN K | PSEUDOMONAS AERUGINOSA | 7–42 | 248–286 | 331–358 | | | | | | |
| PGSPL_ERWCH | PROTEIN L | ERWINIA CHRYSANTHEMI | 39–73 | 297–324 | | | | | | | |
| PGSPL_XANCP | PROTEIN L | XANTHOMONAS CAMPESTRIS | 108–145 | | | | | | | | |
| PGSPM_ERWCA | PROTEIN M | ERWINIA CAROTOVORA | 259–302 | 448–475 | 546–573 | 657–684 | | | | | |
| PGSQD_ERWCH | PROTEIN D PRECURSOR | ERWINIA CHRYSANTHEMI | 42–69 | 177–204 | 212–239 | 464–491 | 1382–1416 | 1495–1529 | | | |
| PGTF1_STRDO | GLUCOSYLTRANSFERASE-I PRECURSOR | STREPTOCOCCUS DOWNEI | 171–198 | 206–233 | 458–485 | 1382–1412 | 1497–1524 | | | | |
| PGTF2_STRDO | GLUCOSYLTRANSFERASE-I PRECURSOR | STREPTOCOCCUS DOWNEI | 297–350 | 110–137 | 161–188 | 199–246 | 313–347 | 592–627 | | | |
| PGTFA_STRMU | GLUCOSYLTRANSFERASE-S PRECURSOR | STREPTOCOCCUS MUTANS | 42–93 | 110–138 | 235–262 | 330–361 | 614–653 | | | | |
| PGTFB_STRMU | GLUCOSYLTRANSFERASE-I PRECURSOR | STREPTOCOCCUS MUTANS | 4–40 | | | | | | | | |
| PGTFC_STRMU | GLUCOSYLTRANSFERASE-SI PRECURSOR | STREPTOCOCCUS MUTANS | | | | | | | | | |
| PGTFS_STRDO | GLUCOSYLTRANSFERASE-S PRECURSOR | STREPTOCOCCUS DOWNEI | 275–316 | 436–463 | 1281–1315 | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PGTMR_METTF | POSSIBLE G-T MISMATCHES REPAIR ENZYME | METHANOBACTERIUM THERMOFORMICICUM | 80–107 | 148–175 | | | | | | | |
| PGUAA_BACSU | GMP SYNTHASE | BACILLUS SUBTILIS | 314–348 | 399–436 | 478–505 | | | | | | |
| PGUAA_ECOLI | GMP SYNTHASE | ESCHERICHIA COLI | 105–132 | | | | | | | | |
| PGUB_BACCI | BETA-GLUCANASE PRECURSOR | BACILLUS CIRCULANS | 164–191 | | | | | | | | |
| PGUB_BACLI | BETA-GLUCANASE PRECURSOR | BACILLUS LICHENIFORMIS | 132–166 | | | | | | | | |
| PGUB_BACMA | BETA-GLUCANASE PRECURSOR | BACILLUS MACERANS | 126–160 | | | | | | | | |
| PGUN1_BACS4 | ENDOGLUCANASE A PRECURSOR | BACILLUS SP | 18–49 | | | | | | | | |
| PGUN1_BACSU | ENDOGLUCANASE A PRECURSOR | BACILLUS SUBTILIS | 270–304 | 376–403 | | | | | | | |
| PGUN1_BUTFI | ENDOGLUCANASE 1 PRECURSOR | BUTYRIVIBRIO FIBRISOLVENS | 154–181 | 452–495 | | | | | | | |
| PGUN2_BACSU | ENDOGLUCANASE PRECURSOR | BACILLUS SUBTILIS | 270–304 | | | | | | | | |
| PGUN2_THEFU | ENDOGLUCANASE E-2 PRECURSOR | THERMOMONOSPORA FUSCA | 201–228 | | | | | | | | |
| PGUN3_BACS4 | ENDOGLUCANASE C PRECURSOR | BACILLUS SP | 110–137 | 348–378 | 538–565 | | | | | | |
| PGUN3_BACSU | ENDOGLUCANASE PRECURSOR | BACILLUS SUBTILIS | 270–304 | | | | | | | | |
| PGUN3_FIBSU | ENDOGLUCANASE 3 PRECURSOR | FIBROBACTER SUCCINOGENES | 542–586 | | | | | | | | |
| PGUN4_THEFU | ENDOGLUCANASE E-4 PRECURSOR | THERMOMONOSPORA FUSCA | 308–342 | | | | | | | | |
| PGUN5_THEFU | ENDOGLUCANASE E-5 PRECURSOR | THERMOMONOSPORA FUSCA | 44–71 | | | | | | | | |
| FGUNA_BACLA | ENDOGLUCANASE A PRECURSOR | BACILLUS LAUTUS | 410–437 | 454–481 | | | | | | | |
| PGUNA_CLOTM | ENDOGLUCANASE A PRECURSOR | CLOSTRIDIUM THERMOCELLUM | 354–384 | | | | | | | | |
| PGUNA_PSEFL | ENDOGLUCANASE A PRECURSOR | PSEUDOMONAS FLUORESCENS | 762–789 | | | | | | | | |
| PGUNA_RUMAL | ENDOGLUCANASE A PRECURSOR | RUMINOCOCCUS ALBUS | 294–321 | | | | | | | | |
| PGUNA_RUMFL | CELLODEXTRINASE A | RUMINOCOCCUS FLAVEFACIENS | 276–303 | | | | | | | | |
| PGUNB_BACLA | ENDOGLUCANASE B PRECURSOR | BACILLUS LAUTUS | 375–450 | | | | | | | | |
| PGUNB_CALSA | ENDOGLUCANASE B PRECURSOR | CALDOCELLUM SACCHAROLYTICUM | 151–182 | 444–478 | | | | | | | |
| PGUNB_CELFI | ENDOGLUCANASE B PRECURSOR | CELLULOMONAS FIMI | 266–293 | | | | | | | | |
| PGUNB_CLOCL | ENDOGLUCANASE B PRECURSOR | CLOSTRIDIUM CELLULOVORANS | 144–171 | 266–300 | | | | | | | |
| PGUNB_CLOTM | ENDOGLUCANASE B PRECURSOR | CLOSTRIDIUM THERMOCELLUM | 514–541 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PGUNC_CELFI | ENDOGLUCANASE C PRECURSOR | CELLULOMONAS FIMI | 881–908 | | | | | | | | |
| PGUNC_PSEFL | ENDOGLUCANASE C PRECURSOR | PSEUDOMONAS FLUORESCENS | 52–82 | | | | | | | | |
| PGUND_CLOCE | ENDOGLUCANASE D PRECURSOR | CLOSTRIDIUM CELLULOLYTICUM | 382–453 | | | | | | | | |
| PGUND_CLOCL | ENDOGLUCANASE D PRECURSOR | CLOSTRIDIUM CELLULOLYTICUM | 145–172 | 271–298 | | | | | | | |
| PGUNE_CLOTM | ENDOGLUCANASE E PRECURSOR | CLOSTRIDIUM THERMOCELLUM | 158–185 | 207–234 | 284–311 | | | | | | |
| PGUNH_CLOTM | ENDOGLUCANASE H PRECURSOR | CLOSTRIDIUM THERMOCELLUM | 46–73 | 425–452 | | | | | | | |
| PGUNS_ERWCA | ENDOGLUCANASE PRECURSOR | ERWINIA CAROTOVORA | 20–47 | 115–149 | | | | | | | |
| PGUNX_CLOTM | PUTATIVE ENDOGLUCANASE X | CLOSTRIDIUM THERMOCELLUM | 105–139 | | | | | | | | |
| PGUNZ_CLOSR | ENDOGLUCANASE Z PRECURSOR | CLOSTRIDIUM STERCORARIUM | 296–326 | 522–549 | | | | | | | |
| PGUN_BACPO | ENDOGLUCANASE | BACILLUS POLYMYXA | 198–225 | | | | | | | | |
| PGUN_BACS1 | ENDOGLUCANASE PRECURSOR | BACILLUS SP | 321–348 | | | | | | | | |
| PGUN_BACS6 | ENDOGLUCANASE PRECURSOR | BACILLUS SP | 198–229 | 501–528 | 623–664 | | | | | | |
| PGUTD_ECOLI | SORBITOL-6-PHOSPHATE 2-DEHYDROGENASE | ESCHERICHIA COLI | 138–165 | | | | | | | | |
| PGVP1_HALHA | GAS VESICLE PROTEIN, PLASMID | HALOBACTERIUM HALOBIUM | 36–63 | | | | | | | | |
| PGVP2_HALHA | GAS VESTILE PROTEIN, CHROMOSOMAL | HALOBACTERIUM HALOBIUM | 36–63 | | | | | | | | |
| PGVPA_APHFL | GAS VESICLE PROTEIN | APHANIZOMENON FLOS-AQUAE | 4–31 | 39–66 | | | | | | | |
| PGVPA_FREDI | GAS VESICLE PROTEIN | FREMYELLA DIPLOSIPHON | 4–31 | 39–66 | | | | | | | |
| PGVPA_HALME | GAS VESICLE PROTEIN | HALOBACTERIUM MEDITERRANEI | 37–64 | | | | | | | | |
| PGVPA_MICBC | GAS VESICLE PROTEIN | MICROCYSTIS SP | 39–66 | | | | | | | | |
| PGVPA_PSEAN | GAS VESICLE PROTEIN | PSEUDONANABAENA SP | 4–31 | 39–66 | | | | | | | |
| PGVPC_APHFL | GAS VESICLE PROTEIN C | APHANIZOMENON FLOS-AQUAE | 8–49 | | | | | | | | |
| PGVPC_HALHA | GAS VESICLE PROTEIN C | HALOBACTERIUM HALOBIUM | 150–249 | | | | | | | | |
| PGVPC_HALME | GAS VESICLE PROTEIN C | HALOBACTERIUM MEDITERRANEI | 139–169 | | | | | | | | |
| PGVPD_HALHA | GVPD PROTEIN, PLASMID | HALOBACTERIUM HALOBIUM | 110–147 | | | | | | | | |
| PGVPD_HALME | GVPD PROTEIN | HALOBACTERIUM MEDITERRANEI | 110–147 | | | | | | | | |
| PGVPF_HALHA | GVPF PROTEIN, PLASMID | HALOBACTERIUM HALOBIUM | 13–47 | 135–169 | | | | | | | |
| PGVPF_HALME | GVPF PROTEIN | HALOBACTERIUM MEDITERRANEI | 13–47 | | | | | | | | |
| PGVPF_HALSA | GVPF PROTEIN | HALOBACTERIUM SALINARIUM | 8–49 | | | | | | | | |
| PGVPG_HALHA | GVPG PROTEIN, PLASMID | HALOBACTERIUM HALOBIUM | 38–65 | | | | | | | | |
| PGVPG_HALME | GVPG PROTEIN | HALOBACTERIUM MEDITERRANEI | 38–72 | | | | | | | | |
| PGVPH_HALHA | GVPH PROTEIN | HALOBACTERIUM HALOBIUM | 10–40 | | | | | | | | |
| PGVPI_HALME | GVPI PROTEIN | HALOBACTERIUM MEDITERRANEI | 5–32 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PGVPK_HALHA | GVPK PROTEIN | HALOBACTERIUM HALOBIUM | 45–76 | | | | | | | | |
| PGVPK_HALME | GVPK PROTEIN | HALOBACTERIUM MEDITERRANEI | 12–39 | 47–74 | | | | | | | |
| PGVPK_HALSA | GVPK PROTEIN | HALOBACTERIUM SALINARIUM | 11–38 | 50–77 | | | | | | | |
| PGVPL_HALME | GVPL PROTEIN | HALOBACTERIUM MEDITERRANEI | 44–78 | | | | | | | | |
| PGVPN_HALHA | GVPN PROTEIN | HALOBACTERIUM HALOBIUM | 113–140 | | | | | | | | |
| PGVPN_HALME | GVPN PROTEIN | HALOBACTERIUM MEDITERRANEI | 15–56 | | | | | | | | |
| PGVPG_HALME | GVPG PROTEIN | HALOBACTERIUM MEDITERRANEI | 69–96 | 105–132 | | | | | | | |
| PGYRA_BACSU | DNA GYRASE SUBUNIT A | BACILLUS SUBTILIS | 380–407 | 429–499 | | | | | | | |
| PGYRA_CAMJE | DNA GYRASE SUBUNIT A | CAMPYLOBACTER JEJUNI | 267–310 | 381–408 | 452–479 | 665–695 | | | | | |
| PGYRA_ECOLI | DNA GYRASE SUBUNIT A | ESCHERICHIA COLI | 266–293 | 449–497 | | | | | | | |
| PGYRA_KLEPN | DNA GYRASE SUBUNIT A | KLEBSIELLA PNEUMONIAE | 266–293 | 448–496 | 518–545 | | | | | | |
| PGYRA_MYCPN | DNA GYRASE SUBUNIT A | MYCOPLASMA PNEUMONIAE | 4–31 | | | | | | | | |
| PGYRA_STAAU | DNA GYRASE SUBUNIT A | STAPHYLOCOCCUS AUREUS | 129–156 | 346–373 | 430–479 | 647–674 | 812–839 | | | | |
| PGYRB_BACSU | DNA GYRASE SUBUNIT B | BACILLUS SUBTILIS | 198–239 | | | | | | | | |
| PGYRB_BORBU | DNA GYRASE SUBUNIT B | BORRELIA BURGDORFERI | 154–191 | | | | | | | | |
| PGYRB_ECOLI | DNA GYRASE SUBUNIT B | ESCHERICHIA COLI | 616–643 | | | | | | | | |
| PGYRB_HALSQ | DNA GYRASE SUBUNIT B | HALOFERAX SP | 230–257 | | | | | | | | |
| PGYRB_MYCPN | DNA GYRASE SUBUNIT B | MYCOPLASMA PNEUMONIAE | 249–283 | | | | | | | | |
| PGYRB_NEIGO | DNA GYRASE SUBUNIT B | NEISSERIA GONORRHOEAE | 524–558 | 618–645 | | | | | | | |
| PGYRB_PSEPU | DNA GYRASE SUBUNIT B | PSEUDOMONAS PUTIDA | 122–149 | 684–711 | | | | | | | |
| PGYRB_SPICI | DNA GYRASE SUBUNIT B | SPIROPLASMA CITRI | 40–74 | 189–238 | 283–310 | 341–368 | 540–579 | | | | |
| PGYRB_STAAU | DNA GYRASE SUBUNIT B | STAPHYLOCOCCUS AUREUS | 252–279 | 291–318 | | | | | | | |
| PHDHA_ECOLI | 7-ALPHA-HYDROXYSTEROID DEHYDROGENASE | ESCHERICHIA COLI | 71–98 | | | | | | | | |
| PHELD_ECOLI | HELICASE IV | ESCHERICHIA COLI | 100–134 | 529–556 | | | | | | | |
| PHEL_HAEIN | LIPROPROTEIN E PRECURSOR | HAEMOPHILUS INFLUENZAE | 58–85 | | | | | | | | |
| PHEM1_CHLVI | GLUTAMYL-TRNA REDUCTASE | CHLOROBIUM VIBRIOFORMES | 232–259 | | | | | | | | |
| PHEM1_ECOLI | GLUTAMYL-TRNA REDUCTASE | ESCHERICHIA COLI | 289–316 | | | | | | | | |
| PHEM1_RHOSH | 5-AMINOLEVULINIC ACID SYNTHASE | RHODOBACTER SPHAEROIDES | 73–100 | | | | | | | | |
| PHEM1_SALTY | GLUTAMYL-TRNA REDUCTASE( | SALMONELLA TYPHIMURIUM | 289–316 | 344–371 | | | | | | | |
| PHEM1_SYNY3 | GLUTAMYL-TRNA REDUCTASE | SYNECHOCYSTIS SP | 163–190 | 350–377 | | | | | | | |
| PHEM2_METSC | DELTA-AMINOLEVULINIC ACID DEHYDRATASE | METHANOTHERMUS SOCIABILIS | 131–158 | | | | | | | | |
| PHEM4_BACSU | PUTATIVE UROPORPHYRINO- GEN-III SYNTHASE | BACILLUS SUBTILIS | 10–37 | | | | | | | | |
| PHEM4_ECOLI | UROPORPHYRINOGEN-III SYNTHASE | ESCHERICHIA COLI | 211–238 | | | | | | | | |
| PHEMM_ECOLI | HEMM PROTEIN | ESCHERICHIA COLI | 147–174 | | | | | | | | |
| PHEMR_YEREN | HEMIN RECEPTOR PRECURSOR | YERSINIA ENTEROCOLITICA | 234–261 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMX_ECOLI | PUTATIVE METHYL-TRANSFERASE | ESCHERICHIA COLI | 69–138 | 185–219 | | | | | | | |
| PHEMY_BACSU | HEMY PROTEIN | BACILLUS SUBTILIS | 217–262 | | | | | | | | |
| PHEMZ_BACSU | FERROCHELATASE | BACILLUS SUBTILIS | 199–226 | | | | | | | | |
| PHETA_ANASP | HETEROCYST DIFFERENTIATION PROTEIN | ANABAENA SP | 184–211 | 357–398 | 521–565 | | | | | | |
| PHEXA_STRPN | DNA MISMATCH REPAIR PROTEIN HEXA | STREPTOCOCCUS PNEUMONIAE | 426–460 | | | | | | | | |
| PHEXB_STRPN | DNA MISMATCH REPAIR PROTEIN HEXB | STREPTOCOCCUS PNEUMONIAE | 470–497 | | | | | | | | |
| PHFAB_CAUCR | POS TRANSACTIVATOR PROTEIN HFAB | CAULOBACTER CRESCENTUS | 98–125 | | | | | | | | |
| PHFLC_ECOLI | HFLC PROTEIN | ESCHERICHIA COLI | 113–140 | | | | | | | | |
| PHFLX_ECOLI | GTP-BINDING PROTEIN HFLX | ESCHERICHIA COLI | 169–196 | | | | | | | | |
| PHFQ_ECOLI | HOST FACTOR-1 PROTEIN | ESCHERICHIA COLI | 24–51 | | | | | | | | |
| PHFC_HAEIN | PILIATION PROTEIN HIFC PRECURSOR | HAEMOPHILUS INFLUENZAE | 356–383 | 404–431 | 447–474 | | | | | | |
| PHIS2_LACLA | PHOSPHORIBOSYL-AMP CYCLOHYDROLASE | LACTOCOCCUS LACTIS | 126–174 | | | | | | | | |
| PHIS4_ECOLI | P-5-A CARBOXAMIDE RIBOTIDE | ESCHERICHIA COLI | 125–159 | | | | | | | | |
| PHIS4_LACLA | P-5-A CARBOXAMIDE RIBOTIDE | LACTOCOCCUS LACTIS | 49–89 | 181–228 | | | | | | | |
| PHIS4_METVA | P-5-A CARBOXAMIDE RIBOTIDE | METHANOCOCCUS VANNIELII | 115–142 | | | | | | | | |
| PHIS4_SALTY | P-5-A CARBOXAMIDE RIBOTIDE | SALMONELLA TYPHIMURIUM | 125–159 | | | | | | | | |
| PHIS5_LACLA | AMIDOTRANSFERASE HISH | LACTOCOCCUS LACTIS | 7–34 | | | | | | | | |
| PHIS6_ECOLI | HISF PROTEIN | ESCHERICHIA COLI | 39–66 | 142–169 | | | | | | | |
| PHIS6_SALTY | HISF PROTEIN | SALMONELLA TYPHIMURIUM | 39–66 | 142–169 | | | | | | | |
| PHIS7_ECOLI | IMIDAZOLEGLYCEROL-PHOSPHATE DEHYDRATASE | ESCHERICHIA COLI | 168–199 | | | | | | | | |
| PHIS7_SALTY | IMIDAZOLEGLYCEROL-PHOSPHATE DEHYDRATASE | SALMONELLA TYPHIMURIUM | 161–199 | | | | | | | | |
| PHIS8_ECOLI | HISTIDINOL-PHOSPHATE AMINOTRANSFERASE | ESCHERICHIA COLI | 290–317 | | | | | | | | |
| PHIS8_HALVO | HISTIDINOL-PHOSPHATE AMINOTRANSFERASE | HALOBACTERIUM VOLCANII | 174–201 | | | | | | | | |
| PHIS8_LACLA | HISTIDINOL-PHOSPHATE AMINOTRANSFERASE | LACTOCOCCUS LACTIS | 161–188 | | | | | | | | |
| PHIS8_SALTY | HISTIDINOL-PHOSPHATE AMINOTRANSFERASE | SALMONELLA TYPHIMURIUM | 293–320 | | | | | | | | |
| PHISQ_SALTY | HISTIDINE PERMEASE MEMBRANE Q PROTEIN | SALMONELLA TYPHIMURIUM | 8–35 | | | | | | | | |
| PHISX_ECOLI | HISTIDINOL DEHYDROGENASE | ESCHERICHIA COLI | 393–434 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHISX_LACLA | HISTIDINOL DEHYDRO-GENASE | LACTOCOCCUS LACTIS | 19–46 | 264–303 | | | | | | | |
| PHISX_MYCSM | HISTIDINOL DEHYDRO-GENASE | MYCOBACTERIUM SMEGMATIS | 288–329 | 399–430 | | | | | | | |
| PHISX_SALTY | HISTIDINOL DEHYDRO-GENASE | SALMONELLA TYPHIMURIUM | 393–434 | | | | | | | | |
| PHLA_STAAU | ALPHA-HEMOLYSIN PRECURSOR | STAPHYLOCOCCUS AUREUS | 69–102 | | | | | | | | |
| PHLY1_ECOLI | HEMOLYSIN A, CHROMO-SOMAL | ESCHERICHIA COLI | 5–32 | 76–103 | 161–224 | 234–261 | 353–380 | 458–492 | 554–581 | 642–728 | |
| PHLY2_ECOLI | HAEMOLYSIN SECRETION PROTEIN, CHROMOSOMA | ESCHERICHIA COLI | 487–514 | | | | | | | | |
| PHLY4_ECOLI | HEMOLYSIN D, CHROMO-SOMAL | ESCHERICHIA COLI | 103–133 | 178–215 | 223–331 | | | | | | |
| PHLYA_ACTPL | HEMOLYSIN | ACTINOBACILLUS PLEURO-PNEUMONIAE | 5–39 | 136–170 | 184–218 | 273–300 | 350–377 | 459–527 | 846–924 | | |
| PHLYA_ACTSU | HEMOLYSIN | ACTINOBACILLUS SUIS | 5–39 | 136–170 | 184–218 | 273–300 | 350–377 | 459–527 | 846–924 | | |
| PHLYA_ECOLI | HEMOLYSIN A, PLASMID | ESCHERICHIA COLI | 5–32 | 76–103 | 161–262 | 354–381 | 452–493 | 555–582 | 643–729 | 705–742 | 747–774 |
| PHLYA_PROMI | HEMOLYSIN PRECURSOR | PROTEUS MIRABILIS | 165–196 789–823 | 299–338 841–868 | 356–400 966–993 | 425–471 1113–1140 | 498–525 1166–1193 | 528–576 1225–1273 | 610–695 1301–1342 | 1391–1461 | 1483–1527 |
| PHLYA_SERMA | HEMOLYSIN PRECURSOR | SERRATIA MARCESCENS | 311–345 1516–1553 | 477–504 | 558–585 | 625–703 | 718–745 | 830–864 | 1081–1108 | 1155–1202 | 1249–1286 |
| PHLYB_VIBCH | HEMOLYSIN PRECURSOR | VIBRIO CHOLERAE | 335–369 | 638–665 | | | | | | | |
| PHLYB_ACTPL | HAEMOLYSIN SECRETION PROTEIN | ACTINOBACILLUS PLEURO-PNEUMONIAE | 34–61 | | | | | | | | |
| PHLYB_ECOLI | HAEMOLYSIN SECRETION PROTEIN, PLASMID | ESCHERICHIA COLI | 487–514 | | | | | | | | |
| PHLYB_PROMI | HEMOLYSIN ACTIVATOR PROTEIN PRECURSOR | PROTEUS MIRABILIS | 16–64 | 499–547 | | | | | | | |
| PHLYB_PROVU | HAEMOLYSIN SECRETION PROTEIN | PROTEUS VULGARIS | 34–68 | 487–514 | | | | | | | |
| PHLYB_SERMA | HEMOLYSIN ACTIVATOR PROTEIN PRECURSOR | SERRATIA MARCESCENS | 110–137 | | | | | | | | |
| PHLYB_VIBCH | HEMOLYSIN SECRETION PROTEIN PRECURSOR | VIBRIO CHOLERAE | 335–398 | 413–447 | 458–524 | | | | | | |
| PHLYC_ACTPL | HEMOLYSIN C | ACTINOBACILLUS PLEURO-PNEUMONIAE | 130–157 | | | | | | | | |
| PHLYD_ACTPL | HEMOLYSIN SECRETION PROTEIN APPD | ACTINOBACILLUS PLEURO-PNEUMONIAE | 191–331 | | | | | | | | |
| PHLYD_ECOLI | HEMOLYSIN D, PLASMID | ESCHERICHIA COLI | 103–133 | 178–215 | 223–331 | | | | | | |
| PHLY_HALI7 | HALOLYSIN PRECURSOR | HALOPHILIC BACTERIA STRAIN 172P1 | 484–516 | | | | | | | | |
| PHMC3_DESVH | 43.2 KD PROTEIN IN HMC OPERON | DESULFOBIVRIO VULGARIS | 156–186 | | | | | | | | |
| PHMD_METKA | H(2)-FORMING DEHYDRO-GENASE | METHANOPYRUS KANDLERI | 36–63 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHNS_SERMA | DNA-BINDING PROTEIN H-NS | SERRATIA MARCESCENS | 35–62 | | | | | | | | |
| PHOLA_ECOLI | DNA POLYMERASE III, DELTA SUBUNIT | ESCHERICHIA COLI | 94–121 | 288–322 | | | | | | | |
| PHOXA_BRAJA | REG PROTEIN HOXA | BRADYRHIZOBIUM JAPONICUM | 113–163 | 444–471 | | | | | | | |
| PHOXF_NOCOP | HOXS ALPHA SUBUNIT | NOCARDIA OPACA | 4–31 | | | | | | | | |
| PHOXQ_ALCEU | HOXQ PROTEIN | ALCALIGENES EUTROPHUS | 76–110 | | | | | | | | |
| PHOXX_BRAJA | HOXX PROTEIN | BRADYRHIZOBIUM JAPONICUM | 356–383 | | | | | | | | |
| PHPL_DEIRA | HEXAGONALLY SURFACE PROTEIN PRECURSOR | DEINOCCCUS RADIODURANS | 585–612 | | | | | | | | |
| PHPRT_LACLA | PHOSPHORIBOSYL-TRANSFERASE | LACTOCOCCUS LACTIS | 3–39 | 71–105 | | | | | | | |
| PHRDD_STRCO | SIGMA FACTOR HRDD | STREPTOMYCES COELICOLOR | 296–323 | | | | | | | | |
| PHRPB_BURSO | REGULATORY PROTEIN HRPB | BURKHOLDERIA SOLANACEARUM | 371–405 | | | | | | | | |
| PHRPH_PSESY | OUTER MEMBRANE PROTEIN HRPH PRECURSOR | PSEUDOMONAS SYRINGAE | 102–129 | 310–344 | | | | | | | |
| PHRPS_PSESH | PROBABLE REGULATORY PROTEIN HRPS | PSEUDOMONAS SYRINGAE | 24–51 | | | | | | | | |
| PHS18_CLOAB | 18 KB HEAT SHOCK PROTEIN | CLOSTRIDIUM ACETOBUTYLICUM | 67–108 | | | | | | | | |
| PHS70_HALMA | HEAT SHOCK 70 KD PROTEIN | HALOARCULA MARISMORTUI | 522–576 | | | | | | | | |
| PHS70_MYCLE | HEAT SHOCK 70 KD PROTEIN | MYCOBACTERIUM LEPRAE | 461–488 | 503–530 | | | | | | | |
| PHS70_MYCPA | HEAT SHOCK 70 KD PROTEIN | MYCOBACTERIUM PARA-TUBERCULOSIS | 460–487 | | | | | | | | |
| PHTPG_ECOLI | HEAT SHOCK PROTEIN C62.5 | ESCHERICHIA COLI | 221–248 | 482–509 | | | | | | | |
| PHTRA_ECOLI | PROTEASE DO PRECURSOR | ESCHERICHIA COLI | 373–400 | | | | | | | | |
| PHTRE_ECOLI | HTRE PROTEIN PRECURSOR | ESCHERICHIA COLI | 454–484 | 524–576 | | | | | | | |
| PHTRJ_HALHA | SENSORY RHODOPSIN I TRANSDUCER | HALOBACTERIUM HALOBIUM | 413–471 | 479–506 | | | | | | | |
| PHTRJ_HALSA | SENSORY RHODOPSIN I TRANSDUCER | HALOBACTERIUM SALINARIUM | 114–159 | 413–471 | 479–506 | | | | | | |
| PHUTP_BACSU | HUT OPERON POSITIVE REGULATORY PROTEIN | BACILLUS SUBTILIS | 5–36 | | | | | | | | |
| PHVTJ_LACHE | HELVETICIN J | LACTOBACILLUS HELVETICUS | 174–212 | 306–333 | | | | | | | |
| PHYCA_ECOLI | FORMATE HYDROGENYLASE SUBUNIT 1 | ESCHERICHIA COLI | 73–100 | 106–133 | | | | | | | |
| PHYDG_ECOLI | TRANSCRIPTIONAL REGULATORY PROTEIN HYDG | ESCHERICHIA COLI | 251–278 | | | | | | | | |
| PHYDG_SALTY | TRANSCRIPTIONAL REGULATORY PROTEIN HYDG | SALMONELLA TYPHIMURIUM | 251–278 | | | | | | | | |
| PHYDH_ECOLI | SENSOR PROTEIN HYDH | ESCHERICHIA COLI | 312–339 | 360–387 | | | | | | | |
| PHYUB_PSESN | HYDANTOIN UTILIZATION PROTEIN B | PSEUDOMONAS SP | 554–581 | | | | | | | | |
| PHYUC_PSESN | HYDANTOIN UTILIZATION PROTEIN | PSEUDOMONAS SP | 6–40 | 96–123 | | | | | | | |
| PIAAL_PSESS | INDOLEACETATE-LYSINE LIGASE | PSEUDOMONAS SYRINGAE | 133–160 | 297–331 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PIAP_ECOLI | ALK PHOS ISOZYME CONVERSION PROTEIN | ESCHERICHIA COLI | 74–101 | | | | | | | | |
| PICEN_ERWAN | ICE NUCLEATION PROTEIN | ERWINIA ANANAS | 326–353 1046–1073 | 422–449 | 534–561 | 614–641 | 662–689 | 721–748 | 758–785 | 854–881 | 950–977 |
| PICEN_ERWHE | ICE NUCLEATION PROTEIN | ERWINIA HERBIOCOLA | 310–337 | 406–433 | 534–561 | 646–673 | 694–721 | 838–865 | 886–913 | 982–1009 | |
| PICEN_PSEFL | ICE NUCLEATION PROTEIN | PSEUDOMONAS FLUORESCENS | 281–308 | 377–404 | 425–452 | 681–708 | 729–781 | 795–852 | | | |
| PICEN_PSESY | ICE NUCLEATION PROTEIN | PSEUDOMONAS SYRINGAE | 564–602 | 772–847 | 868–895 | 909–943 | | | | | |
| PICEN_XANCT | ICE NUCLEATION PROTEIN | XANTHOMONAS CAMPESTRIS | 496–534 | 555–582 | 1168–1204 | 1248–1275 | | | | | |
| PICSB_SHIFL | INTERCELLULAR SPREAD PROTEIN | SHIGELLA FLEXNERI | 41–105 | 438–467 | | | | | | | |
| PIF2_BACST | INITIATION FACTOR IF-2 | BACILLUS STEAROTHERMOPHILUS | 540–567 | 681–708 | | | | | | | |
| PIF2_BACSU | INITIATION FACTOR IF-2 | BACILLUS SUBTILIS | 173–208 | 394–421 | | | | | | | |
| PIF2_ECOLI | INITIATION FACTOR IF-2 | ESCHERICHIA COLI | 686–724 | 835–862 | | | | | | | |
| PIF2_ENTFC | INITIATION FACTOR IF-2 | ENTEROCOCCUS FAECIUM | 579–627 | | | | | | | | |
| PIF3_BACST | INITIATION FACTOR IF-3 | BACILLUS STEAROTHERMOPHILUS | 7–34 | | | | | | | | |
| PIF3_ECOLI | INITIATION FACTOR IF-3 | ESCHERICHIA COLI | 27–54 | 70–97 | | | | | | | |
| PIF3_KLEPN | INITIATION FACTOR IF-3 | KLEBSIELLA PNEUMONIAE | 27–54 | 70–97 | | | | | | | |
| PIF3_MYCFE | INITIATION FACTOR IF-3 | MYCOPLASMA FERMENTANS | 177–211 | | | | | | | | |
| PIF3_PROVU | INITIATION FACTOR IF-3 | PROTEUS VULGARIS | 2–29 | 70–97 | | | | | | | |
| PIF3_SALTY | INITIATION FACTOR IF-3 | SALMONELLA TYPHIMURIUM | 27–54 | 70–97 | | | | | | | |
| PIF3_SERMA | INITIATION FACTOR IF-3 | SERRATIA MARCESCENS | 19–46 | 70–97 | | | | | | | |
| PIGA_NEIGO | IGA-SPECIFIC SERINE ENDOPEPTIDASE | NEISSERIA GONORRHOEAE | 245–272 | 287–314 | 833–860 | 1024–1058 | 1377–1404 | 1483–1531 | | | |
| PIGGB_STRSP | IGG BINDING PROTEIN PRECURSOR | STREPTOCOCCUS SP | 46–76 | 120–150 | 195–222 | | | | | | |
| PIGGG_STRSP | IGG BINDING PROTEIN PRECURSOR | STREPTOCOCCUS SP | 46–76 | 120–150 | 195–225 | 270–297 | | | | | |
| PILVH_ECOLI | ACETOLACTATE SYNTHASE | ESCHERICHIA COLI | 47–81 | 120–147 | | | | | | | |
| PILVH_SALTY | ACETOLACTATE SYNTHASE | SALMONELLA TYPHIMURIUM | 47–81 | 120–147 | | | | | | | |
| PILVN_LACLA | ACETOLACTATE SYNTHASE | LACTOCOCCUS LACTIS | 20–75 | | | | | | | | |
| PIMPB_SALTY | IMPB PROTEIN | SALMONELLA TYPHIMURIUM | 185–212 | | | | | | | | |
| PIMP_ACICA | INOSINE-5′-MONOPHOSPHATE DEHYDROGENASE | ACINETOBACTER CALCOACETICUS | 166–193 | | | | | | | | |
| PIMP_BACSU | E-5′-MONOPHOSPHATE DEHYDROGENASE | BACILLUS SUBTILIS | 159–186 | | | | | | | | |
| PINA_BACTL | IMMUNE INHIBITOR A PRECURSOR | BACILLUS THURINGIENSIS | 103–130 | 324–358 | | | | | | | |
| PINLA_LISMO | INTERNALIN A | LISTERIA MONOCYTOGENES | 106–143 | 161–188 | 196–232 | | | | | | |
| PINLB_LISMO | INTERNALIN B PRECURSOR | LISTERIA MONOCYTOGENES | 53–94 | 166–200 | 385–415 | | | | | | |
| PINVA_YEREN | INVASIN | YERSINIA ENTEROCOLITICA | 501–535 | | | | | | | | |
| PIPA7_SHIFL | 60 KD ANTIGEN | SHIGELLA FLEXNERI | 285–312 | | | | | | | | |
| PIPAA_SHIFL | 70 KD ANTIGEN | SHIGELLA FLEXNERI | 95–136 | 437–475 | 493–557 | 596–630 | | | | | |
| PIPAB_SHIDY | 62 KD MEMBRANE ANTIGEN | SHIGELLA DYSENTERIAE | 28–55 | 71–169 | 480–507 | 522–556 | | | | | |
| PIPAB_SHIFL | 62 KD MEMBRANE ANTIGEN | SHIGELLA FLEXNERI | 28–55 | 71–169 | 480–507 | 522–556 | | | | | |
| PIPAC_SHIDY | 42 KD MEMBRANE ANTIGEN PRECURSOR | SHIGELLA DYSENTERIAE | 21–57 | 113–161 | 273–300 | 324–378 | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PIPAC_SHIFL | 42 KD MEMBRANE ANTIGEN PRECURSOR | SHIGELLA FLEXNERI | 28–57 | 113–161 | 273–300 | 324–372 | | | | | |
| PIPAD_SHIDY | 37 KD MEMBRANE ANTIGEN IPAD | SHIGELLA DYSENTERIAE | 47–86 | 291–318 | | | | | | | |
| PIPAD_SHIFL | 36 KD MEMBRANE ANTIGEN IPGB PROTEIN | SHIGELLA FLEXNERI | 47–86 | 259–286 | 291–318 | | | | | | |
| PIPGB_SHIDY | IPGB PROTEIN | SHIGELLA DYSENTERIAE | 175–202 | | | | | | | | |
| PIPGB_SHIFL | IPGB PROTEIN | SHIGELLA FLEXNERI | 175–202 | | | | | | | | |
| PIPT_PSESS | ISOPENTENYL TRANSFERASE | PSEUDOMONAS SYRINGAE | 53–87 | 143–173 | | | | | | | |
| PIPYR_ECOLI | INORGANIC PYROPHOSPHA-TASE | ESCHERICHIA COLI | 138–172 | | | | | | | | |
| PIRGA_VIBCH | VIRULENCE PROTEIN PRECURSOR | VIBRIO CHOLERAE | 212–239 | 336–377 | | | | | | | |
| PIRGB_VIBCH | VIRULENCE REGULATORY PROTEIN IRGB | VIBRIO CHOLERAE | | 67–97 | | | | | | | |
| PIRPA_SYNP7 | IRON-REGULATED PROTEIN A | SYNECHOCOCCUS SP | 167–194 | | | | | | | | |
| PISBD_SHIDY | INSERTION ELEMENT ISO-ISID PROTEIN INSB | SHIGELLA DYSENTERIAE | 86–113 | | | | | | | | |
| PISBN_SHIDY | INSERTION ELEMENT ISO-ISIN PROTEIN INSB | SHIGELLA DYSENTERIAE | 6–37 | | | | | | | | |
| PISB_ECOLI | INSERTION ELEMENT IS1 PROTEIN INSB | ESCHERICHIA COLI | 122–149 | | | | | | | | |
| PISB_SHIFL | INSERTION ELEMENT IS1 PROTEIN INSB | SHIGELLA FLEXNERI | 86–113 | | | | | | | | |
| PISB_SHISO | INSERTION ELEMENT IS1 PROTEIN INSB | SHIGELLA SONNEI | 86–113 | | | | | | | | |
| PISP1_BACSU | MAJOR INTRACELLULAR SERINE PROTEASE | BACILLUS SUBTILIS | 115–142 | 197–224 | 253–280 | | | | | | |
| PISP_BACPO | INTRACELLULAR SERINE PROTEASE | BACILLUS POLYMYXA | 109–143 | | | | | | | | |
| PISTA_ECOLI | ISTA PROTEIN | ESCHERICHIA COLI | 183–210 | | | | | | | | |
| PISTA_SHISO | ISTA PROTEIN | SHIGELLA SONNEI | 183–210 | | | | | | | | |
| PIUTA_ECOLI | FERRIC AEROBACTIN RECEPTOR PRECURSOR | ESCHERICHIA COLI | 186–213 | 525–552 | 559–593 | | | | | | |
| PJAG_BACSU | JAG PROTEIN | BACILLUS SUBTILIS | 68–95 | | | | | | | | |
| PK6P2_ECOLI | 6-PHOSPHOFRUCTOKINASE ISOZYME 2 | ESCHERICHIA COLI | 143–170 | | | | | | | | |
| PKAD_BACSU | ADENYLATE KINASE | BACILLUS SUBTILIS | 188–215 | | | | | | | | |
| PKAD_LACLA | ADENYLATE KINASE | LACTOCOCCUS LACTIS | 186–213 | | | | | | | | |
| PKANU_BACSP | KANAMYCIN NUCLEOTIDYL-TRANSFERASE | BACILLUS SP | 69–96 | | | | | | | | |
| PKANU_STAAU | KANAMYCIN NUCLEOTIDYL-TRANSFERASE | STAPHYLOCOCCUS AUREUS | 69–96 | | | | | | | | |
| PKDGT_ECOLI | 2-KETO-3-DEOXYGLUCONATE PERMEASE | ESCHERICHIA COLI | 70–97 | | | | | | | | |
| PKDGT_ERWCH | 2-KETO-3-DEOXYGLUCONATE PERMEASE | ERWINIA CHRYSANTHEMI | 126–153 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PKDTA_ECOLI | 3-DEOXY-D-MANNO-OCTULOSONIC-ACID TRANS | ESCHERICHIA COLI | 369–396 | | | | | | | | |
| PKGTP_ECOLI | ALPHA-DETOGLUTARATE PERMEASE | ESCHERICHIA COLI | 7–34 | | | | | | | | |
| PKGUA_ECOLI | GUANYLATE KINASE | ESCHERICHIA COLI | 162–189 | | | | | | | | |
| PKHSE_BACSU | HOMOSERINE KINASE | BACILLUS SUBTILIS | 49–76 | | | | | | | | |
| PKHSE_FREDI | HOMOSERINE KINASE | FREMYELLA DIPLOSIPHON | 52–79 | | | | | | | | |
| PKKA4_BACCI | AMINOGLYCOSIDE 3'-PHOSPHOTRANSFERASE | BACILLUS CIRCULANS | 12–39 | | | | | | | | |
| PKORB_ECOLI | KORB TRANSCRIPTIONAL REPRESSOR PROTEIN | ESCHERICHIA COLI | 228–255 | | | | | | | | |
| PKPY1_SPICI | PYRUVATE KINASE | SPIROPLASMA CITRI | 112–148 | | | | | | | | |
| PKPYK_BACST | PYRUVATE KINASE | BACILLUS STEAROTHERMOPHILUS | 331–374 | | | | | | | | |
| PLACA_STAAU | ISOMERASE LACA SUBUNIT | STAPHYLOCOCCUS AUREUS | 9–64 | | | | | | | | |
| PLACA_STRMU | ISOMERASE LACA SUBUNIT | STAPHYLOCOCCUS MUTANS | 26–60 | | | | | | | | |
| PLACA_STRMU | TAGATOSE-6-PHOSPHATE KINASE | STAPHYLOCOCCUS MUTANS | 56–83 | 283–310 | | | | | | | |
| PLACG_LACCA | 6-PHOSPHO-BETA-GALACTO-SIDASE | LACTOBACILLUS CASEI | 290–317 | | | | | | | | |
| PLACL_ECOLI | LACTOSE OPERON REPRESSOR | ESCHERICHIA COLI | 9–36 | | | | | | | | |
| PLACL_KLEPN | LACTOSE OPERON REPRESSOR | KLEBSIELLA PNEUMONIAE | 195–229 | | | | | | | | |
| PLACR_STAAU | PHOSPHOTRANSFERASE REPRESSOR | STAPHYLOCOCCUS AUREUS | 2–29 | | | | | | | | |
| PLACR_STRMU | PHOSPHOTRANSFERASE REPRESSOR | STREPTOCOCCUS MUTANS | 2–32 | | | | | | | | |
| PLACY_LACDE | LACTOSE PERMEASE | LACTOBACILLUS DELBRUECKII | 196–230 | | | | | | | | |
| PLAFB_VIBPA | FLAGELLAR HOOK-ASSOCIATED PROTEIN 2 | VIBRIO PARAHAEMOLYTICUS | 62–89 | 388–415 | | | | | | | |
| PLAMB_KLEPN | MALTOPORIN PRECURSOR | KLEBSIELLA PNEUMONIAE | 337–364 | | | | | | | | |
| PLAMI_CLOTM | ENDO-1,3(4)-BETA-GLUCANASE PRECURSOR | CLOSTRIDIUM THERMOCELLUM | 132–159 | | | | | | | | |
| PLASI_PSEAE | OHH1 SYNTHESIS PROTEIN LASI | PSEUDOMONAS AERUGINOSA | 171–198 | | | | | | | | |
| PLCCI_LEUGE | PROBABLE LEUCOCIN A IMMUNITY PROTEIN | LEUCONOSTOC GELIDUM | 41–71 | | | | | | | | |
| PLCNC_LACLA | LACTOCOCCIN A SECRETION PROTEIN LCNC | LACTOCOCCUS LACTIS | 162–189 | 207–234 | 388–433 | | | | | | |
| PLCND_LACLA | LACTOCOCCIN A SECRETION PROTEIN LCND | LACTOCOCCUS LACTIS | 99–126 | 140–202 | 237–307 | | | | | | |
| PLCRD_YEREN | LOW CALCIUM RESPONSE LOCUS PROTEIN D | YERSINIA ENTEROCOLITICA | 122–149 | 491–518 | | | | | | | |
| PLCRD_YERPE | LOW CALCIUM RESPONSE LOCUS PROTEIN D | YERSINIA PESTIS | 122–149 | 491–518 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PLCRV_YERPE | VIRULENCE-ASSOCIATED V ANTIGEN | *YERSINIA PESTIS* | 22–49 | 157–184 | 240–267 | | | | | | |
| PLCRV_YERPS | VIRULENCE-ASSOCIATED V ANTIGEN | *YERSINIA PSEUDOTUBERCULOSIS* | 22–49 | 240–267 | | | | | | | |
| PLCTB_BACCA | LCTB PROTEIN | *BACILLUS CALDOTENAX* | 18–45 | | | | | | | | |
| PLCTB_BACST | LCTB PROTEIN | *BACILLUS STEAROTHERMOPHILUS* | 14–45 | | | | | | | | |
| PLDHD_LACPL | D-LACTATE DEHYDRO-GENASE | *LACTOBACILLUS PLANTARUM* | 51–81 | | | | | | | | |
| PLDHP_BACPS | L-LACTATE DEHYDRO-GENASE P | *BACILLUS PSYCHRO-SACCHAROLYTICUS* | 2–43 | 241–272 | 279–306 | | | | | | |
| PLDHX_BACPS | L-LACTATE DEHYDRO-GENASE X | *BACILLUS PSYCHRO-SACCHAROLYTICUS* | 2–43 | 241–275 | 279–306 | | | | | | |
| PLDH_BACME | L-LACTATE DEHYDRO-GENASE | *BACILLUS MEGATERIUM* | 244–274 | | | | | | | | |
| PLDH_BACST | L-LACTATE DEHYDRO-GENASE | *BACILLUS STEAROTHERMOPHILUS* | 241–268 | 279–313 | | | | | | | |
| PLDH_BACSU | L-LACTATE DEHYDRO-GENASE | *BACILLUS SUBTILIS* | 8–42 | 240–267 | | | | | | | |
| PLDH_BIFLO | L-LACTATE DEHYDRO-GENASE | *BIFIDOBACTERIUM LONGUM* | 22–49 | | | | | | | | |
| PLDH_LACPL | L-LACTATE DEHYDRO-GENASE | *LACTOBACILLUS PLANTARUM* | 197–231 | | | | | | | | |
| PLDH_LISMO | L-LACTATE DEHYDRO-GENASE | *LISTERIA MONOCYTOGENES* | 42–69 | | | | | | | | |
| PLDH_MYCHY | L-LACTATE DEHYDRO-GENASE | *MYCOPLASMA HYOPNEUMONIAE* | 276–310 | | | | | | | | |
| PLDH_THEAQ | L-LACTATE DEHYDRO-GENASE | *THERMUS AQUATICUS* | 3–30 | | | | | | | | |
| PLEF_BACAN | LETHAL FACTOR PRECURSOR | *BACILLUS ANTHRACIS* | 165–192 | 304–331 | 480–514 | 548–578 | 619–658 | 737–764 | | | |
| PLEPA_PSEFL | LEPA PROTEIN | *PSEUDOMONAS FLUORESCENS* | 23–50 | | | | | | | | |
| PLEP_BACSU | SIGNAL PEPTIDASE I | *BACILLUS SUBTILIS* | 3–30 | | | | | | | | |
| PLEU1_ECOLI | 2-ISOPROPYLMALATE SYNTHASE | *ESCHERICHIA COLI* | 437–464 | | | | | | | | |
| PLEU1_LACLA | 2-ISOPROPYLMALATE SYNTHASE | *LACTOCOCCUS LACTIS* | 22–49 | 379–484 | | | | | | | |
| PLEU3_BACCO | 3-ISOPROPYLMALATE DEHYDROGENASE | *BACILLUS COAGULANS* | 331–358 | | | | | | | | |
| PLEU3_CLOPA | 3-ISOPROPYLMALATE DEHYDROGENASE | *CLOSTRIDIUM PASTEURIANUM* | 185–212 | | | | | | | | |
| PLEUD_LACLA | 3-ISOPROPYLMALATE DEHYDRATASE | *LACTOCOCCUS LACTIS* | 163–190 | | | | | | | | |
| PLEVR_BACSU | TRANSCRIPTIONAL REGULA-TORY PROTEIN LEVR | *BACILLUS SUBTILIS* | 297–324 | 676–703 | 744–774 | 785–822 | | | | | |
| PLEXA_ERWCA | LEXA REPRESSOR | *ERWINIA CAROTOVORA* | 146–173 | | | | | | | | |
| PLIP1_MORSP | LIPASE 1 | MORAXELLA SP | 26–53 | | | | | | | | |
| PLIP2_MORSP | LIPASE 2 | MORAXELLA SP | 356–383 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PLIPB_ECOLI | LIPB PROTEIN | ESCHERICHIA COLI | 66–93 | | | | | | | | |
| PLIP_BURCE | LIPASE PRECURSOR | BURKHOLDERIA CEPACIA | 176–203 | | | | | | | | |
| PLIP_PSEFL | LIPASE PRECURSOR | PSEUDOMONAS FLUORESCENS | 8–35 | | | | | | | | |
| PLIP_PSES5 | LIPASE PRECURSOR | PSEUDOMONAS SP | 176–203 | | | | | | | | |
| PLIP_STAAU | LIPASE PRECURSOR | STAPHYLOCOCCUS AUREUS | 80–146 | 512–546 | | | | | | | |
| PLIVB_SALTY | LEU/ILE/VAL/THR-BINDING PROTEIN PRECURSOR | SALMONELLA TYPHIMURIUM | 193–220 | | | | | | | | |
| PLIVC_SALTY | LEUCINE-SPECIFIC BINDING PROTEIN PRECURSOR | SALMONELLA TYPHIMURIUM | 195–222 | | | | | | | | |
| PLIVE_SALTY | AMINO ACID TRANSPORT PROTEIN LIVE | SALMONELLA TYPHIMURIUM | 121–148 | | | | | | | | |
| PLIVF_ECOLI | AMINO ACID TRANSPORT PROTEIN LIVF | ESCHERICHIA COLI | 23–50 | | | | | | | | |
| PLIVI_CITFR | LEU/ILE/VAL-BINDING PROTEIN PRECURSOR | CITROBACTER FREUNDII | 195–222 | | | | | | | | |
| PLIVJ_ECOLI | LEU/ILE/VAL-BINDING PROTEIN PRECURSOR | ESCHERICHIA COLI | 195–222 | | | | | | | | |
| PLIVK_ECOLI | LEUCINE-SPECIFIC BINDING PROTEIN PRECURSOR | ESCHERICHIA COLI | 195–222 | | | | | | | | |
| PLIVM_ECOLI | AMINO ACID TRANSPORT PROTEIN LIVM | ESCHERICHIA COLI | 121–148 | | | | | | | | |
| PLKTA_ACTAC | LEUKOTOXIN | ACTINOBACILLUS ACTINO-MYCETEMCOMITANS | 113–147 | 173–213 | 398–443 | 451–488 | 593–620 | 655–711 | | | |
| PLKTB_PASHA | LEUKOTOXIN | PASTEURELLA HAEMOLYTICA | 53–99 | 179–216 | 345–372 | 409–436 | 455–482 | 496–530 | 545–572 | 811–838 | 853–926 |
| PLKTB_ACTAC | LEUKOTOXIN SECRETION PROTEIN | ACTINOBACILLUS ACTINO-MYCETEMCOMITANS | 487–514 | | | | | | | | |
| PLKTB_PASHA | LEUKOTOXIN SECRETION PROTEIN | PASTEURELLA HAEMOLYTICA | 42–69 | 78–105 | 488–515 | | | | | | |
| PLKTC_ACTAC | LTC PROTEIN | ACTINOBACILLUS ACTINO-MYCETEMCOMITANS | 58–85 | 116–150 | | | | | | | |
| PLKTC_PASHA | LKTC PROTEIN | PASTEURELLA HAEMOLYTICA | 123–157 | | | | | | | | |
| PLKTD_ACTAC | LKTD PROTEIN | ACTINOBACILLUS ACTINO-MYCETEMCOMITANS | 116–164 | 205–242 | 278–305 | 364–391 | | | | | |
| PLKTD_PASHA | LKTD PROTEIN | PASTEURELLA HAEMOLYTICA | 184–289 | | | | | | | | |
| PLON_ECOLI | ATP-DEPENDENT PROTEASE LA | ESCHERICHIA COLI | 121–148 | | | | | | | | |
| PLPXA_RICRI | UDP-N-ACETYLGLUCO-SAMINE ACYLTRANSFERASE | RICKETTSIA RICKETTSII | 229–256 | | | | | | | | |
| PLSPA_ECOLI | LIPOPROTEIN SIGNAL PEPTIDASE | ESCHERICHIA COLI | 10–37 | | | | | | | | |
| PLSPA_STAAU | LIPOPROTEIN SIGNAL PEPTIDASE | STAPHYLOCOCCUS AUREUS | 134–161 | | | | | | | | |
| PLUKF_STAAU | LEUKOCIDIN F SUBUNIT PRECURSOR | STAPHYLOCOCCUS AUREUS | 161–195 | | | | | | | | |
| PLUKS_STAAU | LEUKOCIDIN S SUBUNIT PRECURSOR | STAPHYLOCOCCUS AUREUS | 157–207 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PLUXA_KRYAL | ALKANAL MONOOXYGENASE ALPHA CHAIN | KRYPTOPHANARON ALFREDI | 190–217 | | | | | | | | |
| PLUXB_PHOPO | ALKANAL MONOOXYGENASE BETA CHAIN | PHOTOBACTERIUM PHOSPHOREUM | 188–217 | 257–291 | | | | | | | |
| PLUXB_VIBHA | ALKANAL MONOOXYGENASE BETA CHAIN | VIBRIO HARVEYI | 373–400 | | | | | | | | |
| PLUXC_PHOLE | ACYL-COA REDUCTASE | PHOTOBACTERIUM LEIOGNATHI | 44–81 | | | | | | | | |
| PLUXC_PHOPO | ACYL-COA REDUCTASE | PHOTOBACTERIUM PHOSPHOREUM | 54–91 | | | | | | | | |
| PLUXC_VIBFI | ACYL-COA REDUCTASE | VIBRIO FISCHERI | 16–65 | | | | | | | | |
| PLUXC_XENLU | ACYL-COA REDUCTASE | XENORHABDUS LUMINESCENS | 39–69 | | | | | | | | |
| PLUXD_PHOLE | ACYL TRANSFERASE | PHOTOBACTERIUM LEIOGNATHI | 89–119 | 218–245 | | | | | | | |
| PLUXE_VIBHA | LUCIFERIN-COMPONENT LIGASE | VIBRIO HARVEYI | 30–57 | | | | | | | | |
| PLUXF_PHOLE | NON-FLUORESCENT FLAVO-PROTEIN | PHOTOBACTERIUM LEIOGNATHI | 145–172 | | | | | | | | |
| PLUXF_PHOPO | NON-FLUORESCENT FLAVO-PROTEIN | PHOTOBACTERIUM PHOSPHOREUM | 37–85 | 99–126 | | | | | | | |
| PLUXG_VIBFI | PROBABLE FLAVIN REDUCTASE | VIBRIO FISCHERI | 137–168 | | | | | | | | |
| PLUXH_VIBHA | LUXH PROTEIN | VIBRIO HARVEYI | 96–123 | | | | | | | | |
| PLUXI_VIBFI | OHHL SYNTHESIS PROTEIN LUXI | VIBRIO FISCHERI | 30–58 | | | | | | | | |
| PLUXJ_VIBFI | OHHL SYNTHESIS PROTEIN LUXI | VIBRIO FISCHERI | 30–57 | | | | | | | | |
| PLUXP_PHOPO | LUMAZINE PROTEIN | PHOTOBACTERIUM PHOSPHOREUM | 51–85 | 162–189 | | | | | | | |
| PLUXR_VIBHA | LUXR REGULATORY PROTEIN | VIBRIO HARVEYI | 61–88 | | | | | | | | |
| PLXB1_PHOLE | ALKANAL MONOOXYGENASE BETA CHAIN | PHOTOBACTERIUM LEIOGNATHI | 268–295 | | | | | | | | |
| PLXB2_PHOLE | ALKANAL MONOOXYGENASE BETA CHAIN | PHOTOBACTERIUM LEIOGNATHI | 228–255 | | | | | | | | |
| PLYB_BACSU | B-ENZYME | BACILLUS SUBTILIS | 87–114 | | | | | | | | |
| PLYC_CLOAB | AUTOLYTIC LYSOZYME | CLOSTRIDIUM ACETOBUTYLICUM | 91–118 | | | | | | | | |
| PLYSP_ECOLI | LYSINE-SPECIFIC PERMEASE | ESCHERICHIA COLI | 142–176 | 150–177 | 467–513 | 555–585 | | | | | |
| PLYTB_BACSU | AMIDASE ENHANCER PRECURSOR | BACILLUS SUBTILIS | 55–82 | | | | | | | | |
| PLYTB_ECOLI | LYTB PROTEIN | ESCHERICHIA COLI | 210–237 | | | | | | | | |
| PLYTC_BACSU | AMIDASE PRECURSOR | BACILLUS SUBTILIS | 179–213 | 225–252 | | | | | | | |
| PLYTR_BACSU | MEMBRANE-BOUND PROTEIN LYTR | BACILLUS SUBTILIS | 13–64 | 259–303 | | | | | | | |
| PM12_STRPY | M PROTEIN, SEROTYPE 12 PRECURSOR | STREPTOCOCCUS PYOGENES | 46–92 | 114–156 | 191–300 | 305–342 | 383–417 | 436–494 | | | |
| PM24_STRPY | M PROTEIN, SEROTYPE 24 PRECURSOR | STREPTOCOCCUS PYOGENES | 12–46 | 89–128 | 175–202 | 245–272 | 280–313 | 399–457 | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PM49_STRPY | M PROTEIN, SEROTYPE 49 PRECURSOR | STREPTOCOCCUS PYOGENES | 12–174 | 269–327 | | | | | | | |
| PM5_STRPY | M PROTEIN, SEROTYPE 5 PRECURSOR | STREPTOCOCCUS PYOGENES | 5–39 | 56–263 | 306–333 | 352–410 | | | | | |
| PM6_STRPY | M PROTEIN, SEROTYPE 6 PRECURSOR | STREPTOCOCCUS PYOGENES | 12–39 | 70–282 | 290–324 | 343–401 | | | | | |
| PMALE_ECOLI | MALTOSE-BINDING PROTEIN PRECURSOR | ESCHERICHIA COLI | 20–47 | | | | | | | | |
| PMALE_ENTAE | MALTOSE-BINDING PROTEIN PRECURSOR | ENTEROBACTER AEROGENES | 20–47 | | | | | | | | |
| PMALK_ENTAE | INNER MEMBRANE PROTEIN MALK | ENTEROBACTER AEROGENES | 3–30 | | | | | | | | |
| PMALT_ECOLI | MALT REGULATORY PROTEIN | ESCHERICHIA COLI | 852–879 | | | | | | | | |
| PMALX_STRPN | MALX PROTEIN PRECURSOR | STREPTOCOCCUS PNEUMONIAE | 40–67 | 180–207 | | | | | | | |
| PMANB_BACSM | 1,4-BETA-MANNOSIDASE A AND B PREC | BACILLUS SP | 410–441 | | | | | | | | |
| PMANB_CALSA | B-MANNANASE/ENDO-GLUCANASE A PREC | CALDOCELLUM SACCHAROLYTICUM | 389–423 | 592–626 | 1222–1256 | 1296–1323 | | | | | |
| PMAOX_BACST | MALATE OXIDOREDUCTASE | BACILLUS STEAROTHERMOPHILUS | 246–273 | | | | | | | | |
| PMARR_ECOLI | ANTIBIOTIC RESISTANCE PROTEIN MARR | ESCHERICHIA COLI | 95–122 | | | | | | | | |
| PMBEB_ECOLI | MOBILIZATION PROTEIN MBEB | ESCHERICHIA COLI | 38–65 | 100–134 | | | | | | | |
| PMBHL_WOLSU | QUINONE-REAC NI/FE-HYDROGENASE | WOLINELLA SUCCINOGENES | 440–471 | | | | | | | | |
| PMCBB_ECOLI | MCBB PROTEIN | ESCHERICHIA COLI | 47–74 | 122–163 | | | | | | | |
| PMCBD_ECOLI | MCBD PROTEIN | ESCHERICHIA COLI | 172–206 | 226–253 | 306–345 | | | | | | |
| PMCP1_ECOLI | METHYL-ACCEPTING CHEMOTAXIS PROTEIN I | ESCHERICHIA COLI | 272–299 | | | | | | | | |
| PMCP2_ECOLI | METHYL-ACCEPTING CHEMOTAXIS PROTEIN II | ESCHERICHIA COLI | 258–306 | | | | | | | | |
| PMCP2_SALTY | METHYL-ACCEPTING CHEMOTAXIS PROTEIN II | SALMONELLA TYPHIMURIUM | 258–306 | | | | | | | | |
| PMCP3_ECOLI | METHYL-ACCEPTING CHEMOTAXIS PROTEIN III | ESCHERICHIA COLI | 288–315 | | | | | | | | |
| PMC4_ECOLI | METHYL-ACCEPTING CHEMOTAXIS PROTEIN IV | ESCHERICHIA COLI | 111–145 | 164–191 | 277–304 | | | | | | |
| PMCPA_CAUCR | CHEMORECEPTOR MCPA | CAULOBACTER CRESCENTUS | 260–287 | 369–403 | 516–543 | | | | | | |
| PMCPC_SALTY | CHEMOTAXIS CITRATE TRANDUCER | SALMONELLA TYPHIMURIUM | 314–348 | | | | | | | | |
| PMCPD_ENTAE | CHEMOTAXIS ASPARTATE TRANSDUCER | ENTEROBACTER AEROGENES | 275–302 | | | | | | | | |
| PMCPS_ENTAE | CHEMOTAXIS SERINE TRANSDUCER | ENTEROBACTER AEROGENES | 41–68 | 158–208 | 317–351 | 488–522 | | | | | |
| PMCRA_ECOLI | SPECIFIC RESTRICTION ENZYME A | ESCHERICHIA COLI | 37–71 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PMCRA_METBA | METHYL-COENZYME M REDUCTASE | METHANOSARCINA BARKERI | 375–405 | | | | | | | | |
| PMCRA_METVA | METHYL-COENZYME M REDUCTASE | METHANOCOCCUS VANNIELII | 335–362 | | | | | | | | |
| PMCRA_METVO | METHYL-COENZYME M REDUCTASE | METHANOCOCCUS VOLTAE | 336–363 | | | | | | | | |
| PMCRB_METFE | METHYL-COENZYME M REDUCTASE | METHANOTHERMUS FERVIDUS | 267–294 | | | | | | | | |
| PMCRB_METVO | METHYL-COENZYME M REDUCTASE | METHANOCOCCUS VOLTAE | 247–274 | | | | | | | | |
| PMCRC_ECOLI | MCRC PROTEIN | ESCHERICHIA COLI | 111–145 | | | | | | | | |
| PMCRD_METVO | REDUCTASE OPERON PROTEIN D | METHANOCOCCUS VOLTAE | 54–91 | | | | | | | | |
| PMDH_ECOLI | MALATE DEHYDROGENASE | ESCHERICHIA COLI | 127–154 | | | | | | | | |
| PMDH_METFE | MALATE DEHYDROGENASE | METHANOTHERMUS FERVIDUS | 54–88 | | | | | | | | |
| PMDH_SALTY | MALATE DEHYDROGENASE | SALMONELLA TYPHIMURIUM | 127–154 | | | | | | | | |
| PMDL_ECOLI | MDL PROTEIN | ESCHERICHIA COLI | 464–491 | 684–711 | | | | | | | |
| PMDOH_ECOLI | BIOSYNTHESIS PROTEIN MDOH | ESCHERICHIA COLI | 119–152 | | 992–1019 | | | | | | |
| PMECL_STAEP | METHICILLIN RESIS REG PROTEIN MECI | STAPHYLOCOCCUS EPIDERMIDIS & AUREUS | 88–122 | | | | | | | | |
| PMECR_STAEP | METHICILLIN RESISTANCE MECR1 PROTEIN | STAPHYLOCOCCUS EPIDERMIDIS & AUREUS | 439–495 | 546–573 | | | | | | | |
| PMEMB_METCA | METHANE MONOOXYGENASE COMPONENT A | METHYLOCOCCUS CAPSULATUS | 214–248 | | | | | | | | |
| PMEMB_METTR | METHANE MONOOXYGENASE COMPONENT A | METHYLOSINUS TRICHOSPORIUM | 321–348 | | | | | | | | |
| PMEND_ECOLI | SHCHC SYNTHASE | ESCHERICHIA COLI | 333–367 | | | | | | | | |
| PMER4_STRLI | PROBABLE HG TRANSPORT PROTEIN | STREPTOMYCES LIVIDANS | 159–186 | | | | | | | | |
| PMERA_BACSR | MERCURIC REDUCTASE | BACILLUS SP | 146–180 | | | | | | | | |
| PMERA_STAAU | MERCURIC REDUCTASE | STAPHYLOCOCCUS AUREUS | 292–347 | 352–386 | | | | | | | |
| PMERR_STAAU | MERCURIC RESISTANCE OPERON REG PROTEIN | STAPHYLOCOCCUS AUREUS | 86–113 | | | | | | | | |
| PMETB_ECOLI | CYSTATHIONINE GAMMA-SYNTHASE | ESCHERICHIA COLI | 356–383 | | | | | | | | |
| PMETC_ECOLI | CYSTATHIONINE BETA-LYASE | ESCHERICHIA COLI | 363–390 | | | | | | | | |
| PMETC_SALTY | CYSTATHIONINE BETA-LYASE | SALMONELLA TYPHIMURIUM | 2–29 | | | | | | | | |
| PMETE_ECOLI | METHIONINE SYNTHASE | ESCHERICHIA COLI | 448–482 | | | | | | | | |
| PMETH_ECOLI | METHIONINE SYNTHASE | ESCHERICHIA COLI | 371–398 | 642–676 | | | | | | | |
| PMFD_ECOLI | TRANSCRIPTION-REPAIR COUPLING FACTOR | ESCHERICHIA COLI | 185–212 | | | | | | | | |
| PMGLA_ECOLI | GALACTOSIDE-BINDING PROTEIN | ESCHERICHIA COLI | 62–89 | 312–380 | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PMINC_BACSU | SEPTUM SITE-DETERMINING PROTEIN MINC | BACILLUS SUBTILIS | 65–122 | | | | | | | | |
| PMIOC_ECOLI | MIOC PROTEIN | ESCHERICHIA COLI | 102–129 | | | | | | | | |
| PMIP_CHLTR | 27 KD MEMBRANE PROTEIN PRECURSOR | CHLAMYDIA TRACHOMATIS | 41–75 | | | | | | | | |
| PMIP_LEGMI | OUTER MEMBRANE PROTEIN MIP PRECURSOR | LEGIONELLA MICDADEI | 106–133 | | | | | | | | |
| PMLS1_ENTFA | RRNA ADENINE N-6-METHYL-TRANSFERASE | ENTEROCOCCUS FAECALIS | 4–81 | 20–154 | | | | | | | |
| PMLS1_STAAU | RRNA ADENINE N-6-METHYL-TRANSFERASE | STAPHYLOCOCCUS AUREUS | 9–47 | | | | | | | | |
| PMLS2_ENTFA | RRNA ADENINE N-6-METHYL-TRANSFERASE | ENTEROCOCCUS FAECALIS | 4–81 | 120–154 | | | | | | | |
| PMLSB_BACFR | RRNA ADENINE N-6-METHYL-TRANSFERASE | BACTEROIDES FRAGILIS | 16–43 | | | | | | | | |
| PMLSB_ECOLI | RRNA ADENINE N-6-METHYL-TRANSFERASE | ESCHERICHIA COLI | 4–81 | 120–154 | | | | | | | |
| PMLSB_STRPN | RRNA ADENINE N-6-METHYL-TRANSFERASE | STREPTOCOCCUS PNEUMONIAE | 4–81 | 120–154 | | | | | | | |
| PMLSB_STRSA | RRNA ADENINE N-6-METHYL-TRANSFERASE | STREPTOCOCCUS SANGUIS | 4–81 | 120–154 | | | | | | | |
| PMLSC_BACFR | RRNA ADENINE N-6-METHYL-TRANSFERASE | BACTEROIDES FRAGILIS | 16–43 | | | | | | | | |
| PMMOB_METC | METHANE MONOOXYGENASE REG PROTEIN B | METHYLOCOCCUS CAPSULATUS | 34–64 | | | | | | | | |
| PMOAB_ECOLI | MOLYBD COFAC BIOSYN PROTEIN B | ESCHERICHIA COLI | 49–76 | | | | | | | | |
| PMOBA_THIFE | MOBA PROTEIN | THIOBACILLUS FERROOXIDANS | 94–121 | 251–278 | | | | | | | |
| PMOBC_THIFE | MOBC PROTEIN | THIOBACILLUS FERROOXIDANS | 20–47 | | | | | | | | |
| PMOBD_THIFE | MOBD PROTEIN | THIOBACILLUS FERROOXIDANS | 95–132 | | | | | | | | |
| PMOB_ECOLI | MOB PROTEIN | ESCHERICHIA COLI | 45–72 | | | | | | | | |
| PMOEA_ECOLI | MOLYBDOPTERIN BIO-SYNTHESIS MOEA PROTEIN | ESCHERICHIA COLI | 243–270 | | | | | | | | |
| PMOP1_CLOPA | MOLYBDENUM-PTERIN BINDING PROTEIN I | CLOSTRIDIUM PASTEURIANUM | 26–53 | | | | | | | | |
| PMOP2_CLOPA | MOLYBDENUM-PTERIN BINDING PROTEIN II | CLOSTRIDIUM PASTEURIANUM | 26–64 | | | | | | | | |
| PMOXY_PARDE | METHANOL UTIL CONT PROTEIN MOXY | PARACOCCUS DENITRIFICANS | 200–234 | 307–334 | | | | | | | |
| PMPEU_SYNPY | BILIN BIOSYNTHESIS PROTEIN MPEU | SYNECHOCOCCUS SP | 2–36 | 80–107 | 198–225 | | | | | | |
| PMPEV_SYNPY | BILIN BIOSYNTHESIS PROTEIN MPEV | SYNECHOCOCCUS SP | 2–31 | 175–216 | | | | | | | |
| PMPRA_ECOLI | MPRA PROTEIN | ESCHERICHIA COLI | 136–163 | | | | | | | | |
| PMRAY_BACSU | PENTAPEPTIDE-TRANSFERASE | BACILLUS SUBTILIS | 106–133 | 247–281 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PMREB_BACCE | ROD SHAPE-DETERMINING PROTEIN MREB | BACILLUS CEREUS | 186–213 | | | | | | | | |
| PMREC_BACSU | ROD SHAPE-DETERMINING PROTEIN MREC | BACILLUS SUBTILIS | 65–112 | | | | | | | | |
| PMRKB_KLEPN | CHAPERONE PROTEIN MRKB PRECURSOR | KLEBSIELLA PNEUMONIAE | 198–232 | | | | | | | | |
| PMRKC_KLEPN | MRKC PROTEIN PRECURSOR | KLEBSIELLA PNEUMONIAE | 55–82 | 452–489 | 592–622 | | | | | | |
| PMRKD_KLEPN | FIMBRIA ADHESION PROTEIN PRECURSOR | KLEBSIELLA PNEUMONIAE | 222–268 | | | | | | | | |
| PMRKE_KLEPN | MRKE PROTEIN | KLEBSIELLA PNEUMONIAE | 193–220 | | | | | | | | |
| PMR4_STRPY | FIBRINOGEN-/IG-BINDING PROTEIN PRECURSOR | STREPTOCOCCUS PYOGENES | 7–46 | 99–310 | | | | | | | |
| PMRP_STRSU | MURAMIDASE-RELEASED PROTEIN PRECURSOR | STREPTOCOCCUS SUIS | 75–102 | 130–177 | 261–291 | 421–448 | 507–534 | 588–622 | 773–800 | 1058–1085 | |
| PMSBA_ECOLI | PROB ATP-BINDING TRANSPORT PROTEIN MSBA | ESCHERICHIA COLI | 116–150 | 412–449 | | | | | | | |
| PMSRA_STAEP | ERYTHROMYCIN RESISTANCE PROTEIN | STAPHYLOCOCCUS EPIDERMIDIS | 174–223 | 323–350 | | | | | | | |
| PMSYB_ECOLI | ACIDIC PROTEIN MSYB | ESCHERICHIA COLI | 73–100 | | | | | | | | |
| PMT57_ECOLI | MODIFICATION METHYLASE ECO571 | ESCHERICHIA COLI | 250–284 | 474–544 | | | | | | | |
| PMTA1_ACICA | MODIFICATION METHYLASE ACCI | ACINETOBACTER CALCOACETICUS | 503–540 | | | | | | | | |
| PMTAB_SYNP2 | MODIFICATION METHYLASE AQUI BETA SUBUNIT | SYNECHOCOCCUS SP | 19–46 | | | | | | | | |
| PMTB1_BREEP | MODIFICATION METHYLASE BEPI | BREVIBACTERIUM EPIDERMIDIS | 166–200 | 309–336 | | | | | | | |
| PMTB1_HERAU | MODIFICATION METHYLASE HGIBI | HERPETOSIPHON AURANTIACUS | 281–308 | | | | | | | | |
| PMTB2_BACAM | MODIFICATION METHYLASE BAMHI | BACILLUS AMYLOLIQUEFACIENS | 35–62 | | | | | | | | |
| PMTB3_BACAR | MODIFICATION METHYLASE BANII | BACILLUS ANEURINOLYTICUS | 184–211 | | | | | | | | |
| PMTBA_BACAR | MODIFICATION METHYLASE BANI | BACILLUS ANEURINOLYTICUS | 121–148 | 382–409 | | | | | | | |
| PMTBB_BACSU | MODIFICATION METHYLASE BSUBI | BACILLUS SUBTILIS | 231–258 | 467–496 | | | | | | | |
| PMTBF_BACSU | MODIFICATION METHYLASE BSUFI | BACILLUS SUBTILIS | 208–235 | | | | | | | | |
| PMTC1_CITFR | MODIFICATION METHYLASE CFRBI | CITROBACTER FREUNDII | 2–36 | 55–82 | 252–279 | | | | | | |
| PMTC1_HERAU | MODIFICATION METHYLASE HGICI | HERPETOSIPHON AURANTIACUS | 120–147 | | | | | | | | |
| PMTC2_HERAU | MODIFICATION METHYLASE HGICII | HERPETOSIPHON AURANTIACUS | 281–311 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PMTE1_ECOLI | MODIFICATION METHYLASE ECORI | ESCHERICHIA COLI | 76–110 | 145–172 | | | | | | | |
| PMTE1_HERAU | MODIFICATION METHYLASE HGIEI | HERPETOSIPHON AURANTIACUS | 281–308 | | | | | | | | |
| PMTE2_ECOLI | MODIFICATION METHYLASE ECORII | ESCHERICHIA COLI | 4–61 | | | | | | | | |
| PMTE5_ECOLI | MODIFICATION METHYLASE ECO RV | ESCHERICHIA COLI | 73–100 | | | | | | | | |
| PMTEC_ENTCL | MODIFICATION METHYLASE ECIA | ENTEROBACTER CLOACAE | 418–445 | | | | | | | | |
| PMTF1_FLAOK | MODIFICATION METHYLASE FOKI | FLAVOBACTERIUM OKEANOKOITES | 184–211 | 279–306 | 337–366 | 398–425 | 555–646 | | | | |
| PMTF1_FUSNU | MODIFICATION METHYLASE FNUDI | FUSOBACTERIUM NUCLEATUM | 22–49 | | | | | | | | |
| PMTG2_HAEGA | MODIFICATION METHYLASE HGAI-2 | HAEMOPHILUS GALLINARUM | 135–165 | | | | | | | | |
| PMTH2_HAEIN | MODIFICATION METHYLASE HINCII | HAEMOPHILUS INFLUENZAE | 181–208 | 399–426 | | | | | | | |
| PMTHZ_METTF | MODIFICATION METHYLASE MTHZI | METHANOBACTERIUM THERMOFORMICICUM | 188–215 | 296–323 | | | | | | | |
| PMTK1_KLEPN | MODIFICATION METHYLASE KPNI | KLEBSIELLA PNEUMONIAE | 270–297 | | | | | | | | |
| PMTLD_STRMU | MANNITOL-1-PHOSPHATE 5-DEHYDROGENASE | STREPTOCOCCUS MUTANS | 39–66 | 224–258 | 349–376 | | | | | | |
| PMTM1_MORSP | MODIFICATION METHYLASE MSPI | MORAXELLA SP | 5–39 | 49–104 | | | | | | | |
| PMTN3_NEILA | MODIFICATION METHYLASE NLAIII | NEISSERIA LACTAMICA | 124–158 | 183–210 | | | | | | | |
| PMTP2_PROVU | MODIFICATION METHYLASE PVU II | PROTEUS VULGARIS | 308–335 | | | | | | | | |
| PMTPG_SULAC | MEMBRANE-ASSOCIATED ATPASE | SULFOLOBUS ACIDOCALDARIUS | 9–67 | | | | | | | | |
| PMTPS_PROST | MODIFICATION METHYLASE PSTI | PROVIDENCIA STUARTII | 226–264 | | | | | | | | |
| PMTR_ECOLI | TRYPTOPHAN-SPECIFIC TRANSPORT PROTEIN | ESCHERICHIA COLI | 80–107 | | | | | | | | |
| PMTS1_STRSA | MODIFICATION METHYLASE STSI | STREPTOCOCCUS SANGUIS | 116–153 | 434–461 | 600–645 | | | | | | |
| PMTS2_SHISO | MODIFICATION METHYLASE SSOII | SHIGELLA SONNEI | 81–108 | | | | | | | | |
| PMTS9_STAAU | MODIFICATION METHYLASE SAU96I | STAPHYLOCOCCUS AUREUS | 233–274 | | | | | | | | |
| PMTSA_LACLC | MODIFICATION METHYLASE SCRFI-A | LACTOCOCCUS LACTIS | 88–115 | 187–214 | | | | | | | |
| PMTSB_LACLC | MODIFICATION METHYLASE SCRFI-B | LACTOCOCCUS LACTIS | 27–61 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PMTS1_SPISQ | CPG DNA METHYLASE | SPIROPLASMA SP | 188–230 | 256–290 | | | | | | | |
| PMTSM_SERMA | MODIFICATION METHYLASE SMAI | SERRATIA MARCESCENS | 61–88 | | | | | | | | |
| PMT8_THETH | MODIFICATION METHYLASE TTHHB8I | THERMUS AQUATICUS | 120–157 | | | | | | | | |
| PMTV1_VIBS3 | MODIFICATION METHYLASE VSPI | VIBRIO SP | 23–66 | | | | | | | | |
| PMUKB_ECOLI | MUKB PROTEIN | ESCHERICHIA COLI | 320–381 | 1014–1048 | 1216–1252 | | | | | | |
| PMULI_ERWAM | MAJOR OUTER MEMBRANE LIPOPROTEIN PREC | ERWINIA AMYLOVORA | 24–54 | | | | | | | | |
| PMULI_MORMO | MAJOR OUTER MEMBRANE LIPOPROTEIN PREC | MORGANELA MORGANII | 27–54 | | | | | | | | |
| PMULI_PROMI | MAJOR OUTER MEMBRANE LIPOPROTEIN PREC | PROTEUS MIRABILIS | 21–63 | | | | | | | | |
| PMURD_BACSU | UDP-LIGASE | BACILLUS SUBTILIS | 101–132 | 299–326 | | | | | | | |
| PMURE_ECOLI | LIGASE | ESCHERICHIA COLI | 107–134 | | | | | | | | |
| PMURF_ECOLI | UDP-MURNAC-PENTAPEPTIDE SYNTHETASE | ESCHERICHIA COLI | 407–437 | | | | | | | | |
| PMURZ_ECOLI | ENOYLPYRUVATE TRANSFERASE | ESCHERICHIA COLI | 392–419 | | | | | | | | |
| PMURZ_ENTCL | ENOYLPYRUVATE TRANSFERASE | ENTEROBACTER CLOACAE | 392–419 | | | | | | | | |
| PMUTA_STRCM | METHYLMALONYL-COA MUTASE BETA-SUBUNIT | STREPTOMYCES CINNAMONENSIS | 31–58 | | | | | | | | |
| PMUTB_PROFR | METHYLMALONYL-COA MUTASE ALPHA-SUBUNIT | PROPIONIBACTERIUM FREUDENREICHII | 549–576 | | | | | | | | |
| PMUTB_SALTY | SALMONELLA TYPHIMURIUM /G-SPECIFIC ADENINE GLYCOSYLASE | SALMONELLA TYPHIMURIUM | 273–300 | | | | | | | | |
| PMUTB_STRCM | METHYLMALONYL-COA MUTASE ALPHA-SUBUNIT | STREPTOMYCES CINNAMONENSIS | 481–508 | | | | | | | | |
| PMUTL_ECOLI | DNA MISMATCH REPAIR PROTEIN MUTL | ESCHERICHIA COLI | 80–114 | | | | | | | | |
| PMUTL_SALTY | DNA MISMATCH REPAIR PROTEIN MUTL | SALMONELLA TYPHIMURIUM | 80–114 | | | | | | | | |
| PMUTL_VIBCH | PROTEIN MUTL | VIBRIO CHOLERAE | 134–169 | | | | | | | | |
| PMUTS_ECOLI | DNA MISMATCH REPAIR PROTEIN MUTS | ESCHERICHIA COLI | 119–153 | | | | | | | | |
| PMUTT_STRAM | MUTT-LIKE PROTEIN | STREPTOMYCES AMBOFACIENS | 60–87 | | | | | | | | |
| PMVAA_PSEMV | COENZYME A REDUCTASE | PSEUDOMONAS MEVALONII | 341–368 | | | | | | | | |
| PMX_STRPY | M-RELATED PROTEIN PRECURSOR | STREPTOCOCCUS PYOGENES | 5–129 | 148–182 | 190–217 | 240–301 | | | | | |
| PMYCO_STRCI | MYCOLYSIN PRECURSOR | STREPTOMYCES CACAOI | 300–352 | | | | | | | | |
| PMYFC_YEREN | MYFC PROTEIN PRECURSOR | YERSINIA ENTEROCOLITICA | 210–237 | | | | | | | | |
| PNADC_SALTY | NICOTINATE-NUCLEOTIDE PYROPHOSPHORYLASE | SALMONELLA TYPHIMURIUM | 123–154 | 255–289 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PNADR_SALTY | TRANSCRIPTIONAL REGULATOR NADR | SALMONELLA TYPHIMURIUM | 233–260 | | | | | | | | |
| PNAGD_ECOLI | NAGD PROTEIN | ESCHERICHIA COLI | 75–102 | | | | | | | | |
| PNAGH_CLOPE | HYALURONOGLUCOS-AMINIDASE | CLOSTRIDIUM PERFRINGENS | 48–75 | 990–1017 | | | | | | | |
| PNAGR_ECOLI | NAGR PROTEIN | ESCHERICHIA COLI | 119–153 | | | | | | | | |
| PNANH_CLOSE | SIALIDASE PRECURSOR | CLOSTRIDIUM SEPTICUM | 11–42 | 289–330 | 922–988 | | | | | | |
| PNANH_CLOSO | SIALIDASE PRECURSOR | CLOSTRIDIUM SORDELLII | 377–404 | | | | | | | | |
| PNANH_SALTY | SIALIDASE | SALMONELLA TYPHIMURIUM | 290–317 | | | | | | | | |
| PNAPA_ENTHR | NA(+)/H(+) ANTIPORTER | ENTEROCOCCUS HIRAE | 116–150 | | | | | | | | |
| PNARG_ECOLI | RESPIRATORY NITRATE REDUCTASE ALPHA CHAIN | ESCHERICHIA COLI | 386–420 | | | | | | | | |
| PNARL_ECOLI | REGULATOR PROTEIN NARL | ESCHERICHIA COLI | 76–103 | | | | | | | | |
| PNARP_ECOLI | REGULATOR PROTEIN NARP | ESCHERICHIA COLI | 155–189 | | | | | | | | |
| PNARX_ECOLI | NITRATE/NITRITE SENSOR PROTEIN NARX | ESCHERICHIA COLI | 220–247 | 358–385 | 431–458 | 505–538 | | | | | |
| PNDVA_RHIME | BETA-(1→2)GLUCAN EXPORT PROTEIN | RHIZOBIUM MELILOTI | 212–239 | | | | | | | | |
| PNEOR_STRCY | NEOMYCIN RESISTANCE PROTEIN | STREPTOMYCES CYANOGENUS | 348–375 | | | | | | | | |
| PNEUA_ECOLI | ACYLNEURAMINATE CYTIDYLYLTRANSFERASE | ESCHERICHIA COLI | 218–252 | 268–298 | | | | | | | |
| PNFRA_ECOLI | N4 ADSORPTION PROTEIN A PRECURSOR | ESCHERICHIA COLI | 490–517 | | | | | | | | |
| PNFRB_ECOLI | N4 ADSORPTION PROTEIN B | ESCHERICHIA COLI | 2–43 | 186–220 | 511–538 | | | | | | |
| PNFRC_ECOLI | N4 ADSORPTION PROTEIN C | ESCHERICHIA COLI | 315–342 | | | | | | | | |
| PNFSL_ENTCL | NAD(P)H NITROREDUCTASE | ENTEROBACTER CLOACAE | 9–36 | | | | | | | | |
| PNHAA_ECOLI | NA(+)/H(+) ANTIPORTER 1 | ESCHERICHIA COLI | 206–233 | | | | | | | | |
| PNHAB_ECOLI | NA(+)/H(+) ANTIPORTER 2 | ESCHERICHIA COLI | 271–305 | | | | | | | | |
| PNHAB_PSECL | NITRILE HYDRATASE SUBUNIT BETA | PSEUDOMONAS CHLORORAPHIS | 71–101 | | | | | | | | |
| PNHB1_RHORH | NITRILE HYDRATASE SUBUNIT BETA | RHODOCOCCUS RHODOCHROUS | 63–93 | | | | | | | | |
| PNIFA_AZOBR | NIF-SPECIFIC REGULATORY PROTEIN | AZOSPIRILLUM BRASILENSE | 7–44 | | | | | | | | |
| PNIFA_BRAJA | NIF-SPECIFIC REGULATORY PROTEIN | BRADYRHIZOBIUM JAPONICUM | 252–279 | | | | | | | | |
| PNIFA_HERSE | NIF-SPECIFIC REGULATORY PROTEIN | HERBASPIRILLUM SEROPEDICAE | 9–51 | 162–203 | 327–354 | | | | | | |
| PNIFA_RHILE | NIF-SPECIFIC REGULATORY PROTEIN | RHIZOBIUM LEGUMINOSARUM | 100–127 | | | | | | | | |
| PNIFA_RHIME | NIF-SPECIFIC REGULATORY PROTEIN | RHIZOBIUM MELILOTI | 171–198 | | | | | | | | |
| PNIFA_RHOCA | NIF-SPECIFIC REGULATORY PROTEIN | RHODOBACTER CAPSULATUS | 260–287 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences | ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|---|
| PNIFB_AZOVI | NIFB PROTEIN | | AZOTOBACTER VINELANDII | 342–369 | | | | | | | | |
| PNIFB_KLEPN | NIFB PROTEIN | | KLEBSIELLA PNEUMONIAE | 154–181 | | | | | | | | |
| PNIFD_ANASP | NITROG MOLYBD-IRON PROTEIN | | ANABAENA SP | 374–401 | | | | | | | | |
| PNIFD_AZOBR | NITROG MOLYBD-IRON PROTEIN | | AZOSPIRILLUM BRASILENSE | 377–404 | | | | | | | | |
| PNIFD_PLEBO | NITROG MOLYBD-IRON PROTEIN | | PLECTONEMA BORYANUM | 387–414 | | | | | | | | |
| PNIFD_THIFE | NITROG MOLYBD-IRON PROTEIN | | THIOBACILLUS FERROOXIDANS | 383–410 | | | | | | | | |
| PNIFE_CLOPA | BIOSYNTHESIS PROTEIN NIFE | | CLOSTRIDIUM PASTEURIANUM | 359–386 | | | | | | | | |
| PNIFH_FRAGR | NITROGENASE IRON PROTEIN | | FRANKIA SP | 56–83 | | | | | | | | |
| PNIFH_PLEBO | NITROGENASE IRON PROTEIN | | PLECTONEMA BORYANUM | 267–294 | | | | | | | | |
| PNIFK_AZOBR | NITROG MOLYBD-IRON PROTEIN | | AZOSPIRILLUM BRASILENSE | 430–457 | | | | | | | | |
| PNIFK_BRAJA | NITROG MOLYBD-IRON PROTEIN | | BRADYRHIZOBIUM JAPONICUM | 483–510 | | | | | | | | |
| PNIFK_BRASP | NITROG MOLYBD-IRON PROTEIN | | BRADYRHIZOBIUM SP | 478–505 | | | | | | | | |
| PNIFK_CLOPA | NITROG MOLYBD-IRON PROTEIN | | CLOSTRIDIUM PASTEURIANUM | 227–254 | | | | | | | | |
| PNIFK_THIFE | NITROG MOLYBD-IRON PROTEIN | | THIOBACILLUS FERROOXIDANS | 479–506 | | | | | | | | |
| PNIFM_AZOCH | NIFM PROTEIN | | AZOTOBACTER CHROOCOCCUM MCD 1 | 265–292 | | | | | | | | |
| PNIFN_BRAJA | BIOSYNTHESIS PROTEIN NIFN | | BRADYRHIZOBIUM JAPONICUM | 339–366 | | | | | | | | |
| PNIFS_ANASP | NIFS PROTEIN | | ANABAENA SP | 112–139 | | | | | | | | |
| PNIFS_LACDE | NIFS PROTEIN HOMOLOG | | LACTOBACILLUS DELBRUECKII | 59–86 | | | | | | | | |
| PNIFT_AZOVI | NIFT PROTEIN | | AZOTOBACTER VINELANDII | 6–33 | | | | | | | | |
| PNIFU_ANASL | NIFU PROTEIN | | ANABAENA SP | 7–49 | | | | | | | | |
| PNIFU_ANASP | NIFU PROTEIN | | ANABAENA SP | 148–178 | | | | | | | | |
| PNIFU_KLEPN | NIFU PROTEIN | | KLEBSIELLA PNEUMONIAE | 66–93 | | | | | | | | |
| PNIKA_ECOLI | NICKEL TRANSPORT PROTEIN NIKA PRECURSOR | | ESCHERICHIA COLI | 122–149 | 282–309 | 456–483 | | | | | | |
| PNIKE_ECOLI | NICKEL TRANSPORT PROTEIN NIKE | | ESCHERICHIA COLI | 177–204 | | | | | | | | |
| PNIRB_ECOLI | NITRITE REDUCTASE | | ESCHERICHIA COLI | 54–81 | 345–372 | | | | | | | |
| PNIRC_ECOLI | NIRC PROTEIN | | ESCHERICHIA COLI | 212–239 | | | | | | | | |
| PNIRS_PSEST | PSEUDOMONAS CYTO-CHROME OXIDASE PRECURSO | | PSEUDOMONAS STUTZERI | 303–333 | | | | | | | | |
| PNISB_LACLA | 117 KD MEMBRANE ASSOCIATED PROTEIN | | LACTOCOCCUS LACTIS | 202–229 | 287–332 | 663–697 | 886–902 | | | | | |
| PNISC_LACLA | NISIN BIOSYNTHESIS PROTEIN NISC | | LACTOCUCCUS LACTIS | 52–92 | 140–188 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PNIST_LACLA | NISIN TRANSPORT PROTEIN NIST | LACTOCOCCUS LACTIS | 223–257 | 278–305 | 426–470 | | | | | | |
| PNIVA_CLOPA | HOMOCITRATE SYNTHASE, ALPHA SUBUNIT | CLOSTRIDIUM PASTEURIANUM | 100–127 | 234–268 | | | | | | | |
| PNIVO_CLOPA | HOMOCITRATE SYNTHASE, OMEGA SUBUNIT | CLOSTRIDIUM PASTEURIANUM | 63–94 | 103–132 | 213–240 | 283–310 | | | | | |
| PNMPC_ECOLI | PORIN PROTEIN NMPC PRECURSOR | ESCHERICHIA COLI | 22–49 | 69–96 | 335–362 | | | | | | |
| PNODC_BRASP | NODULATION PROTEIN C | BRADYRHIZOBIUM SP | 3–30 | | | | | | | | |
| PNODC_RHILO | NODULATION PROTEIN C | RHIZOBIUM LOTI | 286–313 | | | | | | | | |
| PNODC_RHILT | NODULATION PROTEIN C | RHIZOBIUM LEGUMINOSARUM | 14–48 | | | | | | | | |
| PNODF_RHILV | NODULATION PROTEIN F | RHIZOBIUM LEGUMINOSARUM | 31–58 | | | | | | | | |
| PNODF_RHIMS | NODULATION PROTEIN F | RHIZOBIUM MELILOTI | 39–66 | | | | | | | | |
| PNODG_RHIME | NODULATION PROTEIN G | RHIZOBIUM MELILOTI | 8–35 | | | | | | | | |
| PNODG_RHIMS | NODULATION PROTEIN G | RHIZOBIUM MELILOTI | 8–35 | | | | | | | | |
| PNODL_RHILV | NODULATION PROTEIN L | RHIZOBIUM LEGUMINOSARUM | 26–53 | | | | | | | | |
| PNODQ_AZOBR | NODULATION PROTEIN Q | AZOSPIRILLUM BRASILENSE | 60–87 | | | | | | | | |
| PNODT_RHILT | NODULATION PROTEIN T | RHIZOBIUM LEGUMINOSARUM | 104–134 | 355–382 | 420–454 | | | | | | |
| PNODT_RHILV | NODULATION PROTEIN T | RHIZOBIUM LEGUMINOSARUM | 364–391 | 416–443 | | | | | | | |
| PNODU_RHIFR | NODULATION PROTEIN U | RHIZOBIUM FREDII | 506–536 | | | | | | | | |
| PNODV_BRAJA | NODULATION PROTEIN V | BRADYRHIZOBIUM JAPONICUM | 378–419 | 739–766 | | | | | | | |
| PNODX_RHILV | NODULATION PROTEIN X | RHIZOBIUM LEGUMINOSARUM | 232–259 | | | | | | | | |
| PNOLB_RHIFR | NODULATION PROTEIN NOLB | RHIZOBIUM FREDII | 133–160 | | | | | | | | |
| PNOLR_RHIME | NODULATION PROTEIN NOLR | RHIZOBIUM MELILOTI | 88–115 | | | | | | | | |
| PNOSD_PSEST | NOSD PROTEIN PRECURSOR | PSEUDOMONAS STUTZERI | 319–346 | | | | | | | | |
| PNOSR_PSEST | REGULATORY PROTEIN NOSR | PSEUDOMONAS STUTZERI | 127–154 | | | | | | | | |
| PNOSZ_PSEAE | NITROUS-OXIDE REDUCTASE PRECURSOR | PSEDOMONAS AERUGINOSA | 267–294 | | | | | | | | |
| PNOSZ_PSEST | NITROUS-OXIDE REDUCTASE PRECURSOR | PSEUDOMONAS STUTZERI | 557–591 | | | | | | | | |
| PNPRE_BACAM | BACILLOLYSIN PRECURSOR | BACILLUS AMLOLIQUEFACIENS | 113–147 | 217–244 | | | | | | | |
| PNPRE_BACPO | BACILLOLYSIN PRECURSOR | BACILLUS POLYMYXA | 57–91 | 187–228 | | | | | | | |
| PNPRE_BACSU | BACILLOLYSIN PRECURSOR | BACILLUS SUBTILIS | 116–146 | 307–334 | | | | | | | |
| PNQ05_PARDE | NADH-UBIQUINONE OXIDOREDUCTASE 21 KD CHAI | PARACOCCUS DENITRIFICANS | 4–45 | | | | | | | | |
| PNQO9_PARDE | NADH-UBIQUINONE OXIDOREDUC 20 KD CHAIN | PARACOCCUS DENITRIFICANS | 125–152 | | | | | | | | |
| PNRDD_ECOLI | ANNAER RIBONUC-TRIPHOS REDUCTASE | ESCHERICHIA COLI | 91–125 | | | | | | | | |
| PNRFA_ECOLI | CYTOCHROME C552 PRECURSOR | ESCHERICHIA COLI | 319–346 | | | | | | | | |
| PNRFG_ECOLI | NRFG PROTEIN | ESCHERICHIA COLI | 72–111 | | | | | | | | |
| PNRL1_RHORH | ALIPHATIC NITRILASE | RHODOCOCCUS RHODOCHROUS | 109–136 | | | | | | | | |
| PNSR_LACLA | NISIN-RESISTANCE PROTEIN | LACTOCOCCUS LACTIS | 52–79 | 135–162 | | | | | | | |
| PNTCA_ANASP | DNA-BINDING PROTEIN VF1 | ANABAENA SP | 65–92 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PNTCA_SYNP7 | GLOBAL NITROGEN REGULATOR | SYNECHOCOCCUS SP | 44–91 | | | | | | | | |
| PNTCA_SYNP3 | GLOBAL NITROGEN REGULATOR | SYNECHOCYSTIS SP | 67–94 | | | | | | | | |
| PNTRB_VIBAL | NITROGEN REGULATION PROTEIN NTRB | VIBRIO ALGINOLYTICUS | 194–223 | | | | | | | | |
| PNTRC_PROVU | NITROGEN REGULATION PROTEIN NR | PROTEUS VULGARIS | 385–412 | | | | | | | | |
| PNTRC_RHIME | NITROGEN ASSIMILATION REGULATORY PROTEIN | RHIZOBIUM MELILOTI | 451–478 | | | | | | | | |
| PNU2C_SYNP7 | NADH-PLASTOQUINONE OXIDOREDUCTASE CHAIN | SYNECHOCOCCUS SP | 80–107 | | | | | | | | |
| PNU4C_SYNY3 | NADH-PLASTOQUINONE OXIDOREDUCTASE CHAIN | SYNECHOCYSTIS SP | 27–54 | | | | | | | | |
| PNU5C_SYNP2 | NADH-PLASTOQUINONE OXIDOREDUCTASE CHAIN | SYNECHOCOCCUS SP | 614–641 | | | | | | | | |
| PNUJC_SYNY3 | PROB NADH-UBIQUINONE OXIDOREDUCTASE SUBU | SYNECHOCYSTIS SP | 163–190 | | | | | | | | |
| PNUKC_SYNY3 | PROB NADH-UBIQUINONE OXIDOREDUCTASE SUBU | SYNECHOCYSTIS SP | 169–199 | | | | | | | | |
| PNULX_SYNY3 | NADH-PLASTOQUINONE OXIDOREDUCTASE CHAIN | SYNECHOCYSTIS SP | 46–80 | | | | | | | | |
| PNUOG_ECOLI | NADH DEHYDROGENASE I CHAIN G | ESCHERICHIA COLI | 368–402 | | | | | | | | |
| PNUOL_ECOLI | NADH DEHYDROGENASE I CHAIN L | ESCHERICHIA COLI | 30–57 | 496–523 | | | | | | | |
| PNUON_ECOLI | NADH DEHYDROGENASE I CHAIN N | ESCHERICHIA COLI | 392–419 | | | | | | | | |
| PNUPC_ECOLI | NUCLEOTIDE PERMEASE | ESCHERICHIA COLI | 13–43 | 134–164 | 356–383 | | | | | | |
| PNUSA_ECOLI | NUSA PROTEIN | ESCHERICHIA COLI | 21–62 | | | | | | | | |
| PNUSB_ECOLI | N UTILIZATION SUBSTANCE PROTEIN B | ESCHERICHIA COLI | 17–65 | 70–97 | | | | | | | |
| PNUSG_ECOLI | TRANSCRIPTION ANTI-TERMINATION PROTEIN NUS | ESCHERICHIA COLI | 141–168 | | | | | | | | |
| PNUSG_THEMA | TRANSCRIPTION ANTI-TERMINATION PROTEIN NUS | THERMOTOGA MARITIMA | 203–230 | | | | | | | | |
| PNYLB_FLASP | 6-AMINOHEXANOATE-DIMER HYDROLASE | FLAVOBACTERIUM SP | 223–250 | | | | | | | | |
| PNYLC_FLASP | 6-AMINOHEXANOATE-DIMER HYDROLASE | FLAVOBACTERIUM SP | 223–250 | | | | | | | | |
| PO16G_BACCE | OLIGO-1,6-GLUCOSIDASE | BACILLUS CEREUS | 301–328 | | | | | | | | |
| POCCT_AGRT6 | OCTOPINE-BINDING PROTEIN T PRECURSOR | AGROBACTERIUM TUMEFACIENS | 172–202 | | | | | | | | |
| PODO1_AZOVI | 2-OXOGLUTARATE DEHYDROGENASE E1 COMPONE | AZOTOBACTER VINELANDII | 829–856 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PODO1_BACSU | 2-OXOGLUTARATE DEHYDROGENASE E1 COMPONE | BACILLUS SUBTILIS | 487–524 | 809–850 | | | | | | | |
| PODO1_ECOLI | 2-OXOGLUTARATE DEHYDROGENASE E1 COMPONE | ESCHERICHIA COLI | 6–33 | | | | | | | | |
| PODO2_BACSU | DIHYDROLIPOAMIDE SUC-TRANSF COMP | BACILLUS SUBTILIS | 30–60 | | | | | | | | |
| PODOB_PSEPU | 2-OXOGLUTARATE DEHYDROGENASE E1 COMPONE | PSEUDOMONAS PUTIDA | 223–254 | | | | | | | | |
| PODP1_ECOLI | PYRUVATE DEHYDROGENASE E1 COMPONENT | ESCHERICHIA COLI | 624–651 | | | | | | | | |
| PODP2_AZOVI | DIHYDROLIPOAMIDE ACETRANS COMP | AZOTOBACTER VINELANDII | 518–545 | | | | | | | | |
| PODP2_ECOLI | DIHYDROLIPOAMIDE ACETRANS COMP | ESCHERICHIA COLI | 14–41 | 117–144 | | | | | | | |
| PODPA_BACST | PYRUVATE DEHYDROGENASE E1 COMPONENT | BACILLUS STEAROTHERMOPHILUS | 299–333 | | | | | | | | |
| PODPA_BACSU | PYRUVATE DEHYDROGENASE E1 COMPONENT | BACILLUS SUBTILIS | 305–332 | | | | | | | | |
| PODPB_BACST | PYRUVATE DEHYDROGENASE E1 COMPONENT | BACILLUS STEAROTHERMOPHILUS | 23–50 | | | | | | | | |
| PODPB_BACSU | PYRUVATE DEHYDROGENASE E1 COMPONENT | BACILLUS SUBTILIS | 16–50 | | | | | | | | |
| POM1E_CHLTR | 15 KD CYSTEINE-RICH PROTEIN, SEROVAR E | CHLAMYDIA TRACHOMATIS | 38–65 | | | | | | | | |
| POMA1_NEIGO | OUTER MEMBRANE PROTEIN P.I A PRECURSOR | NEISSERIA GONORRHOEAE | 63–90 | | | | | | | | |
| POMA1_NEIME | OUTER MEMBRANE PROTEIN P.I A PRECURSOR | NEISSERIA MENINGITIDIS | 359–386 | | | | | | | | |
| POMA2_NEIME | OUTER MEMBRANE PROTEIN P.I A PRECURSOR | NEISSERIA MENINGITIDIS | 353–380 | | | | | | | | |
| POMB1_NEIGO | OUTER MEMBRANE PROTEIN P.IB PRECURSOR | NEISSERIA GONORRHOEAE | 63–90 | | | | | | | | |
| POMB1_NEIME | OUTER MEMBRANE PROTEIN P.IB PRECURSOR | NEISSERIA MENINGITIDIS | 63–90 | | | | | | | | |
| POMB2_NEIGO | OUTER MEMBRANE PROTEIN P.IB PRECURSOR | NEISSERIA GONORRHOEAE | 63–90 | | | | | | | | |
| POMB2_NEIME | OUTER MEMBRANE PROTEIN P.IB PRECURSOR | NEISSERIA MENINGITIDIS | 63–90 | | | | | | | | |
| POMB3_NEIME | OUTER MEMBRANE PROTEIN P.IB PRECURSOR | NEISSERIA MENINGITIDIS | 63–90 | | | | | | | | |
| POMB4_NEIME | OUTER MEMBRANE PROTEIN P.IB PRECURSOR | NEISSERIA MENINGITIDIS | 24–51 | 63–90 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| POMB_NEILA | OUTER MEMBRANE PROTEIN P.IB PRECURSOR | NEISSERIA LACTAMICA | 116-143 | | | | | | | | |
| POMB_NEISI | OUTER MEMBRANE PROTEIN P.IB PRECURSOR | NEISSERIA SICCA | 24-51 | 63-90 | | | | | | | |
| POMLA_ACTPL | OUTER MEMBRANE LIPO-PROTEIN PRECURSOR | ACTINOBACILLUS PLEUROPNEUMONIAE | 114-151 | | | | | | | | |
| POMP1_HAEIN | OUTER MEMBRANE PROTEIN P1 PRECURSOR | HAEMOPHILUS INFLUENZAE | 154-184 | 303-330 | 341-368 | | | | | | |
| POMP2_HAEIN | OUTER MEMBRANE PROTEIN P2 PRECURSOR | HAEMOPHILUS INFLUENZAE | 16-71 | 220-254 | 326-353 | | | | | | |
| POMP3_NEIGO | OUTER MEMBRANE PROTEIN P.III PRECURSOR | NEISSERIA GONORRHOEAE | 14-41 | | | | | | | | |
| POMP7_STAAU | 70 KD OUTER MEMBRANE PROTEIN PRECURSOR | STAPHYLOCOCCUS AUREUS | 53-80 | 88-115 | | | | | | | |
| POMPA_THEMA | OUTER MEMBRANE PROTEIN ALPHA PRECURSOR | THERMOTOGA MARITIMA | 100-138 | 151-178 | 183-249 | 255-292 | 301-328 | 351-385 | | | |
| POMPC_ECOLI | OUTER MEMBRANE PROTEIN C PRECURSOR | ESCHERICHIA COLI | 20-47 | 64-94 | | | | | | | |
| POMPC_NEIGO | OUTER MEMBRANE PROTEIN P.IIC PRECURSOR | NEISSERIA GONORRHOEAE | 89-123 | | | | | | | | |
| POMPC_SALTI | OUTER MEMBRANE PROTEIN C PRECURSOR | SALMONELLA TYPHI | 166-193 | | | | | | | | |
| POMPF_ECOLI | OUTER MEMBRANE PROTEIN F PRECURSOR | ESCHERICHIA COLI | 21-55 | 231-258 | | | | | | | |
| POMPH_PHOS9 | OMPH PROTEIN | PHOTOBACTERIUM SP | 292-319 | | | | | | | | |
| POMPT_ECOLI | PROTEASE VII PRECURSOR | ESCHERICHIA COLI | 37-64 | | | | | | | | |
| POP65_NEIGO | OPACITY PROTEIN OPA65 | NEISSERIA GONORRHOEAE | 71-111 | | | | | | | | |
| POP67_NEIGO | OPACITY PROTEIN OPA67 | NEISSERIA GONORRHOEAE | 72-109 | | | | | | | | |
| POPAA_NEIGO | OPACITY PROTEIN OPA53 | NEISSERIA GONORRHOEAE | 71-123 | 140-167 | | | | | | | |
| POPAG_NEIGO | OPACITY PROTEIN OPA52 | NEISSERIA GONORRHOEAE | 80-107 | 140-167 | | | | | | | |
| POPAI_NEIGO | OPACITY PROTEIN OPA54 | NEISSERIA GONORRHOEAE | 80-107 | | | | | | | | |
| POPAJ_NEIGO | OPACITY PROTEIN OPA58 | NEISSERIA GONORRHOEAE | 71-105 | | | | | | | | |
| POPAK_NEIGO | OPACITY PROTEIN OPA57 | NEISSERIA GONORRHOEAE | 71-105 | | | | | | | | |
| POPDA_ECOLI | OLIGOPEPTIDASE A | ESCHERICHIA COLI | 147-174 | | | | | | | | |
| POPDA_SALTY | OLIGOPEPTIDASE A | SALMONELLA TYPHIMURIUM | 147-174 | | | | | | | | |
| POPDE_PSEAE | TRANSCRIPTION FACTOR OPDE | PSEUDOMONAS AUREGINOSA | 64-91 | | | | | | | | |
| POPPA_ECOLI | OLIGOPEPTIDE-BINDING PROTEIN PRECURSOR | ESCHERICHIA COLI | 402-432 | | | | | | | | |
| POPPB_SALTY | OLIGOPEPTIDE PERMEASE PROTEIN OPPB | SALMONELLA TYPHIMURIUM | 265-299 | | | | | | | | |
| POPR1_NEIME | OPACITY-RELATED PROTEIN POPM1 | NEISSERIA MENINGITIDIS | 108-135 | | | | | | | | |
| POPR3_NEIME | OPACITY-RELATED PROTEIN POPM3 | NEISSERIA MENINGITIDIS | 94-135 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| POSMC_ECOLI | OSMOTICALLY INDUCIBLE PROTEIN OSMC | ESCHERICHIA COLI | 5–32 | | | | | | | | |
| POSPA_BORBU | OUTER SURFACE PROTEIN A PRECURSOR | BORRELIA BURGDORFERI | 63–100 | 112–139 | 157–204 | 223–271 | | | | | |
| POSPB_BORBU | OUTER SURFACE PROTEIN B PRECURSOR | BORRELIA BURGDORFERI | 113–259 | 262–296 | | | | | | | |
| POTC2_BACSU | ORNITHINE CARBAMOYL-TRANSFERASE | BACILLUS SUBTILIS | 188–215 | | | | | | | | |
| POTCC_PSEAE | ORNITHINE CARBAMOYL-TRANSFERASE | PSEUDOMONAS AERUGINOSA | 17–44 | | | | | | | | |
| POTCC_PSEPU | ORNITHINE CARBAMOYL-TRANSFERASE | PSEUDOMONAS PUTIDA | 3–33 | | | | | | | | |
| POUTB_BACSU | SPORE OUTGROWTH FACTOR B | BACILLUS SUBTILIS | 225–252 | | | | | | | | |
| POUTO_ERWCA | LEADER PEPTIDASE | ERWINIA CAROTOVORA | 189–216 | | | | | | | | |
| PP18K_STRPA | 18 KD PROTEIN IN FIMA 3' REGION | STREPTOCOCCUS PARASANGUIS | 115–149 | | | | | | | | |
| PP18K_STRSA | 18 KD PROTEIN IN SSAB 3' REGION | STREPTOCOCCUS SANGUIS | 10–37 | 114–148 | | | | | | | |
| PPIP_LACLC | P1-TYPE PROTEINASE PRECURSOR | LACTOCOCCUS LACTIS | 107–155 | 904–950 | 1073–1100 | 1223–1250 | 1466–1496 | 1625–1655 | | | |
| PP29_MYCHR | PROTEIN P29 | MYCOPLASMA HYORHINIS | 5–56 | 101–160 | 202–246 | | | | | | |
| PP2P_LACLA | PII-TYPE PROTEINASE PRECURSOR | LACTOCOCCUS LACTIS | 107–155 | 904–950 | 1073–1100 | 1223–1250 | 1446–1496 | 1625–1689 | | | |
| PP2P_LACPA | II-TYPE PROTEINASE PRECURSOR | LACTOBACILLUS PARACASEI | 107–155 | 904–941 | 1073–1100 | 1223–1250 | 1446–1496 | 1628–1655 | | | |
| PP30_ECOLI | P30 PROTEIN | ESCHERICHIA COLI | 55–82 | | | | | | | | |
| PP34_RICRI | PROTEIN P34 | RICKETTSIA RICKETTSII | 9–47 | 135–173 | | | | | | | |
| PP37_MYCHR | PROTEIN P37 PRECURSOR | MYCOPLASMA HYORHINIS | 38–75 | | | | | | | | |
| PP3P_LACLC | PIII-TYPE PROTEINASE PRECURSOR | LACTOCOCCUS LACTIS | 107–155 | 904–950 | 1073–1100 | 1223–1250 | 1446–1496 | 1628–1655 | | | |
| PP47K_PSECL | 47 KD PROTEIN | PSEUDOMONAS CHLORORAPHIS | 288–315 | | | | | | | | |
| PP54_ENTFC | P54 PROTEIN PRECURSOR | ENTEROCOCCUS FAECIUM | 58–92 | 141–209 | | | | | | | |
| PP60_LISGR | PROTEIN P60 PRECURSOR | LISTERIA GRAYI | 31–61 | 101–142 | 300–334 | 431–458 | | | | | |
| PP60_LISIN | PROTEIN P60 PRECURSOR | LISTERIA INNOCUA | 67–94 | 102–143 | | | | | | | |
| PP60_LISIV | PROTEIN P60 PRECURSOR | LISTERIA IVANOVII | 101–140 | 315–359 | | | | | | | |
| PP60_LISMO | PROTEIN P60 PRECURSOR | LISTERIA MONOCYTOGENES | 103–144 | | | | | | | | |
| PP60_LISSE | PROTEIN P60 PRECURSOR | LISTERIA SEELIGERI | 101–140 | 270–298 | 321–365 | 395–422 | | | | | |
| PP60_LISWE | PROTEIN P60 PRECURSOR | LISTERIA WELSHIMERI | 113–140 | 317–361 | 396–423 | | | | | | |
| PP69_MYCHR | PROTEIN P69 | MYCOPLASMA HYORHINIS | 264–295 | 421–464 | 487–517 | 544–575 | | | | | |
| PPABA_BACSU | ADC SYNTHASE | BACILLUS SUBTILIS | 12–41 | | | | | | | | |
| PPABB_BACSU | 4-AMINO-4-DEOXYCHORISMATE LYASE | BACILLUS SUBTILIS | 250–277 | | | | | | | | |
| PPABC_ECOLI | 4-AMINO-4-DEOXYCHORISMATE LYASE | ESCHERICHIA COLI | 140–167 | | | | | | | | |
| PPABL_STRGR | PROTEIN Y | STREPTOMYCES GRISEUS | 52–79 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPAC_ARTVI | PENICILLIN ACYLASE PRECURSOR | ARTHROBACTER VISCOSUS | 170–197 | 333–363 | 571–606 | 640–674 | | | | | |
| PPAC_BACSH | PENICILLIN ACYLASE | BACILLUS SPHAERICUS | 232–259 | | | | | | | | |
| PPAC_STRMU | PAC PROTEIN PRECURSOR | STREPTOCOCCUS MUTANS | 146–276 | 281–465 | 538–565 | 576–630 | 1075–1102 | 1159–1186 | 1381–1434 | | |
| PPAI1_BACSU | REGULATORY PROTEIN PAI 1 | BACILLUS SUBTILIS | 103–137 | | | | | | | | |
| PPAI2_BACSU | REGULATORY PROTEIN PAI 2 | BACILLUS SUBTILIS | 145–172 | | | | | | | | |
| PPAPE_ECOLI | FIMBRIAL PROTEIN PAPE | ESCHERICHIA COLI | 42–69 | 86–123 | | | | | | | |
| PPAPF_ECOLI | MINOR FIMBRIAL PROTEIN PAPF | ESCHERICHIA COLI | 4–31 | | | | | | | | |
| PPAPG_ECOLI | FIMBRIAL PROTEIN PAPG PRECURSOR | ESCHERICHIA COLI | 282–316 | | | | | | | | |
| PPARA_AGRTU | PARA PROTEIN | AGROBACTERIUM TUMEFACIENS | 60–87 | | | | | | | | |
| PPARB_ECOLI | PLASMID PARTITION PAR B PROTEIN | ESCHERICHIA COLI | 117–154 | 249–283 | | | | | | | |
| PPARE_ECOLI | TOPOISOMERASE IV SUBUNIT B | ESCHERICHIA COLI | 444–471 | 526–553 | | | | | | | |
| PPARE_SALTY | TOPOISOMERASE IV SUBUNIT B | SALMONELLA TYPHIMURIUM | 444–471 | 526–553 | | | | | | | |
| PPA_BACAN | PROTECTIVE ANTIGEN PRECURSOR | BACILLUS ANTHRACIS | 13–52 | 125–152 | 296–335 | 585–615 | 650–684 | | | | |
| PPBP2_ECOLI | PENICILLIN-BINDING PROTEIN 2 | ESCHERICHIA COLI | 95–122 | 178–205 | 207–241 | | | | | | |
| PPBP2_NEIGO | PENICILLIN-BINDING PROTEIN 2 | NEISSERIA GONORRHOEAE | 193–220 | | | | | | | | |
| PPBP2_NEIME | PENICILLIN-BINDING PROTEIN 2 | NEISSERIA MENINGITIDIS | 193–220 | | | | | | | | |
| PPBP2_STRPN | PENICILLIN-BINDING PROTEIN 2B | STREPTOCOCCUS PNEUMONIAE | 144–183 | 216–243 | 259–286 | 605–632 | | | | | |
| PPBP3_ECOLI | PENICILLIN-BINDING PROTEIN 3 PRECURSOR | ESCHERICHIA COLI | 224–251 | 334–368 | | | | | | | |
| PPBP4_BACSU | PENICILLIN-BINDING PROTEIN 4° | BACILLUS SUBTILIS | 374–401 | | | | | | | | |
| PPBP4_ECOLI | PENICILLIN-BINDING PROTEIN 4 PRECURSOR | ESCHERICHIA COLI | 336–363 | | | | | | | | |
| PPBPA_ECOLI | PENICILLIN-BINDING PROTEIN 1A | ESCHERICHIA COLI | 145–172 | | | | | | | | |
| PPBPB_ECOLI | PENICILLIN-BINDING PROTEIN 1B | ESCHERICHIA COLI | 62–96 | 263–290 | | | | | | | |
| PPBPX_STRPN | PENICILLIN-BINDING PROTEIN 2X | STREPTOCOCCUS PNEUMONIAE | 89–116 | 706–733 | | | | | | | |
| PPBP_STAAU | PENICILLIN-BINDING PROTEIN | STAPHYLOCOCCUS AUREUS | 78–108 | 176–203 | 263–324 | 502–529 | | | | | |
| PPCAB_PSEPU | CYCLOISOMERASE | PSEUDOMONAS PUTIDA | 115–142 | 226–253 | | | | | | | |
| PPEL3_ERWCA | PECTATE LYASE III PRECURSOR | ERWINIA CAROTOVORA | 110–137 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPELA_ERWCA | PECTATE LYASE A PRECURSOR | ERWINIA CAROTOVORA | 110–137 | | | | | | | | |
| PPELB_ERWCA | PECTATE LYASE B PRECURSOR | ERWINIA CAROTOVORA | 110–137 | | | | | | | | |
| PPELC_ERWCA | PECTATE LYASE C PRECURSOR | ERWINIA CAROTOVORA | 110–137 | | | | | | | | |
| PPELF_ERWCH | PECTATE LYASE E PRECURSOR | ERWINIA CHRYSANTHEMI | 40–67 | 209–243 | | | | | | | |
| PPELP_ERWCA | PERIPLASMIC PECTATE LYASE PRECURSOR | ERWINIA CAROTOVORA | 455–482 | | | | | | | | |
| PPELP_YERPS | PERIPLASMIC PECTATE LYASE PRECURSOR | YERSINIA PSEUDOTUBERCULOSIS | 459–489 | | | | | | | | |
| PPELX_ERWCA | PUTATIVE PECTATE LYASE X PRECURSOR | ERWINIA CAROTOVORA | 188–218 | | | | | | | | |
| PPELX_ERWCH | EXOPOLYGALACTURONATE LYASE PRECURSOR | ERWINIA CHRYSANTHEMI | 466–493 | | | | | | | | |
| PPEPD_ECOLI | AMINOACYL-HISTIDINE DIPEPTIDASE | ESCHERICHIA COLI | 264–314 | | | | | | | | |
| PPEPQ_ECOLI | X-PRO DIPEPTIDASE | ESCHERICHIA COLI | 251–278 | | | | | | | | |
| PPERT_BORBR | PERTACTIN PRECURSOR | BORDETELLA BRONCHISEPTICA | 617–644 | | | | | | | | |
| PPERT_BORPA | PERTACTIN PRECURSOR | BORDETELLA PARAPERTUSSIS | 628–655 | | | | | | | | |
| PPERT_BORPE | PERTACTIN PRECURSOR | BORDETELLA PERTUSSIS | 616–643 | | | | | | | | |
| PPGK_CORGL | PHOSPHOGLYCERATE KINASE | CORYNEBACTERIUM GLUTMICUM | 83–117 | | | | | | | | |
| PPGK_ECOLI | PHOSPHOGLYCERATE KINASE | ESCHERICHIA COLI | 186–216 | | | | | | | | |
| PPGK_METBR | PHOSPHOGLYCERATE KINASE | METHANOBACTERIUM BRYANTII | 36–63 | | | | | | | | |
| PPGK_THETH | PHOSPHOGLYCERATE KINASE | THERMUS AQUATICUS | 222–249 | | | | | | | | |
| PPGL1_ERWCA | ENDO-POLYGALACTURO- NASE PRECURSOR | ERWINIA CAROTOVORA | 237–271 | | | | | | | | |
| PPGTE_SALTY | OUTER MEMBRANE PROTEASE E PRECURSOR | SALMONELLA TYPHIMURIUM | 66–93 | | | | | | | | |
| PPHA1_FREDI | C-PHYCOCYANIN-1 ALPHA CHAIN | FREMYELLA DIPLOSIPHON | 21–48 | | | | | | | | |
| PPHA2_FREDI | C-PHYCOCYANIN-2 ALPHA CHAIN | FREMYELLA DIPLOSIPHON | 21–48 | | | | | | | | |
| PPHAA_PSEOL | POLY(3-HYDROXY- ALKANOATE) POLYMERASE 1 | PSEUDOMONAS OLEOVORANS | 264–291 | | | | | | | | |
| PPHAB_ANACY | ALLOPHYCOCYANIN BETA CHAIN | ANABAENA CYLINDRICA | 7–48 | | | | | | | | |
| PPHAB_ANAVA | ALLOPHYCOCYANIN BETA CHAIN | ANABAENA VARIABILIS | 14–48 | | | | | | | | |
| PPHAB_FREDI | ALLOPHYCOCYANIN BETA CHAIN | FREMYELLA DIPLOSIPHON | 8–49 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPHAB_MASLA | ALLOPHYCOCYANIN BETA CHAIN | MASTIGOCLADUS LAMINOSUS | 14–41 | | | | | | | | |
| PPHAB_SYNP6 | ALLOPHYCOCYANIN BETA CHAIN | SYNECHOCOCCUS SP | 14–41 | | | | | | | | |
| PPHAC_SYNP6 | ALLOPHYCOCYANIN ALPHA-B CHAIN | SYNECHOCOCCUS SP | 33–60 | | | | | | | | |
| PPHAG_FREDI | ALLOPHYCOCYANIN GAMMA CHAIN | FREMYELLA DIPLOSIPHON | 32–59 | | | | | | | | |
| PPHB3_FREDI | C-PHYCOCYANIN-3 BETA CHAIN | FREMYELLA DIPLOSIPHON | 29–56 | | | | | | | | |
| PPHBB_ALCEU | ACETOACETYL-COA REDUCTASE | ALCALIGENES EUTROPHUS | 55–85 | | | | | | | | |
| PPHCA_SYNY1 | C-PHYCOCYANIN ALPHA CHAIN | SYNECHOCYSTIS SP | 21–55 | | | | | | | | |
| PPHCB_SYNP6 | C-PHYCOCYANIN BETA CHAIN | SYNECHOCOCCUS SP | 28–55 | | | | | | | | |
| PPHCB_SYNP7 | C-PHYCOCYANIN BETA CHAIN | SYNECHOCOCCUS SP | 28–55 | | | | | | | | |
| PPHCB_SYNY1 | C-PHYCOCYANIN BETA CHAIN | SYNECHOCYSTIS SP | 21–55 | | | | | | | | |
| PPHEA_ECOLI | CHORISMATE MUTASE | ESCHERICHIA COLI | 10–37 | | | | | | | | |
| PPHEA_ERWHE | CHORISMATE MUTASE | ERWINIA HERBICOLA | 10–37 | 159–186 | 252–286 | | | | | | |
| PPHEA_PSESP | PHENOL 2-MONOOXYGENASE | PSEUDOMONAS SP | 171–201 | 282–314 | 437–464 | | | | | | |
| PPHEB_MASLA | PHYCOERYTHROCYANIN BETA CHAIN | MASTIGOCLADUS LAMINOSUS | 21–62 | | | | | | | | |
| PPHEB_PSESP | CATHECHOL 1,2-DIOXYGENASE | PSEUDOMONAS SP | 24–51 | | | | | | | | |
| PPHEG_SYNPY | LINKER POLYPEPTIDE | SYNECHOCOCCUS SP | 158–185 | | | | | | | | |
| PPHEP_ECOLI | PHENYLALANINE-SPECIFIC PERMEASE | ESCHERICHIA COLI | 284–311 | | | | | | | | |
| PPHF1_CLOPA | PERIPLASMIC [FE] HYDROGENASE 1 | CLOSTRIDIUM PASTEURIANUM | 434–471 | | | | | | | | |
| PPHL1_BACCE | SPHINGOMYELINASE C PRECURSOR | BACILLUS CEREUS | 2–36 | | | | | | | | |
| PPHL2_BACCE | SPHINGOMYELINASE C PRECURSOR | BACILLUS CEREUS | 2–36 | | | | | | | | |
| PPHL3_BACCE | SPHINGOMYELINASE C PRECURSOR | BACILLUS CEREUS | 2–36 | | | | | | | | |
| PPHLC_BACCE | PHOSPHOLIPASE C PRECURSOR | BACILLUS CEREUS | 32–59 | 179–206 | | | | | | | |
| PPHLC_CLOBI | PHOSPHOLIPASE C PRECURSOR | CLOSTRIDIUM BIFERMENTANS | 50–77 | 335–365 | | | | | | | |
| PPHLC_CLOPE | PHOSPHOLIPASE C PRECURSOR | CLOSTRIDIUM PERFRINGENS | 210–237 | 369–398 | | | | | | | |
| PPHLC_LISMO | PHOSPHOLIPASE C PRECURSOR | LISTERIA MONOCYTOGENES | 147–174 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPHLC_PSEAE | HEMOLYTIC PHOSPHOLIPASE C PRECURSOR | PSEUDOMONAS AERUGINOSA | 685–712 | | | | | | | | |
| PPHLC_STAAU | PHOSPHOLIPASE C PRECURSOR | STAPHYLOCOCCUS AUREUS | 6–33 | | | | | | | | |
| PPHLD_BACCE | PHOSPHOLIPASE C PRECURSOR | BACILLUS CEREUS | 179–206 | | | | | | | | |
| PPHL_LEPIN | SPHINGOMYELINASE C PRECURSOR | LEPTOSPIRA INTERROGANS | 30–57 | 394–428 | | | | | | | |
| PPHND_ECOLI | PHND PROTEIN | ESCHERICHIA COLI | 296–326 | | | | | | | | |
| PPHNK_ECOLI | PHNK PROTEIN | ESCHERICHIA COLI | 178–205 | | | | | | | | |
| PPHNM_ECOLI | PHNM PROTEIN | ESCHERICHIA COLI | 5–35 | | | | | | | | |
| PPHOE_CITFR | OUTER MEMBRANE PORE PROTEIN E PRECURSOR | CITROBACTER FREUNDII | 13–40 | 47–105 | | | | | | | |
| PPHOE_ECOLI | OUTER MEMBRANE PORE PROTEIN E PRECURSOR | ESCHERICHIA COLI | 13–40 | 64–105 | 168–195 | 226–253 | | | | | |
| PPHOE_KLEOX | OUTER MEMBRANE PORE PROTEIN E PRECURSOR | KLEBSIELLA OXYTOCA | 13–40 | 64–91 | | | | | | | |
| PPHOE_KLEPN | OUTER MEMBRANE PORE PROTEIN E PRECURSOR | KLEBSIELLA PNEUMONIAE | 13–40 | 64–105 | | | | | | | |
| PPHOE_SALTY | OUTER MEMBRANE PORE PROTEIN E PRECURSOR | SALMONELLA TYPHIMURIUM | 63–104 | 320–347 | | | | | | | |
| PPHOP_BACSU | ALK PHOS SYNTHESIS TRANS REG PROTEIN | BACILLUS SUBTILIS | 185–219 | | | | | | | | |
| PPHOQ_ECOLI | SENSOR PROTEIN PHOQ | ESCHERICHIA COLI | 244–278 | | | | | | | | |
| PPHOQ_SALTY | VIRULENCE SENSOR PROTEIN PHOQ | SALMONELLA TYPHIMURIUM | 226–260 | | | | | | | | |
| PPHOR_BACSU | ALK PHOS SYNTHESIS SENSOR PROTEIN PHOR | BACILLUS SUBTILIS | 89–145 | 387–425 | | | | | | | |
| PPHRA_ECOLI | PHOTOREPAIR PROTEIN PHRA | ESCHERICHIA COLI | 63–90 | 207–241 | | | | | | | |
| PPHRA_SYNPY | R-PHYCOCYANIN II ALPHA CHAIN | SYNECHOCOCCUS SP | 20–47 | | | | | | | | |
| PPHRA_SYNPZ | R-PHYCOCYANIN II ALPHA CHAIN | SYNECHOCOCCUS SP | 20–47 | | | | | | | | |
| PPHSG_ECOLI | GLYCOGEN PHOSPHORYLASE | ESCHERICHIA COLI | 157–184 | 488–515 | | | | | | | |
| PPHSM_ECOLI | MALTODEXTRIN PHOSPHORYLASE | ESCHERICHIA COLI | 71–108 | | | | | | | | |
| PPILA_NEIGO | PROB SIGNAL RECOGNITION PARTICLE PROTEIN | NEISSERIA GONORRHOEAE | 17–68 | | | | | | | | |
| PPILB_PSEAE | FIMBRIAL ASSEMBLY PROTEIN PILB | PSEUDOMONAS AERUGINOSA | 16–60 | | | | | | | | |
| PPILC_PSEAE | PILC PROTEIN | PSEUDOMONAS AERUGINOSA | 143–170 | | | | | | | | |
| PPILD_NEIGO | LEADER PEPTIDASE | NEISSERIA GONORRHOEAE | 110–137 | | | | | | | | |
| PPILQ_PSEAE | FIMBRIAL ASSEMBLY PROTEIN PILQ PRECURSOR | PSEUDOMONAS AERUGINOSA | 71–115 | 639–666 | | | | | | | |
| PPILS_PSEAE | SENSOR PROTEIN PILS | PSEUDOMONAS AERUGINOSA | 9–46 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPIR_ECOLI | P1 PROTEIN | ESCHERICHIA COLI | 156–188 | | | | | | | | |
| PPIV_MORBO | PININ GENE INVERTING PROTEIN | MORAXELLA BOVIS | 42–69 | 152–182 | | | | | | | |
| PPIV_MORLA | PILIN GENE INVERTING PROTEIN | MORAXELLA LACUNATA | 152–182 | | | | | | | | |
| PPLC_BACCE | PHOSPHODIESTERASE PRECURSOR | BACILLUS CEREUS | 217–245 | | | | | | | | |
| PPLC_BACTU | PHOSPHODIESTERASE PRECURSOR | BACILLUS THURINGIENSIS | 216–245 | | | | | | | | |
| PPLC_LISMO | PHOSPHODIESTERASE PRECURSOR | LISTERIA MONOCYTOGENES | 238–265 | | | | | | | | |
| PPLSC_ECOLI | ACYLTRANSFERASE | ESCHERICHIA COLI | 106–133 | | | | | | | | |
| PPLSX_ECOLI | PLSX PROTEIN | ESCHERICHIA COLI | 241–270 | | | | | | | | |
| PPLYD_ERWCA | PECTIN LYASE | ERWINIA CAROTOVORA | 27–92 | | | | | | | | |
| PPMBA_ECOLI | PMPA PROTEIN | ESCHERICHIA COLI | 9–50 | | | | | | | | |
| PPME_ERWCH | PECTINESTERASE PRECURSOR | ERWINIA CHRYSANTHEMI | 60–87 | | | | | | | | |
| PPMGY_ECOLI | PHOSPHOGLYCERATE MUTASE | ESCHERICHIA COLI | 82–116 | | | | | | | | |
| PPMGY_ZYMM | PHOSPHOGLYCERATE MUTASE | ZYMOMONAS MOBILIS | 13–40 | 80–110 | | | | | | | |
| PPNP_ECOLI | POLYRIBONUC NUCLEOTIDYLTRANSF | ESCHERICHIA COLI | 260–294 | | | | | | | | |
| PPNUC_SALTY | PNUC PROTEIN | SALMONELLA TYPHIMURIUM | 178–205 | | | | | | | | |
| PPODK_BACSY | PYRUVATE, ORTHO-PHOSPHATE DIKINASE | BACTEROIDES SYMBIOSUS | 51–78 | | | | | | | | |
| PPORF_PSESY | OUTER MEMBRANE PORIN F PRECURSOR | PSEUDOMONAS SYRINGAE | 111–138 | | | | | | | | |
| PPORO_PSEAE | PORIN O PRECURSOR | PSEUDOMONAS AERUGINOSA | 390–424 | | | | | | | | |
| PPORP_PSEAE | PORIN P PRECURSOR | PSEUDOMONAS AERUGINOSA | 139–181 | 260–287 | 369–396 | | | | | | |
| PPOTD_ECOLI | BINDING PROTEIN PRECURSOR | ESCHERICHIA COLI | 320–347 | | | | | | | | |
| PPOTE_ECOLI | PUTRESCINE-ORNITHINE ANTIPORTER | ESCHERICHIA COLI | 91–118 | | | | | | | | |
| PPOXB_ECOLI | PYRUVATE DEHYDROGENASE | ESCHERICHIA COLI | 8–38 | | | | | | | | |
| PPPB3_BACSU | ALKALINE PHOSPHATASE III PRECURSOR | BACILLUS SUBTILIS | 109–150 | 433–460 | | | | | | | |
| PPPB4_BACSU | ALKALINE PHOSPHATASE IV PRECURSOR | BACILLUS SUBTILIS | 85–123 | 336–363 | | | | | | | |
| PPPB_ECOLI | ALKALINE PHOSPHATASE PRECURSOR | ESCHERICHIA COLI | 235–262 | | | | | | | | |
| PPPB_ESCFE | ALKALINE PHOSPHATE PRECURSOR | ESCHERICHIA FERGUSONII | 236–263 | | | | | | | | |
| PPPCE_FLAME | PROLYL ENDOPEPTIDASE PRECURSOR | FLAVOBACTERIUM MENINGOSEPTICUM | 158–199 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPPCF_FLAME | PROLYL ENDOPEPTIDASE PRECURSOR | FLAVOBACTERIUM MENINGOSEPTICUM | 158–199 | 256–283 | | | | | | | |
| PPPCK_ECOLI | PHOSPHOENOLPYRUVATE CARBOXYKINASE | ESCHERICHIA COLI | 45–72 | | | | | | | | |
| PPPDA_CLOPE | PROTEIN A PRECURSOR | CLOSTRIDIUM PERFRINGENS | 73–107 | | | | | | | | |
| PPPSA_ECOLI | PHOSPHOENOLPYRUVATE SYNTHASE | ESCHERICHIA COLI | 49–76 | | | | | | | | |
| PPQQ2_ACICA | COENZYME PQQ SYNTHESIS PROTEIN II | ACINETOBACTER CALCOACETICUS | 40–74 | | | | | | | | |
| PPRCA_ANAVA | CALCIUM DEPENDENT PROTEASE PRECURSOR | ANABAENA VARIABILIS | 371–398 | | | | | | | | |
| PPRCA_THEAC | PROTEASOME, ALPHA SUBUNIT | THERMOPLASMA ACIDOPHILUM | 88–115 | | | | | | | | |
| PPRC_ECOLI | TAIL-SPECIFIC PROTEASE PROCURSOR | ESCHERICHIA COLI | 158–192 | 366–393 | | | | | | | |
| PPRE1_STAAU | PLASMID RECOMBINATION ENZYME | STAPHYLOCOCCUS AUREUS | 27–78 | 152–179 | 264–347 | | | | | | |
| PPRE2_STAAU | PLASMID RECOMBINATION ENZYME | STAPHYLOCOCCUS AUREUS | 48–75 | 181–208 | 310–361 | 366–393 | | | | | |
| PPREA_LACPL | PLASMID RECOMBINATION ENZYME | LACTOBACILLUS PLANTARUM | 37–71 | 291–318 | | | | | | | |
| PPRE_BACLI | REGULATORY PROTEIN | BACILLUS LICHENIFORMIS | 2–40 | | | | | | | | |
| PPRE_BACSP | PLASMID RECOMBINATION ENZYME | BACILLUS SP | 181–224 | 288–345 | | | | | | | |
| PPRE_STRAG | PLASMID RECOMBINATION ENZYME | STREPTOCOCCUS AGALACTIAE | 285–319 | 332–359 | 420–454 | | | | | | |
| PPRFA_LISMO | LISTERIOLYSIN REGULATORY PROTEIN | LISTERIA MONOCYTOGENES | 76–110 | 173–204 | | | | | | | |
| PPRIA_ECOLI | PRIMOSOMAL PROTEIN N' | ESCHERICHIA COLI | 218–245 383–433 | | | | | | | | |
| PPRIM_BACSU | DNA PRIMASE | BACILLUS SUBTILIS | 13–43 | | | | | | | | |
| PPRIM_BUCAP | DNA PRIMASE | BUCHNERA APHIDICOLA | 87–114 | 282–319 | | | | | | | |
| PPRIM_CLOAB | DNA PRIMASE | CLOSTRIDIUM ACETOBUTYLICUM | 269–296 | | | | | | | | |
| PPRIM_LACLA | DNA PRIMASE | LACTOCOCCUS LACTIS | 10–37 | 245–286 | 477–504 | 526–593 | | | | | |
| PPRIM_RICPR | DNA PRIMASE | RICKETTSIA PROWAZEKII | 30–57 | | | | | | | | |
| PPRIS_DESDE | PRISMANE PROTEIN | DESULFOVIBRIO DESULFURICANS | 317–344 | | | | | | | | |
| PPRLB_ACHLY | BETA-LYTIC METALLOENDO-PEPTIDASE | ACHROMOBACTER LYTICUS | 121–148 | | | | | | | | |
| PPRLB_LYSEN | BETA-LYTIC METALLOENDO-PEPTIDASE | LYSOBACTER ENZYMOGENES | 111–145 | 275–316 | | | | | | | |
| PPRO1_LISMO | ZINC METALLOPROTEINASE PRECURSOR | LISTERIA MONOCYTOGENES | 111–145 | | | | | | | | |
| PPRO2_LISMO | ZINC METALLOPROTEINASE PRECURSOR | LISTERIA MONOCYTOGENES | 309–336 | | | | | | | | |
| PPROA_SERMA | GAMMA-GLUTAMYL PHOSPHATE REDUCTASE | SERRATIA MARCESCENS | 2–29 | | | | | | | | |
| PPROA_STAAU | PROTEIN A PRECURSOR | STAPHYLOCOCCUS AUREUS | | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPROB_SERMA | GLUTAMATE 5-KINASE | SERRATIA MARCESCENS | 7–34 | | | | | | | | |
| PPROB_STRAG | PROTEIN B | STREPTOCOCCUS AGALACTIAE | 58–85 | | | | | | | | |
| PPROC_PSEAE | PYRROLINE-5-CARBOXYLATE REDUCTASE | PSEUDOMONAS AERUGINOSA | 148–175 | | | | | | | | |
| PPROH_BACSU | PYRROLINE-5-CARBOXYLATE REDUCTASE HOMOL | BACILLUS SUBTILIS | 200–227 | | | | | | | | |
| PPROP_ECOLI | PROLINE/BETAINE TRANSPORTER | ESCHERICHIA COLI | 460–487 | | | | | | | | |
| PPROV_ECOLI | PERIPHERAL MEMBRANE PROTEIN PROV | ESCHERICHIA COLI | 24–54 | | | | | | | | |
| PPROV_SALTY | PERIPHERAL MEMBRANE PROTEIN PROV | SALMONELLA TYPHIMURIUM | 24–54 | | | | | | | | |
| PPRRB_ECOLI | PRRB PROTEIN | ESCHERICHIA COLI | 170–197 | | | | | | | | |
| PPRRC_ECOLI | ANTICODON NUCLEASE | ESCHERICHIA COLI | 282–309 | | | | | | | | |
| PPRRD_ECOLI | PRRD PROTEIN | ESCHERICHIA COLI | 278–305 | | | | | | | | |
| PPRSA_BACSU | PROTEIN EXPORT PROTEIN PRSA PRECURSOR | BACILLUS SUBTILIS | 52–87 | 95–157 | | | | | | | |
| PPRTA_STRGR | PROTEASE A PRECURSOR | STREPTOMYCES GRISEUS | 56–110 | | | | | | | | |
| PPRTC_ERWCH | SECRETED PROTEASE C PRECURSOR | ERWINIA CHRYSANTHEMI | 103–130 | | | | | | | | |
| PPRTC_PORGI | COLLAGENASE PRECURSOR | PORPHYROMONAS GINGIVALIS | 285–312 | | | | | | | | |
| PPRTD_ERWCH | PROTEASES SECRETION PROTEIN PRTD | ERWINIA CHRYSANTHEMI | 328–355 | | | | | | | | |
| PPRTE_BACNO | EXTRACELLULAR SERINE PROTEASE PRECURSOR | BACTEROIDES NODOSUS | 106–133 | 219–265 | 346–384 | | | | | | |
| PPRTE_ERWCH | PROTEASES SECRETION PROTEIN PRTE | ERWINIA CHRYSANTHEMI | 108–135 | 158–192 | 231–290 | | | | | | |
| PPRTF_ERWCH | PROTEASES SECRETION PROTEIN PRTF | ERWINIA CHRYSANTHEMI | 280–310 | | | | | | | | |
| PPRTM_LACLA | PROTEASE MATURATION PROTEIN PRECURSOR | LACTOCOCCUS LACTIS | 76–103 | 112–139 | | | | | | | |
| PPRTM_LACLC | PROTEASE MATURATION PROTEIN PRECURSOR | LACTOCOCCUS LACTIS | 26–53 | 76–103 | 112–139 | | | | | | |
| PPRTM_LACPA | PROTEASE MATURATION PROTEIN PRECURSOR | LACTOBACILLUS PARACASEI | 76–103 | 112–139 | | | | | | | |
| PPRTS_SERMA | EXTRACELLULAR SERINE PROTEASE PRECURSOR | SERRATIA MARCESCENS | 304–331 | 576–607 | 1007–1041 | | | | | | |
| PPRTT_SERMA | EXTRACELLULAR SERINE PROTEASE PRECURSOR | SERRATIA MARCESCENS | 304–331 | 463–491 | 1007–1041 | | | | | | |
| PPRTX_ERWCH | SECRETED PROTEASE C PRECURSOR | ERWINIA CHRYSANTHEMI | 314–341 | | | | | | | | |
| PPSAA_SYNEN | CHLOROPHYLL A APOPROTEIN A1 | SYNECHOCOCCUS ELONGATUS NAEGEL | 120–147 | | | | | | | | |
| PPSAA_SYNP2 | CHLOROPHYLL A APOPROTEIN A1 | SYNECHOCOCCUS SP | 109–136 | 326–356 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPSAA_SYNVU | CHLOROPHYLL A APOPROTEIN A1 | SYNECHOCOCCUS VULCANUS | 120–147 | | | | | | | | |
| PPSAA_SYNY3 | CHLOROPHYLL A APOPROTEIN A1 | SYNECHOCYSTIS SP | 44–71 | 120–147 | 338–368 | | | | | | |
| PPSAB_YERPE | CHAPERONE PROTEIN PSAB PRECURSOR | YERSINIA PESTIS | 244–271 | | | | | | | | |
| PPSAD_SYNP6 | PHOTOSYSTEM 1 REACTION CENTRE SUBUNIT II | SYNECHOCOCCUS SP | 11–38 | | | | | | | | |
| PPSAE_YERPE | PSAE PROTEIN PRECURSOR | YERSINIA PESTIS | 66–118 | | | | | | | | |
| PPSBO_ANANI | STABILIZING POLYPEPTIDE PRECURSOR | ANACYSTIS NIDULANS | 99–126 | 209–243 | | | | | | | |
| PPSPA_ECOLI | PHAGE SHOCK PROTEIN A | ESCHERICHIA COLI | 55–82 | | | | | | | | |
| PPSRA_WOLSU | POLYSULFIDE REDUCTASE CHAIN A PRECURSOR | WOLINELLA SUCCINOGENES | 114–141 | | | | | | | | |
| PSTS_ECOLI | PHOSPHATE-BINDING PROTEIN PRECURSOR | ESCHERICHIA COLI | 40–74 | | | | | | | | |
| PPT1_BACSU | PHOSPHOTRANSFERASE | BACILLUS SUBTILIS | 26–60 | | | | | | | | |
| PPT1_ECOLI | PHOSPHOTRANSFERASE | ESCHERICHIA COLI | 135–162 | 399–426 | | | | | | | |
| PPT1_SALTY | PHOSPHOTRANSFERASE | SALMONELLA TYPHIMURIUM | 232–259 | 399–426 | | | | | | | |
| PPT1_STACA | PHOSPHOTRANSFERASE | STAPHYLOCOCCUS CARNOSUS | 34–61 | | | | | | | | |
| PPT1_STRSL | PHOSPHOTRANSFERASE | STREPTOCOCCUS SALIVARIUS | 34–61 | | | | | | | | |
| PPT2B_ERWCH | PHOSPHOTRANSFERASE ENZYME II | ERWINIA CHRYSANTHEMI | 127–154 | 198–232 | | | | | | | |
| PPT2G_BACSU | PHOSPHOTRANSFERASE ENZYME II | BACILLUS SUBTILIS | 670–697 | | | | | | | | |
| PPT2L_LACCA | PHOSPHOTRANSFERASE ENZYME II | LACTOBACILLUS CASEI | 537–564 | | | | | | | | |
| PPT2L_LACLA | PHOSPHOTRANSFERASE ENZYME II | LACTOCOCCUS LACTIS | 183–214 | 409–436 | | | | | | | |
| PPT2L_STAAU | PHOSPHOTRANSFERASE ENZYME II | STAPHYLOCOCCUS AUREUS | 421–448 | 530–557 | | | | | | | |
| PPT2M_ECOLI | PHOSPHOTRANSFERASE ENZYME II | ESCHERICHIA COLI | 445–489 | | | | | | | | |
| PPT2M_STACA | PHOSPHOTRANSFERASE ENZYME II | STAPHYLOCOCCUS CARNOSUS | 388–415 | | | | | | | | |
| PPT2N_ECOLI | N-ACETYLGLUCOSAMINE-PERMEASE | ESCHERICHIA COLI | 370–400 | | | | | | | | |
| PPT2S_STRMU | PHOSPHOTRANSFERASE ENZYME II | STREPTOCOCCUS MUTANS | 600–627 | | | | | | | | |
| PPT3F_SALTY | PHOSPHOTRANSFERASE FPR PROTEIN | SALMONELLA TYPHIMURIUM | 107–134 | | | | | | | | |
| PPT3L_LACCA | PHOSPHOTRANSFERASE FACTOR III | LACTOBACILLUS CASEI | 40–67 | | | | | | | | |
| PPTHP_ECOLI | PHOSPHOCARRIER PROTEIN HPR | ESCHERICHIA COLI & SALMONELLA TYPHIMURIUM | 31–65 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPTHP_KLEPN | PHOSPHOCARRIER PROTEIN HPR | KLEBSIELLA PNEUMONIAE | 31–65 | | | | | | | | |
| PPTRB_ECOLI | PROTEASE II | ESCHERICHIA COLI | 94–121 | 217–251 | | | | | | | |
| PPULA_KLEAE | PULLULANASE | KLEBSIELLA AEROGENES | 894–928 | | | | | | | | |
| PPULA_KLEPN | PULLULANASE | KLEBSIELLA PNEUMONIAE | 894–918 | | | | | | | | |
| PPULO_KLEPN | LEADER PEPTIDASE | KLEBSIELLA PNEUMONIAE | 178–205 | | | | | | | | |
| PPULS_KLEPN | PULS PRECURSOR | KLEBSIELLA PNEUMONIAE | 70–97 | | | | | | | | |
| PPUPA_PSEPU | UPTAKE PROTEIN PRECURSOR | PSEUDOMONAS PUTIDA | 112–162 | 210–237 | 429–463 | 736–763 | | | | | |
| PPUR1_BACSU | AMIDOPHOSPHORIBOSYL-TRANSF PREC | BACILLUS SUBTILIS | 394–421 | | | | | | | | |
| PPUR2_BACSU | PHOSPHORIBOSYLAMINE-GLYCINE LIGASE | BACILLUS SUBTILIS | 349–376 | | | | | | | | |
| PPUR3_BACSU | FORMYLTRANSFERASE | BACILLUS SUBTILIS | 149–176 | | | | | | | | |
| PPUR3_ECOLI | FORMYLTRANSFERASE | ESCHERICHIA COLI | 27–54 | | | | | | | | |
| PPUR4_BACSU | SYNTHASE I | BACILLUS SUBTILIS | 18–45 | | | | | | | | |
| PPUR5_BACSU | CYCLO-LIGASE | BACILLUS SUBTILIS | 153–194 | | | | | | | | |
| PPUR6_ECOLI | AIR CARBOXYLASE | ESCHERICHIA COLI | 131–158 | | | | | | | | |
| PPUR7_BACSU | SAICAR SYNTHETASE | BACILLUS SUBTILIS | 3–43 | | | | | | | | |
| PPUR8_BACSU | ADENYLOSUCCINATE LYASE | BACILLUS SUBTILIS | 56–130 | 226–253 | | | | | | | |
| PPUR8_ECOLI | ADENYLOSUCCINATE LYASE | ESCHERICHIA COLI | 194–221 | 331–372 | | | | | | | |
| PPUR9_BACSU | AICAR TRANSFORMYLASE | BACILLUS SUBTILIS | 19–53 | 345–372 | | | | | | | |
| PPUR9_ECOLI | AICAR TRANSFORMYLASE | ESCHERICHIA COLI | 239–268 | | | | | | | | |
| PPUR9_SALTY | AICAR TRANSFORMYLASE | SALMONELLA TYPHIMURIUM | 218–247 | | | | | | | | |
| PPURL_BACSU | SYNTHASE II | BACILLUS SUBTILIS | 609–636 | | | | | | | | |
| PPYG1_ANASP | LINKER POLYPEPTIDE CPCG1 | ANABAENA SP | 88–115 | | | | | | | | |
| PPYG1_MASLA | LINKER POLYPEPTIDE CPCG1 | MASTIGOCLADUS LAMINOSUS | 89–116 | | | | | | | | |
| PPYG2_ANASP | LINKER POLYPEPTIDE CPCG2 | ANABAENA SP | 88–115 | | | | | | | | |
| PPYG2_MASLA | LINKER POLYPEPTIDE CPCG2 | MASTIGOCLADUS LAMINOSUS | 89–116 | | | | | | | | |
| PPYG3_MASLA | LINKER POLYPEPTIDE CPCG3 | MASTIGOCLADUS LAMINOSUS | 91–132 | | | | | | | | |
| PPYG4_ANASP | LINKER POLYPEPTIDE CPCG4 | ANABAENA SP | 90–131 | | | | | | | | |
| PPYR1_ANASP | 32.1 KD LINKER POLYPEPTIDE | ANABAENA SP | 35–62 | | | | | | | | |
| PPYR2_FREDI | 27.9 KD LINKER POLYPEPTIDE | FREMYELLA DIPLOSIPHON | 105–132 | | | | | | | | |
| PPYR4_FREDI | 31.6 KD LINKER POLYPEPTIDE | FREMYELLA DIPLOSIPHON | 22–66 | | | | | | | | |
| PPYR5_FREDI | 37.5 KD LINKER POLYPEPTIDE | FREMYELLA DIPLOSIPHON | 106–143 | | | | | | | | |
| PPYR6_FREDI | 30.8 KD LINKER POLYPEPTIDE | FREMYELLA DIPLOSIPHON | 43–70 | 113–140 | | | | | | | |
| PPYRB_BACSU | ASPARTATE CARBAMOYL-TRANSFERASE | BACILLUS SUBTILIS | 9–36 | | | | | | | | |
| PPYRB_SERMA | ASPARTATE CARBAMOYL-TRANSFERASE | SERRATIA MARCESCENS | 70–97 | | | | | | | | |
| PPYRD_ECOLI | DIHYDROOROTATE DEHYDROGENASE | ESCHERICHIA COLI | 115–142 | | | | | | | | |
| PPYRD_SALTY | DIHYDROOROTATE DEHYDROGENASE | SALMONELLA TYPHIMURIUM | 115–142 | 183–210 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPYRG_BACSU | CTP SYNTHASE | BACILLUS SUBTILIS | 275–302 | 322–349 | | | | | | | |
| PPYS1_FREDI | PHYCOBILISOME 9.7 KD LINKER POLYPEPTIDE | FREMYELLA DIPLOSIPHON | 21–48 | | | | | | | | |
| PQOR_ECOLI | QUINONE OXIDOREDUCTASE | ESCHERICHIA COLI | 180–215 | | | | | | | | |
| PQUEA_ECOLI | QUEUOSINE BIOSYNTHESIS PROTEIN QUEA | ESCHERICHIA COLI | 234–261 | | | | | | | | |
| PR34K_CLOPA | 34.2 KD PROTEIN IN RUBREDOXIN OPERON | CLOSTRIDIUM PASTEURIANUM | 23–50 | 157–232 | | | | | | | |
| PRACC_ECOLI | RACC PROTEIN | ESCHERICHIA COLI | 5–32 | | | | | | | | |
| PRACD_STRTR | ASPARTATE RACEMASE | STREPTOCOCCUS THERMOPHILUS | 152–189 | | | | | | | | |
| PRACS_BACSU | PROBABLE AMINO ACID RACEMASE | BACILLUS SUBTILIS | 132–162 | | | | | | | | |
| PRAFA_ECOLI | ALPHA-GALACTOSIDASE | ESCHERICHIA COLI | 89–116 | | | | | | | | |
| PRAFD_ECOLI | RAFFINOSE INVERTASE | ESCHERICHIA COLI | 348–375 | | | | | | | | |
| PRBSC_ECOLI | RIBOSE TRANSPORT SYSTEM COMPONENT | ESCHERICHIA COLI | 65–99 | 195–222 | | | | | | | |
| PRBSK_ECOLI | RIBOKINASE | ESCHERICHIA COLI | 200–239 | | | | | | | | |
| PRBTR_KLEAE | RIBITOL (RBT) OPERON REPRESSOR | KLEBSIELLA AEROGENES | 6–47 | | | | | | | | |
| PRCSA_ECOLI | BIOSYNTHESIS ACTIVATION PROTEIN A | ESCHERICHIA COLI | 170–197 | | | | | | | | |
| PRCSA_ERWAM | BIOSYNTHESIS ACTIVATION PROTEIN A | ERWINIA AMYLOVORA | 92–119 | 174–201 | | | | | | | |
| PRCSA_ERWST | BIOSYNTHESIS ACTIVATION PROTEIN A | ERWINIA STEWARTII | 174–201 | | | | | | | | |
| PRCSA_KLEAE | BIOSYNTHESIS ACTIVATION PROTEIN A | KLEBSIELLA AEROGENES | 168–205 | | | | | | | | |
| PRCSB_ECOLI | CAPSULE SYNTHESIS B COMPONENT | ESCHERICHIA COLI | 14–41 | 159–186 | | | | | | | |
| PREC2_LEGPN | RECA PROTEIN | LEGIONELLA PNEUMOPHILA | 262–310 | | | | | | | | |
| PRECA_ACHLA | RECA PROTEIN | ACHOLEPLASMA LAIDLAWII | 283–310 | | | | | | | | |
| PRECA_AGRTU | RECA PROTEIN | AGROBACTERIUM TUMEFACIENS | 3–30 | 132–159 | 281–308 | | | | | | |
| PRECA_ANAVA | RECA PROTEIN | ANABAENA VARIABILIS | 322–349 | | | | | | | | |
| PRECA_AQUPY | RECA PROTEIN | AQUIFEX PYROPHILUS | 63–90 | 126–153 | | | | | | | |
| PRECA_BACFR | RECA PROTEIN | BACTEROIDES FRAGILIS | 108–135 | | | | | | | | |
| PRECA_BACSU | RECE PROTEIN | BACILLUS SUBTILIS | 267–294 | | | | | | | | |
| PRECA_BRUAB | RECA PROTEIN | BRUCELLA ABORTUS | 3–30 | 132–159 | 280–307 | | | | | | |
| PRECA_BURCE | RECA PROTEIN | BURKHOLDERIA CEPACIA | 75–109 | | | | | | | | |
| PRECA_ERWCA | RECA PROTEIN | ERWINIA CAROTOVORA | 284–311 | | | | | | | | |
| PRECA_LACDE | RECA PROTEIN | LACTOBACILLUS DELBRUECKII | 20–47 | | | | | | | | |
| PRECA_LACHE | RECA PROTEIN | LACTOBACILLUS HELVETICUS | 20–47 | | | | | | | | |
| PRECA_LACLA | RECA PROTEIN | LACTOCOCCUS LACTIS | 135–162 | 232–269 | 288–315 | | | | | | |
| PRECA_METCL | RECA PROTEIN | METHYLOMONAS CLARA | 266–303 | | | | | | | | |
| PRECA_METFL | RECA PROTEIN | METHYLOBACILLUS FLAGELLATUM | 276–303 | | | | | | | | |
| PRECA_MYCPU | RECA PROTEIN | MYCOPLASMA PULMONIS | 30–57 | | | | | | | | |
| PRECA_MYCTU | RECA PROTEIN | MYCOBACTERIUM TUBERCULOSIS | 749–776 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRECA_NEIGO | RECA PROTEIN | NEISSERIA GONORRHOEAE | 263–310 | | | | | | | | |
| PRECA_PROMI | RECA PROTEIN | PROTEUS MIRABILIS | 283–310 | | | | | | | | |
| PRECA_PSEAE | RECA PROTEIN | PSEUDOMONAS AERUGINOSA | 282–309 | | | | | | | | |
| PRECA_RHILP | RECA PROTEIN | RHIZOBIUM LEGUMINOSARUM | 3–30 | 131–158 | 280–307 | | | | | | |
| PRECA_RHILV | RECA PROTEIN | RHIZOBIUM LEGUMINOSARUM | 119–146 | 268–295 | | | | | | | |
| PRECA_RHIME | RECA PROTEIN | RHIZOBIUM MELILOTI | 119–146 | 268–295 | | | | | | | |
| PRECA_RHOSH | RECA PROTEIN | RHODOBACTER SPHAEROIDES | 119–146 | | | | | | | | |
| PRECA_STRPN | RECA PROTEIN | STREPTOCOCCUS PNEUMONIAE | 134–161 | 293–327 | | | | | | | |
| PRECA_SYNP2 | RECA PROTEIN | SYNECHOCOCCUS SP | 124–151 | | | | | | | | |
| PRECA_VIBCH | RECA PROTEIN | VIBRIO CHOLERAE | 290–317 | | | | | | | | |
| PRECF_BACSU | RECF PROTEIN | BACILLUS SUBTILIS | 4–31 | 178–205 | | | | | | | |
| PRECF_ECOLI | RECF PROTEIN | ESCHERICHIA COLI | 82–109 | 147–174 | | | | | | | |
| PRECF_PROMI | RECF PROTEIN | PROTEUS MIRABILIS | 86–113 | | | | | | | | |
| PRECF_PSEPU | RECF PROTEIN | PSEUDOMONAS PUTIDA | 84–111 | | | | | | | | |
| PRECF_SALTY | RECF PROTEIN | SALMONELLA TYPHIMURIUM | 147–174 | | | | | | | | |
| PRECJ_ECOLI | EXONUCLEASE RECJ | ESCHERICHIA COLI | 52–79 | | | | | | | | |
| PRECN_BACSU | RECOMBINATION PROTEIN | BACILLUS SUBTILIS | 21–48 | 156–184 | 192–247 | 299–336 | 344–378 | | | | |
| PRECQ_ECOLI | DNA HELICASE RECQ | ESCHERICHIA COLI | 468–495 | | | | | | | | |
| PRELA_ECOLI | GTP PYROPHOSPHOKINASE | ESCHERICHIA COLI | 680–707 | | | | | | | | |
| PREMA_BACSU | REPLICATION AND MAINTENANCE PROTEIN | BACILLUS SUBTILIS | 2–36 | 81–108 | | | | | | | |
| PREMA_STAAU | REPLICATION AND MAINTENANCE PROTEIN | STAPHYLOCOCCUS AUREUS | 2–36 | 81–108 | | | | | | | |
| PREMA_STAEP | REPLICATION AND MAINTENANCE PROTEIN | STAPHYLOCOCCUS EPIDERMIDIS | 2–36 | 81–108 | | | | | | | |
| PREP5_ECOLI | REPLICATION PROTEIN REPA | ESCHERICHIA COLI | 50–77 | 90–117 | | | | | | | |
| PREPA_BACSU | REPA PROTEIN | BACILLUS SUBTILIS | 342–373 | | | | | | | | |
| PREPA_ECOLI | REPA PROTEIN | ESCHERICHIA COLI | 91–118 | 228–255 | | | | | | | |
| PREPA_NEIGO | REPLICATION PROTEIN | NEISSERIA GONORRHOEAE | 57–84 | 138–172 | | | | | | | |
| PREPB_LACPL | REPLICATION PROTEIN REPB | LACTOBACILLUS PLANTARUM | 184–211 | | | | | | | | |
| PREPM_STAAU | REPLICATION INITIATION PROTEIN | STAPHYLOCOCCUS AUREUS | 254–284 | | | | | | | | |
| PREPN_STAAU | REPLICATION INITIATION PROTEIN | STAPHYLOCOCCUS AUREUS | 258–285 | | | | | | | | |
| PREPR_STRAG | REPR PROTEIN | STREPTOCOCCUS AGALACTIAE | 430–467 | | | | | | | | |
| PREPS_STRPY | REPS PROTEIN | STREPTOCOCCUS PYOGENES | 423–467 | | | | | | | | |
| PREPX_STAAU | REP PROTEIN | STAPHYLOCOCCUS AUREUS | 111–150 | 172–210 | | | | | | | |
| PREPY_ECOLI | REPLICATION INITIATION PROTEIN | ESCHERICHIA COLI | 288–315 | | | | | | | | |
| PREP_CLOPE | REPLICATION PROTEIN | CLOSTRIDIUM PERFRINGENS | 168–195 | 297–324 | 343–375 | | | | | | |
| PREP_ECOLI | REP HELICASE | ESCHERICHIA COLI | 119–146 | 205–243 | | | | | | | |
| PREP_LACPL | REP PROTEIN | LACTOBACILLUS PLANTARUM | 119–199 | 260–287 | | | | | | | |
| PRESP_CLOPE | RESOLVASE | CLOSTRIDIUM PERFRINGENS | 68–102 | 151–185 | | | | | | | |
| PRF2_BACSU | PROBABLE PEPTIDE CHAIN RELEASE FACTOR 2 | BACILLUS SUBTILIS | 34–68 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRF2_ECOLI | PEPTIDE CHAIN RELEASE FACTOR 2 | ESCHERICHIA COLI | 86–113 | 163–204 | | | | | | | |
| PRF2_SALTY | PEPTIDE CHAIN RELEASE FACTOR 2 | SALMONELLA TYPHIMURIUM | 86–113 | 163–204 | | | | | | | |
| PRF3_ECOLI | PEPTIDE CHAIN RELEASE FACTOR 3 | ESCHERICHIA COLI | 180–210 | 443–473 | | | | | | | |
| PRFAB_ECOLI | 1,6-GALACTOSYL-TRANSFERASE | ESCHERICHIA COLI | 199–226 | | | | | | | | |
| PRFAG_ECOLI | BIOSYNTHESIS PROTEIN RFAG | ESCHERICHIA COLI | 185–212 | | | | | | | | |
| PRFAJ_ECOLI | 1,2-GLUCOSYLTRANSFERASE | ESCHERICHIA COLI | 39–66 | 233–268 | | | | | | | |
| PRFAJ_SALTY | 1,2-GLUCOSYLTRANSFERASE | SALMONELLA TYPHIMURIUM | 68–95 | 145–172 | 236–263 | | | | | | |
| PRJAK_SALTY | 1,2-N-ACETYLGLUCOSAMINE-TRANSFERASE | SALMONELLA TYPHIMURIUM | 335–369 | | | | | | | | |
| PRFAL_ECOLI | O-ANTIGEN LIGASE | ESCHERICHIA COLI | 366–393 | | | | | | | | |
| PRFAL_SALTY | O-ANTIGEN LIGASE | SALMONELLA TYPHIMURIUM | 326–360 | | | | | | | | |
| PRFAP_ECOLI | BIOSYNTHESIS PROTEIN RFAP | ESCHERICHIA COLI | 8–35 | | | | | | | | |
| PRFAS_ECOLI | BIOSYNTHESIS PROTEIN RFAS | ESCHERICHIA COLI | 62–89 | 184–240 | | | | | | | |
| PRFAY_ECOLI | BIOSYNTHESIS PROTEIN RFAY | ESCHERICHIA COLI | 18–45 | | | | | | | | |
| PRFAZ_ECOLI | BIOSYNTHESIS PROTEIN RFAZ | ESCHERICHIA COLI | 3–30 | 85–112 | | | | | | | |
| PRFBB_SALTY | DTDP-GLUCOSE 4,6-DEHYDRATASE | SALMONELLA TYPHIMURIUM | 320–359 | | | | | | | | |
| PRFBM_SALTY | MANNOSE-1-PHOSPHATE GUANYLYLTRANSFERASE | SALMONELLA TYPHIMURIUM | 313–361 | | | | | | | | |
| PRFBS_SALTI | PARATOSE SYNTHASE | SALMONELLA TYPHI | 22–56 | 205–232 | | | | | | | |
| PRFEA_VIBAN | PRECURSOR FOR FERRIC ANGUIBACTIN | VIBRIO ANGUILLARUM | 349–376 | | | | | | | | |
| PRFH_ECOLI | PEPTIDE CHAIN RELEASE FACTOR HOMOLOG | ESCHERICHIA COLI | 83–110 | | | | | | | | |
| PRG12_BACTU | PUTATIVE G12 SITE-SPECIFIC RECOMBINASE | BACILLUS THURINGIENSIS | 15–68 | 190–262 | 310–383 | | | | | | |
| PRHAB_ECOLI | RHAMNULOKINASE | ESCHERICHIA COLI | 175–202 | | | | | | | | |
| PRHAB_SALTY | RHAMNULOKINASE | SALMONELLA TYPHIMURIUM | 175–202 | | | | | | | | |
| PRHAR_ECOLI | L-RHAMNOSE OPERON TRANSACTIVATOR | ESCHERICHIA COLI | 10–41 | | | | | | | | |
| PRHAS_ECOLI | L-RHAMNOSE OPERON REG PROTEIN RHAS | ESCHERICHIA COLI | 152–179 | | | | | | | | |
| PRHIR_RHILV | RHIR REGULATORY PROTEIN | RHIZOBIUM LEGUMINOSARUM | 206–233 | | | | | | | | |
| PRHLB_ECOLI | RNA HELICASE RHLB/MMRA | ESCHERICHIA COLI | 138–165 | | | | | | | | |
| PRHO_BORBU | TRANS TERM FACTOR RHO | BORRELIA BURGDORFERI | 215–242 | 327–369 | | | | | | | |
| PRHPR_BACSU | PROTEASE PROD REG PROTEIN HPR | BACILLUS SUBTILIS | 82–109 | | | | | | | | |
| PRHSA_ECOLI | RHSA PROTEIN PRECURSOR | ESCHERICHIA COLI | 667–694 | | | | | | | | |
| PRHSB_ECOLI | RHSB PROTEIN PRECURSOR | ESCHERICHIA COLI | 667–694 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRHSC_ECOLI | RHSC PROTEIN PRECURSOR | ESCHERICHIA COLI | 380–414 | 667–694 | 1056–1083 | | | | | | |
| PRHSD_ECOLI | RHSD PROTEIN PRECURSOR | ESCHERICHIA COLI | 671–712 | 1071–1098 | | | | | | | |
| PRHSE_ECOLI | RHSE PROTEIN | ESCHERICHIA COLI | 345–372 | | | | | | | | |
| PRIML_ECOLI | ACETYLTRANSFERASE | ESCHERICHIA COLI | 93–127 | | | | | | | | |
| PRIR2_ECOLI | RIBONUCLEOSIDE-DIPHOSPHATE REDUCTASE | ESCHERICHIA COLI | 167–194 | | | | | | | | |
| PRISA_PHOLE | RIBOFLAVIN SYNTHASE ALPHA CHAIN | PHOTOBACTERIUM LEIOGNATHI | 2–47 | 131–158 | | | | | | | |
| PRISB_BACSU | RIBOFLAVIN SYNTHASE BETA CHAIN | BACILLUS SUBTILIS | 8–35 | | | | | | | | |
| PRISB_PHOLE | RIBOFLAVIN SYNTHASE BETA CHAIN | PHOTOBACTERIUM LEIOGNATHI | 14–41 | | | | | | | | |
| PRL10_STRAT | 50S RIBOSOMAL PROTEIN L10 | STREPTOMYCES ANTIBIOTICUS | 14–72 | 106–133 | | | | | | | |
| PRL12_SYNY3 | 50S RIBOSOMAL PROTEIN L12 | SYNECHOCYSTIS SP | 2–34 | | | | | | | | |
| PRL12_THEMA | 50S RIBOSOMAL PROTEIN L12 | THERMOTOGA MARITIMA | 8–35 | 56–86 | | | | | | | |
| PRL14_BACST | 50S RIBOSOMAL PROTEIN L14 | BACILLUS STEAROTHERMOPHILUS | 18–45 | | | | | | | | |
| PRL14_MICLU | 50S RIBOSOMAL PROTEIN L14 | MICROCOCCUS LUTEUS | 18–45 | | | | | | | | |
| PRL14_MYCCA | 50S RIBOSOMAL PROTEIN L14 | MYCOPLASMA CAPRICOLUM | 51–92 | | | | | | | | |
| PRL15_BACLI | 50S RIBOSOMAL PROTEIN L15 | BACILLUS LICHENIFORMIS | 21–48 | | | | | | | | |
| PRL15_BACST | 50S RIBOSOMAL PROTEIN L15 | BACILLUS STEAROTHERMOPHILUS | 95–134 | | | | | | | | |
| PRL15_BACSU | 50S RIBOSOMAL PROTEIN L15 | BACILLUS SUBTILIS | 95–122 | | | | | | | | |
| PRL15_CHLTR | 50S RIBOSOMAL PROTEIN L15 | CHLAMYDIA TRACHOMATIS | 110–144 | | | | | | | | |
| PRL15_ECOLI | 50S RIBOSOMAL PROTEIN L15 | ESCHERICHIA COLI | 79–113 | | | | | | | | |
| PRL15_LACLA | 50S RIBOSOMAL PROTEIN L15 | LACTOCOCCUS LACTIS | 8–35 | | | | | | | | |
| PRL15_METVA | 50S RIBOSOMAL PROTEIN L15 | METHANOCOCCUS VANNIELII | 68–102 | | | | | | | | |
| PRL15_MYCCA | 50S RIBOSOMAL PROTEIN L15 | MYCOPLASMA CAPRICOLUM | 63–135 | | | | | | | | |
| PRL18_BACST | 50S RIBOSOMAL PROTEIN L18 | BACILLUS STEAROTHERMOPHILUS | 31–58 | | | | | | | | |
| PRL18_CHLTR | 50S RIBOSOMAL PROTEIN L18 | CHLAMYDIA TRACHOMATIS | 32–86 | | | | | | | | |
| PRL18_HALMA | 50S RIBOSOMAL PROTEIN L18 | HALOARCULA MARISMORTUI | 80–107 | | | | | | | | |
| PRL18_MYCCA | 50S RIBOSOMAL PROTEIN L18 | MYCOPLASMA CAPRICOLUM | 61–88 | | | | | | | | |
| PRL19_ECOLI | 50S RIBOSOMAL PROTEIN L19 | ESCHERICHIA COLI | 25–52 | | | | | | | | |
| PRL19_HALMA | 50S RIBOSOMAL PROTEIN L19 | HALOARCULA MARISMORTUI | 101–128 | | | | | | | | |
| PRL19_METVA | PROBABLE 50S RIBOSOMAL PROTEIN | METHANOCOCCUS VANNIELII | 45–72 | | | | | | | | |
| PRL1_PROVU | 50S RIBOSOMAL PROTEIN L1 | PROTEUS VULGARIS | 159–194 | | | | | | | | |
| PRL1_SULSO | 50S RIBOSOMAL PROTEIN L1 | SULFOLOBUS SOLFATARICUS | 5–32 | 184–211 | | | | | | | |
| PRL20_ECOLI | 50S RIBOSOMAL PROTEIN L20 | ESCHERICHIA COLI | 14–41 | | | | | | | | |
| PRL20_MYCFE | 50S RIBOSOMAL PROTEIN L20 | MYCOPLASMA FERMENTANS | 14–41 | | | | | | | | |
| PRL21_BACSU | 50S RIBOSOMAL PROTEIN L21 | BACILLUS SUBTILIS | 4–38 | | | | | | | | |
| PRL22_ECOLI | 50S RIBOSOMAL PROTEIN L22 | ESCHERICHIA COLI | 28–55 | | | | | | | | |
| PRL23_METVA | 50S RIBOSOMAL PROTEIN L23 | METHANOCOCCUS VANNIELII | 30–57 | | | | | | | | |
| PRL23_MYCCA | 50S RIBOSOMAL PROTEIN L23 | MYCOPLASMA CAPRICOLUM | 32–59 | | | | | | | | |
| PRL24_HALMA | 50S RIBOSOMAL PROTEIN L24 | HALOARCULA MARISMORTUI | 48–75 | | | | | | | | |
| PRL24_METVA | 50S RIBOSOMAL PROTEIN L24 | METHANOCOCCUS VANNIELII | 61–90 | | | | | | | | |
| PRL24_MICLU | 50S RIBOSOMAL PROTEIN L24 | MICROCOCCUS LUTEUS | 36–63 | | | | | | | | |
| PRL29_CHLTR | 50S RIBOSOMAL PROTEIN L29 | CHLAMYDIA TRACHOMATIS | 39–66 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRL29_ECOLI | 50S RIBOSOMAL PROTEIN L29 | ESCHERICHIA COLI | 36–63 | | | | | | | | |
| PRL29_MYCCA | 50S RIBOSOMAL PROTEIN L29 | MYCOPLASMA CAPRICOLUM | 39–85 | | | | | | | | |
| PRL4_BACST | 50S RIBOSOMAL PROTEIN L4 | BACILLUS STEAROTHERMOPHILUS | 141–168 | | | | | | | | |
| PRL4_MYCCA | 50S RIBOSOMAL PROTEIN L4 | MYCOPLASMA CAPRICOLUM | 144–198 | | | | | | | | |
| PRL5_THETH | 50S RIBOSOMAL PROTEIN L5 | THERMUS AQUATICUS | 38–65 | | | | | | | | |
| PRL6_BACST | 50S RIBOSOMAL PROTEIN L6 | BACILLUS STEAROTHERMOPHILUS | 79–106 | | | | | | | | |
| PRL6_ECOLI | 50S RIBOSOMAL PROTEIN L6 | ESCHERICHIA COLI | 19–46 | | | | | | | | |
| PRL6_METVA | 50S RIBOSOMAL PROTEIN L6 | METHANOCOCCUS VANNIELII | 129–159 | | | | | | | | |
| PRL9_BACST | 50S RIBOSOMAL PROTEIN L9 | BACILLUS STEAROTHERMOPHILUS | 47–77 | | | | | | | | |
| PRL9_ECOLI | 50S RIBOSOMAL PROTEIN L9 | ESCHERICHIA COLI | 122–149 | | | | | | | | |
| PRLA0_HALCU | ACIDIC RIBOSOMAL PROTEIN P0 HOMOLOG | HALBACTERIUM CUTIRUBRUM | 138–182 | | | | | | | | |
| PRLA0_HALHA | ACIDIC RIBOSOMAL PROTEIN P0 HOMOLOG | HALOBACTERIUM HALOBIUM | 138–182 | | | | | | | | |
| PRLA0_HALMA | ACIDIC RIBOSOMAL PROTEIN P0 HOMOLOG | HALOARCULA MARISMORTUI | 64–91 | 153–184 | | | | | | | |
| PRLA0_METVA | ACIDIC RIBOSOMAL PROTEIN P0 HOMOLOG | METHANOCOCCUS VANNIELII | 194–221 | | | | | | | | |
| PRLA_HALEU | RIBOSOMAL PROTEIN 'A' | HALOPHILIC EUBACTERIUM NRCC 41227 | 59–86 | | | | | | | | |
| PRLA_HALHA | 50S RIBOSOMAL PROTEIN L20 | HALOBACTERIUM HALOBIUM | 2–29 | | | | | | | | |
| PRLA_HALMA | 50S RIBOSOMAL PROTEIN L12 | HALOARCULA MARISMORTUI | 2–29 | | | | | | | | |
| PRLA_METVA | RIBOSOMAL PROTEIN 'A' | METHANOCOCCUS VANNIELII | 2–29 | | | | | | | | |
| PRLA_MICLU | 50S RIBOSOMAL PROTEIN MA | MICROCOCCUS LUTEUS | 55–82 | 90–117 | | | | | | | |
| PRLX1_SALTY | 43 KD RELAXATION PROTEIN | SALMONELLA TYPHIMURIUM | 226–260 | | | | | | | | |
| PRLX1_STAAU | RLX PROTEIN | STAPHYLOCOCCUS AUREUS | 3–30 | 102–132 | 177–218 | 266–300 | | | | | |
| PRLX2_SALTY | 22 KD RELAXATION PROTEIN | SALMONELLA TYPHIMURIUM | 19–53 | | | | | | | | |
| PRLX2_STAAU | RLX PROTEIN | STAPHYLOCOCCUS AUREUS | 3–30 | 102–133 | 261–295 | | | | | | |
| PRLX3_STAAU | RLX PROTEIN | STAPHYLOCOCCUS AUREUS | 3–30 | 146–216 | | | | | | | |
| PRLX_SULSO | 50S RIBOSOMAL PROTEIN LX | SULFOLOBUS SOLFATARICUS | 32–62 | | | | | | | | |
| PRNBR_BACAM | RIBONUCLEASE PRECURSOR | BACILLUS AMYLOLIQUEFACIENS | 33–67 | 129–156 | | | | | | | |
| PRNC_ECOLI | RIBONUCLEASE III | ESCHERICHIA COLI | 10–37 | 117–144 | | | | | | | |
| PRNE_ECOLI | RIBONUCLEASE E | ESCHERICHIA COLI | 413–440 | 628–662 | | | | | | | |
| PRNPA_BUCAP | RIBONUCLEASE P PROTEIN COMPONENT | BUCHNERA APHIDICOLA | 85–114 | | | | | | | | |
| PRNPH_BACSU | RIBONUCLEASE PH | BACILLUS SUBTILIS | 159–186 | | | | | | | | |
| PRNS_ECOLI | REGULATORY PROTEIN RNS | ESCHERICHIA COLI | 116–160 | | | | | | | | |
| PRN_BACCI | RIBONUCLEASE | BACILLUS CIRCULANS | 82–109 | | | | | | | | |
| PRN_BACIN | RIBONUCLEASE PRECURSOR | BACILLUS INTERMEDIUS | 38–72 | | | | | | | | |
| PRP28_BACTK | RNA POLYMERASE SIGMA-28 FACTOR PRECURSOR | BACILLUS THURINGIENSIS | 73–107 | | | | | | | | |
| PRP32_CITFR | RNA POLYMERASE SIGMA-32 FACTOR | CITROBACTER FREUNDII | 30–57 | | | | | | | | |
| PRP35_BACTK | RNA POLYMERASE SIGMA-35 FACTOR PRECURSOR | BACILLUS THURINGIENSIS | 8–35 | 63–90 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRP54_ALCEU | RNA POLYMERASE SIGMA-54 FACTOR | ALCALIGENES EUTROPHUS | 229–266 | | | | | | | | |
| PRP54_AZOCA | RNA POLYMERASE SIGMA-54 FACTOR | AZORHIZOBIUM CAULINODANS | 174–208 | | | | | | | | |
| PRP54_BACSU | RNA POLYMERASE SIGMA-54 FACTOR | BACILLUS SUBTILIS | 16–43 | 97–124 | 274–308 | 396–423 | | | | | |
| PRP54_BRAJA | RNA POLYMERASE SIGMA-54 FACTOR 1 | BRADYRHIZOBIUM JAPONICUM | 97–124 | | | | | | | | |
| PRP54_KLEPN | RNA POLYMERASE SIGMA-54 FACTOR | KLEBSIELLA PNEUMONIAE | 148–182 | | | | | | | | |
| PRP54_RHOCA | RNA POLYMERASE SIGMA-54 FACTOR | RHODOBACTER CAPSULATUS | 155–185 | | | | | | | | |
| PRP55_BRAJA | RNA POLYMERASE SIGMA-54 FACTOR 2 | BRADYRHIZOBIUM JAPONICUM | 145–172 | | | | | | | | |
| PRP5M_ALCEU | PROBABLE SIGMA (54) MODULATION PROTEIN | ALCALIGENES EUTROPHUS | 21–51 | | | | | | | | |
| PRP5M_ECOLI | PROBABLE SIGMA (54) MODULATION PROTEIN | ESCHERICHIA COLI | 21–67 | | | | | | | | |
| PRP5M_SALTY | PROBABLE SIGMA (54) MODULATION PROTEIN | SALMONELLA TYPHIMURIUM | 21–67 | | | | | | | | |
| PRP70_BUCAP | RNA POLYMERASE SIGMA-70 FACTOR | BUCHNERA APHIDICOLA | 69–96 | 109–136 | 173–217 | 228–255 | 303–337 | | | | |
| PRP70_CHLTR | RNA POLYMERASE SIGMA-70 FACTOR | CHLAMYDIA TRACHOMATIS | 5–32 | | | | | | | | |
| PRP70_ECOLI | RNA POLYMERASE SIGMA-70 FACTOR | ESCHERICHIA COLI | 327–361 | | | | | | | | |
| PRP70_PSEAE | RNA POLYMERASE SIGMA-70 FACTOR | PSEUDOMONAS AERUGINOSA | 334–368 | | | | | | | | |
| PRP70_RICPR | RNA POLYMERASE SIGMA-70 FACTOR | RICKETTSIA PROWAZEKII | 244–321 | 348–382 | | | | | | | |
| PRP80_MYXXA | RNA POLYMERASE SIGMA-80 FACTOR | MYXOCOCCUS XANTHUS | 208–235 | 318–347 | 359–386 | | | | | | |
| PRPCF_SYNPY | BILIN BIOSYNTHESIS PROTEIN RPCF | SYNECHOCOCCUS SP | 180–207 | | | | | | | | |
| PRPOA_BACSU | DNA-DIRECTED RNA POLYMERASE ALPHA CHAIN | BACILLUS SUBTILIS | 55–107 | | | | | | | | |
| PRPOA_ECOLI | DNA-DIRECTED RNA POLYMERASE ALPHA CHAIN | ESCHERICHIA COLI & SALMONELLA TYPHIMURIUM | 57–105 | | | | | | | | |
| PRPOA_HALHA | DNA-DIRECTED RNA POLYMERASE SUBUNIT A | HALOBACTERIUM HALOBIUM | 863–904 | | | | | | | | |
| PRPOA_HALMO | DNA-DIRECTED RNA POLYMERASE SUBUNIT A | HALOCOCCUS MORRHUAE | 229–270 | | | | | | | | |
| PRPOA_METTH | DNA-DIRECTED RNA POLYMERASE SUBUNIT A | METHANOBACTERIUM THERMOAUTOTROPHICU | 218–245 | 486–513 | 642–669 | | | | | | |
| PRPOA_SULAC | DNA-DIRECTED RNA POLYMERASE SUBUNIT A | SULFOLOBUS ACIDOCALDARIUS | 222–256 | 500–527 | 693–720 | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRPOA_THECE | DNA-DIRECTED RNA POLYMERASE SUBUNIT A' | THERMOCOCCUS CELER | 228–262 | | | | | | | | |
| PRPOB_ECOLI | DNA-DIRECTED RNA POLYMERASE BETA CHAIN | ESCHERICHIA COLI | 599–626 | 1011–1038 | | | | | | | |
| PRPOB_MYCLE | DNA-DIRECTED RNA POLYMERASE BETA CHAIN | MYCOBACTERIUM LEPRAE | 723–760 | 1084–1111 | | | | | | | |
| PRPOB_SALTY | DNA-DIRECTED RNA POLYMERASE BETA CHAIN | SALMONELLA TYPHIMURIUM | 599–626 | 958–985 | 1011–1038 | | | | | | |
| PRPOB_SULAC | DNA-DIRECTED RNA A-DIRECTED RNA | SULFOLOBUS ACIDOCALDARIUS | 160–187 | 255–282 | 534–561 | 827–861 | | | | | |
| PRPOB_THEMA | DNA-DIRECTED RNA POLYMERASE SUBUNIT B | THERMOTOGA MARITIMA | 350–377 | | | | | | | | |
| PRPOB_ANASP | DNA-DIRECTED RNA POLYMERASE GAMMA CHAIN | ANABAENA SP | 152–194 | | | | | | | | |
| PRPOC_ECOLI | DNA-DIRECTED RNA POLYMERASE BETA' CHAIN | ESCHERICHIA COLI | 786–813 | 948–994 | 1223–1257 | | | | | | |
| PRPOC_HALHA | DNA-DIRECTED RNA POLYMERASE SUBUNIT C | HALOBACTERIUM HALOBIUM | 175–202 | | | | | | | | |
| PRPOC_HALMO | DNA-DIRECTED RNA POLYMERASE SUBUNIT C | HALOCOCCUS MORRHUAE | 27–54 | 117–144 | 207–234 | | | | | | |
| PRPOC_METTH | DNA-DIRECTED RNA POLYMERASE SUBUNIT C | METHANOBACTERIUM THERMOAUTOTROPHICU | 58–85 | 272–302 | 327–354 | | | | | | |
| PRPOC_MYCLE | DNA-DIRECTED RNA POLYMERASE BETA' CHAIN | MYCOBACTERIUM LEPRAE | 273–300 | 860–887 | 911–938 | 1131–1158 | | | | | |
| PRPOC_NOSCO | DNA-DIRECTED RNA POLYMERASE GAMMA CHAIN | NOSTOC COMMUNE | 150–192 | | | | | | | | |
| PRPOC_SULAC | DNA-DIRECTED RNA POLYMERASE SUBUNIT C | SULFOLOBUS ACIDOCALDARIUS | 36–63 | 172–214 | 224–251 | | | | | | |
| PRPOC_THECE | DNA-DIRECTED RNA POLYMERASE SUBUNIT A" | THERMOCOCCUS CELER | 21–58 | | | | | | | | |
| PRPOD_NOSCO | DNA-DIRECTED RNA POLYMERASE DELTA CHAIN | NOSTOC COMMUNE | 72–116 | 402–449 | 539–566 | | | | | | |
| PRPOE_ECOLI | RNA POLYMERASE SIGMA-E FACTOR | ESCHERICHIA COLI | 5–39 | | | | | | | | |
| PRPOS_ECOLI | RNA POLYMERASE SIGMA FACTOR KATF | ESCHERICHIA COLI | 281–308 | | | | | | | | |
| PRPOU_HALHA | DNA-DIRECTED RNA POLYMERASE SUBUNIT B' | HALOBACTERIUM HALOBIUM | 91–118 | | | | | | | | |
| PRPSA_AGRTU | RNA POLYMERASE SIGMA-A FACTOR | AGROBACTERIUM TUMEFACIENS | 310–347 | 397–427 | | | | | | | |
| PRPSA_ANASP | RNA POLYMERASE SIGMA-A FACTOR | ANABAENA SP | 71–105 | | | | | | | | |
| PRPSA_CLOAB | RNA POLYMERASE SIGMA-A FACTOR | CLOSTRIDIUM ACETOBUTYLICUM | 2–29 | | | | | | | | |
| PRPSA_STRAU | RNA POLYMERASE SIGMA FACTOR RPOD | STREPTOMYCES AUREOFACIENS | 278–305 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRPSB_ANASP | RNA POLYMERASE SIGMA-B FACTOR | ANABAENA SP | 4–31 | | | | | | | | |
| PRPSB_BACSU | RNA POLYMERASE SIGMA-B FACTOR | BACILLUS SUBTILIS | 5–35 | 169–196 | 200–230 | | | | | | |
| PRPSB_MYXXA | RNA POLYMERASE SIGMA-B FACTOR | MYXOCOCCUS XANTHUS | 47–74 | | | | | | | | |
| PRPSB_STIAU | RNA POLYMERASE SIGMA-B FACTOR | STIGMATELLA AURANTIACA | 96–123 | | | | | | | | |
| PRPSC_ANASP | RNA POLYMERASE SIGMA-C FACTOR | ANABAENA SP | 58–85 | | | | | | | | |
| PRPSD_BACSU | RNA POLYMERASE SIGMA-D FACTOR | BACILLUS SUBTILIS | 192–249 | | | | | | | | |
| PRPSE_BACSU | RNA POLYMERASE SIGMA-E FACTOR PRECURSOR | BACILLUS SUBTILIS | 63–90 | | | | | | | | |
| PRPSE_CLOAB | RNA POLYMERASE SIGMA-E FACTOR | CLOSTRIDIUM ACETOBUTYLICUM | 14–41 | 116–160 | | | | | | | |
| PRPSF_BACLI | RNA POLYMERASE SIGMA-F FACTOR | BACILLUS LICHENIFORMIS | 4–31 | 191–248 | | | | | | | |
| PRPSF_BACME | RNA POLYMERASE SIGMA-F FACTOR | BACILLUS MEGATERIUM | 191–225 | | | | | | | | |
| PRPSF_BACSU | RNA POLYMERASE SIGMA-F FACTOR | BACILLUS SUBTILIS | 4–41 | 191–248 | | | | | | | |
| PRPSH_BACLI | RNA POLYMERASE SIGMA-H FACTOR | BACILLUS LICHENIFORMIS | 191–218 | | | | | | | | |
| PRPSH_BACSU | RNA POLYMERASE SIGMA-H FACTOR | BACILLUS SUBTILIS | 186–213 | | | | | | | | |
| PRPSK_BACSU | RNA POLYMERASE SIGMA-K FACTOR | BACILLUS SUBTILIS | 75–109 | 189–216 | | | | | | | |
| PRPSP_STAAU | RNA POLYMERASE SIGMA FACTOR PLAC | STAPHYLOCOCCUS AUREUS | 19–46 | | | | | | | | |
| PRPSW_STRCO | RNA POLYMERASE SIGMA FACTOR WHIG | STREPOMYCES COELICOLOR | 232–273 | | | | | | | | |
| PRPSX_BACTK | POSSIBLE RNA POLYMERASE SIGMA-G FACTOR | BACILLUS THURINGIENSIS | 33–60 | | | | | | | | |
| PRS10_ECOLI | 30S RIBOSOMAL PROTEIN S10 | ESCHERICHIA COLI | 3–30 | | | | | | | | |
| PRS11_BACSU | 30S RIBOSOMAL PROTEIN S11 | BACILLUS SUBTILIS | 8–42 | | | | | | | | |
| PRS13_BACSU | 30S RIBOSOMAL PROTEIN S13 | BACILLUS SUBTILIS | 44–85 | | | | | | | | |
| PRS17_METVA | 30S RIBOSOMAL PROTEIN S17 | METHANOCOCCUS VANNIELII | 34–73 | | | | | | | | |
| PRS1_ECOLI | 30S RIBOSOMAL PROTEIN S1 | ESCHERICHIA COLI | 99–126 | 144–171 | | | | | | | |
| PRS1_PROSP | 30S RIBOSOMAL PROTEIN S1 | PROVIDENCIA SP | 39–66 | 265–292 | 349–376 | | | | | | |
| PRS1_RHIME | 30S RIBOSOMAL PROTEIN S1 | RHIZOBIUM MELILOTI | 91–125 | 172–217 | | | | | | | |
| PRS21_BACST | 30S RIBOSOMAL PROTEIN S21 | BACILLUS STEAROTHERMOPHILUS | 1–28 | | | | | | | | |
| PRS2_SPICI | 30S RIBOSOMAL PROTEIN S2 | SPIROPLASMA CITRI | 91–125 | | | | | | | | |
| PRS3_ACHLA | 30S RIBOSOMAL PROTEIN S3 | ACHOLEPLASMA LAIDLAWII | 83–110 | | | | | | | | |
| PRS3_MYCCA | 30S RIBOSOMAL PROTEIN S3 | MYCOPLASMA CAPRICOLUM | 77–106 | 136–163 | | | | | | | |
| PRS4_ECOLI | 30S RIBOSOMAL PROTEIN S4 | ESCHERICHIA COLI | 50–77 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRS5_HALMA | 30S RIBOSOMAL PROTEIN S5 | HALOARCULA MARISMORTUI | 160–187 | | | | | | | | |
| PRS5_MYCCA | 30S RIBOSOMAL PROTEIN S5 | MYCOPLASMA CAPRICOLUM | 35–62 | 182–216 | | | | | | | |
| PRS6_THETH | 30S RIBOSOMAL PROTEIN S6 | THERMUS AQUATICUS | 16–43 | | | | | | | | |
| PRS7_METVA | 30S RIBOSOMAL PROTEIN S7 | METHANOCOCCUS VANNIELII | 69–96 | | | | | | | | |
| PRS7_MYCLE | 30S RIBOSOMAL PROTEIN S7 | MYCOBACTERIUM LEPRAE | 22–49 | | | | | | | | |
| PRS8_MICLU | 30S RIBOSOMAL PROTEIN S8 | MICROCOCCUS LUTEUS | 103–130 | | | | | | | | |
| PRS8_MYCCA | 30S RIBOSOMAL PROTEIN S8 | MYCOPLASMA CAPRICOLUM | 41–78 | | | | | | | | |
| PRSGA_ECOLI | FERRITIN LIKE PROTEIN | ESCHERICHIA COLI | 80–107 | | | | | | | | |
| PRT67_ECOLI | RNA-DIRECTED DNA POLYMERASE | ESCHERICHIA COLI | 225–268 | | | | | | | | |
| PSACB_BACAM | LEVANSUCRASE PRECURSOR | BACILLUS AMYLOLIQUEFACIENS | 175–202 | 254–281 | | | | | | | |
| PSACB_BACSU | LEVANSUCRASE PRECURSOR | BACILLUS SUBTILIS | 175–202 | 254–288 | | | | | | | |
| PSACB_STRMU | LEVANSUCRASE PRECURSOR | STREPTOCOCCUS MUTANS | 31–65 | 155–189 | 314–369 | | | | | | |
| PSACQ_BACLI | SACQ REGULATORY FACTOR | BACILLUS LICHENIFORMIS | 2–46 | | | | | | | | |
| PSACT_BACSU | SACPA OPERON ANTI-TERMINATOR | BACILLUS SUBTILIS | 102–129 | 189–216 | | | | | | | |
| PSAGP_STRPY | STREPTOCOCCAL ACID GLYCOPROTEIN | STREPTOCOCCUS PYOGENES | 294–331 | 362–389 | | | | | | | |
| PSAOX_BACSN | SARCOSINE OXIDASE | BACILLUS SP | 350–377 | | | | | | | | |
| PSAS2_CLOBI | SPORE PROTEIN | CLOSTRIDIUM BIFERMENTANS | 17–47 | | | | | | | | |
| PSASG_BACCE | SPORE PROTEIN GAMMA-TYPE | BACILLUS CEREUS | 31–58 | | | | | | | | |
| PSASG_BACST | SPORE PROTEIN GAMMA-TYPE | BACILLUS STEAROTHERMOPHILUS | 37–64 | | | | | | | | |
| PSBCC_ECOLI | EXONUCLEASE SBCC | ESCHERICHIA COLI | 218–260 | 337–364 | 535–585 | 622–656 | 778–812 | 821–865 | 915–942 | | |
| PSBCD_ECOLI | EXONUCLEASE SBCD | ESCHERICHIA COLI | 137–164 | 334–397 | 553–580 | | | | | | |
| PSBM_ECOLI | SBM PROTEIN | ESCHERICHIA COLI | 5–32 | 436–470 | | | | | | | |
| PSBP_BACSU | SBP PROTEIN | BACILLUS SUBTILIS | 28–55 | | | | | | | | |
| PSCPA_STRPY | C5A PEPTIDASE PRECURSOR | STREPTOCOCCUS PYOGENES | 126–160 | 784–811 | 831–880 | | | | | | |
| PSCRB_KLEPN | SUCROSE-6-PHOSPHATE HYDROLASE | KLEBSIELLA PNEUMONIAE | 174–201 | | | | | | | | |
| PSCRB_LACLA | SUCROSE-6-PHOSPHATE HYDROLASE | LACTOCOCCUS LACTIS | 182–217 | 354–385 | 395–422 | | | | | | |
| PSCRB_STRMU | SUCROSE-6-PHOSPHATE HYDROLASE | STREPTOCOCCUS MUTANS | 335–362 | | | | | | | | |
| PSCRK_SALTH | FRUCTOKINASE | SALMONELLA THOMPSON | 97–124 | | | | | | | | |
| PSCRK_SALTY | FRUCTOKINASE | SALMONELLA TYPHIMURIUM | 183–210 | | | | | | | | |
| PSCRY_KLEPN | SUCROSE PORIN PRECURSOR | KLEBSIELLA PNEUMONIAE | 61–88 | 240–267 | 240–267 | | | | | | |
| PSCRY_SALTY | SUCROSE PORIN PRECURSOR | SALMONELLA TYPHIMURIUM | 16–54 | 61–88 | | | | | | | |
| PSECA_BACSU | PREPROTEIN TRANSLOCASE SECA SUBUNIT | BACILLUS SUBTILIS | 12–39 | 226–260 | | | | | | | |
| PSECA_ECOLI | PREPROTEIN TRANSLOCASE SECA SUBUNIT | ESCHERICHIA COLI | 360–387 | 453–481 | | | | | | | |
| PSECB_ECOLI | PROTEIN-EXPORT PROTEIN SECB | ESCHERICHIA COLI | 41–68 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PSECD_ECOLI | PROTEIN-EXPORT MEMBRANE PROTEIN SECD | ESCHERICHIA COLI | 46–73 | 378–412 | | | | | | | |
| PSECF_ECOLI | PROTEIN-EXPORT MEMBRANE PROTEIN SECF | ESCHERICHIA COLI | 174–201 | | | | | | | | |
| PSECY_ECOLI | PREPROTEIN TRANSLOCASE SECY SUBUNIT | ESCHERICHIA COLI | 101–128 | | | | | | | | |
| PSECY_LACLA | PREPROTEIN TRANSLOCASE SECY SUBUNIT | LACTOCOCCUS LACTIS | 403–430 | | | | | | | | |
| PSECY_METVA | PREPROTEIN TRANSLOCASE SECY SUBUNIT | METHANOCOCCUS VANNIELII | 131–161 | 396–423 | | | | | | | |
| PSECY_STACA | PREPROTEIN TRANSLOCASE SECY SUBUNIT | STAPHYLOCOCCUS CARNOSUS | 149–191 | | | | | | | | |
| PSEFC_SALEN | SEFC PROTEIN PRECURSOR | SALMONELLA ENTERITIDIS | 137–164 | 475–535 | | | | | | | |
| PSERA_BACSU | D-3-PHOSPHOGLYCERATE DEHYDROGENASE | BACILLUS SUBTILIS | 16–43 | 347–374 | | | | | | | |
| PSFAA_ECOLI | 5-FIMBRIAL PROTEIN SUBUNIT PRECURSOR | ESCHERICHIA COLI | 11–38 | | | | | | | | |
| PSFSA_ECOLI | SUGAR FERMENTATION STIMULATION PROTEIN | ESCHERICHIA COLI | 81–115 | | | | | | | | |
| PSFUA_SERMA | IRON-TRANSPORT SFUA PROTEIN PRECURSOR | SERRATIA MARCESCENS | 34–61 | | | | | | | | |
| PSHU1_ECOLI | SHUFFLON PROTEIN A | ESCHERICHIA COLI | 224–262 | | | | | | | | |
| PSHU2_ECOLI | SHUFFLON PROTEIN A' | ESCHERICHIA COLI | 224–262 | | | | | | | | |
| PSHU3_ECOLI | SHUFFLON PROTEIN B | ESCHERICHIA COLI | 224–262 | | | | | | | | |
| PSHU4_ECOLI | SHUFFLON PROTEIN B' | ESCHERICHIA COLI | 224–262 | 402–429 | | | | | | | |
| PSHU5_ECOLI | SHUFFLON PROTEIN C | ESCHERICHIA COLI | 224–262 | | | | | | | | |
| PSHU6_ECOLI | SHUFFLON PROTEIN C' | ESCHERICHIA COLI | 224–262 | | | | | | | | |
| PSHU7_ECOLI | SHUFFLON PROTEIN D' | ESCHERICHIA COLI | 224–262 | | | | | | | | |
| PSINR_BACLI | SINR PROTEIN | BACILLUS LICHENIFORMIS | 9–36 | 43–80 | | | | | | | |
| PSINR_BACSU | SINR PROTEIN | BACILLUS SUBTILIS | 9–36 | 43–70 | | | | | | | |
| PSLAP_ACEKI | CELL SURFACE PROTEIN PRECURSOR | ACETOGENIUM KIVUI | 237–264 | 282–309 | 313–453 | 458–489 | 517–544 | 563–593 | 641–685 | 726–753 | |
| PSLPA_ECOLI | PROPHAGE CP4-57 INTEGRASE | ESCHERICHIA COLI | 93–136 | | | | | | | | |
| PSMF_ECOLI | SMF PROTEIN | ESCHERICHIA COLI | 24–51 | | | | | | | | |
| PSMPB_ECOLI | SMALL PROTEIN B | ESCHERICHIA COLI | 27–61 | | | | | | | | |
| PSMP_ECOLI | SMP PROTEIN PRECURSOR | ESCHERICHIA COLI | 71–98 | 90–117 | | | | | | | |
| PSMTB_SYNP7 | TRANSCRIPTIONAL REPRESSOR SMTB | SYNECHOCOCCUS SP | 62–96 | | | | | | | | |
| PSODF_COXBU | SUPEROXIDE DISMUTASE | COXIELLA BURNETII | 116–143 | | | | | | | | |
| PSODF_ECOLI | SUPEROXIDE DISMUTASE | ESCHERICHIA COLI | 115–142 | | | | | | | | |
| PSODF_METTH | SUPEROXIDE DISMUTASE | METHANOBACTERIUM THERMOAUTOTROPHICU | 25–52 | | | | | | | | |
| PSODF_PHOLE | SUPEROXIDE DISMUTASE | PHOTOBACTERIUM LEIOGNATHI | 22–63 | | | | | | | | |
| PSODM_PROFR | SUPEROXIDE DISMUTASE | PROPIONIBACTERIUM FREUDENREICHII | 164–191 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PSOHB_ECOLI | SOHB PROTEIN PRECURSOR | ESCHERICHIA COLI | 7–48 | 70–97 | 273–300 | | | | | | |
| PSOPB_ECOLI | SOPB PROTEIN | ESCHERICHIA COLI | 252–279 | | | | | | | | |
| PSOXR_ECOLI | SOXR PROTEIN | ESCHERICHIA COLI | 16–63 | | | | | | | | |
| PSP0J_BACSU | STAGE 0 SPORULATION PROTEIN J | BACILLUS SUBTILIS | 131–158 | | | | | | | | |
| PSP2A_BACME | STAGE II SPORULATION PROTEIN AA | BACILLUS MEGATERIUM | 19–53 | | | | | | | | |
| PSP2A_BACSU | STAGE II SPORULATION PROTEIN AA | BACILLUS SUBTILIS | 21–55 | | | | | | | | |
| PSP2B_BACLI | STAGE II SPORULATION PROTEIN AB | BACILLUS LICHENIFORMIS | 42–69 | | | | | | | | |
| PSP2B_BACME | STAGE II SPORULATION PROTEIN AB | BACILLUS MEGATERIUM | 36–73 | | | | | | | | |
| PSP2D_BACSU | STAGE II SPORULATION PROTEIN D | BACILLUS SUBTILIS | 134–161 | | | | | | | | |
| PSP2G_BACTK | POSSIBLE ASPARTYL PROTEASE | BACILLUS THURINGIENSIS | 4–36 | 117–144 | | | | | | | |
| PSP2J_BACSU | STAGE II SPORULATION PROTEIN J | BACILLUS SUBTILIS | 14–44 | 463–500 | | | | | | | |
| PSP3D_BACSU | STAGE III SPORULATION PROTEIN D | BACILLUS SUBTILIS | 9–36 | 52–86 | | | | | | | |
| PSP3J_BACSU | STAGE III SPORULATION PROTEIN J PRECURSOR | BACILLUS SUBTILIS | 44–75 | | | | | | | | |
| PSP4A_BACSU | STAGE IV SPORULATION PROTEIN A | BACILLUS SUBTILIS | 139–180 | | | | | | | | |
| PSP4B_BACSU | STAGE IV SPORULATION PROTEIN B | BACILLUS SUBTILIS | 39–66 | | | | | | | | |
| PSP4G_BACSU | STAGE IV SPORULATION PROTEIN FB | BACILLUS SUBTILIS | 251–278 | | | | | | | | |
| PSP5A_BACSU | STAGE V SPORULATION PROTEIN AF | BACILLUS SUBTILIS | 9–36 | | | | | | | | |
| PSPAA_STRDO | ANTIGEN I | STREPTOCOCCUS DOWNEI | 184–218 | | | | | | | | |
| PSPAB_BACSU | SUBTILIN BIOSYNTHESIS 117 KD PROTEIN | BACILLUS SUBTILIS | 181–208 | | | | | | | | |
| PSPAC_BACSU | SUBTILIN BIOSYNTHESIS PROTEIN SPAC | BACILLUS SUBTILIS | 311–338 | | | | | | | | |
| PSPAK_BACSU | SENSOR PROTEIN SPAK | BACILLUS SUBTILIS | 80–107 | 224–251 | 290–324 | | | | | | |
| PSPAP_STRMU | CELL SURFACE ANTIGEN I/II PRECURSOR | STREPTOCOCCUS MUTANS | 122–276 | 281–465 | 538–565 | 576–630 | 1071–1098 | 1155–1182 | 1377–1430 | | |
| PSPAR_BACSU | REGULATORY PROTEIN | BACILLUS SUBTILIS | 4–31 | 172–199 | | | | | | | |
| PSPAT_BACSU | SUBTILIN TRANSPORT PROTEIN SPAT | BACILLUS SUBTILIS | 55–82 | 226–267 | | | | | | | |
| PSPEC_STRPY | EXOTOXIN TYPE C PRECURSOR | STREPTOCOCCUS PYOGENES | 12–39 | | | | | | | | |
| PSPIR_SPICI | SPIRALIN | SPIROPLASMA CITRI | 82–109 | 155–182 | | | | | | | |
| PSPIR_SPIME | SPIRALIN | SPIROPLASMA MELLIFERUM | 195–222 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PSPOT_ECOLI | GUAN-3',5'-BIS(DIPHOS) 3'-PYROPHOSPHOHYDROLA | ESCHERICHIA COLI | 637–664 | | | | | | | | |
| PSPPA_ECOLI | PROTEASE IV | ESCHERICHIA COLI | 278–305 | | | | | | | | |
| PSQHC_ZYMMO | SQUALENE-HOPENE CYCLASE | ZYMOMONAS MOBILIS | 590–617 | | | | | | | | |
| PSRFA_BACSU | SURFACTIN SYNTHETASE SUBUNIT A | BACILLUS SUBTILIS | 159–186 | 244–271 | | | | | | | |
| PSRP5_ECOLI | SIGNAL RECOGNITION PARTICLE PROTEIN | ESCHERICHIA COLI | 301–328 | | | | | | | | |
| PSRP5_MYCMY | SIGNAL RECOGNITION PARTICLE PROTEIN | MYCOPLASMA MYCOIDES | 21–65 | 107–141 | 394–428 | | | | | | |
| PSSA1_PASHA | SEROTYPE-SPECIFIC ANTIGEN 1 PRECURSOR | PASTEURELLA HAEMOLYTICA | 151–178 | 358–385 | 465–518 | 529–570 | 860–904 | | | | |
| PSSAB_STRPA | ADHESION B PRECURSOR | STREPTOCOCCUS PARASANGUIS | 32–59 | | | | | | | | |
| PSSAB_STRSA | ADHESION B PRECURSOR | STREPTOCOCCUS SANGUIS | 21–59 | 101–128 | | | | | | | |
| PSSB_ECOLI | SINGLE-STRAND BINDING PROTEIN | ESCHERICHIA COLI | 68–95 | | | | | | | | |
| PSSB_PROMI | SINGLE-STRAND BINDING PROTEIN | PROTEUS MIRABILIS | 63–104 | | | | | | | | |
| PSSB_SERMA | SINGLE-STRAND BINDING PROTEIN | SERRATIA MERCESCENS | 63–104 | | | | | | | | |
| PSSP5_STRSA | AGGLUTININ RECEPTOR PRECURSOR | STREPTOCOCCUS SANGUIS | 131–173 | 178–287 | 295–483 | 565–592 | 676–710 | 1081–1131 | | | |
| PSTAV_STRAV | STREPTAVIDIN PRECURSOR | STREPTOMYCES AVIDINII | 125–152 | | | | | | | | |
| PSTA_ECOLI | STREPTOTHRICIN ACETYL-TRANSFERASE | ESCHERICHIA COLI | 66–91 | | | | | | | | |
| PSTC1_STAAU | STAPHYLOCOAGULASE PRECURSOR | STAPHYLOCOCCUS AUREUS | 90–119 | 172–199 | 280–311 | | | | | | |
| PSTC2_STAAU | STAPHYLOCOAGULASE PRECURSOR | STAPHYLOCOCCUS AUREUS | 90–117 | 264–291 | | | | | | | |
| PSTC_CLOBE | L-TRANSD TRANSC CONTROL PROTEIN | CLOSTRIDIUM BEIJERINCKII | 47–74 | | | | | | | | |
| PSTPA_ECOLI | STPA PROTEIN | ESCHERICHIA COLI | 36–63 | | | | | | | | |
| PSTR1_STRGR | INOSAMINE-PHOSPHATE AMIDINOTRANSFERASE 1 | STREPTOMYCES GRISEUS | 183–210 | | | | | | | | |
| PSTRP_STREQ | STREPTOKINASE C PRECURSOR | STREPTOCOCCUS EQUISIMILIS | 209–236 | 281–308 | | | | | | | |
| PSTRP_STRPY | STREPTOKINASE A PRECURSOR | STREPTOCOCCUS PYOGENES | 209–236 | | | | | | | | |
| PSTRP_STRSP | STREPTOKINASE G PRECURSOR | STREPTOCOCCUS SP | 209–236 | 281–308 | | | | | | | |
| PSUBE_BACSU | MINOR EXTRACELLULAR PROTEASE EPR PREC | BACILLUS SUBTILIS | 435–462 | 522–563 | 639 | | | | | | |
| PSUBF_BACSU | BACILLOPEPTIDASE F PRECURSOR | BACILLUS SUBTILIS | 40–67 | 89–116 | 121–148 | 554–597 | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PSUBL_SALTY | SULFATE-BINDING PROTEIN | SALMONELLA TYPHIMURIUM | 37–74 | | | | | | | | |
| PSUBL_SYNP7 | SULFATE-BINDING PROTEIN PRECURSOR | SYNECHOCOCCUS SP | 63–94 | | | | | | | | |
| PSUBL_SYNY3 | SULFATE-BINDING PROTEIN PRECURSOR | SYNECHOCYSTIS SP | 64–91 | | | | | | | | |
| PSUBT_BACLI | SUBTILISIN CARLSBERG PRECURSOR | BACILLUS LICHENIFORMIS | 191–222 | | | | | | | | |
| PSUBT_BACMS | SUBTILISIN | BACILLUS MESENTERICUS | 91–118 | | | | | | | | |
| PSUBT_BACS9 | SUBTILISIN PRECURSOR | BACILLUS SP | 36–63 | 250–277 | | | | | | | |
| PSUBT_BACSA | SUBTILISIN AMYLO-SACCHARITICUS PRECURSOR | BACILLUS SUBTILIS | 197–224 | | | | | | | | |
| PSUBT_BACSD | SUBTILISIN | BACILLUS SUBTILIS | 86–117 | | | | | | | | |
| PSUBT_BACST | SUBTILISIN J PRECURSOR | BACILLUS STEAROTHERMOPHILUS | 197–224 | | | | | | | | |
| PSUBT_BACSU | SUBTILISIN E PRECURSOR | BACILLUS SUBTILIS | 197–224 | | | | | | | | |
| PSUBV_BACSU | MINOR EXTRACELLULAR PROTEASE VPR PRECUR | BACILLUS SUBTILIS | 55–108 | 613–654 | 741–768 | | | | | | |
| PSUCC_ECOLI | SUCCINYL-COA SYNTHETASE BETA | ESCHERICHIA COLI | 62–89 | | | | | | | | |
| PSUCP_AGRVI | SUCROSE PHOSPHORYLASE | AGROBACTERIUM VITIS | 449–476 | | | | | | | | |
| PSULA_ENTAE | CELL DIVISION INHIBITOR | ENTEROBACTER AEROGENES | 112–139 | | | | | | | | |
| PSYA_ECOLI | ALANYL-TRNA SYNTHETASE | ESCHERICHIA COLI | 257–287 | 725–752 | 790–821 | | | | | | |
| PSYD_ECOLI | ASPARTYL-TRNA SYNTHETASE | ESCHERICHIA COLI | 330–357 | | | | | | | | |
| PSYE_BACST | GLUTAMYL-TRNA SYNTHETASE | BACILLUS STEAROTHERMOPHILUS | 49–76 | | | | | | | | |
| PSYE_BACSU | GLUTAMYL-TRNA SYNTHETASE | BACILLUS SUBTILIS | 49–76 | 351–386 | | | | | | | |
| PSYE_THETH | GLUTAMYL-TRNA SYNTHETASE | THERMUS AQUATICUS | 405–432 | | | | | | | | |
| PSYFA_BACSU | PHENYLALANYL-TRNA SYNTHETASE A CHAIN | BACILLUS SUBTILIS | 7–34 | | | | | | | | |
| PSYFB_BACSU | PHENYLALANYL-TRNA SYNTHETASE BETA CHAIN | BACILLUS SUBTILIS | 340–367 | 407–441 | | | | | | | |
| PSYFB_ECOLI | PHENYLALANYL-TRNA SYNTHETASE BETA CHAIN | ESCHERICHIA COLI | 546–573 | 607–634 | 744–771 | | | | | | |
| PSYGB_ECOLI | GLYCYL-TRNA SYNTHETASE BETA CHAIN | ESCHERICHIA COLI | 354–381 | 487–514 | | | | | | | |
| PSYH_STREQ | HISTIDYL-TRNA SYNTHETASE | STREPTOCOCCUS EQUISIMILIS | 376–403 | | | | | | | | |
| PSYI_METTH | ISOLEUCYL-TRNA SYNTHETASE | METHANOBACTERIUM THERMOAUTOTROPHICU | 1010–1037 | | | | | | | | |
| PSYK1_ECOLI | LYSYL-TRNA SYNTHETASE | ESCHERICHIA COLI | 283–310 | | | | | | | | |
| PSYK2_ECOLI | LYSYL-TRNA SYNTHETASE, HEAT INDUCIBLE | ESCHERICHIA COLI | 45–72 | 283–310 | | | | | | | |
| PSYL_ECOLI | LEUCYL-TRNA SYNTHETASE | ESCHERICHIA COLI | 220–247 | | | | | | | | |
| PSYM_BACST | METHIONYL-TRNA SYNTHETASE | BACILLUS STEAROTHERMOPHILUS | 69–99 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PSYM_ECOLI | METHIONYL-TRNA SYNTHETASE | ESCHERICHIA COLI | 87–124 | | | | | | | | |
| PSYP_ECOLI | PROLYL-TRNA SYNTHETASE | ESCHERICHIA COLI | 541–568 | | | | | | | | |
| PSYQ_ECOLI | GLUTAMINYL-TRNA SYNTHETASE | ESCHERICHIA COLI | 394–421 | | | | | | | | |
| PSYRD_PSESY | SYRD PROTEIN | PSEUDOMONAS SYRINGAE | 449–483 | | | | | | | | |
| PSYR_ECOLI | ARGINYL-TRNA SYNTHETASE | ESCHERICHIA COLI | 540–574 | | | | | | | | |
| PSYT1_BACSU | THREONYL-TRNA SYNTHETASE | BACILLUS SUBTILIS | 401–428 | 605–639 | | | | | | | |
| PSYV_BACST | VALYL-TRNA SYNTHETASE | BACILLUS STEAROTHERMOPHILUS | 603–630 | 809–843 | | | | | | | |
| PSYV_ECOLI | VALYL-TRNA SYNTHETASE | ESCHERICHIA COLI | 300–327 | 882–912 | 924–951 | | | | | | |
| PSYW_BACST | TRYPTOPHANYL-TRNA SYNTHETASE | BACILLUS STEAROTHERMOPHILUS | 204–231 | 239–266 | | | | | | | |
| PSYY1_BACSU | TYROSYL-TRNA SYNTHETASE 1 | BACILLUS SUBTILIS | 81–115 | 375–409 | | | | | | | |
| PSYY2_BACSU | TYROSYL-TRNA SYNTHETASE 2 | BACILLUS SUBTILIS | 69–96 | | | | | | | | |
| PSYY_BACCA | TYROSYL-TRNA SYNTHETASE | BACILLUS CALDOTENAX | 295–322 | 372–416 | | | | | | | |
| PSYY_BACST | TYROSYL-TRNA SYNTHETASE | BACILLUS STEAROTHERMOPHILUS | 295–322 | 372–416 | | | | | | | |
| PT1MI_ECOLI | ENZYME ECOR124/3 1 M PROTEIN | ESCHERICHIA COLI | 126–167 | 405–432 | 485–512 | | | | | | |
| PT1R1_ECOLI | ENZYME ECOR124/3 R PROTEIN | ESCHERICHIA COLI | 30–57 | 624–651 | 702–736 | 768–795 | 843–870 | 966–1000 | | | |
| PT1R_ECOLI | ENZYME ECOK 1 R PROTEIN | ESCHERICHIA COLI | 158–263 | | | | | | | | |
| PT1S1_ECOLI | ENZYME ECOR124/3 1 SPECIFICITY PROTEIN | ESCHERICHIA COLI | 154–181 | | | | | | | | |
| PT1SA_ECOLI | ENZYME ECOA I SPECIFICITY PROTEIN | ESCHERICHIA COLI | 279–306 | | | | | | | | |
| PT1SB_ECOLI | ENZYME ECOB I SPECIFICITY PROTEIN | ESCHERICHIA COLI | 278–312 | | | | | | | | |
| PT1SD_ECOLI | ENZYME ECOD I SPECIFICITY PROTEIN | ESCHERICHIA COLI | 249–283 | | | | | | | | |
| PT1SE_ECOLI | ENZYME ECOE I SPECIFICITY PROTEIN | ESCHERICHIA COLI | 279–306 | | | | | | | | |
| PT1S_SALPO | ENZYME SPECIFICITY PROTEIN | SALMONELLA POTSDAM | 396–423 | | | | | | | | |
| PT1S_SALTY | ENZYME SPECIFICITY PROTEIN | SALMONELLA TYPHIMURIUM | 194–221 | 276–304 | 402–429 | | | | | | |
| PT257_ECOLI | TYPE IIS RESTRICTION ENZYME ECO57I | ESCHERICHIA COLI | 138–196 | 265–295 | 406–440 | 639–682 | 687–728 | 926–954 | | | |
| PT2A1_ACICA | TYPE II RESTRICTION ENZYME ACCI | ACINETOBACTER CALCOACETICUS | 49–76 | | | | | | | | |
| PT2BF_BACSU | TYPE II RESTRICTION ENZYME BSUFI | BACILLUS SUBTILIS | 3–43 | 135–223 | 236–280 | | | | | | |
| PT2BR_BACSU | TYPE II RESTRICTION ENZYME BSURI | BACILLUS SUBTILIS | 3–45 | 338–384 | 401–430 | 532–559 | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PT2C1_CITFR | TYPE II RESTRICTION ENZYME CFRBI | CITROBACTER FREUNDII | 35–62 | | | | | | | | |
| PT2C1_HERAU | TYPE II RESTRICTION ENZYME HGICI | HERPETOSIPHON AURANTIACUS | 176–215 | | | | | | | | |
| PT2C2_HERAU | TYPE II RESTRICTION ENZYME HGICII | HERPETOSIPHON AURANTIACUS | 243–273 | | | | | | | | |
| PT2D1_DESDN | TYPE II RESTRICTION ENZYME DDEI | DESULFOVIBRIO DESULFURICANS | 85–122 | | | | | | | | |
| PT2D1_STRPN | TYPE II RESTRICTION ENZYME DPNI | STREPTOCOCCUS PNEUMONIAE | 213–240 | | | | | | | | |
| PT2E1_ECOLI | TYPE II RESTRICTION ENZYME ECORI | ESCHERICHIA COLI | 2–29 | | | | | | | | |
| PT2E2_ECOLI | TYPE II RESTRICTION ENZYME ECORII | ESCHERICHIA COLI | 333–360 | | | | | | | | |
| PT2E5_ECOLI | TYPE II RESTRICTION ENZYME ECORV | ESCHERICHIA COLI | 128–155 | 214–241 | | | | | | | |
| PT2F1_FLAOK | TYPE IIS RESTRICTION ENZYME FOKI | FLAVOBACTERIUM OKEANOKOITES | 302–336 | | | | | | | | |
| PT2H1_HAEIN | TYPE II RESTRICTION ENZYME HINFI | HAEMOPHILUS INFLUENZAE | 6–38 | 69–96 | | | | | | | |
| PT2H1_HAEPA | TYPE II RESTRICTION ENZYME HPAI | HAEMOPHILUS PARAINFLUENZAE | 77–125 | | | | | | | | |
| PT2H2_HAEHA | TYPE II RESTRICTION ENZYME HHAII | HAEMOPHILUS HAEMOLYTICUS | 23–50 | | | | | | | | |
| PT2H2_HAEIN | TYPE II RESTRICTION ENZYME HINCII | HAEMOPHILUS INFLUENZAE | 97–138 | | | | | | | | |
| PT2K1_KLEPN | TYPE II RESTRICTION ENZYME KPNI | KLEBSIELLA PNEUMONIAE | 18–45 | 178–205 | | | | | | | |
| PT2M1_MORBO | TYPE II RESTRICTION ENZYME MBOI | MORAXELLA BOVIS | 15–61 | 187–215 | 225–252 | | | | | | |
| PT2M2_MORBO | TYPE IIS RESTRICTION ENZYME MBOII | MORAXELLA BOVIS | 3–30 | 158–185 | 337–364 | | | | | | |
| PT2MZ_METTF | POSSIBLE TYPE II RESTRICTION ENZYME MTHZI | METHANOBACTERIUM THERMOFORMICICUM | 105–151 | | | | | | | | |
| PT2NG_NEIGO | TYPE II RESTRICTION ENZYME NGOPII | NEISSERIA GONORRHOEAE | 117–144 | 231–258 | | | | | | | |
| PT2S1_STRSA | TYPE II RESTRICTION ENZYME STSI | STREPTOCOCCUS SANGUIS | 5–32 | 41–68 | 395–446 | | | | | | |
| PT2S2_SHISO | TYPE II RESTRICTION ENZYME SSOII | SHIGELLA SONNEI | 206–243 | 258–288 | | | | | | | |
| PT2S3_STAAU | TYPE II RESTRICTION ENZYME SAU3A1 | STAPHYLOCOCCUS AUREUS | 70–102 | | | | | | | | |
| PT2SI_SALIN | TYPE II RESTRICTION ENZYME SINI | SALMONELLA INFANTIS | 144–181 | | | | | | | | |
| PT2SM_SERMA | TYPE II RESTRICTION ENZYME SMAI | SERRATIA MARCESCENS | 61–88 | | | | | | | | |

TABLE VIII-continued

| PCGENE FILE NAME | 107 × 178 × 4 PROTEIN | Prokaryotic Sequences ORGANISM | 107 × 178 × 4 SEARCH MOTIF RESULTS SUMMARY FOR ALL PROCARYOTIC PROTEINS | | | | | | | |
|---|---|---|---|---|---|---|---|---|---|---|
| | | | AREA 1 | AREA 2 | AREA 3 | AREA 4 | AREA 5 | AREA 6 | AREA 7 | AREA 8 | AREA 9 |
| PT2TA_THEAQ | TYPE II RESTRICTION ENZYME TAQI | THERMUS AQUATICUS | 147–181 | 203–237 | | | | | | | |
| PT3MO_ECOLI | SYSTEM ECOP15 ENZYME MOD | ESCHERICHIA COLI | 37–71 | 75–102 | 236–296 | 378–405 | | | | | |
| PT3RE_BACCE | SYSTEM ENZYME RES | BACILLUS CEREUS | 62–89 | 256–283 | | | | | | | |
| PTA47_TREPA | 47 KD MEMBRANE ANTIGEN PRECURSOR | TREPONEMA PALLIDUM | 26–53 | | | | | | | | |
| PTA53_TREDE | 53 KD MEMBRANE ANTIGEN A PRECURSOR | TREPONEMA DENTICOLA | 99–126 | 298–329 | | | | | | | |
| PTACY_BACAL | ALVEOLYSIN PRECURSOR | BACILLUS ALVEI | 272–302 | 374–401 | | | | | | | |
| PTACY_CLOPE | PERFRINGOLYSIN O PRECURSOR | CLOSTRIDIUM PERFRINGENS | 270–311 | 372–434 | | | | | | | |
| PTACY_LISIV | IVANOLYSIN PRECURSOR | LISTERIA IVANOVII | 93–120 | 167–195 | 396–423 | | | | | | |
| PTACY_LISMO | LISTERIOLYSIN O PRECURSOR | LISTERIA MONOCYTOGENES | 98–125 | 168–196 | 295–329 | 397–424 | | | | | |
| PTACY_LISSE | SEELIGERIOLYSIN PRECURSOR | LISTERIA SEELIGERI | 99–126 | 296–323 | 349–376 | 398–463 | | | | | |
| PTACY_STRPN | PNEUMOLYSIN | STREPTOCOCCUS PNEUMONIAE | 234–272 | | | | | | | | |
| PTACY_STRPY | STREPTOLYSIN O PRECURSOR | STREPTOCOCCUS PYOGENES | 86–133 | 355–382 | 440–470 | | | | | | |
| PTAGB_BACSU | TECHOIC ACID BIOSYN PROTEIN B PREC | BACILLUS SUBTILIS | 42–69 | | | | | | | | |
| PTACG_BACSU | TECHOIC ACID BIO-SYNTHESIS PROTEIN C | BACILLUS SUBTILIS | 348–375 | | | | | | | | |
| PTAGE_BACSU | TECHOIC ACID BIO-SYNTHESIS PROTEIN E | BACILLUS SUBTILIS | 59–93 | 144–181 | 185–243 | 565–592 | 600–627 | | | | |
| PTAGF_BACSU | TECHOIC ACID BIO-SYNTHESIS PROTEIN F | BACILLUS SUBTILIS | 182–209 | | | | | | | | |
| PTBP1_NEIGO | TRANSFERRIN-BINDING PROTEIN 1 PRECURSOR | NEISSERIA GONORRHOEAE | 39–73 | 127–164 | 398–425 | 810–841 | | | | | |
| PTBUD_PSEPI | PHENOL 2-MONOOXYGENASE | PSEUDOMONAS PICKETTII | 38–65 | 227–254 | 375–402 | | | | | | |
| PTCDT_SALTY | TRANSCRIPTIONAL REGULATORY PROTEIN TCDT | SALMONELLA TYPHIMURIUM | 105–132 | | | | | | | | |
| PTCPC_VIBCH | MEMBRANE PROTEIN TCPC | VIBRIO CHOLERAE | 20–47 | 83–128 | 199–233 | 263–290 | 344–375 | 459–486 | | | |
| PTCPE_VIBCH | TCP PILUS BIOSYNTHESIS PROTEIN TCPE | VIBRIO CHOLERAE | 24–59 | 77–111 | | | | | | | |
| PTCPF_VIBCH | TCP PILUS SECRETION PROTEIN TCPF | VIBRIO CHOLERAE | 32–66 | 211–238 | | | | | | | |
| PTCPH_VIBCH | TCP PILUS BIOSYNTHESIS PROTEIN TCPH | VIBRIO CHOLERAE | 95–122 | | | | | | | | |
| PTCIP_VIBCH | TCP PILUS VIRULENCE REGULATORY PROTEIN | VIBRIO CHOLERAE | 25–52 | 234–261 | 279–306 | 346–379 | | | | | |
| PTCPN_VIBCH | TCP PILUS BIOSYNTHESIS PROTEIN TCPI | VIBRIO CHOLERAE | 48–75 | | | | | | | | |
| PTCPO_VIBCH | TCP PILUS BIOSYNTHESIS PROTEIN TCPO | VIBRIO CHOLERAE | 230–257 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTCPY_VIBCH | TCP PILUS BIOSYNTHESIS PROTEIN TCPY | VIBRIO CHOLERAE | 121–148 | | | | | | | | |
| PTCPZ_VIBCH | TCP PILUS BIOSYNTHESIS PROTEIN TCPZ | VIBRIO CHOLERAE | 44–85 | | | | | | | | |
| PTCR2_BACSU | TETRACYCLINE RESISTANCE PROTEIN | BACILLUS SUBTILIS | 404–434 | | | | | | | | |
| PTCR_BACST | TETRACYCLINE RESISTANCE PROTEIN | BACILLUS STEAROTHERMOPHILUS | 422–453 | | | | | | | | |
| PTCR_STAAU | TETRACYCLINE RESISTANCE PROTEIN | STAPHYLOCOCCUS AUREUS | 404–431 | | | | | | | | |
| PTCR_STRAG | TETRACYCLINE RESISTANCE PROTEIN | STREPTOCOCCUS AGALACTIAE | 422–453 | | | | | | | | |
| PTCR_STRPN | TETRACYCLINE RESISTANCE PROTEIN | STREPTOCOCCUS PNEUMONIAE | 422–453 | | | | | | | | |
| PTDCA_ECOLI | TDCABC OPERON TRANSCRIPTIONAL ACTIVATOR | ESCHERICHIA COLI | 210–239 | | | | | | | | |
| PTDCC_ECOLI | TDCC PROTEIN | ESCHERICHIA COLI | 334–361 | | | | | | | | |
| PTEE6_STRPY | TRYPSIN-RESIST SURFACE T6 PROTEIN PREC | STREPTOCOCCUS PYOGENES | 137–164 | 361–395 | 400–437 | | | | | | |
| PTER2_ECOLI | TETRACYCLINE REPRESSOR PROTEIN CLASS B | ESCHERICHIA COLI | 8–36 | | | | | | | | |
| PTER4_ECOLI | TETRACYCLINE REPRESSOR PROTEIN CLASS D | ESCHERICHIA COLI | 183–210 | | | | | | | | |
| PTERA_ALCSP | TELLURIUM RESISTANCE PROTEIN TERA | ALCALIGENES SP | 48–86 | | | | | | | | |
| PTESB_ECOLI | ACYL-COA THIOESTERASE II | ESCHERICHIA COLI | 4–31 | | | | | | | | |
| PTET5_ENTFA | TETRACYCLINE RESISTANCE PROTEIN TETM | ENTEROCOCCUS FAECALIS | 2–36 | 130–159 | 179–206 | 217–244 | | | | | |
| PTET9_ENTFA | TETRACYCLINE RESISTANCE PROTEIN TETM | ENTEROCOCCUS FAECALIS | 2–36 | 130–159 | 217–244 | 260–287 | | | | | |
| PTETC_ECOLI | TRANSPOSON TN10 TETC PROTEIN | ESCHERICHIA COLI | 72–106 | 116–158 | | | | | | | |
| PTETM_STRLI | TETRACYCLINE RESISTANCE PROTEIN | STREPTOMYCES LIVIDANS | 82–109 | | | | | | | | |
| PTETM_UREUR | TETRACYCLINE RESISTANCE PROTEIN TETM | UREAPLASMA UREALYTICUM | 2–36 | 130–159 | 217–244 | 260–287 | | | | | |
| PTETO_CAMCO | TETRACYCLINE RESISTANCE PROTEIN TETO | CAMPYLOBACTER COLI | 2–29 | | | | | | | | |
| PTETO_CAMJE | TETRACYCLINE RESISTANCE PROTEIN TETO | CAMPYLOBACTER JEJUNI | 2–36 | | | | | | | | |
| PTETO_STRMU | TETRACYCLINE RESISTANCE PROTEIN TETO | STREPTOCOCCUS MUTANS | 2–29 | | | | | | | | |
| PTETX_BACFR | TETRACYCLINE RESISTANCE PROTEIN | BACTEROIDES FRAGILIS | 25–62 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTETX_CLOTE | TETANUS TOXIN PRECURSOR | CLOSTRIDIUM TETANI | 274–304 | 540–567 | 615–642 | 692–719 | 985–1012 | 1240–1277 | | | |
| PTF2B_PYRWO | TRANS INITIATION FACTOR HB HOMOLOG | PYROCOCCUS WOESEI | 218–258 | | | | | | | | |
| PTFDC_ALCEU | CHLOROCATECHOL 1,2-DIOXYGENASE | ALCALIGENES EUTROPHUS | 2–33 | | | | | | | | |
| PTGT_ECOLI | QUEUINE TRNA-RIBOSYL-TRANSFERASE | ESCHERICHIA COLI | 173–200 | | | | | | | | |
| PTHD1_LACLA | THREONINE DEHYDRATASE BIOSYNTHETIC | LACTOCOCCUS LACTIS | 267–303 | | | | | | | | |
| PTHD2_ECOLI | THREONINE DEHYDRATASE CATABOLIC | ESCHERICHIA COLI | 293–320 | | | | | | | | |
| PTHDF_BACSU | FURAN OXIDATION PROTEIN THDF | BACILLUS SUBTILIS | 153–180 | 192–226 | 282–316 | 391–418 | | | | | |
| PTHDF_ECOLI | FURAN OXIDATION PROTEIN THDF | ESCHERICHIA COLI | 226–260 | 404–431 | | | | | | | |
| PTHDF_PSEPU | FURAN OXIDATION PROTEIN THDF | PSEUDOMONAS PUTIDA | 226–260 | | | | | | | | |
| PTHER_BACCE | THERMOLYSIN | BACILLUS CEREUS | 4–38 | 240–267 | | | | | | | |
| PTHER_BACST | THERMOLYSIN PRECURSOR | BACILLUS STEAROTHERMOPHILUS | 45–72 | | | | | | | | |
| PTHER_BACTH | THERMOLYSIN | BACILLUS THERMOPROTEOLYTICUS | 86–113 | | | | | | | | |
| PTHET_THEVU | THERMITASE | THERMOACTINOMYCES VULGARIS | 131–161 | | | | | | | | |
| PTHIC_ECOLI | THIC PROTEIN | ESCHERICHIA COLI | 232–263 | 301–328 | | | | | | | |
| PTHIG_ECOLI | THIG PROTEIN | ESCHERICHIA COLI | 138–165 | | | | | | | | |
| PTHPS_SULAC | THERMOPSIN PRECURSOR | SULFOLOBUS ACIDOCALDARIUS | 135–172 | 199–233 | | | | | | | |
| PTHRC_BRELA | THREONINE SYNTHASE | BREVIBACTERIUM LACTOFERMENTUM | 288–315 | | | | | | | | |
| PTHTR_SACER | PUTATIVE THIOSULFATE SULFURTRANSFERASE | SACCHAROPOLYSPORA ERYTHRAEA | 69–96 | | | | | | | | |
| PTIG_ECOLI | TRIGGER FACTOR | ESCHERICHIA COLI | 144–171 | | | | | | | | |
| PTMPA_TREPA | TREPONEMAL MEMBRANE PROTEIN A PRECURSOR | TREPONEMA PALLIDUM | 236–266 | | | | | | | | |
| PTMPB_TREPA | TREPONEMAL MEMBRANE PROTEIN B PRECURSOR | TREPONEMA PALLIDUM | 44–71 | | | | | | | | |
| PTMPB_TREPH | TREPONEMAL MEMBRANE PROTEIN B PRECURSOR | TREPONEMA PHAGEDENIS | 41–68 | | | | | | | | |
| PTNAB_ECOLI | LOW AFFINITY TRYPTOPHAN PERMEASE | ESCHERICHIA COLI | 74–108 | | | | | | | | |
| PTNP4_STAAU | TRANSPOSASE | STAPHYLOCOCCUS AUREUS | 52–79 | 322–349 | | | | | | | |
| PTNP7_ENTFA | TRANSPOSON TN917 RESOLVASE | ENTEROCOCCUS FAECALIS | 59–97 | 111–138 | | | | | | | |
| PTNPA_STAAU | TRANSPOSASE A | STAPHYLOCOCCUS AUREUS | 151–178 | | | | | | | | |
| PTNPB_STAAU | TRANSPOSASE B | STAPHYLOCOCCUS AUREUS | 589–625 | | | | | | | | |
| PTNPI_BACTU | TNP I RESOLVASE | BACILLUS THURINGIENSIS | 7–62 | 65–92 | 174–201 | | | | | | |
| PTNSB_ECOLI | TRANSPOSON TN7 TRANSPOSITION PROTEIN TNSB | ESCHERICHIA COLI | 99–126 | 510–537 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTNSC_ECOLI | TRANSPOSON TN7 TRANSPOSITION PROTEIN TNSC | ESCHERICHIA COLI | 32–59 | 314–341 | | | | | | | |
| PTNSD_ECOLI | TRANSPOSON TN7 TRANSPOSITION PROTEIN TNSD | ESCHERICHIA COLI | 339–366 | | | | | | | | |
| PTNSE_ECOLI | TRANSPOSON TN7 TRANSPOSITION PROTEIN TNSE | ESCHERICHIA COLI | 463–490 | | | | | | | | |
| PTOD1_PSEPU | TOLUENE 1,2-DIOXYGENASE ALPHA SUBUNIT | PSEUDOMONAS PUTIDA | 36–63 | | | | | | | | |
| PTOD2_PSEPU | TOLUENE 1,2-DIOXYGENASE BETA SUBUNIT | PSEUDOMONAS PUTIDA | 119–153 | | | | | | | | |
| PTODA_PSEPU | TOLUENE 1,2-DIOXYGENASE SYSTEM | PSEUDOMONAS PUTIDA | 179–213 | | | | | | | | |
| PTODJ_PSEPU | TODF PRODUCT HYDRATASE | PSEUDOMONAS PUTIDA | 143–170 | | | | | | | | |
| PTOLA_ECOLI | TOLA PROTEIN | ESCHERICHIA COLI | 101–138 | | | | | | | | |
| PTOLC_ECOLI | OUTER MEMBRANE PROTEIN TOLC PRECURSOR | ESCHERICHIA COLI | 144–178 | 184–211 | 239–266 | 348–375 | 383–443 | | | | |
| PTOP1_SYNP7 | DNA TOPOISOMERASE I | SYNECHOCOCCUS SP | 203–230 | | | | | | | | |
| PTORA_ECOLI | TRIMETHYLAMINE-N-OXIDE REDUCTASE | ESCHERICHIA COLI | 797–824 | | | | | | | | |
| PTOX1_BORPE | PERTUSSIS TOXIN SUBUNIT 1 (S1) PRECURSOR | BORDETELLA PERTUSSIS | 179–206 | | | | | | | | |
| PTOX2_BORPE | PERTUSSIS TOXIN SUBUNIT 2 (S2) PRECURSOR | BORDETELLA PERTUSSIS | 58–85 | | | | | | | | |
| PTOXA_CLODI | TOXIN A | CLOSTRIDIUM DIFFICILE | 20–88 | 99–159 | 204–231 | 342–369 | 373–414 | 847–962 | 966–994 | 997–1024 | 1348–1402 |
| PTOXA_PSEAE | EXOTOXIN A PRECURSOR | PSEUDOMONAS AERUGINOSA | 470–497 | | | | | | | | |
| PTOXB_CLODI | TOXIN B | CLOSTRIDIUM DIFFICILE | 38–72 | 133–163 | 199–241 | 825–869 | 923–950 | 1334–1388 | 1403–1433 | 1506–1565 | 1716–1747 |
| PTOXS_VIBCH | TRANSMEMBRANE REGULATORY PROTEIN TOXS | VIBRIO CHOLERAE | 13–40 | | | | | | | | |
| PTPF1_TREPA | ANTIGEN TPF 1 | TREPONEMA PALLIDUM | 106–143 | | | | | | | | |
| PTPIS_ECOLI | TRIOSEPHOSPHATE ISOMERASE | ESCHERICHIA COLI | 83–110 | | | | | | | | |
| PTPIS_MORSP | TRIOSEPHOSPHATE ISOMERASE | MORAXELLA SP | 139–166 | | | | | | | | |
| PTPR_PORGI | THIOL PROTEASE PRECURSOR | PORPHYROMONAS GINGIVALIS | 117–144 | | | | | | | | |
| PTR2M_AGRT3 | TRYPTOPHAN 2-MONO-OXYGENASE | AGROBACTERIUM TUMEFACIENS | 239–266 | 501–529 | | | | | | | |
| PTR2M_AGRT4 | TRYPTOPHAN 2-MONO-OXYGENASE | AGROBACTERIUM TUMEFACIENS | 239–266 | 502–529 | | | | | | | |
| PTR2M_PSESS | TRYPTOPHAN 2-MONO-OXYGENASE | PSEUDOMONAS SYRINGAE | 41–68 | | | | | | | | |
| PTRA1_STAAU | TRANSPOSASE | STAPHYLOCOCCUS AUREUS | 58–113 | | | | | | | | |
| PTRA2_STAAU | TRANSPOSASE | STAPHYLOCOCCUS AUREUS | 11–38 | 58–113 | | | | | | | |
| PTRA3_ECOLI | TRANSPOSASE | ESCHERICHIA COLI | 721–755 | | | | | | | | |
| PTRA3_RHIME | TRANSPOSASE | RHIZOBIUM MELILOTI | 179–206 | | | | | | | | |
| PTRA3_STAAU | TRANSPOSASE | STAPHYLOCOCCUS AUREUS | 33–60 | 68–95 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTRA4_ECOLI | TRANSPOSASE | ESCHERICHIA COLI | 181–208 | 308–340 | 720–754 | | | | | | |
| PTRA6_ECOLI | TRANSPOSASE | ESCHERICHIA COLI | 51–78 | | | | | | | | |
| PTRA6_SHISO | TRANSPOSASE | SHIGELLA SONNEI | 51–78 | 200–227 | 231–258 | | | | | | |
| PTRA7_ECOLI | TRANSPOSASE | ESCHERICHIA COLI | 729–756 | | | | | | | | |
| PTRA9_MYCTU | PUTATIVE TRANSPOSASE | MYCOBACTERIUM TUBERCULOSIS | 159–186 | | | | | | | | |
| PTRAB_BACTB | IS231B PROBABLE TRANSPOSASE | BACILLUS THURINGINESIS | 281–308 | 419–446 | | | | | | | |
| PTRAC_BACTB | IS231C PROBABLE TRANSPOSASE | BACILLUS THURINGIENSIS | 281–308 | 419–446 | | | | | | | |
| PTRAC_STAAU | TRANSPOSASE | STAPHYLOCOCCUS AUREUS | 4–31 | 45–72 | | | | | | | |
| PTRAX_BACTB | IS231 PROBABLE TRANSPOSASE | BACILLUS THURINGIENSIS | 281–308 | 419–446 | | | | | | | |
| PTRA_BACTU | TRANSPOSASE | BACILLUS THURINGIENSIS | 93–127 | 509–539 | | | | | | | |
| PTRA_PSEAE | TRANSPOSASE | PSEUDOMONAS AERUGINOSA | 127–154 | 721–755 | | | | | | | |
| PTRB1_ECOLI | TRAB PROTEIN | ESCHERICHIA COLI | 113–143 | | | | | | | | |
| PTRBF_ECOLI | TRBF PROTEIN | ESCHERICHIA COLI | 12–39 | | | | | | | | |
| PTRBI_ECOLI | TRBI PROTEIN | ESCHERICHIA COLI | 70–97 | | | | | | | | |
| PTRC1_ECOLI | TRAC-1 PROTEIN | ESCHERICHIA COLI | 1006–1058 | | | | | | | | |
| PTRC2_ECOLI | TRAC-2 PROTEIN | ESCHERICHIA COLI | 1102–1149 | | | | | | | | |
| PTRC3_ECOLI | TRAC-3 PROTEIN | ESCHERICHIA COLI | 884–931 | | | | | | | | |
| PTRD1_ECOLI | TRAD PROTEIN | ESCHERICHIA COLI | 297–348 | | | | | | | | |
| PTREA_ECOLI | PERIPLASMIC TREHALASE PRECURSOR | ESCHERICHIA COLI | 362–403 | 477–508 | | | | | | | |
| PTREC_ECOLI | AMYLOTREHALASE | ESCHERICHIA COLI | 280–307 | | | | | | | | |
| PTRFA_ECOLI | TRFA TRANSCRIPTIONAL REPRESSOR PROTEIN | ESCHERICHIA COLI | 5–32 | 105–132 | | | | | | | |
| PTRG1_ECOLI | TRAG PROTEIN | ESCHERICHIA COLI | 61–88 | 630–657 | 831–858 | 865–895 | | | | | |
| PTRG5_ECOLI | TRAG PROTEIN | ESCHERICHIA COLI | 196–223 | | | | | | | | |
| PTRG6_ECOLI | TRAG PROTEIN | ESCHERICHIA COLI | 195–222 | 518–545 | | | | | | | |
| PTRI1_ECOLI | TRAI PROTEIN | ESCHERICHIA COLI | 155–209 | 597–624 | 887–914 | 1350–1377 | | | | | |
| PTRI2_ECOLI | TRAI PROTEIN | ESCHERICHIA COLI | 155–209 | 597–624 | 887–914 | 1350–1377 | | | | | |
| PTRI5_ECOLI | TRAI PROTEIN | ESCHERICHIA COLI | 47–74 | 328–371 | | | | | | | |
| PTRJ4_ECOLI | TRAJ PROTEIN | ESCHERICHIA COLI | 36–63 | | | | | | | | |
| PTRM8_ECOLI | TRAM PROTEIN | ESCHERICHIA COLI | 5–32 | | | | | | | | |
| PTRMA_ECOLI | TRNA (URACIL-5-)-METHYL-TRANSFERASE | ESCHERICHIA COLI | 107–137 | | | | | | | | |
| PTRMD_ECOLI | TRNA (GUANINE-N1)-METHYLTRANSFERASE | ESCHERICHIA COLI | 115–142 | 226–253 | | | | | | | |
| PTRPA_BACSU | TRYPTOPHAN SYNTHASE ALPHA CHAIN | BACILLUS SUBTILIS | 220–247 | | | | | | | | |
| PTRPA_CAUCR | TRYPTOPHAN SYNTHASE ALPHA CHAIN | CAULOBACTER CRESCENTUS | 241–275 | | | | | | | | |
| PTRPA_PSEAE | TRYPTOPHAN SYNTHASE ALPHA CHAIN | PSEUDOMONAS AERUGINOSA | 176–203 | | | | | | | | |
| PTRPB_ACICA | TRYPTOPHAN SYNTHASE BETA CHAIN | ACINETOBACTER CALCOACETICUS | 79–113 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTRPB_BACSU | TRYPTOPHAN SYNTHASE BETA CHAIN | BACILLUS SUBTILIS | 76–103 | 318–345 | | | | | | | |
| PTRPB_BRELA | TRYPTOPHAN SYNTHASE BETA CHAIN | BREVIBACTERIUM LACTOFERMENTUM | 172–199 | | | | | | | | |
| PTRPB_LACCA | TRYPTOPHAN SYNTHASE BETA CHAIN | LACTOBACILLUS CASEI | 83–117 | | | | | | | | |
| PTRPB_LACLA | TRYPTOPHAN SYNTHASE BETA CHAIN | LACTOBACILLUS LACTIS | 77–104 | 164–191 | | | | | | | |
| PTRPB_VIBPA | TRYPTOPHAN SYNTHASE BETA CHAIN | VIBRIO PARAHAEMOLYTICUS | 56–83 | | | | | | | | |
| PTRPC_BRELA | INDOLE-3-GLYCEROL PHOSPHATE SYNTHASE | BREVIBACTERIUM LACTOFERMENTUM | 229–256 | | | | | | | | |
| PTRPC_ECOLI | INDOLE-3-GLYCEROL PHOSPHATE SYNTHASE | ESCHERICHIA COLI | 205–232 | | | | | | | | |
| PTRPC_LACLA | INDOLE-3-GLYCEROL PHOSPHATE SYNTHASE | LACTOCOCCUS LACTIS | 148–175 | | | | | | | | |
| PTRPC_VIBPA | INDOLE-3-GLYCEROL PHOSPHATE SYNTHASE | VIBRIO PARAHAEMOLYTICUS | 346–376 | | | | | | | | |
| PTRPD_ACICA | ANTHRANILATE PHOSPHOR-IBOSYLTRANSFERASE | ACINETOBACTER CALCOACETICUS | 223–250 | 260–294 | | | | | | | |
| PTRPD_PSEAE | ANTHRANILATE PHOSPHOR-IBOSYLTRANSFERASE | PSEUDOMONAS AERUGINOSA | 205–232 | | | | | | | | |
| PTRPD_PSEPU | ANTHRANILATE PHOSPHOR-IBOSYLTRANSFERASE | PSEUDOMONAS PUTIDA | 205–232 | | | | | | | | |
| PTRPD_VIBPA | ANTHRANILATE PHOSPHOR-IBOSYLTRANSFERASE | VIBRIO PARAHAEMOLYTICUS | 2–29 | | | | | | | | |
| PTRPE_BACPU | ANTHRANILATE SYNTHASE COMPONENT I | BACILLUS PUMILUS | 33–60 | | | | | | | | |
| PTRPE_CLOTM | ANTHRANILATE SYNTHASE COMPONENT I | CLOSTRIDIUM THERMOCELLUM | 165–226 | | | | | | | | |
| PTRPE_LACLA | ANTHRANILATE SYNTHASE COMPONENT I | LACTOCOCCUS LACTIS | 142–191 | | | | | | | | |
| PTRPE_LEPBI | ANTHRANILATE SYNTHASE COMPONENT I | LEPTOSPIRA BIFLEXA | 145–179 | | | | | | | | |
| PTRPE_RHIME | ANTHRANILATE SYNTHASE COMPONENT I | RHIZOBIUM MELILOTI | 139–166 | | | | | | | | |
| PTRPE_SALTY | ANTHRANILATE SYNTHASE COMPONENT I | SALMONELLA TYPHIMURIUM | 191–218 | | | | | | | | |
| PTRPE_SULSO | ANTHRANILATE SYNTHASE COMPONENT I | SULFOLOBUS SOLFATARICUS | 143–183 | 298–328 | | | | | | | |
| PTRPE_VIBPA | ANTHRANILATE SYNTHASE COMPONENT I | VIBRIO PARAHAEMOLYTICUS | 9–36 | 54–81 | | | | | | | |
| PTRPG_ACICA | ANTHRANILATE SYNTHASE COMPONENT II | ACINETOBACTER CALCOACETICUS | 12–39 | | | | | | | | |
| PTRPG_AZOBR | ANTHRANILATE SYNTHASE COMPONENT II | AZOSPIRILLUM BRASILENSE | 4–31 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTRPG_ECOLI | ANTHRANILATE SYNTHASE COMPONENT II | ESCHERICHIA COLI | 5–32 | | | | | | | | |
| PTRPG_LACLA | ANTHRANILATE SYNTHASE COMPONENT II | LACTOCOCCUS LACTIS | 4–31 | | | | | | | | |
| PTRPG_PSEAE | ANTHRANILATE SYNTHASE COMPONENT II | PSEUDOMONAS AERUGINOSA | 12–39 | | | | | | | | |
| PTRPG_SALTY | ANTHRANILATE SYNTHASE COMPONENT II | SALMONELLA TYPHIMURIUM | 5–32 | | | | | | | | |
| PTRPG_SERMA | ANTHRANILATE SYNTHASE COMPONENT II | SERRATIA MARCESCENS | 9–43 | | | | | | | | |
| PTRPG_SHIDY | ANTHRANILATE SYNTHASE COMPONENT II | SHIGELLA DYSENTERIAE | 5–32 | | | | | | | | |
| PTRPO_PSEAE | PUTATIVE TRANSCRIPTIONAL REGULATOR | PSEUDOMONAS AERUGINOSA | 147–174 | | | | | | | | |
| PTRS2_ECOLI | TRANS PROTEIN | ESCHERICHIA COLI | 85–119 | | | | | | | | |
| PTRT3_ECOLI | RESISTANCE PROTEIN PRECURSOR | ESCHERICHIA COLI | 184–221 | | | | | | | | |
| PTRY1_SALTY | TRAY PROTEIN | SALMONELLA TYPHIMURIUM | 30–57 | | | | | | | | |
| PTRYP_STRGR | TRYPSIN PRECURSOR | STREPTOMYCES GRISEUS | 80–107 | | | | | | | | |
| PTSR_STRAZ | RRNA METHYLTRANSFERASE | STREPTOMYCES AZUREUS | 126–153 | | | | | | | | |
| PTSST_STAAU | TOXIC SHOCK SYNDROME TOXIN-1 PRECURSOR | STAPHYLOCOCCUS AUREUS | 29–63 | 102–129 | | | | | | | |
| PTSX_ECOLI | CHANNEL-FORMING PROTEIN TSX PRECURSOR | ESCHERICHIA COLI | 225–252 | | | | | | | | |
| PTTK_ECOLI | HYPOTHETICAL 24.3 KD PROTEIN | ESCHERICHIA COLI | 81–115 | | | | | | | | |
| PTUS_ECOLI | SITE-BINDING PROTEIN | ESCHERICHIA COLI | 57–91 | 107–134 | | | | | | | |
| PTYCA_BACBR | TRYOCIDINE SYNTHETASE I | BACILLUS BREVIS | 117–147 | 534–561 | 1019–1051 | | | | | | |
| PTYF1_TREPE | ANTIGEN TYF1 | TREPONEMA PERTENUE | 106–143 | | | | | | | | |
| PTYRA_BACSU | POSSIBLE PREPHENATE DEHYDROGENASE | BACILLUS SUBTILIS | 244–271 | 312–342 | | | | | | | |
| PTYRA_ECOLI | CHORISMATE MUTASE | ESCHERICHIA COLI | 329–370 | | | | | | | | |
| PTYRR_ECOLI | TRANSCRIPTIONAL REGULATORY PROTEIN TYRR | ESCHERICHIA COLI | 483–510 | | | | | | | | |
| PTYSY_LACCA | THYMIDYLATE SYNTHASE | LACTOBACILLUS CASEI | 139–173 | | | | | | | | |
| PTYSY_LACLA | THYMIDYLATE SYNTHASE | LACTOCOCCUS LACTIS | 75–109 | | | | | | | | |
| PTYSY_STAAU | THYMIDYLATE SYNTHASE | STAPHYLOCOCCUS AUREUS | 69–96 | | | | | | | | |
| PUHPB_ECOLI | SENSOR PROTEIN UHPB | ESCHERICHIA COLI | 276–303 | 316–343 | | | | | | | |
| PUHPB_SALTY | SENSOR PROTEIN UHPB | SALMONELLA TYPHIMURIUM | 276–303 | 316–343 | | | | | | | |
| PUMUC_SALTY | UMUC PROTEIN | SALMONELLA TYPHIMURIUM | 204–231 | | | | | | | | |
| PUPP_ECOLI | URACIL PHOSPHORIBOSYL-TRANSFERASE | ESCHERICHIA COLI | 30–57 | | | | | | | | |
| PURAA_ECOLI | URACIL PERMEASE | ESCHERICHIA COLI | 350–384 | | | | | | | | |
| PURE1_HELPY | UREASE ALPHA SUBUNIT | HELICOBACTER PYLORI | 15–42 | | | | | | | | |
| PURE1_PROMI | UREASE ALPHA SUBUNIT | PROTEUS MIRABILIS | 72–99 | | | | | | | | |
| PURE1_PROVU | UREASE ALPHA SUBUNIT | PROTEUS VULGARIS | 72–99 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PURE1_UREUR | UREASE ALPHA SUBUNIT | UREAPLASMA UREALYTICUM | 13–40 | 483–517 | | | | | | | |
| PURE2_HELPY | UREASE BETA SUBUNIT | HELICOBACTER PYLORI | 62–99 | | | | | | | | |
| PURED_HELPY | UREASE OPERON URED PROTEIN | HELICOBACTER PYLORI | 17–44 | | | | | | | | |
| PUREE_PROMI | UREASE ACCESSORY PROTEIN UREE | PROTEUS MIRABILIS | 57–84 | | | | | | | | |
| PUREF_KLEAE | UREASE ACCESSORY PROTEIN UREF PRECURSOR | KLEBSIELLA AEROGENES | 20–47 | | | | | | | | |
| PUS45_LACLA | SECRETED 45 KD PROTEIN PRECURSOR | LACTOCOCCUS LACTIS | 44–98 | 150–223 | 276–303 | | | | | | |
| PUSHA_ECOLI | P-SUGAR HYDROLASE PRECURSOR | ESCHERICHIA COLI | 56–83 | | | | | | | | |
| PUSHA_SALTY | SILENT PROTEIN USHA (0) PRECURSOR | SALMONELLA TYPHIMURIUM | 56–83 | | | | | | | | |
| PUVRA_ECOLI | EXCINUCLEASE ABC SUBUNIT A | ESCHERICHIA COLI | 527–554 | 871–898 | | | | | | | |
| PUVRA_MICLU | EXCINUCLEASE ABC SUBUNIT A | MICROCOCCUS LUTEUS | 579–606 | 619–646 | 684–718 | 922–949 | | | | | |
| PUVRA_PARDE | EXCINUCLEASE ABC SUBUNIT A | PARACOCCUS DENITRIFICANS | 33–60 | | | | | | | | |
| PUVRC_BACSU | EXCINUCLEASE ABC SUBUNIT C | BACILLUS SUBTILIS | 342–372 | 511–538 | | | | | | | |
| PUVRC_ECOLI | EXCINUCLEASE ABC SUBUNIT C | ESCHERICHIA COLI | 37–64 | 332–362 | | | | | | | |
| PUVRD_ECOLI | HELICASE II | ESCHERICHIA COLI | 280–307 | | | | | | | | |
| PVANA_ENTFC | VANCOMYCIN RESISTANCE PROTEIN VANA | ENTEROCOCCUS FAECIUM | 182–209 | | | | | | | | |
| PVANC_ENTGA | VANCOMYCIN RESISTANCE PROTEIN VANC | ENTEROCOCCUS GALLINARUM | 177–211 | | | | | | | | |
| PVIB4_AGRT5 | VIRB4 PROTEIN PRECURSOR | AGROBACTERIUM TUMEFACIENS | 138–172 | | | | | | | | |
| PVIB6_AGRT5 | VIRB6 PROTEIN | AGROBACTERIUM TUMEFACIENS | 190–227 | | | | | | | | |
| PVIB6_AGRT6 | VIRB6 PROTEIN | AGROBACTERIUM TUMEFACIENS | 190–227 | | | | | | | | |
| PVIB6_AGRT9 | VIRB6 PROTEIN | AGROBACTERIUM TUMEFACIENS | 190–227 | | | | | | | | |
| PVIBX_AGRT5 | VIRB10 PROTEIN | AGROBACTERIUM TUMEFACIENS | 32–59 | 212–239 | | | | | | | |
| PVIBX_AGRT6 | VIRB10 PROTEIN | AGROBACTERIUM TUMEFACIENS | 32–59 | 211–238 | | | | | | | |
| PVIBX_AGRT9 | VIRB10 PROTEIN | AGROBACTERIUM TUMEFACIENS | 32–59 | 212–239 | | | | | | | |
| PVIC1_AGRRA | VIRC1 PROTEIN | AGROBACTERIUM RHIZOGENES | 81–108 | | | | | | | | |
| PVIC1_AGRT5 | VIRC1 PROTEIN | AGROBACTERIUM TUMEFACIENS | 81–108 | | | | | | | | |
| PVIC1_AGRT6 | VIRC1 PROTEIN | AGROBACTERIUM TUMEFACIENS | 81–108 | | | | | | | | |
| PVID3_AGRRA | VIRD3 PROTEIN | AGROBACTERIUM RHIZOGENES | 149–176 | 265–292 | | | | | | | |
| PVIRA_AGRT5 | WIDE HOST RANGE (WHR) VIRA PROTEIN | AGROBACTERIUM TUMEFACIENS | 42–76 | 113–147 | 657–684 | | | | | | |
| PVIRA_AGRT6 | WIDE HOST RANGE (WHR) VIRA PROTEIN | AGROBACTERIUM TUMEFACIENS | 42–69 | 84–125 | 653–680 | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVIRA_AGRT9 | WIDE HOST RANGE (WHR) VIRA PROTEIN | AGROB

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PXYLK_STAXY | XYLULOSE KINASE | STAPHYLOCOCCUS XYLOSUS | 4–31 | 96–130 | 209–236 | 246–273 | | | | | |
| PXYLR_BACSU | XYLOSE REPRESSOR | BACILLUS SUBTILIS | 75–102 | 260–287 | | | | | | | |
| PXYLR_LACPE | XYLOSE REPRESSOR | LACTOBACILLUS PENTOSUS | 262–289 | | | | | | | | |
| PXYLR_STAXY | XYLOSE REPRESSOR | STAPHYLOCOCCUS XYLOSUS | 20–64 | 101–158 | 181–215 | 221–255 | 274–301 | | | | |
| PXYLZ_PSEPU | ELECTRON TRANSFER COMPONENT | PSEUDOMONAS PUTIDA | 51–78 | 104–131 | | | | | | | |
| PXYN4_CALSA | PUTATIVE ENDO-1,4-BETA-XYLANASE | CALDOCELLUM SACCHAROLYTICUM | 198–225 | | | | | | | | |
| PXYNA_BACCI | O-1,4-BETA-XYLANASE PRECURSOR | BACILLUS CIRCULANS | 47–74 | | | | | | | | |
| PXYNA_BACSS | ENDO-1,4-BETA-XYLANASE PRECURSOR | BACILLUS SP | 173–200 | | | | | | | | |
| PXYNA_BACSU | ENDO-1,4-BETA-XYLANASE PRECURSOR | BACILLUS SUBTILIS | 47–74 | | | | | | | | |
| PXYNA_CALSA | ENDO-1,4-BETA-XYLANASE A PRECURSOR | CALDOCELLUM SACCHAROLYTICUM | 132–159 | 226–256 | | | | | | | |
| PXYNA_PSEFL | ENDO-1,4-BETA-XYLANASE PRECURSOR | PSEUDOMONAS FLUORESCENS | 33–82 | | | | | | | | |
| PXYNB_BACPU | BETA-XYLOSIDASE | BACILLUS PUMILUS | 459–486 | | | | | | | | |
| PXYNB_CALSA | BETA-XYLOSIDASE | CALDOCELLUM SACCHAROLYTICUM | 440–474 | | | | | | | | |
| PXYNB_PSEFL | ENDO-1,4-BETA-XYLANASE PRECURSOR | PSEUDOMONAS FLUORESCENS | 51–78 | 251–278 | 317–344 | 475–502 | | | | | |
| PXYNC_PSEFL | ENDO-1,4-BETA-XYLANASE | PSEUDOMONAS FLUORESCENS | 51–78 | 251–278 | | | | | | | |
| PXYNC_STRLI | ALPHA-L-ARABINOFURAN-OSIDASE C PRECURSOR | STREPTOMYCES LIVIDANS | 183–210 | | | | | | | | |
| PXYNC_STRLI | ENDO-1,4-BETA-XYLANASE C PRECURSOR | | | 172–218 | | | | | | | |
| PY14K_HALMO | HYPOTHETICAL 14.9 KD PROTEIN | HALOCOCCUS MORRHUAE | 56–83 | | | | | | | | |
| PY23K_STROR | HYPOTHETICAL 23.1 KD PROTEIN | STREPTOCOCCUS ORALIS | 78–105 | | | | | | | | |
| PY36K_METSM | HYPOTHETICAL 36.7 KD PROTEIN | METHANOBREVIBACTER SMITHII | 128–162 | | | | | | | | |
| PYAAC_ECOLI | HYPOTHETICAL 34.6 KD PROTEIN | ESCHERICHIA COLI | 271–298 | | | | | | | | |
| PYAAC_PSEFL | HYPOTHETICAL 33.9 KD PROTEIN | PSEUDOMONAS FLUORESCENS | 274–301 | | | | | | | | |
| PYAAM_ECOLI | HYPOTHETICAL 59.1 KD PROTEIN | ESCHERICHIA COLI | 45–72 | | | | | | | | |
| PYAAP_ECOLI | HYPOTHETICAL 56.6 KD PROTEIN | ESCHERICHIA COLI | 352–379 | | | | | | | | |
| PYAAQ_ECOLI | HYPOTHETICAL 28.5 KD PROTEIN | ESCHERICHIA COLI | 155–182 | | | | | | | | |
| PYABC_ECOLI | HYPOTHETICAL 34.9 KD PROTEIN | ESCHERICHIA COLI | 131–158 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYABG_ECOLI | HYPOTHETICAL 89.7 KD PROTEIN | ESCHERICHIA COLI | 446–480 | 627–654 | | | | | | | |
| PYABN_ECOLI | HYPOTHETICAL 63.9 KD PROTEIN | ESCHERICHIA COLI | 428–455 | | | | | | | | |
| PYAC3_PSEAE | HYPOTHETICAL 23.9 KD PROTEIN | PSEUDOMONAS AERUGINOSA | 48–75 | 150–177 | | | | | | | |
| PYAD2_CLOAB | HYPOTHETICAL 21.6 KD PROTEIN | CLOSTRIDIUM ACETOBUTYLICUM | 75–109 | 114–144 | | | | | | | |
| PYAD3_CLOAB | HYPOTHETICAL 36.9 KD PROTEIN | CLOSTRIDIUM ACETOBUTYLICUM | 132–159 | 165–196 | 210–237 | | | | | | |
| PYAD6_CLOAB | HYPOTHETICAL PROTEIN | CLOSTRIDIUM ACETOBUTYLICUM | 21–55 | | | | | | | | |
| PYADA_YEREN | INVASIN PRECURSOR | YERSINIA ENTEROCOLITICA | 196–230 | 247–274 | 318–381 | | | | | | |
| PYADA_YERPS | INVASIN PRECURSOR | YERSINIA PSEUDOTUBERCULOSIS | 255–282 | 297–360 | | | | | | | |
| PYADC_ECOLI | HYPOTHETICAL PROTEIN | ESCHERICHIA COLI | 13–40 | 101–131 | | | | | | | |
| PYAEA_RICRI | 17 KD PROTEIN | RICKETTSIA RICKETTSII | 107–134 | | | | | | | | |
| PYAFB_ECOLI | HYPOTHETICAL 29.4 KD PROTEIN | ESCHERICHIA COLI | 221–248 | | | | | | | | |
| PYAFD_ECOLI | HYPOTHETICAL 29.1 KD PROTEIN | ESCHERICHIA COLI | 34–71 | | | | | | | | |
| PYAFE_ECOLI | HYPOTHETICAL 23.0 KD PROTEIN | ESCHERICHIA COLI | 123–150 | | | | | | | | |
| PYA1B_ESCFE | HYPOTHETICAL PROTEIN | ESCHERICHIA FERGUSONII | 2–35 | | | | | | | | |
| PYAM1_SALTY | PUTATIVE AMIDASE | SALMONELLA TYPHIMURIUM | 73–100 | | | | | | | | |
| PYAT1_SYNY3 | HYPOTHETICAL 13.0 KD PROTEIN | SYNECHOCYSTIS SP | 26–60 | | | | | | | | |
| PYATP_MYCLE | HYPO PROTEIN PUTATIVE ATP OPERON | MYCOBACTERIUM LEPRAE | 23–57 | 91–158 | 511–538 | | | | | | |
| PYATR_BACFI | HYPO L ATP-BINDING TRANSPORT PROTEIN | BACILLUS FIRMUS | 211–238 | | | | | | | | |
| PYATS_MYCGA | HYPOTHETICAL PROTEIN | MYCOPLASMA GALLISEPTICUM | 7–41 | | | | | | | | |
| PYATU_MYCGA | HYPOTHETICAL PROTEIN | MYCOPLASMA GALLISEPTICUM | 29–56 | 60–87 | | | | | | | |
| PYAV5_XANCV | HYPOTHETICAL 50 KD AVIRULENCE PROTEIN | XANTHOMONAS CAMPESTRIS | 68–98 | 199–226 | | | | | | | |
| PYBAH_ECOLI | HYPOTHETICAL 24.8 KD PROTEIN | ESCHERICHIA COLI | 49–79 | | | | | | | | |
| PYBBA_ECOLI | HYPOTHETICAL ABC TRANSPORTER | ESCHERICHIA COLI | 6–69 | | | | | | | | |
| PYBED_ECOLI | HYPOTHETICAL 9.8 KD PROTEIN | ESCHERICHIA COLI | 51–82 | | | | | | | | |
| PYBID_ECOLI | HYPOTHETICAL 14.1 KD PROTEIN | ESCHERICHIA COLI | 97–124 | | | | | | | | |
| PYCAE_ECOLI | HYPOTHETICAL 24.5 KD PROTEIN | ESCHERICHIA COLI | 34–61 | | | | | | | | |
| PYCBA_ECOLI | HYPOTHETICAL PROTEIN | ESCHERICHIA COLI | 38–65 | | | | | | | | |
| PYCBL_BACUN | HYPOTHETICAL 17.3 KD PROTEIN | BACTEROIDES UNIFORMIS | 66–100 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYCEA_BACLA | HYPOTHETICAL PROTEIN | BACILLUS LAUTUS | 111–138 | | | | | | | | |
| PYCFC_ECOLI | HYPOTHETICAL 22.9 KD PROTEIN | ESCHERICHIA COLI | 52–79 | | | | | | | | |
| PYCHR_ALCEU | HYPOTHETICAL PROTEIN | ALCALIGENES EUTROPHUS | 21–48 | | | | | | | | |
| PYC1B_ECOLI | HYPOTHETICAL 20.8 KD PROTEIN | ESCHERICHIA COLI | 16–43 | | | | | | | | |
| PYC1F_ECOLI | 18.6 KD PROTEIN | ESCHERICHIA COLI | 7–68 | 134–166 | | | | | | | |
| PYC1K_ECOLI | HYPOTHETICAL PROTEIN | ESCHERICHIA COLI | 35–62 | | | | | | | | |
| PYC11_ECOLI | HYPOTHETICAL 43.3 KD PROTEIN | ESCHERICHIA COLI | 54–81 | | | | | | | | |
| PYCP3_SYNPY | HYPOTHETICAL 29.3 KD PROTEIN | SYNECHOCOCCUS SP | 194–221 | | | | | | | | |
| PYCP3_SYNY3 | HYPOTHETICAL 28.0 KD PROTEIN | SYNECHOCYSTIS SP | 7–34 | 120–154 | | | | | | | |
| PYCP5_SYNY3 | HYPOTHETICAL 39.5 KD PROTEIN | SYNECHOCYSTIS SP | 277–308 | | | | | | | | |
| PYCPG_MASLA | HYPOTHETICAL PROTEIN | MASTIGOCLADUS LAMINOSUS | 2–29 | | | | | | | | |
| PYCPY_PSEA9 | HYPO PHYCOCYANIN OPERON PROTEIN Y | PSEUDANABAENA SP | 380–407 | | | | | | | | |
| PYCR2_BACTK | HYPOTHETICAL 29.1 KD PROTEIN | BACILLUS THURINGIENSIS | 42–84 | 153–180 | | | | | | | |
| PYCS5_ECOLI | HYPOTHETICAL PROTEIN PRECURSOR | ESCHERICHIA COLI | 32–59 | | | | | | | | |
| PYCW5_BACSU | HYPOTHETICAL PROTEIN | BACILLUS SUBTILIS | 3–30 | 59–86 | | | | | | | |
| PYD3M_HERAU | HYPOTHETICAL 68.4 KD PROTEIN | HERPETOSIPHON AURANTIACUS | 12–39 | 151–178 | 360–416 | | | | | | |
| PYDBA_ECOLI | HYPOTHETICAL PROTEIN | ESCHERICHIA COLI | 32–66 | 117–144 | 163–216 | 233–267 | 295–329 | 458–485 | 676–717 | 1136–1163 | 1499–1530 |
| PYDBD_ECOLI | HYPOTHETICAL PROTEIN | ESCHERICHIA COLI | 80–107 | 683–714 | 726–753 | | | | | | |
| PYDDB_ECOLI | HYPOTHETICAL 86.7 KD PROTEIN | ESCHERICHIA COLI | 606–641 | | | | | | | | |
| PYDDC_ECOLI | HYPOTHETICAL 80.8 KD PROTEIN | ESCHERICHIA COLI | 373–400 | 421–452 | 621–648 | | | | | | |
| PYDDD_ECOLI | HYPOTHETICAL 24.1 KD PROTEIN | ESCHERICHIA COLI | 133–174 | | | | | | | | |
| PYDEH_ECOLI | HYPOTHETICAL 20.5 KD PROTEIN | ESCHERICHIA COLI | 96–130 | | | | | | | | |
| PYDEJ_ECOLI | HYPOTHETICAL 18.3 KD PROTEIN | ESCHERICHIA COLI | 4–38 | | | | | | | | |
| PYDEK_ECOLI | HYPOTHETICAL 65.5 KD PROTEIN | ESCHERICHIA COLI | 333–360 | 524–551 | 565–592 | | | | | | |
| PYDNN_BORBU | HYPOTHETICAL 11.2 KD PROTEIN | BORRELIA BURGDORFERI | 6–36 | | | | | | | | |
| PYDO1_SULSO | HYPOTHETICAL 14.7 KD PROTEIN | SULFOLOBUS SOLFATARICUS | 17–58 | 71–103 | | | | | | | |
| PYDO3_SULSO | HYPOTHETICAL 16.9 KD PROTEIN | SULFOLOBUS SOLFATARICUS | 11–38 | | | | | | | | |

TABLE VIII-continued

107 x 178 x 4 SEARCH MOTIF RESULTS SUMMARY FOR ALL PROCARYOTIC PROTEINS

| PCGENE FILE NAME | 107 x 178 x 4 | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYEBA_ECOLI | HYPOTHETICAL PROTEIN | ESCHERICHIA COLI | 93–120 | | | | | | | | |
| PYEBG_ECOLI | HYPOTHETICAL 10.7 KD PROTEIN | ESCHERICHIA COLI | 50–77 | | | | | | | | |
| PYEEE_ECOLI | HYPOTHETICAL 38.1 KD PROTEIN | ESCHERICHIA COLI | 43–70 | | | | | | | | |
| PYEEF_ECOLI | HYPO 49.8 KD TRANSPORT PROTEIN | ESCHERICHIA COLI | 147–174 | | | | | | | | |
| PYEGA_ECOLI | HYPOTHETICAL IN DCD 3' REGION | ESCHERICHIA COLI | 145–172 | | | | | | | | |
| PYEHA_ECOLI | HYPOTHETICAL 36.9 KD PROTEIN | ESCHERICHIA COLI | 69–106 | 283–310 | | | | | | | |
| PYEHB_ECOLI | HYPOTHETICAL 92.3 KD PROTEIN | ESCHERICHIA COLI | 151–178 | 501–545 | | | | | | | |
| PYEHD_ECOLI | HYPOTHETICAL 19.1 KD PROTEIN | ESCHERICHIA COLI | 96–123 | | | | | | | | |
| PYEHF_ECOLI | HYPOTHETICAL 140.0 KD PROTEIN | ESCHERICHIA COLI | 543–570 | | | | | | | | |
| PYEHI_ECOLI | HYPOTHETICAL 138.1 KD PROTEIN | ESCHERICHIA COLI | 35–70 | 102–129 | | | | | | | |
| PYEHU_ECOLI | HYPOTHETICAL 62.1 KD PROTEIN | ESCHERICHIA COLI | 326–353 | | | | | | | | |
| PYEIC_ECOLI | HYPOTHETICAL 33.6 KD PROTEIN | ESCHERICHIA COLI | 46–80 | | | | | | | | |
| PYEIF_ECOLI | HYPOTHETICAL PROTEIN | ESCHERICHIA COLI | 61–88 | | | | | | | | |
| PYEII_ECOLI | HYPOTHETICAL 43.4 KD PROTEIN | ESCHERICHIA COLI | 15–42 | | | | | | | | |
| PYEJA_ECOLI | HYPOTHETICAL ABC TRANSPORTER | ESCHERICHIA COLI | 83–110 | | | | | | | | |
| PYEJF_ECOLI | HYPOTHETICAL PROTEIN | ESCHERICHIA COLI | 453–480 | | | | | | | | |
| PYEJO_ECOLI | HYPOTHETICAL 91.2 KD PROTEIN | ESCHERICHIA COLI | 399–433 | | | | | | | | |
| PYFHD_ECOLI | HYPOTHETICAL 40.6 KD PROTEIN | ESCHERICHIA COLI | 175–202 | | | | | | | | |
| PYFU2_BACST | HYPOTHETICAL 30.6 KD PROTEIN | BACILLUS STEAROTHERMOPHILUS | 133–160 | | | | | | | | |
| PYFXK_BRAJA | HYPOTHETICAL PROTEIN | BRADYRHIZOBIUM JAPONICUM | 109–150 | | | | | | | | |
| PYGAP_BACME | HYPOTHETICAL 37.7 KD PROTEIN | BACILLUS MEGATERIUM | 40–67 | | | | | | | | |
| PYGFD_ECOLI | HYPOTHETICAL 29.4 KD PROTEIN | ESCHERICHIA COLI | 214–241 | | | | | | | | |
| PYGGB_ECOLI | HYPOTHETICAL 30.9 KD PROTEIN | ESCHERICHIA COLI | 225–252 | | | | | | | | |
| PYGGG_ECOLI | HYPOTHETICAL 31.8 KD PROTEIN | ESCHERICHIA COLI | 209–236 | | | | | | | | |
| PYG12_BACTU | HYPOTHETICAL 22.8 KD PROTEIN | BACILLUS THURINGIENSIS | 26–61 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYG12_PSEPU | HYPOTHETICAL 32.4 KD PROTEIN | PSEUDOMONAS PUTIDA | 145–172 | | | | | | | | |
| PYG1F_ECOLI | HYPOTHETICAL 48.4 KD PROTEIN | ESCHERICHIA COLI | 223–264 | | | | | | | | |
| PYG14_BACST | HYPOTHETICAL 35.5 KD PROTEIN | BACILLUS STEAROTHERMOPHILUS | 6–33 | | | | | | | | |
| PYG15_BACST | HYPOTHETICAL PROTEIN | BACILLUS STEAROTHERMOPHILUS | 182–209 | | | | | | | | |
| PYGLN_BACCE | HYPOTHETICAL 15 KD PROTEIN | BACILLUS CEREUS | 79–124 | | | | | | | | |
| PYGRD_BACSU | HYPOTHETICAL PROTEIN | BACILLUS SUBTILIS | 20–47 | | | | | | | | |
| PYGRE_BACSU | HYPOTHETICAL 17.1 KD PROTEIN | BACILLUS SUBTILIS | 84–111 | | | | | | | | |
| PYGRP_BACSU | HYPOTHETICAL 39.0 KD PROTEIN | BACILLUS SUBTILIS | 98–125 | | | | | | | | |
| PYGRP_CLOAB | HYPOTHETICAL 38.8 KD PROTEIN | CLOSTRIDIUM ACETOBUTYLICUM | 160–210 | | | | | | | | |
| PYGT2_STRMU | HYPOTHETICAL PROTEIN 2 | STREPTOCOCCUS MUTANS | 4–40 | 110–138 | 235–262 | | | | | | |
| PYHAB_ECOLI | HYPOTHETICAL 20.6 KD PROTEIN | ESCHERICHIA COLI | 20–65 | | | | | | | | |
| PYHAC_ECOLI | HYPOTHETICAL 45.2 KD PROTEIN | ESCHERICHIA COLI | 69–96 | | | | | | | | |
| PYHAF_ECOLI | HYPOTHETICAL PROTEIN | ESCHERICHIA COLI | 44–71 | 138–165 | | | | | | | |
| PYHBG_ECOLI | PROBABLE ABC TRANSPORTER | ESCHERICHIA COLI | 176–203 | | | | | | | | |
| PYHBG_PSEPU | PROBABLE ABC TRANSPORTER | PSEUDOMONAS PUTIDA | 74–101 | 106–133 | 147–174 | | | | | | |
| PYHBG_THIFE | PROBABLE ABC TRANSPORTER | THIOBACILLUS FERROOXIDANS | 113–140 | | | | | | | | |
| PYHDF_ECOLI | HYPOTHETICAL 55.4 KD PROTEIN | ESCHERICHIA COLI | 267–297 | | | | | | | | |
| PYHEM_BACSU | HYPOTHETICAL 32.0 KD PROTEIN | BACILLUS SUBTILIS | 222–253 | | | | | | | | |
| PYHET_ANASP | HYPOTHETICAL PROTEIN | ANABAENA SP | 72–99 | | | | | | | | |
| PYHHA_ECOLI | HYPOTHETICAL 16.6 KD PROTEIN | ESCHERICHIA COLI | 56–84 | | | | | | | | |
| PYHIG_ECOLI | HYPOTHETICAL 15.1 KD PROTEIN | ESCHERICHIA COLI | 43–77 | | | | | | | | |
| PYHHH_ECOLI | HYPOTHETICAL 14.5 KD PROTEIN | ESCHERICHIA COLI | 43–73 | | | | | | | | |
| PYHI1_LACLA | HYPOTHETICAL PROTEIN | LACTOCOCCUS LACTIS | 167–194 | | | | | | | | |
| PYHI3_LACLA | HYPOTHETICAL 38.0 KD PROTEIN | LACTOCOCCUS LACTIS | 90–124 | 132–159 | | | | | | | |
| PYHI6_LACLA | HYPOTHETICAL 30.7 KD PROTEIN | LACTOCOCCUS LACTIS | 92–148 | | | | | | | | |
| PYHI8_LACLA | HYPOTHETICAL 30.7 KD PROTEIN | LACTOCOCCUS LACTIS | 77–104 | 156–183 | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYHLB_STAAU | HYPOTHETICAL PROTEIN | STAPHYLOCOCCUS AUREUS | 18–67 | | | | | | | | |
| PYHLB_VIBCH | HYPOTHETICAL 18.3 KD PROTEIN | VIBRIO CHOLERAE | 99–126 | | | | | | | | |
| PYHMF_METFE | HYPOTHETICAL 32.2 KD PROTEIN | METHANOTHERMUS FERVIDUS | 106–133 | | | | | | | | |
| PYHS1_CLOAB | HYPOTHETICAL 11.0 KD PROTEIN | CLOSTRIDIUM ACETOBUTYLICUM | 41–85 | | | | | | | | |
| PYHSA_CLOAB | HYPOTHETICAL 20.6 KD PROTEIN | CLOSTRIDIUM ACETOBUTYLICUM | 98–125 | | | | | | | | |
| PYHSC_CLOAB | HYPOTHETICAL 42.4 KD PROTEIN | CLOSTRIDIUM ACETOBUTYLICUM | 25–52 | 208–253 | 276–310 | | | | | | |
| PYHV1_LACHE | HYPOTHETICAL PROTEIN | LACTOBACILLUS HELVETICUS | 93–120 | 127–154 | | | | | | | |
| PYHYA_PSESN | HYPOTHETICAL PROTEIN | PSEUDOMONAS SP | 217–266 | | | | | | | | |
| PYI11_HALHA | HYPOTHETICAL 38.0 KD PROTEIN | HALOBACTERIUM HALOBIUM | 245–272 | | | | | | | | |
| PYI32_MYCTU | IS986 HYPOTHETICAL 6.6 KD PROTEIN | MYCOBACTERIUM TUBERCULOSIS | 19–46 | | | | | | | | |
| PYI42_PSEAY | HYPOTHETICAL 42.6 KD PROTEIN | PSEUDOMONAS AMYLODERAMOSA | 9–36 | | | | | | | | |
| PYI48_METSM | ISM1 HYPOTHETICAL 48.3 KD PROTEIN | METHANOBREVIBACTER SMITHII | 73–100 | 154–184 | 338–365 | | | | | | |
| PYI52_HALHA | HYPOTHETICAL 31 KD PROTEIN | HALOBACTERIUM HALOBIUM | 86–113 | | | | | | | | |
| PYIBB_ECOLI | HYPOTHETICAL 34.0 KD PROTEIN | ESCHERICHIA COLI | 202–239 | | | | | | | | |
| PYIBD_ECOLI | HYPOTHETICAL PROTEIN | ESCHERICHIA COLI | 9–43 | | | | | | | | |
| PYIBF_ECOLI | HYPOTHETICAL 22.6 KD PROTEIN | ESCHERICHIA COLI | 131–158 | | | | | | | | |
| PYIBG_ECOLI | HYPOTHETICAL 18.1 KD PROTEIN | ESCHERICHIA COLI | 70–97 | | | | | | | | |
| PYICC_ECOLI | HYPOTHETICAL 33.2 KD PROTEIN | ESCHERICHIA COLI | 143–170 | | | | | | | | |
| PYICD_ECOLI | HYPOTHETICAL 31.1 KD PROTEIN | ESCHERICHIA COLI | 132–159 | | | | | | | | |
| PYICE_ECOLI | HYPOTHETICAL 62.3 KD PROTEIN | ESCHERICHIA COLI | 408–435 | | | | | | | | |
| PYICL_ECOLI | HYPOTHETICAL 88.1 KD PROTEIN | ESCHERICHIA COLI | 122–149 | | | | | | | | |
| PYICN_ECOLI | HYPOTHETICAL 18.2 KD PROTEIN | ESCHERICHIA COLI | 76–103 | | | | | | | | |
| PYICO_ECOLI | HYPOTHETICAL 49.9 KD PROTEIN | ESCHERICHIA COLI | 320–347 | | | | | | | | |
| PYIDB_ECOLI | HYPOTHETICAL 13.8 KD PROTEIN | ESCHERICHIA COLI | 34–78 | | | | | | | | |
| PYIDE_ECOLI | HYPOTHETICAL 58.9 KD PROTEIN | ESCHERICHIA COLI | 86–113 | 182–209 | 277–304 | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYIDI_ECOLI | HYPOTHETICAL 15.7 KD PROTEIN | ESCHERICHIA COLI | 56–83 | | | | | | | | |
| PYIDK_ECOLI | HYPOTHETICAL 62.1 KD PROTEIN | ESCHERICHIA COLI | 2–39 | | | | | | | | |
| PYIDP_ECOLI | HYPOTHETICAL 27.3 KD PROTEIN | ESCHERICHIA COLI | 63–97 | | | | | | | | |
| PYIEA_ECOLI | HYPOTHETICAL 49.2 KD PROTEIN | ESCHERICHIA COLI | 221–248 | | | | | | | | |
| PYIEC_ECOLI | HYPOTHETICAL 60.6 KD PROTEIN | ESCHERICHIA COLI | 20–58 | 270–297 | | | | | | | |
| PYIEC_ERWCH | HYPOTHETICAL PROTEIN | ERWINIA CHRYSANTHEMI | 22–67 | | | | | | | | |
| PYIED_ECOLI | HYPOTHETICAL 34.8 KD PROTEIN | ESCHERICHIA COLI | 86–120 | | | | | | | | |
| PYIEG_ECOLI | HYPOTHETICAL 46.9 KD PROTEIN | ESCHERICHIA COLI | 293–327 | | | | | | | | |
| PYIEH_ECOLI | HYPOTHETICAL 24.7 KD PROTEIN | ESCHERICHIA COLI | 51–78 | | | | | | | | |
| PYIEM_ECOLI | HYPOTHETICAL 15.0 KD PROTEIN | ESCHERICHIA COLI | 73–105 | | | | | | | | |
| PYIEO_ECOLI | HYPOTHETICAL 51.5 KD PROTEIN | ESCHERICHIA COLI | 201–242 | 380–407 | | | | | | | |
| PYIFC_ECOLI | HYPOTHETICAL 39.6 KD PROTEIN | ESCHERICHIA COLI | 175–202 | | | | | | | | |
| PYIGJ_ECOLI | HYPOTHETICAL 14.0 KD PROTEIN | ESCHERICHIA COLI | 51–92 | | | | | | | | |
| PYIGM_ECOLI | HYPOTHETICAL 33.7 KD PROTEIN | ESCHERICHIA COLI | 120–154 | | | | | | | | |
| PYIGN_ECOLI | HYPOTHETICAL 54.7 KD PROTEIN | ESCHERICHIA COLI | 207–234 | | | | | | | | |
| PYIGO_ECOLI | HYPOTHETICAL 28.1 KD PROTEIN | ESCHERICHIA COLI | 67–94 | | | | | | | | |
| PYIGP_ECOLI | HYPOTHETICAL 22.3 KD PROTEIN | ESCHERICHIA COLI | 173–200 | | | | | | | | |
| PYIGT_ECOLI | HYPOTHETICAL 27.8 KD PROTEIN | ESCHERICHIA COLI | 132–159 | | | | | | | | |
| PYIHB_ECOLI | HYPOTHETICAL 21.2 KD PROTEIN | ESCHERICHIA COLI | 13–40 | | | | | | | | |
| PYIHD_ECOLI | HYPOTHETICAL 10.3 KD PROTEIN | ESCHERICHIA COLI | 28–55 | | | | | | | | |
| PYIHF_ECOLI | HYPOTHETICAL 54.1 KD PROTEIN | ESCHERICHIA COLI | 272–306 | | | | | | | | |
| PYIHI_ECOLI | HYPOTHETICAL 19.1 KD PROTEIN | ESCHERICHIA COLI | 112–139 | | | | | | | | |
| PYIHK_ECOLI | HYPOTHETICAL 65.4 KD PROTEIN | ESCHERICHIA COLI | 4–31 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYIHM_ECOLI | HYPOTHETICAL 36.9 KD PROTEIN | ESCHERICHIA COLI | 83–110 | 120–154 | 297–324 | | | | | | |
| PYIHO_ECOLI | HYPOTHETICAL 81.8 KD PROTEIN | ESCHERICHIA COLI | 612–646 | | | | | | | | |
| PYIHP_ECOLI | HYPOTHETICAL 53.1 KD PROTEIN | ESCHERICHIA COLI | 357–384 | | | | | | | | |
| PYIHV_ECOLI | HYPOTHETICAL 31.9 KD PROTEIN | ESCHERICHIA COLI | 72–99 | | | | | | | | |
| PYIHX_ECOLI | HYPOTHETICAL 23.5 KD PROTEIN | ESCHERICHIA COLI | 9–36 | | | | | | | | |
| PYIHZ_ECOLI | HYPOTHETICAL 15.9 KD PROTEIN | ESCHERICHIA COLI | 6–33 | | | | | | | | |
| PYIIP_ECOLI | HYPOTHETICAL 32.9 KD PROTEIN | ESCHERICHIA COLI | 22–63 | | | | | | | | |
| PYIIU_ECOLI | HYPOTHETICAL 9.6 KD PROTEIN | ESCHERICHIA COLI | 28–71 | | | | | | | | |
| PYIIC_ECOLI | HYPOTHETICAL 26.6 KD PROTEIN | ESCHERICHIA COLI | 136–163 | | | | | | | | |
| PYIIH_ECOLI | HYPOTHETICAL 78.3 KD PROTEIN | ESCHERICHIA COLI | 225–263 | | | | | | | | |
| PYIIK_ECOLI | HYPOTHETICAL 11.2 KD PROTEIN | ESCHERICHIA COLI | 26–53 | | | | | | | | |
| PYIIO_ECOLI | HYPOTHETICAL 32.1 KD PROTEIN | ESCHERICHIA COLI | 214–241 | | | | | | | | |
| PYIIP_ECOLI | HYPOTHETICAL 66.6 KD PROTEIN | ESCHERICHIA COLI | 110–137 | 419–446 | | | | | | | |
| PYINL_LISMO | HYPOTHETICAL 26.8 KD PROTEIN | LISTERIA MONOCYTOGENES | 7–34 | | | | | | | | |
| PYIS1_SHISO | INSERITON ELEMENT IS600 | SHIGELLA SONNEI | 62–89 | | | | | | | | |
| PYIS1_STRCO | IS110 HYPOTHETICAL 43.6 KD PROTEIN | STREPTOMYCES COELICOLOR | 125–152 | | | | | | | | |
| PYIS3_SHISO | INSERITON LEMENT IS629 | SHIGELLA SONNEI | 66–100 | | | | | | | | |
| PYISP_BACSP | HYPOTHETICAL 42.1 KD PROTEIN | BACILLUS SP | 312–339 | | | | | | | | |
| PYIAG_ECOLI | HYPOTHETICAL 22.6 KD PROTEIN | ESCHERICHIA COLI | 51–78 | | | | | | | | |
| PYIAJ_ECOLI | HYPOTHETICAL 20.4 KD PROTEIN | ESCHERICHIA COLI | 88–122 | | | | | | | | |
| PYIBH_ECOLI | HYPOTHETICAL 78.5 KD PROTEIN | ESCHERICHIA COLI | 93–120 | | | | | | | | |
| PYIBL_ECOLI | HYPOTHETICAL 9.7 KD PROTEIN | ESCHERICHIA COLI | 30–57 | | | | | | | | |
| PYIBM_ECOLI | HYPOTHETICAL 26.7 KD PROTEIN | ESCHERICHIA COLI | 112–149 | | | | | | | | |
| PYIBQ_ECOLI | HYPOTHETICAL 15.7 KD PROTEIN | ESCHERICHIA COLI | 2–29 | | | | | | | | |

TABLE VIII-continued 107 x 178 x 4 SEARCH MOTIF RESULTS SUMMARY FOR ALL PROCARYOTIC PROTEINS

| PCGENE FILE NAME | 107 x 178 x 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYICC_ECOLI | HYPOTHETICAL 60.8 KD PROTEIN | ESCHERICHIA COLI | 38–65 | 414–441 | 451–492 | | | | | | |
| PYICE_ECOLI | HYPOTHETICAL 60.5 KD PROTEIN | ESCHERICHIA COLI | 454–481 | | | | | | | | |
| PYICG_ECOLI | HYPOTHETICAL 59.2 KD PROTEIN | ESCHERICHIA COLI | 394–421 | | | | | | | | |
| PYICO_ECOLI | HYPOTHETICAL 25.1 KD PROTEIN | ESCHERICHIA COLI | 91–118 | | | | | | | | |
| PYICP_ECOLI | HYPOTHETICAL 53.4 KD PROTEIN | ESCHERICHIA COLI | 242–269 | | | | | | | | |
| PYICS_ECOLI | HYPOTHETICAL 73.7 KD PROTEIN | ESCHERICHIA COLI | 366–396 | | | | | | | | |
| PYICW_ECOLI | HYPOTHETICAL ABC TRANSPORTER | ESCHERICHIA COLI | 50–94 | | | | | | | | |
| PYIDA_ECOLI | HYPOTHETICAL 84.2 KD PROTEIN | ESCHERICHIA COLI | 2–29 | 451–485 | | | | | | | |
| PYIDB_ECOLI | HYPOTHETICAL PROTEIN | ESCHERICHIA COLI | 103–134 | | | | | | | | |
| PYIJA_ECOLI | HYPOTHETICAL 17.5 KD PROTEIN | ESCHERICHIA COLI | 35–69 | 88–129 | | | | | | | |
| PYKAB_BACFI | HYPOTHETICAL 48.8 KD PROTEIN | BACILLUS FIRMUS | 321–355 | | | | | | | | |
| PYLA1_LACAC | HYPOTHETICAL PROTEIN | LACTOBACILLUS ACIDOPHILUS | 47–74 | | | | | | | | |
| PYLA2_LACAC | HYPOTHETICAL 14.5 KD PROTEIN | LACTOBACILLUS ACIDOPHILUS | 15–42 | | | | | | | | |
| PYLA3_LACAC | HYPOTHETICAL 14.4 KD PROTEIN | LACTOBACILLUS ACIDOPHILUS | 47–74 | | | | | | | | |
| PYLAC_SULSO | HYPOTHETICAL 24.4 KD PROTEIN | SULFOLOBUS SOLFATARICUS | 23–50 | | | | | | | | |
| PYLP3_PSEPU | HYPOTHETICAL 44.7 KD PROTEIN | PSEUDOMONAS PUTIDA | 186–213 | 314–341 | | | | | | | |
| PYLPA_YEREN | YLPA LIPOPROTEIN PRECURSOR | YERSINIA ENTEROCOLITICA | 184–221 | | | | | | | | |
| PYLT3_ANAVA | HYPOTHETICAL 22.6 KD PROTEIN | ANABAENA VARIABILIS | 172–199 | | | | | | | | |
| PYLUD_LACLA | HYPOTHETICAL 29.7 KD PROTEIN | LACTOCOCCUS LACTIS | 35–70 | | | | | | | | |
| PYME2_BACSU | HYOPTHETICAL 35.3 KD PROTEIN | BACILLUS SUBTILIS | 52–79 | | | | | | | | |
| PYMG2_MYCGE | HYPOTHETICAL 114.4 KD PROTEIN PRECURSOR | MYCOPLASMA GENITALIUM | 56–83 | 159–193 | 420–445 | 981–1008 | | | | | |
| PYNGA_CLOPE | HYPOTHETICAL PROTEIN | CLOSTRIDIUM PERFRINGENS | 139–166 | | | | | | | | |
| PYNGB_CLOPE | HYPOTHETICAL 31.2 KD PROTEIN | CLOSTRIDIUM PERFRINGENS | 12–49 | 63–97 | 182–211 | | | | | | |
| PYNI1_METTL | HYPOTHETICAL PROTEIN | METHANOCOCCUS THERMOLITHOTROPHICUS | 55–89 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYNQ1_PARDE | HYPOTHETICAL 9.3 KD PROTEIN | PARACOCCUS DENITRIFICANS | 52–86 | | | | | | | | |
| PYNT3_ANASP | HYPOTHETICAL 28.1 KD PROTEIN | ANABAENA SP | 171–198 | | | | | | | | |
| PYNT5_ANASP | HYPOTHETICAL PROTEIN | ANABAENA SP | 87–165 | | | | | | | | |
| PYOHD_ECOLI | HYPOTHETICAL 21.4 KD PROTEIN | ESCHERICHIA COLI | 5–32 | | | | | | | | |
| PYOHG_ECOLI | HYPOTHETICAL 43.3 KD PROTEIN | ESCHERICHIA COLI | 104–171 | 289–316 | | | | | | | |
| PYOJA_ECOLI | HYPOTHETICAL 15.0 KD PROTEIN | ESCHERICHIA COLI | 17–44 | | | | | | | | |
| PYOJE_ECOLI | HYPOTHETICAL 93.5 KD PROTEIN | ESCHERICHIA COLI | 221–248 | | | | | | | | |
| PYOIF_ECOLI | HYPOTHETICAL 9.5 KD PROTEIN | ESCHERICHIA COLI | 41–82 | | | | | | | | |
| PYOIH_ECOLI | HYPOTHETICAL 54.3 KD PROTEIN | ESCHERICHIA COLI | 145–193 | | | | | | | | |
| PYOJJ_ECOLI | HYPOTHETICAL 36.2 KD PROTEIN | ESCHERICHIA COLI | 94–121 | | | | | | | | |
| PYOMA2_PHOS9 | HYPOTHETICAL PROTEIN IN OMPH 3' REGION | PHOTOBACTERIUM SP | 32–59 | | | | | | | | |
| PYOPH_YEREN | PROTEIN-TYROSINE PHOSPHATASE YOPH | YERSINIA ENTEROCOLITICA | 63–105 | | | | | | | | |
| PYOPH_YERPS | PROTEIN-TYROSINE PHOSPHATASE YOPH | YERSINIA PSEUDOTUBERCULOSIS | 63–105 | | | | | | | | |
| PYOPN_YEREN | OUTER MEMBRANE PROTEIN YOPN | YERSINIA ENTEROCOLITICA | 23–50 | 66–93 | 235–262 | | | | | | |
| PYOPN_YERPS | OUTER MEMBRANE PROTEIN YOPN | YERSINIA PSEUDOTUBERCULOSIS | 23–50 | 66–93 | 235–262 | | | | | | |
| PYOPQ_YEREN | YOPQ PROTEIN PRECURSOR | YERSINIA ENTEROCOLITICA | 61–88 | | | | | | | | |
| PYORA_HAEIN | HYPOTHETICAL 31.5 KD PROTEIN | HAEMOPHILUS INFLUENZAE | 147–174 | | | | | | | | |
| PYORA_LISMO | HYPOTHETICAL 25.6 KD PROTEIN | LISTERIA MONOCYTOGENES | 32–77 | | | | | | | | |
| PYORA_PYRWO | HYPOTHETICAL 24.7 KD PROTEIN | PYROCOCCUS WOESEI | 183–210 | | | | | | | | |
| PYORB_HAEIN | HYPOTHETICAL 19.8 KD PROTEIN | HAEMOPHILUS INFLUENZAE | 39–66 | | | | | | | | |
| PYORC_HAEIN | HYPOTHETICAL 19.9 KD PROTEIN | HAEMOPHILUS INFLUENZAE | 49–79 | | | | | | | | |
| PYORE_HAEIN | 8 KD PROTEIN | HAEMOPHILUS INFLUENZAE | 47–74 | 82–109 | | | | | | | |
| PYORF_HAEIN | 26.8 KD PROTEIN | HAEMOPHILUS INFLUENZAE | 199–229 | | | | | | | | |
| PYORH_HAEIN | HYPOTHETICAL 13.7 KD PROTEIN | HAEMOPHILUS INFLUENZAE | 7–34 | | | | | | | | |

TABLE VIII-continued

| PCGENE FILE NAME | 107 × 178 × 4 | Prokaryotic Sequences ORGANISM | 107 × 178 × 4 SEARCH MOTIF RESULTS SUMMARY FOR ALL PROCARYOTIC PROTEINS | | | | | | | | |
|---|---|---|---|---|---|---|---|---|---|---|---|
| | | | AREA 1 | AREA 2 | AREA 3 | AREA 4 | AREA 5 | AREA 6 | AREA 7 | AREA 8 | AREA 9 |
| PYORI_HAEIN | 95.4 KD PROTEIN | HAEMOPHILUS INFLUENZAE | 416-450 | 688-722 | | | | | | | |
| PYORQ_BACSU | HYPOTHETICAL 34 KD PROTEIN | BACILLUS SUBTILIS | 148-175 | | | | | | | | |
| PYORX_PYRWO | HYPOTHETICAL PROTEIN | PYROCOCCUS WOESEI | 66-93 | | | | | | | | |
| PYORZ_LISMO | HYPOTHETICAL 16.9 KD PROTEIN | LISTERIA MONOCYTOGENES | 27-54 | | | | | | | | |
| PYP15_STAAU | HYPOTHETICAL 15.5 KD PROTEIN | STAPHYLOCOCCUS AUREUS | 71-98 | 110-137 | | | | | | | |
| PYP23_BACSU | HYPOTHETICAL 22.5 KD PROTEIN | BACILLUS SUBTILIS | 57-84 | | | | | | | | |
| PYP23_STAAU | HYPOTHETICAL 22.2 KD PROTEIN | STAPHYLOCOCCUS AUREUS | 29-70 | | | | | | | | |
| PYP2A_STAAU | HYPOTHETICAL 26.9 KD PROTEIN | STAPHYLOCOCCUS AUREUS | 34-104 | | | | | | | | |
| PYP2B_STAAU | HYPOTHETICAL 27.0 KD PROTEIN | STAPHYLOCOCCUS AUREUS | 23-60 | 62-89 | 179-206 | | | | | | |
| PYP2C_STAAU | HYPOTHETICAL 27.7 KD PROTEIN | STAPHYLOCOCCUS AUREUS | 13-83 | 129-176 | | | | | | | |
| PYP7_AGRT4 | HYPOTHETICAL PROTEIN 7 | AGROBACTERIUM TUMEFACIENS | 29-56 | | | | | | | | |
| PYPA2_LEGPN | HYPOTHETICAL PROTEIN | LEGIONELLA PNEUMOPHILA | 94-135 | | | | | | | | |
| PYPAS_ENTFA | HYPOTHETICAL 13 KD PROTEIN | ENTEROCOCCUS FAECALIS | 79-106 | | | | | | | | |
| PYPA_BACAN | HYPOTHETICAL 21.6 KD PROTEIN | BACILLUS ANTHRACIS | 13-47 | 115-162 | | | | | | | |
| PYPC1_ECOLI | HYPOTHETICAL 27.6 KD PROTEIN | ESCHERICHIA COLI | 5-32 | | | | | | | | |
| PYPDA_BACSU | HYPOTHETICAL 27.3 KD PROTEIN | BACILLUS SUBTILIS | 184-222 | | | | | | | | |
| PYPFT_ECOLI | HYPOTHETICAL 12.6 KD PROTEIN | ESCHERICHIA COLI | 16-43 | | | | | | | | |
| PYPH1_SYNP2 | HYPOTHETICAL 18.1 KD PROTEIN | SYNECHOCOCCUS SP | 34-61 | | | | | | | | |
| PYP16_CLOPE | HYPOTHETICAL 19.7 KD PROTEIN | CLOSTRIDIUM PERFRINGENS | 7-34 | 43-77 | 83-149 | | | | | | |
| PYP19_CLOPE | HYPOTHETICAL 14.5 KD PROTEIN | CLOSTRIDIUM PERFRINGENS | 2-59 | | | | | | | | |
| PYPIX_CLOPE | HYPOTHETICAL 38.4 KD PROTEIN | CLOSTRIDIUM PERFRINGENS | 110-137 | 263-290 | 303-340 | | | | | | |
| PYPIY_PSEAE | HYPOTHETICAL 38.5 KD PROTEIN | PSEUDOMONAS AERUGINOSA | 22-52 | | | | | | | | |
| PYPP_BACSU | HYPOTHETICAL PROCESSING PROTEASE | BACILLUS SUBTILIS | 329-356 | | | | | | | | |
| PYPQQ_KLEPN | HYPOTHETICAL PROTEIN | KLEBSIELLA PNEUMONIAE | 243-270 | | | | | | | | |
| PYPS2_PLEBO | HYPOTHETICAL 13.1 KD PROTEIN | LECTONEMA BORYANUM | 27-54 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYPV1_METTF | HYPOTHETICAL 40.7 KD PROTEIN | METHANOBACTERIUM THERMOFORMICICUM | 58–85 | 308–335 | | | | | | | |
| PYPV3_METTF | HYPOTHETICAL 22.5 KD PROTEIN | METHANOBACTERIUM THERMOFORMICICUM | 3–30 | | | | | | | | |
| PYPV7_METTF | HYPOTHETICAL 17.3 KD PROTEIN | METHANOBACTERIUM THERMOFORMICICUM | 69–117 | | | | | | | | |
| PYPVB_METTF | HYPOTHETICAL 49.6 KD PROTEIN | METHANOBACTERIUM THERMOFORMICICUM | 333–360 | 389–430 | | | | | | | |
| PYPYB_BACSU | HYPOTHETICAL 72.4 KD PROTEIN | BACILLUS SUBTILIS | 602–636 | | | | | | | | |
| PYPZ1_METTF | HYPOTHETICAL 40.6 KD PROTEIN | METHANOBACTERIUM THERMOFORMICICUM | 58–85 | 308–335 | | | | | | | |
| PYPZ2_METTF | HYPOTHETICAL 33.1 KD PROTEIN | METHANOBACTERIUM THERMOFORMICICUM | 38–65 | 154–188 | | | | | | | |
| PYPZ5_METTF | HYPOTHETICAL 54.1 KD PROTEIN | METHANOBACTERIUM THERMOFORMICICUM | 193–220 | 226–253 | 381–408 | | | | | | |
| PYPZ7_METTF | HYPOTHETICAL 9.7 KD PROTEIN | METHANOBACTERIUM THERMOFORMICICUM | 5–78 | | | | | | | | |
| PYR18_THEPE | HYPOTHETICAL 18.7 KD PROTEIN | THERMOFILUM PENDENS | 82–109 | | | | | | | | |
| PYRB1_HALCU | HYPOTHETICAL 40 KD OF PROTEIN | HALOBACTERIUM CUTIRUBRUM | 20–51 | | | | | | | | |
| PYREC_SYNP2 | HYPOTHETICAL 28.7 KD PROTEIN | GTP-BINDING PROTEIN SYNECHOCOCCUS SP | 49–76 | | | | | | | | |
| PYRF0_SALTY | HYPOTHETICAL 40.6 KD PROTEIN | SALMONELLA TYPHIMURIUM | 143–190 | | | | | | | | |
| PYRF2_SALTY | HYPOTHETICAL 51.0 KD PROTEIN | SALMONELLA TYPHIMURIUM | 428–455 | | | | | | | | |
| PYRF5_SALTY | HYPOTHETICAL 20.6 KD PROTEIN | SALMONELLA TYPHIMURIUM | 29–56 | | | | | | | | |
| PYRF6_SALTY | HYPOTHETICAL 36.6 KD PROTEIN | SALMONELLA TYPHIMURIUM | 130–157 | | | | | | | | |
| PYRG2_LACLA | HYPOTHETICAL PROTEIN | LACTOCOCCUS LACTIS | 140–167 | | | | | | | | |
| PYRL1_METVA | HYPOTHETICAL PROTEIN | METHANOCOCCUS VANNIELII | 40–93 | 129–156 | | | | | | | |
| PYRP2_METVA | HYPOTHETICAL 11.6 KD PROTEIN | METHANOCOCCUS VANNIELII | 13–40 | | | | | | | | |
| PYRP2_SULAC | HYPOTHETICAL 11.5 KD PROTEIN | SULFOLOBUS ACIDOCALDARIUS | 5–51 | | | | | | | | |
| PYRP3_SULAC | HYPOTHETICAL 14.5 KD PROTEIN | SULFOLOBUS ACIDOCALDARIUS | 37–71 | | | | | | | | |
| PYRTP_BACSU | HYPOTHETICAL 25.3 KD PROTEIN | BACILLUS SUBTILIS | 29–56 | | | | | | | | |
| PYRTS_BACSU | HYPOTHETICAL 11.4 KD PROTEIN | BACILLUS SUBTILIS | 3–30 | 44–81 | | | | | | | |
| PYSCB_YEREN | HYPOTHETICAL YSC OPERON PROTEIN B | YERSINIA ENTEROCOLITICA | 90–121 | | | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYSCC_YEREN | YSC OPERON PROTEIN C PRECURSOR | *YERSINIA ENTEROCOLITICA* | 38–72 | 365–399 | | | | | | | |
| PYSCD_YEREN | YSC OPERON PROTEIN D | *YERSINIA ENTEROCOLITICA* | 242–269 | | | | | | | | |
| PYSCH_YEREN | YSC OPERON PROTEIN H | *YERSINIA ENTEROCOLITICA* | 28–58 | | | | | | | | |
| PYSCH_YERPS | YSC OPERON PROTEIN H | *YERSINIA PSEUDOTUBERCULOSIS* | 28–58 | | | | | | | | |
| PYSCI_YEREN | YSC OPERON PROTEIN I | *YERSINIA ENTEROCOLITICA* | 49–76 | | | | | | | | |
| PYSCI_YERPS | YSC OPERON PROTEIN I | *YERSINIA PSEUDOTUBERCULOSIS* | 49–76 | | | | | | | | |
| PYSCJ_YEREN | YSC OPERON LIPOPROTEIN J PRECURSOR | *YERSINIA ENTEROCOLITICA* | 99–126 | | | | | | | | |
| PYSCJ_YEREN | YSC OPERON LIPOPROTEIN J PRECURSOR | *YERSINIA PSEUDOTUBERCULOSIS* | 99–126 | | | | | | | | |
| PYSCL_YEREN | YSC OPERON PROTEIN L | *YERSINIA ENTEROCOLITICA* | 41–68 | | | | | | | | |
| PYSCL_YERPS | YSC OPERON PROTEIN L | *YERSINIA PSEUDOTUBERCULOSIS* | 41–68 | | | | | | | | |
| PYSMA_SERMA | HYPOTHETICAL 9.5 KD PROTEIN | *SERRATIA MARCESCENS* | 11–70 | | | | | | | | |
| PYSO2_DESAM | HYPOTHETICAL 28.3 KD PROTEIN | *DESULFUROLOBUS AMBIVALENS* | 68–109 | | | | | | | | |
| PYSO3_DESAM | HYPOTHETICAL PROTEIN | *DESULFUROLOBUS AMBIVALENS* | 65–155 | | | | | | | | |
| PYSP2_LEPIT | HYPOTHETICAL PROTEIN | *LEPTOSPIRA INTERROGANS* | 6–33 | 60–94 | | | | | | | |
| PYSR1_MYCMY | HYPOTHETICAL PROTEIN | *MYCOPLASMA MYCOIDES* | 35–99 | 185–227 | 300–327 | | | | | | |
| PYSY3_BACSU | HYPOTHETICAL 19.6 KD PROTEIN | *BACILLUS SUBTILIS* | 72–99 | | | | | | | | |
| PYSYN_METFE | HYPOTHETICAL PROTEIN | *METHANOTHERMUS FERVIDUS* | 78–105 | | | | | | | | |
| PYT37_STRFR | HYPOTHETICAL 37.1 KD PROTEIN | *STREPTOMYCES FRADIAE* | 246–273 | | | | | | | | |
| PYTDK_BACSU | HYPOTHETICAL 35.6 KD PROTEIN | *BACILLUS SUBTILIS* | 244–271 | 279–306 | | | | | | | |
| PYTRE_LEPBI | HYPOTHETICAL 22 KD PROTEIN | *LEPTOSPIRA BIFLEXA* | 84–113 | | | | | | | | |
| PYTRP_LACLA | HYPOTHETICAL 13.3 KD PROTEIN | *LACTOCOCCUS LACTIS* | 76–112 | | | | | | | | |
| PYTS1_BACSU | HYPOTHETICAL 20 KD PROTEIN | *BACILLUS SUBTILIS* | 37–64 | | | | | | | | |
| PYTSF_SPICI | HYPOTHETICAL 23.8 KD PROTEIN | *SPIROPLASMA CITRI* | 102–149 | | | | | | | | |
| PYX04_BACSU | HYPOTHETICAL 12.8 KD PROTEIN | *BACILLUS SUBTILIS* | 37–64 | 68–95 | | | | | | | |
| PYX06_BACSU | HYPOTHETICAL 21.0 KD PROTEIN | *BACILLUS SUBTILIS* | 142–169 | | | | | | | | |
| PYX13_BACSU | HYPOTHETICAL 26.0 KD PROTEIN | *BACILLUS SUBTILIS* | 17–51 | | | | | | | | |
| PYX15_BACSU | HYPOTHETICAL 61.8 KD PROTEIN | *BACILLUS SUBTILIS* | 165–207 | 262–289 | | | | | | | |
| PYX18_BACSU | HYPOTHETICAL 66.8 KD PROTEIN | *BACILLUS SUBTILIS* | 3–30 | 34–61 | 94–142 | | | | | | |

TABLE VIII-continued

107 × 178 × 4 SEARCH MOTIF RESULTS SUMMARY FOR ALL PROCARYOTIC PROTEINS

| PCGENE FILE NAME | 107 × 178 × 4 PROTEIN | Prokaryotic Sequences ORGANISM | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYX19_BACSU | HYPOTHETICAL 31.3 KD PROTEIN | BACILLUS SUBTILIS | 56–83 | 85–112 | | | | | | | |
| PYX20_BACSU | HYPOTHETICAL 23.2 KD PROTEIN | BACILLUS SUBTILIS | 24–58 | | | | | | | | |
| PYX12_ANASP | HYPOTHETICAL 18.9 KD PROTEIN | ANABAENA SP | 77–104 | | | | | | | | |
| PYXYB_CALSA | HYPOTHETICAL 10.7 KD PROTEIN | CALDOCELLUM SACCHAROLYTICUM | 9–39 | | | | | | | | |
| PYXYC_CALSA | HYPOTHETICAL PROTEIN | CALDOCELLUM SACCHAROLYTICUM | 41–94 | | | | | | | | |
| PYZE_ECOLI | HYPOTHETICAL 16.7 KD PROTEIN | ESCHERICHIA COLI | 41–78 | | | | | | | | |

TABLE IX

107 × 174 × 4 SEARCH MOTIF RESULTS SUMMARY FOR ALL HUMAN PROTEINS

107 × 178 × 4 Motif Search on All Human Protein Sequences

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| P143F_HUMAN | 14-3-3 PROTEIN ETA (PROTEIN AS1) (FRAGMENT) | 101–135 | | | | | | | | |
| P143S_HUMAN | 14-3-3 PROTEIN HOMOLOG STRATIFIN | 45–72 | | | | | | | | |
| P143T_HUMAN | 14-3-3 PROTEIN THETA (14-3-3 PROTEIN T-CELL) (HS1 PROTEIN) | 61–92 | | | | | | | | |
| P143Z_HUMAN | 14-3-3 PROTEIN ZETA (PROTEIN KINASE C INHIBITOR PROTEIN-1) (KCIP-1) | 28–55 | | | | | | | | |
| P1A23_HUMAN | HLA CLASS I HISTOCOMPATIBILITY ANTIGEN, A-29 (AW-19) A*2901 ALPHA CHAIN | 84–114 | | | | | | | | |
| P1A24_HUMAN | HLA CLASS I HISTOCOMPATIBILITY ANTIGEN, A-29 (AW-19) A*2902 ALPHA CHAIN | 87–114 | | | | | | | | |
| P1B02_HUMAN | HLA CLASS I HISTOCOMPATIBILITY ANTIGEN, B-7 B*0702 ALPHA CHAIN | 87–114 | | | | | | | | |
| P1B05_HUMAN | HLA CLASS I HISTOCOMPATIBILITY ANTIGEN, B-13 B*1301 ALPHA CHAIN | 87–114 | 148–182 | | | | | | | |
| P1B10_HUMAN | HLA CLASS I HISTOCOMPATIBILITY ANTIGEN, BW-75 (B-15) B*1502 ALPHA CHAIN | 87–114 | | | | | | | | |
| P1B11_HUMAN | HLA CLASS I HISTOCOMPATIBILITY ANTIGEN, BW-72 (BW-70) B*1503 ALPHA | 84–115 | | | | | | | | |
| P1B12_HUMAN | HLA CLASS I HISTOCOMPATIBILITY ANTIGEN, B-62 B*1504 ALPHA CHAIN | 76–107 | | | | | | | | |
| P1B13_HUMAN | HLA CLASS I HISTOCOMPATIBILITY ANTIGEN, B-18 B*1801 ALPHA CHAIN | 84–115 | | | | | | | | |
| P1B21_HUMAN | HLA CLASS I HISTOCOMPATIBILITY ANTIGEN, B-35 B*3501 ALPHA CHAIN | 84–115 | | | | | | | | |
| P1B22_HUMAN | HLA CLASS I HISTOCOMPATIBILITY ANTIGEN, B-35 B*3502 ALPHA CHAIN | 84–115 | | | | | | | | |
| P1B23_HUMAN | HLA CLASS I HISTOCOMPATIBILITY ANTIGEN, B-35 B*3503 ALPHA CHAIN | 84–115 | | | | | | | | |
| P1B24_HUMAN | HLA CLASS I HISTOCOMPATIBILITY ANTIGEN, B-35 B*3504 ALPHA CHAIN | 76–107 | | | | | | | | |
| P1B25_HUMAN | HLA CLASS I HISTOCOMPATIBILITY ANTIGEN, B-35 B*3505 ALPHA CHAIN | 84–115 | | | | | | | | |
| P1B26_HUMAN | HLA CLASS I HISTOCOMPATIBILITY ANTIGEN, B-35 B*3506 ALPHA CHAIN | 84–115 | | | | | | | | |
| P1B27_HUMAN | HLA CLASS I HISTOCOMPATIBILITY ANTIGEN, B-35 B*3507 ALPHA CHAIN | 84–115 | | | | | | | | |
| P1B28_HUMAN | HLA CLASS I HISTOCOMPATIBILITY ANTIGEN, B-35 B*3508 ALPHA CHAIN | 84–115 | | | | | | | | |
| P1B29_HUMAN | HLA CLASS I HISTOCOMPATIBILITY ANTIGEN, B-37 B*3701 ALPHA CHAIN | 88–115 | | | | | | | | |
| P1B32_HUMAN | HLA CLASS I HISTOCOMPATIBILITY ANTIGEN, B-39 B*3902 ALPHA CHAIN | 87–114 | | | | | | | | |
| P1B33_HUMAN | HLA CLASS I HISTOCOMPATIBILITY ANTIGEN, BW-60 (B-40) B*4001 ALPHA CHAIN | 60–91 | | | | | | | | |
| P1B34_HUMAN | HLA CLASS I HISTOCOMPATIBILITY ANTIGEN, B-40 B*4002 ALPHA CHAIN | 84–115 | | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| P1B35_HUMAN | HLA CLASS I HISTOCOMPATIBILITY ANTIGEN, B-40 B*4003 ALPHA CHAIN | 84–115 | | | | | | | | |
| P1B36_HUMAN | HLA CLASS I HISTOCOMPATIBILITY ANTIGEN, B-40 B*4004 ALPHA CHAIN | 84–115 | | | | | | | | |
| P1B38_HUMAN | HLA CLASS I HISTOCOMPATIBILITY ANTIGEN, BW-41 B*4101 ALPHA CHAIN | 84–115 | | | | | | | | |
| P1B39_HUMAN | HLA CLASS I HISTOCOMPATIBILITY ANTIGEN, BW-42 B*4201 ALPHA CHAIN | 87–114 | | | | | | | | |
| P1B40_HUMAN | HLA CLASS I HISTOCOMPATIBILITY ANTIGEN, BW-44 (B-12) B*4401 ALPHA CHAIN | 84–111 | | | | | | | | |
| P1B41_HUMAN | HLA CLASS I HISTOCOMPATIBILITY ANTIGEN, BW-44 (B-12) B*4402 ALPHA CHAIN | 87–114 | | | | | | | | |
| P1B42_HUMAN | HLA CLASS I HISTOCOMPATIBILITY ANTIGEN, BW-44 (B-12) B*4403 ALPHA CHAIN | 87–114 | | | | | | | | |
| P1B43_HUMAN | HLA CLASS I HISTOCOMPATIBILITY ANTIGEN, BW-45 (B-12) B*4501 ALPHA CHAIN | 84–115 | | | | | | | | |
| P1B44_HUMAN | HLA CLASS I HISTOCOMPATIBILITY ANTIGEN, BW-46 B*4601 ALPHA CHAIN | 87–114 | | | | | | | | |
| P1B45_HUMAN | HLA CLASS I HISTOCOMPATIBILITY ANTIGEN, BW-47 B*4701 ALPHA CHAIN | 88–115 | | | | | | | | |
| P1B46_HUMAN | HLA CLASS I HISTOCOMPATIBILITY ANTIGEN, BW-48 B*4801 ALPHA CHAIN | 84–115 | | | | | | | | |
| P1B47_HUMAN | HLA CLASS I HISTOCOMPATIBILITY ANTIGEN, BW-49 (B-21) B*4901 ALPHA CHAIN | 87–114 | | | | | | | | |
| P1B48_HUMAN | HLA CLASS I HISTOCOMPATIBILITY ANTIGEN, BW-50 (B-21) B*5001 ALPHA CHAIN | 84–115 | | | | | | | | |
| P1B53_HUMAN | HLA CLASS I HISTOCOMPATIBILITY ANTIGEN, BW-52 (B-5) B*5201 ALPHA CHAIN | 87–114 | | | | | | | | |
| P1B55_HUMAN | HLA CLASS I HISTOCOMPATIBILITY ANTIGEN, BW-54 (BW-22) B*5401 ALPHA | 87–114 | | | | | | | | |
| P1B56_HUMAN | HLA CLASS I HISTOCOMPATIBILITY ANTIGEN, BW-55 (BW-22) B*5501 ALPHA | 87–114 | | | | | | | | |
| P1B57_HUMAN | HLA CLASS I HISTOCOMPATIBILITY ANTIGEN, BW-55 (BW-22) B*5502 ALPHA | 87–114 | | | | | | | | |
| P1B58_HUMAN | HLA CLASS I HISTOCOMPATIBILITY ANTIGEN, BW-56 (BW-22) B*5601 ALPHA | 87–114 | | | | | | | | |
| P1B59_HUMAN | HLA CLASS I HISTOCOMPATIBILITY ANTIGEN, BW-56 (BW-22) B*5602 ALPHA | 87–114 | | | | | | | | |
| P1C01_HUMAN | HLA CLASS I HISTOCOMPATIBILITY ANTIGEN, CW-1 CW*0101 ALPHA CHAIN | 87–114 | | | | | | | | |
| P1C02_HUMAN | HLA CLASS I HISTOCOMPATIBILITY ANTIGEN, CW-1 CW*0102 ALPHA CHAIN | 87–114 | | | | | | | | |
| P1C03_HUMAN | HLA CLASS I HISTOCOMPATIBILITY ANTIGEN, CW-2 CW*0201 ALPHA CHAIN | 87–114 | | | | | | | | |
| P1C04_HUMAN | HLA CLASS I HISTOCOMPATIBILITY ANTIGEN, CW-2 CW*0202 ALPHA CHAIN | 87–114 | | | | | | | | |

TABLE IX-continued

107 × 178 × 4 SEARCH MOTIF RESULTS SUMMARY FOR ALL HUMAN PROTEINS

| PCGENE FILE NAME | 107 × 174 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| P1C06_HUMAN | HLA CLASS I HISTOCOMPATIBILITY ANTIGEN, CW-3 CW*0302 ALPHA CHAIN | 87–114 | | | | | | | | |
| P1C12_HUMAN | HLA CLASS I HISTOCOMPATIBILITY ANTIGEN, CW-8 CW*0801 ALPHA CHAIN | 87–114 | | | | | | | | |
| P1C13_HUMAN | HLA CLASS I HISTOCOMPATIBILITY ANTIGEN, CW-8 CW*0802 ALPHA CHAIN | 87–114 | | | | | | | | |
| P1C14_HUMAN | HLA CLASS I HISTOCOMPATIBILITY ANTIGEN, CW-8 CW*0803 ALPHA CHAIN | 87–114 | | | | | | | | |
| P1C17_HUMAN | HLA CLASS I HISTOCOMPATIBILITY ANTIGEN, CW*1401 ALPHA CHAIN PRECURSOR | 87–114 | | | | | | | | |
| P25A6_HUMAN | 69/71 KD (2'–5') OLIGOADENYLATE SYNTHETASE | 593–620 | | | | | | | | |
| P2AAA_HUMAN | PROTEIN PHOSPHATASE PP2A, 65 KD REGULATORY SUBUNIT, ALPHA ISOFORM | 12–49 | 54–81 | | | | | | | |
| P2AAB_HUMAN | PROTEIN PHOSPHATASE PP2A, 65 KD REGULATORY SUBUNIT, BETA ISOFORM | 9–36 | 41–68 | 79–106 | | | | | | |
| P2ABA_HUMAN | PROTEIN PHOSPHATASE PP2A, 55 KD REGULATORY SUBUNIT, ALPHA ISOFORM | 177–218 | | | | | | | | |
| P411_HUMAN | ERYTHROID PROTEIN 4.1 (BAND 4.1, ERYTHROCYTE FORM) | 32–66 | | | | | | | | |
| P412_HUMAN | NON-ERYTHROID PROTEIN 4.1 (BAND 4.1, LYMPHOID FORM) | 3–30 | 708–735 | | | | | | | |
| P42_HUMAN | ERYTHROCYTE MEMBRANE PROTEIN BAND 4.2 | 173–200 | 518–545 | | | | | | | |
| P4F2_HUMAN | 4F2 CELL-SURFACE ANTIGEN HEAVY CHAIN (4F2HC) (LYMPHOCYTE ACTIVATION | 281–322 | | | | | | | | |
| P5H1E_HUMAN | 5-HYDROXYTRYPTAMINE 1E RECEPTOR (5-HT-1E) (SEROTONIN RECEPTOR) | 311–338 | | | | | | | | |
| P5H1F_HUMAN | 5-HYDROXYTRYPTAMINE 1F RECEPTOR (5-HT-1F) (SEROTONIN RECEPTOR) | 222–253 | | | | | | | | |
| P5H2A_HUMAN | 5-HYDROXYTRYPTAMINE 2A RECEPTOR (5-HT-2A) (SEROTONIN RECEPTOR) | 22–56 | | | | | | | | |
| P5H7_HUMAN | 5-HYDROXYTRYPTAMINE 7 RECEPTOR (5-HT-7) (5-HT-X) (SEROTONIN RECEPTOR) | 72–99 | | | | | | | | |
| PA1AC_HUMAN | ALPHA-1-ANTICHYMORTYPSIN PRECURSOR (ACT) | 98–132 | 330–357 | | | | | | | |
| PA1AG_HUMAN | ALPHA-1-ACID GLYCOPROTEIN 1 PRECURSOR (OROSOMUCOID) ((OMD) | 92–119 | | | | | | | | |
| PA1AT_HUMAN | ALPHA-1-ANTITRYPSIN PRECURSOR (ALPHA-1 PROTEASE INHIBITOR) (ALPHA-1- | 168–202 | | | | | | | | |
| PA1AU_HUMAN | ALPHA-1-ANTITRYPSIN-REALATED PROTEIN PRECURSOR | 163–197 | | | | | | | | |
| PA2AP_HUMAN | ALPHA-2-ANTIPLASMIN PRECURSOR (ALPHA-2-PLASMIN INHIBITOR) (ALPHA-2- | 191–218 | 365–395 | | | | | | | |
| PA2GL_HUMAN | LEUCINE-RICH ALPHA-2-GLYCOPROTEIN (LRG) | 104–134 | | | | | | | | |
| PA2MG_HUMAN | ALPHA-2-MACROGLOBULIN PRECURSOR (ALPHA-2-M) | 53–80 | 319–349 | | 1085–1112 | 1402–1429 | | | | |
| PA4_HUMAN | ALZHIMER'S DESEASE AMYLOID A4 PROTEIN PRECURSOR (PROTEASE NEXIN-11) | 428–455 | | | | | | | | |
| PAACT_HUMAN | ALPHA-ACTININ (F-ACTIN CROSS LINKING PROTEIN) | 92–119 | 720–747 | | | | | | | |
| PAATM_HUMAN | ASPARTATE AMINOTRANSFERASE, MITOCHONDRIAL PRECURSOR (EC 2.6.1.1) | 109–136 | | | | | | | | |

TABLE IX-continued

107 × 178 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PABP2_HUMAN | ENDOTHELIAL ACTIN-BINDING PROTEIN (ABP-280) (NONMUSCLE FILAMIN) | 61–88 | 119–147 | 2604–2633 | | | | | | |
| PAC12_HUMAN | ACTIVATOR 1 37 KD SUBUNIT (REPLICATION FACTOR C 37 KD SUBUNIT) (A1 | 306–333 | | | | | | | | |
| PAC15_HUMAN | ACTIVATOR 1 140 KD SUBUNIT (REPLICATION FACTOR C LARGE SUBUNIT) (A1 | 14–51 | 182–209 | 668–700 | | | | | | |
| PACDL_HUMAN | ACYL-COA DEHYDROGENASE PRECURSOR, LONG-CHAIN SPECIFIC (EC 1.3.99.13) | 78–108 | 179–206 | 313–340 | | | | | | |
| PACET_HUMAN | ANGIOTENSIN-CONVERTING ENZYME PRECURSOR, TESTIS-SPECIFIC (EC 3.4.15.1) | 78–115 | 126–153 | 676–710 | | | | | | |
| PACE_HUMAN | ANGIOTENSIN-CONVERTING ENZYME PRECURSOR, SOMATIC (EC 3.4.15.1) (ACE) | 652–689 | 700–727 | 1250–1284 | | | | | | |
| PACHA_HUMAN | ACETYLCHOLINE RECEPTOR PROTEIN, ALPHA CHAIN PRECURSOR | 48–80 | | | | | | | | |
| PACHE_HUMAN | ACETYLCHOLINE RECEPTOR PROTEIN, EPSILON CHAIN PRECURSOR | 46–98 | | | | | | | | |
| PACHG_HUMAN | ACETYLCHOLINE RECEPTOR PROTEIN, GAMMA CHAIN PRECURSOR | 45–79 | 304–331 | | | | | | | |
| PACHIP_HUMAN | NEURONAL ACETYLCHOLINE RECEPTOR PROTEIN, BETA-4 CHAIN (FRAGMENT) | 29–56 | 70–97 | | | | | | | |
| PACRO_HUMAN | ACROSIN PRECURSOR (EC 3.4.21.10) | 112–149 | | | | | | | | |
| PACYM_HUMAN | ACYLPHOSPHATASE, MUSCLE TYPE ISOZYME (EC 3.6.1.7) (ACYLPHOSPHATE | 26–53 | | | | | | | | |
| PADT2_HUMAN | ADP,ATP CARRIER PROTEIN, FIBROBLAST ISOFORM (ADP/ATP TRANSLOCASE 2) | 162–189 | | | | | | | | |
| PADT3_HUMAN | ADP,ATP CARRIER PROTEIN, LIVER ISOFORM T2 (ADP/ATP TRANSLOCASE 3) | 163–190 | | | | | | | | |
| PAK79_HUMAN | A-KINASE ANCHOR PROTEIN 79 (AKAP 79) (CAMP-DEPENDENT PROTEIN KINASE | 197–238 | 381–414 | | | | | | | |
| PALFA_HUMAN | FRUCTOSE-BISPHOSPHATE ALDOLASE (EC 4.1.2.13) A (MUSCLE) | 36–63 | | | | | | | | |
| PALFB_HUMAN | FRUCTOSE-BISPHOSPHATE ALDOLASE (EC 4.1.2.13) B (LIVER) | 79–113 | | | | | | | | |
| PAMD1_HUMAN | AMP DEAMINASE 1 (EC 3.5.4.6) (MYOADENYLATE DEAMINASE) (AMP DEAMINASE | 59–86 | | | | | | | | |
| PAMD3_HUMAN | AMP DEAMINASE 3 (EC 3.5.4.6) (AMP DEAMINASE ISOFORM E) | 49–76 | | | | | | | | |
| PAMPN_HUMAN | AMINOPEPTIDASE N (EC 3.4.11.2) (MICROSOMAL AMINOPEPTIDASE) (GP150) | 492–523 | 604–648 | 926–964 | | | | | | |
| PAMPR_HUMAN | AMPHIRGEULIN PRECURSOR (AR) | 213–247 | | | | | | | | |
| PAMRP_HUMAN | ALPHA-2-MACROGLOBULIN RECEPTOR-ASSOCIATED PROTEIN PRECURSOR | 173–236 | 263–290 | | | | | | | |
| PANFB_HUMAN | BRAIN NATRIURETIC PEPTIDE PRECURSOR | 36–63 | | | | | | | | |
| PANK1_HUMAN | ANKYRIN R (ANKYRINS 2.1 AND 2.2) (ERYTHROCYTE ANKYRIN) | 812–839 | 1004–1031 | 1617–1644 | | | | | | |
| PANKB_HUMAN | ANKYRIN, BRAIN VARIANT 1 (ANKYRIN B) (ANKYRIN, NONERYTHROID) | 1544–1571 | | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PANKC_HUMAN | ANKYRIN, BRAIN VARIANT 2 (ANKYRIN B) (ANKYRIN, NONERYTHROID) | 1811–1838 | | | | | | | | |
| PANPA_HUMAN | ATRIAL NATRIURETIC PEPTIDE RECEPTOR A PRECURSOR (ANP-A) (ANPRA) (GC-A) | 553–580 | 825–852 | | | | | | | |
| PANPB_HUMAN | ATRIAL NATRIURETIC PEPTIDE RECEPTOR B PRECURSOR (ANP-B) (ANPRA) (GC-B) | 810–837 | | | | | | | | |
| PANT3_HUMAN | ANTITHROMBIN-III PRECURSOR (ATIII) | 162–196 | | | | | | | | |
| PANX2_HUMAN | ANNEXIN II (LIPOCORTIN II) (CALPACTIN I HEAVY CHAIN) (CHROMOBINDIN 8) | 40–67 | 306–333 | | | | | | | |
| PANX3_HUMAN | ANNEXIN III (LIPOCORTIN III) (PLACENTAL ANTICOAGULANT PROTEIN III) | 215–242 | | | | | | | | |
| PANX6_HUMAN | ANNEXIN VI (LIPOCORTIN VI) (P68) (P70) (PROTEIN III) (CHROMOBINDIN 20) | 60–87 | 626–653 | | | | | | | |
| PANXI_HUMAN | ANNEXIN, INTESTIN-SPECIFIC (ISA) | 37–78 | 137–164 | | | | | | | |
| PAOFA_HUMAN | AMINE OXIDASE (FLAVIN-CONTAINING) A (EC 1.4.3.4) (MONOAMINE OXIDASE) | 16–43 | 74–104 | | | | | | | |
| PAOFB_HUMAN | AMINE OXIDASE (FLAVIN-CONTAINING) B (EC 1.4.3.4) (MONOAMINE OXIDASE) | 68–95 | | | | | | | | |
| PAPA1_HUMAN | APOLIPOPROTEIN A-I PRECURSOR (APO-AI) | 57–84 | | | | | | | | |
| PAPB_HUMAN | APOLIPOPROTEIN B-100 PRECURSOR (APO B-100/APO B-48) | 585–619 2466–2507 4247–4301 | 1073–1100 2529–2559 4397–4438 | 1353–1380 2850–3000 4465–4492 | 1524–1584 3360–3390 4499–4544 | 2074–2113 3480–3570 | 2132–2159 3620–3654 | 2181–2215 4040–4074 | 2240–2271 4090–4120 | 2360–2389 4135–4167 |
| PAPC2_HUMAN | APOLIPOPROTEIN C-II PRECURSOR (APO-CII) | 36–63 | | | | | | | | |
| PAPC_HUMAN | ADENOMATOUS POLYPOSIS COLI PROTEIN (APC PROTEIN) | 145–172 | 617–651 | 247–274 | 834–861 | 1795–1822 | 2172–2212 | 2572–2609 | | |
| PAPE_HUMAN | APOLIPOPROTEIN E PRECURSOR (APO-E) | 48–81 | | | | | | | | |
| PAPOA_HUMAN | APOLIPOPROTEIN (A) PRECURSOR (EC 3.4.21.-) (APO (A)) (LP (A)) | 4448–4475 | | | | | | | | |
| PAQP1_HUMAN | AQUAPORIN-CHIP (WATER CHANNEL PROTEIN FOR RED BLOOD CELLS AND KIDNEY | 39–73 | | | | | | | | |
| PARK1_HUMAN | BETA-ADRENERGIC RECEPTOR KINASE 1 (EC 2.7.1.126) (BETA-ARK-1) | 523–553 | | | | | | | | |
| PARLY_HUMAN | ARGININOSUCCINATE LYASE (EC 4.3.2.1) (ARGINOSUCCINASE) | 69–103 | | | | | | | | |
| PARNT_HUMAN | ARYL HYDROCARBON RECEPTOR NUCLEAR TRANSLOCATOR (ARNT PROTEIN) (DIO | 223–250 | | | | | | | | |
| PARRC_HUMAN | BETA-ARRESTIN 2 | 215–242 | 305–332 | | | | | | | |
| PARRS_HUMAN | ARRESTIN (RETINAL S-ANTIGEN) (48 KD PROTEIN) (S-AG) | 299–352 | | | | | | | | |
| PARY1_HUMAN | ARYLAMINE N-ACETYL TRANSFERASE, MONOMORPHIC (EC 2.3.1.5) (MNAT) | 7–34 | | | | | | | | |
| PARY2_HUMAN | ARYLAMINE N-ACETYLTRANSFERASE, POLYMORPHIC (EC 2.3.1.5) (PNAT) | 7–34 | | | | | | | | |
| PASNS_HUMAN | ASPARAGINE SYNTHETASE (GLUTAMINE-HYDROLYZING) (EC 6.3.5.4) (TS11 CELL | 311–338 | 347–374 | | | | | | | |
| PATCD_HUMAN | CALCIUM-TRANSPORTING ATPASE SARCOPLASMIC RETICULUM TYPE (EC 3.6.1.38) | 163–190 | | | | | | | | |
| PATCE_HUMAN | CALCIUM-TRANSPORTING ATPASE ENDOPLASMIC RETICULUM TYPE (EC 3.6.1.38) | 163–190 | | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PATF1_HUMAN | TRANSCRIPTION FACTOR ATF-1 (FRAGMENT) | 203–230 | | | | | | | | |
| PATF3_HUMAN | TRANSCRIPTION FACTOR ATF-3 (FRAGMENT) | 155–183 | | | | | | | | |
| PATF5_HUMAN | TRANSCRIPTION FACTOR ATF-5 (FRAGMENT) | 30–61 | | | | | | | | |
| PATF6_HUMAN | TRANSCRIPTION FACTOR ATF-6 (FRAGMENT) | 34–68 | | | | | | | | |
| PATFA_HUMAN | TRANSCRIPTION FACTOR ATF-A AND AFTA-DELTA | 351–394 | | | | | | | | |
| PATPF_HUMAN | ATP SYNTHASE B CHAIN, MITOCHONDRIAL PRECURSOR (EC 3.6.1.34) | 129–163 | | | | | | | | |
| PB232_HUMAN | NUCLEOLAR PHOSPHOPROTEIN B23 (NUCLEOPHOSMIN) (NUMATRIN) | 114–141 | | | | | | | | |
| PB2AR_HUMAN | BETA-2-ADRENERGIC RECEPTOR | 292–319 | 345–372 | | | | | | | |
| PB3A2_HUMAN | ANION EXCHANGE PROTEIN 2 (NON-ERYTHROID BAND 3-LIKE PROTEIN) (BND3L) | 1081–1111 | | | | | | | | |
| PB94_HUMAN | B94 PROTEIN | 115–142 | 525–562 | 609–636 | | | | | | |
| PBAN7_HUMAN | ERYTHROCYTE BAND 7 INTEGRAL MEMBRANE PROTEIN | 106–140 | | | | | | | | |
| PBASO_HUMAN | BASONUCLIN | 120–147 | 310–337 | 773–807 | | | | | | |
| PBC2B_HUMAN | TRANSFORMING PROTEIN BCL-2-BETA | 178–205 | | | | | | | | |
| PBCGF_HUMAN | B-CELL GROWTH FACTOR PRECURSOR (BCGF-12 KD) | 33–63 | | | | | | | | |
| PBCR_HUMAN | BREAKPOINT CLUSTER REGION PROTEIN | 784–825 | | | | | | | | |
| PBGLR_HUMAN | BETA-GLUCURONIDASE PRECURSOR (EC 3.2.1.31) | 246–280 | 504–531 | | | | | | | |
| PBMP2_HUMAN | BONE MORPHOGENETIC PROTEIN 2 PRECURSOR (BMP-2) (BMP-2A) | 216–250 | | | | | | | | |
| PBMP5_HUMAN | BONE MORPHOGENETIC PROTEIN 5 PRECURSOR (BMP-5) | 202–229 | | | | | | | | |
| PBMP6_HUMAN | BONE MORPHOGENETIC PROTEIN 6 PRECURSOR (BMP-6) | 274–301 | | | | | | | | |
| BPMP7_HUMAN | BONE MORPHOGENETIC PROTEIN 7 PRECURSOR (BMP-7) (OSTEOGENIC PROTEIN 1) | 192–219 | | | | | | | | |
| PBN51_HUMAN | BN51 PROTEIN | 284–311 | | | | | | | | |
| PBPI_HUMAN | BACTERICIDAL PERMEABILITY INCREASING PROTEIN PRECURSOR (BPI) (CAP 57) | 168–195 | | | | | | | | |
| PBRS3_HUMAN | BOMBESIN RECEPTOR SUBTYPE-3 (BRS-3) | 10–37 | | | | | | | | |
| BPTF2_HUMAN | BASIC TRANSCRIPTION FACTOR 62 KD SUBUNIT (P62) | 128–162 | 353–385 | | | | | | | |
| PBTG1_HUMAN | BTG1 PROTEIN (B-CELL TRANSLOCATION GENE 1 PROTEIN) | 26–53 | | | | | | | | |
| PCITC_HUMAN | C-1-TETRAHYDROFOLATE SYNTHASE, CYTOPLASMIC (METHYLENETETRAYDROFO | 330–363 | | | | | | | | |
| PC2TA_HUMAN | MHC CLASS II TRANSACTIVATOR CIITA | 921–948 | | | | | | | | |
| PCA19_HUMAN | COLLAGEN ALPHA 1 (IX) CHAIN PRECURSOR | 120–150 | | | | | | | | |
| PCA1B_HUMAN | COLLAGEN ALPHA 1 (IX) CHAIN PRECURSOR | 341–368 | | | | | | | | |
| PCABV_HUMAN | CALBINDIN (VITAMIN D-DEPENDENT CALCIUM-BINDING PROTEIN (CABP), AVIAN- | 27–54 | | | | | | | | |
| PCAD5_HUMAN | CADHERIN 5 PRECURSOR (7B4 ANTIGEN) | 723–750 | | | | | | | | |
| PCADE_HUMAN | EPITHELIAL-CADHERIN PRECURSOR (E-CADHERIN) (UVOMORULIN) (CAM 120/80) | 838–865 | | | | | | | | |
| PCADN_HUMAN | NEURAL-CADHERIN PRECURSOR (N-CADHERIN) | 95–122 | 323–350 | | | | | | | |
| PCADP_HUMAN | PLACENTAL-CADHERIN PRECURSOR (P-CADHERIN) | 384–411 | 580–607 | | | | | | | |
| PCAGA_HUMAN | CALGRANULIN A (MIGRATION INHIBITORY FACTOR-RELATED PROTEIN 8) (MRP-8) | 2–29 | | | | | | | | |
| PCALR_HUMAN | CALCITONIN RECEPTOR PRECURSOR (CT-R) | 140–167 | | | | | | | | |
| PCAMA_HUMAN | CARTLIAGE MATRIX PROTEIN PRECURSOR | 297–324 | 467–494 | | | | | | | |

TABLE IX-continued

107 × 174 × 4 SEARCH MOTIF RESULTS SUMMARY FOR ALL HUMAN PROTEINS

107 × 178 × 4 Motif Search on All Human Protein Sequences

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PCAP1_HUMAN | CALPAIN 1, LARGE (CATALYTIC) SUBUNIT (EC 3.4.22.17) (CALCIUM-ACTIVATED | 561–588 | | | | | | | | |
| PCAP2_HUMAN | CALPAIN 2, LARGE (CATALYTIC) SUBUNIT (EC 3.4.22.17) (CALCIUM-ACTIVATED | 257–284 | 502–529 | | | | | | | |
| PCAP3_HUMAN | CALPAIN P94, LARGE (CATALYTIC) SUBUNIT (EC 3.4.22.17) (CALCIUM- | 674–701 | | | | | | | | |
| PCAPL_HUMAN | PLACENTAL CALCIUM-BINDING PROTEIN | 13–40 | | | | | | | | |
| PCAP_HUMAN | ADENYLYL CYCLASE-ASSOCIATED PROTEIN (CAP) | 111–138 | 163–197 | 321–355 | | | | | | |
| PCART_HUMAN | CALRETININ (29 KD CALBINDIN) | 217–244 | | | | | | | | |
| PCASB_HUMAN | BETA CASIN PRECURSOR | 14–48 | | | | | | | | |
| PCATA_HUMAN | CATALASE (EC 1.11.1.6) | 422–456 | | | | | | | | |
| PCATD_HUMAN | CATHEPSIN D PRECURSOR (EC 3.4.23.5) | 253–282 | | | | | | | | |
| PCATH_HUMAN | CATHEPSIN H PRECURSOR (EC 3.4.22.16) | 41–68 | | | | | | | | |
| PCATL_HUMAN | CATHEPSIN L PRECURSOR (EC 3.4.22.15) (MAJOR EXCRETED PROTEIN (MEP) | 278–305 | | | | | | | | |
| PCATS_HUMAN | CATHEPSIN S PRECURSOR (EC 3.4.22.27) | 30–57 | 142–169 | | | | | | | |
| PCBFB_HUMAN | CCAAT-BINDING TRANSCRIPTION FACTOR SUBUNIT B (CBF-B) (NF-Y PROTEIN | 24–58 | 138–165 | | | | | | | |
| PCBG_HUMAN | CORTICOSTEROID-BINDING GLOBINULIN PRECURSOR (CBG) (TRANSCORTIN) | 88–122 | | | | | | | | |
| PCBPB_HUMAN | CARBOXYPEPTIDASE B PRECURSOR (EC 3.4.17.2) (PARCREAS-SPECIFIC PROTEIN) | 69–129 | 278–305 | 319–346 | | | | | | |
| PCBPH_HUMAN | CARBOXYPEPTIDASE H PRECURSOR (EC 3.4.17.10) (CARBOXYPEPTIDASE E) (CPE) | 355–382 | | | | | | | | |
| PCC21_HUMAN | CDC21 HOMOLOG (P1-CDC21) (FRAGMENT) | 35–62 | | | | | | | | |
| PCC27_HUMAN | PROTEIN CDC27HS | 209–240 | | | | | | | | |
| PCCG1_HUMAN | TRANSCRIPTION INITIATION FACTOR TFIID 250 KD SUBUNIT (TBP-ASSOCIATED | 1298–1342 | | | | | | | | |
| PCE14_HUMAN | MONOCYTE DIFFERENTIATION ANTIGEN CD14 PRECURSOR (MYELOID CELL-SPECIFI | 142–169 | | | | | | | | |
| PCD1A_HUMAN | T-CELL SURFACE CLYCOPROTEIN CD1A PRECURSOR (CD1A ANTIGEN) (T-CELL | 32–63 | 281–308 | | | | | | | |
| PCD1E_HUMAN | T-CELL SURFACE CLYCOPROTEIN CD1E PRECURSOR (CD1E ANTIGEN) (R2G1) | 71–104 | | | | | | | | |
| PCD20_HUMAN | B-LYMPHOCYTE ANTIGEN CD20 (B-LYMPHOCYTE SURFACE ANTIGEN B1) (LEU-16) | 226–255 | | | | | | | | |
| PCD24_HUMAN | CD20 RECEPTOR PRECURSOR | 226–255 | | | | | | | | |
| PCD2_HUMAN | T-CELL SURFACE ANTIGEN CD2 PRECURSOR (T-CELL SURFACE ANTIGEN | 88–19 | | | | | | | | |
| PCD34_HUMAN | HEMOPOIETIC PROGENITOR CELL ANTIGEN CD34 PRECURSOR | 74–108 | | | | | | | | |
| PCD37_HUMAN | LEUKOCYTE ANTIEN CD37 | 101–128 | | | | | | | | |
| PCD3G_HUMAN | T-CELL SURFACE GLYCOPROTEIN CD3 GAMMA CHAIN PRECURSOR (T-CELL RECEPT | 7–34 | | | | | | | | |
| PCD3L_HUMAN | CD30 LIGAND (CD30-L) | 96–130 | 183–217 | | | | | | | |
| PCD4X_HUMAN | CD44 ANTIGEN, EPITHELIAL FORM PRECURSOR (CD44E) (PHAGOCYTIC | 328–355 | | | | | | | | |

TABLE IX-continued

107 × 178 × 4 Motif Search on All Human Protein Sequences
107 × 174 × 4 SEARCH MOTIF RESULTS SUMMARY FOR ALL HUMAN PROTEINS

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PCD4_HUMAN | T-CELL SURFACE GLYCOPROTEIN CD4 PRECURSOR (T-CELL SURFACE ANTIGEN | 44–71 | 240–267 | | | | | | | |
| PCD53_HUMAN | LEUKOCYTE SURFACE ANTIGEN CD53 | 87–114 | | | | | | | | |
| PCD72_HUMAN | B-CELL DIFFERENTIATION ANTIGEN CD72 (LYB-2) | 118–177 | | | | | | | | |
| PCDK3_HUMAN | CELL DIVISION PROTEIN KINASE 3 (EC 2.7.1.-) | 5–32 | | | | | | | | |
| PCDK5_HUMAN | CELL DIVISION PROTEIN KINASE 5 (EC 2.7.1.-) (KINASE PSSALRE) | 5–32 | | | | | | | | |
| PCEBB_HUMAN | CCAA/ENHANCER BINDING PROTEIN BETA (C/EBP BETA) (NUCLEAR FACTOR | 296–330 | | | | | | | | |
| PCENB_HUMAN | MAJOR CENTROMERE AUTOANTIGEN B (CENTROMERE PROTEIN B) (CENP-B) | 568–595 | | | | | | | | |
| PCENC_HUMAN | CENTROMERE PROTEIN C (CENP-C) (CENTROMERE AUTOANTIGEN C) | 433–460 | | | | | | | | |
| PCENE_HUMAN | CENTROMERIC PROTEIN E (CENP-E PROTEIN) | 372–399 1122–1149 1852–1883 | 493–520 1179–1239 1890–1917 | 553–607 1250–1277 1940–1988 | 715–752 1340–1367 2021–2048 | 767–825 1440–1481 2288–2318 | 850–884 1486–1556 2440–2478 | 903–947 1646–1680 2498–2563 | 963–995 1684–1724 | 1080–1107 1808–1846 |
| PCERU_HUMAN | CERULOPLASMIN PRECURSOR (EC 1.16.3.1) (FERROXIDASE) | 913–940 | | | | | | | | |
| PCETP_HUMAN | CHOLESTERYL ESTER TRANSFER PROTEIN PRECURSOR | 71–108 | | | | | | | | |
| PCFTR_HUMAN | CYSTIC FIBROSIS TRANASMEMBRANE CONDUCTANCE REGULATOR (CFTR) | 158–189 | 803–922 | 1243–1270 | | | | | | |
| PCGCC_HUMAN | CGMP-GATED CATION CHANNEL PROTEIN (CYCLIC NUCLEOTIDE | 216–243 | | | | | | | | |
| PCGL_HUMAN | CYSTATHIONINE GAMMA-LYASE (EC 4.4.1.1) | 315–349 | | | | | | | | |
| PCHLR_HUMAN | CHLORDECONE REDUCTASE (EC 1.1.1.225) (CDR) | 17–51 | | | | | | | | |
| PCHOL_HUMAN | CHOROIDERAEMIA-LIKE PROTEIN | 56–97 | 230–257 | 451–478 | | | | | | |
| PCHOR_HUMAN | CHOROIDERAEMIA PROTEIN (TCD PROTEIN) | 112–139 | | | | | | | | |
| PCINA_HUMAN | SODIUM CHANNEL PROTEIN, CARDIAC AND SKELETAL MUSCLE ALPHA-SUBUNIT | 787–814 | 943–970 | | | | | | | |
| PCLCA_HUMAN | CLATHRIN LIGHT CHAIN A (BRAIN AND LYMPHOCYTE LCA) | 121–148 | | | | | | | | |
| PCLCB_HUMAN | CLATHRIN LIGHT CHAIN B (BRAIN AND LYMPHOCYTE LCB) | 123–157 | | | | | | | | |
| PCLCY_HUMAN | CALCYCLIN (PROLACTIN RECEPTOR ASSOCIATED PROTEIN) (PRA) (GROWTH | 9–50 | | | | | | | | |
| PCLUS_HUMAN | CLUSTERIN PRECURSOR (COMPLEMENT-ASSOCIATED PROTEIN SP-40,40) | 36–98 | 323–350 | 367–394 | | | | | | |
| PCMGA_HUMAN | CHROMOGRANIN A PRECURSOR (CGA) (CONTAINS: PANCREASTATIN AND WE-14) | 93–120 | 430–457 | | | | | | | |
| PCNTF_HUMAN | CILIARY NEUROTROPHIC FACTOR (CNTF) | 66–93 | 95–148 | | | | | | | |
| PCO02_HUMAN | TUMOR-ASSOCIATED ANTIGEN CO-029 | 29–56 | 593–620 | 837–867 | | | | | | |
| PCO3_HUMAN | COMPLEMENT C3 PRECURSOR | 242–276 1292–1319 | | | | | | | | |
| PCO4_HUMAN | COMPLEMENT C4 PRECURSOR | 298–342 | 537–564 | 970–997 | 1270–1304 | | | | | |
| PCO5_HUMAN | COMPLEMENT C5 PRECURSOR | 367–398 | | | | | | | | |
| PCO6_HUMAN | COMPLEMENT C6 PRECURSOR | 225–261 | | | | | | | | |
| PCO7_HUMAN | COMPLEMENT C7 PRECURSOR | 353–380 | | | | | | | | |
| PCOXL_HUMAN | CYTOCHROME C OXIDASE POLYPEPTIDE I (EC 1.9.3.1) | 263–290 | 346–373 | | | | | | | |
| PCP70_HUMAN | CYTOCHROME P450 VII (CHOLESTEROL 7-ALPHA-MONOOXYGENASE) | | | | | | | | | |
| PCPCH_HUMAN | CYTOCHROME P450 IIC17 (EC 1.14.14.1) (P450-254C) (FRAGMENT) | 109–136 | | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PCPE1_HUMAN | CYTOCHROME P450 IIE1 (EC 1.14.14.1) (P450-J) (ETHANOL INDUCIBLE) | 231–258 | | | | | | | | |
| PCPSM_HUMAN | CARBAMOYL-PHOSPHATE SYNTHASE (AMMONIA) MITOCHONDRIAL PRECURSOR | 112–146 | 420–447 | | | | | | | |
| PCPT2_HUMAN | MITOCHONDRIAL CARNITINE PALMITOYLTRANSFERASE II PRECURSOR | 410–437 | | | | | | | | |
| PCPT7_HUMAN | CYTOCHROME P450 XVIIA1 (P450-C17) (EC 1.14.99.9) (STERIOD 17-ALPHA- | 226–257 | | | | | | | | |
| PCPV1_HUMAN | CYTOCHROME P450 XIXA1 (AROMATASE) (EC 1.14.14.1) (ESTROGEN | 234–271 | | | | | | | | |
| PCR2_HUMAN | COMPLEMENT RECEPTOR TYPE 2 PRECURSOR (CR2) (COMPLEMENT C3D RECEPTOR) | 986–1013 | | | | | | | | |
| PCRCM_HUMAN | COLORECTAL MUTANT CANCER PROTEIN (MCC PROTEIN) | 68–126 | 379–420 | 633–678 | 724–754 | 763–790 | | | | |
| PCREB_HUMAN | CAMP RESPONSE ELEMENT BINDING PROTEINS A AND B (CREB-1 AND CREB-B) | 94–125 | | | | | | | | |
| PCREP_HUMAN | CAMP RESPONSE ELEMENT BINDING PROTEIN CRE-BP1 | 380–414 | | | | | | | | |
| PCRP_HUMAN | C-REACTIVE PROTEIN PRECURSOR | 60–87 | 150–177 | | | | | | | |
| PCS1_HUMAN | CLEAVAGE SIGNAL-1 PROTEIN (CS-1) | 203–233 | | | | | | | | |
| PCSF1_HUMAN | MACROPHAGE COLONY STIMULATING FACTOR-1 PRECURSOR (CSF-1) (MCSF) | 143–170 | | | | | | | | |
| PCST3_HUMAN | CLEAVAGE STIMULATION FACTOR, 50 KD SUBUNIT (CSTF 50 KD SUBUNIT) (CF-1 | 6–33 | | | | | | | | |
| PCTNA_HUMAN | ALPHA-CATENIN (CADHERIN-ASSOCIATED PROTEIN) | 681–718 | | | | | | | | |
| PCTNR_HUMAN | ALPHA-CATENIN RELATED PROTEIN (CATENIN ALPHA-2) | 680–717 | | | | | | | | |
| PCX26_HUMAN | GAP JUNCTION BETA-2 PROTEIN (CONNEXIN 26) (CX26) | 108–139 | 126–153 | 352–396 | | | | | | |
| PCS32_HUMAN | GAP JUNCTION BETA-1 PROTEIN (CONNEXIN 32) (CX32) | 117–144 | | | | | | | | |
| PCX37_HUMAN | GAP JUNCTION ALPHA-4 PROTEIN (CONNEXIN 37) (CX37) | 88–115 | | | | | | | | |
| PCYB5_HUMAN | CYTOCHROME B5 | 3–42 | | | | | | | | |
| PCYG1_HUMAN | GUANYLATE CYCLASE SOLUBLE, BETA-1 CHAIN (EC 4.6.1.2) (70 KD CHAIN) | 80–107 | | | | | | | | |
| PCYG4_HUMAN | GUANYLATE CYCLASE SOLUBLE, ALPHA-4 CHAIN (EC 4.6.1.2) | 106–133 | | | | | | | | |
| PCYGR_HUMAN | RETINAL GUANYLYL CYCLASE PRECURSOR (EC 4.6.1.2) | 824–851 | | | | | | | | |
| PCYRG_HUMAN | CYTOKINE RECEPTOR COMMON GAMMA CHAIN PRECURSOR (GAMMA-C) | 293–320 | | | | | | | | |
| PCYTA_HUMAN | CYSTATIN A (STEFIN A) (CYSTATIN AS) | 27–58 | | | | | | | | |
| PDBL_HUMAN | PROTO-ONCOGENE DBL PRECURSOR (CONTAINS: MCF2) | 233–283 | 485–524 | 766–793 | 801–845 | | | | | |
| PDESM_HUMAN | DESMIN | 153–180 | 272–312 | | | | | | | |
| PDESP_HUMAN | DESMOPLAKIN I AND II (DPI AND DPII) (FRAGMENT) | 31–79 | 113–143 | 217–244 | 269–317 | 382–434 | 437–467 | 528–558 | 563–598 | 630–674 |
| | | 697–734 | 738–789 | 1456–1493 | 1508–1535 | | | | | |
| PDHAP_HUMAN | ALDEHYDE DEHYDROGENASE, DIMERIC NADP-PREFERRING (EC 1.2.1.5) | 31–58 | | | | | | | | |
| PDMD_HUMAN | DYSTROPHIN | 86–116 | 338–365 | 484–511 | 753–780 | 976–1003 | 1012–1228 | 1201–1228 | 1364–1394 | 1615–1674 |
| | | 1838–1865 | 2158–2185 | 2313–2343 | 2752–2779 | 2786–2830 | 2912–2958 | 3014–3041 | 3499–3533 | |
| PDNJ1_HUMAN | DNAJ PROTEIN HOMOLOG | 45–76 | | | | | | | | |
| PDNL1_HUMAN | DNA LIGASE I (EC 6.5.1.1) (POLYDEOXYRIBONUCLEOTIDE SYNTHASE (ATP) | 130–157 | 355–392 | 732–759 | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PDPOA_HUMAN | DNA POLYMERASE ALPHA (EC 2.7.7.7) | 25–74 | 1009–1057 | 1100–1127 | | | | | | |
| PDPOD_HUMAN | DNA POLYMERASE DELTA CATALYTIC CHAIN (EC 2.7.7.7) | 729–756 | | | | | | | | |
| PDPP4_HUMAN | DIPDPTIDYL PEPTIDASE IV (EC 3.4.14.5) (DPP IV) (T-CELL ACTIVATION | 29–77 | 114–148 | | | | | | | |
| PDRN1_HUMAN | DEOXYRIBONCULEASE I PRECURSOR (EC 3.1.21.1) (DNASE I) | 44–71 | | | | | | | | |
| PDSC2_HUMAN | DESMOCOLLIN 3A/3B PRECURSOR (DESMOSOMAL GLYCOPROTEIN II AND III) | 80 107 | 355–398 | | | | | | | |
| PDSG1_HUMAN | DESMOGLEIN 1 PRECURSOR (DESMOSOMAL GLYCOPROTEIN 1) (DG1) | 15–42 | 271–298 | 497–531 | | | | | | |
| PDSG3_HUMAN | DESMOGLEIN 3 PRECURSOR (130 KD PEMPHIGUS VULGARIS ANTIGEN) (PVA) | 211–248 | 325–352 | | | | | | | |
| PDUG_HUMAN | DIVERENT UPSTREAM PROTEIN (DUP) | 584–618 | | | | | | | | |
| PEAR1_HUMAN | V-ERBA RELATED PROTEIN EAR-1 | 523–550 | | | | | | | | |
| PEB12_HUMAN | EBV-INDUCED G PROTEIN-COUPLED RECEPTOR 2 (EBI2) | 44–78 | | | | | | | | |
| PEF1B_HUMAN | ELONGATION FACTOR 1-BETA (EF-1-BETA) | 105–132 | | | | | | | | |
| PEF1D_HUMAN | ELONGATION FACTOR 1-DELTA (EF-1-DELTA) | 84–118 | | | | | | | | |
| PEGFR_HUMAN | EPIDERMAL GROWTH FACTOR RECEPTOR PRECURSOR (EC 2.7.1.112) | 64–91 | 440–467 | | | | | | | |
| PEGF_HUMAN | EPIDERMAL GROWTH FACTOR PRECURSOR, KIDNEY (EGF) (UROGASTRONE) | 47–74 | | | | | | | | |
| PELF1_HUMAN | ETS-RELATED TRANSCRIPTION FACTOR ELF-1 | 551–588 | | | | | | | | |
| PENPL_HUMAN | ENDOPLASMIN PRECURSOR (94 KD GLUCOSE-REGULATED PROTEIN) (GRP94) (GP96 | 47–74 | 246–273 | | | | | | | |
| PENV1_HUMAN | RETROVIRUS-RELATED ENV POLYPROTEIN | 382–420 | | | | | | | | |
| PEPC_HUMAN | IG EPSILON CHAIN C REGION | 161–188 | | | | | | | | |
| PEPMO_HUMAN | EPIMORPHIN | 35–62 | 67–94 | 249–283 | | | | | | |
| PER72_HUMAN | PROTEIN DISULFIDE ISOMERASE-RELATED PRECURSOR (ERP72) | 58–85 | 142–169 | 458–485 | | | | | | |
| PERC1_HUMAN | DNA EXCISION REPAIR PROTEIN ERCC-1 | 240–270 | | | | | | | | |
| PERC6_HUMAN | EXCISION REPAIR PROTEIN ERCC-6 | 160–209 | | | | | | | | |
| PERTR_HUMAN | ESTROGEN RECEPTOR (ER) | 451–488 | | | | | | | | |
| PET2_HUMAN | ENDOTHELIN-2 PRECURSOR (ET2) | 133–160 | | | | | | | | |
| PET3_HUMAN | ENDOTHELIN-3 PRECURSOR (ET3) | 182–209 | | | | | | | | |
| PEV2A_HUMAN | EV12A PROTEIN PRECURSOR | 29–56 | | | | | | | | |
| PEZRI_HUMAN | EZRIN (P81) (CYTOVILLIN) (VILLIN-2) | 119–146 | 351–392 | 402–429 | 512–539 | | | | | |
| PFA5_HUMAN | COAGULATION FACTOR V PRECURSOR | 2103–2137 | | | | | | | | |
| PFA8_HUMAN | COAGULATION FACTOR VIII PRECURSOR (PROCOAGULANT COMPONENT) | 871–908 | 1007–1034 | 1194–1230 | | | | | | |
| PFA9_HUMAN | COAGULATION FACTOR IX PRECURSOR (EC 3.4.21.22) (CHRISTMAS FACTOR) | 271–298 | | | | | | | | |
| PFABL_HUMAN | FATTY ACID-BINDING PROTEIN, INTESTINAL | 98–125 | | | | | | | | |
| PFASA_HUMAN | APOPTOSIS-MEDIATING SURFACE ANTIGEN FAS PRECURSOR (APO-1 ANTIGEN) | 23–50 | 249–301 | 306–333 | | | | | | |
| PFCE2_HUMAN | LOW AFFINITY IMMUNOGLOBULIN EPSILON FC RECEPTOR (LYMPHOCYTE IGE | 81 115 | | | | | | | | |

TABLE IX-continued

107 × 178 × 4 Motif Search on All Human Protein Sequences

107 × 174 × 4 SEARCH MOTIF RESULTS SUMMARY FOR ALL HUMAN PROTEINS

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PFCEA_HUMAN | HIGH AFFINITY IMMUNOGLOBULIN EPSILON RECEPTOR ALPHA SUBUNIT (FCERI) | 140–174 | | | | | | | | |
| PFIBA_HUMAN | FIBRINOGEN ALPHA CHAIN PRECURSOR | 131–165 | 427–457 | | | | | | | |
| PFIBB_HUMAN | FIBRINOGEN BETA CHAIN PRECURSOR | 149–186 | | | | | | | | |
| PFIBG_HUMAN | FIBRINOGEN GAMMA-A CHAIN PRECURSOR | 59–93 | 125–160 | | | | | | | |
| PFIBH_HUMAN | FIBRINOGEN GAMMA-G CHAIN (FIBRINOGEN GAMMA') | 59–93 | 125–160 | | | | | | | |
| PFINC_HUMAN | FIBRONECTIN PRECURSOR | 2168–2199 | | | | | | | | |
| PFLI1_HUMAN | FLI-1 ONCOGENE (ERGB TRANSCRIPTION FACTOR) | 172–209 | | | | | | | | |
| PFMO3_HUMAN | DIMETHYLANILINE MONOOXYGENASE (N-OXIDE FORMING) 3 (EC 1.14.13.8) | 184–218 | 256–283 | 301–328 | | | | | | |
| PFOS_HUMAN | P55-FOS PROTO-ONCOGENE PROTEIN | 162–193 | | | | | | | | |
| PFRA1_HUMAN | FOS-RELATED ANTIGEN 1 | 133–168 | | | | | | | | |
| PFRA2_HUMAN | FOS-RELATED ANTIGEN 2 | 149–180 | | | | | | | | |
| PFRIH_HUMAN | FERRITIN HEAVY CHAIN | 7–34 | | | | | | | | |
| PFRIL_HUMAN | FERRITIN LIGHT CHAIN | 3–33 | | | | | | | | |
| PFSHR_HUMAN | FOLLICLE STIMULATING HORMONE RECEPTOR PRECURSOR (FSH-R) | 364–395 | | | | | | | | |
| PFUCO_HUMAN | TISSUE ALPHA-L-FUCOSIDASE PRECURSOR (EC 3.2.1.51) (ALPHA-L-FUCOSIDASE | 308–335 | | | | | | | | |
| PFUMH_HUMAN | FUMARATE HYDRATASE, MITOCHONDRIAL (EC 4.2.1.2) (FUMARASE) | 424–451 | | | | | | | | |
| PGOS2_HUMAN | PUTATIVE LYMPHOCYTE G0/G1 SWITCH PROTEIN | 56–83 | | | | | | | | |
| PG19P_HUMAN | PROTEIN KINASE C SUBSTRATE, 80 KD PROTEIN, HEAVY CHAIN (PKCSH) | 146–173 | | | | | | | | |
| PG6P1_HUMAN | GLUCOSE-6-PHOSPHATE ISOMERASE (GPI) (EC 5.3.1.9) (PHOSPHOGLUCOSE | 16–50 | | | | | | | | |
| PG732_HUMAN | MAJOR GASTROINTESTINAL TUMOR-ASSOCIATED PROTEIN GA733-2 PRECURSOR | 181–215 | | | | | | | | |
| PGASR_HUMAN | GASTRIN/CHOLECYSTOKININ TYPE B RECEPTOR (CCK-B RECEPTOR) | 75–105 | | | | | | | | |
| PGA12_HUMAN | GALACTOKINASE 2 (EC 2.7.1.6) | 254–281 | | | | | | | | |
| PGAA1_HUMAN | GAMMA-AMINOBUTYRIC-ACID RECEPTOR ALPHA-1 SUBUNIT PRECURSOR (GABA(A) | 210–237 | | | | | | | | |
| PGAA3_HUMAN | GAMMA-AMINOBUTYRIC-ACID RECEPTOR ALPHA-3 SUBUNIT PRECURSOR (GABA(A) | 211–255 | | | | | | | | |
| PGB01_HUMAN | GUANINE NUCLEOTIDE-BINDING PROTEIN G(O), ALPHA SUBUNIT 1 | 22–49 | | | | | | | | |
| PGB02_HUMAN | GUANINE NUCLEOTIDE-BINDING PROTEIN G(O), ALPHA SUBUNIT 2 | 22–49 | | | | | | | | |
| PGBAK_HUMAN | GUANINE NUCLEOTIDE-BINDING PROTEIN G(K), ALPHA SUBUNIT G(I) ALPHA-3) | 22–49 | | | | | | | | |
| PGBAS_HUMAN | GUANINE NUCLEOTIDE-BINDING PROTEIN G(S), ALPHA SUBUNIT (ADENYLATE | 7–34 | | | | | | | | |
| PGBAY_HUMAN | GUANINE NUCLEOTIDE-BINDING PROTEIN G(Y), ALPHA SUBUNIT (ALPHA-11) | 95–122 | | | | | | | | |
| PGBB3_HUMAN | GUANINE NUCLEOTIDE-BINDING PROTEIN G(I)/G(S)/G(T) BETA SUBUNIT 3 | 65–92 | | | | | | | | |

TABLE IX-continued

107 × 174 × 4 SEARCH MOTIF RESULTS SUMMARY FOR ALL HUMAN PROTEINS

107 × 178 × 4 Motif Search on All Human Protein Sequences

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PGBLP_HUMAN | GUANINE NUCLEOTIDE-BINDING PROTEIN BETA SUBUNIT-LIKE PROTEIN 12.3 | 110–137 | 255–282 | 289–316 | | | | | | |
| PGBP2_HUMAN | INTERFERON-INDUCED GUANYLATE-BINDING PROTEIN 2 (GUANINE NUCLEOTIDE- | 454–488 | | | | | | | | |
| PGBT2_HUMAN | GUANINE NUCLEOTIDE-BINDING PROTEIN G(T), ALPHA-2 SUBUNIT (TRANSDUCIN | 22–49 | | | | | | | | |
| PGCF_HUMAN | GC-RICH SEQUENCE DNA-BINDING FACTOR (GCF) (TRANSCRIPTION FACTOR 9) | 200–227 | 293–320 | 367–394 | 396–423 | 647–674 | | | | |
| PGCH1_HUMAN | GTP CYCLOHYDROLASE I (EC 3.5.4.16) | 165–192 | | | | | | | | |
| PGCRA_HUMAN | GLUCOCORTICOID RECEPTOR, ALPHA (GR) | 167–194 | | | | | | | | |
| PGCRB_HUMAN | GLUCOCORTICOID RECEPTOR, BETA (GR) | 167–194 | | | | | | | | |
| PGCSP_HUMAN | GLYCINE DEHYDROGENASE (DECARBOXYLATING) PRECURSOR (EC 1.4.4.2) | 460–487 | | | | | | | | |
| PGDN_HUMAN | GLIA DERIVED NEXIN (GDN) (PROTEASE NEXIN 1) | 83–110 | | | | | | | | |
| PGELS_HUMAN | GELSOLIN PRECURSOR, PLASMA (ACTIN-DEPOLYMERIZING FACTOR) (ADF) | 701–728 | | | | | | | | |
| PGFAP_HUMAN | GLIAL FIBRILLARY ACIDIC PROTEIN, ASTROCYTE | 189–216 | 349–376 | 384–411 | | | | | | |
| PGL6S_HUMAN | N-ACETYLGLUCOSAMINE-6-SULFATASE PRECURSOR (EC 3.1.6.14) (G6S) | 170–211 | | | | | | | | |
| PGLPK_HUMAN | GLYCEROL KINASE (EC 2.7.1.30) (APT: GLYCEROL 3-PHOSPHOTRANSFERASE) | 78–112 | 251–278 | | | | | | | |
| PGLY1_HUMAN | SERINE HYDROXYMETHYLTRANSFERASE, CYTOSOLIC (EC 2.1.2.1) (SERINE | 32–59 | 344–371 | | | | | | | |
| PGLY2_HUMAN | SERINE HYDROXYMETHYLTRANSFERASE, MITOCHONDRIAL (EC 2.1.2.1) (SERINE | 417–444 | | | | | | | | |
| PGR78_HUMAN | 78 KD GLUCOSE REGULATED PROTEIN PRECURSOR (GRP 78) (IMMUNOGLOBULIN | 564–591 | 598–625 | | | | | | | |
| PGRA2_HUMAN | GLYCINE RECEPTOR ALPHA-2 CHAIN PRECURSOR | 142–169 | 341–368 | | | | | | | |
| PGRAV_HUMAN | GRAVIN (FRAGMENT) | 9–43 | 61–88 | | | | | | | |
| PGRFR_HUMAN | GROWTH HORMONE-RELEASING HORMONE RECEPTOR PRECURSOR (GHRH RECEPT | 128–155 | | | | | | | | |
| PGTH2_HUMAN | GLUTATHIONE S-TRANSFERASE HA SUBUNIT 2 (EC 2.5.1.18) (GTH2) (CLASS- | 64–91 | | | | | | | | |
| PGTPA_HUMAN | GTPASE-ACTIVATING PROTEIN (GAP) (RAS P21 PROTEIN ACTIVATOR) | 474–501 | 1012–1047 | | | | | | | |
| PGTR1_HUMAN | GLUCOSE TRANSPORTER TYPE 1, ERYTHROCYTE/BRAIN | 274–301 | | | | | | | | |
| PGTR3_HUMAN | GLUCOSE TRANSPORTER TYPE 3, BRAIN | 272–299 | | | | | | | | |
| PGTR4_HUMAN | GLUCOSE TRANSPORTER TYPE 4, INSULIN-RESPONSIVE | 290–317 | | | | | | | | |
| PH10_HUMAN | ISTONE H1' | 44–89 | | | | | | | | |
| PH1A_HUMAN | HISTONE H1A (H1.1) | 73–104 | | | | | | | | |
| PH1B_HUMAN | HISTONE H1B (H1.4) | 70–101 | | | | | | | | |
| PH1C_HUMAN | HISTONE H1C (H1.3) | 71–102 | | | | | | | | |
| PH1D_HUMAN | HISTONE H1D (H1.2) | 70–101 | | | | | | | | |
| PH1T_HUMAN | HISTONE H1T | 74–105 | | | | | | | | |
| PH2B0_HUMAN | HISTONE H2B.1 | 20–47 | | | | | | | | |
| PH2B2_HUMAN | HISTONE H2B.2 | 20–47 | | | | | | | | |
| PH2B_HUMAN | HISTONE H2B (H2B.1 A) | 20–47 | | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PHA25_HUMAN | HLA CLASS II HISTOCOMPATIBILITY ANTIGEN, DQ(5) ALPHA CHAIN PRECURSOR | 142–169 | | | | | | | | |
| PHA2K_HUMAN | HLA CLASS II HISTOCOMPATIBILITY ANTIGEN, DR-W53 BETA CHAIN PRECURSOR | 56–83 | | | | | | | | |
| PHA2P_HUMAN | HLA CLASS II HISTOCOMPATIBILITY ANTIGEN, DP(W4) BETA CHAIN PRECURSOR | 50–77 | | | | | | | | |
| PHA2Q_HUMAN | HLA CLASS II HISTOCOMPATIBILITY ANTIGEN, DP(W2) BETA CHAIN PRECURSOR | 50–77 | | | | | | | | |
| PHA2S_HUMAN | HLA CLASS II HISTOCOMPATIBILITY ANTIGEN, SB BETA CHAIN PRECURSOR | 16–43 | | | | | | | | |
| PHBG1_HUMAN | HEPARIN-BINDING GROWTH FACTOR PRECURSOR 1 (HBGF-1) (ACIDIC FIBROBLAST | 102–129 | | | | | | | | |
| PHBG3_HUMAN | INT-2 PROTO-ONCOGENE PROTEIN PRECURSOR (HBGF-3) | 61–91 | | | | | | | | |
| PHBG6_HUMAN | FIBROBLAST GROWTH FACTOR-6 PRECURSOR (FGF-6) (HBGF-6) (HST-2) | 41–75 | 159–186 | | | | | | | |
| PHBI_HUMAN | P59 PROTEIN (HSP BINDING IMMUNOPHILIN) (HBI) (POSSIBLE PEPTIDYL-PROLYL | 264–312 | | | | | | | | |
| PHEM4_HUMAN | UROPORPHYRINOGEN-III SYNTHASE (EC 4.2.1.75) (UROPORPHYRINOGEN-III | 74–118 | | | | | | | | |
| PHEP2_HUMAN | HEPARIN COFACTOR II PRECURSOR (HC-II) (PROTEASE INHIBITOR LEUSERPIN 2) | 169–196 | | | | | | | | |
| PHEPS_HUMAN | SERIN PROTEASE HEPSIN (EC 3.4.21.-) | 22–49 | | | | | | | | |
| PHEXA_HUMAN | BETA-HEXOSAMINIDASE ALPHA CHAIN PRECUROSR (EC 3.2.1.52) (N-ACETYL- | 356–383 | | | | | | | | |
| PHEXB_HUMAN | BETA-HEXOSAMINIDASE BETA CHAIN PRECUROSR (EC 3.2.1.52) (N-ACETYL-BETA | 388–415 | | | | | | | | |
| PHMX1_HUMAN | HOMEOBOX PROTEIN MSX-1 (HOX-7) | 178–212 | | | | | | | | |
| PHNFA_HUMAN | HEPATOCYTE NUCLEAR FACTOR 1-ALPHA (HNF-1A) (LIVER SPECIFIC | 2–29 | | | | | | | | |
| PHO1_HUMAN | HEME OXYGENASE 1 (EC 1.14.99.3) (HO-1) | 197–224 | | | | | | | | |
| PHPPD_HUMAN | 4-HYDROXYPHENYLPYRUVATE DIOXYGENASE (EC 1.13.11.27) (4HPPD) | 306–333 | | | | | | | | |
| PHRX_HUMAN | ZINC FINGER PROTEIN HRX | 521–548 | 914–974 | 1637–1666 | 2215–2286 | 2289–2316 | 3317–3344 | 3448–3475 | | |
| PHS1_HUMAN | HEMATOPOIETIC LINEAGE CELL SPECIFIC PROTEIN | 43–70 | | | | | | | | |
| PHS9A_HUMAN | HEAT SHOCK PROTEIN HSP 90-ALPHA (HSP 86) | 443–470 | 640–674 | | | | | | | |
| PHSER_HUMAN | HEAT-STABLE ENTEROTOXIN RECEPTOR PRECURSOR (GC-C) (INTESTINAL | 511–545 | | | | | | | | |
| PHSF1_HUMAN | HEAT SHOCK FACTOR PROTEIN 1 (HSF 1) (HEAT SHOCK TRANSCRIPTION FACTOR | 113–140 | 168–209 | | | | | | | |
| PHSF2_HUMAN | HEAT SHOCK FACTOR PROTEIN 2 (HSF 2) (HEAT SHOCK TRANSCRIPTION FACTOR | 117–198 | | | | | | | | |
| PHV2L_HUMAN | IG HEAVY CHAIN PRECURSOR V-II REGION (ARH-77) | 67–108 | | | | | | | | |
| PHV3T_HUMAN | IG HEAVY CHAIN V-III REGION (GAL) | 47–74 | | | | | | | | |
| PHX11_HUMAN | HOMEOBOX PROTEIN HOX-II (TCL-3 PROTO-ONOGENE) | 262–289 | | | | | | | | |
| PHXB7_HUMAN | HOMEOBOX PROTEIN HOX-B7 (HOX-2C) (HHO.C1) | 135–162 | | | | | | | | |
| PIAPP_HUMAN | ISLET AMYLOID POLYPEPTIDE | 53–80 | | | | | | | | |

TABLE IX-continued 107 x 174 x 4 SEARCH MOTIF RESULTS SUMMARY FOR ALL HUMAN PROTEINS

| PCGENE FILE NAME | 107 x 178 x 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PIBP3_HUMAN | INSULIN-LIKE GROWTH FACTOR BINDING PROTEIN 3 PRECURSOR (IGFBP-3) | 183–210 | | | | | | | | |
| PIC1_HUMAN | PLASMA PROTEASE C1 INHIBITOR PRECURSOR (C1 INH) | 251–278 | | | | | | | | |
| PICA2_HUMAN | INTERCELLULAR ADHESION MOLECULE-2 PRECURSOR (ICAM-2) | 57–84 | | | | | | | | |
| PIDE_HUMAN | INSULIN-DEGRADING ENZYME (EC 3.4.99.45) (INSULINASE) (INSULIN | 474–504 | 907–941 | | | | | | | |
| PIF4I_HUMAN | EUKARYOTIC INITIATION FACTOR 4A-1 (EIF-4A-I) | 232–259 | 322–349 | | | | | | | |
| PIF4B_HUMAN | INTRINSIC FACTOR PRECURSOR (IF) (GASTRIC INTRINSIC FACTOR) | 149–176 | 406–433 | | | | | | | |
| PIF_HUMAN | INHIBIN BETA A CHAIN PRECURSOR (ACTIVIN BETA-A CHAIN) (ERYTHROID | 308–349 | | | | | | | | |
| PIHBA_HUMAN | INTERLEUKIN-1 ALPHA PRECURSOR (IL-1 ALPHA) (HEMATOPOIETIN-1) | 80–107 | 183–210 | | | | | | | |
| PIL1A_HUMAN | INTERLEUKIN-1 RECEPTOR, TYPE I PRECURSOR (IL-1R1) (P80) | 76–110 | 172–199 | | | | | | | |
| PIL1R_HUMAN | INTERLEUKIN-1 RECEPTOR, TYPE I PRECURSOR (IL-1R1) (P80) | 437–467 | | | | | | | | |
| PIL1S_HUMAN | INTERLEUKIN-1 RECEPTOR, TYPE II PRECURSOR (IL-1R2) | 159–186 | | | | | | | | |
| PIL5R_HUMAN | INTERLEUKIN-5 RECEPTOR ALPHA CHAIN PRECURSOR (IL-5R-ALPHA) | 87–114 | | | | | | | | |
| PIL6_HUMAN | INTERLEUKIN-6 PRECURSOR (IL-6) (B-CELL STIMULATOR FACTOR 2) (BSF-2) | 112–139 | | | | | | | | |
| PINAL_HUMAN | INTERFERON ALPHA-1 PRECURSOR | 94–121 | | | | | | | | |
| PINAR_HUMAN | INTERFERON ALPHA RECEPTOR PRECURSOR (IFN-ALPHA-REC) | 90–117 | 164–191 | 300–327 | 508–535 | | | | | |
| PINB_HUMAN | INTERFERON BETA PRECURSOR (FIBROBLAST | 88–129 | | | | | | | | |
| BINI1_HUMAN | INTERFERON-INDUCED 17 KD PROTEIN (CONTAINS: INTERFERON-INDUCED 15 KD | 83–121 | | | | | | | | |
| BINI6_HUMAN | INTERFERON-INDUCED 56 KD PROTEIN (IFI-56K) | 51–78 | 216–245 | 393–430 | | | | | | |
| PINSR_HUMAN | INSULIN RECEPTOR PRECURSOR (EC 2.7.1.112) (IR) | 592–619 | | | | | | | | |
| PINVO_HUMAN | INVOLUCRIN | 119–146 | 229–273 | 326–363 | 386–450 | | | | | |
| PIP3K_HUMAN | 1D-MYO-INOSITOL-TRISPHOSPHATE 3-KINASE A (EC 2.7.1.127) (INOSITOL | 121–162 | | | | | | | | |
| PIPSP_HUMAN | PLASMA SERINE PROTEASE (PROTEIN C) INHIBITOR PRECURSOR (PCI) | 90–117 | 206–233 | | | | | | | |
| PIRBP_HUMAN | INTERPHOTORECEPTOR RETINOID-BINDING PROTEIN PRECURSOR (IRBP) | 670–697 | | | | | | | | |
| PIRF2_HUMAN | INTERFERON REGULATORY FACTOR 2 (IRF-2) | 157–193 | | | | | | | | |
| PIT5P_HUMAN | 75 KD INOSITOL-1,4,5-TRISPHOSPHATE 5-PHOSPHATASE PRECURSOR | 235–262 | | | | | | | | |
| PITA2_HUMAN | PLATELET MEMBRANE GLYCOPROTEIN IA PRECURSOR (GPIA) (COLLAGEN RECEPTO | 579–606 | 900–927 | | | | | | | |
| PITA5_HUMAN | FIBRONECTIN RECEPTOR ALPHA SUBUNIT PRECURSOR (INTEGRIN ALPHA-F) | 250–284 | 657–695 | 765–792 | | | | | | |
| PITA6_HUMAN | INTEGRIN ALPHA-6 PRECURSOR (VLA-6) (INTEGRIN ALPHA-E) (CD49F) | 884–911 | 944–974 | | | | | | | |
| PITAL_HUMAN | LEUKOCYTE ADHESION GLYCOPROTEIN LFA1 ALPHA CHAIN PRECURSOR (LEUKOC | 256–283 | 310–341 | 795–822 | | | | | | |

TABLE IX-continued

107 × 178 × 4 Motif Search on All Human Protein Sequences

107 × 174 × 4 SEARCH MOTIF RESULTS SUMMARY FOR ALL HUMAN PROTEINS

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PITAM_HUMAN | CELL SURFACE GLYCOPROTEIN MAC-1 ALPHA SUBUNIT PRECURSOR (CR-3 ALPHA | 1044–1078 | | | | | | | | |
| PITAV_HUMAN | VITRONECTIN RECEPTOR ALPHA SUBUNIT PRECURSOR (INTEGRIN ALPHA-V) | 230–264 | | | | | | | | |
| PITB1_HUMAN | FIBRONECTIN RECEPTOR BETA SUBUNIT PRECURSOR (INTEGRIN BETA-1) (CD29) | 218–245 | 354–399 | | | | | | | |
| PITB2_HUMAN | CELL SURFACE ADHESION GLYCOPROTEINS LFA-1, CR3 AND P150,95, BETA- | 339–366 | 705–732 | | | | | | | |
| PITB3_HUMAN | PLATELET MEMBRANE GLYCOPROTEIN IIIA PRECURSOR (GPIIIA) (INTEGRIN BETA- | 324–351 | | | | | | | | |
| PITB4_HUMAN | INTEGRIN BETA-4 SUBUNIT PRECURSOR (GP150) | 342–369 | | | | | | | | |
| PITB5_HUMAN | INTEGRIN BETA-5 SUBUNIT PRECURSOR | 724–751 | | | | | | | | |
| PITB6_HUMAN | INTEGRIN BETA-6 SUBUNIT PRECURSOR | 311–338 | 352–393 | | | | | | | |
| PITB8_HUMAN | INTEGRIN BETA-8 SUBUNIT PRECURSOR | 362–399 | 696–737 | | | | | | | |
| PITI2_HUMAN | INTER-ALPHA-TRYPSIN INHIBITOR COMPLEX COMPONENT II PRECURSOR | 134–161 | 425–452 | 772–818 | | | | | | |
| PK1CJ_HUMAN | KERATIN, TYPE I CYTOSKELETAL 10 (CYTOKERATIN 10) (K10) | 154–187 | 196–227 | 337–399 | 428–462 | | | | | |
| PK1CM_HUMAN | KERATIN, TYPE I CYTOSKELETAL 13 (CYTOKERATIN 13) (K13) | 12–142 | | | | | | | | |
| PK1CN_HUMAN | KERATIN, TYPE I CYTOSKELETAL 14 (CYTOKERATIN 14) (K14) | 122–152 | 306–335 | 393–424 | | | | | | |
| PK1CO_HUMAN | KERATIN, TYPE I CYTOSKELETAL 15 (CYTOKERATIN 15) (K15) | 113–143 | | | | | | | | |
| PK1CP_HUMAN | KERATIN, TYPE I CYTOSKELETAL 16 (CYTOKERATIN 16) (K16) | 308–339 | | | | | | | | |
| PK1CQ_HUMAN | KERATIN, TYPE I CYTOSKELETAL 17 (CYTOKERATIN 17) (K17) | 122–152 | 302–346 | 393–431 | | | | | | |
| PK1CR_HUMAN | KERATIN, TYPE I CYTOSKELETAL 18 (CYTOKERATIN 18) (K18) | 87–114 | 251–298 | 337–385 | | | | | | |
| PK1CS_HUMAN | KERATIN, TYPE I CYTOSKELETAL 19 (CYTOKERATIN 19) (K19) | 88–118 | 317–362 | 370–397 | | | | | | |
| PK2C1_HUMAN | KERATIN, TYPE II CYTOSKELETAL 1 (CYTOKERATIN 1) (K1) (CYTOSKELETAL 67 | 196–226 | 346–384 | 390–467 | | | | | | |
| PK2C2_HUMAN | KERATIN, TYPE II CYTOSKELETAL 65 KD | 215–248 | 364–405 | 461–488 | | | | | | |
| PK2C4_HUMAN | KERATIN, TYPE II CYTOSKELETAL 4 (CYTOKERATIN 4) (K4) (FRAGMENT) | 42–73 | 126–153 | 189–248 | | | | | | |
| PK2C5_HUMAN | KERATIN, TYPE II CYTOSKELETAL 5 (CYTOKERATIN 5) (K5) (58 KD | 185–246 | 332–373 | | | | | | | |
| PK2C6_HUMAN | KERATIN, TYPE II CYTOSKELETAL 6 (CYTOKERATIN 6) (K6) (K6B KERATIN) | 178–239 | 325–366 | 422–449 | | | | | | |
| PK2C8_HUMAN | KERATIN, TYPE II CYTOSKELETAL 8 (CYTOKERATIN 8) (K8) | 140–167 | 120–161 | 217–244 | | | | | | |
| PK2CA_HUMAN | KERATIN, TYPE II CYTOSKELETAL 56 KD (K6A KERATIN) (FRAGMENT) | 7–34 | | | | | | | | |
| KP6PF_HUMAN | 6-PHOSPHOFRUCTOKINASE, MUSCLE TYPE (EC 2.7.1.11) (PHOSPHOFRUCTOKINASE | 140–167 | | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PK6PL_HUMAN | 6-PHOSPHOFRUCTOKINASE, LIVER TYPE (EC 2.7.1.11) (PHOSPHOFRUCTOKINASE | 49–80 | 128–159 | | | | | | | |
| PKABL_HUMAN | PROTO-ONCOGENE TYROSINE-PROTEIN KINASE ABL (EC 2.7.1.112) (P150) | 498–525 | | | | | | | | |
| PKAC_HUMAN | IG KAPPA CHAIN C REGION | 37–85 | | | | | | | | |
| PKALM_HUMAN | KALLMANN SYNDROME PROTEIN PRECURSOR (ADHESION MOLECULE-LIKE X-LINK | 380–414 | | | | | | | | |
| PKAP0_HUMAN | CAMP-DEPENDENT PROTEIN KINASE TYPE I-ALPHA REGULATORY CHAIN | 179–206 | | | | | | | | |
| PKAP1_HUMAN | CAMP-DEPENDENT PROTEIN KINASE TYPE I-BETA REGULATORY CHAIN | 177–204 | | | | | | | | |
| PKAP2_HUMAN | CAMP-DEPENDENT PROTEIN KINASE TYPE II-ALPHA REGULATORY CHAIN | 175–202 | 290–317 | | | | | | | |
| PKBF1_HUMAN | NUCLEAR FACTOR KAPPA-B SUBUNIT-1 (NF-KAPPA-B P105 SUBUNIT | 529–570 | | | | | | | | |
| PKCRB_HUMAN | CREATINE KINASE, B CHAIN (EC 2.7.3.2) | 301–328 | | | | | | | | |
| PKECK_HUMAN | TYROSINE PROTEIN-KINASE ECK PRECURSOR (EC 2.7.1.112) (EPITHELIAL CELL | 466–493 | | | | | | | | |
| PKFER_HUMAN | PROTO-ONCOGENE TYROSINE-PROTEIN KINASE FER (EC 2.7.1.112) (P94-FER) | 219–246 | 564–591 | | | | | | | |
| PKFER_HUMAN | PROTO-ONCOGENE TYROSINE-PROTEIN KINASE FER (EC 2.7.1.112) (C-FES) | 101–145 | 295–322 | | | | | | | |
| PKFLT_HUMAN | RECEPTOR-RELATED TYROSINE KINASE FLT PRECURSOR (EC 2.7.1.112) | 208–235 | 319–353 | | | | | | | |
| PKFMS_HUMAN | MACROPHAGE COLONY STIMULATION FACTOR I RECEPTOR PRECURSOR (CSF-1-R) | 293–320 | | | | | | | | |
| PKFYN_HUMAN | PROTO-ONCOGENE TYROSINE-PROTEIN KINASE FYN (EC 2.7.1.112) (P59-FYN) | 199–233 | | | | | | | | |
| KGGPB_HUMAN | CGMP-DEPENDENT PROTEIN KINASE, BETA ISOZYME (CGK) (EC 2.7.1.37) | 17–54 | | | | | | | | |
| PKHEK_HUMAN | TYROSINE KINASE HEK RECEPTOR PRECURSOR (EC 2.7.1.112) | 646–673 | 425–452 | 471–542 | 633–680 | 689–716 | 872–899 | | | |
| PKINH_HUMAN | KINESIN HEAVY CHAIN | 125–155 | | | | | | | | |
| PKKIT_HUMAN | KIT PROTO-ONCOGENE TYROSINE KINASE PRECURSOR (EC 2.7.1.112) | 235–263 | | | | | | | | |
| PKMET_HUMAN | HEPATOCYTE GROWTH FACTOR RECEPTOR PRECURSOR (MET PROTO-ONCOGENE | 898–925 | | | | | | | | |
| PHNH_HUMAN | KININOGEN, HMW PRECURSOR (ALPHA-2-THIOL PROTEINASE INHIBITOR) | 505–532 | | | | | | | | |
| PKP58_HUMAN | GALACTOSYLTRANSFERASE ASSOCICATED PROTEIN KINASE P58/GTA (EC 2.7.1.-) | 81–108 | | | | | | | | |
| PKP68_HUMAN | INTERFERON-INDUCED, DOUBLE-STRANDED RNA-ACTIVATED PROTEIN KINASE | 149–179 | 191–225 | 285–312 | | | | | | |
| PKP78_HUMAN | PUTATIVE SERINE/THREONINE-PROTEIN KINASE P78 (EC 2.7.1.-) | 582–609 | | | | | | | | |
| PKPCL_HUMAN | PROTEIN KINASE C, ETA TYPE (EC 2.7.1.-) (NPKC-ETA) (PKC-L) | 318–345 | | | | | | | | |
| PKPT1_HUMAN | SERINE/THREONINE-PROTEIN KINASE PCTAIRE-1 (EC 2.7.1.-) | 149–176 | 209–253 | | | | | | | |

TABLE IX-continued

107 × 174 × 4 SEARCH MOTIF RESULTS SUMMARY FOR ALL HUMAN PROTEINS

107 × 178 × 4 Motif Search on All Human Protein Sequences

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PKPY1_HUMAN | PYRUVATE KINASE, M1 (MUSCLE) ISOZYME (EC 2.7.1.40) (CYTOSOLIC THYROID | 243–289 | | | | | | | | |
| PKPY2_HUMAN | PYRUVATE KINASE, M2 (MUSCLE) (EC 2.7.1.40) | 243–289 | | | | | | | | |
| PKPYR_HUMAN | PYRUVATE KINASE, ISOZYME R (EC 2.7.1.40) | 2–29 | | | | | | | | |
| PKRET_HUMAN | PROTO-ONCOGENE TYROSINE-PROTEIN KINASE RET (EC 2.7.1.112) | 183–217 | | | | | | | | |
| PKROS_HUMAN | ROS PROTO-ONCOGENE TYROSINE KINASE (EC 2.7.1.112) (FRAGMENT) | 157–203 | | | | | | | | |
| PKSRC_HUMAN | PROTO-ONCOGENE TYROSINE-PROTEIN KINASE SRC (EC 2.7.1.112) (P60-SRC) | 143–170 | | | | | | | | |
| PKU7_HUMAN | LUPUS KU AUTOANTIGEN PROTEIN P70 (70 KD SUBUNIT OF KU ANTIGEN) | 235–279 | | | | | | | | |
| PKU86_HUMAN | LUPUS KU AUTOANTIGEN PROTEIN P86 (86 KD SUBUNIT OF KU ANTIGEN) | 258–292 | | | | | | | | |
| PKYES_HUMAN | PROTO-ONCOGENE TYROSINE-PROTEIN KINASE YES (EC 2.7.1.112) (P61-YES) | 209–243 | | | | | | | | |
| PLAM1_HUMAN | LAMIN B1 | 32–66 | 117–144 | 152–193 | 214–241 | 397–424 | 480–507 | 510–539 | | |
| PLAMA_HUMAN | LAMIN A (70 KD LAMIN) | 32–88 | 114–165 | 292–343 | | | | | | |
| PLAMC_HUMAN | LAMIN C | 32–88 | 114–165 | 292–343 | | | | | | |
| PLAR_HUMAN | LAR PROTEIN PRECURSOR (LEUKOCYTE ANTIGEN RELATED) (EC 3.1.3.48) | 935–969 | | | | | | | | |
| PLA_HUMAN | LUPUS LA PROTEIN (SJOGREN SYNDROME TYPE B ANTIGEN (SS-B)) | 191–222 | 295–342 | | | | | | | |
| PLCAT_HUMAN | PHOSPHATIDYLCHOLINE-STEROL ACYLTRANSFERASE PRECURSOR (EC 2.3.1.43) | 131–158 | | | | | | | | |
| PLDHH_HUMAN | L-LACTATE DEHYDROGENASE H CHAIN (EC 1.1.1.27) (LDH-B) | 81–108 | 302–329 | | | | | | | |
| PLDHM_HUMAN | L-LACTATE DEHYDROGENASE M CHAIN (EC 1.1.1.27) (LDH-A) | 225–252 | | | | | | | | |
| PLDLR_HUMAN | LOW-DENSITY LIPOPROTEIN RECEPTOR PRECURSOR | 483–510 | | | | | | | | |
| PLECH_HUMAN | ASIALOGLYCOPROTEIN RECEPTOR 1 (HEPATIC LECTIN H1) (ASGPR) | 62–96 | | | | | | | | |
| PLEM3_HUMAN | P-SELECTIN PRECURSOR (GRANULE MEMBRANE PROTEIN 140) (GMP-140) (PADGEM) | 32–59 | 87–116 | | | | | | | |
| PLGU1_HUMAN | LACTOYLGLUTATHIONE LYASE (EC 4.4.1.5) (METHYLGLYOXALASE) | 83–117 | | | | | | | | |
| PLIF_HUMAN | LEUKAEMIA INHIBITORY FACTOR PRECURSOR (LIF) (DIFFERENTIATION- | 95–122 | | | | | | | | |
| PLIN1_HUMAN | LINE-1 REVERSE TRANSCRIPTASE HOMOLOG | 152–179 | 232–263 | 298–358 | 671–698 | 874–901 | 1036–1066 | | | |
| PLIPG_HUMAN | TRIACYLGLYCEROL LIPASE PRECURSOR (EC 3.1.1.3) (LIPASE, GASTRIC) | 158–185 | | | | | | | | |
| PLIPS_HUMAN | HORMONE SENSITIVE LIPASE (EC 3.1.1.-) (HSL) | 305–332 | | | | | | | | |
| PLKHA_HUMAN | LEUKOTRIENE A-4 HYDROLASE (EC 3.3.2.6) (LTA-4 HYDROLASE) (LEUKTRIENE | 42–83 | 290–324 | | | | | | | |
| PLMA_HUMAN | LAMININ A CHAIN PRECURSOR | 1318–1345 | 1741–1771 | 1785–1812 | 1824–1851 | 1884–1921 | 1965–1999 | 2026–2059 | 2091–2118 | |
| PLMB1_HUMAN | LAMININ B1 CHAIN PRECURSOR | 1267–1314 | 1364–1394 | 1597–1631 | 1651–1714 | 1722–1781 | | | | |
| PLMB2_HUMAN | LAMININ B2 CHAIN PRECURSOR | 1103–1135 | 1513–1547 | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PLMP2_HUMAN | LYSOSOME-ASSOCIATED MEMBRANE GLYCOPROTEIN 2 PRECURSOR (LAMP-2) | 155–182 | | | | | | | | |
| PLOX2_HUMAN | ARACHIDONATE 12-LIPOXYGENASE (EC 1.13.11.31) (12-LOX) | 341–368 | | | | | | | | |
| PLOX5_HUMAN | ARACHIDONATE 5-LIPOXYGENASE (EC 1.13.11.31) (5-LIPOXYGENASE) (5-LO) | 50–87 | | | | | | | | |
| PLPH_HUMAN | LACTASE-PHLORIZIN HYDROLASE PRECURSOR (EC 3.2.1.108) (EC 3.2.1.62) | 776–803 | | | | | | | | |
| PLRPB_HUMAN | PROTEIN-TYROSINE PHOSPHATASE BETA PRECURSOR (EC 3.1.3.48) (PTP-BETA) | 140–167 | 589–637 | | | | | | | |
| PLRPG_HUMAN | PROTEIN-TYROSINE PHOSPHATASE GAMMA PRECURSOR (EC 3.1.3.48) | 1081–1108 | | | | | | | | |
| PLRPZ_HUMAN | PROTEIN-TYROSINE PHOSPHATASE ZETA PRECURSOR (EC 3.1.3.48) (PTP-ZETA) | 553–587 | 1024–1051 | 1973–2000 | | | | | | |
| PLSHR_HUMAN | LUTROPIN-CHORIOGONADOTROPIC HORMONE RECEPTOR PRECURSOR (LG/CG-5) | 66–114 | 448–480 | | | | | | | |
| PLV2B_HUMAN | IG LAMBDA CHAIN V-II REGION (NEI) | 61–88 | | | | | | | | |
| PLYAG_HUMAN | LYSOSOMAL ALPHA-GLUCOSIDASE PRECURSOR (EC 3.2.1.20) (ACID MALTASE) | 885–912 | | | | | | | | |
| PM2OM_HUMAN | MITOCHONDRIAL 2-OXOGLUTARATE/MALATE CARRIER PROTEIN (OGCP) | 50–77 | | | | | | | | |
| PMAC2_HUMAN | GALACTOSE-SPECIFIC LECTIN (MAC-2 ANTIGEN) (IGE-BINDING PROTEIN) (35 KD | 219–246 | | | | | | | | |
| PMAN9_HUMAN | MAN(9)-ALPHA-MANNOSIDASE (EC 3.2.1.-) | 414–441 | | | | | | | | |
| PMAMA_HUMAN | MANNOSE-6-PHOSPHATE ISOMERASE (EC 5.3.1.8) (PHOSPHOMANNOSE ISOMERASE) | 60–87 | | | | | | | | |
| PMANR_HUMAN | MACROPHAGE MANNOSE RECEPTOR PRECURSOR | 248–284 | 1147–1182 | | | | | | | |
| PMAP2_HUMAN | MICROTUBULE-ASSOCIATED PROTEIN 2 (FRAGMENT) | 434–478 | | | | | | | | |
| PMAP4_HUMAN | MICROTUBULE-ASSOCIATED PROTEIN 4 | 408–449 | | | | | | | | |
| PMAX_HUMAN | MAX PROTEIN | 117–144 | | | | | | | | |
| PMDM2_HUMAN | MDM2 PROTEIN (P53-ASSOCIATED PROTEIN) | 235–288 | | | | | | | | |
| PMDR1_HUMAN | MULTIDRUG RESISTANCE PROTEIN 1 (P-GLYCOPROTEIN 1) | 377–407 | 532–566 | | | | | | | |
| PMERL_HUMAN | MERLIN (SCHWANNMIN) | 71–105 | 139–173 | 431–458 | 791–818 | | | | | |
| PMERO_HUMAN | MEROSIN HEAVY CHAIN (LAMININ CHAIN A2) (FRAGMENT) | 91–118 | | | | | | | | |
| PMGMT_HUMAN | METHYLATED-DNA-PROTEIN-CYSTEINE METHYLTRANSFERASE (EC 2.1.1.63) (6-O- | 207–234 | 319–346 | 510–537 | 549–608 | | | | | |
| PMKLP_HUMAN | MITOTIC KINESIN-LIKE PROTEIN-1 | 8–35 | | | | | | | | |
| PMLCH_HUMAN | MELANIN-CONCENTRATING HORMONE PRECURSOR | 130–157 | 321–348 | | | | | | | |
| PMLK1_HUMAN | MIXED LINEAGE KINASE 1 (EC 2.7.1.-) (FRAGMENT) | 393–420 | | | | | | | | |
| PMMSA_HUMAN | METHYLMALONATE-SEMIALDEHYDE DEHYDROGENASE | 119–146 | 351–403 | | | | | | | |
| PMOES_HUMAN | MOESIN (MEMBRANE-ORGANIZING EXTENSION SPIKE PROTEIN) | 286–313 | | | | | | | | |
| PMPCP_HUMAN | MITOCHONDRIAL PHOSPHATE CARRIER PROTEIN PRECURSOR | 72–99 | | | | | | | | |
| PMPI3_HUMAN | M-PHASE INDUCER PHOSPHATASE 3 (EC 3.1.3.48) | 19–50 | | | | | | | | |
| PMPKK_HUMAN | DUAL SPECIFICITY MITOGEN-ACTIVATED PROTEIN KINASE KINASE (EC 2.7.1.-) | 1569–1596 | 2437–2478 | | | | | | | |
| PMPRL_HUMAN | CATION-INDEPENDENT MANNOSE-6-PHOSPHATE RECEPTOR PRECURSOR (CI MAN-6- | | | | | | | | | |

TABLE IX-continued

107 × 178 × 4 Motif Search on All Human Protein Sequences

107 × 174 × 4 SEARCH MOTIF RESULTS SUMMARY FOR ALL HUMAN PROTEINS

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PMRP_HUMAN | MULTIDRUG RESISTANCE-ASSOCIATED PROTEIN | 396–423 | 507–548 | | | | | | | |
| PMSHR_HUMAN | MELANOCYTE STIMULATING HORMONE RECEPTOR (MSH-R) (MELANOTROPIN | 38–65 | | | | | | | | |
| PMSRE_HUMAN | MACROPHAGE SCAVENGER RECEPTOR TYPES I AND II (MACROPHAGE ACETYLATED | 173–204 | 230–260 | | | | | | | |
| PMTDM_HUMAN | DNA (CYTOSINE-5)-METHYLTRANSFERASE (EC 2.1.1.37) (DNA | 387–414 | 601–628 | | | | | | | |
| PMTF1_HUMAN | MITOCHONDRIAL TRANSCRIPTION FACTOR 1 PRECURSOR (MTTF1) | 181–212 | | | | | | | | |
| PMUTA_HUMAN | METHYLMALONYL-COA MUTASE PRECURSOR (EC 5.4.99.2) (MCM) | 468–519 | | | | | | | | |
| PMX1_HUMAN | INTERFERON-REGULATED RESISTANCE GTP-BINDING PROTEIN MXA (INTERFERON- | 108–150 | | | | | | | | |
| PMX2_HUMAN | INTERFERON-REGULATED RESISTANCE GTP-BINDING PROTEIN MXB (P78 RELATED | 451–489 | 670–697 | | | | | | | |
| PMYBA_HUMAN | MYB-RELATED PROTEIN A (FRAGMENT) | 619–646 | | | | | | | | |
| PMYBB_HUMAN | MYB-RELATED PROTEIN B | 87–117 | | | | | | | | |
| PMYCN_HUMAN | N-MYC PROTO-ONCOGENE PROTEIN | 263–300 | 413–461 | | | | | | | |
| PMYC_HUMAN | MYC PROTO-ONCOGENE PROTEIN | 393–422 | | | | | | | | |
| PMYF4_HUMAN | MYOGENIC FACTOR MYF-4 (MYOGENIN) | 119–146 | | | | | | | | |
| PMYF5_HUMAN | MYOGENIC FACTOR MYF-5 | 121–148 | | | | | | | | |
| PMYP2_HUMAN | MYOGENIC P2 PROTEIN | 70–110 | | | | | | | | |
| PMYPR_HUMAN | MYELIN PROTEOLIPID PROTEIN (PLP) (LIPOPHILIN) (CONTAINS: MYELIN | 43–70 | | | | | | | | |
| PMYSA_HUMAN | MYOSIN HEAVY CHAIN, CARDIAC MUSCLE ALPHA ISOFORM (FRAGMENT) | 38–75 | 84–111 | 137–178 | 236–324 | 398–435 | 440–485 | | | |
| PMYSB_HUMAN | MYOSIN HEAVY CHAIN, CARDIAC MUSCLE BETA ISOFORM | 48–75 1541–1582 | 951–981 1640–1681 | 997–1044 1683–1710 | 1088–1122 1801–1838 | 1192–1234 | 1266–1332 | 1360–1408 | 1442–1479 | 1488–1532 |
| PMYSE_HUMAN | MYOSIN HEAVY CHAIN, FAST SKELETAL MUSCLE, EMBRYONIC | 46–73 1707–1734 | 860–903 1827–1858 | 952–1077 | 1119–1146 | 1193–1235 | 1267–1340 | 1364–1411 | 1483–1597 | 1641–1675 |
| PMYSP_HUMAN | MYOSIN HEAVY CHAIN, PERINATAL CARDIAC MUSCLE (FRAGMENT) | 50–77 | 95–125 | 141–188 | 215–272 | 403–483 | 507–552 | 586–624 | 685–736 | 784–818 |
| PMYSS_HUMAN | MYOSIN HEAVY CHAIN, SKELETAL MUSCLE (FRAGMENT) | 823–907 133–160 | 946–987 193–280 846–873 | 1049–1076 304–349 | 423–460 | 468–526 | 581–608 | 645–681 | 743–798 | 808–835 |
| PMYT1_HUMAN | MYELIN TRANSCRIPTION FACTOR 1 (MYTI) (FRAGMENT) | 640–678 | | 705–735 | | | | | | |
| PNACA_HUMAN | SODIUM/CALCIUM EXCHANGER PRECURSOR (NA+/CA2+ EXCHANGE PROTEIN) | 492–519 | 594–621 | | | | | | | |
| PNCA2_HUMAN | NEURAL CELL ADHESION MOLECULE, PHOSPHATIDYLINOSITOL-LINKED ISOFORM | 255–282 | | | | | | | | |
| PNCF1_HUMAN | NEUTROPHIL CYTOSOL FACTOR 1 (NCF-47K) (47 KD AUTOSOMAL CHRONIC | 234–261 | 310–337 | | | | | | | |
| PNCF2_HUMAN | NEUTROPHIL NADPH OXIDASE FACTOR (P67-PHOX) | 5–32 | | | | | | | | |
| PNEFA_HUMAN | DNA-BINDING PROTEIN NEFA PRECURSOR | 50–77 | 82–112 | 343–395 | | | | | | |
| PNEP_HUMAN | NEPRILYSIN (EC 3.4.24.11) (NEUTRAL ENDOPEPTIDASE) (NEP) | 170–216 | 644–671 | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PNFL_HUMAN | NEUROFIBROMIN (NEUROFIBROMATOSIS-RELATED PROTEIN NF-1) (FRAGMENT) | 1145–1172 | 1388–1422 | 1639–1666 | | | | | | |
| PNFH_HUMAN | NEUROFILAMENT TRIPLET H PROTEIN (200 KD NEUROFILAMENT PROTEIN) (NF-H) | 91–128 | 431–490 | | | | | | | |
| PNFL_HUMAN | NEUROFILAMENT TRIPLET L PROTEIN (68 KD NEUROFILAMENT PROTEIN) (NF-L) | 92–126 | 441–468 | | | | | | | |
| PNFM_HUMAN | NEUROFILAMENT TRIPLET M PROTEIN (160 KD NEUROFILAMENT PROTEIN) (NF-M) | 101–141 | 164–194 | 215–280 | 315–372 | 737–764 | 794–826 | 872–913 | | |
| PNK1R_HUMAN | SUBSTANCE-P RECEPTOR (SPR) (NK-1 RECEPTOR) (NK-1R) | 338–365 | | | | | | | | |
| PNK4_HUMAN | NATURAL KILLER CELLS PROTEIN 4 PRECURSOR | 166–193 | | | | | | | | |
| PNKCR_HUMAN | NK-TUMOR RECOGNITION PROTEIN (NATURAL-KILLER CELLS CYCLOPHILIN- | 187–214 | 448–475 | 559–599 | 701–742 | 816–843 | 1080–1133 | | | |
| PNKGA_HUMAN | NKG2-A AND NKG2-B TYPE II INTEGRAL MEMBRANE PROTEINS | 28–55 | | | | | | | | |
| PNOSL_HUMAN | NITRIC-OXIDE SYNTHASE, BRAIN (EC 1.14.13.39) (NOS, TYPE I) | 389–416 | 1116–1146 | 1292–1319 | | | | | | |
| PNOS3_HUMAN | NITRIC-OXIDE SYNTHASE, ENDOTHELIAL (EC 1.14.13.39) (EC-NOS) (NOS, | 389–416 | | | | | | | | |
| PNTGL_HUMAN | SODIUM- AND CHLORIDE-DEPENDENT GABA TRANSPORTER 1 | 131–158 | | | | | | | | |
| PNTR_HUMAN | NEUROTENSIN RECEPTOR (NT-R) | 57–84 | | | | | | | | |
| PNTSE_HUMAN | SODIUM DEPENDENT SEROTONIN TRANSPORTER (5HT TRANSPORTER) (5HTT) | 71–98 | | | | | | | | |
| PNTTA_HUMAN | SODIUM- AND CHLORIDE-DEPENDENT TAURINE TRANSPORTER | 120–147 | | | | | | | | |
| PNU2M_HUMAN | NADH-UBIQUINONE OXIDOREDUCTASE CHAIN 2 (EC 1.6.5.3) | 202–240 | 372–399 | | | | | | | |
| PNU4M_HUMAN | NADH-UBIQUINONE OXIDOREDUCTASE CHAIN 4 (EC 1.6.5.3) | 164–191 | 360–387 | | | | | | | |
| PNUBN_HUMAN | NUCLEOBINDIN PRECURSOR | 46–73 | | | | | | | | |
| PNUCL_HUMAN | NUCLEOLIN (PROTEIN C23) | 462–508 | | | | | | | | |
| PNY3R_HUMAN | PUTATIVE NEUROPEPTIDE Y RECEPTOR TYPE 3 (PNY3-R) (FB22) (NPYRL) | 115–142 | | | | | | | | |
| POAT_HUMAN | ORNITHINE AMINOTRANSFERASE PRECURSOR (EC 2.6.1.13) (ORNITHINE-OXO- | 98–128 | | | | | | | | |
| POC3A_HUMAN | OCTAMER-BINDING TRANSCRIPTION FACTOR 3A (OCT-3A) | 139–173 | | | | | | | | |
| POC3B_HUMAN | OCTAMER-BINDING TRANSCRIPTION FACTOR 3B (OCT-3B) | 37–78 | | | | | | | | |
| POCRL_HUMAN | LOWE'S OCULOCEREBRORENAL SYNDROME PROTEIN | 704–735 | | | | | | | | |
| PODB2_HUMAN | LIPOAMIDE ACYLTRANSFERASE COMPONENT (E2) PRECURSOR OF BRANCHED-CHAI | 100–127 | 375–402 | | | | | | | |
| PODP2_HUMAN | DIHYDROLIPOAMIDE ACETYLTRANSFERASE COMPONENT (E2) OF PYRUVATE | 72–99 | | | | | | | | |
| POMGP_HUMAN | OLIODENDROCYTE-MYELIN GLYCOPROTEIN PRECURSOR (OMG) | 53–80 | | | | | | | | |
| POPSB_HUMAN | BLUE-SENSITIVE OPSIN (BLUE CONE PHOTORECEPTOR PIGMENT) | 220–247 | | | | | | | | |
| POPSG_HUMAN | GREEN-SENSITIVE OPSIN (GREEN CONE PHOTORECEPTOR PIGMENT) | 90–117 | 239–266 | | | | | | | |
| POPSR_HUMAN | RED-SENSITIVE OPSIN (RED CONE PHOTORECEPTOR PIGMENT) | 90–117 | 239–266 | | | | | | | |
| POSTP_HUMAN | OSTEOPONTIN PRECURSOR (BONE SIALOPROTEIN 1) (URINARY STONE PROTEIN) | 239–266 | | | | | | | | |

TABLE IX-continued

107 × 178 × 4 Motif Search on All Human Protein Sequences / 107 × 174 × 4 SEARCH MOTIF RESULTS SUMMARY FOR ALL HUMAN PROTEINS

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| POTC_HUMAN | ORNITHINE CARBAMOYLTRANSFERASE PERCURSOR (EC 2.1.3.3) | 170–204 | | | | | | | | |
| POTNC_HUMAN | OSTEONECTIN PRECURSOR (BASEMENT MEMBRANE PROTEIN BM-40) | 173–207 | | | | | | | | |
| POXYB_HUMAN | OXYSTEROL-BINDING PROTEIN | 89–123 | 190–217 | 290–317 | 577–604 | | | | | |
| POXYR_HUMAN | OXYTOCIN RECEPTOR (OT-R) | 350–377 | 422–449 | | | | | | | |
| PP107_HUMAN | RETINOBLASTOMA-ASSOCIATED PROTEIN-LIKE 107 KD HOMOLOG (P107) | 159–186 | | | | | | | | |
| PP1DP_HUMAN | DNA POLYMERASE ALPHA HOLOENZYME-ASSOCIATED PROTEIN P1 | 19–60 | 637–664 | | | | | | | |
| PP47_HUMAN | PLECKSTRIN (P47) | 298–325 | | | | | | | | |
| PP4HA_HUMAN | PROLYL 4-HYDROXYLASE ALPHA SUBUNIT PRECURSOR (EC 1.14.11.2) | 26–69 | 191–218 | | | | | | | |
| PP60_HUMAN | MITOCHONDRIAL MATRIX PROTEIN P1 PRECURSOR (P60 LYMPHOCYTE PROTEIN) | 72–99 | 271–298 | 361–407 | | | | | | |
| PP85A_HUMAN | PHOSPHATIDYLINOSITOL 3-KINASE REGULATORY ALPHA SUBUNIT (P13-KINASE | 12–39 | 428–476 | 586–613 | 688–715 | | | | | |
| PPAP1_HUMAN | PANCREATITIS ASSOCIATED PROTEIN 1 PRECURSOR | 77–104 | | | | | | | | |
| PPAX5_HUMAN | PAIRED BOX PROTEIN PAX-5 (B-CELL SPECIFIC TRANSCRIPTION FACTOR) | 157–187 | | | | | | | | |
| PPDGA_HUMAN | PLATELET-DERIVED GROWTH FACTOR, A CHAIN PRECURSOR (PDGF A-CHAIN) | 38–65 | | | | | | | | |
| PPEC1_HUMAN | PLATELET ENDOTHELIAL CELL ADHESION MOLECULE PRECURSOR (PECAM-1) | 685–719 | | | | | | | | |
| PPENK_HUMAN | PROENKEPHALIN A PRECURSOR | 142–176 | | | | | | | | |
| PPERE_HUMAN | EOSINOPHIL PEROXIDASE PRECURSOR (EC 1.11.1.7) (EPO) (FRAGMENT) | 308–335 | | | | | | | | |
| PPERF_HUMAN | PERFORIN 1 PRECURSOR (P1) (LYMPHOCYTE PORE FORMING PROTEIN) (PFP) | 411–438 | | | | | | | | |
| PPF4L_HUMAN | PLATELET BASIC PROTEIN PRECURSOR (PBP) (CONTAINS: CONNECTIVE-TISSUE | 21–55 | | | | | | | | |
| PPGCA_HUMAN | CARTILAGE-SPECIFIC PROTEOGLYCAN CORE PROTEIN PRECURSOR (CSPCP) | 73–100 | | | | | | | | |
| PPGCS_HUMAN | LARGE FIBROBLAST PROTEOGLYCAN PRECURSOR (VERSICAN) (CHONDROITIN) | 64–98 | 1390–1417 | 1553–1580 | | | | | | |
| PPGDH_HUMAN | 15-HYDROXYPROSTAGLANDIN DEHYDROGENASE (NAD(+)) (EC 1.1.1.141) (PGDH) | 87–118 | | | | | | | | |
| PPGDR_HUMAN | BETA PLATELET-DERIVED GROWTH FACTOR RECEPTOR PRECURSOR (EC 2.7.1.112) | 294–321 | 354–384 | 465–495 | | | | | | |
| PPGDS_HUMAN | ALPHA PLATELET-DERIVED GROWTH FACTOR RECEPTOR PRECURSOR | 64–94 | 347–395 | 461–488 | 524–551 | 986–1058 | | | | |
| PPGHS_HUMAN | PROSTAGLANDIN G/H SYNTHASE PRECURSOR (EC 1.14.99.1) (CYCLOOXYGENSE) | 331–358 | | | | | | | | |
| PPGS1_HUMAN | BONE/CARTILAGE PROTEOGLYCAN I PRECURSOR (BIGLYCAN) (PG-S1) | 100–127 | | | | | | | | |
| PPH4H_HUMAN | PHENYLALANINE-4-HYDROXYLASE (EC 1.14.16.1) (PAH) (PHE-4- | 239–266 | | | | | | | | |
| PPHB_HUMAN | PROHIBITIN | 41–68 | | | | | | | | |

TABLE IX-continued

107 × 178 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PHOS_HUMAN | PHOSDUCIN (33 KD PHOTOTRANSDUCING PROTEIN) (MEKA PROTEIN) | 184–225 | | | | | | | | |
| PPHS1_HUMAN | GLYCOGEN PHOSPHORYLASE, LIVER FORM (EC 2.4.1.1) | 116–143 | | | | | | | | |
| PPHS2_HUMAN | GLYCOGEN PHOSPHORYLASE, MUSCLE FORM (EC 2.4.1.1) | 532–559 | | | | | | | | |
| PPHS3_HUMAN | GLYCOGEN PHOSPHORYLASE, BRAIN FORM (EC 2.4.1.1) | 533–560 | | | | | | | | |
| PPIP4_HUMAN | 1-PHOSPHATIDYLINOSITOR-4,5-BISPHOSPHATE PHOSPHODIESTERASE BETA 2 | 908–935 | | | | | | | | |
| PPIP5_HUMAN | 1-PHOSPHATIDYLINOSITOR-4,5-BISPHOSPHATE PHOSPHODIESTERASE GAMMA 2 | 142–169 | 239–266 | | | | | | | |
| PPLAK_HUMAN | PLAKOGLOBIN (DESMOPLAKIN III) | 373–400 | | | | | | | | |
| PPLSL_HUMAN | L-PLASTIN (FIMBRIN) | 507–534 | | | | | | | | |
| PPLST_HUMAN | T-PLASTIN (FIMBRIN) | 510–561 | | | | | | | | |
| PPM22_HUMAN | PHERIPHERAL MYELIN PROTEIN 22 (PMP-22) | 3–33 | | | | | | | | |
| PPMGB_HUMAN | PHOSPHOGLYCERATE MUTASE, BRAIN FORM (EC 5.4.2.1) (PGAM-B) (EC 5.4.2.4) | 81–111 | | | | | | | | |
| PPMGM_HUMAN | PHOSPHOGLYCERATE MUTASE, MUSCLE FORM (EC 5.4.2.1) (PGAM-M) | 81–115 | | | | | | | | |
| PPML1_HUMAN | PROBABLE TRANSCRIPTION FACTOR PML-1 | 551–585 | | | | | | | | |
| PPMLX_HUMAN | PROBABLE TRANSCRIPTION FACTOR PML-X | 551–585 | | | | | | | | |
| PPMSC_HUMAN | AUTOANTIGEN PM-SCL | 103–130 | | | | | | | | |
| PPOGA_HUMAN | DNA-BINDING PROTEIN PO-GA | 14–51 | 182–209 | 610–637 | 667–699 | | | | | |
| PPOL1_HUMAN | RETROVIRUS-RELATED POL POLYPROTEIN (REVERSE TRANSCRIPTASE | 774–804 | | | | | | | | |
| PPOL2_HUMAN | RETROVIRUS-RELATED POL POLYPROTEIN (FRAGMENT) | 78–138 | 171–205 | | | | | | | |
| PPOR1_HUMAN | OUTER MITOCHONDRIAL MEMBRANE PROTEIN PORIN (VOLTAGE-DEPENDENT ANIO | 33–76 | 189–216 | | | | | | | |
| PPPAP_HUMAN | PROSTATIC ACID PHOSPHATASE PRECURSOR (EC 3.1.3.2) | 235–269 | | | | | | | | |
| PPPAS_HUMAN | RED CELL ACID PHOPHATASE 1, ISOZYME S (EC 3.1.3.2) (ACP1) | 26–53 | | | | | | | | |
| PPPOL_HUMAN | NAD(+) ADP-RIBOSYLTRANSFERASE (EC 2.4.2.30) (POLY(ADP-RIBOSE) | 699–729 | 972–1003 | | | | | | | |
| PPRC2_HUMAN | PROTEASOME COMPONENT C2 (EC 3.4.99.46) (MACROPAIN SUBUNIT C2) | 39–66 | | | | | | | | |
| PPRC3_HUMAN | PROTEASOME COMPONENT C3 (EC 3.4.99.46) (MACROPAIN SUBUNIT C3) | 34–61 | | | | | | | | |
| PPRC9_HUMAN | PROTEASOME COMPONENT C9 (EC 3.4.99.46) (MACROPAIN SUBUNIT C9) | 203–261 | | | | | | | | |
| PPRGR_HUMAN | PROGESTERONE RECEPTOR (PR) (FORMS A AND B) | 846–890 | | | | | | | | |
| PPRTS_HUMAN | VITAMIN K-DEPENDENT PROTEIN S (BLOOD CLOTTING) PRECURSOR | 337–371 | | | | | | | | |
| PPRTZ_HUMAN | VITAMIN K-DEPENDENT PROTEIN Z PRECURSOR | 29–56 | | | | | | | | |
| PPSOR_HUMAN | PSORIASIN | 65–92 | | | | | | | | |
| PPSPD_HUMAN | PULMONARY SURFACTANT-ASSOCIATED PROTEIN D PRECURSOR (PSP-D) (SP-D) | 224–251 | | | | | | | | |
| PPTHY_HUMAN | PARATHYROID HORMONE PRECURSOR (PARATHYRIN) | 86–113 | | | | | | | | |
| PPTN1_HUMAN | PROTEIN-TYROSINE PHOSPHATASE 1B (EC 3.1.3.48) (PTP-1B) | 136–177 | | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PTN2_HUMAN | T-CELL PROTEIN-TYROSINE PHOSPHATASE (EC 3.1.3.48) (TCPTP) | 59–86 | 138–178 | | | | | | | |
| PPTN6_HUMAN | PROTEIN-TYROSINE PHOSPHATASE 1C (EC 3.1.3.48) (PTP-1C) (HEMATOPOIETIC | 227–261 | 512–580 | | | | | | | |
| PPTNB_HUMAN | PROTEIN-TYROSINE PHOSPHATASE 2C (EC 3.1.3.48) (PTP-2C) (PTP-1D) | 41–68 | 218–245 | | | | | | | |
| PPTNC_HUMAN | PROTEIN-TYROSINE PHOSPHATASE G1 (EC 3.1.3.48) (PTPG1) | 618–645 | 695–722 | | | | | | | |
| PPTRR_HUMAN | PARATHYROID HORMONE/PARATHYROID HORMONE-RELATED PEPTIDE | 368–395 | | | | | | | | |
| PPTX3_HUMAN | PENTAXIN-RELATED PROTEIN PTX3 PRECURSOR | 74–101 | | | | | | | | |
| PPUR2_HUMAN | PHOSPHORIBOSYLAMINE-GLYCINE LIGASE (EC 6.3.4.13) (GARS) (GLYCINAMIDE | 803–830 | | | | | | | | |
| PPUR6_HUMAN | MULTIFUNCTIONAL PROTEIN ADE2H1 (PHOSPHORIBOSYLAMINOIMIDAZOLE- | 391–418 | | | | | | | | |
| PPUR8_HUMAN | ADENYLOSUCCINATE LYASE (EC 4.3.2.2) (ADENYLOSUCCINASE) (ASL) | 204–231 | | | | | | | | |
| PPYR5_HUMAN | URIDINE 5'-MONOPHOSPHATE SYNTHASE (UMP SYNTHASE (UMP SYNTHASE) (OROTATE | 120–150 | | | | | | | | |
| PPYRG_HUMAN | CTP SYNTHASE (EC 6.3.4.2) (UTP-AMMONIA LIGASE) (CTP SYNTHETASE) | 86–113 | 300–334 | | | | | | | |
| PPZP_HUMAN | PREGNANCY ZONE PROTEIN PRECURSOR | 315–354 | 990–1024 | 1162–1189 | | | | | | |
| PRA74_HUMAN | TRANSCRIPTION FACTOR IIF, ALPHA SUBUNIT (TFIIF, ALPHA SUBUNIT) | 474–501 | | | 1405–1432 | | | | | |
| PRAB4_HUMAN | RAS-RELATED PROTEIN RAB-4 | 38–65 | | | | | | | | |
| PRAB6_HUMAN | RAS-RELATED PROTEIN RAB-6 | 123–150 | | | | | | | | |
| PRADI_HUMAN | RADIXIN | 308–335 | 414–463 | 510–537 | | | | | | |
| PRB11_HUMAN | RAS-RELATED PROTEIN RAB-11 (24KG) (YL-8) | 151–178 | | | | | | | | |
| PRBB3_HUMAN | RETINOBLASTOMA BINDING PROTEIN 3 (RBBP-3) (PRB-BINDING PROTEIN E2F-1) | 129–156 | 161–223 | | | | | | | |
| PRDP_HUMAN | RD PROTEIN | 9–53 | | | | | | | | |
| PRENL_HUMAN | RENIN PRECURSOR, RENAL (EC 3.4.23.15) (ANGIOTENSINOGENASE) | 136–163 | | | | | | | | |
| PREST_HUMAN | RESTIN (CYTOPLASMIC LINKER PROTEIN-170 ALPHA-2) (CLIP-170) | 190–217 1216–1306 | 333–370 | 445–472 | 571–619 | 744–771 | 784–852 | 1023–1050 | 1088–1139 | 1157–1184 |
| PRFA1_HUMAN | REPLICATION PROTEIN A 70 KD DNA-BINDING SUBUNIT (RP-1) (RF-A) | 208–235 | 425–455 | | | | | | | |
| PRFP_HUMAN | TRANSFORMING PROTEIN (RFP) (RET FINGER PROTEIN) | 183–217 | | | | | | | | |
| PRH_HUMAN | BLOOD GROUP RH(D) POLYPEPTIDE | 361–388 | | | | | | | | |
| PRIB1_HUMAN | RIBOPHORIN I PRECURSOR | 81–108 | 496–530 | | | | | | | |
| PRIB1_HUMAN | RIBOPHORIN II PRECURSOR | 142–172 | 361–388 | | | | | | | |
| PRIR1_HUMAN | RIBONUCLEOSIDE-DIPHOSPHATE REDUCTASE M1 CHAIN (EC 1.17.4.1) | 42–69 | 370–400 | | | | | | | |
| PRL22_HUMAN | 60S RIBOSOMAL PROTEIN L22 (EPSTEIN-BARR VIRUS SMALL RNA ASSOCIATED | 78–112 | | | | | | | | |
| PRL26_HUMAN | 60S RIBOSOMAL PROTEIN L26 | 55–89 | 103–137 | | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PRL9_HUMAN | 60S ROBOSOMAL PROTEIN L9 | 146–192 | | | | | | | | |
| PRLA0_HUMAN | 60S ACIDIC ROBOSOMAL PROTEIN P0 (L10E) | 138–165 | | | | | | | | |
| PRO5_HUMAN | 52 KD RO PROTEIN (SJOREN SYNDROME TYPE A ANTIGEN (SS-A)) | 190–235 | 238–265 | | | | | | | |
| PRO6_HUMAN | 60 KD RO PROTEIN (SJOREN SYNDROME TYPE A ANTIGEN (SS-A)) | 192–245 | | | | | | | | |
| PROC_HUMAN | HETEROGENEOUS NUCLEAR RIBONUCLEOPROTEINS C1/C2 (HNRNP C1 AND HNPNP | 16–43 | | | | | | | | |
| PROL_HUMAN | HETEROGENEOUS RIBONUCLEOPROTEIN L (HRNPL) | 501–528 | | | | | | | | |
| PROU_HUMAN | HETEROGENEOUS RIBONUCLEOPROTEIN U | 630–657 | | | | | | | | |
| PRPB1_HUMAN | DNA-DIRECTED RNA POLYMERASE II 215 KD POLYPEPTIDE | 269–296 | 665–720 | 879–906 | 1314–1341 | 1371–1398 | | | | |
| PRPB2_HUMAN | DNA-DIRECTED RNA POLYMERASE II 140 KD POLYPEPTIDE | 626–667 | 1008–1035 | | | | | | | |
| PRPB3_HUMAN | DNA-DIRECTED RNA POLYMERASE II 33 KD POLYPEPTIDE | 242–274 | | | | | | | | |
| PRRXA_HUMAN | RETINOIC ACID RECEPTOR RXR-ALPHA | 318–352 | | | | | | | | |
| PRRXB_HUMAN | RETINOIC ACID RECEPTOR RXR-BETA ISOFORM 1 | 376–403 | | | | | | | | |
| PRRXC_HUMAN | RETINOIC ACID RECEPTOR RXR-BETA ISOFORM 2 | 396–423 | | | | | | | | |
| PRS12_HUMAN | 40S RIBOSOMAL PROTEIN S12 | 60–87 | | | | | | | | |
| PRS16_HUMAN | 40S RIBOSOMAL PROTEIN S16 | 89–116 | | | | | | | | |
| PRS25_HUMAN | 40S RIBOSOMAL PROTEIN S25 | 26–53 | | | | | | | | |
| PRS27_HUMAN | 40S RIBOSOMAL PROTEIN S27A | 14–41 | | | | | | | | |
| PRS7_HUMAN | 40S RIBOSOMAL PROTEIN S7 (S8) | 73–100 | | | | | | | | |
| PRS8_HUMAN | 40S RIBOSOMAL PROTEIN S8 | 136–163 | | | | | | | | |
| PRTC1_HUMAN | RAS-LIKE PROTEIN TC21 | 123–150 | | | | | | | | |
| PRU1A_HUMAN | U1 SMALL NUCLEAR RIPONUCLEOPROTEIN A (U1 SNRNP A PROTEIN) | 13–47 | | | | | | | | |
| PRU2B_HUMAN | U2 SMALL NUCLEAR RIPONUCLEOPROTEIN B" | 17–44 | | | | | | | | |
| PRYNR_HUMAN | RYANODINE RECEPTOR, SKELETAL MUSCLE | 154–188 | 495–522 | 866–893 | 2750–2777 | 2820–2847 | 3304–3331 | 3529–3556 | 3912–3939 | 4921–4948 |
| PS10A_HUMAN | S-100 PROTEIN, ALPHA CHAIN | 12–54 | | | | | | | | |
| PS10B_HUMAN | S-100 PROTEIN, BETA CHAIN | 14–56 | | | | | | | | |
| PS10D_HUMAN | S-100D PROTEIN | 31–58 | | | | | | | | |
| PSAHH_HUMAN | ADENOSYLHOMOCYSTEINASE (EC 3.3.1.1) (S-ADENOSYL-L-HOMOCYSTEINE | 389–416 | | | | | | | | |
| PAST1_HUMAN | DNA-BINDING PROTEIN SATB1 | 709–736 | | | | | | | | |
| PSCCA_HUMAN | SQUAMOUS CELL CARCINOMA ANTIGEN (SCCA) (PROTEIN T4-A) | 78–105 | | | | | | | | |
| PSCF_HUMAN | STEM CELL FACTOR PRECURSOR (SCF) | 74–101 | | | | | | | | |
| PSEM1_HUMAN | SEMENOGELIN I PROTEIN PRECURSOR (SGI) (CONTAINS: SEMINAL BASIC | 64–98 | 176–226 | 228–329 | 334–368 | 405–439 | 539–575 | | | |
| PSEM2_HUMAN | SEMENOGELIN II PRECURSOR (SGII) | 71–98 | 183–226 | 304–355 | | | | | | |
| PSET_HUMAN | SET PROTEIN | 38–65 | 154–181 | | | | | | | |
| PSG1_HUMAN | SECRETOGRANIN I PRECURSOR (CHROMOGRANIN B) | 144–178 | | | | | | | | |
| PSG2_HUMAN | SECRETOGRANIN II PRECURSOR (CHROMOGRANIN C) | 254–281 | 290–317 | 534–561 | | | | | | |
| PSIAL_HUMAN | BONE SIALOPROTEIN II PRECURSOR (BSP II) | 84–113 | 155–193 | 256–283 | | | | | | |
| PSN2L_HUMAN | POSSIBLE GLOBAL TRANSCRIPTION ACTIVATOR SNF2L | 231–258 | 545–572 | | | | | | | |
| PSNOB_HUMAN | SK1-RELATED ONCOGENE SNON | 414–441 | | | | | | | | |
| PSPCA_HUMAN | SPECTRIN ALPHA CHAIN | 193–220 2346–2373 | 570–621 | 655–712 | 1099–1126 | 1461–1502 | 1882–1901 | 1988–2022 | 2120–2154 | 2223–2250 |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PSPCB_HUMAN | SPECTRIN BETA CHAIN, ERYTHROCYTE | 150–177 | 316–350 | 486–520 | 648–675 | 987–1021 | 1027–1083 | 1287–1324 | 1347–1374 | 1834–1861 |
| PSPRE_HUMAN | SEPIAPTERIN REDUCTASE (EC 1.1.1.153) (SPR) | 90–124 | | | | | | | | |
| PSRF_HUMAN | SERUM RESPONSE FACTOR (SRF) | 77–104 | 480–507 | | | | | | | |
| PSRPR_HUMAN | SIGNAL RECOGNITION PARTICLE RECEPTOR ALPHA SUBUNIT (SR-ALPHA) | 76–110 | | | | | | | | |
| PSSR1_HUMAN | SOMATOSTATIN RECEPTOR TYPE 1 | 289–316 | | | | | | | | |
| PSTHM_HUMAN | STATHMIN (PHOSPHOPROTEIN P19) (ONCOPROTEIN P18) (LEUKEMIA-ASSOCIATED | 47–74 | | | | | | | | |
| PSUIS_HUMAN | SUCRASE-ISOMALTASE, INTESTINAL (EC 3.2.1.48)/ (EC 3.2.1.10) | 1748–1775 | | | | | | | | |
| PSYB1_HUMAN | SYNAPTOBREVIN 1 | 31–67 | | | | | | | | |
| PSYD2_HUMAN | ASPARTYL-TRNA SYNTHETASE ALPHA-2 SUBUNIT (EC 6.1.1.12) (ASPARTATE- | 44–71 | | | | | | | | |
| PSYEP_HUMAN | MULTIFUNCTIONAL AMINOACYL-TRNA SYNTHETASE (CONTAINS: GLUTAMYL-TRN | 174–201 | 740–771 | | | | | | | |
| PSYH_HUMAN | HISTIDYL-TRAN SYNTHETASE (EC 6.1.1.21) (HISTIDINE-TRNA LIGASE) | 380–442 | 468–502 | | | | | | | |
| PSYT1_HUMAN | SYNAPTOTAGMIN 1 (P65) | 140–167 | 250–277 | | | | | | | |
| PSYTC_HUMAN | THREONYL-TRAN SYNTHETASE, CYTOPLASMIC (EC 6.1.1.3) (THREONINE-TRNA | 497–524 | 658–685 | | | | | | | |
| PSYV_HUMAN | VALYL-TRNA SYNTHETASE (EC 6.1.1.9) (VALINE-TRNA LIGASE) (VALRS) | 230–257 | 413–440 | | | | | | | |
| PSYW_HUMAN | TRYPTOPHANYL-TRNA SYNTHETASE (EC 6.1.1.2) (TRYPTOPHAN-TRNA LIGASE) | 93–127 | 196–223 | | | | | | | |
| PT2EB_HUMAN | TRANSCRIPTION INITIATION FACTOR IIE-BETA CHAIN (TFIIE-BETA) | 34–68 | | | | | | | | |
| PTAP4_HUMAN | TRANSCRIPTION FACTOR AP-4 (FRAGMENT) | 169–196 | 245–272 | | | | | | | |
| PTAPB_HUMAN | TRANSCRIPTION FACTOR JUN-B | 296–323 | | | | | | | | |
| PTAPD_HUMAN | TRANSCRIPTION FACTOR JUN-D | 291–333 | | | | | | | | |
| PTAU1_HUMAN | MICROTUBULE-ASSOCIATED PROTEIN TAU | 278–305 | | | | | | | | |
| PTAU2_HUMAN | MICROTUBULE-ASSOCIATED PROTEIN TAU, FETAL | 211–238 | | | | | | | | |
| PTCO1_HUMAN | TRANSCOBALAMIN I PRECURSOR | 201–241 | 330–357 | | | | | | | |
| PTCP1_HUMAN | T-COMPLEX PROTEIN 1 (TCP-1) | 316–343 | | | | | | | | |
| PTDT_HUMAN | DNA NUCLEOTIDYLEXOTRANSFERASE (EC 2.7.7.31) (TERMINAL ADDITION ENZYME) | 61–95 | | | | | | | | |
| PTEK_HUMAN | RECEPTOR TYROSINE-PROTEIN KINASE TEK PRECURSOR (EC 2.7.1.112) (HPK-6) | 644–678 | 969–996 | 1007–1036 | | | | | | |
| PTF2B_HUMAN | TRANSCRIPTION INITIATION FACTOR 11B (FT11B) | 135–162 | | | | | | | | |
| PTFE3_HUMAN | TRANSCRIPTION FACTOR E3 (FRAGMENT) | 43–70 | 122–149 | 178–226 | | | | | | |
| PTFS2_HUMAN | TRANSCRIPTION ELONGATION FACTOR S-II | 29–56 | | | | | | | | |
| PTF_HUMAN | TISSUE FACTOR PRECURSOR (TF) (COAGULATION FACTOR III) | 148–175 | | | | | | | | |
| PTGF1_HUMAN | TRANSFORMING GROWTH FACTOR BETA 1 PRECURSOR (TGF-BETA 1) | 148–185 | | | | | | | | |
| PTGF2_HUMAN | TRANSFORMING GROWTH FACTOR BETA 2 PRECURSOR (TGF-BETA 2) (GLIOBLASTO | 243–270 | | | | | | | | |
| PTGFA_HUMAN | TRANSFORMING GROWTH FACTOR ALPHA PRECURSOR (TGF-ALPHA) (EGF-LIKE TGR | 87–114 | | | | | | | | |

TABLE IX-continued

107 × 178 × 4 Motif Search on All Human Protein Sequences
107 × 174 × 4 SEARCH MOTIF RESULTS SUMMARY FOR ALL HUMAN PROTEINS

| PCGENE FILE NAME | PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PTGLK_HUMAN | PROTEIN-GLUTAMINE GAMMA-GLUTAMYLTRANSFERASE K (EC 2.3.2.13) | 258–285 | | | | | | | | |
| PTHBS_HUMAN | THROMBOSPONDIN PRECURSOR | 110–165 | 284–314 | | | | | | | |
| PTHIK_HUMAN | 3-KETOACYL-COA THIOLASE PEROXISOMAL PRECURSOR (EC 2.3.1.16) (BETA- | 185–212 | | | | | | | | |
| PTKNB_HUMAN | PROTACHYKININ BETA PRECURSOR (CONTAINS: SUBSTANCE P, NEUROKININ A | 11–38 | | | | | | | | |
| PTLE1_HUMAN | TRANSDUCIN-LIKE ENHANCER PROTEIN 1 | 626–653 | | | | | | | | |
| PTLE2_HUMAN | TRANSDUCIN-LIKE ENHANCER PROTEIN 2 | 94–125 | | | | | | | | |
| PTLE4_HUMAN | TRANSDUCIN-LIKE ENHANCER PROTEIN 4 (FRAGMENT) | 304–331 | | | | | | | | |
| PTOPA_HUMAN | DNA TOPOISOMERASE II, ALPHA ISOZYME (EC 5.99.1.3) | 19–46 | 503–532 | | | | | | | |
| PTOPB_HUMAN | DNA TOPOISOMERASE II, BETA ISOZYME (EC 5.99.1.3) | 35–65 | 616–647 | | | | | | | |
| PTPM3_HUMAN | TROPOMYOSIN, FIBROBLAST ISOFORM TM3 | 16–74 | 82–116 | | | | | | | |
| PTPMA_HUMAN | TROPOMYOSIN ALPHA CHAIN, SKELETAL MUSCLE | 16–43 | 47–74 | 82–116 | 147–174 | 191–237 | 243–277 | | | |
| PTPMB_HUMAN | TROPOMYOSIN BETA CHAIN, SKELETAL MUSCLE | 37–116 | 193–240 | 193–277 | | | | | | |
| PTPMC_HUMAN | TROPOMYOSIN ALPHA CHAIN, CARDIAC MUSCLE | 16–74 | 82–116 | 243–270 | | | | | | |
| PTPMF_HUMAN | TROPOMYOSIN, FIBROBLAST AND EPITHELIAL MUSCLE-TYPE (TM36) (TME1) | 37–116 | 210–240 | | | | | | | |
| PTPMG_HUMAN | TROPOMYOSIN, FIBROBLAST NON-MUSCLE TYPE (TM30PL) | 46–80 | 111–138 | 158–199 | 207–234 | | | | | |
| PTPM1_HUMAN | TROPOMYOSIN, CYTOSKELETAL TYPE (TM30NM) | 46–80 | 111–138 | 172–199 | | | | | | |
| PTPMS_HUMAN | TROPOMYOSIN ALPHA CHAIN, SMOOTH MUSCLE (FRAGMENT) | 25–59 | 147–178 | | | | | | | |
| PTPP2_HUMAN | TRIPEPTIDYL-PEPTIDASE II (EC 3.4.14.10) (TPP II) (TRIPEPTIDYL | 153–187 | 1004–1031 | 1160–1187 | | | | | | |
| PTPR_HUMAN | TPR ONCOGENE (FRAGMENT) | 82–147 | | | | | | | | |
| PTR36_HUMAN | TREB36 PROTEIN | 18–45 | 242–269 | | | | | | | |
| PTRFR_HUMAN | THYROTROPIN-RELEASING HORMONE RECEPTOR (TRH-R) (THYROLIBERIN | 349–383 | | | | | | | | |
| PTRIC_HUMAN | TROPONIN I, CARDIAC MUSCLE | 36–63 | | | | | | | | |
| PTRKA_HUMAN | HIGH AFFINITY NERVE GROWTH FACTOR RECEPTOR PRECURSOR (EC 2.7.1.112) | 66–93 | 117–148 | | | | | | | |
| PTRSR_HUMAN | TRANSFERRIN RECEPTOR PROTEIN (TR) (ANTIGEN CD71) (T9) | 188–215 | 366–393 | | | | | | | |
| PTSHR_HUMAN | THYROTROPIN RECEPTOR PRECURSOR (TSH-R) | 87–117 | 420–447 | | | | | | | |
| PTTK_HUMAN | PROTEIN KINASE TKK (EC 2.7.1.-) | 170–197 | 324–359 | 510–544 | 549–583 | | | | | |
| PTYK2_HUMAN | NON-RECEPTOR TYROSINE-PROTEIN KINASE TYK2 (EC 2.7.1.112) | 150–177 | | | | | | | | |
| PUBA1_HUMAN | UBIQUITIN-ACTIVATING ENZYME E1 (A1S9 PROTEIN) | 448–475 | | | | | | | | |
| PUBF1_HUMAN | NUCLEOLAR TRANSCRIPTION FACTOR 1 (UPSTREAM BINDING FACTOR 1) (UBF-1) | 227–254 | | | | | | | | |
| PUDP0_HUMAN | UDP-GLUCURONOSYLTRANSFERASE PRECURSOR MICROSOMAL (EC 2.4.1.17) | | | | | | | | | |
| PUFO_HUMAN | RECEPTOR TYROSINE-PROTEIN KINASE UFO PRECURSOR (EC 2.7.1.112) | 488–522 | | | | | | | | |
| PUSF1_HUMAN | UPSTREAM STIMULATORY FACTOR 1 | 251–295 | | | | | | | | |
| PVATC_HUMAN | VACULAR ATP SYNTHASE SUBUNIT C (EC 3.6.1.34) (V-ATPASE C SUBUNIT) | 47–74 | 117–147 | | | | | | | |
| PVIL1_HUMAN | VILLIN | 338–372 | 427–461 | 717–744 | | | | | | |

TABLE IX-continued

107 × 174 × 4 SEARCH MOTIF RESULTS SUMMARY FOR ALL HUMAN PROTEINS

| PCGENE FILE NAME | 107 × 178 × 4 Motif Search on All Human Protein Sequences PROTEIN | AREA 1 | AREA 2 | AREA 3 | AREA 4 | AREA 5 | AREA 6 | AREA 7 | AREA 8 | AREA 9 |
|---|---|---|---|---|---|---|---|---|---|---|
| PVIME_HUMAN | VIMENTIN | 119–146 | 233–260 | | | | | | | |
| PVINC_HUMAN | VINCULIN | 108–135 | | | | | | | | |
| PVPRT_HUMAN | RETROVIRUS-RELATED PROTEASE (EC 3.4.23.-) | 95–134 | | | | | | | | |
| PWEE1_HUMAN | WEE1-LIKE PROTEIN KINASE (EC 2.7.1.112) | 354–388 | | | | | | | | |
| PWT1_HUMAN | WILMS' TUMOR PROTEIN (WT33) | 247–274 | | | | | | | | |
| PXBP1_HUMAN | X BOX BINDING PROTEIN-1 (XBP-1) (TREB5 PROTEIN) | 97–135 | | | | | | | | |
| PXPAC_HUMAN | DNA-REPAIR PROTEIN COMPLEMENTING XP-A CELLS (XERODERMA PIGMENTOSUM | 180–211 | | | | | | | | |
| PXPCC_HUMAN | DNA-REPAIR PROTEIN COMPLEMENTING XP-C CELLS (XERODERMA PIGMENTOSUM | 134–168 | 701–728 | | | | | | | |
| PXPDC_HUMAN | DNA-REPAIR PROTEIN COMPLEMENTING XP-D CELLS (XERODERMA PIGMENTOSUM | 264–291 | | | | | | | | |
| PXPGC_HUMAN | DNA-REPAIR PROTEIN COMPLEMENTING XP-G CELLS (XERODERMA PIGMENTOSUM | 83–110 | 715–766 | 1047–1081 | | | | | | |
| PXRCC_HUMAN | DNA-REPAIR PROTEIN XRCC1 | 23–57 | | | | | | | | |
| PZN10_HUMAN | ZINC FINGER PROTEIN 10 (ZINC FINGER PROTEIN KOX1) (FRAGMENT) | 29–56 | | | | | | | | |
| PZN40_HUMAN | ZINC FINGER PROTEIN 40 (HUMAN IMMUNODEFICIENCY VIRUS TYPE I ENHANCER- | 17–62 | 307–334 | 1071–1098 | 1469–1500 | 2013–2057 | 2146–2180 | | | |
| PZN45_HUMAN | ZINC FINGER PROTEIN 45 (BRC1744) (FRAGMENT) | 3–30 | 201–228 | | | | | | | |
| PZN46_HUMAN | ZINC FINGER PROTEIN 46 (ZINC FINGER PROTEIN KUP) | 121–149 | | | | | | | | |

TABLE X

Search Results Summary for PCTLZIP, P1CTLZIP, and P2CTLZIP Motifs

| PCTLZIP LIBRARY FILE | | P1CTLZIP LIBRARY FILE | | P2CTLZIP LIBRARY FILE | |
|---|---|---|---|---|---|
| PENV_FOAMV | 481–496 | PENV_BIVO6 | 434–450 | PENV_BIVO6 | 525–542 |
| PENV_HV1MA | 438–453 | PENV_BIV27 | 463–479 | PENV_BIV27 | 554–571 |
| PENV_HV1MF | 183–198 | PENV_FOAMV | 481–496 | PENV_FENV1 | 30–47 |
| PENV_HV1RH | 445–460 | PENV_HV1KB | 752–768 | PENV_FIVPE | 781–798 |
| PENV_HV1SC | 186–201 | PENV_HV1MA | 437–453 | PENV_FIVSD | 779–796 |
| PENV_HV1Z2 | 123–138 | PENV_HV1MF | 183–198 | PENV_FIVT2 | 780–797 |
| PENV_HV1ZH | 438–453 | PENV_HV1RH | 444–460 | PENV_FLVC6 | 38–55 |
| PENV_HV2BE | 750–765 | PENV_HV1S1 | 738–754 | PENV_FLVGL | 605–622 |
| PENV_HV2D1 | 741–756 | PENV_HV1SC | 186–201 | PENV_FLVLB | 625–642 |
| PENV_HV2G1 | 741–756 | PENV_HV1Z2 | 123–138 | PENV_FLVSA | 602–619 |
| PENV_HV2NZ | 742–757 | PENV_HV1Z3 | 117–133 | PENV_FOAMV | 710–727 |
| PENV_HV2RO | 751–766 | PENV_HV1ZH | 437–453 | PENV_FSVGA | 625–642 |
| PENV_HV2SB | 743–758 | PENV_HV2BE | 750–765 | PENV_FSVGB | 605–622 |
| PENV_HV2ST | 745–760 | PENV_HV2D1 | 741–756 | PENV_FSVSM | 608–625 |
| PENV_JSRV | 104–119 | PENV_HV2G1 | 741–756 | PENV_HV1OY | 123–140 |
| PENV_MMTVB | 618–633 | PENV_HV2NZ | 742–757 | PENV_HV1Z2 | 410–427 |
| PENV_MMTVG | 618–633 | PENV_HV2RO | 751–766 | PENV_HV1Z3 | 154–171 |
| PENV_SIVMK | 139–154 | PENV_HV2SB | 743–758 | PENV_HV2CA | 750–767 |
| PENV_SIVML | 139–154 | PENV_HV2ST | 745–760 | PENV_MCFF | 600–617 |
| PHEMA_CVBLY | 391–406 | PENV_JSRV | 104–119 | 541–557 | PENV_MCFF3 | 601–618 |
| PHEMA_CVBM | 391–406 | PENV_MCFF | 397–413 | PENV_MLVAV | 630–647 | 630–647 |
| PHEMA_CVBQ | 391–406 | PENV_MCFF3 | 397–413 | PENV_MLVCB | 625–642 |
| PHEMA_CVHOC | 391–406 | PENV_MLVAV | 427–443 | PENV_MLVF5 | 639–656 |
| PHEMA_CVMA5 | 402–417 | PENV_MLVCB | 422–438 | PENV_MLVFF | 639–656 |
| PHEMA_CVMS | 403–418 | PENV_MLVHO | 423–439 | PENV_MLVFP | 639–656 |
| PHEMA_INBAA | 295–310 | PENV_MLVMO | 426–442 | PENV_MLVHO | 626–643 |
| PHEMA_INBBE | 303–318 | PENV_MLVRD | 424–440 | PENV_MLVKI | 167–184 |
| PHEMA_INBBO | 293–308 | PENV_MLVRK | 424–440 | PENV_MLVMO | 629–646 |
| PHEMA_INBEN | 301–316 | PENV_MMTVB | 618–633 | PENV_MLVRD | 624–641 | 624–641 |
| PHEMA_INBFU | 286–301 | PENV_MMTVG | 618–633 | PENV_MLVRK | 624–641 |
| PHEMA_INBGL | 296–311 | PENV_SFV1 | 864–880 | PENV_MSVFB | 170–187 |
| PHEMA_INBHK | 293–308 | PENV_SFV3L | 861–877 | PENV_RMCFV | 603–620 |
| PHEMA_INBIB | 288–303 | PENV_SFV3L | 93–109 | PENV_SFV1 | 710–727 | 957–974 |
| PHEMA_INBID | 299–314 | PENV_SIVGB | 139–154 | PENV_SFV3L | 707–724 | 954–971 |
| PHEMA_INBLE | 302–317 | PENV_SIVMK | 139–154 | PENV_SIVMI | 766–783 |
| PHEMA_INBMD | 292–307 | PENV_SIVML | 806–822 | 802–818 | PENV_SIVMK | 765–782 |
| PHEMA_INBME | 296–311 | PENV_SIVS4 | 810–826 | 801–817 | PENV_SIVML | 764–781 |
| PHEMA_INBNA | 288–303 | PENV_SIVSP | 36–52 | PENV_SIVS4 | 769–786 |
| PHEMA_INBOR | 301–316 | PHEMA_CDVO | 391–406 | PENV_SIVSP | 773–790 |
| PHEMA_INBSI | 301–316 | PHEMA_CVBLY | 391–406 | PENV_SMRVH | 536–553 |
| PHEMA_INBSJ | 296–313 | PHEMA_CVBM | 391–406 | PENV_SMSAV | 42–59 |
| PHEMA_INBUS | 294–309 | PHEMA_CVBQ | 391–406 | PHEMA_CDVO | 36–53 | 200–217 |
| PHEMA_INBV1 | 296–311 | PHEMA_CVHOC | 402–417 | PHEMA_CVBLY | 391–408 |
| PHEMA_INBVK | 303–318 | PHEMA_CVMA5 | 403–418 | PHEMA_CVBM | 391–408 |
| PHEMA_INBYB | 286–301 | PHEMA_CVMS | 237–253 | PHEMA_CVBQ | 391–408 |
| PHEMA_MUMPM | 133–148 | PHEMA_IAAIC | 221–237 | PHEMA_CVHOC | 391–408 |
| | | PHEMA_IABAN | | | |

TABLE X-continued

Search Results Summary for PCTLZIP, P1CTLZIP, and P2CTLZIP Motifs

| PCTLZIP LIBRARY FILE | | | P1CTLZIP LIBRARY FILE | | P2CTLZIP LIBRARY FILE | |
|---|---|---|---|---|---|---|
| PHEMA__MUMPR | 133–148 | | PHEMA__IABUD | 234–250 | PHEMA__IAAIC | 322–339 |
| PHEMA__MUMPS | 133–148 | | PHEMA__IACKA | 234–250 | PHEMA__IABAN | 306–323 |
| PHEMA__PI1HW | 345–360 | | PHEMA__IACKG | 231–247 | PHEMA__IABUD | 320–337 |
| PHEMA__PI2H | 65–80 | | PHEMA__IACKV | 230–246 | PHEMA__IACKA | 320–337 |
| PHEMA__PI2HT | 65–80 | | PHEMA__IADA1 | 234–250 | PHEMA__IACKG | 316–333 |
| PHEMA__RINDK | 368–383 | | PHEMA__IADA3 | 237–253 | PHEMA__IACKP | 302–319 |
| PHEMA__SV5 | 7–94 | | PHEMA__IADCZ | 234–250 | PHEMA__IACKQ | 302–319 |
| PHEMA__SV5CM | 7–94 | | PHEMA__IADH1 | 221–237 | PHEMA__IACKS | 319–336 |
| PHEMA__SV5CP | 7–94 | | PHEMA__IADH2 | 221–237 | PHEMA__IACKV | 315–332 |
| PHEMA__SV5LN | 7–94 | | PHEMA__IADH3 | 221–237 | PHEMA__IADA1 | 320–337 |
| PVENV__DHVI1 | 42–57 | | PHEMA__IADH4 | 221–237 | PHEMA__IADA3 | 322–339 |
| PVFP7__CAPVK | 89–104 | | PHEMA__IADH5 | 221–237 | PHEMA__IADCZ | 320–337 |
| PVFUS__VACC6 | 72–87 | | PHEMA__IADH6 | 221–237 | PHEMA__IADH1 | 306–323 |
| PVGO1__BPP22 | 242–257 | | PHEMA__IADH7 | 221–237 | PHEMA__IADH2 | 306–323 |
| PVGO1__HSVEB | 169–184 | | PHEMA__IADM2 | 237–253 | PHEMA__IADH3 | 306–323 |
| PVGO1__HSVI1 | 210–225 | 317–332 | PHEMA__IADNZ | 234–250 | PHEMA__IADH4 | 306–323 |
| PVGO6__BPT4 | 184–199 | | PHEMA__IAEN6 | 221–237 | PHEMA__IADH6 | 306–323 |
| PVGO7__BPT4 | 885–900 | | PHEMA__IAEN7 | 237–253 | PHEMA__IADH7 | 306–323 |
| PVGO8__HSVI1 | 134–149 | | PHEMA__IAFPR | 230–246 | PHEMA__IADM2 | 322–339 |
| PVG10__BPPH2 | 183–198 | | PHEMA__IAHAL | 236–252 | PHEMA__IADNZ | 320–337 |
| PVG10__BPPZA | 183–198 | | PHEMA__IAHAR | 235–251 | PHEMA__IADU3 | 322–339 |
| PVG10__HSVSA | 109–124 | | PHEMA__IAHC6 | 230–246 | PHEMA__IAEN6 | 306–323 |
| PVG16__BPP1 | 81–96 | | PHEMA__IAHC7 | 230–246 | PHEMA__IAEN7 | 322–339 |
| PVG18__BPT4 | 468–483 | | PHEMA__IAHCD | 230–246 | PHEMA__IAFPR | 315–332 |
| PVG25__BPT4 | 97–112 | | PHEMA__IAHDE | 230–246 | PHEMA__IAGRE | 320–337 |
| PVG29__HSVI1 | 20–35 | | PHEMA__IAHFO | 236–252 | PHEMA__IAGU2 | 320–337 |
| PVG30__BPPH8 | 11–94 | | PHEMA__IAHK6 | 236–252 | PHEMA__IAGUA | 319–336 |
| PVG36__BPOX2 | 22–37 | | PHEMA__IAHK7 | 236–252 | PHEMA__IAHAL | 321–338 |
| PVG36__HSVSA | 108–123 | | PHEMA__IAHLE | 230–246 | PHEMA__IAHC6 | 315–332 |
| PVG37__BPT2 | 1253–1268 | | PHEMA__IAHLO | 230–246 | PHEMA__IAHC7 | 315–332 |
| PVG37__HSVI1 | 284–299 | | PHEMA__IAHMI | 236–252 | PHEMA__IAHCD | 315–332 |
| PVG55__HSVI1 | 22–37 | 143–158 | PHEMA__IAHNM | 236–252 | PHEMA__IAHDE | 315–332 |
| PVG56__HSVI1 | 268–283 | | PHEMA__IAHRO | 236–252 | PHEMA__IAHFO | 321–338 |
| PVG56__HSVI1 | 102–117 | | PHEMA__IAHSA | 236–252 | PHEMA__IAHK6 | 321–338 |
| PVG59__HSVI1 | 267–282 | | PHEMA__IAHSP | 230–246 | PHEMA__IAHK7 | 321–338 |
| PVG65__HSVI1 | 518–533 | | PHEMA__IAHSW | 230–246 | PHEMA__IAHLE | 315–332 |
| PVG9__BPPH2 | 234–249 | | PHEMA__IAHTE | 236–252 | PHEMA__IAHLO | 315–332 |
| PVG9__BPPZA | 234–249 | | PHEMA__IAHTO | 236–252 | PHEMA__IAHMI | 321–338 |
| PVG9__SPV1R | 57–72 | | PHEMA__IAHUR | 236–252 | PHEMA__IAHNM | 321–338 |
| PVGF__BPPHX | 234–249 | | PHEMA__IAKIE | 235–251 | PHEMA__IAHNN | 815–332 |
| PVGL2__CVBF | 264–279 | | PHEMA__IALEN | 235–251 | PHEMA__IAHPR | 315–332 |
| PVGL2__CFBL9 | 264–279 | | PHEMA__IAMAA | 233–249 | PHEMA__IAHRO | 321–338 |
| PVGL2__CVBLY | 264–279 | | PHEMA__IAMAB | 238–254 | PHEMA__IAHSA | 321–338 |
| PVGL2__CVBM | 264–279 | | PHEMA__IAMAO | 237–253 | PHEMA__IAHSP | 315–332 |
| PVGL2__CVBQ | 264–279 | | PHEMA__IAME1 | 237–253 | PHEMA__IAHSW | 315–332 |
| PVGL2__CVBV | 264–279 | | PHEMA__IAME2 | 237–253 | PHEMA__IAHTE | 321–338 |
| PVGL2__CVPFS | 442–457 | | PHEMA__IAME6 | 221–237 | PHEMA__IAHTO | 321–338 |

TABLE X-continued

Search Results Summary for PCTLZIP, P1CTLZIP, and P2CTLZIP Motifs

| PCTLZIP LIBRARY FILE | | P1CTLZIP LIBRARY FILE | | | P2CTLZIP LIBRARY FILE | |
|---|---|---|---|---|---|---|
| PVGL2_CVPPU | 440–455 | PHEMA_IAMIN | 85–101 | | PHEMA_IAHUR | 321–338 |
| PVGL2_CVPR8 | 218–233 | PHEMA_IANT6 | 237–253 | 231–247 | PHEMA_IAJAP | 317–334 |
| PVGL2_CVPRM | 218–233 | PHEMA_IAQU7 | 221–237 | | PHEMA_IAMAA | 319–336 |
| PVGL2_IBV6 | 1056–1071 | PHEMA_IARUD | 234–250 | | PHEMA_IAMAB | 324–341 |
| PVGL2_IBVB | 1055–1070 | PHEMA_IASE2 | 234–250 | | PHEMA_IAMAO | 322–339 |
| PVGL2_IBVD2 | 1056–1071 | PHEMA_IASH2 | 234–250 | | PHEMA_IAME1 | 322–339 |
| PVGL2_IBVK | 1055–1070 | PHEMA_IASTA | 230–246 | | PHEMA_IAME2 | 322–339 |
| PVGL2_IBVM | 1055–1070 | PHEMA_IATAI | 235–251 | | PHEMA_IAME6 | 306–323 |
| PVGLB_HSVBA | 701–716 | PHEMA_IATKM | 234–250 | | PHEMA_IAMIN | 316–333 |
| PVGLB_PRVIF | 203–216 | PHEMA_IATKO | 233–249 | | PHEMA_IANT6 | 322–339 |
| PVGLC_HSVBC | 475–490 | PHEMA_IATKR | 230–246 | | PHEMA_IAPIL | 320–337 |
| PVGLC_HSVE4 | 444–459 | PHEMA_IATKW | 229–245 | | PHEMA_IAQU7 | 306–323 |
| PVGLC_HSVEB | 427–442 | PHEMA_IAUDO | 237–253 | | PHEMA_IARUD | 320–337 |
| PV

TABLE X-continued

Search Results Summary for PCTLZIP, P1CTLZIP, and P2CTLZIP Motifs

| PCTLZIP LIBRARY FILE | | P1CTLZIP LIBRARY FILE | | | | P2CTLZIP LIBRARY FILE | |
|---|---|---|---|---|---|---|---|
| PVMT2_IALE2 | 25–40 | PHEMA_PI3H4 | 324–340 | | | PHEMA_SV5 | 84–101 |
| PVMT2_IAMAN | 25–40 | PHEMA_PI3HA | 324–340 | | | PHEMA_SV5CM | 84–101 |
| PVMT2_IAPUE | 25–40 | PHEMA_PI3HT | 324–340 | | | PHEMA_SV5CP | 84–101 |
| PVMT2_IASIN | 25–40 | PHEMA_PI3HU | 324–340 | | | PHEMA_SV5LN | 84–101 |
| PVMT2_IAUDO | 25–40 | PHEMA_PI3HV | 324–340 | | | PVFO5_VACCC | 280–297 |
| PVMT2_IAWIL | 25–40 |

TABLE X-continued

Search Results Summary for PCTLZIP, P1CTLZIP, and P2CTLZIP Motifs

| PCTLZIP LIBRARY FILE | P1CTLZIP LIBRARY FILE | | | | | P2CTLZIP LIBRARY FILE | |
|---|---|---|---|---|---|---|---|
| | PVGL2_CVM4 | 95–111 | 1267–1283 | | | PVMAT_MEASI | 87–104 |
| | PVGL2_CVMA5 | 95–111 | 1216–1231 | | | PVMP_CAMVC | 147–164 |
| | PVGL2_CVMJH | 95–111 | 1126–1142 | | | PVMP_CAMVD | 147–164 |
| | PVGL2_CVPFS | 442–457 | 800–818 | 1274–1290 | | PVMP_CAMVE | 147–164 |
| | PVGL2_CVPPU | 440–455 | 504–519 | 798–814 | 1272–1288 | PVMP_CAMVN | 147–164 |
| | PVGL2_CVPR8 | 218–233 | 576–592 | 1050–1066 | | PVMP_CAMVS | 147–164 |
| | PVGL2_CVPRM | 218–233 | 576–592 | 1050–1066 | | PVMP_CAMVW | 147–164 |
| | PVGL2_FIPV | 803–819 | 1277–1293 | | | PVMSA_HPBVO | 11–94 |
| | PVGL2_IBV6 | 1056–1071 | | | | PVMSA_HPBV2 | 185–202 |
| | PVGL2_IBVB | 1055–1070 | | | | PVMSA_HPBV4 | 185–202 |
| | PVGL2_IBVD2 | 1056–1071 | | | | PVMSA_HPBVA | 174–191 |
| | PVGL2_IBVK | 1055–1070 | | | | PVMSA_HPBVD | 11–94 |
| | PVGL2_IBVM | 1055–1070 | | | | PVMSA_HPBVJ | 174–191 |
| | PVGLB_HSVSA | 701–716 | | | | PVMSA_HPBVL | 174–191 |
| | PVGLB_PRVIF | 203–218 | | | | PVMSA_HPBVN | 11–94 |
| | PVGLB_VZVD | 522–538 | | | | PVMSA_HPBVO | 174–191 |
| | PVGLC_HSVBC | 475–490 | | | | PVMSA_HPBVP | 185–202 |
| | PVGLC_HSVE4 | 444–459 | | | | PVMSA_HPBVR | 185–202 |
| | PVGLC_HSVEB | 427–442 | | | | PVMSA_HPBVS | 11–94 |
| | PVGLC_PRVIF | 446–461 | | | | PVMSA_HPBVW | 174–191 |
| | PVGLC_VZVD | 150–166 | | | | PVMSA_HPBVY | 174–191 |
| | PVGLC_VZVS | 150–166 | | | | PVMSA_HPBVZ | 174–191 |
| | PVGLD_HSV11 | 79–94 | | | | PVMT2_IAANN | 25–42 |
| | PVGLD_HSV2 | 79–94 | | | | PVMT2_IABAN | 25–42 |
| | PVGLE_PRVRI | 3–94 | | | | PVMT2_IAFOW | 25–42 |
| | PVGLF_BRSVA | 205–221 | 265–280 | | | PVMT2_IAFPR | 25–42 |
| | PVGLF_BRSVC | 205–221 | 265–280 | | | PVMT2_IAFPW | 25–42 |
| | PVGLF_BRSVR | 205–221 | 265–280 | | | PVMT2_IALE1 | 25–42 |
| | PVGLF_COVO | 398–414 | | | | PVMT2_IALE2 | 25–42 |
| | PVGLF_HRSV1 | 205–221 | 265–280 | | | PVMT2_IAMAN | 25–42 |
| | PVGLF_HRSVA | 205–221 | 265–280 | | | PVMT2_IAPUE | 25–42 |
| | PVGLF_HRSVL | 205–221 | 265–280 | | | PVMT2_IASIN | 25–42 |
| | PVGLF_HRSVR | 205–221 | 265–280 | | | PVMT2_IAUDO | 25–42 |
| | PVGLF_MEASE | 286–302 | | | | PVMT2_IAWIL | 25–42 |
| | PVGLF_MEASI | 289–305 | | | | | |
| | PVGLF_MEASY | 286–302 | | | | | |
| | PVGLF_MUMPM | 276–292 | | | | | |
| | PVGLF_MUMPR | 276–292 | | | | | |
| | PVGLF_MUMPS | 5–94 | 276–292 | | | | |
| | PVGLF_NDVA | 273–289 | | | | | |
| | PVGLF_NDVB | 273–289 | | | | | |
| | PVGLF_NDVM | 273–289 | | | | | |
| | PVGLF_NDVT | 273–289 | | | | | |
| | PVGLF_NDVTG | 273–289 | | | | | |
| | PVGLF_NDVU | 273–289 | | | | | |
| | PVGLF_PHODV | 269–285 | 367–383 | | | | |
| | PVGLF_RINDK | 282–298 | | | | | |

TABLE X-continued

Search Results Summary for PCTLZIP, P1CTLZIP, and P2CTLZIP Motifs

| PCTLZIP LIBRARY FILE | P1CTLZIP LIBRARY FILE | | P2CTLZIP LIBRARY FILE |
|---|---|---|---|
| | PVGLF_RINDL | 282–298 | |
| | PVGLF_TRITV | 175–191 | |
| | PVGLI_VZVD | 278–293 | |
| | PVGLM_HANTB | 355–371 | 900–915 |
| | PVGLM_HANTH | 499–515 | |
| | PVGLM_HANTL | 499–515 | |
| | PVGLM_HANTV | 499–515 | |
| | PVGLM_PTPV | 743–758 | |
| | PVGLM_PUUMH | 509–525 | |
| | PVGLM_PUUMS | 509–525 | |
| | PVGLM_SEOUR | 355–371 | 901–916 |
| | PVGLM_SEOUS | 355–371 | 900–915 |
| | PVGLM_UUK | 826–842 | |
| | PVGLP_BEV | 869–885 | |
| | PVGLY_LASSG | 12–94 | 426–441 |
| | PVGLY_LASSJ | 12–94 | 427–442 |
| | PVGLY_LYCVA | 12–94 | |
| | PVGLY_LYCVW | 12–94 | |
| | PVGLY_MOPEI | 12–94 | 425–440 |
| | PVGLY_PIARV | 12–94 | |
| | PVGNM_CPMV | 1021–1037 | |
| | PVM3_REOVD | 521–536 | |
| | PVMAT_MUMPS | 191–207 | |
| | PVMAT_NDVA | 135–151 | |
| | PVMAT_NDVB | 135–151 | |
| | PVMAT_PI2HT | 189–205 | |
| | PVMAT_SV41 | 189–205 | |
| | PVMAT_SV5 | 98–114 | 132–148 |
| | PVMP_CAMVC | 118–134 | |
| | PVMP_CAMVD | 118–134 | |
| | PVMP_CAMVE | 118–134 | |
| | PVMP_CAMVN | 118–134 | |
| | PVMP_CAMVS | 118–134 | |
| | PVMP_CAMVW | 118–134 | |
| | PVMP_FMVD | 115–131 | |
| | PVMSA_HPBGS | 380–395 | |
| | PVMSA_HPBV9 | 187–202 | |
| | PVMSA_WHV1 | 378–393 | |
| | PVMSA_WHV59 | 383–398 | |
| | PVMSA_WHV7 | 383–398 | |
| | PVMSA_WHV8 | 383–398 | |
| | PVMSA_WHVSI | 383–398 | |
| | PVMSA_WHVW6 | 234–249 | |
| | PVMT2_IAANN | 25–40 | |
| | PVMT2_IABAN | 25–40 | |
| | PVMT2_IAFOW | 25–40 | |
| | PVMT2_IAFPR | 25–40 | |

TABLE X-continued

Search Results Summary for PCTLZIP, P1CTLZIP, and P2CTLZIP Motifs

| PCTLZIP LIBRARY FILE | P1CTLZIP LIBRARY FILE | | P2CTLZIP LIBRARY FILE |
|---|---|---|---|
| | PVMT2_IAFPW | 25-40 | |
| | PVMT2_IALE1 | 25-40 | |
| | PVMT2_IALE2 | 25-40 | |
| | PVMT2_IAMAN | 25-40 | |
| | PVMT2_IAPUE | 25-40 | |
| | PVMT2_IASIN | 25-40 | |
| | PVMT2_IAUDO | 25-40 | |
| | PVMT2_IAWIL | 25-40 | |
| |

TABLE XI

Search Results Summary for P3CTLZIP, P4CTLZIP, P5CTLZIP, and P6CTLZIP Motifs

| P3CTLZIP LIBRARY FILE | | | P4CTLZIP LIBRARY FILE | | | P5CTLZIP LIBRARY FILE | | | P6CTLZIP LIBRARY FILE | | | |
|---|---|---|---|---|---|---|---|---|---|---|---|---|
| PENV_BIV27 | 147–165 | | PENV1_FRSFV | 380–399 | | PENV1_FRSFV | 380–400 | | PENV_BIVO6 | 47–68 | 525–546 | |
| PENV_CAEVC | 810–828 | | PENV_AVISU | 98–117 | | PENV2_FRSFV | 380–400 | | PENV_BIV27 | 47–68 | 147–168 | 564–575 |
| PENV_CAEVG | 808–826 | | PENV_BIV27 | 147–166 | | PENV_BAEVM | 170–190 | | PENV_FENV1 | 225–246 | 630–651 | |
| PENV_HV2BE | 750–768 | | PENV_HV1ZH | 123–142 | | PENV_FIVPE | 781–801 | | PENV_FLVC6 | 624–645 | | |
| PENV_HV2D1 | 741–759 | | PENV_HV2D2 | 9–29 | | PENV_FIVSD | 779–799 | | PENV_FLVGL | 447–468 | 605–626 | |
| PENV_HV2G1 | 741–759 | | PENV_HV2SB | 778–797 | | PENV_FIVT2 | 780–800 | | PENV_FLVLB | 467–488 | 625–646 | |
| PENV_HV2NZ | 742–760 | | PENV_JSRV | 541–560 | | PENV_FLVGL | 9–29 | | PENV_FLVSA | 444–465 | 602–623 | |
| PENV_HV2RO | 751–769 | | PENV_RSVP | 533–552 | | PENV_FOAMV | 255–275 | 924–944 | PENV_FOAMV | 153–174 | 957–978 | |
| PENV_HV2SB | 743–761 | | PHEMA_VACCC | 173–192 | | PENV_FSVGA | 9–29 | | PENV_FSVGA | 467–488 | 625–646 | |
| PENV_HV2ST | 745–763 | | PHEMA_VACCI | 173–192 | | PENV_HV1C4 | 428–448 | | PENV_FSVGB | 447–468 | 605–626 | |
| PENV_JSRV | 376–394 | | PHEMA_VACCT | 173–192 | | PENV_HV2CA | 750–770 | | PENV_FSVSM | 450–471 | 608–629 | |
| PHEMA_PI2H | 118–136 | | PHEMA_VACCV | 173–192 | | PENV_MLVF5 | 400–420 | | PENV_FSVST | 467–488 | | |
| PHEMA_PI2HT | 118–136 | | PVENV_BEV | 62–81 | | PENV_MMTVB | 643–663 | | PENV_GALV | 52–73 | 519–540 | |
| PHEMA_SV41 | 55–73 | | PVENV_MCV1 | 61–80 | | PENV_MMTVG | 643–663 | | PENV_HV2BE | 750–771 | | |
| PVENV_THOGV | 473–491 | | PVENV_MCV2 | 61–80 | | PENV_OMVVS | 75–95 | | PENV_HV2G1 | 741–702 | | |
| PVG16_BPP22 | 83–101 | | PVFUS_ORFNZ | 29–48 | | PENV_RSVP | 42–62 | | PENV_HV2NZ | 742–763 | | |
| PVG24_BPT4 | 115–133 | | PVGO1_HSVEB | 169–188 | | PENV_SFV1 | 924–944 | | PENV_HV2RO | 751–772 | | |
| PVG36_HSVSA | 344–362 | | PVGO1_VACCC | 376–395 | | PENV_SFV3L | 921–941 | | PENV_HV2ST | 745–766 | | |
| PVG40_HSVI1 | 14–32 | | PVGO1_VACCV | 315–334 | | PENV_SIVM1 | 766–786 | | PENV_MCFF | 600–621 | | |
| PVG50_HSVSA | 5–94 | | PVGO1_VARV | 376–395 | | PENV_SIVMK | 765–785 | | PENV_MCFF3 | 601–622 | | |
| PVG51_BPT4 | 63–81 | | PVGO6_BPT4 | 627–646 | | PENV_SIVML | 764–784 | | PENV_MLVAV | 630–651 | | |
| PVG51_HSVI1 | 84–102 | | PVG10_HSVI1 | 35–54 | | PENV_SIVS4 | 769–789 | | PENV_MLVCB | 625–646 | | |
| PVG65_HSVI1 | 155–173 | | PVG11_HSVI1 | 103–122 | 150–169 | PENV_SIVSP | 773–793 | | PENV_MLVF5 | 639–660 | | |
| PVGF1_IBVB | 2788–2806 | 3374–3392 | PVG1_BPPH2 | 31–50 | | PHEMA_CDVO | 493–513 | | PENV_MLVFF | 639–660 | | |
| PVGL2_CVH22 | 1053–1071 | | PVG1_SPV1R | 659–678 | | PHEMA_CVBLY | 391–411 | | PENV_MLVFP | 639–660 | | |
| PVGL2_IBV6 | 1056–1074 | | PVG20_BPT4 | 231–250 | | PHEMA_CVBM | 391–411 | | PENV_MLVHO | 626–647 | | |
| PVGL2_IBVB | 1055–1073 | | PVG32_VZVD | 90–109 | | PHEMA_CVBQ | 391–411 | | PENV_MLVKI | 167–188 | | |
| PVGL2_IBVD2 | 1056–1074 | | PVG36_BPK3 | 132–151 | | PHEMA_CVHOC | 391–411 | | PENV_MLVMO | 629–650 | | |
| PVGL2_IBVK | 1055–1073 | | PVG37_BPT2 | 19–38 | 629–648 | PHEMA_CVMA5 | 402–422 | | PENV_MLVRD | 624–645 | | |
| PVGL2_IBVM | 1055–1073 | | PVG37_BPT4 | 19–38 | 625–644 | PHEMA_IACKG | 81–101 | | PENV_MLVRK | 624–645 | | |
| PVGLB_HSVB1 | 560–578 | 689–707 | PVG39_HSVI1 | 1038–1057 | | PHEMA_IADMA | 81–101 | | PENV_MSVFB | 170–191 | | |
| PVGLB_HSVBC | 692–710 | | PVG41_HSVI1 | 62–81 | | PHEMA_MUMPM | 397–417 | | PENV_RMCFV | 603–624 | | |
| PVGLB_HSVSA | 584–602 | | PVG43_BPPF3 | 380–399 | | PHEMA_MUMPR | 397–417 | | PENV_SFV1 | 957–978 | | |
| PVGLB_ILTV6 | 740–758 | | PVG46_BPPF1 | 337–356 | | PHEMA_MUMPS | 397–417 | | PENV_SFV3L | 157–178 | 954–975 | |
| PVGLB_ILTVS | 750–768 | | PVG59_HSVI1 | 142–161 | | PHEMA_PHODV | 493–513 | | PENV_SIVA1 | 437–458 | | |
| PVGLB_ILTVT | 750–768 | | PVG61_HSVI1 | 117–136 | | PHEMA_PI1HW | 322–342 | | PENV_SIVAG | 442–463 | | |
| PVGLC_VZVD | 431–449 | | PVG67_HSVI1 | 318–337 | 1072–1091 | PHEMA_PI2H | 13–33 | | PENV_SIVAI | 421–442 | | |
| PVGLC_VZVS | 431–449 | | PVGF1_IBVB | 1587–1606 | 2108–2127 | PHEMA_PI2HT | 13–33 | | PENV_SIVAT | 435–456 | | |
| PVGLF_PI3H4 | 2–94 | | PVGL2_CVBF | 991–1010 | | PHEMA_RINDL | 497–517 | | PENV_SMSAV | 42–63 | | |
| PVGLH_HSV6G | 314–332 | | PVGL2_CVBL9 | 991–1010 | | PHEMA_SEND5 | 322–342 | | PHEMA_CVMA5 | 402–423 | | |
| PVGLH_HSVE4 | 814–832 | | PVGL2_CVBLY | 991–1010 | | PHEMA_SENDF | 322–342 | | PHEMA_IADE1 | 266–287 | | |
| PVGLH_HSVEB | 807–825 | | PVGL2_CVBM | 991–1010 | | PHEMA_SENDH | 322–342 | | PHEMA_MUMPM | 225–246 | | |
| PVGLI_HSV11 | 5–94 | | PVGL2_CVBQ | 991–1010 | | PHEMA_SENDJ | 322–342 | | PHEMA_MUMPR | 225–246 | | |
| PVGNM_BPMV | 678–696 | | PVGL2_CVBV | 991–1010 | | PHEMA_SENDZ | 322–342 | | PHEMA_MUMPS | 225–246 | | |
| PVMO1_VACCC | 134–152 | 177–195 | PVGL2_CVH22 | 768–787 | 1115–1134 | PVENV_LELV | 27–47 | 148–168 | PHEMA_PHODV | 213–234 | | |
| PVMO1_VACCV | 63–101 | 126–144 | PVGL2_CVM4 | 999–1018 | | PVENV_THOGV | 356–376 | | PHEMA_PI2H | 13–34 | | |

TABLE XI-continued

Search Results Summary for P3CTLZIP, P4CTLZIP, P5CTLZIP, and P6CTLZIP Motifs

| P3CTLZIP LIBRARY FILE | | P4CTLZIP LIBRARY FILE | | P5CTLZIP LIBRARY FILE | | P6CTLZIP LIBRARY FILE | |
|---|---|---|---|---|---|---|---|
| PVM1_REOVD | 227–245 | PVGL2_CVMA5 | 947–966 | PVGO1_VACCC | 298–318 | PHEMA_PI2HT | 13–34 |
| PVM1_REOVL | 227–245 | PVGL2_CVMIH | 858–877 | PVGO1_VACCV | 237–257 | PHEMA_SV5 | 7–28 |
| PVMAT_HRSVA | 44–62 | PVGL2_CVPFS | 64–83 | PVGO1_VARV | 298–318 | PHEMA_SV5CM | 7–28 |
| PVMAT_NDVA | 190–208 | PVGL2_CVPPU | 64–83 | 1038–1057 | PVGO6_VACCC | 31–51 | PHEMA_SV5CP | 7–28 |
| PVMAT_NDVB | 190–208 | PVGL2_CVPR8 | 814–833 | 1036–1055 | PVGO6_VARV | 31–51 | PHEMA_SV5LN | 7–28 |
| PVMP_CAMVC | 183–201 | PVGL2_CVPRM | 814–833 | PVGO9_BPPF1 | 25–45 | PVGO1_HSVEB | 169–190 |
| PVMP_CAMVD | 183–201 | PVGL2_FIPV | 1041–1060 | PVG12_HSVI1 | 151–171 | PVGO1_HSVI1 | 589–610 |
| PVMP_CAMVE | 183–201 | PVGL2_IBV6 | 588–607 | 771–790 | PVG22_HSVI1 | 300–320 | PVG23_HSVI1 | 314–335 |
| PVMP_CAMVN | 183–201 | PVGL2_IBVB | 587–606 | 770–789 | PVG39_HSVI1 | 648–668 | 970–990 | PVG37_BPOX2 | 65–86 |
| PVMP_CAMVS | 183–201 | PVGL2_IBVD2 | 588–607 | 771–790 | PVG51_HSVI1 | 29–49 | PVG43_HSVI1 | 157–178 |
| PVMP_CAMVW | 183–201 | PVGL2_IBVK | 587–606 | 770–789 | PVG63_HSVI1 | 336–356 | PVG55_HSVI1 | 288–309 |
| PVMP_FMVD | 180–198 | PVGL2_IBVM | 587–606 | PVG65_HSVI1 | 117–137 | PVG56_HSVI1 | 85–106 |
| | | PVGLB_HCMVA | 706–725 | PVG74_HSVSA | 124–144 | PVG58_HSVSA | 1155–1176 |
| | | PVGLB_HCMVT | 707–726 | PVG12_IBV6 | 328–348 | PVG60_HSVI1 | 266–287 |
| | | PVGLB_HSV6U | 117–136 | PVG12_IBVB | 327–347 | PVGF1_IBVB | 30–51 |
| | | PVGLB_IIITV6 | 256–275 | PVG12_IBVD2 | 328–348 | PVGH3_HCMVA | 1856–1877 |
| | | PVGLB_IIITVS | 266–285 | PVG12_IBVD3 | 328–348 | PVGL2_CVBF | 157–178 |
| | | PVGLB_IIITVT | 266–285 | PVG12_IBVK | 327–347 | 378–398 | PVGL2_CVBL9 | 1259–1280 |
| | | PVGLC_HSVI1 | 3–94 | 467–486 | PVG12_IBVM | 327–347 | PVGL2_CVBIY | 1259–1280 |
| | | PVGLC_HSVI1K | 3–94 | 467–486 | PVG12_IBVU2 | 310–330 | PVGL2_CVBM | 1259–1280 |
| | | PVGLC_HSVBC | 475–494 | PVGLB_EBV | 732–752 | PVGL2_CVBQ | 1259–1280 |
| | | PVGLG_CHAV | 436–455 | PVGLB_HCMVA | 750–770 | PVGL2_CVBV | 1259–1280 |
| | | PVGLG_RABVH | 372–391 | PVGLB_HCMVT | 751–771 | PVGL2_CVM4 | 1317–1338 |
| | | PVGLI_HSVEB | 44–63 | PVGLB_HSV23 | 79–99 | PVGL2_CVMA5 | 1265–1286 |
| | | PVGL1_VZVD | 278–297 | PVGLB_HSV2H | 79–99 | PVGL2_CVMJH | 1176–1197 |
| | | PVGLM_BUNGE | 117–136 | PVGLB_HSV2S | 65–85 | PVGLB_HSV11 | 83–104 |
| | | PVGLM_PHV | 152–171 | PVGLB_HSV6U | 72–92 | PVGLB_HSV1F | 82–103 |
| | | PVGLM_PTPV | 997–1016 | PVGLB_HSVB2 | 279–299 | PVGLB_HSV1K | 82–103 |
| | | PVGLM_PUUMH | 155–174 | PVGLB_HSVSA | 63–83 | PVGLB_HSV1P | 83–104 |
| | | PVGLM_PUUMS | 155–174 | PVGLB_MCMVS | 738–758 | PVGLB_MCMVS | 135–156 |
| | | PVGLM_RVFV | 830–849 | PVGLF_PI3H4 | 283–303 | PVGLC_PRVIF | 446–467 |
| | | PVGLM_RVFVZ | 830–849 | PVGLG_RABVE | 454–474 | PVGLF_CDVO | 336–357 |
| | | PVGLM_UUK | 655–674 | PVGLG_RABVH | 454–474 | PVGLF_MEASE | 224–245 |
| | | PVGLY_LYCVW | 89–108 | PVGLG_RABVP | 454–474 | PVGLF_MEASI | 227–248 |
| | | PVGNB_CPMV | 1165–1184 | PVGLG_RABVT | 454–474 | PVGLF_MEASY | 224–245 |
| | | PVM3_REOVD | 521–540 | PVGLH_MCMVS | 670–690 | PVGLF_MUMPM | 446–467 |
| | | PVME1_CVBM | 171–190 | PVGLM_BUN1.7 | 1325–1345 | PVGLF_MUMPR | 446–467 |
| | | PVME1_CVH22 | 136–155 | PVGLM_BUNSH | 1325–1345 | PVGLF_MUMPS | 446–467 |
| | | PVME1_CVPFS | 174–193 | PVGLM_BUNYW | 996–1016 | PVGLF_PHODV | 305–326 |
| | | PVME1_CVPPU | 174–193 | PVGLM_HANTB | 999–1019 | PVGLF_PI1HC | 456–477 |
| | | PVME1_CVPRM | 174–193 | PVGLM_HANTH | 1000–1020 | PVGLF_PI2H | 450–471 |
| | | PVME1_CVTKE | 171–190 | PVGLM_HANTL | 1001–1021 | PVGLF_PI2HG | 450–471 |
| | | | | PVGLM_HANTV | 1156–1176 | PVGLF_PI2HT | 450–471 |
| | | | | PVGLM_RVFVZ | 670–690 | PVGLF_PI3B | 405–426 | 453–474 |
| | | | | PVGLM_SEOUR | 1000–1020 | PVGLF_PI3H4 | 453–474 |
| | | | | PVGLM_SEOUS | 999–1019 | | |

TABLE XI-continued

Search Results Summary for P3CTLZIP, P4CTLZIP, P5CTLZIP, and P6CTLZIP Motifs

| P3CTLZIP LIBRARY FILE | P4CTLZIP LIBRARY FILE | P5CTLZIP LIBRARY FILE | | P6CTLZIP LIBRARY FILE | | |
|---|---|---|---|---|---|---|
| | | PVGLM__UUK | 925–945 | PVGLF__RINDK | 220–241 | |
| | | PVGLY__LYCVA | 12–32 | PVGLF__RINDL | 220–241 | |
| | | PVGLY__LYCVW | 12–32 | PVGLF__SEND5 | 460–481 | |
| | | PVGLY__PIARV | 12–32 | PVGLF__SENDF | 460–481 | |
| | | PVGNB__CPMV | 141–161 | PVGLF__SENDH | 460–481 | |
| | | PVMAT__MUMPS | 310–330 | PVGLF__SENDJ | 460–481 | |
| | | PVMAT__NDVA | 309–329 | PVGLF__SENDZ | 460–481 | |
| | | PVMAT__NDVB | 309–329 | PVGLF__SV41 | 453–474 | |
| | | PVMAT__PI2HT | 308–328 | PVGLF__SV5 | 446–467 | |
| | | PVMAT__PI4HA | 312–332 | PVGLH__HCMVA | 691–712 | |
| | | PVMAT__PI4HB | 312–332 | PVGLH__HCMVT | 690–711 | |
| | | PVMAT__SV41 | 308–328 | PVGLH__HSVE4 | 304–325 | |
| | | PVMAT__SV5 | 308–328 | PVGLH__HSVEB | 297–318 | |
| | | PVME1__IBV6 | 74–94 | PVGLH__HSVSA | 658–679 | |
| | | PVME1__IBVB | 74–94 | PVGLI__HSV2 | 2–23 | |
| | | PVME1__IBVB2 | 74–94 | PVGLI__HSV23 | 2–23 | |
| | | PVME1__IBVK | 74–94 | PVGLM__BUNGE | 197–218 | |
| | | PVMSA__HPBDB | 201–221 | PVGLM__BUNL7 | 190–211 | |
| | | PVMSA__HPBGS | 209–229 | PVGLM__BUNSH | 190–211 | |
| | | PVMSA__HPBHE | 293–313 | PVGLM__BUNYW | 193–214 | |
| | | PVMSA__WHV1 | 207–227 | PVGLY__LASSG | 237–258 | |
| | | PVMSA__WHV59 | 212–232 | PVGLY__LASSJ | 238–259 | |
| | | PVMSA__WHV7 | 212–232 | PVGP8__EBV | 67–88 | |
| | | PVMSA__WHV8 | 212–232 | PVMO1__VACCC | 281–302 | |
| | | PVMSA__WHVBI | 212–232 | PVMO1__VACCV | 230–251 | |
| | | PVMSA__WHVW6 | 63–83 | PVMAT__HRSVA | 139–160 | |
| | | | | PVMAT__RINDK | 200–221 | 239–260 |
| | | | | PVMAT__TRTV | 122–143 | |
| | | | | PVME1__CVHOC | 64–85 | |
| | | | | PVMSA__HPBDB | 201–222 | |
| | | | | PVMSA__HPBVO | 70–91 | |
| | | | | PVMSA__HPBV2 | 244–265 | |
| | | | | PVMSA__HPBV4 | 244–265 | |
| | | | | PVMSA__HPBV9 | 244–265 | |
| | | | | PVMSA__HPBVA | 233–254 | |
| | | | | PVMSA__HPBVD | 70–91 | |
| | | | | PVMSA__HPBVI | 233–254 | |
| | | | | PVMSA__HPBVJ | 233–254 | |
| | | | | PVMSA__HPBVL | 233–254 | |
| | | | | PVMSA__HPBVN | 70–91 | |
| | | | | PVMSA__HPBVO | 233–254 | |
| | | | | PVMSA__HPBVP | 244–265 | |
| | | | | PVMSA__HPBVR | 244–265 | |
| | | | | PVMSA__HPBVS | 70–91 | |
| | | | | PVMSA__HPBVW | 233–254 | |
| | | | | PVMSA__HPBVY | 233–254 | |
| | | | | PVMSA__HPBVZ | 233–254 | |

TABLE XI-continued

Search Results Summary for P3CTLZIP, P4CTLZIP, P5CTLZIP, and P6CTLZIP Motifs

| P3CTLZIP LIBRARY FILE | P4CTLZIP LIBRARY FILE | P5CTLZIP LIBRARY FILE | P6CTLZIP LIBRARY FILE | |
|---|---|---|---|---|
| | | | PVMT2_IAANN | 25-46 |
| | | | PVMT2_IABAN | 25-46 |
| | | | PVMT2_IAFOW | 25-46 |
| | | | PVMT2_IAFPR | 25-46 |
| | | | PVMT2_IAFPW | 25-46 |
| | | | PVMT2_IALE1 | 25-46 |
| | | | PVMT2_IALE2 | 25-46 |
| | | | PVMT2_IAMAN | 25-46 |
| | | | PVMT2_IAPUE | 25-46 |
| | | | PVMT2_IASIN | 25-46 |
| | | | PVMT2_IAUDO | 25-46 |
| | | | PVMT2_IAWIL | 25-46 |

TABLE XII

Search Results Summary for P7CTLZIP, P8CTLZIP, and P9CTLZIP Motifs

| P7CTLZIP | | | P8CTLZIP | | | P9CTLZIP | | |
|---|---|---|---|---|---|---|---|---|
| LIBRARY FILE | | | LIBRARY FILE | | | LIBRARY | | |
| PENV_BAEVM | 202–224 | | PENV1_FRSFV | 380–403 | | PENV_BLVAF | 303–327 | |
| PENV_HV1B1 | 498–520 | | PENV2_FRSFV | 380–403 | | PENV_BLVAU | 303–327 | |
| PENV_HV1B8 | 493–516 | | PENV_BIV06 | 178–201 | | PENV_BLVAV | 303–327 | |
| PENV_HV1BN | 494–516 | | PENV_BIV27 | 207–230 | | PENV_BLVB2 | 303–327 | |
| PENV_HV1BA | 603–526 | | PENV_FOAMV | 804–867 | | PENV_BLVBG | 303–327 | |
| PENV_HV1EL | 495–517 | | PENV_HV123 | 175–198 | | PENV_BLVJ | 303–327 | |
| PENV_HV1H2 | 495–520 | | PENV_HV2BE | 3–26 | 781–804 | PENV_FIVPE | 781–806 | |
| PENV_HV1H3 | 498–520 | | PENV_HV2CA | 750–773 | | PENV_FIVSD | 779–803 | |
| PENV_HV1J3 | 610–532 | | PENV_HV2D1 | 3–26 | 772–706 | PENV_FIVT2 | 780–804 | |
| PENV_HV1JR | 490–512 | | PENV_HV2G1 | 772–795 | | PHEMA_CVBLY | 391–415 | |
| PENV_HV1KB | 504–526 | | PENV_HV2NZ | 777–800 | | PHEMA_CVBM | 391–415 | |
| PENV_HV1MA | 500–522 | | PENV_JSRV | 541–564 | | PHEMA_CVBQ | 391–415 | |
| PENV_HV1MF | 495–516 | | PENV_SFV1 | 664–887 | | PHEMA_CVHOC | 391–415 | |
| PENV_HV1ND | 488–510 | | PENV_SFV3L | 861–884 | | PHEMA_INCCA | 442–466 | |
| PENV_HV1PV | 498–520 | | PENV_SIVM1 | 803–826 | | PHEMA_INCEN | 430–454 | |
| PENV_HV1S1 | 489–511 | | PENV_SIVMK | 802–825 | | PHEMA_INCGL | 430–454 | |
| PENV_HV1Z2 | 123–146 | 495–517 | PENV_SIVML | 801–824 | | PHEMA_INCHY | 429–453 | |
| PENV_HV1Z6 | 497–519 | | PENV_SIVS4 | 806–829 | | PHEMA_INCJH | 443–467 | |
| PENV_HV1Z8 | 505–527 | | PENV_SIVSP | 810–833 | | PHEMA_INCKY | 429–453 | |
| PENV_HV1ZH | 498–520 | | PHEMA_COVO | 200–223 | | PHEMA_INCMI | 429–453 | |
| PENV_JSRV | 376–398 | | PHEMA_PI2H | 85–88 | | PHEMA_INCNA | 429–453 | |
| PENV_MPMV | 213–235 | | PHEMA_PI2HT | 85–88 | | PHEMA_INCP1 | 430–454 | |
| PENV_SRV1 | 213–235 | | PVF11_VACCC | 181–184 | | PHEMA_INCP2 | 430–454 | |
| PHEMA_IAAIC | 37–59 | | PVF15_VACCC | 25–48 | | PHEMA_INCP3 | 430–454 | |
| PHEMA_IABAN | 21–43 | | PVF15_VACCP | 3–26 | | PHEMA_INCTA | 430–454 | |
| PHEMA_IADA3 | 37–59 | | PVG1L_AMEPV | 313–336 | | PHEMA_INCYA | 430–454 | |
| PHEMA_IADH2 | 21–43 | | PVG28_HSVI1 | 491–514 | | PHEMA_MUMPM | 101–125 | |
| PHEMA_IADH3 | 21–43 | | PVG43_HSVI1 | 322–345 | | PHEMA_MUMPR | 101–125 | |
| PHEMA_IADH4 | 21–43 | | PVG52_HSVI1 | 229–262 | | PHEMA_MUMPS | 101–125 | |
| PHEMA_IADH5 | 21–43 | | PVG67_HSVI1 | 722–745 | | PHEMA_PI1HW | 29–53 | |
| PHEMA_IADH6 | 21–43 | | PVGL2_CVBF | 10–33 | | PVENV_BEV | 62–86 | |
| PHEMA_IADH7 | 21–43 | | RVGL2_CVBL9 | 651–674 | | PVFO5_VACCC | 280–304 | |
| PHEMA_IADM2 | 37–59 | | PVGL2_CVBLY | 10–33 | | PVFO5_VACCP | 280–304 | |
| PHEMA_IADMA | 28–50 | | PVGL2_CVM4 | 1267–1290 | | PVF05_VACCV | 281–305 | |
| PHEMA_IADU3 | 37–59 | | PVGL2_CVMA5 | 1215–1238 | | PVF09_VACCC | 176–200 | |
| PHEMA_IAEN6 | 21–43 | | PVGL2_CVMJH | 1126–1149 | | PVF09_VACCV | 176–200 | |
| PHEMA_IAEN7 | 37–59 | | PVGL2_CVPF8 | 1274–1207 | | PVG01_V2VD | 58–82 | |
| PHEMA_IAMAO | 37–59 | | PVGL2_CVPPU | 1272–1295 | | PVG10_HSVSA | 355–379 | |
| PHEMA_IAME1 | 37–59 | | PVGL2_CVPR8 | 1050–1073 | | PVG12_HSVSA | 68–92 | |
| PHEMA_IAME2 | 37–59 | | PVGL2_CVPRM | 1050–1073 | | PVG19_HSVI1 | 68–112 | |
| PHEMA_IAME8 | 21–43 | | PVGL2_FIPV | 1277–1300 | | PVG28_HSVI1 | 173–197 | |
| PHEMA_IANT8 | 37–59 | | PVGL2_IBV6 | 196–219 | | PVG43_HSVI1 | 109–133 | |
| PHEMA_IAQU7 | 21–43 | | PVGL2_IBVB | 195–218 | | PVG67_HSVI1 | 108–132 | 1005–1029 |
| PHEMA_IATKM | 33–55 | | PVGL2_IBVD2 | 196–219 | | PVG72_HSVI1 | 720–744 | |
| PHEMA_IAUDO | 37–59 | | PVGL2_IBVD3 | 196–219 | | PVGF1_IBVB | 3601–3626 | |
| PHEMA_IAVI7 | 38–60 | | PVGL2_IBVK | 195–218 | | PVGLB_HSVMD | 589–613 | |
| PHEMA_IAX31 | 37–59 | | PVGL2_IBVM | 195–218 | | PVGLB_ILTV6 | 597–621 | |
| PHEMA_IAZCO | 37–59 | | PVGL2_IBVU1 | 178–201 | | PVGLB_ILTVS | 607–631 | |
| PHEMA_IAZH2 | 21–43 | | PVGL2_IBVU2 | 178–201 | | PVGLB_ILTVT | 607–631 | |
| PHEMA_IAZH3 | 21–43 | | PVGL2_IBVU3 | 178–201 | | PVGLE_HSVI1 | 413–437 | |
| PHEMA_IAZUK | 37–59 | | PVGLB_HCMVA | 635–558 | | PVGLE_VZVD | 469–493 | |
| PHEMA_PHODV | 38–58 | | PVGLB_HCMVT | 530–559 | | PVGLF_SV6 | 401–426 | |
| PHEMA_PI2H | 65–87 | | PVGLB_HSVSA | 483–508 | | PVGLH_HCMVA | 574–598 | |
| PHEMA_PI2HT | 65–87 | | PVGLB_MCMVS | 586–589 | | PVGLH_HCMVT | 573–597 | |
| PVFP7_CAPVK | 89–111 | | PVGLC_HSV11 | 487–490 | | PVGLH_HSV11 | 443–467 | 803–827 |
| PVFU8_VACC6 | 72–94 | | PVGLC_HSV1K | 487–490 | | PVGLH_HSV1E | 443–467 | 603–827 |
| PVG01_HSVI1 | 317–339 | | PVGLC_HSV2 | 435–458 | | PVGLM_BUNL7 | 31–55 | |
| PVG03_VACCC | 50–72 | | PVGLC_HSV23 | 436–459 | | PVGLM_BUNSH | 31–55 | |
| PVG03_VARV | 50–72 | | PVGLM_BUNL7 | 1387–1410 | | PVGLM_HANTH | 694–718 | |
| PVG04_VACCC | 11–33 | | PVGLM_BUNSH | 1387–1410 | | PVGLM_RVFV | 344–368 | |
| PVG04_VARV | 11–33 | | PVGLM_UUK | 988–989 | | PVGLM_RVFVZ | 344–368 | |
| PVG19_HSVI1 | 85–110 | | PVGLY_JUNIN | 12–35 | | PVGLM_UUK | 581.585 | |
| PVG28_HSVI1 | 173–195 | | PVGLM_LAS8G | 12–35 | | PVGLM_CPVM | 311–335 | |
| PVG29_HSVI1 | 20–42 | | PVGLY_LASSJ | 12–35 | | PVGP2_EBV | 657–681 | |
| PVG48_HSVI1 | 134–158 | | PVGLY_LYCVA | 12–35 | | PVGP3_EBV | 854–878 | |
| PVG48_HSVSA | 71–93 | | PVGLY_LYCVW | 12–35 | | PVM1_REOVD | 280–304 | |
| PVG58_HSVSA | 286–288 | | PVGLY_MOPEI | 12–35 | | PVM1_REOVL | 280–304 | |
| PVG59_HSVI1 | 287–289 | | PVGLY_TACV | 12–35 | | PVM21_REOVD | 168–192 | |
| PVG5_SPV4 | 42–64 | | PVGLY_TACV5 | 12–35 | | PVM22_REOVD | 168–192 | |
| PVG80_HSVI1 | 63–75 | | PVGLY_TACV7 | 12–35 | | PVM2_REOVJ | 168–192 | |
| PVG85_HSVI1 | 1347–1369 | | PVGLY_TACVT | 12–35 | | PVM2_REOVL | 168–192 | |
| PVG8_SPV1R | 60–82 | | PVGNM_CPMV | 741–764 | | PVMAT_MEASI | 87–111 | |
| PVGL2_IBV6 | 1058–1078 | | PVM1_REOVD | 324–347 | 454–477 | PVMAT_SSPVB | 314–338 | |
| PVGL2_IBVB | 1055–1077 | | PVM1_REOVL | 467–477 | | PVME1_CVBM | 137–161 | |

TABLE XII-continued

Search Results Summary for P7CTLZIP, P8CTLZIP, and P9CTLZIP Motifs

| P7CTLZIP | | | P8CTLZIP | | P9CTLZIP | |
|---|---|---|---|---|---|---|
| PVGL2_IBVD2 | 1056–1078 | | PVMAT_MUMPS | 227–250 | PVME1_CVHOC | 137–161 |
| PVGL2_IBVK | 1055–1077 | | PVMSA_HPBDB | 269–292 | PVME1_CVTKE | 137–161 |
| PVGL2_IBVM | 1055–1077 | | PVMSA_HPBDC | 268–291 | PVME1_IBV8 | 74–98 |
| PVGLB_HSVBU | 117–139 | | PVMSA_HPBDU | 231–254 | PVME1_IBVB | 74–98 |
| PVGLB_HSVB2 | 745–787 | | PVMSA_HPBDW | 289–292 | PVME1_IBVB2 | 74–98 |
| PVGLC_HSVMB | 399–421 | | PVMSA_HPBHE | 236–259 | PVME1_IBVK | 74–98 |
| PVGLC_HSVMG | 398–420 | | | | PVMSA_HPBGS | 271–295 |
| PVGLC_HSVMM | 399–421 | | | | PVMSA_WHV1 | 289–293 |
| PVGLF_BRSVA | 285–287 | 482–504 | | | PVMSA_WHV59 | 274–298 |
| PVGLF_BRSVC | 484–506 | | | | PVMSA_WHV7 | 274–298 |
| PVGLF_BRSVR | 484–506 | | | | PVMSA_WHV8 | 274–298 |
| PVGLF_HRSV1 | 484–506 | | | | PVMSA_WHV8I | 274–298 |
| PVGLF_HRSVA | 484–506 | | | | PVMSA_WHVW8 | 125–149 |
| PVGLF_HRSVL | 484–506 | | | | | |
| PVGLF_HRSVR | 484–506 | | | | | |
| PVGLF_TRTV | 452–474 | | | | | |
| PVGLG_IHNV | 77–99 | | | | | |
| PVGLG_VH8VO | 406–428 | | | | | |
| PVGLH_HSVE4 | 814–838 | | | | | |
| FVGLH_HSVEB | 807–829 | | | | | |
| PVGLI_HCMVA | 186–180 | | | | | |
| PVGLM_PTPV | 743–765 | | | | | |
| PVGLP_BEV | 430–452 | 1646–1688 | | | | |
| PVGLY_LASSG | 428–448 | | | | | |
| PVGLY_LASSJ | 427–449 | | | | | |
| PVGLY_MOPEI | 425–447 | | | | | |
| PVGP2_EBV | 657–679 | | | | | |
| PVGP3_EBV | 854–878 | | | | | |
| PVM1_REOVD | 414–436 | | | | | |
| PVM1_REOVL | 414–436 | | | | | |
| PVM3_REOVD | 304–326 | | | | | |
| PVMAT_PI1HC | 195–217 | | | | | |
| PVMAT_PI2HT | 132–154 | | | | | |
| PVMAT_SENDF | 195–217 | | | | | |
| PVMAT_SENDH | 195–217 | | | | | |
| PVMAT_SENDZ | 195–217 | | | | | |
| PVMAT_SV41 | 132–154 | | | | | |
| PVMEM_EBV | 131–153 | | | | | |
| PVMP_CERV | 293–315 | | | | | |

TABLE XIII

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| P194K_TRVSY | POTENTIAL 194 KD PROTEIN | TOBACCO RATTLE VIRUS (STRAIN SYM) | 360–378 | 463–478 | 600–619 | 641–668 | 1011–1030 | 1299–1325 | 1385–1409 | | |
| P3BHS_VACCC | 3BETA-HSD | VACCINIA VIRUS (STRAIN COPENHAGEN) | 41–56 | 297–321 | | | | | | | |
| P3BHS_VACCV | 3BETA-HSD | VACCINIA VIRUS (STRAIN WR) | 41–56 | 297–321 | | | | | | | |
| P3BHS_VARV | 3BETA-HSD | VARIOLA VIRUS | 41–56 | | | | | | | | |
| PAT3H_FOWPM | ANTITHROMBIN-III HOMOLOG | FOWLPOX VIRUS (ISOLATE HP-438[MUNICH]) | 47–69 | | | | | | | | |
| PATI1_VACCV | 94 KD A-TYPE INCLUSION PROTEIN | VACCINIA VIRUS (STRAIN WR) | 387–410 | | | | | | | | |
| PATI1_VARV | 81 KD A-TYPE INCLUSION PROTEIN | VARIOLA VIRUS | 388–411 | | | | | | | | |
| PATI2_HSV11 | UL46 | HERPES SIMPLEX VIRUS (TYPE I/STRAIN 27) | 279–305 | | | | | | | | |
| PATI2_HSV1F | UL46 | HERPES SIMPLEX VIRUS (TYPE I/STRAIN F) | 279–305 | | | | | | | | |
| PATI2_HSVEB | ALPHA TRANS-INDUCING FACTOR 82 KD PROTEIN | EQUINE HERPESVIRUS TYPE I (STRAIN AB4P) | 197–222 | | | | | | | | |
| PATI2_VACCC | PUTATIVE A-TYPE INCLUSION PROTEIN | VACCINIA VIRUS (STRAIN COPENHAGEN) | 215–241 | | | | | | | | |
| PATI2_VZVD | ALPHA TRANS-INDUCING FACTOR 74 KD PROTEIN | VARICELLA-ZOSTER VIRUS (STRAIN DUMAS) | 61–79 | 377–397 | | | | | | | |
| PATI3_VACCV | PUTATIVE A-TYPE INCLUSION PROTEIN | VACCINIA VIRUS (STRAIN WR) | 47–73 | | | | | | | | |
| PATIN_HSVBP | ALPHA TRANS-INDUCING PROTEIN | BOVINE HERPESVIRUS TYPE I (STRAIN P8-2) | 101–120 | 277–292 | | | | | | | |
| PATIN_HSVE4 | ALPHA TRANS-INDUCING PROTEIN | EQUINE HERPESVIRUS TYPE 4 | 104–123 | | | | | | | | |
| PATIN_HSVEB | ALPHA TRANS-INDUCING PROTEIN | EQUINE HERPESVIRUS TYPE 1 (STRAIN AB4P) | 129–148 | | | | | | | | |
| PATIN_VZVD | ALPHA TRANS-INDUCING PROTEIN | VARICELLA-ZOSTER VIRUS (STRAIN DUMAS) | 203–230 | | | | | | | | |
| PATI_COWPX | A-TYPE INCLUSION PROTEIN | COWPOX VIRUS | 389–412 | 1102–1128 | | | | | | | |
| PB2_BBV | B2 PROTEIN | BLACK BEETLE VIRUS | 31–52 | | | | | | | | |
| PB701–HSV6G | TRANSCRIPTIONAL REGULATORY PROTEIN | HERPES SIMPLEX VIRUS (TYPE 6/STRAIN GS) | 55–78 | | | | | | | | |
| PBCRF_EBV | BCRF1 PROTEIN PRECURSOR | E[001b]PSTEIN-BARR VIRUS (STRAIN B95-8) | 96–123 | | | | | | | | |
| PBRL1_EBV | TRANSCRIPTION ACTIVATOR BRLF1 | EPSTEIN-BARR VIRUS (STRAIN B95-8) | 16–32 | 200–224 | | | | | | | |
| PCAHH_VACCC | CELL SURFACE-BINDING PROTEIN | VACCINIA VIRUS (STRAIN COPENHAGEN) | 188–203 | | | | | | | | |
| PCAHH_VACCV | CELL SURFACE-BINDING PROTEIN | VACCINIA VIRUS (STRAIN WR) | 188–203 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PCAHH_VARV | CELL SURFACE-BINDING PROTEIN | VARIOLA VIRUS | 188–203 | | | | | | | | |
| PCCPH_HSVSA | COMPL CONTROL PROTEIN HOMOLOG PREC | HERPESVIRUS SAIMIRI (STRAIN 11) | 326–348 | | | | | | | | |
| PCELF_HSV11 | CELL FUSION PROTEIN PRECURSOR | HERPES SIMPLEX VIRUS (TYPE I/STRAIN 17) | 178–196 | 212–238 | 286–309 | | | | | | |
| HCELF_HSVIK | CELL FUSION PROTEIN PRECURSOR | HERPES SIMPLEX VIRUS (TYPE I/STRAIN KOS) | 178–196 | 212–238 | | | | | | | |
| PCELF_HSV2H | CELL FUSION PROTEIN PRECURSOR | HERPES SIMPLEX VIRUS (TYPE 2/STRAIN HG52) | 178–196 | 212–238 | 285–309 | | | | | | |
| PCELF_HSVEB | CELL FUSION PROTEIN PRECURSOR | HERPESVIRUS TYPE (STRAIN KENTUCKY A) | 205–223 | 249–268 | | | | | | | |
| PCELF_VZVD | CELL FUSION PROTEIN PRECURSOR | VARICELLA-ZOSTER VIRUS (STRAIN DUMAS) | 246–269 | | | | | | | | |
| PCGH2_HSVSA | CYCLIN HOMOLOG | HERPESVIRUS SAIMIRI (STRAIN 11) | 35–61 | 216–242 | | | | | | | |
| PCOA1_BFDV | COAT PROTEIN VP1 | BUDGERIGAR FLEDGLING DISEASE VIRUS | 93–110 | | | | | | | | |
| PCOA1_POVBA | COAT PROTEIN VP1 | POLYOMAVIRUS BK (STRAIN AS) | 25–52 | 97–123 | 233–251 | | | | | | |
| CPOA1_POVBK | COAT PROTEIN VP1 | POLYOMAVIRUS BK | 25–52 | 97–123 | 233–251 | | | | | | |
| PCOA1_POVBO | COAT PROTEIN VP1 | BOVINE POLYOMAVIRUS | 96–120 | | | | | | | | |
| PCOA1_POVHA | COAT PROTEIN VP1 | HAMSTER POLYOMAVIRUS | 16–43 | | | | | | | | |
| PCOA1_POVJC | COAT PROTEIN VP1 | POLYOMAVIRUS JC | 17–44 | 89–115 | 225–243 | | | | | | |
| PCOA1_POVLY | COAT PROTEIN VP1 | LYMPHOTROPIC POLYOMAVIRUS | 97–123 | | | | | | | | |
| PCOA1_POVMK | COAT PROTEIN VP1 | MOUSE POLYOMAVIRUS (STRAIN KILHAM) | 142–160 | 231–249 | | | | | | | |
| PCOA1_SV40 | COAT PROTEIN VP1 | SIMIAN VIRUS 40 | 27–44 | 99–125 | 235–253 | | | | | | |
| PCOA1_TTV1 | COAT PROTEIN TP1 | THERMOPROTEUS TENAX VIRUS (STRAIN KRA1) | 80–103 | | | | | | | | |
| PCOA2_POVBO | COAT PROTEIN VP2 | BOVINE POLYOMAVIRUS | 77–104 | | | | | | | | |
| PCOA2_POVLY | COAT PROTEIN VP2 | LYMPHOTROPIC POLYOMAVIRS | 79–102 | | | | | | | | |
| PCOA2_POVM3 | COAT PROTEIN VP2 | MOUSE POLYOMAVIRUS (STRAIN 3) | 205–226 | | | | | | | | |
| PCOA3_TTV1 | COAT PROTEIN TP3 | THERMOPROTEUS TENAX VIRUS I (STRAIN KRA1) | 33–55 | | | | | | | | |
| PCOAT_ABMVW | COAT PROTEIN | ABUTILON MASAIC VIRUS (ISOLATE WEST INDIA) | 148–171 | | | | | | | | |
| PCOAT_BOOLV | COAT PROTEIN PRECURSOR | BOOLARRA VIRUS | 383–401 | | | | | | | | |
| PCOAT_CHVP1 | MAJOR CAPSID PROTEIN | PARAMECIUM BURSARIA CHLORELLA VIRUS 1 | 364–387 | 392–409 | | | | | | | |
| PCOAT_CLVK | COAT PROTEIN | CASSAVA LATENT VIRUS (STRAIN WEST KENYAN 844) | 165–188 | | | | | | | | |
| PCOAT_CLVN | COAT PROTEIN | CASSAVA LATENT VIRUS (STRAIN NIGERIAN) | 165–188 | | | | | | | | |
| PCOAT_CMVSI | COAT PROTEIN | CYMBIDIUM MOSAIC VIRUS (STRAIN SINGAPORE) | 58–76 | | | | | | | | |
| PCOAT_CNV | COAT PROTEIN | CUCUMBER NECROSIS VIRUS | 19–42 | | | | | | | | |

TABLE XIII-continued

| PCGENE FILE NAME | P12CTLZIP PROTEIN | SEARCH RESULTS SUMMARY FOR P12LZIPC MOTIF All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PCOAT_CSMV | COAT PROTEIN | CHLORIS STRIATE MOSAIC VIRUS | 219–238 | | | | | | | | |
| PCOAT_CTV36 | COAT PROTEIN | CITRUS TRISTEZA VIRUS (ISOLATE T36) | 72–94 | | | | | | | | |
| PCOAT_FCVC6 | COAT PROTEIN | FELINE CALICIVIRUS (STRAIN CF1/68 FIV) | 564–587 | 642–664 | | | | | | | |
| PCOAT_FCVF4 | COAT PROTEIN | FELINE CALICIVIRUS (STRAIN JAPANESE F4) | 564–587 | 642–657 | | | | | | | |
| PCOAT_FCVF9 | COAT PROTEIN | FELINE CALICIVIRUS (STRAIN F9) | 567–590 | 645–660 | | | | | | | |
| PCOAT_FPV | COAT PROTEIN VP1 | FELINE PANLEUKOPENIA VIRUS | 690–705 | | | | | | | | |
| PCOAT_FPV19 | COAT PROTEIN VP1 | FELINE PANLEUKOPENIA VIRUS (STRAIN 193) | 690–705 | | | | | | | | |
| PCOAT_HEVS | COAT PROTEIN | HELENIUM VIRUS S | 47–66 | | | | | | | | |
| PCOAT_MEVA | COAT PROTEIN VP1 | MINK ENTERITIS VIRUS (STRAIN ABASHIRI) | 685–700 | | | | | | | | |
| PCOAT_MNSV | COAT PROTEIN | MELON NECROTIC SPOT VIRUS | 37–53 | | | | | | | | |
| PCOAT_MSTV | COAT PROTEIN | MAIZE STRIPE VIRUS | 176–197 | 204–227 | | | | | | | |
| PCOAT_NMV | COAT PROTEIN | NARCISSUS MOSAIC VIRUS | 67–86 | | | | | | | | |
| PCOAT_NODAV | COAT PROTEIN PRECURSOR | NODAMURA VIRUS | 379–394 | | | | | | | | |
| PCOAT_ORSV | COAT PROTEIN | ODONTOGLOSSUM RINGSPOT VIRUS | 104–130 | | | | | | | | |
| PCOAT_OYMV | COAT PROTEIN | ONONIS YELLOW MOSAIC VIRUS | 35–52 | | | | | | | | |
| PCOAT_PAVC2 | COAT PROTEIN VP2 | CANINE PARVOVIRUS (TYPE 2/STRAIN A72) | 547–562 | | | | | | | | |
| PCOAT_PAVC7 | COAT PROTEIN VP1 | CANINE PARVOVIRUS (STRAIN 780929) | 685–700 | | | | | | | | |
| PCOAT_PAVCD | COAT PROTEIN VP1 | CANINE PARVOVIRUS (STRAIN CPV-D CORNELL 320) | 700–715 | | | | | | | | |
| PCOAT_PAVCN | COAT PROTEIN VP1 | CANINE PARVOVIRUS (STRAIN N) | 711–726 | | | | | | | | |
| PCOAT_PEMV | COAT PROTEIN PRECURSOR | PEPPER MOTTLE VIRUS | 273–295 | | | | | | | | |
| PCOAT_PMV | COAT PROTEIN | PAPAYA MOSAIC POTEXVIRUS | 85–103 | | | | | | | | |
| PCOAT_PPMVS | COAT PROTEIN | PEPPER MILD MOTTLE VIRUS (STRAINI SPAIN) | 64–84 | 103–129 | | | | | | | |
| PCOAT_PVSP | COAT PROTEIN | POTATO VIRUS (STRAIN PERUVIAN) | 129–147 | | | | | | | | |
| PCOAT_RSV | COAT PROTEIN | RICE STRIPE VIRUS | 128–152 | | | | | | | | |
| PCOAT_SMWLM | COAT PROTEIN | SATELLITE MAIZE WHITE LINE MOSAIC VIRUS | 51–67 | | | | | | | | |
| PCOAT_SMYEA | COAT PROTEIN | STRAWBERRY MILD YELLOW EDGE-ASSOCAITED VIRUS | 57–72 | | | | | | | | |
| PCOAT_TAMV | GENOME POLYPROTEIN | TAMARILLO MOSAIC VIRUS | 222–237 | | | | | | | | |
| PCOAT_TBSVB | COAT PROTEIN | TOMATO BUSHY STUNT VIRUS (STRAIN BS-3) | 359–383 | | | | | | | | |
| PCOAT_TCV | COAT PROTEIN | TURNIP CRINKLE VIRUS | 73–89 | | | | | | | | |
| PCOAT_TGMV | COAT PROTEIN | TOMATO GOLDEN MOSAIC VIRUS | 154–177 | | | | | | | | |
| PCOAT_TMGMV | COAT PROTEIN | TOBACCO MILD GREEN MOSAIC VIRUS (TMV STRAIN U2) | 102–128 | | | | | | | | |

TABLE XIII-continued

| SEARCH RESULTS SUMMARY FOR P12LZIPC MOTIF | | | | | | | | | | | |
|---|---|---|---|---|---|---|---|---|---|---|---|
| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
| PCOAT_TMV | COAT PROTEIN | TOBACCO MOSAIC VIRUS (VULGARE) | 102–128 | | | | | | | | |
| PCOAT_TMV06 | COAT PROTEIN | TOBACCO MOSAIC VIRUS (STRAIN 06) | 102–128 | | | | | | | | |
| PCOAT_TMVDA | COAT PROTEIN | TOBACCO MOSAIC VIRUS (STRAIN DAHLEMENSE) | 102–128 | | | | | | | | |
| PCOAT_TMVER | COAT PROTEIN | TOBACCO MOSAIC VIRUS (STRAIN ER) | 102–128 | | | | | | | | |
| PCOAT_TMVHR | COAT PROTEIN | TOBACCO MOSAIC VIRUS (STRAIN HOLMES RIBGRASS (HR)) | 102–128 | | | | | | | | |
| PCOAT_TMVO | COAT PROTEIN | TOBACCO MOSAIC VIRUS (STRAIN O) | 102–128 | | | | | | | | |
| PCOAT_TMVOM | COAT PROTEIN | TOBACCO MOSAIC VIRUS (STRAIN OM) | 102–128 | | | | | | | | |
| PCOAT_TMVTO | COAT PROTEIN | TOBACCO MOSAIC VIRUS (STRAIN TOMATO/L) | 102–128 | | | | | | | | |
| PCOAT_TNVA | COAT PROTEIN | TOBACCO NECROSIS VIRUS (STRAIN A) | 119–142 | | | | | | | | |
| PCOAT_TNVD | COAT PROTEIN | TOBACCO NECROSIS VIRUS (STRAIN D) | 108–134 | | | | | | | | |
| PCOLL_HSVSC | COLLAGEN-LIKE PROTEIN | HERPESVIRUS SAIMIRI (SUBGROUP C/STRAIN 488) | 71–96 | | | | | | | | |
| PCORA_HPBV2 | CORE ANTIGEN | HEPATITIS B VIRUS (SUBTYPE ADW2) | 79–100 | | | | | | | | |
| PCORA_HPBVA | CORE ANTIGEN | HEPATITIS B VIRUS (STRAIN ALPHA1) | 15–31 | | | | | | | | |
| PCORA_HPBVZ | CORE ANTIGEN | HEPATITIS B VIRUS (SUBTYPE ADYW) | 79–100 | | | | | | | | |
| PDNBI_ADE02 | PROBABLE DNA-BINDING PROTEIN | HUMAN ADENOVIRUS TYPE 2 | 71–93 | | | | | | | | |
| PDNBI_EBV | MAJOR DNA-BINDING PROTEIN | EPSTEIN-BARR VIRUS (STRAIN B95-8) | 649–673 | | | | | | | | |
| PDNBI_HCMVA | MAJOR DNA-BINDING PROTEIN | HUMAN CYTOMEGALOVIRUS (STRAIN AD169) | 681–708 | | | | | | | | |
| PDNBI_HSV11 | MAJOR DNA-BINDING PROTEIN | HERPES SIMPLEX VIRUS (TYPE 1/STRAIN 17) | 459–476 | 597–620 | | | | | | | |
| PDNBI_HSV1F | MAJOR DNA-BINDING PROTEIN | HERPES SIMPLEX VIRUS (TYPE 1/STRAIN F) | 459–476 | 597–620 | | | | | | | |
| PDNBI_HSV1K | MAJOR DNA-BINDING PROTEIN | HERPES SIMPLEX VIRUS (TYPE 1/STRAIN KOS) | 459–476 | 597–620 | | | | | | | |
| PDNBI_HSVB2 | MAJOR DNA-BINDING PROTEIN | BOVINE HERPESVIRUS TYPE 2 (STRAIN BMV) | 455–472 | 596–616 | | | | | | | |
| PDNBI_HSVEB | MAJOR DNA-BINDING PROTEIN | EQUINE HERPESVIRUS TYPE 1 (STRAIN AD4P) | 810–831 | | | | | | | | |
| PDNBI_HSVSA | MAJOR DNA-BINDING PROTEIN | HERPESVIRUS SAIMIRI (STRAIN 11) | 108–127 | 610–629 | 869–887 | 974–1000 | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDNBL_MCMVS | MAJOR DNA-BINDING PROTEIN | MURINE CYTOMEGALOVIRUS (STRAIN SMITH) | 657–684 | | | | | | | | |
| PDNBL_SCMVC | MAJOR DNA-BINDING PROTEIN | SIMIAN CYTOMEGALOVIRUS (STRAIN COLBURN) | 188–212 | 643–670 | | | | | | | |
| PDNL1_VARV | DNA LIGASE | VARIOLA VIRUS | 269–294 | | | | | | | | |
| PDPOL_ADE02 | DNA POLYMERASE | HUMAN ADENOVIRUS TYPE 2 | 264–283 | 828–850 | | | | | | | |
| PDPOL_ADE05 | DNA POLYMERASE | HUMAN ADENOVIRUS TYPE 5 | 264–283 | 828–850 | | | | | | | |
| PDPOL_ADE07 | DNA POLYMERASE | HUMAN ADENOVIRUS TYPE 7 | 331–350 | 494–517 | 894–916 | | | | | | |
| PDPOL_ADE12 | DNA POLYMERASE | HUMAN ADENOVIRUS TYPE 12 | 262–281 | 562–583 | 826–848 | | | | | | |
| PDPOL_CBEPV | DNA POLYMERASE | CHORISTONEURA BIENNIS ENTOMOPOXVIRUS | 430–454 | 654–678 | 732–757 | | | | | | |
| PDPOL_CHVN2 | DNA POLYMERASE | CHLORELLA VIRUS NY-2A | 424–442 | | | | | | | | |
| PDPOL_CHVP1 | DNA POLYMERASE | PARAMECIUM BURSARIA CHLORELLA VIRUS 1 | 153–172 | 424–442 | | | | | | | |
| PDPOL_EBV | DNA POLYMERASE | EPSTEIN-BARR VIRUS (STRAIN B95-8) | 354–374 | 438–463 | 524–542 | 667–687 | | | | | |
| PDPOL_FOWPV | DNA POLYMERASE | FOWLPOX VIRUS | 60–77 | 220–247 | | | | | | | |
| PDPOL_HCMVA | DNA POLYMERASE | HUMAN CYTOMEGALOVIRUS (STRAIN AD169) | 569–587 | 945–960 | 1029–1053 | | | | | | |
| PDPOL_HPBDB | DNA POLYMERASE | DUCK HEPATITIS B VIRUS (BROWN SHANGHAI DUCK ISOLATE S5) | 4–29 | 157–174 | 522–541 | 554–572 | 973–990 | | | | |
| PDPOL_HPBDC | DNA POLYMERASE | DUCK HEPATITIS B VIRUS (STRAIN CHINA) | 4–29 | 157–174 | 521–540 | 553–571 | | | | | |
| PDPOL_HPBDU | DNA POLYMERASE | DUCK HEPATITIS B VIRUS | 181–200 | 213–231 | | | | | | | |
| PDPOL_HPBDW | DNA POLYMERASE | DUCK HEPATITIS B VIRUS (WHITE SHANGHAI DUCK ISOLATE S31) | 4–29 | 157–174 | 522–541 | 554–572 | | | | | |
| PDPOL_HPBGS | DNA POLYMERASE | GROUND SQUIRREL HEPATITIS VIRUS | 448–475 | | | | | | | | |
| PDPOL_HPBHE | DNA POLYMERASE | HERON HEPATITIS B VIRUS | 4–29 | 554–572 | | | | | | | |
| PDPOL_HPBV2 | DNA POLYMERASE | HEPATITIS B VIRUS (SUBTYPE ADW2) | 412–439 | 447–463 | 761–780 | | | | | | |
| PDPOL_HPBV4 | DNA POLYMERASE | HEPATITIS B VIRUS (SUBTYPE ADR4) | 410–417 | | | | | | | | |
| PDPOL_HPBV9 | DNA POLYMERASE | HEPATITIS B VIRUS (SUBTYPE ADW/STRAIN 991) | 412–439 | 447–463 | 763–780 | | | | | | |
| PDPOL_HPBVA | DNA POLYMERASE | HEPATITIS B VIRUS (STRAIN ALPHA1) | 80–96 | 399–426 | 434–450 | 750–767 | | | | | |
| PDPOL_HPBV1 | DNA POLYMERASE | HEPATITIS B VIRUS (SUBTYPE ADW/STRAIN INDONESIA/PIDW420) | 80–96 | 410–437 | 445–468 | 761–778 | | | | | |
| PDPOL_HPBVJ | DNA POLYMERASE | HEPATITIS B VIRUS (SUBTYPE ADW/STRAIN JAPAN/PIDW233) | 80–96 | 410–437 | 445–468 | 761–778 | | | | | |
| PDPOL_PHBVL | DNA POLYMERASE | HEPATITIS B VIRUS (STRAIN LSH/CHIMPANZEE ISOLATE) | 80–96 | 399–426 | 434–457 | 750–767 | | | | | |
| PDPOL_HPBVM | DNA POLYMERASE | HEPATITIS B VIRUS (SUBTYPE ADR/MUTANT) | 80–96 | 410–437 | 760–777 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDPOL_HPBVO | DNA POLYMERASE | HEPATITIS B VIRUS (SUBTYPE ADW/STRAIN OKINAWA/PODW282) | 80–96 | 410–437 | 445–468 | 761–778 | | | | | |
| PDPOL_HPBVP | DNA POLYMERASE | HEPATITIS B VIRUS (SUBTYPE ADW/STRAIN PHILIPPINO/PFDW294) | 412–439 | 447–463 | | | | | | | |
| PDPOL_HPBVR | DNA POLYMERASE | HEPATITIS B VIRUS (SUBTYPE ADR) | 80–96 | 410–437 | 761–778 | | | | | | |
| PDPOL_HPBVW | DNA POLYMERASE | HEPATITIS B VIRUS (SUBTYPE ADW) | 82–98 | 405–432 | 440–456 | | | | | | |
| PDPOL_HPBVY | DNA POLYMERASE | HEPATITIS B VIRUS (SUBTYPE AYW) | 80–96 | 399–426 | 434–457 | 750–767 | | | | | |
| PDPOL_HPBVZ | DNA POLYMERASE | HEPATITIS B VIRUS (SUBTYPE ADYW) | 80–96 | 399–426 | 434–457 | | | | | | |
| PDPOL_HSVI1 | DNA POLYMERASE | HERPES SIMPLEX VIRUS (TYPE I/STRAIN 17) | 797–817 | 877–897 | 1073–1090 | | | | | | |
| PDPOL_HSV1A | DNA POLYMERASE | HERPES SIMPLEX VIRUS (TYPE I/STRAIN ANGELOTTI) | 797–817 | 877–897 | 1073–1090 | | | | | | |
| PDPOL_HSV1K | DNA POLYMERASE | HERPES SIMPLEX VIRUS (TYPE I/STRAIN KOS) | 797–817 | 877–897 | 1073–1090 | | | | | | |
| PDPOL_HSV1S | DNA POLYMERASE | HERPES SIMPLEX VIRUS (TYPE I/STRAIN SC16) | 797–817 | 877–897 | 1073–1090 | | | | | | |
| PDPOL_HSV21 | DNA POLYMERASE | HERPES SIMPLEX VIRUS (TYPE 2/STRAIN 186) | 802–822 | 882–902 | 1078–1095 | | | | | | |
| PDPOL_HSV6U | DNA POLYMERASE | HERPES SIMPLEX VIRUS (TYPE 6/STRAIN UGANDA-1102) | 652–672 | 786–803 | 858–882 | | | | | | |
| PDPOL_HSVEB | DNA POLYMERASE | EQUINE HERPESVIRUS TYPE 1 (STRAIN AB4P) | 283–299 | 377–392 | 454–477 | 798–818 | 878–898 | | | | |
| PDPOL_HSVI1 | DNA POLYMERASE | ICTALURID HERPESVIRUS 1 | 257–275 | 397–418 | | | | | | | |
| PDPOL_HSVSA | DNA POLYMERASE | HERPESVIRUS SAIMIRI (STRAIN 11) | 118–137 | 297–319 | 344–364 | 514–532 | 955–972 | | | | |
| PDPOL_MCMVS | DNA POLYMERASE | MURINE CYTOMEGALOVIRUS (STRAIN SMITH) | 303–322 | 535–553 | 780–802 | | | | | | |
| PDPOL_NPVAC | DNA POLYMERASE | AUTOGRAPHA CALIFORNICA NUCLEAR POLYHEDROSIS VIRUS | 518–536 | 676–697 | | | | | | | |
| PDPOL_VARV | DNA POLYMERASE | VARIOLA VIRUS | 421–437 | | | | | | | | |
| PDPOL_VZVD | DNA POLYMERASE | VARICELLA-ZOSTER VIRUS (STRAIN DUMAS) | 312–331 | 363–382 | 440–463 | 713–740 | 757–781 | 1006–1024 | | | |
| PDPOL_WHV1 | DNA POLYMERASE | WOODCHUCK HEPATITIS VIRUS 1 | 446–473 | | | | | | | | |
| PDPOL_WHV59 | DNA POLYMERASE | WOODCHUCK HEPATITIS VIRUS 59 | 451–478 | | | | | | | | |
| PDPOL_WHV7 | DNA POLYMERASE | WOODCHUCK HEPATITIS VIRUS 7 | 451–478 | | | | | | | | |
| PDPOL_WHV8 | DNA POLYMERASE | WOODCHUCK HEPATITIS VIRUS 8 | 450–477 | 554–571 | | | | | | | |
| PDPOL_HEV8I | DNA POLYMERASE | WOODCHUCK HEPATITIS VIRUS 8 | 451–478 | | | | | | | | |
| PDPOL_WHVW6 | DNA POLYMERASE | WOODCHUCK HEPATITIS VIRUS W64 (ISOLATE PWS23) | 123–150 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PDPOM_HPBVY | DNA POLYMERASE | HEPATITIS B VIRUS (SUBTYPE AYW) | 399–426 | 434–450 | 750–767 | | | | | | |
| PDUT_HCMVA | DUTPASE | HUMAN CYTOMEGALOVIRUS (STRAIN AD169) | 107–126 | | | | | | | | |
| PDUT_HSVE4 | DUTPASE | EQUINE HERPESVIRUS TYPE 4 (STRAIN 1942) | 130–154 | | | | | | | | |
| PDUT_HSVEB | DUTPASE | EQUINE HERPESVIRUS TYPE 1 (STRAIN AB4P) | 130–149 | | | | | | | | |
| PDUT_HDVI1 | DUTPASE | ICTALURID HERPESVIRUS 1 | 72–95 | | | | | | | | |
| PDUT_HSVSA | DUTPASE | HERPESVIRUS SAIMIRI (STRAIN 11) | 22–45 | 79–104 | 168–183 | | | | | | |
| PE111_ADEM1 | EARLY E1A 11 KD PROTEIN | MOUSE ADENOVIRUS TYPE 1 | 24–47 | | | | | | | | |
| PE146_ADE07 | EARLY E1A 63 KD PROTEIN | HUMAN ADENOVIRUS TYPE 7 | 8–35 | | | | | | | | |
| PE1A_ADE04 | EARLY E1A 28 KD PROTEIN | HUMAN ADENOVIRUS TYPE 4 | 104–120 | | | | | | | | |
| PE1A_ADE07 | EARLY E1A 28 KD PROTEIN | HUMAN ADENOVIRUS TYPE 7 | 8–35 | | | | | | | | |
| PE1A_ADES7 | EARLY E1A 28 KD PROTEIN | SIMIAN ADENOVIRUS TYPE 7 | 173–189 | 238–254 | | | | | | | |
| PE1BL_ADE12 | E1B PROTEIN, LARGE T-ANTIGEN | HUMAN ADENOVIRUS TYPE 12 | 451–467 | | | | | | | | |
| PE1BL_ADEC2 | E1B PROTEIN, LARGE T-ANTIGEN | CANINE ADENOVIRUS TYPE 2 | 101–122 | | | | | | | | |
| PR1BL_ADENT | EARLY E1B 44 KD PROTEIN | TUPAIA ADENOVIRUS | 75–101 | | | | | | | | |
| PE1BS_ADEC2 | E1B PROTEIN, SMALL T-ANTIGEN | CANINE ADENOVIRUS TYPE 2 | 55–77 | | | | | | | | |
| PE1BS_ADEM1 | E1B PROTEIN, SMALL T-ANTIGEN | MOUSE ADENOVIRUS TYPE 1 | 118–138 | | | | | | | | |
| PE310_ADE02 | EARLY E1B 10 4 KD PROTEIN PRECURSOR | HUMAN ADENOVIRUS TYPE 2 | 3–21 | 34–60 | | | | | | | |
| PE310_ADE05 | EARLY E1B 10 4 KD PROTEIN PRECURSOR | HUMAN ADENOVIRUS TYPE 5 | 3–21 | 33–60 | | | | | | | |
| PE310_ADE07 | EARLY E3B 4 KD PROTEIN PRECURSOR | HUMAN ADENOVIRUS TYPE 7 | 3–24 | | | | | | | | |
| PE311_ADE02 | EARLY E3A 11 6 KD GLYCOPROTEIN | HUMAN ADENOVIRUS TYPE 2 | 27–53 | | | | | | | | |
| PE311_ADE03 | EARLY E3 9 0 KD GLYCOPROTEIN | HUMAN ADENOVIRUS TYPE 3 | 19–45 | | | | | | | | |
| PE311_ADE05 | EARLY E3A 10 5 KD GLYCOPROTEIN | HUMAN ADENOVIRUS TYPE 5 | 20–46 | | | | | | | | |
| PE311_ADE07 | EARLY E3 7 7 KD PROTEIN | HUMAN ADENOVIRUS TYPE 7 | 36–62 | | | | | | | | |
| PE314_ADE05 | EARLY E3 14 5 KD PROTEIN | HUMAN ADENOVIRUS TYPE 5 | 108–125 | | | | | | | | |
| PE315_ADE03 | EARLY E3B 14 5 KD PROTEIN | HUMAN ADENOVIRUS TYPE 3 | 52–72 | | | | | | | | |
| PE315_ADE07 | EARLY E3B 14 9 KD PROTEIN PRECURSOR | HUMAN ADENOVIRUS TYPE 7 | 52–72 | | | | | | | | |
| PE316_ADE03 | EARLY E3 16 KD GLYCOPROTEIN | HUMAN ADENOVIRUS TYPE 3 | 102–125 | | | | | | | | |
| PE321_ADE03 | EARLY E3 20 5 KD GLYCOPROTEIN | HUMAN ADENOVIRUS TYPE 3 | 146–167 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PE321_ADE07 | EARLY E3 20 5 KD GLYCOPROTEIN | HUMAN ADENOVIRUS TYPE 7 | 146–167 | | | | | | | | |
| PE322_ADEC1 | EARLY E3 22 2 KD GLYCOPROTEIN | CANINE ADENOVIRUS TYPE 1 (STRAIN GLAXO) | 155–177 | | | | | | | | |
| PE3GL_ADEM1 | EARLY E3 17 7 GLYCOPROTEIN | MOUSE ADENOVIRUS TYPE 1 | 105–127 | | | | | | | | |
| PE411_ADE02 | PROBABLE EARLY E4 11 KD PROTEIN | HUMAN ADENOVIRUS TYPE 2 | 56–77 | | | | | | | | |
| PE411_ADE05 | PROBABLE EARLY E4 11 KD PROTEIN | HUMAN ADENOVIRUS TYPE 5 | 56–77 | | | | | | | | |
| PE433_ADEM1 | PROBABLE EARLY E4 33 KD PROTEIN | MOUSE ADENOVIRUS TYPE 1 | 61–80 | | | | | | | | |
| PE434_ADE02 | EARLY E4 34 KD PROTEIN | HUMAN ADENOVIRUS TYPE 2 | 80–106 | | | | | | | | |
| PEAD_EBV | EARLY ANTIGEN PROTEIN D | EPSTEIN-BARR VIRUS (STRAIN B95-8) | 263–286 | | | | | | | | |
| PEAR_EBV | EARLY ANTIGEN PROTEIN R | EPSTEIN-BARR VIRUS (STRAIN B95-8) | 159–184 | | | | | | | | |
| PEBN2_EBV | EBNA-2 NUCLEAR PROTEIN | EPSTEIN-BARR VIRUS (STRAIN B95-8) | 126–141 | | | | | | | | |
| PEBN3_EBV | EBNA-3 NUCLEAR PROTEIN | EPSTEIN-BARR VIRUS (STRAIN B95-8) | 113–131 | 662–683 | | | | | | | |
| PEFT1_VARV | EARLY TRANSCRIPTION FACTOR 70 KD SUBUNIT | VARIOLA VIRUS | 21–41 | | | | | | | | |
| PENV1_FRSFV | ENV POLYPROTEIN PRECURSOR | FRIEND SPLEEN FOCUS-FORMIMG VIRUS | 380–407 | | | | | | | | |
| PENV2_FRSFV | ENV POLYPROTEIN PRECURSOR | FRIEND SPLEEN FOCUS-FORMING VIRUS | 380–407 | | | | | | | | |
| PENV_AVIR3 | ENV POLYPROTEIN | AVIAN RETROVIRUS RPL30 | 206–225 | | | | | | | | |
| PENV_AVISU | COAT PROTEIN GP37 | AVIAN SARCOMA VIRUS (STRAIN UR2) | 98–117 | | | | | | | | |
| PENV_BAEVM | ENV POLYPROTEIN | BABOON ENDOGENOUS VIRUS (STRAIN M7) | 170–190 | 202–224 | | | | | | | |
| PENV_BIV06 | ENV POLYPROTEIN PRECURSOR | BOVINE IMMUNODEFICIENCY VIRUS (ISOLATE 106) | 47–68 | 178–201 | 434–450 | 525–546 | | | | | |
| PENV_BIV27 | ENV POLYPROTEIN PRECURSOR | BOVINE IMMUNODEFICIENCY VIRUS (ISOLATE 127) | 47–68 | 147–168 | 207–230 | 463–479 | 554–575 | | | | |
| PENV_BLVAF | ENV POLYPROTEIN | BOVINE LEUKEMIA VIRUS (AMERICAN ISOLATE FLK) | 303–327 | | | | | | | | |
| PENV_BLVAU | ENV POLYPROTEIN | BOVINE LEUKEMIA VIRUS (AUSTRALIAN ISOLATE) | 303–327 | | | | | | | | |
| PENV_BLVAV | ENV POLYPROTEIN | BOVINE LEUKEMIA VIRUS (AMERICAN ISOLATE VDM) | 303–327 | | | | | | | | |
| PENV_BLVB2 | ENV POLYPROTEIN | BOVINE LEUKEMIA VIRUS (BELGIUM ISOLATE LB285) | 303–327 | | | | | | | | |
| PENV_BLVB5 | ENV POLYPROTEIN | BOVINE LEUKEMIA VIRUS (BELGIUM ISOLATE LB59) | 303–327 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PENV_BLVJ | ENV POLYPROTEIN | BOVINE LEUKEMIA VIRUS (JAPANESE ISOLATE BLV-1) | 303–327 | | | | | | | | |
| PENV_FENV1 | ENV POLYPROTEIN PRECURSOR | FELINE ENDOGENOUS VIRUS ECE1 | 30–47 | 225–246 | 630–651 | | | | | | |
| PENV_FIVPE | ENV POLYPROTEIN PRECURSOR | FELINE ENDOGENOUS VIRUS ECE1 | 30–47 | 225–246 | 630–651 | | | | | | |
| PENV_FLVC6 | ENV POLYPROTEIN PRECURSOR | FELINE LEUKEMIA PROVIRUS (CLONE CFE-6) | 38–55 | 624–645 | | | | | | | |
| PENV_FLVGL | ENV POLYPROTEIN PRECURSOR | FELINE LEUKEMIA VIRUS (STRAIN A/GLASGOW-1) | 9–29 | 447–468 | 605–626 | | | | | | |
| PENV_FLVLB | ENV POLYPROTEIN PRECURSOR | FELINE LEUKEMIA VIRUS (STRAIN LAMBDA-B1) | 467–488 | 625–646 | | | | | | | |
| PENV_FLVSA | ENV POLYPROTEIN PRECURSOR | FELINE LEUKEMIA VIRUS (STRAIN SARMA) | 444–465 | 602–623 | | | | | | | |
| PENV_FOAMV | ENV POLYPROTEIN | HUMAN SPUMARETROVIRUS (FOAMY VIRUS) | 153–174 | 255–275 | 300–325 | 481–496 | 710–727 | 864–887 | 924–951 | 957–978 | |
| PENV_FSVGA | ENV POLYPROTEIN PRECURSOR | FELINE SARCOMA VIRUS (STRAIN GARDNER-ARNSTEIN) | 467–488 | 625–646 | | | | | | | |
| PENV_FSVGB | ENV POLYPROTEIN PRECURSOR | FELINE SARCOMA VIRUS (STRAIN GA) | 447–468 | 605–626 | | | | | | | |
| PENV_FSVSM | ENV POLYPROTEIN PRECURSOR | FELINE SARCOMA VIRUS (STRAIN SM) | 450–471 | 608–629 | | | | | | | |
| PENV_FSVST | ENV POLYPROTEIN PRECURSOR | FELINE SARCOMA VIRUS (STRAIN SNYDER-THEILEN) | 467–488 | | | | | | | | |
| PENV_GALV | ENV POLYPROTEIN PRECURSOR | GIBBON APE LEUKEMIA VIRUS | 519–540 | | | | | | | | |
| PENV_HV1B1 | GP160 PRECURSOR | HUMAN IMMUNODEFICIENCY VIRUS TYPE 1 (BH10 ISOLATE) | 498–520 | | | | | | | | |
| PENV_HV1B8 | GP160 PRECURSOR | HUMAN IMMUNODEFICIENCY VIRUS TYPE 1 (BH8 ISOLATE) | 493–515 | | | | | | | | |
| PENV_HV1BN | GP160 PRECURSOR | HUMAN IMMUNODEFICIENCY VIRUS TYPE 1 (BRAIN ISOLATE) | 494–516 | | | | | | | | |
| PENV_HV1BR | GP160 PRECURSOR | HUMAN IMMUNODEFICIENCY VIRUS TYPE 1 (BRU ISOLATE) | 503–525 | | | | | | | | |
| PENV_HV1C4 | GP160 PRECURSOR | HUMAN IMMUNODEFICIENCY VIRUS TYPE 1 (CDC-451 ISOLATE) | 428–448 | | | | | | | | |
| PENV_HV1EL | GP160 PRECURSOR | HUMAN IMMUNODEFICIENCY VIRUS TYPE 1 (ELI ISOLATE) | 495–517 | | | | | | | | |
| PENV_HV1H2 | GP160 PRECURSOR | HUMAN IMMUNODEFICIENCY VIRUS TYPE 1 (HXB2 ISOLATE) | 498–520 | | | | | | | | |
| PENV_HV1H3 | GP160 PRECURSOR | HUMAN IMMUNODEFICIENCY VIRUS TYPE 1 (HXB3 ISOLATE) | 498–520 | | | | | | | | |
| PENV_HV1J3 | GP160 PRECURSOR | HUMAN IMMUNODEFICIENCY VIRUS TYPE 1 (JH3 ISOLATE) | 510–532 | | | | | | | | |
| PENV_HV1JR | GP160 PRECURSOR | HUMAN IMMUNODEFICIENCY VIRUS TYPE 1 (JRCSF ISOLATE) | 490–512 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PENV_HV1KB | GP160 PRECURSOR | HUMAN IMMUNODEFICIENCY VIRUS TYPE 1 (STRAIN KB-1-GP32) | 504–526 | 552–579 | 752–768 | | | | | | |
| PENV_HV1MA | GP160 PRECURSOR | HUMAN IMMUNODEFICIENCY VIRUS TYPE 1 (MAL ISOLATE) | 500–522 | | | | | | | | |
| PENV_HV1MF | GP160 PRECURSOR | HUMAN IMMUNODEFICIENCY VIRUS TYPE 1 (MFA ISOLATE) | 496–518 | | | | | | | | |
| PENV_HV1N5 | GP160 PRECURSOR | HUMAN IMMUNODEFICIENCY VIRUS TYPE 1 (NEW YORK-5 ISOLATE) | 178–203 | | | | | | | | |
| PENV_HV1ND | GP160 PRECURSOR | HUMAN IMMUNODEFICIENCY VIRUS TYPE 1 (NDK ISOLATE) | 488–510 | | | | | | | | |
| PENV_HV1OY | GP160 PRECURSOR | HUMAN IMMUNODEFICIENCY VIRUS TYPE 1 (OYI ISOLATE) | 123–140 | | | | | | | | |
| PENV_HV1PV | GP160 PRECURSOR | HUMAN IMMUNODEFICIENCY VIRUS TYPE 1 (PV22 ISOLATE) | 498–520 | | | | | | | | |
| PENV_HV1RH | GP160 PRECURSOR | HUMAN IMMUNODEFICIENCY VIRUS TYPE 1 (RF/HAT ISOLATE) | 445–460 | | | | | | | | |
| PENV_HV1S1 | GP160 PRECURSOR | HUMAN IMMUNODEFICIENCY VIRUS TYPE 1 (SF162 ISOLATE) | 489–511 | 738–754 | | | | | | | |
| PENV_HV1S3 | GP160 PRECURSOR | HUMAN IMMUNODEFICIENCY VIRUS TYPE 1 (SF33 ISOLATE) | 300–322 | | | | | | | | |
| PENV_HV122 | GP160 PRECURSOR | HUMAN IMMUNODEFICIENCY VIRUS TYPE 1 (Z2/CDC-Z34 ISOLATE) | 123–145 | 410–427 | 495–517 | | | | | | |
| PENV_HV1Z3 | GP160 PRECURSOR | HUMAN IMMUNODEFICIENCY VIRUS TYPE 1 (ZAIRE 3 ISOLATE) | 117–133 | 175–198 | | | | | | | |
| PENV_HV1Z6 | GP160 PRECURSOR | HUMAN IMMUNODEFICIENCY VIRUS TYPE 1 (ZAIRE 6 ISOLATE) | 497–519 | | | | | | | | |
| PENV_HV1Z8 | GP160 PRECURSOR | HUMAN IMMUNODEFICIENCY VIRUS TYPE 1 (Z-84 ISOLATE) | 505–527 | | | | | | | | |
| PENV_HV1ZH | GP160 PRECURSOR | HUMAN IMMUNODEFICIENCY VIRUS TYPE 1 (ZAIRE HZ321 ISOLATE) | 123–142 | 438–453 | 498–520 | | | | | | |
| PENV_HV2BE | GP160 PRECURSOR | HUMAN IMMUNODEFICIENCY VIRUS TYPE 2 (ISOLATE BEN) | 3–26 | 750–775 | 781–804 | | | | | | |
| PENV_HV2CA | GP160 PRECURSOR | HUMAN IMMUNODEFICIENCY VIRUS TYPE 2 (ISOLATE CAM2) | 750–777 | | | | | | | | |
| PENV_HV2D1 | GP160 PRECURSOR | HUMAN IMMUNODEFICIENCY VIRUS TYPE 2 (ISOLATE D194) | 3–26 | 741–766 | 772–795 | | | | | | |
| PENV_HV2D2 | GP160 PRECURSOR | HUMAN IMMUNODEFICIENCY VIRUS TYPE 2 (ISOLATE D205.7) | 9–28 | | | | | | | | |
| PENV_HV2G1 | GP160 PRECURSOR | HUMAN IMMUNODEFICIENCY VIRUS TYPE 2 (ISOLATE GHANA-1) | 741–766 | 772–795 | | | | | | | |
| PENV_HV2NZ | GP160 PRECURSOR | HUMAN IMMUNODEFICIENCY VIRUS TYPE 2 (ISOLATE NIH-Z) | 742–767 | 777–800 | | | | | | | |
| PENV_HV2RO | GP160 PRECURSOR | HUMAN IMMUNODEFICIENCY VIRUS TYPE 2 (ISOLATE ROD) | 751–776 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PENV_HV2SB | GP160 PRECURSOR | HUMAN IMMUNODEFICIENCY VIRUS TYPE 2 (ISOLATE SBLISY) | 743–768 | 778–804 | | | | | | | |
| PENV_HV2ST | GP160 PRECURSOR | HUMAN IMMUNODEFICIENCY VIRUS TYPE 2 (ISOLATE ST) | 745–770 | | | | | | | | |
| PENV_JSRV | ENV POLYPROTEIN PRECURSOR | SHEEP PULMONARY ADENOMATOSIS VIRUS | 104–119 | 299–325 | 376–398 | 541–564 | | | | | |
| PENV_MCFF | ENV POLYPROTEIN PRECURSOR | MINK CELL FOCUS-FORMING MURINE LEUKEMIA VIRUS | 600–621 | | | | | | | | |
| PENV_MCFF3 | ENV POLYPROTEIN PRECURSOR | MINK CELL FOCUS-FORMING MURINE LEUKEMIA VIRUS (ISOLATE CI- | 601–622 | | | | | | | | |
| PENV_MLVAV | ENV POLYPROTEIN PRECURSOR | AKV MURINE LEUKEMIA VIRUS | 630–651 | | | | | | | | |
| PENV_MLVCB | ENV POLYPROTEIN PRECURSOR | CAS-BR-E MURINE LEUKEMIA VIRUS | 625–646 | | | | | | | | |
| PENV_MLVF5 | ENV POLYPROTEIN PRECURSOR | FRIEND MURINE LEUKEMIA VIRUS (ISOLATE 57) | 639–660 | | | | | | | | |
| PENV_MLVFF | ENV POLYPROTEIN PRECURSOR | FRIEND MURINE LEUKEMIA VIRUS (ISOLATE FB29) | 639–660 | | | | | | | | |
| PENV_MLVFP | ENV POLYPROTEIN PRECURSOR | FRIEND MURINE LEUKEMIA VIRUS (ISOLATE PVC-211) | 639–660 | | | | | | | | |
| PENV_MLVHO | ENV POLYPROTEIN PRECURSOR | HOMULV MURINE LEUKEMIA VIRUS (MUS HORTULANUS VIRUS) | 626–647 | | | | | | | | |
| PENV_MLVK1 | ENV POLYPROTEIN PRECURSOR | KRISTEN MURINE LEUKEMIA VIRUS | 167–188 | | | | | | | | |
| PENV_MLVMO | ENV POLYPROTEIN PRECURSOR | MOLONEY MURINE LEUKEMIA VIRUS | 629–650 | | | | | | | | |
| PENV_MLVRD | ENV POLYPROTEIN PRECURSOR | RADIATION MURINE LEUKEMIA VIRUS | 624–645 | | | | | | | | |
| PENV_MLVRK | ENV POLYPROTEIN PRECURSOR | RADIATION MURINE LEUKEMIA VIRUS (STRAIN KAPLAN) | 624–645 | | | | | | | | |
| PENV_MMTVB | ENV POLYPROTEIN PRECURSOR | MOUSE MAMMARY TUMOR VIRUS (STRAIN BR6) | 643–663 | | | | | | | | |
| PENV_MMTVG | ENV POLYPROTEIN | MOUSE MAMMARY TUMOR VIRUS (STRAIN GR) | 643–663 | | | | | | | | |
| PENV_MPMV | ENV POLYPROTEIN PRECURSOR | SIMIA MASON-PFIZER VIRUS | 213–235 | | | | | | | | |
| PENV_MSVFB | ENV POLYPROTEIN PRECURSOR | FBJ MURINE OSTEOSARCOMA VIRUS | 170–191 | | | | | | | | |
| PENV_OMVVS | ENV POLYPROTEIN PRECURSOR | OVINE LENTIVIRUS (STRAIN SA-OMVV) | 658–683 | | | | | | | | |
| PENV_RMCFV | ENV POLYPROTEIN PRECURSOR | RAUSCHER MINK CELL FOCUS-INDUCING VIRUS | 603–624 | | | | | | | | |
| PENV_RSVP | ENV POLYPROTEIN | ROUS SARCOMA VIRUS (STRAIN PRAGUE C) | 42–69 | 533–552 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PENV_SFV1 | ENV POLYPROTEIN | SIMIAN FOAMY VIRUS (TYPE 1) | 300–325 | 710–727 | 864–887 | 924–951 | 957–978 | | | | |
| PENV_SFV3L | ENV POLYPROTEIN | SIMIAN FOAMY VIRUS (TYPE 3/STRAIN LK3) | 157–178 | 304–329 | 707–724 | 861–884 | 921–948 | 954–975 | | | |
| PENV_SIVA1 | GP160 PRECURSOR | SIMIAN IMMUNODEFICIENCY VIRUS (AGM155 ISOLATE) | 437–458 | | | | | | | | |
| PENV_SIVAG | GP160 PRECURSOR | SIMIAN IMMUNODEFICIENCY VIRUS (AGM3 ISOLATE) | 442–463 | | | | | | | | |
| PENV_SIVA1 | GP160 PRECURSOR | SIMIAN IMMUNODEFICIENCY VIRUS (ISOLATE AGM/CLONE GRI-1) | 421–442 | | | | | | | | |
| PENV_SIVAT | GP160 PRECURSOR | SIMIAN IMMUNODEFICIENCY VIRUS (TYO-1 ISOLATE) | 435–456 | | | | | | | | |
| PENV_SIVGB | GP160 PRECURSOR | SIMIAN IMMUNODEFICIENCY VIRUS (ISOLATE GB1) | 93–109 | | | | | | | | |
| PENV_SIVM1 | GP160 PRECURSOR | SIMIAN IMMUNODEFICIENCY VIRUS (MM142-83 ISOLATE) | 766–793 | 803–826 | | | | | | | |
| PENV_SIVMK | GP160 PRECURSOR | SIMIAN IMMUNODEFICIENCY VIRUS (K6W ISOLATE) | 139–154 | 765–792 | 802–825 | | | | | | |
| PENV_SIVML | GP160 PRECURSOR | SIMIAN IMMUNODEFICIENCY VIRUS (K78 ISOLATE) | 139–154 | 764–791 | 801–824 | | | | | | |
| PENV_SIVS4 | GP160 PRECURSOR | SIMIAN IMMUNODEFICIENCY VIRUS (F236/SMH4 ISOLATE) | 769–789 | 806–829 | | | | | | | |
| PENV_SIVSP | GP160 PRECURSOR | SIMIAN IMMUNODEFICIENCY VIRUS (BPJ/BC13 ISOLATE) | 773–793 | 810–833 | | | | | | | |
| PENV_SMSAV | P15E PROTEIN | SIMIAN SARCOMA VIRUS | 42–63 | | | | | | | | |
| PENV_SRV1 | EVN POLYPROTEIN | SIMIAN RETROVIRUS SRV-1 | 213–235 | | | | | | | | |
| PERBA_AVIER | ERBA ONCOGENE PROTEIN | AVIAN ERYTHROBLASTOSIS VIRUS (STRAIN ES4) | 227–249 | | | | | | | | |
| PERG1_FOWP1 | EARLY TRANSCRIPTION FACTOR | FOWLPOX VIRUS (STRAIN FP-1) | 21–41 | 73–92 | | | | | | | |
| PETF1_SFVKA | EARLY TRANSCRIPTION FACTOR | SHOPE FIBROMA VIRUS (STRAIN KASZA) | 21–41 | | | | | | | | |
| PETF1_VACCC | EARLY TRANSCRIPTION FACTOR | VACCINIA VIRUS (STRAIN COPENHAGEN) | 21–41 | | | | | | | | |
| PETF1_VACCV | EARLY TRANSCRIPTION FACTOR | VACCINIA VIRUS (STRAIN WR) | 21–41 | | | | | | | | |
| PETF2_VACCC | EARLY TRANSCRIPTION FACTOR 82 KD SUBUNIT | VACCINIA VIRUS (STRAIN COPENHAGEN) | 50–73 | 101–117 | 165–187 | 285–308 | 558–582 | | | | |
| PETF2_VACCV | EARLY TRANSCRIPTION FACTOR 82 KD SUBUNIT | VACCINIA VIRUS (STRAIN WR) | 48–72 | | | | | | | | |
| PETF2_VARV | EARLY TRANSCRIPTION FACTOR 82 KD SUBUNIT | VARIOLA VIRUS | 50–73 | 101–117 | 165–187 | 285–308 | 558–582 | | | | |
| PEXON_HSV11 | ALKALINE EXONULEASE | HERPES SIMPLEX VIRUS (TYPE 1/STRAIN 17) | 165–180 | | | | | | | | |
| PEXON_HSV2 | ALKALINE EXONULEASE | HERPES SIMPLEX VIRUS (TYPE 2) | 155–170 | | | | | | | | |
| PEXON_HSVEB | ALKALINE EXONULEASE | EQUINE HERPES VIRUS TYPE 1 (STRAIN AB4P) | 276–291 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PEXON_PRVN3 | ALKALINE EXONULEASE | PSEUDORABIES VIRUS (STRAIN NIA-3) | 36–51 | | | | | | | | |
| PEXON_VZVD | ALKALINE EXONULEASE | VARICELLA-ZOSTER VIRUS (STRAIN DUMAS) | 28–44 | 217–262 | | | | | | | |
| PFIB2_ADE40 | 41 4 KD FIBER PROTEIN | HUMAN ADENOVIRUS TYPE 40 | 116–133 | | | | | | | | |
| PFIB2_ADE41 | 41 4 KD FIBER PROTEIN | HUMAN ADENOVIRUS TYPE 41 | 116–133 | | | | | | | | |
| PFIBP_ADE03 | FIBER PROTEIN | HUMAN ADENOVIRUS TYPE 3 | 152–173 | | | | | | | | |
| PFIBP_ADE05 | FIBER PROTEIN | HUMAN ADENOVIRUS TYPE 5 | 447–473 | | | | | | | | |
| PFIBP_ADEB3 | FIBER PROTEIN | BOVINE ADENOVIRUS TYPE 3 (MASTADENOVIRUS BOS3) | 347–372 | 775–801 | | | | | | | |
| PFIBP_ADEC1 | FIBER PROTEIN | CANINE ADENOVIRUS TYPE 1 (STRAIN GLAXO) | 382–397 | | | | | | | | |
| FP1BP_ADEM1 | FIBER PROTEIN | MOUSE ADENOVIRUS TYPE 1 | 191–215 | 227–252 | 493–513 | 548–571 | 579–599 | | | | |
| PGAG_AVEV1 | GAG POLYPROTEIN | AVIAN ENDOGENOUS VIRUS EV-1 | 53–78 | | | | | | | | |
| PGAG_AVEV2 | GAG POLYPROTEIN | AVIAN ENDOGENOUS ROUS-ASSOCIATED VIRUS-0 | 2–27 | | | | | | | | |
| PGAG_AVIMC | GAG POLYPROTEIN | AVIAN MYELOCYTOMATOSIS VIRUS MC29 | 53–78 | | | | | | | | |
| PGAG_AVIMD | GAG POLYPROTEIN | AVIAN MYELOCTYOMATOSIS VIRUS HB1 | 53–78 | | | | | | | | |
| PGAG_AVISU | CORE PROTEIN P19 | AVIAN SARCOMA VIRUS (STRAIN UR2) | 53–78 | | | | | | | | |
| PGAG_AVISY | GAG POLYPROTEIN | AVIAN SARCOMA VIRUS (STRAIN Y73) | 53–78 | | | | | | | | |
| PGAG_BAEVM | GAG POLYPROTEIN | BABOON ENDOGENOUS VIRUS (STRAIN M7) | 397–422 | | | | | | | | |
| PGAG_BLVAU | GAG POLYPROTEIN | BOVINE LEUKEMIA VIRUS (AUSTRALIAN ISOLATE) | 212–238 | | | | | | | | |
| PGAG_BLVJ | GAG POLYPROTEIN | BOVINE LEUKEMIA VIRUS (JAPANESE ISOLATE BLV-1) | 213–239 | | | | | | | | |
| PGAG_CAEVC | GAG POLYPROTEIN | CAPRINE ARTHRITIS ENCEPHALITIS VIRUS (STRAIN CORK) | 102–119 | | | | | | | | |
| PGAG_FUJSV | GAG POLYPROTEIN | FUJINAMI SARCOMA VIRUS | 53–78 | | | | | | | | |
| PGAG_HTL1A | GAG POLYPROTEIN | HUMAN T-CELL LEUKEMIA VIRUS TYPE 1 (STRAIN ATK) | 77–94 | | | | | | | | |
| PGAG_HTL1C | GAG POLYPROTEIN | HUMAN T-CELL LEUKEMIA VIRUS TYPE 1 (CARIBBEAN ISOLATE) | 77–94 | | | | | | | | |
| PGAG_HTL1M | GAG POLYPROTEIN | HUMAN T-CELL LEUKEMIA VIRUS TYPE 1 (ISOLATE MT-2) | 77–94 | | | | | | | | |
| PGAG_HV1A2 | GAG POLYPROTEIN | HUMAN IMMUNODEFICIENCY VIRUS TYPE 1 (ARV2/SF2 ISOLATE) | 65–91 | | | | | | | | |
| PGAG_HV1B1 | GAG POLYPROTEIN | HUMAN IMMUNODEFICIENCY VIRUS TYPE 1 (BH10 ISOLATE) | 65–91 | | | | | | | | |
| PGAG_HV1B5 | GAG POLYPROTEIN | HUMAN IMMUNODEFICIENCY VIRUS TYPE 1 (BH5 ISOLATE) | 65–91 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PGAG_HV1BR | GAG POLYPROTEIN | HUMAN IMMUNODEFICIENCY VIRUS TYPE 1 (BRU ISOLATE) | 65–91 | | | | | | | | |
| PGAG_HV1C4 | GAG POLYPROTEIN | HUMAN IMMUNODEFICIENCY VIRUS TYPE 1 (CDC-451 ISOLATE) | 65–91 | | | | | | | | |
| PGAG_HV1EL | GAG POLYPROTEIN | HUMAN IMMUNODEFICIENCY VIRUS TYPE 1 (ELI ISOLATE) | 65–91 | | | | | | | | |
| PGAG_HV1H2 | GAG POLYPROTEIN | HUMAN IMMUNODEFICIENCY VIRUS TYPE 1 (HXB2 ISOLATE) | 65–91 | | | | | | | | |
| PGAG_HV1J3 | GAG POLYPROTEIN | HUMAN IMMUNODEFICIENCY VIRUS TYPE 1 (JH3 ISOLATE) | 65–91 | | | | | | | | |
| PGAG_HV1JR | GAG POLYPROTEIN | HUMAN IMMUNODEFICIENCY VIRUS TYPE 1 (JRCSF ISOLATE) | 65–91 | | | | | | | | |
| PGAG_HV1MA | GAG POLYPROTEIN | HUMAN IMMUNODEFICIENCY VIRUS TYPE 1 (MAL ISOLATE) | 262–285 | | | | | | | | |
| PGAG_HV1MN | GAG POLYPROTEIN | HUMAN IMMUNODEFICIENCY VIRUS TYPE 1 (MN ISOLATE) | 65–91 | | | | | | | | |
| PGAG_HV1N5 | GAG POLYPROTEIN | HUMAN IMMUNODEFICIENCY VIRUS TYPE 1 (NEW YORK-5 ISOLATE) | 65–91 | | | | | | | | |
| PGAG_HV1ND | GAG POLYPROTEIN | HUMAN IMMUNODEFICIENCY VIRUS TYPE 1 (NDK ISOLATE) | 65–91 | 352–373 | | | | | | | |
| PGAG_HV1OY | GAG POLYPROTEIN | HUMAN IMMUNODEFICIENCY VIRUS TYPE 1 (OY1 ISOLATE) | 65–91 | | | | | | | | |
| PGAG_HV1PV | GAG POLYPROTEIN | HUMAN IMMUNODEFICIENCY VIRUS TYPE 1 (PV22 ISOLATE) | 65–91 | | | | | | | | |
| PGAG_HV1RH | GAG POLYPROTEIN | HUMAN IMMUNODEFICIENCY VIRUS TYPE 1 (RF/HAT ISOLATE) | 65–91 | | | | | | | | |
| PGAG_HV1U4 | GAG POLYPROTEIN | HUMAN IMMUNODEFICIENCY VIRUS TYPE 1 (STRAIN UGANDAN/ISO) | 65–91 | | | | | | | | |
| PGAG_HV1W2 | GAG POLYPROTEIN | HUMAN IMMUNODEFICIENCY VIRUS TYPE 1 (WM12 ISOLATE) | 65–91 | | | | | | | | |
| PGAG_HV1Z2 | GAG POLYPROTEIN | HUMAN IMMUNODEFICIENCY VIRUS TYPE 1 (Z2/CDC-Z34 ISOLATE) | 65–91 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PGAG__SFV1 | GAG POLYPROTEIN | SIMIAN FOAMY VIRUS (TYPE 1) | 85–103 | | | | | | | | |
| PGAG__SFV3L | GAG POLYPROTEIN | SIMIAN FOAMY VIRUS (TYPE 3/STRAIN LK3) | 83–101 | | | | | | | | |
| PGAG__SIVA1 | GAG POLYPROTEIN | SIMIAN IMMUNODEFICIENCY VIRUS (AGM155 ISOLATE) | 189–213 | | | | | | | | |
| PGAG__SIVAG | GAG POLYPROTEIN | SIMIAN IMMUNODIFICIENCY VIRUS (AGM3 ISOLATE) | 193–217 | | | | | | | | |
| PGAG__SIVAT | GAG POLYPROTEIN | SIMIAN IMMUNODEFICIENCY VIRUS (TYO-1 ISOLATE) | 189–213 | | | | | | | | |
| PGAG__SIVCZ | GAG POLYPROTEIN | CHIMPANZEE IMMUNODEFICIENCY VIRUS (SIV(CPZ)) | 66–92 | | | | | | | | |
| PGAG__SIVGB | GAG POLYPROTEIN | SIMIAN IMMUNODIFICIENCY VIRUS (ISOLATE GB) | 66–92 | | | | | | | | |
| PGAG__SIVM1 | GAG POLYPROTEIN | SIMIAN IMMUNODEFCICENCY VIRUS (MM142-83 ISOLATE) | | | | | | | | | |
| PGAG__SMRVH | GAG POLYPROTEIN | SQUIRREL MONKEY RETROVIRUS (SMRV-H) | 286–307 | | | | | | | | |
| PGLRX__VACCC | POSSIBLE GLUTAREDOXIN | VACCINIA VIRUS (STRAIN COPENHAGEN), AND (STRAIN L-IVP) | 71–87 | | | | | | | | |
| PGLRX__VARV | POSSIBLE GLUTAREDOXIN | VARIOLA VIRUS | 71–87 | | | | | | | | |
| PGRAN__GVAS | GRANULIN | AGROTIS SEGETUM GRANULOSIS VIRUS | 208–226 | | | | | | | | |
| PGRAN__GVTN | GRANULIN | TRICHOPLUSIA NI GRANULOSIS VIRUS | 209–227 | | | | | | | | |
| PGRFA__VACCC | GROWHT FACTOR | VACCINIA VIRUS (STRAIN COPENHAGEN) | 104–124 | | | | | | | | |
| PGRFA__VACCV | GROWTH FACTOR | VACCINIA VIRUS (STRAIN WR) | 104–123 | | | | | | | | |
| PGRFA__VARV | GROWTH FACTOR | VARIOLA VIRUS | 104–122 | | | | | | | | |
| PHELI__EBV | PROBABLE HELICASE | EPSTEIN-BARR VIRUS (STRAIN B95-8) | 180–207 | 338–361 | 438–464 | | | | | | |
| PHELI__HCMVA | PROBABLE HELICASE | HUMAN CYTOMEGALOVIRUS (STRAIN AD169) | 397–420 | 539–560 | 826–852 | | | | | | |
| PHELI__HSV11 | PROBABLE HELICASE | HERPES SIMPLEX VIRUS (TYPE 1/STRAIN 17) | 389–408 | 628–646 | | | | | | | |
| PHELI__HSV2H | PROBABLE HELICASE | HERPES SIMPLEX VIRUS (TYPE 2/STRAIN HG52) | 290–309 | 529–554 | | | | | | | |
| PHELI__HSVEB | PROBABLE HELICASE | EQUINE HERPESVIRUS TYPE 1 (STRAIN AB4P) | 181–204 | 243–266 | 394–413 | | | | | | |
| PHELI__HSVSA | PROBABLE HELICASE | HERPESVIRUS SAIMIRI (STRAIN 11) | 327–350 | 389–411 | 658–683 | | | | | | |
| PHELI__VZVD | PROBABLE HELICASE | VARICELLA-ZOSTER VIRUS (STRAIN DUMAS) | 165–189 | 383–402 | 561–578 | 761–786 | | | | | |
| PHEMA__CDVO | HEMAGGLUTININ-NEURAMINIDASE | CANINE DISTEMPER VIRUS (STRAIN ONDERSTEPOORT) | 36–53 | 200–223 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_CVBF | HEMAGGLUTININ-ESTERASE PRECURSOR | BOVINE CORONAVIRUS (STRAIN F15) | 391–415 | | | | | | | | |
| PHEMA_CVBLY | HEMAGGLUTININ-ESTERASE PRECURSOR | BOVINE CORONAVIRUS (STRAIN LY-138) | 391–415 | | | | | | | | |
| PHEMA_

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IADH4 | HEMAGGLUTININ PRECURSOR | INFLUENZA A VIRUS (STRAIN A/DUCK/HOKKAIDO/7/82) | 21–43 | 306–323

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IAHLO | HEMAGGLUTININ PRECURSOR | INFLUENZA A VIRUS (STRAIN A/EQUINE/LONDON/1416/73) | 230–246 | 315–332 | | | | | | | |
| PHEMA_IAHMI | HEMAGGLUTININ PRECURSOR | INFLUENZA A VIRUS (STRAIN A/EQUINE/MIANI/1/63) | 236–252 | 321–338 | | | | | | | |
| PHEMA_IAHNM | HEMAGGLUTININ PRECURSOR | INFLUENZA A VIRUS (STRAIN A/EQUINE/NEW MARKET/76) | 236–252 | 321–338 | | | | | | | |
| PHEMA_IAHNN | HEMAGGLUTININ PRECURSOR | INFLUENZA A VIRUS (STRAIN A/EQUINE/NEW MARKET/1/77) | 315–332 | | | | | | | | |
| PHEMA_IAHPR | HEMAGGLUTININ PRECURSOR | INFLUENZA A VIRUS (STRAIN A/EQUINE/PRAGUE/1/56) | 315–332 | | | | | | | | |
| PHEMA_IAHRO | HEMAGGLUTININ PRECURSOR | INFLUENZA A VIRUS (STRAIN A/EQUINE/ROMANIA/80) | 236–252 | 321–338 | | | | | | | |
| PHEMA_IAHSA | HEMAGGLUTININ PRECURSOR | INFLUENZA A VIRUS (STRAIN A/EQUINE/SANTIAGO/1/85) | 236–252 | 321–338 | | | | | | | |
| PHEMA_IAHSP | HEMAGGLUTININ PRECURSOR | INFLUENZA A VIRUS (STRAIN A/EQUINE/SAO PAULO/1/76) | 230–246 | 315–332 | | | | | | | |
| PHEMA_IAHSW | HEMAGGLUTININ PRECURSOR | INFLUENZA A VIRUS (STRAIN A/EQUINE/SWITZERLAND/137/72) | 230–246 | 315–332 | | | | | | | |
| PHEMA_IAHTE | HEMAGGLUTININ PRECURSOR | INFLUENZA A VIRUS (STRAIN A/EQUINE/TENNESSEE/5/86) | 236–252 | 321–338 | | | | | | | |
| PHEMA_IAHTO | HEMAGGLUTININ PRECURSOR | INFLUENZA A VIRUS (STRAIN A/EQUINE/TOKYO/71) | 236–252 | 321–338 | | | | | | | |
| PHEMA_IAHUR | HEMAGGLUTININ PRECURSOR | INFLUENZA A VIRUS (STRAIN A/EQUINE/URUGUAY/1/63) | 236–252 | 321–338 | | | | | | | |
| PHEMA_IAJAP | HEMAGGLUTININ PRECURSOR | INFLUENZA A VIRUS (STRAIN A/JAPAN/305/57) | 317–334 | | | | | | | | |
| PHEMA_IAMAA | HEMAGGLUTININ PRECURSOR | INFLUENZA A VIRUS (STRAIN A/MALLARD/ASTRAKHAN/244/82) | 197–223 | 319–336 | | | | | | | |
| PHEMA_IAMAB | HEMAGGLUTININ PRECURSOR | INFLUENZA A VIRUS (STRAIN A/MALLARD/ASTRAKHAN/263/82) | 202–228 | 324–341 | | | | | | | |
| PHEMA_IAMAO | HEMAGGLUTININ PRECURSOR | INFLUENZA A VIRUS (STRAIN A/MALLARD/NEW YORK/6874/78) | 37–59 | 322–339 | | | | | | | |
| PHEMA_IAME1 | HEMAGGLUTININ PRECURSOR | INFLUENZA A VIRUS (STRAIN A/MEMPHIS/1/71) | 37–59 | 322–339 | | | | | | | |
| PHEMA_IAME2 | HEMAGGLUTININ PRECURSOR | INFLUENZA A VIRUS (STRAIN A/MEMPHIS/102/72) | 37–59 | 322–339 | | | | | | | |
| PHEMA_IAME6 | HEMAGGLUTININ PRECURSOR | INFLUENZA A VIRUS (STRAIN A/MEMPHIS/6/86) | 21–43 | 306–323 | | | | | | | |
| PHEMA_IAMIN | HEMAGGLUTININ PRECURSOR | INFLUENZA A VIRUS (STRAIN A/MINK/SWEDEN/84) | 85–101 | 231–247 | 316–333 | | | | | | |
| PHEMA_IANT6 | HEMAGGLUTININ PRECURSOR | INFLUENZA A VIRUS (STRAIN A/NT/60/68) | 37–59 | 322–339 | | | | | | | |
| PHEMA_IAPIL | HEMAGGLUTININ PRECURSOR | INFLUENZA A VIRUS (STRAIN A/PILOT WHALE/MAINE/328/84) | 320–337 | | | | | | | | |
| PHEMA_IAQU7 | HEMAGGLUTININ PRECURSOR | INFLUENZA A VIRUS (STRAIN A/QU/T/70) | 21–43 | 306–323 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_IARUD | HEMAGGLUTININ PRECURSOR | INFLUENZA A VIRUS (STRAIN A/RUDDY TURNSTONE/ NEW JERSEY/4/47 | 320–337 | | | | | | | | |
| PHEMA_IASE2 | HEMAGGLUTININ PRECURSOR | INFLUENZA A VIRUS (STRAIN A/SEAL/MASSACHUSETT TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_INBID | HEMAGGLUTININ PRECURSOR | INFLUENZA B VIRUS (STRAIN B/ID/86) | 120–136 | 299–314 | | | | | | | |
| PHEMA_INBLE | HEMAGGLUTININ PRECURSOR | INFLUENZA B VIRUS (STRAIN B/LEE/40) | 123–139 | 302–317 | | | | | | | |
| PHEMA_INBMD | HEMAGGLUTININ PRECURSOR | INFLUENZA B VIRUS (STRAIN B/MARYLAND/59) | 113–129 | 292–307 | | | | | | | |
| PHEMA_INBME | HEMAGGLUTININ PRECURSOR | INFLUENZA B VIRUS (STRAIN B/MEMPHIS/6/86) | 116–132 | 296–311 | | | | | | | |
| PHEMA_INBNA | HEMAGGLUTININ PRECURSOR | INFLUENZA B VIRUS (STRAIN B/NAGASAKI/1/87) | 108–124 | 288–303 | | | | | | | |
| PHEMA_INBOR | HEMAGGLUTININ PRECURSOR | INFLUENZA B VIRUS (STRAIN B/OREGON/5/80) | 123–139 | 301–316 | | | | | | | |
| PHEMA_INBSI | HEMAGGLUTININ PRECURSOR | INFLUENZA B VIRUS (STRAIN B/SINGAPORE/222/79) | 123–139 | 301–316 | | | | | | | |
| PHEMA_INBSJ | HEMAGGLUTININ PRECURSOR | INFLUENZA B VIRUS (STRAIN B/SINGAPORE/64) | 119–135 | 298–313 | | | | | | | |
| PHEMA_INBUS | HEMAGGLUTININ PRECURSOR | INFLUENZA B VIRUS (STRAIN B/USSR/100/83) | 116–132 | 294–309 | | | | | | | |
| PHEMA_INBVI | HEMAGGLUTININ PRECURSOR | INFLUENZA B VIRUS (STRAIN B/VICTORIA/3/85) | 116–132 | 296–311 | | | | | | | |
| PHEMA_INBVK | HEMAGGLUTININ PRECURSOR | INFLUENZA B VIRUS (STRAIN B/VICTORIA/2/87) | 123–139 | 303–318 | | | | | | | |
| PHEMA_INBYB | HEMAGGLUTININ I | INFLUENZA B VIRUS (STRAIN B/YAMAGATA/16/88) | 108–124 | 286–301 | | | | | | | |
| PHEMA_INCCA | HEMAGGLUTININ PRECURSOR | INFLUENZA C VIRUS (STRAIN C/CALIFORNIA/78) | 442–466 | | | | | | | | |
| PHEMA_INCEN | HEMAGGLUTININ PRECURSOR | INFLUENZA C VIRUS (STRAIN C/ENGLAND/892/83) | 430–454 | | | | | | | | |
| PHEMA_INCGL | HEMAGGLUTININ PRECURSOR | INFLUENZA C VIRUS (STRAIN C/GREAT LAKES/1167/54) | 430–454 | | | | | | | | |
| PHEMA_INCHY | HEMAGGLUTININ PRECURSOR | INFLUENZA C VIRUS (STRAIN C/HYOGO/1/83) | 429–453 | | | | | | | | |
| PHEMA_INCJH | HEMAGGLUTININ PRECURSOR | INFLUENZA C VIRUS (STRAIN C/JOHANNESBURG/1/66) | 443–467 | | | | | | | | |
| PHEMA_INCKY | HEMAGGLUTININ PRECURSOR | INFLUENZA C VIRUS (STRAIN C/KYOTO/41/82) | 429–453 | | | | | | | | |
| PHEMA_INCMI | HEMAGGLUTININ PRECURSOR | INFLUENZA C VIRUS (STRAIN C/MISSISSIPPI/80) | 429–453 | | | | | | | | |
| PHEMA_INCNA | HEMAGGLUTININ PRECURSOR | INFLUENZA C VIRUS (STRAIN C/NARA/82) | 429–453 | | | | | | | | |
| PHEMA_INCP1 | HEMAGGLUTININ PRECURSOR | INFLUENZA C VIRUS (STRAIN C/PIG/BEIJING/10/81) | 430–454 | | | | | | | | |
| PHEMA_INCP2 | HEMAGGLUTININ PRECURSOR | INFLUENZA C VIRUS (STRAIN C/PIG/BEIJING/115/81) | 430–454 | | | | | | | | |
| PHEMA_INCP3 | HEMAGGLUTININ PRECURSOR | INFLUENZA C VIRUS (STRAIN C/PIG/BEIJING/439/82) | 430–454 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_INCTA | HEMAGGLUTININ PRECURSOR | INFLUENZA C VIRUS (STRAIN C/TAYLOR/1233/47) | 430–454 | | | | | | | | |
| PHEMA_INCYA | HEMAGGLUTININ PRECURSOR | INFLUENZA C VIRUS (STRAIN C/YAMAGATA/10/81) | 430–454 | | | | | | | | |
| PHEMA_MUMP1 | HEMAGGLUTININ-NEURAMINIDASE | MUMPS VIRUS (STRAIN SBL-1) | 101–125 | 133–148 | 225–246 | 367–394 | 397–417 | | | | |
| PHEMA_MUMPM | HEMAGGLUTININ-NEURAMINIDASE | MUMPS VIRUS (STRAIN MIYAHARA VACCINE) | 101–125 | 133–148 | 225–246 | 367–394 | 397–417 | | | | |
| PHEMA_MUMPR | HEMAGGLUTININ-NEURAMINIDASE | MUMPS VIRUS (STRAIN RW) | 101–125 | 133–148 | 225–246 | 367–394 | 397–417 | | | | |
| PHEMA_MUMPS | HEMAGGLUTININ-NEURAMINIDASE | MUMPS VIRUS (STRAIN SBL) | 101–125 | 133–148 | | | | | | | |
| PHEMA_NDVA | HEMAGGLUTININ-NEURAMINIDASE | NEWCASTLE DISEASE VIRUS (STRAIN AUSTRALIA-VICTORIA/32) | 93–110 | | | | | | | | |
| PHEMA_NDVB | HEMAGGLUTININ-NEURAMINIDASE | NEWCASTLE DISEASE VIRUS (STRAIN BEAUDETTE C/45) | 93–110 | | | | | | | | |
| PHEMA_NDVD | HEMAGGLUTININ-NEURAMINIDASE | NEWCASTLE DISEASE VIRUS (STRAIN D26/76) | 93–110 | | | | | | | | |
| PHEMA_NDVH4 | HEMAGGLUTININ-NEURAMINIDASE | NEWCASTLE DISEASE VIRUS (STRAIN B1-HITCHNER/47) | 93–110 | | | | | | | | |
| PHEMA_NDVI | HEMAGGLUTININ-NEURAMINIDASE | NEWCASTLE DISEASE VIRUS (STRAIN ITALIEN/45) | 93–110 | | | | | | | | |
| PHEMA_NDVM | HEMAGGLUTININ-NEURAMINIDASE | NEWCASTLE DISEASE VIRUS (STRAIN MIYADERA/51) | 93–110 | | | | | | | | |
| PHEMA_NDVQ | HEMAGGLUTININ-NEURAMINIDASE | NEWCASTLE DISEASE VIRUS (STRAIN QUEENSLAND/66) | 93–110 | | | | | | | | |
| PHEMA_NDVTG | HEMAGGLUTININ-NEURAMINIDASE | NEWCASTLE DISEASE VIRUS (STRAIN TEXAS G B/48) | 93–110 | | | | | | | | |
| PHEMA_NDVU | HEMAGGLUTININ-NEURAMINIDASE | NEWCASTLE DISEASE VIRUS (STRAIN ULSTER/67) | 93–110 | | | | | | | | |
| PHEMA_PHODV | HEMAGGLUTININ-NEURAMINIDASE | PHOCINE DISTEMPER VIRUS | 36–58 | 213–234 | 493–513 | | | | | | |
| PHEMA_PI1HW | HEMAGGLUTININ-NEURAMINIDASE | HUMAN PARAINFLUENZA 1 VIRUS (STRAIN WASHINGTON/1957) | 29–53 | 322–342 | 345–360 | 486–503 | | | | | |
| PHEMA_PI2H | HEMAGGLUTININ-NEURAMINIDASE | HUMAN PARAINFLUENZA 2 VIRUS (PIV-2) | 13–40 | 65–88 | 118–136 | | | | | | |
| PHEMA_PI2HT | HEMAGGLUTININ-NEURAMINIDASE | HUMAN PARAINFLUENZA 2 VIRUS (STRAIN TOSHIBA) | 13–40 | 65–88 | 118–136 | | | | | | |
| PHEMA_PI3B | HEMAGGLUTININ-NEURAMINIDASE | BOVINE PARAINFLUENZA 3 VIRUS | 111–128 | 272–299 | 324–340 | | | | | | |
| PHEMA_PI3H4 | HEMAGGLUTININ-NEURAMINIDASE | HUMAN PARAINFLUENZA 3 VIRUS (STRAIN N1H 47885) | 111–128 | 272–299 | 324–340 | | | | | | |
| PHEMA_PI3HA | HEMAGGLUTININ-NEURAMINIDASE | HUMAN PARAINFLUENZA 3 VIRUS (STRAIN AUS/124854/74) | 111–128 | 272–299 | 324–340 | | | | | | |
| PHEMA_PI3HT | HEMAGGLUTININ-NEURAMINIDASE | HUMAN PARAINFLUENZA 3 VIRUS (STRAIN TEX/545/80) | 111–128 | 272–299 | 324–340 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEMA_PI3HU | HEMAGGLUTININ-NEURAMINIDASE | HUMAN PARAINFLUENZA 3 VIRUS (STRAIN TEX/9305/82) | 111–128 | 272–299 | 324–340 | | | | | | |
| PHEMA_PI3HV | HEMAGGLUTININ-NEURAMINIDASE | HUMAN PARAINFLUENZA 3 VIRUS (STRAIN TEX/12677/83) | 111–128 | 272–299 | 324–340 | | | | | | |
| PHEMA_PI3HW | HEMAGGLUTININ-NEURAMINIDASE | HUMAN PARAINFLUENZA 3 VIRUS (STRAIN WASH/641/79) | 111–128 | 272–299 | 324–340 | | | | | | |
| PHEMA_PI3HX | HEMAGGLUTININ-NEURAMINIDASE | HUMAN PARAINFLUENZA 3 VIRUS (STRAIN WASH/1511/73) | 111–128 | 272–299 | 324–340 | | | | | | |
| PHEMA_PI4HA | HEMAGGLUTININ-NEURAMINIDASE | HUMAN PARAINFLUENZA 4A VIRUS (STRAIN TOSHIBA) | 50–67 | | | | | | | | |
| PHEMA_RINDK | HEMAGGLUTININ-NEURAMINIDASE | RINDERPEST VIRUS (STRAIN KABETE O) | 368–383 | | | | | | | | |
| PHEMA_RINDL | HEMAGGLUTININ-NEURAMINIDASE | RINDERPEST VIRUS (STRAIN L) | 4–30 | | | | | | | | |
| PHEMA_SEND5 | HEMAGGLUTININ-NEURAMINIDASE | SENDAI VIRUS (STRAIN Z/HOST MUTANTS) | 322–342 | | | | | | | | |
| PHEMA_SENDF | HEMAGGLUTININ-NEURAMINIDASE | SENDAI VIRUS (STRAIN FUSHIMI) | 322–342 | | | | | | | | |
| PHEMA_SENDH | HEMAGGLUTININ-NEURAMINIDASE | SENDAI VIRUS (STRAIN HARRIS) | 322–342 | | | | | | | | |
| PHEMA_SENDJ | HEMAGGLUTININ-NEURAMINIDASE | SENDAI VIRUS (STRAIN HVJ) | 322–342 | | | | | | | | |
| PHEMA_SENDZ | HEMAGGLUTININ-NEURAMINIDASE | SENDAI VIRUS (STRAIN Z) | 322–342 | | | | | | | | |
| PHEMA_SV41 | HEMAGGLUTININ-NEURAMINIDASE | SIMIAN VIRUS 41 | 55–73 | 85–102 | 107–132 | | | | | | |
| PHEMA_SV5 | HEMAGGLUTININ-NEURAMINIDASE | SIMIAN VIRUS 5 (STRAIN W3) | 7–28 | 84–101 | 379–400 | | | | | | |
| PHEMA_SV5CM | HEMAGGLUTININ-NEURAMINIDASE | SIMIAN VIRUS 5 (ISOLATE CANINE/CP1–) | 7–28 | 84–101 | 379–400 | | | | | | |
| PHEMA_SV5CP | HEMAGGLUTININ-NEURAMINIDASE | SIMIAN VIRUS 5 (ISOLATE CANINE/CP1+) | 7–28 | 84–101 | 379–400 | | | | | | |
| PHEMA_SV5LN | HEMAGGLUTININ-NEURAMINIDASE | | 7–28 | 84–101 | 379–400 | | | | | | |
| PHEMA_VACCC | HEMAGGLUTININ PRECURSOR | VACCINIA VIRUS (STRAIN COPENHAGEN) | 173–192 | | | | | | | | |
| PHEMA_VACCI | HEMAGGLUTININ PRECURSOR | VACCINIA VIRUS (STRAIN IHD-J) | 173–192 | | | | | | | | |
| PHEMA_VACCT | HEMAGGLUTININ PRECURSOR | VACCINIA VIRUS (STRAIN TIAN TAN) | 173–192 | | | | | | | | |
| PHEMA_VACCV | HEMAGGLUTININ PRECURSOR | VACCINIA VIRUS (STRAIN WR) | 173–192 | | | | | | | | |
| PHEMA_VARV | HEMAGGLUTININ PRECURSOR | VARIOLA VIRUS | 175–194 | | | | | | | | |
| PHEX8_ADE02 | HEXON-ASSOCIATED PROTEIN PRECURSOR | HUMAN ADENOVIRUS TYPE 2 | 38–61 | 119–140 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PHEX8_ADE03 | HEXON-ASSOCIATED PROTEIN PRECURSOR | HUMAN ADENOVIRUS TYPE 3 | 27–48 | | | | | | | | |
| PHEX8_ADE05 | HEXON-ASSOCIATED PROTEIN PRECURSOR | HUMAN ADENOVIRUS TYPE 5 | 38–61 | 119–140 | | | | | | | |
| PHEX8_ADE41 | HEXON-ASSOCIATED PROTEIN PRECURSOR | HUMAN ADENOVIRUS TYPE 41 | 38–61 | 128–146 | | | | | | | |
| PHEX8_ADEM1 | HEXON-ASSOCIATED PROTEIN PRECURSOR | MOUSE ADENOVIRUS TYPE 1 | 36–52 | | | | | | | | |
| PHEX9_ADE07 | HEXON-ASSOCIATED PROTEIN | HUMAN ADENOVIRUS TYPE 7 AND 3 | 92–117 | | | | | | | | |
| PHEX9_ADEC2 | HEXON-ASSOCIATED PROTEIN | CANINE ADENOVIRUS TYPE 2 | 52–77 | | | | | | | | |
| PHEX9_ADENT | HEXON-ASSOCIATED PROTEIN | TUPAIA ADENOVIRUS | 60–82 | | | | | | | | |
| PHRG_COWPX | HOST RANGE PROTEIN | COWPOX VIRUS | 517–533 | 558–583 | 609–636 | | | | | | |
| PI177_ASFB7 | LATE PROTEIN I177L | AFRICAN SWINE FEVER VIRUS (STRAIN BA71V) | 68–83 | | | | | | | | |
| PI196_ASFB7 | LATE PROTEIN I196L | AFRICAN SWINE FEVER VIRUS (STRAIN BA71V) | 169–190 | | | | | | | | |
| PI226_ASFB7 | LATE PROTEIN I226R | AFRICAN SWINE FEVER VIRUS (STRAIN BA71V) | 60–77 | | | | | | | | |
| PI329_ASFB7 | LATE PROTEIN I329L PRECURSOR | AFRICAN SWINE FEVER VIRUS (STRAIN BA71V) | 239–260 | | | | | | | | |
| PI78_ASFB7 | EARLY PROTEIN I78R | AFRICAN SWINE FEVER VIRUS (STRAIN BA71V) | 2–29 | | | | | | | | |
| PIBMP_SOCMV | INCLUSION BODY MATRIX PROTEIN | SOYBEAN CHLOROTIC MOTTLE VIRUS | 97–119 | | | | | | | | |
| PIC18_EBV | PROBABLE PROCESSING AND TRANSPORT PROTEIN | EPSTEIN-BARR VIRUS (STRAIN B95-8) | 101–123 | 131–153 | 759–777 | | | | | | |
| PIC18_HCMVA | PROBABLE PROCESSING AND TRANSPORT PROTEIN | HUMAN CYTOMEGALOVIRUS (STRAIN AD169) | 156–176 | 202–222 | | | | | | | |
| PIC18_HSV11 | PROBABLE PROCESSING AND TRANSPORT PROTEIN | HERPEX SIMPLEX VIRUS (TYPE 1/STRAIN 17) | 8–29 | 45–61 | 122–143 | 751–768 | | | | | |
| PIC18_HSV1A | PROBABLE PROCESSING AND TRANSPORT PROTEIN | HERPES SIMPLEX VIRUS (TYPE 1/STRAIN ANGELOTTI) | 8–29 | 45–61 | 122–143 | 751–768 | | | | | |
| PIC18_HSV1F | PROBABLE PROCESSING AND TRANSPORT PROTEIN | HERPES SIMPLEX VIRUS (TYPE 1/STRAIN F) | 8–29 | 122–143 | 746–763 | | | | | | |
| PIC18_HSVB2 | PROBABLE PROCESSING AND TRANSPORT PROTEIN | BOVINE HERPESVIRUS TYPE 2 (STRAIN BMV) | 12–37 | 130–151 | | | | | | | |
| PIC18_HSVEB | PROBABLE PROCESSING AND TRANSPORT PROTEIN | EQUINE HERPESVIRUS TYPE 1 | 37–56 | 129–144 | 732–755 | | | | | | |
| PIC18_HSVSA | PROBABLE PROCESSING AND TRANSPORT PROTEIN | HERPESVIRUS SAIMIRI (STRAIN 11) | 27–29 | 51–78 | 647–672 | | | | | | |
| PIC18_MCMVS | PROBABLE PROCESSING AND TRANSPORT PROTEIN | MURINE CYTOMEGALOVIRUS (STRAIN SMITH) | 126–144 | 202–229 | 386–411 | | | | | | |
| PIC18_PRVIF | PROBABLE PROCESSING AND TRANSPORT PROTEIN | PSEUDORABIES VIRUS (STRAIN INDIANA-FUNKHAUSER/BECKER) | 285–307 | 698–718 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PIC18_VZVD | PROBABLE PROCESSING AND TRANSPORT PROTEIN | VARICELLA-ZOSTER VIRUS (STRAIN DUMAS) | 69–88 | 619–639 | 725–744 | | | | | | |
| PICP0_HSV11 | IMMEDIATE-EARLY PROTEIN | HERPES SIMPLEX VIRUS (TYPE 1/STRAIN 17) | 668–684 | | | | | | | | |
| PICP0_HSV2H | VMW118 PROTEIN | HERPES SIMPLEX VIRUS (TYPE 2/STRAIN HG52) | 713–729 | | | | | | | | |
| PICP0_PRVIF | EARLY PROTEIN 0 | PSEUDORABIES VIRUS (STRAIN INDIANA-FUNKHAUSER/BECKER) | 82–102 | | | | | | | | |
| PICP3_HSV1F | INFECTED CELL PROTEIN | HERPES SIMPLEX VIRUS (TYPE 1/STRAIN F) | 211–227 | | | | | | | | |
| PICP4_HSV11 | TRANS-ACTING TRANSCRIPTIONAL PROTEIN | HERPES SIMPLEX VIRUS (TYPE 1/STRAIN 17) | 81–98 | 621–637 | | | | | | | |
| PICP4_HSVEB | TRANS-ACTING TRANSCRIPTIONAL PROTEIN | EQUINE HERPESVIRUS TYPE 1 (STRAIN AB4P) | 708–725 | 736–759 | | | | | | | |
| PICP4_HSVEK | TRANS-ACTING TRANSCRIPTIONAL PROTEIN | EQUINE HERPESVIRUS TYPE 1 (STRAIN KENTUCKY A) | 708–725 | 736–759 | | | | | | | |
| PICP4_HSVMG | TRANS-ACTING TRANSACTIVATOR PROTEIN | MAREK'S DISEASE HERPESVIRUS (STRAIN GA) | 488–506 | 585–611 | 1202–1218 | | | | | | |
| PICP4_VZVD | TRANS-ACTING TRANSCRIPTIONAL PROTEIN | VARICELLA-ZOSTER VIRUS (STRAIN DUMAS) | 547–563 | | | | | | | | |
| PIE18_PRVIF | IMMEDIATE-EARLY PROTEIN IE180 | PSEUDORABIES VIRUS (STRAIN INDIANA-FUNKHAUSER/BECKER) | 731–748 | | | | | | | | |
| PIE18_PRVKA | IMMEDIATE-EARLY PROTEIN IE180 | PSEUDORABIES VIRUS (STRAIN KAPLAN) | 720–737 | | | | | | | | |
| PIE63_HCMVA | TRANSCRIPTIONAL REGULATOR IE63 HOMOLOG ( | HUMAN CYTOMEGALOVIRUS (STRAIN AD169) | 286–304 | 364–383 | | | | | | | |
| PIE63_HSV11 | TRANSCRIPTIONAL REGULATOR IE63 | HERPES SIMPLEX VIRUS (TYPE 1/STRAIN 17) | 378–394 | | | | | | | | |
| PIE63_HSV2H | TRANSCRIPTIONAL REGULATOR IE63 | HERPES SIMPLEX VIRUS (TYPE 2/STRAIN HG52) | 378–394 | | | | | | | | |
| PIE63_HSVEB | TRANSCRIPTIONAL REGULARTOR IE63 HOMOLOG | EQUINE HERPESVIRUS TYPE 1 (STRAIN AB4P) | 337–353 | 385–406 | | | | | | | |
| PIE63_HSVSA | 52 KD IMMEDIATE-EARLY PHOSPHOPROTEIN | HERPESVIRUS SAIMIRI (STRAIN 11) | 301–326 | | | | | | | | |
| PIE68_HSV11 | IMMEDIATE-EARLY PROTEIN IE68 | HERPES SIMPLEX VIRUS (TYPE 1/STRAIN 17) | 189–205 | | | | | | | | |
| PIE68_HSVE4 | IMMEDIATE-EARLY PROTEIN IE68 | EQUINE HERPESVIRUS TYPE 4 | 81–104 | | | | | | | | |
| PIE68_HSVEB | IMMEDIATE-EARLY PROTEIN | EQUINE HERPESVIRUS TYPE 1 | 93–116 | | | | | | | | |
| PIE68_PRVKA | IMMEDIATE-EARLY PROTEIN | PSEUDORABIES VIRUS (STRAIN KAPLAN) | 85–108 | | | | | | | | |
| PEI68_VZVD | GENE 63/70 PROTEIN | VARICELLA-ZOSTER VIRUS (STRAIN DUMAS) | 57–78 | | | | | | | | |
| PIR14_HCMVA | HYPOTHETICAL PROTEIN | HUMAN CYTOMEGALOVIRUS (STRAIN AD169) | 117–137 | | | | | | | | |
| PKERB_AVIER | ERBB TYROSINE KINASE TRANSFORMING PROTEIN | AVIAN ERYTHROBLASTOSIS VIRUS | 64–84 | 297–324 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PKFES_FSVGA | TYROSINE-PROTEIN KINASE TRANSFORMING PROTEIN | FELINE SARCOMA VIRUS (STRAIN GARDNER-ARNSTEIN) | 73–88 | | | | | | | | |
| PKFES_FSVST | TYROSINE-PROTEIN KINASE TRANSFORMING PROTEIN | FELINE SARCOMA VIRUS (STRAIN SNYDER-THEILEN) | 2–22 | | | | | | | | |
| PKFGR_FSVGR | TYROSINE-PROTEIN KINASE TRANSFORMING PROTEIN | FELINE SARCOMA VIRUS (STRAIN GARDNER-RASHEED) | 269–288 | | | | | | | | |
| PKFMS_FSVMD | FMS TYROSINE KINASE TRANSFORMING PROTEIN | FELINE SARCOMA VIRUS (STRAIN MCDONOUGH) | 141–159 | 243–263 | 434–450 | 548–563 | 781–801 | 856–877 | | | |
| PKFPS_AVISP | TYROSINE-PROTEIN KINASE TRANSFORMING PROTEIN | AVIAN SARCOMA VIRUS (STRAIN PRC11) | 247–274 | | | | | | | | |
| PKFPS_FUJSV | TYROSINE-PROTEIN KINASE TRANSFORMING PROTEIN | FUJIAMI SARCOMA VIRUS | 259–275 | 346–370 | 400–420 | 587–614 | | | | | |
| PKITH_ASFB7 | THYMIDINE KINASE | AFRICAN SWINE FEVER VIRUS (STRAIN BA71V) | 18–41 | | | | | | | | |
| PKITH_EBV | THYMIDINE KINASE | EPSTEIN-BARR VIRUS (STRAIN B95-8) | 403–418 | 428–446 | | | | | | | |
| PKITH_FLDV | THYMIDINE KINASE | FISH LYMPHOCYSTSITIS DISEASE VIRUS | 96–117 | 252–275 | | | | | | | |
| PKITH_HSV11 | THYMIDINE KINASE | HERPES SIMPLEX VIRUS (TYPE 1/STRAIN 17) | 223–249 | | | | | | | | |
| PKITH_HSV1C | THYMIDINE KINASE | HERPES SIMPLEX VIRUS (TYPE 1/STRAIN CL101) | 223–249 | | | | | | | | |
| PKITH_HSV1E | THYMIDINE KINASE | HERPES SIMPLEX VIRUS (TYPE 1/STRAIN HFEM) | 223–249 | | | | | | | | |
| PKITH_HSV1K | THYMIDINE KINASE | HERPES SIMPLEX VIRUS (TYPE 1/STRAIN KOS) | 223–249 | | | | | | | | |
| PKITH_HSV1S | THYMIDINE KINASE | HERPES SIMPLEX VIRUS (TYPE 1/STRAIN SC16) | 223–249 | | | | | | | | |
| PKITH_HSV23 | THYMIDINE KINASE | HERPES SIMPLEX VIRUS (TYPE 2/STRAIN 333) | 224–250 | 333–348 | | | | | | | |
| PKITH_HSVB6 | THYMIDINE KINASE | BOVINE HERPESVIRUS TYPE 1 (STRAIN 6660) | 193–219 | 280–304 | | | | | | | |
| PKITH_HSVBH | THYMIDINE KINASE | BOVINE HERPESVIRUS TYPE 2 (STRAIN BHM-1) | 180–202 | | | | | | | | |
| PKITH_HSVBM | THYMIDINE KINASE | BOVINE HERPERVIRUS TYPE 3 (STRAIN WC11) | 381–399 | 609–633 | | | | | | | |
| PKITH_HSVBQ | THYMIDINE KINASE | BOVINE HERPESVIRUS TYPE 1 2 (STRAIN Q3932) | 194–220 | 282–306 | | | | | | | |
| PKITH_HSVE4 | THYMIDINE KINASE | EQUINE HERPESVIRUS TYPE 4 (STRAIN 1942) | 174–193 | 261–284 | | | | | | | |
| PKITH_HSVEB | THYMIDINE KINASE | EQUINE HERPESVIRUS TYPE 1 (STRAIN AB4P) AND (ISOLATE HVS25A) | 18–33 | 174–193 | 274–298 | | | | | | |
| PKITH_HSVF | THYMIDINE KINASE | FELINE HERPESVIRUS (FELID HERPESVIRUS 1) | 171–189 | | | | | | | | |
| PKITH_HSV11 | THYMIDINE KINASE | ICTALURID HERPESVIRUS 1 | 14–32 | | | | | | | | |
| PKITH_HSVMR | THYMIDINE KINASE | MARMOSET HERPESVIRUS | 189–215 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PKITH_HSVSA | THYMIDINE KINASE | HERPESVIRUS SAIMIRI (STRAIN 11) | 208–232 | | | | | | | | |
| PKITH_ILTVT | THYMIDINE KINASE | INFECTIOUS LARYNGOTRACHEITIS VIRUS (STRAIN THORNE V882) | 183–202

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PKRB1_VACCC | 30 KD PROTEIN KINASE HOMOLOG | VACCINIA VIRUS (STRAIN COPENHAGEN) | 199–214 | | | | | | | | |
| PKRB1_VACCV | 30 KD PROTEIN KINASE HOMOLOG | VACCINIA VIRUS (STRAIN WR) | 199–214 | | | | | | | | |
| PKRB1_VARV | 30 KD PROTEIN KINASE HOMOLOG | VARIOLA VIRUS | 199–214 | | | | | | | | |
| PKRF1_SFVKA | POSSIBLE PROTEIN KINASE C20 | SHOPE FIBROMA VIRUS (STRAIN KASZA) | 83–98 | | | | | | | | |
| PKRF1_VACCC | POSSIBLE PROTEIN KINASE F10 | VACCINIA VIRUS (STRAIN COPENHAGEN) | 85–100 | | | | | | | | |
| PKRF1_VACCP | POSSIBLE PROTEIN KINASE F10 | VACCINIA VIRUS (STRAIN L-IVP) | 52–67 | | | | | | | | |
| PKRF1_VARV | POSSIBLE PROTEIN KINASE F10 | VARIOLA VIRUS | 85–100 | | | | | | | | |
| PKROS_AVISU | ROS TYR KINASE TRANSFORMING PROTEIN | AVIAN SARCOMA VIRUS (STRAIN UR2) | 6–29 | 202–223 | 284–305 | | | | | | |
| PKRYK_AVIR3 | TYR-PROTEIN KINASE TRANSFORMING PROTEIN R | AVIAN RETROVIRUS RPL30 | 154–172 | 221–241 | | | | | | | |
| PKSEA_AVIET | TYR-PROTEIN KINASE TRANSFORMING PROTEIN SE | AVIAN ERYTHROBLASTOSIS VIRUS (STRAIN S13) | 158–177 | | | | | | | | |
| PKSRC_AVIS2 | TYR-PROTEIN KINASE TRANSFORMING PROTEIN SR | AVIAN SARCOMA VIRUS (STRAIN PR2257) | 361–377 | | | | | | | | |
| PKSRC_AVISR | TYR-PROTEIN KINASE TRANSFORMING PROTEIN SR | AVIAN SARCOMA VIRUS (STRAIN RASV1441) | 361–377 | | | | | | | | |
| PKSRC_AVISS | TYR-PROTEIN KINASE TRANSFORMING PROTEIN SR | AVIAN SARCOMA VIRUS (STRAIN S1) | 361–377 | | | | | | | | |
| PKSRC_AVIST | TYR-PROTEIN KINASE TRANSFORMING PROTEIN SR | AVIAN SARCOMA VIRUS (STRAIN S2) | 361–377 | | | | | | | | |
| PKSRC_RSVH1 | TYR-PROTEIN KINASE TRANSFORMING PROTEIN SR | ROUS SARCOMA VIRUS (STRAIN H-19) | 361–377 | | | | | | | | |
| PKSRC_RSVP | TYR-PROTEIN KINASE TRANSFORMING PROTEIN SR | ROUS SARCOMA VIRUS (STRAIN PRAGUE C) | 361–377 | | | | | | | | |
| PKSRC_RSVPA | TYR-PROTEIN KINASE TRANSFORMING PROTEIN SR | ROUS SARCOMA VIRUS (STRAIN PA101T) | 358–374 | | | | | | | | |
| PKSRC_RSVSR | TYR-PROTEIN KINASE TRANSFORMING PROTEIN SR | ROUS SARCOMA VIRUS (STRAIN SCHMIDT-RUPPIN) | 361–377 | | | | | | | | |
| PKYES_AVISY | TYR-PROTEIN KINASE TRANSFORMING PROTEIN Y | AVIAN SARCOMA VIRUS (STRAIN Y73 | 361–377 | | | | | | | | |
| PL100_ADE02 | LATE 100 KD PROTEIN | HUMAN ADENOVIRUS TYPE 2 | 489–511 | | | | | | | | |
| PL100_ADE05 | LATE 100 KD PROTEIN | HUMAN ADENOVIRUS TYPE 5 | 489–511 | | | | | | | | |
| PL100_ADE41 | LATE 100 KD PROTEIN | HUMAN ADENOVIRUS TYPE 41 | 458–480 | | | | | | | | |
| PL52_ADE02 | LATE L1 52 KD PROTEIN | HUMAN ADENOVIRUS TYPE 2 | 237–259 | | | | | | | | |
| PL52_ADE05 | LATE L1 52 KD PROTEIN | HUMAN ADENOVIRUS TYPE 5 | 237–259 | | | | | | | | |
| PLEC1_FOWPM | HEPATIC LECTIN HOMOLOG | FOWLPOX VIRUS (ISOLATE HP-438(MUNICH)) | 2–26 | | | | | | | | |
| PLMP1_EBV | LATENT MEMBRANE PROTEIN 1 | EPSTEIN-BARR VIRUS (STRAIN B95-8) | 20–43 | 79–100 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PLMP1_EBVC | LATENT MEMBRANE PROTEIN 1 | EPSTEIN-BARR VIRUS (STRAIN B95-8) | 20–43 | 79–100 | | | | | | | |
| PLMP1_EBVR | LATENT MEMBRANE PROTEIN 1 | EPSTEIN-BARR VIRUS (STRAIN B95-8) | 20–43 | 79–100 | | | | | | | |
| PLMP2_EBV | GENE TERMINAL PROTEIN | EPSTEIN-BARR VIRUS (STRAIN B95-8) | 181–196 | 204–226 | 267–288 | 291–315 | 346–369 | 390–410 | | | |
| PMCEL_SFVKA | MRNA CAPPING ENZYME, LARGE SUBUNIT | SHOPE FIBROMA VIRUS (STRAIN KASZA) | 244–260 | 556–578 | 679–699 | | | | | | |
| PMCEL_VACCC | MRNA CAPPING ENZYME, LARGE SUBUNIT | VACCINIA VIRUS (STRAIN COPENHAGEN) | 81–102 | 265–282 | 289–312 | 687–707 | | | | | |
| PMCEL_VACCV | MRNA CAPPING ENZYME, LARGE SUBUNIT | VACCINIA VIRUS (STRAIN WR) | 81–102 | 265–282 | 289–312 | 687–707 | | | | | |
| PMCEL_VARV | MRNA CAPPING ENZYME, LARGE SUBUNIT | VARIOLA VIRUS | 81–102 | 265–282 | 289–312 | 687–707 | | | | | |
| PMCE_ASFB7 | MRNA CAPPING ENZYME | AFRICAN SWINE FEVER VIRUS (STRAIN BA71V) | 217–243 | | | | | | | | |
| PMCE_REOVD | MRNA CAPPING ENZYME | REOVIRUS (TYPE 3/STRAIN DEARING) | 358–383 | 567–588 | 714–741 | | | | | | |
| PMOVP_CGMVS | MOVEMENT PROTEIN | CUCUMBER GREEN MOTTLE MOSAIC VIRUS (WATERMELON STRAIN S) | 157–172 | | | | | | | | |
| PMOVP_CGMVW | MOVEMENT PROTEIN | CUCUMBER GREEN MOTTLE MOSAIC VIRUS (WATERMELON STRAIN | 157–172 | | | | | | | | |
| PMOVP_ORSV | MOVEMENT PROTEIN | ODONTOGLOSSUM RINGSPOT VIRUS | 49–74 | 178–205 | | | | | | | |
| PMOVP_PPMVS | MOVEMENT PROTEIN | PEPPER MILD MOTTLE VIRUS (STRAIN SPAIN) | 25–50 | 186–201 | | | | | | | |
| PMOVP_TMGMV | MOVEMENT PROTEIN | TOBACCO MILD GREEN MOSAIC (TMV STRAIN U2) | 186–201 | | | | | | | | |
| PMOVP_TMVCO | MOVEMENT PROTEIN | TOBACCO MOSAIC VIRUS (STRAIN COWPEA) | 88–107 | 156–171 | | | | | | | |
| PMTC1_CHVN1 | MODIFICATION METHYLASE CVIBI | CHOLRELLA VIRUS NC-1A | 129–156 | | | | | | | | |
| PMTC2_CHVP1 | MODIFICATION METHYLASE CVIAII | PARAMECIUM BURSARIA CHLORELLA VIRUS 1 ( | 72–94 | | | | | | | | |
| PMTC3_CHVN1 | MODIFICATION METHYLASE CVIBII | CHLORELLA VIRUS NC-1A | 177–192 | 265–286 | | | | | | | |
| PMYBE_AVILE | P135-GAG-MYB-ETS TRANSORMING PROTEIN ( | AVIAN LEUKEMIA VIRUS E26 | 104–124 | | | | | | | | |
| PMYB_AVIMB | MYB TRANFORMING PROTEIN | AVIAN MYELOBLASTOSIS VIRUS | 218–238 | 301–326 | | | | | | | |
| PNCAP_AINOV | NUCLEOCAPSID PROTEIN | AINO VIRUS | 159–181 | | | | | | | | |
| PNCAP_BUNLC | NUCLEOCAPSID PROTEIN | BUNYAVIRUS LA CROSSE | 84–99 | | | | | | | | |
| PNCAP_BUNSH | NUCLEOCAPSID PROTEIN | BUNYAVIRUS SNOWSHOE HARE | 84–99 | | | | | | | | |
| PNCAP_CDVO | NUCLEOCAPSID PROTEIN | CANINE DISTEMPER VIRUS (STRAIN ONDERSTEPOORT) | 31–50 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PNCAP_FIPV | NUCLEOCAPSID PROTEIN | FELINE INFECTIOUS PERITONITIS VIRUS (STRAIN 79-1146) | 57–74 | | | | | | | | |
| PNCAP_HANTV | NUCLEOCAPSID PROTEIN | HANTAAN VIRUS (STRAIN 76-118) | 317–342 | | | | | | | | |
| PNCAP_HAZVJ | NUCLEOCAPSID PROTEIN | HAZARA VIRUS (ISOLATE JC280) | 428–446 | | | | | | | | |
| PNCAP_IHNV | NUCLEOCAPSID PROTEIN | INFECTIOUS HEMATOPOIETIC NECROSIS VIRUS (STRAIN ROUND BUT | 110–137 | 239–265 | | | | | | | |
| PNCAP_INSV | NUCLEOCAPSID PROTEIN | IMPATIENS NECROTIC SPOT VIRUS | 155–179 | | | | | | | | |
| PNCAP_MEASE | NUCLEOCAPSID PROTEIN | MEASLES VIRUS (STRAIN EDMONSTON) | 40–59 | | | | | | | | |
| PNCAP_MEASH | NUCLEOCAPSID PROTEIN | MEASLES VIRUS (STRAIN HALLE) | 40–59 | | | | | | | | |
| PNCAP_MEASY | NUCLEOCAPSID PROTEIN | MEASLES VIRUS (STRAIN YAMAGATA-1) | 40–59 | | | | | | | | |
| PNCAP_MUMP1 | NUCLEOCAPSID PROTEIN | MUMPS VIRUS (STRAIN SBL-1) | 156–178 | | | | | | | | |
| PNCAP_MUMPM | NUCLEOCAPSID PROTEIN | MUMPS VIRUS (STRAIN MIYAHARA VACCINE) | 156–178 | | | | | | | | |
| PNCAP_PHV | NUCLEOCAPSID PROTEIN | PROSPECT HILL VIRUS | 36–58 | 218–236 | 256–277 | 321–346 | | | | | |
| PNCAP_PI1HC | NUCLEOCAPSID PROTEIN | HUMAN PARAINFLUENZA 1 VIRUS (STRAIN C39) | 42–58 | 86–102 | | | | | | | |
| PNCAP_PI1HW | NUCLEOCAPSID PROTEIN | HUMAN PARAINFLUENZA 1 VIRUS (STRAIN WASHINGTON/1957) | 42–58 | 86–102 | | | | | | | |
| PNCAP_PI3B | NUCLEOCAPSID PROTEIN | BOVINE PARAINFLUENZA 3 VIRUS | 163–184 | | | | | | | | |
| PNCAP_HI3H4 | NUCLEOCAPSID PROTEIN | HUMAN PARAINFLUENZA 3 VIRUS (STRAIN NIH 47885) | 163–184 | | | | | | | | |
| PNCAP_PUUMP | NUCLEOCAPSID PROTEIN | PUUMALA VIRUS (STRAIN HALLNAS B1) | 36–58 | 321–346 | | | | | | | |
| PNCAP_PUUMS | NUCLEOCAPSID PROTEIN | PUUMALA VIRUS (STRAIN SOTKAMO) | 36–58 | 218–236 | 321–346 | | | | | | |
| PNCAP_RABVA | NUCLEOCAPSID PROTEIN | RABIES VIRUS (STRAIN AVOI) | 299–322 | | | | | | | | |
| PNCAP_RABVP | NUCLEOCAPSID PROTEIN | RABIES VIRUS (STRAIN PV) | 299–322 | | | | | | | | |
| PNCAP_RABVS | NUCLEOCAPSID PROTEIN | RABIES VIRUS (STRAIN SAD B19) | 299–322 | | | | | | | | |
| PNCAP_RVFVZ | NUCLEOCAPSID PROTEIN | RIFT VALLEY FEVER VIRUS (STRAIN ZH-548 M12) | 158–180 | | | | | | | | |
| PNCAP_SEND5 | NUCLEOCAPSID PROTEIN | SENDAI VIRUS (STRAIN Z/ HOST MUTANTS) | 29–51 | 86–102 | | | | | | | |
| PNCAP_SENDE | NUCLEOCAPSID PROTEIN | SENDAI VIRUS (STRAIN ENDERS) | 42–58 | 86–102 | | | | | | | |
| PNCAP_SENDH | NUCLEOCAPSID PROTEIN | SENDAI VIRUS (STRAIN HARRIS) | 42–58 | 86–102 | | | | | | | |
| PNCAP_SENDZ | NUCLEOCAPSID PROTEIN | SENDAI VIRUS (STRAIN Z) | 29–51 | 86–102 | | | | | | | |
| PNCAP_SEOUS | NUCLEOCAPSID PROTEIN | SEOUL VIRUS (STRAIN SR-11) | 112–138 | 317–342 | | | | | | | |
| PNCAP_SFSV | NUCLEOCAPSID PROTEIN | SANDFLY FEVER SICILIAN VIRUS | 156–181 | | | | | | | | |
| PNCAP_TACV | NUCLEOCAPSID PROTEIN | TACARIBE VIRUS | 219–241 | | | | | | | | |
| PNCAP_UUK | NUCLEOCAPSID PROTEIN | UUKUNIEMI VIRUS | 167–189 | | | | | | | | |
| PNCAP_VHSV0 | NUCLEOCAPSID PROTEIN | VIRAL HEMORRHAGIC SEPTICEMIA VIRUS (STRAIN 07-71) | 240–266 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PNCAP__VHSVM | NUCLEOCAPSID PROTEIN | VIRAL HEMORRHAGIC SPETICEMIA VIRUS (STRAIN MAKAH) | 240–266 | | | | | | | | |
| PNCAP__VSVJO | NUCLEOCAPSID PROTEIN | VESICULAR STOMATITIS VIRUS SEROTYPE NEW JERSEY/ STRAIN OG | 64–80 | | | | | | | | |
| PNCAP__VSVSJ | | | | | | | | | | | |
| PNEF__HV2RO | NEGATIVE FACTOR | HUMAN IMMUNODEFICIENCY VIRUS TYPE 2 (ISOLATE ROD) | 110–129 | | | | | | | | |
| PNEF__HV2ST | NEGATIVE FACTOR | HUMAN IMMUNODEFICIENCY VIRUS TYPE 2 (ISOLSTE ST) | 106–128 | | | | | | | | |
| PNRAM__IABDA | NEURAMINIDASE | INFLUENZA A VIRUS (STRAIN A/BLACK DUCK/AUSTRALIA/ 702/78) | 3–29 | | | | | | | | |
| PNRAM__IACHI | NEURAMINIDASE | INFLUENZA A VIRUS (STRAIN A/CHILE/1/83) | 3–24 | | | | | | | | |
| PNRAM__IADA1 | NEURAMINIDASE | INFLUENZA A VIRUS (STRAIN A/DUCK/ALBERTA/28/76) | 3–24 | | | | | | | | |
| PNRAM__IADGE | NEURAMINIDASE | INFLUENZA A VIRUS (STRAIN A/DUCK/GERMANY/49) | 3–29 | | | | | | | | |
| PNRAM__IAFPW | NEURAMINIDASE | INFLUENZA A VIRUS (STRAIN A/FOWL PLAGUE VIRUS/ WEYBRIDGE) | 3–29 | 301–317 | | | | | | | |
| PNRAM__IAHCO | NEURAMINIDASE | INFLUENZA A VIRUS (STRAIN A/EQUINE/COR/16/74) | 299–315 | | | | | | | | |
| PNRAM__IAHK1 | NEURAMINIDASE | INFLUENZA A VIRUS (STRAIN A/EQUINE/KENTUCKY/1/81) | 3–29 | | | | | | | | |
| PNRAM__IAKIE | NEURAMINIDASE | INFLUENZA A VIRUS (STRAIN A/KIEV/59/79) | 3–24 | | | | | | | | |
| PNRAM__IALEN | NEURAMINIDASE | INFLUENZA A VIRUS (STRAIN A/LENINGRAD/54/1) | 3–24 | | | | | | | | |
| PNRAM__IAME1 | NEURAMINIDASE | INFLUENZA A VIRUS (STRAIN A/MEMPHIS/1/71H-A/ BELLAMY/42N) | 3–30 | | | | | | | | |
| PNRAM__IAPAR | NEURAMINIDASE | INFLUENZA A VIRUS (STRAIN A/PARROT/ULSTER/73) | 3–30 | | | | | | | | |
| PNRAM__IAPUE | NEURAMINIDASE | INFLUENZA A VIRUS (STRAIN A/PUERTO RICO/8/34) | 3–30 | | | | | | | | |
| PNRAM__IARUE | NEURAMINIDASE | INFLUENZA A VIRUS (STRAIN A/RUDDY TURNSTONE/ NEW JERSEY/60/ | 3–29 | | | | | | | | |
| PNRAM__IASH2 | NEURAMINIDASE | INFLUENZA A VIRUS (STRAIN A/SHEARWATER/AUSTRALIA/72) | 3–29 | | | | | | | | |
| PNRAM__IATKR | NEURAMINIDASE | INFLUENZA A VIRUS (STRAIN A/TURKEY/OREGON/71) | 3–24 | 56–77 | | | | | | | |
| PNRAM__IATRA | NEURAMINIDASE | INFLUENZA A VIRUS (STRAIN A/TERN/AUSTRALIA/G70C/75) | 3–29 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PNRAM_IAUSS | NEURAMINIDASE | INFLUENZA A VIRUS (STRAIN A/USSR/90/77) | 3–24 | | | | | | | | |
| PNRAM_IAWHM | NEURAMINIDASE | INFLUENZA A VIRUS (STRAIN A/WHALE/MAINE/1/84) | 3–29 | | | | | | | | |
| PNRAM_IAWIL | NEURAMINIDASE | INFLUENZA A VIRUS (STRAIN A/WILSON-SMITH/33) | 3–30 | | | | | | | | |
| PNRAM_INBBE | NEURAMINIDASE | INFLUENZA B VIRUS (STRAIN B/BEIJING/1/87) | 3–20 | | | | | | | | |
| PNRAM_INBHK | NEURAMINIDASE | INFLUENZA B VIRUS (STRAIN B/HONG KONG/8/73) | 3–20 | | | | | | | | |
| PNRAM_INBLE | NEURAMINIDASE | INFLUENZA B VIRUS (STRAIN B/LEE/40) | 3–20 | | | | | | | | |
| PNRAM_INBLN | NEURAMINIDASE | INFLUENZA B VIRUS (STRAIN B/LENNINGRAD/179/86) | 3–20 | | | | | | | | |
| PNRAM_INBMD | NEURAMINIDASE | INFLUENZA B VIRUS (STRAIN B/MARYLAND/59) | 3–20 | | | | | | | | |
| PNRAM_INBMF | NEURAMINIDASE | INFLUENZA B VIRUS (STRAIN B/MEMPHIS/3/89) | 3–20 | | | | | | | | |
| PNRAM_INBOR | NEURAMINIDASE | INFLUENZA B VIRUS (STRAIN B/OREGON/5/80) | 3–20 | | | | | | | | |
| PNRAM_INBSI | NEURAMINIDASE | INFLUENZA B VIRUS (STRAIN B/SINGAPORE/222/79) | 3–20 | | | | | | | | |
| PNRAM_INBUS | NEURAMINIDASE | INFLUENZA B VIRUS (STRAIN B/USSR/100/83) | 3–20 | | | | | | | | |
| PNRAM_INBVI | NEURAMINIDASE | INFLUENZA B VIRUS (STRAIN B/VICTORIA/3/85) | 3–20 | | | | | | | | |
| PNS1_SIDEV | PROBABLE NONSTRUCTURAL PROTEIN PRECURSO | BOMBYX DENSONUCLEOSIS VIRUS | 135–151 | | | | | | | | |
| PNS2_SIDEV | PROBABLE STRUCTURAL PROTEIN PRESURSOR | BOMBYX DENSONUCLEOSIS VIRUS | 2–26 | 196–221 | 783–806 | | | | | | |
| PNS3_SIDEV | PROBABLE NONSTRUCTURAL PROTEIN PRECURSOR | BOMBYX DENSONUCLEOSIS VIRUS | 60–78 | | | | | | | | |
| PNSS_TSWVB | NON-STRUCTURAL PROTEIN | TOMATO SPOTTED WILT VIRUS (BRAZILIAN IOSLOATE CPNH1/BR-01) | 80–105 | 431–455 | | | | | | | |
| PNSS_TSWVL | NON-STRUCTURAL PROTEIN | TOMATO SPOTTED WILT VIRUS (STRAIN L3) | 80–105 | 436–458 | | | | | | | |
| PNTP1_VACCC | NUCLEOSIDE TRIPHOSPHATASE I | VACCINIA VIRUS (STRAIN COPENHAGEN) | 20–45 | 387–403 | | | | | | | |
| PNTP1_VACCV | NUCLEOSIDE TRIPHOSPHATASE I | VACCINIA VIRUS (STRAIN WR) | 20–45 | 387–403 | | | | | | | |
| PNTP1_VARV | NUCLEOSIDE TRIPHOSPHATASE I | VARIOLA VIRUS | 293–309 | | | | | | | | |
| PP100_HSV6U | MAJOR ANTIGENIC STRUCTURAL PROTEIN | HERPES SIMPLEX VIRUS (TYPE 6/ STRAIN UGANDA-1102) | 182–204 | 250–270 | 344–366 | | | | | | |
| PPAP2_FOWPV | POLY(A) POLYMERASE REGULATORY SUBUNIT | FOWLPOX VIRUS | 79–100 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPAP2__MYXVA | POLY(A) POLYMERASE REGULATORY SUBUNIT | MYXOMA VIRUS (ISOLATE AUST/ URIARRA/VERG-86/1) | 101–116 | | | | | | | | |
| PPAP2__VACCC | POLY(A) POLYMERASE REGULATORY SUBUNIT | VACCINIA VIRUS (STRAIN COPENHAGEN) | 101–116 | | | | | | | | |
| PPAP2__VACCV | POLY(A) POLYMERASE REGULATORY SUBUNIT | VACCINIA VIRUS (STRAIN WR) | 101–116 | | | | | | | | |
| PPAP2__VARV | POLY(A) POLYMERASE REGULATORY SUBUNIT | VARIOLA VIRUS | 101–116 | | | | | | | | |
| PPCNA__NPVAC | PROLIFERATING CELL NUCLEAR ANTIGEN | AUTOGRAPHA CALIFORNICA NUCLEAR POLYHEDROSIS VIRUS | 67–89 | 227–244 | | | | | | | |
| PPE21__NPVOP | 21 2 KD PROTEIN IN PE 5'REGION | ORGYIA PSEUDOTSUGATA MULTICAPSID POLYHEDROSIS VIRUS | 117–139 | | | | | | | | |
| PPE25__NPVAC | 25 1 KD PROTEIN IN PE-P26 INTERGENIC REGION | AUTOGRAPHA CALIFORNICA NUCLEAR POLYHEDROSIS VIRUS | 57–83 | | | | | | | | |
| PPE38__NPVAC | MAJOR IMMEDIATE EARLY PROTEIN | AUTOGRAPHA CALIFORNICA NUCLEAR POLYHEDROSIS VIRUS | 17–33 | | | | | | | | |
| PPEN3__ADE02 | PENTON PROTEIN | HUMAN ADENOVIRUS TYPE 2 | 171–195 | | | | | | | | |
| PPEN3__ADE05 | PENTON PROTEIN | HUMAN ADENOVIRUS TYPE 5 | 171–195 | | | | | | | | |
| PPEN3__ADEGX | PENTON PROTEIN | AVIAN ADENOVIRUS GAL10 (STRAIN SA2) | 194–214 | 307–324 | | | | | | | |
| PPIV2__ADE07 | MATURATION PROTEIN | HUMAN ADENOVIRUS TYPE 7 | 412–431 | | | | | | | | |
| PPIV2__ADEM1 | MATURATION PROTEIN | MOUSE ADENOVIRUS TYPE 1 | 409–428 | | | | | | | | |
| PPOL1__BAYMG | GENOME POLYPROTEIN 1 | BARLEY TELLOW MOSAIC VIRUS (GERMAN ISOLATE) | 739–755 | 835–856 | 1072–1094 | 1889–1910 | | | | | |
| PPOL1__BAYMJ | GENOME POLYPROTEIN 1 | BARLEY TELLOW MOSAIC VIRUS (JAPANESE STRAIN II-1) | 739–755 | 835–856 | 1072–1094 | 1465–1485 | 1888–1909 | | | | |
| PPOL1__GCMV | RNA1 POLYPROTEIN | HUMGARIAN GRAPEVINE CHROME MOSAIC VIRUS | 691–717 | 1040–1062 | 1116–1143 | | | | | | |
| PPOL1__GFLV | RNA1 POLYPROTEIN | GRAPEVINE FANLEAF VIRUS | 380–396 | 477–503 | 545–564 | 1079–1098 | 1149–1171 | 1341–1356 | 1761–1785 | 1821–1848 | 2020–2044 |
| PPOL1__TBRVS | RNA1 POLYPROTEIN | TOMATO BLACK RING VIRUS (STRAIN S) | 1132–1159 | | | | | | | | |
| PPOL2__ARMV | RNA2 POLYPROTEIN | ARABIS MOSAIC VIRUS | 129–150 | 243–266 | 346–367 | | | | | | |
| PPOL2__BAYMG | GENOME POLYPROTEIN 2 | BARLEY YELLOW MOSAIC VIRUS (GERMAN ISOLATE) | 325–350 | 463–485 | | | | | | | |
| PPOL2__BAYMJ | GENOME POLYPROTEIN 2 | BARLEY YELLOW MOSAIC VIRUS (JAPANSES STRAIN II-1) | 325–350 | 463–485 | | | | | | | |
| PPOL2__GFLV | RNA2 POLYPROTEIN | GRAPEVINE FANLEAF VIRUS | 808–829 | 1021–1045 | | | | | | | |
| PPOL2__TBRVS | RNA2 POLYPROTEIN | TOMATO BLACK RING VIRUS (STRAIN S) | 425–446 | 541–557 | 856–876 | 1203–1223 | | | | | |
| PPOL2__TRSVR | RNA2 POLYPROTEIN | TOMATO RINGSPOT VIRUS (ISOLATE RASPBERRY) | 316–340 | 427–448 | 1527–1554 | | | | | | |
| PPOLG__BOVEV | GENOME POLYPROTEIN | BOVINE ENTEROVIRUS (STRAIN VG-5-27) | 1833–1859 | | | | | | | | |
| PPOLG__BVDVN | GENOME POLYPROTEIN | BOVINE VIRAL DIARRHEA VIRUS (ISOLATE NADL) | 627–653 | 943–965 | 1119–1134 | 1282–1297 | 1363–1387 | 1868–1892 | 2460–2487 | 2608–2628 | 2883–2898 |
| | | | 3141–3161 | 3220–3241 | 3856–3871 | 3967–3986 | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLG_BVDVS | GENOME POLYPROTEIN | BOVINE VIRAL DIARRHEA VIRUS (STRAIN SD-1) | 627–653 | 943–965 | 1119–1134 | 1138–1134 | 1189–1205 | 1282–1297 | 1363–1387 | 1778–1802 | 2370–2397 |
| | | | 2518–2538 | 2741–2766 | 2793–2808 | 3766–3781 | | | | | |
| PPOLG_COXA2 | GENOME POLYPROTEIN | COXSACKIEVIRUS A21 (STRAIN COE) | 850–867 | | | | | | | | |
| PPOLG_COXA3 | GENOME POLYPROTEIN | COXSACKIEVIRUS A23 (ECHO 9 VIRUS) | 67–92 | | | | | | | | |
| PPOLG_COXA9 | GENOME POLYPROTEIN | COXSACKIEVIRUS A9 (STRAIN GRIGGS) | 1491–1517 | 1601–1626 | | | | | | | |
| PPOLG_COXB1 | GENOME POLYPROTEIN | COXSACKIEVIRUS B1 | 1472–1498 | 1582–1607 | | | | | | | |
| PPOLG_COXB3 | GENOME POLYPROTEIN | COXSACKEIVIRUS B3 | 228–255 | 1475–1501 | 1585–1610 | | | | | | |
| PPOLG_COXB4 | GENOME POLYPROTEIN | COXSACKIEVIRUS B4 | 821–846 | 1473–1499 | 1583–1608 | | | | | | |
| PPOLG_COXB5 | GENOME POLYPROTEIN | COXSACKIEVIRUS B5 | 1475–1501 | 1585–1610 | | | | | | | |
| PPOLG_DENIS | GENOME POLYPROTEIN | DENGUE VIRUS TYPE 1 (STRAIN SINGAPORE S275/90) | 918–943 | 1111–1138 | 1211–1236 | 1243–1260 | 1612–1628 | 2222–2248 | 2348–2365 | 2401–2426 | 3050–3069 |
| PPOLG_DEN1W | GENOME POLYPROTEIN | DENGUE VIRUS TYPE 1 (STRAIN WESTERN PACIFIC) | 919–944 | 1112–1139 | | | | | | | |
| PPOLG_DEN23 | GENOME POLYPROTEIN | DENGUE VIRUS TYPE 2 (ISOLATE MALAYSIA M3) | 336–354 | | | | | | | | |
| PPOLG_DEN26 | GENOME POLYPROTEIN | DENGUE VIRUS TYPE 2 (STRAIN 16681) | 848–868 | 919–944 | 1112–1139 | 1244–1261 | 1283–1301 | 1613–1629 | 2293–2318 | 2347–2364 | 2405–2425 |
| | | | 2700–2726 | | | | | | | | |
| PPOLG_DEN27 | GENOME POLYPROTEIN | DENGUE VIRUS TYPE 2 (STRAIN 16681-PDK53) | 848–868 | 919–944 | 1112–1139 | 1244–1261 | 1283–1301 | 1376–1396 | 1613–1629 | 2293–2318 | 2347–2364 |
| | | | 2405–2425 | 2700–2726 | | | | | | | |
| PPOLG_DEN2D | GENOME POLYPROTEIN | DENGUE VIRUS TYPE 2 (STRAIN D2-04) | 848–868 | 919–944 | | | | | | | |
| PPOLG_DEN2J | GENOME POLYPROTEIN | DENGUE VIRUS TYPE 2 (STRAIN JAMAICA) | 848–868 | 919–944 | 1112–1139 | 1244–1261 | 1376–1396 | 1613–1629 | 2293–2318 | 2347–2364 | 2405–2425 |
| | | | 2700–2726 | | | | | | | | |
| PPOLG_DEN2N | GENOME POLYPROTEIN | DENGUE VIRUS TYPE 2 (STRAIN NEW GUINEA C) | 100–120 | 171–196 | 364–391 | | | | | | |
| PPOLG_DEN2P | GENOME POLYPROTEIN | DENGUE VIRUS TYPE 2 (STRAIN PR159/51) | 919–944 | 1112–1139 | 1244–1261 | 1283–1301 | 1376–1396 | 1613–1629 | 2290–2315 | 2344–2361 | 2402–2422 |
| | | | 2697–2723 | | | | | | | | |
| PPOLG_DEN2T | GENOME POLYPROTEIN | DENGUE VIRUS TYPE 2 (STRAIN TONGA 1974) | 639–664 | 832–859 | 964–981 | 1203–1219 | | | | | |
| PPOLG_DEN3 | GENOME POLYPROTEIN | DENGUE VIRUS TYPE 3 | 917–942 | 1210–1228 | 1242–1259 | 1174–1194 | 1611–1627 | 2141–2162 | 2221–2247 | 2146–2361 | 2199–2424 |
| | | | 2698–2724 | 3048–3067 | | | | | | | |
| PPOLG_DEN4 | GENOME POLYPROTEIN | DENGUE VIRUS TYPE 4 | 1209–1227 | 1241–1258 | 1611–1627 | 2220–2246 | 2342–2359 | 2400–2420 | 3045–3064 | | |
| PPOLG_EC11G | GENOME POLYPROTEIN | ECHOVIRUS 11 (STRAIN GREGORY | 664–690 | 774–799 | | | | | | | |
| PPOLG_EMCV | GENOME POLYPROTEIN | ENCEPHALOMYOCARDITIS VIRUS | 225–247 | 558–578 | 1194–1215 | 1650–1667 | | | | | |
| PPOLG_EMCVB | GENOME POLYPROTEIN | ENCEPHALOMYOCARDITIS VIRUS (STRAIN EMC-B NONDIABETOGENI | 560–580 | 1120–1141 | 1196–1217 | | | | | | |
| PPOLG_EMCVD | GENOME POLYPROTEIN | ENCEPHALOMYOCARDITIS VIRUS (STRAIN EMC-D DIABETOGENIC) | 560–580 | 1120–1141 | 1196–1217 | | | | | | |
| PPOLG_ENMG3 | GENOME POLYPROTEIN | MENGO ENCEPHALOMYOCAR-DITIS VIRUS (STRAIN 37A) | 560–580 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLG_ENMGO | GENOME POLYPROTEIN | MENGO ENCEPHALOMYOCAR-DITIS VIRUS | 493–513 | | | | | | | | |
| PPOLG_FMDV1 | GENOME POLYPROTEIN | FOOT-AND-MOUTH DISEASE VIRUS (STRAIN A10-61) | 121–141 | 984–1003 | 1036–1057 | 1396–1411 | 1465–1487 | 1764–1791 | | | |
| PPOLG_FMDVS | GENOME POLYPROTEIN | FOOT-AND-MOUTH DISEASE VIRUS (STRAIN A5) | 162–187 | | | | | | | | |
| PPOLG_FMDVA | GENOME POLYPROTEIN | FOOT-AND-MOUTH DISEASE VIRUS (STRAIN A12) | 121–140 | 984–1003 | 1036–1057 | 1396–1411 | 1465–1487 | 1763–1790 | | | |
| PPOLG_FMDVO | GENOME POLYPROTEIN | FOOT-AND-MOUTH DISEASE VIRUS (STRAINS OIL AND OIBFS)( | 121–141 | 984–1003 | 1036–1057 | 1396–1411 | 1465–1487 | 1763–1790 | | | |
| PPOLG_FMDV5 | GENOME POLYPROTEIN | FOOT-AND-MOUTH DISEASE VIRUS (STRAIN C1-SANTA PAU [C-S8]) | 301–320 | | | | | | | | |
| PPOLG_FMDVT | GENOME POLYPROTEIN | FOOT-AND-MOUTH DISEASE VIRUS (STRAIN C1) | 121–141 | 979–998 | | | | | | | |
| PPOLG_HCV1 | GENOME POLYPROTEIN | HEPATITIS C VIRUS (ISOLATE 1) | 112–133 | 143–169 | 619–640 | 683–699 | 833–857 | 2327–2347 | 2442–2457 | 2837–2859 | |
| PPOLG_HCVA | GENOME POLYPROTEIN | HOG CHOLERA VIRUS (STRAIN ALFORT) | 102–128 | 1143–1163 | 1282–1301 | 1778–1802 | 2370–2397 | 2518–2538 | 3131–3152 | 3737–3753 | 3767–3782 |
| | | | 3877–3893 | | | | | | | | |
| PPOLG_HCVB | GENOME POLYPROTEIN | HOG CHOLERA VIRUS (STRAIN BRESCIA) | 102–128 | 1143–1163 | 1282–1301 | 1778–1802 | 2370–2397 | 2518–2538 | 3131–3152 | 3737–3753 | 3767–3782 |
| | | | 3877–3893 | | | | | | | | |
| PPOLG_HCVBK | GENOME POLYPROTEIN | HEPATITIS C VIRUS (ISOLATE BK) | 112–133 | 143–169 | 619–640 | 683–699 | 2327–2347 | 2441–2456 | 2836–2858 | 2988–3007 | |
| PPOLG_HCVE1 | GENOME POLYPROTEIN | HEPATITIS C VIRUS (ISOLATE EC1) | 27–53 | | | | | | | | |
| PPOLG_HCVH | GENOME POLYPROTEIN | HEPATITIS C VIRUS (ISOLATE H) | 112–133 | 143–169 | 619–640 | 683–699 | 833–853 | 863–880 | 2442–2457 | 2837–2859 | |
| PPOLG_HCVH4 | GENOME POLYPROTEIN | HEPATITIS C VIRUS (ISOLATE HCV-476) | 112–133 | 143–169 | | | | | | | |
| PPOLG_HCVH7 | GENOME POLYPROTEIN | HEPATITIS C VIRUS (ISOLATE HCT27) | 15–41 | | | | | | | | |
| PPOLG_HCVH8 | GENOME POLYPROTEIN | HEPATITIS C VIRUS (ISOLATE HCT18) | 27–53 | | | | | | | | |
| PPOLG_HCVHK | GENOME POLYPROTEIN | HEPATITIS C VIRUS (ISOLATE HCV-KF) | 112–133 | 143–169 | | | | | | | |
| PPOLG_HCVJ2 | GENOME POLYPROTEIN | HEPATITIS C VIRUS (ISOLATE HC-J2) | 112–133 | 143–169 | | | | | | | |
| PPOLG_HCVJ5 | GENOME POLYPROTEIN | HEPATITIS C VIRUS (ISOLATE HC-J5) | 112–133 | 143–169 | 623–644 | 687–703 | | | | | |
| PPOLG_JCVJ6 | GENOME POLYPROTEIN | HEPATITIS C VIRUS (ISOLATE HC-J6) | 112–133 | 143–169 | 623–644 | 687–703 | 837–861 | 1827–1853 | 2327–2347 | 2859–2881 | 3011–3030 |
| PPOLG_HCVJ7 | GENOME POLYPROTEIN | HEPATITIS C VIRUS (ISOLATE HC-J7) | 143–169 | 623–644 | 687–703 | | | | | | |
| PPOLG_HCVJ8 | GENOME POLYPROTEIN | HEPATITIS C VIRUS (ISOLATE HC-J8) | 112–133 | 143–169 | 837–861 | 867–884 | 1172–1188 | 1827–1853 | 2859–2881 | 3011–3030 | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLG_HCVJA | GENOME POLYPROTEIN | HEPATITIS C VIRUS (ISOLATE JAPANESE) | 112–133 | 143–169 | 619–640 | 683–699 | 833–857 | 863–880 | 2327–2347 | 2836–2858 | 2988–3007 |
| PPOLG_HCVJT | GENOME POLYPROTEIN | HEPATITIS C VIRUS (ISOLATE HC-JT) | 112–133 | 143–169 | 619–640 | 683–699 | 833–857 | 2327–2347 | 2441–2456 | 2836–2858 | |
| PPOLG_HCVTH | GENOME POLYPROTEIN | HEPATITIS C VIRUS (ISOLATE TH) | 27–53 | | | | | | | | |
| PPOLG_HCVTW | GENOME POLYPROTEIN | HEPATITIS C VIRUS (ISOLATE TAIWAN) | 112–133 | 143–169 | 619–640 | 683–699 | 833–857 | 2327–2347 | 2441–2456 | 2836–2858 | 2988–3007 |
| PPOLG_HPAV1 | GENOME POLYPROTEIN | HEPATITIS A VIRUS (STRAIN LCDC-1) | 303–323 | | | | | | | | |
| PPOLG_HPAV2 | GENOME POLYPROTEIN | HEPATITIS A VIRUS (STRAIN 24A) | 401–428 | 799–819 | 1195–1708 | 1687–1708 | 2008–2033 | 2068–2092 | | | |
| PPOLG_HPAV4 | GENOME POLYPROTEIN | HEPATITIS A VIRUS (STRAIN 43C) | 799–819 | 1195–1210 | 1687–1708 | 2008–2033 | 2068–2092 | | | | |
| PPOLG_HPAV8 | GENOME POLYPROTEIN | HEPATITIS A VIRUS (STRAIN 18F) | 799–819 | 1195–1210 | 1687–1708 | 2008–2033 | 2068–2092 | | | | |
| PPOLG_HPAVC | GENOME POLYPROTEIN | HEPATITIS A VIRUS (STRAIN CR326) | 799–819 | | | | | | | | |
| PPOLG_HPAVG | GENOME POLYPROTEIN | HEPATITIS A VIRUS (STRAIN GA76) | 778–798 | | | | | | | | |
| PPOLG_HPAVH | GENOME POLYPROTEIN | HEPATITIS A VIRUS (STRAIN HM-175) | 799–819 | 1195–1210 | 1688–1709 | 2009–2034 | 2069–2093 | | | | |
| PPOLG_HPAVL | GENOME POLYPROTEIN | HEPATITIS A VIRUS (STRAIN LA) | 799–819 | 1195–1210 | 1688–1709 | 2009–2034 | 2069–2093 | | | | |
| PPOLG_HPAVM | GENOME POLYPROTEIN | HEPATITIS A VIRUS (STRAIN MBB) | 799–819 | 1195–1210 | 1688–1709 | 2009–2034 | 2069–2093 | | | | |
| PPOLG_HPAVS | GENOME POLYPROTEIN | SIMIAN HEPATITIS A VIRUS (STRAIN AGM-27) | 1199–1214 | 1690–1711 | 2012–2037 | 2072–2096 | | | | | |
| PPOLG_HRV14 | GENOME POLYPROTEIN | HUMAN RHINOVIRUS 14 (HRV-14) | 1383–1406 | 1962–1982 | | | | | | | |
| PPOLG_HRV1A | GENOME POLYPROTEIN | HUMAN RHINOVIRUS 1A (HRV-1A) | 361–379 | 547–562 | | | | | | | |
| PPOLG_HRV1B | GENOME POLYPROTEIN | HUMAN RHINOVIRUS 1B (HRV-1B) | 386–404 | 572–587 | 859–876 | 1029–1052 | 1453–1478 | 1625–1641 | 1816–1842 | 1941–1961 | |
| PPOLG_HRV2 | GENOME POLYPROTEIN | HUMAN RHINOVIRUS 2 (HRV-2) | 569–584 | 694–713 | 1022–1045 | 1446–1469 | 1618–1634 | 1809–1835 | 1843–1866 | | |
| PPOLG_HRV89 | GENOME POLYPROTEIN | HUMAN RHINOVIRUS 89 (HRV-89) | 576–591 | 1038–1061 | 1229–1253 | 1332–1358 | 1460–1485 | 1632–1648 | 1823–1849 | 1948–1968 | |
| PPOLG_HUBV7 | GENOME POLYPROTEIN | HUMAN RHINOVIRUS 70 (STRAIN J670/71) | 1492–1515 | | | | | | | | |
| PPOLG_1BDVO | STRUCTURAL POLYPROTEIN | AVAIN INFECTIOUS BURSAL DISEASE VIRUS (STRAIN OH) | 905–922 | | | | | | | | |
| PPOLG_JAEV1 | GENOME POLYPROTEIN | JAPANESE ENCEPHALITIS VIRUS (STRAIN SA-14) | 938–963 | 1306–1325 | 1642–1658 | 2245–2270 | 2326–2351 | 2462–2481 | | | |
| PPOLG_JAEV5 | GENOME POLYPROTEIN | JAPANESE ENCEPHALITIS VIRUS (STRAIN SA(V)) | 938–963 | 1306–1325 | 1642–1658 | 2245–2270 | 2326–2351 | 2462–2481 | | | |
| PPOLG_JAEVJ | GENOME POLYPROTEIN | JAPANESE ENCEPHALITIS VIRUS (STRAIN JAORAS982) | 938–963 | 1306–1325 | 1642–1658 | 2245–2270 | 2326–2351 | 2462–2481 | | | |
| PPOLG_JAEVN | GENOME POLYPROTEIN | JAPANESE ENCEPHALITIS VIRUS (STRAIN NAKAYAMA) | 866–891 | 1234–1253 | 1307–1326 | 1643–1659 | 2246–2271 | 2327–2352 | 2440–2460 | 2463–2483 | |
| PPOLG_KUNJM | GENOME POLYPROTEIN | KUNJIN VIRUS (STRAIN MRM61C) | 561–576 2798–2814 | 935–960 | 1307–1326 | 1643–1659 | 2246–2271 | 2327–2352 | 2440–2460 | 2463–2483 | 2641–2658 |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLG_LANVT | GENOME POLYPROTEIN | LANGAT VIRUS (STRAIN TP21) | 67–89<br>2366–2387 | 527–551<br>2424–2451 | 736–756<br>2766–2784 | 835–862 | 1157–1178 | 1519–1544 | 1630–1653 | 2158–2182 | 2230–2257 |
| PPOLG_LANVY | GENOME POLYPROTEIN | LANGAT VIRUS (STRAIN YELANTSEV) | 67–89 | 527–551 | | | | | | | |
| PPOLG_LIV | GENOME POLYPROTEIN | LOUPING ILL VIRUS (LI) | 67–89 | 527–551 | 835–862 | | | | | | |
| PPOLG_LIVSB | GENOME POLYPROTEIN | LOUPING ILL VIRUS (STRAIN SB 526) | 247–271 | | | | | | | | |
| PPOLG_MCFA | GENOME POLYPROTEIN | MOSQUITO CELL FUSING AGENT (CFA FLAVIVIRUS) | 120–137 | 1174–1199 | 1402–1428 | 1788–1805 | 1872–1887 | 2012–2029 | 2810–2827 | | |
| PPOLG_MDMV | GENOME POLYPROTEIN | MAIZE DWARF MOSAIC VIRUS | 39–56 | | | | | | | | |
| PPOLG_MVEV | GENOME POLYPROTEIN | MURRAY VALLEY ENCEPHALITIS VIRUS | 331–347 | 563–578 | 937–962 | 1305–1324 | 1523–1548 | 1585–1602 | 1641–1657 | | |
| PPOLG_OMV | GENOME POLYPROTEIN | ORNITHOGLAUM MOSAIC VIRUS | 90–110 | 111–696 | 678–696 | 898–914 | | | | | |
| PPOLG_PEMVC | GENOME POLYPROTEIN | PEPPER MOTTLE VIRUS (CALIFORNIA ISOLATE) | 690–717 | 826–846 | 1009–1034 | 1301–1348 | 1455–1482 | 1484–1500 | 1676–1697 | 1921–1945 | 2002–2022 |
| PPOLG_POLIM | GENOME POLYPROTEIN | POLIOVIRUS TYPE 1 (STRAIN MAHONEY) | 1409–1432 | | | | | | | | |
| PPOLG_POLIS | GENOME POLYPROTEIN | POLIOVIRUS TYPE I (STRAIN SABIN) | 1410–1433 | | | | | | | | |
| PPOLG_POL2L | GENOME POLYPROTEIN | POLIOVIRUS TYPE 2 (STRAIN LANSING) | 1408–1431 | | | | | | | | |
| PPOLG_POL2W | GENOME POLYPROTEIN | POLIOVIRUS TYPE 2 (STRAIN W-2) | 1408–1431 | | | | | | | | |
| PPOLG_POL32 | GENOME POLYPROTEIN | POLIOVIRUS TYPE 3 (STRAIN 23127) | 577–594 | 1407–1430 | | | | | | | |
| PPOLG_POL3L | GENOME POLYPROTEIN | POLIOVIRUS TYPE 3 (STRAINS P3/LEON/37 AND P3/LEON 12A[1]B) | 577–594 | 1407–1430 | | | | | | | |
| PPOLG_PPVD | GENOME POLYPROTEIN | PLUM POX POTYVIRUS (STRAIN D) | 153–178 | 551–571 | 714–741 | 1098–1115 | 1468–1495 | 1497–1513 | 2606–2624 | 3084–3106 | |
| PPOLG_PPVEA | GENOME POLYPROTEIN | PLUM POX POTYVIRUS (STRAIN ELAMAR) | 981–999 | 1461–1483 | | | | | | | |
| PPOLG_PPVNA | GENOME POLYPROTEIN | PLUM POX POTYVIRUS (ISOLATE NAT) | 153–178 | 713–740 | 1097–1114 | 1467–1494 | 1496–1512 | 2605–2623 | 3068–3090 | | |
| PPOLG_PPVRA | GENOME POLYPROTEIN | PLUM POX POTY VIRUS (STRAIN RANKOVIC) | 153–178 | 713–740 | 1097–1114 | 1467–1494 | 1496–1512 | 2605–2623 | 3083–3105 | | |
| PPOLG_PRSVH | GENOME POLYPROTEIN | PAPAYA RINGSPOT VIRUS (STRAIN P/MUTANT HA) | 272–290 | | | | | | | | |
| PPOLG_PRSVP | GENOME POLYPROTEIN | PAPAYA RINGSPOT VIRUS (STRAIN P/MUTANT HA-5-1) | 163–181 | | | | | | | | |
| PPOLG_PRSVW | GENOME POLYPROTEIN | PAPAYA RINGSPOT VIRUS (STRAIN W) | 163–181 | | | | | | | | |
| PPOLG_PSBMV | GENOME POLYPROTEIN | PEA SEED-BORNE MOSAIC VIRUS (STRAIN DPD1) | 47–62 | 251–268 | 339–357 | 654–674 | 981–1001 | 1411–1428 | 1565–1592 | 2708–2726 | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLG_PVYC | GENOME POLYPROTEIN | POTATO VIRUS Y (STRAIN C) | 755–776 | | | | | | | | |
| PPOLG_PVYHU | GENOME POLYPROTEIN | POTATO VIRUS Y (STRAIN HUNGARIAN) | 755–776 | 964–982 | 1010–1036 | 1109–1125 | 1456–1483 | 1485–1501 | 1677–1698 | 1922–1946 | 2588–2606 |
| | | | 3004–3026 | | | | | | | | |
| PPOLG_PVYN | GENOME POLYPROTEIN | POTATO VIRUS Y (STRAIN N) | 755–776 | 964–982 | 1010–1036 | 1109–1125 | 1456–1483 | 1485–1501 | 1677–1698 | 1922–1946 | 2590–2608 |
| PPOLG_PVYO | GENOME POLYPROTEIN | POTATO VIRUS Y (STRAIN O) | 755–776 | | | | | | | | |
| PPOLG_PYFV1 | GENOME POLYPROTEIN | PARSNIP YELLOW FLECK VIRUS (ISOLATE P-121) | 592–616 | 1326–1353 | 1626–1651 | 1903–1924 | 2621–2642 | 2702–2729 | 2766–2783 | | |
| PPOLG_STEVM | GENOME POLYPROTEIN | ST LOUIS ENCEPHALITIS VIRUS (STRAIN MS1-7) | 1301–1324 | | | | | | | | |
| PPOLG_SUMVS | GENOME POLYPROTEIN | SUGARCANE MOSAIC VIRUS (STRAIN SC) | 39–56 | | | | | | | | |
| PPOLG_SVDVH | GENOME POLYPROTEIN | SWINE VESICULAR DISEASE VIRUS (STRAIN H/3 '76) | 1475–1501 | 1585–1610 | | | | | | | |
| PPOLG_SVDVU | GENOME POLYPROTEIN | SWINE VESICULAR DISEASE VIRUS (STRAIN UKG/27/72) | 1475–1501 | 1585–1610 | | | | | | | |
| PPOLG_TBEVS | GENOME POLYPROTEIN | TICK-BORNE ENCEPHALITIS VIRUS (STRAIN SOFJIN) | 67–89 | 527–551 | 1363–1378 | 1519–1544 | 1630–1653 | 1740–1761 | 2230–2257 | 2366–2387 | 2765–2783 |
| PPOLG_TBEVW | GENOME POLYPROTEIN | TICK-BORNE ENCEPHALITIS (VIRSU (WESTERN SUBTYPE) | 67–89 | 527–551 | 835–862 | 1519–1544 | 1630–1653 | 2230–2257 | 2366–2387 | 2766–2784 | |
| PPLLG_TEV | GENOME POLYPROTEIN | TOBACCO ETCH VIRUS (TEV | 827–853 | 953–980 | 1016–1042 | 1114–1130 | 1307–1324 | 1490–1506 | | | |
| PPOLG_TMEVB | GENOME POLYPROTEIN | THEILER'S MURINE ENCEPHALOMYELITIS VIRUS (STRAIN BEAN 8386) | 924–941 | 1074–1095 | 1119–1140 | 1520–1546 | 1658–1677 | | | | |
| PPOLG_TMEVD | GENOME POLYPROTEIN | THEILER'S MURINE ENCEPHALOMYELITIS VIRUS (STRAIN DA) | 1072–1093 | 1117–1138 | 1518–1544 | 1656–1675 | | | | | |
| PPOLG_TMEVG | GENOME POLYPROTEIN | THEILER'S MURINE ENCEPHALOMYELITIS VIRUS (STRAIN GDV11) | 645–670 | 924–941 | 1074–1095 | 1119–1140 | 1520–1546 | 1658–1677 | | | |
| PPOLG_TUMV | GENOME POLYPROTEIN | TURNIP MOSAIC VIRUS | 23–39 | 970–991 | 1138–1156 | 1573–1595 | | | | | |
| PPOLG_TVMV | GENOME POLYPROTEIN | TOBACCO VEIN MOTTLING VIRUS | 404–428 | 497–517 | 660–687 | 850–866 | 967–992 | 1257–1274 | 2537–2562 | | |
| PPOLG_WMV2 | GENOME POLYPROTEIN | WATERMELON MOSAIC VIRUS II | 198–218 | | | | | | | | |
| PPOLG_WNV | GENOME POLYPROTEIN | WEST NILE VIRUS | 557–572 | 931–956 | 1303–1322 | 1639–1655 | 2240–2267 | 2324–2349 | 2437–2457 | 2638–2655 | 2795–2811 |
| PPOLG_YEFV1 | GENOME POLYPROTEIN | YELLOW FEVER VIRUS (STRAIN 17D) | 74–95 | 1157–1179 | 1228–1248 | 1385–1405 | 1495–1511 | 1625–1641 | 1761–1778 | 2229–2254 | |
| PPOLG_YEFV2 | GENOME POLYPROTEIN | YELLOW FEVER VIRUS (STRAIN PASTEUR 17D-204) | 74–95 | 1157–1179 | 1228–1248 | 1385–1405 | 1495–1511 | 1625–1641 | 1761–1778 | 2229–2254 | |
| PPOLG_YEFV8 | GENOME POLYPROTEIN | YELLOW FEVER VIRUS (STRAIN 1899/81) | 74–95 | | | | | | | | |
| PPOLH_POLIM | GENOME POLYPROTEIN | POLIOVIRUS TYPE 1 (STRAIN MAHONEY) | 1410–1433 | | | | | | | | |
| PPOLN_EEVVT | NONSTRUCTURAL POLYPROTEIN | VENEZUELAN EQUINE ENCEPHALITIS VIRUS (STRAIN TRINIDAD DON | 90–107 | 235–254 | 613–634 | 1001–1018 | 1153–1178 | 1923–1939 | 2129–2144 | 2201–2221 | |
| PPOLN_FCVC6 | NON-STRUCTURAL POLYPROTEIN | FELINE CACICIVIRUS (STRAIN CF1/68 FIV) | 443–469 | 748–766 | 902–923 | 1069–1088 | | | | | |

TABLE XIII-continued

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| SEARCH RESULTS SUMMARY FOR P12LZIPC MOTIF | | | | | | | | | | | |
| PPOLN_FCVF4 | NON-STRUCTURAL POLYPROTEIN | FELINE CACICIVIRUS (STRAIN JAPANESE F4) | 300–326 | | | | | | | | |
| PPOLN_FCVF9 | NON-STRUCTURAL POLYPROTEIN | FELINE CACICIVIRUS (STRAIN F9) | 171–186 | 262–283 | 919–945 | 1224–1242 | 1378–1399 | 1545–1564 | | | |
| PPOLN_HEVBU | NON-STRUCTURAL POLYPROTEIN | HEPATITIS E VIRUS (STRAIN BURMA) | 250–266 | 1274–1291 | | | | | | | |
| PPOLN_HEVME | NON-STRUCTURAL POLYPROTEIN | HEPATITIS E VIRUS (STRAIN MEXICO) | 250–266 | 1272–1289 | | | | | | | |
| PPOLN_HEVMY | NON-STRUCTURAL POLYPROTEIN | HEPATITIS E VIRUS (STRAIN MYANMAR) | 250–266 | 1274–1291 | | | | | | | |
| PPOLN_HEVPA | NON-STRUCTURAL POLYPROTEIN | HEPATITIS E VIRUS (STRAIN PAKISTAN) | 249–265 | 1273–1290 | | | | | | | |
| PPOLN_MIDDV | NONSTRUCTURAL POLYPROTEIN | MIDDLEBURG VIRUS | 488–512 | 628–643 | 700–720 | | | | | | |
| PPOLN_ONNVG | NONSTRUCTURAL POLYPROTEIN | ONYONG-NYONG VIRUS (STRAIN GULU) | 90–107 | 613–634 | 2148–2163 | 2220–2240 | | | | | |
| PPOLN_RHDV | NON-STRUCTURAL POLYPROTEIN | RABBIT HEMORRHAGIC DISEASE VIRUS | 156–180 | 270–292 | 299–320 | 479–502 | 1330–1353 | 1429–1455 | 1471–1490 | | |
| PPOLN_RHDV3 | NON-STRUCTURAL POLYPROTEIN | RABBIT HEMORRHAGIC DISEASE VIRUS (STRAIN V-351) | 115–135 | | | | | | | | |
| PPOLN_RRVN | NONSTRUCTURAL POLYPROTEIN | ROSS RIVER VIRUS (STRAIN NB5092) | 89–106 | 611–632 | 2113–2128 | 2185–2205 | | | | | |
| PPOLN_RRVT | NONSTRUCTURAL POLYPROTEIN | ROSS RIVER VIRUS (STRAIN T48) | 782–797 | 854–874 | | | | | | | |
| PPOLN_RUBVT | NONSTRUCTURAL POLYPROTEIN | RUBELLA VIRUS (STRAIN THERIEN) | 14–37 | 97–113 | 263–279 | 670–694 | 901–918 | 1374–1393 | 2035–2052 | | |
| PPOLN_SFV | NONSTRUCTURAL POLYPROTEIN | SEMLIKI FOREST VIRUS | 91–108 | 617–643 | 2062–2077 | 2134–2154 | | | | | |
| PPOLN_SINDO | NONSTRUCTURAL POLYPROTEIN | SINDBIS VIRUS (SUBTYPE OCKELBO/STRAIN EDSBYN 82-5) | 620–646 | 1123–1150 | 1790–1814 | 2148–3163 | 2220–2240 | | | | |
| PPOLN_SINDV | NONSTRUCTURAL POLYPROTEIN | SINDBIS VIRUS (STRAIN HRSP) | 620–646 | 1123–1150 | 1744–1763 | 1790–1812 | 2146–2161 | 2218–2238 | | | |
| PPOLR_EPMV | RNA REPLICASE POLYPROTEIN | EGGPLANT MOSAIC VIRUS | 8908–833 | | | | | | | | |
| PPOLR_OYMV | RNA REPLICASE POLYPROTEIN | ONONIS YELLOW MOSAIC VIRUS | 707–727 | 941–962 | | | | | | | |
| PPOLR_TYMV | RNA REPLICASE POLYPROTEIN | TURNIP YELLOW MOSAIC VIRUS | 212–233 | 436–453 | 1173–1192 | | | | | | |
| PPOLR_TYMVA | RNA REPLICASE POLYPROTEIN | TURNIP YELLOW MOSAIC VIRUS (AUSTRAILIA ISOLATE) | 212–233 | 436–453 | 1173–1192 | | | | | | |
| PPOLR_TYMVC | RNA REPLICASE POLYPROTEIN | YURNIP YELLOW MOSAIC VIRUS (ISOLATE TYMC) | 212–233 | 436–453 | 1173–1192 | | | | | | |
| PPOLS_EEEV | STRUCTURAL POLYPROTEIN | EASTER EQUINE ENCEPHALITIS VIRUS | 35–50 | 213–229 | 491–507 | | | | | | |
| PPOLS_EEEV3 | STRUCTURAL POLYPROTEIN | EASTER EQUINE ENCEPHALITIS VIRUS | 35–50 | 214–230 | 492–508 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOLS_EEVV8 | STRUCTURAL POLYPROTEIN | VENEZUELAN EQUINE ENCEPHALITIS VIRUS (STRAIN TC-83) | 32–48 | 229–245 | 504–522 | | | | | | |
| PPOLS_EEVVT | STRUCTURAL POLYPROTEIN | VENEZUELAN EQUINE ENCEPHALITIS VIRUS (STRAIN TRINIDAD DON | 32–48 | 229–245 | 504–522 | | | | | | |
| PPOLS_IBVD5 | STRUCTURAL POLYPROTEIN | AVIAN INFECTIOUS BURSAL DISEASE VIRUS (STRAIN 52/70) | 900–922 | | | | | | | | |
| PPOLS_IBDVA | STRUCTURAL POLYPROTEIN | AVIAN INFECTIOUS BURSAL DISEASE VIRUS (STRAIN AUSTRA-LIAN 00 | 900–922 | | | | | | | | |
| PPOLS_IBDVC | STRUCTURAL POLYPROTEIN | AVIAN INFECTIOUS BURSAL DISEASE VIRUS (STRAIN CU-1) | 900–922 | | | | | | | | |
| PPOLS_IBDVP | STRUCTURAL POLYPROTEIN | AVIAN INFECTIOUS BURSAL DISEASE VIRUS (STRAIN PBG-98) | 881–903 | | | | | | | | |
| PPOLS_IBDVS | STRUCTURAL POLYPROTEIN | AVIAN INFECTIOUS BURSAL DISEASE VIRUS (STRAIN STC) | 900–922 | | | | | | | | |
| PPOLS_ONNVG | STRUCTURAL POLYPROTEIN | O'NYONG-NYONG VIRUS (STRAIN GULU) | 688–708 | | | | | | | | |
| PPOLS_RRVT | STRUCTURAL POLYPROTEIN | ROSS RIVER VIRUS (STRAIN T48) | 1216–1243 | | | | | | | | |
| PPOLS_RUBVH | STRUCTURAL POLYPROTEIN | RUBELLA VIRUS (VACCINE STRAIN HPV77) | 281–302 | | | | | | | | |
| PPOLS_RUBVM | STRUCTURAL POLYPROTEIN | RUBELLA VIRUS (STRAIN M33) | 280–301 | | | | | | | | |
| PPOLS_RUBVR | STRUCTURAL POLYPROTEIN | RUBELLA VIRUS (VACCINE STRAIN RA27/3 | 281–302 | | | | | | | | |
| PPOLS_RUBVT | STRUCTURAL POLYPROTEIN | RUBELLA VIRUS (STRAIN THERIEN | 281–302 | 1041–1060 | | | | | | | |
| PPOLS_SFV | STRUCTURAL POLYPROTEIN | SEMLIKI FOREST VIRUS | 35–59 | 751–772 | 780–801 | | | | | | |
| PPOLS_SINDO | STRUCTURAL POLYPROTEIN | SINDBIS VIRUS (SUBTYPE OCKELBO/STRAIN EDSBYN 82-5) | 33–52 | | | | | | | | |
| PPOLS_SINDV | STRUCTURAL POLYPROTEIN | SINDBIS VIRUS (STRAIN HRSP AND HRLP) | 33–52 | | | | | | | | |
| PPOLS_WEEV | STRUCTURAL POLYPROTEIN | WESTERN EQUINE ENCEPHALITIS VIRUS | 36–51 | 909–933 | | | | | | | |
| PPOL_AVIRE | POL POLYPROTEIN | AVIAN RETICULOENDOTHELIOSIS VIRUS | 283–303 | | | | | | | | |
| PPOL_BAEVM | POL POLYPROTEIN | BABOON ENDOGENOUS VIRUS (STRAIN M7) | 526–544 | 973–993 | 999–1019 | 1070–1091 | | | | | |
| PPOL_BIV06 | POL POLYPROTEIN | BOVINE IMMUNODEFICIENCY VIRUS (ISOLATE 106) | 101–119 | 742–768 | 868–889 | | | | | | |
| PPOL_BIV27 | POL POLYPROTEIN | BOVINE IMMUNODEFICIENCY VIRUS (ISOLATE 127) | 101–119 | 742–768 | 868–889 | | | | | | |
| PPOL_BLVAU | POL POLYPROTEIN | BOVINE LEUKEMIA VIRUS (AUSTRALIAN ISOLATE) | 487–504 | | | | | | | | |
| PPOL_BLVJ | POL POLYPROTEIN (REVERSE TRANSCRIPTASE | BOVINE LEUKEMIA VIRUS (JAPANESE ISOLATE BVL-1) | 487–504 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOL_CAEVC | POL POLYPROTEIN | CAPRINE ARTHRITIS ENCEPHALITIS VIRUS (STRAIN CORK) | 393–419 | 656–671 | | | | | | | |
| PPOL_CAMVC | ENZYMATIC POLYPROTEIN | CAULIFLOWER MOSAIC VIRUS (STRAIN CM-1841) | 184–204 | 380–407 | 471–494 | | | | | | |
| PPOL_CAMVD | ENZYMATIC POLYPROTEIN | CAULIFLOWER MOSAIC VIRUS (STRAIN D/H) | 175–199 | 375–402 | 466–489 | | | | | | |
| PPOL_CAMVE | ENZYMATIC POLYPROTEIN | CAULIFLOWER MOSAIC VIRUS (STRAIN BBC) | 184–204 | 380–407 | 471–494 | | | | | | |
| PPOL_CAMVN | ENZYMATIC POLYPROTEIN | CAULIFLOWER MOSAIC VIRUS (STRAIN NY8153) | 70–97 | 185–205 | 381–408 | 472–495 | | | | | |
| PPOL_CAMVS | ENZYMATIC POLYPROTEIN | CAULIFLOWER MOSAIC VIRUS (STRAIN STRASBOURG) | 184–204 | 380–407 | 471–494 | | | | | | |
| PPOL_CERV | ENZYMATIC POLYPROTEIN | CARNATION ETCHED RING VIRUS | 161–186 | 455–478 | | | | | | | |
| PPOL_COYMV | PUTATIVE POLYPROTEIN | COMMELINE YELLOW MOTTLE VIRUS | 320–343 | 1286–1311 | 1606–1622 | 1641–1665 | | | | | |
| PPOL_EIAV9 | POL POLYPROTEIN | EQUINE INFECTIOUS ANEMIA VIRUC (CLONE 1369) | 437–456 | | | | | | | | |
| PPOL_EIAVC | POL POLYPROTEIN | EQUINE INFECTIOUS ANEMIA VIRUS (CLONE CL22) | 437–456 | | | | | | | | |
| PPOL_EIAVY | POL POLYPROTEIN | EQUINE INFECTIOUS ANEMIA VIRUS (ISOLATE WYOMING) | 436–455 | | | | | | | | |
| PPOL_FENV1 | POL POLYPROTEIN | FELINE EDNOGENOUS VIRUS ECE1 | 383–401 | 856–876 | | | | | | | |
| PPOL_FIVPE | POL POLYPROTEIN | FELINE IMMUNODEFICIENCY VIRUS (ISOLATE PETALUMA) | 407–426 | 755–775 | | | | | | | |
| PPOL_FIVSD | POL POLYPROTEIN | FELINE IMMUNODEFICIENCY VIRUS (ISOLATE SAN DIEGO) | 407–426 | 755–775 | | | | | | | |
| PPOL_FIVT2 | POL POLYPROTEIN | FELINE IMMUNODEFICIENCY VIRUS (ISOLATE TM2) | 406–425 | 665–690 | 755–775 | 1041–1060 | | | | | |
| PPOL_FMVD | ENZYMATIC POLYPROTEIN | FIGWORT MOSAIC VIRUS (STRAIN DXS) | 191–212 | 464–487 | | | | | | | |
| PPOL_FOAMV | POL POLYPROTEIN | HUMAN SPUMARETROVIRUS | 126–147 | 768–788 | | | | | | | |
| PPOL_GALV | POL POLYPROTEIN | GIBBON APE LEUKEMIA VIRUS | 59–80 | 971–991 | 1048–1071 | | | | | | |
| PPOL_HTL1A | POL POLYPROTEIN | HUMAN T-CELL LEUKEMIA VIRUS TYPE I (STRAIN ATK) | 330–346 | | | | | | | | |
| PPOL_HTL1C | POL POLYPROTEIN | HUMAN T-CELL LEUKEMIA VIRUS TYPE I (CARIBBEAN ISOLATE) | 330–346 | | | | | | | | |
| PPOL_TTLV2 | POL POLYPROTEIN | HUMAN T-CELL LEUKEMIA VIRUS TYPE II | 609–627 | | | | | | | | |
| PPOL_HV1A2 | POL POLYPROTEIN | HUMAN IMMUNODEFICIENCY VIRUS TYPE 1 (ARV2/SF2 ISOLATE) | 860–887 | | | | | | | | |
| PPOL_HV1B1 | POL POLYPROTEIN | HUMAN IMMUNODEFICIENCY VIRUS TYPE 1 (BH10 ISOLATE) | 635–660 | 872–899 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOL_HV1B5 | POL POLYPROTEIN | HUMAN IMMUNODEFICIENCY VIRUS TYPE 1 (BH5 ISOLATE) | 872–899 | | | | | | | | |
| PPOL_HV1BR | POL POLYPROTEIN | HUMAN IMMUNODEFICIENCY VIRUS TYPE 1 (BRU ISOLATE) | 872–899 | | | | | | | | |
| PPOL_HE1EL | POL POLYPROTEIN | HUMAN IMMUNODEFICIENCY VIRUS TYPE 1 (ELI ISOLATE) | 622–647 | 859–886 | | | | | | | |
| PPOL_HV1H2 | POL POLYPROTEIN | HUMAN IMMUNODEFICIENCY VIRUS TYPE 1 (HXB2 ISOLATE) | 860–887 | | | | | | | | |
| PPOL_HV1JR | POL POLYPROTEIN | HUMAN IMMUNODEFICIENCY VIRUS TYPE 1 (JRCSF ISOLATE) | 864–891 | | | | | | | | |
| PPOL_HV1MA | POL POLYPROTEIN | HUMAN IMMUNODEFICIENCY VIRUS TYPE 1 (MAL ISOLATE) | 859–886 | | | | | | | | |
| PPOL_HV1MN | POL POLYPROTEIN | HUMAN IMMUNODEFICIENCY VIRUS TYPE 1 (MN ISOLATE) | 863–890 | | | | | | | | |
| PPOL_HV1N5 | POL POLYPROTEIN | HUMAN IMMUNODEFICIENCY VIRUS TYPE 1 (NEW YORK-5 ISOLATE) | 623–648 | 860–887 | | | | | | | |
| PPOL_HV1ND | POL POLYPROTEIN | HUMAN IMMUNODEFICIENCY VIRUS TYPE 1 (NDK ISOLATE) | 622–647 | 859–886 | | | | | | | |
| PPOL_HV1OY | POL POLYPROTEIN | HUMAN IMMUNODEFICIENCY VIRUS TYPE 1 (OY1 ISOLATE) | 860_887 | | | | | | | | |
| PPOL_HVIPV | POL POLYPROTEIN | HUMAN IMMUNODEFICIENCY VIRUS TYPE 1 (PV22 ISOLATE) | 635–660 | 872–899 | | | | | | | |
| PPOL_HV1RH | POL POLYPROTEIN | HUMAN IMMUNODEFICIENCY VIRUS TYPE 1 (RF/HAT ISOLATE) | 859–886 | | | | | | | | |
| PPOL_HV1U4 | POL POLYPROTEIN | HUMAN IMMUNODEFICIENCY VIRUS TYPE 1 (STRAIN UGANDAN/ISO | 859–886 | | | | | | | | |
| PPOL_HV1Z2 | POL POLYPROTEIN | HUMAN IMMUNODEFICIENCY VIRUS TYPE 1 (Z2/CDC-Z34 ISOLATE) | 622–647 | 859–886 | | | | | | | |
| PPOL_HV1Z6 | POL POLYPROTEIN | HUMAN IMMUNODEFICIENCY VIRUS TYPE 1 (ZAIRE 6 ISOLATE) | 5–32 | | | | | | | | |
| PPOL_HV2BE | POL POLYPROTEIN | HUMAN IMMUNODEFICIENCY VIRUS TYPE 2 (ISOLATE BEN) | 379–406 | 907–934 | | | | | | | |
| PPOL_HV2CA | POL POLYPROTEIN | HUMAN IMMUNODEFICIENCY VIRUS TYPE 2 (ISOLATE CAM2) | 886–913 | | | | | | | | |
| PPOL_HV2D1 | POL POLYPROTEIN | HUMAN IMMUNODEFICIENCY VIRUS TYPE 2 (ISOLATE D194) | 397–424 | 925–952 | | | | | | | |
| PPOL_HV2D2 | POL POLYPROTEIN | HUMAN IMMUNODEFICIENCY VIRUS TYPE 2 (ISOLATE D205.7) | 907–934 | | | | | | | | |
| PPOL_HV2G1 | POL POLYPROTEIN | HUMAN IMMUNODEFICIENCY VIRUS TYPE 2 (ISOLATE GHANA-1) | 359–386 | 887–914 | | | | | | | |
| PPOL_HV2NZ | POL POLYPROTEIN | HUMAN IMMUNODEFICIENCY VIRUS TYPE 2 (ISOLATE NIH-Z) | 543–564 | 771–792 | 887–914 | | | | | | |
| PPOL_HV2RO | POL POLYPROTEIN | HUMAN IMMUNODEFICIENCY VIRUS TYPE 2 (ISOLATE ROD) | 888–915 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOL_HV2SB | POL POLYPROTEIN | HUMAN IMMUNODEFICIENCY VIRUS TYPE 2 (ISOLATE SBLISY) | 359–386 | 887–907 | | | | | | | |
| PPOL_HV2ST | POL POLYPROTEIN | HUMAN IMMUNOCEFICIENCY VIRUS TYPE 2 (ISOLATE ST) | 379–406 | 907–934 | | | | | | | |
| PPOL_IPHA | PUTATIVE POL POLYPROTEIN | HAMSTER INTRACISTERNAL A-PARTICLE | 166–190 | 198–225 | 460–477 | | | | | | |
| PPOL_IPMA | PUTATIVE POL POLYPROTEIN | MOUSE INTRACISTERNAL A-PARTICLE | 183–201 | 209–236 | 506–523 | 531–552 | 769–789 | | | | |
| PPOL_IPMAI | PROBABLE POL POLYPROTEIN | MOUSE INTRACISTERNAL A-PARTICLE | 102–120 | 128–155 | 407–423 | 425–442 | | | | | |
| PPOL_JSRV | POL POLYPROTEIN | SHEEP PULMONARY ADENO-MATOSIS VIRUS (JAAGSIEKTE SHEEP RET | 186–213 | 507–526 | 660–679 | | | | | | |
| PPOL_MCFF3 | POL POLYPROTEIN | MINK CELL FOCUS-FORMING MURINE LEUKEMIA VIRUS (ISOLATE CI- | 37–53 | | | | | | | | |
| PPOL_MLVAK | POL POLYPROTEIN | AKR MURINE LEUKEMIA VIRUS | 651–671 | 728–744 | | | | | | | |
| PPOL_MLVAV | POL POLYPROTEIN | AKV MURINE LEUKEMIA VIRUS | 335–354 | 978–998 | 1004–1024 | 1081–1097 | | | | | |
| PPOL_MLVCB | POL POLYPROTEIN | CAS-BR-E MURINE LEUKEMIA VIRUS | 64–84 | 90–110 | 167–183 | | | | | | |
| PPOL_MLVF5 | POL POLYPROTEIN | FRIEND MURINE LEUKEMIA VIRUS (ISOLATE 57) | 340–359 | 983–1003 | 1009–1029 | 1086–1102 | | | | | |
| PPOL_MLVFF | POL POLYPROTEIN | FRIEND MURINE LEUKEMIA VIRUS (ISOLATE FB29) | 340–359 | 983–1003 | 1009–1029 | 1086–1102 | | | | | |
| PPOL_MLVFP | POL POLYPROTEIN | FRIEND MURINE LEUKEMIA (ISOLATE PVC-211) | 340–359 | 983–1003 | 1009–1029 | 1086–1102 | | | | | |
| PPOL_MLVMO | POL POLYPROTEIN | MOLONEY MURINE LEUKEMIA VIRUS | 335–354 | 978–998 | | | | | | | |
| PPOL_MLVRD | POL POLYPROTEIN | RADIATION MURINE LEUKEMIA VIRUS | 335–354 | 978–998 | 1004–1024 | 1081–1097 | | | | | |
| PPOL_MLVRK | POL POLYPROTEIN | RADIATION MURINE LEUKEMIA VIRUS (STRAIN KAPLAN) | 363–383 | 389–409 | 466–482 | | | | | | |
| PPOL_MMTVB | POL POLYPROTEIN | MOUSE MAMMARY TUMOR VIRUS (STRAIN BR6) | 196–219 | 731–751 | | | | | | | |
| PPOL_MPMV | POL POLYPROTEIN | SIMIAN MASON-PFIZER VIRUS | 743–763 | | | | | | | | |
| PPOL_OMVVS | POL POLYPROTEIN | OVINE LENTIVIRUS (STRAIN SA-OMVV) | 369–395 | 469–488 | 632–647 | 1045–1063 | | | | | |
| PPOL_RSVP | POL POLYPROTEIN | ROUS SARCOMA VIRUS (STRAIN PRAGUE C) | 719–742 | | | | | | | | |
| PPOL_RTBV | POLYPROTEIN | RICE TUNGRO BACILLIFORM VIRUS (RTBV) | 891–915 | 1058–1083 | | | | | | | |
| PPOL_RTBVP | POLYPROTEIN | RICE TUNGRO BACILLIFORM VIRUS (ISOLATE PHILIPPINES) | 891–915 | 1058–1083 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPOL_SFV1 | POL POLYPROTEIN | SIMIAN FOAMY VIRUS (TYPE 1) | 188–204 | 335–356 | 845–869 | 976–996 | | | | | |
| PPOL_SFV3L | POL POLYPROTEIN | SIMIAN FOAMY VIRUS (TYPE 3/STRAIN LK3) | 186–206 | 337–358 | 847–871 | 978–998 | | | | | |
| PPOL_SIVA1 | POL POLYPROTEIN | SIMAIN IMMUNODEFICIENCY VIRUS (AGM155 ISOLATE) | 895–915 | | | | | | | | |
| PPOL_SIVAG | POL POLYPROTEIN | SIMAIN IMMUNODEFICIENCY VIRUS (AGM3 ISOLATE) | 711–726 | 900–920 | | | | | | | |
| PPOL_SIVA1 | POL POLYPROTEIN | SIMAIN IMMUNODEFICIENCY VIRUS (ISOLATE AGM/CLONE GR1-1) | 899–926 | | | | | | | | |
| PPOL_SIVAT | POL POLYPROTEIN | SIMIAN IMMUNODEFICIENCY VIRUS (TYO-1 ISOLATE) | 726–741 | 915–935 | | | | | | | |
| PPOL_SIVCZ | POL POLYPROTEIN | CHIMPANZEE IMMUNODEFICIENCY VIRUS | 884–911 | | | | | | | | |
| PPOL_SIVGB | POL POLYPROTEIN | SIMAIN IMMUNODEFICIENCY VIRUS (ISOLATE GB1) | 680–695 | 869–896 | | | | | | | |
| PPOL_SIVMI | POL POLYPROTEIN | SIMAIN IMMUNODEFICIENCY VIRUS (MM142-83 ISOLATE) | 380–407 | 908–935 | | | | | | | |
| PPOL_SIVMK | POL POLYPROTEIN | SIMAIN IMMUNODEFICIENCY VIRUS (K6W ISOLATE) | 380–407 | 712–737 | 906–933 | | | | | | |
| PPOL_SIVS4 | POL POLYPROTEIN | SIMAIN IMMUNODEFICIENCY VIRUS (F235/SMH4 ISOLATE) | 343–370 | 871–898 | | | | | | | |
| PPOL_SIVSP | POL POLYPROTEIN | SIMAIN IMMUNODEFICIENCY VIRUS (PBJ/BC13 ISOLATE) | 346–373 | 874–901 | | | | | | | |
| PPOL_SMRVH | POL POLYPROTEIN | SQUIRREL MONKEY RETROVIRUS | 748–768 | | | | | | | | |
| PPOL_SMSAV | POL POLYPROTEIN | SIMIAN SARCOMA VIRUS | 100–120 | 177–200 | | | | | | | |
| PPOL_SOCMV | ENZYMATIC POLYPROTEIN | SOYBEAN CHLOROTIC MOTTLE VIRUS | 131–155 | | | | | | | | |
| PPOL_SRV1 | POL POLYPROTEIN | SIMIAN RETROVIRUS | 743–763 | | | | | | | | |
| PPOL_VILV | POL POLYPROTEIN | VISNA LENTIVIRUS (STRAIN 1514) | 488–507 | 651–666 | 971–991 | | | | | | |
| PPOL_VILV1 | POL POLYPROTEIN | VISNA LENTIVIRUS (STRAIN 1514/CLONE LV1-1KS1) | 488–507 | 651–666 | 971–991 | | | | | | |
| PPOL_VILV2 | POL POLYPROTEIN | VISNA LENTIVIRUS (STRAIN 1514/CLONE LV1-1KS2) | 488–507 | 651–666 | 971–991 | | | | | | |
| PPP15_HCMVA | LARGE STRUCTURAL PHOSPHOPROTEIN PP150 | HUMAN CYTOMEGALOVIRUS (STRAIN AD169) | 153–171 | 183–210 | | | | | | | |
| PPP28_HCMVA | 28 KD STRUCTURAL PHOSPHOPROTEIN | HUMAN CYTOMEGALOVIRUS (STRAIN AD169) | 116–141 | | | | | | | | |
| PPP41_HSV6G | PHOSPHOPROTEIN P41 | HERPES SIMPLEX VIRUS (TYPE 6/STRAIN GS) | 158–175 | 396–411 | | | | | | | |
| PPP65_HCMVA | 65 KD LOWER MATRIX PHOSPHOPROTEIN | HUMAN CYTOMEGALOVIRUS (STRAIN AD169) | 311–333 | | | | | | | | |
| PPP65_HCMVT | 64 KD LOWER MATRIX PHOSPHOPROTEIN | HUMAN CYTOMEGALOVIRUS (STRAIN TOWNE) | 301–323 | | | | | | | | |
| PPP71_HCMVA | 71 KD UPPER MATRIX PHOSPHOPROTEIN | HUMAN CYTOMEGALOVIRUS (STRAIN AD169) | 79–102 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PPR73_MMTVB | PROTEIN PR73 | MOUSE MAMMARY TUMOR VIRUS (STRAIN BR6) | 40–61 | | | | | | | | |
| PPR73_MMTVG | PROTEIN PR73 | MOUSE MAMMARY TUMOR VIRUS (STRAIN GR) | 40–61 | | | | | | | | |
| PPR7L_MMTVG | PROTEIN PR73 | MOUSE MAMMARY TUMOR VIRUS (STRAIN GR) | 44–65 | | | | | | | | |
| PPR7R_MMTVG | PROTEIN PR73 | MOUSE MAMMARY TUMOR VIRUS (STRAIN GR) | 40–61 | | | | | | | | |
| PRASH_MSVHA | TRANSFORMING PROTEINS P21 AND P29 | HARVEY MURINE SARCOMA VIRUS | 49–73 | | | | | | | | |
| PRASH_RRASV | TRANSFORMING PROTEINS P21 AND P29 | RASHEED RAT SARCOMA VIRUS | 56–80 | | | | | | | | |
| PREEP_CSV | REPEAT ELEMENT PROTEIN | CAMPOLETIC SONORENSIS VIRUS | 14–36 | | | | | | | | |
| PREFR_VACCV | RIFAMPICIN RESISTANCE PROTEIN | VACCINIA VIRUS (STRAIN WR), AND (STRAIN COPENHAGEN) | 274–298 | 316–335 | 517–535 | | | | | | |
| PREFR_VARV | RIFAMPICIN RESISTANCE PROTEIN | VARIOLA VIRUS | 274–298 | 316–335 | 517–535 | | | | | | |
| PREV_SIVAG | REV PROTEIN | SIMIAN IMMUNODEFICIENCY VIRUS (AGM3 ISOLATE) | 2–17 | | | | | | | | |
| PREV_SIVGB | REV PROTEIN | SIMIAN IMMUNODEFICIENCY VIRUS (ISOLATE GB1) | 45–72 | | | | | | | | |
| PRIR1_ASFM2 | RIBONUCLEOSIDE-DIPHOSPHATE REDUCTASE | AFRICAN SWINE FEVER VIRUS (ISOLATE MALAWI LIL 20/1) | 139–164 | 189–210 | 495–510 | | | | | | |
| PRIR1_EBV | RIBONUCLEOTIDE REDUCTASE | EPSTEIN-BARR VIRUS (STRAIN B95-8) | 793–812 | | | | | | | | |
| PRIR1_HCMVA | RIBONUCLEOTIDE REDUCTASE | HUMAN CYTOMEGALOVIRUS (STRAIN AD169) | 192–212 | 669–684 | | | | | | | |
| PRIR1_HSV11 | RIBONUCLEOTIDE REDUCTASE | HERPES SIMPLEX VIRUS (TYPE 1/STRAIN 17) | 415–430 | 587–613 | | | | | | | |
| PRIR1_HSVEB | RIBONUCLEOTIDE REDUCTASE | EQUINE HERPESVIRUS TYPE 1 (STRAIN AB4P) | 60–85 | 266–288 | 668–694 | | | | | | |
| PRIR1_HSVSA | RIBONUCLEOTIDE REDUCTASE | HERPESVIRUS SAIMIRI (STRAIN 11) | 136–151 | | | | | | | | |
| PRIR1_VACCC | RIBONUCLEOTIDE REDUCTASE | VACCINIA VIRUS (STRAIN COPENHAGEN) | 36–51 | | | | | | | | |
| PRIR1_VACCV | RIBONUCLEOTIDE REDUCTASE | VACCINIA VIRUS (STRAIN WR) | 36–51 | | | | | | | | |
| PRIR1_VARV | RIBONUCLEOTIDE REDUCTASE | VARIOLA VIRUS | 36–51 | | | | | | | | |
| PRIR1_VZVD | RIBONUCLEOTIDE REDUCTASE | VARICELLA-ZOSTER VIRUS (STRAIN DUMAS) | 34–58 | 221–247 | 258–280 | | | | | | |
| PRIR2_EBV | RIBONUCLEOTIDE REDUCTASE | EPSTEIN-BARR VIRUS (STRAIN B95-8) | 209–236 | | | | | | | | |
| PRIR2_HSV11 | RIBONUCLEOTIDE REDUCTASE | HERPES SIMPLEX VIRUS (TYPE 1/STRAIN 17) | 44–66 | 275–292 | | | | | | | |
| PRIR2_HSVIK | RIBONUCLEOTIDE REDUCTASE | HERPES SIMPLEX VIRUS (TYPE 1/STRAIN KOS) | 43–65 | 245–261 | 274–291 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRIR2_HSV23 | RIBONUCLEOTIDE REDUCTASE | HERPES SIMPLEX VIRUS (TYPE 2/STRAIN 333) | 41–63 | 272–289 | | | | | | | |
| PRIR2_HSVB3 | RIBONUCLEOTIDE REDUCTASE | BOVINE HERPESVIRUS TYPE 1 (STRAIN 34) | 244–266 | | | | | | | | |
| PRIR2_HSVEB | RIBONUCLEOTIDE REDUCTASE | EQUINE HERPESVIRUS TYPE 1 (STRAIN AB4P) | 61–88 | 251–273 | | | | | | | |
| PRIR2_HSVSA | RIBONUCLEOTIDE REDUCTASE | HERPESVIRUS SAIMIRI (STRAIN 11) | 212–239 | | | | | | | | |
| PRIR2_SFVKA | RIBONUCLEOTIDE REDUCTASE | SHOPE FIBROMA VIRUS (STRAIN KASZA) | 184–206 | 215–237 | | | | | | | |
| PRIR2_VACCC | RIBONUCLEOTIDE REDUCTASE | VACCINIA VIRUS (STRAIN COPENHAGEN) | 184–206 | | | | | | | | |
| PRIR2_VACCP | RIBONUCLEOTIDE REDUCTASE | VACCINIA VIRUS (STRAIN L-IVP | 184–206 | | | | | | | | |
| PRIR2_VACCV | RIBONUCLEOTIDE REDUCTASE | VACCINIA VIRUS (STRAIN WR) | 184–206 | | | | | | | | |
| PRIR2_VARV | RIBONUCLEOTIDE REDUCTASE | VARIOLA VIRUS | 184–206 | 215–237 | | | | | | | |
| PRIR2_VZVD | RIBONUCLEOTIDE REDUCTASE | VARICELLA-ZOSTER VIRUS (STRAIN DUMAS) | 237–258 | | | | | | | | |
| PRMIL_AVEVR | RMIL SER/THR-PROTEIN TRANSFORMING P | AVIAN ROUS-ASSOCIATED VIRUS TYPE 1 | 380–405 | | | | | | | | |
| PRP94_VACCV | RNA-POL-ASSOCIATED TRANSCRIPTION SPEC FACT | VACCINIA VIRUS (STRAIN WR), AND (STRAIN COPENHAGEN) | 173–189 | 265–290 | 371–394 | 561–578 | | | | | |
| PRP94_VARV | RNA-POL-ASSOCIATED TRANSCRIPTION SPEC FACT | VARIOLA VIRUS | 173–189 | 265–290 | 371–394 | 561–578 | | | | | |
| PRPO1_VACCC | DNA-DIRECTED RNA POL 147 KD POLYPEPTIDE | VACCINIA VIRUS (STRAIN COPENHAGEN) | 76–96 | 304–329 | 848–871 | 1005–1032 | | | | | |
| PRPO1_VACCV | DNA-DIRECTED RNA POLYMERASE 147 KD POLYPE | VACCINIA VIRUS (STRAIN WR) | 76–96 | 304–329 | 848–871 | | | | | | |
| PRPO1_VARV | DNA-DIRECTED RNA POLYMERASE 147 KD POLYPE | VARIOLA VIRUS | 76–96 | 304–329 | 848–871 | 1005–1032 | | | | | |
| PRPO2_CAPVK | DNA-DIRECTED RNA POLYMERASE 132 KD POLYPE | CAPRIPOXVIRUS (STRAIN KS-1) | 12–29 | 477–498 | | | | | | | |
| PRPO2_COWPX | DNA-DIRECTED RNA POLYMERASE 132 KD POLYPE | COWPOX VIRUS | 150–170 | 258–274 | 480–505 | | | | | | |
| PRPO2_VACCV | DNA-DIRECTED RNA POLYMERASE 132 KD POLYPE | VACCINIA VIRUS (STRAIN WR), AND (STRAIN COPENHAGEN) | 150–170 | 258–274 | 480–505 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRPO2_VARV | DNA-DIRECTED RNA POLYMERASE 132 KD POLYPE | VARIOLA VIRUS | 150–170 | 258–274 | 480–505 | | | | | | |
| PRPO4_VACCC | DNA-DIRECTED RNA POLYMERASE 35 KD POLYPEP | VACCINIA VIRUS (STRAIN COPENHAGEN) | 33–48 | | | | | | | | |
| PRPO4_VACCV | DNA-DIRECTED RNA POLYMERASE 35 KD POLYPEP | VACCINAI VIRUS (STRAIN WR) | 33–48 | | | | | | | | |
| PRPO4_VARV | DNA-DIRECTED RNA POLYMERASE 35 KD POLYPEP | VARIOLA VIRUS | 33–55 | | | | | | | | |
| PRPO6_VACCV | DNA-DIRECTED RNA POLYMERASE 19 KD POLYPEP | VACCINAI VIRUS (STRAIN WR), AND (STRAIN COPENHAGEN) | 38–59 | | | | | | | | |
| PRPO7_VACCV | DNA-DIRECTED RNA POLYMERASE 19 KD POLYPEP | VACCINIA VIRUS (STRAIN WR), AND (STRAIN COPENHAGEN) | 38–59 | | | | | | | | |
| PRPO7_VARV | DNA-DIRECTED RNA POLYMERASE 19 KD POLYPEP | VARIOLA VIRUS | 38–59 | | | | | | | | |
| PRPO8_FOWP1 | DNA-DIRECTED RNA POLYMERASE 18 KD POLYPEP | FOWLPOX VIRUS (STRAIN FP-1) | 57–81 | | | | | | | | |
| PRPOA_LELV | RNA-DIRECTED RNA POLYMERASE | LELYSTAD VIRUS | 175–197 | 707–729 | 1164–1180 | 1233–1258 | 1513–1530 | 1534–1546 | 1955–1977 | 2320–2343 | 2802–2823 |
| | | | 3133–3156 | | | | | | | | |
| PRPOL_EAV | RNA-DIRECTED RNA POLYMERASE | EQUINE ARTERITIS VIRUS | 97–118 | 602–617 | 754–774 | 825–851 | 2530–2553 | 3041–3068 | | | |
| PRRP1_DHV11 | RNA-DIRECTED RNA POLYMERASE SUBUNIT P1 | DHORI VIRUS (STRAIN INDIAN/1313/61) | 247–264 | 275–299 | 337–359 | 377–394 | 569–591 | | | | |
| PRRP1_IAANN | RNA-DIRECTED RNA POLYMERASE SUBUNIT P1 | INFLUENZA A VIRUS (STRAIN A/ANN ARBOR/6/60) | 244–262 | | | | | | | | |
| PRRP1_IABEI | RNA-DIRECTED RNA POLYMERASE SUBUNIT P1 | INFLUENZA A VIRUS (STRAIN A/BEIJING/11/56) | 244–262 | | | | | | | | |
| PRRP1_IADUN | RNA-DIRECTED RNA POLYMERASE SUBUNIT P1 | INFLUENZA A VIRUS (STRAIN A/DUNEDIN/4/73) | 244–262 | | | | | | | | |
| PRRP1_IAGU2 | RNA-DIRECTED RNA POLYMERASE SUBUNIT P1 | INFLUENZA A VIRUS (STRAIN A/GULL/MARYLAND/704/77) | 244–262 | | | | | | | | |
| PRRP1_IAHLO | RNA-DIRECTED RNA POLYMERASE SUBUNIT P1 | INFLUENZA A VIRUS (STRAIN A/EQUINE/LONDON/1416/73) | 244–262 | | | | | | | | |
| PRRP1_IAHTE | RNA-DIRECTED RNA POLYMERASE SUBUNIT P1 | INFLUENZA A VIRUS (STRAIN A/EQUINE/TENNESSEE/5/86) | 244–262 | | | | | | | | |
| PRRP1_IAKIE | RNA-DIRECTED RNA POLYMERASE SUBUNIT P1 | INFLUENZA A VIRUS (STRAIN A/KIEV/59/79) | 244–262 | | | | | | | | |
| PRRP1_IAKOR | RNA-DIRECTED RNA POLYMERASE SUBUNIT P1 | INFLUENZA A VIRUS (STRAIN A/KOREAN/426/68) | 244–262 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRP1__IALE1 | RNA-DIRECTED RNA POLYMERASE SUBUNIT P1 | INFLUENZA A VIRUS (STRAIN A/LENINGRAD/134/57) | 244–262 | | | | | | | | |
| PRRP1__IALE2 | RNA-DIRECTED RNA POLYMERASE SUBUNIT P1 | INFLUENZA A VIRUS (STRAIN A/LENINGRAD/134/17/57) | 244–262 | | | | | | | | |
| PRRP1__IALE3 | RNA-DIRECTED RNA POLYMERASE SUBUNIT P1 | INFLUENZA A VIRUS (STRAIN A/LENINGRAD/134/47/57) | 244–262 | | | | | | | | |
| PRRP1__IAMAN | RNA-DIRECTED RNA POLYMERASE SUBUNIT P1 | INFLUENZA A VIRUS (STRAIN A/MALLARD/NEW YORK/6750/78) | 244–262 | | | | | | | | |
| PRRP1__IAME8 | RNA-DIRECTED RNA POLYMERASE SUBUNIT P1 | INFLUENZA A VIRUS (STRAIN A/MEMPHIS 8/88) | 244–262 | | | | | | | | |
| PRRP1__IANT6 | RNA-DIRECTED RNA POLYMERASE SUBUNIT P1 | INFLUENZA A VIRUS (STRAIN A/NT/60/68) | 244–262 | | | | | | | | |
| PRRP1__IAPUE | RNA-DIRECTED RNA POLYMERASE SUBUNIT P1 | INFLUENZA A VIRUS (STRAIN A/PUERTO RICO/8/34) | 244–262 | | | | | | | | |
| PRRP1__IASIN | RNA-DIRECTED RNA POLYMERASE SUBUNIT P1 | INFLUENZA A VIRUS (STRAIN A/SINGAPORE/1/57) | 244–262 | | | | | | | | |
| PRRPI__IATKM | RNA-DIRECTED RNA POLYMERASE SUBUNIT P1 | INFLUENZA A VIRUS (STRAIN A/TURKEY/MINNESOTA/833/80) | 244–262 | | | | | | | | |
| PRRP1__IAVI7 | RNA-DIRECTED RNA POLYMERASE SUBUNIT P1 | INFLUENZA A VIRUS (STRAIN A/VICTORIA/3/75) | 138–163 | 244–262 | | | | | | | |
| PRRP1__IAWIL | RNA-DIRECTED RNA POLYMERASE SUBUNIT P1 | INFLUENZA A VIRUS (STRAIN A/WILSON-SMITH/33) | 244–262 | | | | | | | | |
| PRRP1__IAWIS | RNA-DIRECTED RNA POLYMERASE SUBUNIT P1 | INFLUENZA A VIRUS (STRAIN A/WISCONSIN/3523/88) | 244–262 | | | | | | | | |
| PRRP1__IAZH3 | RNA-DIRECTED RNA POLYMERASE SUBUNIT P1 | INFLUENZA A VIRUS (STRAIN A/SWINE/HONG KONG/126/82) | 244–262 | | | | | | | | |
| PRRP1__IAZON | RNA-DIRECTED RNA POLYMERASE SUBUNIT P1 | INFLUENZA A VIRUS (STRAIN A/SWINE/ONTARIO/2/81) | 244–262 | | | | | | | | |
| PRRP1__IAZTF | RNA-DIRECTED RNA POLYMERASE SUBUNIT P1 | INFLUENZA A VIRUS (STRAIN A/SWINE/TENNESSEE/26/77) | 244–262 | | | | | | | | |
| PRRP1__INBAC | RNA-DIRECTED RNA POLYMERASE SUBUNIT P1 | INFLUENZA B VIRUS (STRAIN B/ANN ARBOR/1/66 [COLD-ADAPTED]) | 205–222 | | | | | | | | |
| PRRP1__INBAD | RNA-DIRECTED RNA POLYMERASE SUBUNIT P1 | INFLUENZA B VIRUS (STRAIN B/ANN ARBOR/1/66 [WILD-TYPE]) | 205–222 | | | | | | | | |
| PRRP1__INBLE | RNA-DIRECTED RNA POLYMERASE SUBUNIT P1 | INFLUENZA B VIRUS (STRAIN B/LEE/40) | 205–222 | | | | | | | | |
| PRRP1__INCJJ | RNA-DIRECTED RNA POLYMERASE SUBUNIT P1 | INFLUENZA C VIRUS (STRAIN C/JJ/50) | 317–341 | 564–591 | | | | | | | |
| PRRP2__IAANN | RNA-DIRECTED RNA POLYMERASE SUBUNIT P2 | INFLUENZA A VIRUS (STRAIN A/ANN ARBOR/6/60) | 534–557 | | | | | | | | |
| PRRP2__IADH2 | RNA-DIRECTED RNA POLYMERASE SUBUNIT P2 | INFLUENZA A VIRUS (STRAIN A/DUCK/HOKKAIDO/8/80) | 534–557 | | | | | | | | |
| PRRP2__IAFPR | RNA-DIRECTED RNA POLYMERASE SUBUNIT P2 | INFLUENZA A VIRUS (STRAIN A/FOWL PLAGUE VIRUS/ ROSTOCK/34) | 534–557 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRP2_IAGU2 | RNA-DIRECTED RNA POLYMERASE SUBUNIT P2 | INFLUENZA A VIRUS (STRAIN A/GULL/MARYLAND/704/77) | 534–557 | | | | | | | | |
| PRRP2_IAHLO | RNA-DIRECTED RNA POLYMERASE SUBUNIT P2 | INFLUENZA A VIRUS (STRAIN A/EQUINE/LONDON/1416/73) | 534–557 | | | | | | | | |
| PRRP2_IALE1 | RNA-DIRECTED RNA POLYMERASE SUBUNIT P2 | INFLUENZA A VIRUS (STRAIN (A/LENINGRAD/134/57) | 534–557 | | | | | | | | |
| PRRP2_IALE2 | RNA-DIRECTED RNA POLYMERASE SUBUNIT P2 | INFLUENZA A VIRUS (STRAIN A/LENINGRAD/134/17/57) | 534–557 | | | | | | | | |
| PRRP2_IAP10 | RNA-DIRECTED RNA POLYMERASE SUBUNIT P2 | INFLUENZA A VIRUS (STRAIN A/PINTAIL/ALBERTA/119/79) | 534–557 | | | | | | | | |
| PRRP2_IAPUE | RNA-DIRECTED RNA POLYMERASE SUBUNIT P2 | INFLUENZA A VIRUS (STRAIN A/PUERTO RICO/8/34) | 534–557 | | | | | | | | |
| PRRP2_IARUD | RNA-DIRECTED RNA POLYMERASE SUBUNIT P2 | INFLUENZA A VIRUS (STRAIN A/RUDDY TURNSTONE/NEW JERSEY/47/ | 534–557 | | | | | | | | |
| PRRP2_IASIN | RNA-DIRECTED RNA POLYMERASE SUBUNIT P2 | INFLUENZA A VIRUS (STRAIN A/SINGAPORE/1/57) | 534–557 | | | | | | | | |
| PRRP2_IATKM | RNA-DIRECTED RNA POLYMERASE SUBUNIT P2 | INFLUENZA A VIRUS (STRAIN A/TURKEY/MINNESOTA/833/80) | 534–557 | | | | | | | | |
| PRRP2_IAWIL | RNA-DIRECTED RNA POLYMERASE SUBUNIT P2 | INFLUENZA A VIRUS (STRAIN A/WILSON-SMITH/33) | 68–86 | 534–557 | | | | | | | |
| PRRP2_IAZH2 | RNA-DIRECTED RNA POLYMERASE SUBUNIT P2 | INFLUENZA A VIRUS (STRAIN A/SWINE/HONG KONG/81/78) | 534–557 | | | | | | | | |
| PRRP2_IAZH3 | RNA-DIRECTED RNA POLYMERASE SUBUNIT P2 | INFLUENZA A VIRUS (STRAIN A/SWINE/HONG KONG/126/82) | 534–557 | | | | | | | | |
| PRRP2_IAZ11 | RNA-DIRECTED RNA POLYMERASE SUBUNIT P2 | INFLUENZA A VIRUS (STRAIN A/SWINE/IOWA/15/30) | 534–557 | | | | | | | | |
| PRRP2_IAZTF | RNA-DIRECTED RNA POLYMERASE SUBUNIT P2 | INFLUENZA A VIRUS (STRAIN A/SWINE/TENNESSEE/26/77) | 530–557 | | | | | | | | |
| PRRP2_INBAC | RNA-DIRECTED RNA POLYMERASE SUBUNIT P2 | INFLUENZA B VIRUS (STRAIN (B/ANN ARBOR/1/66 [COLD-ADAPED]) | 32–54 | | | | | | | | |
| PRRP2_INBAD | RNA-DIRECTED RNA POLYMERASE SUBUNIT P2 | INFLUENZA B VIRUS (STRAIN B/ANN ARBOR/1/66 [WILD-TYPE]) | 32–54 | | | | | | | | |
| PRRP2_INBSI | RNA-DIRECTED RNA POLYMERASE SUBUNIT P2 | INFLUENZA B VIRUS (STRAIN B/SINGAPORE/222/79) | 32–54 | | | | | | | | |
| PRRP2_INCJI | RNA-DIRECTED RNA POLYMERASE SUBUNIT P2 | INFLUENZA C VIRUS (STRAIN C/JJ/50) | 406–425 | | | | | | | | |
| PRRP3_IAANN | RNA-DIRECTED RNA POLYMERASE SUBUNIT P3 | INFLUENZA A VIRUS (STRAIN A/ANN ARBOR/6/60) | 219–234 | 542–560 | | | | | | | |
| PRRP3_IABUD | RNA-DIRECTED RNA POLYMERASE SUBUNIT P3 | INFLUENZA A VIRUS (STRAIN A/BUDERIGARI/IOKKAIDO/1/77) | 219–234 | | | | | | | | |
| PRRP3_IACHI | RNA-DIRECTED RNA POLYMERASE SUBUNIT P3 | INFLUENZA A VIRUS (STRAIN A/CHILE/1/83) | 219–234 | 542–560 | | | | | | | |
| PRRP3_IAFPR | RNA-DIRECTED RNA POLYMERASE SUBUNIT P3 | INFLUENZA A VIRUS (STRAIN A/FOWL PLAGUE VIRUS/ ROSTOCK/34) | 219–234 | 542–567 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRP3_IAFPW | RNA-DIRECTED RNA POLYMERASE SUBUNIT P3 | INFLUENZA A VIRUS (STRAIN A/FOWL PLAGUE VIRUS/ WEYBRIDGE) | 219–234 | 542–560 | | | | | | | |
| PRRP3_IAGU2 | RNA-DIRECTED RNA POLYMERASE SUBUNIT P3 | INFLUENZA A VIRUS (STRAIN A/GULL/MARYLAND/704/77) | 219–234 | 542–560 | | | | | | | |
| PRRP3_IAGUA | RNA-DIRECTED RNA POLYMERASE SUBUNIT P3 | INFLUENZA A VIRUS (STRAIN A/GULL/ASTRAKHAN/227/84) | 219–234 | 542–560 | | | | | | | |
| PRRP3_IAKH6 | RNA-DIRECTED RNA POLYMERASE SUBUNIT P3 | INFLUENZA A VIRUS (STRAIN A/EQUINE/KENTUCKY/2/86) | 219–234 | 542–560 | | | | | | | |
| PRRP3_IAHLO | RNA-DIRECTED RNA POLYMERASE SUBUNIT P3 | INFLUENZA A VIRUS (STRAIN A/EQUINE/LONDON/1416/73) | 219–234 | 542–560 | | | | | | | |
| PRRP3_IAHPR | RNA-DIRECTED RNA POLYMERASE SUBUNIT P3 | INFLUENZA A VIRUS (STRAIN A/EQUINE/PRAGUE/1/56) | 219–234 | 542–560 | | | | | | | |
| PRRP3_IAKIE | RNA-DIRECTED RNA POLYMERASE SUBUNIT P3 | INFLUENZA A VIRUS (STRAIN A/KEIV/59/79) | 542–560 | | | | | | | | |
| PRRP3_IAKOR | RNA-DIRECTED RNA POLYMERASE SUBUNIT P3 | INFLUENZA A VIRUS (STRAIN A/KOREA/426/68) | 219–234 | 542–560 | | | | | | | |
| PRRP3_IALE1 | RNA-DIRECTED RNA POLYMERASE SUBUNIT P3 | INFLUENZA A VIRUS (STRAIN A/LENINGRAD/134/57) | 219–234 | 542–560 | | | | | | | |
| PRRP3_IALE2 | RNA-DIRECTED RNA POLYMERASE SUBUNIT P3 | INFLUENZA A VIRUS (STRAIN A/LENINGRAD/134/17/57) | 219–234 | 542–560 | | | | | | | |
| PRRP3_IALE3 | RNA-DIRECTED RNA POLYMERASE SUBUNIT P3 | INFLUENZA A VIRUS (STRAIN A/LENINGRAD/134/47/57) | 219–234 | 542–560 | | | | | | | |
| PRRP3_IAMAN | RNA-DIRECTED RNA POLYMERASE SUBUNIT P3 | INFLUENZA A VIRUS (STRAIN A/MALLARD/NEW YORK/6750/78) | 219–234 | 542–560 | | | | | | | |
| PRRP3_IAME8 | RNA-DIRECTED RNA POLYMERASE SUBUNIT P3 | | 219–234 | 542–560 | | | | | | | |
| PRRP3_IANT6 | RNA-DIRECTED RNA POLYMERASE SUBUNIT P3 | INFLUENZA A VIRUS (STRAIN A/NT/60/68) | 219–234 | 542–560 | | | | | | | |
| PRRP3_IAUPE | RNA-DIRECTED RNA POLYMERASE SUBUNIT P3 | INFLUENZA A VIRUS (STRAIN A/PUERTO RICO/8/34) | 219–234 | 469–485 | 542–560 | | | | | | |
| PRRP3_IAURD | RNA-DIRECTED RNA POLYMERASE SUBUNIT P3 | INFLUENZA A VIRUS (STRAIN A/RUDDY TURNSTONE/ NEW JERSEY/47/ | 219–234 | 542–560 | | | | | | | |
| PRRP3_IASE2 | RNA-DIRECTED RNA POLYMERASE SUBUNIT P3 | INFLUENZA A VIRUS (STRAIN A/SEAL/MASSACHUSETTS/133/82) | 219–234 | 542–560 | | | | | | | |
| PRRP3_IASIN | RNA-DIRECTED RNA POLYMERASE SUBUNIT P3 | INFLUENZA A VIRUS (STRAIN A/SINGAPORE/1/57) | 219–234 | 542–560 | | | | | | | |
| PRRP3_IATKM | RNA-DIRECTED RNA POLYMERASE SUBUNIT P3 | INFLUENZA A VIRUS (STRAIN A/TURKEY/MINNESOTA/833/80) | 219–234 | 542–560 | | | | | | | |
| PRRP3_IAVI7 | RNA-DIRECTED RNA POLYMERASE SUBUNIT P3 | INFLUENZA A VIRUS (STRAIN A/VICTORIA/3/75) | 219–234 | 542–560 | | | | | | | |
| PRRP3_IAWIL | RNA-DIRECTED RNA POLYMERASE SUBUNIT P3 | INFLUENZA A VIRUS (STRAIN A/WILSON-SMITH/33) | 219–234 | 542–560 | | | | | | | |
| PRRP3_IAZI1 | RNA-DIRECTED RNA POLYMERASE SUBUNIT P3 | INFLUENZA A VIRUS (STRAIN A/SWINE/IOWA/15/30) | 219–234 | 542–560 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRP3_IAZTE | RNA-DIRECTED RNA POLYMERASE SUBUNIT P3 | INFLUENZA A VIRUS (STRAIN A/SWINE/TENNESSEE/24/77) | 219–234 | 542–560 | | | | | | | |
| PRRP3_INBAC | RNA-DIRECTED RNA POLYMERASE SUBUNIT P3 | INFLUENZA B VIRUS (STRAIN B/ANN ARBOR/1/66 [COLD-ADAPTED]) | 71–86 | 535–561 | | | | | | | |
| PRRP3_INBAD | RNA-DIRECTED RNA POLYMERASE SUBUNIT P3 | INFLUENZA B VIRUS (STRAIN B/ANN ARBOR/1/66 [WILD-TYPE]) | 71–86 | 535–561 | | | | | | | |
| PRRP3_INCBE | RNA-DIRECTED RNA POLYMERASE SUBUNIT P3 | INFLUENZA C VIRUS (STRAIN C/BERLIN/1/85) | 74–96 | 552–571 | | | | | | | |
| PRRP3_INCJJ | RNA-DIRECTED RNA POLYMERASE SUBUNIT P3 | INFLUENZA C VIRUS (STRAIN C/JJ/50) | 74–96 | 552–571 | | | | | | | |
| PRRP3_THOGV | RNA-DIRECTED RNA POL SUBUNIT P3 | THOGOTO VIRUS | 85–101 | | | | | | | | |
| PRRPA_CVH22 | RNA-DIRECTED RNA POLYMERASE | HUMAN CORONAVIRUS (STRAIN 229E) | 82–104 | 410–436 | 858–878 | 1482–1507 | 1523–1542 | 1543–1568 | 2125–2149 | 2974–2992 | 3537–3559 |
| PRRPA_CVMJD | RNA-DIRECTED RNA POLYMERASE | MURINE HEPATITIS VIRUS (STRAIN DEFECTIVE JHM) | 440–467 | | | | | | | | |
| PRRPA_CVMJH | RNA-DIRECTED RNA POLYMERASE | MURINE CORONAVIRUS MHV (STRAIN JHM) | 917–938 | 1188–1215 | 1338–1354 | 1422–1449 | 1461–1480 | 1567–1585 | 1783–1806 | 2165–2192 | 2337–2354 |
| | | | 2470–2494 | 2660–2676 | 2944–2961 | 3229–3255 | 3405–3425 | 3933–3954 | | | |
| PRRPB_BEV | RNA-DIRECTED RNA POLYMERASE | BERNE VIRUS | 806–832 | 1509–1527 | 1738–1757 | 2137–2154 | | | | | |
| PRRPB_CVMA5 | RNA-DIRECTED RNA POLYMERASE | MURINE CORONAVIRUS MHV (STRAIN A59) | 385–412 | 1302–1324 | 1835–1850 | 2698–2723 | | | | | |
| PRRPB_CVMJH | RNA-DIRECTED RNA POLYMERASE | MURINE CORONAVIRUS MHV (STRAIN JHM) | 385–412 | 746–770 | 1302–1324 | 1833–1848 | 2696–2721 | | | | |
| PRRPB_CVPFS | RNA-DIRECTED RNA POLYMERASE | PORCINE TRANSMISSIBLE GASTROENTERITIS CORONA-VIRUS (STRAIN | 173–200 | 482–508 | | | | | | | |
| PRRPB_CVPR8 | RNA-DIRECTED RNA POLYMERASE | PORCINE RESPIRATORY CORONAVIRUS (STRAIN 86/137004/BRITISH I | 80–106 | | | | | | | | |
| PRRPB_IBVB | RNA-DIRECTED RNA POLYMERASE | AVIAN INFECTIOUS BRONCHITIS VIRUS (STRAIN BEAUDETTE) | 140–164 | 338–365 | 887–911 | 1335–1352 | 1654–1674 | | | | |
| PRRPL_BVT10 | RNA-DIRECTED RNA POLYMERASE | BLUETONGUE VIRUS (SEROTYPE 10/ISOLATE USA) | 21–41 | 146–161 | | | | | | | |
| PRRPL_BUNYW | RNA POLYMERASE | BUNYAMWERA VIRUS | 78–104 | 303–324 | 440–465 | 1096–1116 | 1317–1338 | 1343–1365 | 1539–1554 | 1869–1886 | 2001–2027 |
| PRRPL_EBOV | RNA-DIRECTED RNA POLYMERASE | EBOLA VIRUS | 16–31 | | | | | | | | |
| PRRPL_HANTV | RNA POLYMERASE | HANTAAN VIRUS (STRAIN 76–118) | 151–168 | 173–194 | 596–611 | 1561–1585 | 2081–2105 | | | | |
| PRRPL_HRSV | RNA POLYMERASE BETA SUBUNIT | HUMAN RESPIRATORY SYNCYTIAL VIRUS | 3–19 | | | | | | | | |
| PRRPL_HRSVA | RNA POLYMERASE BETA SUBUNIT | HUMAN RESPIRATORY SYNCYTIAL VIRUS (STRAIN A2) | 3–19 | 1181–1206 | 1425–1447 | 1633–1653 | 1929–1948 | 2018–2037 | | | |
| PRRPL_MABVM | RNA-DIRECTED RNA POLYMERASE | MARBURG VIRUS (STRAIN MUSOKE) | 15–30 | 144–169 | 223–248 | 317–341 | 471–492 | 546–569 | 931–946 | 1042–1067 | 1410–1436 |
| | | | 1711–1731 | 1990–2017 | 2071–2094 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRPL_MABVP | RNA-DIRECTED RNA POLYMERASE | MARBURG VIRUS (STRAIN POPP) | 15–30 | 144–169 | 223–248 | 471–492 | 546–569 | 931–946 | 1042–1067 | 1410–1436 | 1677–1696 |
| | | | 1715–1731 | 1805–1832 | 1990–2017 | 2071–2094 | 2223–2246 | | | | |
| PRRPL_MEASE | RNA POLYMERASE BETA SUBUNIT | MEASLES VIRUS (STRAIN EDMONSTON) | 285–312 | 617–632 | 998–1023 | 1160–1185 | 1279–1304 | 1920–1940 | 2038–2063 | | |
| PRRPL_MUMPM | RNA POLYMERASE BETA SUBUNIT | MUMPS VIRUS (STRAIN MIYAHARA VACCINE) | 43–66 | 110–135 | 265–280 | 962–988 | 1100–1124 | 1132–1153 | 1601–1622 | 2128–2143 | |
| PRRPL_NDVB | RNA POLYMERASE BETA SUBUNIT | NEWCASTLE DISEASE VIRUS (STRAIN BEAUDETTE C/45) | 704–724 | 1571–1592 | 1967–1994 | 2040–2067 | | | | | |
| PRRPL_P12HT | RNA POLYMERASE BETA SUBUNIT | HUMAN PARAINFLUENZA 2 VIRUS (STRAIN TOSHIBA) | 109–124 | 268–291 | 308–334 | 1309–1335 | 1562–1588 | 1985–2010 | 2215–2334 | | |
| PRRPL_P13H4 | RNA POLYMERASE BETA SUBUNIT | HUMAN PARAINFLUENZA 3 VIRUS (STRAIN NIH 47885) | 172–193 | 304–330 | 844–861 | 885–900 | 1848–1868 | 2068–2084 | 2111–2134 | | |
| PRRPL_PUUMH | RNA-DIRECTED RNA POLYMERASE | PUUMALA VIRUS (STRAIN HALLNAS B1) | 173–194 | 596–611 | 1561–1585 | 1677–1696 | 2086–2110 | | | | |
| PRRPL_RABVP | RNA POLYMERASE BETA SUBUNIT | RABIES VIRUS (STRAIN PV) | 266–286 | 542–563 | 741–762 | 1446–1461 | 1492–1517 | | | | |
| PRRPL_RABVS | RNA POLYMERASE BETA SUBUNIT | RABIES VIRUS (STRAIN SAD B19) | 266–286 | 542–563 | 741–762 | 1446–1461 | 1492–1517 | 1744–1761 | | | |
| PRRPL_RDV | RNA-DIRECTED RNA POLYMERASE | RICE DWARF VIRUS | 10–27 | 533–560 | 680–697 | 1293–1316 | | | | | |
| PRRPL_RVFVZ | RNA-DIRECTED RNA POLYMERASE | RIFT VALLEY FEVER VIRUS (STRAIN ZH-548 M12) | 582–609 | 2009–2035 | | | | | | | |
| PRRPL_SEND5 | RNA POLYMERASE BETA SUBUNIT | SENDAI VIRUS (STRAIN Z/ HOST MUTANTS) | 64–83 | 104–120 | 194–218 | 844–861 | 885–900 | 1405–1420 | 1844–1864 | 2107–2128 | |
| PRRPL_SENDE | RNA POLYMERASE BETA SUBUNIT | SENDAI VIRUS (STRAIN ENDERS) | 14–38 | 664–681 | 705–720 | 1225–1240 | 1664–1684 | 1927–1948 | | | |
| PRRPL_SENDZ | RNA POLYMERASE BETA SUBUNIT | SENDAI VIRUS (STRAIN Z) | 64–83 | 104–120 | 194–218 | 844–861 | 885–900 | 1405–1420 | 1884–1864 | 2107–2128 | |
| PRRPL_SEOU8 | RNA-DIRECTED RNA POLYMERASE | SEOUL VIRUS (STRAIN 80-39) | 151–168 | 173–194 | 394–419 | 596–611 | 1561–1585 | 2081–2105 | | | |
| PRRPL_SV5WR | RNA POLYMERASE BETA SUBUNIT | SIMIAN VIRUS 5 (STRAIN 21004-WR) | 43–66 | 108–124 | 263–289 | 1094–1118 | 1124–1147 | 1558–1580 | 2117–2137 | | |
| PRRPL_SYNV | RNA POLYMERASE BETA SUBUNIT | SONCHUS YELLOW NET VIRUS | 126–146 | 391–406 | 605–627 | 704–731 | 863–883 | 886–911 | 1484–1510 | 1776–1792 | |
| PRRPL_TSWVB | RNA-DIRECTED RNA POLYMERASE | TOMATO SPOTTED WILT VIRUS (BRAZILIAN ISOLATE CPNH/BR-01) | 958–974 | 1385–1410 | 1778–1800 | 2609–2627 | 2678–2702 | | | | |
| PRRPL_UUK | RNA POLYMERASE | UUKUNIEME VIRUS | 698–714 | 923–948 | 1404–1431 | 1570–1591 | 2060–2081 | | | | |
| PRRPL_VSVJH | RNA POLYMERASE BETA SUBUNIT | VESICULAR STOMATITIS VIRUS (SEROTYPE NEW JERSEY/ STRAIN HA | 156–183 | 312–339 | 903–928 | 1956–1982 | 2080–2097 | | | | |
| PRRPL_VSVJO | RNA POLYMERASE BETA SUBUNIT | VESICULAR STOMATITIS VIRUS (SEROTYPE NEW JERSEY/ STRAIN OG | 156–183 | 312–339 | 1956–1982 | 2080–2101 | | | | | |
| PRRPL_VSVSJ | RNA POLYMERASE BETA SUBUNIT | VESICULAR STOMATITS VIRUS (STRAIN SAN JUAN) | 1956–1982 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRPO_ACLSV | RNA-DIRECTED RNA POLYMERASE | APPLE CHLOROTIC LEAF SPOT VIRUS | 226–247 | 1036–1054 | 1132–1155 | 1775–1201 | | | | | |
| PRRPO_BWYVF | PUTATIVE RNA-DIRECTED RNA POL | BEET WESTERN YELLOWS VIRUS (ISOLATE FL-1) | 299–326 | | | | | | | | |
| PRRPO_BYDV1 | PUTATIVE RNA-DIRECTED RNA POL | BARLEY YELLOW DWARF VIRUS (ISOLATE MAV-PS1) | 359–386 | 391–416 | 505–532 | | | | | | |
| PRRPO_BYDVP | PUTATIVE RNA-DIRECTED RNA POL | BARLEY YELLOW DWARF VIRUS (ISOLATE PAV) | 359–386 | 391–416 | 505–532 | | | | | | |
| PRRPO_BYDVR | PUTATIVE RNA-DIRECTED RNA POL | BARLEY YELLOW DWARF VIRUS (ISOLATE P-PAV) | 359–386 | 391–416 | 505–532 | | | | | | |
| PRRPO_CARMV | PROBABLE RNA-DIRECTED RNA POL | CARNATION MOTTLE VIRUS | 4–30 | 92–107 | 327–350 | 818–833 | | | | | |
| PRRPO_CGMVS | PUTATIVE RNA-DIRECTED RNA POL | CUCUMBER GREEN MOTTLE MOSAIC VIRUS (WATERMELON STRAIN S | 443–466 | 574–591 | 1017–1032 | 1523–1539 | | | | | |
| PRRPO_CNV | PROBABLE RNA-DIRECTED RNA POL | CUCUMBER NECROSIS VIRUS | 277–300 | 345–371 | 470–494 | | | | | | |
| PRRPO_CRV | PROBABLE RNA-DIRECTED RNA POL | CYMBIDIUM RINGSPOT VIRUS | 96–111 | 345–371 | 470–494 | | | | | | |
| PRRPO_IPNVJ | PUTATIVE RNA-DIRECTED RNA POL | INFECTIOUS PANCREATIC NECROSIS VIRUS (SEROTYPE JASPER) | 221–238 | | | | | | | | |
| PRRPO_LYCVA | RNA POLYMERASE | LYMPHOCYTIC CHORIOMENINGI-TIS VIRUS (STRAIN ARMSTRONG) | 35–52 | 597–613 | 659–682 | 988–1008 | 1234–1258 | 1770–1795 | 2077–2099 | | |
| PRRPO_LYCVW | RNA POLYMERASE | LYMPHOCYTIC CHORIOMENINGI-TIS VIRUS (STRAIN WE) | 35–52 | | | | | | | | |
| PRRPO_MCMV | PROBABLE RNA-DIRECTED RNA POL | MAIZE CHLOROTIC MOTTLE VIRUS | 16–41 | 101–127 | 573–599 | | | | | | |
| PRRPO_PEAMV | RNA-DIRECTED RNA POLYMERASE | PEA ENATION MOSAIC VIRUS | 144–161 | 316–336 | 431–456 | 558–574 | | | | | |
| PRRPO_PLRV1 | PUTATIVE RNA-DIRECTED RNA POL | POTATO LEAFROLL VIRUS (STRAIN 1) | 331–358 | 576–600 | | | | | | | |
| PRRPO_PLRVW | PUTATIVE RNA-DIRECTED RNA POL | POTATO LEAFROLL VIRUS (STRAIN WAGENINGEN) | 331–358 | 576–600 | | | | | | | |
| PRRPO_PPMVS | PUTATIVE RNA-DIRECTED RNA POL | PEPPER MILD MOTTLE VIRUS (STRAIN SPAIN) | 375–395 | 702–726 | 1069–1096 | 1491–1507 | | | | | |
| PRRPO_RCNMV | PUTATIVE RNA-DIRECTED RNA POL | RED CLOVER NECROTIC MOSAIC VIRUS | 278–300 | | | | | | | | |
| PRRPO_REOVJ | RNA-DIRECTED RNA POLYMERASE | REOVIRUS (TYPE 2/STRAIN D5/JONES) | 161–176 | | | | | | | | |
| PRRPO_REOVL | RNA-DIRECTED RNA POLYMERASE | REOVIRUS (TYPE 1/STRAIN LANG) | 161–176 | | | | | | | | |
| PRRPO_ROTBR | RNA-DIRECTED RNA SUBUNIT VP1 | BOVINE ROTAVIRUS (STRAIN RF) | 132–156 | 247–269 | 844–861 | 904–921 | 942–967 | 1027–1046 | | | |
| PRRPO_ROTBU | RNA-DIRECTED RNA SUBUNIT VP1 | BOVINE ROTAVIRUS (STRAIN UK) | 132–156 | 247–269 | 844–861 | 904–921 | 942–967 | 1027–1046 | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRPO_ROTPC | RNA-DIRECTED RNA SUBUNIT VP1 | PORCINE ROTAVIRUS (GROUP C/STRAIN COWDEN) | 198–223 | 254–274 | 318–337 | 769–784 | 856–878 | 936–952 | | | |
| PRRPO_ROTPG | RNA-DIRECTED RNA SUBUNIT VP1 | PORCINE ROTAVIRUS (STRAIN GOTTFRIED) | 32–53 | 57–72 | 132–156 | 247–269 | 844–861 | 904–921 | 942–967 | 1027–1046 | |
| PRRPO_ROTS1 | RNA-DIRECTED RNA SUBUNIT VP1 | SIMIAN 11 ROTAVIRUS (STRAIN SA11) | 132–156 | 247–269 | 844–861 | 904–921 | 942–967 | 1027–1046 | | | |
| PRRPO_SBMV | PROBABLE RNA-DIRECTED RNA POL | SOUTHERN BEAN MOSAIC VIRUS | 38–64 | 122–143 | 188–206 | 287–302 | 444–466 | 625–643 | 825–846 | | |
| PRRPO_TACV | RNA POLYMERASE | TACARIBE VIRUS | 88–1 07 | 369–389 | 1281–1301 | 1676–1692 | 2019–2046 | | | | |
| PRRPO_TBSVC | PUTATIVE RNA-DIRECTED RNA POL | TOMATO BUSHY STUNT VIRUS (STRAIN CHERRY) | 277–300 | 345–371 | 470–494 | | | | | | |
| PRRPO_TCV | PUTATIVE RNA-DIRECTED RNA POL | TURNIP CRINKLE VIRUS | 31–58 | 241–263 | | | | | | | |
| PRRPO_TMGMV | PUTATIVE RNA-DIRECTED RNA POL | TOBACCO MILD GREEN MOSAIC VIRUS (TMV STRAIN U2) | 209–231 | 1085–1100 | | | | | | | |
| PRRPO_TMV | PUTATIVE RNA-DIRECTED RNA POL | TOBACCO MOSAIC VIRUS (VULGARE) | 700–724 | 1090–1105 | 1587–1610 | | | | | | |
| PRRPO_TMVKR | PUTATIVE RNA-DIRECTED RNA POL | TOBACCO MOSAIC VIRUS (STRAIN KOREAN) | 700–724 | 1090–1105 | 1587–1610 | | | | | | |
| PRRPO_TMVTO | PUTATIVE RNA-DIRECTED RNA POL | TOBACCO MOSAIC VIRUS (STRAIN TOMATO/L) | 700–724 | 1090–1105 | 1151–1170 | 1587–1610 | | | | | |
| PRRPO_TNVA | RNA-DIRECTED RNA POLYMERASE | TOBACCO NECROSIS VIRUS (STRAIN A) | 113–135 | | | | | | | | |
| PRRPO_TNVD | RNA-DIRECTED RNA POLYMERASE | TOBACCO NECROSIS VIRUS (STRAIN D) | 5–26 | | | | | | | | |
| PRRPP_CHAV | RNA POLYMERASE ALPHA SUBUNIT | CHANDIPURA VIRUS (STRAIN 1653514) | 124–146 | | | | | | | | |
| PRRPP_MUMP1 | RNA POLYMERASE ALPHA SUBUNIT | MUMPS VIRUS (STRAIN SBL-1) | 211–238 | | | | | | | | |
| PRRPP_MUMPE | RNA POLYMERASE ALPHA SUBUNIT | MUMPS VIRUS (STRAIN ENDERS) | 212–239 | | | | | | | | |
| PRRPP_MUMPM | RNA POLYMERASE ALPHA SUBUNIT | MUMPS VIRUS (STRAIN MIYAHARA VACCINE) | 212–239 | | | | | | | | |
| PRRPP_NDVA | RNA POLYMERASE ALPHA SUBUNIT | NEWCASTLE DISEASE VIRUS (STRAIN AUSTRALIA-VICTORIA/32) | 256–276 | | | | | | | | |
| PRRPP_NDVB | RNA POLYMERASE ALPHA SUBUNIT | NEWCASTLE DISEASE VIRUS (STRAIN BEAUDETTE C/45) | 256–276 | | | | | | | | |
| PRRPP_P12H | RNA POLYMERASE ALPHA SUBUNIT | HUMAN PARAINFLUENZA 2 VIRUS | 216–243 | | | | | | | | |
| PRRPP_P12HT | RNA POLYMERASE ALPHA SUBUNIT | HUMAN PARAINFLUENZA 2 VIRUS (STRAIN TOSHIBA) | 216–243 | | | | | | | | |
| PRRPP_P14HA | RNA POLYMERASE ALPHA SUBUNIT | HUMAN PARAINFLUENZA 4A VIRUS (STRAIN TOSHIBA) | 220–247 | | | | | | | | |
| PRRPP_P14HB | RNA POLYMERASE ALPHA SUBUNIT | HUMAN PARAINFLUENZA 4B VIRUS (STRAIN 68-333) | 220–247 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PRRPP_PIRYV | RNA POLYMERASE ALPHA SUBUNIT | PIRY VIRUS | 134–161 | | | | | | | | |
| PRRPP_RABVA | RNA POLYMERASE ALPHA SUBUNIT | RABIES VIRUS (STRAIN AVO1) | 8–32 | | | | | | | | |
| PRRPP_RABVC | RNA POLYMERASE ALPHA SUBUNIT | RABIES VIRUS (STRAIN CVS-11) | 8–32 | | | | | | | | |
| PRRPP_RABVE | RNA POLYMERASE ALPHA SUBUNIT | RABIES VIRUS (STRAIN ERA), AND (STRAIN PM) | 8–32 | 216–237 | | | | | | | |
| PRRPP_RABVP | RNA POLYMERASE ALPHA SUBUNIT | RABIES VIRUS (STRAIN PV) | 8–32 | 216–237 | | | | | | | |
| PRRPP_RABVS | RNA POLYMERASE ALPHA SUBUNIT | RABIES VIRUS (STRAIN SAD B19) | 8–32 | 216–237 | | | | | | | |
| PRRPP_SV5 | RNA POLYMERASE ALPHA SUBUNIT | SIMINA VIRUS 5 (STRAIN W3) | 199–226 | 282–301 | | | | | | | |
| PRRPP_VSVIO | RNA POLYMERASE ALPHA SUBUNIT | VESICULAR STOMATITIS VIRUS (SEROTYPE NEW JERSEY/ STRAIN OG | 197–223 | | | | | | | | |
| PS27R_ASFB7 | 5273R PROTEIN | AFRICAN SWINE FEVER VIRUS (STRAIN BA71V) | 196–218 | | | | | | | | |
| PSODC_VACCC | SUPEROXIDE DISMUTASE LIKE PROTEIN | VACCINIA VIRUS (STRAIN COPENHAGEN) | 19–40 | | | | | | | | |
| PSODC_VACCV | SUPEROXIDE DISMUTASE LIKE PROTEIN | VACCINIA VIRUS (STRAIN WR) | 19–40 | | | | | | | | |
| PSODC_VARV | SUPEROXIDE DISMUTASE LIKE PROTEIN | VARIOLA VIRUS | 19–40 | | | | | | | | |
| PSPHR_AMEPV | SHEROIDIN | AMSACTA MOOREI ENTOMOMPOXVIRUS | 58–79 | 627–646 | | | | | | | |
| PSPHR_CBEPV | SHEROIDIN PRECURSOR | CHORISTONEURA BIENNIS ENTOMOPOXVIRUS | 177–201 | | | | | | | | |
| PSPT1_MYXVL | SERPIN 1 | MYXOMA VIRUS (STRAIN LAUSANNE) | 62–80 | 217–243 | | | | | | | |
| PSWFA_SPVKA | SWF8A PROTEIN | SWINEPOX VIRUS (STRAIN KASZA) | 61–83 | | | | | | | | |
| PTALA_BFDV | LARGE T ANTIGEN | BUDGERIGAR FLEDGLING DISEASE VIRUS | 354–369 | | | | | | | | |
| PTALA_POVBA | LARGE T ANTIGEN | POLYOMAVIRUS BK (STRAIN AS) | 202–224 | 429–444 | | | | | | | |
| PTALA_POVBK | LARGE T ANTIGEN | POLYOMAVIRUS BK | 202–224 | 429–444 | | | | | | | |
| PTALA_POVBO | LARGE T ANTIGEN | BOVINE POLYOMAVIRUS | 385–400 | | | | | | | | |
| PTALA_POVHA | LARGE T ANTIGEN | HAMSTER POLYOMAVIRUS | 43–69 | 549–564 | | | | | | | |
| PTALA_POVJC | LARGE T ANTIGEN | POLYOMAVIRUS VIRUS JC | 201–223 | 428–443 | | | | | | | |
| PTATAL_POVLY | LARGE T ANTIGEN | LYMPHOTROPIC POLYOMAVIRUS | 43–69 | 516–542 | | | | | | | |
| PTATAL_POVM3 | LARGE T ANTIGEN | MOUSE POLYOMAVIRUS (STRAIN 3) | 576–591 | | | | | | | | |
| PTALA_POVMA | LARGE T ANTIGEN | MOUSE POLYOMAVIRUS (STRAIN A2) | 574–589 | | | | | | | | |
| PTALA_POVMC | LARGE T ANTIGEN | MOUSE POLYOMAVIRUS (STRAIN CRAWFORD SMALL-PLAQUE) | 571–586 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTALA_POVMK | LARGE T ANTIGEN | MOUSE POLYOMAVIRUS (STRAIN KILHAM) | 173–191 | 278–304 | 446–472 | | | | | | |
| PTALA_SV40 | LARGE T ANTIGEN | SIMIAN VIRUS 40 (SV40) | 200–222 | 427–442 | | | | | | | |
| PTAMI_POVHA | MIDDLE T ANTIGEN | HAMSTER POLYOMAVIRUS | 43–69 | | | | | | | | |
| PTASM_POVHA | SMALL T ANTIGEN | HAMSTER POLYOMAVIRUS | 43–69 | | | | | | | | |
| PTASM_POVLY | SMALL T ANTIGEN | LYMPHOTROPIC POLOMAVIRUS | 43–69 | | | | | | | | |
| PTASM_POVMK | SMALL T ANTIGEN | MOUSE POLYOMAVIRUS (STRAIN KILHAM) | 43–69 | 67–89 | | | | | | | |
| PTATR_NPVAC | TRANS-ACTIVATING TRANS REG PROTEIN | AUTOGRAPHA CALIFORNICA NUCLEAR POLYHEDROSIS VIRUS | 406–431 | | | | | | | | |
| PTATR_NPVBM | TRANS-ACTIVATING TRANS REG PROTEIN | BOMBYX MORI NUCLEAR POLYHEDROSIS VIRUS | 411–436 | | | | | | | | |
| PTATR_NPVOP | TRANS-ACTIVATING TRANS REG PROTEIN | ORGYIA PSEUDOTSUGATA MULTICAPSID POLYHEDROSIS VIRUS | 389–414 | | | | | | | | |
| PTAT_BIV06 | TRANS-ACTIVATING TRANS REG PROTEIN | BOVINE IMMUNODEFICIENCY VIRUS (ISOLATE 106) | 44–59 | | | | | | | | |
| PTAT_BIV27 | TRANS-ACTIVATING TRANS REG PROTEIN | BOVINE IMMUNODEFICIENCY VIRUS (ISOLATE 127) | 44–59 | | | | | | | | |
| PTAT_HTL1A | TRANS-ACTIVATING TRANS REG PROTEIN | HUMAN T-CELL LEUKEMIA VIRUS TYPE 1 (STRAIN ATK) | 192–210 | | | | | | | | |
| PTAT_HTL1C | TRANS-ACTIVATING TRANS REG PROTEIN | HUMAN T-CELL LEUKEMIA VIRUS TYPE 1 (CARIBBEAN ISOLATE) | 192–210 | | | | | | | | |
| PTAT_HV1U4 | TAT PROTEIN | HUMAN IMMUNODEFICIENCY VIRUS TYPE 1 (STRAIN UNANDAN/ISO | 18–43 | | | | | | | | |
| PTCB_FLV | T-CELL RECEPTOR BETA CHAIN PRECURSOR | FELINE LEUKEMIA VIRUS | 6–22 | 98–118 | | | | | | | |
| PTEGP_HSVEB | PROBABLE TEGUMENT PHOSPHOPROTEIN | EQUINE HERPESVIRUS TYPE 1 (STRAIN AB4P) | 101–118 | | | | | | | | |
| PTEGP_HSVEK | TEGUMENT PROTEIN | EQUINE HERPESVIRUS TYPE 1 (STRAIN KENTUCKY A) | 101–118 | | | | | | | | |
| PTEGU_EBV | LARGE TEGUMENT PROTEIN | EPSTEIN-BARR VIRUS (STRAIN B95-8) | 143–166 | 767–789 | 814–835 | 1052–1075 | 1194–1220 | 1469–1496 | 1869–1893 | 3061–3077 | 3102–3126 |
| PTEGU_HCMVA | PROBABLE LARGE TEGUMENT PROTEIN | HUMAN CYTOMEGALOVIRUS (STRAIN AD169) | 342–358 | 644–668 | 1061–1077 | 1307–1322 | 1323–1345 | 1410–1446 | 1509–1536 | 1957–1974 | 2199–2221 |
| PTEGU_HSV11 | LARGE TEGUMENT PROTEIN | HERPES SIMPLEX VIRUS (TYPE 1/STRAIN 17) | 12–27 | 623–646 | 1732–1759 | | | | | | |
| PTEGU_HSV6G | LARGE TEGUMENT PROTEIN | HERPES SIMPLEX VIRUS (TYPE 6/STRAIN GS) | 131–152 | 345–365 | 615–636 | 1027–1043 | 1308–1328 | 1562–1579 | | | |
| PTEGU_HSVEB | LARGE TEGUMENT PROTEIN | EQUINE HERPESVIRUS TYPE 1 (STRIN AB4P) | 432–456 | 559–582 | 1072–1099 | 1107–1132 | 1618–1640 | 1764–1791 | 2263–2285 | | |
| PTEGU_HSVSA | PROBABLE LARGE TEGUMENT PROTEIN | HERPESVIRUS SAIMIRI (STRAIN 11) | 467–491 2421–2349 | 714–737 | 989–1008 | 1121–1137 | 1155–1174 | 1177–1193 | 1503–1525 | 1607–1622 | 1898–1915 |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PTEGU_VZVD | LARGE TEGUMENT PROTEIN | VARICELLA-ZOSTER VIRUS (STRAIN DUMAS) | 433–456 | 494–511 | 711–728 | 801–823 | 895–920 | 1013–1034 | 1360–1376 | 1632–1657 | 1780–1807 |
| | | | 2008–2029 | 2270–2287 | 2694–2711 | | | | | | |
| PTERM_ADE02 | DNA TERMINAL PROTEIN | HUMAN ADENOVIRUS TYPE 2 | 63–80 | 593–616 | | | | | | | |
| PTERM_ADE05 | DNA TERMINAL PROTEIN | HUMAN ADENOVIRUS TYPE 5 | 63–80 | 593–616 | | | | | | | |
| PTERM_ADE07 | DNA TERMINAL PROTEIN | HUMAN ADENOVIRUS TYPE 7 | 63–80 | 580–603 | | | | | | | |
| PTERM_ADE12 | DNA TERMINAL PROTEIN | HUMAN ADENOVIRUS TYPE 12 | 46–63 | 334–350 | 546–569 | | | | | | |
| PTOP2_ASFB7 | DNA TOPOISOMERASE II | AFRICAN SWINE FEVER VIRUS (STRAIN BA71V) | 119–146 | 686–707 | | | | | | | |
| PTOP2_ASFM2 | DNA TOPOISOMERASE II | AFRICAN SWINE FEVER VIRUS (ISOLATE MALAWI LIL 20/1) | 119–146 | 685–706 | | | | | | | |
| PTR14_HCMVA | HYPOTHETICAL PROTEIN TRL14 | HUMAN CYTOMEGALOVIRUS (STRAIN AD169) | 139–165 | | | | | | | | |
| PTREL_AVIRE | REL TRANSFORMING PROTEIN | AVIAN RETICULOENDOTHELIOSIS VIRUS | 56–74 | | | | | | | | |
| PTYSY_VZVD | THYMIDYLATE SYNTHASE | VARICELLA-ZOSTER VIRUS (STRAIN DUMAS) | 11–29 | | | | | | | | |
| PU15R_HSV6U | POSSIBLE GANCICLOVIR KINASE | HERPES SIMPLEX VIRUS (TYPE 6/STRAIN UGANDA-1102) | 400–415 | | | | | | | | |
| PU2L_HSV6U | PROTEIN 2L | HERPES SIMPLEX VIRUS (TYPE 6/STRAIN UGANDA-1102) | 4–27 | | | | | | | | |
| PUDPE_NPVAC | UDP-GLUCOSYLTRANSFER-ASE PRECURSOR | AUTOGRAPHA CALIFORNICA NUCLEAR POLYHEDROSIS VIRUS | 452–477 | | | | | | | | |
| PUL02_HCMVA | HYPOTHETICAL PROTEIN UL2 | HUMAN CYTOMEGALOVIRUS (STRAIN AD169) | 25–49 | | | | | | | | |
| PUL05_HCMVA | HYPOTHETICAL PROTEIN UL5 | HUMAN CYTOMEGALOVIRUS (STRAIN AD169) | 11–37 | | | | | | | | |
| PUL06_EBV | VIRION PROTEIN BBRF1 | EPSTEIN-BARR VIRUS (STRAIN B95-8) | 253–268 | | | | | | | | |
| PUL06_HCMVA | HYPOTHETICAL PROTEIN UL6 | HUMAN CYTOMEGALOVIRUS (STRAIN AD169) | 191–208 | | | | | | | | |
| PUL06_HSV11 | VIRION PROTEIN UL6 | HERPES SIMPLEX VIRUS (TYPE 1/STRAIN 17) | 404–429 | | | | | | | | |
| PUL06_HSVEB | VIRION GENE 56 PROTEIN | EQUINE HERPESVIRUS TYPE 1 (STRAIN AB4P) | 437–461 | | | | | | | | |
| PUL06_HSVSA | VIRION GENE 43 PROTEIN | HERPES VIRUS SAIMIRI (STRAIN 11) | 44–60 | | | | | | | | |
| PUL07_EBV | BBRF2 PROTEIN | EPSTEIN-BARR VIRUS (STRAIN B95-8) | 127–149 | | | | | | | | |
| PUL07_HCMVA | HYPOTHETICAL PROTEIN UL7 | HUMAN CYTOMEGALOVIRUS (STRAIN AD169) | 88–108 | 186–209 | | | | | | | |
| PUL07_HSV11 | PROTEIN UL7 | HERPES SIMPLEX VIRUS (TYPE 1/STRAIN 17) | 177–200 | | | | | | | | |
| PUL07_HSVEB | GENE 55 PROTEIN | EQUINE HERPES VIRUS TYPE 1 (STRAIN AB4P) | 11–32 | | | | | | | | |
| PUL07_HSVSA | GENE 42 PROTEIN | HERPESVIRUS SAIMIRI (STRAIN 11) | 44–61 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUL07_VZVD | GENE 53 PROTEIN | VARICELLA-ZOSTER VIRUS (STRAIN DUMAS) | 158–176 | 202–224

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUL21_HSV11 | PROTEIN UL21 | HERPES SIMPLEX VIRUS (TYPE 1/STRAIN 17) | 98–114 | 130–146 | | | | | | | |
| PUL21_USV1E | PROTEIN UL21 | HERPES SIMPLEX VIRUS (TYPE 1/STRAIN HFEM) | 98–114 | 130–146 | | | | | | | |
| PUL21_HSVEB | GENE 40 PROTEIN | EQUINE HERPESVIRUS TYPE 1 (STRAIN AB4P) | 119–142 | 294–321 | 379–403 | 412–427 | | | | | |
| PUL21_VZVD | GENE 38 PROTEIN | VARICELLA-ZOSTER VIRUS (STRAIN DUMAS) | 270–293 | 300–327 | | | | | | | |
| PUL22_HCMVA | HYPOTHETICAL PROTEIN UL22 | HUMAN CYTOMEGALOVIRUS (STRAIN AD169) | 44–67 | | | | | | | | |
| PUL24_EBV | PROTEIN BXRF1 | EPSTEIN-BARR VIRUS (STRAIN B95-8) | 134–155 | | | | | | | | |
| PUL24_HCMVA | HYPOTHETICAL PROTEIN UL24 | HUMAN CYTOMEGALOVIRUS (STRAIN AD169) | 206–222 | | | | | | | | |
| PUL24_HSV11 | PROTEIN UL24 | HERPES SIMPLEX VIRUS (TYPE 1/STRAIN 17) | 147–166 | | | | | | | | |
| PUL24_ILTVT | PROTEIN UL24 HOMOLOG | INFECTIOUS LARYNGOTRACHEI-TIS VIRUS (STRAIN THORNE V882) | 158–179 | | | | | | | | |
| PUL25_HCMVA | HYPOTHETICAL PROTEIN UL25 | HUMAN CYTOMEGALOVIRUS (STRAIN AD169) | 484–500 | | | | | | | | |
| PUL25_HSV11 | VIRION PROTEIN UL25 | HERPES SIMPLEX VIRUS (TYPE 1/STRAIN 17) | 86–101 | | | | | | | | |
| PUL25_HSVEB | VIRION PROTEIN UL25 | EQUINE HERPESVIRUS TYPE 1 (STRAIN AB4P) | 89–104 | 130–147 | | | | | | | |
| PUL25_HSVSA | VIRION GENE 19 PROTEIN | HERPESVIRUS SAIMIRI (STRAIN 11) | 244–265 | 344–368 | | | | | | | |
| PUL25_ILTVT | 64 1 KD VIRION PROTEIN | INFECTIOUS LARYNGOTRACHEI-TIS VIRUS (STRAIN THRONE V882) | 270–287 | 316–336 | | | | | | | |
| PUL27_HCMVA | HYPOTHETICAL PROTEIN UL27 | HUMAN CYTOMEGALOVIRUS (STRAIN AD169) | 307–324 | 486–507 | | | | | | | |
| PUL29_HCMVA | HYPOTHETICAL PROTEIN UL29 | HUMAN CYTOMEGALOVIRUS (STRAIN AD169) | 239–266 | | | | | | | | |
| PUL30_HCMVA | HYPOTHETICAL PROTEIN UL30 | HUMAN CYTOMEGALOVIRUS (STRAIN AD169) | 9–32 | | | | | | | | |
| PUL31_EBV | PROTEIN BFLF2 | EPSTEIN-BARR VIRUS (STRAIN B95-8) | 273–296 | | | | | | | | |
| PUL31_HCMVA | HYPOTHETICAL PROTEIN UL31 | HUMAN CYTOMEGALOVIRUS (STRAIN AD169) | 410–437 | 582–602 | | | | | | | |
| PUL31_HSV11 | PROTEIN UL31 | HERPES SIMPLEX VIRUS (TYPE 1/STRAIN 17) | 95–116 | | | | | | | | |
| PUL31_HSVEB | GENE 29 PROTEIN | EQUINE HERPESVIRUS TYPE 1 (STRAIN AB4P) | 104–125 | 288–309 | | | | | | | |
| PUL31_HSVSA | GENE 69 PROTEIN | HERPESVIRUS SAIMIRI (STRAIN 11) | 145–161 | 163–190 | | | | | | | |
| PUL31_VZVD | GENE 27 PROTEIN | VARICELLA-ZOSTER VIRUS (STRAIN DUMAS) | 117–138 | 295–316 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUL32_HSV11 | PROBABLE MAJOR ENV GLYCOPROTEIN UL32 | HERPES SIMPLEX VIRUS (TYPE 1/STRAIN 17) | 127–143 | 564–585 | | | | | | | |
| PUL32_HSVEB | MAJOR ENVELOPE GLYCOPROTEIN 300 | EQUINE HERPESVIRUS TYPE 1 (STRAIN AB4P) | 81–108 | | | | | | | | |
| PUL32_VZVD | PROBABLE MAJOR ENV GLYCOPROTEIN 26 | VARICELL-ZOSTER VIRUS (STRAIN DUMAS) | 553–574 | | | | | | | | |
| PUL33_HCMVA | G-PROTEIN COUPLED REC HOMOLOG UL33 | HUMAN CYTOMEGALOVIRUS (STRAIN AD169) | 76–102 | | | | | | | | |
| PUL34_HCMVA | HYPOTHETICAL PROTEIN UL34 | HUMAN CYTOMEGALOVIRUS (STRAIN AD169) | 214–232 | 297–321 | | | | | | | |
| PUL34_HSV11 | VIRION PROTEIN UL34 | HERPES SIMPLEX VIRUS (TYPE 1/STRAIN 17) | 251–275 | | | | | | | | |
| PUL34_HSVEB | VIRION GENE 26 PROTEIN | EQUINE HERPESVIRUS TYPE 1 (STRAIN AB4P) | 249–264 | | | | | | | | |
| PUL34_HSVSA | GENE 67 PROTEIN | HERPESVIRUS SAIMIRI (STRAIN 11) | 207–229 | | | | | | | | |
| PUL34_VZVD | VIRION GENE 24 PROTEIN | VARICELL-ZOSTER VIRUS (STRAIN DUMAS) | 244–266 | | | | | | | | |
| PUL35_HCMVA | HYPOTHETICAL PROTEIN UL35 | HUMAN CYTOMEGALOVIRUS (STRAIN AD169) | 229–252 | 310–329 | 331–348 | | | | | | |
| PUL36_HCMVA | HYPOTHETICAL PROTEIN UL36 | HUMAN CYTOMEGALOVIRUS (STRAIN AD169) | 143–168 | 387–410 | | | | | | | |
| PUL37_EBV | PROTEIN BOLF1 | EPSTEIN-BARR VIRUS (STRAIN B95-8) | 21–36 | 135–155 | 707–730 | 984–1004 | | | | | |
| PUL37_HSV11 | PROTEIN UL37 | HERPES SIMPLEX VIRUS (TYPE 1/STRAIN 17) | 229–252 | 262–277 | 445–467 | 665–681 | 758–777 | 925–947 | 1009–1028 | | |
| PUL37_HSVEB | GENE 23 PROTEIN | EQUINE HERPESVIRUS TYPE 1 (STRAIN AB4P) | 414–440 | 491–510 | 664–690 | 778–805 | 901–919 | | | | |
| PUL37_HSVSA | GENE 63 PROTEIN | HERPESVIRUS SAIMIRI (STRAIN 11) | 5–20 | | | | | | | | |
| PUL37_VZVD | GENE 21 PROTEIN | VARICELLA-ZOSTER VIRUS (STRAIN DUMAS) | 4–19 | 104–124 | 140–165 | 168–191 | 196–212 | 229–244 | 248–269 | 670–694 | 776–803 |
| PUL38_HCMVA | HYPOTHETICAL PROTEIN UL38 | HUMAN CYTOMEGALOVIRUS (STRAIN AD169) | 904–923 199–220 | | | | | | | | |
| PUL40_HCMVA | HYPOTHETICAL PROTEIN UL40 | HUMAN CYTOMEGALOVIRUS (STRAIN AD169) | 18–35 | 116–134 | | | | | | | |
| PUL41_HCMVA | HYPOTHETICAL PROTEIN UL41 | HUMAN CYTOMEGALOVIRUS (STRAIN AD169) | 15–31 | | | | | | | | |
| PUL43_HSV11 | MEMBRANE PROTEIN UL43 | HERPES SIMPLEX VIRUS (TYPE 1/STRAIN 17) | 41–63 | 139–160 | 343–365 | 394–421 | | | | | |
| PUL43_HSVEB | GENE 17 MEMBRANE PROTEIN | EQUINE HERPESVIRUS TYPE 1 (STRAIN AB4P) | 34–60 | 86–107 | | | | | | | |
| PUL43_VZVD | GENE 17 MEMBRANE PROTEIN | VARICELLA-ZOSTER VIRUS (STRAIN DUMAS) | 88–114 | 127–146 | 160–180 | 277–299 | 374–400 | | | | |
| PUL45_HSV11 | PROTEIN UL45 | HERPES SIMPLEX VIRUS (TYPE 1/STRAIN 17) | 25–46 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUL45_HSV1K | PROTEIN UL45 | HERPES SIMPLEX VIRUS (TYPE 1/STRAIN KOS) | 25–46 | | | | | | | | |
| PUL45_HSV1M | PROTEIN UL45 | HERPES SIMPLEX VIRUS (TYPE 1/STRAIN MP) | 25–46 | | | | | | | | |
| PUL47_HCMVA | PROTEIN UL47 | HUMAN CYTOMEGALOVIRUS (STRAIN AD169) | 193–218 | 438–464 | 533–556 | 614–640 | 741–766 | | | | |
| PUL47_HSV11 | VIRION PROTEIN UL47 | HERPES SIMPLEX VIRUS (TYPE 1/STRAIN 17) | 404–425 | | | | | | | | |
| PUL47_HSV1F | VIRION PROTEIN UL47 | HERPES SIMPLEX VIRUS (TYPE 1/STRAIN F) | 404–425 | | | | | | | | |
| PUL47_HSVBP | 80 7 KD ALPHA TRANS-INDUCING PROTEIN | BOVINE HERPESVIRUS TYPE 1 (STRAIN P8-2) | 681–702 | | | | | | | | |
| PUL47_HSVE4 | 97 KD ALPHA TRANS-INDUCING PROTEIN | EQUINE HERPESVIRUS TYPE 4 | 580–601 | | | | | | | | |
| PUL47_HSVEB | 97 KD ALPHA TRANS-INDUCING PROTEIN | EQUINE HERPESVIRUS TYPE 1 (STRAIN AB4P) | 587–608 | | | | | | | | |
| PUL47_VZVD | ALPHA TRANS-INDUCING FACTOR 91 8 KD PROTEIN | VARICELLA-ZOSTER VIRUS (STRAIN DUMAS) | 42–58 | 608–627 | | | | | | | |
| PUL49_EBV | HYPOTHETICAL BFRF2 PROTEIN | EPSTEIN-BARR VIRUS (STRAIN B95-8) | 336–358 | | | | | | | | |
| PUL49_HCMVA | HYPOTHETICAL PROTEIN UL49 | HUMAN CYTOMEGALOVIRUS (STRAIN AD169) | 248–264 | 528–543 | | | | | | | |
| PUL49_HSV11 | TEGUMENT PROTEIN UL49 | HERPES SIMPLEX VIRUS (TYPE 1/STRAIN 17) | 226–252 | | | | | | | | |
| PUL49_HSVSA | HYPOTHETICAL GENE 66 PROTEIN | HERPESVIRUS SAIMIRI (STRAIN 11) | 232–253 | | | | | | | | |
| PUL50_HCMVA | PROTEIN UL50 | HUMAN CYTOMEGALOVIRUS (STRAIN AD169) | 96–119 | | | | | | | | |
| PUL51_HSV11 | PROTEIN UL51 | HERPES SIMPLEX VIRUS (TYPE 1/STRAIN 17) | 49–66 | | | | | | | | |
| PUL51_HSVE4 | GENE 8 PROTEIN | EQUINE HERPESVIRUS TYPE 4 (STRAIN 1942) | 169–190 | | | | | | | | |
| PUL51_HSVEB | GENE 8 PROTEIN | EQUINE HERPESVIRUS TYPE 1 (STRAIN AB4P) | 166–189 | | | | | | | | |
| PUL51_VZVD | GENE 7 PROTEIN | VARICELLA-ZOSTER VIRUS (STRAIN DUMAS) | 30–49 | | | | | | | | |
| PUL52_EBV | PROBABLE DNA REPLICATION PROTEIN BSLF1 | EPSTEIN-BARR VIRUS | 44–59 | | | | | | | | |
| PUL52_HSV11 | DNA REPLICATION PROTEIN UL52 | HERPES SIMPLEX VIRUS (TYPE 1/STRAIN 17) | 17–37 | 65–91 | | | | | | | |
| PUL52_HSVE4 | DNA REPLICATION PROTEIN UL52 | EQUINE HERPESVIRUS TYPE 4 (STRAIN 1942) | 8–27 | | | | | | | | |
| PUL52_HSVEB | DNA REPLICATION PROTEIN UL52 | EQUINE HERPESVIRUS TYPE 1 (STRAIN AD4P) | 8–27 | 135–159 | 316–337 | | | | | | |
| PUL52_HSVSA | PROBABLE DNA REPLICATION GENE 56 PROTEIN | HERPESVIRUS SAIMIRI (STRAIN 11) | 489–508 | 586–605 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUL52_VZVD | PROBABLE DNA REPLICATION GENE 6 PROTEIN | VARICELLA-ZOSTER VIRUS (STRAIN DUMAS) | 446–466 | 645–670 | | | | | | | |
| PUL53_HCMVA | PROTEIN UL53 | HUMAN CYTOMEGALOVIRUS (STRAIN AD169) | 173–188 | | | | | | | | |
| PUL53_HSV6U | UL53 PROTEIN HOMOLOG | HERPES SIMPLEX VIRUS (TYPE 6/STRAIN UGANDA-1102) | 64–80 | | | | | | | | |
| PUL60_HCMVA | HYPOTHETICAL PROTEIN UL60 | HUMAN CYTOMEGALOVIRUS (STRAIN AD169) | 120–141 | | | | | | | | |
| PUL62_HCMVA | HYPOTHETICAL PROTEIN UL62 | HUMAN CYTOMEGALOVIRUS (STRAIN AD169) | 62–84 | 178–205 | | | | | | | |
| PUL68_HCMVA | HYPOTHETICAL PROTEIN UL68 | HUMAN CYTOMEGALOVIRUS (STRAIN AD169) | 87–107 | | | | | | | | |
| PUL70_HCMVA | PROBABLE DNA REPLICATION PROTEIN UL70 | HUMAN CYTOMEGALOVIRUS (STRAIN AD169) | 225–252 | 409–430 | 499–514 | 626–645 | 770–793 | | | | |
| PUL71_HCMVA | HYPOTHETICAL PROTEIN UL71 | HUMAN CYTOMEGALOVIRUS (STRAIN AD169) | 234–250 | | | | | | | | |
| PUL73_EBV | HYPOTHETICAL BLRF1 PROTEIN | EPSTEIN-BARR VIRUS (STRAIN B95-8) | 62–87 | | | | | | | | |
| PUL73_HSVSA | HYPOTHETICAL GENE 53 PROTEIN | HERPESVIRUS SAIMIRI (STRAIN 11) | 51–73 | | | | | | | | |
| PUL74_HCMVA | HYPOTHETICAL PROTEIN UL74 | HUMAN CYTOMEGALOVIRUS (STRAIN AD169) | 12–32 | | | | | | | | |
| PUL77_HCMVA | VIRION PROTEIN UL77 | HUMAN CYTOMEGALOVIRUS (STRAIN AD169) | 268–291 | 607–628 | | | | | | | |
| PUL78_HCMVA | HYPOTHETICAL PROTEIN UL78 | HUMAN CYTOMEGALOVIRUS (STRAIN AD169) | 71–90 | 190–205 | | | | | | | |
| PUL79_HCMVA | HYPOTHETICAL PROTEIN UL79 | HUMAN CYTOMEGALOVIRUS (STRAIN AD169) | 40–58 | | | | | | | | |
| PUL84_HCMVA | 65 KD EARLY NONSTRUCTURAL PROTEIN | HUMAN CYTOMEGALOVIRUS (STRAIN AD169) | 100–116 | | | | | | | | |
| PUL84_HCMVT | 65 KD EARLY NONSTRUCTURAL PROTEIN | HUMAN CYTOMEGALOVIRUS (STRAIN TOWNE) | 100–116 | | | | | | | | |
| PUL87_EBV | HYPOTHETICAL PROTEIN B(C)RF1 | EPSTEIN-BARR VIRUS (STRAIN B95-8) | 406–422 | 530–557 | | | | | | | |
| PUL87_HCMVA | HYPOTHETICAL PROTEIN UL87 | HUMAN CYTOMEGALOVIRUS (STRAIN AD169) | 205–231 | 309–335 | 606–628 | 633–653 | 757–781 | | | | |
| PUL87_HSV6U | HYPOTHETICAL PROTEIN 5R | HERPES SIMPLEX VIRUS (TYPE 6/STRAIN UGANDA-1102) | 301–322 | 507–529 | | | | | | | |
| PUL87_HSVSA | HYPOTHERICAL GENE 24 PROTEIN | HERPESVIRUS SAIMIRI (STRAIN 11) | 365–387 | 402–422 | 579–595 | | | | | | |
| PUL88_HCMVA | HYPOTHETICAL PROTEIN UL88 | HUMAN CYTOMEGALOVIRUS (STRAIN AD169) | 173–191 | 252–279 | | | | | | | |
| PUL88_HSV6U | HYPOTHETICAL PROTEIN 6R | HERPES SIMPLEX VIRUS (TYPE 6/STRAIN UGANDA-1102) | 150–173 | | | | | | | | |
| PUL90_HCMVA | HYPOTHETICAL PROTEIN UL90 | HUMAN CYTOMEGALOVIRUS (STRAIN AD169) | 35–50 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUL91_HSV6U | HYPOTHETICAL PROTEIN 8R | HERPES SIMPLEX VIRUS (TYPE 6/STRAIN UGANDA-1102) | 43–65 | | | | | | | | |
| PUL92_HCMVA | HYPOTHETICAL PROTEIN UL92 | HUMAN CYTOMEGALOVIRUS (STRAIN AD169) | 76–99 | | | | | | | | |
| PUL92_HSV6U | HYPOTHETICAL PROTEIN 9R | HERPES SIMPLEX VIRUS (TYPE 6/STRAIN UGANDA-1102) | 36–55 | 100–119 | | | | | | | |
| PUL94_HCMVA | PROTEIN UL94 | HUMAN CYTOMEGALOVIRUS | 49–70 | | | | | | | | |
| PUL95_EBV | HYPOTHETICAL PROTEIN BGLF3 | EPSTEIN-BARR VIRUS (STRAIN B95-8) | 201–223 | | | | | | | | |
| PUL95_HCMVA | HYPOTHETICAL PROTEIN UL95 | HUMAN CYTOMEGALOVIRUS (STRAIN AD169) | 508–526 | | | | | | | | |
| PUL95_HSV6U | HYPOTHETICAL PROTEIN 13R | HERPES SIMPLEX VIRUS (TYPE 6/STRAIN UGANDA-1102) | 9–30 | 328–346 | | | | | | | |
| PUL95_HSVSA | HYPOTHETICAL GENE 34 PROTEIN | HERPESVIRUS SAIMIRI (STRAIN 11) | 187–209 | | | | | | | | |
| PUL97_HCMVA | GANCICLOVIR KINASE | HUMAN CYTOMEGALOVIRUS (STRAIN AD169) | 208–228 | 541–567 | | | | | | | |
| PULA2_HCMVA | HYPOTHETICAL PROTEIN UL102 | HUMAN CYTOMEGALOVIRUS (STRAIN AD169) | 168–185 | | | | | | | | |
| PULA3_HCMVA | PROTEIN UL103 | HUMAN CYTOMEGALOVIRUS (STRAIN AD169) | 26–47 | | | | | | | | |
| PULA4_HCMVA | VIRION PROTEIN UL104 | HUMAN CYTOMEGALOVIRUS (STRAIN AD169) | 215–235 | 423–450 | | | | | | | |
| PULA8_HCMVA | HYPOTHETICAL PROTEIN UL108 | HUMAN CYTOMEGALOVIRUS (STRAIN AD169) | 93–118 | | | | | | | | |
| PILB1_HCMVA | HYPOTHETICAL PROTEIN UL111 | HUMAN CYTOMEGALOVIRUS (STRAIN AD169) | 60–81 | | | | | | | | |
| PULB3_HCMVA | HYPOTHETICAL PROTEIN UL113 | HUMAN CYTOMEGALOVIRUS (STRAIN AD169) | 298–319 | | | | | | | | |
| PULB7_HCMVA | HYPOTHETICAL PROTEIN UL117 | HUMAN CYTOMEGALOVIRUS (STRAIN AD169) | 178–195 | | | | | | | | |
| PULB8_HCMVA | HYPOTHETICAL PROTEIN UL118 | HUMAN CYTOMEGALOVIRUS (STRAIN AD169) | 103–130 | | | | | | | | |
| PULC1_HCMVA | HYPOTHETICAL PROTEIN UL121 | HUMAN CYTOMEGALOVIRUS (STRAIN AD169) | 129–153 | | | | | | | | |
| PULD2_HCMVA | HYPOTHETICAL PROTEIN UL132 | HUMAN CYTOMEGALOVIRUS (STRAIN AD169) | 4–22 | | | | | | | | |
| PUNG_FOWP1 | URACIL-DNA GLUCOSYLASE | FOWLPOX VIRUS (STRAIN FP-1) | 12–37 | | | | | | | | |
| PUNG_HSVEB | URACIL-DNA GLUCOSYLASE | EQUINE HERPESVIRUS TYPE 1 (STRAIN AB4P) | 224–250 | | | | | | | | |
| PUNG_VACCC | URACIL-DNA GLUCOSYLASE | VACCINIA VIRUS (STRAIN COPENHAGEN) | 82–103 | | | | | | | | |
| PUNG_VACCV | URACIL-DNA GLUCOSYLASE | VACCINIA VIRUS (STRAIN WR) | 82–103 | | | | | | | | |
| PUNG_VARV | URACIL-DNA GLUCOSYLASE | VARIOLA VIRUS | 82–103 | | | | | | | | |
| PUNG_VZVD | URACIL-DNA GLUCOSYLASE | VARICELLA-ZOSTER VIRUS (STRAIN DUMAS) | 217–243 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUS02_HSVEB | GENE 68 PROTEIN | EQUINE HERPESVIRUS TYPE 1 (STRAIN AB4P) | 48–63 | | | | | | | | |
| PUS02_HSVEK | US1 PROTEIN | EQUINE HERPESVIRUS TYPE 1 (STRAIN KENTUCKY A) | 48–63 | | | | | | | | |
| PUS02_PRVN3 | PROTEIN US2 HOMOLOG | PSEUDORABIES VIRUS (STRAIN NIA-3) | 120–136 | | | | | | | | |
| PUS03_HCMVA | HQLF1 PROTEIN | HUMAN CYTOMEGALOVIRUS (STRAIN AD169) | 24–39 | | | | | | | | |
| PUS05_HSV11 | PUTATIVE GLYCOPROTEIN US5 | HERPES SIMPLEX VIRUS (TYPE 1/STRAIN 17) | 53–70 | | | | | | | | |
| PUS05_HSV2 | PUTATIVE GLYCOPROTEIN US5 | HERPES SIMPLEX VIRUS (TYPE 2) | 53–70 | | | | | | | | |
| PUS09_HCMVA | HYPOTHETICAL PROTEIN HXLF3 | HUMAN CYTOMEGALOVIRUS (STRAIN AD169) | 179–206 | | | | | | | | |
| PUS11_HCMVA | HYPOTHETICAL PROTEIN HXLF1 | HUMAN CYTOMEGALOVIRUS (STRAIN AD169) | 98–113 | | | | | | | | |
| PUS12_HCMVA | HYPOTHETICAL PROTEIN HVLF6 | HUMAN CYTOMEGALOVIRUS (STRAIN AD169) | 29–50 | 113–135 | 195–222 | | | | | | |
| PUS13_HCMVA | HYPOTHETICAL PROTEIN HVLF5 | HUMAN CYTOMEGALOVIRUS (STRAIN AD169) | 11–33 | 208–231 | | | | | | | |
| PUS14_HCMVA | HYPOTHETICAL PROTEIN HVLF4 | HUMAN CYTOMEGALOVIRUS (STRAIN AD169) | 236–260 | | | | | | | | |
| PUS15_HCMVA | HYPOTHETICAL PROTEIN HVLF3 | HUMAN CYTOMEGALOVIRUS (STRAIN AD169) | 378–402 | 443–466 | | | | | | | |
| PUS16_HCMVA | HYPOTHETICAL PROTEIN HVLF2 | HUMAN CYTOMEGALOVIRUS (STRAIN AD169) | 151–174 | 243–267 | | | | | | | |
| PUS17_HCMVA | HYPOTHETICAL PROTEIN HVLF1 | HUMAN CYTOMEGALOVIRUS (STRAIN AD169) | 110–126 | | | | | | | | |
| PUS19_HCMVA | MEMBRANE PROTEIN HWLF4 | HUMAN CYTOMEGALOVIRUS (STRAIN AD169) | 120–142 | 178–202 | 214–232 | | | | | | |
| PUS21_HCMVA | HYPOTHETICAL PROTEIN HWLF2 | HUMAN CYTOMEGALOVIRUS (STRAIN AD169) | 41–67 | 155–182 | | | | | | | |
| PUS22_HCMVA | EARLY NUCLEAR PROTEIN HWLF1 | HUMAN CYTOMEGALOVIRUS (STRAIN AD169) | 270–292 | | | | | | | | |
| PUS23_HCMVA | HYPOTHETICAL PROTEIN HHLF7 | HUMAN CYTOMEGALOVIRUS (STRAIN AD169) | 292–310 | | | | | | | | |
| PUS24_HCMVA | HYPOTHETICAL PROTEIN HHLF6 | HUMAN CYTOMEGALOVIRUS (STRAIN AD169) | 352–373 | | | | | | | | |
| PUS28_HCMVA | G-PROTEIN COUPLED REC HOMOLOG US28 | HUMAN CYTOMEGALOVIRUS (STRAIN AD169) | 34–49 | 140–160 | | | | | | | |
| PUS28_HCMVT | G-PROTEIN COUPLED REC HOMOLOG US28 | HUMAN CYTOMEGALOVIRUS (STRAIN TOWNE) | 34–49 | 140–160 | | | | | | | |
| PUS29_HCMVA | HYPOTHETICAL PROTEIN HHRF4 | HUMAN CYTOMEGALOVIRUS (STRAIN AD169) | 246–269 | | | | | | | | |
| PUS30_HCMVA | HYPOTHETICAL PROTEIN HHRF5 | HUMAN CYTOMEGALOVIRUS (STRAIN AD169) | 102–128 | 208–233 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PUS33_HCMVA | HYPOTHETICAL PROTEIN HHLF3 | HUMAN CYTOMEGALOVIRUS (STRAIN AD169) | 41–59 | | | | | | | | |
| PV07K_LSV | 7 KD PROTEIN | LILY SYMPTOMLESS VIRUS | 27–46 | | | | | | | | |
| PV07K_NMV | 7 KD PROTEIN | POTATO VIRUS S (STRAIN PERUVIAN) | 28–49 | | | | | | | | |
| PV07K_PVSP | 7 KD PROTEIN | POTATO VIRUS X (PVX) | 31–48 | | | | | | | | |
| PV07K_PVX | 7 KD PROTEIN | POTATO VIRUS X (STRAIN X3) | 31–48 | | | | | | | | |
| PV07K_PVXX3 | 7 KD PROTEIN | POTATO VIRUS X (STRAIN XC) (STRAIN CP) | 31–48 | | | | | | | | |
| PV117_ASFL5 | LIS 121-1 PROTEIN | AFRICAN SWINE FEVER VIRUS (STRAIN LIS57) | 73–94 | | | | | | | | |
| PV121_ASFL5 | 125 KD PROTEIN | ALFALFA MOSAIC VIRUS (STRAIN 425/ISOLATE LEIDEN) | 59–79 | | | | | | | | |
| PV12K_PVMR | 12 KD PROTEIN | POTATO VIRUS M (STRAIN RUSSIAN) | 79–96 | | | | | | | | |
| P

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PV2A_TAV | 2A PROTEIN | TOMATO ASPERMY VIRUS | 234–255 | | | | | | | | |
| PV30K_TRVTC | 29 1 KD PROTEIN | TOBACCO RATTLE VIRUS (STRAIN TCM) | 62–82 | | | | | | | | |
| PV31K_TOBSV | 31 7 KD PROTEIN | TOBACCO STREAK VIRUS (STRAIN WC) | 226–250 | | | | | | | | |
| PV362_ASFB7 | K 362 PROTEIN | AFRICAN SWINE FEVER VIRUS (STRAIN BA71V) | 145–164 | | | | | | | | |
| PV375_ASFL5 | LIS 375 PROTEIN | AFRICAN SWINE FEVER VIRUS (STRAIN LIS57) | 114–135 | | | | | | | | |
| PV382_ASFL5 | LIS 382 PROTEIN | AFRICAN SWINE FEVER VIRUS (STRAIN LIS57) | 114–135 | | | | | | | | |
| PV3A_CCMV | COWPEA CHLOROTIC MOTTLE VIRUS | | 160–187 | | | | | | | | |
| PV3A_CMVFN | 3A PROTEIN | CUCUMBER MOSAIC VIRUS (STRAIN FNY) | 214–235 | | | | | | | | |
| PV3A_CMVM | 3A PROTEIN | CUCUMBER MOSAIC VIRUS (STRAIN M) | 214–235 | | | | | | | | |
| PV3A_CMVO | 3A PROTEIN | CUCUMBER MOSAIC VIRUS (STRAIN O) | 214–235 | | | | | | | | |
| PV3A_CMVQ | 3A PROTEIN | CUCUMBER MOSAIC VIRUS (STRAIN Q) | 214–235 | | | | | | | | |
| PV3A_CMVY | CUCUMBER MOSAIC VIRUS (STRAIN Y) | | 214–235 | | | | | | | | |
| PV3A_IBVB | 3A PROTEIN | AVAIN INFECTIOUS BRONCHITIS VIRUS (STRAIN BEAUDETTE) | 5–28 | | | | | | | | |
| PV3A_IBVM | 3A PROTEIN | AVAIN INFECTIOUS BRONCHITIS VIRUS (STRAIN M41) | 5–28 | | | | | | | | |
| PV3A_IBVP3 | 3A PROTEIN | AVAIN INFECTIOUS BRONCHITIS VIRUS (STRAIN PORTUGAL/322/82) | 5–28 | | | | | | | | |
| PV3A_IBVU5 | 3A PROTEIN | AVAIN INFECTIOUS BRONCHITIS VIRUS (STRAIN UK/183/66) | 5–28 | | | | | | | | |
| PV3A_TAV | 3A PROTEIN | TOMATO ASPERMY VIRUS | 147–168 | | | | | | | | |
| PV58K_BSMV | 58 KD PROTEIN | BARLEY STRIPE MOSAIC VIRUS | 320–340 | | | | | | | | |
| PV66K_BWYVF | PROTEIN 6B | CANINE ENTERIC CORONAVIRUS (STRAIN K378) | 97–116 | | | | | | | | |
| PV70K_TYMVA | 69 KD PROTEIN | TURNIP YELLOW MOSAIC VIRUS (AUSTRALIAN ISOLATE) | 12–35 | | | | | | | | |
| PV90K_AMVLE | 90 KD PROTEIN | ALFALFA MOSAIC VIRUS (STRAIN 425/ISOLATE LEIDEN) | 44–59 | | | | | | | | |
| PVA04_VACCC | PROTEIN A4 | VACCINIA VIRUS (STRAIN COPENHAGEN) | 217–244 | | | | | | | | |
| PVA04_VACCV | PROTEIN A4 | VACCINIA VIRUS (STRAIN WR) | 217–244 | | | | | | | | |
| PVA04_VARV | PROTEIN A4 | VARIOLA VIRUS | 207–234 | | | | | | | | |
| PVA09_VACCC | PROTEIN A9 | VACCINIA VIRUS (STRAIN COPENHAGEN) | 41–66 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVA09_VARV | PROTEIN A9 | VARIOLA VIRUS | 41–66 | | | | | | | | |
| PVA11_VACCC | PROTEIN A11 | VACCINIA VIRUS (STRAIN COPENHAGEN) | 23–44 | 140–159 | 299–317 | | | | | | |
| PVA11_VARV | PROTEIN A11 | VARIOLA VIRUS | 23–44 | 141–160 | 300–318 | | | | | | |
| PVA14_VACCC | PROTEIN A14 | VACCINIA VIRUS (STRAIN COPENHAGEN) | 39–62 | | | | | | | | |
| PVA14_VARV | PROTEIN A14 | VARIOLA VIRUS | 39–62 | | | | | | | | |
| PVA16_VACCC | PROTEIN A16 | VACCINIA VIRUS (STRAIN COPENHAGEN) | 341–362 | | | | | | | | |
| PVA16_VARV | PROTEIN A16 | VARIOLA VIRUS | 340–361 | | | | | | | | |
| PVA18_VACCC | 56 KD ABORTIVE LATE PROTEIN | VACCINIA VIRUS (STRAIN COPENHAGEN) | 429–447 | | | | | | | | |
| PVA18_VACCV | 56 KD ABORTIVE LATE PROTEIN | VACCINIA VIRUS (STRAIN WR) | 429–447 | | | | | | | | |
| PVA18_VARV | 56 KD ABORTIVE LATE PROTEIN | VARIOLA VIRUS | 429–447 | | | | | | | | |
| PVA20_VACCC | PROTEIN A20 | VACCINIA VIRUS (STRAIN COPENHAGEN) | 107–131 | 193–209 | | | | | | | |
| PVA20_VARV | PROTEIN A20 | VARIOLA VIRUS | 107–131 | 193–209 | | | | | | | |
| PVA23_VARV | PROTEIN A23 | VARIOLA VIRUS | 58–82 | | | | | | | | |
| PVA28_VACCV | PROTEIN A28 | VACCINIA VIRUS (STRAIN WR), AND (STRAIN COPENHAGEN) | 53–76 | | | | | | | | |
| PVA28_VARV | PROTEIN A28 | VARIOLA VIRUS | 53–76 | | | | | | | | |
| PVA32_VACCV | PROTEIN A32 | VACCINIA VIRUS (STRAIN WR), AND (STRAIN COPENHAGEN) | 205–220 | | | | | | | | |
| PVA32_VARV | PROTEIN A32 | VARIOLA VIRUS | 175–190 | | | | | | | | |
| PVA35_VACCC | PROTEIN A35 PRECURSOR | VACCINIA VIRUS (STRAIN COPENHAGEN) | 33–49 | | | | | | | | |
| PVA35_VACCV | PROTEIN A35 PRECURSOR | VACCINIA VIRUS (STRAIN WR) | 33–49 | 141–164 | | | | | | | |
| PVA37_VACCC | PROTEIN A37 | VACCINIA VIRUS (STRAIN COPENHAGEN) | 66–90 | | | | | | | | |
| PVA37_VACCV | PROTEIN A37 | VACCINIA VIRUS (STRAIN WR) | 66–90 | | | | | | | | |
| PVA40_VACCC | PROTEIN A40 | VACCINIA VIRUS (STRAIN COPENHAGEN) | 4–30 | | | | | | | | |
| PVA41_VACCC | PROTEIN A41 PRECURSOR | VACCINIA VIRUS (STRAIN COPENHAGEN) | 47–71 | | | | | | | | |
| PVA41_VACCV | PROTEIN A41 PRECURSOR | VACCINIA VIRUS (STRAIN WR) | 47–71 | | | | | | | | |
| PVA41_VARV | PROTEIN A41 PRECURSOR | VARIOLA VIRUS | 47–71 | | | | | | | | |
| PVA47-VACCC | PROTEIN A47 | VACCINIA VIRUS (STRAIN COPENHAGEN) | 59–79 | 201–226 | | | | | | | |
| PVA47_VACCV | PROTEIN A47 | VACCINIA VIRUS (STRAIN WR) | 59–79 | 201–226 | | | | | | | |
| PVA47_VARV | PROTEIN A47 | VARIOLA VIRUS | 59–79 | 201–226 | | | | | | | |
| PVA55-VACCC | PROTEIN A55 | VACCINIA VIRUS (STRAIN COPENHAGEN) | 247–266 | 384–404 | | | | | | | |
| PVA55_VACCV | PROTEIN A55 | VACCINIA VIRUS (STRAIN WR) | 247–266 | 384–404 | | | | | | | |
| PVAL1_BCTV | AL1 PROTEIN | BEET CURLY TOP VIRUS | 56–75 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| VAL1_CLVK | AL1 PROTEIN | CASSAVA LATENT VIRUS (STRAIN WEST KENYAN 844) | 55–74 | | | | | | | | |
| PVAL1_CLVN | AL1 PROTEIN | CASSAVA LATENT VIRUS (STRAIN NIGERIAN) | 55–74 | | | | | | | | |
| PVAL3_BCTV | AL3 PROTEIN | BEET CURLY TOP VIRUS | 82–108 | | | | | | | | |
| PVAL3_CLVK | AL3 PROTEIN | CASSAVA LATENT VIRUS (STRAIN WEST KENYAN 844) | 77–97 | | | | | | | | |
| PVAL3_CLVN | AL3 PROTEIN | CASSAVA LATENT VIRUS (STRAIN NIGERIAN) | 77–97 | | | | | | | | |
| PVAL3_TYLCM | AL3 PROTEIN | TOMATO YELLOW LEAF CURL VIRUS (STRAIN MARMANDE) | 78–97 | | | | | | | | |
| PVAL3_TYLCV | AL3 PROTEIN | TOMATO YELLOW LEAF CURL VIRUS | 77–97 | | | | | | | | |
| PVAT_CAMVC | APHID TRANSMISSION PROTEIN | CAULIFLOWER MOSAIC VIRUS (STRAIN CM-1841) | 134–157 | | | | | | | | |
| PVAT_CAMVD | APHID TRANSMISSION PROTEIN | CAULIFLOWER MOSAIC VIRUS (STRAIN D/H) | 134–157 | | | | | | | | |
| PVAT_CAMVE | APHID TRANSMISSION PROTEIN | CAULIFLOWER MOSAIC VIRUS (STRAIN BBC) | 134–157 | | | | | | | | |
| PVAT_CAMVN | APHID TRANSMISSION PROTEIN | CAULIFLOWER MOSAIC VIRUS (STRAIN NY8153) | 134–157 | | | | | | | | |
| PVAT_CAMVP | APHID TRANSMISSION PROTEIN | CAULIFLOWER MOSAIC VIRUS (STRAIN PV147) | 134–157 | | | | | | | | |
| PVAT_CAMVS | APHID TRANSMISSION PROTEIN | CAULIFLOWER MOSAIC VIRUS (STRAIN STRASBOURG) | 134–157 | | | | | | | | |
| PVAT_CAMVW | APHID TRANSMISSION PROTEIN | CAULIFLOWER MOSAIC VIRUS (STRAIN W260) | 34–60 | | | | | | | | |
| PVAT_CERV | APHID TRANSMISSION PROTEIN | CARNATION ETCHED RING VIRUS | 141–161 | | | | | | | | |
| PVAT_FMVD | APHID TRANSMISSION PROTEIN | FIGWORT MOSAIC VIRUS (STRAIN DXS) | 132–159 | | | | | | | | |
| PVB02_VACCC | PROTEIN B2 | VACCINIA VIRUS (STRAIN COPENHAGEN) | 155–170 | | | | | | | | |
| PVB02_VACCC | PROTEIN B2 | VACCINIA VIRUS (STRAIN WR) | 155–170 | | | | | | | | |
| PVB04_VACCC | PROTEIN B4 | VACCINIA VIRUS (STRAIN COPENHAGEN) | 155–170 | | | | | | | | |
| PVB04_VACCV | PROTEIN B4 | VACCINIA VIRUS (STRAIN WR) | 489–511 | | | | | | | | |
| PVB04_VARV | PROTEIN B4 | VARIOLA VIRUS | 489–511 | | | | | | | | |
| PVB05_VACC0 | PLAQUE-SIZE/HOST RANGE PROTEIN PRECURSOR | VACCINIA VIRUS (STRAIN LC16MO) | 251–271 | | | | | | | | |
| PVB05_VACCC | PLAQUE-SIZE/HOST RANGE PROTEIN PRECUROSR | VACCINIA VIRUS (STRAIN COPENHAGEN) | 251–271 | | | | | | | | |
| PVB05_VACCL | PLAQUE-SIZE/HOST RANGE PROTEIN PRECURSOR | VACCINIA VIRUS (STRAIN LISTER) | 251–271 | | | | | | | | |
| PVB05_VACCV | PLAQUE-SIZE/HOST RANGE PROTEIN PRECURSOR | VACCINIA VIRUS (STRAIN WR) | 251–271 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVB06_VACCV | PROTEIN B6 | VACCINIA VIRUS (STRAIN WR) AND (STRAIN COPENHAGEN) | 59–82 | | | | | | | | |
| PVB15_VACCC | PROTEIN B15 | VACCINIA VIRUS (STRAIN COPENHAGEN) | 121–143 | | | | | | | | |
| PVB15_VACCV | PROTEIN B15 | VACCINIA VIRUS (STRAIN WR) | 121–143 | | | | | | | | |
| PVB15_VARV | PROTEIN B15 | VARIOLA VIRUS | 121–143 | | | | | | | | |
| PVB17_VACCC | PROTEIN B17 | VACCINIA VIRUS (STRAIN COPENHAGEN) | 157–179 | | | | | | | | |
| PVB17_VACCV | PROTEIN B17 | VACCINIA VIRUS (STRAIN WR) | | | | | | | | | |
| PVBL1_CLVK | BL1 PROTEIN | CASSAVA LATENT VIRUS (STRAIN WEST KENYAN 844) | 34–51 | | | | | | | | |
| PVBL1_CLVN | BL1 PROTEIN | CASSAVA LATENT VIRUS (STRAIN NIGERIAN) | 34–51 | | | | | | | | |
| PVBL1_SLCV | BL1 PROTEIN | SQUASH LEAF CURL VIRUS | 245–268 | | | | | | | | |
| PVBRL1_ABMVW | BR1 PROTEIN | ABUTILON MOSAIC VIRUS (ISOLATE WEST INDIA) | 166–191 | | | | | | | | |
| PVBR1_BGMV | BR1 PROTEIN | BEAN GOLDEN MOSAIC VIRUS | 166–191 | | | | | | | | |
| PVBR1_PYMVV | BR1 PROTEIN | POTATO YELLOW MOSAIC VIRUS (ISOLATE VENEZUELA) | 166–191 | | | | | | | | |
| PVBR1_SLCV | BR1 PROTEIN | SQUASH LEAF CURL VIRUS | | | | | | | | | |
| PVC01_VACCC | PROTEIN C1 | VACCINIA VIRUS (STRAIN COPENHAGEN) | 70–90 | | | | | | | | |
| PVC01_VACCV | PROTEIN C1 | VACCINIA VIRUS (STRAIN WR) | 75–95 | | | | | | | | |
| PVC01_VARV | PROTEIN C1 | VARIOLA VIRUS | 58–78 | | | | | | | | |
| PVC02_SFVKA | HYPOTHETICAL PROTEIN C2 | SHOPE FIBROMA VIRUS (STRAIN KASZA) | 8–31 | | | | | | | | |
| PVC03_SFVKA | G-PROTEIN COUPLED RECEPTOR HOMOLOG C3 | SHOPE FIBROMA VIRUS (STRAIN KASZA) | 98–123 | 179–197 | | | | | | | |
| PVC04_VACCC | PROTEIN C4 | VACCINIA VIRUS (STRAIN COPENHAGEN) | 182–209 | | | | | | | | |
| PVC04_VACCV | PROTEIN C4 | VACCINIA VIRUS (STRAIN WR) | 183–208 | | | | | | | | |
| PVC05_SFVKA | HYPOTHETICAL PROTEIN C6 | SHOPE FIBROMA VIRUS (STRAIN KASZA) | 20–47 | | | | | | | | |
| PVC08_SFVKA | HYPOTHETICAL PROTEIN C8 | SHOPE FIBROMA VIRUS (STRAIN KASZA) | 14–30 | | | | | | | | |
| PVC09_VACCC | PROTEIN C9 | VACCINIA VIRUS (STRAIN COPENHAGEN) | 40–59 | | | | | | | | |
| PVC09_VACCV | PROTEIN C9 | VACCINIA VIRUS (STRAIN WR) | 40–59 | | | | | | | | |
| PVC10_SFVKA | HYPOTHETICAL PROTEIN C10 | SHOPE FIBROMA VIRUS (STRAIN KASZA) | 85–109 | | | | | | | | |
| PVC10_VACCC | PROTEIN C10 | VACCINIA VIRUS (STRAIN COPENHAGEN) | 42–64 | | | | | | | | |
| PVC10_VACCV | PROTEIN C10 | VACCINIA VIRUS (STRAIN WR) | 42–64 | | | | | | | | |
| PVC10_VARV | PROTEIN C10 | VARIOLA VIRUS | 42–64 | | | | | | | | |
| PVC16_VACCC | PROTEIN C16/B22 | VACCINIA VIRUS (STRAIN COPENHAGEN) | 41–68 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVC17_VACCC | PROTEIN C17/B23 | VACCINIA VIRUS (STRAIN COPENHAGEN) | 301–326 | | | | | | | | |
| PVC21_VACCC | PROTEIN C21/B27 | VACCINIA VIRUS (STRAIN COPENHAGEN) | 3–28 | | | | | | | | |
| PVCAP_EBV | MAJOR CAPSID PROTEIN | EPSTEIN-BARR VIRUS (STRAIN B95-8) | 148–172 | 366–381 | 1072–1095 | | | | | | |
| PVCAP_HCMVA | MAJOR CAPSID PROTEIN | HUMAN CYTOMEGALOVIRUS (STRAIN AD169) | 668–684 | 842–860 | 871–893 | | | | | | |
| PVCAP_HSV11 | MAJOR CAPSID PROTEIN | HERPES SIMPLEX VIRUS (TYPE 1/STRAIN 17) | 283–302 | 358–384 | 1137–1152 | | | | | | |
| PVCAP_HSVEB | MAJOR CAPSID PROTEIN | EQUINE HERPESVIRUS TYPE 1 (STRAIN AB4P) | 357–383 | 872–898 | | | | | | | |
| PVCAP_HSVSA | MAJOR CAPSID PROTEIN | HERPESVIRUS SAIMIRI (STRAIN 11) | 144–168 | 269–287 | 357–372 | 1062–1089 | | | | | |
| PVCAP_PRVIS | MAJOR CAPSID PROTEIN | PSEUDORABIES VIRUS (STRAIN INDIANA S) | 335–362 | | | | | | | | |
| PVCAP_VZVD | MAJOR CAPSID PROTEIN | VARICELLA-ZOSTER VIRUS (STRAIN DUMAS) | 381–401 | 891–910 | 1156–1176 | | | | | | |
| PVCG3_NPVAC | DNA-BINDING PROTEIN | AUTOGRAPHA CALIFORNICA NUCLEAR POLYHEDROSIS VIRUS | 60–81 | | | | | | | | |
| PVD03_VACCC | PROTEIN D3 | VACCINIA VIRUS (STRAIN COPENHAGEN) | 12–39 | | | | | | | | |
| PVD03_VACCV | PROTEIN D3 | VACCINIA VIRUS (STRAIN WR) | 12–39 | | | | | | | | |
| PVD03_VARV | PROTEIN D3 | VARIOLA VIRUS | 12–39 | | | | | | | | |
| PVD05_FOWP1 | 92 6 KD PROTEIN | FOWLPOX VIRUS (STRAIN FP-1) | 246–265 | 315–337 | | | | | | | |
| PVD05_SFVKA | PROTEIN D5 | SHOPE FIBROMA VIRUS (STRAIN KASZA) | 54–78 | 171–198 | | | | | | | |
| PVD05_VACCC | PROTEIN D5 | VACCINIA VIRUS (STRAIN COPENHAGEN) | 320–340 | 694–714 | 715–734 | | | | | | |
| PVD05_VACCV | PROTEIN D5 | VACCINIA VIRUS (STRAIN WR) | 320–340 | 694–714 | 715–734 | | | | | | |
| PVD05_VARV | PROTEIN D5 | VARIOLA VIRUS | 320–340 | 694–714 | 715–734 | | | | | | |
| PVDBP_CMAVC | DNA-BINDING PROTEIN | CAULIFLOWER MOSAIC VIRUS (STRAIN CM-1841) | 37–56 | | | | | | | | |
| PVDBP_CMAVD | DNA-BINDING PROTEIN | CAULIFLOWER MOSAIC VIRUS (STRAIN D/H) | 37–56 | | | | | | | | |
| PVDBP_CAMVE | DNA-BINDING PROTEIN | CAULIFLOWER MOSAIC VIRUS (STRAIN BBC) | 37–56 | | | | | | | | |
| PVDBP_CAMVN | DNA-BINDING PROTEIN | CAULIFLOWER MOSAIC VIRUS (STRAIN NY8153) | 37–56 | | | | | | | | |
| PVDBP_CAMVS | DNA-BINDING PROTEIN | CAULIFLOWER MOSAIC VIRUS (STRAIN STRASBOURG) | 37–56 | | | | | | | | |
| PVE02_VACCC | PROTEIN E2 | VACCINIA VIRUS (STRAIN COPENHAGEN) | 70–97 | 355–380 | 540–558 | | | | | | |
| PVE02_VACCV | PROTEIN E2 | VACCINIA VIRUS (STRAIN WR) | 70–97 | 355–380 | 540–558 | | | | | | |
| PVE02_VARV | PROTEIN E2 | VARIOLA VIRUS | 70–97 | 355–380 | 540–558 | | | | | | |
| PVE05_VACCC | PROTEIN E5 | VACCINIA VIRUS (STRAIN COPENHAGEN) | 314–329 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVE05_VACCD | PROTEIN E5 | VACCINIA VIRUS (STRAIN DAIREN I) | 324–339 | | | | | | | | |
| PVE05_VACCV | PROTEIN E5 | VACCINIA VIRUS (STRAIN WR) | 324–339 | | | | | | | | |
| PVE05_VARV | PROTEIN E5 | VARIOLA VIRUS | 324–339 | | | | | | | | |
| PVE06_VACCC | PROTEIN E6 | VACCINIA VIRUS (STRAIN COPENHAGEN) | 430–451 | | | | | | | | |
| PVE06_VACCV | PROTEIN E6 | VACCINIA VIRUS (STRAIN WR) | 430–451 | | | | | | | | |
| PVE06_VARV | PROTEIN E6 | VARIOLA VIRUS | 251–267 | 430–451 | | | | | | | |
| PVE08_VACCC | PROTEIN E8 | VACCINIA VIRUS (STRAIN COPENHAGEN) | 254–270 | | | | | | | | |
| PVEO8_VACCV | PROTEIN E8 | VACCINIA VIRUS (STRAIN WR) | 254–270 | | | | | | | | |
| PVE08_VARV | PROTEIN E8 | VARIOLA VIRUS | 254–270 | | | | | | | | |
| PVE12_HPV16 | PROBABLE E1 PROTEIN 2 | HUMAN PAPILLOMAVIRUS TYPE 16 | 167–183 | | | | | | | | |
| PVE18_NPVAC | EARLY 18 5 KD PROTEIN | AUTOGRAPHA CALIFORNICA NUCLEAR POLYHEDROSIS VIRUS | 106–113 | | | | | | | | |
| PVE1_BPV1 | E1 PROTEIN | BOVINE PAPILLOMAVIRUS TYPE 1 | 265–282 | 517–533 | | | | | | | |
| PVE1_BPV2 | E1 PROTEIN | BOVINE PAPILLOMAVIRUS TYPE 2 | 265–281 | 516–532 | | | | | | | |
| PVE1_CRPVK | E1 PROTEIN | COTTONTAIL RABBIT (SHOPE) PAPILLOMAVIRUS (STRAIN KANSAS) | 7–22 | | | | | | | | |
| PVE1_HPV11 | E1 PROTEIN | HUMAN PAPILLOMAVIRUS TYPE 11 | 258–275 | 311–334 | | | | | | | |
| PVE1_HPV13 | E1 PROTEIN | HUMAN PAPILLOMAVIRUS TYPE 13 | 308–324 | | | | | | | | |
| PVE1_HPV18 | E1 PROTEIN | HUMAN PAPILLOMAVIRUS TYPE 18 | 264–281 | 317–333 | 344–364 | | | | | | |
| PVE1_HPV31 | E1 PROTEIN | HUMAN PAPILLOMAVIRUS TYPE 31 | 237–254 | | | | | | | | |
| PVE1_HPV33 | E1 PROTEIN | HUMAN PAPILLOMAVIRUS TYPE 33 | 238–260 | | | | | | | | |
| PVE1_HPV39 | E1 PROTEIN | HUMAN PAPILLOMAVIRUS TYPE 39 | 334–354 | | | | | | | | |
| PVE1_HPV41 | E1 PROTEIN | HUMAN PAPILLOMAVIRUS TYPE 41 | 363–380 | | | | | | | | |
| PVE1_HPV42 | E1 PROTEIN | HUMAN PAPILLOMAVIRUS TYPE 42 | 304–320 | | | | | | | | |
| PVE1_HPV58 | E1 PROTEIN | HUMAN PAPILLOMAVIRUS TYPE 58 | 238–260 | | | | | | | | |
| PVE1_HPV6B | E1 PROTEIN | HUMAN PAPILLOMAVIRUS TYPE 6B | 258–275 | 311–334 | | | | | | | |
| PVE1_PCPV1 | E1 PROTEIN | PYGMY CHIMPANZEE PAPILLOMAVIRUS TYPE 1 | 257–274 | 310–326 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVE1_RHPV1 | E1 PROTEIN | RHESUS PAPILLOMAVIRUS TYPE 1 | 286–309 | | | | | | | | |
| PVE2_CRPVK | PROBABLE E2 PROTEIN | COTTONTAIL RABBIT (SHOPE) PAPILLOMAVIRUS (STRAIN KANSAS) | 308–333 | | | | | | | | |
| PVE2_HPV11 | E2 PROTEIN | HUMAN PAPILLOMAVIRUS TYPE 11 | 285–310 | | | | | | | | |
| PVE2_HPV13 | E2 PROTEIN | HUMAN PAPILLOMAVIRUS TYPE 13 | 295–320 | | | | | | | | |
| PVE2_HPV18 | E2 PROTEIN | HUMAN PAPILLOMAVIRUS TYPE 18 | 288–306 | | | | | | | | |
| PVE2_HPV1A | E2 PROTEIN | HUMAN PAPILLOMAVIRUS TYPE 1A | 284–300 | | | | | | | | |
| PVE2_HPV2A | E2 PROTEIN | HUMAN PAPILLOMAVIRUS TYPE 2A | 311–336 | | | | | | | | |
| PVE2_HPV31 | E2 PROTEIN | HUMAN PAPILLOMAVIRUS TYPE 31 | 294–312 | | | | | | | | |
| PVE2_HPV33 | E2 PROTEIN | HUMAN PAPILLOMAVIRUS TYPE 33 | 275–293 | | | | | | | | |
| PVE2_HPV35 | E2 PROTEIN | HUMAN PAPILLOMAVIRUS TYPE 35 | 289–307 | | | | | | | | |
| PVE2_HPV39 | E2 PROTEIN | HUMAN PAPILLOMAVIRUS TYPE 39 | 292–310 | | | | | | | | |
| PVE2_HPV42 | E2 PROTEIN | HUMAN PAPILLOMAVIRUS TYPE 42 | 321–338 | | | | | | | | |
| PVE2_HPV57 | E2 PROTEIN | HUMAN PAPILLOMAVIRUS TYPE 57 | 303–328 | | | | | | | | |
| PVE2_HPV6B | E2 PROTEIN | HUMAN PAPILLOMAVIRUS TYPE 6B | 286–311 | | | | | | | | |
| PVE2_PAPVD | PROBABLE E2 PROTEIN | DEER PAPIOLMAVIRUS | 333–351 | | | | | | | | |
| PVE2_PCPV1 | E2 PROTEIN | PYGMY CHIMPANZEE PAPILLOMAVIRUS TYPE 1 | 295–320 | | | | | | | | |
| PVE2_RHPV1 | E2 PROTEIN | RHESUS PAPILLOMAVIRUS TYPE 1 | 290–308 | | | | | | | | |
| PVE4_HPV18 | PROBABLE E4 PROTEIN | HUMAN PAPILLOMAVIRUS TYPE 18 | 39–59 | | | | | | | | |
| PVE4_HPV41 | PROBABLE E4 PROTEIN | HUMAN PAPILLOMAVIRUS TYPE 41 | 56–76 | | | | | | | | |
| PVE4_HPV51 | PROBABLE E4 PROTEIN | HUMAN PAPILLOMAVIRUS TYPE 51 | 59–83 | | | | | | | | |
| PVE4_RHPV1 | PROBABLE E4 PROTEIN | HUMAN PAPILLOMAVIRUS TYPE 1 | 63–87 | | | | | | | | |
| PVE5A_HPV11 | PROBABLE E5A PROTEIN | HUMAN PAPILLOMAVIRUS TYPE 11 | 19–42 | | | | | | | | |
| PVE5A_HPV6C | PROBABLE E5A PROTEIN | HUMAN PAPILLOMAVIRUS TYPE 6C | 19–42 | | | | | | | | |
| PVE5_BPV1 | E5 PROTEIN | BOVINE PAPILLOMAVIRUS TYPE 1 AND TYPE 2 | 2–26 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVE5_HPV13 | PROBABLE E5 PROTEIN | HUMAN PAPILLOMAVIRUS TYPE 13 | 19–42 | | | | | | | | |
| PVE5_HPV31 | PROBABLE E5 PROTEIN | HUMAN PAPILLOMAVIRUS TYPE 31 | 31–52 | | | | | | | | |
| PVE5_HPV42 | PROBABLE E5 PROTEIN | HUMAN PAPILLOMAVIRUS TYPE 42 | 45–65 | | | | | | | | |
| PVE5_HPV51 | PROBABLE E5 PROTEIN | HUMAN PAPILLOMAVIRUS TYPE 51 | 31–52 | | | | | | | | |
| PVE5_HPV5B | PROBABLE E5 PROTEIN | HUMAN PAPILLOMAVIRUS TYPE 5B | 89–113 | | | | | | | | |
| PVE5_RHPV1 | PROBABLE E5 PROTEIN | RHESUS PAPILLOMAVIRUS TYPE 1 | 109–132 | | | | | | | | |
| PVE6_BPV1 | E6 PROTEIN | BOVINE PAPILLOMAVIRUS TYPE 1 | 23–41 | | | | | | | | |
| PVE6_CRPVK | E6 PROTEIN | COTTONTAIL RABBIT (SHOPE) PAPILLOMAVIRUS (STRAIN KAN-SAS) | 6–23 | | | | | | | | |
| PVE6_HPV08 | E6 PROTEIN | HUMAN PAPILLOMAVIRUS TYPE 8 | 133–151 | | | | | | | | |
| PVE6_HPV2A | E6 PROTEIN | HUMAN PAPILLOMAVIRUS TYPE 2A | 8–27 | | | | | | | | |
| PVE6_HPV33 | E6 PROTEIN | HUMAN PAPILLOMAVIRUS TYPE 33 | 9–26 | | | | | | | | |
| PVE6_HPV35 | E6 PROTEIN | HUMAN PAPILLOMAVIRUS TYPE 35 | 9–26 | | | | | | | | |
| PVE6_HPV51 | E6 PROTEIN | HUMAN PAPILLOMAVIRUS TYPE 51 | 9–26 | | | | | | | | |
| PVE6_HPV57 | E6 PROTEIN | HUMAN PAPILLOMAVIRUS TYPE 57 | 8–27 | | | | | | | | |
| PVE6_HPV58 | E6 PROTEIN | HUMAN PAPILLOMAVIRUS TYPE 58 | 9–26 | | | | | | | | |
| PVE6_MMPV | E6 PROTEIN | MICROMYS MINUTUS PAPILLOMAVIRUS | 7–33 | 36–60 | | | | | | | |
| PVE7_CRPVK | E7 PROTEIN | COTTONTAIL RABBIT (SHOPE) PAPILLOMAVIRUS (STRAIN KAN-SAS) | 71–88 | | | | | | | | |
| PVE7_HPV13 | E7 PROTEIN | HUMAN PAPILLOMAVIRUS TYPE 13 | 77–93 | | | | | | | | |
| PVE7_HPV51 | E7 PROTEIN | HUMAN PAPILLOMAVIRUS TYPE 51 | 61–87 | | | | | | | | |
| PVE7_HPV6B | E7 PROTEIN | HUMAN PAPILLOMAVIRUS TYPE 6B | 20–37 | | | | | | | | |
| PVE7_RHPV1 | E7 PROTEIN | RHESUS PAPILLOMAVIRUS TYPE 1 | 79–105 | | | | | | | | |
| PVE94_NPVAC | EARLY 94 KD PROTEIN | AUTOGRAPHA CALIFORNICA NUCLEAR POLYHEDROSIS VIRUS | 78–99 | 203–222 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVEF_GVTN | VIRAL ENHANCING FACTOR | TRICHOPLUSIA NI GRANULOSIS VIRUS | 154–175 | 237–260 | 677–696 | | | | | | |
| PVENV_BEV | ENVELOPE PROTEIN | BERNE VIRUS | 62–86 | 87–114 | | | | | | | |
| PVENV_DHV11 | ENVELOPE GLYCOPROTEIN PRECURSOR | DHORI VIRUS (STRAIN INDIAN/1313/61) | 42–57 | 484–511 | | | | | | | |
| PVENV_EAV | PROBABLE ENVELOPE PROTEIN | EQUINE ARTERITIS VIRUS | 25–41 | | | | | | | | |
| PVENV_LELV | PROBABLE ENVELOPE PROTEIN | LELYSTAD VIRUS | 27–47 | 148–168 | | | | | | | |
| PVENNV_MCV1 | MAJOR ENVELOPE PROTEIN | MOLLUSCUM CONTAGIOSUM VIRUS SUBTYPE 1 | 61–80 | | | | | | | | |
| PVENV_MCV2 | MAJOR ENVELOPE PROTEIN | MOLLUSCUM CONTAGIOSUM VIRUS SUBTYPE 2 | 61–80 | 306–333 | | | | | | | |
| PVENV_THOGV | ENVELOPE GLYCOPROTEIN PRECURSOR | THOGOTO VIRUS | 196–221 | 356–383 | 473–491 | | | | | | |
| PVETM_NPVAC | ECORI-T SITE PROTEIN ETM | AUTOGRAPHA CALIFORNICA NUCLEAR POLYHEDROSIS VIRUS | 82–105 | | | | | | | | |
| PVF05_VACCC | 36 KD MAJOR MEMBRANE PROTEIN PRECURSOR | VACCININA VIRUS (STRAIN COPENHAGEN) | 280–305 | | | | | | | | |
| PVF05_VACCP | 36 KD MAJOR MEMEBRANE PROTEIN PRECURSOR | VACCINIA VIRUS (STRAIN L-IVP) | 280–305 | | | | | | | | |
| PVF05_VACCV | 36 KD MAJOR MEMBRANE PROTEIN PRECURSOR | VACCINIA VIRUS (STRAIN WR) | 281–306 | | | | | | | | |
| PVF05_VARV | 36 KD MAJOR MEMBRANE PROTEIN PRECURSOR | VARIOLA VIRUS | 280–305 | | | | | | | | |
| PVF09_VACCC | PROTEIN F9 | VACCINIA VIRUS (STRAIN COPENHAGEN), AND (STRAIN L-IVP) | 176–200 | | | | | | | | |
| PVF09_VACCV | PROTEIN F9 | VACCINIA VIRUS (STRAIN WR) | 176–200 | | | | | | | | |
| PVF09_VARV | PROTEIN F9 | VARIOLA VIRUS | 176–200 | | | | | | | | |
| PFV11_VACCC | PROTEIN F11 | VACCINIA VIRUS (STRAIN COPENHAGEN) | 161–184 | | | | | | | | |
| PVF11_VARV | PROTEIN F11 | VARIOLA VIRUS | 161–184 | | | | | | | | |
| PVF15_VACCC | PROTEIN F15 | VACCINIA VIRUS (STRAIN COPENHAGEN) | 25–48 | | | | | | | | |
| PVF15_VACCP | PROTEIN F15 | VACCINIA VIRUS (STRAIN L-IVP) | 3–26 | | | | | | | | |
| PVF15_VARV | PROTEIN F15 | VARIOLA VIRUS | 28–51 | | | | | | | | |
| PVFP1_FOWPV | PROTEIN FP1 | FOWLPOX VIRUS | 297–333 | | | | | | | | |
| PVFP2_FOWPV | PROTEIN FP2 | FOWLPOX VIRUS | 88–104 | | | | | | | | |
| PVFP7_CAPVK | PROTEIN F7 | CAPRIPOXIVIRUS (STRAIN KS-1) | 89–111 | | | | | | | | |
| PVFP7_FOWPV | PROTEIN FP7 | FOWLPOX VIRUS | 65–90 | | | | | | | | |
| PVFP8_CAPVK | CF8A PROTEIN | CAPRIPOXVIRUS (STRAIN KS-1) | 51–76 | | | | | | | | |
| PVFUS_ORFNZ | 10 KD FUSION PROTEIN | ORF VIRUS (STRAIN NZ2) | 29–48 | | | | | | | | |
| PVFUS_VACC6 | 14 KD FUSION PROTEIN | VACCINIA VIRUS (STRAIN WR 65-16) | 72–94 | | | | | | | | |
| PVG01_HSVEB | HYPOTHETICAL GENE 1 PROTEIN | EQUINE HERPESVIRUS TYPE 1 (STRAIN AB4P) | 169–195 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVG01_HSV11 | HYPOTHETICAL GENE 1 PROTEIN | ICTALURID HERPESVIRUS 1 | 210–225 | 317–339 | 589–616 | | | | | | |
| PVG01_VACCC | PROTEIN G1 | VACCINIA VIRUS (STRAIN COPENHAGEN) | 298–318 | 376–395 | | | | | | | |
| PVG01_VACCV | PROTEIN G1 | VACCINIA VIRUS (STRAIN WR) | 237–257 | 315–334 | | | | | | | |
| PVG01_VARV | PROTEIN G1 | VARIOLA VIRUS | 298–318 | 376–395 | | | | | | | |
| PVG01_VZVD | HYPOTHETICAL GENE 1 PROTEIN | VARICELLA-ZOSTER VIRUS (STRAIN DUMAS) | 58–82 | | | | | | | | |
| PVG03_VACCC | PROTEIN G3 | VACCINIA VIRUS (STRAIN COPENHAGEN) | 50–72 | | | | | | | | |
| PVG03_VARV | PROTEIN G3 | VARIOLA VIRUS | 50–72 | | | | | | | | |
| PVG04_VACCC | PROTEIN G4 | VACCINIA VIRUS (STRAIN COPENHAGEN) | 11–33 | | | | | | | | |
| PVG04_VARV | PROTEIN G4 | VARIOLA VIRUS | 11–33 | | | | | | | | |
| PVG06_VACCC | PROTEIN G6 | VACCINIA VIRUS (STRAIN COPENHAGEN) | 31–51 | | | | | | | | |
| PVG06_VARV | PROTEIN G6 | VARIOLA VIRUS | 31–51 | | | | | | | | |
| PVG08_HSV11 | HYPOTHETICAL GENE 8 MEMBRANE PROTEIN | ICTALURID HERPESVIRUS 1 | 134–149 | 159–185 | | | | | | | |
| PVG10_HSV11 | HYPOTHETICAL GENE 10 MEMBRANE PROTEIN | ICTALURID HERPESVIRUS 1 | 35–54 | | | | | | | | |
| PVG10_HSVSA | HERPESVIRUS SAIMIRI | HERPESVIRUS SAIMIRI (STRAIN 11) | 109–124 | 355–379 | | | | | | | |
| PVG11_HSV11 | HYPOTHETICAL GENE 11 ZINE-BINDING PROTEIN | ICTALURID HERPESVIRUS 1 | 103–122 | 150–176 | | | | | | | |
| PVG12_HSV11 | HYPOTHETICAL GENE 12 ZINC-BINDING PROTEIN | ICTALURID HERPESVIRUS 1 | 151–178 | 270–286 | | | | | | | |
| PVG12_HSVSA | HYPOTHETICAL GENE 12 PROTEIN | HERPESVIRUS SAIMIRI (STRAIN 11) | 68–92 | | | | | | | | |
| PVG19_HSV11 | HYPOTHETICAL GENE 19 MEMBRANE PROTEIN | ICTALURID HERPESVIRUS 1 | 88–112 | | | | | | | | |
| PVG1L_AMEPV | G1L PROTEIN | AMSACTA MOOREI ENTOMOPOXVIRUS | 313–336 | | | | | | | | |
| PVG1_SPV1R | CAPSID PROTEIN | SPIROPLASMA VIRUS SPV1-R8A2 B | 76–92 | 659–678 | | | | | | | |
| PVG22_HSV11 | HYPOTHETICAL GENE 22 PROTEIN | ICTALURID HERPESVIRUS 1 | 300–327 | | | | | | | | |
| PVG23_HSV11 | HYPOTHETICAL GENE 23 PROTEIN | ICTALURID HERPESVIRUS 1 | 314–335 | | | | | | | | |
| PVG27_HSV11 | HYPOTHETICAL GENE 27 PROTEIN | ICTALURID HERPESVIRUS 1 | 158–184 | | | | | | | | |
| PVG27_HSVSA | HYPOTHETICAL GENE 27 PROTEIN | HERPESVIRUS SAIMIRI (STRAIN 11) | 209–226 | | | | | | | | |
| PVG28-_HSV11 | HYPOTHETICAL GENE 28 PROTEIN | ICTALURID HERPESVIRUS 1 | 173–197 | 491–518 | | | | | | | |
| PVG28_HSVSA | HYPOTHETICAL GENE 28 PROTEIN | HERPESVIRUS SAIMIRI (STRAIN 11) | 14–40 | | | | | | | | |

TABLE XIII-continued

| PCGENE FILE NAME | P12CTLZIP PROTEIN | All Viruses (No Bacteriophages) VIRUS | SEARCH RESULTS SUMMARY FOR P12LZIPC MOTIF AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVG29_HSV11 | HYPOTHETICAL GENE 29 PROTEIN | ICTALURID HERPESVIRUS 1 | 20–42 | | | | | | | | |
| PVG30_HSV11 | HYPOTHETICAL GENE 30 PROTEIN | ICTALURID HERPESVIRUS 1 | 166–191 | | | | | | | | |
| PVG32_VZVD | GENE 32 PROTEIN | VARICELLA-ZOSTER VIRUS (STRAIN DUMAS) | 90–109 | | | | | | | | |
| PVG36_HSVSA | POSSIBLE TYROSINE-PROTEIN KINASE | HERPESVIRUS SAIMIRI (STRAIN 11) | 108–123 | 344–362 | | | | | | | |
| PVG37_HSV11 | HYPOTHETICAL GENE 37 PROTEIN | ICTALURID HERPESVIRUS 1 | 284–299 | | | | | | | | |
| PVG39_HSV11 | HYPOTHETICAL GENE 39 PROTEIN | ICTALURID HERPESVIRUS 1 | 648–675 | 970–990 | 1038–1065 | | | | | | |
| PVG40_HSV11 | HYPOTHETICAL GENE 40 PROTEIN | ICTALURID HERPESVIRUS 1 | 14–32 | | | | | | | | |
| PVG41_HSV11 | HYPOTHETICAL GENE 41 PROTEIN | ICTALURID HERPESVIRUS 1 | 11–38 | 62–81 | 244–260 | | | | | | |
| PVG43_HSV11 | HYPOTHETICAL GENE 43 PROTEIN | ICTALURID HERPESVIRUS 1 | 109–133 | 157–178 | 322–345 | 521–538 | | | | | |
| PVG46_HSV11 | PROBABLE MAJOR GLYCOPROTEIN | ICTALURID HERPESVIRUS 1 | 134–156 | 580–607 | 937–963 | 1244–1270 | | | | | |
| PVG48_HSV11 | HYPOTHETICAL GENE 48 PROTEIN | ICTALURID HERPESVIRUS 1 | 71–93 | | | | | | | | |
| PVG50_HSVSA | PROB TRANSCRIPTION ACTIVATOR EDRF1 | HERPESVIRUS SAIMIRI (STRAIN 11) | 5–30 | 58–83 | | | | | | | |
| PVG51_HSV11 | HYP GENE 51 MEMBRANE PROTEIN | ICTALURID HERPESVIRUS 1 | 29–49 | 84–102 | | | | | | | |
| PVG52_HSV11 | HYPOTHETICAL GENE 52 PROTEIN | ICTALURID HERPESVIRUS 1 | 229–252 | | | | | | | | |
| PVG55_HSV11 | HYPOTHETICAL GENE 55 PROTEIN | ICTALURID HERPESVIRUS 1 | 22–37 | 143–158 | 288–309 | | | | | | |
| PVG55_HSVSA | HYPOTHETICAL GENE 55 PROTEIN | HERPESVIRUS SAIMIRI (STRAIN 11) | 85–106 | | | | | | | | |
| PVG56_HSV11 | HYPOTHETICAL GENE 56 PROTEIN | ICTALURID HERPESVIRUS 1 | 1155–1176 | | | | | | | | |
| PVG58_HSVSA | GENE 58 PROTEIN | HERPESVIRUS SAIMIRI (STRAIN 11) | 130–146 | 266–288 | 293–319 | 330–346 | | | | | |
| PVG59_HSV11 | HYP GENE 59 MEMBRANE PROTEIN | ICTALURID HERPESVIRUS 1 | 142–161 | 267–289 | | | | | | | |
| PVG5_SPV4 | GENE 5 PROTEIN | SPIROPLASMA VIRUS 4 | 42–64 | | | | | | | | |
| PVG60_HSV11 | HYPOTHETICAL GENE 60 PROTEIN | ICTALURID HERPESVIURS 1 | 30–51 | 53–75 | | | | | | | |
| PVG61_HSV11 | HYPOTHETICAL GENE 61 PROTEIN | ICTALURID HERPESVIRUS 1 | 76–102 | 117–136 | | | | | | | |
| PVG63_HSV11 | HYPOTHETICAL GENE 63 PROTEIN | ICTALURID HERPESVIRUS 1 | 238–259 | 336–363 | | | | | | | |
| PVG64_HSV11 | HYPOTHETICAL GENE 64 PROTEIN | ICTALURID HERPESVIRUS 1 | 420–445 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVG65_HSV11 | HYPOTHETICAL GENE 65 PROTEIN | ICTALURID HERPESVIRUS 1 | 117–137 | 155–173 | 362–378 | 518–533 | 1147–1174 | 1347–1369 | | | |
| PVG67_HSV11 | HYPOTHETICAL GENE 67 PROTEIN | ICTALURID HERPESVIRUS 1 | 108–132 | 171–188 | 318–344 | 722–745 | 1005–1029 | 1072–1091 | 1315–1341 | | |
| PVG6_SPVIR | GENE 6 PROTEIN | SPIROPLASMA VIRUS SPV1-R8A2 B | 60–82 | | | | | | | | |
| PVG70_HSV11 | HYPOTHETICAL GENE 70 PROTEIN | ICTALURID HERPESVIRUS 1 | 184–209 | | | | | | | | |
| PVG71_HSVSA | HYPOTHETICAL GENE 71 PROTEIN | HERPESVIRUS SAIMIRI (STRAIN 11) | 89–105 | | | | | | | | |
| PVG72_HSV11 | HYPOTHETICAL GENE 72 PROTEIN | ICTALURID HERPESVIRUS 1 | 445–471 | 535–561 | 720–744 | 1252–1269 | | | | | |
| PVG74_HSVSA | G-PROTEIN COUPLED REC HOMOLOG ECRF3 | HERPESVIRUS SAIMIRI (STRAIN 11) | 124–151 | | | | | | | | |
| PVG9_SPV1R | GENE 9 PROTEIN | SPIROPLASMA VIRUS SPV1-R8A2 B | 57–72 | | | | | | | | |
| PVGF1_IBVB | F1 PROTEIN | AVIAN INFECTIOUS BRONCHITIS VIRUS (STRAIN BEAUDETTE) | 1587–1606 3601–3625 | 1856–1877 | 2108–2127 | 2210–2226 | 2788–2806 | 2973–2999 | 3073–3090 | 3120–3145 | 3374–3399 |
| PVGH3_HCMVA | GLYCOPROTEIN H301 PRECURSOR | HUMAN CYTOMEGALOVIRUS (STRAIN AD169) | 157–178 | | | | | | | | |
| PVGL1_CVPR8 | E1 GLYCOPROTEIN PRECURSOR | PROCINE RESPIRATORY CORONAVIRUS (STRAIN 86/137004/BRITISH IS | 174–193 | | | | | | | | |
| PVGL2_CVBF | E2 GLYCOPROTEIN PRECURSOR | BOVINE CORONAVIRUS (STRAIN F15) | 10–33 | 123–139 | 174–190 | 264–279 | 991–1017 | 1259–1280 | | | |
| PVGL2_CVBL9 | E2 GLYCOPROTEIN PRECURSOR | BOVINE CORONAVIRUS (STRAIN L9) | 123–139 | 174–190 | 264–279 | 651–674 | 991–1017 | 1259–1280 | | | |
| PVGL2_CVBLY | E2 GLYCOPROTEIN PRECURSOR | BOVINE CORONAVIRUS (STRAIN LY-138) | 10–33 | 123–139 | 174–190 | 264–279 | 991–1017 | 1259–1280 | | | |
| PVGL2_CVBM | E2 GLYCOPROTEIN PRECURSOR | BOVINE CORONAVIRUS (STRAIN MEBUS) | 123–139 | 174–190 | 264–279 | 991–1017 | 1259–1280 | | | | |
| PVGL2_CVBQ | E2 GLYCOPROTEIN PRECURSOR | BOVINE CORONAVIRUS (STRAIN QUEBEC) | 31–47 | 123–139 | 174–190 | 264–279 | 991–1017 | 1259–1280 | | | |
| PVGL2_CVBV | E2 GLYCOPROTEIN PRECURSOR | BOVINE CORONAVIRUS (STRAIN VACCINE) | 123–139 | 174–190 | 264–279 | 991–1017 | 1259–1280 | | | | |
| PVGL2_CVH22 | E2 GLYCOPROTEIN PRECURSOR | HUMAN CORONAVIRUS (STRAIN 229E) | 768–794 | 1053–1071 | 1115–1134 | | | | | | |
| PVGL2_CVM4 | E2 GLYCOPROTEIN PRECURSOR | MURINE CORONAVIRUS (STRAIN WILD TYPE 4) | 95–111 | 999–1025 | 1267–1290 | 1317–1338 | | | | | |
| PVGL2_CVMA5 | E2 GLYCOPROTEIN PRECURSOR | MURINE CORONAVIRUS (STRAIN A59) | 95–111 | 947–973 | 1215–1238 | 1265–1286 | | | | | |
| PVGL2_CVMJC | E2 GLYCOPROTEIN PRECURSOR | MURINE CORONAVIRUS (STRAIN JHMV/VARIANT CL-2) | 95–111 | 999–1025 | 1267–1290 | 1317–1358 | | | | | |
| PVGL2_CVMJH | E2 GLYCOPROTEIN PRECURSOR | MURINE CORONAVIRUS (STRAIN JHM) | 95–111 | 858–884 | 1126–1149 | 1176–1197 | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGL2_CVPFS | E2 GLYCOPROTEIN PRECURSOR | PORCINE TRANSMISSIBLE GASTROENTERITIS CORONAVIRUS (STRAIN | 64–83 | 442–457 | 800–816 | 1038–1064 | 1274–1297 | | | | |
| PVGL2_CVPMI | E2 GLYCOPROTEIN PRECURSOR | PORCINE TRANSMISSIBLE GASTROENTERITIS CORONAVIRUS (STRAIN | 64–83 | 442–457 | 506–521 | 800–816 | 1038–1064 | 1274–1297 | | | |
| PVGL2_CVPPR | E2 GLYCOPROTEIN PRECURSOR | PORCINE TRANSMISSIBLE GASTROENTERITIS CORONAVIRUS (STRAIN | 64–83 | 440–455 | 504–519 | 798–814 | 1036–1062 | 1272–1295 | | | |
| PVGL2_CVPPU | E2 GLYCOPROTEIN PRECURSOR | PORCINE TRANSMISSIBLE GASTROENTERITIS CORONAVIRUS (STRAIN | 64–83 | 440–455 | 504–519 | 798–814 | 1036–1062 | 1272–1295 | | | |
| PVGL2_CVPR8 | E2 GLYCOPROTEIN PRECURSOR | PORCINE RESPIRATORY CORONAVIRUS (STRAIN 86/137004/BRITISH I | 218–233 | 576–592 | 814–840 | 1050–1073 | | | | | |
| PVGL2_CVPRM | E2 GLYCOPROTEIN PRECURSOR | PORCINE RESPIRATORY CORONAVIRUS (STRAIN RM4) | 218–233 | 576–592 | 814–840 | 1050–1073 | | | | | |
| PVGL2_CVPRT | E2 GLYCOPROTEIN PRECURSOR | PORCINE TRANSMISSIBLE GASTROENTERITIS CORONAVIRUS (STRAIN | 64–83 | 440–455 | 504–519 | 798–814 | 1036–1062 | 1272–1295 | | | |
| PVGL2_FIPV | E2 GLYCOPROTEIN PRECURSOR | FELINE INFECTIOUS PERITONITIS VIRUS (STRAIN 79-1146) | 803–819 | 1041–1067 | 1277–1300 | | | | | | |
| PVGL2_IBV6 | E2 GLYCOPROTEIN PRECURSOR | AVIAN INFECTIOUS BRONCHITIS VIRUS (STRAIN 6/82) | 196–219 | 588–607 | 771–797 | 1056–1081 | 1094–1111 | | | | |
| PVGL2_IBVB | E2 GLYCOPROTEIN PRECURSOR | AVIAN INFECTIOUS BRONCHITIS VIRUS (STRAIN BEAUDETTE) | 195–218 | 587–606 | 770–796 | 1055–1080 | | | | | |
| PVGL2_IBVD2 | E2 GLYCOPROTEIN PRECURSOR | AVIAN INFECTIOUS BRONCHITIS VIRUS (STRAIN D274) ( | 196–219 | 588–607 | 771–797 | 1056–1081 | | | | | |
| PVGL2_IBVD3 | E2 GLYCOPROTEIN PRECURSOR | AVIAN INFECTIOUS BRONCHITIS VIRUS (STRAIN D3896) | 196–219 | | | | | | | | |
| PVGL2_IBVK | E2 GLYCOPROTEIN PRECURSOR | AVIAN INFECTIOUS BRONCHITIS VIRUS (STRAIN KB8523) | 195–218 | 587–606 | 770–796 | 1055–1080 | | | | | |
| PVGL2_IBVM | E2 GLYCOPROTEIN PRECURSOR | AVIAN INFECTIOUS BRONCHITIS VIRUS (STRAIN M41) | 195–218 | 378–398 | 587–606 | 770–796 | 1055–1080 | | | | |
| PVGL2_IBVU1 | E2 GLYCOPROTEIN | AVIAN INFECTIOUS BRONCHITIS VIRUS (STRAIN UK/123/82) | 178–201 | | | | | | | | |
| PVGL2_IBVU2 | E2 GLYCOPROTEIN | AVIAN INFECTIOUS BRONCHITIS VIRUS (STRAIN UK/142/86) | 178–201 | | | | | | | | |
| PVGL2_IBVU3 | E2 GLYCOPROTEIN | AVIAN INFECTIOUS BRONCHITIS VIRUS (STRAIN UK/167/84) | 178–201 | | | | | | | | |
| PVGLB_EBV | GLYCOPROTEIN GP110 PRECURSOR | EPSTEIN-BARR VIRUS (STRAIN B95-8) | 732–752 | | | | | | | | |
| PVGLB_HCMVA | GLYCOPROTEIN B PRECURSOR | HUMAN CYTOMEGALOVIRUS (STRAIN AD169) | 535–558 | 706–732 | 750–777 | | | | | | |
| PVGLB_HCMVT | GLYCOPROTEIN B PRECURSOR | HUMAN CYTOMEGALOVIRUS (STRAIN TOWNE) | 536–559 | 707–733 | 751–778 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLB_HSV11 | GLYCOPROTEIN B PRECURSOR | HERPES SIMPLEX VIRUS (TYPE 1/STRAIN 17) | 83–104 | | | | | | | | |
| PVGLB_HSV1F | GLYCOPROTEIN B PRECURSOR | HERPES SIMPLEX VIRUS (TYPE 1/STRAIN F) | 82–103 | | | | | | | | |
| PVGLB_HSV1K | GLYCOPROTEIN B PRECURSOR | HERPES SIMPLEX VIRUS (TYPE 1/STRAIN KOS) | 82–103 | | | | | | | | |
| PVGLB_HSV1P | GLYCOPROTEIN B PRECURSOR | HERPES SIMPLEX VIRUS (TYPE 1/STRAIN PATTON) | 83–104 | | | | | | | | |
| PVGLB_HSV23 | GLYCOPROTEIN B PRECURSOR | HERPES SIMPLEX VIRUS (TYPE 2/STRAIN 333)/ | 79–99 | | | | | | | | |
| PVGLB_HSV2H | GLYCOPROTEIN B PRECURSOR | HERPES SIMPLEX VIRUS (TYPE 2/STRAIN HG52) | 79–99 | | | | | | | | |
| PVGLB_HSV2S | GLYCOPROTEIN B PRECURSOR | HERPES SIMPLEX VIRUS (TYPE 2/STRAIN 58A) | 65–85 | | | | | | | | |
| PVGLB_HSV6U | GLYCOPROTEIN B (FRAGMENT) | HERPES SIMPLEX VIRUS (TYPE 6/STRAIN UGANDA-1102) | 72–92 | 117–144 | | | | | | | |
| PVGLB_HSVB1 | GLYCOPROTEIN 1 PRECURSOR | BOVINE HERPESVIRUS TYPE 1 | 560–578 | 689–707 | | | | | | | |
| PVGLB_HSVB2 | GLYCOPROTEIN B-1 PRECURSOR | BOVINE HERPESVIRUS TYPE 2 (STRAIN BMV) (BOVINE MAMMILLITIS | 279–299 | 745–767 | | | | | | | |
| PVGLB_HSVBC | GLYCOPROTEIN 1 PRECURSOR | BOVINE HERPESVIRUS TYPE 1 (STRAIN COOPER) | 692–710 | | | | | | | | |
| PVG;B_HSVE1 | GLYCOPROTEIN B PRECURSOR | EQUINE HERPESVIRUS TYPE 1 (ISOLATE HVS25A) (EHV-1) | 736–753 | | | | | | | | |
| PVGLB_HSVE4 | GLYCOPROTEIN B PRECURSOR | EQUINE HERPESVIRUS TYPE 1 (STRAIN AB1) | 675–692 | | | | | | | | |
| PVGLB_HSVEA | GLYCOPROTEIN B PRECURSOR | EQUINE HERPESVIRUS TYPE 1 (STRAIN AB1) | 736–753 | | | | | | | | |
| PVGLB_HSVEB | GLYCOPROTEIN B PRECURSOR | EQUINE HERPESVIRUS TYPE 1 (STRAIN AB4P) | 736–753 | | | | | | | | |
| PVGLB_HSVEL | GLYCOPROTEIN B PRECURSOR | EQUINE HERPESVIRUS TYPE 1 (STRAIN KENTUCKY D) | 736–753 | | | | | | | | |
| PVGLB_HSVMD | GLYCOPROTEIN B PRECURSOR | MAREK'S DISEASE HERPESVIRUS (STRAIN RB-1B) | 589–613 | | | | | | | | |
| PVGLB_HSVSA | GLYCOPROTEIN B PRECURSOR | HERPESVIRUS SAIMIRI (STRAIN 11) | 483–506 | 584–602 | 701–716 | | | | | | |
| PVGLB_ILTV6 | GLYCOPROTEIN B PRECURSOR | INFECTIOUS LARYNGOTRACHEI-TIS VIRUS (STRAIN 632) | 256–275 | 597–621 | 740–758 | | | | | | |
| PVGLB_ILTIVS | GLYCOPROTEIN B PRECURSOR | INFECTIOUS LARYNGOTRACHEI-TIS VIRUS (STRAIN SA-2) | 266–285 | 607–631 | 750–768 | | | | | | |
| PVGLB_ILTVT | GLYCOPROTEIN B PRECURSOR | INFECTIOUS LARYNGOTRACHEI-TIS VIRUS (STRAIN THRONE V882) | 266–285 | 607–631 | 750–768 | | | | | | |
| PVGLB_MCMVS | GLYCOPROTEIN B PRECURSOR | MURINE CYTOMEGALOVIRUS (STRAIN SMITH) | 135–156 | 566–589 | 738–765 | | | | | | |
| PVGLB_PRVIF | GLYCOPROTEIN GII PRECURSOR | PSEUDORABIES VIRUS (STRAIN INDIANA-FUNKHAUSER/BECKER) | 203–218 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLB_VZVD | GLYCOPROTEIN B PRECURSOR | VARICELLA-ZOSTER VIRUS (STRAIN DUMAS) | 522–538 | | | | | | | | |
| PVGLC_HSV11 | GLYCOPROTEIN C PRECURSOR | HERPES SIMPLEX VIRUS (TYPE 1/STRAIN 17) | 3–22 | 467–493 | | | | | | | |
| PVGLC_HSV1K | GLYCOPROTEIN C PRECURSOR | HERPES SIMPLEX VIRUS (TYPE 1/STRAIN 17) | 3–22 | 467–493 | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLF_BRSVR | FUSION GLYCOPROTEIN PRECURSOR | BOVIN TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLF_NDVTG | FUSION GLYCOPROTEIN PRECURSOR | NEWCASTLE DISEASE VIRUS (STRAIN TEXAS G B/48) | 273–289 | | | | | | | | |
| PVGLF_NDVU | FUSION GLYCOPROTEIN PRECURSOR | NEWCASTLE DISEASE VIRUS (STRAIN ULSTER/67) | 273–289 | | | | | | | | |
| PVGLF_PHODV | FUSION GLYCOPROTEIN PRECURSOR | PHOCINE DISTEMPER VIRUS | 269–285 | 305–326 | 367–383 | 531–558 | | | | | |
| PVGLF_P11HC | FUSION GLYCOPROTEIN PRECURSOR | HUMAN PARAINFLUENZA 1 VIRUS (STRAIN C39) | 456–477 | | | | | | | | |
| PVGLF_P12H | FUSION GLYCOPROTEIN PRECURSOR | HUMAN PARAINFLUENZA 2 VIRUS (PIV-2) | 450–471 | | | | | | | | |
| PVGLF_P12HG | FUSION GLYCOPROTEIN PRECURSOR | HUMAN PARAINFLUENZA 2 VIRUS (STRAIN GREER) | 450–471 | | | | | | | | |
| PVGLF_P12HT | FUSION GLYCOPROTEIN PRECURSOR | HUMAN PARAINFLUENZA 2 VIRUS (STRAIN TOSHIBA) | 450–471 | | | | | | | | |
| PVGLF_P13B | FUSION GLYCOPROTEIN PRECURSOR | BOVINE PARAINFLUENZA 3 VIRUS | 405–426 | 453–474 | | | | | | | |
| PVGLF_P13H4 | FUSION GLYCOPROTEIN PRECURSOR | HUMAN PARAINFLUENZA 3 VIRUS (STRAIN N1H 47885) | 2–20 | 283–310 | 453–474 | | | | | | |
| PVGLF_RINDK | FUSION GLYCOPROTEIN PRECURSOR | RINDERPEST VIRUS (STRAIN KABETE O) | 220–241 | 282–298 | 447–473 | | | | | | |
| PVGLF_RINDL | FUSION GLYCOPROTEIN PRECURSOR | RINDERPEST VIRUS (STRAIN L) | 220–241 | 282–298 | 447–473 | | | | | | |
| PVGLF_SEND5 | FUSION GLYCOPROTEIN PRECURSOR | SENDAI VIRUS (STRAIN Z/ HOST MUTANTS) | 460–481 | | | | | | | | |
| PVGLF_SENDF | FUSION GLYCOPROTEIN PRECURSOR | SENDAI VIRUS (STRAIN FUSHIMI) | 460–481 | | | | | | | | |
| PVGLF_SENDH | FUSION GLYCOPROTEIN PRECURSOR | SENDAI VIRUS (STRAIN HARRIS) | 460–481 | | | | | | | | |
| PVGLF_SENDJ | FUSION GLYCOPROTEIN PRECURSOR | SENDAI VIRUS (STRAIN HVJ) | 460–481 | | | | | | | | |
| PVGLF_SENDZ | FUSION GLYCOPROTEIN PRECURSOR | SENDAI VIRUS (STRAIN Z) | 460–481 | | | | | | | | |
| PCGLF_SV41 | FUSION GLYCOPROTEIN PRECURSOR | SIMIAN VIRUS 41 | 453–474 | | | | | | | | |
| PVGLF_SV5 | FUSION GLYCOPROTEIN PRECURSOR | SIMIAN VIRUS 5 (STRAIN W3) | 401–425 | 446–467 | | | | | | | |
| PVGLF_TRTV | FUSION GLYCOPROTEIN PRECURSOR | TURKEY RHINOTRACHEITIS VIRUS | 175–191 | 452–474 | | | | | | | |
| PVGLG_INHV | SPIKE GLYCOPROTEIN PRECURSOR | INFECTIOUS HEMATOPOIETIC NECROSIS VIRUS (STRAIN ROUND BUT | 77–99 | | | | | | | | |
| PVGLG_RABVE | SPIKE GLYCOPROTEIN PRECURSOR | RABIES VIRUS (STRAIN ERA) | 454–474 | | | | | | | | |
| PVGLG_RABVH | SPIKE GLYCOPROTEIN PRECURSOR | RABIES VIRUS (STRAIN HEP-FLURY) | 372–391 | 454–474 | | | | | | | |
| PVGLG_RABVP | SPIKE GLYCOPROTEIN PRECURSOR | RABIES VIRUS (STRAIN PV) | 454–474 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLG_RABVS | SPIKE GLYCOPROTEIN PRECURSOR | RABIES VIRUS (STRAIN SAD B19) | 454–474 | | | | | | | | |
| PVGLG_RABVT | SPIKE GLYCOPROTEIN PRECURSOR | RABIES VIRUS (STRAIN STREET) | 454–474 | | | | | | | | |
| PVGLG_TRTV | MAJOR SURFACE GLYCOPROTEIN G | TURKEY RHINOTRACHEITIS VIRUS | 199–216 | | | | | | | | |
| PVGLG_VHSV0 | SPIKE GLYCOPROTEIN PRECURSOR | VIRAL HEMORRHAGIC SEPTICEMIA VIRUS (STRAIN 07-71) | 406–428 | | | | | | | | |
| PVGLH_HCMVA | GLYCOPROTEIN H PRECURSOR | HUMAN CYTOMEGALOVIRUS (STRAIN AD169) | 211–237 | 365–382 | 574–598 | 691–712 | | | | | |
| PVGLH_HCMVT | GLYCOPROTEIN H PRECURSOR | HUMAN CYTOMEGALOVIRUS (STRAIN TOWNE) | 210–236 | 364–381 | 573–597 | 690–711 | | | | | |
| PVGLH_HSV11 | GLYCOPROTEIN H PRECURSOR | HERPES SIMPLEX VIRUS (TYPE 1/STRAIN 17) | 245–262 | 443–467 | 803–827 | | | | | | |
| PVGLH_HSV1E | GLYCOPROTEIN H PRECURSOR | HERPES SIMPLEX VIRUS (TYPE 1/STRAIN HFEM) | 245–262 | 443–467 | 803–827 | | | | | | |
| PVGLH_HSV6G | GLYCOPROTEIN H PRECURSOR | HERPES SIMPLEX VIRUS (TYPE 6/STRAIN GS) | 314–332 | | | | | | | | |
| PVGLH_HSVE4 | GLYCOPROTEIN H PRECURSOR | EQUINE HERPESVIRUS TYPE 4 (STRAIN 1942) | 304–325 | 814–839 | | | | | | | |
| PVGLH_HSVEB | GLYCOPROTEIN H PRECURSOR | EQUINE HERPESVIRUS TYPE 1 (STRAIN AB4P) and (ISOLATE HVS25A) | 297–318 | 807–832 | | | | | | | |
| PVGLH_HSVSA | GLYCOPROTEIN H PRECURSOR | HERPESVIRUS SAIMIRI (STRAIN 11) | 454–479 | 658–679 | | | | | | | |
| PVGLH_MCMVS | GLYCOPROTEIN H PRECURSOR | MURINE CYTOMEGALOVIRUS (STRAIN SMITH) | 670–690 | | | | | | | | |
| PVGL1_HCMVA | IE GLYCOPROTEIN PRECURSOR | HUMAN CYTOMEGALOVIRUS (STRAIN AD169) | 158–180 | | | | | | | | |
| PVGLL_HSV11 | GLYCOPROTEIN I | HERPES SIMPLEX VIRUS (TYPE 1/STRAIN 17) | 43–60 | | | | | | | | |
| PVGLL_HSVEB | GLYCOPROTEIN I | EQUINE HERPESVIRUS TYPE 1 | 44–63 | | | | | | | | |
| PVGLL_VZVD | GLYCOPROTEIN I | VARICELLA-ZOSTER VIRUS (STRAIN DUMAS) | 278–297 | | | | | | | | |
| PVGLM-BUNGE | M POLYPROTEIN PRECURSOR | BUNYAVIRUS GERMISTON | 117–136 | 197–222 | | | | | | | |
| PVGLM_BUNL7 | M POLYPROTEIN PRECURSOR | BUNYAVIRUS LA CROSSE (ISOLATE L74) | 31–55 | 81–98 | 190–211 | 1325–1345 | 1387–1410 | | | | |
| PVGLM_BUNSH | M POLYPROTEIN PRECURSOR | BUNYAVIRUS SNOWSHOE HARE | 31–55 | 81–98 | 190–211 | 1325–1345 | 1387–1410 | | | | |
| PVGLM_BUNYW | M POLYPROTEIN PRECURSOR | BUNYAMWERA VIRUS | 193–218 | 1379–1404 | | | | | | | |
| PVGLM_DUGBV | M POLYPROTEIN PRECURSOR | DUGBE VIRUS | | | | | | | | | |
| PVGLM_HANTB | M POLYPROTEIN PRECURSOR | HANTAAN VIRUS (STRAIN B-1) | 355–371 | 692–717 | 900–915 | 999–1019 | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLM_HANTH | M POLYPROTEIN PRECURSOR | HANTAAN VIRUS (STRAIN HOJO) | 499–515 | 694–718 | 1000–1020 | | | | | | |
| PVGLM_HANTL | M POLYPROTEIN PRECURSOR | HANTAAN VIRUS (STRAIN LEE) | 499–515 | 694–719 | 1001–1021 | | | | | | |
| PVGLM_HANTV | M POLYPROTEIN PRECURSOR | HANTAAN VIRUS (STRAIN 76-118) | 499–515 | 694–719 | 1001–1021 | | | | | | |
| PVGLM_INSV | M POLYPROTEIN PRECURSOR | IMPATIENS NECROTIC SPOT VIRUS (INSV) | 18–44 | 269–293 | 348–367 | 531–551 | 815–841 | | | | |
| PVGLM_PHV | M POLYPROTEIN PRECURSOR | PROSPECT HILL VIRUS | 152–171 | | | | | | | | |
| PVGLM_PTPV | M POLYPROTEIN PRECURSOR | PUNTA TORO PHLEBOVIRUS | 743–765 | 997–1016 | 1275–1302 | | | | | | |
| PVGLM_PUUMH | M POLYPROTEIN PRECURSOR | PUUMALA VIRUS (STRAIN HALLNAS B1) | 155–174 | 509–525 | 712–729 | | | | | | |
| PVGLM_PUUMS | M POLYPROTEIN PRECURSOR | PUUMALA VIRUS (STRAIN SOTKAMO) | 155–174 | 509–525 | 712–729 | 1092–1117 | | | | | |
| PVGLM_RVRF | M POLYPROTEIN PRECURSOR | RIFT VALLEY FEVER VIRUS | 53–80 | 344–368 | 830–856 | | | | | | |
| PVGLM_RVFVZ | M POLYPROTEIN PRECURSOR | RIFT VALLEY FEVER VIRUS (STRAIN ZH-548-M12) | 53–80 | 344–368 | 830–856 | 1156–1176 | | | | | |
| PVGLM_SEOU8 | M POLYPROTEIN PRECURSOR | SEOUL VIRUS (STRAIN 80-39) | 355–371 | 692–717 | 900–915 | 999–1019 | | | | | |
| PVGLM_SEOUR | M POLYPROTEIN PRECURSOR | SEOUL VIRUS (STRAIN R22) | 355–371 | 693–718 | 901–916 | 1000–1020 | | | | | |
| PVGLM_SEOUS | M POLYPROTEIN PRECURSOR | SEOUL VIRUS (STRAIN ST-11) (SAPPORO RAT VIRUS) | 355–371 | 692–717 | 900–915 | 999–1019 | | | | | |
| PVGLM_UUK | M POLYPROTEIN PRECURSOR | UUKUNIEMI VIRUS | 561–585 | 655–674 | 826–842 | 925–952 | 966–989 | | | | |
| PVGLP_EVB | PEPLOMER GLYCOPROTEIN PRECURSOR | BERNE VIRUS | 430–452 | 869–885 | 1099–1124 | 1546–1568 | | | | | |
| PVGLX_HSVEB | GLYCOPROTEIN X PRECURSOR | EQUINE HERPESVIRUS TYPE 1 (STRAIN AB4P) | | | | | | | | | |
| PVGLX_HSVEK | GLYCOPROTEIN GX PRECURSOR | EQUINE HERPESVIRUS TYPE 1 (STRAIN KENTUCKY A) | | | | | | | | | |
| PVGLX_HSVEL | GLYCOPROTEIN GX | EQUINE HERPESVIRUS TYPE 1 (STRAIN KENTUCKY D) | | | | | | | | | |
| PVGLX_PRVR1 | SECRETED GLYCOPROTEIN GX | PESUDORABIES VIRUS (STRAIN RICE) | 149–176 | | | | | | | | |
| PVGLY_JUNIN | GLYCOPROTEIN POLYPROTEIN PRECURSOR | JUNIN AREANVIRUS | 12–38 | | | | | | | | |
| PVGLY_LASSG | GLYCOPROTEIN POLYPROTEIN PRECURSOR | LASSA VIRUS (STRAIN GA39) | 12–38 | 237–259 | 426–448 | | | | | | |
| PVGLY_LASSJ | GLYCOPROTEIN POLYPROTEIN PRECURSOR | LASSA VIRUS (STRAIN JOSIAH) | 12–35 | 238–259 | 427–449 | | | | | | |
| PVGLY_LYCVA | GLYCOPROTEIN POLYPROTEIN PRECURSOR | LYMPHOCYTIC CHORIOMENINGITIS VIRUS (STRAIN ARMSTRONG) | 12–35 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVGLY_LYCVW | GLYCOPROTEIN POLYPROTEIN PRECURSOR | LYMPHOCYTIC CHORIOMENINGITIS VIRUS (STRAIN WE) | 12–35 | 89–108 | | | | | | | |
| PVGLY_MOPE1 | GLYCOPROTEIN POLYPROTEIN PRECURSOR | MOPIEA VIRUS | 12–35 | 425–447 | | | | | | | |
| PVGLY_PIARV | GLYCOPROTEIN POLYPROTEIN PRECURSOR | PICHINDE ARENA VIRUS | 12–38 | 441–466 | | | | | | | |
| PVGLY_TACV | GLYCOPROTEIN POLYPROTEIN PRECURSOR | TACARIBE VIRUS | 12–38 | | | | | | | | |
| PVGLY_TACV5 | GLYCOPROTEIN POLYPROTEIN PRECURSOR | TACARIBE VIRUS (STRAIN V5) | 12–38 | | | | | | | | |
| PVGLY_TACV7 | GLYCOPROTEIN POLYPROTEIN PRECURSOR | TACARIBE VIRUS (STRAIN V7) | 12–38 | | | | | | | | |
| PVGLY_TACVT | GLYCOPROTEIN POLYPROTEIN PRECURSOR | TACARIBE VIRUS (STRAIN TRVL 11598) | 12–38 | | | | | | | | |
| PVGNB_CPMV | GENOME POLYPROTEIN B | COWPEA MOSAIC VIRUS | 141–161 | 569–594 | 757–783 | 1110–1135 | 1165–1184 | | | | |
| PVGNM_CPMV | GENOME POLYPROTEIN M | COWPEA MOSAIC VIRUS | 311–335 | 741–764 | | | | | | | |
| PVGP2_EBV | PROBABLE MEMBRANE ANTIGEN GP220 | EPSTEIN-BARR VIRUS (STRAIN B95-8) (HUMAN HERPESVIRUS 4) | 657–681 | | | | | | | | |
| PVGP3_EBV | ENVELOPE GLYCOPROTEIN GP340 | EPSTEIN-BARR VIRUS (STRAIN B95-8) (HUMAN HERPESVIRUS 4) | 854–878 | | | | | | | | |
| PVGP8_EBV | PROBABLE MEMBRANE ANTIGEN GP85 | EPSTEIN-BARR VIRUS (STRAIN B95-8) (HUMAN HERPESVIRUS 4) | 67–88 | | | | | | | | |
| PVGP_EBOV | STRUCTURAL GLYCOPROTEIN PRECURSOR | EBOLA VIRUS | 34–52 | 537–561 | 653–675 | | | | | | |
| PVGP_MABVM | STRUCTURAL GLYCOPROTEIN PRECURSOR | MARBURG VIRUS (STRAIN MUSOKE) | 538–562 | 607–627 | | | | | | | |
| PVGP_MABVP | STRUCTURAL GLYCOPROTEIN PRECURSOR | MARBURG VIRUS (STRAIN POPP) | 538–562 | 607–627 | | | | | | | |
| PVH01_VACCC | PROTEIN-TYROSINE PHOSPHATASE | VACCINIA VIRUS (STRAIN COPENHAGEN) | 76–92 | 105–121 | | | | | | | |
| PVH01_VACCV | PROTEIN-TYROSINE PHOSPHATASE | VACCINIA VIRUS (STRAIN WR) | 76–92 | 105–121 | | | | | | | |
| PVH01_VARV | PROTEIN-TYROSINE PHOSPHATASE | VARIOLA VIRUS | 76–92 | 105–121 | | | | | | | |
| PVH07_VACCV | LATE PROTEIN H7 | VACCINIA VIRUS (STRAIN WR) | 70–97 | | | | | | | | |
| PVH07_VARV | LATE PROTEIN H7 | VARIOLA VIRUS | 70–97 | | | | | | | | |
| PVHEL_FXMV | PROBABLE HELICASE | FOXTAIL MOSAIC VIRUS | 182–205 | | | | | | | | |
| PVHEL_PMV | PROBABLE HELICASE | PAPAYA MOSAIC POTEXVIRUS | 153–168 | | | | | | | | |
| PV101_VACCC | PROTEIN I1 | VACCINIA VIRUS (STRAIN COPENHAGEN) | 120–135 | | | | | | | | |
| PV101_VARV | PROTEIN I1 | VARIOLA VIRUS | 120–135 | | | | | | | | |
| PV103_VACCC | PROTEIN I3 | VACCINIA VIRUS (STRAIN COPENHAGEN) | 194–220 | | | | | | | | |
| PV103_VACCV | PROTEIN I3 | VACCINIA VIRUS (STRAIN WR) | 194–220 | | | | | | | | |
| PV103_VARV | PROTEIN I3 | VARIOLA VIRUS | 194–220 | | | | | | | | |
| PV106_VACCV | PROTEIN I6 | VACCINIA VIRUS (STRAIN WR) | 106–128 | 133–155 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PV106_VARV | PROTEIN I6 | VARIOLA VIRUS | 106–128 | 133–155 | | | | | | | |
| PV107_VACCC | PROTIEN I7 | VACCINIA VIRUS (STRAIN COPENHAGEN) | 13–34 | 344–367 | | | | | | | |
| PV107_VACCV | PROTEIN I7 | VACCINIA VIRUS (STRAIN WR) | 13–34 | 344–367 | | | | | | | |
| PV107_VARV | PROTEIN I7 | VARIOLA VIRUS | 13–34 | 344–367 | | | | | | | |
| PV108_VACCC | PUTATIVE RNA HELICASE 18 | VACCINIA VIRUS (STRAIN COPENHAGEN) | 196–212 | 418–438 | | | | | | | |
| PV108_VACCV | PUTATIVE RNA HELICASE 18 | VACCINIA VIRUS (STRAIN WR) | 196–212 | 418–438 | | | | | | | |
| PV108_VARV | PUTATIVE RNA HELICASE 18 | VARIOLA VIRUS | 196–212 | 418–438 | | | | | | | |
| PVIE1_HCMVA | 55 KD IMMEDIATE-EARLY PROTEIN 1 | HUMAN CYTOMEGALOVIRUS (STRAIN AD169) | 77–100 | 333–350 | | | | | | | |
| PVIE1_HCMVT | 55 KD IMMEDIATE-EARLY PROTEIN 1 | HUMAN CYTOMEGALOVIRUS (STRAIN TOWNE) | 77–100 | 333–350 | | | | | | | |
| PVIE2_HCMVA | 45 KD IMMEDIATE-EARLY PROTEIN 2 | HUMAN CYTOMEGALOVIRUS (STRAIN AD169) | 14–32 | 389–406 | | | | | | | |
| PVIE2_HCMVT | 45 KD IMMEDIATE-EARLY PROTEIN 2 | HUMAN CYTOMEGALOVIRUS (STRAIN TOWNE) | 14–32 | 388–405 | | | | | | | |
| PVIE2_MCMVS | IMMEDIATE-EARLY PROTEIN 2 | MUTINE CYTOMEGALOVIRUS (STRAIN SMITH) | 251–272 | | | | | | | | |
| PVIE3_HCMVT | 30 KD IMMEDIATE-EARLY PROTEIN 2 | HUMAN CYTOMEGALOVIRUS (STRAIN TOWNE) | 14–32 | | | | | | | | |
| PVIEG_HSVSA | IMMEDIATE-EARLY PROTEIN IE-G | HERPESVIRUS SAIMIRI (STRAIN 11) | 65–80 | | | | | | | | |
| PVIEN_NPVAC | IMMEDIATE-EARLY REG PROTEIN 1E-N | AUTOGRAPHA CALIFORNICA NUCLEAR POLYHEDROSIS VIRUS | 100–116 | 273–290 | | | | | | | |
| PVIMP_EBV | PROB INTEGRAL MEMBRANE PROTEIN BBRF3 | EPSTEIN-BARR VIRUS (STRAIN B95-8) | 75–100 | 125–152 | 203–222 | | | | | | |
| PVIMP_HCMVA | PROBABLE INTEGRAL MEMBRANE PROTEIN | HUMAN CYTOMEGALOVIRUS (STRAIN AD169) | 68–89 | 190–217 | | | | | | | |
| PVIMP_HSV11 | PROBABLE INTEGRAL MEMBRANE PROTEIN | HERPES SIMPLEX VIRUS (TYPE 1/STRAIN 17) | 83–110 | 250–270 | | | | | | | |
| PVIMP_HSVEB | PROBABLE INTEGRAL MEMBRANE PROTEIN | EQUINE HERPESVIRUS TYPE 1 (STRAIN AB4P) | 24–49 | 93–120 | 145–172 | 247–263 | 301–321 | 332–358 | | | |
| PVIMP_HSVSA | INTEGRAL MEMBRANE PROTEIN | HERPESVIRUS SAIMIRI (STRAIN 11) | 76–101 | 313–331 | | | | | | | |
| PVIMP_VZVD | PROBABLE INTEGRAL MEMBRANE PROTEIN | VARICELLA-ZOSTER VIRUS (STRAIN DUMAS) | 21–47 | 154–181 | 230–252 | | | | | | |
| PVJ01_VACCC | PROTEIN J1 | VACCINIA VIRUS (STRAIN COPENHAGEN) | 89–110 | | | | | | | | |
| PVJ01_VACCV | PROTEIN J1 | VACCINIA VIRUS (STRAIN WR) | 89–110 | | | | | | | | |
| PVJ01_VARV | PROTEIN J1 | VARIOLA VIRUS | 89–110 | | | | | | | | |
| PVK04_VACCC | PROTEIN K4 | VACCINIA VIRUS (STRAIN COPENHAGEN) | 87–113 | 208–234 | 319–337 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVK04_VACCV | PROTEIN K4 | VACCINIA VIRUS (STRAIN WR) | 87–113 | 208–234 | 319–337 | | | | | | |
| PVK05_VACCC | PROTEIN K5 | VACCINIA VIRUS (STRAIN COPENHAGEN) | 106–133 | | | | | | | | |
| PVL02_VACCC | PROTEIN L2 | VACCINIA VIRUS (STRAIN COPENHAGEN) | 39–61 | | | | | | | | |
| PVL02_VACCV | PROTEIN L2 | VACCINIA VIRUS (STRAIN WR) | 39–61 | | | | | | | | |
| PVL02_VARV | PROTEIN L2 | VARIOLA VIRUS | 39–61 | | | | | | | | |
| PVL03_VACCC | PROTEIN L3 | VACCINIA VIRUS (STRAIN COPENHAGEN) | 148–164 | 186–208 | 292–315 | | | | | | |
| PVL03_VACCV | PROTEIN L3 | VACCINIA VIRUS (STRAIN WR) | 148–164 | 186–208 | 292–315 | | | | | | |
| PVL03_VARV | PROTEIN L3 | VARIOLA VIRUS | 147–163 | /185–207 | 291–314 | | | | | | |
| PVL05_VACCV | PROTEIN L5 | VACCINIA VIRUS (STRAIN WR), AND (STRAIN COPENHAGEN) | 16–39 | | | | | | | | |
| PVL05_VARV | PROTEIN L5 | VARIOLA VIRUS | 16–39 | | | | | | | | |
| PVL1_CRPVK | PROBABLE L1 PROTEIN | COTTONTAIL RABBIT (SHOPE) PAPILLOMAVIRUS (STRAIN KANSAS) | 299–317 | | | | | | | | |
| PVL1_HPV18 | PROBABLE L1 PROTEIN | HUMAN PAPILLOMAVIRUS TYPE 18 | 28–55 | | | | | | | | |
| PVL1_HPV41 | PROBABLE L1 PROTEIN | HUMAM PAPILLOMAVIRUS TYPE 41 | 38–63 | | | | | | | | |
| PVL1_REOVD | MAJOR CORE PROTEIN LAMBDA 1 | REOVIRUS (TYPE 3/STRAIN DEARING) | 327–346 | 351–366 | 752–774 | | | | | | |
| PVL2_HPV08 | PROBABLE L2 PROTEIN | HUMAN PAPILLOMAVIRUS TYPE 8 | 254–270 | | | | | | | | |
| PVL2_HPV11 | PROBABLE L2 PROTEIN | HUMAN PAPILLOMAVIRUS TYPE 11 | 32–58 | | | | | | | | |
| PVL2_HPV13 | PROBABLE L2 PROTEIN | HUMAN PAPILLOMAVIRUS TYPE 13 | 33–59 | | | | | | | | |
| PVL2_HPV16 | PROBABLE L2 PROTEIN | HUMAN PAPILLOMAVIRUS TYPE 16 | 34–60 | | | | | | | | |
| PVL2_HPV18 | PROBABLE L2 PROTEIN | HUMAN PAPILLOMAVIRUS TYPE 18 | 33–59 | | | | | | | | |
| PVL2_HPV1A | PROBABLE L2 PROTEIN | HUMAN PAPILLOMAVIRUS TYPE 1A | 213–228 | | | | | | | | |
| PVL2_HSV2A | PROBABLE L2 PROTEIN | HUMAN PAPILLOMAVIRUS TYPE 2A | 88–114 | | | | | | | | |
| PVL2_HPV31 | PROBABLE L2 PROTEIN | HUMAN PAPILLOMAVIRUS TYPE 31 | 34–60 | 443–462 | | | | | | | |
| PVL2_HPV33 | PROBABLE L2 PROTEIN | HUMAN PAPILLOMAVIRUS TYPE 33 | 33–59 | 99–114 | | | | | | | |
| PVL2_HPV35 | PROBABLE L2 PROTEIN | HUMAN PAPILLOMAVIRUS TYPE 35 | 34–60 | | | | | | | | |
| PVL2_HPV41 | PROBABLE L2 PROTEIN | HUMAN PAPILLOMAVIRUS TYPE 41 | 39–58 | 414–436 | | | | | | | |
| PVL2_HPV42 | PROBABLE L2 PROTEIN | HUMAN PAPILLOMAVIRUS TYPE 42 | 33–59 | 344–370 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVL2_HPV47 | PROBABLE L2 PROTEIN | HUMAN PAPILLOMAVIRUS TYPE 47 | 250–265 | | | | | | | | |
| PVL2_HPV57 | PROBABLE L2 PROTEIN | HUMAN PAPILLOMAVIRUS TYPE 57 | 32–58 | | | | | | | | |
| PVL2_HPV58 | PROBABLE L2 PROTEIN | HUMAN PAPILLOMAVIRUS TYPE 58 | 33–59 | 99–114 | | | | | | | |
| PVL2_HPV6B | PROBABLE L2 PROTEIN | HUMAN PAPILLOMAVIRUS TYPE 6B | 33–59 | | | | | | | | |
| PVL2_PAPVE | PROBABLE L2 PROTEIN | EUROPEAN ELK PAPILLOMAVIRUS | 30–56 | | | | | | | | |
| PVL2_RHPV1 | PROBABLE L2 PROTEIN | RHESUS PAPILLOMAVIRUS TYPE 1 | 45–71 | | | | | | | | |
| PVL3_HPV5B | PROBABLE L3 PROTEIN | HUMAN PAPILLOMAVIRUS TYPE 5B | 6–28 | | | | | | | | |
| PVL3_REOVD | MINOR CORE PROTEIN LAMBDA 3 | REOVIRUS (TYPE 3/STRAIN DEARING | 714–737 | | | | | | | | |
| PVL3_REOVJ | MINOR CORE PROTEIN LAMBDA 3 | REOVIRUS (TYPE 2/STRAIN D5/JONES) | 714–737 | 1213–1236 | | | | | | | |
| PVL3_REOVL | MINOR CORE PROTEIN LAMBDA 3 | REOVIRUS (TYPE 1/STRAIN LANG) | 714–737 | | | | | | | | |
| PVL96_IRV1 | L96 PROTEIN | TIPULA IRIDESCENT VIRUS (TIV) (INSECT IRIDESCENT VIRUS TYPE 1) | 144–170 | 196–220 | 686–711 | 845–861 | | | | | |
| PVM01_VACCC | PROTEIN M1 | VACCINIA VIRUS (STRAIN COPENHAGEN) | 134–159 | 177–195 | 281–302 | | | | | | |
| PVM01_VACCV | PROTEIN M1 | VACCINIA VIRUS (STRAIN WR) | 83–108 | 126–144 | 230–251 | | | | | | |
| PVM01_VARV | PROTEIN M1 | VARIOLA VIRUS | 81–106 | 124–142 | 228–249 | | | | | | |
| PVM1_REOVD | MINOR VIRION STRUCTURAL PROTEIN MU-2 | REOVIRUS (TYPE 3/STRAIN DEARING) | 141–168 | 227–245 | 280–304 | 324–347 | 414–436 | 454–477 | | | |
| PVM1_REOVL | MINOR VIRION STRUCTURAL PROTEIN MU-2 | REOVIRUS (TYPE 1/STRAIN LANG) | 141–168 | 227–245 | 280–304 | 414–436 | 454–477 | | | | |
| PVM21_REOVD | MAJOR VIRION STRUCTURAL PROTEIN MU-1/MU-1C | REOVIRUS (TYPE 3/STRAIN DEARING) | 168–192 | | | | | | | | |
| PVM22_REOVD | MAJOR VIRION STRUCTURAL PROTEIN MU-1/MU-1C | REOVIRUS (TYPE 3/STRAIN DEARING) | 168–192 | | | | | | | | |
| PVM2_REOVJ | MAJOR VIRION STRUCTURAL PROTEIN MU-1/MU-1C | REOVIRUS (TYPE 2/STRAIN D5/JONES) | 168–192 | | | | | | | | |
| PVM2_REOVL | MAJOR VIRION STRUCTURAL PROTEIN MU-1/MU-1C | REOVIRUS (TYPE 1/STRAIN LANG) | 168–192 | | | | | | | | |
| PVM3_REOVD | MAJOR NONSTRUCTURAL PROTEIN MU-NS | REOVIRUS (TYPE 3/STRAIN DEARING) | 304–326 | 521–540 | | | | | | | |
| PVMAT_BRSVA | MATRIX PROTEIN | BOVINE RESPIRATORY SYNCYTIAL VIRUS (STRAIN A51908) | 37–62 | | | | | | | | |
| PVMAT_CDVO | MATRIX PROTEIN | CANINE DISTEMPER VIRUS (STRAIN ONDERSTEPOORT) | 148–165 | 283–309 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVMAT_HRSVA | MATRIX PROTEIN | HUMAN RESPIRATORY SYNCYTIAL VIRUS (STRAIN A2) | 44–62 | 139–160 | | | | | | | |
| PVMAT_LPMV | MATRIX PROTEIN | LA PIEDAD-MICHOACAN-MEXICO VIRUS | 311–338 | | | | | | | | |
| PVMAT_MEASE | MATRIX PROTEIN | MEASLES VIRUS (STRAIN EDMONSTON) | 283–309 | | | | | | | | |
| PVMAT_MEASH | MATRIX PROTEIN | MEASLES VIRUS (STRAIN HALLE) | 283–309 | | | | | | | | |
| PVMAT_MEASI | MATRIX PROTEIN | MEASLES VIRUS (STRAIN IP-3-CA) | 87–111 | | | | | | | | |
| PVMAT_MEASU | MATRIX PROTEIN | MEASLES VIRUS (STRAIN HU2) | 283–309 | | | | | | | | |
| PVMAT_MUMP1 | MATRIX PROTEIN | MUMPS VIRUS (STRAIN SBL-1) | 191–207 | 227–250 | 310–330 | | | | | | |
| PVMAT_MUMPS | MATRIX PROTEIN | MUMPS VIRUS (STRAIN SBL) | 191–207 | 227–250 | 310–330 | | | | | | |
| PVMAT_NDVA | MATRIX PROTEIN | NEWCASTLE DIESEASE VIRUS (STRAIN AUSTRAULIA-VICTORIA/32) | 135–151 | 190–208 | 309–329 | | | | | | |
| PVMAT_NDVB | MATRIX PROTEIN | NEWCASTLE DIESEASE VIRUS (STRAIN BEAUDETTE C45) | 135–151 | 190–208 | 309–329 | | | | | | |
| PVMAT_PI1HC | MATRIX PROTEIN | HUMAN PARAINFLUENZA 1 VIRUS (STRAIN C39) | 195–217 | | | | | | | | |
| PVMAT_P12HT | MATRIX PROTEIN | HUMAN PARAINFLUENZA 2 VIRUS (STRAIN TOSHIBA) (PIV-2) | 132–154 | 189–205 | 308–328 | | | | | | |
| PVMAT_P14HA | MATRIX PROTEIN | HUMAN PARAINFLUENZA 4A VIRUS (STRAIN TOSHIBA) (PIV-4A) | 312–332 | | | | | | | | |
| PVMAT_P14HB | MATRIX PROTEIN | HUMAN PARAINFLUENZA 4B VIRUS (STRAIN 68-333) (PIV-4B) | 312–332 | | | | | | | | |
| PVMAT_RINDK | MATRIX PROTEIN | RINDERPEST VIRUS (STRAIN KABETE O) | 200–221 | 239–260 | 283–309 | | | | | | |
| PVMAT_SENDF | MATRIX PROTEIN | SENDAI VIRUS (STRAIN FUSHIMI) | 195–217 | | | | | | | | |
| PVMAT_SENDH | MATRIX PROTEIN | SENDAI VIRUS (STRAIN HARRIS) | 195–217 | | | | | | | | |
| PVMAT_SENDZ | MATRIX PROTEIN | SENDAI VIRUS (STRAIN Z) | 195–217 | | | | | | | | |
| PVMAT_SSPVB | MATRIX PROTEIN | SUBACUTE SCLEROSING PANENCEPHALITIS VIRUS (STRAIN BIKEN) | 283–309 | 314–338 | | | | | | | |
| PVMAT_SV41 | MATRIX PROTEIN | SIMINA VIRUS 41 | 132–154 | 189–205 | 308–328 | | | | | | |
| PVMAT_SV5 | MATRIX PROTEIN | SIMIAN VIRUS 5 (STRAIN W3) | 98–114 | 132–148 | 308–335 | | | | | | |
| PVMAT_SVCV | MATRIX PROTEIN | SPRING VIREMIA OF CARP VIRUS (RHABDOVIRUS CARPIA) | 141–167 | | | | | | | | |
| PVMAT_TRTV | MATRIX PROTEIN | TURKEY RHINOTRACHEITIS VIRUS | 122–143 | | | | | | | | |
| PVME1_CVBM | E1 GLYCOPROTEIN | BOVINE CORONAVIRUS (STRAIN MEBUS) | 9–36 | 137–161 | 171–190 | | | | | | |
| PVME1_CVH22 | E1 GLYCOPROTEIN | HUMAN CORONAVIRUS (STRAIN 229E) | 136–155 | | | | | | | | |
| PVME1_CVHOC | E1 GLYCOPROTEIN | HUMAN CORONAVIRUS (STRAIN OC43) | 9–36 | 64–85 | 137–161 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVME1_CVMA5 | E1 GLYCOPROTEIN | MURINE COROANVIRUS MHV (STRAIN A59) | 10–37 | | | | | | | | |
| PVEM1-CVMJH | E1 GLYCOPROTEIN | MURINE COROANVIRUS MHV (STRAIN JHM) | 10–37 | | | | | | | | |
| PVME1_CVPFS | E1 GLYCOPROTEIN PRECURSOR | PORCINE TRANSMISSIBLE GASTROENTERITIS CORONA-VIRUS (STRAIN | 174–193 | | | | | | | | |
| PVME1_CVPPU | E1 GLYCOPROTEIN PRECURSOR | PORCINE TRANSMISSIBLE GASTROENTERITIS CORONA-VIRUS (STRAIN | 169–193 | 174–193 | | | | | | | |
| PVME1_CVPRM | E1 GLYCOPROTEIN PRECURSOR | PORCINE RESPIRATORY CORONAVIRUS (STRAIN RM4) | 174–193 | | | | | | | | |
| PVME1_CVTKE | E1 GLYCOPROTEIN | TURKEY ENTERIC CORONAVIRUS | 9–36 | 137–161 | 171–190 | | | | | | |
| PVME1_IBV6 | E1 GLYCOPROTEIN | AVIAN INFECTIOUS BRONCHITIS VIRUS (STRAIN 6/82) | 74–98 | | | | | | | | |
| PVME1_IBVB | E1 GLYCOPROTEIN | AVIAN INFECTIOUS BRONCHITIS VIRUS (STRAIN BEAUDETTE) | 74–101 | | | | | | | | |
| PVME1_IBVB2 | E1 GLYCOPROTEIN | AVIAN INFECTIOUS BRONCHITIS VIRUS (STRAIN BEAUDETTE M42) | 74–101 | | | | | | | | |
| PVME1_IBVK | E1 GLYCOPROTEIN | AVIAN INFECTIOUS BRONCHITIS VIRUS (STRAIN KB8523) | 74–98 | | | | | | | | |
| PVMEM_EBV | PROBABLE MEMBRANE PROTEIN | EPSTEIN-BARR VIRUS (STRAIN B95-8) | 131–157 | 178–203 | | | | | | | |
| PVMP_CAMVC | MOVEMENT PROTEIN | CAULIFLOWER MOSAIC VIRUS (STRAIN CM-1841) | 118–134 | 147–164 | 183–201 | | | | | | |
| PVMP_CAMVD | MOVEMENT PROTEIN | CAULIFLOWER MOSAIC VIRUS (STRAIN D/H) | 118–134 | 147–164 | 183–201 | | | | | | |
| PVMP_CAMVE | MOVEMENT PROTEIN | CAULIFLOWER MOSAIC VIRUS (STRAIN BBC) | 118–134 | 147–164 | 183–201 | | | | | | |
| PVMP_CAMVN | MOVEMENT PROTEIN | CAULIFLOWER MOSAIC VIRUS (STRAIN NY8153) | 118–134 | 147–164 | 183–201 | | | | | | |
| PVMP_CAMVS | MOVEMENT PROTEIN | CAULIFLOWER MOSAIC VIRUS (STRAIN STRASBOURG) | 118–134 | 147–164 | 183–201 | | | | | | |
| PVMP_CAMVW | MOVEMENT PROTEIN | CAULIFLOWER MOSAIC VIRUS STRAIN W260) | 118–134 | 147–164 | 183–201 | | | | | | |
| PVMP_CERV | MOVEMENT PROTEIN | CARNATION ETCHED RING VIRUS | 293–318 | | | | | | | | |
| PVMP_FMVD | MOVEMENT PROTEIN | FIGWORT MOSAIC VIRUS (STRAIN DXS) | 115–131 | 180–198 | | | | | | | |
| PVMP_SOCMV | MOVEMENT PROTEIN | SOYBEAN CHLOROTIC MOTTLE VIRUS | 122–147 | 273–299 | | | | | | | |
| PVMSA_HPBDB | MAJOR SURFACE ANTIGEN PRECURSOR | DUCK HEPATITIS B VIRUS (BROWN SHANGHAI DUCK ISOLATE S5) | 201–228 | 269–295 | | | | | | | |
| PVMSA_HPBDC | MAJOR SURFACE ANTIGEN PRECURSOR | DUCK HEPATITIS B VIRUS (STRAIN CHINA) | 194–221 | 268–294 | | | | | | | |
| PVMSA_HPBDU | MAJOR SURFACE ANTIGEN PRECURSOR | DUCK HEPATITIS B VIRUS | 157–184 | 231–257 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVMSA_HPBDW | MAJOR SURFACE ANTIGEN PRECURSOR | DUCK HEPATITIS B VIRUS (WHITE SHANGHAI DUCK ISOLATE S31) | 194–221 | 269–295 | | | | | | | |
| PVMSA_HPBGS | MAJOR SURFACE ANTIGEN PRECURSOR | GROUND SQUIRREL HEPATITIS VIRUS | 209–236 | 271–295 | 380–395 | | | | | | |
| PVMSA_HPBHE | MAJOR SURFACE ANTIGEN PRECURSOR | HERON HEPATITIS B VIRUS | 236–262 | 293–320 | | | | | | | |
| PVMSA_HPBV0 | MAJOR SURFACE ANTIGEN | HEPATITIS B VIRUS | 11–28 | 70–96 | | | | | | | |
| PVMSA_HPBV2 | MAJOR SURFACE ANTIGEN PRECURSOR | HEPATITIS B VIRUS (SUBTYPE ADW2) | 185–202 | 244–270 | | | | | | | |
| PVMSA_HPBV4 | MAJOR SURFACE ANTIGEN PRECURSOR | HEPATITIS B VIRUS (SUBTYPE ADR4) | 185–202 | 244–270 | | | | | | | |
| PVMSA_HPBV9 | MAJOR SURFACE ANTIGEN PRECURSOR | HEPATITIS B VIRUS (SUBTYPE ADW/STRAIN 991) | 244–270 | | | | | | | | |
| PVMSA_HPBVA | MAJOR SURFACE ANTIGEN PRECURSOR | HEPATITIS B VIRUS (STRAIN ALPHA) | 174–191 | 233–259 | | | | | | | |
| PVMSA_HPBVD | MAJOR SURFACE ANTIGEN | HEPATITIS B VIRUS (SUBTYPE AD) | 11–28 | 70–96 | | | | | | | |
| PVMSA_HPBV1 | MAJOR SURFACE ANTIGEN PRECURSOR | HEPATITIS B VIRUS (SUBTYPE ADW/STRAIN INDONESIA/PIDW420) | 233–259 | | | | | | | | |
| PVMSA_HPBVJ | MAJOR SURFACE ANTIGEN PRECURSOR | HEPATITIS B VIRUS (SUBTYPE ADW/STRAIN JAPAN/PJDW233) | 174–191 | 233–259 | | | | | | | |
| PVMSA_HPBVL | MAJOR SURFACE ANTIGEN PRECURSOR | HEPATITIS B VIRUS (STRAIN LSH/CHIMPANZEE ISOLATE | 174–191 | 233–259 | | | | | | | |
| PVMSA_HPBVN | MAJOR SURFACE ANTIGEN | HEPATITIS B VIRUS (SUBTYPE ADR/STRAIN NC-1) | 11–28 | 70–96 | | | | | | | |
| PVMSA_HPBVO | MAJOR SURFACE ANTIGEN PRECURSOR | HEPATITIS B VIRUS (SUBTYPE ADW/STRAIN OKINAWA PODW282) | 174–191 | 233–259 | | | | | | | |
| PVMSA_HPBVP | MAJOR SURFACE ANTIGEN PRECURSOR | HEPATITIS B VIRUS (SUBTYPE ADW/STRAIN PHILIPPINO/PFDW294) | 185–202 | 244–270 | | | | | | | |
| PVMSA_HPBVR | MAJOR SURFACE ANTIGEN PRECURSOR | HEPATITIS B VIRUS (SUBTYPE ADR) | 185–202 | 244–270 | | | | | | | |
| PVMSA_HPBVS | MAJOR SURFACE ANTIGEN | HEPATITIS B VIRUS (SUBTYPE AR) | 11–28 | 70–96 | | | | | | | |
| PVMSA_HPBVW | MAJOR SURFACE ANTIGEN PRECURSOR | HEPATITIS B VIRUS (SUBTYPE ADW) | 174–191 | 233–259 | | | | | | | |
| PVMSA_HPBVY | MAJOR SURFACE ANTIGEN PRECURSOR | HEPATITIS B VIRUS (SUBTYPE ADW) | 174–191 | 233–259 | | | | | | | |
| PVMSA_HPBVZ | MAJOR SURFACE ANTIGEN PRECURSOR | HEPATITIS B VIRUS (SUBTYPE ADYW) | 174–191 | 233–259 | | | | | | | |
| PVMSA_WHV1 | MAJOR SURFACE ANTIGEN PRECURSOR | WOODCHUCK HEPATITIS VIRUS 1 | 207–234 | 269–293 | 378–393 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVMSA_WHV59 | MAJOR SURFACE ANTIGEN PRECURSOR | WOODCHUCK HEPATITIS VIRUS 59 | 212–239 | 274–298 | 383–398 | | | | | | |
| PVMSA_WHV7 | MAJOR SURFACE ANTIGEN PRECURSOR | WOODCHUCK HEPATITIS VIRUS 7 | 212–239 | 274–398 | 383–398 | | | | | | |
| PVMSA_WHV8 | MAJOR SURFACE ANTIGEN PRECURSOR | WOODCHUCK HEPATITIS VIRUS 8 | 212–239 | 274–298 | 383–398 | | | | | | |
| PVMSA_WHV8I | PROB MAJOR SURFACE ANTIGEN PREC | WOODCHUCK HEPATITIS VIRUS 8 (INFECTIOUS CLONE) | 212–239 | 274–298 | 383–398 | | | | | | |
| PVMSA_WHVW6 | MAJOR SURFACE ANTIGEN PRECURSOR | WOODCHUCK HEPATITIS VIRUS W64 (ISOLATE PWS23) | 125–149 | 234–249 | | | | | | | |
| PVMT2_IAANN | MATRIX (M2) PROTEIN | INFLUENZA A VIRUS (STRAIN A/ANN ARBOR/6/60) | 25–46 | | | | | | | | |
| PVMT2_IABAN | MATRIX (M2) PROTEIN | INFLUENZA A VIRUS (STRAIN A/BANGKOK/1/79) | 25–46 | | | | | | | | |
| PVMT2_IAFOW | MATRIX (M2) PROTEIN | INFLUENZA A VIRUS (STRAIN A/FORT WARREN/1/50) | 25–46 | | | | | | | | |
| PVMT2_IAFPR | MATRIX (M2) PROTEIN | INFLUENZA A VIRUS (STRAIN A/FOWL PLAGUE VIRUS/ROSTOCK/34) | 25–46 | | | | | | | | |
| PVMT2_IAFPW | MATRIX (M2) PROTEIN | INFLUENZA A VIRUS (STRAIN A/FOWL PLAGUE VIRUS/WEYBRIDE) | 25–46 | | | | | | | | |
| PVMT2_IALE1 | MATRIX (M2) PROTEIN | INFLUENZA A VIRUS (STRAIN A/LENINGRAD/134/57) | 25–46 | | | | | | | | |
| PVMT2_IALE2 | MATRIX (M2) PROTEIN | INFLUENZA A VIRUS (STRAIN A/LENINGRAD/134/17/57) | 25–46 | | | | | | | | |
| PVMT2_IAMAN | MATRIX (M2) PROTEIN | INFLUENZA A VIRUS (STRAIN A/MALLARD/NEW YORK/6750/78) | 25–46 | | | | | | | | |
| PVMT2_IAPUE | MATRIX (M2) PROTEIN | INFLUENZA A VIRUS (STRAIN A/PUERTO RICO/8/34) | 25–46 | | | | | | | | |
| PVMT2_IASIN | MATRIX (M2) PROTEIN | INFLUENZA A VIRUS (STRAIN A/SINGAPORE/1/57) | 25–46 | | | | | | | | |
| PVMT2_IAUDO | MATRIX (M2) PROTEIN | INFLUENZA A VIRUS (STRAIN A/UDORN/307/72) | 25–46 | | | | | | | | |
| PVMT2_IAWIL | MATRIX (M2) PROTEIN | INFLUENZA A VIRUS (STRAIN A/WILSON-SMITH/33) | 25–46 | | | | | | | | |
| PVMT9_MYXVL | MT-9 PROTEIN | MYXOMA VIRUS (STRAIN LAUSANNE) | 226–241 | | | | | | | | |
| PVN34_ROTBS | NONSTRUCTURAL PROTEIN NS34 | BOVINE ROTAVIRUS (GROUP C/STRAIN SHINTOKU) | 334–351 | | | | | | | | |
| PVNBP_PVSP | 10 7 KD PROTEIN | POTATO VIRUS S (STRAIN PERUVIAN) | 21–36 | | | | | | | | |
| PVNB_INBBE | NB GLYCOPROTEIN | INFLUENZA B VIRUS (STRAIN B/BEIJING/1/87) | 13–39 | | | | | | | | |
| PVNB_INBHK | NB GLYCOPROTEIN | INFLUENZA B VIRUS (STRAIN B/HONK KONG/8/73) | 13–39 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNB_INBLE | NB GLYCOPROTEIN | INFLUENZA B VIRUS (STRAIN B/LEE/40) | 13–39 | | | | | | | | |
| PVNB_INBLN | NB GLYCOPROTEIN | INFLUENZA B VIRUS (STRAIN B/LENINGRAD/179/86) | 13–39 | | | | | | | | |
| PVNB_INBMD | NB GLYCOPROTEIN | INFLUENZA B VIRUS (STRAIN B/MARYLAND/59) | 13–39 | | | | | | | | |
| PVNB_INBMF | NB GLYCOPROTEIN | INFLUENZA B VIRUS (STRAIN B/MEMPHIS/3/89) | 13–39 | | | | | | | | |
| PVNB_INBOR | NB GLYCOPROTEIN | INFLUENZA B VIRUS (STRAIN B/OREGON/5/80) | 13–39 | | | | | | | | |
| PVNCS_ADVG | NONCAPSID PROTEIN NS-1 | ALEUTIAN MINK DISEASE PAR VOVIRUS (STRAIN G) | 81–96 | 169–190 | | | | | | | |
| PVNCS_AEDEV | NONCAPSID PROTEIN NS-1 | AEDES DENSONUCLEOSIS VIRUS (STRAIN GKV 002 002) (AEDES DENS | 675–690 | | | | | | | | |
| PVNCS_PAVHB | NONCAPSID PROTEIN NS-1 | HUMAN PARVOVIRUS B19 | 575–597 | | | | | | | | |
| PVNCS_PAVHH | NONCAPSID PROTEIN NS-1 | HAMSTER PARVOVIRUS H1 | 140–165 | | | | | | | | |
| PVNS1_AHSV4 | NONSTRUCTURAL PROTEIN NS1 | AFRICAN HORSE SICKNESS VIRUS (SEROTYPE 4/ STRAIN VACCINE) | 256–272 | | | | | | | | |
| PVNS1_IAALA | NONSTRUCTURAL PROTEIN NS1 | INFLUENZA A VIRUS (STRAIN A/ALASKA/6/77) | 31–50 | 114–137 | 167–192 | | | | | | |
| PVNS1_IAANN | NONSTRUCTURAL PROTEIN NS1 | INFLUENZA A VIRUS (STRAIN A/ANN ARBOR/6/60) | 31–50 | 114–137 | 167–192 | | | | | | |
| PVNS1_IACAO | NONSTRUCTURAL PROTEIN NS1 | INFLUENZA A VIRUS (STRAIN A/CAMEL/MONGOLIA/82) | 19–38 | | | | | | | | |
| PVNS1_IACHI | NONSTRUCTURAL PROTEIN NS1 | INFLUENZA A VIRUS (STRAIN A/CHILE/1/83) | 31–50 | 114–137 | 167–192 | | | | | | |
| PVNS1_IACKG | NONSTRUCTURAL PROTEIN NS1 | INFLUENZA A VIRUS (STRAIN A/CHICKEN/GERMANY/N/49) | 31–50 | 167–192 | | | | | | | |
| PVNS1_IACKJ | NONSTRUCTURAL PROTEIN NS1 | INFLUENZA A VIRUS (STRAIN A/CHICKEN/JAPAN/24) | 28–47 | 164–189 | | | | | | | |
| PVNS1_IADA2 | NONSTRUCTURAL PROTEIN NS1 | INFLUENZA A VIRUS (STRAIN A/DUCK/ALBERTA/60/76) | 31–50 | 167–192 | | | | | | | |
| PVNS1_IADE1 | NONSTRUCTURAL PROTEIN NS1 | INFLUENZA A VIRUS (STRAIN A/DUCK/ENGLAND/1/56) | 28–47 | 164–189 | | | | | | | |
| PVNS1_IADU3 | NONSTRUCTURAL PROTEIN NS1 | INFLUENZA A VIRUS (STRAIN A/DUCK/UKRAINE/1/63) | 28–47 | 164–189 | | | | | | | |
| PVNS1_IAFOM | NONSTRUCTURAL PROTEIN NS1 | INFLUENZA A VIRUS (STRAIN A/FORT MONMOUTH/1/47) | 31–50 | 114–137 | 167–192 | | | | | | |
| PVNS1_IAFOW | NONSTRUCTURAL PROTEIN NS1 | INFLUENZA A VIRUS (STRAIN A/FORT WARREN/1/50), AND (STRAIN A/ | 31–50 | 114–137 | 167–192 | | | | | | |
| PVNS1_IAFPR | NONSTRUCTURAL PROTEIN NS1 | INFLUENZA A VIRUS (STRAIN A/FOWL PLAGUE VIRUS/ ROSTOCK/34) | 31–50 | 167–192 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNS1__IALE1 | NONSTRUCTURAL PROTEIN NS1 | INFLUENZA A VIRUS (STRAIN A/LENINGRAD/134/57) | 31–50 | 114–137 | 167–192 | | | | | | |
| PVNS1__IALEN | NONSTRUCTURAL PROTEIN NS1 | INFLUENZA A VIRUS (STRAIN A/LENINGRAD/54/71) | 31–50 | 114–137 | 167–192 | | | | | | |
| PVNS1__IAMA6 | NONSTRUCTURAL PROTEIN NS1 | INFLUENZA A VIRUS (STRAIN A/MALLARD/ALBERTA/88/76) | 31–50 | 167–192 | | | | | | | |
| PVNS1__IAMAN | NONSTRUCTURAL PROTEIN NS1 | INFLUENZA A VIRUS (STRAIN A/MALLARD/NEW YORK/6750/78) | 31–50 | 167–192 | | | | | | | |
| PVNS1__IAMAO | NONSTRUCTURAL PROTEIN NS1 | INFLUENZA A VIRUS (STRAIN A/MALLARD/NEW YORK/6874/78) | 31–50 | 167–192 | | | | | | | |
| PNVS1__IAMYN | NONSTRUCTURAL PROTEIN NS1 | INFLUENZA A VIRUS (STRAIN A/MYNAH/HANEDA-THAI/76) | 28–47 | 164–189 | | | | | | | |
| PVNS1__IAP10 | NONSTRUCTURAL PROTEIN NS1 | INFLUENZA A VIRUS (STRAIN A/PINTAIL/ALBERTA/119/79) | 167–192 | | | | | | | | |
| PVNS1__IAPI1 | NONSTRUCTURAL PROTEIN NS1 | INFLUENZA A VIRUS (STRAIN A/PINTAIL/ALBERTA/121/79) | 31–50 | 167–192 | | | | | | | |
| PVNS1__IAPI2 | NONSTRUCTURAL PROTEIN NS1 | INFLUENZA A VIRUS (STRAIN A/PINTAIL/ALBERTA/268/78) | 31–50 | 167–192 | | | | | | | |
| PVNS1__IAPI3 | NONSTRUCTURAL PROTEIN NS1 | INFLUENZA A VIRUS (STRAIN A/PINTAIL/ALBERTA/358/79) | 31–50 | 167–192 | | | | | | | |
| PVNS1__IAPUE | NONSTRUCTURAL PROTEIN NS1 | INFLUENZA A VIRUS (STRAIN A/PUERTO RICO/8/34) | 31–50 | 114–137 | 167–192 | | | | | | |
| PVNS1__IATKB | NONSTRUCTURAL PROTEIN NS1 | INFLUENZA A VIRUS (STRAIN A/TURKEY/BETHLEHEM-GLILIT/1492-B | 31–50 | 167–192 | | | | | | | |
| PVNS1__IATKC | NONSTRUCTURAL PROTEIN NS1 | INFLUENZA A VIRUS (STRAIN A/TURKEY/CANADA/63) | 31–50 | 167–192 | | | | | | | |
| PVNS1__IATKR | NONSTRUCTURAL PROTEIN NS1 | INFLUENZA A VIRUS (STRAIN A/TURKEY/OREGON/71) | 31–50 | | | | | | | | |
| PVNS1__IATRS | NONSTRUCTURAL PROTEIN NS1 | INFLUENZA A VIRUS (STRAIN A/TERN/SOUTH AFRICA/61) | 28–47 | 164–189 | | | | | | | |
| PVNS1__IATRT | NONSTRUCTURAL PROTEIN NS1 | INFLUENZA A VIRUS (STRAIN A/TERN/TURKMENIA/18/72) | 31–50 | 167–192 | | | | | | | |
| PVNS1__IAUDO | NONSTRUCTURAL PROTEIN NS1 | INFLUENZA A VIRUS (STRAIN A/UDORN/307/72) | 31–50 | 114–137 | 167–192 | | | | | | |
| PVNS1__IAUSS | NONSTRUCTURAL PROTEIN NS1 | INFLUENZA A VIRUS (STRAIN A/USSR/90/77) | 31–50 | 114–137 | 167–192 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNS1_IAZI1 | NONSTRUCTURAL PROTEIN NS1 | INFLUENZA A VIRUS (STRAIN A/SWINE/IOWA/15/30) | 31–50 | 167–192 | | | | | | | |
| PVNS1_INCAA | NONSTRUCTURAL PROTEIN NS1 | INFLUENZA C VIRUS (STRAIN C/ANN ARBOR/1/50) | 222–248 | | | | | | | | |
| PVNS1_INCCA | NONSTRUCTURAL PROTEIN NS1 | INFLUENZA C VIRUS (STRAIN C/CALIFORNIA/78) | 222–248 | | | | | | | | |
| PVNS2_BTV10 | NONSTRUCTURAL PROTEIN NS2 | BLUETONGUE VIRUS (SEROTYPE 10/ISOLATE USA) | 145–161 | 201–223 | | | | | | | |
| PVNS2_BTV17 | NONSTRUCTURAL PROTEIN NS2 | BLUETONGUE VIRUS (SEROTYPE 17/ISOLATE USA) | 145–161 | 201–223 | | | | | | | |
| PVNS2_BTV1S | NONSTRUCTURAL PROTEIN NS2 | BLUETONGUE VIRUS (SEROTYPE 1/ISOLATE SOUTH AFRICA) | 145–161 | | | | | | | | |
| PVNS2_BTV1X | NONSTRUCTURAL PROTEIN NS2 | BLUETONGUE VIRUS (SEROTYPE 10) | 145–161 | | | | | | | | |
| PVNS2_EHDV2 | NONSTRUCTURAL PROTEIN NS2 | EPIZOOTIC HEMORRHAGIC DISEASE VIRUS (SEROTYPE 2/ STRAIN AL | 145–161 | | | | | | | | |
| PVNS2_IAPUE | NONSTRUCTURAL PROTEIN NS2 | INFLUENZA A VIRUS (STRAIN A/PUERTO RICO/8/34) | 3–28 | | | | | | | | |
| PVNS2_IATRS | NONSTRUCTURAL PROTEIN NS2 | INFLUENZA A VIRUS (STRAIN A/TERN/SOUTH AFRICA/61) | 56–80 | | | | | | | | |
| PVNS2_PVM | NONSTRUCTURAL PROTEIN 2 | PNEUMONIA VIRUS OF MICE | 52–68 | | | | | | | | |
| PVNS3_CVPFS | NONSTRUCTURAL PROTEIN 3-1 | PORCINE TRANSMISSIBLE GASTROENTERITIS CORONA-VIRUS (STRAIN | 177–201 | | | | | | | | |
| PVNS3_CVPPU | NONSTRUCTURAL PROTEIN 3-1 | PORCINE TRANSMISSIBLE GASTROENTERITIS CORONAVIRUS (STRAIN | 98–122 | | | | | | | | |
| PVNS3_CVPRM | NONSTRUCTURAL PROTEIN 3-1 | PORCINE RESPIRATORY CORONAVIRUS (STRAIN RM4) | 177–201 | | | | | | | | |
| PVNS3_RSV | NONSTRUCTURAL PROTEIN NS3 | RICE STRIPE VIRUS | 16–40 | | | | | | | | |
| PVNS4_CVH22 | NONSTRUCTURAL PROTEIN 4 | HUMAN CORONAVIRUS (STRAIN 229E) | 84–100 | | | | | | | | |
| PVNS4_CVMS | NONSTRUCTURAL PROTEIN 4 | MURINE CORONAVIRUS MHV (STRAIN S) | 17–38 | | | | | | | | |
| PVNS4_CVPFS | NONSTRUCTURAL PROTEIN 4 | PORCINE TRANSMISSIBLE GASTROENTERITIS CORNOA-VIRUS (STRAIN | 4–31 | | | | | | | | |
| PVNS4_CVPPU | NONSTRUCTURAL PROTEIN 4 | PROCINE TRANSMISSIBLE GASTROENTERITIS CORNOA-VIRUS (STRAIN | 4–31 | | | | | | | | |
| PVNS4_CVPRM | NONSTRUCTURAL PROTEIN 4 | PORCINE REPSIRATORY CORONAVIRUS (STRAIN RM4) | 4–31 | | | | | | | | |
| PVNS4_MSIV | NONSTRUCTURAL PROTEIN NS4 | MAIZE STRIPE VIRUS | 41–56 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNS4_RSV | NONSTRUCTURAL PROTEIN NS4 | RICE STRIPE VIRUS | 41–56 | 60–82 | 152–167 | | | | | | |
| PVNS7_CVFE3 | NONSTRUCTURAL PROTEIN 7 | FELINE ENTERIC CORONAVIRUS (STRAIN 79-1683) | 59–84 | | | | | | | | |
| PVNS7_FIPV | NONSTRUCTURAL PROTEIN 7 | FELINE INFECTIOUS PERITONITIS VIRUS (STRAIN 79-1146) | 59–84 | | | | | | | | |
| PVNSC_PI1HB | NONSTRUCTURAL PROTEIN C | HUMAN PARAINFLUENZA 1 VIRUS (STRAIN C35) | 76–92 | | | | | | | | |
| PVNSC_PI1HC | NONSTRUCTURAL PROTEIN C | HUMAN PARAINFLUENZA 1 VIRUS (STRAIN C39) | 76–92 | | | | | | | | |
| PVNSC_PI1HD | NONSTRUCTURAL PROTEIN C | HUMAN PARAINFLUENZA 1 VIRUS (STRAIN CI-5/73) | 76–92 | 179–197 | | | | | | | |
| PVNSC_PI1HE | NONSTRUCTURAL PROTEIN C | HUMAN PARAINFLUENZA 1 VIRUS (STRAIN CI-14/83) | 76–92 | | | | | | | | |
| PVNST_CVBQ | 32 KD NONSTRUCTURAL PROTEIN | BOVINE CORONAVIRUS (STRAIN QUEBEC) | 88–109 | | | | | | | | |
| PVNST_INCGL | NONSTRUCTURAL PROTEIN NS1-NS2 | INFLUENZA C VIRUS (STRAIN C/GREAT LAKES/1167/54) | 222–248 | | | | | | | | |
| PVNST_INCJH | NONSTRUCTURAL PROTEIN NS1-NS2 | INFLUENZA C VIRUS (STRAIN C/JOHANNESBURG/1/66) | 222–248 | | | | | | | | |
| PVNST_INCMI | NONSTRUCTURAL PROTEIN NS1-NS2 | INFLUENZA C VIRUS (STRAIN C/MISSISSIPPI/80) | 222–248 | | | | | | | | |
| PVNST_INCYA | NONSTRUCTURAL PROTEIN NS1-NS2 | INFLUENZA C VIRUS (STRAIN C/YAMAGATA/10/81) | 222–248 | | | | | | | | |
| PVNST_PTPV | NONSTRUCTURAL PROTEIN NS-S | PUNTA TORO PHLEBOVIRUS | 48–63 | | | | | | | | |
| PVNST_SFSV | NONSTRUCTURAL PROTEIN NS-S | SANDFLY FEVER SILICIAN VIRUS | 16–34 | | | | | | | | |
| PVNST_UUK | NONSTRUCTURAL PROTEIN NS-S | UUKUNIEMI VIRUS | 52–73 | 89–104 | | | | | | | |
| PVNUA_PRVKA | PROBABLE NUCLEAR ANTIGEN | PSEUDORABIES VIRUS (STRAIN KAPLAN) | 756–777 | 1563–1583 | | | | | | | |
| PVNUC_DHVII | NUCLEOPROTEIN | DHORI VIRUS (STRAIN INDIAN/1313/61) | 123–139 | 297–324 | | | | | | | |
| PVNUC_EBOV | NUCLEOPROTEIN | EBOLA VIRUS | 159–176 | | | | | | | | |
| PVNUC_IAANA | NUCLEOPROTEIN | INFLUENZA A VIRUS (STRAIN A/ANAS ACUTA/PRIMORJE/695/76) | 173–197 | 266–287 | | | | | | | |
| PVNUC_IAANN | NUCLEOPROTEIN | INFLUENZA A VIRUS (STRAIN A/ANN ARBOR/6/60) | 173–197 | | | | | | | | |
| PVNUC_IABRA | NUCLEOPROTEIN | INFLUENZA A VIRUS (STRAIN A/BRAZIL/11/78) | 173–197 | | | | | | | | |
| PVNUC_IABUD | NUCLEOPROTEIN | INFLUENZA A VIRUS (STRAIN A/BUDGERIGAR/HOKKAIDO/1/77) | 173–197 | | | | | | | | |
| PVNUC_IACAL | NUCLEOPROTEIN | INFLUENZA A VIRUS (STRAIN A/CALIFORNIA/10/78) | 173–197 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNUC_IACKG | NUCLEOPROTEIN | INFLUENZA A VIRUS (STRAIN A/CHICKEN/GERMANY/N/49) | 173–197 | | | | | | | | |
| PVNUC_IACKP | NUCLEOPROTEIN | INFLUENZA A VIRUS (STRAIN A/CHICKEN/PENNSYLVANIA/1/83) | 173–197 | | | | | | | | |
| PVNUC_IADAU | NUCLEOPROTEIN | INFLUENZA A VIRUS (STRAIN A/DUCK/AUSTRALIA/749/80 | 173–197 | | | | | | | | |
| PVNUC_IADBE | NUCLEOPROTEIN | INFLUENZA A VIRUS (STRAIN A/DUCK/BEIJING/1/78) | 173–197 | | | | | | | | |
| PVNUC_IADCZ | NUCLEOPROTEIN | INFLUENZA A VIRUS (STRAIN A/DUCK/CZECHOSLOVAKIA/56) | 173–197 | | | | | | | | |
| PVNUC_IADE1 | NUCLEOPROTEIN | INFLUENZA A VIRUS (STRAIN A/DUCK/ENGLAND/1/56) | 173–197 | | | | | | | | |
| PVNUC_IADE2 | NUCLEOPROTEIN | INFLUENZA A VIRUS (STRAIN A/DUCK/ENGLAND/1/62) | 173–197 | | | | | | | | |
| PVNUC_IADHK | NUCLEOPROTEIN | INFLUENZA A VIRUS (STRAIN A/DUCK/HONG KONG/7/75) | 173–197 | | | | | | | | |
| PVNUC_IADM2 | NUCLEOPROTEIN | INFLUENZA A VIRUS (STRAIN A/DUCK/MEMPHIS/928/74) | 173–197 | | | | | | | | |
| PVNUC_IADMA | NUCLEOPROTEIN | INFLUENZA A VIRUS (STRAIN A/DUCK/MANITOBA/1/53) | 173–197 | | | | | | | | |
| PVNUC_IADNZ | NUCLEOPROTEIN | INFLUENZA A VIRUS (STRAIN A/DUCK/NEW ZEALAND/31/76) | 173–197 | | | | | | | | |
| PVNUC_IADU2 | NUCLEOPROTEIN | INFLUENZA A VIRUS (STRAIN A/DUCK/UKRAINE/2/60) | 173–197 | | | | | | | | |
| PVNUC_IAEN5 | NUCLEOPROTEIN | INFLUENZA A VIRUS (STRAIN A/ENGLAND/19/55) | 173–197 | | | | | | | | |
| PVNUC_IAFOM | NUCLEOPROTEIN | INFLUENZA A VIRUS (STRAIN A/FORT MONMOUTH/1/47) | 173–197 | | | | | | | | |
| PVNUC_IAFOW | NUCLEOPROTEIN | INFLUENZA A VIRUS (STRAIN A/FORT WARREN/1/50) | 173–197 | | | | | | | | |
| PVNUC_IAFPD | NUCLEOPROTEIN | INFLUENZA A VIRUS (STRAIN A/FOWL PLAGUE VIRUS/ DOBSON/DUTC | 173–197 | | | | | | | | |
| PVNUC_IAFPR | NUCLEOPROTEIN | INFLUENZA A VIRUS (STRAIN A/FOWL PLAGUE VIRUS/ ROSTOCK/34) | 173–197 | | | | | | | | |
| PVNUC_IAGRE | NUCLEOPROTEIN | INFLUENZA A VIRUS (STRAIN A/GREY TEAL/AUSTRALIA/2/79) | 173–197 | | | | | | | | |
| PVNUC_IAGU1 | NUCLEOPROTEIN | INFLUENZA A VIRUS (STRAIN A/GULL/MARYLAND/5/77) | 173–197 | | | | | | | | |
| PVNUC_IAGU2 | NUCLEOPROTEIN | INFLUENZA A VIRUS (STRAIN A/GULL/MARYLAND/704/77) | 173–197 | | | | | | | | |
| PVNUC_IAGU3 | NUCLEOPROTEIN | INFLUENZA A VIRUS (STRAIN A/GULL/MARYLAND/1824/78) | 173–197 | | | | | | | | |
| PVNUC_IAGU4 | NUCLEOPROTEIN | INFLUENZA A VIRUS (STRAIN A/GULL/MARYLAND/1815/79) | 173–197 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNUC_IAGUA | NUCLEOPROTEIN | INFLUENZA A VIRUS (STRAIN A/GULL/ASTRAKHAN/227/84) | 173–197 | | | | | | | | |
| PVNUC_IAGUM | NUCLEOPROTEIN | INFLUENZA A VIRUS (STRAIN A/GULL/MASSACHUSETTS/26/80) | 173–197 | | | | | | | | |
| PVNUC_IAGUN | NUCLEOPROTEIN | INFLUENZA A VIRUS (STRAIN A/GULL/MINNESOTA/945/80) | 173–197 | | | | | | | | |
| PVNUC_IAHIC | NUCLEOPROTEIN | INFLUENZA A VIRUS (STRAIN A/HICKOX/40) | 173–197 | | | | | | | | |
| PVNUC_IAHJI | NUCLEOPROTEIN | INFLUENZA A VIRUS (STRAIN A/EQUINE/JILLIN/1/89) | 173–197 | | | | | | | | |
| PVNUC_IAHLO | NUCLEOPROTEIN | INFLUENZA A VIRUS (STRAIN A/EQUINE/LONDON/1416/73) | 173–197 | | | | | | | | |
| PVNUC_IAHMI | NUCLEOPROTEIN | INFLUENZA A VIRUS (STRAIN A/EQUINE/MIAMI/1/63) | 173–197 | | | | | | | | |
| PVNUC_IAHO1 | NUCLEOPROTEIN | INFLUENZA A VIRUS (STRAIN A/HONG KONG/1/68) | 173–197 | | | | | | | | |
| PVNUC_IAHO2 | NUCLEOPROTEIN | INFLUENZA A VIRUS (STRAIN A/HONG KONG/5/83) | 173–197 | | | | | | | | |
| PVNUC_IAHPR | NUCLEOPROTEIN | INFLUENZA A VIRUS (STRAIN A/EQUINE/PRAGUE/1/56) | 173–197 | | | | | | | | |
| PVNUC_IAHTE | NUCLEOPROTEIN | INFLUENZA A VIRUS (STRAIN A/EQUINE/TENNESSEE/5/86) | 173–197 | | | | | | | | |
| PVNUC_IAKIE | NUCLEOPROTEIN | INFLUENZA A VIRUS (STRAIN A/KEIV/59/79) | 173–197 | | | | | | | | |
| PVNUC_IALEN | NUCLEOPROTEIN | INFLUENZA A VIRUS (STRAIN A/LENINGRAD/54/1) | 173–197 | | | | | | | | |
| PVNUC_IAMAA | NUCLEOPROTEIN | INFLUENZA A VIRUS (STRAIN A/MALLARD/ASTRAKHAN/244/82) | 173–197 | | | | | | | | |
| PVNUC_IAMAN | NUCLEOPROTEIN | INFLUENZA A VIRUS (STRAIN A/MALLARD/NEW YORK/6750/78) | 173–197 | | | | | | | | |
| PVNUC_IAMIN | NUCLEOPROTEIN | INFLUENZA A VIRUS (STRAIN A/MINK/SWEDEN/84) | 173–197 | | | | | | | | |
| PVNUC_IANT6 | NUCLEOPROTEIN | INFLUENZA A VIRUS (STRAIN A/NT/60/68) | 173–197 | | | | | | | | |
| PVNUC_IAOHI | NUCLEOPROTEIN | INFLUENZA A VIRUS (STRAIN A/OHIO/4/83) | 173–197 | | | | | | | | |
| PVNUC_IAPAR | NUCLEOPROTEIN | INFLUENZA A VIRUS (STRAIN A/PARROT/ULSTER/73) | 173–197 | | | | | | | | |
| PVNUC_IAPUE | NUCLEOPROTEIN | INFLUENZA A VIRUS (STRAIN A/PUERTO RICO/8/34) | 173–197 | | | | | | | | |
| PVNUC_IARUD | NUCLEOPROTEIN | INFLUENZA A VIRUS (STRAIN A/RUDDY TURNSTONE/NEW JERSEY/47/ | 173–197 | | | | | | | | |
| PVNUC_IASE0 | NUCLEOPROTEIN | INFLUENZA A VIRUS (STRAIN A/SEAL/MASSCHUSETTES/1/80) | 173–197 | | | | | | | | |
| PVNUC_IASH2 | NUCLEOPROTEIN | INFLUENZA A VIRUS (STRAIN A/SHEARWATER/AUSTRALIA/72) | 173–197 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNUC_IASIN | NUCLEOPROTEIN | INFLUENZA A VIRUS (STRAIN A/SINGAPORE/1/57) | 173–197 | | | | | | | | |
| PVNUC_IATE1 | NUCLEOPROTEIN | INFLUENZA A VIRUS (STRAIN A/TEAL/ICELAND/29/80) | 173–197 | | | | | | | | |
| PVNCU_IATKN | NUCLEOPROTEIN | INFLUENZA A VIRUS (STRAIN A/TURKEY/MINNESOTA/1661/81) | 173–197 | | | | | | | | |
| PVNUC_IATKO | NUCLEOPROTEIN | INFLUENZA A VIRUS (STRAIN A/TURKEY/ONTARIO/7732/66) | 173–197 | | | | | | | | |
| PVNUC_IATRS | NUCLEOPROTEIN | INFLUENZA A VIRUS (STRAIN A/TERN/SOUTH AFRICA/61) | 173–197 | | | | | | | | |
| PVNUC_IATRT | NUCLEOPROTEIN | INFLUENZA A VIRUS (STRAIN A/TERN/TURKEYMENAI/18/72) | 173–197 | | | | | | | | |
| PVNUC_IATX7 | NUCLEOPROTEIN | INFLUENZA A VIRUS (STRAIN A/TEXAS/1/77) | 173–197 | | | | | | | | |
| PVNUC_IAUDO | NUCLEOPROTEIN | INFLUENZA A VIRUS (STRAIN A/UDORN/307/72) | 173–197 | | | | | | | | |
| PVNUC_IAUSS | NUCLEOPROTEIN | INFLUENZA A VIRUS (STRAIN A/USSR/90/77) | 173–197 | | | | | | | | |
| PVNUC_IAVI6 | NUCLEOPROTEIN | INFLUENZA A VIRUS (STRAIN A/VICTORIA/5/68) | 173–197 | | | | | | | | |
| PVNUC_IAWHN | NUCLEOPROTEIN | INFLUENZA A VIRUS (STRAIN A/WHALE/MAINE/328/84) | 173–197 | | | | | | | | |
| PVNUC_IAWHP | NUCLEOPROTEIN | INFLUENZA A VIRUS (STRAIN A/WHALE/PACIFIC OCEAN/19/76) | 173–197 | | | | | | | | |
| PVNUC_IAWIL | NUCLEOPROTEIN | INFLUENZA A VIRUS (STRAIN A/WILSON-SMITH/33) | 173–197 | | | | | | | | |
| PVNUC_IAZ29 | NUCLEOPROTEIN | INFLUENZA A VIRUS (STRAIN A/SWINE/29/3) | 173–197 | | | | | | | | |
| PVNUC_IAZ41 | NUCLEOPROTEIN | INFLUENZA A VIRUS (STRAIN A/SWINE/41/49) | 173–197 | | | | | | | | |
| PVNUC_IAZCA | NUCLEOPROTEIN | INFLUENZA A VIRUS (STRAIN A/SWINE/CAMBRIDGE/1/35) | 173–197 | | | | | | | | |
| PVNUC_IAZDA | NUCLEOPROTEIN | INFLUENZA A VIRUS (STRAIN A/SWINE/DANDONG/9/83) | 173–197 | | | | | | | | |
| PVNUC_IAZGE | NUCLEOPROTEIN | INFLUENZA A VIRUS (STRAIN A/SWINE/GERMANY/2/81) | 173–197 | | | | | | | | |
| PVNUC_IAZH1 | NUCLEOPROTEIN | INFLUENZA A VIRUS (STRAIN A/SWINE/HONG KONG/6/76) | 173–197 | | | | | | | | |
| PVNUC_IAZH3 | NUCLEOPROTEIN | INFLUENZA A VIRUS (STRAIN A/SWINE/HONG KONG/126/82) | 173–197 | | | | | | | | |
| PVNUC_IAZJ1 | NUCLEOPROTEIN | INFLUENZA A VIRUS (STRAIN A/SWINE/IOWA/15/30) | 173–197 | | | | | | | | |
| PVNUC_IAZJ2 | NUCLEOPROTEIN | INFLUENZA A VIRUS (STRAIN A/SWINE/IOWA/1976/31) | 173–197 | | | | | | | | |
| PVNUC_IAZJ3 | NUCLEOPROTEIN | INFLUENZA A VIRUS (STRAIN A/SWINE/IOWA/46) | 173–197 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVNUC_IAZJ4 | NUCLEOPROTEIN | INFLUENZA A VIRUS (STRAIN A/SWINE/ITALY/839/89) | 173–197 | | | | | | | | |
| PVNUC_IAZJA | NUCLEOPROTEIN | INFLUENZA A VIRUS (STRAIN A/SWINE/JAMESBURG/42) | 173–197 | | | | | | | | |
| PVNUC_IAZMA | NUCLEOPROTEIN | INFLUENZA A VIRUS (STRAIN A/SWINE/MAY/54) | 173–197 | | | | | | | | |
| PVNUC_IAZNE | NUCLEOPROTEIN | INFLUENZA A VIRUS (STRAIN A/SWINE/NETHERLANDS/12/85) | 173–197 | | | | | | | | |
| PVNUC_IAZOH | NUCLEOPROTEIN | INFLUENZA A VIRUS (STRAIN A/SWINE/OHIO/23/35) | 173–197 | | | | | | | | |
| PVNUC_IAZW1 | NUCLEOPROTEIN | INFLUENZA A VIRUS (STRAIN A/SWINE/WISCONSIN/1/57) | 173–197 | | | | | | | | |
| PVNUC_IAZW2 | NUCLEOPROTEIN | INFLUENZA A VIRUS (STRAIN A/SWINE/WISCONSIN/1/61) | 173–197 | | | | | | | | |
| PVNUC_INBAC | NUCLEOPROTEIN | INFLUENZA B VIRUS (STRAIN B/ANN ARBOR/1/66 [COLD-ADAPTED] | 234–258 | | | | | | | | |
| PVNUC_INBAD | NUCLEOPROTEIN | INFLUENZA B VIRUS (STRAIN B/ANN ARBOR/1/66 [WILD-TYPE]) | 234–258 | | | | | | | | |
| PVNUC_INBLE | NUCLEOPROTEIN | INFLUENZA B VIRUS (STRAIN B/LEE/40) | 234–258 | | | | | | | | |
| PVNUC_INBSI | NUCLEOPROTEIN | INFLUENZA B VIRUS (STRAIN B/SINGAPORE/222/79) | 234–258 | | | | | | | | |
| PVNUC_MABVM | NUCLEOPROTEIN | MARBURG VIRUS (STRAIN MUSOKE) | 16–39 | 141–158 | | | | | | | |
| PVNUC_MABVP | NUCLEOPROTEIN | MARBURG VIRUS (STRAIN POPP) | 16–39 | 141–158 | | | | | | | |
| PVO01_VACCC | PROTEIN O1 | VACCINIA VIRUS (STRAIN COPENHAGEN) | 189–204 | 242–252 | 336–358 | | | | | | |
| PVO01_VARV | PROTEIN O1 | VARIOLA VIRUS | 189–204 | 242–252 | 336–358 | | | | | | |
| PVOR1_FXMV | 152 KD PROTEIN | FOXTAIL MOSAIC VIRUS | 846–865 | | | | | | | | |
| PVOR1_NMV | 186 KD PROTEIN | NARCISSUS MOSAIC VIRUS | 409–424 | 990–1010 | | | | | | | |
| PVOR1_PVMR | 223 KD PROTEIN | POTATO VIRUS M (STRAIN RUSSIAN) | 87–104 | 986–1009 | 1251–1270 | 1893–1909 | | | | | |
| PVOR1_PVSP | 223 KD PROTEIN | POTATO VIRUS S (STRAIN PERUVIAN) | 279–295 | | | | | | | | |
| PVOR1_PVX | 165 KD PROTEIN | POTATO VIRUS X | 128–153 | 234–256 | 306–322 | 1010–1030 | | | | | |
| PVOR1_PVXCP | 165 KD PROTEIN | POTATO VIRUS X (STRAIN CP) | 128–153 | 234–256 | 306–322 | 385–404 | 1010–1030 | | | | |
| PVOR1_PVXX3 | 165 KD PROTEIN | POTATO VIRUS X (STRAIN X3) | 128–153 | 234–256 | 306–322 | 1010–1030 | | | | | |
| PVOR1_SMYEA | 150 KD PROTEIN | OS STRAWBERRY MILD YELLOW EDGE-ASSOCIATED VIRUS | 121–146 | 155–175 | | | | | | | |
| PVOR1_WCMVM | 147 KD PROTEIN | WHITE CLOVER MOSAIC VIRUS (STRAIN M) | 121–146 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVOR1_WCMVO | 147 KD PROTEIN | WHITE CLOVER MOSAIC VIRUS (STRAIN O) | 121–146 | 408–430 | | | | | | | |
| PVP03_HSVSA | PROBABLE MEMBRANE ANTIGEN 3 | HERPESVIRUS SAIMIRI (STRAIN 11) | 424–446 | 462–486 | 551–575 | 579–595 | 1051–1072 | | | | |
| PVP10_NPVAC | P10 PROTEIN | AUTOGRAPHA CALIFORNICA NUCLEAR POLYHEDROSIS VIRUS | 4–26 | 42–59 | | | | | | | |
| PVP10_NPVOP | P10 PROTEIN | ORGYIA PSEUDOTSUGATA MULTI-CAPSID POLYHEDROSIS VIRUS | 4–31 | | | | | | | | |
| PVP10_NPVSE | P10 PROTEIN | SPODOPTERA EXIGUA NUCLEAR POLYHEDROSIS VIRUS (STRAIN US) | 35–58 | | | | | | | | |
| PVP10_RBSDV | PROTEIN S10 | RICE BLACK STREAKED DWARF VIRUS | 31–49 | 52–77 | 105–129 | 195–914 | 260–283 | 504–528 | | | |
| PVP10_WTV | NONSTRUCTURAL PROTEIN PNS10 | WOUND TUMOR VIRUS (WTV) | 90–107 | 265–291 | | | | | | | |
| VPV14_EBV | PROBABLE MEMBRANE ANTIGEN P140 | EPSTEIN-BARR VIRUS (STRAIN B95-8) | 694–715 | 857–879 | 1124–1145 | | | | | | |
| PVP19_EBV | PROB CAPSID ASSEMBLY AND DNA MATUR PROTEI | EPSTEIN-BARR VIRUS (STRAIN B95-8) | | 346–364 | | | | | | | |
| PVP19_HCMVA | PROB CAPSID ASSEMBLY AND DNA MATUR PROTEI | HUMAN CYTOMEGALOVIRUS (STRAIN AD 169) | 77–101 | 122–149 | 200–216 | | | | | | |
| PVP19_HSVSA | PROB CAPSID ASSEMBLY AND DNA MATUR PROTEI | HERPESVIRUS SAIMIRI (STRAIN 11) | 238–265 | | | | | | | | |
| PVP19_VZVD | CAPSID ASSEMBLY AND DNA MATUR PROTEIN | VARICELLA-ZOSTER VIRUS (STRAIN DUMAS) | 5–31 | | | | | | | | |
| PVP1_SSV1 | STRUCTURAL PROTEIN VP1 PRECURSOR | SULFOLOBUS VIRUS-LIKE PARTICLE SSV1 | 8–35 | | | | | | | | |
| PVP21_AMCV | CORE PROTEIN P21 | ARTICHOKE MOTTLED CRINKLE VIRUS | 37–63 | | | | | | | | |
| PVP21_CNV | CORE PROTEIN P21 | CUCUMBER NECROSIS VIRUS | 40–65 | | | | | | | | |
| PVP21_CRV | CORE PROTEIN P21 | CYMBIDIUM RINGSPOT VIRUS | 40–63 | | | | | | | | |
| PVP21_TBSVC | CORE PROTEIN P21 | TOMATO BUSHY STUNT VIRUS (STRAIN CHERRY) | 40–63 | | | | | | | | |
| PVP23_HCMVA | PROBABLE CAPSID PROTEIN VP23 | HUMAN CYTOMEGALOVIRUS (STRAIN AD 169) | 141–165 | 187–202 | 261–282 | | | | | | |
| PVP23_HSVI1 | CAPSID PROTEIN VP23 | HERPES SIMPLEX VIRUS (TYPE 1/STRAIN 17) | 197–220 | | | | | | | | |
| PVP23_HSV6U | PROBABLE CAPSID PROTEIN VP23 | HERPES SIMPLEX VIRUS (TYPE 6/STRAIN UGANDA-1102) | 206–232 | | | | | | | | |
| PVP23_VZVD | PROBABLE CAPSID PROTEIN VP23 | VARICELLA-ZOSTER VIRUS (STRAIN DUMAS) | 117–132 | | | | | | | | |
| PVP26_NPVAC | P26 PROTEIN | AUTOGRAPHA CALIFORNICA NUCLEAR POLYHEDROSIS VIRUS | 12–31 | 58–76 | 117–141 | | | | | | |
| PVP2_AHSV4 | OUTER CAPSID PROTIEN VP2 | AFRICAN HORSE SICKNESS VIRUS (SEROTYPE 4/STRAIN VACCINE) | 868–891 | 974–994 | | | | | | | |
| PVP2_BTV10 | OUTER CAPSID PROTEIN VP2 | BLUETONGUE VIRUS (SEROTYPE 10/ISOLATE USA | 361–381 | 399–424 | 564–586 | 829–849 | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVP2_BTV11 | OUTER CAPSID PROTEIN VP2 | BLUETONGUE VIRUS (SEROTYPE 11/ISOLATE USA) | 361–381 | 399–424 | 829–849 | | | | | | |
| PVP2_BTV13 | OUTER CAPSID PROTEIN VP2 | BLUETONGUE VIRUS (SEROTYPE 13/ISOLATE USA) | 362–382 | 420–438 | 617–642 | 657–676 | | | | | |
| PVP2_BTV17 | OUTER CAPSID PROTEIN VP2 | BLUETONGUE VIRUS (SEROTYPE 17/ISOLATE USA) | 361–381 | | | | | | | | |
| PVP2_BTV1A | OUTER CAPSID PROTEIN VP2 | BLUETONGUE VIRUS (SEROTYPE 1/ISOLATE AUSTRALIA) | 420–438 | 654–681 | | | | | | | |
| PVP2_BTV1S | OUTER CAPSID PROTEIN VP2 | BLUETONGUE VIRUS (SEROTYPE 1/ISOLATE SOUTH AFRICA) | 14–31 | 117–140 | 420–438 | 654–681 | | | | | |
| PVP2_EHDV1 | OUTER CAPSID PROTEIN VP2 | EPIZOOTIC HEMORRHAGIC DISEASE VIRUS (SEROTYPE 1) | 153–168 | 229–252 | | | | | | | |
| PVP2_ROTBR | RNA-BINDING PROTEIN VP2 | BOVINE ROTAVIRUS (STRAIN RF) | 301–317 | 334–360 | 522–543 | 673–699 | 764–789 | | | | |
| PVP2_ROTBU | RNA-BINDING PROTEIN VP2 | BOVINE ROTAVIRUS (STRAIN UK) | 301–317 | 334–360 | 523–544 | 765–790 | | | | | |
| PVP2_ROTHW | RNA-BINDING PROTEIN VP2 | HUMAN ROTAVIRUS (SEROTYPE 1/STRAIN WA) | 309–325 | 432–363 | 532–553 | 674–700 | 774–799 | | | | |
| PVP2_ROTPC | RNA-BINDING PROTEIN VP2 | PORCINE ROTAVIRUS (GROUP C/STRAIN COWDEN) | 51–75 | 303–319 | 408–425 | 514–535 | 665–691 | | | | |
| PVP2_ROTS1 | RNA-BINDING PROTEIN VP2 | SIMIAN 11 ROTAVIRUS (STRAIN SA11) | 34–57 | 219–240 | 302–318 | 335–360 | 523–544 | 674–700 | 765–790 | | |
| PVP30_MABVP | MINOR NUCLEOPROTEIN VP30 | MARBURG VIRUS (STRAIN MUSOKE) | 50–75 | | | | | | | | |
| PVP32_ASFB7 | PHOSPHOPROTEIN P32 | AFRICAN SWINE FEVER VIRUS (STRAIN BA71V) | 174–197 | | | | | | | | |
| PVP35_EBOV | POLYMERASE COMPLEX PROTEIN VP35 | EBOLA VIRUS | 233–256 | | | | | | | | |
| PVP35_MABVM | POLYMERASE COMPLEX PROTEIN VP35 | MARBURG VIRUS (STRAIN MUSOKE) | 49–75 | 78–104 | | | | | | | |
| PVP35_MABVP | POLYMERASE COMPLEX VP35 | MARBURG VIRUS (STRAIN POPP) | 49–75 | 78–104 | | | | | | | |
| PVP35_VACCC | IMMUNODOMINANT ENVELOPE PROTEIN P35 | VACCINIA VIRUS (STRAIN COPENHAGEN) | 278–304 | | | | | | | | |
| PVP35_VACCV | IMMUNODOMINANT ENVELOPE PROTEIN P35 | VACCINIA VIRUS (STRAIN WR) | 278–304 | | | | | | | | |
| PVP35_VARV | IMMUNODOMINANT ENVELOPE PROTEIN P35 | VARIOLA VIRUS | 279–305 | | | | | | | | |
| PVP38_HSVMG | 38 KD PHOSPHOPROTEIN | MAREK'S DISEASE HERPESVIRUS (STRAIN GA) | 255–270 | | | | | | | | |
| PVP38_HSVMN | 38 KD PHOSPHOPROTEIN | MAREK'S DISEASE HERPESVIRUS (STRAIN MD11/75C/R2) | 255–270 | | | | | | | | |
| PVP39_NPVAC | MAJOR CAPSID PROTEIN | AUTOGRAPHA CALIFORNICA NUCLEAR POLYHEDROSIS VIRUS | 296–311 | | | | | | | | |
| PVP39_NPVOP | MAJOR CAPSID PROTEIN | ORGYIA PSEUDOTSUGATA MULTICAPSID POLYHEDROSIS VIRUS | 107–134 | 214–240 | 295–316 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVP3_ASHV4 | VP3 CORE PROTEIN | AFRICAN HORSE SICKNESS VIRUS (SEROTYPE 4/STRAIN VACCINE) | 65–85 | 126–147 | 215–230 | 845–862 | | | | | |
| PVP3_BTV10 | VP3 CORE PROTEIN | BLUETONGUE VIRUS (SEROTYPE 10/ISOLATE USA) | 123–144 | 212–227 | | | | | | | |
| PVP3_BTV17 | VP3 CORE PROTEIN | BLUETONGUE VIRUS (SEROTYPE 17/ISOLATTE USA) | 123–144 | 212–227 | | | | | | | |
| PVP3_BTV1A | VP3 CORE PROTEIN | BLUETONGUE VIRUS (SEROTYPE 1/ISOLATE AUSTRALIA) | 123–144 | 212–227 | | | | | | | |
| PVP3_EHDV1 | VP3 CORE PROTEIN | EPIZOOTIC HEMORRHAGIC DISEASE VIRUS (SEROTYPE 1) | 121–142 | 671–695 | | | | | | | |
| PVP3_EHDVA | VP3 CORE PROTEIN | EPIZOOTIC HEMORRHAGIC DISEASE VIRUS (SEROTYPE 2/STRAIN AUS | 121–142 | 675–695 | | | | | | | |
| PVP3_RDV | MAJOR 114 KD STRUCTURAL PROTEIN | RICE DWARF VIRUS (RDV) | 89–108 | 340–360 | 367–393 | 690–717 | 742–768 | 748–768 | 960–975 | | |
| PVP3_ROTPC | INNER CORE PROTEIN VP3 | PORCINE ROTAVIRUS (GROUP C/ STRAIN COWDEN) | 405–429 | | | | | | | | |
| PVP3_ROTS1 | INNER CORE PROTEIN VP3 | SIMIAN 11 ROTATVIRUS (STRAIN SA11) | 401–425 | 426–444 | 512–536 | 796–822 | | | | | |
| PVP40_EBV | CAPSID PROTEIN P40 | EPSTEIN-BARR VIRUS (STRAIN B95-8) | 429–454 | | | | | | | | |
| PVP40_HSV11 | CAPSID PROTEIN P40 | HERPES SIMPLEX VIRUS (TYPE 1/STRAIN 17) | 141–168 | 472–492 | | | | | | | |
| PVP40_HSVEB | CAPSID PROTEIN P40 | EQUINE HERPESVIRUS TYPE 1 (STRAIN AB4P) | 50–67 | 95–119 | 483–504 | | | | | | |
| PVP40_HSVSA | CAPSID PROTEIN P40 | HERPESVIRUS SAIMIRI (STRAIN 11) | 342–368 | | | | | | | | |
| PVP40_ILTVT | CAPSID PROTEIN P40 | INFECTIOUS LARYNGOTRACHEI-TIS VIRUS (STRAIN THRONE V882) | 506–528 | | | | | | | | |
| PVP40_MABVM | MATRIX PROTEIN VP40 | MARBURG VIRUS (STRAIN MUSOKE) | 95–110 | | | | | | | | |
| PVP40_MABVP | MATRIX PROTEIN VP40 | MARBURB VIRUS (STRAIN POPP) | 95–110 | | | | | | | | |
| PVP40_NPVBM | STRUCTURAL GLYCOPROTEIN P40 | BOMBYX MORI NUCLEAR POLYHEDROSIS VIRUS | 223–242 | 256–272 | | | | | | | |
| PVP40_VZVD | CAPSID PROTEIN VP24 | VARICELLA-ZOSTER VIRUS (STRAIN DUMAS) | 47–64 | | | | | | | | |
| PVP41_NPVAC | STRUCTURAL GLYCOPROTEIN GP41 | AUTOGRAPHA CALIFORNICA NUCLEAR POLYHEDROSIS VIRUS | 229–248 | 262–278 | | | | | | | |
| PVP41_ROTS1 | OUTER CAPSID PROTEIN VP4 | SIMIAN 11 ROTAVIRUS (STRAIN SA11) | 483–508 | | | | | | | | |
| PVP42_ROTS1 | OUTER CAPSID PROTEIN VP4 | SIMIAN 11 ROTAVIRUS (STRAIN SA11) | 395–411 | 483–508 | | | | | | | |
| PVP47_NPVAC | VIRAL TRANSCRIPTION REGULATOR P47 | AUTOGRAPHA CALIFORNICA NUCLEAR POLYHEDROSIS VIRUS | 14–38 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVP48_NPVOP | P48 PROTEIN | ORGYIA PSEUDOSUGATA MULTICAPSID POLYHEDROSIS VIRUS | 136–157 | | | | | | | | |
| PVP4A_VARV | MAJOR CORE PROTEIN P4A PRECURSOR | VARIOLA VIRUS | 273–288 | | | | | | | | |
| PVP4B_VACCC | MAJOR CORE PROTEIN P4B PRECURSOR | VACCINIA VIRUS (STRAIN COPENHAGEN) | 331–358 | | | | | | | | |
| PVP4B_VACCV | MAJOR CORE PROTEIN P4B PRECURSOR | VACCINIA VIRUS (STRAIN WR) | 331–358 | | | | | | | | |
| PVP4B_VARV | MAJOR CORE PROTEIN P4B PRECURSOR | VARIOLA VIRUS | 331–358 | | | | | | | | |
| PVP4_BTV10 | VP4 CORE PROTEIN | BLUETONGUE VIRUS (SEROTYPE 10/ISOLATE USA) | 174–191 | 233–249 | 545–561 | | | | | | |
| PVP4_BTV11 | VP4 CORE PROTEIN | BLUETONGUE VIRUS (SEROTYPE 11/ISOLATE USA) | 174–191 | 233–249 | 535–551 | | | | | | |
| PVP4_BTV13 | VP4 CORE PROTEIN | BLUETONGUE VIRUS (SEROTYPE 13/ISOLATE USA) | 174–191 | 233–249 | 535–551 | | | | | | |
| PVP4_BTV2A | VP4 CORE PROTEIN | BLUETONGUE VIRUS (SEROTYPE 2/ISOLATE USA) | 174–193 | 233–249 | 535–551 | | | | | | |
| PVP4_NCDV | OUTER CAPSID PROTEIN VP4 | NEBRASKA CALF DIARRHEA VIRUS (STRAIN NCDV-LINCOLN) | 483–508 | | | | | | | | |
| PVP4_RDV | NONSTRUCTURAL PROTEIN PNS4 | RICE DWARF VIRUS | 386–407 | 493–514 | 626–645 | | | | | | |
| PVP4_ROTB4 | OUTER CAPSID PROTEIN VP4 | BOVINE ROTAVIRUS (SEROTYPE 6/STRAIN B64) | 483–508 | | | | | | | | |
| PVP4_ROTBC | OUTER CAPSID PROTEIN VP4 | BOVINE ROTAVIRUS (STRAIN C486) | 483–508 | | | | | | | | |
| PVP4_ROTBU | OUTER CAPSID PROTEIN VP4 | BOVINE ROTAVIRUS (STRAIN UK) | 483–508 | | | | | | | | |
| PVP4_ROTEH | OUTER CAPSID PROTEIN VP4 | EQUINE ROTAVIRUS (STRAIN H-2) | 226–250 | 483–508 | | | | | | | |
| PVP4_ROTH1 | OUTER CAPSID PROTEIN VP4 | HUMAN ROTAVIRUS (SEROTYPE/ 1/STRAIN 1076) | 181–207 | 234–249 | 482–507 | | | | | | |
| PVP4_ROTH5 | OUTER CAPSID PROTEIN VP4 | HUMAN ROTAVIRUS (SEROTYPE/ 2/STRAIN RV-5) | 181–207 | 234–249 | 482–507 | | | | | | |
| PVP4_ROTH6 | OUTER CAPSID PROTEIN VP4 | HUMAN ROTAVIRUS (SEROTYPE 1/STRAIN 69M) | 483–508 | | | | | | | | |
| PVP4_ROTHD | OUTER CAPSID PROTEIN VP4 | HUMAN ROTAVIRUS (SEROTYPE 2/STRAIN DS1) | 181–207 | 234–249 | 482–507 | | | | | | |
| PVP4_ROTHJ | OUTER CAPSID PROTEIN VP4 | HUMAN ROTAVIRUS (STRAIN K8) | 483–508 | 524–548 | | | | | | | |
| PVP4_ROTHK | OUTER CAPSID PROTEIN VP4 | HUMAN ROTAVIRUS (STRAIN KU) | 76–91 | 181–207 | 234–249 | 482–507 | | | | | |
| PVP4_ROTHL | OUTER CAPSID PROTEIN VP4 | HUMAN ROTAVIRUS (STRAIN L26) | 181–207 | 234–249 | 482–507 | | | | | | |
| PVP4_ROTHM | OUTER CAPSID PROTEIN VP4 | HUMAN ROTAVIRUS (SEROTYPE 1/STRAIN M37) | 181–207 | 234–249 | 482–507 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVP4_ROTHN | OUTER CAPSID PROTEIN VP4 | HUMAN ROTAVIRUS (SEROTYPE/ 3/STRAIN MCN13) | 181–208 | 235–250 | 483–508 | | | | | | |
| PVP4_ROTHP | OUTER CAPSID PROTEIN VP4 | HUMAN ROTAVIRUS (SEROTYPE 3/STRAIN P) | 181–207 | 234–249 | 482–507 | | | | | | |
| PVP4_ROTHT | OUTER CAPSID PROTEIN VP4 | HUMAN ROTAVIRUS (SEROTYPE 4/STRAIN ST THOMAS 3) | 181–207 | 234–249 | 482–507 | | | | | | |
| PVP4_ROTHV | OUTER CAPSID PROTEIN VP4 | HUMAN ROTAVIRUS (SEROTYPE 4/STRAIN VA70) | 181–207 | 482–507 | | | | | | | |
| PVP4_ROTHW | OUTER CAPSID PROTEIN VP4 | HUMAN ROTAVIRUS (SEROTYPE 1/STRAIN WA) | 181–207 | 482–507 | | | | | | | |
| PVP4_ROTP5 | OUTER CAPSID PROTEIN VP4 | PORCINE ROTAVIRUS (SEROTYPE 5/STRAIN OSU) | 235–250 | 483–508 | | | | | | | |
| PVP4_ROTPC | OUTER CAPSID PROTEIN VP4 | PORCINE ROTAVIRUS (GROUP C/STRAIN COWDEN) | 487–512 | | | | | | | | |
| PVP4_ROTPG | OUTER CAPSID PROTEIN VP4 | PORCINE ROTAVIRUS (SEROTYPE GOTTFRIED) | 234–249 | 482–507 | | | | | | | |
| PVP4_ROTPY | OUTER CAPSID PROTEIN VP4 | PORCINE ROTAVIRUS (SEROTYPE YM) | 235–250 | 483–508 | | | | | | | |
| PVP4_ROTRH | OUTER CAPSID PROTEIN VP4 | RHESUS ROTA VIRUS | 483–508 | | | | | | | | |
| PVP4_ROTSF | OUTER CAPSID PROTEIN VP4 | SIMIAN 11 ROTAVIRUS (STRAIN SA11-FEM) | 483–508 | | | | | | | | |
| PVP4_ROTSS | OUTER CAPSID PROTEIN VP4 | SIMIAN 11 ROTAVIRUS (STRAIN SA11-SEM) | 395–411 | 483–508 | | | | | | | |
| PVP4_SBMV | P4 PROTEIN | SOUTHERN BEAN MOSAIC VIRUS | 90–114 | | | | | | | | |
| PVP4_WTV | NONSTRUCTURAL PROTEIN PNS4 | WOUND TUMOR VIRUS | 192–215 | 416–438 | 498–519 | 564–591 | | | | | |
| PVP5_BTV10 | OUTER CAPSID PROTEIN VP5 | BLUETONGUE VIRUS (SEROTYPE 10/ISOLATE USA) | 295–317 | 326–345 | 494–517 | | | | | | |
| PVP5_BTV11 | OUTER CAPSID PROTEIN VP5 | BLUETONGUE VIRUS (SEROTYPE 11/ISOLATE USA) | 295–317 | 326–345 | 494–517 | | | | | | |
| PVP5_BTV13 | OUTER CAPSID PROTEIN VP5 | BLUETONGUE VIRUS (SEROTYPE 13/ISOLATE USA) | 295–317 | 494–517 | | | | | | | |
| PVP5_BTV1A | OUTER CAPSID PROTEIN VP5 | BLUETONGUE VIRUS (SEROTYPE 1/ISOLATE AUSTRALIA) | 87–102 | 295–317 | | | | | | | |
| PVP5_BTV1S | OUTER CAPSID PROTEIN VP5 | BLUETONGUE VIRUS (SEROTYPE 1/ISOLATE SOUTH AFRICA) | 295–317 | | | | | | | | |
| PVP5_BTV2A | OUTER CAPSID PROTEIN VP5 | BLUETONGUE VIRUS (SEROTYPE 2/ISOLATE USA) | 295–317 | | | | | | | | |
| PVP5_RDV | OUTER COAT PROTEIN P5 | RICE DWARF VIRUS | 265–284 | 622–639 | 690–715 | | | | | | |
| PVP61_BTV10 | VP6 PROTEIN | BLUETONGUE VIRUS (SEROTYPE 10/ISOLATE USA) | 9–27 | 232–249 | 261–276 | | | | | | |
| PVP61_NPVAC | 61 KD PROTEIN | AUTOGRAPHA CALIFORNICA NUCLEAR POLYHEDROSIS VIRUS | 321–337 | 438–462 | | | | | | | |
| PVP62_BTV10 | VP6 PROTEIN | BLUETONGUE VIRUS (SEROTYPE 10/ISOLATE USA) | 5–23 | 257–372 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVP62_MRDV | PROB NONSTRUCTURAL 36 3 KD PROTEIN | MAIZE ROUGH DWARF VIRUS | 130–146 | | | | | | | | |
| PVP64_NPVOP | MAJOR ENV GLYCOPROTEIN PREC | ORGYIA PSEUDOTSUGATA MULTICAPSID POLYHEDROSIS VIRUS | 81–99 | 235–252 | 286–313 | | | | | | |
| PVP67_NPVAC | MAJOR ENV GLYCOPROTEIN PREC | AUTOGRAPHA CALIFORNICA NUCLEAR POLYHEDROSIS VIRUS GALLERIA MELLONELLA | 84–102 | 238–255 | | | | | | | |
| PVP67_MPVGM | MAJOR ENVELOPE GLYCOPROTEIN | NUCLEAR POLYHEDROSIS VIRUS | 155–172 | | | | | | | | |
| PVP6_BTV11 | VP6 PROTEIN | BLUETONGUE VIRUS (SEROTYPE 11/ISOLATE USA) | 5–23 | 228–245 | 257–272 | | | | | | |
| PVP6_BTV13 | VP6 PROTEIN | BLUETONGUE VIRUS (SEROTYPE 13/ISOLATE USA) | 5–23 | 228–245 | 257–272 | | | | | | |
| PVP6_BTV17 | VP6 PROTEIN | BLUETONGUE VIRUS (SEROTYPE 17/ISOLATE USA) | 5–23 | 228–245 | 257–272 | | | | | | |
| PVP6_BTV1S | VP6 PROTEIN | BLUETONGUE VIRUS (SEROTYPE 1/ISOLATE SOUTH AFRICA) | 9–27 | 232–249 | 261–276 | | | | | | |
| PVP6_BTV2A | VP6 PROTEIN | BLUETONGUE VIRUS (SEROTYPE 2/ISOLATE USA) | 204–221 | 233–248 | | | | | | | |
| PVP6_WTV | STRUCTURAL PROTEIN P6 | WOUND TUMOR VIRUS | 374–397 | | | | | | | | |
| PVP6_WTVNJ | STRUCTURAL PROTEIN P6 | WOUND TUMOR VIRUS (STRAIN NJ) | 374–397 | | | | | | | | |
| PVP74_NPVAC | P74 PROTEIN | AUTOGRAPHA CALIFORNICA NUCLEAR POLYHEDROSIS VIRUS | 254–275 | | | | | | | | |
| PVP75_HSVSA | PROBABLE MEMBRANE ANTIGEN 75 | HERPESVIRUS SAIMIRI (STRAIN 11) | 127–147 | | | | | | | | |
| PVP79_NPVAC | 79 KD PROTEIN | AUTOGRAPHA CALIFORNICA NUCLEAR POLYHEDROSIS VIRUS | 274–301 | 405–420 | 678–704 | | | | | | |
| PVP7_BTV13 | VP7 CORE PROTEIN | BLUETONGUE VIRUS (SEROTYPE 13/ISOLATE USA) | 197–222 | | | | | | | | |
| PVP7_EHDV1 | VP7 CORE PROTEIN | EPIZOOTIC HEMORRHAGIC DISEASE VIRUS (SEROTYPE 1) | 205–222 | 301–323 | | | | | | | |
| PVP7_RDV | NONSTRUCTURAL PROTEIN PNS7 | RICE DWARF VIRUS | 400–416 | | | | | | | | |
| PVP7_WTV | NONSTRUCTURAL PROTEIN PNS7 | WOUND TUMOR VIRUS | 262–285 | | | | | | | | |
| PVP80_NPVAC | CAPSID PROTEIN P80 | AUTOGRAPHA CALIFORNICA NUCLEAR POLYHEDROSIS VIRUS | 98–123 | 638–660 | | | | | | | |
| PVP87_NPVOP | CAPSID PROTEIN P87 | ORGYIA PSEUDOTSUGATA MULTICAPSID POLYHYDROSIS VIRUS | 571–593 | | | | | | | | |
| PVP8_BTV10 | NONSTRUCTURAL PROTEIN P8 | BLUETONGUE VIRUS (SEROTYPE 10/ISOLATE USA) | 104–120 | | | | | | | | |
| PVP8_BTV11 | NONSTRUCTURAL PROTEIN P8 | BLUETONGUE VIRUS (SEROTYPE 11/ISOLATE USA) | 104–120 | | | | | | | | |
| PVP8_BTV13 | NONSTRUCTURAL PROTEIN P8 | BLUETONGUE VIRUS (SEROTYPE 13/ISOLATE USA) | 104–120 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVP8_BTV17 | NONSTRUCTURAL PROTEIN P8 | BLUETONGUE VIRUS (SEROTYPE 17/ISOLATE USA) | 104–120 | | | | | | | | |
| PVP8_BTV1A | NONSTRUCTURAL PROTEIN P8 | BLUETONGUE VIRUS (SEROTYPE 1/ISOLATE AUSTRALIA) | 104–120 | | | | | | | | |
| PVP8_BTV1S | NONSTRUCTURAL PROTEIN P8 | BLUETONGUE VIRUS (SEROTYPE 1/ISOLATE SOUTH AFRICA) | 104–120 | | | | | | | | |
| PVP8_BTV2A | NONSTRUCTURAL PROTEIN P8 | BLUETONGUE VIRUS (SEROTYPE 1/ISOLATE SOUTH USA) | 104–120 | | | | | | | | |
| PVP8_RDV | OUTER CAPSID PROTEIN P8 ( | RICE DWARF VIRUS | 374–400 | | | | | | | | |
| PVP8_RGDV | OUTER CAPSID PROTEIN P8 | RICE GALL DWARF VIRUS | 177–202 | 216–242 | 398–425 | | | | | | |
| PVP8_VACCC | STRUCTURAL PROTEIN VP8 PRECURSOR | VACCINIA VIRUS (STRAIN COPENHAGEN) | 225–242 | | | | | | | | |
| PVP8_VACCV | STRUCTURAL PROTEIN VP8 PRECURSOR | VACCINIA VIRUS (STRAIN WR) | 225–242 | | | | | | | | |
| PVP8_VARV | STRUCTURAL PROTEIN VP8 PRECURSOR | VARIOLA VIRUS | 225–242 | | | | | | | | |
| PVP8_WTV | OUTER CAPSID PROTEIN P8 | WOUND TUMOR VIRUS | 111–129 | 214–241 | 251–271 | 379–405 | | | | | |
| PVP9_RDV | NONSTRUCTURAL PROTEIN PN59 | RICE DWARF VIRUS | 51–72 | | | | | | | | |
| PVP9_RGDV | NONSTRUCTURAL PROTEIN 59 | RICE GALL DWARF VIRUS | 151–175 | | | | | | | | |
| PVPHE_NPVAC | 29 KD POLYHEDRAL ENVELOPE PROTEIN | AUTOGRAPHA CALIFONICA NU-CLEAR POLYHEDROSIS VIRUS | 145–166 | 225–245 | | | | | | | |
| PVPHE_NPVOP | 32 KD POLYHEDRAL ENVELOPE PROTEIN | ORGYIA PSEUDOTSUGATA MUL-TICAPSID POLYHEDROSIS VIRUS | 122–144 | | | | | | | | |
| PVPRT_ADE12 | ENDOPROTEASE | HUMAN ADENOVIRUS TYPE 12 | 161–181 | | | | | | | | |
| PVPRT_MMTVB | PROTEASE | MOUSE MAMMARY TUMOR VIRUS (STRAIN BR6) | 42–63 | | | | | | | | |
| PVPRT_MPMV | PROTEASE | SIMIAN MASON-PFIZER VIRUS | 80–99 | | | | | | | | |
| PVPRT_SMRVH | PROTEASE | SQUIRREL MONKEY RETROVIRUS | 256–271 | | | | | | | | |
| PVPRT_SRV1 | PROTEASE | SIMIAN RETROVIRUS SRV-1 | 80–99 | | | | | | | | |
| PVPU_HV1B1 | VPU PROTEIN | HUMAN IMMUNODEFICIENCY VIRUS TYPE 1 (BH10 ISOLATE HXB3) | 3–27 | | | | | | | | |
| PVPU_HV1B8 | VPU PROTEIN | HUMAN IMMUNODEFICIENCY VIRUS TYPE 1 (BH8 ISOLATE) | 4–27 | | | | | | | | |
| PVPU_HV1BN | VPU PROTEIN | HUMAN IMMUNODEFICIENCY VIRUS TYPE 1 (BRAIN ISOLATE) | 3–28 | | | | | | | | |
| PVPU_HV1BR | VPU PROTEIN | HUMAN IMMUNODEFICIENCY VIRUS TYPE 1 (BRU ISOLATE) | 3–27 | | | | | | | | |
| PVPU_HV1EL | VPU PROTEIN | HUMAN IMMUNODEFICIENCY VIRUS TYPE 1 (EL1ISOLATE) | 3–26 | | | | | | | | |
| PVPU_HV1H2 | VPU PROTEIN | HUMAN IMMUNODEFICIENCY VIRUS TYPE 1 (HXB2 ISOLATE) | 4–27 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVPU_HV1JR | VPU PROTEIN | HUMAN IMMUNODEFICIENCY VIRUS TYPE 1 (JRCSF ISOLATE) | 3–28 | | | | | | | | |
| PVPU_HV1MA | VPU PROTEIN | HUMAN IMMUNODEFICIENCY VIRUS TYPE 1 (MAL ISOLATE) | 2–27 | | | | | | | | |
| PVPU_HV1MN | VPU PROTEIN | HUMAN IMMUNODEFICIENCY VIRUS TYPE 1 (MN ISOLATE) | 3–20 | | | | | | | | |
| PVPU_HV1ND | VPU PROTEIN | HUMAN IMMUNODEFICIENCY VIRUS TYPE 1 (NDK ISOLATE) | 3–28 | | | | | | | | |
| PVPU_HV1PV | VPU PROTEIN | HUMAN IMMUNODEFICIENCY VIRUS TYPE 1 (PV22 ISOLATE) | 3–27 | | | | | | | | |
| PVPU_HV1S1 | VPU PROTEIN | HUMAN IMMUNODEFICIENCY VIRUS TYPE 1 (SF162 ISOLATE) | 3–28 | | | | | | | | |
| PVPU_HV1SC | VPU PROTEIN | HUMAN IMMUNODEFICIENCY VIRUS TYPE 1 (SC ISOLATE) | 3–28 | | | | | | | | |
| PVPU_HV1Z2 | VPU PROTEIN | HUMAN IMMUNODEFICIENCY VIRUS TYPE 1 (Z2/CDC-Z34 ISOLATE) | 3–28 | | | | | | | | |
| PVPU_JSRV | VPU PROTEIN | SHEEP PULMONARY ADENO-MATOSIS VIRUS (JAAGSIEKTE SHEEP RET | 24–45 | | | | | | | | |
| PVPX_HV2BE | VPX PROTEIN | HUMAN IMMUNODEFICIENCY VIRUS TYPE 2 (ISOLATE BEN) | 10–32 | | | | | | | | |
| PVPX_HV2CA | VPX PROTEIN | HUMAN IMMUNODEFICIENCY VIRUS TYPE 2 (ISOLATE CAM2) | 10–32 | | | | | | | | |
| PVPX_HV2D1 | VPX PROTEIN | HUMAN IMMUNODEFICIENCY VIRUS TYPE 2 (ISOLATE D194) | 10–32 | | | | | | | | |
| PVPX_HV2D2 | VPX PROTEIN | HUMAN IMMUNODEFICIENCY VIRUS TYPE 2 (ISOLATE D205.7) | 9–31 | | | | | | | | |
| PVPX_HV2G1 | VPX PROTEIN | HUMAN IMMUNODEFICIENCY VIRUS TYPE 2 (ISOLATE GHANA-1) | 10–32 | | | | | | | | |
| PVPX_HV2NZ | VPX PROTEIN | HUMAN IMMUNODEFICIENCY VIRUS TYPE 2 (ISOLATE NIH-Z) | 10–32 | | | | | | | | |
| PVPX_HV2RO | VPX PROTEIN | HUMAN IMMUNODEFICIENCY VIRUS TYPE 2 (ISOLATE ROD) | 10–32 | | | | | | | | |
| PVPX_HV2SB | VPX PROTEIN | HUMAN IMMUNODEFICIENCY VIRUS TYPE 2 (ISOLATE SBLISY) | 10–32 | | | | | | | | |
| PVPX_HV2ST | VPX PROTEIN | HUMAN IMMUNODEFICIENCY VIRUS TYPE 2 (ISOLATE ST) | 10–32 | | | | | | | | |
| PVPX_LDV | VPX PROTEIN | LACTATE DEHYDROGENASE-ELEVATING VIRUS | 145–165 | | | | | | | | |
| PVPX_SIVAI | VPX PROTEIN | SIMIAM IMMUNODEFICIENCY VIRUS (ISOLATE AGM/CLONE GR1-1)(S | 66–84 | | | | | | | | |
| PVPX_SIVMI | VPX PROTEIN | SIMIAN IMMUNODEFICIENCY VIRUS (MM142-83 ISOLATE) (SIV-MAC) | 10–32 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVPX_SIVMK | VPX PROTEIN | SIMIAN IMMUNODEFICIENCY VIRUS (K6W ISOLATE)(SIV-MAC) | 10–32 | | | | | | | | |
| PVPX_SIVML | VPX PROTEIN | SIMIAN IMMUNODEFICIENCY VIRUS (K78 ISOLATE)(SIV-MAC) | 10–32 | | | | | | | | |
| PVPX_SIVS4 | VPX PROTEIN | SIMIAN IMMUNODEFICIENCY VIRUS (F236/SMH4 ISOLATE) (SOOTY M | 10–32 | | | | | | | | |
| PVPX_SIVSP | VPX PROTEIN | SIMIAN IMMUNODEFICIENCY VIRUS (PBJ/BC13 ISOLATE) (SOOTY MA | 10–32 | | | | | | | | |
| PVRNA_BSMV | ALPHA-A PROTEIN | BARLEY STRIPE MOSAIC VIRUS (BSMV) | 290–312 | 904–929 | | | | | | | |
| PVS05_ROTBR | NONSTRUCTURAL PROTEIN NCVP2 | BOVINE ROTAVIRUS (STRAIN RF) | 140–157 | 461–487 | | | | | | | |
| PVS05_ROTH1 | NONSTRUCTURAL PROTEIN NCVP2 | HUMAN ROTAVIRUS (STRAIN IGV-80-3) | 140–157 | 428–450 | 457–473 | | | | | | |
| PVS05_ROTPC | NONSTRUCTURAL PROTEIN NS53 | PORCINE ROTAVIRUS (GROUP C/STRAIN COWDEN) | 88–112 | | | | | | | | |
| PVS05_ROTS1 | NONSTRUCTURAL PROTEIN NCVP2 | SIMINA 11 ROTAVIRUS (STRAIN SA11) | 399–414 | | | | | | | | |
| PVS06_ROTBR | VP6 PROTEIN | BOVINE ROTAVIRUS (STRAIN RF) | 202–225 | | | | | | | | |
| PVS06_ROTBS | VP6 PROTEIN | BOVINE ROTAVIRUS (GROUP C/ STRAIN SHINTOKU) | 64–85 | | | | | | | | |
| PVS06_ROTBU | VP6 PROTEIN | BOVINE ROTAVIRUS (STRAIN UK) | 202–225 | | | | | | | | |
| PVS06_ROTEF | VP6 PROTEIN | EQUINE ROTAVIRUS (STRAIN F1-14) | 202–225 | | | | | | | | |
| PVS06_ROTEH | VP6 PROTEIN | EQUINE ROTAVIRUS (STRAIN H-2) | 202–225 | | | | | | | | |
| PVS06_ROTGA | VP6 PROTEIN | ROTAVIRUS (GROUP B/STRAIN ADRV) (ADULT DIARRHEA ROTAVIRUS) | 22–40 | | | | | | | | |
| PVS06_ROTG1 | VP6 PROTEIN | ROTAVIRUS (GROUP B/ STRAIN IDIR) | 22–40 | | | | | | | | |
| PVS06_ROTH1 | VP6 PROTEIN | HUMAN ROTAVIRUS (SEROTYPE 1/STRAIN 1076) | 202–225 | | | | | | | | |
| PVS06_ROTHC | VP6 PROTEIN | HUMAN ROTAVIRUS (GROUP C/ STRAIN BRISTOL) | 64–85 | | | | | | | | |
| PVS06_ROTHS | VP6 PROTEIN | HUMAN ROTAVIRUS (SEROTYPE 2/STRAIN S2) | 202–225 | | | | | | | | |
| PVS06_ROTHW | VP6 PROTEIN | HUMAN ROTAVIRUS (SEROTYPE 1/STRAIN WA) | 202–225 | | | | | | | | |
| PVS06_ROTPC | VP6 PROTEIN | PORCINE ROTAVIRUS (GROUP C/ STRAIN COWDEN) | 64–85 | 314–340 | | | | | | | |
| PVS06_ROTPG | VP6 PROTEIN | PORCINE ROTAVIRUS (STRAIN GOTTFRIED) | 202–225 | | | | | | | | |
| PVS07_ROTBJ | GLYCOPROTEIN VP7 | BOVINE ROTAVIRUS (STRAIN KN-4) | 131–155 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVS08_RPTPC | GLYCOPROTEIN VP7 | PORCINE ROTAVIRUS (GROUP C/ STRAIN COWDEN) | 117–136 | | | | | | | | |
| PVS08_ROTS1 | NONSTRUCTURAL PROTEIN NCVP4 | SIMINA 11 ROTAVIRUS (STRAIN SA11) | 274–295 | | | | | | | | |
| PVS09_ROTB6 | GLYCOPROTEIN VP7 | BOVINE ROTAVIRUS (SEROTYPE 6/STRAIN 61A) | 131–155 | | | | | | | | |
| PVS09_ROTBA | GLYCOPROTEIN VP7 | BOVINE ROTAVIRUS (STRAIN A44) | 131–155 | | | | | | | | |
| PVS09_ROTBB | GLYCOPROTEIN VP7 | BOVINE ROTAVIRUS (SEROTYPE 10/STRAIN B223) | 131–155 | | | | | | | | |
| PVS09_ROTBK | GLYCOPROTEIN VP7 | BOVINE ROTAVIRUS (STRAIN KK3) | 131–155 | | | | | | | | |
| PVS09_ROTBT | GLYCOPROTEIN VP7 1/STRAIN T449) | BOVINE ROTAVIRUS (SEROTYPE | 131–155 | | | | | | | | |
| PVS09_ROTC7 | GLYCOPROTEIN VP7 | CHICKEN ROTAVIRIUS A (SEROTYPE 7/STRAIN CH2) | 134–158 | | | | | | | | |
| VPS09_ROTEL | GLYCOPROTEIN VP7 | EQUINE ROTATVIRUS (STRAIN L338) | 131–155 | | | | | | | | |
| PVS09_ROTG1 | GLYCOPROTEIN VP7 PRECURSOR | ROTAVIRUS (GROUP B/ IDIR) | 205–232 | | | | | | | | |
| PVS09_ROTH4 | GLYCOPROTEIN VP7 | HUMAN ROTAVIRUS (SEROTYPE 4/STRAIN RV-4) | 131–155 | 197–212 | | | | | | | |
| PVS09_ROTHA | GLYCOPROTEIN VP7 | HUMAN ROTAVIRUS (SEROTYPE 2/STRAIN HU5) | 197–212 | | | | | | | | |
| PVS09_ROTHD | GLYCOPROTEIN VP7 | HUMAN ROTAVIRUS (SEROTYPE 2/STRAIN DS1) | 197–212 | | | | | | | | |
| PVS09_TOTHH | GLYCOPROTEIN VP7 | HUMAN ROTAVIRUS (SEROTYPE 2/STRAIN HN126) | 197–212 | | | | | | | | |
| PVS09_ROTHL | GLYCOPROTEIN VP7 | HUMAN ROTAVIRUS (STRAIN L26) | 131–155 | 197–212 | | | | | | | |
| PVS09_ROTHM | GLYCOPROTEIN VP7 | HUMAN ROTAVIRUS (SEROTYPE 1/STRAIN M37) | 131–155 | 197–212 | | | | | | | |
| PVS09_ROTHO | GLYCOPROTEIN VP7 | HUMAN ROTAVIRUS (SEROTYPE 1/STRAIN MO AND STRAIN D) | 131–155 | 197–212 | | | | | | | |
| PVS09_ROTHP | GLYCOPROTEIN VP7 | HUMAN ROTAVIRUS (SERPTYPE 3/STRAIN P) | 131–155 | | | | | | | | |
| PVS09_ROTHR | GLYCOPROTEIN VP7 | HUMAN ROTAVIRUS (SEROTYPE 3/STRAIN RRV) | 131–155 | | | | | | | | |
| PVS09_ROTHS | GLYCOPROTEIN VP7 | HUMAN ROTAVIRUS (SEROTYPE 2/STRAIN S2) | 197–212 | | | | | | | | |
| PVS09_ROTHV | GLYCOPROTEIN VP7 | HUMAN ROTAVIRUS (SEROTYPE 4/STRAIN VA70) | 197–212 | | | | | | | | |
| PVS09_ROTHW | GLYCOPROTEIN VP7 | HUMAN ROTAVIRUS (SEROTYPE 1/STRAIN WA) | 131–155 | 197–212 | | | | | | | |
| PVS09_ROTP5 | GLYCOPROTEIN VP7 | PORCINE ROTAVIRUS (SEROTYPE 5/STRAIN OSU) | 131–155 | 197–212 | | | | | | | |
| PVS09_ROTP6 | GLYCOPROTEIN VP7 | PORCINE ROTAVIRUS (SEROTYPE 5/STRAIN TFR-41) | 131–155 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVS09_ROTPB | GLYCOPROTEIN VP7 | PORCINE ROTAVIRUS (SEROTYPE 4/STRAIN BEN-144) | 197–212 | | | | | | | | |
| PVS09_ROTPM | GLYCOPROTEIN VP7 | PORCINE ROTAVIRUS (SEROTYPE 4/STRAIN BM1-1) | 197–212 | | | | | | | | |
| PVS09_ROTRH | GLYCOPROTEIN VP7 | RHESUS ROTAVIRUS | 131–155 | | | | | | | | |
| PVS09_ROTS1 | GLYCOPROTEIN VP7 | SIMIAN 11 ROTAVIRUS (STRAIN SA11) | 131–155 | | | | | | | | |
| PVS11_ROTGA | NONSTRUCTURAL PROTEIN | ROTAVIRUS (GROUP B/STRAIN ADRV) (ADULT DIARRHEA ROTAVIRUS) | 136–153 | | | | | | | | |
| PVSH_HRSVA | SMALL HYDROPHOBIC PROTEIN | HUMAN RESPIRATORY SYNCYTIAL VIRUS (STRAIN A2) | 16–41 | | | | | | | | |
| PVSH_MUMP1 | SMALL HYDROPHOBIC PROTEIN | MUMPS VIRUS (STRAIN SBL-1), AND MUMPS VIRUS (STRAIN SBL) | 7–29 | | | | | | | | |
| PVSH_MUMP2 | SMALL HYDROPHOBIC PROTEIN | MUMPS VIRUS (STRAIN EDINGBURGH 2 –6) | 7–29 | | | | | | | | |
| PVSH_MUMP4 | SMALL HYDROPHOBIC PROTEIN | MUMPS VIRUS (STRAIN EDINGBURGH 4) | 7–29 | | | | | | | | |
| PVSH_MUMPA | SMALL HYDROPHOBIC PROTEIN | MUMPS VIRUS (STRAIN MATSUYAMA) | 10–29 | | | | | | | | |
| PVSH_MUMPB | SMALL HYDROPHOBIC PROTEIN | MUMPS VIRUS (STRAIN BELFAST) | 7–29 | | | | | | | | |
| PVSH_MUMPE | SMALL HYDROPHOBIC PROTEIN | MUMPS VIRUS (STRAIN ENDERS) | 7–29 | | | | | | | | |
| PVSH_MUMPJ | SMALL HYDROPHOBIC PROTEIN | MUMPS VIRUS (STRAIN JERYL-LYNN) | 7–29 | | | | | | | | |
| PVSH_MUMPK | SMALL HYDROPHOBIC PROTEIN | MUMPS VIRUS (STRAIN KILHAM) | 7–29 | | | | | | | | |
| PVSH_MUMPL | SMALL HYDROPHOBIC PROTEIN | MUMPS VIRUS (STRAIN BRISTOL I) | 6–29 | | | | | | | | |
| PVSH_MUMPM | SMALL HYDROPHOBIC PROTEIN | MUMPS VIRUS (STRAIN MIYAHRARA VACCINE) | 10–29 | | | | | | | | |
| PVSH_MUMPR | SMALL HYDROPHOBIC PROTEIN | MUMPS VIRUS (STRAIN RW) | 7–29 | | | | | | | | |
| PVSH_MUMPT | SMALL HYDROPHOBIC PROTEIN | MUMPS VIRUS (STRAIN TAKAJIASHI) | 10–29 | | | | | | | | |
| PVSH_MUMPU | SMALL HYDROPHOBIC PROTEIN | MUMPS VIRUS (STRAIN URABE VACCINE AM9) | 10–29 | | | | | | | | |
| PVSI1_REOVL | SIGMA 1 PROTEIN PRECURSOR | REOVIRUS (TYPE 1/ STRAIN LANG) | 110–136 | | | | | | | | |
| PVSI3_REOVD | SIGMA 3 PROTEIN | REOVIRUS (TYPE 3/ STRAIN DEARING) | 152–170 | | | | | | | | |
| PVSI3_REOVJ | SIGMA 3 PROTEIN | REOVIRUS (TYPE 2/ STRAIN D5/JONES) | 152–170 | | | | | | | | |
| PVSI3_REOVL | SIGMA 3 PROTEIN | REOVIRUS (TYPE 1/ STRAIN LANG) | 152–170 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PVSIS_REOVL | SIGMA 1-S PROTEIN | REOVIRUS (TYPE 1/STRAIN LANG) | 79–101 | | | | | | | | |
| PVST2_HEVBU | STRUCTURAL PROTEIN 2 PRECURSOR | HEPATITIS E VIRUS (STRAIN BURMA) | 292–311 | | | | | | | | |
| PVST2_HEVME | STRUCTURAL PROTEIN 2 PRECURSOR | HEPATITIS E VIRUS (STRAIN MEXICO) | 292–311 | | | | | | | | |
| PVST2_HEVMY | STRUCTURAL PROTEIN 2 PRECURSOR | HEPATITIS E VIRUS (STRAIN MYANMAR) | 292–311 | | | | | | | | |
| PVST2_HEVPA | STRUCTURAL PROTEIN 2 PRECURSOR | HEPATITIS E VIRUS (STRAIN PAKISTAN) | 292–311 | | | | | | | | |
| PVST2_HEVRH | STRUCTURAL PROTEIN 2 | HEPATITIS E VIRUS (ISOLATE RHESUS) | 160–179 | | | | | | | | |
| PVT2_MYSVL | TUMOR NECROSIS FACTOR SOL RECEPTOR PREC | MYXOMA VIRUS (STRAIN LAUSANNE) | 261–283 | | | | | | | | |
| PVT2_SFVKA | TUMOR NECROSIS FACTOR SOL RECEPTOR PREC | SHOPE FIBROMA VIRUS (STRAIN KASZA) | 270–289 | | | | | | | | |
| PVT3A_CAPVI | PROTEIN T3A | CAPRIPOSVIRUS (STRAIN INS-1) | 116–138 | | | | | | | | |
| PVT4_SFVKA | T4 PROTEIN | SHOPE FIBROMA VIRUS (STRAIN KASZA) | 125–148 | | | | | | | | |
| PVTER_EBV | PROBABLE DNA PACKAGING PROTEIN | EPSTEIN-BARR VIRUS (STRAIN B95-8) | 117–139 | 166–192 | 227–250 | | | | | | |
| PVTER_HCMVA | PROBABLE DNA PACKAGING PROTEIN | HUMAN CYTOMEGALOVIRUS (STRAIN AD169) | 409–430 | | | | | | | | |
| PVTER_HSVII | PROBABLE DNA PACKAGING PROTEIN | HERPES SIMPLEX VIRUS (TYPE 1/STRAIN 17) | 363–380 | | 673–688 | | | | | | |
| PVTER_HSV6U | PROBABLE DNA PACKAGING PROTEIN | HERPES SIMPLEX VIRUS (TYPE 6/STRAIN UGANDA-1102) | 260–278 | | | | | | | | |
| PVTER_HSVEB | PROBABLE DNA PACKAGING PROTEIN | EQUINE HERPESVIRUS TYPE 1 (STRAIN AB4P) | 364–381 | | | | | | | | |
| PVTER_HSVII | PROBABLE DNA PACKAGING PROTEIN | ICTALURID HERPESVIRUS 1 | 309–333 | 756–781 | | | | | | | |
| PVTER_HSVSA | PROBABLE DNA PACKAGING PROTEIN | HERPES VIRUS SAIMIRI (STRAIN 11) | 218–241 | | | | | | | | |
| PVTER_VZVD | PROBABLE DNA PACKAGING PROTEIN | VARICELLA-ZOSTER VIRUS (STRAIN DUMAS) | 372–389 | | | | | | | | |
| PX_HPBGS | PROTEIN X | GROUND SQUIRREL HEPATITIS VIRUS | 68–85 | | | | | | | | |
| PX_WHV1 | PROTEIN X | WOODCHUCK HEPATITIS VIRUS 1 | 68–85 | | | | | | | | |
| PX_WHV59 | PROTEIN X | WOODCHUCK HEPATITIS VIRUS 59 | 68–85 | | | | | | | | |
| PX_WHV7 | PROTEIN X | WOODCHUCK HEPATITIS VIRUS 7 | 68–85 | | | | | | | | |
| PX_WHV8 | PROTEIN X | WOODCHUCK HEPATITIS VIRUS 8 | 68–85 | | | | | | | | |
| PX_WHV81 | PROTEIN X | WOODCHUCK HEPATITIS VIRUS 8 (INFECTIOUS CLONE) | 68–85 | | | | | | | | |

TABLE XIII-continued

| SEARCH RESULTS SUMMARY FOR P12LZIPC MOTIF | | | | | | | | | | | |
|---|---|---|---|---|---|---|---|---|---|---|---|
| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
| PX_WHVW6 | PROTEIN X | WOODCHUCK HEPATITIS VIRUS W64 (ISOLATE PWS23) | 68–85 | | | | | | | | |
| PY104_ADE07 | HYPOTHETICAL 10 4 KD EARLY PROTEIN | HUMAN ADENOVIRUS TYPE 7 | 55–73 | | | | | | | | |
| PY108_SSV1 | HYPOTHETICAL 10 8 KD PROTEIN | SULFOLOBUS VIRUS-LIKE PARTICLE SSV1 | 66–90 | | | | | | | | |
| PY10K_MSMV | HYPOTHETICAL 10 9 KD PROTEIN | MAIZE STREAK VIRUS (SOUTH-AFRICAN ISOLATE) | 24–47 | | | | | | | | |
| PY118_SSV1 | HYPOTHETICAL 11 8 KD PROTEIN | SULFOLOBUS VIRUS-LIKE PARTICLE SSV1 | 42–59 | | | | | | | | |
| PY11K_PASV | HYPOTHETICAL 11 9 KD PROTEIN | PANICUM STREAK VIRUS | 29–52 | | | | | | | | |
| PY12K_BNYVG | RNA-3 HYPOTHETICAL 11 6 KD PROTEIN | BEET NECROTIC YELLOW VEIN MOSIAC VIRUS (ISOLATE G1) | 15–42 | | | | | | | | |
| PY12K_CMVSI | HYPOTHETICAL 12 4 KD PROTEIN | CYMBIDIUM MOSAIC VIRUS (STRAIN SINGAPORE) | 8–30 | | | | | | | | |
| PY137_ADE02 | HYPOTHETICAL PROTEIN B-137 | HUMAN ADENOVIRUS TYPE 2 | 28–50 | | | | | | | | |
| PY13K_CLVK | HYPOTHETICAL 13 1 KD PROTEIN | CASSA VA LETENT VIRUS (STRAIN WEST KENYAN 844) | 34–55 | | | | | | | | |
| PY13K_CLVN | HYPOTHETICAL 13 1 KD PROTEIN | CASSA VA LETENT VIRUS (STRAIN NIGERIAN) | 34–55 | | | | | | | | |
| PY13K_TYLCM | HYPOTHETICAL 13 3 KD PROTEIN | TOMATO YELLOW LEAF CURL VIRUS (STRAIN MARMANDE) | 10–27 | | | | | | | | |
| PY13K_TYLCV | HYPOTHETICAL 13 4 KD PROTEIN | TOMATO YELLOW LEAF CURL VIRUS | 34–55 | | | | | | | | |
| PY145_ADE07 | HYPOTHETICAL 14 5 KD EARLY PROTEIN | HUMAN ADENOVIRUS TYPE 7 | 108–132 | | | | | | | | |
| PY145_CSMV | HYPOTHETICAL 14 5 KD PROTEIN | CHLORIS STRIATE MOSAIC VIRUS | 54–80 | | | | | | | | |
| PY18K_SSV1 | HYPOTHETICAL 18 0 KD PROTEIN | SULFOLOBUS VIRUS-LIKE PARTICLE SSV1 | 100–125 | 141–162 | | | | | | | |
| PY206_ADE07 | HYPOTHETICAL 20 6 KD EARLY PROTEIN | HUMAN ADENOVIRUS TYPE 1 | 50–73 | | | | | | | | |
| PY25K_BNYVF | RNA-3 HYPOTHETICAL 24 7 KD PROTEIN | BEET NECROTIC YELLOW VEIN MOSIAC VIRUS (ISOLATE F2) | 163–188 | | | | | | | | |
| PY29K_NPVAC | HYPOTHETICAL 29 9 KD PROTEIN | AUTOGRAPHA CALIFORNICA NUCLEAR POLYHEDROSIS VIRUS | 90–106 | | | | | | | | |
| PY2_SOCMV | HYPOTHETICAL PROTEIN 2 | SOYBEAN CHLOROTIC MOTTLE VIRUS | 65–90 | | | | | | | | |
| PY32K_SSV1 | HYPOTHETICAL 31 7 KD PROTEIN | SULFOLOBUS VIRUS-LIKE PARTICLE SSV1 | 122–142 | | | | | | | | |
| PY6K0_SSV1 | HYPOTHETICAL 6 0 KD PROTEIN | SULFOLOBUS VIRUS-LIKE PARTICLE SSV1 | 23–44 | | | | | | | | |
| PY7K4_VACCV | HYPOTHETICAL 7 4 KD PROTEIN | VACCINIA VIRUS (STRAIN WR) | 21–36 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PY7K_MEASH | HYPOTHETICAL 7 KD PROTEIN | MEASLES VIRUS (STRAIN HALLE) | 3–25 | | | | | | | | |
| PY7_SOCMV | HYPOTHETICAL PROTEIN 7 | SOYBEAN CHLOROTIC MOTTLE VIRUS | 96–120 | | | | | | | | |
| PY85K_SSV1 | HYPOTHETICAL 85 7 KD PROTEIN | SULFOLOBUS VIRUS-LIKE PARTICLE SSV1 | 80–105 | 155–173 | 543–565 | 657–675 | 764–784 | | | | |
| PY8_SOCMV | HYPOTHETICAL PROTEIN 8 | SOYBEAN CHLOROTIC MOTTLE VIRUS | 10–27 | | | | | | | | |
| PY97_ADE07 | HYPOTHETICAL 9 7 KD EARLY PROTEIN | HUMAN ADENOVIRUS TYPE 7 | 54–77 | | | | | | | | |
| PY9K2_SSV1 | HYPOTHETICAL 9 2 KD PROTEIN | SULFOLOBUS VIRUS-LIKE PARTICLE SSV1 | 16–41 | 62–77 | | | | | | | |
| PYAL1_EBV | HYPOTHETICAL BALF1 PROTEIN | EPSTEIN-BARR VIRUS (STRAIN B95-8) | 205–220 | | | | | | | | |
| PYB01_FOWPM | HYPOTHETICAL BAMHI-ORF1 PROTEIN | FOWLPOX VIRUS (ISOLATE HP-438[MUNICH]) | 354–374 | | | | | | | | |
| PYB07_FOWPM | HYPOTHETICAL BAMHI-ORF7 PROTEIN | FOWLPOX VIRUS (ISOLATE HP-438[MUNICH]) | 104–121 | | | | | | | | |
| PYB09_FOWPM | HYPOTHETICAL BAMHI-ORF9 PROTEIN | FOWLPOX VIRUS (ISOLATE HP-438[MUNICH]) | 49–67 | | | | | | | | |
| PYB10_FOWPM | HYPOTHETICAL BAMHI-ORF10 PROTEIN | FOWLPOX VIRUS (ISOLATE HP-438[MUNICH]) | 84–100 | | | | | | | | |
| PYB12_FOWPM | HYPOTHETICAL BAMHI-ORF12 PROTEIN | FOWLPOX VIRUS (ISOLATE HP-438[MUNICH]) | 114–134 | 154–169 | | | | | | | |
| PYBL2_SFV3L | BEL-2 PROTEIN | SIMIAN FOAMY VIRUS (TYPE 3/STRAIN LK3) | 113–128 | | | | | | | | |
| PYBL3_FOAMV | BEL-3 PROTEIN | HUMAN SPUMARETROVIRUS | 52–78 | | | | | | | | |
| PYDH1_HSVSC | HYP 28 7 KD PROTEIN IN DHFR 3'REGION | HERPESVIRUS SAIMIRI (SUBGROUP C/STRAIN 488) | 206–230 | | | | | | | | |
| PYDH3_HSVSC | HYP 9 5 KD PROTEIN IN DHFR 3'REGION | HERPESVIRUS SAIMIRI (SUBGROUP C/STRAIN 488) | 69–90 | | | | | | | | |
| PYEC4_EBV | HYPOTHETICAL EC-RF4 PROTEIN | EPSTEIN-BARR VIRUS (STRAIN B95-8) | 200–222 | | | | | | | | |
| PYGA1_HSVMB | HYPOTHETICAL 23 6 KD PROTEIN | MAREK'S DISEASE HERPESVIRUS (STRAIN BC-1) | 175–190 | | | | | | | | |
| PYGA1_HSVMM | HYPOTHETICAL 23 6 KD PROTEIN | MAREK'S DISEASE HERPESVIRUS (STRAIN MD5) | 175–190 | | | | | | | | |
| PYHL4_HCMVA | HYPOTHETICLA PROTEIN HHLF4 | HUMAN CYTOMEGALOVIRUS (STRAIN AD169) | 101–121 | | | | | | | | |
| PYHR3_VACCV | HYP HOST RANGE 27 4 KD PROTEIN | VACCINIA VIRUS (STRAIN WR) | 86–102 | | | | | | | | |
| PYIO2_CVMAS | HYP PROTEIN IN NUCLEOCAPSID ORF | MURINE CORONAVIRUS MHV | 141–156 | | | | | | | | |
| PYIOR_CVM1 | HYP PROTEIN IN NUCLEOCAPSID ORF | MURINE CORONAVIRUS MHV | 141–156 | | | | | | | | |
| PYIOR_CVMS | HYP PROTEIN IN NUCLEOCAPSID ORF | MURINE CORONAVIRUS MHV | 7–33 | | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYKR2_EBV | HYPOTHETICAL BKRF2 PROTEIN | EPSTEIN-BARR VIRUS (STRAIN B95-8) | 67–90 | | | | | | | | |
| PYL12_ADE41 | HYPOTHETICAL 8 0 KD PROTEIN | HUMAN ADENOVIRUS TYPE 41 | 53–73 | | | | | | | | |
| PYMR2_EBV | BMRF2 PROTEIN | EPSTEIN-BARR VIRUS (STRAIN B95-8) | 76–100 | 128–155 | 215–241 | 330–350 | | | | | |
| PYMSP_IRV22 | HYPOTHETICAL 15 9 KD PROTEIN | SIMULIUM IRIDESCENT VIRUS (INSECT IRIDESCENT VIRUS TYPE 22) | 23–46 | | | | | | | | |
| PYOR1_ADEG1 | HYPOTHETICAL PROTEIN | AVIAN ADENOVIRUS GAL1 (STRAIN PHELPS)(FOWL ADENOVIRUS 1) | 59–80 | | | | | | | | |
| PYOR1_COYMV | HYPOTHETICAL 23 KD PROTEIN | COMMELINA YELOW MOTTLE VIRUS | 56–83 | | | | | | | | |
| PYOR1_TTV1 | HYPOTHETICAL 7 9 KD PROTEIN | THERMOPROTEUS TENAX VIRUS 1 (STRAIN KRA1) | 13–40 | | | | | | | | |
| PYOR2_COYMV | HYPOTHETICAL 15 KD PROTEIN | COMMELINA YELLOW MOTTLE VIRUS | 23–49 | | | | | | | | |
| PYOR2_EAV | HYPOTHETICAL 25 6 KD PROTEIN | EQUINE ARTERITIS VIRUS | 165–192 | | | | | | | | |
| PYOR2_LELV | HYPOTHETICAL 28 4 KD PROTEIN | LELYSTAD VIRUS | 196–212 | | | | | | | | |
| PYOR3_LVX | HYPOTHETICAL 11 8 KD PROTEIN | LILY VIRUX X | 71–92 | | | | | | | | |
| PYOR3_NMV | HYPOTHETICAL 14 KD PROTEIN | NARCISSUS MOSAIC VIRUS | 7–30 | | | | | | | | |
| PYOR3_PVX | HYPOTHETICAL 12 KD PROTEIN | POTATO VIRUS X | 11–34 | | | | | | | | |
| PYOR3_PVXCP | HYPOTHETICAL 12 KD PROTEIN | POTATO VIRUS X (STRAIN CP) | 11–34 | | | | | | | | |
| PYOR3_WCMVM | HYPOTHETICAL 13 KD PROTEIN | WHITE CLOVER MOSAIC VIRUS (STRAIN M) | 9–29 | | | | | | | | |
| PYOR3_WCMVO | HYPOTHETICAL 13 KD PROTEIN | WHITE CLOVER MOSAIC VIRUS (STRAIN O) | 9–31 | | | | | | | | |
| PYOR5_ADEG1 | HYPOTHETICAL 31 5 KD PROTEIN | AVIAN ADENOVIRUS GAL1 (STRAIN PHELPS) (FOWL AND ADENOVIRUS 1) | 69–86 | | | | | | | | |
| PYOR5_EAV | HYPOTHETICAL 28 7 KD PROTEIN | EQUINE ARTERITIS VIRUS | 139–158 | | | | | | | | |
| PYOR6_NMV | HYPOTHETICAL 10 KD PROTEIN | NARCISSUS MOSAIC VIRUS | 10–26 | | | | | | | | |
| PYORL_TTV1 | HYPOTHETICAL 16 6 KD PROTEIN | THERMOPROTEUS TENAX VIRUS 1 (STRAIN KRA 1) | 13–32 | | | | | | | | |
| PYORL_TTV1 | HYPOTHETICAL 16 5 KD PROTEIN | THERMOPROTEUS TENAX VIRUS 1 (STRAIN KRA 1) | 16–39 | | | | | | | | |
| PYORM_TTV1 | HYPOTHETICAL 38 6 KD PROTEIN | THERMOPROTEUS TENAX VIRUS 1 (STRAIN KRA 1) | 82–102 | 233–256 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYORP_TTV1 | HYPOTHETICAL 20 2 KD PROTEIN | THERMOPROTEUS TEXAX VIRUS (STRAIN KRA1) | 91–115 | | | | | | | | |
| PYR24_RTBV | HYPOTHETICAL P24 PROTEIN | RICE TUNGRO BACILLIFORM VIRUS | 2–25 | 104–126 | | | | | | | |
| PYP24_RTBVP | HYPOTHETICAL P24 PROTEIN | RICE TUNGRO BACILLIFORM VIRUS (ISOLATE PHILIPPINES) | 2–25 | 104–126 | | | | | | | |
| PYP47_NPVAC | HYPOTHETICAL 43 5 KD PROTEIN | AUTOGRAPHA CALIFORNICA NUCLEAR POLYHEDROSIS VIRUS | 211–234 | | | | | | | | |
| PYP62_NPVOP | HYPOTHETICAL 12 2 KD PROTEIN | ORGYIA PSEUDOSUGATA MULTICAPSID POLYHEDROSIS VIRUS (OP | 82–108 | | | | | | | | |
| PYP63_NPVOP | HYPOTHETICAL 40 0 KD PROTEIN | ORGYIA PSEUDOSUGATA MULTICAPSID POLYHEDROSIS VIRUS (OP | 27–54 | 215–230 | | | | | | | |
| PYP7B_TNVD | HYPOTHETICAL P7B PROTEIN | TOBACCO NECROSIS VIRUS (STRAIN D) (TNV) | 13–31 | | | | | | | | |
| PYPO4_NPVLD | HYPOTHETICAL 8 5 KD PROTEIN | LYMANTRIA DISPAR MULTI-CAPSID NUCLEAR POLYHEDROSIS VIRUS | 16–35 | | | | | | | | |
| PYRF1_HSV6G | HYPOTHETICAL PROTEIN RF1 | HERPES SIMPLEX VIRUS (TYPE 6/STRAIN GS) | 42–66 | | | | | | | | |
| PYRF2_HSV6G | HYPOTHETICAL PROTEIN RF2 | HERPES SIMPLEX VIRUS (TYPE 6/STRAIN GS) | 55–74 | | | | | | | | |
| PYRF3_HSV6G | HYPOTHETICAL PROTEIN RF3 | HERPES SIMPLEX VIRUS (TYPE 6/STRAIN GS) | 32–56 | | | | | | | | |
| PYRP1_IRV6 | REPETITIVE PROTEIN ORF1 | CHILD IRIDESCENT VIRUS (CIV) (INSECT IRIDESCENT VIURS TYPE 6) | 20–43 | | | | | | | | |
| PYRP4_IRV6 | REPETITIVE PROTEIN ORF4 | CHILD IRIDESCENT VIRUS (CIV) (INSECT IRIDESCENT VIURS TYPE 6) | 44–69 | | | | | | | | |
| PYRP5_IRV6 | REPETITIVE PROTEIN ORF5 | CHILD IRIDESCENT VIRUS (CIV) (INSECT IRIDESCENT VIURS TYPE 6) | 98–123 | 179–204 | 260–285 | | | | | | |
| PYRR1_EBV | HYPOTHETICAL BRRF1 PROTEIIN | EPSTEIN-BARR VIRUS (STRAIN B95-8) | 199–223 | | | | | | | | |
| PYRR2_EBV | HYPOTHETICAL BRRF1 PROTEIIN | EPSTEIN-BARR VIRUS (STRAIN B95-8) | 164–182 | | | | | | | | |
| PYsR1_EBV | HYPOTHETICAL BRRF1 PROTEIIN | EPSTEIN-BARR VIRUS (STRAIN B95-8) | 92–113 | | | | | | | | |
| PYtR1_EBV | HYPOTHETICAL BRRF1 PROTEIIN | EPSTEIN-BARR VIRUS (STRAIN B95-8) | 383–401 | | | | | | | | |
| PYUB2_NPVOP | HYPOTHETICAL 24 0 KD PROTEIN | ORGYIA PSEUDOTSUGATA MULTICAPSID POLYHEDROSIS VIRUS (OP | 133–152 | | | | | | | | |
| PYVAE_VACCC | HYPOTHETICAL 18 2 KD PROTEIN | VACCINIA VIRUS (STRAIN COPENHAGEN) | 82–99 | 140–156 | | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYVAF_VACCC | HYPOTHETICAL 8 4 KD PROTEIN | VACCINIA VIRUS (STRAIN COPENHAGEN) | 17–40 | 51–68 | | | | | | | |
| PYVAL_VACCV | HYPOTHETICAL 9 9 KD PROTEIN | VACCINIA VIRUS (STRAIN WR), AND VACCINIA VIRUS (STRAIN COPE | 21–43 | | | | | | | | |
| PYVAT_VACCV | HYPOTHETICAL 8 9 KD PROTEIN | VACCINIA VIRUS (STRAIN WR), AND VACCINIA VIRUS (STRAIN COPE | 28–46 | | | | | | |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PY6K0_SSV1 | HYPOTHETICAL 6 0 KD PROTEIN |

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|
| PYIO2_CVMA5 | HYPOTHETICAL PROTEIN IN NUCLEOCAPSID ORF | MURINE CORONAVIRUS M

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|

TABLE XIII-continued

SEARCH RESULTS SUMMARY FOR P12LZIPC MOTIF

| PCGENE FILE NAME | P12CTLZIP PROTEIN | All Viruses (No Bacteriophages) VIRUS | AREA 1 | AREA 2 | AREA 3 | AREA 4 | AREA 5 | AREA 6 | AREA 7 | AREA 8 | AREA 9 |
|---|---|---|---|---|---|---|---|---|---|---|---|

TABLE XIV

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PPOL2__TBRVS | RNA2 POLYPROTEIN | TOMATO BLACK RING VIRUS (STRAIN S) (TBRV) | 617–651 | 1041–1077 | | | | | |
| PPOL2__TRSVR | RNA2 POLYPROTEIN | TOMATO RINGSPOT VIRUS (ISOLATE RASPBERRY)(TOMRSV) | 316–347 | | | | | | |
| PPOLG__BOVEV | GENOME POLYPROTEIN | BOVINE ENTEROVIRUS (STRAIN VG-5-27)(BEV) | 1833–1866 | 2001–2037 | | | | | |
| PPOLG__BVDVN | GENOME POLYPROTEIN | BOVINE VIRAL DIARRHEA VIRUS (ISOLATE NADL) | 102–135 | 1650–1678 | 3220–3248 | | | | |
| PPOLG__BVDVS | GENOME POLYPROTEIN | BOVINE VIRAL DIARRHEA VIRUS (STRAIN SD-1) | 102–135 | 1560–1588 | 3130–3158 | | | | |
| PPOLG__BYMV | GENOME POLYPROTEIN | BEAN YELLOW MOSAIC VIRUS | 226–255 | | | | | | |
| PPOLG__COXA2 | GENOME POLYPROTEIN | COXSACKIEVIRUS A21 (STRAIN COE) | 1120–1157 | | | | | | |
| PPOLG__COXA3 | GENOME POLYPROTEIN | COXSACKIEVIRUS A23 (ECHO 9 VIRUS)(EC-9-V) | 67–99 | | | | | | |
| PPOLG__COXA9 | GENOME POLYPROTEIN | COXSACKIEVIRUS A9 (STRAIN GRIGGS) | 1601–1633 | | | | | | |
| PPOLG__COXB1 | GENOME POLYPROTEIN | COXSACKIEVIRUS B1 | 1582–1614 | | | | | | |
| PPOLG__COXB3 | GENOME POLYPROTEIN | COXSACKIEVIRUS B3 | 1585–1617 | | | | | | |
| PPOLG__COXB4 | GENOME POLYPROTEIN | COXSACKIEVIRUS B4 | 1583–1615 | | | | | | |
| PPOLG__COXB5 | GENOME POLYPROTEIN | COXSACKIEVIRUS B5 | 835–868 | 1585–1617 | | | | | |
| PPOLG__DEN1S | GENOME POLYPROTEIN | DENGUE VIRUS TYPE 1 (STRAIN SINGAPORE S275/90) | 1111–1145 | 1485–1519 | 2401–2434 | | | | |
| PPOLG__DEN1W | GENOME POLYPROTEIN | DENGUE VIRUS TYPE 1 (STRAIN WESTERN PACIFIC) | 1112–1146 | | | | | | |
| PPOLG__DEN26 | GENOME POLYPROTEIN | DENGUE VIRUS TYPE 2 (STRAIN 16681) | 61–95 | 1112–1146 | | | | | |
| PPOLG__DEN27 | GENOME POLYPROTEIN | DENGUE VIRUS TYPE 2 (STRAIN 16681-PDK53) | 61–95 | 1112–1146 | | | | | |
| PPOLG__DEN2D | GENOME POLYPROTEIN | DENGUE VIRUS TYPE 2 (STRAIN D2-04) | 61–95 | | | | | | |
| PPOLG__DEN2J | GENOME POLYPROTEIN | DENGUE VIRUS TYPE 2 (STRAIN JAMAICA) | 61–95 | 1112–1146 | | | | | |
| PPOLG__DEN2N | GENOME POLYPROTEIN | DENGUE VIRUS TYPE 2 (STRAIN NEW GUINEA C) | 364–398 | | | | | | |
| PPOLG__DEN2P | GENOME POLYPROTEIN | DENGUE VIRUS TYPE 2 (STRAIN PR 159/S1) | 61–95 | 1112–1146 | | | | | |
| PPOLG__DEN2T | GENOME POLYPROTEIN | DENGUE VIRUS TYPE 2 (STRAIN TONGA 1974 | 832–866 | | | | | | |
| PPOLG__DEN3 | GENOME POLYPROTEIN | DENGUE VIRUS TYPE 3 | 61–95 | 2399–2432 | | | | | |
| PPOLG__DEN4 | GENOME POLYPROTEIN | DENGUE VIRUS TYPE 4 | 60–94 | | | | | | |
| PPOLG__ECHG | GENOME POLYPROTEIN | ECHOVIRUS II (STRAIN GREGORY) | 774–806 | | | | | | |
| PPOLG__EMCV | GENOME POLYPROTEIN | ENCEPHALOMYOCARDITIS VIRUS | 1194–1226 | 1463–1501 | | | | | |
| PPOLG__EMCVB | GENOME POLYPROTEIN | ENCEPHALOMYOCARDITIS VIRUS (STRAIN EMC-B NONDIABETOGENIC) | 1196–1228 | 1465–1503 | | | | | |
| PPOLG__EMCVD | GENOME POLYPROTEIN | ENCEPHALOMYOCARDITIS VIRUS (STRAIN EMC-D DIABETOGENIC) | 1196–1228 | 1465–1503 | | | | | |
| PPOLG__FMDVI | GENOME POLYPROTEIN | FOOT-AND-MOUTH DISEASE VIRUS (STRAIN A10-61)(APHTHOVIRUS A) | 1036–1064 | 1098–1133 | 1167–1199 | 1465–1501 | | | |
| PPOLG__FMDVA | GENOME POLYPROTEIN | FOOT-AND-MOUTH DISEASE VIRUS (STRAIN A12)(APHTHOVIRUS A) | 1036–1074 | 1098–1133 | 1167–1199 | 1465–1501 | | | |
| PPOLG__FMDVO | GENOME POLYPROTEIN | FOOT-AND-MOUTH DISEASE VIRUS (STRAINS OIK AND OIBFS) | 1098–1133 | 1167–1199 | 1465–1501 | | | | |
| PPOLG__HCV1 | GENOME POLYPROTEIN | HEPATITIS C VIRUS (ISOLATE 1)(HCV) | 1640–1670 | | | | | | |
| PPOLG__HCVA | GENOME POLYPROTEIN | HOG CHOLERA VIRUS (STRAIN ALFORT)(SWINE FEVER VIRUS) | 1363–1393 | 1560–1588 | 3131–3159 | | | | |
| PPOLG__HDVB | GENOME POLYPROTEIN | HOG CHOLERA VIRUS (STRAIN BRESCIA)(SWINE FEVER VIRUS) | 102–135 | 1560–1588 | 3131–3159 | | | | |
| PPOLG__HDVBK | GENOME POLYPROTEIN | HEPATITIS C VIRUS (ISOLATE BK)(HCV) | 1640–1670 | | | | | | |

TABLE XIV-continued

| PCGENE FILE NAME | P23CTLZIP PROTEIN | SEARCH RESULTS SUMMARY FOR P23TLZIPC MOTIF All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PPOLG_HDVH | GENOME POLYPROTEIN | HEPATITIS C VIRUS (ISOLATE H)(HCV) | 1640–1670 | | | | | | |
| PPOLG_HDVH4 | GENOME POLYPROTEIN | HEPATITIS C VIRUS (ISOLATE HCV-476)(HCV) | 254–291 | | | | | | |
| PPOLG_HCVJ6 | GENOME POLYPROTEIN | HEPATITIS C VIRUS (ISOLATE HC-J6)(HCV) | 711–742 | | | | | | |
| PPOLG_HCVJ8 | GENOME POLYPROTEIN | HEPATITIS C VIRUS (ISOLATE HC-J8)(HCV) | 711–742 | 1893–1924 | | | | | |
| PPOLG_HCVJA | GENOME POLYPROTEIN | HEPATITIS C VIRUS (ISOLATE JAPANESE)(HCV) | 1640–1670 | | | | | | |
| PPOLG_HCVJT | GENOME POLYPROTEIN | HEPATITIS C VIRUS (ISOLATE HC-JT)(HCV) | 1640–1670 | | | | | | |
| PPOLG_HCVTW | GENOME POLYPROTEIN | HEPATITIS C VIRUS (ISOLATE TAIWAN)(HCV | 1640–1670 | | | | | | |
| PPOLG_HPAV2 | GENOME POLYPROTEIN | HEPATITIS A VIRUS (STRAIN 24A) | 1514–1550 | 2068–2099 | | | | | |
| PPOLG_HPAV4 | GENOME POLYPROTEIN | HEPATITIS A VIRUS (STRAIN 43C) | 1514–1550 | 2068–2099 | | | | | |
| PPOLG_HPAV8 | GENOME POLYPROTEIN | HEPATITIS A VIRUS (STRAIN 18F) | 1514–1550 | 2068–2099 | | | | | |
| PPOLG_HPAVH | GENOME POLYPROTEIN | HEPATITIS A VIRUS (STRAIN HM-175) | 1515–1551 | 2069–2100 | | | | | |
| PPOLG_HPAVL | GENOME POLYPROTEIN | HEPATITIS A VIRUS (STRAIN LA) | 1515–1551 | 2069–2100 | | | | | |
| PPOLG_HPAVM | GENOME POLYPROTEIN | HEPATITIS A VIRUS (STRAIN MBB) | 1515–1551 | 2069–2100 | | | | | |
| PPOLG_HPAVS | GENOME POLYPROTEIN | SIMIAN HEPATITIS A VIRUS (STRAIN AGM-27) | 831–868 | 1517–1553 | | | | | |
| PPOLG_HPB14 | GENOME POLYPROTEIN | HUMAN RHINOVIRUS 14 (HRV-14) | 1094–1132 | 2005–2041 | | | | | |
| PPOLG_HRV1B | GENOME POLYPROTEIN | HUMAN RHINOVIRUS 1B (HRV-1B) | 1453–1485 | 1816–1849 | 1983–2019 | | | | |
| PPOLG_HRV2 | GENOME POLYPROTEIN | HUMAN RHINOVIRUS 2 (HRV-2) | 1446–1475 | 1809–1842 | 1976–2012 | | | | |
| PPOLG_HRV89 | GENOME POLYPROTEIN | HUMAN RHINOVIRUS 89 (HRV-89) | 1460–1492 | 1823–1856 | 1990–2026 | | | | |
| PPOLG_HUEV7 | GENOME POLYPROTEIN | HUMAN ENTEROVIRUS 70 (STRAIN J670/71 | 1108–1145 | | | | | | |
| PPOLG_IBDVO | STRUCTURAL POLYPROTEIN | AVIAN INFECTIOUS BURSAL DISEASE VIRUS (STRAIN OH) | 222–260 | | | | | | |
| PPOLG_JAEV1 | GENOME POLYPROTEIN | JAPANESE ENCEPHALITIS VIRUS (STRAIN SA-14) | 61–95 | 1233–1269 | 1516–1549 | 2779–2813 | 3274–3311 | | |
| PPOLG_JAEV5 | GENOME POLYPROTEIN | JAPANESE ENCEPHALITIS VIRUS (STRAIN SA(V)) | 61–95 | 1233–1269 | 1516–1549 | 2779–2813 | 3274–3311 | | |
| PPOLG_JAEVJ | GENOME POLYPROTEIN | JAPANESE ENCEPHALITIS VIRUS (STRAIN JAOARS982) | 61–95 | 1233–1269 | 1516–1549 | 2779–2813 | 3274–3311 | | |
| PPOLG_JAEVN | GENOME POLYPROTEIN | JAPANESE ENCEPHALITIS VIRUS (STRAIN NAKAYAMA) | 1161–1197 | | | | | | |
| PPOLG_KUNJM | GENOME POLYPROTEIN | KUNJIN VIRUS (STRAIN MRM61C) | 61–95 | 561–594 | 3275–3312 | | | | |
| PPOLG_LANVT | GENOME POLYPROTEIN | LANGAT VIRUS (STAIN TP21) | 1157–1188 | 1519–1551 | 2230–2264 | 2366–2398 | 3095–3132 | | |
| PPOLG_MCFA | GENOME POLYPROTEIN | MOSQUITO CELL FUSING AGENT (CFA FLAVIVIRUS) | 1174–1206 | 1330–1359 | | | | | |
| PPOLG_MDMV | GENOME POLYPROTEIN | MAIZE DWARF MOSAIC VIRUS (MDMV) | 322–351 | | | | | | |
| PPOLG_MVEV | GENOME POLYPROTEIN | MURRAY VALLEY ENCEPHALITIS VIRUS | 61–95 | 1305–1342 | | | | | |
| PPOLG_OMV | GENOME POLYPROTEIN | ORNITHOGALUM MOSAIC VIRUS | 344–376 | | | | | | |
| PPOLG_PEMVC | GENOME POLYPROTEIN | PEPPER MOTTLE VIRUS (CALIFORNIA ISOLATE)(PEMV) | 826–859 | 1086–1124 | | | | | |
| PPOLG_POL1M | GENOME POLYPROTEIN | POLIOVIRUS TYPE 1 (STRAIN MAHONEY) | 1121–1158 | | | | | | |

TABLE XIV-continued

| PCGENE FILE NAME | P23CTLZIP PROTEIN | SEARCH RESULTS SUMMARY FOR P23TLZIPC MOTIF All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PPOLG_POL1S | GENOME POLYPROTEIN | POLIOVIRUS TYPE 1 (STRAIN SABIN) | 1122–1159 | | | | | | |
| PPOLG_POL2L | GENOME POLYPROTEIN | POLIOVIRUS TYPE 2 (STRAIN LANSING) | 1120–1157 | | | | | | |
| PPOLG_POL2W | GENOME POLYPROTEIN | POLIOVIRUS TYPE 2 (STRAIN W-2) | 1120–1157 | | | | | | |
| PPOLG_POL32 | GENOME POLYPROTEIN | POLIOVIRUS TYPE 3 (STRAIN 23127) | 1119–1156 | | | | | | |
| PPOLG_POL3L | GENOME POLYPROTEIN | POLIOVIRUS TYPE 3 (STRAINS P3/LEON/37 AND P3/LEON 12A[1]B) | 1119–1156 | | | | | | |
| PPOLG_PPVD | GENOME POLYPROTEIN | PLUM POX POTYVIRUS (STRAIN D)(PPV) | 2960–2991 | 3084–3113 | | | | | |
| PPOLG_PPVEA | GENOME POLYPROTEIN | PLUM POX POTYVIRUS (STRAIN EL AMAR)(PPV) | 1337–1368 | 1461–1490 | | | | | |
| PPOLG_PPVNA | GENOME POLYPROTEIN | PLUM POX POTYVIRUS (ISOLATE NAT)(PPV) | 2944–2975 | 3068–3097 | | | | | |
| PPOLG_PPVRA | GENOME POLYPROTEIN | PLUM POX POTYVIRUS (STRAIN RANKOVIC)(PPV) | 2959–2990 | 3083–3112 | | | | | |
| PPOLG_PSBMV | GENOME POLYPROTEIN | PEA SEED-BORNE MOSAIC VIRUS (STRAIN DPDI) | 931–966 | 1411–1445 | 3149–3178 | | | | |
| PPOLG_PVYHU | GENOME POLYPROTEIN | POTATO VIRUS Y (STRAIN HUNGARIAN)(PVY) | 1302–1336 | 3004–3033 | | | | | |
| PPOLG_PVYN | GENOME POLYPROTEIN | POTATO VIRUS Y (STRAIN N)(PVY) | 1302–1336 | | | | | | |
| PPOLG_PYFVI | GENOME POLYPROTEIN | PARSNIP YELLOW FLECK VIRUS (ISOLATE P-121)(PYI-V) | 230–262 | 1110–1139 | 1903–1931 | | | | |
| PPOLG_SBMVN | GENOME POLYPROTEIN | SOYBEAN MOSAIC VIRUS (STRAIN N) | 245–274 | | | | | | |
| PPOLG_STEVM | GENOME POLYPROTEIN | ST LOUIS ENCEPHALITIS VIRUS (STRAIN M51-7) | 61–95 | 1301–1331 | | | | | |
| PPOLG_SUMVS | GENOME POLYPROTEIN | SUGARCANE MOSAIC VIRUS (STRAIN SC) | 307–336 | | | | | | |
| PPOLG_SVDVH | GENOME POLYPROTEIN | SWINE VESICULAR DISEASE VIRUS (STRAIN H/3'76) | 1585–1617 | | | | | | |
| PPOLG_SVDVU | GENOME POLYPROTEIN | SWINE VESICULAR DISEASE VIRUS (STRAIN UKG/27/72) | 1585–1617 | | | | | | |
| PPOLG_TBEVS | GENOME POLYPROTEIN | TICK-BORNE ENCEPHALITIS VIRUS (STRAIN SOFJIN)(TBEV) | 835–869 | 1157–1188 | 2366–2398 | 3093–3130 | | | |
| PPOLG_TBEVW | GENOME POLYPROTEIN | TICK-BORNE ENCEPHALITIS VIRUS (WESTERN SUBTYPE)(THEV) | 1157–1188 | 2366–2398 | 3095–3132 | | | | |
| PPOLG_TEV | GENOME POLYPROTEIN | TOBACCO ETCH VIRUS (TEV) | 827–865 | 2998–3027 | | | | | |
| PPOLG_TMEVB | GENOME POLYPROTEIN | THEILER'S MURINE ENCEPHALOMYELITIS VIRUS (STRAIN BEAN 8386) | 1074–1102 | 1193–1221 | 1470–1508 | 1908–1939 | | | |
| PPOLG_TMEVD | GENOME POLYPROTEIN | THEILER'S MURINE ENCEPHALOMYELITIS VIRUS (STRAIN DA) | 1072–1100 | 1191–1219 | 1468–1506 | 1906–1937 | | | |
| PPOLG_TMEVG | GENMOE POLYPROTEIN | THEILER'S MURINE ENCEPHALOMYELITIS VIRUS (STRAIN GDVH) | 1074–1102 | 1193–1221 | 1407–1508 | 1908–1939 | | | |
| PPOLG_TUMV | GENOME POLYPROTEIN | TURNIP MOSAIC VIRUS (TUMV) | 1573–1602 | | | | | | |
| PPOLG_TVMV | GENOME POLYPROTEIN | TOBACCO VEIN MOTTLING VIRUS (TVMV) | 2698–2733 | | | | | | |
| PPOLG_WMV2 | GENOME POLYPROTEIN | WATERMELON MOSAIC VIRUS II | 958–987 | | | | | | |
| PPOLG_WNV | GENOME POLYPROTEIN | WEST NILE VIRUS | 61–95 | 557–590 | 3272–3309 | | | | |
| PPOLG_YEFV1 | GENOME POLYPROTEIN | YELLOW FEVER VIRUS (STRAIN 17D) | 1157–1186 | 1228–1266 | 1495–1531 | 2308–2340 | 3092–3127 | | |
| PPOLG_YEFV2 | GENOME POLYPROTEIN | YELLOW FEVER VIRUS (STRAIN PASTEUR 17D-204) | 1157–1186 | 1228–1266 | 1495–1531 | 2308–2340 | 3092–3127 | | |
| PPOLG_ZYMV | GENOME POLYPROTEIN | ZUCCHINI YELLOW MOSAIC VIRUS (ZYMV) | 329–358 | | | | | | |
| PPOLH_POLIM | GENOME POLYPROTEIN | POLIOVIRUS TYPE I (STRAIN MAHONEY) | 1122–1159 | | | | | | |
| PPOLH_WMV2 | GENOME POLYPROTEIN | WATERMELON MOSAIC VIRUS II | 244–273 | | | | | | |
| PPOLN_EEVVT | NONSTRUCTURAL POLYPROTEIN | VENEZUELAN EQUINE ENCEPHALITIS VIRUS (STRAIN TRINIDAD DONKEY) | 613–648 | 1436–1468 | | | | | |
| PPOLN_FCVC6 | NON-STRUCTURAL POLYPROTEIN | FELINE CALICIVIRUS (STRAIN DFI/68 FIV)(FCV) | 327–365 | | | | | | |
| PPOLN_FCVF4 | NON-STRUCTURAL POLYPROTEIN | FELINE CALICIVIRUS (STRAIN JAPANESE F4)(FCV) | 300–333 | | | | | | |
| PPOLN_FCVF9 | NON-STRUCTURAL POLYPROTEIN | FELINE CALICIVIRUS (STRAIN F9)(FCV) | 803–841 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PPOLN_HEVBU | NON-STRUCTURAL POLYPROTEIN | HEPATITIS E VIRUS (STRAIN BURMA)(HEV) | 1618–1652 | | | | | | |
| PPOLN_HEVME | NON-STRUCTURAL POLYPROTEIN | HEPATITIS E VIRUS (STRAIN MEXICO)(HEV) | 1616–1650 | | | | | | |
| PPOLN_HEVMY | NON-STRUCTURAL POLYPROTEIN | HEPATITIS E VIRUS (STRAIN MYANMAR)(HEV) | 1618–1652 | | | | | | |
| PPOLN_HEVPA | NON-STRUCTURAL POLYPROTEIN | HEPATITIS E VIRUS (STRAIN PAKISTAN)(HEV) | 1617–1651 | | | | | | |
| PPOLN_MIDDV | NONSTRUCTURAL POLYPROTEIN | MIDDELBURG VIRUS | 25–57 | | | | | | |
| PPOLN_ONRVG | NONSTRUCTURAL POLYPROTEIN | O'NYONG-NYONG VIRUS (STRAIN GULU)(ONN) | 1144–1180 | 1404–1439 | | | | | |
| PPOLN_RHDV | NON-STRUCTURAL POLYPROTEIN | RABBIT HEMORRHAGIC DISEASE VIRUS (RHDV | 299–337 | 1562–1594 | | | | | |
| PPOLN_SFV | NONSTRUCTURAL POLYPROTEIN | SEMLIKI FOREST VIRUS | 1146–1175 | 1406–1441 | | | | | |
| PPOLN_SINDO | NONSTRUCTURAL POLYPROTEIN | SINDBIS VIRUS (SUBTYPE OCKELBO/STRAIN EDSBYN 82-5) | 1454–1486 | | | | | | |
| PPOLN_SINDV | NONSTRUCTURAL POLYPROTEIN | SINDBIS VIRUS (STRAIN HRSP) | 1454–1486 | | | | | | |
| PPOLS_EEEV | STRUCTURAL POLYPROTEIN | EASTERN EQUINE ENCEPHALITIS VIRUS | 524–556 | | | | | | |
| PPOLS_EEEV3 | STRUCTURAL POLYPROTEIN | EASTERN EQUINE ENCEPHALITIS VIRUS (STRAIN VA33[TEN BROECK]) | 525–557 | | | | | | |
| PPOLS_EEVV8 | STRUCTURAL POLYPROTEIN | VENEZUELAN EQUINE ENCEPHALITIS VIRUS (STRAIN TC-83) | 1203–1239 | | | | | | |
| PPOLS_EEVVT | STRUCTURAL POLYPROTEIN | VENEZUELAN EQUINE ENCEPHALITIS VIRUS (STRAIN TRINIDAD DONKEY) | 1203–1239 | | | | | | |
| PPOLS_ONNVG | STRUCTURAL POLYPROTEIN | O'NYONG-NYONG VIRUS (STRAIN GULU)(ONN) | 1150–1182 | 1201–1235 | | | | | |
| PPOLS_RRVN | STRUCTURAL POLYPROTEIN | ROSS RIVER VIRUS (STRAIN NB5092)(RRV) | 1216–1250 | | | | | | |
| PPOLS_RRVT | STRUCTURAL POLYPROTEIN | ROSS RIVER VIRUS (STRAIN T48)(RRV) | 1216–1250 | | | | | | |
| PPOLS_SFV | STRUCTURAL POLYPROTEIN | SEMLIKI FOREST VIRUS | 1215–1251 | | | | | | |
| PPOLS_SINDO | STRUCTURAL POLYPROTEIN | SINDBIS VIRUS (SUBTYPE OCKELBO/STRAIN EDSBYN 82-5) | 1197–1233 | | | | | | |
| PPOLS_SINDV | STRUCTURAL POLYPROTEIN | SINDBIS VIRUS (STRAINS HRSP AND HRLP) | 1197–1233 | | | | | | |
| PPOLS_WEEV | STRUCTURAL POLYPROTEIN | WESTERN EQUINE ENCEPHALITIS VIRUS | 1188–1224 | | | | | | |
| PPOL_BIV06 | POL POLYPROTEIN | BOVINE IMMUNODEFICIENCY VIRUS (ISOLATE 106)(BIV) | 742–773 | | | | | | |
| PPOL_BIV27 | POL POLYPROTEIN | BOVINE IMMUNODEFICIENCY VIRUS (ISOLATE 127)(BIV) | 742–773 | | | | | | |
| PPOL_BLVAU | POL POLYPROTEIN | BOVINE LEUKEMIA VIRUS (AUSTRALIAN ISOLATE)(BLV) | 343–374 | | | | | | |
| PPOL_CAEVC | POL POLYPROTEIN | CAPRINE ARTHRITIS ENCEPHALITIS VIRUS (STRAIN CORK)(CAEV) | 206–240 | 322–355 | | | | | |
| PPOL_COYMV | PUTATIVE POLYPROTEIN | COMMELINA YELLOW MOTTLE VIRUS (COYMV) | 1234–1267 | 1484–1518 | 1750–1788 | 1800–1831 | | | |
| PPOL_EIAV9 | POL POLYPROTEIN | EQUINE INFECTIOUS ANEMIA VIRUS (CLONE 1369)(EIAV) | 166–198 | 506–539 | | | | | |
| PPOL_EIAVC | POL POLYPROTEIN | EQUINE INFECTIOUS ANEMIA VIRUS (CLONE CL22)(EIAV) | 166–198 | 506–539 | | | | | |
| PPOL_EIAVY | POL POLYPROTEIN | EQUINE INFECTIOUS ANEMIA VIRUS (ISOLATE WYOMING)(EIAV) | 166–198 | 505–538 | | | | | |
| PPOL_FOAMV | POL POLYPROTEIN | HUMAN SPUMARETROVIRUS (FOAMY VIRUS) | 126–154 | | | | | | |
| PPOL_GALV | POL POLYPROTEIN | GIBBON APE LEUKEMIA VIRUS | 348–378 | | | | | | |
| PPOL_HTL1A | POL POLYPROTEIN | HUMAN T-CELL LEUKEMIA VIRUS TYPE 1 (STRAIN ATK)(HTLV-1) | | 657–688 | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PPOL_HTL1C | POL POLYPROTEIN | HUMAN T-CELL LEUKEMIA VIRUS TYPE 1 (CARIBBEAN ISOLATE)(HTLV-1) | 657–688 | | | | | | |
| PPOL_HV1A2 | POL POLYPROTEIN | HUMAN IMMUNODEFICIENCY VIRUS TYPE 1 (ARV2/SF2 ISOLATE)(HIV-1) | 331–364 | 500–537 | | | | | |
| PPOL_HV1B1 | POL POLYPROTEIN | HUMAN IMMUNODEFICIENCY VIRUS TYPE 1 (BH10 ISOLATE)(HIV-1) | 343–376 | 512–549 | | | | | |
| PPOL_HV1B5 | POL POLYPROTEIN | HUMAN IMMUNODEFICIENCY VIRUS TYPE 1 (BH5 ISOLATE)(HIV-1) | 343–376 | 512–549 | | | | | |
| PPOL_HV1BR | POL POLYPROTEIN | HUMAN IMMUNODEFICIENCY VIRUS TYPE 1 (BRU ISOLATE)(HIV-1) | 343–376 | 512–549 | | | | | |
| PPOL_HV1EL | POL POLYPROTEIN | HUMAN IMMUNODEFICIENCY VIRUS TYPE 1 (ELI ISOLATE)(HIV-1) | 330–363 | 499–536 | | | | | |
| PPOL_HV1H2 | POL POLYPROTEIN | HUMAN IMMUNODEFICIENCY VIRUS TYPE 1 (HXB2 ISOLATE)(HIV-1) | 331–364 | 500–537 | | | | | |
| PPOL_HV1JR | POL POLYPROTEIN | HUMAN IMMUNODEFICIENCY VIRUS TYPE 1 (JRCSF ISOLATE)(HIV-1) | 335–368 | 504–541 | | | | | |
| PPOL_HV1MA | POL POLYPROTEIN | HUMAN IMMUNODEFICIENCY VIRUS TYPE 1 (MAL ISOLATE)(HIV-1) | 330–363 | | | | | | |
| PPOL_HV1MN | POL POLYPROTEIN | HUMAN IMMUNODEFICIENCY VIRUS TYPE 1 (MN ISOLATE)(HIV-1) | 343–367 | 503–540 | | | | | |
| PPOL_HV1N5 | POL POLYPROTEIN | HUMAN IMMUNODEFICIENCY VIRUS TYPE 1 (NEW YORK-5 ISOLATE)(HIV-1) | 331–364 | 500–537 | | | | | |
| PPOL_HV1ND | POL POLYPROTEIN | HUMAN IMMUNODEFICIENCY VIRUS TYPE 1 (NDK ISOLATE)(HIV-1) | 330–363 | 499–536 | | | | | |
| PPOL_HV1OY | POL POLYPROTEIN | HUMAN IMMUNODEFICIENCY VIRUS TYPE 1 (OYI ISOLATE)(HIV-1) | 331–364 | 500–537 | | | | | |
| PPOL_HV1PV | POL POLYPROTEIN | HUMAN IMMUNODEFICIENCY VIRUS TYPE 1 (PV22 ISOLATE)(HIV-1) | 343–376 | 512–549 | | | | | |
| PPOL_HV1RH | POL POLYPROTEIN | HUMAN IMMUNODEFICIENCY VIRUS TYPE 1 (RF/HAT ISOLATE)(HIV-1) | 330–363 | 499–536 | | | | | |
| PPOL_HV1U4 | POL POLYPROTEIN | HUMAN IMMUNODEFICIENCY VIRUS TYPE 1 (STRAIN UGANDAN/ISOLATE | 330–363 | 499–536 | | | | | |
| PPOL_HV1Z2 | POL POLYPROTEIN | HUMAN IMMUNODEFICIENCY VIRUS TYPE 1 (Z2/CDC-Z34 ISOLATE)(HIV-1) | 330–363 | 499–536 | | | | | |
| PPOL_HV2CA | POL POLYPROTEIN | HUMAN IMMUNODEFICIENCY VIRUS TYPE 2 (ISOLATE CAM2)(HIV-2) | 353–386 | | | | | | |
| PPOL_HV2NZ | POL POLYPROTEIN | HUMAN IMMUNODEFICIENCY VIRUS TYPE 2 (ISOLATE NH-Z)(HIV-2) | 353–386 | | | | | | |
| PPOL_HV2RO | POL POLYPROTEIN | HUMAN IMMUNODEFICIENCY VIRUS TYPE 2 (ISOLATE ROD)(HIV-2) | 354–387 | | | | | | |
| PPOL_IPHA | PUTATIVE POL POLYPROTEIN | HAMSTER INTRACISTERNAL A-PARTICLE (IAP-H18 | 460–496 | | | | | | |
| PPOL_JSRV | POL POLYPROTEIN | SHEEP PULMONARY ADENOMATOSIS VIRUS | 186–220 | | | | | | |
| PPOL_MPMV | POL POLYPROTEIN | SIMIAN MASON-PFIZER VIRUS (MPMV) | 650–681 | | | | | | |
| PPOL_OMVVS | POL POLYPROTEIN | OVINE LENTIVIRUS (STRAIN SA-OMVV) | 61–98 | 102–130 | 182–216 | 298–331 | | | |
| PPOL_RTBV | POLYPROTEIN | RICE TUNGRO BACILLIFORM VIRUS (RTBV) | 788–824 | 891–919 | 1399–1433 | | | | |

TABLE XIV-continued

| PCGENE FILE NAME | P23CTLZIP PROTEIN | SEARCH RESULTS SUMMARY FOR P23TLZIPC MOTIF All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PPOL_RTBVP | POLYPROTEIN | RICE TUNGRO BACILLIFORM VIRUS (ISOLATE PHILIPPINES)(RTBV) | 788–824 | 891–919 | 1399–1433 | | | | |
| PPOL_SFV3L | POL POLYPROTEIN | SIMIAN FOAMY VIRUS (TYPE 3/STRAIN LK3)(SFV-3) | 337–365 | | | | | | |
| PPOL_SIVCE | POL POLYPROTEIN | CHIMPANZEE IMMUNODEFICIENCY VIRUS (SIV(CPZ))(CIV) | 355–388 | 524–561 | | | | | |
| PPOL_SOCMV | ENZYMATIC POLYPROTEIN | SOYBEAN CHLOROTIC MOTTLE VIRUS | 17–55 | 524–561 | | | | | |
| PPOL_SRV | POL POLYPROTEIN | SIMIAN RETROVIRUS SRV-1 | 650–681 | | | | | | |
| PPOL_VILV | POL POLYPROTEIN | VISNA LENTIVIRUS (STRAIN 1514) | 80–117 | 201–235 | 317–350 | | | | |
| PPOL_VILV1 | POL POLYPROTEIN | VISNA LENTIVIRUS (STRAIN 1514/CLONE LV1-1KS1) | 80–117 | 317–350 | | | | | |
| PPOL_VILV2 | POL POLYPROTEIN | VISNA LENTIVIRUS (STRAIN 1514/CLONE LV1-1KS2) | 80–117 | 201–235 | 317–350 | | | | |
| PPP41_HSV6G | PHOSPHOPROTEIN P41 | HERPES SIMPLEX VIRUS (TYPE 6/STRAIN GS) | 60–91 | | | | | | |
| PPTP_NPVAC | PROTEIN-TYROSINE PHOSPHATASE | AUTOGRAPHA CALIFORNICA NUCLEAR POLYHEDROSIS VIRUS | 53–85 | | | | | | |
| PREEP_CSV | REPEAT ELEMENT PROTEIN | CAMPOLETIS SONORENSIS VIRUS (CSV) | 113–149 | | | | | | |
| PREV_BIV27 | REV PROTEIN | BOVINE IMMUNODEFICIENCY VIRUS (ISOLATE 127)(BIV) | 74–109 | | | | | | |
| PREV_EIAV9 | REV PROTEIN | EQUINE INFECTIOUS ANEMIA VIRUS (CLONE 1369)(EIAV) | 44–79 | | | | | | |
| PREV_EIAVC | REV PROTEIN | EQUINE INFECTIOUS ANEMIA VIRUS (CLONE CL22)(EIAV) | 44–79 | | | | | | |
| PREV_EIAVY | REV PROTEIN | EQUINE INFECTIOUS ANEMIA VIRUS (ISOLATE WYOMING)(EIAV) | 74–109 | | | | | | |
| PREV_SIVAT | REV PROTEIN | SIMIAN IMMUNODEFICIENCY VIRUS (TYP-1 ISOLATE)(SIV-AGM) | 25–62 | | | | | | |
| PRIRI_ASFM2 | RIBONUCLEOSIDE-DIPHOSPHATE REDUCTASE LARGE CH | AFRICAN SWINE FEVER VIRUS (ISOLATE MALAWILIL 20/1)(ASFV) | 630–666 | | | | | | |
| PRIRI_HCMVA | RIBONUCLEOSIDE-DIPHOSPHATE REDUCTASE LARGE CH | HUMAN CYTOMEGALOVIRUS (STRAIN AD169) | 279–311 | 393–430 | 449–477 | | | | |
| PRIRI_HSVEB | RIBONUCLEOSIDE-DIPHOSPHATE REDUCTASE LARGE CH | EQUINE HERPESVIRUS TYPE 1 (STRAIN AB4P)(EHV-1) | 60–92 | 503–531 | | | | | |
| PRIRI_VACCC | RIBONUCLEOSIDE-DIPHOSPHATE REDUCTASE LARGE CH | VACCINIA VIRUS (STRAIN COPENHAGEN) | 203–235 | | | | | | |
| PRIRI_VACCV | RIBONUCLEOSIDE-DIPHOSPHATE REDUCTASE LARGE CH | VACCINIA VIRUS (STRAIN WR) | 203–235 | | | | | | |
| PRIRI_VARV | RIBONUCLEOSIDE-DIPHOSPHATE REDUCTASE LARGE CH | VARIOLA VIRUS | 203–235 | | | | | | |
| PRIRI_V2VD | RIBONUCLEOSIDE-DIPHOSPHATE REDUCTASE LARGE CH | VARICELLA-ZOSTER VIRUS (STRAIN DUMAS)(V2V) | 34–72 | 221–254 | 488–516 | | | | |
| PRMIL_AVEVR | RMIL SERINE/THREONINE-PROTEIN KINASE TRANSFORM | AVIAN ROUS-ASSOCIATED VIRUS TYPE 1 | 149–177 | | | | | | |
| PRMIL_AVII1 | RMIL SERINE/THREONINE-PROTEIN KINASE TRANSFORM | AVIAN RETROVIRUS IC10 | 133–161 | | | | | | |
| PRP94_VACCV | RNA-POLYMERASE-ASSOCIATED TRANSCRIPTION SPECIF | VACCINIA VIRUS (STRAIN WR), AND VACCINIA VIRUS (STRAIN COPENHAGE | 399–427 | | | | | | |
| PRP94_VARV | RNA-POLYMERASE-ASSOCIATED TRANSCRIPTION SPECIF | VARIOLA VIRUS | 399–427 | | | | | | |

TABLE XIV-continued

| PCGENE FILE NAME | P23CTLZIP PROTEIN | SEARCH RESULTS SUMMARY FOR P23TLZIPC MOTIF All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PRPO1_VACCV | DNA-DIRECTED RNA POLY-MERASE 147 KD POLYPEPTIDE | VACCINIA VIRUS (STRAIN WR) | 1005–1033 | | | | | | |
| PRPO2_CAPVK | DNA-DIRECTED RNA POLY-MERASE 132 KD POLYPEPTIDE | CAPRIPOXVIRUS (STRAIN KS-1) | 297–333 | 667–696 | | | | | |
| PRPO2_COWPX | DNA-DIRECTED RNA POLY-MERASE 132 KD POLYPEPTIDE | COWPOX VIRUS (CPV) | 202–236 | 542–578 | | | | | |
| PRPO2_VACCV | DNA-DIRECTED RNA POLY-MERASE 132 KD POLYPEPTIDE | VACCINIA VIRUS (STRAIN WR), AND VACCINIA VIRUS (STRAIN COPENHAE | 202–236 | 542–578 | | | | | |
| PRPO2_VARV | DNA-DIRECTED RNA POLY-MERASE 132 KD POLYPEPTIDE | VARIOLA VIRUS | 202–236 | 542–578 | | | | | |
| PRPO7_VACCV | DNA-DIRECTED RNA POLY-MERASE 19 KD POLYPEPTIDE | VACCINIA VIRUS (STRAIN WR), AND VACCINIA VIRUS (STRAIN COPENHAGE | 38–66 | | | | | | |
| PRPO7_VARV | DNA-DIRECTED RNA POLY-MERASE 19 KD POLYPEPTIDE | VARIOLA VIRUS | 38–66 | | | | | | |
| PRPO8_FOWP1 | DNA-DIRECTED RNA POLY-MERASE 18 KD POLYPEPTIDE | FOWLPOX VIRUS (STRAIN FP-1) | 57–88 | | | | | | |
| PRPOA_LEVL | RNA-DIRECTED RNA POLY-MERASE | LELYSTAD VIRUS (LV) | 1233–1268 | 3133–3163 | 3426–3457 | | | | |
| PRPOL_EAV | RNA-DIRECTED RNA POLY-MERASE | EQUINE ARTERITIS VIRUS (EAV) | 171–207 | 3041–3072 | | | | | |
| PRRP1_DHVI1 | RNA-DIRECTED RNA POLY-MERASE SUBUNIT P1 | DHORI VIRUS (STRAIN INDIAN/1313/61)(DHO) | 96–125 | 199–234 | | | | | |
| PRRP1_IAVI7 | RNA-DIRECTED RNA POLY-MERASE SUBUNIT P1 | INFLUENZA A VIRUS (STRAIN A/VICTORIA/3/75) | 138–170 | | | | | | |
| PRRP1_INCJJ | RNA-DIRECTED RNA POLY-MERASE SUBUNIT P1 | INFLUENZA C VIRUS (STRAIN C/JJ/50) | 564–598 | | | | | | |
| PRRP2_IAANN | RNA-DIRECTED RNA POLY-MERASE SUBUNIT P2 | INFLUENZA A VIRUS (STRAIN A/ANN ARBOR/6/60) | 398–435 | 484–518 | | | | | |
| PRRP2_IADH2 | RNA-DIRECTED RNA POLY-MERASE SUBUNIT P2 | INFLUENZA A VIRUS (STRAIN A/DUCK/HOKKAIDO/8/80) | 484–518 | | | | | | |
| PRRP2_IAFPR | RNA-DIRECTED RNA POLY-MERASE SUBUNIT P2 | INFLUENZA A VIRUS (STRAIN A/FOWL PLAGUE VIRUS/ROSTOCK/34) | 484–518 | | | | | | |
| PRRP2_IAGU2 | RNA-DIRECTED RNA POLY-MERASE SUBUNIT P2 | INFLUENZA A VIRUS (STRAIN A/GULL/MARYLAND/704/77) | 484–518 | | | | | | |
| PRRP2_IAHLO | RNA-DIRECTED RNA POLY-MERASE SUBUNIT P2 | INFLUENZA A VIRUS (STRAIN A/EQUINE/LONDON/1416/73) | 484–518 | | | | | | |
| PRRP2_IAHTE | RNA-DIRECTED RNA POLY-MERASE SUBUNIT P2 | INFLUENZA A VIRUS (STRAIN A/EQUINE/TENNESSEE/5/86) | 484–518 | | | | | | |
| PRRP2_IAKOR | RNA-DIRECTED RNA POLY-MERASE SUBUNIT P2 | INFLUENZA A VIRUS (STRAIN A/KOREA/426/68) | 484–518 | | | | | | |
| PRRP2_IALE1 | RNA-DIRECTED RNA POLY-MERASE SUBUNIT P2 | INFLUENZA A VIRUS (STRAIN A/LENINGRAD/134/57) | 484–518 | | | | | | |
| PRRP2_IALE2 | RNA-DIRECTED RNA POLY-MERASE SUBUNIT P2 | INFLUENZA A VIRUS (STRAIN A/LENINGRAD/134/17/57) | 484–518 | | | | | | |
| PRRP2_IAMAN | RNA-DIRECTED RNA POLY-MERASE SUBUNIT P2 | INFLUENZA A VIRUS (STRAIN A/MALLARD/NEW YORK/6750/78) | 484–518 | | | | | | |

TABLE XIV-continued

| PCGENE FILE NAME | P23CTLZIP PROTEIN | All Viruses (no bacteriophages) VIRUS | SEARCH RESULTS SUMMARY FOR P23TLZIPC MOTIF AREA 1 | AREA 2 | AREA 3 | AREA 4 | AREA 5 | AREA 6 | AREA 7 |
|---|---|---|---|---|---|---|---|---|---|
| PRRP2_IANT6 | RNA-DIRECTED RNA POLYMERASE SUBUNIT P2 | INFLUENZA A VIRUS (STRAIN A/NT/60/68) | 484–518 | | | | | | |
| PRRP2_IAPI0 | RNA-DIRECTED RNA POLYMERASE SUBUNIT P2 | INFLUENZA A VIRUS (STRAIN A/PINTAIL/ALBERTA/119/79) | 484–518 | | | | | | |
| PRRP2_IAPUE | RNA-DIRECTED RNA POLYMERASE SUBUNIT P2 | INFLUENZA A VIRUS (STRAIN A/PUERTO RICO/8/34) | 484–518 | | | | | | |
| PRRP2_IARUD | RNA-DIRECTED RNA POLYMERASE SUBUNIT P2 | INFLUENZA A VIRUS (STRAIN A/RUDDY TURNSTONE/NEW JERSEY/47/85) | 484–518 | | | | | | |
| PRRP2_IASIN | RNA-DIRECTED RNA POLYMERASE SUBUNIT P2 | INFLUENZA A VIRUS (STRAIN A/SINGAPORE/1/57) | 484–518 | | | | | | |
| PRRP2_IATKM | RNA-DIRECTED RNA POLYMERASE SUBUNIT P2 | INFLUENZA A VIRUS (STRAIN A/TURKEY/MINNESOTA/833/80) | 484–518 | | | | | | |
| PRRP2_IAVI7 | RNA-DIRECTED RNA POLYMERASE SUBUNIT P2 | INFLUENZA A VIRUS (STRAIN A/VICTORIA/3/75) | 484–518 | | | | | | |
| PRRP2_IAWIL | RNA-DIRECTED RNA POLYMERASE SUBUNIT P2 | INFLUENZA A VIRUS (STRAIN A/WILSON-SMITH/33) | 484–518 | | | | | | |
| PRRP2_IAZH2 | RNA-DIRECTED RNA POLYMERASE SUBUNIT P2 | INFLUENZA A VIRUS (STRAIN A/SWINE/HONG KONG/81/78) | 484–518 | | | | | | |
| PRRP2_IAZH3 | RNA-DIRECTED RNA POLYMERASE SUBUNIT P2 | INFLUENZA A VIRUS (STRAIN A/SWINE/HONG KONG/126/82) | 484–518 | | | | | | |
| PRRP2_IAZI1 | RNA-DIRECTED RNA POLYMERASE SUBUNIT P2 | INFLUENZA A VIRUS (STRAIN A/SWINE/IOWA/15/30) | 484–518 | | | | | | |
| PRRP2_IAZTF | RNA-DIRECTED RNA POLYMERASE SUBUNIT P2 | INFLUENZA A VIRUS (STRAIN A/SWINE/TENNESSEE/26/77) | 484–518 | | | | | | |
| PRRP3_IABUD | RNA-DIRECTED RNA POLYMERASE SUBUNIT P3 | INFLUENZA A VIRUS (STRAIN A/BUDGERIGAR/HOKKAIDO/1/77) | 515–553 | 585–613 | | | | | |
| PRRP3_IAFPR | RNA-DIRECTED RNA POLYMERASE SUBUNIT P3 | INFLUENZA A VIRUS (STRAIN A/FOWL PLAGUE VIRUS/ROSTOCK/34) | 585–613 | | | | | | |
| PRRP3_IAFPW | RNA-DIRECTED RNA POLYMERASE SUBUNIT P3 | INFLUENZA A VIRUS (STRAIN A/FOWL PLAGUE VIRUS/WEYBRIDGE) | 579–613 | | | | | | |
| PRRP3_IAGUE | RNA-DIRECTED RNA POLYMERASE SUBUNIT P3 | INFLUENZA A VIRUS (STRAIN A/GULL/MARYLAND/704/77) | 585–613 | | | | | | |
| PRRP3_IAGUA | RNA-DIRECTED RNA POLYMERASE SUBUNIT P3 | INFLUENZA A VIRUS (STRAIN A/GULL/ASTRAKHAN/227/84) | 585–613 | | | | | | |
| PRRP3_IAHPR | RNA-DIRECTED RNA POLYMERASE SUBUNIT P3 | INFLUENZA A VIRUS (STRAIN A/EQUINE/PRAGUE/1/56) | 585–613 | | | | | | |
| PRRP3_IAMAN | RNA-DIRECTED RNA POLYMERASE SUBUNIT P3 | INFLUENZA A VIRUS (STRAIN A/MALLARD/NEW YORK/6750/78) | 585–613 | | | | | | |
| PRRP3_IARUD | RNA-DIRECTED RNA POLYMERASE SUBUNIT P3 | INFLUENZA A VIRUS (STRAIN A/RUDDY TURNSTONE/NEW JERSEY/47/85) | 585–613 | | | | | | |
| PRRP3_IASE2 | RNA-DIRECTED RNA POLYMERASE SUBUNIT P3 | INFLUENZA A VIRUS (STRAIN A/SEAL/MASSACHUSETTS/133/82) | 585–613 | | | | | | |
| PRRP3_IATKM | RNA-DIRECTED RNA POLYMERASE SUBUNIT P3 | INFLUENZA A VIRUS (STRAIN A/TURKEY/MINNESOTA/833/80) | 585–613 | | | | | | |
| PRRP3_IAZI1 | RNA-DIRECTED RNA POLYMERASE SUBUNIT P3 | INFLUENZA A VIRUS (STRAIN A/SWINE/IOWA/15/30) | 585–613 | | | | | | |

TABLE XIV-continued

| PCGENE FILE NAME | P23CTLZIP PROTEIN | All Viruses (no bacteriophages) VIRUS | SEARCH RESULTS SUMMARY FOR P23TLZIPC MOTIF AREA 1 | AREA 2 | AREA 3 | AREA 4 | AREA 5 | AREA 6 | AREA 7 |
|---|---|---|---|---|---|---|---|---|---|
| PRRP3_IAZTE | RNA-DIRECTED RNA POLY-MERASE SUBUNIT P3 | INFLUENZA A VIRUS (STRAIN A/SWINE/TENNESSE/24/77) | 735–769 | | | | | | |
| PRRP3_INBAC | RNA-DIRECTED RNA POLY-MERASE SUBUNIT P3 | INFLUENZA B VIRUS (STRAIN B/ANN ARBOR/1/66[COLD-ADAPTED]) | 735–769 | | | | | | |
| PRRP3_INBAD | RNA-DIRECTED RNA POLY-MERASE SUBUNIT P3 | INFLUENZA B VIRUS (STRAIN B/ANN ARBOR/1/66[WILD-TYPE]) | 735–769 | | | | | | |
| PRRP3_INCBE | RNA-DIRECTED RNA POLY-MERASE SUBUNIT P3 | INFLUENZA C VIRUS (STRAIN C/BERLIN/1/85) | 609–641 | | | | | | |
| PRRP3_INCJJ | RNA-DIRECTED RNA POLY-MERASE SUBUNIT P3 | INFLUENZA C VIRUS (STRAIN C/JJ/50) | 609–641 | | | | | | |
| PRRP3_THOGV | RNA-DIRECTED RNA POLY-MERASE SUBUNIT P3 | THOGOTO VIRUS (THO) | 109–145 | 324–356 | | | | | |
| PRRPA_CVH22 | RNA-DIRECTED RNA POLY-MERASE | HUMAN CORONAVIRUS (STRAIN 229E) | 410–443 | 712–745 | 1262–1295 | 1963–1999 | 2078–2112 | 2474–2508 | 3153–3191 |
| PRRPA_CVMJH | RNA-DIRECTED RNA POLY-MERASE | MURINE CORONAVIRUS MHV (STRAIN JHM) | 708–740 | 3544–3577 | 3757–3785 | 3933–3961 | | | |
| PRRPB_BEV | RNA-DIRECTED RNA POLY-MERASE | BERNE VIRUS (BEV) | 941–969 | 2137–2169 | 2178–2206 | | | | |
| PRRPB_CVMA5 | RNA-DIRECTED RNA POLY-MERASE | MURINE CORONAVIRUS MHV (STRAIN A59) | 346–380 | 684–714 | 1689–1722 | 2698–2730 | | | |
| PRRPB_CVMJH | RNA-DIRECTED RNA POLY-MERASE | MURINE CORONAVIRUS MHV (STRAIN JHM) | 346–380 | 684–714 | 1687–1720 | 2356–2391 | 2696–2728 | | |
| PRRPB_CVPFS | RNA-DIRECTED RNA POLY-MERASE | PORCINE TRANSMISSIBLE GASTROENTERITIS CORONAVIRUS | 173–207 | 322–350 | 482–515 | | | | |
| PRRPB_CVPR8 | RNA-DIRECTED RNA POLY-MERASE | PORCINE RESPIRATORY CORONAVIRUS | 80–113 | | | | | | |
| PRRPB_IBVB | RNA-DIRECTED RNA POLY-MERASE | AVIAN INFECTIOUS BRONCHITIS VIRUS (STRAIN BEAUDETTE)(IBV) | 636–670 | | | | | | |
| PRRPL_BUNYW | RNA POLYMERASE | BUNYAMWERA VIRUS | 303–331 | 1096–1128 | | | | | |
| PRRPL_HANTV | RNA POLYMERASE | HANTAAN VIRUS (STRAIN 76-118) (KOREAN HEMORRHAGIC FEVER VIRUS) | 1938–1971 | | | | | | |
| PRRPL_HRSVA | RNA POLYMERASE BETA SUBUNIT | HUMAN RESPIRATORY SYNCYTIAL VIRUS (STRAIN A2) | 892–922 | 1181–1213 | | | | | |
| PRRPL_MABVM | RNA-DIRECTED RNA POLY-MERASE | MARBURG VIRUS (STRAIN MUSOKE) | 144–176 | 698–736 | 1042–1074 | 1797–1832 | | | |
| PRRPL_MABVP | RNA-DIRECTED RNA POLY-MERASE | MARBURG VIRUS (STRAIN POPP) | 144–176 | 698–736 | 1042–1074 | 2223–2253 | | | |
| PRRPL_MEASE | RNA POLYMERASE BETA SUBUNIT | MEASLES VIRUS (STRAIN EDMONSTON) | 193–227 | 647–683 | 788–825 | 1160–1192 | 1886–1914 | | |
| PRRPL_MUMPM | RNA POLYMERASE BETA SUBUNIT | MUMPS VIRUS (STRAIN MIYAHARA VACCINE) | 1882–1913 | | | | | | |
| PRRPL_NDVB | RNA POLYMERASE BETA SUBUNIT | NEWCASTLE DISEASE VIRUS (STRAIN BEAUDETTE C/45)(NDV) | 626–661 | 1571–1603 | | | | | |
| PRRPL_PI2HT | RNA POLYMERASE BETA SUBUNIT | HUMAN PARAINFLUENZA 2 VIRUS (STRAIN TOSHIBA)(PIV-2) | 268–305 | 558–595 | 654–688 | 1562–1599 | 1881–1912 | 2025–2053 | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PRRPL_PI3H4 | RNA POLYMERASE BETA SUBUNIT | HUMAN PARAINFLUENZA 3 VIRUS (STRAIN NIH 47885) | 41–76 | 735–764 | 784–814 | 2111–2139 | | | |
| PRRPL_RABVP | RNA POLYMERASE BETA SUBUNIT | RABIES VIRUS (STRAIN PV) | 60–90 | 804–837 | 1365–1394 | 1930–1962 | | | |
| PRRPL_RABVS | RNA POLYMERASE BETA SUBUNIT | RABIES VIRUS (STRAIN SAD B19) | 60–90 | 804–837 | 1365–1394 | 1930–1962 | | | |
| PRRPL_RDV | RNA-DIRECTED RNA POLYMERASE | RICE DWARF VIRUS (RDV) | 1293–1323 | | | | | | |
| PRRPL_RVFVZ | RNA-DIRECTED RNA POLYMERASE | RIFT VALLEY FEVER VIRUS (STRAIN ZH-548 M12)(RVFV) | 1018–1055 | 2009–2044 | | | | | |
| PRRPL_SEND5 | RNA POLYMERASE BETA SUBUNIT | SENDAI VIRUS (STRAIN Z/HOST MUTANTS) | 194–231 | 233–269 | 735–764 | 784–814 | 2140–2177 | | |
| PRRPL_SENDE | RNA POLYMERSE BETA SUBUNIT | SENDAI VIRUS (STRAIN ENDERS) | 14–51 | 53–89 | 555–584 | 1927–1955 | 1960–1997 | | |
| PRRPL_SENDZ | RNA POLYMERSE BETA SUBUNIT | SENDAI VIRUS (STRAIN Z) | 194–231 | 233–269 | 735–764 | 784–814 | 2140–2177 | | |
| PRRPL_SEOU8 | RNA-DIRECTED RNA POLYMERASE | SEOUL VIRUS (STRAIN 80-39) | 394–431 | 1938–1971 | 2081–2119 | | | | |
| PRRPL_SV5WR | RNA POLYMERSE BETA SUBUNIT | SIMIAN VIRUS 5 (STRAIN 21004-WR)(SV5) | 557–594 | 1094–1122 | 2020–2051 | | | | |
| PRRPL_SYNV | RNA POLYMERASE BETA SUBUNIT | SONCHUS YELLOW NET VIRUS (SYNV) | 126–164 | 605–634 | 820–856 | 918–951 | 1484–1517 | | |
| PRRPL_TSWVB | RNA-DIRECTED RNA POLYMERASE | TOMATO SPOTTED WILT VIRUS (BRAZILIAN ISOLATE CPNH1/BR-01)(TSWV) | 43–79 | 843–880 | 2266–2298 | 2369–2403 | 2481–2511 | 2805–2840 | |
| PRRPL_UUK | RNA POLYMERASE | UUKUNIEMI VIRUS (UUK) | 1017–1051 | 1147–1177 | 1293–1321 | 2060–2095 | | | |
| PRRPL_VSVIH | RNA POLYMERSE BETA SUBUNIT | VESICULAR STOMATITIS VIRUS | 209–246 | 312–349 | 1011–1039 | 1662–1697 | 1956–1989 | | |
| PRRPL_VSVIO | RNA POLYMERSE BETA SUBUNIT | VESICULAR STOMATITIS VIRUS | 1011–1039 | 1956–1989 | | | | | |
| PRRPL_VSVSJ | RNA POLYMERSE BETA SUBUNIT | VESICULAR STOMATITIS VIRUS (STRAIN SAN JUAN) | 138–171 | 209–246 | 312–349 | 961–999 | 1011–1039 | 1739–1772 | 2051–2087 |
| PRRPO_BWYVF | PUTATIVE RNA-DIRECTED RNA POLYMERASE | BEET WESTERN YELLOWS VIRUS (ISOLATE FL-1)(BWYV) | 346–374 | | | | | | |
| PRRPO_BYDVI | PUTATIVE RNA-DIRECTED RNA POLYMERASE | BARLEY YELLOW DWARF VIRUS (ISOLATE MAV-PS1)(BYDV) | 722–755 | | | | | | |
| PRRPO_BYDVP | PUTATIVE RNA-DIRECTED RNA POLYMERASE | BARLEY YELLOW DWARF VIRUS (ISOLATE PAV)(BYDV) | 722–755 | | | | | | |
| PRRPO_BYDVR | PUTATIVE RNA-DIRECTED RNA POLYMERASE | BARLEY YELLOW DWARF VIRUS (ISOLATE P-PAV)(BYDV) | 722–755 | | | | | | |
| PRRPO_CARMV | PROBABLE RNA-DIRECTED RNA POLYMERASE | CARNATION MOTTLE VIRUS (CARMV) | 4–37 | | | | | | |
| PRRPO_CGMVS | PUTATIVE RNA-DIRECTED RNA POLYMERASE | CUCUMBER GREEN MOTTLE MOSAIC VIRUS (WATERMELON STRAIN S14) | 443–481 | 725–755 | 1095–1132 | 1565–1597 | | | |
| PRRPO_CNV | PROBABLE RNA-DIRECTED RNA POLYMERASE | CUCUMBER NECROSIS VIRUS (CNV) | 470–501 | | | | | | |
| PRRPO_CRM | PROBABLE RNA-DIRECTED RNA POLYMERASE | CYMBIDIUM RINGSPOT VIRUS | 28–62 | 267–300 | 470–501 | | | | |
| PRRPO_IBDV5 | PUTATIVE RNA-DIRECTED RNA POLYMERASE | AVIAN INFECTIOUS BURSAL DISEASE VIRUS (STRAIN 52/70)(IBDV) | 186–218 | 274–302 | | | | | |
| PRRPO_IBDVA | PUTATIVE RNA-DIRECTED RNA POLYMERASE | AVIAN INFECTIOUS BURSAL DISEASE VIRUS | 260–288 | 511–543 | 599–627 | | | | |
| PRRPO_IPNVJ | PUTATIVE RNA-DIRECTED RNA POLYMERASE | INFECTIOUS PANCREATIC NECROSIS VIRUS (SEROTYPE JASPER) | 360–390 | 749–778 | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PRRPO_IPNVS | PUTATIVE RNA-DIRECTED RNA POLYMERASE | INFECTIOUS PANCREATIC NECROSIS VIRUS (SEROTYPE SP)(IPNV) | 360–390 | 749–778 | | | | | |
| PRRPO_LYCVA | RNA POLYMERASE | LYMPHOCYTIC CHORIOMENINGITIS VIRUS (STRAIN ARMSTRONG) | 109–137 | 263–291 | 2077–2106 | | | | |
| PRRPO_LYCVW | RNA POLYMERASE | LYMPHOCYTIC CHORIOMENINGITIS VIRUS (STRAIN WE) | 109–137 | | | | | | |
| PRRPO_MCMV | PROBABLE RNA-DIRECTED RNA POLYMERASE | MAIZE CHLOROTIC MOTTLE VIRUS (MCMV) | 16–48 | 53–81 | | | | | |
| PRRPO_PLRV1 | PUTATIVE RNA-DIRECTED RNA POLYMERASE | POTATO LEAFROLL VIRUS (STRAIN 1)(PLRV | 576–607 | | | | | | |
| PRRPO_PLRVW | PUTATIVE RNA-DIRECTED RNA POLYMERASE | POTATO LEAFROLL VIRUS (STRAIN WAGENINGEN)(PLRV) | 576–607 | | | | | | |
| PRRPO_PPMV5 | PUTATIVE RNA-DIRECTED RNA POLYMERASE | PEPPER MILD MOTTLE VIRUS (STRAIN SPAIN)(PPMV) | 375–407 | 702–730 | 859–891 | 1069–1106 | 1533–1565 | | |
| PRRPO_RCNMV | PUTATIVE RNA-DIRECTED RNA POLYMERASE | RED CLOVER NECROTIC MOSAIC VIRUS (RCNMV) | 278–314 | 320–353 | | | | | |
| PRRPO_REOVJ | RNA-DIRECTED RNA POLYMERASE | REOVIRUS (TYPE 2/STRAIN D5/JONES) | 284–315 | | | | | | |
| PRRPO_ROTBR | RNA-DIRECTED RNA POLYMERASE SUBUNIT VPI | BOVINE ROTAVIRUS (STRAIN RF) | 25–60 | 200–231 | 247–276 | | | | |
| PRRPO_ROTBU | RNA-DIRECTED RNA POLYMERASE SUBUNIT VPI | BOVINE ROTAVIRUS (STRAIN UR) | 200–231 | 247–276 | | | | | |
| PRRPO_ROTPG | RNA-DIRECTED RNA POLYMERASE SUBUNIT VPI | PORCINE ROTAVIRUS (STRAIN GOTTFRIED) | 200–231 | 247–276 | | | | | |
| PRRPO_ROTS1 | RNA-DIRECTED RNA POLYMERASE SUBUNIT VPI | SIMIAN II ROTAVIRUS (STRAIN SA11) | 25–60 | 200–231 | 247–276 | | | | |
| PRRPO_TACV | RNA POLYMERASE | TACARIBE VIRUS | 17–52 | 109–138 | 2078–2112 | | | | |
| PRRPO_TBSVC | PROBABLE RNA-DIRECTED RNA POLYMERASE | TOMATO BUSHY STUNT VIRUS (STRAIN CHERRY)(TBSV) | 470–501 | | | | | | |
| PRRPO_TCV | PROBABLE RNA-DIRECTED RNA POLYMERASE | TURNIP CRINKLE VIRUS (TCV) | 280–318 | | | | | | |
| PRRPO_TMGMV | PUTATIVE RNA-DIRECTED RNA POLYMERASE | TOBACCO MILD GREEN MOSAIC VIRUS (TMV STRAIN U2) | 67–97 | 128–159 | 209–244 | 376–406 | 450–483 | 855–887 | 1527–1559 |
| PRRPO_TMV | PUTATIVE RNA-DIRECTED RNA POLYMERASE | TOBACCO MOSAIC VIRUS (VULGARE)(TMV) | 128–159 | 376–406 | 700–728 | 1533–1565 | | | |
| PRRPO_TMVKR | PUTATIVE RNA-DIRECTED RNA POLYMERASE | TOBACCO MOSAIC VIRUS (STRAIN KOREAN)(TMV) | 128–159 | 376–406 | 700–728 | 1533–1565 | | | |
| PRRPO_TMVTO | PUTATIVE RNA-DIRECTED RNA POLYMERASE | TOBACCO MOSAIC VIRUS (STRAIN TOMATO/L)(TMV) | 128–159 | 376–406 | 700–728 | 857–889 | 1533–1565 | | |
| PRRPO_TNVA | RNA-DIRECTED RNA POLYMERASE | TOBACCO NECROSIS VIRUS (STRAIN A)(TNV) | 231–263 | | | | | | |
| PRRPO_TNVD | RNA-DIRECTED RNA POLYMERASE | TOBACCO NECROSIS VIRUS (STRAIN D)(TNV) | 5–40 | 234–270 | | | | | |
| PRRPP_CDVO | RNA POLYMERASE ALPHA SUBUNIT | CANINE DISTEMPER VIRUS (STRAIN ONDERSTEPOORT)(CDV) | 295–332 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PRRPP_MEASE | RNA POLYMERASE ALPHA SUBUNIT | MEASLES VIRUS (STRAIN EDMONSTON) | 295–332 | | | | | | |
| PRRPP_MEAS1 | RNA POLYMERASE ALPHA SUBUNIT | MEASLES VIRUS (STRAIN IP-3-CA) | 295–332 | | | | | | |
| PRRPP_MEASY | RNA POLYMERASE ALPHA SUBUNIT | MEASLES VIRUS (STRAIN YAMAGATA-1) | 295–332 | | | | | | |
| PRRPP_MUMP1 | RNA POLYMERASE ALPHA SUBUNIT | MUMPS VIRUS (STRAIN SBL-1) | 211–248 | | | | | | |
| PRRPP_MUMPE | RNA POLYMERASE ALPHA SUBUNIT | MUMPS VIRUS (STRAIN ENDERS) | 212–249 | | | | | | |
| PRRPP_MUMPM | RNA POLYMERASE ALPHA SUBUNIT | MUMPS VIRUS (STRAIN MIYAHARA VACCINE) | 212–249 | | | | | | |
| PRRPP_NDVA | RNA POLYMERASE ALPHA SUBUNIT | NEWCASTLE DISEASE VIRUS (STRAIN AUSTRALIA-VICTORIA/32)(NDV) | 220–255 | | | | | | |
| PRRPP_NDVB | RNA POLYMERASE ALPHA SUBUNIT | NEWCASTLE DISEASE VIRUS (STRAIN BEAUDETTE C/45)(NDV) | 220–255 | | | | | | |
| PRRPP_P12H | RNA POLYMERASE ALPHA SUBUNIT | HUMAN PARAINFLUENZA 2 VIRUS (PIV-2 STRAIN TOSHIBA)(PIV-2) | 216–253 | | | | | | |
| PRRPP_P12HT | RNA POLYMERASE ALPHA SUBUNIT | HUMAN PARAINFLUENZA 2 VIRUS (STRAIN TOSHIBA)(PIV-2) | 216–253 | | | | | | |
| PRRPP_P14HA | RNA POLYMERASE ALPHA SUBUNIT | HUMAN PARAINFLUENZA 4A VIRUS (STRAIN TOSHIBA)(PIV-4A) | 220–257 | 332–364 | | | | | |
| PRRPP_P14HB | RNA POLYMERASE ALPHA SUBUNIT | HUMAN PARAINFLUENZA 4B VIRUS (STRAIN 68-333)(PIV-4B) | 220–257 | 332–364 | | | | | |
| PRRPP_PIRYV | RNA POLYMERASE ALPHA SUBUNIT | PIRY VIRUS | 134–168 | | | | | | |
| PRRPP_RABVA | RNA POLYMERASE ALPHA SUBUNIT | RABIES VIRUS (STRAIN AVO1) | 216–244 | | | | | | |
| PRRPP_RABVC | RNA POLYMERASE ALPHA SUBUNIT | RABIES VIRUS (STRAIN CVS-11) | 216–244 | | | | | | |
| PRRPP_RABVE | RNA POLYMERASE ALPHA SUBUNIT | RABIES VIRUS (STRAIN ERA), AND RABIES VIRUS (STRAIN PM) | 216–244 | | | | | | |
| PRRPP_RABVP | RNA POLYMERASE ALPHA SUBUNIT | RABIES VIRUS (STRAIN PV) | 89–122 | 216–244 | | | | | |
| PRRPP_RABVS | RNA POLYMERASE ALPHA SUBUNIT | RABIES VIRUS (STRAIN SAD B19) | 216–244 | | | | | | |
| PRRPP_SEND5 | RNA POLYMERASE ALPHA SUBUNIT | SENDAI VIRUS (STRAIN Z/HOST MUTANTS) | 530–566 | | | | | | |
| PRRPP_SEND6 | RNA POLYMERASE ALPHA SUBUNIT | SENDAI VIRUS (STRAIN 6/94) | 530–566 | | | | | | |
| PRRPP_SENDF | RNA POLYMERASE ALPHA SUBUNIT | SENDAI VIRUS (STRAIN FUSHIMI) | 530–566 | | | | | | |
| PRRPP_SENDH | RNA POLYMERASE ALPHA SUBUNIT | SENDAI VIRUS (STRAIN HARRIS) | 530–566 | | | | | | |
| PRRPP_SENDZ | RNA POLYMERASE ALPHA SUBUNIT | SENDAI VIRUS (STRAIN Z) | 530–566 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PRRPP_SV5 | RNA POLYMERASE ALPHA SUBUNIT | SIMIAN VIRUS 5 (STRAIN W3)(SV5) | 199–236 | | | | | | |
| PRRPP_VSVJM | RNA POLYMERASE ALPHA SUBUNIT | VESICULAR STOMATITIS VIRUS (SEROTYPE NEW JERSEY/STRAIN MISSOUR | 198–230 | | | | | | |
| PRRPP_VSVJO | RNA POLYMERASE ALPHA SUBUNIT | VESICULAR STOMATITIS VIRUS (SEROTYPE NEW JERSEY/STRAIN OGDEN) | 197–230 | | | | | | |
| PSODC_VACCC | SUPEROXIDE DISMUTASE LIKE PROTEIN | VACCINIA VIRUS (STRAIN COPENAGEN) | 19–55 | | | | | | |
| PSODC_VACCV | SUPEROXIDE DISMUTASE LIKE PROTEIN | VACCINIA VIRUS (STRAIN WR) | 19–55 | | | | | | |
| PSODC_VARV | SUPEROXIDE DISMUTASE LIKE PROTEIN | VARIOLA VIRUS | 19–55 | | | | | | |
| PSPHR_AMEPV | SHEROIDIN | AMSACTA MOOREIENTOMOPOXVIRUS (AMEPV) | 58–86 | 138–172 | 627–659 | 671–701 | | | |
| PSPI1_MYXVL | SERPIN 1 | MYXOMA VIRUS (STRAIN LAUSANNE) | 167–200 | | | | | | |
| PSPI3_VACCC | SERINE PROTEINASE INHIBITOR 3 | VACCINIA VIRUS (STRAIN COPENHAGEN) | 112–140 | | | | | | |
| PSPI3_VACCV | SERINE PROTEINASE INHIBITOR 3 | VACCINIA VIRUS (STRAIN WR) | 112–140 | | | | | | |
| PSPI3_VARV | SERINE PROTEINASE INHIBITOR 3 | VARIOLA VIRUS | 116–144 | | | | | | |
| PIAG8_FOWPV | TRANS-ACTIVATOR PROTEIN FP0 | FOWLPOX VIRUS | 199–230 | | | | | | |
| PTALA_BFDV | LARGE T ANTIGEN | BUDGERIGAR FLEDGLING DISEASE VIRUS (BFDV) | 99–129 | 172–210 | 461–491 | | | | |
| PTAMI_POVHA | MIDDLE T ANTIGEN | HAMSTER POLYOMAVIRUS | 106–138 | | | | | | |
| PTAMI_POVM3 | MIDDLE T ANTIGEN | MOUSE POLYOMAVIRUS (STRAIN 3) | 43–80 | | | | | | |
| PTAMI_POVMA | MIDDLE T ANTIGEN | MOUSE POLYOMAVIRUS (STRAIN A2) | 43–80 | | | | | | |
| PTAMI_POVMC | MIDDLE T ANTIGEN | MOUSE POLYOMAVIRUS (STRAIN CRAWFORD SMALL-PLAQUE) | 43–80 | | | | | | |
| PTASM_POVBA | SMALL T ANTIGEN | POLYOMAVIRUS BK (STRAIN AS) | 130–162 | | | | | | |
| PTASM_POVBK | SMALL T ANTIGEN | POLYOMAVIRUS BK | 130–162 | | | | | | |
| PTASM_POVHA | SMALL T ANTIGEN | HAMSTER POLYOMAVIRUS | 106–138 | | | | | | |
| PTASM_POVMA | SMALL T ANTIGEN | MOUSE POLYOMAVIRUS (STRAIN A2) | 43–80 | | | | | | |
| PTASM_SV40 | SMALL T ANTIGEN | SIMIAN VIRUS 40 (SV40) | 132–164 | | | | | | |
| PTEGU_EBV | LARGE TEGUMENT PROTEIN | EPSTEIN-BARR VIRUS (STRAIN B95-8)(HUMAN HERPESVIRUS 4) | 143–173 | 1469–1503 | 1791–1819 | 3102–3137 | | | |
| PTEGU_HCMVA | PROBABLE LARGE TEGUMENT PROTEIN | HUMAN CYTOMEGALOVIRUS (STRAIN AD169) | 161–192 | 699–736 | 812–840 | 2199–2228 | | | |
| PTEGU_HSV6G | LARGE TEGUMENT PROTEIN | HERPES SIMPLEX VIRUS (TYPE 6/STRAIN GS) | 222–259 | 566–601 | 615–643 | 1436–1469 | 2037–2072 | | |
| PTEGU_HSVEB | LARGE TEGUMENT PROTEIN | EQUINE HERPESVIRUS TYPE 1 (STRAIN AB4P)(EHV-1) | 265–297 | 569–589 | 1072–1106 | 3363–3392 | | | |
| PTEGU_HSVSA | PROBABLE LARGE TEGUMENT PROTEIN | HERPESVIRUS SAIMIRI (STRAIN 11) | 467–505 | 714–751 | 823–861 | 926–960 | 1503–1536 | 2421–2457 | |
| PTERM_ADE07 | DNA TERMINAL PROTEIN | HUMAN ADENOVIRUS TYPE 7 | 369–400 | | | | | | |
| PTMAF_AVIS4 | TRANSFORMING PROTEIN MAP | AVIAN MUSCULOAPONEUROTIC FIBROSARCOMA VIRUS A542 | 230–267 | | | | | | |
| PTOP2_ASFB7 | DNA TOPOISOMERASE II | AFRICAN SWINE FEVER VIRUS (STRAIN BA71V) | 119–153 | 1105–1142 | | | | | |
| PTOP2_ASFM2 | DNA TOPOISOMERASE II | AFRICAN SWINE FEVER VIRUS (ASFV)(ISOLATE MALAWILIL 20/1)(ASFV) | 119–153 | 1104–1141 | | | | | |
| PTREL_AVIRE | REL TRANSFORMING PROTEIN | AVIAN RETICULOENDOTHELIOSIS VIRUS | 189–226 | | | | | | |
| PTYSY_V2VD | THYMIDYLATE SYNTHASE | VARICELLA-ZOSTER VIRUS (STRAIN DUMAS)(VZV) | 121–156 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PUIL_HSV6U | PROTEIN IL | HERPES SIMPLEX VIRUS (TYPE 6/ STRAIN UGANDA-1102) | 171–203 | | | | | | |
| PUDPE_NPVAC | ECDYSTEROID UDP-GLUCOS-YLTRANSFERASE PRECURSO | AUTOGRAPHA CALIFORNICA NUCLEAR POLY-HEDROSIS VIRUS (ACMNPV) | 185–219 | 387–425 | 452–484 | | | | |
| PUL02_HCMVA | HYPOTHETICAL PROTEIN UL2 | HUMAN CYTOMEGALOVIRUS (STRAIN AD169) | 25–59 | | | | | | |
| PUL06_EBV | VIRION PROTEIN BDRF1 | EPSTEIN-BARR VIRUS (STRAIN B95-8)(HUMAN HERPESVIRUS 4) | 355–386 | | | | | | |
| PUL06_HSVI1 | VIRION PROTEIN UL6 | HERPES SIMPLEX VIRUS (TYPE 1/STRAIN 17) | 404–436 | | | | | | |
| PUL06_HSVEB | VIRION GENE 56 PROTEIN | EQUINE HERPESVIRUS TYPE 1 (STRAIN AB4P)(EHV-1) | 222–251 | 437–475 | | | | | |
| PUL06_HSVSA | VIRION GENE 43 PROTEIN | HERPESVIRUS SAIMIRI (STRAIN 11) | 299–330 | | | | | | |
| PUL06_VZVD | VIRION GENE 54 PROTEIN | VARICELLA-ZOSTER VIRUS (STRAIN DUMAS)(VZV) | 223–252 | 502–530 | | | | | |
| PUL07_HCMVA | HYPOTHETICAL PROTEIN UL7 | HUMAN CYTOMEGALOVIRUS (STRAIN AD169) | 186–216 | | | | | | |
| PUL07_HSVEB | GENE 55 PROTEIN | EQUINE HERPESVIRUS TYPE 1 (STRAIN AB4P)(EHV-1) | Nov-39 | | | | | | |
| PUL08_HCMVA | HYPOTHETICAL PROTEIN UL8 | HUMAN CYTOMEGALOVIRUS (STRAIN AD169) | 65–96 | | | | | | |
| PUL08_HSVI1 | PROTEIN UL8 | HERPES SIMPLEX VIRUS (TYPE 1/STRAIN 17) | 614–648 | | | | | | |
| PUL08_VZVD | GENE 52 PROTEIN | VARICELLA-ZOSTER VIRUS (STRAIN DUMAS)(VZV) | 227–255 | | | | | | |
| PUL09_HSVI1 | ORIGIN OF REPLICATION BINDING PROTEIN | HERPES SIMPLEX VIRUS (TYPE 1/STRAIN 17) | 678–713 | | | | | | |
| PUL09_VZVD | ORIGIN OF REPLICATION BINDING PROTEIN | VARICELLA-ZOSTER VIRUS (STRAIN DUMAS)(VZV) | 168–204 | | | | | | |
| PUL14_PRVN3 | UL14 PROTEIN HOMOLOG | PSEUDORABIES VIRUS (STRAIN NIA-3)(PRV) | 40–76 | | | | | | |
| PUL16_H5VI1 | PROTEIN UL16 | HERPES SIMPLEX VIRUS (TYPE 1/STRAIN 17) | 22–52 | | | | | | |
| PUL17_HSV6U | PROTEIN 10R | HERPES SIMPLEX VIRUS (TYPE 6/STRAIN UGANDA-1102) | 302–339 | | | | | | |
| PUL21_HSVEB | GENE 40 PROTEIN | EQUINE HERPESVIRUS TYPE 1 (STRAIN AB4P)(EHV-1) | 294–328 | | | | | | |
| PUL21_PRVN3 | PROTEIN UL21 HOMOLOG | PSEUDORABIES VIRUS (STRAIN NIA-3)(PRV) | 242–271 | | | | | | |
| PUL21_VZVD | GENE 38 PROTEIN | VARICELLA-ZOSTER VIRUS (STRAIN DUMAS)(VZV) | 56–92 | 375–412 | | | | | |
| PUL24_HCMVA | HYPOTHETICAL PROTEIN UL24 | HUMAN CYTOMEGALOVIRUS (STRAIN AD169) | 52–87 | | | | | | |
| PUL24_ILTVT | PROTEIN UL24 HOMOLOG | INFECTIOUS LARYNGOTRACHEITIS VIRUS (STRAIN THORNE V882) | 158–196 | | | | | | |
| PUL25_HSVEB | VIRION PROTEIN UL25 | EQUINE HERPESVIRUS TYPE 1 (STRAIN AB4P)(EHV-1) | 343–379 | | | | | | |
| PUL25_HSVSA | VIRION GENE 19 PROTEIN | HERPES VIRUS SAIMIRI (STRAIN 11) | 290–323 | | | | | | |
| PUL25_VZVD | VIRION GENE 34 PROTEIN | VARICELLA-ZOSTER VIRUS (STRAIN DUMAS)(VZV) | 540–571 | | | | | | |
| PUL28_HCMVA | HYPOTHETICAL PROTEIN UL28 | HUMAN CYTOMEGALOVIRUS (STRAIN AD169) | 287–316 | | | | | | |
| PUL31_HCMVA | HYPOTHETICAL PROTEIN UL31 | HUMAN CYTOMEGALOVIRUS (STRAIN AD169) | 464–501 | | | | | | |
| PUL31_HSVA | GENE 69 PROTEIN | HERPESVIRUS SAIMIRI (STRAIN 11) | 163–197 | | | | | | |
| PUL32_EBV | PROBABLE MAJOR ENVELOPE GLYCOPROTEIN BFLF1 | EPSTEIN-BARR VIRUS (STRAIN B95-8)(HUMAN HERPESVIRUS 4) | 367–405 | | | | | | |
| PUL32_HSVI1 | PROBABLE MAJOR ENVELOPE GLYCOPROTEIN UL32 | HERPES SIMPLEX VIRUS (TYPE 1/STRAIN 17) | 404–438 | 564–592 | | | | | |
| PUL32_HSVEB | MAJOR ENVELOPE GLYCO-PROTEIN 300 | EQUINE HERPESVIRUS TYPE 1 | 81–115 | | | | | | |
| PUL32_HSVSA | PROBABLE MAJOR ENVELOPE GLYCOPROTEIN 68 | HERPESVIRUS SAIMIRI (STRAIN 11) | 276–307 | | | | | | |
| PUL32_VZVD | PROBABLE MAJOR ENVELOPE GLYCOPROTEIN 26 | VARICELLA-ZOSTER VIRUS (STRAIN DUMAS)(VZV) | 553–581 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PUL34_HSVSA | GENE 67 PROTEIN | HERPESVIRUS SAIMIRI (STRAIN 11) | 98–130 | | | | | | |
| PUL35_HCMVA | HYPOTHETICAL PROTEIN UL35 | HUMAN CYTOMEGALOVIRUS (STRAIN AD169) | 138–169 | | | | | | |
| PUL36_HCMVA | HYPOTHETICAL PROTEIN UL36 | HUMAN CYTOMEGALOVIRUS (STRAIN AD169) | 186–223 | | | | | | |
| PUL37_EBV | PROTEIN BOLF1 | EPSTEIN-BARR VIRUS (STRAIN B95-8)(HUMAN HERPESVIRUS 4) | 85–123 | | | | | | |
| PUL37_HSVEB | GENE 23 PROTEIN | EQUINE HERPESVIRUS TYPE 1 (STRAIN AB4P)(EHV-1) | 702–732 | 778–812 | | | | | |
| PUL37_HSVSA | GENE 63 PROTEIN | HERPESVIRUS SAIMIRI (STRAIN 11) | 566–602 | | | | | | |
| PUL37_VZVD | GENE 21 PROTEIN | VARICELLA-ZOSTER VIRUS (STRAIN DUMAS)(VZV) | 598–629 | 706–736 | 776–806 | | | | |
| PUL38_HCMVA | HYPOTHETICAL PROTEIN UL38 | HUMAN CYTOMEGALOVIRUS (STRAIN AD169) | 157–188 | | | | | | |
| PUL41_VZVD | HOST SHUTOFF VIRION PROTEIN | VARICELLA-ZOSTER VIRUS (STRAIN DUMAS)(VZV) | 274–307 | | | | | | |
| PUL43_HSVI1 | MEMBRANE PROTEIN UL43 | HERPES SIMPLEX VIRUS (TYPE 1/STRAIN 17) | 41–70 | | | | | | |
| PUL45_HSVI1 | GENE 15 MEMBRANE PROTEIN | VARICELLA-ZOSTER VIRUS (STRAIN DUMAS)(VZV) | 34–64 | 277–308 | | | | | |
| PUL47_HCMVA | PROTEIN UL47 | HUMAN CYTOMEGALOVIRUS (STRAIN AD169) | 438–471 | 741–777 | | | | | |
| PUL47_HSVE4 | 97 KD ALPHA TRANS-INDUCING PROTEIN | EQUINE HERPESVIRUS TYPE 4 | 580–615 | | | | | | |
| PUL47_HSVEB | 97 KD ALPHA TRANS-INDUCING PROTEIN | EQUINE HERPESVIRUS TYPE 1 (STRAIN AB4P)(EHV-1) | 587–622 | | | | | | |
| PUL49_HSVI1 | TEGUMENT PROTEIN UL49 | HERPES SIMPLEX VIRUS (TYPE 1/STRAIN 17 | 226–259 | | | | | | |
| PUL49_HSVBP | TEGUMENT PROTEIN UL49 HOMOLOG | BOVINE HERPESVIRUS TYPE 1 (STRAIN P8-2) | 135–168 | | | | | | |
| PUL52_EBV | PROBABLE DNA REPLI-CATION PROTEIN BSLF1 | EPSTEIN-BARR VIRUS (STRAIN B95-8)(HUMAN HERPESVIRUS 4) | 582–617 | | | | | | |
| PUL52_HSVI1 | DNA REPLICATION PROTEIN UL52 | HERPES SIMPLEX VIRUS (TYPE 1/STRAIN 17) | 599–629 | 771–805 | | | | | |
| PUL52_HSVEB | DNA REPLICATION PROTEIN UL52 | EQUINE HERPESVIRUS TYPE 1 (STRAIN AB4P)(EHV-1) | 316–344 | 580–618 | 912–947 | | | | |
| PUL52_HSVSA | PROBABLE DNA REPLI-CATION GENE 56 PROTEIN | HERPESVIRUS SAIMIRI (STRAIN 11) | 229–267 | 374–411 | | | | | |
| PUL53_HCMVA | PROTEIN UL53 | HUMAN CYTOMEGALOVIRUS (STRAIN AD169) | 213–248 | | | | | | |
| PUL53_HSV6U | UL53 PROTEIN HOMOLOG | HERPES SIMPLEX VIRUS (TYPE 67 STRAIN UGANDA-1102) | 105–139 | | | | | | |
| PUL60_HCMVA | HYPOTHETICAL PROTEIN UL60 | HUMAN CYTOMEGALOVIRUS (STRAIN AD169) | 120–148 | | | | | | |
| PUL70_HCMVA | PROBABLE REPLICATION PROTEIN UL70 | HUMAN CYTOMEGALOVIRUS (STRAIN AD169) | 36–65 | 626–664 | | | | | |
| PUL77_HCMVA | VIRION PROTEIN UL77 | HUMAN CYTOMEGALOVIRUS (STRAIN AD169) | 381–413 | 565–598 | | | | | |
| PUL78_HCMVA | HYPOTHETICAL PROTEIN UL78 | HUMAN CYTOMEGALOVIRUS (STRAIN AD169) | 262–290 | 303–341 | | | | | |
| PUL79_HSVSA | HYPOTHETICAL GENE 18 PROTEIN | HERPESVIRUS SAIMIRI (STRAIN 11) | 158–195 | | | | | | |
| PUL87_HSV6U | HYPOTHETICAL PROTEIN 5R | HERPES SIMPLEX VIRUS (TYPE 6/STRAIN UGANDA-1102) | 130–159 | | | | | | |
| PUL87_HSVSA | HYPOTHETICAL GENE 24 PROTEIN | HERPESVIRUS SAIMIRI (STRAIN 11) | 322–355 | | | | | | |
| PUL88_HCMVA | HYPOTHETICAL PROTEIN UL88 | HUMAN CYTOMEGALOVIRUS (STRAIN AD169) | 309–337 | | | | | | |
| PUL88_HSV6U | HYPOTHETICAL PROTEIN 6R | HERPES SIMPLEX VIRUS (TYPE 6/STRAIN UGANDA-1102) | 150–187 | 238–272 | | | | | |
| PUL91_HSVSA | HYPOTHETICAL GENE 30 PROTEIN | HERPESVIRUS SAIMIRI (STRAIN 11) | 23–53 | | | | | | |
| PUL92_EBV | HYPOTHETICAL PROTEIN BDLF4 | EPSTEIN-BARR VIRUS (STRAIN B95-8)(HUMAN HERPESVIRUS 4) | 106–144 | | | | | | |
| PUL92_HSVSA | HYPOTHETICAL GENE 31 PROTEIN | HERPESVIRUS SAIMIRI (STRAIN 11) | 123–157 | | | | | | |
| PUL93_HDMVA | PROTEIN UL93 | HUMAN CYTOMEGALOVIRUS (STRAIN AD169) | 387–420 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PUL95_EBV | HYPOTHETICAL PROTEIN BGLF3 | EPSTEIN-BARR VIRUS (STRAIN B95-8)(HUMAN HERPESVIRUS 4) | 111–145 | | | | | | |
| PULB8_HCMVA | HYPOTHETICAL PROTEIN UL118 | HUMAN CYTOMEGALOVIRUS (STRAIN AD169) | 102–130 | 152–181 | | | | | |
| PULC1_HCMVA | HYPOTHETICAL PROTEIN UL121 | HUMAN CYTOMEGALOVIRUS (STRAIN AD169) | 129–165 | | | | | | |
| PULC8_HCMVA | HYPOTHETICAL PROTEIN UL128 | HUMAN CYTOMEGALOVIRUS (STRAIN AD169) | 64–96 | | | | | | |
| PULC9_HCMVA | HYPOTHETICAL PROTEIN UL129 | HUMAN CYTOMEGALOVIRUS (STRAIN AD169) | 66–99 | | | | | | |
| PULD0_HCMVA | HYPOTHETICAL PROTEIN UL130 | HUMAN CYTOMEGALOVIRUS (STRAIN AD169) | 81–114 | | | | | | |
| PUNG_EBV | URACIL-DNA GLYCOSYLASE | EPSTEIN-BARR VIRUS (STRAIN B95-8)(HUMAN HERPESVIRUS 4) | 159–189 | | | | | | |
| PUNG_VACCC | URACIL-DNA GLYCOSYLASE | VACCINIA VIRUS (STRAIN COPENHAGEN) | 82–117 | | | | | | |
| PUNG_VACCV | URACIL-DNA GLYCOSYLASE | VACCINIA VIRUS (STRAIN WR) | 82–117 | | | | | | |
| PUNG_VARV | URACIL-DNA GLYCOSYLASE | VARIOLA VIRUS | 82–117 | | | | | | |
| PUS02_HCMVA | HYPOTHETICAL PROTEIN HOLF2 | HUMAN CYTOMEGALOVIRUS (STRAIN AD169) | 43–73 | | | | | | |
| PUS07_HCMVA | HYPOTHETICAL PROTEIN HXLF5 | HUMAN CYTOMEGALOVIRUS (STRAIN AD169) | 153–190 | | | | | | |
| PUS09_HCMVA | HYPOTHETICAL PROTEIN HXLF3 | HUMAN CYTOMEGALOVIRUS (STRAIN AD169) | 179–213 | | | | | | |
| PUS10_HCMVA | HYPOTHETICAL PROTEIN HXLF2 | HUMAN CYTOMEGALOVIRUS (STRAIN AD169) | 137–170 | | | | | | |
| PUS12_HCMVA | HYPOTHETICAL PROTEIN HVLF6 | HUMAN CYTOMEGALOVIRUS (STRAIN AD169) | 29–67 | 113–142 | | | | | |
| PUS13_HCMVA | HYPOTHETICAL PROTEIN HVLF5 | HUMAN CYTOMEGALOVIRUS (STRAIN AD169) | 11–45 | | | | | | |
| PUS15_HCMVA | HYPOTHETICAL PROTEIN HVLF3 | HUMAN CYTOMEGALOVIRUS (STRAIN AD169) | 343–375 | | | | | | |
| PUS16_HCMVA | HYPOTHETICAL PROTEIN HVLF2 | HUMAN CYTOMEGALOVIRUS (STRAIN AD169) | 151–188 | 243–274 | | | | | |
| PUS18_HCMVA | MEMBRANE PROTEIN HWLF5 | HUMAN CYTOMEGALOVIRUS (STRAIN AD169) | 185–222 | | | | | | |
| PUS22_HCMVA | EARLY NUCLEAR PROTEIN HWLF1 | HUMAN CYTOMEGALOVIRUS (STRAIN AD169) | 270–299 | | | | | | |
| PUS26_HCMVA | HYPOTHETICAL PROTEIN HHLF5 | HUMAN CYTOMEGALOVIRUS (STRAIN AD169) | 132–164 | | | | | | |
| PUS27_HCMVA | G-PROTEIN COUPLED RECEPTOR HOMOLOG US27 | HUMAN CYTOMEGALOVIRUS (STRAIN AD169) | 247–285 | | | | | | |
| PUS29_HCMVA | HYPOTHETICAL PROTEIN HHRF4 | HUMAN CYTOMEGALOVIRUS (STRAIN AD169) | 246–276 | | | | | | |
| PUS30_HCMVA | HYPOTHETICAL PROTEIN HHRF5 | HUMAN CYTOMEGALOVIRUS (STRAIN AD169) | 208–246 | | | | | | |
| PV125_AMVLE | 125 KD PROTEIN | ALFALFA MOSAIC VIRUS (STRAIN 425/ISOLATE LEIDEN | 263–292 | | | | | | |
| PV13K_TRVPL | 16 KD PROTEIN | TOBACCO RATTLE VIRUS (STRAIN PLB) | 24–62 | | | | | | |
| PV143_NPVAC | HELICASE | AUTOGRAPHA CALIFORNICA NUCLEAR POLYHEDROSIS VIRUS | 312–342 | | | | | | |
| PV17K_BSMV | 17 KD PROTEIN | BARLEY STRIPE MOSAIC VIRUS (BSMV) | 40–75 | | | | | | |
| PV1A_CMVFN | 1A PROTEIN | CUCUMBER MOSAIC VIRUS (STRAIN FNY)(CMV) | 674–709 | | | | | | |
| PV270_ASFB7 | L270 PROTEIN | AFRICAN SWINE FEVER VIRUS (STRAIN BA71V)(ASFV) | 103–135 | | | | | | |
| PV2A_BBMV | 2A PROTEIN | BROAD BEAN MOTTLE VIRUS | 636–673 | | | | | | |
| PV2A_CCMV | 2A PROTEIN | COWPEA CHLOROTIC MOTTLE VIRUS (CCMV) | 325–363 | 639–673 | 762–799 | | | | |
| PV2A_CMVFN | 2A PROTEIN | CUCUMBER MOSAIC VIRUS (STRAIN FNY)(CMV) | 208–243 | 292–320 | | | | | |
| PV2A_CMVQ | 2A PROTEIN | CUCUMBER MOSAIC VIRUS (STRAIN Q)(CMV) | 205–240 | | | | | | |
| PV2A_TAV | 2A PROTEIN | TOMATO ASPERMY VIRUS (TAV) | 297–325 | | | | | | |
| PV30K_TRVTC | 29.1 KD PROTEIN | TOBACCO RATTLE VIRUS (STRAIN TCM) | 102–133 | | | | | | |
| PV3A_BBMV | 3A PROTEIN | BROAD BEAN MOTTLE VIRUS | 155–187 | | | | | | |
| PV3A_BMV | 3A PROTEIN | BROME MOSAIC VIRUS (BMV) | 159–189 | | | | | | |
| PV3A_CCMV | 3A PROTEIN | COWPEA CHLOROTIC MOTTLE VIRUS (CCMV) | 160–188 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PV3A_IBVB | 3A PROTEIN | AVIAN INFECTIOUS BRONCHITIS VIRUS (STRAIN BEAUDETTE)(IBV) | 5–43 | | | | | | |
| PV3A_IBVM | 3A PROTEIN | AVIAN INFECTIOUS BRONCHITIS VIRUS (STRAIN M41)(IBV) | 5–42 | | | | | | |
| PV3A_IBVP3 | 3A PROTEIN | AVIAN INFECTIOUS BRONCHITIS VIRUS | 5–42 | | | | | | |
| PV3A_IBVU5 | 3A PROTEIN | AVIAN INFECTIOUS BRONCHITIS VIRUS (STRAIN UK/183/66)(IBV) | 5–42 | | | | | | |
| PV51K_ACLSV | 50.8 KD PROTEIN | APPLE CHLOROTC LEAF SPOT VIRUS (ACLSV) | 70–106 | | | | | | |
| PV51K_BWYVF | 51 KD PROTEIN | BEET WESTERN YELLOWS VIRUS (ISOLATE FL-1)(BWYV) | 366–398 | | | | | | |
| PV51K_BWYVG | 51 KD PROTEIN | BEET WESTERN YELLOWS VIRUS (ISOLATE GB1)(BWYV) | 366–398 | | | | | | |
| PV56K_PLRV1 | 56 KD PROTEIN | POTATO LEAFROLL VIRUS (STRAIN 1)(PLRV) | 360–392 | | | | | | |
| PV56K_PLRVW | 56 KD PROTEIN | POTATO LEAFROLL VIRUS (STRAIN WAGENINGEN)(PLRV) | 360–392 | | | | | | |
| PV58K_BSMV | 58 KD PROTEIN | BARLEY STRIPE MOSAIC VIRUS (BSMV) | 320–353 | | | | | | |
| PV70K_PLRV1 | 69.7 KD PROTEIN | POTATO LEAFROLL VIRUS (STRAIN 1)(PLRV) | 220–257 | | | | | | |
| PV70K_PLRVW | 69.7 KD PROTEIN | POTATO LEAFROLL VIRUS (STRAIN WAGENINGEN)(PLRV) | 220–257 | | | | | | |
| PV90K_AMVLE | 90 KD PROTEIN | ALFALFA MOSAIC VIRUS (STRAIN 425/ISOLATE LEIDEN) | 103–131 | | | | | | |
| PVA04_VACCC | PROTEIN A4 | VACCINIA VIRUS (STRAIN COPENHAGEN) | 217–251 | | | | | | |
| PVA04_VACCV | PROTEIN A4 | VACCINIA VIRUS (STRAIN WR) | 217–251 | | | | | | |
| PVA04_VARV | PROTEIN A4 | VARIOLA VIRUS | 207–241 | | | | | | |
| PVA11_VACCC | PROTEIN A11 | VACCINIA VIRUS (STRAIN COPENHAGEN) | 95–132 | | | | | | |
| PVA11_VARV | PROTEIN A11 | VARIOLA VIRUS | 96–133 | | | | | | |
| PVA18_VACCC | 56 KD ABORTIVE LATE PROTEIN | VACCINIA VIRUS (STRAIN COPENHAGEN) | 390–421 | | | | | | |
| PVA18_VACCV | 56 KD ABORTIVE LATE PROTEIN | VACCINIA VIRUS (STRAIN WR) | 390–421 | | | | | | |
| PVA18_VARV | 56 KD ABORTIVE LATE PROTEIN | VARIOLA VIRUS | 390–421 | | | | | | |
| PVA23_VACCC | PROTEIN A23 | VACCINIA VIRUS (STRAIN COPENHAGEN) | 81–111 | 170–203 | | | | | |
| PVA23_VARV | PROTEIN A23 | VARIOLA VIRUS | 81–111 | 170–203 | | | | | |
| PVA31_VACCC | PROTEIN A31 | VACCINIA VIRUS (STRAIN COPENHAGEN) | 42–76 | | | | | | |
| PVA31_VACCV | PROTEIN A31 | VACCINIA VIRUS (STRAIN WR) | 42–76 | | | | | | |
| PVA31_VARV | PROTEIN A31 | VARIOLA VIRUS | 42–76 | | | | | | |
| PVA32_VACCV | PROTEIN A32 | VACCINIA VIRUS (STRAIN WR), AND VACCINIA VIRUS (STRAIN COPENHAG | 48–79 | | | | | | |
| PVA32_VARV | PROTEIN A32 | VARIOLA VIRUS | 18–49 | | | | | | |
| PVA40_VACCC | PROTEIN A40 | VACCINIA VIRUS (STRAIN COPENHAGEN) | 4–37 | | | | | | |
| PVA43_VACCC | PROTEIN A43 | VACCINIA VIRUS (STRAIN COPENHAGEN) | 94–129 | | | | | | |
| PVA43_VACCV | PROTEIN A43 | VACCINIA VIRUS (STRAIN WR) | 94–129 | | | | | | |
| PVA43_VARV | PROTEIN A43 | VARIOLA VIRUS | 95–130 | | | | | | |
| PVA51_VACCC | PROTEIN A51 | VACCINIA VIRUS (STRAIN COPENHAGEN) | 109–143 | | | | | | |
| PVA51_VACCV | PROTEIN A51 | VACCINIA VIRUS (STRAIN WR) | 109–143 | | | | | | |
| PVAL1_BCV | AL1 PROTEIN | BEET CURLY TOP VIRUS (BCTV) | 89–118 | | | | | | |
| PVAL1_BGMV | AL1 PROTEIN | BEAN GOLDEN MOSAIC VIRUS | 89–118 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVAL1_CLVK | AL1 PROTEIN | CASSAVA LATENT VIRUS (STRAIN WEST KENYAN 844 | 88–117 | | | | | | |
| PVAL1_CLVN | AL1 PROTEIN | CASSAVA LATENT VIRUS (STRAIN NIGERIAN) | 88–117 | | | | | | |
| PVAL1_PYMVV | AL1 PROTEIN | POTATO YELLOW MOSAIC VIRUS (ISOLATE VENEZUELA) | 89–118 | | | | | | |
| PVAL1_TGMV | AL1 PROTEIN | TOMATO GOLDEN MOSAIC VIRUS (TGMV) | 90–119 | | | | | | |
| PVAL1_TYLCM | AL1 PROTEIN | TOMATO YELLOW LEAF CURL VIRUS (STRAIN MARMANDE)(TYLCV) | 89–118 | | | | | | |
| PLAL1_TYLCV | AL1 PROTEIN | TOMATO YELLOW LEAF CURL VIRUS (TYLCV) | 87–116 | | | | | | |
| PVAL3_BCTV | AL3 PROTEIN | BEET CURLY TOP VIRUS (BCTV) | 82–115 | | | | | | |
| PVAL3_CLVK | AL3 PROTEIN | CASSAVA LATENT VIRUS (STRAIN WEST KENYAN 844) | 77–113 | | | | | | |
| PVAL3_CLVN | AL3 PROTEIN | CASSAVA LATENT VIRUS (STRAIN NIGERIAN) | 77–113 | | | | | | |
| PVAL3_TYLCM | AL3 PROTEIN | TOMATO YELLOW LEAF CURL VIRUS (STRAIN MARMANDE)(TYLCV) | 78–116 | | | | | | |
| PVAL3_TYLCV | AL3 PROTEIN | TOMATO YELLOW LEAF CURL VIRUS (TYLCV | 77–113 | | | | | | |
| PVAT_CAMVC | APHID TRANSMISSION PROTEIN | CAULIFLOWER MOSAIC VIRUS (STRAIN CM-1841)(CAMV) | 20–53 | 81–116 | | | | | |
| PVAT_CAMVD | APHID TRANSMISSION PROTEIN | CAULIFLOWER MOSAIC VIRUS (STRAIN D/H)(CAMV | 20–53 | 102–130 | | | | | |
| PVAT_CAMVE | APHID TRANSMISSION PROTEIN | CAULIFLOWER MOSAIC VIRUS (STRAIN BBC)(CAMV) | 20–53 | 81–116 | | | | | |
| PVAT_CAMVN | APHID TRANSMISSION PROTEIN | CAULIFLOWER MOSAIC VIRUS (STRAIN NY8153)(CAMV) | 20–53 | 81–116 | | | | | |
| PVAT_CAMVP | APHID TRANSMISSION PROTEIN | CAULIFLOWER MOSAIC VIRUS (STRAIN PV147)(CAMV) | 20–53 | 81–116 | | | | | |
| PVAT_CAMVS | APHID TRANSMISSION PROTEIN | CAULIFLOWER MOSAIC VIRUS (STRAIN STRASBOURG)(CAMV) | 20–53 | 81–116 | | | | | |
| PVB04_VACCC | PROTEIN B4 | VACCINIA VIRUS (STRAIN COPENHAGEN) | 124–156 | 489–525 | | | | | |
| PVB04_VACCV | PROTEIN B4 | VACCINIA VIRUS (STRAIN WR) | 124–156 | 489–525 | | | | | |
| PVB04_VARV | PROTEIN B4 | VARIOLA VIRUS | 489–525 | | | | | | |
| PVB16_COWPX | INTERLEUKIN-1 BINDING PROTEIN PRECURSOR | COWPOX VIRUS (CPV) | 89–126 | | | | | | |
| PVB16_VACCV | INTERLEUKIN-1 BINDING PROTEIN PRECURSOR | VACCINIA VIRUS (STRAIN WR) | 89–126 | | | | | | |
| PVB19_VACCC | SURFACE ANTIGEN S PRECURSOR | VACCINIA VIRUS (STRAIN COPENHAGEN) | 213–244 | | | | | | |
| PVB19_VACCD | SURFACE ANTIGEN S PRECURSOR | VACCINIA VIRUS (STRAIN DAIREN 1) | 211–242 | | | | | | |
| PVB19_VACCV | SURFACE ANTIGEN S PRECURSOR | VACCINIA VIRUS (STRAIN WR) | 211–242 | | | | | | |
| PVB19_VARV | SURFACE ANTIGEN S PRECURSOR | VARIOLA VIRUS | 211–242 | | | | | | |
| PVBR1_BGMV | BR1 PROTEIN | BEAN GOLDEN MOSAIC VIRUS | 166–198 | | | | | | |
| PVC03_SFVKA | G-PROTEIN COUPLED RECEPTOR HOMOLOG C3 | SHOPE FIBROMA VIRUS (STRAIN KASZA)(SFV) | 98–130 | | | | | | |
| PVC04_VACCC | PROTEIN C4 | VACCINIA VIRUS (STRAIN COPENHAGEN) | 109–139 | 182–216 | | | | | |
| PVC04_VACCV | PROTEIN C4 | VACCINIA VIRUS (STRAIN WR) | 109–139 | 183–215 | | | | | |
| PVC04_VARV | PROTEIN C4 | VARIOLA VIRUS | 109–139 | | | | | | |
| PVC06_VACCC | PROTEIN C6 | VACCINIA VIRUS (STRAIN COPENHAGEN) | 36–67 | | | | | | |
| PVC06_VACCV | PROTEIN C6 | VACCINIA VIRUS (STRAIN WR) | 36–67 | | | | | | |
| PVC06_VARV | PROTEIN C6 | VARIOLA VIRUS | 36–67 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVC07_SFVKA | HYPOTHETICAL PROTEIN C7 | SHOPE FIBROMA VIRUS (STRAIN KASZA)(SFV) | 60–97 | | | | | | |
| PVC09_VACCC | PROTEIN C9 | VACCINIA VIRUS (STRAIN COPENHAGEN) | 573–610 | | | | | | |
| PVC09_VACCV | PROTEIN C9 | VACCINIA VIRUS (STRAIN WR) | 573–610 | | | | | | |
| PVC10_SFVKA | HYPOTHETICAL PROTEIN C10 | SHOPE FIBROMA VIRUS (STRAIN KASZA)(SFV) | 85–121 | | | | | | |
| PVC10_VACCC | PROTEIN C10 | VACCINIA VIRUS (STRAIN COPENHAGEN) | 121–158 | | | | | | |
| PVC10_VACCV | PROTEIN C10 | VACCINIA VIRUS (STRAIN WR) | 121–158 | | | | | | |
| PVC10_VARV | PROTEIN C10 | VARIOLA VIRUS | 121–158 | | | | | | |
| PVC21_VACCC | PROTEIN C21/B27 | VACCINIA VIRUS (STRAIN COPENHAGEN) | 3–34 | | | | | | |
| PVCAP_EBV | MAJOR CAPSID PROTEIN | EPSTEIN-BARR VIRUS (STRAIN B95-8) (HUMAN HERPESVIRUS 4) | 148–183 | 200–230 | | | | | |
| PVCAP_HCMVA | MAJOR CAPSID PROTEIN | HUMAN CYTOMEGALOVIRUS (STRAIN AD169) | 43–78 | 128–161 | 258–286 | | | | |
| PVCAP_HSVI1 | MAJOR CAPSID PROTEIN | HERPES SIMPLEX VIRUS (TYPE 1/STRAIN 17) | 19–49 | | | | | | |
| PVCAP_HSV6U | MAJOR CAPSID PROTEIN | HERPES SIMPLEX VIRUS (TYPE 6/STRAIN UGANDA-1102) | 124–161 | 666–696 | 841–869 | | | | |
| PVCAP_HSVEB | MAJOR CAPSID PROTEIN | EQUINE HERPESVIRUS TYPE 1 (STRAIN AB4P)(EHV-1) | 17–54 | 198–232 | 272–301 | | | | |
| PVCAP_HSVSA | MAJOR CAPSID PROTEIN | HERPESVIRUS SAIMIRI (STRAIN 11) | 144–179 | 196–226 | 734–769 | 1062–1096 | | | |
| PVCAP_PRVIS | MAJOR CAPSID PROTEIN | PSEUDORABIES VIRUS (STRAIN INDIANA S)(PRV) | 189–221 | 260–289 | | | | | |
| PVCAP_VZVD | MAJOR CAPSID PROTEIN | VARICELLA-ZOSTER VIRUS (STRAIN DUMAS)(VZV) | 31–68 | | | | | | |
| PVCOM_ADE02 | MINOR CORE PROTEIN | HUMAN ADENOVIRUS TYPE 2 | 86–115 | | | | | | |
| PVCOM_ADE05 | MINOR CORE PROTEIN | HUMAN ADENOVIRUS TYPE 5 | 85–114 | | | | | | |
| PVD03_VACCC | PROTEIN D3 | VACCINIA VIRUS (STRAIN COPENHAGEN) | 12–50 | 146–182 | | | | | |
| PVD03_VACCV | PROTEIN D3 | VACCINIA VIRUS (STRAIN WR) | 12–50 | 146–182 | | | | | |
| PVD03_VARV | PROTEIN D3 | VARIOLA VIRUS | 12–50 | 146–182 | | | | | |
| PVD05_FOWP1 | 92.6 KD PROTEIN | FOWLPOX VIRUS (STRAIN FP-1) | 315–352 | | | | | | |
| PVD05_VACCC | PROTEIN D5 | VACCINIA VIRUS (STRAIN COPENHAGEN) | 320–348 | | | | | | |
| PVD05_VACCV | PROTEIN D5 | VACCINIA VIRUS (STRAIN WR) | 320–348 | | | | | | |
| PVD05_VARV | PROTEIN D5 | VARIOLA VIRUS | 320–348 | | | | | | |
| PVD10_FOWP1 | PROTEIN D10 | FOWLPOX VIRUS (STRAIN FP-1) | 114–143 | | | | | | |
| PVE05_VACCD | PROTEIN E5 | VACCINIA VIRUS (STRAIN DAIREN 1) | 31–60 | | | | | | |
| PVE06_VACCC | PROTEIN E6 | VACCINIA VIRUS (STRAIN COPENHAGEN) | 226–260 | 430–458 | 511–540 | | | | |
| PVE06_VACCV | PROTEIN E6 | VACCINIA VIRUS (STRAIN WR) | 226–260 | 430–458 | 511–540 | | | | |
| PVE06_VARV | PROTEIN E6 | VARIOLA VIRUS | 430–458 | 511–540 | | | | | |
| PVE10_VACCC | PROTEIN E10 | VACCINIA VIRUS (STRAIN COPENHAGEN) | 3–41 | | | | | | |
| PVE10_VACCV | PROTEIN E10 | VACCINIA VIRUS (STRAIN WR) | 3–41 | | | | | | |
| PVE10_VARV | PROTEIN E10 | VARIOLA VIRUS | 3–41 | | | | | | |
| PVE12_HPV16 | PROBABLE E1 PROTEIN 2 | HUMAN PAPILLOMAVIRUS TYPE 16 | 102–131 | | | | | | |
| PVE18_NPVAC | EARLY 18.5 KD PROTEIN | AUTOGRAPHA CALIFORNICA NUCLEAR POLYHEDROSIS VIRUS (ACMNPV) | 45–77 | | | | | | |
| PVE1_HPV05 | E1 PROTEIN | HUMAN PAPILLOMAVIRUS TYPE 5 | 4–35 | | | | | | |
| PVE1_HPV11 | E1 PROTEIN | HUMAN PAPILLOMAVIRUS TYPE 11 | 258–291 | | | | | | |
| PVE1_HPV13 | E1 PROTEIN | HUMAN PAPILLOMAVIRUS TYPE 13 | 255–288 | | | | | | |
| PVE1_HPV33 | E1 PROTEIN | HUMAN PAPILLOMAVIRUS TYPE 33 | 238–267 | 519–547 | | | | | |
| PVE1_HPV35 | E1 PROTEIN | HUMAN PAPILLOMAVIRUS TYPE 35 | 230–263 | | | | | | |
| PVE1_HPV39 | E1 PROTEIN | HUMAN PAPILLOMAVIRUS TYPE 39 | 242–271 | | | | | | |
| PVE1_HPV31 | E1 PROTEIN | HUMAN PAPILLOMAVIRUS TYPE 41 | 105–138 | 193–231 | | | | | |
| PVE1_HPV58 | E1 PROTEIN | HUMAN PAPILLOMAVIRUS TYPE 58 | 238–267 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVE1_HPV5B | E1 PROTEIN | HUMAN PAPILLOMAVIRUS TYPE 5B | 6–35 | | | | | | |
| PVE1_HPV6B | E1 PROTEIN | HUMAN PAPILLOMAVIRUS TYPE 6B | 258–291 | | | | | | |
| PVE1_PAPVD | E1 PROTEIN | DEER PAPILLOMAVIRUS | 163–201 | | | | | | |
| PVE1_PCPV1 | E1 PROTEIN | PYGMY CHIMPANZEE PAPILLOMAVIRUS TYPE 1 | 257–290 | | | | | | |
| PVE26_NPVAC | EARLY 25.9 KD PROTEIN | AUTOGRAPHA CALIFORNICA NUCLEAR POLYHEDROSIS VIRUS (ACMNPV) | 118–150 | | | | | | |
| PVE2_HPV57 | E2 PROTEIN | HUMAN PAPILLOMAVIRUS TYPE 57 | 151–182 | | | | | | |
| PVE2_RHPV1 | E2 PROTEIN | RHESUS PAPILLOMAVIRUS TYPE 1 (RHPV 1) | 117–147 | | | | | | |
| PVE41_NPVAC | EARLY 40.9 KD PROTEIN | AUTOGRAPHA CALIFORNICA NUCLEAR POLYHEDROSIS VIRUS (ACMNPV) | 14–52 | | | | | | |
| PVE5A_HPV11 | PROBABLE E5A PROTEIN | HUMAN PAPILLOMAVIRUS TYPE 11 | 19–56 | | | | | | |
| PVE5A_HPV6B | PROBABLE E5A PROTEIN | HUMAN PAPILLOMAVIRUS TYPE 6B | 19–56 | | | | | | |
| PVE5A_HPV6C | PROBABLE E5A PROTEIN | HUMAN PAPILLOMAVIRUS TYPE 6C | 19–56 | | | | | | |
| PVE5_HPV13 | PROBABLE E5 PROTEIN | HUMAN PAPILLOMAVIRUS TYPE 13 | 19–56 | | | | | | |
| PVE5_HPV5B | PROBABLE E5 PROTEIN | HUMAN PAPILLOMAVIRUS TYPE 5B | 89–118 | | | | | | |
| PVE5_PCPV1 | PROBABLE E5 PROTEIN | PYGMY CHIMPANZEE PAPILLOMAVIRUS TYPE 1 | 21–58 | | | | | | |
| PVE5_RHPV1 | PROBABLE E5 PROTEIN | RHESUS PAPILLOMAVIRUS TYPE 1 (RHPV 1) | 109–140 | | | | | | |
| PVE6_HPV1A | E6 PROTEIN | HUMAN PAPILLOMAVIRUS TYPE 1A | 91–128 | | | | | | |
| PVE7_HPV05 | E7 PROTEIN | HUMAN PAPILLOMAVIRUS TYPE 5 | 55–90 | | | | | | |
| PVE7_HPV08 | E7 PROTEIN | HUMAN PAPILLOMAVIRUS TYPE 8 | 55–90 | | | | | | |
| PVE7_HPV11 | E7 PROTEIN | HUMAN PAPILLOMAVIRUS TYPE 11 | 47–83 | | | | | | |
| PVE7_HPV16 | E7 PROTEIN | HUMAN PAPILLOMAVIRUS TYPE 16 | 47–83 | | | | | | |
| PVE7_HPV1A | E7 PROTEIN | HUMAN PAPILLOMAVIRUS TYPE 1A | 45–77 | | | | | | |
| PVE7_HPV31 | E7 PROTEIN | HUMAN PAPILLOMAVIRUS TYPE 31 | 47–83 | | | | | | |
| PVE7_HPV33 | E7 PROTEIN | HUMAN PAPILLOMAVIRUS TYPE 33 | 47–83 | | | | | | |
| PVE7_HPV35 | E7 PROTEIN | HUMAN PAPILLOMAVIRUS TYPE 35 | 48–84 | | | | | | |
| PVE7_HPV41 | E7 PROTEIN | HUMAN PAPILLOMAVIRUS TYPE 41 | 63–94 | | | | | | |
| PVE7_HPV47 | E7 PROTEIN | HUMAN PAPILLOMAVIRUS TYPE 47 | 55–90 | | | | | | |
| PVE7_HPV51 | E7 PROTEIN | HUMAN PAPILLOMAVIRUS TYPE 51 | 61–94 | | | | | | |
| PVE7_HPV58 | E7 PROTEIN | HUMAN PAPILLOMAVIRUS TYPE 58 | 48–84 | | | | | | |
| PVE7_HPV5B | E7 PROTEIN | HUMAN PAPILLOMAVIRUS TYPE 5B | 55–90 | | | | | | |
| PVE7_HPV6B | E7 PROTEIN | HUMAN PAPILLOMAVIRUS TYPE 6B | 47–83 | | | | | | |
| PVE7_PAPVD | E7 PROTEIN | DEEP PAPILLOMAVIRUS | 48–86 | | | | | | |
| PVE7_PAPVE | E7 PROTEIN | EUROPEAN ELK PAPILLOMAVIRUS (EEPV) | 60–93 | | | | | | |
| PVE94_NPVAC | EARLY 94 KD PROTEIN | AUTOGRAPHA CALIFORNICA NUCLEAR POLYHEDROSIS VIRUS (ACMNPV) | 123–157 | | | | | | |
| PVEF_GVIN | VIRAL ENHANCING FACTOR | TRICHOPLUSIA N1 GRANULOSIS VIRUS (TNGV) | 154–182 | | | | | | |
| PVENV_BEV | ENVELOPE PROTEIN | BERNE VIRUS (BEV) | 16–51 | 650–678 | | | | | |
| PVENV_DHV11 | ENVELOPE GLYCOPROTEIN | DHORI VIRUS (STRAIN INDIAN/1313/61)(DHO) PRECURSOR | 297–335 | 87–117 | | | | | |
| PVENV_MCV1 | MAJOR ENVELOPE PROTEIN | MOLLUSCUM CONTAGIOUSUM VIRUS SUBTYPE 1 (MCV1) | 203–236 | | | | | | |
| PVENV_MCV2 | MAJOR ENVELOPE PROTEIN | MOLLUSCUM CONTAGIOUSUM VIRUS SUBTYPE 2 (MCV11) | 203–236 | | | | | | |
| PVENV_VACCC | MAJOR ENVELOPE PROTEIN | VACCINIA VIRUS (STRAIN COPENHAGEN) | 208–241 | | | | | | |
| PVENV_VACCI | MAJOR ENVELOPE PROTEIN | VACCINIA VIRUS (STRAIN 1HD-J) | 208–241 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVENV_VACCP | MAJOR ENVELOPE PROTEIN | VACCINIA VIRUS (STRAIN L-IVP) | 208–241 | | | | | | |
| PVENV_VACCV | MAJOR ENVELOPE PROTEIN | VACCINIA VIRUS (STRAIN WR) | 208–241 | | | | | | |
| PVENV_VARV | MAJOR ENVELOPE PROTEIN | VARJOLA VIRUS | 155–187 | 208–241 | | | | | |
| PVF03_VACCC | PROTEIN F3 | VACCINIA VIRUS (STRAIN COPENHAGEN) | 2–40 | 61–93 | | | | | |
| PVF03_VACCV | PROTEIN F3 | VACCINIA VIRUS (STRAIN WR) | 2–40 | 61–93 | | | | | |
| PVFP1_FOWPV | PROTEIN FP1 | FOWLPOX VIRUS | 297–330 | | | | | | |
| PVFP4_FOWPV | PROTEIN FP4 | FOWLPOX VIRUS | 237–267 | | | | | | |
| PVFP7_CAPVK | PROTEIN F7 | CAPRIPOX VIRUS (STRAIN K5-1) | 89–118 | | | | | | |
| PVFUS_VACCC | 14 KD FUSION PROTEIN | VACCINIA VIRUS (STRAIN COPENHAGEN) | 28–61 | | | | | | |
| PVFUS_VACCV | 14 KD FUSION PROTEIN | VACCINIA VIRUS (STRAIN WR) | 28–61 | | | | | | |
| PVFUS_VARV | 14 KD FUSION PROTEIN | VARJOLA VIRUS | 28–61 | | | | | | |
| PVG01_HSV11 | HYPOTHETICAL GENE 1 PROTEIN | ICTALURID HERPESVIRUS 1 (CHANNEL CATFISH VIRUS)(CCV) | 317–346 | | | | | | |
| PVG02_HSVEB | HYPOTHETICAL GENE 2 PROTEIN | EQUINE HERPESVIRUS TYPE 1 (STRAIN AB4P)(EHV-1) | 163–196 | | | | | | |
| PVG02_VACCV | ISATIN-BETA-THIOSEM-ICARBAZONE DEPENDENT PROTEI | VACCINIA VIRUS (STRAIN WR), AND VACCINIA VIRUS (STRAIN COPENHAGE | 92–120 | | | | | | |
| PVG02_VARV | ISATIN-BETA-THIOSEM-ICARBAZONE DEPENDENT PROTEI | VARJOLA VIRUS | 92–120 | | | | | | |
| PVG03_HSVI1 | HYPOTHETICAL GENE 3 PROTEIN | ICTALURID HERPESVIRUS 1 (CHANNEL CATFISH VIRUS)(CCV) | 108–136 | | | | | | |
| PVG06_HSVI1 | HYPOTHETICAL GENE 6 MEMBRANE PROTEIN | ICTALURID HERPESVIRUS 1 (CHANNEL CATFISH VIRUS)(CCV) | 54–83 | | | | | | |
| PVG06_VACCC | PROTEIN G6 | VACCINIA VIRUS (STRAIN COPENHAGEN) | 99–136 | | | | | | |
| PVG06_VARV | PROTEIN G6 | VARJOLA VIRUS | 99–136 | | | | | | |
| PVG07_VACCC | PROTEIN G7 | VACCINIA VIRUS (STRAIN COPENHAGEN) | 113–145 | | | | | | |
| PVG07_VARV | PROTEIN G7 | VARJOLA VIRUS | 113–145 | | | | | | |
| PVG09_VACCC | PROTEIN F1 | VACCINIA VIRUS (STRAIN COPENHAGEN) | 303–338 | | | | | | |
| PVG09_VACCV | PROTEIN F1 | VACCINIA VIRUS (STRAIN WR) | 266–301 | | | | | | |
| PVG09_VARV | PROTEIN F1 | VARJOLA VIRUS | 303–338 | | | | | | |
| PVG11_HSV11 | HYPOTHETICAL GENE 11 ZINC-BINDING PROTEIN | ICTALURID HERPESVIRUS 1 (CHANNEL CATFISH VIRUS)(CCV) | 150–183 | | | | | | |
| PVG12_HSV11 | HYPOTHETICAL GENE 12 ZINC-BINDING PROTEIN | ICTALURID HERPESVIRUS 1 (CHANNEL CATFISH VIRUS)(CCV) | 206–243 | | | | | | |
| PVG12_HSVSA | HYPOTHETICAL GENE 12 PROTEIN | HERPESVIRUS SAIMIRI (STRAIN 11) | 68–106 | | | | | | |
| PVG1_SPVIR | CAPSID PROTEIN | SPIROPLASMA VIRUS SPVI-R8A2 B | 254–292 | 303–337 | 414–452 | | | | |
| PVG22_HSV11 | HYPOTHETICAL GENE 22 PROTEIN | ICTALURID HERPESVIRUS 1 (CHANNEL CATFISH VIRUS)(CCV) | 300–337 | 647–678 | | | | | |
| PGV23_HSV11 | HYPOTHETICAL GENE 23 PROTEIN | ICTALURID HERPESVIRUS 1 (CHANNEL CATFISH VIRUS)(CCV) | 70–108 | | | | | | |
| PVG26_HSV11 | HYPOTHETICAL GENE 26 PROTEIN | ICTALURID HERPESVIRUS 1 (CHANNEL CATFISH VIRUS)(CCV) | 94–125 | | | | | | |
| PVG27_HSVSA | HYPOTHETICAL GENE 27 PROTEIN | HERPESVIRUS SAIMIRI (STRAIN 11) | 36–74 | | | | | | |
| PVG28_HSV11 | HYPOTHETICAL GENE 28 PROTEIN | ICTALURID HERPESVIRUS 1 (CHANNEL CATFISH VIRUS)(CCV) | 491–521 | | | | | | |
| PVG2R_AMEPV | HYPOTHETICAL G2R PROTEIN | AMSACTA MOOREI ENTOMOPOXVIRUS (AMEPV) | 180–217 | | | | | | |
| PVG2_SPV4 | GENE 2 PROTEIN | SPIROPLASMA VIRUS 4 (SPV4) | 209–244 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVG35_HSV11 | HYPOTHETICAL GENE 35 PROTEIN | ICTALURID HERPESVIRUS 1 (CHANNEL CATFISH VIRUS)(CCV) | 15–46 | 190–226 | | | | | |
| PVG36_HSVSA | POSSIBLE TYROSINE -PROTEIN KINASE | HERPESVIRUS SAIMIRI (STRAIN 11) | 151–185 | | | | | | |
| PVG39_HSV11 | HYPOTHETICAL GENE 39 PROTEIN | ICTALURID HERPESVIRUS 1 (CHANNEL CATFISH VIRUS)(CCV) | 543–577 | 648–682 | | | | | |
| PVG40_HSVSA | HYPOTHETICAL GENE 40 PROTEIN | HERPESVIRUS SAIMIRI (STRAIN 11) | 187–216 | | | | | | |
| PVG41_HSV11 | HYPOTHETICAL GENE 41 PROTEIN | ICTALURID HERPESVIRUS 1 (CHANNEL CATFISH VIRUS)(CCV) | 11–45 | 202–233 | | | | | |
| PVG42_HSV11 | HYPOTHETICAL GENE 42 PROTEIN | ICTALURID HERPESVIRUS 1 (CHANNEL CATFISH VIRUS)(CCV) | 91–125 | | | | | | |
| PVG43_HSV11 | HYPOTHETICAL GENE 43 PROTEIN | ICTALURID HERPESVIRUS 1 (CHANNEL CATFISH VIRUS)(CCV) | 109–140 | 157–185 | | | | | |
| PVG46_HSV11 | PROBABLE MAJOR GLYCOPROTEIN | ICTALURID HERPESVIRUS 1 (CHANNEL CATFISH VIRUS)(CCV) | 888–925 | | | | | | |
| PVG48_HSVSA | HYPOTHETICAL GENE 48 PROTEIN | HERPESVIRUS SAIMIRI (STRAIN 11) | 329–357 | | | | | | |
| PVG50_HSVSA | PROBABLE TRANSCRIPTION ACTIVAOR EDRF1 | HERPESVIRUS SAIMIRI (STRAIN 11) | 113–141 | | | | | | |
| PVG51_HSV11 | HYPOTHETICAL GENE 51 MEMBRANE PROTEIN | ICTALURID HERPESVIRUS 1 (CHANNEL CATFISH VIRUS)(CCV) | 29–64 | 84–120 | | | | | |
| PVG52_HSV11 | HYPOTHETICAL GENE 52 PROTEIN | ICTALURID HERPESVIRUS 1 (CHANNEL CATFISH VIRUS)(CCV) | 96–134 | | | | | | |
| PVG55_HSV11 | HYPOTHETICAL GENE 55 PROTEIN | ICTALURID HERPESVIRUS 1 (CHANNEL CATFISH VIRUS)(CCV) | 100–129 | | | | | | |
| PVG56_HSV11 | HYPOTHETICAL GENE 56 PROTEIN | ICTALURID HERPESVIRUS 1 (CHANNEL CATFISH VIRUS)(CCV) | 364–396 | 631–667 | 1091–1126 | | | | |
| PVG58_HSV11 | HYPOTHETICAL GENE 58 PROTEIN | ICTALURID HERPESVIRUS 1 (CHANNEL CATFISH VIRUS)(CCV) | 342–375 | 480–508 | | | | | |
| PVG58_HSVSA | GENE 58 PROTEIN | HERPESVIRUS SAIMIRI (STRAIN 11) | 25–60 | 195–233 | | | | | |
| PVG59_HSV11 | HYPOTHETICAL GENE 59 PROTEIN | ICTALURID HERPESVIRUS 1 82–118 (CHANNEL CATFISH VIRUS)(CCV) | | | | | | | |
| PVG61_HSV11 | HYPOTHETICAL GENE 61 PROTEIN | ICTALURID HERPESVIRUS 1 (CHANNEL CATFISH VIRUS)(CCV) | 76–109 | | | | | | |
| PVG64_HSV11 | HYPOTHETICAL GENE 64 PROTEIN | ICTALURID HERPESVIRUS 1 (CHANNEL CATFISH VIRUS)(CCV) | 55–89 | 363–401 | 420–452 | | | | |
| PVG65_HSV11 | HYPOTHETICAL GENE 65 PROTEIN | ICTALURID HERPESVIRUS 1 (CHANNEL CATFISH VIRUS)(CCV) | 801–836 | 1146–1174 | 1290–1326 | | | | |
| PVG67_HSV11 | HYPOTHETICAL GENE 67 PROTEIN | ICTALURID HERPESVIRUS 1 (CHANNEL CATFISH VIRUS)(CCV) | 1150–1185 | | | | | | |
| PVG6_SPV1R | GENE 6 PROTEIN | SPIROPLASMA VIRUS SPV1-R8A2 B | 60–89 | | | | | | |
| PVG71_HSVSA | HYPOTHETICAL GENE 71 PROTEIN | HERPESVIRUS SAIMIRI (STRAIN 11) | 128–158 | | | | | | |
| PVG72_HSV11 | HYPOTHETICAL GENE 72 PROTEIN | ICTALURID HERPESVIRUS 1 (CHANNEL CATFISH VIRUS)(CCV) | 445–478 | 720–751 | 1158–1189 | 1252–1285 | | | |
| PVG75_HSV11 | HYPOTHETICAL GENE 75 PROTEIN | ICTALURID HERPESVIRUS 1 (CHANNEL CATFISH VIRUS)(CCV) | 263–291 | 387–422 | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVG76_HSV11 | HYPOTHETICAL GENE 76 PROTEIN | ICTALURID HERPESVIRUS 1 (CHANNEL CATFISH VIRUS)(CCV) | 187–221 | | | | | | |
| PVG7_SPVIR | GENE 7 PROTEIN | SPIROPLASMA VIRUS SPV1-R8A2 B | 18–46 | | | | | | |
| PVGF1_IBVB | F1 PROTEIN | AVIAN INFECTIOUS BRONCHITIS VIRUS (STRAIN BEAUDETTE)(IBV) | 1719–1747 | 1856–1891 | 2108–2146 | 3601–3633 | | | |
| PVGH3_HCMVA | GLYCOPROTEIN H301 PRECURSOR | HUMAN CYTOMEGALOVIRUS (STRAIN AD169) | 80–115 | 157–185 | | | | | |
| PVGL2_CVBF | E2 GLYCOPROTEIN PRECURSOR | BOVINE CORONAVIRUS (STRAIN F15) | 1259–1294 | | | | | | |
| PVGL2_CVBL9 | E2 GLYCOPROTEIN PRECURSOR | BOVINE CORONAVIRUS (STRAIN L9) | 651–681 | | | | | | |
| PVGL2_CVBLY | E2 GLYCOPROTEIN PRECURSOR | BOVINE CORONAVIRUS (STRAIN LY-138) | 1259–1294 | | | | | | |
| PVGL2_CVMB | E2 GLYCOPROTEIN PRECURSOR | BOVINE CORONAVIRUS (STRAIN MEBUS) | 1259–1294 | | | | | | |
| PVGL2_CVBQ | E2 GLYCOPROTEIN PRECURSOR | BOVINE CORONAVIRUS (STRAIN QUEBEC) | 1259–1294 | | | | | | |
| PVGL2_CVBV | E2 GLYCOPROTEIN PRECURSOR | BOVINE CORONAVIRUS (STRAIN VACCINE) | 1259–1294 | | | | | | |
| PVGL2_CVH22 | E2 GLYCOPROTEIN PRECURSOR | HUMAN CORONAVIRUS (STRAIN 229E) | 1053–1088 | | | | | | |
| PVGL2_CVM4 | E2 GLYCOPROTEIN PRECURSOR | MURINE CORONAVIRUS MHV (STRAIN WILD TYPE 4)(MHV-4) | 1267–1304 | | | | | | |
| PVGL2_CVMA5 | E2 GLYCOPROTEIN PRECURSOR | MURINE CORONAVIRUS MHV (STRAIN A59 | 1215–1252 | | | | | | |
| PVGL2_CMVJC | E2 GLYCOPROTEIN PRECURSOR | MURINE CORONAVIRUS MHV (STRAIN JHMV/VARIANT CL-2) | 1267–1304 | | | | | | |
| PVGL2_CVMJH | E2 GLYCOPROTEIN PRECURSOR | MURINE CORONAVIRUS MHV (STRAIN JHM) | 1126–1163 | | | | | | |
| PVGL2_CVPFS | E2 GLYCOPROTEIN PRECURSOR | PORCINE TRANSMISSIBLE GASTROENTERITIS CORONAVIRUS | 632–665 | 736–764 | 1328–1363 | | | | |
| PVGL2_CVPMI | E2 GLYCOPROTEIN PRECURSOR | PORCINE TRANSMISSIBLE GASTROENTERITIS CORONAVIRUS | 632–665 | 736–764 | 1328–1363 | | | | |
| PVGL2_CVPPR | E2 GLYCOPROTEIN PRECURSOR | PORCINE TRANSMISSIBLE GASTROENTERITIS CORONAVIRUS | 630–663 | 734–762 | 1326–1361 | | | | |
| PVGL2_CVPPU | E2 GLYCOPROTEIN PRECURSOR | PORCINE TRANSMISSIBLE GASTROENTERITIS CORONAVIRUS | 630–663 | 734–762 | 1326–1361 | | | | |
| PVGL2_CVPR8 | E2 GLYCOPROTEIN PRECURSOR | PORCINE RESPIRATORY CORONAVIRUS | 512–540 | 1104–1139 | | | | | |
| PVGL2_CVPRM | E2 GLYCOPROTEIN PRECURSOR | PORCINE RESPIRATORY CORONAVIRUS (STRAIN RM4)(PRCV) | 408–441 | 512–540 | 1104–1139 | | | | |
| PVGL2_CVPRT | E2 GLYCOPROTEIN PRECURSOR | PORCINE TRANSMISSIBLE GASTROENTERITIS CORONAVIRUS (STRAIN NEB7) | 630–663 | 734–762 | 1326–1361 | | | | |
| PVGL2_FIPV | E2 GLYCOPROTEIN PRECURSOR | FELINE INFECTIOUS PERITONTIS VIRUS (STRAIN 79-1146)(FIPV) | 635–668 | 739–767 | 1331–1366 | | | | |
| PVGL2_IBVB | E2 GLYCOPROTEIN PRECURSOR | AVIAN INFECTIOUS BRONCHITIS VIRUS (STRAIN BEAUDETTE)(IBV) | 153–188 | | | | | | |
| PVGLB_HCMVA | GLYCOPROTEIN B PRECURSOR | HUMAN CYTOMEGALOVIRUS (STRAIN AD169) | 116–147 | 706–743 | | | | | |
| PVGLB_HCMVT | GLYCOPROTEIN B PRECURSOR | HUMAN CYTOMEGALOVIRUS (STRAIN TOWNE) | 116–147 | 707–744 | | | | | |
| PVGLB_HSV6U | GLYCOPROTEIN B | HERPES SIMPLEX VIRUS (TYPE 6/STRAIN UGANDA-1102) | 72–110 | | | | | | |
| PVGLB_HSVB1 | GLYCOPROTEIN 1 PRECURSOR | BOVINE HERPESVIRUS TYPE 1 | 254–288 | | | | | | |
| PVGLB_HSVB2 | GLYCOPROTEIN B-1 PRECURSOR | BOVINE HERPESVIRUS 2 (STRAIN BMV)(BOVINE MAMMILLITIS VIRUS | 745–774 | | | | | | |
| PVGLB_HSVBC | GLYCOPROTEIN 1 PRECURSOR | BOVINE HERPESVIRUS 1 (STRAIN COOPER | 253–287 | | | | | | |
| PVGLB_ILTV6 | GLYCOPROTEIN B PRECURSOR | INFECTIOUS LARYNGOTRACHEITIS VIRUS (STRAIN 632)(ILIV) | 442–472 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVGLB_ILTVS | GLYCOPROTEIN B PRECURSOR | INFECTIOUS LARYNGOTRACHEITIS VIRUS (STRAIN SA-2)(ILTV) | 452–482 | | | | | | |
| PVGLB_ILTVT | GLYCOPROTEIN B PRECURSOR | INFECTIOUS LARYNGOTRACHEITIS VIRUS (STRAIN THORNE V882)(ILTV) | 452–482 | | | | | | |
| PVGLB_MCMVS | GLYCOPROTEIN B PRECURSOR | MURINE CYTOMEGALOVIRUS (STRAIN SMITH) | 135–163 | 738–776 | | | | | |
| PVGLC_HSV11 | GLYCOPROTEIN C PRECURSOR | HERPES SIMPLEX VIRUS (TYPE 1/STRAIN 17) | 467–500 | | | | | | |
| PVGLC_HSVIK | GLYCOPROTEIN C PRECURSOR | HERPES SIMPLEX VIRUS (TYPE 1/STRAIN KOS) | 467–500 | | | | | | |
| PVGLC_HSV2 | GLYCOPROTEIN C PRECURSOR | HERPES SIMPLEX VIRUS (TYPE 2) | 435–465 | | | | | | |
| PVGLC_HSV23 | GLYCOPROTEIN C PRECURSOR | HERPES SIMPLEX VIRUS (TYPE 2/STRAIN 333) | 436–466 | | | | | | |
| PVGLC_HSVBC | GLYCOPROTEIN G111 PRECURSOR | BOVINE HERPESVIRUS TYPE 1 (STRAIN COOPER) | 475–507 | | | | | | |
| PVGLC_VZVD | GLYCOPROTEIN GPV | VARICELLA-ZOSTER VIRUS (STRAIN DUMAS)(VZV) | 351–388 | 513–548 | | | | | |
| PVGLC_VZVS | GLYCOPROTEIN GPV | VARICELLA-ZOSTER VIRUS (STRAIN SCOTT)(VZV) | 351–388 | 513–548 | | | | | |
| PVGLD_HSVEA | GLYCOPROTEIN D PRECURSOR | EQUINE HERPESVIRUS TYPE 1 (STRAIN AB1)(EHV-1) | 340–370 | | | | | | |
| PVGLD_HSVEB | GLYCOPROTEIN D PRECURSOR | EQUINE HERPESVIRUS TYPE 1 | 41–70 | 390–420 | | | | | |
| PVGLD_HSVEK | GLYCOPROTEIN D PRECURSOR | EQUINE HERPESVIRUS TYPE 1 | 41–70 | 390–420 | | | | | |
| PVGLE_HSVE4 | GLYCOPROTEIN E | EQUINE HERPESVIRUS TYPE 4 | 95–125 | | | | | | |
| PVGLE_HSVEB | GLYCOPROTEIN E PRECURSOR | EQUINE HERPESVIRUS TYPE 1 | 63–100 | 390–420 | | | | | |
| PVGLE_HSVEL | GLYCOPROTEIN E PRECURSOR | EQUINE HERPESVIRUS TYPE 1 | 63–100 | 392–422 | | | | | |
| PVGLE_PRVR1 | GLYCOPROTEIN G1 PRECURSOR | PSEUDORABIES VIRUS (STRAIN RICE)(PRV) | 332–369 | | | | | | |
| PVGLE_BRSVA | FUSION GLYCOPROTEIN PRECURSOR | BOVINE RESPIRATORY SYNCYTIAL VIRUS (STRAIN A51908)(BRS) | 265–301 | 482–511 | | | | | |
| PVGLF_BRSVC | FUSION GLYCOPROTEIN PRECURSOR | BOVINE RESPIRATORY SYNCYTIAL VIRUS (STRAIN COPENHAGEN)(BRS) | 484–513 | | | | | | |
| PVGLF_BRSVR | FUSION GLYCOPROTEIN PRECURSOR | BOVINE RESPIRATORY SYNCYTIAL VIRUS (STRAIN RB94)(BRS) | 484–513 | | | | | | |
| PVGLF_CDVO | FUSION GLYCOPROTEIN PRECURSOR | CANINE DISTEMPER VIRUS (STRAIN ONDERSTEPOORT)(CDV) | 562–596 | | | | | | |
| PVGLF_HRSV1 | FUSION GLYCOPROTEIN PRECURSOR | HUMAN RESPIRATORY SYNCYTIAL VIRUS (SUBGROUP B/STRAIN 18537) | 484–513 | | | | | | |
| PVGLF_HRSVA | FUSION GLYCOPROTEIN PRECURSOR | HUMAN RESPIRATORY SYNCYTIAL VIRUS (STRAIN A2) | 484–513 | | | | | | |
| PVGLF_HRSVL | FUSION GLYCOPROTEIN PRECURSOR | HUMAN RESPIRATORY SYNCYTIAL VIRUS (SUBGROUP A/STRAIN LONG) | 484–513 | | | | | | |
| PVGLF_HRSVR | FUSION GLYCOPROTEIN PRECURSOR | HUMAN RESPIRATORY SYNCYTIAL VIRUS (STRAIN RSS-2) | 484–513 | | | | | | |
| PVGLF_MEASE | FUSION GLYCOPROTEIN PRECURSOR | MEASLES VIRUS (STRAIN EDMONSTON) | 224–256 | 451–484 | | | | | |
| PVGLF_MEAS1 | FUSION GLYCOPROTEIN PRECURSOR | MEASLES VIRUS (STRAIN IP-J-CA | 227–259 | 454–487 | | | | | |
| PVGLF_MEASY | FUSION GLYCOPROTEIN PRECURSOR | MEASLES VIRUS (STRAIN YAMAGATA-1) | 224–256 | 451–484 | | | | | |
| PVGLF_MUMP1 | FUSION GLYCOPROTEIN PRECURSOR | MUMPS VIRUS (STRAIN SBL-1) | 5–38 | 446–474 | | | | | |
| PVGLF_MUMPM | FUSION GLYCOPROTEIN PRECURSOR | MUMPS VIRUS (STRAIN MIYAHARA VACCINE) | 446–474 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVGLF_MUMPR | FUSION GLYCOPROTEIN PRECURSOR | MUMPS VIRUS (STRAIN RW) | 446–474 | | | | | | |
| PVGLF_MUMPS | FUSION GLYCOPROTEIN PRECURSOR | MUMPS VIRUS (STRAIN SBL) | 5–38 | 446–474 | | | | | |
| PVGLF_NDV1 | FUSION GLYCOPROTEIN PRECURSOR | NEWCASTLE DISEASE VIRUS (STRAIN ITALIEN/45)(NDV) | 132–165 | | | | | | |
| PVGLF_NDVL | FUSION GLYCOPROTEIN PRECURSOR | NEWCASTLE DISEASE VIRUS (STRAIN LA5/46)(NDV) | 132–165 | | | | | | |
| PVGLF_PHODV | FUSION GLYCOPROTEIN PRECURSOR | PHOCINE DISTEMPER VIRUS | 531–565 | | | | | | |
| PVGLF_PHHC | FUSION GLYCOPROTEIN PRECURSOR | HUMAN PARAINFLUENZA 1 VIRUS (STRAIN C39) | 456–484 | | | | | | |
| PVGLF_P13B | FUSION GLYCOPROTEIN PRECURSOR | BOVINE PARAINFLUENZA 3 VIRUS | 453–481 | | | | | | |
| PVGLF_P13H4 | FUSION GLYCOPROTEIN PRECURSOR | HUMAN PARAINFLUENZA 3 VIRUS (STRAIN NIH 47885 | 453–481 | | | | | | |
| PVGLF_RINDK | FUSION GLYCOPROTEIN PRECURSOR | RINDERPEST VIRUS (STRAIN KABETTE O)(RDV) | 220–252 | 447–480 | | | | | |
| PVGLF_RINDL | FUSION GLYCOPROTEIN PRECURSOR | RINDERPEST VIRUS (STRAIN L)(RDV) | 220–252 | 447–480 | | | | | |
| PVGLF_SEND5 | FUSION GLYCOPROTEIN PRECURSOR | SENDAI VIRUS (STRAIN Z/HOST MUTANTS) | 460–488 | | | | | | |
| PVGLF_SENDF | FUSION GLYCOPROTEIN PRECURSOR | SENDAI VIRUS (STRAIN FUSHIMI) | 460–488 | | | | | | |
| PVGLF_SENDH | FUSION GLYCOPROTEIN PRECURSOR | SENDAI VIRUS (STRAIN HARRIS) | 460–488 | | | | | | |
| PVGLF_SENDJ | FUSION GLYCOPROTEIN PRECURSOR | SENDAI VIRUS (STRAIN HVJ) | 460–480 | | | | | | |
| PVGLF_SENDZ | FUSION GLYCOPROTEIN PRECURSOR | SENDAI VIRUS (STRAIN Z) | 460–488 | | | | | | |
| PVGLF_SV5 | FUSION GLYCOPROTEIN PRECURSOR | SIMIAN VIRUS 5 (STRAIN W3)(SV5) | 446–474 | | | | | | |
| PVGLF_TRTV | FUSION GLYCOPROTEIN PRECURSOR | TURKEY RHINOTRACHEITIS VIRUS (TRTV) | 452–481 | | | | | | |
| PVGLG_HSVEB | GLYCOPROTEIN G PRECURSOR | EQUINE HERPESVIRUS TYPE 1 (STRAIN AB4P)(EHV-1) | 327–364 | | | | | | |
| PVGLG_SYNV | SPIKE GLYCOPROTEIN PRECURSOR | SONCHUS YELLOW NET VIRUS (SYNV) | 524–553 | | | | | | |
| PVGLG_VSVIG | SPIKE GLYCOPROTEIN PRECURSOR | VESICULAR STOMATITIS VIRUS (SEROTYPE INDIANA/STRAIN GLASGOW) | 450–488 | | | | | | |
| PVGLG_VSVJO | SPIKE GLYCOPROTEIN PRECURSOR | VESICULAR STOMATITIS VIRUS (SEROTYPE NEW JERSEY/STRAIN OGDEN) | 457–492 | | | | | | |
| PVGLG_VSVO | SPIKE GLYCOPROTEIN PRECURSOR | VESICULAR STOMATITIS VIRUS (STRAIN ORSAY) | 450–488 | | | | | | |
| PVGLG_VSVSJ | SPIKE GLYCOPROTEIN PRECURSOR | VESICULAR STOMATITIS VIRUS (STRAIN SAN JUAN) | 450–488 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVGLH_HCMVA | GLYCOPROTEIN H PRECURSOR | HUMAN CYTOMEGALOVIRUS (STRAIN AD169) | 691–719 | | | | | | |
| PVGLH_HCMVT | GLYCOPROTEIN H PRECURSOR | HUMAN CYTOMEGALOVIRUS (STRAIN TOWNE) | 690–718 | | | | | | |
| PVGLH_HSV6G | GLYCOPROTEIN H PRECURSOR | HERPES SIMPLEX VIRUS (TYPE 6/STRAIN GS) | 215–247 | 640–677 | | | | | |
| PVGLH_HSVE4 | GLYCOPROTEIN H PRECURSOR | EQUINE HERPESVIRUS TYPE 4 | 814–850 | | | | | | |
| PVGLH_HSVEB | GLYCOPROTEIN H PRECURSOR | EQUINE HERPESVIRUS TYPE 1 | 807–843 | | | | | | |
| PVGLL_HCMVA | IMMEDIATE EARLY GLYCOPROTEIN PRECURSOR | HUMAN CYTOMEGALOVIRUS (STRAIN AD169) | 158–194 | | | | | | |
| PVGLM_BUNGE | M POLYPROTEIN PRECURSOR | BUNYAVIRUS GERMISTON | 197–227 | 438–468 | 982–1020 | 1049–1084 | | | |
| PVGLM_BUNL7 | M POLYPROTEIN PRECURSOR | BUNYAVIRUS LA CROSSE (ISOLATE L74) | 190–220 | | | | | | |
| PVGLM_BUNSH | M POLYPROTEIN PRECURSOR | BUNYAVIRUS SNOWSHOE HARE | 190–220 | 344–381 | 823–854 | | | | |
| PVGLM_BUNYW | M POLYPROTEIN PRECURSOR | BUNYAMWERA VIRUS | 193–228 | 434–472 | 886–915 | 935–965 | 1403–1441 | | |
| PVGLM_DUGBV | M POLYPROTEIN PRECURSOR | DUGBE VIRUS | 244–273 | 637–672 | | | | | |
| PVGLM_HANTB | M POLYPROTEIN PRECURSOR | HANTANN VIRUS (STRAIN B-1)(KOREAN HEMORRHAGIC FEVER VIRUS) | 610–641 | 1081–1119 | | | | | |
| PVGLM_HANTH | M POLYPROTEIN PRECURSOR | HANTANN VIRUS (STRAIN HOJO) | 188–222 | 612–643 | 1082–1120 | | | | |
| PVGLM_HANTL | M POLYPROTEIN PRECURSOR | HANTANN VIRUS (STRAIN LEE) | 188–222 | 612–643 | 1083–1121 | | | | |
| PVGLM_HANTV | M POLYPROTEIN PRECURSOR | HANTANN VIRUS (STRAIN 76-118) | 188–222 | 612–643 | 1083–1121 | | | | |
| PVGLM_INSV | M POLYPROTEIN PRECURSOR | IMPATIENS NECROTIC SPOT VIRUS (INSV) | 269–307 | 1028–1062 | | | | | |
| PVGLM_PHV | M POLYPROTEIN PRECURSOR | PROSPECT HILL VIRUS (PHV) | 616–649 | 1088–1121 | | | | | |
| PVGLM_PTPV | M POLYPROTEIN PRECURSOR | PUNTA TOTO PHLEBOVIRUS | 949–982 | 1275–1309 | | | | | |
| PVGLM_PUUMH | M POLYPROTEIN PRECURSOR | PUUMALA VIRUS (STRAIN HALLNAS B1) | 620–653 | 1092–1125 | | | | | |
| PVGLM_PUUMS | M POLYPROTEIN PRECURSOR | PUUMALA VIRUS (STRAIN SOTKAMO) | 620–653 | 1092–1125 | | | | | |
| PVGLM_RVFV | M POLYPROTEIN PRECURSOR | RIFT VALLEY FEVER VIRUS (RVFV) | 620–650 | 830–863 | | | | | |
| PVGLM_RVFVZ | M POLYPROTEIN PRECURSOR | RIFT VALLEY FEVER VIRUS (STRAIN ZH-648 M12)(RVFV) | 620–650 | 830–863 | 1156–1185 | | | | |
| PVGLM_SEOU8 | M POLYPROTEIN PRECURSOR | SEOUL VIRUS (STRAIN 80-39) | 610–641 | 1081–1119 | | | | | |
| PVGLM_SEOUR | M POLYPROTEIN PRECURSOR | SEOUL VIRUS (STRAIN R22) | 605–641 | 1082–1120 | | | | | |
| PVGLM_SEOUS | M POLYPROTEIN PRECURSOR | SEOUL VIRUS (STRAIN SR-11)(SAPPORO RAT VIRUS) | 610–641 | 1081–1119 | | | | | |
| PVGLM_UUK | M POLYPROTEIN PRECURSOR | UUKUNIEMI VIRUS (UUK) | 431–468 | 966–995 | | | | | |
| PVGLP_BEY | REPLOMER GLYCOPORTEIN PRECURSOR | BERNE VIRUS (BEV) | 1491–1526 | | | | | | |
| PVGLY_JUNN | GLYCOPROTEIN POLYPROTEIN PRECURSOR | JUNIN ARENAVIRUS | 12–45 | | | | | | |
| PVGLY_LASSG | GLYCOPROTEIN POLYPROTEIN PRECURSOR | LASSA VIRUS (STRAIN GA391) | 237–265 | | | | | | |
| PVGLY_LASSJ | GLYCOPROTEIN POLYPROTEIN PRECURSOR | LASSA VIRUS (STRAIN JOSIAH) | 238–266 | | | | | | |
| PVGLY_PIARV | GLYCOPROTEIN POLYPROTEIN PRECURSOR | PICHINDE ARENAVIRUS | 12–50 | | | | | | |
| PVGLY_TACV | GLYCOPROTEIN POLYPROTEIN PRECURSOR | TACARBIDE VIRUS | 12–50 | | | | | | |
| PVGLY_TACV5 | GLYCOPROTEIN POLYPROTEIN PRECURSOR | TACARBIDE VIRUS (STRAIN V5) | 12–50 | 89–124 | | | | | |
| PVGLY_TACV7 | GLYCOPROTEIN POLYPROTEIN PRECURSOR | TACARBIDE VIRUS (STRAIN V7) | 12–50 | 89–124 | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVGLY_TACVT | GLYCOPROTEIN POLYPROTEIN PRECURSOR | TACARBIDE VIRUS (STRAIN TRVL 11598) | 12–50 | 89–124 | | | | | |
| PVGNB_CPMV | GENOME POLYPROTEIN B | COWPEA MOSAIC VIRUS (CPMV) | 1527–1555 | | | | | | |
| PVGNM_CPMV | GENOME POLYPROTEIN M | COWPEA MOSAIC VIRUS (CPMV) | 209–242 | 741–771 | | | | | |
| PVGNM_CPSMV | GENOME POLYPROTEIN M | COWPEA SEVERE MOSAIC VIRUS (STRAIN DG) | 50–86 | 479–515 | | | | | |
| PVGNM_RCMV | GENOME POLYPROTEIN M | RED CLOVER MOTTLE VIRUS (RCMV) | 766–799 | | | | | | |
| PVGP2_EBV | PROBABLE MEMBRANE ANTIGEN GP220 | EPSTEIN-BARR VIRUS (STRAIN B95-8)(HUMAN HERPESVIRUS 4) | 78–111 | | | | | | |
| PVGP3_EBV | ENVELOPE GLYCOPROTEIN GP340 | EPSTEIN-BARR VIRUS (STRAIN B95-8)(HUMAN HERPESVIRUS 4) | 78–111 | | | | | | |
| PVH02_VACCC | LATE PROTEIN H2 | VACCINIA VIRUS (STRAIN COPENHAGEN) | 54–89 | | | | | | |
| PVH02_VACCV | LATE PROTEIN H2 | VACCINIA VIRUS (STRAIN WR) | 54–89 | | | | | | |
| PVH02_VARV | LATE PROTEIN H2 | VARJOLA VIRUS | | | | | | | |
| PVH05_VACCC | PROTEIN H5 | VACCINIA VIRUS (STRAIN COPENHAGEN) | 115–149 | | | | | | |
| PVH05_VACCV | PROTEIN H5 | VACCINIA VIRUS (STRAIN WR) | 115–149 | | | | | | |
| PVH05_VARV | PROTEIN H5 | VARJOLA VIRUS | 133–167 | | | | | | |
| PVHEL_LSV | PROBABLE HELICASE | LILY SYMPTOMLESS VIRUS (LSV) | 107–143 | | | | | | |
| PV101_VACCC | PROTEIN 11 | VACCINIA VIRUS (STRAIN COPENHAGEN) | 54–82 | | | | | | |
| PV101_VARV | PROTEIN 11 | VARJOLA VIRUS | 54–82 | | | | | | |
| PV106_VACCV | PROTEIN 16 | VACCINIA VIRUS (STRAIN WR) | 55–88 | | | | | | |
| PV106_VARV | PROTEIN 16 | VARJOLA VIRUS | 55–88 | | | | | | |
| PV108_VACCC | PUTATIVE RNA HELICASE 18 | VACCINIA VIRUS (STRAIN COPENHAGEN) | 591–624 | | | | | | |
| PV108_VACCV | PUTATIVE RNA HELICASE 18 | VACCINIA VIRUS (STRAIN WR) | 591–624 | | | | | | |
| PV108_VARV | PUTATIVE RNA HELICASE 18 | VARJOLA VIRUS | 591–624 | | | | | | |
| PV1E1_HCMVA | 55 KD IMMEDIATE-EARLY PROTEIN 1 | HUMAN CYTOMEGALOVIRUS (STRAIN AD169) | 243–271 | | | | | | |
| PV1E1_HCMVT | 55 KD IMMEDIATE-EARLY PROTEIN 1 | HUMAN CYTOMEGALOVIRUS (STRAIN TOWNE) | 243–271 | | | | | | |
| PVIF_BIV06 | VIRION INFECTIVITY FACTOR | BOVINE IMMUNODEFICIENCY VIRUS (ISOLATE 106)(BIV) | 42–78 | | | | | | |
| PVIF_BIV27 | VIRION INFECTIVITY FACTOR | BOVINE IMMUNODEFICIENCY VIRUS (ISOLATE 127)(BIV) | 42–78 | | | | | | |
| PVIF_SIVGB | VIRION INFECTIVITY FACTOR | SIMIAN IMMUNODEFICIENCY VIRUS (ISOLATE GB1) | 46–78 | | | | | | |
| PVIF_SIVMK | VIRION INFECTIVITY FACTOR | SIMIAN IMMUNODEFICIENCY VIRUS (K6W ISOLATE)(SIV-MAC) | 82–111 | | | | | | |
| PVIMP_EBV | PROBABLE INTEGRAL MEMBRANE PROTEIN BBRF3 | EPSTEIN-BARR VIRUS (STRAIN B95-8)(HUMAN HERPESVIRUS 4) | 125–159 | | | | | | |
| PVIMP_HCMVA | PROBABLE INTEGRAL MEMBRANE PROTEIN | HUMAN CYTOMEGALOVIRUS (STRAIN AD169 | 68–100 | | | | | | |
| PVIMP_HSV11 | PROBABLE INTEGRAL MEMBRANE PROTEIN | HERPES SIMPLEX VIRUS (TYPE 1/STRAIN 17) | 83–114 | 136–171 | 250–282 | | | | |
| PVIMP_HSVEB | PROBABLE INTEGRAL MEMBRANE PROTEIN | EQUINE HERPESVIRUS TYPE 1 (STRAIN AB4P)(EHV-1) | 24–56 | 93–127 | 145–180 | 332–361 | | | |
| PVIMP_HSVSA | INTEGRAL MEMBRANE PROTEIN | HERPESVIRUS SAIMIRI (STRAIN 11) | 76–111 | | | | | | |
| PVINT_SSV1 | PROBABLE INTEGRASE | SULFOLOBUS VIRUS-LIKE PARTICLE SSV1 | 253–291 | | | | | | |
| PVJ05_VACCC | PROTEIN J5 | VACCINIA VIRUS (STRAIN COPENHAGEN) | 54–85 | | | | | | |

TABLE XIV-continued

| PCGENE FILE NAME | P23CTLZIP PROTEIN | All Viruses (no bacteriophages) VIRUS | SEARCH RESULTS SUMMARY FOR P23TLZIPC MOTIF AREA 1 | AREA 2 | AREA 3 | AREA 4 | AREA 5 | AREA 6 | AREA 7 |
|---|---|---|---|---|---|---|---|---|---|
| PVJ05_VACCV | PROTEIN J5 | VACCINIA VIRUS (STRAIN WR) | 54–85 | | | | | | |
| PVJ05_VARV | PROTEIN J5 | VARJOLA VIRUS | 54–85 | | | | | | |
| PVK04_VACCC | PROTEIN K4 | VACCINIA VIRUS (STRAIN COPENHAGEN) | 87–120 | | | | | | |
| PVK04_VACCV | PROTEIN K4 | VACCINIA VIRUS (STRAIN WR) | 87–120 | | | | | | |
| PVK05_VACCC | PROTEIN K5 | VACCINIA VIRUS (STRAIN COPENHAGEN) | 74–103 | | | | | | |
| PVK05_VACCV | PROTEIN K5 | VACCINIA VIRUS (STRAIN WR) | 87–116 | | | | | | |
| PVL02_VACCC | PROTEIN L2 | VACCINIA VIRUS (STRAIN COPENHAGEN) | 39–76 | | | | | | |
| PVL02_VACCV | PROTEIN L2 | VACCINIA VIRUS (STRAIN WR) | 39–76 | | | | | | |
| PVL02_VARV | PROTEIN L2 | VARJOLA VIRUS | 39–76 | | | | | | |
| PLV03_VACCC | PROTEIN L3 | VACCINIA VIRUS (STRAIN COPENHAGEN) | 292–322 | | | | | | |
| PVL03_VACCV | PROTEIN L3 | VACCINIA VIRUS (STRAIN WR) | 292–322 | | | | | | |
| PVL03_VARV | PROTEIN L3 | VARJOLA VIRUS | 291–321 | | | | | | |
| PVL05_VACCV | PROTEIN L5 | VACCINIA VIRUS (STRAIN WR), AND VACCINIA VIRUS (STRAIN COPENHAGE | 16–45 | | | | | | |
| PVL05_VARV | PROTEIN L5 | VARJOLA VIRUS | 16–45 | | | | | | |
| PVL1_HPV5B | PROBABLE L1 PROTEIN | HUMAN PAPILLOMAVIRUS TYPE 5B | 373–406 | | | | | | |
| PVL2_CRPVK | PROBABLE L2 PROTEIN | COTTONTAIL RABBIT (SHOPE) PAPILLOMAVIRUS (STRAIN KANSAS)(CRPV) | 26–57 | | | | | | |
| PVL2_HPV05 | PROBABLE L2 PROTEIN | HUMAN PAPILLOMAVIRUS TYPE 5 | 27–57 | | | | | | |
| PVL2_HPV08 | PROBABLE L2 PROTEIN | HUMAN PAPILLOMAVIRUS TYPE 8 | 27–57 | | | | | | |
| PVL2_HPV1A | PROBABLE L2 PROTEIN | HUMAN PAPILLOMAVIRUS TYPE 1A | 26–56 | | | | | | |
| PVL2_HPV39 | PROBABLE L2 PROTEIN | HUMAN PAPILLOMAVIRUS TYPE 39 | 29–59 | 285–313 | | | | | |
| PVL2_HPV42 | PROBABLE L2 PROTEIN | HUMAN PAPILLOMAVIRUS TYPE 42 | 344–379 | | | | | | |
| PVL2_HPV47 | PROBABLE L2 PROTEIN | HUMAN PAPILLOMAVIRUS TYPE 47 | 26–57 | | | | | | |
| PVL2_HPV51 | PROBABLE L2 PROTEIN | HUMAN PAPILLOMAVIRUS TYPE 51 | 29–59 | | | | | | |
| PVL2_HPV5B | PROBABLE L2 PROTEIN | HUMAN PAPILLOMAVIRUS TYPE 5B | 27–57 | | | | | | |
| PVL2_HPVME | PROBABLE L2 PROTEIN | HUMAN PAPILLOMAVIRUS TYPE ME180 | 29–59 | | | | | | |
| PVL2_PCPV1 | PROBABLE L2 PROTEIN | PYGMY CHIMPANZEE PAPILLOMAVIRUS TYPE 1 | 29–59 | | | | | | |
| PVL96_IRV1 | L96 PROTEIN | TIPULA IRIDESCENT VIRUS (TIV) (INSECT IRRIDESCENT VIRUS TYPE 1) | 144–177 | 686–718 | | | | | |
| PVM1_REOVD | MINOR VIRION STRUCTURAL PROTEIN MU-2 | REOVIRUS (TYPE 3/STRAIN DEARING | 280–318 | 324–361 | | | | | |
| PVM1_REOVL | MINOR VIRION STRUCTURAL PROTEIN MU-2 | REOVIRUS (TYPE 1/STRAIN LANG) | 280–318 | | | | | | |
| PVM21_REOVD | MAJOR VIRION STRUCTURAL PROTEIN MU-1/MU-1C | REOVIRUS (TYPE 3/STRAIN DEARING) | 168–199 | | | | | | |
| PVM22_REOVD | MAJOR VIRION STRUCTURAL PROTEIN MU-1/MU-1C | REOVIRUS (TYPE 3/STRAIN DEARING) | 168–199 | | | | | | |
| PVM2_REOVJ | MAJOR VIRION STRUCTURAL PROTEIN MU-1/MU-1C | REOVIRUS (TYPE 2/STRAIN D5/JONES) | 168–199 | | | | | | |
| PVM2_REOVL | MAJOR VIRION STRUCTURAL PROTEIN MU-1/MU-1C | REOVIRUS (TYPE 1/STRAIN LANG) | 168–199 | | | | | | |
| PVM3_REOVD | MAJOR NONSTRUCTURAL PROTEIN MU-NS | REOVIRUS (TYPE 3/STRAIN DEARING) | 333–364 | | | | | | |
| PVMAT_SV5 | MATRIX PROTEIN | SIMIAN VIRUS 5 (STRAIN W3)(SV5) | 308–342 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVMAT_TRTV | MATRIX PROTEIN | TURKEY RHINOTRACHEITIS VIRUS (TRTV) | 122–150 | | | | | | |
| PVME1_CVBM | E1 GLYCOPROTEIN | BOVINE CORONAVIRUS (STRAIN MEBUS) | 64–102 | | | | | | |
| PVME1_CVHOC | E1 GLYCOPROTEIN | HUMAN CORONAVIRUS (STRAIN OC43) | 64–102 | | | | | | |
| PVME1_CVMA5 | E1 GLYCOPROTEIN | MURINE CORONAVIRUS MHV (STRAIN A59) | 65–103 | | | | | | |
| PVME1_CVMJH | E1 GLYCOPROTEIN | MURINE CORONAVIRUS MHV (STRAIN JHM) | 65–103 | | | | | | |
| PVME1_CVTKE | E1 GLYCOPROTEIN | TURKEY ENTERIC CORONAVIRUS (TCV) | 64–102 | | | | | | |
| PVME1_1BVB | E1 GLYCOPROTEIN | AVIAN INFECTIOUS BRONCHITIS VIRUS (STRAIN BEAUDETTE)(IBV) | 73–101 | | | | | | |
| PVME1_1BVB2 | E1 GLYCOPROTEIN | AVIAN INFECTIOUS BRONCHITIS VIRUS (STRAIN BEAUDETTE M42)(IBV) | 73–101 | | | | | | |
| PVMEM_EBV | PROBABLE MEMBRANE PROTEIN | EPSTEIN-BARR VIRUS (STRAIN B95-8)(HUMAN HERPESVIRUS 4) | 178–213 | | | | | | |
| PVMP_CERV | MOVEMENT PROTEIN | CARNATION ETCHED RING VIRUS (CERV) | 93–126 | | | | | | |
| PVMP_SOCMV | MOVEMENT PROTEIN | SOYBEAN CHLOROTIC MOTTLE VIRUS | 66–98 | 273–303 | | | | | |
| PVMSA_HPBDB | MAJOR SURFACE ANTIGEN PRECURSOR | DUCK HEPATITIS B VIRUS (BROWN SHANGHAI DUCK ISOLATE S5)(DHBV) | 201–238 | 269–302 | | | | | |
| PVMSA_HPBDC | MAJOR SURFACE ANTIGEN PRECURSOR | DUCK HEPATITIS B VIRUS (STRAIN CHINA)(DHBV) | 194–227 | 268–301 | | | | | |
| PVMSA_HPBDU | MAJOR SURFACE ANTIGEN PRECURSOR | DUCK HEPATITIS B VIRUS (DHBV) | 157–190 | 231–264 | | | | | |
| PVMSA_HPBDW | MAJOR SURFACE ANTIGEN PRECURSOR | DUCK HEPATITIS B VIRUS (WHITE SHANGHAI DUCK ISOLATE S31)(DHBV) | 194–228 | 269–302 | | | | | |
| PVMSA_HPBGS | MAJOR SURFACE ANTIGEN PRECURSOR | GROUND SQUIRREL HEPATITIS VIRUS (GSHV) | 209–243 | 271–307 | | | | | |
| PVMSA_HPBHE | MAJOR SURFACE ANTIGEN PRECURSOR | HERON HEPATITIS B VIRUS | 159–195 | 236–269 | | | | | |
| PVMSA_HPBV0 | MAJOR SURFACE ANTIGEN | HEPATITIS B VIRUS | 70–98 | | | | | | |
| PVMSA_HPBV2 | MAJOR SURFACE ANTIGEN PRECURSOR | HEPATITIS B VIRUS (SUBTYPE ADW2) | 244–272 | | | | | | |
| PVMSA_HPBV4 | MAJOR SURFACE ANTIGEN PRECURSOR | HEPATITIS B VIRUS (SUBTYPE ADR4) | 244–272 | | | | | | |
| PVMSA_HPBV9 | MAJOR SURFACE ANTIGEN PRECURSOR | HEPATITIS B VIRUS (SUBTYPE ADW/STRAIN 991) | 244–272 | | | | | | |
| PVMSA_HPBVA | MAJOR SURFACE ANTIGEN PRECURSOR | HEPATITIS B VIRUS (STRAIN ALPHA1) | 233–261 | | | | | | |
| PVMSA_HPBVD | MAJOR SURFACE ANTIGEN | HEPATITIS B VIRUS (SUBTYPE AD) | 70–98 | | | | | | |
| PVMSA_HPBV1 | MAJOR SURFACE ANTIGEN PRECURSOR | HEPATITIS B VIRUS (SUBTYPE ADW/ STRAIN INDONESIA/PIDW420) | 233–261 | | | | | | |
| PVMSA_HPBVJ | MAJOR SURFACE ANTIGEN PRECURSOR | HEPATITIS B VIRUS (SUBTYPE ADW/STRAIN JAPAN/PJDW233) | 233–261 | | | | | | |
| PVMSA_HPBVL | MAJOR SURFACE ANTIGEN PRECURSOR | HEPATITIS B VIRUS (STRAIN LSH/CHIMPANZEE ISOLATE) | 233–261 | | | | | | |
| PVMSA_HPBVN | MAJOR SURFACE ANTIGEN | HEPATITIS B VIRUS (SUBTYPE ADR/STRAIN NC-1) | 70–98 | | | | | | |
| PVMSA_HPBVO | MAJOR SURFACE ANTIGEN PRECURSOR | HEPATITIS B VIRUS (SUBTYPE ADW/ STRAIN OKINAWA/PODW282) | 233–261 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVMSA_HPBVP | MAJOR SURFACE ANTIGEN PRECURSOR | HEPATITIS B VIRUS (SUBTYPE ADW/ STRAIN PHILIPPINO/PFDW294) | 244–272 | | | | | | |
| PVMSA_HPBVR | MAJOR SURFACE ANTIGEN PRECURSOR | HEPATITIS B VIRUS (SUBTYPE ADR) | 244–272 | | | | | | |
| PVMSA_HPBVS | MAJOR SURFACE ANTIGEN | HEPATITIS B VIRUS (SUBTYPE AR) | 70–98 | | | | | | |
| PVMSA_HPBVW | MAJOR SURFACE ANTIGEN PRECURSOR | HEPATITIS B VIRUS (SUBTYPE ADW) | 233–261 | | | | | | |
| PVMSA_HPBVY | MAJOR SURFACE ANTIGEN PRECURSOR | HEPATITIS B VIRUS (SUBTYPE AYW) | 233–261 | | | | | | |
| PVMSA_HPBVZ | MAJOR SURFACE ANTIGEN PRECURSOR | HEPATITIS B VIRUS (SUBTYPE ADYW) | 233–261 | | | | | | |
| PVMSA_WHV1 | MAJOR SURFACE ANTIGEN PRECURSOR | WOODCHUCK HEPATITIS VIRUS 1 | 207–241 | 269–305 | | | | | |
| PVMSA_WHV59 | MAJOR SURFACE ANTIGEN PRECURSOR | WOODCHUCK HEPATITIS VIRUS 59 | 212–246 | 274–310 | | | | | |
| PVMSA_WHV7 | MAJOR SURFACE ANTIGEN PRECURSOR | WOODCHUCK HEPATITIS VIRUS 7 | 212–246 | 274–310 | | | | | |
| PVMSA_WHV8 | MAJOR SURFACE ANTIGEN PRECURSOR | WOODCHUCK HEPATITIS VIRUS 8 | 212–246 | 274–310 | | | | | |
| PVMSA_WHV81 | PROBABLE MAJOR SURFACE ANTIGEN PRECURSOR | WOODCHUCK HEPATITIS VIRUS 8 (INFECTIOUS CLONE) | 212–246 | 274–305 | | | | | |
| PVMSA_WHVW6 | MAJOR SURFACE ANTIGEN PRECURSOR | WOODCHUCK HEPATITIS VIRUS W64 (ISOLATE PWS23) | 125–161 | | | | | | |
| PVMT2_IAZH | MATRIX (M2) PROTEIN | INFLUENZA A VIRUS (STRAIN A/SWINE/IOWA/15/30) | 10–42 | | | | | | |
| PVMT8_MYXVL | M-T8 PROTEIN | MYXOMA VIRUS (STRAIN LAUSANNE) | 5–34 | 141–170 | | | | | |
| PVMT9_MYXVL | MT-9 PROTEIN | MYXOMA VIRUS (STRAIN LAUSANNE) | 246–282 | | | | | | |
| PVN02_VACCC | PROTEIN N2 | VACCINIA VIRUS (STRAIN COPENHAGEN) | 31–68 | | | | | | |
| PVN02_VACCV | PROTEIN N2 | VACCINIA VIRUS (STRAIN WR) | 31–68 | | | | | | |
| PVN02_VARV | PROTEIN N2 | VARIOLA VIRUS | 31–68 | | | | | | |
| PVN34_ROTPC | NONSTRUCTURAL PROTEIN NS34 | PORCINE ROTAVIRUS (GROUP C/STRAIN COWDEN) | 336–366 | | | | | | |
| PVNCA_AAV2 | DNA REPLICATION PROTEIN | ADENO-ASSOCIATED VIRUS 2 (AAV2) | 163–196 | 365–401 | | | | | |
| PVNCS_PAVBO | PROBABLE NONCAPSID PROTEIN NS1 | BOVINE PARVOVIRUS (BPV) | 180–217 | 346–377 | 439–471 | | | | |
| PVNS1_AHSV4 | NONSTRUCTURAL PROTEIN NS1 | AFRICAN HORSE SICKNESS VIRUS (SEROTYPE 4/STRAIN VACCINE) | 351–380 | | | | | | |
| PVNS1_IAALA | NONSTRUCTURAL PROTEIN NS1 | INFLUENZA A VIRUS (STRAIN A/ALASKA/6/77) | 114–144 | | | | | | |
| PVNS1_IAANN | NONSTRUCTURAL PROTEIN NS1 | INFLUENZA A VIRUS (STRAIN A/ANN ARBOR/6/60) | 114–144 | | | | | | |
| PVNS1_IACHI | NONSTRUCTURAL PROTEIN NS1 | INFLUENZA A VIRUS (STRAIN A/CHILE/1/8) | 114–144 | | | | | | |
| PVNS1_IACKG | NONSTRUCTURAL PROTEIN NS1 | INFLUENZA A VIRUS (STRAIN A/CHICKEN/GERMANY/N/49) | 107–144 | | | | | | |
| PVNS1_IACKJ | NONSTRUCTURAL PROTEIN NS1 | INFLUENZA A VIRUS (STRAIN A/CHICKEN/JAPAN/24) | 104–141 | | | | | | |

TABLE XIV-continued

| PCGENE FILE NAME | P23CTLZIP PROTEIN | All Viruses (no bacteriophages) VIRUS | SEARCH RESULTS SUMMARY FOR P23TLZIPC MOTIF AREA 1 | AREA 2 | AREA 3 | AREA 4 | AREA 5 | AREA 6 | AREA 7 |
|---|---|---|---|---|---|---|---|---|---|
| PVNS1_IADA2 | NONSTRUCTURAL PROTEIN NS1 | INFLUENZA A VIRUS (STRAIN A/DUCK/ALBERTA/60/76) | 107–144 | | | | | | |
| PVNS1_IADE1 | NONSTRUCTURAL PROTEIN NS1 | INFLUENZA A VIRUS (STRAIN A/DUCK/ENGLAND/1/56) | 104–141 | | | | | | |
| PVNS1_IADU3 | NONSTRUCTURAL PROTEIN NS1 | INFLUENZA A VIRUS (STRAIN A/DUCK/UKRAINE/1/63) | 104–141 | | | | | | |
| PVNS1_IAFOM | NONSTRUCTURAL PROTEIN NS1 | INFLUENZA A VIRUS (STRAIN A/FORT MONMOUTH/1/47) | 114–144 | | | | | | |
| PVNS1_IAFOW | NONSTRUCTURAL PROTEIN NS1 | INFLUENZA A VIRUS (STRAIN A/FORT WARREN/1/50) | 114–144 | | | | | | |
| PVNS1_IAFPR | NONSTRUCTURAL PROTEIN NS1 | INFLUENZA A VIRUS (STRAIN A/FOWL PLAGUE VIRUS/ROSTOCK/34) | 107–144 | | | | | | |
| PVNS1_IALE1 | NONSTRUCTURAL PROTEIN NS1 | INFLUENZA A VIRUS (STRAIN A/LENINGRAD/134/57) | 114–144 | | | | | | |
| PVNS1_IALEN | NONSTRUCTURAL PROTEIN NS1 | INFLUENZA A VIRUS (STRAIN A/LENINGRAD/54/1) | 114–144 | | | | | | |
| PVNS1_IAMA6 | NONSTRUCTURAL PROTEIN NS1 | INFLUENZA A VIRUS (STRAIN A/MALLARD/ALBERTA/88/76) | 107–144 | | | | | | |
| PVNS1_IAMAN | NONSTRUCTURAL PROTEIN NS1 | INFLUENZA A VIRUS (STRAIN A/MALLARD/NEW YORK/6750/78) | 107–144 | | | | | | |
| PVNS1_IAMAO | NONSTRUCTURAL PROTEIN NS1 | INFLUENZA A VIRUS (STRAIN A/MALLARD/NEW YORK/6874/78) | 107–144 | | | | | | |
| PVNS1_IAMYN | NONSTRUCTURAL PROTEIN NS1 | INFLUENZA A VIRUS (STRAIN A/MYNAH/HANEDA-THAI/76) | 104–141 | | | | | | |
| PVNS1_IAP10 | NONSTRUCTURAL PROTEIN NS1 | INFLUENZA A VIRUS (STRAIN A/PINTAIL/ALBERTA/119/79) | 107–144 | | | | | | |
| PVNS1_IAP11 | NONSTRUCTURAL PROTEIN NS1 | INFLUENZA A VIRUS (STRAIN A/PINTAIL/ALBERTA/121/79) | 107–144 | | | | | | |
| PVNS1_IAP12 | NONSTRUCTURAL PROTEIN NS1 | INFLUENZA A VIRUS (STRAIN A/PINTAIL/ALBERTA/268/78) | 107–144 | | | | | | |
| PVNS1_IAP13 | NONSTRUCTURAL PROTEIN NS1 | INFLUENZA A VIRUS (STRAIN A/ PINTAIL/ALBERTA/358/79) | 107–144 | | | | | | |
| PVNS1_IAPUE | NONSTRUCTURAL PROTEIN NS1 | INFLUENZA A VIRUS (STRAIN A/PUERTO RICO/8/34) | 114–144 | | | | | | |
| PVNS1_IATKB | NONSTRUCTURAL PROTEIN NS1 | INFLUENZA A VIRUS (STRAIN A/TURKEY/ BETHLEHEM-GLILIT/1492-B/82) | 107–144 | | | | | | |
| PVNS1_IATKC | NONSTRUCTURAL PROTEIN NS1 | INFLUENZA A VIRUS (STRAIN A/ TURKEY/CANADA/63) | 107–144 | | | | | | |
| PVNS1_IATRS | NONSTRUCTURAL PROTEIN NS1 | INFLUENZA A VIRUS (STRAIN A/ TERN/SOUTH AFRICA/61) | 104–141 | | | | | | |
| PVNS1_IATRT | NONSTRUCTURAL PROTEIN NS1 | INFLUENZA A VIRUS (STRAIN A/ TERN/TURKMENIA/18/72) | 107–144 | | | | | | |
| PVNS1_IAUDO | NONSTRUCTURAL PROTEIN NS1 | INFLUENZA A VIRUS (STRAIN A/UDORN/307/72) | 114–144 | | | | | | |
| PVNS1_IAUSS | NONSTRUCTURAL PROTEIN NS1 | INFLUENZA A VIRUS (STRAIN A/USSR/90/77) | 114–144 | | | | | | |
| PVNS1_IAZ11 | NONSTRUCTURAL PROTEIN NS1 | INFLUENZA A VIRUS (STRAIN A/SWINE/IOWA/15/30 | 107–144 | | | | | | |
| PVNS1_INBPA | NONSTRUCTURAL PROTEIN NS1 | INFLUENZA B VIRUS (STRAIN B/PA/79) | 266–295 | | | | | | |
| PVNS1_INCAA | NONSTRUCTURAL PROTEIN NS1 | INFLUENZA C VIRUS (STRAIN C/ANN ARBOR/1/50) | 222–255 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVNS1_INCCA | NONSTRUCTURAL PROTEIN NS1 | INFLUENZA C VIRUS (STRAIN C/CALIFORNIA/78) | 222–255 | | | | | | |
| PVNS2_HRSV1 | NONSTRUCTURAL PROTEIN 2 | HUMAN RESPIRATORY SYNCYTIAL VIRUS (SUBGROUP B/STRAIN 18537) | 20–49 | | | | | | |
| PVNS2_HRSVA | NONSTRUCTURAL PROTEIN 2 | HUMAN RESPIRATORY SYNCYTIAL VIRUS (STRAIN A2) | 20–49 | | | | | | |
| PVNS2_INBLE | NONSTRUCTURAL PROTEIN NS2 | INFLUENZA B VIRUS (STRAIN B/LEE/40 | 48–77 | | | | | | |
| PVNS2_INBYA | NONSTRUCTURAL PROTEIN NS2 | INFLUENZA B VIRUS (STRAIN B/YAMAGATA/1/73) | 48–77 | | | | | | |
| PVNS4_CVMS | NONSTRUCTURAL PROTEIN 4 | MURINE CORONAVIRUS MHV (STRAIN S) | 17–45 | | | | | | |
| PVNS4_CVPFS | NONSTRUCTURAL PROTEIN 4 | PORCINE TRANSMISSIBLE GASTROENTERITIS CORONAVIRUS (STRAIN FS77 | 4–34 | | | | | | |
| PVNS4_CVPPU | NONSTRUCTURAL PROTEIN 4 | PORCINE TRANSMISSIBLE GASTROENTERITIS CORONAVIRUS (STRAIN PUR | 4–39 | | | | | | |
| PVNS4_CVPRM | NONSTRUCTURAL PROTEIN 4 | PORCINE REPIRATORY CORONAVIRUS | 4–39 | | | | | | |
| PVNST_CVMA5 | 30 KD NONSTRUCTURAL PROTEIN | MURINE CORONAVIRUS MHV (STRAIN A59) | 45–80 | | | | | | |
| PVNST_CVMJH | 30 KD NONSTRUCTURAL PROTEIN | MURINE CORONAVIRUS MHV (STRAIN JHM) | 49–84 | | | | | | |
| PVNST_INCGL | NONSTRUCTURAL PROTEINS NS1-NS2 | INFLUENZA C VIRUS (STRAIN C/GREAT LAKES/1167/54) | 222–255 | | | | | | |
| PVNST_INCH | NONSTRUCTURAL PROTEINS NS1-NS2 | INFLUENZA C VIRUS (STRAIN C/JOHANNESBURG/1/66) | 222–255 | | | | | | |
| PNVST_INCM1 | NONSTRUCTURAL PROTEINS NS1-NS2 | INFLUENZA C VIRUS (STRAIN C/MISSISSIPPI/80) | 222–255 | | | | | | |
| PVNST_INCYA | NONSTRUCTURAL PROTEINS NS1-NS2 | INFLUENZA C VIRUS (STRAIN C/YAMAGATA/10/81) | 222–255 | | | | | | |
| PVNUA_PRVKA | PROBABLE NUCLEAR ANTIGEN | PSEUDORABIES VIRUS (STRAIN KAPLAN)(PRV) | 756–784 | | | | | | |
| PVNUC_DHVH | NUCLEOPROTEIN | DHORI VIRUS (STRAIN INDIAN/1313/61)(DHO) | 297–331 | 441–470 | | | | | |
| PVNUC_IACKP | NUCLEOPROTEIN | INFLUENZA A VIRUS (STRAIN A/CHICKEN/PENNSYLVANIA/1/83) | 354–388 | | | | | | |
| PVNUC_IAHLO | NUCLEOPROTEIN | INFLUENZA A VIRUS (STRAIN A/EQUINE/LONDON/1416/73) | 354–388 | | | | | | |
| PVNUC_IAHPR | NUCLEOPROTEIN | INFLUENZA A VIRUS (STRAIN A/EQUINE/PRAGUE/1/56) | 354–388 | | | | | | |
| PVNUC_IAHTE | NUCLEOPROTEIN | INFLUENZA A VIRUS (STRAIN A/EQUINE/TENNESSEE/5/86) | 354–388 | | | | | | |
| PVNUC_MABVM | NUCLEOPROTEIN | MARBURG VIRUS (STRAIN MUSOKE) | 16–46 | | | | | | |
| PVNUC_MABVP | NUCLEOPROTEIN | MARBURG VIRUS (STRAIN POPP) | 16–46 | | | | | | |
| PVO01_VACCC | PROTEIN O1 | VACCINIA VIRUS (STRAIN COPENHAGEN) | 511–539 | 550–581 | | | | | |
| PVO01_VARV | PROTEIN O1 | VARIOLA VIRUS | 511–539 | | | | | | |
| PVOR1_NMV | 186 KD PROTEIN | NARCISSUS MOSAIC VIRUS (NMV) | 121–150 | 641–671 | | | | | |
| PVOR1_PVMR | 223 KD PROTEIN | POTATO VIRUS M (STRAIN RUSSIAN)(PVM) | 1667–1703 | | | | | | |
| PVOR1_SMYEA | 150 KD PROTEIN | STRAWBERRY MILD YELLOW EDGE-ASSOCIATED VIRUS (SMYEAV) | 121–153 | | | | | | |
| PVP03_HSVSA | PROBABLE MEMBRANE ANTIGEN 3 | HERPESVIRUS SAIMIRI (STRAIN 11) | 462–493 | | | | | | |
| PVP10_NPVAC | P10 PROTEIN | AUTOGRAPHA CALIFORNICA NUCLEAR POLYHEDROSIS VIRUS (ACMNPV) | 4–38 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVP10_NPVOP | P10 PROTEIN | ORGYIA PSEUDOTSUGATA MULTICAPSID POLYHEDROSIS VIRUS (OPMNPV) | 4–38 | | | | | | |
| PVP10_RBSDV | PROTEIN S10 | RICE BLACK STREAKED DWARF VIRUS (RBSDV) | 260–291 | | | | | | |
| PVP19_HSVEB | CAPSID ASSEMBLY AND DNA MATURATION PROTEIN | EQUINE HERPESVIRUS TYPE 1 (STRAIN AB4P)(EHV-1) | 239–268 | 287–325 | | | | | |
| PVP23_HCMVA | PROBABLE CAPSID PROTEIN VP23 | HUMAN CYTOMEGALOVIRUS (STRAIN AD169) | 141–172 | | | | | | |
| PVP23_HSV6U | PROBABLE CAPSID PROTEIN VP23 | HERPES SIMPLEX VIRUS (TYPE 6/STRAIN UGANDA-1102) | 46–79 | 206–238 | | | | | |
| PVP23_HSVEB | PROBABLE CAPSID PROTEIN VP23 | EQUINE HERPESVIRUS TYPE 1 (STRAIN AB4P)(EHV-1) | 18–48 | | | | | | |
| PVP23_VZVD | PROBABLE CAPSID PROTEIN VP23 | VARICELLA-ZOSTER VIRUS (STRAIN DUMAS)(VZV) | 224–253 | | | | | | |
| PVP2_AHSV4 | OUTER CAPSID PROTEIN VP2 | AFRICAN HORSE SICKNESS VIRUS (SEROTYPE 4/STRAIN VACCINE) | 408–441 | | | | | | |
| PVP2_BTV10 | OUTER CAPSID PROTEIN VP2 | BLUETONGUE VIRUS (SEROTYPE 10/ISOLATE USA) | 649–683 | | | | | | |
| PVP2_BTV11 | OUTER CAPSID PROTEIN VP2 | BLUETONGUE VIRUS (SEROTYPE 11/ISOLATE USA) | 558–586 | 649–683 | | | | | |
| PVP2_BTV17 | OUTER CAPSID PROTEIN VP2 | BLUETONGUE VIRUS (SEROTYPE 17/ISOLATE USA) | 391–424 | 564–593 | | | | | |
| PVP2_BTV1A | OUTER CAPSID PROTEIN VP2 | BLUETONGUE VIRUS (SEROTYPE 1/ ISOLATE AUSTRALIA) | 654–688 | | | | | | |
| PVP2_BTV1S | OUTER CAPSID PROTEIN VP2 | BLUETONGUE VIRUS (SEROTYPE 1/ ISOLATE SOUTH AFRICA) | 654–688 | | | | | | |
| PVP2_EHDV1 | OUTER CAPSID PROTEIN VP2 | EPIZOOTIC HEMORRHAGIC DISEASE VIRUS (SEROTYPE 1)(EHDV-1) | 878–915 | | | | | | |
| PVP2_ROTBR | RNA-BINDING PROTEIN VP2 | BOVINE ROTAVIRUS (STRAIN RF) | 334–367 | 522–557 | | | | | |
| PVP2_ROTBU | RNA-BINDING PROTEIN VP2 | BOVINE ROTAVIRUS (STRAIN UK) | 334–367 | 523–558 | | | | | |
| PVP2_ROTHW | RNA-BINDING PROTEIN VP2 | HUMAN ROTAVIRUS (SEROTYPE 1/STRAIN WA) | 342–377 | 532–567 | | | | | |
| PVP2_ROTPC | RNA-BINDING PROTEIN VP2 | PORCINE ROTAVIRUS (GROUP C/STRAIN COWDEN) | 514–549 | 589–617 | 811–841 | | | | |
| PVP2_ROTS1 | RNA-BINDING PROTEIN VP2 | SIMIAN 11 ROTAVIRUS (STRAIN SA11) | 335–368 | 523–558 | | | | | |
| PVP35_VACCC | IMMUNODOMINANT ENVELOPE PROTEIN P35 | VACCINIA VIRUS (STRAIN COPENHAGEN) | 278–311 | | | | | | |
| PVP35_VACCV | IMMUNODOMINANT ENVELOPE PROTEIN P35 | VACCINIA VIRUS (STRAIN WR) | 278–311 | | | | | | |
| PVP35_VARV | IMMUNODOMINANT ENVELOPE PROTEIN P35 | VARIOLA VIRUS | 279–312 | | | | | | |
| PVP39_NPVOP | MAJOR CAPSID PROTEIN | ORGYIA PSEUDOTSUGATA MULTICAPSID POLYHEDROSIS VIRUS (OPMNPV) | 107–141 | | | | | | |
| PVP3_EHDV1 | VP3 CORE PROTEIN | EPIZOOTIC HEMORRHAGIC DISEASE VIRUS (SEROTYPE 1)(EHDV-1) | 383–412 | 734–770 | | | | | |
| PVP3_EHDVA | VP3 CORE PROTEIN | EPIZOOTIC HEMORRHAGIC DISEASE VIRUS | 383–412 | 734–770 | | | | | |
| PVP3_RDV | MAJOR 114 KD STRUCTURAL PROTEIN | RICE DWARF VIRUS (RDV) | 297–330 | | | | | | |
| PVP3_ROTS1 | INNER CORE PROTEIN VP3 | SIMIAN 11 ROTAVIRUS (STRAIN SA11) | 652–688 | | | | | | |
| PVP40_EBV | CAPSID PROTEIN P40 | EPSTEIN-BARR VIRUS (STRAIN B95-8)(HUMAN HERPESVIRUS 4) | 429–457 | | | | | | |
| PVP40_HSVSA | CAPSID PROTEIN P40 | HERPESVIRUS SAIMIRI (STRAIN 11 | 119–152 | | | | | | |
| PVP40_ILTVT | CAPSID PROTEIN P40 | INFECTIOUS LARYNGOTRACHEITIS VIRUS (STRAIN THORNE V882)(ILTV) | 84–119 | | | | | | |

TABLE XIV-continued

| PCGENE FILE NAME | P23CTLZIP PROTEIN | SEARCH RESULTS SUMMARY FOR P23TLZIPC MOTIF All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVP40_VZVD | CAPSID PROTEIN P40 | VARICELLA-ZOSTER VIRUS (STRAIN DUMAS)(VZV | 485–516 | | | | | | |
| PVP47_NPVAC | VIRAL TRANSCRIPTION REGULATOR P47 | AUTOGRAPHA CALIFORNICA NUCLEAR POLYHEDROSIS VIRUS (ACMNPV) | 239–270 | | | | | | |
| PVP4A_VACCC | MAJOR CORE PROTEIN P4A PRECURSOR | VACCINIA VIRUS (STRAIN COPENHAGEN) | 553–591 | | | | | | |
| PVP4A_VACCV | MAJOR CORE PROTEIN P4A PRECURSOR | VACCINIA VIRUS (STRAIN WR) | 553–591 | | | | | | |
| PVP4A_VARV | MAJOR CORE PROTEIN P4A PRECURSOR | VARJOLA VIRUS | 554–592 | | | | | | |
| PVP4_ROTG1 | OUTER CAPSID PROTEIN VP4 | ROTAVIRUS (GROUP B/STRAIN IDIR) | 93–122 | 468–499 | | | | | |
| PVP4_WTV | NONSTRUCTURAL PROTEIN PNS4 | WOUND TUMOR VIRUS (WTV) | 278–308 | 624–659 | | | | | |
| PVP5_BRD | OUTER CAPSID PROTEIN VP5 | BROADHAVEN VIRUS (BRD) | 96–133 | 295–326 | | | | | |
| PVP5_BTVIA | OUTER CAPSID PROTEIN VP5 | BLUETONGUE VIRUS (SEROTYPE 1/ISOLATE AUSTRALIA) | 295–324 | | | | | | |
| PVP5_BTV1 | OUTER CAPSID PROTEIN VP5 | BLUETONGUE VIRUS (SEROTYPE 1/ ISOLATE SOUTH AFRICA) | 295–324 | | | | | | |
| PVP5_BTV2A | OUTER CAPSID PROTEIN VP5 | BLUETONGUE VIRUS (SEROTYPE 2/ISOLATE USA) | 295–324 | | | | | | |
| PVP5_EHDV1 | OUTER CAPSID PROTEIN VP5 | EPIZOOTIC HEMORRHAGIC DISEASE VIRUS (SEROTYPE 1)(EHVD-1) | 290–325 | | | | | | |
| PVP5_WTV | OUTER COAT PROTEIN P5 | WOUND TUMOR VIRUS (WTV) | 691–719 | | | | | | |
| PVP61_BTV10 | VP6 PROTEIN | BLUETONGUE VIRUS (SEROTYPE 10/ISOLATE USA) | 159–187 | | | | | | |
| PVP62_BTV10 | VP6 PROTEIN | BLUETONGUE VIRUS (SEROTYPE 10/ISOLATE USA) | 155–183 | 210–245 | | | | | |
| PVP62_MRDV | PROBABLE NONSTRUCTURAL 36.3 KD PROTEIN | MAIZE ROUGH DWARF VIRUS (MRDV) | 25–61 | 222–257 | | | | | |
| PVP64_NPVOP | MAJOR ENVELOPE GLYCOPROTEIN PRECURSOR | ORGYIA PSEUDOTSUGATA MULTICAPSID POLYHEDROSIS VIRUS (OPMNPV) | 285–313 | | | | | | |
| PVP67_NPVAC | MAJOR ENVELOPE GLYCOPROTEIN PRECURSOR | AUTOGRAPHA CALIFORNICA NUCLEAR POLYHEDROSIS VIRUS (ACMNPV) | 281–316 | | | | | | |
| PVP67_NPVGM | MAJOR ENVELOPE GLYCOPROTEIN | GALLERIA MELLONELLA NUCLEAR POLYHEDROSIS VIRUS (GMNPV) | 198–233 | | | | | | |
| PVP6_BTV11 | VP6 PROTEIN | BLUETONGUE VIRUS (SEROTYPE 11/ISOLATE USA) | 155–183 | | | | | | |
| PVP6_BTV17 | VP6 PROTEIN | BLUETONGUE VIRUS (SEROTYPE 17/ISOLATE USA) | 155–183 | | | | | | |
| PVP6_BTV15 | VP6 PROTEIN | BLUETONGUE VIRUS (SEROTYPE 17/ ISOLATE SOUTH AFRICA) | 159–187 | | | | | | |
| PVP6_BTV2A | VP6 PROTEIN | BLUETONGUE VIRUS (SEROTYPE 2/ISOLATE USA) | 131–159 | | | | | | |
| PVP6_WTV | STRUCTURAL PROTEIN P6 | WOUND TUMOR VIRUS (WTV) | 180–209 | | | | | | |
| PVP6_WTVNJ | STRUCTURAL PROTEIN P6 | WOUND TUMOR VIRUS (STRAIN NJ)(WTV) | 180–209 | | | | | | |
| PVP79_NPVAC | 79 KD PROTEIN | AUTOGRAPHA CALIFORNICA NUCLEAR POLYHEDROSIS VIRUS (ACMNPV) | 405–442 | | | | | | |
| PVP7_WTV | NONSTRUCTURAL PROTEIN PNS7 | WOUND TUMOR VIRUS (WTV) | 454–490 | | | | | | |
| PVP87_NPVOP | CAPSID PROTEIN P87 | ORGYIA PSEUDOTSUGATA MULTICAPSID POLYHDEDROSIS VIRUS (OPMNPV) | 77–112 | | | | | | |
| PVP8_BTV10 | NONSTRUCTURAL PROTEIN P8 | BLUETONGUE VIRUS (SEROTYPE 10/ISOLATE USA) | 104–139 | | | | | | |
| PVP8_BTV11 | NONSTRUCTURAL PROTEIN P8 | BLUETONGUE VIRUS (SEROTYPE 11/ISOLATE USA) | 104–139 | | | | | | |
| PVP8_BTV13 | NONSTRUCTURAL PROTEIN P8 | BLUETONGUE VIRUS (SEROTYPE 13/ISOLATE USA) | 104–139 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVP8_BTV17 | NONSTRUCTURAL PROTEIN P8 | BLUETONGUE VIRUS (SEROTYPE 17/ISOLATE USA) | 104–139 | | | | | | |
| PVP8_BTV1A | NONSTRUCTURAL PROTEIN P8 | BLUETONGUE VIRUS (SEROTYPE 1/ ISOLATE AUSTRALIA) | 104–139 | | | | | | |
| PVP8_BTV1S | NONSTRUCTURAL PROTEIN P8 | BLUETONGUE VIRUS (SEROTYPE 1/ ISOLATE SOUTH AFRICA) | 104–139 | | | | | | |
| PVP8_BTV2A | NONSTRUCTURAL PROTEIN P8 | BLUETONGUE VIRUS (SEROTYPE 2/ISOLATE USA) | 104–139 | | | | | | |
| PVP8_RDV | OUTER CAPSID PROTEIN P8 | RICE DWARF VIRUS (RDV) | 374–412 | | | | | | |
| PVP8_WTV | OUTER CAPSID PROTEIN P8 | WOUND TUMOR VIRUS (WTV) | 164–195 | 379–412 | | | | | |
| PVPHE_NPVAC | 29 KD POLYHEDRAL ENVELOPE PROTEIN | AUTOGRAPHA CALIFORNICA NUCLEAR POLYHEDROSIS VIRUS (ACMNPV) | 145–173 | | | | | | |
| PVPHE_NPVOP | 32 KD POLYHEDRAL ENVELOPE PROTEIN | ORGYIA PSEUDOTSUGATA MULTICAPSID POLYHEDROSIS VIRUS (OPMNPV) | 122–151 | | | | | | |
| PVPR_HV1A2 | VPR PROTEIN | HUMAN IMMUNODEFICIENCY VIRUS TYPE 1 (ARV2/SF2 ISOLATE)(HIV-1) | 37–74 | | | | | | |
| PVPR_HV2BE | VPR PROTEIN | HUMAN IMMUNODEFICIENCY VIRUS TYPE 2 (ISOLATE BEN)(HIV-2) | 41–73 | | | | | | |
| PVPR_HV2CA | VPR PROTEIN | HUMNA IMMUNODEFICIENCY VIRUS TYPE 2 (ISOLATE CAM2)(HIV-2) | 41–73 | | | | | | |
| PVPR_HV2D1 | VPR PROTEIN | HUMAN IMMUNODEFICIENCY VIRUS TYPE 2 (ISOLATE D194)(HIV-2) | 41–73 | | | | | | |
| PVPR_HV2D2 | VPR PROTEIN | HUMAN IMMUNODEFICIENCY VIRUS TYPE 2 (ISOLATE D205,7)(HIV-2) | 41–73 | | | | | | |
| PVPR_HV2NZ | VPR PROTEIN | HUMAN IMMUNODEFICIENCY VIRUS TYPE 2 (ISOLATE NIH-Z)(HIV-2) | 41–73 | | | | | | |
| PVPR_HV2RO | VPR PROTEIN | HUMAN IMMUNODEFICIENCY VIRUS TYPE 2 (ISOLATE ROD)(HIV-2) | 41–73 | | | | | | |
| PVPR_HV2SB | VPR PROTEIN | HUMAN IMMUNODEFICIENCY VIRUS TYPE 2 (ISOLATE SBLISY)(HIV-2) | 41–73 | | | | | | |
| PVPR_HV2ST | VPR PROTEIN | HUMAN IMMUNODEFICIENCY VIRUS TYPE 2 (ISOLATE ST)(HIV-2) | 40–72 | | | | | | |
| PVPR_SIVCZ | VPR PROTEIN | CHIMPANZEE IMMUNODEFICIENCY VIRUS (SIV(CPZ))(CIV) | 37–74 | | | | | | |
| PVPR_SIVM1 | VPR PROTEIN | SIMIAN IMMUNODEFICIENCY VIRUS (MM142-83 ISOLATE)(SIV-MAC) | 37–69 | | | | | | |
| PVPR_SIVMK | VPR PROTEIN | SIMIAN IMMUNODEFICIENCY VIRUS (K6W ISOLATE)(SIV-MAC) | 37–69 | | | | | | |
| PVPR_SIVML | VPR PROTEIN | SIMIAN IMMUNODEFICIENCY VIRUS (K78 ISOLATE)(SIV-MAC) | 37–69 | | | | | | |
| PVPR_SIVS4 | VPR PROTEIN | SIMIAN IMMUNODEFICIENCY VIRUS (F236/SMH4 ISOLATE)(SOOTY MANGA | 37–69 | | | | | | |
| PVPR_SIVSP | VPR PROTEIN | SIMIAN IMMUNODEFICIENCY VIRUS (PBJ/BC13 ISOLATE)(SOOTY MANGABE | 37–69 | | | | | | |
| PVPU_HV1B1 | VPU PROTEIN | HUMAN IMMUNODEFICIENCY VIRUS TYPE 1 (BH10 ISOLATE, HXB3 ISOLATE) | 3–33 | | | | | | |
| PVPU_HV1B8 | VPU PROTEIN | HUMAN IMMUNODEFICIENCY VIRUS TYPE 1 (BH8 ISOLATE)(HIV-1) | 4–33 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVPU_HV1BN | VPU PROTEIN | HUMAN IMMUNODEFICIENCY VIRUS TYPE 1 (BRAIN ISOLATE)(HIV-1) | 3–34 | | | | | | |
| PVPU_HV1BR | VPU PROTEIN | HUMAN IMMUNODEFICIENCY VIRUS TYPE 1 (BRU ISOLATE)(HIV-1) | 3–33 | | | | | | |
| PVPU_HV1J12 | VPU PROTEIN | HUMAN IMMUNODEFICIENCY VIRUS TYPE 1 (HXB2 ISOLATE)(HIV-1) | 4–33 | | | | | | |
| PVPU_HV1JR | VPU PROTEIN | HUMAN IMMUNODEFICIENCY VIRUS TYPE 1 (JRCSF ISOLATE)(HIV-1) | 3–34 | | | | | | |
| PVPU_HV1PV | VPU PROTEIN | HUMAN IMMUNODEFICIENCY VIRUS TYPE 1 (PV22 ISOLATE)(HIV-1) | 3–33 | | | | | | |
| PVPU_JSRV | VPU PROTEIN | SHEEP PULMONARY ADENOMATOSIS VIRUS | 116–154 | | | | | | |
| PVPX_LDV | VPX PROTEIN | LACTATE DEHYDROGENASE-ELEVATING VIRUS (LDV) | 25–55 | | | | | | |
| PVPY_BIV2 | ORF-Y PROTEIN | BOVINE IMMUNODEFICIENCY VIRUS (ISOLATE 127)(BIV) | 35–71 | | | | | | |
| PVRNA_BSMV | ALPHA-A PROTEIN | BARLEY STRIPE MOSAIC VIRUS (BSMV) | 290–319 | 676–705 | | | | | |
| PVS05_ROTH1 | NONSTRUCTURAL PROTEIN NCVP2 | HUMAN ROTAVIRUS (STRAIN IGV-80-3) | 198–230 | | | | | | |
| PVS05_ROTPC | NONSTRUCTURAL PROTEIN NS53 | PORCINE ROTAVIRUS (GROUP C/STRAIN COWDEN) | 88–119 | 358–392 | | | | | |
| PVS05_ROTS1 | NONSTRUCTURAL PROTEIN-NCVP2 | SIMIAN 11 ROTAVIRUS (STRAIN SA11) | 315–347 | | | | | | |
| PVS06_ROTBR | VP6 PROTEIN | BOVINE ROTAVIRUS (STRAIN RF) | 55–92 | | | | | | |
| PVS06_ROTBS | VP6 PROTEIN | BOVINE ROTAVIRUS (GROUP C/STRAIN SHINTOKU) | 64–92 | 312–340 | | | | | |
| PVS06_ROTBU | VP6 PROTEIN | BOVINE ROTAVIRUS (STRAIN UK) | 55–92 | | | | | | |
| PVS06_ROTEF | VP6 PROTEIN | EQUINE ROTAVIRUS (STRAIN FI-14) | 55–92 | | | | | | |
| PVS06_ROTEH | VP6 PROTEIN | EQUINE ROTAVIRUS (STRAIN H-2) | 55–92 | | | | | | |
| PVS06_ROTH1 | VP6 PROTEIN | HUMAN ROTAVIRUS (SEROTYPE 1/STRAIN 1076) | 55–92 | | | | | | |
| PVS06_ROTHC | VP6 PROTEIN | HUMAN ROTAVIRUS (GROUP C/STRAIN BRISTOL) | 64–92 | 312–340 | | | | | |
| PVS06_ROTHS | VP6 PROTEIN | HUMAN ROTAVIRUS (SEROTYPE 2/STRAIN S2) | 55–92 | | | | | | |
| PVS06_ROTHW | VP6 PROTEIN | HUMAN ROTAVIRUS (SEROTYPE 1/STRAIN WA) | 55–92 | 313–349 | | | | | |
| PVS06_ROTPC | VP6 PROTEIN | PORCINE ROTAVIRUS (GROUP C/STRAIN COWDEN) | 64–92 | | | | | | |
| PVS06_ROTPG | VP6 PROTEIN | PORCINE ROTAVIRUS (STRAIN GOTTFRIED) | 55–92 | 313–349 | | | | | |
| PVS06_ROTS1 | VP6 PROTEIN | SIMIAN 11 ROTAVIRUS (STRAIN SA11) | 55–92 | 313–349 | | | | | |
| PVS08_ROTS1 | NONSTRUCTURAL PROTEIN NCVP4 | SIMIAN 11 ROTAVIRUS (STRAIN SA11) | 274–302 | | | | | | |
| PVS09_ROTHT | GLYCOPROTEIN VP7 | HUMAN ROTAVIRUS (SEROTYPE 4/STRAIN ST. THOMAS 3) | 131–159 | | | | | | |
| PVS09_ROTPB | GLYCOPROTEIN VP7 | PORCINE ROTAVIRUS (SEROTYPE 4/STRAIN BEN-144) | 131–159 | | | | | | |
| PVS10_ROTBN | NONSTRUCTURAL GLYCO-PROTEIN NCVP5 | BOVINE ROTAVIRUS (STRAIN NCDV) | 52–89 | | | | | | |
| PVS10_ROTBU | NONSTRUCTURAL GLYCO-PROTEIN NCVP5 | BOVINE ROTAVIRUS (STRAIN UK) | 52–89 | | | | | | |
| PVS10_ROTH2 | NONSTRUCTURAL GLYCO-PROTEIN NCVP5 | HUMAN ROTAVIRUS (STRAIN A28) | 52–89 | | | | | | |
| PVS10_ROTH7 | NONSTRUCTURAL GLYCO-PROTEIN NCVP5 | HUMAN ROTAVIRUS (STRAIN A64/CLONE 2) | 52–89 | | | | | | |

TABLE XIV-continued

| PCGENE FILE NAME | P23CTLZIP PROTEIN | SEARCH RESULTS SUMMARY FOR P23TLZIPC MOTIF All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PVS10_ROTH8 | NONSTRUCTURAL GLYCO-PROTEIN NCVP5 | HUMAN ROTAVIRUS (STRAIN A64/CLONE 6 | 52–89 | | | | | | |
| PSV10_ROTHW | NONSTRUCTURAL GLYCO-PROTEIN NCVP5 | HUMAN ROTAVIRUS (SEROTYPE 1/STRAIN WA) | 52–89 | | | | | | |
| PVS10_ROTS1 | NONSTRUCTURAL GLYCO-PROTEIN NCVP5 | SIMIAN 11 ROTAVIRUS (STRAIN SA11) | 52–89 | | | | | | |
| PVS11_ROTHW | MINOR OUTER CAPSID PROTEIN | HUMAN ROTAVIRUS (SEROTYPE 1/STRAIN WA) | 99–130 | | | | | | |
| PVS11_REOVJ | SIGMA 1 PROTEIN PRECURSOR | REOVIRUS (TYPE 2/STRAIN D5/JONES) | 346–384 | | | | | | |
| PVS11_REOVL | SIGMA 1 PROTEIN PRECURSOR | REOVIRUS (TYPE 1/STRAIN LANG) | 110–147 | | | | | | |
| PVT1_SFVKA | PROTEIN T1 PRECURSOR | SHOPE FIBROMA VIRUS (STRAIN KASZA)(SFV) | 147–182 | | | | | | |
| PVT2_MYXVL | TUMOR NECROSIS FACTOR SOLUBLE RECEPTOR PRECUR | MYXOMA VIRUS (STRAIN LAUSANNE) | 261–290 | | | | | | |
| PVT2_SFVKA | TUMOR NECROSIS FACTOR SOLUBLE RECEPTOR PRECUR | SHOPE FIBROMA VIRUS (STRAIN KASZA)(SFV) | 211–249 | | | | | | |
| PVT3A_CAPV1 | PROTEIN T3A | CAPRIPOXVIRUS (STRAIN INS-1) | 116–150 | | | | | | |
| PVTER_EBV | PROBABLE DNA PACK-AGING PROTEIN | EPSTEIN-BARR VIRUS (STRAIN B95-8)(HUMAN HERPESVIRUS 4) | 166–199 | 505–543 | | | | | |
| PVTER_HCMVA | PROBABLE DNA PACK-AGING PROTEIN | HUMAN CYTOMEGALOVIRUS (STRAIN AD169) | 176–209 | | | | | | |
| PVTER_HSV11 | PROBABLE DNA PACK-AGING PROTEIN | ICTALURID HERPESVIRUS 1 (CHANNEL CATFISH VIRUS)(CCV) | 756–788 | | | | | | |
| PVX_SEND6 | X PROTEIN | SENDAI VIRUS (STRAIN 6/94) | 57–93 | | | | | | |
| PY104_ADE07 | HYPOTHETICAL 10.4 KD EARLY PROTEIN | HUMAN ADENOVIRUS TYPE 7 | 55–83 | | | | | | |
| PY10K_MSVS | HYPOTHETICAL 10.9 KD PROTEIN | MAIZE STREAK VIRUS (SOUTH-AFRICAN ISOLATE)(MSV) | 24–54 | | | | | | |
| PY10K_WDV | HYPOTHETICAL 10 KD PROTEIN | WHEAT DWARF VIRUS (WDV) | 22–59 | | | | | | |
| PY119_SSV1 | HYPOTHETICAL 11.9 KD PROTEIN | SULFOLOBUS VIRUS-LIKE PARTICLE SSV1 | 29–64 | | | | | | |
| PY11K_PASV | HYPOTHETICAL 11.9 KD PROTEIN (ORF VI) | PANICUM STREAK VIRUS | 29–61 | | | | | | |
| PY11K_ROTS1 | HYPOTHETICAL 11 KD PROTEIN IN SEGMENT S11 | SIMIAN 11 ROTAVIRUS (STRAIN SA11) | 53–87 | | | | | | |
| PY11K_TYDVA | HYPOTHETICAL 11.2 KD PROTEIN | TOBACCO YELLOW DWARF VIRUS (STRAIN AUSTRALIA)(TYDV) | 28–62 | | | | | | |
| PY14K_NPVAC | HYPOTHETICAL 13.8 KD PROTEIN IN 39 KD PROTEIN 5'REG | AUTOGRAPHA CALIFORNICA NUCLEAR POLY-HEDROSIS VIRUS (ACMNPV) | 65–101 | | | | | | |
| PY18K_SSV1 | HYPOTHETICAL 18.0 KD PROTEIN (ORF B-166) | SULFOLOBUS VIRUS-LIKE PARTICLE SSV1 | 100–132 | | | | | | |
| PY20K_SSV1 | HYPOTHETICAL 20.4 KD PROTEIN (ORF E-178) | SULFOLOBUS VIRUS-LIKE PARTICLE SSV1 | 129–167 | | | | | | |
| PY21K_MSVN | HYPOTHETICAL 21.7 KD PROTEIN | MAIZE STREAK VIRUS (NIGERIAN ISOLATE)(MSV) | 122–155 | | | | | | |
| PY2_SOCMV | HYPOTHETICAL PROTEIN 2 (ORF 11) | SOYBEAN CHLOROTIC MOTTLE VIRUS | 99–137 | | | | | | |
| PY38K_NPVAC | HYPOTHETICAL 37.7 KD PROTEIN (ORF2) | AUTOGRAPHA CALIFORNICA NUCLEAR POLYHEDROSIS VIRUS (ACMNPV) | 250–282 | | | | | | |

TABLE XIV-continued

SEARCH RESULTS SUMMARY FOR P23TLZIPC MOTIF

| PCGENE FILE NAME | P23CTLZIP PROTEIN | All Viruses (no bacteriophages) VIRUS | AREA 1 | AREA 2 | AREA 3 | AREA 4 | AREA 5 | AREA 6 | AREA 7 |
|---|---|---|---|---|---|---|---|---|---|
| PY85K_SSV1 | HYPOTHETICAL 85.7 KD PROTEIN (ORF C-792) | SULFOLOBUS VIRUS-LIKE PARTICLE SSV1 | 274–312 | 543–580 | | | | | |
| PYB13_FOWPM | HYPOTHETICAL BAMHI-ORF13 PROTEIN (FRAGMENT) | FOWLPOX VIRUS (ISOLATE HP-438[MUNICH]) | 114–150 | | | | | | |
| PYDH1_HSVSC | HYPOTHETICAL 28.7 KD PROTEIN IN DHFR 3'REGION (ORF | HERPESVIRUS SAIMIRI (SUBGROUP C/STRAIN 488) | 206–244 | | | | | | |
| PYDH3_HSVSC | HYPOTHETICAL 9.5 KD PROTEIN IN DHFR 3'REGION (ORF3) | HERPESVIRUS SAIMIRI (SUBGROUP C/STRAIN 488) | 69–97 | | | | | | |
| PYEC4_EBV | HYPOTHETICAL EC-RF4 PROTEIN | EPSTEIN-BARR VIRUS (STRAIN B95-8)(HUMAN HERPESVIRUS 4) | 34–68 | | | | | | |
| PYIO1_CVBM | HYPOTHETICAL PROTEIN IORF1 | BOVINE CORONAVIRUS | 84–122 | | | | | | |
| PYIOR_CVBF | HYPOTHETICAL PROTEIN IN NUCLEOCAPSID ORF (IORF) | BOVINE CORONAVIRUS (STRAIN F15) | 41–75 | 137–165 | | | | | |
| PYIOR_CVBM | HYPOTHETICAL PROTEIN IN NUCLEOCAPSID ORF (IORF) | BOVINE CORONAVIRUS (STRAIN MEBUS) | 41–74 | 137–165 | | | | | |
| PYIOR_CVTKE | HYPOTHETICAL PROTEIN IN NUCLEOCAPSID ORF (IORF) | TURKEY ENTERIC CORONAVIRUS (TCV) | 41–74 | 137–165 | | | | | |
| PYKR2_EBV | HYPOTHETICAL BKRF2 PROTEIN | EPSTEIN-BARR VIRUS (STRAIN B95-8) (HUMAN HERPESVIRUS 4) | 67–100 | | | | | | |
| PYMR2_EBV | BMRF2 PROTEIN (HUMAN HERPESVIRUS 4) | EPSTEIN-BARR VIRUS (STRAIN B95-8) | 250–284 | | | | | | |
| PYOR1_COYMV | HYPOTHETICAL 23 KD PROTEIN (ORF1) | COMMELINA YELLOW MOTTLE VIRUS (COYMV) | 93–130 | 166–198 | | | | | |
| PYOR2_COYMV | HYPOTHETICAL 15 KD PROTEIN (ORF2) | COMMELINA YELLOW MOTTLE VIRUS (COYMV) | 23–56 | | | | | | |
| PYOR3_PVXXC | HYPOTHETICAL 12 KD PROTEIN (ORF3)(FRAGMENT) | POTATO VIRUS X (STRAIN XC)(PVX) | 7–39 | | | | | | |
| PYOR3_WCMVM | HYPOTHETICAL 13 KD PROTEIN (ORF 3) | WHITE CLOVER MOSAIC VIRUS (STRAIN M)(WCMV) | 63–94 | | | | | | |
| PYOR3_WCMVO | HYPOTHETICAL 13 KD PROTEIN (ORF 3) | WHITE CLOVER MOSAIC VIRUS (STRAIN O)(WCMV) | 64–95 | | | | | | |
| PYOR5_ADEG1 | HYPOTHETICAL 31.5 KD PROTEIN (ORF 5) | AVIAN ADENOVIRUS GAL1 | 237–272 | | | | | | |
| PYORG_TTV1 | HYPOTHETICAL 7.1 KD PROTEIN | THERMOPROTEUS TENAX VIRUS 1 (STRAIN KRA1)(TTV1) | 5–34 | | | | | | |
| PYORM_TTV1 | HYPOTHETICAL 38.6 KD PROTEIN | THERMOPROTEUS TENAX VIRUS 1 (STRAIN KRA1)(TTV1) | 233–263 | | | | | | |
| PYORP_TTV1 | HYPOTHETICAL 20.2 KD PROTEIN | THERMOPROTEUS TENAX VIRUS 1 (STRAIN KRA1)(TTV1a) | 91–124 | | | | | | |
| PYP24_RTBV | HYPOTHETICAL P24 PROTEIN (ORF 1 | RICE TUNGRO BACILLIFORM VIRUS (RTBV) | 104–133 | 159–191 | | | | | |
| PVP24_RTBVP | HYPOTHETICAL P24 PROTEIN (ORF 1) | RICE TUNGRO BACILLIFORM VIRUS (ISOLATE PHILIPPINES)(RTBV) | 104–133 | 159–191 | | | | | |
| PYP47_NPVAC | HYPOTHETICAL 43.5 KD PROTEIN IN P47 3'REGION | AUTOGRAPHA CALIFORNICA NUCLEAR POLYHEDROSIS VIRUS (ACMNPV) | 23–51 | | | | | | |
| PYRF5_HSV6G | HYPOTHETICAL PROTEIN RF5 | HERPES SIMPLEX VIRUS (TYPE 6/STRAIN GS) | 180–216 | | | | | | |

TABLE XIV-continued

| PCGENE FILE NAME | P23CTLZIP PROTEIN | All Viruses (no bacteriophages) VIRUS | SEARCH RESULTS SUMMARY FOR P23TLZIPC MOTIF AREA 1 | AREA 2 | AREA 3 | AREA 4 | AREA 5 | AREA 6 | AREA 7 |
|---|---|---|---|---|---|---|---|---|---|
| PYRR2_EBV | HYPOTHETICAL BRRF2 PROTEIN | EPSTEIN-BARR VIRUS (STRAIN B95-8)(HUMAN HERPESVIRUS 4) | 13–42 | | | | | | |
| PYSR1_EBV | HYPOTHETICAL BSRF1 PROTEIN | EPSTEIN-BARR VIRUS (STRAIN B95-8)(HUMAN HERPESVIRUS 4) | 92–120 | | | | | | |
| PYTR1_EBV | HYPOTHETICAL BTRF1 PROTEIN | EPSTEIN-BARR VIRUS (STRAIN B95-8)(HUMAN HERPESVIRUS 4) | 306–336 | | | | | | |
| PYVAE_VACCC | HYPOTHETICAL 18.2 KD PROTEIN | VACCINIA VIRUS (STRAIN COPENHAGEN) | 21–53 | | | | | | |
| PYVAL_VACCV | HYPOTHETICAL 9.9 KD PROTEIN | VACCINIA VIRUS (STRAIN WR), AND VACCINIA VIRUS (STRAIN COPENHAGE | 21–49 | | | | | | |
| PYVBC_VACCC | HYPOTHETICAL 10.8 KD PROTEIN | VACCINIA VIRUS (STRAIN COPENHAGEN) | 22–53 | | | | | | |
| PYVDG_VACCV | HYPOTHETICAL 10.4 KD PROTEIN | VACCINIA VIRUS (STRAIN WR), AND VACCINIA VIRUS (STRAIN COPENHAGE | 31–64 | | | | | | |
| PYVEF_VACCC | HYPOTHETICAL 12.9 KD PROTEIN | VACCINIA VIRUS (STRAIN COPENHAGEN) | 8–42 | | | | | | |
| PYVFC_VACCC | HYPOTHETICAL 11.6 KD PROTEIN | VACCINIA VIRUS (STRAIN COPENHAGEN) | 7–35 | | | | | | |
| PZNFP_LYCVA | ZINC FINGER PROTEIN | LYMPHOCYTIC CHORIOMENINGITIS VIRUS (STRAIN ARMSTRONG) | 29–57 | | | | | | |
| PZNFP_LYCVP | ZINC FINGER PROTEIN (FRAGMENT) | LYMPHOCYTIC CHORIOMENINGITIS VIRUS (STRAIN PASTEUR) | 8–32 | | | | | | |

TABLE XV

RESPIRATORY SYNCYTIAL VIRUS DP107 F2 REGION ANALOG CARBOXY TRUNCATIONS

X-YTS-Z
X-YTSV-Z
X-YTSVI-Z
X-YTSVIT-Z
X-YTSVITI-Z
X-YTSVITIE-Z
X-YTSVITIEL-Z
X-YTSVITIELS-Z
X-YTSVITIELSN-Z
X-YTSVITIELSNI-Z
X-YTSVITIELSNIK-Z
X-YTSVITIELSNIKE-Z
X-YTSVITIELSNIKEN-Z
X-YTSVITIELSNIKENK-Z
X-YTSVITIELSNIKENKC-Z
X-YTSVITIELSNIKENKCN-Z
X-YTSVITIELSNIKENKCNG-Z
X-YTSVITIELSNIKENKCNGT-Z
X-YTSVITIELSNIKENKCNGTD-Z
X-YTSVITIELSNIKENKCNGTDA-Z
X-YTSVITIELSNIKENKCNGTDAK-Z
X-YTSVITIELSNIKENKCNGTDAKV-Z
X-YTSVITIELSNIKENKCNGTDAKVK-Z
X-YTSVITIELSNIKENKCNGTDAKVKL-Z
X-YTSVITIELSNIKENKCNGTDAKVKLI-Z
X-YTSVITIELSNIKENKCNGTDAKVKLIK-Z
X-YTSVITIELSNIKENKCNGTDAKVKLIKQ-Z
X-YTSVITIELSNIKENKCNGTDAKVKLIKQE-Z
X-YTSVITIELSNIKENKCNGTDAKVKLIKQEL-Z
X-YTSVITIELSNIKENKCNGTDAKVKLIKQELD-Z
X-YTSVITIELSNIKENKCNGTDAKVKLIKQELDK-Z
X-YTSVITIELSNIKENKCNGTDAKVKLIKQELDKY-Z
X-YTSVITIELSNIKENKCNGTDAKVKLIKQELDKYK-Z
X-YTSVITIELSNIKENKCNGTDAKVKLIKQELDKYKN-Z
X-YTSVITIELSNIKENKCNGTDAKVKLIKQELDKYKNA-Z
X-YTSVITIELSNIKENKCNGTDAKVKLIKQELDKYKNAV-Z
X-YTSVITIELSNIKENKCNGTDAKVKLIKQELDKYKNAVT-Z
X-YTSVITIELSNIKENKCNGTDAKVKLIKQELDKYKNAVTE-Z
X-YTSVITIELSNIKENKCNGTDAKVKLIKQELDKYKNAVTEL-Z
X-YTSVITIELSNIKENKCNGTDAKVKLIKQELDKYKNAVTELQ-Z
X-YTSVITIELSNIKENKCNGTDAKVKLIKQELDKYKNAVTELQL-Z
X-YTSVITIELSNIKENKCNGTDAKVKLIKQELDKYKNAVTELQLL-Z
X-YTSVITIELSNIKENKCNGTDAKVKLIKQELDKYKNAVTELQLLM-Z
X-YTSVITIELSNIKENKCNGTDAKVKLIKQELDKYKNAVTELQLLMQ-Z
X-YTSVITIELSNIKENKCNGTDAKVKLIKQELDKYKNAVTELQLLMQS-Z
X-YTSVITIELSNIKENKCNGTDAKVKLIKQELDKYKNAVTELQLLMQST-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE XVI

RESPIRATORY SYNCYTIAL VIRUS F2 DP178/DP107 REGION ANALOG AMINO TRUNCATIONS

X-QST-Z
X-MQST-Z
X-LMQST-Z
X-LLMQST-Z
X-QLLMQST-Z
X-LQLLMQST-Z
X-ELQLLMQST-Z
X-TELQLLMQST-Z
X-VTELQLLMQST-Z
X-AVTELQLLMQST-Z
X-NAVTELQLLMQST-Z
X-KNAVTELQLLMQST-Z
X-YKNAVTELQLLMQST-Z

TABLE XVI-continued

RESPIRATORY SYNCYTIAL VIRUS F2 DP178/DP107 REGION ANALOG AMINO TRUNCATIONS

X-KYKNAVTELQLLMQST-Z
X-DKYKNAVTELQLLMQST-Z
X-LDKYKNAVTELQLLMQST-Z
X-ELDKYKNAVTELQLLMQST-Z
X-QELDKYKNAVTELQLLMQST-Z
X-KQELDKYKNAVTELQLLMQST-Z
X-IKQELDKYKNAVTELQLLMQST-Z
X-LIKQELDKYKNAVTELQLLMQST-Z
X-KLIKQELDKYKNAVTELQLLMQST-Z
X-VKLIKQELDKYKNAVTELQLLMQST-Z
X-KVKLIKQELDKYKNAVTELQLLMQST-Z
X-AKVKLIKQELDKYKNAVTELQLLMQST-Z
X-DAKVKLIKQELDKYKNAVTELQLLMQST-Z
X-TDAKVKLIKQELDKYKNAVTELQLLMQST-Z
X-GTDAKVKLIKQELDKYKNAVTELQLLMQST-Z
X-NGTDAKVKLIKQELDKYKNAVTELQLLMQST-Z
X-CNGTDAKVKLIKQELDKYKNAVTELQLLMQST-Z
X-KCNGTDAKVKLIKQELDKYKNAVTELQLLMQST-Z
X-NKCNGTDAKVKLIKQELDKYKNAVTELQLLMQST-Z
X-KENKCNGTDAKVKLIKQELDKYKNAVTELQLLMQST-Z
X-IKENKCNGTDAKVKLIKQELDKYKNAVTELQLLMQST-Z
X-NIKENKCNGTDAKVKLIKQELDKYKNAVTELQLLMQST-Z
X-SNIKENKCNGTDAKVKLIKQELDKYKNAVTELQLLMQST-Z
X-LSNIKENKCNGTDAKVKLIKQELDKYKNAVTELQLLMQST-Z
X-ELSNIKENKCNGTDAKVKLIKQELDKYKNAVTELQLLMQST-Z
X-IELSNIKENKCNGTDAKVKLIKQELDKYKNAVTELQLLMQST-Z
X-TIELSNIKENKCNGTDAKVKLIKQELDKYKNAVTELQLLMQST-Z
X-ITIELSNIKENKCNGTDAKVKLIKQELDKYKNAVTELQLLMQST-Z
X-VITIELSNIKENKCNGTDAKVKLIKQELDKYKNAVTELQLLMQST-Z
X-SVITIELSNIKENKCNGTDAKVKLIKQELDKYKNAVTELQLLMQST-Z
X-TSVITIELSNIKENKCNGTDAKVKLIKQELDKYKNAVTELQLLMQST-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE XVII

RESPIRATORY SYNCYTIAL VIRUS F1 DP178 REGION ANALOG CARBOXY TRUNCATIONS

X-FYD-Z
X-FYDP-Z
X-FYDPL-Z
X-FYDPLV-Z
X-FYDPLVF-Z
X-FYDPLVFP-Z
X-FYDPLVFPS-Z
X-FYDPLVFPSD-Z
X-FYDPLVFPSDE-Z
X-FYDPLVFPSDEF-Z
X-FYDPLVFPSDEFD-Z
X-FYDPLVFPSDEFDA-Z
X-FYDPLVFPSDEFDAS-Z
X-FYDPLVFPSDEFDASI-Z
X-FYDPLVFPSDEFDASIS-Z
X-FYDPLVFPSDEFDASISQ-Z
X-FYDPLVFPSDEFDASISQV-Z
X-FYDPLVFPSDEFDASISQVN-Z
X-FYDPLVFPSDEFDASISQVNE-Z
X-FYDPLVFPSDEFDASISQVNEK-Z
X-FYDPLVFPSDEFDASISQVNEKI-Z
X-FYDPLVFPSDEFDASISQVNEKIN-Z
X-FYDPLVFPSDEFDASISQVNEKINQ-Z
X-FYDPLVFPSDEFDASISQVNEKINQS-Z
X-FYDPLVFPSDEFDASISQVNEKINQSL-Z
X-FYDPLVFPSDEFDASISQVNEKINQSLA-Z
X-FYDPLVFPSDEFDASISQVNEKINQSLAF-Z
X-FYDPLVFPSDEFDASISQVNEKINQSLAFI-Z
X-FYDPLVFPSDEFDASISQVNEKINQSLAFIR-Z
X-FYDPLVFPSDEFDASISQVNEKINQSLAFIRK-Z
X-FYDPLVFPSDEFDASISQVNEKINQSLAFIRKS-Z
X-FYDPLVFPSDEFDASISQVNEKINQSLAFIRKSD-Z
X-FYDPLVFPSDEFDASISQVNEKINQSLAFIRKSDE-Z
X-FYDPLVFPSDEFDASISQVNEKINQSLAFIRKSDEL-Z
X-FYDPLVFPSDEFDASISQVNEKINQSLAFIRKSDELL-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE XVIII

RESPIRATORY SYNCYTIAL VIRUS F1 DP178 REGION ANALOG AMINO TRUNCATIONS

X-DELL-Z
X-SDELL-Z
X-KSDELL-Z
X-RKSDELL-Z
X-IRKSDELL-Z
X-FIRKSDELL-Z
X-AFIRKSDELL-Z
X-LAFIRKSDELL-Z
X-SLAFIRKSDELL-Z
X-QSLAFIRKSDELL-Z
X-NQSLAFIRKSDELL-Z
X-INQSLAFIRKSDELL-Z
X-KINQSLAFIRKSDELL-Z
X-EKINQSLAFIRKSDELL-Z
X-NEKINQSLAFIRKSDELL-Z
X-VNEKINQSLAFIRKSDELL-Z
X-QVNEKINQSLAFIRKSDELL-Z
X-SQVNEKINQSLAFIRKSDELL-Z
X-ISQVNEKINQSLAFIRKSDELL-Z
X-SISQVNEKINQSLAFIRKSDELL-Z
X-ASISQVNEKINQSLAFIRKSDELL-Z
X-DASISQVNEKINQSLAFIRKSDELL-Z
X-FDASISQVNEKINQSLAFIRKSDELL-Z
X-EFDASISQVNEKINQSLAFIRKSDELL-Z
X-DEFDASISQVNEKINQSLAFIRKSDELL-Z
X-SDEFDASISQVNEKINQSLAFIRKSDELL-Z
X-PSDEFDASISQVNEKINQSLAFIRKSDELL-Z
X-FPSDEFDASISQVNEKINQSLAFIRKSDELL-Z
X-VFPSDEFDASISQVNEKINQSLAFIRKSDELL-Z
X-LVFPSDEFDASISQVNEKINQSLAFIRKSDELL-Z
X-PLVFPSDEFDASISQVNEKINQSLAFIRKSDELL-Z
X-DPLVFPSDEFDASISQVNEKINQSLAFIRKSDELL-Z
X-YDPLVFPSDEFDASISQVNEKINQSLAFIRKSDELL-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE XIX

HUMAN PARAINFLUENZA VIRUS 3 F1 REGION DP178 ANALOG CARBOXY TRUNCATIONS

X-ITL-Z
X-ITLN-Z
X-ITLNN-Z
X-ITLNNS-Z
X-ITLNNSV-Z
X-ITLNNSVA-Z
X-ITLNNSVAL-Z
X-ITLNNSVALD-Z
X-ITLNNSVALDP-Z
X-ITLNNSVALDPI-Z
X-ITLNNSVALDPID-Z
X-ITLNNSVALDPIDI-Z
X-ITLNNSVALDPIDIS-Z
X-ITLNNSVALDPIDISI-Z
X-ITLNNSVALDPIDISIE-Z
X-ITLNNSVALDPIDISIEL-Z
X-ITLNNSVALDPIDISIELN-Z
X-ITLNNSVALDPIDISIELNK-Z
X-ITLNNSVALDPIDISIELNKA-Z
X-ITLNNSVALDPIDISIELNKAK-Z
X-ITLNNSVALDPIDISIELNKAKS-Z
X-ITLNNSVALDPIDISIELNKAKSD-Z
X-ITLNNSVALDPIDISIELNKAKSDL-Z
X-ITLNNSVALDPIDISIELNKAKSDLE-Z
X-ITLNNSVALDPIDISIELNKAKSDLEE-Z
X-ITLNNSVALDPIDISIELNKAKSDLEES-Z
X-ITLNNSVALDPIDISIELNKAKSDLEESK-Z
X-ITLNNSVALDPIDISIELNKAKSDLEESKE-Z
X-ITLNNSVALDPIDISIELNKAKSDLEESKEW-Z
X-ITLNNSVALDPIDISIELNKAKSDLEESKEWI-Z
X-ITLNNSVALDPIDISIELNKAKSDLEESKEWIR-Z
X-ITLNNSVALDPIDISIELNKAKSDLEESKEWIRR-Z
X-ITLNNSVALDPIDISIELNKAKSDLEESKEWIRRS-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE XX

HUMAN PARAINFLUENZA VIRUS 3 F1 REGION DP178 ANALOG AMINO TRUNCATIONS

X-RRS-Z
X-IRRS-Z
X-WIRRS-Z
X-EWIRRS-Z
X-KEWIRRS-Z
X-SKEWIRRS-Z
X-ESKEWIRRS-Z
X-EESKEWIRRS-Z
X-LEESKEWIRRS-Z
X-DLEESKEWIRRS-Z
X-SDLEESKEWIRRS-Z
X-KSDLEESKEWIRRS-Z
X-AKSDLEESKEWIRRS-Z
X-KAKSDLEESKEWIRRS-Z
X-NKAKSDLEESKEWIRRS-Z
X-LNKAKSDLEESKEWIRRS-Z
X-ELNKAKSDLEESKEWIRRS-Z
X-IELNKAKSDLEESKEWIRRS-Z
X-SIELNKAKSDLEESKEWIRRS-Z
X-ISIELNKAKSDLEESKEWIRRS-Z
X-DISIELNKAKSDLEESKEWIRRS-Z
X-IDISIELNKAKSDLEESKEWIRRS-Z
X-PIDISIELNKAKSDLEESKEWIRRS-Z
X-DPIDISIELNKAKSDLEESKEWIRRS-Z
X-LDPIDISIELNKAKSDLEESKEWIRRS-Z
X-ALDPIDISIELNKAKSDLEESKEWIRRS-Z
X-VALDPIDISIELNKAKSDLEESKEWIRRS-Z
X-SVALDPIDISIELNKAKSDLEESKEWIRRS-Z
X-NSVALDPIDISIELNKAKSDLEESKEWIRRS-Z
X-NNSVALDPIDISIELNKAKSDLEESKEWIRRS-Z
X-LNNSVALDPIDISIELNKAKSDLEESKEWIRRS-Z
X-TLNNSVALDPIDISIELNKAKSDLEESKEWIRRS-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE XIX-continued

HUMAN PARAINFLUENZA VIRUS 3 F1 REGION DP178 ANALOG CARBOXY TRUNCATIONS

X-ITLNNSVALDPIDISIELNKAKSDLEES-Z
X-ITLNNSVALDPIDISIELNKAKSDLEESK-Z
X-ITLNNSVALDPIDISIELNKAKSDLEESKE-Z
X-ITLNNSVALDPIDISIELNKAKSDLEESKEW-Z
X-ITLNNSVALDPIDISIELNKAKSDLEESKEWI-Z
X-ITLNNSVALDPIDISIELNKAKSDLEESKEWIR-Z
X-ITLNNSVALDPIDISIELNKAKSDLEESKEWIRR-Z
X-ITLNNSVALDPIDISIELNKAKSDLEESKEWIRRS-Z

TABLE XXI

HUMAN PARAINFLUENZA VIRUS 3 F1 REGION DP107 ANALOG CARBOXY TRUNCATIONS

X-ALG-Z
X-ALGV-Z
X-ALGVA-Z
X-ALGVAT-Z
X-ALGVATS-Z
X-ALGVATSA-Z
X-ALGVATSAQ-Z
X-ALGVATSAQI-Z
X-ALGVATSAQIT-Z
X-ALGVATSAQITA-Z
X-ALGVATSAQITAA-Z
X-ALGVATSAQITAAV-Z
X-ALGVATSAQITAAVA-Z
X-ALGVATSAQITAAVAL-Z
X-ALGVATSAQITAAVALV-Z
X-ALGVATSAQITAAVALVE-Z
X-ALGVATSAQITAAVALVEA-Z
X-ALGVATSAQITAAVALVEAK-Z
X-ALGVATSAQITAAVALVEAKQ-Z
X-ALGVATSAQITAAVALVEAKQA-Z
X-ALGVATSAQITAAVALVEAKQAR-Z
X-ALGVATSAQITAAVALVEAKQARS-Z
X-ALGVATSAQITAAVALVEAKQARSD-Z
X-ALGVATSAQITAAVALVEAKQARSDI-Z
X-ALGVATSAQITAAVALVEAKQARSDIE-Z
X-ALGVATSAQITAAVALVEAKQARSDIEK-Z
X-ALGVATSAQITAAVALVEAKQARSDIEKL-Z
X-ALGVATSAQITAAVALVEAKQARSDIEKLK-Z
X-ALGVATSAQITAAVALVEAKQARSDIEKLKE-Z
X-ALGVATSAQITAAVALVEAKQARSDIEKLKEA-Z
X-ALGVATSAQITAAVALVEAKQARSDIEKLKEAI-Z
X-ALGVATSAQITAAVALVEAKQARSDIEKLKEAIR-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethyl-carbonyl (FMOC) group; a macromolecular carrier group including but not limited to lipid-fatty acid conjugates, polyethylene glycol, or carbohydrates.
"Z" may represent a carboxyl group, an amido group; a T-butyloxycarbonyl group; a macromolecular carrier group including but not limited to lipid-fatty acid conjugates, polyethylene glycol, or carbohydrates.

TABLE XXII

HUMAN PARAINFLUENZA VIRUS 3 F1 REGION DP107 ANALOG AMINO TRANCATIONS

X-IRD-Z
X-AIRD-Z
X-EAIRD-Z
X-KEAIRD-Z
X-LKEAIRD-Z
X-KLKEAIRD-Z
X-EKLKEAIRD-Z
X-IEKLKEAIRD-Z
X-DIEKLKEAIRD-Z
X-SDIEKLKEAIRD-Z
X-RSDIEKLKEAIRD-Z
X-ARSDIEKLKEAIRD-Z
X-QARSDIEKLKEAIRD-Z
X-KQARSDIEKLKEAIRD-Z
X-AKQARSDIEKLKEAIRD-Z
X-EAKQARSDIEKLKEAIRD-Z
X-VEAKQARSDIEKLKEAIRD-Z
X-LVEAKQARSDIEKLKEAIRD-Z
X-ALVEAKQARSDIEKLKEAIRD-Z
X-VALVEAKQARSDIEKLKEAIRD-Z
X-AVALVEAKQARSDIEKLKEAIRD-Z
X-AAVALVEAKQARSDIEKLKEAIRD-Z
X-TAAVALVEAKQARSDIEKLKEAIRD-Z
X-ITAAVALVEAKQARSDIEKLKEAIRD-Z
X-QITAAVALVEAKQARSDIEKLKEAIRD-Z
X-AQITAAVALVEAKQARSDIEKLKEAIRD-Z

TABLE XXII-continued

HUMAN PARAINFLUENZA VIRUS 3 F1 REGION DP107 ANALOG AMINO TRANCATIONS

X-SAQITAAVALVEAKQARSDIEKLKEAIRD-Z
X-TSAQITAAVALVEAKQARSDIEKLKEAIRD-Z
X-ATSAQITAAVALVEAKQARSDIEKLKEAIRD-Z
X-VATSAQITAAVALVEAKQARSDIEKLKEAIRD-Z
X-GVATSAQITAAVALVEAKQARSDIEKLKEAIRD-Z
X-LGVATSAQITAAVALVEAKQARSDIEKLKEAIRD-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE XXIII

REPRESENTATIVE DP107/DP178 ANALOG ANTIVIRAL PEPTIDES

Anti-Respiratory syncytial virus peptides

X-TSVITIELSNIKENKCNGTDAKVKLIKQELDKYKN-Z
X-SVITIELSNIKENKCNGTDAKVKLIKQELDKYKNA-Z
X-VITIELSNIKENKCNGTDAKVKLIKQELDKYKNAV-Z
X-VAVSKVLHLEGEVNKIALLSTNKAVVSLSNGVS-Z
X-AVSKVLHLEGEVNKIALLSTNKAVVSLSNGVSV-Z
X-VSKVLHLEGEVNKIALLSTNKAVVSLSNGVSVL-Z
X-SKVLHLEGEVNKIALLSTNKAVVSLSNGVSVLT-Z
X-KVLHLEGEVNKIALLSTNKAVVSLSNGVSVLTS-Z
X-LEGEVNKIALLSTNKAVVSLSNGVSVLTSKVLD-Z
X-GEVNKIALLSTNKAVVSLSNGVSVLTSKVLDLK-Z
X-EVNKIALLSTNKAVVSLSNGVSVLTSKVLDLKN-Z
X-VNKIALLSTNKAVVSLSNGVSVLTSKVLDLKNY-Z
X-NKIALLSTNKAVVSLSNGVSVLTSKVLDLKNYI-Z
X-KIALLSTNKAVVSLSNGVSVLTSKVLDLKNYID-Z
X-IALLSTNKAVVSLSNGVSVLTSKVLDLKNYIDK-Z
X-ALLSTNKAVVSLSNGVSVLTSKVLDLKNYIDKQ-Z
X-VAVSKVLHLEGEVNKIALLSTNKAVVSLSNGVS-Z
X-AVSKVLHLEGEVNKIALLSTNKAVVSLSNGVSV-Z
X-VSKVLHLEGEVNKIALLSTNKAVVSLSNGVSVL-Z
X-SKVLHLEGEVNKIALLSTNKAVVSLSNGVSVLT-Z
X-KVLHLEGEVNKIALLSTNKAVVSLSNGVSVLTS-Z
X-LEGEVNKIALLSTNKAVVSLSNGVSVLTSKVLD-Z
X-GEVNKIALLSTNKAVVSLSNGVSVLTSKVLDLK-Z
X-EVNKIALLSTNKAVVSLSNGVSVLTSKVLDLKN-Z
X-VNKIALLSTNKAVVSLSNGVSVLTSKVLDLKNY-Z
X-NKIALLSTNKAVVSLSNGVSVLTSKVLDLKNYI-Z
X-KIALLSTNKAVVSLSNGVSVLTSKVLDLKNYID-Z
X-IALLSTNKAVVSLSNGVSVLTSKVLDLKNYIDK-Z
X-ALLSTNKAVVSLSNGVSVLTSKVLDLKNYIDKQ-Z
(SEQ ID NOS: 210–238, respectively)

Anti-human parainfluenza virus 3 peptides

X-TLNNSVALKPIDISIELNKAKSDLEESKEWIRRSN-Z
X-LNNSVALDPIDISIELNKAKSDLEESKEWIRRSNQ-Z
X-NNSVALDPIDISIELNKAKSDLEESKEWIRRSNQK-Z
X-NSVALDPIDISIELNKAKSDLEESKEWIRRSNQKL-Z
X-SVALDPIDISIELNKAKSDLEESKEWIRRSNQKLD-Z
X-VALDPIDISIELNKAKSDLEESKEWIRRSNQKLDS-Z
X-ALDPIDISIELNKAKSDLEESKEWIRRSNQKLDSI-Z
X-LDPIDISIELNKAKSDLEESKEWIRRSNQKLDSIG-Z
X-DPIDISIELNKAKSDLEESKEWIRRSNQKLDSIGN-Z
X-PIDISIELNKAKSDLEESKEWIRRSNQKLDSIGNW-Z
X-IDISIELNKAKSDLEESKEWIRRSNQKLDSIGNWH-Z
X-DISIELNKAKSDLEESKEWIRRSNQKLDSIGNWHQ-Z
X-ISIELNKAKSDLEESKEWIRRSNQKLDSIGNWHQS-Z
X-SIELNKAKSDLEESKEWIRRSNQKLDSIGNWHQSS-Z
X-IELNKAKSDLEESKEWIRRSNQKLDSIGNWHQSST-Z
X-ELNKAKSDLEESKEWIRRSNQKLDSIGNWHQSSTT-Z
X-TAAVALVEAKQARSDIEKLKEAIRDTNKAVQSVQS-Z
X-AVALVEAKQARSDIEKLKEAIRDTNKAVQSVQSSI-Z
X-LVEAKQARSDIEKLKEAIRDTNKAVQSVQSSIGNL-Z

TABLE XXIII-continued

REPRESENTATIVE DP107/DP178 ANALOG ANTIVIRAL PEPTIDES

X-VEAKQARSDIEKLKEAIRDTNKAVQSVQSSIGNLI-Z
X-EAKQARSDIEKLKEAIRDTNKAVQSVQSSIGNLIV-Z
X-AKQARSDIEKLKEAIRDTNKAVQSVQSSIGNLIVA-Z
X-KQARSDIEKLKEAIRDTNKAVQSVQSSIGNLIVAI-Z
X-QARSDIEKLKEAIRDTNKAVQSVQSSIGNLIVAIK-Z
X-ARSDIEKLKEAIRDTNKAVQSVQSSIGNLIVAIKS-Z
X-RSDIEKLKEAIRDTNKAVQSVQSSIGNLIVAIKSV-Z
X-SDIEKLKEAIRDTNKAVQSVQSSIGNLIVAIKSVQ-Z
X-KLKEAIRDTNKAVQSVQSSIGNLIVAIKSVQDYVN-Z
X-LKEAIRDTNKAVQSVQSSIGNLIVAIKSVQDYVNK-Z
X-AIRDTNKAVQSVQSSIGNLIVAIKSVQDYVNKEIV-Z
Anti-simian immunodeficiency virus peptides X-WQEWERKVDFLEENITALLEEAQIQQEKNMYELQK-Z
X-QEWERKVDFLEENITALLEEAQIQQEKNMYELQKL-Z
X-EWERKVDFLEENITALLEEAQIQQEKNMYELQKLN-Z
X-WERKVDFLEENITALLEEAQIQQEKNMYELQKLNSW-Z
X-ERKVDFLEENITALLEEAQIQQEKNMYELQKLNSW-Z
X-RKVDFLEENITALLEEAQIQQEKNMYELQKLNSWD-Z
X-KVDFLEENITALLEEAQIQQEKNMYELQKLNSWDV-Z
X-VDFLEENITALLEEAQIQQEKNMYELQKLNSWDVF-Z
X-DFLEENITALLEEAQIQQEKNMYELQKLNSWDVFG-Z
X-FLEENITALLEEAQIQQEKNMYELQKLNSWDVFGN-Z
Anti-measles virus peptides X-LHRIDLGPPISLERLDVGTNLGNAIAKLEAKELL-Z
X-HRIDLGPPISLERLDVGTNLGNAIAKLEAKELLE-Z
X-RIDLGPPISLERLDVGTNLGNAIAKLEAKELLES-Z
X-IDLGPPISLERLDVGTNLGNAIAKLEAKELLESS-Z
X-DLGPPISLERLDVGTNLGNAIAKLEAKELLESSD-Z
X-LGPPISLERLDVGTNLGNAIAKLEAKELLESSDQ-Z
X-GPPISLERLDVGTNLGNAIAKLEAKELLESSDQI-Z
X-PPISLERLDVGTNLGNAIAKLEAKELLESSDQIL-Z
X-PISLERLDVGTNLGNAIAKLEAKELLESSDQILR-Z
X-SLERLDVGTNLGNAIAKLEAKELLESSDQILRSM-Z
X-LERLDVGTNLGNAIAKLEAKELLESSDQILRSMK-Z The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

5.4. Synthesis of Peptides

The peptides of the invention may be synthesized or prepared by techniques well known in the art. See, for example, Creighton, 1983, Proteins:. Structures and Molecular Principles, W.H. Freeman and Co., NY, which is incorporated herein by reference in its entirety. Short peptides, for example, can be synthesized on a solid support or in solution. Longer peptides may be made using recombinant DNA techniques. Here, the nucleotide. sequences encoding the peptides of the invention may be synthesized, and/or cloned, and expressed according to techniques well known to those of ordinary skill in the art. See, for example, Sambrook, et al., 1989, Molecular Cloning, A Laboratory Manual, Vols. 1–3, Cold Spring Harbor Press, NY.

The peptides of the invention may alternatively be synthesized such that one or more of the bonds which link the amino acid residues of the peptides are non-peptide bonds. These alternative non-peptide bonds may be formed by utilizing reactions well known to those in the art, and may include, but are not limited. to imino, ester, hydrazide, semicarbazide, and azo bonds, to name but a few. In yet another embodiment of the invention, peptides comprising the sequences described above may be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the peptides' amino termini. Likewise, an acetyl group or a 9-fluorenylmethoxy-carbonyl group may be placed at the peptides' amino termini. (See "X" in Tables I to IV, above.) Additionally, the hydrophobic group, t-butyloxycarbonyl, or an amido group may be added to the peptides' carboxy termini. (See "Z" in Tables I to IV, above.)

Further, the peptides of the invention may be synthesized such that their steric configuration is altered. For example, the D-isomer of one or more of the amino acid residues of the peptide may be used, rather than the usual L-isomer.

Still further, at least one of the amino acid residues of the peptides of the invention may be substituted by one of the well known non-naturally occurring amino acid residues. Alterations such as these may serve to increase the stability, bioavailability and/or inhibitory action of the peptides of the invention.

Any of the peptides described above may, additionally, have a macromolecular carrier group covalently attached to their amino and/or carboxy termini. Such macromolecular carrier groups may include, for example, lipid-fatty acid conjugates, polyethylene glycol, carbohydrates or additional peptides. "X", in Tables I to IV, above, may therefore additionally represent any of the above macromolecular carrier groups covalently attached to the amino terminus of a peptide, with an additional peptide group being preferred. Likewise, "Z", in Tables I to IV, may additionally represent any of the macromolecular carrier groups described above.

5.5. Assays for Anti-membrane Fusion Activity

Described herein, are methods for ability of a compound, such as the peptides of the invention, to inhibit membrane fusion events. Specifically, assays for cell fusion events are described in Section 5.5.1, below, and assays for antiviral activity are described in Section 5.5.2, below.

5.5.1 Assays for Cell Fusion Events

Assays for cell fusion events are well known to those of skill in the art, and may be used in conjunction, for example, with the peptides of the invention to test the peptides antifusogenic capabilities.

Cell fusion assays are generally performed in vitro. Such an assay may comprise culturing cells which, in the absence of any treatment would undergo an observable level of syncytial formation. For example, uninfected cells may be incubated in the presence of cells chronically infected with a virus that induces cell fusion. Such viruses may include, but are not limited to, HIV, SIV, or respiratory syncytial virus.

For the assay, cells are incubated in the presence of a peptide to be assayed. For each peptide, a range of peptide concentrations may be tested. This range should include a control culture wherein no peptide has been added.

Standard conditions for culturing cells, well known to those of ordinary skill in the art, are used. After incubation for an appropriate period (24 hours at 37° C., for example) the culture is examined microscopically for the presence of multinucleated giant cells, which are indicative of cell fusion and syncytial formation. Well known stains, such as crystal violet stain, may be used to facilitate the visualization of syncytial formation.

5.5.2 Assays for Antiviral Activity

The antiviral activity exhibited by the peptides of the invention may be measured, for example, by easily performed in vitro assays, such as those described below, which can test the peptides' ability to inhibit syncytia formation, or their ability to inhibit infection by cell-free virus. Using these assays, such parameters as the relative antiviral activity of the peptides, exhibit against a given strain of virus and/or the strain specific inhibitory activity of the peptide can be determined.

A cell fusion assay may be utilized to test the peptides' ability to inhibit viral-induced, such as HIV-induced, syncytia formation in vitro. Such an assay may comprise culturing uninfected cells in the presence of cells chronically infected with a syncytial-inducing virus and a peptide to be assayed. For each peptide, a range of peptide concentrations may be tested. This range should include a control culture wherein no peptide has been added. Standard conditions for culturing, well known to those of ordinary skill in the art, are used. After incubation for an appropriate period (24 hours at 37° C., for example) the culture is examined microscopically for the presence of multinucleated giant cells, which are indicative of cell fusion and syncytia formation. Well known stains, such as crystal violet stain, may be used to facilitate syhcytial visualization. Taking HIV as an example, such an assay would comprise CD-4+ cells (such as Molt or CEM cells, for example) cultured in the presence of chronically HIV-infected cells and a peptide to be assayed.

Other well known characteristics of viral infection may also be assayed to test a peptide's antiviral capabilities. Once again taking HIV as an example, a reverse transcriptase. (RT) assay may be utilized to test the peptides' ability to inhibit infection of CD-4+ cells by cell-free HIV. Such an assay may comprise culturing an appropriate concentration (i.e., $TCID_{50}$) of virus and CD-4+ cells in the presence of the peptide to be tested. Culture conditions well known to those in the art are used. As above, a range of peptide concentrations may be used, in addition to a control culture wherein no peptide has been added. After incubation for an appropriate period (e.g., 7 days) of culturing, a cell-free supernatant is prepared, using standard procedures, and tested for the present of RT activity as a measure of successful infection. The RT activity may be tested using standard techniques such as those described by, for example, Goff et al. (Goff, S. et al., 1981, J. Virol. 38:239–248) and/or Willey et al. (Willey, R. et al., 1988, J. Virol. 62:139–147). These references are incorporated herein by reference in their entirety.

Standard methods which are well-known to those of skill in the art may be utilized for assaying non-retroviral activity. See, for example, Pringle et al. (Pringle, C. R. et al., 1985, J. Medical Virology 17:377–386) for a discussion of respiratory syncytial virus and parainfluenza virus activity assay techniques. Further, see, for example, "Zinsser Microbiology", 1988, Joklik, W. K. et al., eds., Appleton & Lange, Norwalk, Conn., 19th ed., for a general review of such techniques. These references are incorporated by reference herein in their entirety. In addition, the Examples presented below, in Sections 17, 18, 26 and 27 each provide additional assays for the testing of a compound's antiviral capability.

In vivo assays may also be utilized to test, for example, the antiviral activity of the peptides of the invention. To test for anti-HIV activity, for example, the in vivo model described in Barnett et al. (Barnett, S. W. et al., 1994, Science 266:642–646) may be used.

Additionally, anti-RSV activity can be assayed in vivo via well known mouse models. For example, RSV can be administered intranasally to mice of various inbred strains. Virus replicates in lungs of all strains, but the highest titers are obtained in P/N, C57L/N and DBA/2N mice. Infection of BALB/c mice produces an asymptomatic bronchiolitis characterized by lymphocytic infiltrates and pulmonary virus titers of $10^4$ to $10^5$ pfu/g of lung tissue (Taylor, G. et al., 1984, Infect. Immun. 43:649–655).

Cotton rat models of RSV are also well known. Virus replicates to high titer in the nose and lungs of the cotton rat but produces. few if any signs of inflammation.

5.6. Uses, of the Peptides of the Invention

The peptides of the invention may be utilized as antifusogenic or antiviral compounds, or as compounds which modulate intracellular processes involving coiled coil peptide structures. Further, such peptides may be used to identify agents which exhibit antifusogenic, antiviral or intracellular modulatory activity. Still further, the peptides of the invention may be utilized as organism or viral type/subtype-specific diagnostic tools.

The antifusogenic capability of the peptides of the invention may additionally be utilized to inhibit or treat/ ameliorate symptoms caused by processes involving membrane fusion events. Such events may include, for example, virus transmission via cell-cell fusion, abnormal neurotransmitter exchange via cell-fusion, and sperm-egg fusion. Further, the peptides of the invention may be used to inhibit free viral, such as retroviral, particularly HIV, transmission to uninfected cells wherein such viral infection involves membrane fusion events or involves fusion of a viral structure with a cell membrane. Among the intracellular disorders involving coiled coil peptides structures which may be ameliorated by the peptides of the invention are disorders involving, for example, bacterial toxins.

With respect to antiviral activity, the viruses whose transmission may be inhibited by the peptides of the invention include, but are not limited to all strains of the viruses listed above, in Tables V through VII, and IX through XIV.

These viruses include, for example, human retroviruses, particularly HIV-1 and HIV-2 and the human T-lymphocyte viruses.(HTLV-I and II). The non-human retroviruses whose transmission may be inhibited by the peptides of the invention include, but are not limited to bovine leukosis virus, feline sarcoma and leukemia viruses, simian immunodeficiency, sarcoma and leukemia viruses, and sheep progress pneumonia viruses.

Non retroviral viruses whose transmission may be inhibited by the peptides of the invention include, but are not limited to human respiratory syncytial virus, canine distemper virus, newcastle disease virus, human parainfluenza virus, influenza viruses, measles viruses, Epstein-Barr viruses, hepatitis B viruses, and simian Mason-Pfizer viruses.

Non enveloped viruses whose transmission may be inhibited by the peptides of the invention include, but are not limited to picornaviruses such as polio viruses, hepatitis A virus, enterovirus, echoviruses and coxsackie viruses, papovaviruses such as papilloma virus, parvoviruses, adenoviruses and reoviruses.

As discussed more fully, below, in Section 5.5.1 and in the Example presented, below, in Section 8, DP107, DP178, DP107 analog and DP178 analog peptides form non-covalent protein-protein interactions which are required for normal activity of the virus. Thus, the peptides of the invention may also be utilized as components in assays for the identification of compounds that interfere with such protein-protein interactions and may, therefore, act as antiviral agents. These assays are discussed, below, in Section 5.5.1.

As demonstrated in the Example presented below in Section 6, the antiviral activity of the peptides of the invention may show a pronounced type and subtype. specificity, i.e., specific peptides may be effective in inhibiting the activity of only specific viruses. This feature of the invention presents many advantages. One such advantage, for example, lies in. the field of diagnostics, wherein one can use the antiviral specificity of the peptide of the invention to ascertain the identity of a viral isolate. With respect to HIV, one may easily determine whether a viral isolate consists of an HIV-1 or HIV-2 strain. For example, uninfected CD-4+ cells may be co-infected with an isolate which has been identified as containing HIV the DP178 (SEQ ID:1) peptide, after which the retroviral activity of cell supernatants may be assayed, using, for example, the techniques described above in Section 5.2. Those isolates whose retroviral activity is completely or nearly completely inhibited contain HIV-1. Those isolates whose viral activity is unchanged or only reduced by a small amount, may be considered to not contain HIV-1. Such an isolate may then be treated with one or more of the. other DP178 peptides of the invention, and subsequently be tested for its viral activity in order to determine the identify of the viral isolate. The DP107 and DP178 analogs of the invention may also be utilized in a diagnostic capacity specific to the type and subtype of virus or organism in which the specific peptide sequence is found. A diagnostic procedure as described, above, for DP178, may be used in conjunction with the DP107/DP178 analog of interest.

5.5.1. Screening Assays

As demonstrated in the Example presented in Section 8, below, DP107 and DP178 portions of the TM protein gp41 form non-covalent protein-protein interactions. As is also demonstrated, the maintenance of such interactions is necessary for. normal viral infectivity. Thus, compounds which bind DP107, bind DP178, and/or act to disrupt normal DP107/DP178 protein-protein interactions may act as antifusogenic, antiviral or cellular modulatory agents. Described below are assays for the identification of such compounds. Note that, while, for ease and clarity of discussion, DP107 and DP178 peptides will be used as components of the assays described, but it is to be understood that any of the DP107 analog or DP178 analog peptides described, above, in Sections 5.1 through 5.3 may also be utilized as part of these screens for compounds.

Compounds which may be tested for an ability to bind DP107, DP178, and/or disrupt DP107/DP178 interactions, and which therefore, potentially represent antifusogenic, antiviral or intracellular modulatory compounds, include, but are not limited to, peptides made of D- and/or L-configuration amino acids (in, for example, the form of random peptide libraries; see Lam, K. S. et al., 1991, Nature 354:82–84), phosphopeptides (in, for example, the form of random or partially degenerate, directed phosphopeptide libraries; see, for example, Songyang, Z. et al., 1993, Cell 72:767–778), antibodies, and small organic or inorganic molecules. Synthetic compounds, natural products, and other sources of potentially effective materials may be screened in a variety of ways, as described in this Section.

The compounds, antibodies, or other molecules identified may be tested, for example, for an ability to inhibit cell fusion or viral activity, utilizing, for example, assays such as those described, above, in Section 5.5.

Among the peptides which may be tested are soluble peptides comprising DP107 and/or DP178 domains, and peptides comprising DP107 and/or DP178 domains having one or more mutations within one or both of the domains, such as the M41-P peptide described, below, in the Example presented in Section 8, which contains a isoleucine to proline mutation within the DP178 sequence.

In one embodiment of such screening methods is a method for identifying a compound to be tested for antiviral ability comprising:

(a) exposing at least one compound to a peptide comprising a DP107 peptide for a time sufficient to allow binding of the compound to the DP107 peptide;

(b) removing non-bound compounds; and (c) determining the presence of the compound bound to the DP107 peptide, thereby identifying an agent to be tested for antiviral ability.

In a second embodiment of such screening methods is a method for identifying a compound to be tested for antiviral ability comprising:

(a) exposing at least one compound to a peptide comprising a DP178 peptide for a time sufficient to allow binding of the compound to the DP178 peptide;

(b) removing non-bound compounds; and (c) determining the presence of the compound bound to the DP178 peptide, thereby identifying an agent to be tested for antiviral ability.

One method utilizing these types of approaches that may be pursued in the isolation of such DP107-binding or DP178-binding compounds is an assay which would include the attachment of either the DP107 or the DP178 peptide to a solid matrix, such as, for example, agarose or plastic beads, microtiter plate wells, petri dishes, or membranes composed of, for example, nylon or nitrocellulose. In such an assay system, either the DP107 or DP178 protein may be anchored onto a solid surface, and the compound, or test substance, which is not anchored, is labeled, either directly or indirectly. In practice, microtiter plates are conveniently utilized. The anchored component may be immobilized by non-covalent or covalent attachments. Non-covalent attachment may be accomplished simply by coating the solid surface with a solution of the protein and drying.

Alternatively, an immobilized antibody, preferably a monoclonal antibody, specific for the protein may be used to anchor the protein to the solid surface. The surfaces may be prepared in advance and stored.

In order to conduct the assay, the labeled compound is added to the coated surface containing the anchored DP107 or DP178 peptide. After the reaction is complete, unreacted components are removed (e.g., by washing) under conditions such that any complexes formed will remain immobilized on the solid surface. The detection of complexes anchored on the solid surface can be accomplished in a number of ways. Where the compound is pre-labeled, the detection of label immobilized on the surface indicates that complexes were formed. Where the labeled component is not pre-labeled, an indirect label can be used to detect complexes anchored on the surface; e.g., using a labeled antibody specific for the compound (the antibody, in turn, may be directly labeled or indirectly labeled with a labeled anti-Ig antibody).

Alternatively, such an assay can be conducted in a liquid phase, the reaction products separated from unreacted components, and complexes detected; e.g., using an-immobilized antibody specific for DP107 or DP178, whichever is appropriate for the given assay, or ab antibody specific for the compound, i.e., the test substance, in order to anchor any complexes formed in solution, and a labeled antibody specific for the other member of the complex to detect anchored complexes.

By utilizing procedures such as this, large numbers of types of molecules may be simultaneously screened for DP107 or DP178-binding capability, and thus potential antiviral activity.

Further, compounds may be screened for an ability to inhibit the formation of or, alternatively, disrupt DP107/

DP178 complexes. Such compounds may then be tested for antifusogenic, antiviral or intercellular modulatory capability. For ease of description, DP107 and DP178 will be referred to as "binding partners." Compounds that disrupt such interactions may exhibit antiviral activity. Such compounds may include, but are not limited to molecules such as antibodies, peptides, and the like described above.

The basic principle of the assay systems used to identify compounds that interfere with the interaction between the DP107 and DP178 peptides involves preparing a reaction mixture containing peptides under conditions and for a time sufficient to allow the two peptides to interact and bind, thus forming a complex.

In order to test a compound for disruptive activity, the reaction is conducted in the presence and absence of the test compound, i.e., the test compound may be initially included in the reaction mixture, or added at a time subsequent to the addition of one of the binding partners; controls are incubated without the test compound or with a placebo. The formation of any complexes between the binding partners is then detected. The formation of a complex in the control reaction, but not in the reaction mixture containing the test compound indicates that the compound interferes with the interaction of the DP107 and DP178 peptides.

The assay for compounds that interfere with the interaction of the binding partners can be conducted in a heterogeneous or. homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the binding partners. On the other hand, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, one binding partner, e.g., either the DP107 or DP178 peptide, is. anchored onto a solid surface, and its binding partner, which is not anchored, is labeled, either directly or indirectly. In practice, microtiter plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is added to the coated surface with or without the test compound. After the reaction is complete, unreacted components are removed (e.g., by washing) and any complexes formed will remain immobilized on the solid surface. The detection of complexes anchored on. the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for. the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products-separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the DP107 and DP178 peptides is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt DP-107/DP-178 protein-protein interaction can be identified.

In an alternative screening assay, test compounds may be assayed for the their ability to disrupt a DP178/DP107 interaction, as measured immunometrically using an antibody specifically reactive to a DP107/DP178 complex (i.e., an antibody that recognizes neither DP107 nor DP178 individually). Such an assay acts as a competition assay, and is based on techniques well known to those of skill in the art.

The above competition assay may be described, by way of. example, and not by way of limitation, by using the DP178 and M41Δ178 peptides and by assaying test compounds for the disruption of the complexes formed by these two peptides by immunometrically visualizing DP178/M41Δ178 complexes via the human recombinant Fab, Fab-d, as described, below, in the Example presented in Section 8. M41Δ178 is a maltose binding fusion protein containing a gp41 region having its DP178 domain deleted, and is described, below, in the Example presented in Section 8.

Utilizing such an assay, M41Δ178 may be immobilized onto solid supports such as microtiter wells. A series of dilutions of a test compound may then be added to each M41Δ178-containing well in the presence of a constant concentration of DP-178 peptide. After incubation, at, for example, room temperature for one hour, unbound DP-178 and test compound are removed from the wells and wells are then incubated with the DP178/M41Δ178-specific Fab-d antibody. After incubation and washing, unbound Fab-d is removed from the plates and bound Fab-d is quantitated. A no-inhibitor control should also be conducted. Test compounds showing an ability to disrupt DP178/M41Δ178 complex formation are identified by their concentration-dependent decrease in the level of Fab-d binding.

A variation of such an assay may be utilized to perform a rapid, high-throughput binding assay which is capable of directly measuring DP178 binding to M41Δ178 for the determination of binding constants of the ligand of inhibitory constants for competitors of DP178 binding.

Such an assay takes advantage of accepted radioligand and receptor binding principles. (See, for example, Yamamura, H. I. et al., 1985, "Neurotransmitter Receptor Binding", 2nd ed., Raven Press, NY.) As above, M41Δ178 is immobilized onto a solid support such as a microtiter well. DP178 binding to M41Δ178 is then quantitated by measuring the fraction of DP178 that is bound as $^{125}$I-DP178 and calculating the total amount bound using a value for specific activity (dpm/μg peptide) determined for each labeled DP178 preparation. Specific binding to M41Δ178 is defined as the difference of the binding of the labeled DP178 preparation in the microtiter wells (totals) and the binding in identical wells containing, in addition, excess unlabeled DP178 (nonspecifics).

5.5 Pharmaceutical Formulations, Dosages and Modes of Administration

The peptides of the invention may be administered using techniques well known to those in the art. Preferably, agents are formulated and administered systemically. Techniques for formulation and administration may be found in "Remington's Pharmaceutical Sciences", 18th ed., 1990, Mack Publishing Co., Easton, Pa. Suitable routes may include oral, rectal, transmucosal, or intestinal administration; parenteral delivery, including intramuscular, subcutaneous, intramedullary injections, as well as, intrathecal, direct intraventricular, intravenous, intraperitoneal, intranasal, or intraocular injections, just to name a few. For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In instances wherein intracellular administration of the peptides of the invention or other inhibitory agents is preferred, techniques well known to those of ordinary skill in the art may be utilized. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are effectively delivered into the cell cytoplasm. Additionally, due to their hydrophobicity, when small molecules are to be administered, direct intracellular administration may be achieved.

Nucleotide sequences encoding the peptides of the invention which are to be intracellularly administered may be expressed in cells of interest, using techniques well known to those of skill in the art. For example, expression vectors derived from viruses such as retroviruses, vaccinia viruses, adeno-associated viruses, herpes viruses, or bovine papilloma viruses, may be used for delivery and expression of such nucleotide sequences into the targeted cell population. Methods for the construction of such vectors and expression constructs are well known. See, for example, Sambrook et al., 1989, Molecular Cloning, A Laboratory Manual, Cold Spring Harbor Press, Cold Spring Harbor N.Y., and Ausubel et al., 1989, Current Protocols in Molecular Biology,.Greene Publishing Associates and Wiley Interscience, NY.

With respect to HIV, peptides of the invention, particularly DP107 and DP178, may be used as therapeutics in the treatment of AIDS. In addition, the peptides may be used as prophylactic measures in previously uninfected individuals after acute exposure to an HIV virus. Examples of such prophylactic use of the peptides may include, but are not limited to, prevention of virus transmission from mother to infant and other settings where the likelihood of HIV transmission exists, such as, for example, accidents in health care settings wherein workers are exposed to HIV-containing blood products. The successful use of such treatments do. not rely upon the generation of a host immune response directed against such peptides.

Effective dosages of the peptides of the invention to be administered may be determined through procedures well known to those in the art which address such parameters as biological half-life, bioavailability, and toxicity. Given the data presented below in Section 6, DP178, for example, may prove efficacious in vivo at doses required to achieve circulating levels of about 1 to about 10 ng per ml of peptide.

A therapeutically effective dose refers to that. amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the ED50 (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture. assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (e.g., the concentration of the test compound which achieves a half-maximal inhibition of the fusogenic event, such as a half-maximal inhibition of viral infection relative to the amount of the event in the absence of the test compound) as determined in cell culture. Such information can be used to more accurately determine useful doses in humans. Levels in plasma may be measured, for example, by high performance liquid chromatography (HPLC).

The peptides of the invention may, further, serve the role of a prophylactic vaccine, wherein the host raises antibodies against the peptides of the invention, which then serve to neutralize HIV viruses by, for example, inhibiting further HIV infection.

Administration of the peptides of the invention as a prophylactic vaccine, therefore, would comprise administering to a host a concentration of peptides effective in raising an immune response which is sufficient to neutralize HIV, by, for example, inhibiting HIV ability to infect cells. The exact concentration will depend upon the specific peptide to be administered, but may be determined by using standard techniques for assaying the development of an immune response which are well known to those of ordinary skill in the art. The peptides to be used as vaccines are usually administered intramuscularly.

The peptides may be formulated with a suitable adjuvant in order to enhance the immunological response. Such adjuvants may include, but are not limited to mineral gels such as aluminum hydroxide;

surface active substances such as lysolecithin, pluronic polyols, polyanions; other peptides; oil emulsions; and potentially useful human adjuvants such as BCG and Corynebacterium parvum. Many methods may be used to introduce the vaccine formulations described here. These methods include but are not limited to oral, intradermal, intramuscular, intraperitoneal, intravenous, subcutaneous, and intranasal routes.

Alternatively, an effective concentration of polyclonal or monoclonal antibodies raised against the peptides of the invention may be administered to a host so that no uninfected cells become infected by HIV. The exact concentration of such antibodies will vary according to each specific antibody preparation, but may be determined using standard techniques well known to those of ordinary skill in the art. Administration of the antibodies may be accomplished using a variety of techniques, including, but not limited to those described in this section.

For all such treatments described above, the exact formulation, route of administration and dosage can be chosen by the individual physician in view of the patient's condition. (See e.g. Fingl et al., 1975, in "The Pharmacological Basis of Therapeutics",. Ch. 1 p1).

It should be noted that the attending physician would know how to and when to terminate, interrupt., or adjust administration due. to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and the route of administration. The dose and perhaps dose frequency, will also vary according to the age, body weight, and response of the individual patient. A program comparable to that discussed above may be used in veterinary medicine.

Use of pharmaceutically acceptable carriers to formulate the compounds herein disclosed for the practice of the invention into dosages suitable for. systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilifzing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran optionally, the suspension may also contain suitable stabilizers or agents which increase the solubility of the compounds to allow for the preparation of highly concentrated solutions.

Pharmaceutical preparations for oral use can. be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active. compounds may be dissolved or suspended in suitable liquids, such as fatty oils, liquid paraffin, or liquid polyethylene glycols. In addition, stabilizers may be added.

6. EXAMPLE

DP178 (SEQ ID:1) is a Potent Inhibitor of HIV-1 Infection

In this example, DP178 (SEQ ID:1) is shown to be a potent inhibitor of HIV-1 mediated CD-4$^+$ cell-cell fusion and infection by cell free virus. In the fusion assay, this peptide completely blocks virus induced syncytia formation at concentrations of from 1–10 ng/ml. In the infectivity assay the inhibitory concentration is somewhat higher, blocking infection at 90 ng/ml. It is further shown that DP178 (SEQ ID:1) shows that the antiviral activity of DP178 (SEQ ID:1) is highly specific for HIV-1. Additionally, a synthetic peptide, DP-185 (SEQ ID:3), representing a HIV-1-derived DP178 homolog is also found to block HIV-1-mediated syncytia formation.

6.1. Materials and Methods 6.1.1. Peptide Synthesis

Peptides were synthesized using Fast Moc chemistry-on an Applied Biosystems Model 431A peptide synthesizer. Generally, unless otherwise noted, the peptides contained amidated carboxy termini and acetylated amino termini.

Amidated peptides were prepared using Rink resin (Advanced Chemtech) while. peptides containing free carboxy termini were synthesized on Wang (p-alkoxy-benzyl-alcohol) resin (Bachem). First residues were double coupled to the appropriate resin and subsequent residues were single coupled. Each coupling step was followed by acetic anhydride capping. Peptides were cleaved from the resin by treatment with trifluoracetic acid (TFA) (10 ml), $H_2O$ (0.5 ml), thioanisole (0.5 ml), ethanedithiol (0.25 ml), and crystalline phenol (0.75 g). Purification was carried out by reverse phase HPLC. Approximately 50 mg samples of crude peptide were chromatographed on a Waters Delta Pak C18 column (19 mm×30 cm, 15μ spherical) with a linear gradient; $H_2O$/acetonitrile 0.1% TFA. Lyophilized peptides were stored desiccated and peptide solutions were made in water at about 1 mg/ml. Electrospray mass spectrometry yielded the following results: DP178 (SEQ ID:1):4491.87 (calculated 4491.94); DP-180 (SEQ ID:2):4491.45 (calculated 4491.94); DP-185 (SEQ ID:3):not done (calculated 4546.97).

6.1.2. Virus

The HIV-$1_{LAI}$ virus was obtained from R. Gallo (Popovic, M. et al., 1984, Science 224:497–508) and propagated in CEM cells cultured in RPMI 1640 containing 10% fetal calf serum. Supernatant from the infected CEM cells was passed through a 0.2 μm filter and the infectious titer estimated in a microinfectivity assay using the AA5-cell line to support virus replication. For this purpose, 25 μl of serial diluted virus was added to 75 μl AA5 cells at a concentration of $2\times10^5$/ml in a 96-well microtitre plate. Each virus dilution was tested in triplicate. Cells were cultured for eight days by addition of fresh medium every other day. On day 8 post infection, supernatant'samples were tested for virus replication as evidenced by reverse transcriptase activity released to the supernatant. The $TCID_{50}$ was calculated according to the Reed and Muench formula (Reed, L. J. et al., 1938, Am. J. Hyg. 27:493–497). The titer of the HIV-$1_{LAI}$ and HIV-$1_{MN}$ stocks used for these studies, as measured on the AA5 cell line, was approximately $1.4\times10^6$ and $3.8\times10^4$ $TCID_{50}$/ml, respectively.

6.1.3. Cell Fusion Assay

Approximately $7\times10^4$ Molt cells were incubated with $1\times10^4$ CEM cells chronically infected with the HIV-$1_{LAI}$ virus in 96-well plates (one-half area cluster plates; Costar, Cambridge, Mass.) in a final volume of 100 μl culture medium as previously described (Matthews, T. J. et al., 1987, Proc. Natl. Acad. Sci. USA 84: 5424–5428). Peptide inhibitors were added in a volume of 10 μl and the cell mixtures were incubated for 24 hr. at 37° C. At that time, multinucleated giant cells were estimated by microscopic examination at a 40×magnification which allowed visualization of the entire well in a single field.

6.1.4. Cell Free Virus Infection Assay

Synthetic peptides were incubated at 37° C. with either 247 $TCID_{50}$ (for experiment depicted in FIG. 2), or 62 $TCID_{50}$ (for experiment depicted in FIG. 3) units of HIV-$1_{LAI}$ virus or 25 $TCID_{50}$ units of HIV-$2_{NIHZ}$ and CEM $CD4^+$ cells at:peptide concentrations of 0, 0.04, 0.4, 4.0, and 40 μg/ml for 7 days. The resulting reverse transcriptase (RT) activity in counts per minute was determined using the assay described, below, in Section 6.1.5. See, Reed, L. J. et al., 1938, Am. J. Hyg. 27: 493–497 for an explanation of $TCID_{50}$ calculations.

6.1.5. Reverse Transcriptase Assay

The micro-reverse transcriptase (RT) assay was adapted from Goff et al. (Goff, S. et al., 1981, J. Virol. 38:239–248) and Willey et al. (Willey, R. et al., 1988, J. Virol. 62:139–147). Supernatants from virus/cell cultures are adjusted to 1% Triton-X100. A 10 μl sample of supernatant was added to 50 μl of RT cocktail in a 96-well U-bottom microtitre plate and the samples incubated at 37° C. for 90 min. The RT cocktail contained 75 mM KCl, 2 mM dithiothreitol, 5 mM $MgCl_2$, 5 μg/ml poly A (Pharmacia, cat. No. 27-4110-01), 0.25 units/ml oligo dT (Pharmacia, cat. No. 27-7858-01), 0.05% NP40, 50 mM Tris-HCl, pH 7.8, 0.5 μM non-radioactive dTTP, and 10 μCi/ml 32P-dTTP (Amersham, cat. No. PB.10167).

After the incubation period, 40 μl of reaction mixture was applied to a Schleicher and Schuell (S+S) NA45 membrane (or DE81 paper) saturated in 2×SSC buffer (0.3M NaCl and 0.003M sodium citrate) held in a S+S Minifold over one sheet of GB003 (S+S) filter paper, with partial vacuum applied. -Each well of the minifold was washed four times with 200 μl 2×SSC, under full vacuum. The membrane was removed from the minifold and washed 2 more times in a pyrex dish with an excess of 2×SSC. Finally, the membrane was drained on absorbent paper, placed on Whatman #3 paper, covered with Saran wrap, and exposed to film overnight at −70° C.

6.2. Results 6.2.1. Peptide Inhibition of Infected Cell-inducted Syncytia Formation The initial screen for antiviral activity assayed peptides' ability to block syncytium formation induced by overnight co-cultivation of uninfected Molt4 cells with chronically HIV-1 infected CEM cells. The results of several such experiments are presented herein. In the first of these experiments, serial DP178 (SEQ ID:1) peptide concentrations between 10 μg/ml and 12.5 ng/ml were tested for blockade of the cell fusion process. For these experiments, CEM cells chronically infected with either HIV-$1_{LAI}$, HIV-$1_{MN}$, HIV-$1_{RF}$, or HIV-$1_{SF2}$ virus were cocultivated overnight with uninfected Molt 4 cells. The results (FIG. 4) show that DP178 (SEQ ID:1) afforded complete protection against each of the HIV-l isolates down to the lowest concentration of DP178 (SEQ ID:1) used. For HIV$_{LAI}$ inhibition, the lowest concentration tested was 12.5 ng/ml; for all other HIV-1 viruses, the lowest concentration of DP178 (SEQ ID:1) used in this study was 100 ng/ml. A second peptide, DP-180 (SEQ ID:2), containing the same amino acid residues as DP178 (SEQ ID:1) but arranged in a random order exhibited no evidence of anti-fusogenic activity even at the high concentration of 40 g/ml (FIG. 4). These observations indicate that the inhibitory effect of DP178 (SEQ ID:1) is primary sequence-specific and not related to non-specific peptide/protein interactions. The actual endpoint (i.e., the lowest effective inhibitory concentration) of DP178 inhibitory action is within the range of-1–10 ng/ml.

The next series of experiments involved the preparation and testing of a DP178 (SEQ ID:1) homolog for its ability to inhibit HIV-1-induced syncytia formation. As shown in FIG. 1, the sequence of DP-185 (SEQ ID:3) is slightly different from DP178 (SEQ ID:1) in that its primary sequence is taken from the HIV-$1_{SF2}$ isolate and contains several amino acid differences relative to DP178 (SEQ ID:1) near the N terminus. As shown in FIG. 4, DP-185 (SEQ ID:3), exhibits. inhibitory activity even at 312.5 ng/ml, the lowest concentration tested.

The next series of experiments involved a comparison of DP178 (SEQ ID:1) HIV-1 and HIV-2 inhibitory activity. As shown in FIG. 5, DP178 (SEQ ID:1) blocked HIV-1-mediated syncytia formation at peptide concentrations below 1 ng/ml. DP178 (SEQ ID:1) failed, however, to block HIV-2 mediated syncytia formation at concentrations as high as 10 μg/ml. This striking 4 log selectivity of DP178 (SEQ ID:1) as an inhibitor of HIV-1-mediated cell fusion demonstrates an unexpected HIV-1-specificity in the action of DP178 (SEQ ID:1). DP178 (SEQ ID:1) inhibition of HIV-1-mediated cell fusion, but the peptide's inability to inhibit HIV-2 medicated cell fusion in the same cell type at the concentrations tested provides further evidence for the high degree of selectivity associated with the antiviral action of DP178 (SEQ ID:1).

6.2.2. Peptide Inhibition of Infection by Cell-free Virus

DP178 (SEQ ID:1) was next tested for its ability to block CD-4+ CEM cell infection by cell free HIV-1 virus. The results, shown in FIG. 2, are from an experiment in which DP178 (SEQ ID:1) was assayed for its ability to block infection of CEM cells by an HIV-1$_{LAI}$ isolate. Included in the experiment were three control peptides, DP-116 (SEQ ID:9), DP-125 (SEQ ID:8), and DP-118 (SEQ ID:10). DP-116 (SEQ ID:9). represents a peptide previously shown to be inactive using this assay, and DP-125 (SEQ ID:8; Wild, C. et al., 1992, Proc. Natl. Acad, Sci. USA 89:10,537) and DP-118 (SEQ ID:10) are peptides which have previously been shown to be active in this assay. Each concentration (0, 0.04, 0.4., 4, and 40 μg/ml) of peptide was incubated with 247 TCID$_{50}$ units of HIV-1$_{LAI}$ virus and CEM cells. After 7 days of culture, cell-free supernatant was tested for the presence of RT activity as a measure of successful infection. The results, shown in FIG. 2, demonstrate that DP178 (SEQ ID:1) inhibited the de novo infection process mediated by the HIV-1 viral isolate at concentrations as low as 90 ng/ml (IC50=90 ng/ml). In contrast, the two positive control peptides, DP-125 (SEQ: ID:8) and DP-118 (SEQ ID:10), had over 60-fold higher IC50 concentrations of approximately 5 μg/ml.

In a separate experiment, the HIV-1 and HIV-2 inhibitory action of DP178 (SEQ ID:1) was tested with CEM cells and either HIV-1$_{LAI}$ or HIV-2$_{NIHZ}$. 62 TCID$_{50}$ HIV-1$_{LAI}$ or 25 GCID$_{50}$ HIV-2$_{NIHZ}$ were used in these experiments, and were incubated for 7 days. As may be seen in FIG. 3, DP178 (SEQ ID:1) inhibited HIV-1 infection with an IC50 of about 31 ng/ml. In contrast, DP178 (SEQ ID:1) exhibited a much higher IC50 for HIV$^2$$_{NIHZ}$, thus making DP178 (SEQ ID:1) two logs more potent as a HIV-1 inhibitor than a HIV-2 inhibitor. This finding is consistent with the results of the fusion inhibition assays described, above, in Section 6.2.1, and further supports a significant level of selectivity (i.e., for HIV-1 over HIV-2).

7. EXAMPLE

The HIV-1 Inhibitor, DP178 (SEQ ID:1) is Non-cytotoxic

In this Example, the 36 amino acid synthetic peptide inhibitor DP178 (SEQ ID:1) is shown to be non-cytotoxic to cells in culture, even at the highest peptide concentrations (40 μg/ml) tested.

7.1. Materials and Methods

Cell proliferation and toxicity assay: Approximately 3.8× 10$^5$ CEM cells for each peptide concentration were incubated for 3 days at 37° C. in T25 flasks. Peptides tested were DP178 (SEQ ID:1) and DP-116 (SEQ.ID:9), as described in FIG. 1. Peptides were synthesized as described, above, in Section 6.1. The concentrations of each peptide used were 0, 2.5, 10, and 40 μg/ml. Cell counts were taken at incubation times of 0, 24, 48, and 72 hours.

7.2. Results

Whether the potent HIV-1 inhibitor DP178 (SEQ ID:1) exhibited any cytotoxic effects was assessed by assaying-the peptide's effects on the proliferation and viability of cells in culture. CEM cells were incubated in the presence of varying concentrations of DP178 (SEQ ID:1), and DP-116 (SEQ ID:9), a peptide previously shown to be ineffective as a HIV inhibitor (Wild, C. et al., 1992, Proc. Natl. Acad. Sci. USA 89:10,537–10,541). Additionally, cells were incubated in the absence of either peptide.

The results of the cytotoxicity study demonstrate that DP178 (SEQ ID:1) exhibits no cytotoxic effects on cells in culture. As can be seen, below, in Table XXIV, even the proliferation and viability characteristics of cells cultured for 3 days in the presence of the highest concentration of DP178 (SEQ ID:1) tested (40 82 g/ml) do not significantly differ from the DP-116 (SEQ ID:9) or the no-peptide controls. The cell proliferation data is also represented in graphic form in FIG. 6. As was demonstrated in the Working Example presented above in Section 6, DP178 (SEQ ID:1) completely inhibits HIV-1 mediated syncytia formation at peptide concentrations between 1 and 10 ng/ml, and completely inhibits cell-free viral infection at concentrations of at least 90 ng/ml. Thus, this study demonstrates that even at peptide concentrations greater than 3 log higher than the HIV inhibitory dose, DP178 (SEQ ID:1) exhibits no cytotoxic effects.

TABLE XXIV

| Peptide | Concentration μg/ml | % Viability at time (hours) | | | |
| --- | --- | --- | --- | --- | --- |
| | | 0 | 24 | 48 | 72 |
| DP178 | 40 | 98 | 97 | 95 | 97 |
| (SEQ | 10 | 98 | 97 | 98 | 98 |
| ID:1) | 2.5 | 98 | 93 | 96 | 96 |
| DP116 | 40 | 98 | 95 | 98 | 97 |
| (SEQ | 10 | 98 | 95 | 93 | 98 |
| ID:9) | 2.5 | 98 | 96 | 98 | 99 |
| No Peptide | 0 | 98 | 97 | 99 | 98 |

8. EXAMPLE

The Interaction of DP178 and DP107

Soluble recombinant forms of gp41 used in the example described below provide evidence that the DP178 peptide associates with a distal site on gp41 whose interactive structure is influenced by the DP107 leucine zipper motif. A single mutation disrupting the coiled-coil structure of the leucine zipper domain transformed the soluble recombinant gp41 protein from an inactive to an active inhibitor of HIV-1 fusion. This transformation may result from liberation of the potent DP178 domain from a molecular clasp-with the leucine zipper, DP107, determinant. The results also indicate that the anti-HIV activity of various gp41 derivatives (peptides and recombinant proteins) may be due to their ability to form complexes with viral gp41 and interfere with its fusogenic process.

8.1. Materials and Methods 8.1.1. Construction of Fusion Proteins and GP41 Mutants Construction of fusion proteins and mutants shown in FIG. 7 was accomplished as follows: the DNA sequence corresponding to the extracellular domain of gp41 (540–686) was cloned into the Xmn I site of the expression vector pMal-p2 (New England Biolab) to give M41. The gp41 sequence was amplified from pgtat (Malim et al., 1988, Nature 355: 181–183) by using polymerase chain reaction (PCR) with upstream primer 5'-ATGACGCTGACGGTACAGGCC-3' (primer A) and. downstream primer 5'-TGACTAAGCTTAATACCACAGCCAATTTGTTAT-3' (primer B). M41-P was constructed by using the T7-Gen in vitro mutagenesis kit from United States Biochemicals (USB) following the supplier's instructions. The mutagenic primer (5'-GGAGCTGCTTGGGGCCCCAGAC-3') introduces. an Ile to Pro mutation-in M41 at position 578. M41Δ107, from which the DP-107 region has been deleted, was made using a deletion mutagenic primer 5'-CCAAATCCCCAGGAGCTGCTCGAGCTGCACTAT ACCAGAC-3' (primer C) following the USB T7-Gen mutagenesis protocol. M41Δ178, from which the DP-178 region has been deleted, was made by cloning the DNA fragment corresponding to gp41 amino acids 540–642 into the Xmn I site of-pMal-p2. Primer A and 5'-ATAGCTTCTAGATTAATTGTTAATTTCTCTGTCCC-3' (primer D) were used in the PCR with the template pgtat to generate the inserted DNA fragments. M41-P was used as the template with primer A and D in PCR to generate M41PΔ178. All inserted sequences and mutated residues were checked by restriction enzyme analysis and confirmed by DNA sequencing.

8.1.2. Purification and Characterization of Fusion Proteins

The fusion proteins were purified according to the protocol described in the manufacturer's brochure of protein fusion and purification systems from New England Biolabs (NEB). Fusion proteins (10 ng) were analyzed by electrophoresis on 8% SDS polyacrylamide gels. Western blotting analysis was performed as described by Sambrook et al., 1989, Molecular Cloning: A Laboratory Manual., 2d Ed, Cold Spring Harbor Laboratory Press, Cold Spring Harbor, N.Y., Ch. 18, pp. 64–75. An HIV-1 positive serum diluted 1000-fold, or a human Fab derived from repertoire cloning was used to react with the fusion proteins. The second antibody was HRP-conjugated goat antihuman Fab. An ECL Western blotting detection system (Amersham) was used to detect the bound antibody. A detailed protocol for this detection system was provided by the manufacturer. Rainbow molecular weight markers (Amersham) were used to estimate the size of fusion proteins.

8.1.3. Cell Fusion Assays for Anti-HIV Activity

Cell fusion assays were performed as previously described (Matthews et al., 1987; Proc. Natl. Acad. Sci. USA 84: 5424–5481). CEM cells ($7 \times 10^4$) were incubated with HIV-1$_{IIIB}$ chronically infected CEM cells ($10^4$) in 96-well flat-bottomed half-area plates (Costar) in 100 μl culture medium. Peptide and fusion proteins at various concentrations in 10 μl culture medium were incubated with the cell mixtures at 37° C. for 24 hours. Multinucleated syncytia were estimated with microscopic examination. Both M41 and M41-P did show cytotoxicity at the concentrations tested and shown in FIG. 8.

Inhibition of HIV-1 induced cell-cell fusion activity was carried out in the presence of 10 nM DP178 and various concentrations of M41Δ178 or M41-PΔ178 as indicated in FIG. 9. There was no observable syncytia in the presence of 10 nM DP178. No peptide or fusion protein was added in the control samples.

8.1.4. Elisa Analysis of DP178 Binding to the Leucine Zipper Motif of GP41

The amino acid sequence of DP178 used is: YTSLIHSLIEESQNQQEKNEQELLELDKWASLWNWF. For enzyme linked immunoassay (ELISA), M41Δ178 or M41-PΔ178(5 μg/ml) in 0.1M NaHCO3, pH 8.6, were coated on 96 wells Linbro ELISA plates (Flow Lab, Inc.) overnight. Each well was washed three times with distilled water then blocked with 3% bovine serum albumin (BSA) for 2 hours. After blocking, peptides with 0.5% BSA in TBST (40 mM Tris-HCl pH7.5, 150 mM NaCl, 0.05% Tween 20) were added to the ELISA plates and incubated at room temperature for 1 hour. After washing three times with TBST, Fab-d was added at a concentration of 10 ng/ml with 0.5% BSA in TBST. The plates were washed three times with TBST after incubation at room temperature for 1 hour. Horse radish peroxidase (HRP) conjugated goat antihuman Fab antiserum at a 2000 fold dilution in TBST with 0.5% BSA was added to each well and incubated at room temperature for 45 minutes. The plates were then washed four times with TBST. The peroxidase substrate o-phenylene diamine (2.5 mg/ml) and 0.15% $H_2O_2$ were added to develop the color. The reaction was stopped with an equal volume of 4.5 N $H_2SO_4$ after incubation at room temperature for 10 minutes. The optical density of the stopped reaction mixture was measured with a micro plate reader (Molecular Design) at 490 nm. Results are shown in FIG. 10.

8.2. Results 8.2.1. The Expression and Characterization of the Ectodomain of gp41

As a step toward understanding the roles of the two helical regions in gp41 structure and function, the ectodomain of gp41 was expressed as a maltose binding fusion protein (M41) (FIG. 7). The fusogenic peptide sequence at the N-terminal of gp41 was omitted from this recombinant protein and its derivatives to improve solubility. The maltose binding protein facilitated purification of the fusion proteins under relatively mild, non-denaturing conditions. Because the M41 soluble recombinant gp41 was not glycosylated, lacked several regions of the transmembrane protein (i.e., the fusion peptide, the membrane spanning, and the cytoplasmic domains), and was expressed in the absence of gp120, it was not expected to precisely reflect the structure of native gp41 on HIV-1 virions. Nevertheless, purified M41 folded in a manner that preserved certain discontinuous epitopes as evidenced by reactivity with human monoclonal antibodies, 98–6, 126–6, and 50–69, previously shown to bind conformational epitopes on native gp41 expressed in eukaryotic cells (Xu et al., 1991, J. Virol. 65: 4832–4838; Chen, 1994, J. Virol. 68:2002–2010). Thus, at least certain regions of native gp41 defined by these antibodies appear to be reproduced in the recombinant fusion protein M41. Furthermore, M41 reacted with a human recombinant Fab (Fab-d) that recognizes a conformational epitope on gp41 and binds HIV-1 virions as well as HIV-1 infected cells-but not uninfected cells as analyzed by FACS. Deletion of either helix motif, i.e., DP107 or DP178, of the M41 fusion protein eliminated reactivity with Fab-d. These results indicate that both helical regions, separated by 60 amino acids in the primary sequence, are required to maintain the Fab-d epitope.

8.2.2. Anti-HIV Activity of the Recombinant Ectodomain of GP41

The wild-type M41 fusion protein was tested for anti-HIV-1 activity. As explained, supra, synthetic peptides corresponding to the leucine zipper (DP107) and the C-terminal putative helix (DP178) show potent anti-HIV activity. Despite inclusion of both these regions, the recombinant M41 protein did not affect HIV-1 induced membrane fusion at concentrations as high. as 50 μM (Table XXV, below).

TABLE XXV

DISRUPTION OF THE LEUCINE ZIPPER OF GP41 FREES THE ANTI-HIV MOTIF

|  | DP107 | DP178 | M41 | M41-P | M41-PΔ178 |
|---|---|---|---|---|---|
| Cell fusion (IC$_{90}$) | 1 μM | 1 nM | >50 μM | 83 nM | >50 μM |
| Fab-D binding (k$_D$) | — | — | 3.5 × 10$^{-9}$ | 2.5 × 10$^{-8}$ | — |
| HIV infectivity (IC$_{90}$) | 1 μM | 80 nM | >16 μM | 66 nM | >8 μM |

[1]The affinity constants of Fab-d binding to the fusion proteins were determined using a protocol described by B. Friguet et al., 1985, J. Immunol. Method. 77:305–319.
— = No detectable binding of Fab-d to the fusion proteins.
Antiviral Infectivity Assays. 20 μl of serially diluted virus stock was incubated for 60 minutes at ambient temperature with 20 μl of the indicated-concentration of purified recombinant fusion protein in RPMI 1640 containing 10% fetal bovine serum and antibiotics in a 96-well microteter plate. 20 μl of CEM4 cells at 6 × 10$^5$ cells/ml were added to each well, and cultures were incubated at 37° C. in a humidified CO$_2$ incubator. Cells were cultured for 9 days by the addition of fresh medium every 2 to 3 days. On days 5, 7, and 9 postinfection, supernatant samples were assayed for reverse transcriptase (RT) activity, as described below, to minitor viral replication. The 50% tissure culture infectious dose (TCID$_{50}$) was calculated for each condition according to the formula of Reed & Muench, 1937, Am. J. Hyg. 27:493–497. RT activity was determined by a modification of the published methods of Goff et al., 1981, J. Virol. 38:239–248 and Willey et al., 1988, J. Virol. 62:139–147 as described in Chen et al., 1993, AIDS Res. Human Retroviruses 9:1079–1086.

Surprisingly, a single amino acid substitution, proline in place of isoleucine in the middle of the leucine zipper motif, yielded a fusion protein (M41-P) which did exhibit antiviral activity (Table XXV and FIG. 8). As seen in Table XXV, M41-P blocked syncytia formation by 90% at approximately 85 nM and neutralized HIV-1$_{IIIB}$ infection by 90% at approximately 70 nM concentrations. The anti-HIV-1 activity of M41-P appeared to be mediated by the C-terminal helical sequence since deletion of that region from M41-P yielded an inactive fusion protein, M41-PΔ178 (Table XXV). This interpretation was reinforced by experiments demonstrating that a truncated fusion protein lacking the DP178 sequence, M41Δ178, abrogated the potent anti-fusion activity of the DP178 peptide in a concentration-dependent manner (FIG. 9). The same truncated fusion protein containing the proline mutation disrupting the leucine zipper, M41-PΔ178, was not active in similar-competition experiments (FIG. 9). The results indicate that the DP178 peptide associates with a second site on gp41 whose interactive structure is dependent on a wild type leucine zipper sequence. A similar interaction may occur within the wild type fusion protein, M41, and. act to form an intramolecular clasp-which sequesters the DP178 region, making it unavailable for anti-viral activity.

A specific association between these two domains is also indicated by other human monoclonal Fab-d studies. For example, Fab-d failed to bind either the DP178 peptide or the fusion protein M41Δ178, but its epitope was reconstituted by simply mixing these two reagents together (FIG. 10). Again, the proline mutation in the leucine zipper domain of the fusion protein, M41-PΔ178, failed to reconstitute the epitope in similar mixing experiments.

9. EXAMPLE

Method for Computer-Assisted Identification of DP107-like and DP178-like Sequences A number of known coiled-coil sequences have been well described in the literature and contain heptad repeat positioning for each amino acid. Coiled-coil nomenclature labels each of seven amino acids of a heptad repeat A through G, with amino acids A and D tending to be hydrophobic positions. Amino acids E and G tend to be charged. These four positions (A, D, E, and G) form the amphipathic backbone structure of a monomeric alpha-helix. The backbones of two or more amphipathic helices interact with each other to form di-, tri-, tetrameric, etc., coiled-coil structures. In order to begin to design computer search motifs, a series of well characterized coiled coils were chosen including yeast transcription factor GCN4, Influenza Virus hemagglutinin loop 36, and human proto-oncogenes c-Myc, c-Fos, and c-Jun. For each peptide sequence, a strict homology for the A and D positions, and a list of the amino acids which could be excluded for the B, C, E, F, and G positions (because they are not observed in these positions) was determined. Motifs were tailored to the DP107 and DP178 sequences by deducing the most likely possibilities for heptad positioning of the amino acids of HIV-1 Bru DP-107, which is known to have coiled-coil structure, and HIV-1 Bru DP178, which is still structurally undefined. The analysis of each of the sequences is contained in FIG. 12. For example, the motif for GCN4 was designed as follows:

1. The only amino acids (using standard single letter amino acid codes) found in the A or D positions of GCN4 were [LMNV].
2. All amino acids were found at B, C, E, F, and G positions except {CFGIMPTW}.
3. The PESEARCH motif would, therefore, be written as follows:

[LMNV]-{CFGIMPTW} (2)-[LMNV]-{CFGIMPTW} (3)-

[LMNV]-{CFGIMPTW} (2)-[LMNV]-{CFGIMPTW} (3)-

[LMNV]-{CFGIMPTW} (2)-[LMNV]-{CFGIMPTW} (3)-

[LMNV]-{CFGIMPTW} (2)-[LMNV]-{CFGIMPTW} (3)-

Translating or reading the motif: "at the first A position either L, M, N, or V must occur; at positions B and C (the next two positions) accept everything except C, F, G, I, M, P., T, or W; at the D position either L, M, N, or V must occur; at positions E, F, and G (the next 3 positions) accept everything except C, F, G, I, M, P, T, or W." This statement is contained four times in a 28-mer motif and five times in a 35-mer motif. The basic motif key then would be: [LMNV]-{CFGIMPTW}. The motif keys for the remaining well described coiled-coil sequences are summarized in FIG. 12.

The motif design for DP107 and DP178 was slightly different than the 28-mer model sequences described above due to the fact that heptad repeat positions are not defined and the peptides are both longer than 28 residues. FIG. 13 illustrates several possible sequence alignments for both DP107 and DP178 and also includes motif designs based on 28-mer, 35-mer, and full-length peptides. Notice that only slight differences occur in the motifs as the peptides are lengthened. Generally, lengthening the base peptide results in a less stringent motif. This is very useful in broadening the possibilities for identifying DP107-or DP-178-like primary amino acid sequences referred to in this document as "hits".

In addition to making highly specific motifs for each type peptide sequence to be searched, it is also possible to make "hybrid" motifs. These motifs are made by "crossing" two or more very stringent motifs to make a new search algorithm which will find not only both "parent" motif sequences but also any peptide sequences which have similarities to one, the other, or both "parents". For example, in FIG. 14 the "parent" sequence of GCN4 is crossed with each of the possible "parent" motifs of DP-107. Now the hybrid motif must contain all of the amino acids found in the A and D positions of both parents, and exclude all of the amino acids not found in either parent at the other positions. The resulting hybrid from crossing GCN4 or [LMNV] {CFGIMPTW} and DP107 (28-mer with the first L in the D position) or [ILQT] {CDFIMPST}, is [ILMNQTV] {CFIMPT}. Notice that now only two basic hybrid motifs exist which cover both framing possibilities, as well as all peptide lengths of the parent DP-107 molecule. FIG. 15 represents the "hybridizations" of GCN4 with DP-178. FIG. 16 represents the "hybridizations" of DP107 and DP178. It is important to keep in mind that the represented motifs, both parent and hybrid, are motif keys and not the depiction of the full-length motif needed to actually do the computer search.

Hybridizations can be performed on any combination of two or more motifs. FIG. 17 summarizes several three-motif hybridizations including GCN4, DP107 (both frames), and DP178 (also both frames). Notice that the resulting motifs are now becoming much more similar to each other. In fact, the first and third hybrid motifs are actually subsets of the second and fourth hybrid motifs respectively. This means that the first and third hybrid motifs are slightly more stringent than the second and fourth. It should also be noted that with only minor changes in these four motifs, or by hybridizing them, a single motif could be obtained which would find all of the sequences. However, it should be remembered that stringency is also reduced. Finally, the most broad-spectrum and least-stringent hybrid motif is described in FIG. 18 which summarizes the hybridization of GCN4, DP107 (both frames), DP178 (both frames), c-Fos, c-Jun,: c-Myc, and Flu loop 36.

A special set of motifs was designed based on the fact that DP-178 is located only approximately ten amino acids upstream of the transmembrane spanning region of gp41 and just C-terminal to a proline which separates DP107 and DP178. It has been postulated that DP178 may be an amphipathic helix when membrane associated, and that the proline might aid in the initiation of the helix formation. The same arrangement was observed in Respiratory. Syncytial Virus; however, the DP178-like region in this virus also had a leucine zipper just C-terminal to the proline. Therefore, N-terminal proline-leucine zipper motifs were designed to analyze whether any other viruses might contain this same pattern. The motifs are summarized in FIG. 19.

The PC/Gene protein database contains 5879 viral amino acid sequences (library file PVIRUSES; CD-ROM release 11.0). Of these, 1092 are viral enveloped or glycoprotein sequences (library file PVIRUSE1). Tables V through XIV contain lists of protein sequence names and motif hit locations for all the motifs searched.

10. EXAMPLE computer-assisted Identification of DP107 and DP178-like Sequences in Human Immunodeficiency Virus FIG. 20 represents search results for HIV-1 BRU isolate gp41 (PC/Gene protein sequence PENV_HV1BR). Notice that the hybrid motif which crosses DP-107 and DP-178 (named 107×178×4; the same motif as found in FIG. 16 found three hits including amino acids 550–599, 636–688, and 796–823. These areas include DP-107 plus eight N-terminal and four C-terminal amino acids; DP178 plus seven N-terminal and ten C-terminal amino acids; and an area inside the transmembrane region (cytoplasmic). FIG. 20 also contains the results obtained from searching with the motif named ALLMOTI5, for which the key is found in FIG. 17 ({CDGHP} {CFP}x5). This motif also found three hits including DP107 (amino acids 510–599), DP178 (615–717), and a cytoplasmic region (772–841). These hits overlap the hits found by the motif 107×178×4 with considerable additional sequences on both the amino and carboxy termini. This is not surprising in that 107×178×4 is a subset of the ALLMOTI5 hybrid motif. Importantly, even though the stringency of ALLMOTI5 is considerably. less than 107× 178×4, it still selectively identifies the DP107 and DP178 regions of gp41 shown to contain sequences for inhibitory peptides-of HIV-1. The results of these two motif searches are summarized in Table V under the PC/Gene protein sequence name PENV HV1BR. The proline-leucine zipper motifs also gave several hits in HIV-1 BRU including 503–525 which is at the very C-terminus of gp120, just upstream of the cleavage site (P7LZIPC and P12LZIPC); and 735–768 in the cytoplasmic domain of gp41 (P23LZIPC). These results are found in Tables VIII, IX, and X under the same sequence name as mentioned above. Notice that the only area of HIV-1 BRU which is predicted by. the Lupas algorithm to contain a coiled-coil region, is from amino acids 635–670. This begins eight amino acids N-terminal to the start and ends eight amino acids N-terminal to the end of DP178. DP107, despite the fact that it is a known coiled coil, is not predicted to contain a coiled-coil region using the Lupas method.

11. EXAMPLE

Computer-assisted Identification of DP107-like and DP178-like Sequences in Human Respiratory Syncytial Virus FIG. 21 represents search results for Human Respiratory Syncytial Virus (RSV; Strain A2) fusion glycoprotein F1 (PC/Gene protein sequence name PVGLF_HRSVA). Motif 107×178×4 finds three hits including amino acids 152–202, 213–243, and 488–515. The arrangement of these hits is similar to what is found in HIV-1 except that the motif finds two regions with similarities to DP-178, one just downstream of what would be called the DP107 region or amino acids 213–243, and one just upstream of the transmembrane region (also similar to DP178) or amino acids 488–515. Motif ALLMOTI5 also finds three areas including amino acids 116–202, 267–302, and 506–549. The proline-leucine zipper motifs also gave several hits including amino acids 205–2.21 and 265–287 (P1LZIPC 265–280, P12LZIPC), and 484–513 (P7LZIPC and P12LZIPC 484–506, P23LZIPC). Notice that the PLZIP motifs also identify regions which share location similarities with DP-178 of HIV-1.

12. EXAMPLE

Computer Assisted Identification op DP107-like and DP178-like Sequences in Simian Immunodeficiency Virus Motif hits for Simian immunodeficiency Virus gp41 (AGM3 isolate; PC/Gene protein sequence name PENV_ SIVAG) are shown in FIG. 22. Motif 107×178×4 finds three hits including amino acids 566–593, 597–624, and 703–730. The first two hits only have three amino acids between them and could probably be combined into one hit from 566–624 which would represent a DP107-like hit. Amino acids 703 to 730 would then represent a DP178-like hit. ALLMOTI5 also finds three hits including amino acids 556–628 (DP107 like), 651–699 (DP178-like), and 808–852 which represents the transmembrane spanning region. SIV also has one region from 655–692 with a high propensity to form a coiled coil as predicted by the Lupas algorithm. Both 107×178×4 and ALLMOTI5 motifs find the same region. SIV does not have any PLZIP motif hits in gp41.

The identification of DP178/DP107 analogs for a second SIV isolate (MM251) is demonstrated in the Example presented, below, in Section 19.

13. EXAMPLE

Computer-assisted Identification of DP107-like AND DP178 Like Sequences in Canine Distemper Virus Canine Distemper Virus (strain Onderstepoort) fusion glycoprotein F1 (PC/Gene Protein sequence name PVGLF_CDVO) has regions similar to Human RSV which are predicted to be DP107-like and DP178-like (FIG. 23). Motif 107×178×4 highlights one area just C-terminal to the fusion peptide at amino acids 252–293. Amino acids 252–286 are also predicted to be coiled coil using the Lupas algorithm. Almost 100 amino acids C-terminal to the first region is a DP178-like area at residues 340–367. ALLMOTI5 highlights three areas of interest including: amino acids 228–297, which completely overlaps both the Lupas prediction and the DP107-like 107×178×4 hit; residues 340–381, which overlaps the second 107×178×4 hit; and amino acids 568–602, which is DP178-like in that it is located just N-terminal to the transmembrane region. It also overlaps another region (residues 570–602) predicted by the Lupas method to have a high propensity to form a coiled coil. Several PLZIP motifs successfully identified areas of interest including P6 and P12LZIPC which highlight residues 336–357 and 336–361 respectively; P1 and P12LZIPC which find residues 398–414; and P12 and P23LZIPC which find residues 562–589 and 562–592 respectively.

14. EXAMPLE

Computer-assisted Identification of DP107-like and DP178-like Sequences in Newcastle Disease Virus FIG. 24 shows the motif hits found in Newcastle Disease Virus (strain Australia-Victoria/32; PC Gene protein sequence name PVGLF_NDVA). Motif 107×178×4 finds two areas including a DP107-like hit at amino acids 151–178 and a DP178-like hit at residues 426–512. ALLMOTI5 finds three areas including residues. 117–182, 231–272, and 426–512. The hits from 426–512 include a region which is predicted by the Lupas method to have a high coiled-coil propensity (460–503). The PLZIP motifs identify only one region of interest at amino acids 273–289 (P1 and 12LZIPC).

15. EXAMPLE

Computer-assisted Identification of DP107-like and DP178-like Sequences in Human Parainfluenza Virus Both motifs 107×178×4 and ALLMOTI5 exhibit DP107-like hits in the same region, 115–182 and 117–182 respectively, of Human Parainfluenza Virus (strain NIH 47885; PC/Gene protein sequence name PVGLF_p13H4; (FIG. 25). In addition, the two motifs have a DP178 like hit just slightly C-terminal at amino acids 267–241. Both motifs also have DP178-like hits nearer the transmembrane region including amino acids 457–497 and 462–512 respectively. Several PLZIP motif hits are also observed including 283–303 (P5LZIPC), 283–310 (P12LZIPC), 453-4-74 (P6LZIPC), and 453–481 (P23LZIPC). The Lupas algorithm predicts that amino acids 122–176 may have a propensity to form a coiled-coil.

16. EXAMPLE

Computer-assisted Identification of DP107-like and DP178-like Sequences of Influenza A Virus FIG. 26 illustrates the Lupas prediction for a coiled coil in Influenza A Virus (strain A/Aichi/2/68) at residues 379–436, as well as the motif hits for 107×178×4 at amino acids 387–453, and for ALLMOTI5 at residues 380–456. Residues 383–471 (38–125 of HA2) were shown by Carr and Kim to be an extended coiled coil when. under acidic pH (Carr and Kim, 1993, Cell 73: 823–832). The Lupas algorithm predicts a coiled-coil at residues 379–436. All three methods successfully predicted the region shown to actually have coiled-coil structure; however, ALLMOTI5 predicted the greatest portion of the 88-residue stretch.

17. EXAMPLE

Potential Respiratory Syncytial Virus DP178/DP107 Analogs: CD and Antiviral Characterization In the Example presented herein, respiratory syncytial virus (RSV) peptides identified by utilizing the computer-assisted search motifs described in the Examples presented in Sections 9 and 11, above, were tested for anti-RSV activity. Additionally, circular dichroism (CD) structural analyses were conducted on the peptides, as discussed below. It is demonstrated that several of the identified peptides exhibit potent antiviral capability. Additionally, it is shown that several of these peptides exhibit a substantial helical character.

17.1 Materials and Methods

Structural analyses: The CD spectra were measured in a 10 mM sodium phosphate, 150 mM sodium chloride, pH 7.0, buffer at approximately 10 mM concentrations, using a 1 cm pathlength cell on a Jobin/Yvon Autodichrograph Mark V CD spectrophotometer. Peptides. were synthesized according to the methods described, above, in Section 6.1. Peptide concentrations were determined from $A_{280}$ using Edlehoch's method (1967, Biochemistry 6:1948).

Anti-RSV antiviral activity assays: The assay utilized herein tested the ability of the peptides to disrupt the ability of HEp2 cells acutely infected with RSV (i.e., cells which are infected with a multiplicity of infection of greater than 2) to fuse and cause syncytial formation on a monolayer of uninfected an uninfected line of Hep-2 cells. The lower-the observed level of fusion, the greater the antiviral activity of the peptide was determined to be.

Uninfected confluent monolayers of Hep-2 cells were grown in microtiter wells in 3% EMEM (Eagle Minimum Essential Medium w/o L-glutamine [Bio Whittaker Cat. No. 12-125F], with fetal bovine serum [FBS; which had been heat inactivated for 30 minutes at 56° C.; Bio Whittaker Cat. No. 14-501F) supplemented at 3%, antibiotics (penicillin/streptomycin; Bio Whittaker Cat. No. 17-602E) added at 1%, and glutamine added at 1%.

To prepare Hep2 cells for addition to uninfected cells, cultures of acutely infected Hep2 cells were washed with DPBS (Dulbecco's Phosphate Buffered Saline w/o calcium or magnesium; Bio Whittaker Cat. No. 17-512F) and cell monolayers were removed with Versene (1:5000; Gibco Life Technologies Cat. No. 15040-017). The cells were spun 10 minutes and resuspended in 3% FBS. Cell counts were performed using a hemacytometer. Persistent cells were added to the uninfected Hep-2 cells.

The antiviral assay was conducted by, first, removing all media from the wells containing uninfected Hep-2 cells, then adding peptides (at the dilutions described below) in 3% EMEM, and 100 acutely RSV-infected Hep2 cells per well. Wells were then incubated at 37° C. for 48 hours.

After incubation, cells in control wells were checked for fusion centers, media was removed from the wells, followed by addition, to each well, of either Crystal Violet stain or XTT. With respect to Crystal Violet, approximately 50 µl 0.25% Crystal Violet stain in methanol were added to each well. The wells were rinsed immediately, to remove excess stain, and were allowed to dry. The number of syncytia per well were then counted, using a dissecting microscope.

With respect to XTT (2,3-bis[2-Methoxy-4-nitro-5-sulfophenyl]-2H-tetrazolium-5-carboxyanilide inner salt), 50 µl XTT (1 mg/ml in RPMI buffered with 100 mM HEPES, pH 7.2–7.4, plus 5% DMSO) were added to each well. The $OD_{450/690}$ was measured (after blanking against growth medium without cells or reagents, and against reagents) according to standard procedures.

Peptides: The peptides characterized in the study presented herein were:
1) peptides T-142 to T-155 and T-575, as shown in FIG. 27A, and peptides T-22 to T-27, T-68, T-334 and T-371 to T-375 and T-575, as shown in FIG. 27B;
2) peptides T-120 to T-141 and T-576, as shown in FIG. 27B, and peptides T-12, T-13, T-15, T-19, T-28 to T-30, T-66, T-69, T-70 and T-576, as shown in FIG. 27D; and
3) peptides T-67 and T-104 to T-119 and T-384, as shown in FIG. 28A, and peptides T-71, T-613 to T-617, T-662 to T-676 and T-730, as shown in FIG. 28B.

The peptides of group 1 represent portions of the RSV F2 protein DP178/107-like region. The peptides of group 2 represent portions of the RSV F1 protein DP107-like region. The peptides of groups 3 represent portions of the RSV F1 protein DP178-like region.

Each peptide was tested at 2-fold serial dilutions ranging from 100 µg/ml to approximately 100 ng/ml. For each of the assays, a well containing no peptide was also used. The $IC_{50}$ data for each peptide represents the average of several experiments conducted utilizing that peptide.

17.2 Results

The data summarized in FIGS. 27A–B and 28A–B represent antiviral and structural information obtained from peptides derived from the RSV F2 DP178/DP107-like F2 region (FIGS. 27A–B), the RSV F1 DP-107-like region (FIGS. 27C–D) and the RSV DP178-like F2 region (FIGS. 28A–B).

As shown in FIGS. 27A–D, a number of the RSV DP178/DP107-like peptides exhibited a detectable level of antiviral activity. Peptides from the RSV DP178/DP107-like F2 region (FIGS. 27A–B), for example, T-142 to T-145 and T-334 purfied peptides, exhibited detectable levels of antiviral activity, as evidenced by their $IC_{50}$ values. Further, a number of RSV F1 DP107-like peptides (FIGS. 27C–D) exhibited a sizable level of antiviral activity as purified peptides, including, for example, peptides T-124 to T-127, T-131, T-135 and T-137 to T-139, as demonstrated by their low $IC_{50}$ values. In addition, CD analysis FIGS. 27A, 27C) reveals that many of the peptides exhibit some detectable level of helical structure.

The results summarized in FIGS. 28A–B demonstrate that a number of DP178-like purified peptides exhibit a range of potent anti-viral activity. These peptides include, for example, T-67, T-104, T-105 and T-107 to T-119, as listed in FIG. 28A, and T-665 to T-669 and T-671 to T-673, as listed in FIG. 28B. In addition, some of the DP178-like peptides exhibited some level of helicity.

Thus, the computer assisted searches described, hereinabove, successfully identified viral peptide domains that represent highly promising anti-RSV antiviral compounds.

18. EXAMPLE

Potential Human Parainfluenza Virus Type 3 DP178/DP107 Analogs: CD and Antiviral Characterization In the Example presented herein, human parainfluenza virus type 3 (HPIV3) peptides identified by utilizing the computer-assisted search motifs described in the Examples presented in Sections 9 and 15, above, were tested for anti-HPIV3 activity. Additionally, circular dichroism (CD) structural analyses were conducted on the peptides, as discussed below. It is demonstrated that several of the identified peptides exhibit potent antiviral capability. Additionally, it is shown that several of these peptides exhibit a substantial helical character.

18.1 Materials and Methods

Structural analyses: Structural analyses consisted of circular dichroism (CD) studies. The CD spectra were measured in a 10 mM sodium phosphate, 150 mM sodium chloride, pH 7.0, buffer at approximately 10 mM concentrations, using a 1 cm pathlength cell on a Jobin/Yvon Autodichrograph Mark V CD spectrophotometer. Peptide concentrations were determined from $A_{280}$ using Edlehoch's method (1967, Biochemistry 6:1948).

Anti-HPIV3 antiviral activity assays: The assay utilized herein tested the ability of the peptides to disrupt the ability of Hep2 cells chronically infected with HPIV3 to fuse and cause syncytial formation on a monolayer of an uninfected line of CV-1W cells. The more potent the lower the observed level of fusion, the greater the antiviral activity of the peptide.

Uninfected confluent monolayers of CV-1W cells were grown in microtiter wells in 3% EMEM (Eagle Minimum Essential Medium w/o L-glutamine [Bio Whittaker Cat. No. 12-125F], with fetal bovine serum [FBS; which had been heat inactivated for 30 minutes at 56° C.; Bio Whittaker Cat. No. 14-501F) supplemented at 3%, antibiotics/antimycotics (Gibco BRL Life Technologies Cat. No. 15040-017) added at 1%, and glutamine added at 1%.

To prepare Hep2 cells for addition to uninfected cells, cultures of chronically infected Hep2 cells were washed with DPBS (Dulbecco's Phosphate Buffered Saline w/o calcium or magnesium; Bio Whittaker Cat. No. 17-512F) and cell monolayers were removed with Versene (1:5000; Gibco Life Technologies Cat. No. 15040-017). The cells were spun 10 minutes and resuspended in 3% FBS. Cell counts were performed using a hemacytometer. Persistent cells were added to the uninfected CV-1W cells.

The antiviral assay was conducted by, first, removing all media from the wells containing uninfected CV-1W cells, then adding peptides (at the dilutions described below) in 3% EMEM, and 500 chronically HPIV3-infected Hep2 cells per well. Wells were then incubated at 37° C. for 24 hours.

On day 2, after cells in control wells were checked for fusion centers, media was removed from the wells, followed by addition, to each well, of approximately 50 µl 0.25% Crystal Violet stain in methanol. Wells were rinsed immediately, to remove excess stain and were then allowed to dry. The number of syncytia per well were then counted, using a dissecting microscope.

Alternatively, instead of Crystal Violet analysis, cells were assayed with XTT, as described, above, in Section 17.1.

Figure 29B:
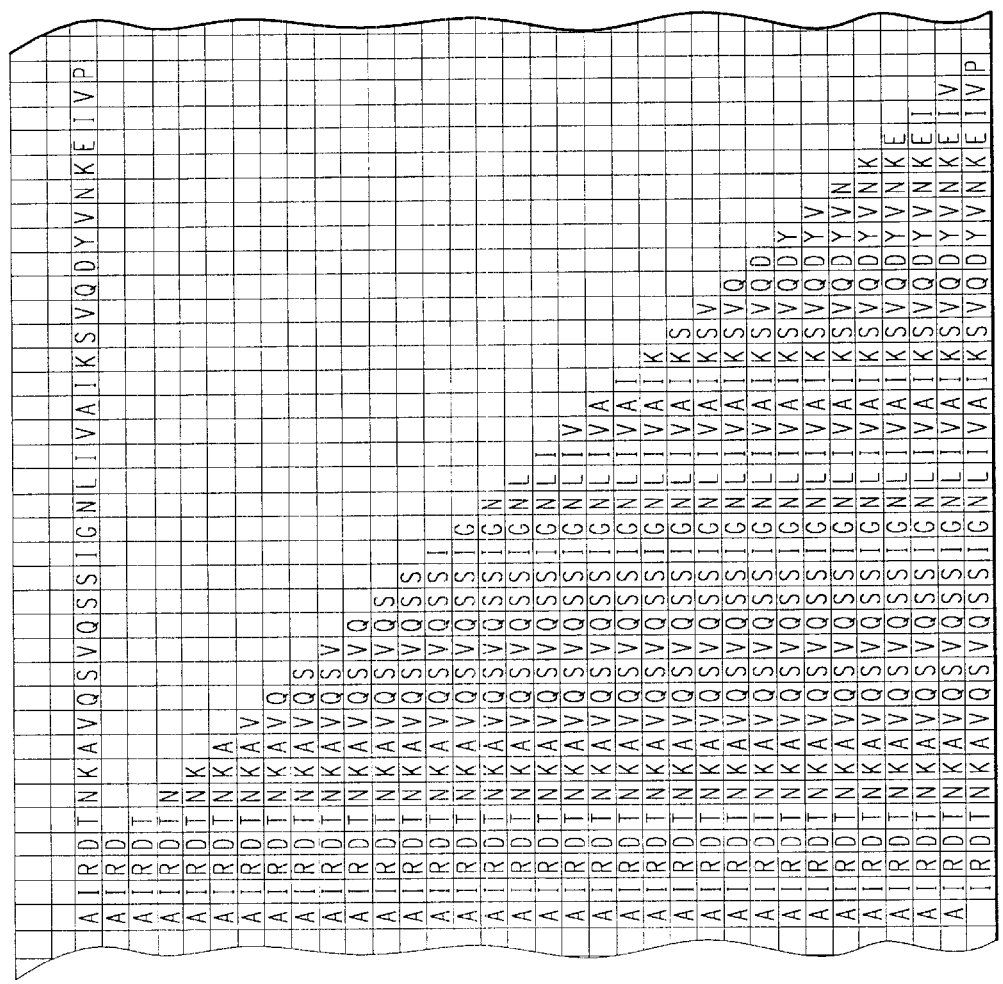

Peptides: The peptides characterized in the study presented herein were:

1) Peptides 157 to 188, as shown in FIG. 29A, and peptides T-38 to T-40, T-42 to T-46 and T-582, as shown in FIG. 29B. These peptides are derived from the DP107 region of the HPIV3 F1 fusion protein (represented by HPF3 107, as shown in FIG. 29A); and 2) Peptides 189 to 210, as shown in FIG. 30A, and T-269, T-626, T-383 and T-577 to T-579, as shown in FIG. 30B. These peptides are primarily derived. from the DP178 region of the HPIV3 F1 fusion protein (represented by HPF3 178, as shown in FIG. 30A). Peptide T-626 contains two mutated amino acid resides (represented by a shaded background). Additionally, peptide T-577 represents F1 amino acids 65–100, T-578 represents F1 amino acids 207–242 and T-579 represents F1 amino acids 273–309.

Each peptide was tested at 2-fold serial dilutions ranging from 500 μg/ml to approximately 500 ng/ml. For each of the assays, a well containing no peptide was also used.

18. Results

The data summarized in FIGS. 29A–B and 30A–B represent antiviral and structural information obtained from peptides derived from the HPIV3 fusion protein DP107-like region (FIGS. 29A–C) and the HPIV3 fusion protein DP178-like region (FIGS. 30A–B).

As shown in FIGS. 29A–B, a number of the HPIV3 DP107-like peptides exhibited potent levels of antiviral activity. These peptides include, for example, peptides T-40, T-172 to T-175, T-178, T-184 and T-185.

CD analysis reveals that a number of the peptides exhibit detectable to substantial level of helical structure.

The results summarized in FIGS. 30A–B demonstrate that a number of the DP178-like peptides tested exhibit a range of anti-viral activity. These peptides include, for example, peptides 194 to 211, as. evidenced by their low $IC_{50}$ values. In fact, peptides 201 to 205 exhibit $IC_{50}$ values in the nanogram/ml range. In addition, many of the DP178-like peptides exhibited some level of helicity.

Thus, the computer assisted searches described, hereinabove, have successfully identified viral peptide domains that represent highly promising anti-HPIV3 anti-viral compounds.

19. EXAMPLE

Computer-assisted Identification of DP178/DP107 Analogs in Simian Immunodeficiency Virus FIG. 31 represents search results for SIV isolate MM251 (PC/Gene® protein sequence PENV_SIVM2). Both 107×178×4 and ALLMOTI5 search motifs identified two regions with similarities to DP107 and/or DP178.

The peptide regions found by 107×178×4 were located at amino acid residues 156–215 and 277–289. The peptide regions found by ALLMOTI5 were located at amino acid residues 156–219 and 245–286. Both motifs, therefore, identify similar regions.

Interestingly, the first SIV peptide region (i.e., from amino acid residue 156 to approximately amino acid residue 219) correlates with a DP107 region, while the second region identified (i.e., from approximately amino acid residue 245 to approximately amino acid residue 289) correlates with the DP178 region of HIV. In-fact, an alignment-of SIV isolate MM251 and HIV isolate BRU, followed by -a selection of the best peptide matches for HIV DP107 and DP178, reveals that the best matches are found within the peptide regions identified by the 107×178×4 and ALLMOTI5 search-motifs.

It should be noted that a potential coiled-coil region at amino acid residues 242–282 is predicted by the Lupas program. This is similar to the-observation in HIV in which the coiled-coil is predicted by the Lupas program to be in the DP178 rather than in the DP107 region. It is possible, therefore, that SIV may be similar to HIV in that it may contain a coiled-coil structure in the DP107 region, despite such a structure being missed by the Lupas algorithm. Likewise, it may be that the region corresponding to a DP178 analog in SIV may exhibit an undefined structure, despite the Lupas program's prediction of a coiled-coil structure.

20. EXAMPLE

Computer-assisted Identification of DP178/DP107 Analogs in Epstein-Barr Virus The results presented herein describe the identification of DP178/DP107 analogs within two different Epstein-Barr Virus proteins. Epstein-Barr is a human herpes virus which is the causative agent of, for example, infectious mononucleosis (IM), and is also associated with nasopharyngeal carcinomas (NPC), Burkitt's lymphoma and other diseases. The virus predominantly exists in the latent form and is activated by a variety of stimuli.

FIG. 32 depicts the search motif results for the Epstein-Barr Virus (Strain B95-8; PC/Gene® protein sequence PVGLB_EBV) glycoprotein gp110 precursor (gp115). The 107×178×4 motif identified two regions of interest, namely the regions covered by amino acid residues 95–122 and 631–658. One PZIP region was identified at amino acid residue 732–752 which is most likely a cytoplasmic region of the protein. The Lupas algorithm predicts a coiled-coil structure for amino acids 657–684. No ALLMOTI5 regions were identified.

FIG. 33 depicts the search motif results for the Zebra (or EB1) trans-activator protein (BZLF1) of the above-identified Epstein-Barr virus. This protein is a transcription factor which represents the primary mediator of viral reactivation. It is a member of the b-ZIP family of transcription factors and shares significant homology with the basic DNA-binding and dimerization domains of the cellular oncogenes c-fos and C/EBP. The Zebra protein functions as a homodimer.

Search results demonstrate that the Zebra protein exhibits a single region which is predicted to be either of DP107 or DP178 similarity, and is found between the known DNA binding and dimerization regions of the protein. Specifically, this region is located at amino acid residues 193–220, as shown in FIG. 33. The Lupas program predicted no coiled-coil regions.

21. EXAMPLE

Computer-assisted Identification of DP178/DP107 Analogs in Measles Virus

FIG. 34 illustrates the motif search results for the fusion protein F1 of measles virus, strain Edmonston (PC Genes protein sequence PVGLF_MEASE), successfully identifying DP178/DP107 analogs.

The 107×178×4 motif identifies a single region at amino acid residues 228–262. The ALLMOTI5 search motif identifies three regions, including amino acid residues 116–184, 228–269 and 452–500. Three regions containing proline residues followed by a leucine zipper-like sequence were found beginning at proline residues 214, 286 and 451.

The Lupas program identified two regions it predicted had potential for coiled-coil structure, which include amino acid residues 141–172 and 444–483.

22. EXAMPLE

Computer-assisted Identification of DP178/DP107 Analogs in Hepatitis B Virus FIG. 35 depicts the results of a PZIP motif search conducted on the Hepatitis B virus subtype AYW. Two regions of interest within the major surface antigen precursor S protein were identified. The first lies just C-terminal to the proposed fusion peptide of the major surface antigen (Hbs) which is found at amino acid residues 174–191. The second region is located at amino acid residues 233–267. The Lupas program predicts no coiled-coil repeat regions.

In order to test the potential anti-HBV antiviral activity of these D178/DP107 analog regions, peptides derived from area around the analog regions are synthesized, as shown in FIGS. 52A–B. These peptides represent one amino acid peptide "walks" through the putative DP178/DP107 analog regions. The peptides are synthesized according to standard Fmoc chemistry on Rinkamide MBHA resins to provide for carboxy terminal blockade (Chang, C. D. and Meinhofer, J., 1978, Int. J. Pept. Protein Res. 11:246–249; Fields, G. B. and Noble, R. L., 1990, Int. J. Pept. Protein Res. 35:161–214). Follwing complete synthesis, the peptide amino-terminus is blocked through automated acetylation,and the peptide is cleaved with trifluoroacetic acid (TFA) and the appropriate scavengers (King, D. S. et al., 1990, Int. J. Pept. Res. 36:255–266). After cleavage, the peptide is precipitated with ether and dried under vacuum for 24 hours.

The anti-HBV activity of the peptides is tested by utilizing standard assays to determine the test peptide concentration required to cause an acceptable (e.g., 90%) decrease in the amount of viral progeny formed by cells exposed to an HBV viral inoculum. Candidate antivial peptides are further characterized in model systems such as wood chuck tissue culture and animal systems, prior to testing on humans.

23. EXAMPLE

Computer-assisted Identification of DP178/DP107 Analogs in Simian Mason-Pfizer Monkey Virus The results depicted herein illustrate the results of search motifs conducted on the Simian Mason-Pfizer monkey virus. The motifs reveal DP178/DP107 analogs within the enveloped (TM) protein GP20, as shown in FIG. 36.

The 107×178×4 motifs identifies a region at amino acid residues 422–470. The ALLMOTI5 finds a region at amino acid residues 408–474. The Lupas program predicted a coiled-coil structure a amino acids 424–459.

24. EXAMPLE

Computer-assisted Identification of DP178/DP107 Analogs in Bacterial Proteins The results presented herein demonstrate the identification of DP178/DP107 analogs corresponding to sequences present in proteins of a variety of bacterial species.

FIG. 37 depicts the search motif results for the *Pseudomonas aeruginosa* fimbrial protein (Pilin). Two regions were identified by motifs 107×178×4 and ALLMOTI5. The regions located at amino acid residues 30–67 and 80–144 were identified by the 107×178×4 motif. The regions at amino acid residues 30–68 and 80–125 were identified by the ALLMOTI5.

FIG. 38 depicts the search motif results for the *Pseudomonas gonorrhoeae* fimbrial protein (Pilin). A single region was identified by both the 107×178×4 and the ALLMOTI5 motifs. The region located at amino acid residues 66–97 was identified by the 107×178×4 motif. The region located at amino acid residues 66–125 were identified by the ALLMOTI5 search motif. No coiled-coil regions were predicted by the Lupas program.

FIG. 39 depicts the search motif results for the Hemophilus Influenza fimbrial protein (Pilin). A single region was identified by both the 107×178×4 and the ALLMOTI5 motifs. The region located at amino acid residues 102–129 was identified by the 107×178×4 motif. The region located at amino acid residues 102–148 were identified by the ALLMOTI5 search motif. No coiled-coil regions were predicted by the Lupas program.

FIG. 40 depicts the search motif results for the *Staphylococcus aureus* toxic shock syndrome Hemophilus Influenza fimbrial protein (Pilin). A single region was identified by both the 107×178×4 and the ALLMOTI5 motifs. The region located at amino acid residues 102–129 was identified by the 107×178×4 motif. The region located at amino acid residues 102–148 were identified by the ALLMOTI5 search motif. No coiled-coil regions were predicted by the Lupas program.

FIG. 41 summarizes the motif search results conducted on the *Staphylococcus aureus* enterotoxin Type E protein. These results demonstrate the successful identification of DP178/DP107 analogs corresponding to peptide sequences within this protein, as described below.

The ALLMOTI5 motif identified a region at amino acid residues 22–27. The 107×178×4 motif identified two regions, with the first at amino acid residues 26–69 and the second at 88–115. A P12LZIPC motif search identified two regions, at amino acid residues 163–181 and 230–250.

The Lupas program predicted a region with a high propensity for coiling at amino acid residues 25–54. This sequence is completely contained within the first region identified by both ALLMOTI5 and 107×178×4 motifs.

FIG. 42 depicts the search motif results conducted on a second *Staphylococcus aureus* toxin, enterotoxin A. Two regions were identified by the ALLMOTI5 motif, at amino acid residues 22–70 and amino acid residues 164–205. The 107×178×4 motif found two regions, the first at amino acid residues 26–69 and the second at amino acid residues 165–192. A P23LZIPC motif search revealed a region at amino acid residues 216–250. No coiled-coil regions were predicted by the Lupas program.

FIG. 43 shows the motif search results conducted on the *E. coli* heat labile enterotoxin A protein, demonstrating that identification of DP178/DP107 analogs corresponding to peptides located within this protein. Two regions were identified by the ALLMOTI5 motif, with the first residing at amino acid residues 55–115, and the second residing at amino acid residues 216–254. The 107×178×4 motif identified a single region at amino acid residues 78–105. No coiled-coil regions were predicted by the Lupas program.

25. EXAMPLE

Computer-assisted Identification of DP178/DP107 Analogs Within Various Human Proteins The results presented herein demonstrate the identification of DP178/DP107 analogs corresponding to peptide sequences present within several different human proteins.

FIG. 44 illustrates the search motif results conducted on the human c-fos oncoprotein. The ALLMOTI5 motif identified a single region at amino acid residues 155–193. The 107×178×4 motif identified one region at amino acid residues 162–193. The Lupas program predicted a region at amino acid residues 148–201 to have coiled-coil structure.

FIG. 45 illustrates the search motif results conducted on the human lupus KU autoantigen protein P70. The ALLMOTI5 motif identified a single region .at amino acid residues 229–280. The 107×178×4 motif identified one region at amino acid residues 235–292. The Lupas program predicted a region at amino acid residues 232–267 to have coiled-coil structure.

FIG. 46 illustrates the search motif results conducted on the human zinc finger protein 10. The ALLMOTI5 motif identified a single region at amino acid residues 29–81. The 107×178×4 motif identified one region at amino acid residues 29–56. A P23LZIPC motif search found a single region at amino acid residues 420–457. The Lupas program predicted no coiled-coil regions.

26. EXAMPLE

Potential Measles Virus DP178/DP107 Analogs: CD and Antiviral Characterization

In the Example presented herein, measles (MeV) virus DP178-like peptides identified by utilizing the computer-assisted search motifs described in the Examples presented in Sections 9 and 21, above, are tested for anti-MeV activity. Additionally, circular dichroism (CD) structural analyses are conducted on the peptides, as discussed below. it is demonstrated that several of the identified peptides exhibit potent antiviral capability. Additionally, it is shown that none of the these peptides exhibit a substantial helical character.

26.1 Materials and Methods

Structural analyses: The CD spectra were measured in a 10 mM sodium phosphate, 150 mM sodium chloride, pH 7.0, buffer at approximately 10 mM concentrations, using a 1 cm pathlength cell on a Jobin/Yvon Autodichrograph Mark V CD spectrophotometer. Peptide concentrations were determined from $A_{280}$ using Edlehoch's method (1967, Biochemistry 6:1948).

Anti-MeV antiviral activity syncytial reduction assay: The assay utilized herein tested the ability of the peptides to disrupt the ability of Vero cells acutely infected with MeV (i.e., cells which are infected with a multiplicity of infection of 2–3) to fuse and cause syncytial formation on a monolayer of an uninfected line of Vero cells. The more potent the peptide, the lower the observed level of fusion, the greater the antiviral activity of the peptide.

Uninfected confluent monolayers of Vero cells were grown in microtiter wells in 10% FBS EMEM (Eagle Minimum Essential Medium w/o L-glutamine [Bio Whittaker Cat. No. 12-125F.], with fetal bovine serum [FBS; which had been heat inactivated for 30 minutes at 56° C.; Bio Whittaker Cat. No. 14-501F) supplemented at 10%, antibiotics/antimycotics (Bio Whittaker Cat. No. 17-602E) added at 1%, and glutamine added at 1%.

To prepare acutely infected Vero cells for addition to the uninfected cells, cultures of acutely infected Vero cells were washed twice with HBSS (Bio Whittaker Cat. No. 10-543F) and cell monolayers were removed with trypsin (Bio Whittaker Cat. No. 17-161E).

Once cells detached, media was added, any remaining clumps of cells were dispersed, and hemacytometer cell counts were performed.

The antiviral assay was conducted by, first, removing all media from the wells containing uninfected Vero cells, then adding peptides (at the dilutions described below) in 10% FBS EMEM, and 50–100 acutely MeV-infected Vero cells per well. Wells were then incubated at 37° C. for a maximum of 18 hours.

On day 2, after cells-in control wells were checked for fusion. centers, media was removed from the wells, followed by addition, to each well, of approximately 50 µl 0.25% Crystal Violet stain in methanol. Wells were rinsed twice with water immediately, to remove excess stain and were then allowed to dry. The number of syncytia per well were then counted, using a dissecting microscope.

Anti-MeV antiviral activity plaque reduction assay: The assay utilized herein tested the ability of the peptides to disrupt the ability of MeV to infect permissive, uninfected. Vero cells, leading to the infected cells' fusing with uninfected cells to produce syncytia. The lower the observed level of syncytial formation, the greater the antiviral activity of the peptide.

Monolayers of uninfected Vero cells are grown as described above.

The antiviral assay was conducted by, first, removing all media. from the wells containing uninfected Vero cells, then adding peptides.(at the dilutions described below) in 10% FBS EMEM, and MeV stock virus at a final concentration of 30 plaque forming units (PFU).per well. Wells were then incubated at 37° C. for a minimum of 36 hours and a maximum of 48 hours.

On day 2, after cells in control wells were checked for fusion centers, media was removed from the wells, followed by addition, to each well, of approximately 50 µl 0.25% Crystal Violet stain in methanol. Wells were rinsed twice with water immediately, to remove excess stain and were then allowed to dry. The number of syncytia per well were then counted, using a dissecting microscope.

Peptides: The peptides characterized in the study presented herein were peptides T-252A0 to T-256A0, T-257B1/C1, and T-258B1 to T-265B0, and T-266A0 to T-268A0, as shown in FIG. 47. These peptides represent a walk through the DP178-like region of the MeV fusion protein.

Each peptide was tested at 2-fold serial dilutions ranging from 100 µg/ml to approximately 100 ng/ml. For each of the assays, a well containing no peptide was also used.

26.2 Results

The data summarized in FIG. 47 represents antiviral and structural information obtained via "peptide walks" through the DP178-like region of the MeV fusion protein.

As shown in FIG. 47, the MeV DP178-like peptides exhibited a range of antiviral activity as crude peptides. Several of these peptides were chosen for purification and further antiviral characterization. The $IC_{50}$ values for such peptides were determined, as shown in FIG. 47, and ranged from 1.35 µg/ml (T257B1/C1) to 0.072 µg/ml (T-265B1). None of the DP178-like peptides showed, by CD analysis, a detectable. level of helicity.

Thus, the computer assisted searches described, hereinabove, as in for example, the Example presented in Section 9, for example, successfully identified. viral peptide domains that represent highly promising anti-MeV antiviral compounds.

27. EXAMPLE

Potential SIV DP178/DP107 Analogs: Antiviral Characterization

In the Example presented herein, simian immunodeficiency virus (SIV) DP178-like peptides identified by utilizing the computer-assisted search motifs described in the Examples presented in Sections 9, 12 and 19, above, were tested for anti-SIV activity. It is demonstrated that several of the identified peptides exhibit potent antiviral capability.

27.1 Materials and Methods

Anti-SIV antiviral assays: The assay utilized. herein were as reported in Langolis et al. (Langolis, A. J. et al., 1991, AIDS Research and Human Retroviruses 7:713–720).

Peptides: The peptides characterized in the study presented herein were peptides T-391 to T-400, as shown in FIG. 48. These peptides represent a walk through the DP178-like region of the SIV TM protein.

Each peptide was tested at 2-fold serial dilutions ranging from 100 µg/ml to approximately 100 ng/ml. For each of the assays, a well containing no peptide was also used.

27.2 Results

The data summarized in FIG. 48 represents antiviral information obtained via "peptide walks" through the DP178-like region of the SIV TM protein.

As shown in FIG. 48, peptides T-391 to T-400 were tested and exhibited a potent antiviral activity as crude peptides.

Thus, the computer assisted searches described, hereinabove, as in for example, the Example presented in Section 9, for example, successfully identified viral peptide domains that represent highly promising anti-SIV antiviral compounds.

28. EXAMPLE

Anti-viral Activity of DP107 and DP178-Peptide Truncations and Mutations

The Example presented in this Section represents a study of the antiviral activity of DP107 and DP178 truncations and mutations. It is demonstrated that several of these DP107 and DP178 modified peptides exhibit substantial antiviral activity.

28.1 Materials and Methods

Anti-HIV assays: The antiviral assays performed were as those described, above, in Section 6.1.

Assays utilized HIV-1/IIIb and/or HIV-2 NIHZ isolates. Purified peptides were used, unless otherwise noted in FIGS. 49A–C.

Peptides: The peptides characterized in the study presented herein were:

1) FIGS. 49A–C present peptides derived from the region around and containing the DP178 region of the HIV-1 BRU isolate.

Specifically, this region spanned from gp41 amino acid residue 615 to amino acid residue 717. The peptides listed. contain truncations of this region and/or mutations which vary from the DP178 sequence amino acid sequence. Further, certain of the peptides have had amino- and/or carboxy-terminal groups either added or removed, as indicated in the figures; and 2) FIG. 50. presents peptides which represent truncations of DP107 and/or the gp41 region surrounding the DP107 amino acid sequence of HIV-1 BRU isolate. Certain of the peptides are unblocked or biotinylated, as indicated in the figure.

Blocked peptides contained an acyl N-terminus and an amido C-terminus.

28.2 Results

Anti-HIV antiviral data was obtained with the group 1 DP178-derived peptides listed in FIGS. 49A–C. The full-length, non-mutant DP178 peptide (referred to in FIGS. 49A–C as T20) results shown are for 4 ng/ml.

In FIG. 49A, a number of the DP178 truncations exhibited a high level of antiviral activity, as evidenced by their low $IC_{50}$ values. These include, for example, test peptides T-50, T-624, T-636 to T-641, T-645 to T-650, T-652 to T-654 and T-656. T-50 represents a test peptide which contains a point mutation, as indicated by the residue's shaded background. The HIV-1-derived test peptides exhibited a distinct strain-specific antiviral activity, in that none of the peptides tested on the. HIV-2 NIHZ isolate demonstrated appreciable anti-HIV-2 antiviral activity.

Among the peptides listed in FIG. 49B, are test peptides representing the amino (T-4) and carboxy (T-3) terminal halves of DP178 were tested. The amino terminal peptide was not active ($IC_{50}$>400 μg/ml) whereas the carboxy terminal peptide showed potent antiviral activity ($IC_{50}$=3 μg/ml). A number of additional test peptides also exhibited a high level of antiviral activity. These included, for example, T-61/T-102, T-217 to T-221, T-235, T-381, T-677, T-377, T-590, T-378, T-591, T-271 to T-272, T-611, T-222 to T-223 and T-60/T-224. Certain of the antiviral peptides contain point mutations and/or amino acid residue additions which vary from the DP178 amino acid sequence.

In FIG. 49C, point mutations and/or amino and/or carboxy-terminal modifications are introduced into the DP178 amino acid sequence itself. As shown in the figure, the majority of the test peptides listed exhibit potent antiviral activity.

Truncations of the DP107 peptide (referred to in IG. 50 as T21) were also produced and tested, as shown in FIG. 50. FIG. 50 also presents data concerning blocked and unblocked peptides which contain additional amino acid residues from the gp41 region in which the DP107 sequence resides. Most of these peptides showed antiviral activity, as evidenced by their low $IC_{50}$ values.

Thus, the results presented in this Section demonstrate that not only do the full length DP107 and DP178 peptides exhibit potent antiviral activity, but truncations and/or mutant versions of these-peptides can also possess substantial antiviral character.

29: EXAMPLE

Potential Epstein-Barr DP178/DP107 Analogs: Antiviral Characterization

In the Example presented herein, peptides derived from the Epstein-Barr (EBV) DP-178/DP107 analog region of the Zebra protein identified, above, in the Example presented in Section 20 are described and tested for anti-EBV activity. It is demonstrated that among these peptides are ones which exhibit potential anti-viral activity.

29.1 Materials and Methods

Electrophoretic Mobility Shift Assays (EMSA): Briefly, an EBV Zebra protein was synthesized utilizing SP6 RNA polymerase in vitro transcription and wheat germ in vitro translation systems (Promega Corporation recommendations; Butler, E. T. and Chamberlain, M. J., 1984. J. Biol. Chem. 257:5772; Pelham, H. R. B. and Jackson, R. J., 1976, Eur. J. Biochem. 67:247). The in vitro translated Zebra protein was then preincubated with increasing amounts of peptide up to 250 ng/ml prior to the addition of 10,000 to 20,000 c.p.m. of a $^{32}P$-labeled Zebra response element DNA fragment. After a 20 minute incubation in the presence of the response element, the reaction was analyzed on a 4% non-denaturing polyacrylamide gel, followed by autoradiography, utilizing standard gel-shift procedures. The ability of a test peptide to prevent Zebra homodimer DNA binding was assayed by the peptide's ability to abolish the response element gel migration retardation characteristic of a protein-bound nucleic acid molecule.

Peptides: The peptides characterized in this study represent peptide walks through the region containing, and flanked on both sides by, the DP178/DP107 analog region identified in the Example presented in Section 20, above, and shown as shown in FIG. 33. Specifically, the peptide walks covered the region from amino acid residue 173 to amino acid residue 246 of the EBV Zebra protein.

Each of the tested peptides were analyzed at a range of concentrations, with 150 ng/ml being the lowest concentration at which any of the peptides exerted an inhibitory effect.

29.2 Results

The EBV Zebra protein transcription factor contains a DP178/DP107 analog region, as demonstrated in the Example presented, above, in Section 20. This protein appears to be the primary factor responsible for the reactivation capability of the virus. A method by which the DNA-binding function of the Zebra virus may be abolished may, therefore, represent an effective antiviral technique. In order to identify potential anti-EBV DP178/DP107 peptides, therefore, peptides derived from the region identified in Section 20, above, were tested for their ability to inhibit Zebra protein DNA binding.

The test peptides' ability to inhibit Zebra protein DNA binding was assayed via the EMSA assays described, above, in Section 28.1. The data summarized in FIGS. 51A–B presents the results of EMSA assays of the listed EBV test peptides. These peptides represent one amino acid "walks" through the region containing, and flanked on both sides by, the DP178/DP107 analog region identified in the Example presented in Section 20, above, and shown as shown in FIG. 33. As shown in FIGS. 51A–B, the region from which these peptides are derived lies from EBV Zebra protein amino acid residue 173 to 246. A number of the test peptides which were assayed exhibited an ability to inhibit Zebra protein homodimer DNA binding, including 439, 441, 444 and 445.

Those peptides which exhibit an ability to inhibit Zebra protein DNA binding represent potential anti-EBV antiviral compounds whose ability to inhibit EBV infection can be further characterized.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

SEQUENCE LISTING (1) GENERAL INFORMATION:

(iii) NUMBER OF SEQUENCES: 273

(2) INFORMATION FOR SEQ ID NO:1:

(i) SEQUENCE CHARACTERISTICS:
      (A) LENGTH: 36 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:1:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

(2) INFORMATION FOR SEQ ID NO:2:

(i) SEQUENCE CHARACTERISTICS:
      (A) LENGTH: 36 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:2:

Ser Ser Glu Ser Phe Thr Leu Leu Glu Gln Trp Asn Asn Trp Lys Leu
1               5                   10                  15

Gln Leu Ala Glu Gln Trp Leu Glu Gln Ile Asn Glu Lys His Tyr Leu
            20                  25                  30

```
Glu Asp Ile Ser
        35

(2) INFORMATION FOR SEQ ID NO:3:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:3:

Tyr Thr Asn Thr Ile Tyr Thr Leu Leu Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

(2) INFORMATION FOR SEQ ID NO:4:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:4:

Tyr Thr Gly Ile Ile Tyr Asn Leu Leu Glu Glu Ser Gln Asn Gln Gln
1               5                   10                  15

Glu Lys Asn Glu Gln Glu Leu Leu Glu Leu Asp Lys Trp Ala Asn Leu
            20                  25                  30

Trp Asn Trp Phe
        35

(2) INFORMATION FOR SEQ ID NO:5:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:5:

Tyr Thr Ser Leu Ile Tyr Ser Leu Leu Glu Lys Ser Gln Thr Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

(2) INFORMATION FOR SEQ ID NO:6:

(i) SEQUENCE CHARACTERISTICS:
        (A) LENGTH: 36 amino acids
        (B) TYPE: amino acid
        (C) STRANDEDNESS:
        (D) TOPOLOGY: unknown
```

```
        (ii) MOLECULE TYPE: peptide (xi) SEQUENCE DESCRIPTION: SEQ ID NO:6:

Leu Glu Ala Asn Ile Ser Lys Ser Leu Glu Gln Ala Gln Ile Gln Gln
1               5                   10                  15

Glu Lys Asn Met Tyr Glu Leu Gln Lys Leu Asn Ser Trp Asp Ile Phe
                20                  25                  30

Gly Asn Trp Phe
        35

(2) INFORMATION FOR SEQ ID NO:7:

(i) SEQUENCE CHARACTERISTICS:
            (A) LENGTH: 36 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:7:

Leu Glu Ala Asn Ile Ser Gln Ser Leu Glu Gln Ala Gln Ile Gln Gln
1               5                   10                  15

Glu Lys Asn Met Tyr Glu Leu Gln Lys Leu Asn Ser Trp Asp Val Phe
                20                  25                  30

Thr Asn Trp Leu
        35

(2) INFORMATION FOR SEQ ID NO:8:

(i) SEQUENCE CHARACTERISTICS:
            (A) LENGTH: 41 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:8:

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
                20                  25                  30

Ala Val Glu Arg Tyr Leu Lys Asp Gln
        35                  40

(2) INFORMATION FOR SEQ ID NO:9:

(i) SEQUENCE CHARACTERISTICS:
            (A) LENGTH: 17 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:9:

Leu Gln Ala Arg Ile Leu Ala Val Glu Arg Tyr Leu Lys Asp Gln Gln
1               5                   10                  15

Gln (2) INFORMATION FOR SEQ ID NO:10:

(i) SEQUENCE CHARACTERISTICS:
```

(A) LENGTH: 38 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:10:

Gln Gln Leu Leu Asp Val Val Lys Arg Gln Gln Glu Met Leu Arg Leu
1               5                   10                  15

Thr Val Trp Gly Thr Lys Asn Leu Gln Ala Arg Val Thr Ala Ile Glu
            20                  25                  30

Lys Tyr Leu Lys Asp Gln
        35

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

ATGACGCTGA CGGTACAGGC C                                              21

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TGACTAAGCT TAATACCACA GCCAATTTGT TAT                                 33

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GGAGCTGCTT GGGGCCCCAG AC                                             22

(2) INFORMATION FOR SEQ ID NO:14:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CCAAATCCCC AGGAGCTGCT CGAGCTGCAC TATACCAGAC                          40

-continued (2) INFORMATION FOR SEQ ID NO:15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

ATAGCTTCTA GATTAATTGT TAATTTCTCT GTCCC                          35

(2) INFORMATION FOR SEQ ID NO:16:

(i) SEQUENCE CHARACTERISTICS:
        (A) LENGTH: 48 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino
            group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:16:

```
Tyr Thr Ser Val Ile Thr Ile Glu Leu Ser Asn Ile Lys Glu Asn Lys
1               5                   10                  15

Cys Asn Gly Thr Asp Ala Lys Val Lys Leu Ile Lys Gln Glu Leu Asp
            20                  25                  30

Lys Tyr Lys Asn Ala Val Thr Glu Leu Gln Leu Leu Met Gln Ser Thr
        35                  40                  45
```

(2) INFORMATION FOR SEQ ID NO:17:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino
            group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl group, or a macromolecular carrier group."

(xi) SEQUENCE DESCRIPTION: SEQ ID NO:17:

```
Phe Tyr Asp Pro Leu Val Phe Pro Ser Asp Glu Phe Asp Ala Ser Ile
1               5                   10                  15

Ser Gln Val Asn Glu Lys Ile Asn Gln Ser Leu Ala Phe Ile Arg Lys
                20                  25                  30

Ser Asp Glu Leu Leu
        35
```

(2) INFORMATION FOR SEQ ID NO:18:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino group, a hydrophobic group, an acetyl group, a 9-fluorenylmethoxycarbonyl group, or a macromolecular carrier group."

(ix) FEATURE:
        (A) NAME/KEY: Modified-site
        (B) LOCATION: 48
        (D) OTHER INFORMATION: /label= B
            /note= "Following this amino acid, there may be a carboxyl group, an amido group, a T-butyloxycarbonyl group, or a macromolecular carrier group."

(xi) SEQUENCE DESCRIPTION: SEQ ID NO:18:

```
Ile Thr Leu Asn Asn Ser Val Ala Leu Asp Pro Ile Asp Ile Ser Ile
1               5                   10                  15

Glu Leu Asn Lys Ala Lys Ser Asp Leu Glu Glu Ser Lys Glu Trp Ile
                20                  25                  30

Arg Arg Ser
        35
```

(2) INFORMATION FOR SEQ ID NO:19:

(i) SEQUENCE CHARACTERISTICS:
        (A) LENGTH: 34 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino group, a hydrophobic group, an acetyl group, a 9-fluorenylmethoxycarbonyl group, or a macromolecular carrier group."

(ix) FEATURE:
        (A) NAME/KEY: Modified-site
        (B) LOCATION: 48
        (D) OTHER INFORMATION: /label= B
            /note= "Following this amino acid, there may be a carboxyl group, an amido group, a T-butyloxycarbonyl group, or a macromolecular carrier group."

(xi) SEQUENCE DESCRIPTION: SEQ ID NO:19:

Ala Leu Gly Val Ala Thr Ser Ala Gln Ile Thr Ala Ala Val Ala Leu
1               5                   10                  15

Val Glu Ala Lys Gln Ala Arg Ser Asp Ile Glu Lys Leu Lys Glu Ala
                20                  25                  30

Ile Arg (2) INFORMATION FOR SEQ ID NO:20:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:20:

Val Ala Val Ser Lys Val Leu His Leu Glu Gly Glu Val Asn Lys Ile
1               5                   10                  15

Ala Leu Leu Ser Thr Asn Lys Ala Val Val Ser Leu Ser Asn Gly Val
                20                  25                  30

Ser (2) INFORMATION FOR SEQ ID NO:21:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino
            group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:21:

```
Ala Val Ser Lys Val Leu His Leu Glu Gly Glu Val Asn Lys Ile Ala
1               5                   10                  15

Leu Leu Ser Thr Asn Lys Ala Val Val Ser Leu Ser Asn Gly Val Ser
                20                  25                  30

Val
```

(2) INFORMATION FOR SEQ ID NO:22:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino
            group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:22:

```
Val Ser Lys Val Leu His Leu Glu Gly Glu Val Asn Lys Ile Ala Leu
1               5                   10                  15

Leu Ser Thr Asn Lys Ala Val Val Ser Leu Ser Asn Gly Val Ser Val
                20                  25                  30

Leu
```

(2) INFORMATION FOR SEQ ID NO:23:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino
            group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:23:

```
Ser Lys Val Leu His Leu Glu Gly Glu Val Asn Lys Ile Ala Leu Leu
1               5                   10                  15
```

-continued

```
Ser Thr Asn Lys Ala Val Val Ser Leu Ser Asn Gly Val Ser Val Leu
            20                  25                  30
Thr (2) INFORMATION FOR SEQ ID NO:24:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino
            group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:24:

Lys Val Leu His Leu Glu Gly Glu Val Asn Lys Ile Ala Leu Leu Ser
1               5                  10                  15

Thr Asn Lys Ala Val Val Ser Leu Ser Asn Gly Val Ser Val Leu Thr
            20                  25                  30

Ser (2) INFORMATION FOR SEQ ID NO:25:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:25:

Leu Glu Gly Glu Val Asn Lys Ile Ala Leu Leu Ser Thr Asn Lys Ala
1               5                  10                  15

Val Val Ser Leu Ser Asn Gly Val Ser Val Leu Thr Ser Lys Val Leu
            20                  25                  30
```

Asp (2) INFORMATION FOR SEQ ID NO:26:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino
            group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:26:

```
Gly Glu Val Asn Lys Ile Ala Leu Leu Ser Thr Asn Lys Ala Val Val
1               5                   10                  15

Ser Leu Ser Asn Gly Val Ser Val Leu Thr Ser Lys Val Leu Asp Leu
            20                  25                  30

Lys
```

(2) INFORMATION FOR SEQ ID NO:27:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:27:

```
Glu Val Asn Lys Ile Ala Leu Leu Ser Thr Asn Lys Ala Val Val Ser
1               5                   10                  15

Leu Ser Asn Gly Val Ser Val Leu Thr Ser Lys Val Leu Asp Leu Lys
            20                  25                  30

Asn
```

-continued (2) INFORMATION FOR SEQ ID NO:28:

(i) SEQUENCE CHARACTERISTICS:
    (A) LENGTH: 33 amino acids
    (B) TYPE: amino acid
    (C) STRANDEDNESS:
    (D) TOPOLOGY: unknown (ii) MOLECULE TYPE: peptide (ix) FEATURE:
    (A) NAME/KEY: Modified-site
    (B) LOCATION: 1
    (D) OTHER INFORMATION: /label= A
        /note= "Preceeding this amino acid, there may be an
        amino group, a hydrophobic group, an acetyl group, a
        9-fluorenylmethoxycarbonyl group, or a macromolecular
        carrier group."

(ix) FEATURE:
    (A) NAME/KEY: Modified-site
    (B) LOCATION: 48
    (D) OTHER INFORMATION: /label= B
        /note= "Following this amino acid, there may be a
        carboxyl group, an amido group, a T-butyloxycarbonyl
        group, or a macromolecular carrier group."

(xi) SEQUENCE DESCRIPTION: SEQ ID NO:28:

Val Asn Lys Ile Ala Leu Leu Ser Thr Asn Lys Ala Val Val Ser Leu
 1               5                  10                  15

Ser Asn Gly Val Ser Val Leu Thr Ser Lys Val Leu Asp Leu Lys Asn
            20                  25                  30

Tyr (2) INFORMATION FOR SEQ ID NO:29:

(i) SEQUENCE CHARACTERISTICS:
    (A) LENGTH: 33 amino acids
    (B) TYPE: amino acid
    (C) STRANDEDNESS:
    (D) TOPOLOGY: unknown (ii) MOLECULE TYPE: peptide (ix) FEATURE:
    (A) NAME/KEY: Modified-site
    (B) LOCATION: 1
    (D) OTHER INFORMATION: /label= A
        /note= "Preceeding this amino acid, there may be an
        amino group, a hydrophobic group, an acetyl group, a
        9-fluorenylmethoxycarbonyl group, or a macromolecular
        carrier group."

(ix) FEATURE:
    (A) NAME/KEY: Modified-site
    (B) LOCATION: 48
    (D) OTHER INFORMATION: /label= B
        /note= "Following this amino acid, there may be a
        carboxyl group, an amido group, a T-butyloxycarbonyl
        group, or a macromolecular carrier group."

(xi) SEQUENCE DESCRIPTION: SEQ ID NO:29:

Asn Lys Ile Ala Leu Leu Ser Thr Asn Lys Ala Val Val Ser Leu Ser
 1               5                  10                  15

Asn Gly Val Ser Val Leu Thr Ser Lys Val Leu Asp Leu Lys Asn Tyr
            20                  25                  30

Ile (2) INFORMATION FOR SEQ ID NO:30:

(i) SEQUENCE CHARACTERISTICS:

```
            (A) LENGTH: 33 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, a hydrophobic group, an acetyl group, a
                9-fluorenylmethoxycarbonyl group, or a macromolecular
                carrier group."

(ix) FEATURE:
            (A) NAME/KEY: Modified-site
            (B) LOCATION: 48
            (D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:30:

Lys Ile Ala Leu Leu Ser Thr Asn Lys Ala Val Val Ser Leu Ser Asn
1               5                  10                  15

Gly Val Ser Val Leu Thr Ser Lys Val Leu Asp Leu Lys Asn Tyr Ile
            20                  25                  30

Asp (2) INFORMATION FOR SEQ ID NO:31:

(i) SEQUENCE CHARACTERISTICS:
            (A) LENGTH: 33 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, a hydrophobic group, an acetyl group, a
                9-fluorenylmethoxycarbonyl group, or a macromolecular
                carrier group."

(ix) FEATURE:
            (A) NAME/KEY: Modified-site
            (B) LOCATION: 48
            (D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:31:

Ile Ala Leu Leu Ser Thr Asn Lys Ala Val Val Ser Leu Ser Asn Gly
1               5                  10                  15

Val Ser Val Leu Thr Ser Lys Val Leu Asp Leu Lys Asn Tyr Ile Asp
            20                  25                  30

Lys (2) INFORMATION FOR SEQ ID NO:32:

(i) SEQUENCE CHARACTERISTICS:
            (A) LENGTH: 33 amino acids
            (B) TYPE: amino acid
            (C) STRANDEDNESS:
```

```
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:32:

Ala Leu Leu Ser Thr Asn Lys Ala Val Val Ser Leu Ser Asn Gly Val
1               5                   10                  15

Ser Val Leu Thr Ser Lys Val Leu Asp Leu Lys Asn Tyr Ile Asp Lys
            20                  25                  30

Gln (2) INFORMATION FOR SEQ ID NO:33:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:33:

Thr Leu Asn Asn Ser Val Ala Leu Asp Pro Ile Asp Ile Ser Ile Glu
1               5                   10                  15

Leu Asn Lys Ala Lys Ser Asp Leu Glu Glu Ser Lys Glu Trp Ile Arg
            20                  25                  30

Arg Ser Asn
        35

(2) INFORMATION FOR SEQ ID NO:34:

(i) SEQUENCE CHARACTERISTICS:
        (A) LENGTH: 35 amino acids
        (B) TYPE: amino acid
        (C) STRANDEDNESS:
        (D) TOPOLOGY: unknown
```

```
        (ii) MOLECULE TYPE: peptide (ix) FEATURE:
              (A) NAME/KEY: Modified-site
              (B) LOCATION: 1
              (D) OTHER INFORMATION: /label= A
                    /note= "Preceeding this amino acid, there may be an
                    amino group, a hydrophobic group, an acetyl group, a
                    9-fluorenylmethoxycarbonyl group, or a macromolecular
                    carrier group."

(ix) FEATURE:
              (A) NAME/KEY: Modified-site
              (B) LOCATION: 48
              (D) OTHER INFORMATION: /label= B
                    /note= "Following this amino acid, there may be a
                    carboxyl group, an amido group, a T-butyloxycarbonyl
                    group, or a macromolecular carrier group."

(xi) SEQUENCE DESCRIPTION: SEQ ID NO:34:

Leu Asn Asn Ser Val Ala Leu Asp Pro Ile Asp Ile Ser Ile Glu Leu
1               5                   10                  15

Asn Lys Ala Lys Ser Asp Leu Glu Glu Ser Lys Glu Trp Ile Arg Arg
            20                  25                  30

Ser Asn Gln
        35

(2) INFORMATION FOR SEQ ID NO:35:

(i) SEQUENCE CHARACTERISTICS:
              (A) LENGTH: 35 amino acids
              (B) TYPE: amino acid
              (C) STRANDEDNESS:
              (D) TOPOLOGY: unknown (ii) MOLECULE TYPE: peptide (ix) FEATURE:
              (A) NAME/KEY: Modified-site
              (B) LOCATION: 1
              (D) OTHER INFORMATION: /label= A
                    /note= "Preceeding this amino acid, there may be an
                    amino group, a hydrophobic group, an acetyl group, a
                    9-fluorenylmethoxycarbonyl group, or a macromolecular
                    carrier group."

(ix) FEATURE:
              (A) NAME/KEY: Modified-site
              (B) LOCATION: 48
              (D) OTHER INFORMATION: /label= B
                    /note= "Following this amino acid, there may be a
                    carboxyl group, an amido group, a T-butyloxycarbonyl
                    group, or a macromolecular carrier group."

(xi) SEQUENCE DESCRIPTION: SEQ ID NO:35:

Asn Asn Ser Val Ala Leu Asp Pro Ile Asp Ile Ser Ile Glu Leu Asn
1               5                   10                  15

Lys Ala Lys Ser Asp Leu Glu Glu Ser Lys Glu Trp Ile Arg Arg Ser
            20                  25                  30

Asn Gln Lys
        35

(2) INFORMATION FOR SEQ ID NO:36:

(i) SEQUENCE CHARACTERISTICS:
              (A) LENGTH: 35 amino acids
              (B) TYPE: amino acid
              (C) STRANDEDNESS:
              (D) TOPOLOGY: unknown (ii) MOLECULE TYPE: peptide
```

```
        (ix) FEATURE:
             (A) NAME/KEY: Modified-site
             (B) LOCATION: 1
             (D) OTHER INFORMATION: /label= A
                  /note= "Preceeding this amino acid, there may be an
                  amino group, a hydrophobic group, an acetyl group, a
                  9-fluorenylmethoxycarbonyl group, or a macromolecular
                  carrier group."

(ix) FEATURE:
             (A) NAME/KEY: Modified-site
             (B) LOCATION: 48
             (D) OTHER INFORMATION: /label= B
                  /note= "Following this amino acid, there may be a
                  carboxyl group, an amido group, a T-butyloxycarbonyl
                  group, or a macromolecular carrier group."

(xi) SEQUENCE DESCRIPTION: SEQ ID NO:36:

Asn Ser Val Ala Leu Asp Pro Ile Asp Ile Ser Ile Glu Leu Asn Lys
1               5                  10                  15

Ala Lys Ser Asp Leu Glu Glu Ser Lys Glu Trp Ile Arg Arg Ser Asn
            20                  25                  30

Gln Lys Leu
        35

(2) INFORMATION FOR SEQ ID NO:37:

(i) SEQUENCE CHARACTERISTICS:
         (A) LENGTH: 35 amino acids
         (B) TYPE: amino acid
         (C) STRANDEDNESS:
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
              /note= "Preceeding this amino acid, there may be an
              amino group, a hydrophobic group, an acetyl group, a
              9-fluorenylmethoxycarbonyl group, or a macromolecular
              carrier group."

(ix) FEATURE:
         (A) NAME/KEY: Modified-site
         (B) LOCATION: 48
         (D) OTHER INFORMATION: /label= B
              /note= "Following this amino acid, there may be a
              carboxyl group, an amido group, a T-butyloxycarbonyl
              group, or a macromolecular carrier group."

(xi) SEQUENCE DESCRIPTION: SEQ ID NO:37:

Ser Val Ala Leu Asp Pro Ile Asp Ile Ser Ile Glu Leu Asn Lys Ala
1               5                  10                  15

Lys Ser Asp Leu Glu Glu Ser Lys Glu Trp Ile Arg Arg Ser Asn Gln
            20                  25                  30

Lys Leu Asp
        35

(2) INFORMATION FOR SEQ ID NO:38:

(i) SEQUENCE CHARACTERISTICS:
         (A) LENGTH: 35 amino acids
         (B) TYPE: amino acid
         (C) STRANDEDNESS:
         (D) TOPOLOGY: unknown (ii) MOLECULE TYPE: peptide
```

```
    (ix) FEATURE:
         (A) NAME/KEY: Modified-site
         (B) LOCATION: 1
         (D) OTHER INFORMATION: /label= A
             /note= "Preceeding this amino acid, there may be an
             amino group, a hydrophobic group, an acetyl group, a
             9-fluorenylmethoxycarbonyl group, or a macromolecular
             carrier group."

(ix) FEATURE:
         (A) NAME/KEY: Modified-site
         (B) LOCATION: 48
         (D) OTHER INFORMATION: /label= B
             /note= "Following this amino acid, there may be a
             carboxyl group, an amido group, a T-butyloxycarbonyl
             group, or a macromolecular carrier group."

(xi) SEQUENCE DESCRIPTION: SEQ ID NO:38:

Val Ala Leu Asp Pro Ile Asp Ile Ser Ile Glu Leu Asn Lys Ala Lys
1               5                   10                  15

Ser Asp Leu Glu Glu Ser Lys Glu Trp Ile Arg Arg Ser Asn Gln Lys
            20                  25                  30

Leu Asp Ser
        35

(2) INFORMATION FOR SEQ ID NO:39:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, a hydrophobic group, an acetyl group, a
             9-fluorenylmethoxycarbonyl group, or a macromolecular
             carrier group."

(ix) FEATURE:
         (A) NAME/KEY: Modified-site
         (B) LOCATION: 48
         (D) OTHER INFORMATION: /label= B
             /note= "Following this amino acid, there may be a
             carboxyl group, an amido group, a T-butyloxycarbonyl
             group, or a macromolecular carrier group."

(xi) SEQUENCE DESCRIPTION: SEQ ID NO:39:

Ala Leu Asp Pro Ile Asp Ile Ser Ile Glu Leu Asn Lys Ala Lys Ser
1               5                   10                  15

Asp Leu Glu Glu Ser Lys Glu Trp Ile Arg Arg Ser Asn Gln Lys Leu
            20                  25                  30

Asp Ser Ile
        35

(2) INFORMATION FOR SEQ ID NO:40:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
```

(A) NAME/KEY: Modified-site
                (B) LOCATION: 1
                (D) OTHER INFORMATION: /label= A
                    /note= "Preceeding this amino acid, there may be an
                    amino group, a hydrophobic group, an acetyl group, a
                    9-fluorenylmethoxycarbonyl group, or a macromolecular
                    carrier group."

(ix) FEATURE:
                (A) NAME/KEY: Modified-site
                (B) LOCATION: 48
                (D) OTHER INFORMATION: /label= B
                    /note= "Following this amino acid, there may be a
                    carboxyl group, an amido group, a T-butyloxycarbonyl
                    group, or a macromolecular carrier group."

(xi) SEQUENCE DESCRIPTION: SEQ ID NO:40:

Leu Asp Pro Ile Asp Ile Ser Ile Glu Leu Asn Lys Ala Lys Ser Asp
1               5                   10                  15

Leu Glu Glu Ser Lys Glu Trp Ile Arg Arg Ser Asn Gln Lys Leu Asp
            20                  25                  30

Ser Ile Gly
        35

(2) INFORMATION FOR SEQ ID NO:41:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:41:

Asp Pro Ile Asp Ile Ser Ile Glu Leu Asn Lys Ala Lys Ser Asp Leu
1               5                   10                  15

Glu Glu Ser Lys Glu Trp Ile Arg Arg Ser Asn Gln Lys Leu Asp Ser
            20                  25                  30

Ile Gly Asn
        35

(2) INFORMATION FOR SEQ ID NO:42:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site (B) LOCATION: 1
            (D) OTHER INFORMATION: /label= A
                /note= "Preceeding this amino acid, there may be an
                amino group, a hydrophobic group, an acetyl group, a
                9-fluorenylmethoxycarbonyl group, or a macromolecular
                carrier group."

(ix) FEATURE:
            (A) NAME/KEY: Modified-site
            (B) LOCATION: 48
            (D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:42:

Pro Ile Asp Ile Ser Ile Glu Leu Asn Lys Ala Lys Ser Asp Leu Glu
1               5                   10                  15

Glu Ser Lys Glu Trp Ile Arg Arg Ser Asn Gln Lys Leu Asp Ser Ile
            20                  25                  30

Gly Asn Trp
        35

(2) INFORMATION FOR SEQ ID NO:43:

(i) SEQUENCE CHARACTERISTICS:
            (A) LENGTH: 35 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, a hydrophobic group, an acetyl group, a
                9-fluorenylmethoxycarbonyl group, or a macromolecular
                carrier group."

(ix) FEATURE:
            (A) NAME/KEY: Modified-site
            (B) LOCATION: 48
            (D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:43:

Ile Asp Ile Ser Ile Glu Leu Asn Lys Ala Lys Ser Asp Leu Glu Glu
1               5                   10                  15

Ser Lys Glu Trp Ile Arg Arg Ser Asn Gln Lys Leu Asp Ser Ile Gly
            20                  25                  30

Asn Trp His
        35

(2) INFORMATION FOR SEQ ID NO:44:

(i) SEQUENCE CHARACTERISTICS:
            (A) LENGTH: 35 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1

(D) OTHER INFORMATION: /label= A
                        /note= "Preceeding this amino acid, there may be an
                        amino group, a hydrophobic group, an acetyl group, a
                        9-fluorenylmethoxycarbonyl group, or a macromolecular
                        carrier group."

(ix) FEATURE:
                    (A) NAME/KEY: Modified-site
                    (B) LOCATION: 48
                    (D) OTHER INFORMATION: /label= B
                        /note= "Following this amino acid, there may be a
                        carboxyl group, an amido group, a T-butyloxycarbonyl
                        group, or a macromolecular carrier group."

(xi) SEQUENCE DESCRIPTION: SEQ ID NO:44:

Asp Ile Ser Ile Glu Leu Asn Lys Ala Lys Ser Asp Leu Glu Ser
1               5                   10                  15

Lys Glu Trp Ile Arg Arg Ser Asn Gln Lys Leu Asp Ser Ile Gly Asn
            20                  25                  30

Trp His Gln
        35

(2) INFORMATION FOR SEQ ID NO:45:

(i) SEQUENCE CHARACTERISTICS:
                (A) LENGTH: 35 amino acids
                (B) TYPE: amino acid
                (C) STRANDEDNESS:
                (D) TOPOLOGY: unknown (ii) MOLECULE TYPE: peptide (ix) FEATURE:
                (A) NAME/KEY: Modified-site
                (B) LOCATION: 1
                (D) OTHER INFORMATION: /label= A
                    /note= "Preceeding this amino acid, there may be an
                    amino group, a hydrophobic group, an acetyl group, a
                    9-fluorenylmethoxycarbonyl group, or a macromolecular
                    carrier group."

(ix) FEATURE:
                (A) NAME/KEY: Modified-site
                (B) LOCATION: 48
                (D) OTHER INFORMATION: /label= B
                    /note= "Following this amino acid, there may be a
                    carboxyl group, an amido group, a T-butyloxycarbonyl
                    group, or a macromolecular carrier group."

(xi) SEQUENCE DESCRIPTION: SEQ ID NO:45:

Ile Ser Ile Glu Leu Asn Lys Ala Lys Ser Asp Leu Glu Glu Ser Lys
1               5                   10                  15

Glu Trp Ile Arg Arg Ser Asn Gln Lys Leu Asp Ser Ile Gly Asn Trp
            20                  25                  30

His Gln Ser
        35

(2) INFORMATION FOR SEQ ID NO:46:

(i) SEQUENCE CHARACTERISTICS:
                (A) LENGTH: 35 amino acids
                (B) TYPE: amino acid
                (C) STRANDEDNESS:
                (D) TOPOLOGY: unknown (ii) MOLECULE TYPE: peptide (ix) FEATURE:
                (A) NAME/KEY: Modified-site
                (B) LOCATION: 1
                (D) OTHER INFORMATION: /label= A /note= "Preceeding this amino acid, there may be an
                amino group, a hydrophobic group, an acetyl group, a
                9-fluorenylmethoxycarbonyl group, or a macromolecular
                carrier group."

(ix) FEATURE:
        (A) NAME/KEY: Modified-site
        (B) LOCATION: 48
        (D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:46:

Ser Ile Glu Leu Asn Lys Ala Lys Ser Asp Leu Glu Glu Ser Lys Glu
1               5                   10                  15

Trp Ile Arg Arg Ser Asn Gln Lys Leu Asp Ser Ile Gly Asn Trp His
            20                  25                  30

Gln Ser Ser
        35

(2) INFORMATION FOR SEQ ID NO:47:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
                /note= "Preceeding this amino acid, there may be an
                amino group, a hydrophobic group, an acetyl group, a
                9-fluorenylmethoxycarbonyl group, or a macromolecular
                carrier group."

(ix) FEATURE:
        (A) NAME/KEY: Modified-site
        (B) LOCATION: 48
        (D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:47:

Ile Glu Leu Asn Lys Ala Lys Ser Asp Leu Glu Glu Ser Lys Glu Trp
1               5                   10                  15

Ile Arg Arg Ser Asn Gln Lys Leu Asp Ser Ile Gly Asn Trp His Gln
            20                  25                  30

Ser Ser Thr
        35

(2) INFORMATION FOR SEQ ID NO:48:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
                /note= "Preceeding this amino acid, there may be an

```
            amino group, a hydrophobic group, an acetyl group, a
            9-fluorenylmethoxycarbonyl group, or a macromolecular
            carrier group."

(ix) FEATURE:
         (A) NAME/KEY: Modified-site
         (B) LOCATION: 48
         (D) OTHER INFORMATION: /label= B
             /note= "Following this amino acid, there may be a
             carboxyl group, an amido group, a T-butyloxycarbonyl
             group, or a macromolecular carrier group."

(xi) SEQUENCE DESCRIPTION: SEQ ID NO:48:

Glu Leu Asn Lys Ala Lys Ser Asp Leu Glu Glu Ser Lys Glu Trp Ile
1               5                   10                  15

Arg Arg Ser Asn Gln Lys Leu Asp Ser Ile Gly Asn Trp His Gln Ser
            20                  25                  30

Ser Thr Thr
        35

(2) INFORMATION FOR SEQ ID NO:49:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, a hydrophobic group, an acetyl group, a
             9-fluorenylmethoxycarbonyl group, or a macromolecular
             carrier group."

(ix) FEATURE:
         (A) NAME/KEY: Modified-site
         (B) LOCATION: 48
         (D) OTHER INFORMATION: /label= B
             /note= "Following this amino acid, there may be a
             carboxyl group, an amido group, a T-butyloxycarbonyl
             group, or a macromolecular carrier group."

(xi) SEQUENCE DESCRIPTION: SEQ ID NO:49:

Thr Ala Ala Val Ala Leu Val Glu Ala Lys Gln Ala Arg Ser Asp Ile
1               5                   10                  15

Glu Lys Leu Lys Glu Ala Ile Arg Asp Thr Asn Lys Ala Val Gln Ser
            20                  25                  30

Val Gln Ser
        35

(2) INFORMATION FOR SEQ ID NO:50:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, a hydrophobic group, an acetyl group, a
```

-continued

```
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:50:

Ala Val Ala Leu Val Glu Ala Lys Gln Ala Arg Ser Asp Ile Glu Lys
1               5                   10                  15

Leu Lys Glu Ala Ile Arg Asp Thr Asn Lys Ala Val Gln Ser Val Gln
            20                  25                  30

Ser Ser Ile
        35

(2) INFORMATION FOR SEQ ID NO:51:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:51:

Leu Val Glu Ala Lys Gln Ala Arg Ser Asp Ile Glu Lys Leu Lys Glu
1               5                   10                  15

Ala Ile Arg Asp Thr Asn Lys Ala Val Gln Ser Val Gln Ser Ser Ile
            20                  25                  30

Gly Asn Leu
        35

(2) INFORMATION FOR SEQ ID NO:52:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
``` carrier group."

(ix) FEATURE:
    (A) NAME/KEY: Modified-site
    (B) LOCATION: 48
    (D) OTHER INFORMATION: /label= B
        /note= "Following this amino acid, there may be a carboxyl group, an amido group, a T-butyloxycarbonyl group, or a macromolecular carrier group."

(xi) SEQUENCE DESCRIPTION: SEQ ID NO:52:

```
Val Glu Ala Lys Gln Ala Arg Ser Asp Ile Glu Lys Leu Lys Glu Ala
1               5                   10                  15

Ile Arg Asp Thr Asn Lys Ala Val Gln Ser Val Gln Ser Ser Ile Gly
            20                  25                  30

Asn Leu Ile
        35
```

(2) INFORMATION FOR SEQ ID NO:53:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino group, a hydrophobic group, an acetyl group, a 9-fluorenylmethoxycarbonyl group, or a macromolecular carrier group."

(ix) FEATURE:
        (A) NAME/KEY: Modified-site
        (B) LOCATION: 48
        (D) OTHER INFORMATION: /label= B
            /note= "Following this amino acid, there may be a carboxyl group, an amido group, a T-butyloxycarbonyl group, or a macromolecular carrier group."

(xi) SEQUENCE DESCRIPTION: SEQ ID NO:53:

```
Glu Ala Lys Gln Ala Arg Ser Asp Ile Glu Lys Leu Lys Glu Ala Ile
1               5                   10                  15

Arg Asp Thr Asn Lys Ala Val Gln Ser Val Gln Ser Ser Ile Gly Asn
            20                  25                  30

Leu Ile Val
        35
```

(2) INFORMATION FOR SEQ ID NO:54:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an amino group, a hydrophobic group, an acetyl group, a 9-fluorenylmethoxycarbonyl group, or a macromolecular carrier group."

(ix) FEATURE:
    (A) NAME/KEY: Modified-site
    (B) LOCATION: 48
    (D) OTHER INFORMATION: /label= B
        /note= "Following this amino acid, there may be a
        carboxyl group, an amido group, a T-butyloxycarbonyl
        group, or a macromolecular carrier group."

(xi) SEQUENCE DESCRIPTION: SEQ ID NO:54:

```
Ala Lys Gln Ala Arg Ser Asp Ile Glu Lys Leu Lys Glu Ala Ile Arg
1               5                   10                  15
Asp Thr Asn Lys Ala Val Gln Ser Val Gln Ser Ser Ile Gly Asn Leu
            20                  25                  30
Ile Val Ala
        35
```

(2) INFORMATION FOR SEQ ID NO:55:

(i) SEQUENCE CHARACTERISTICS:
    (A) LENGTH: 35 amino acids
    (B) TYPE: amino acid
    (C) STRANDEDNESS:
    (D) TOPOLOGY: unknown (ii) MOLECULE TYPE: peptide (ix) FEATURE:
    (A) NAME/KEY: Modified-site
    (B) LOCATION: 1
    (D) OTHER INFORMATION: /label= A
        /note= "Preceeding this amino acid, there may be an
        amino group, a hydrophobic group, an acetyl group, a
        9-fluorenylmethoxycarbonyl group, or a macromolecular
        carrier group."

(ix) FEATURE:
    (A) NAME/KEY: Modified-site
    (B) LOCATION: 48
    (D) OTHER INFORMATION: /label= B
        /note= "Following this amino acid, there may be a
        carboxyl group, an amido group, a T-butyloxycarbonyl
        group, or a macromolecular carrier group."

(xi) SEQUENCE DESCRIPTION: SEQ ID NO:55:

```
Lys Gln Ala Arg Ser Asp Ile Glu Lys Leu Lys Glu Ala Ile Arg Asp
1               5                   10                  15
Thr Asn Lys Ala Val Gln Ser Val Gln Ser Ser Ile Gly Asn Leu Ile
            20                  25                  30
Val Ala Ile
        35
```

(2) INFORMATION FOR SEQ ID NO:56:

(i) SEQUENCE CHARACTERISTICS:
    (A) LENGTH: 35 amino acids
    (B) TYPE: amino acid
    (C) STRANDEDNESS:
    (D) TOPOLOGY: unknown (ii) MOLECULE TYPE: peptide (ix) FEATURE:
    (A) NAME/KEY: Modified-site
    (B) LOCATION: 1
    (D) OTHER INFORMATION: /label= A
        /note= "Preceeding this amino acid, there may be an
        amino group, a hydrophobic group, an acetyl group, a
        9-fluorenylmethoxycarbonyl group, or a macromolecular
        carrier group."

```
    (ix) FEATURE:
         (A) NAME/KEY: Modified-site
         (B) LOCATION: 48
         (D) OTHER INFORMATION: /label= B
             /note= "Following this amino acid, there may be a
             carboxyl group, an amido group, a T-butyloxycarbonyl
             group, or a macromolecular carrier group."

(xi) SEQUENCE DESCRIPTION: SEQ ID NO:56:

Gln Ala Arg Ser Asp Ile Glu Lys Leu Lys Glu Ala Ile Arg Asp Thr
 1               5                  10                  15

Asn Lys Ala Val Gln Ser Val Gln Ser Ser Ile Gly Asn Leu Ile Val
                20                  25                  30

Ala Ile Lys
        35

(2) INFORMATION FOR SEQ ID NO:57:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:57:

Ala Arg Ser Asp Ile Glu Lys Leu Lys Glu Ala Ile Arg Asp Thr Asn
 1               5                  10                  15

Lys Ala Val Gln Ser Val Gln Ser Ser Ile Gly Asn Leu Ile Val Ala
                20                  25                  30

Ile Lys Ser
        35

(2) INFORMATION FOR SEQ ID NO:58:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
```

(A) NAME/KEY: Modified-site
            (B) LOCATION: 48
            (D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:58:

```
Arg Ser Asp Ile Glu Lys Leu Lys Glu Ala Ile Arg Asp Thr Asn Lys
1               5                   10                  15

Ala Val Gln Ser Val Gln Ser Ser Ile Gly Asn Leu Ile Val Ala Ile
            20                  25                  30

Lys Ser Val
        35
```

(2) INFORMATION FOR SEQ ID NO:59:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:59:

```
Ser Asp Ile Glu Lys Leu Lys Glu Ala Ile Arg Asp Thr Asn Lys Ala
1               5                   10                  15

Val Gln Ser Val Gln Ser Ser Ile Gly Asn Leu Ile Val Ala Ile Lys
            20                  25                  30

Ser Val Gln
        35
```

(2) INFORMATION FOR SEQ ID NO:60:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:60:

Lys Leu Lys Glu Ala Ile Arg Asp Thr Asn Lys Ala Val Gln Ser Val
1               5                  10                  15

Gln Ser Ser Ile Gly Asn Leu Ile Val Ala Ile Lys Ser Val Gln Asp
            20                  25                  30

Tyr Val Asn
        35

(2) INFORMATION FOR SEQ ID NO:61:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:61:

Leu Lys Glu Ala Ile Arg Asp Thr Asn Lys Ala Val Gln Ser Val Gln
1               5                  10                  15

Ser Ser Ile Gly Asn Leu Ile Val Ala Ile Lys Ser Val Gln Asp Tyr
            20                  25                  30

Val Asn Lys
        35

(2) INFORMATION FOR SEQ ID NO:62:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48

(D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:62:

Ala Ile Arg Asp Thr Asn Lys Ala Val Gln Ser Val Gln Ser Ser Ile
1               5                   10                  15

Gly Asn Leu Ile Val Ala Ile Lys Ser Val Gln Asp Tyr Val Asn Lys
                20                  25                  30

Glu Ile Val
        35

(2) INFORMATION FOR SEQ ID NO:63:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:63:

Trp Gln Glu Trp Glu Arg Lys Val Asp Phe Leu Glu Glu Asn Ile Thr
1               5                   10                  15

Ala Leu Leu Glu Glu Ala Gln Ile Gln Gln Glu Lys Asn Met Tyr Glu
                20                  25                  30

Leu Gln Lys
        35

(2) INFORMATION FOR SEQ ID NO:64:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B /note= "Following this amino acid, there may be a
carboxyl group, an amido group, a T-butyloxycarbonyl
group, or a macromolecular carrier group."

(xi) SEQUENCE DESCRIPTION: SEQ ID NO:64:

Gln Glu Trp Glu Arg Lys Val Asp Phe Leu Glu Glu Asn Ile Thr Ala
1               5                   10                  15

Leu Leu Glu Glu Ala Gln Ile Gln Gln Glu Lys Asn Met Tyr Glu Leu
            20                  25                  30

Gln Lys Leu
        35

(2) INFORMATION FOR SEQ ID NO:65:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:65:

Glu Trp Glu Arg Lys Val Asp Phe Leu Glu Glu Asn Ile Thr Ala Leu
1               5                   10                  15

Leu Glu Glu Ala Gln Ile Gln Gln Glu Lys Asn Met Tyr Glu Leu Gln
            20                  25                  30

Lys Leu Asn
        35

(2) INFORMATION FOR SEQ ID NO:66:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a carboxyl group, an amido group, a T-butyloxycarbonyl
            group, or a macromolecular carrier group."

(xi) SEQUENCE DESCRIPTION: SEQ ID NO:66:

Trp Glu Arg Lys Val Asp Phe Leu Glu Glu Asn Ile Thr Ala Leu Leu
1               5                   10                  15

Glu Glu Ala Gln Ile Gln Gln Glu Lys Asn Met Tyr Glu Leu Gln Lys
            20                  25                  30

Leu Asn Ser
        35

(2) INFORMATION FOR SEQ ID NO:67:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:67:

Glu Arg Lys Val Asp Phe Leu Glu Glu Asn Ile Thr Ala Leu Leu Glu
1               5                   10                  15

Glu Ala Gln Ile Gln Gln Glu Lys Asn Met Tyr Glu Leu Gln Lys Leu
            20                  25                  30

Asn Ser Trp
        35

(2) INFORMATION FOR SEQ ID NO:68:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl group, or a macromolecular carrier group."

(xi) SEQUENCE DESCRIPTION: SEQ ID NO:68:

Arg Lys Val Asp Phe Leu Glu Glu Asn Ile Thr Ala Leu Leu Glu Glu
1               5                   10                  15

Ala Gln Ile Gln Gln Glu Lys Asn Met Tyr Glu Leu Gln Lys Leu Asn
                20                  25                  30

Ser Trp Asp
        35

(2) INFORMATION FOR SEQ ID NO:69:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:69:

Lys Val Asp Phe Leu Glu Glu Asn Ile Thr Ala Leu Leu Glu Glu Ala
1               5                   10                  15

Gln Ile Gln Gln Glu Lys Asn Met Tyr Glu Leu Gln Lys Leu Asn Ser
                20                  25                  30

Trp Asp Val
        35

(2) INFORMATION FOR SEQ ID NO:70:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:70:

Val Asp Phe Leu Glu Glu Asn Ile Thr Ala Leu Leu Glu Glu Ala Gln
1               5                   10                  15

Ile Gln Gln Glu Lys Asn Met Tyr Glu Leu Gln Lys Leu Asn Ser Trp
                20                  25                  30

Asp Val Phe
        35

(2) INFORMATION FOR SEQ ID NO:71:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:71:

Asp Phe Leu Glu Glu Asn Ile Thr Ala Leu Leu Glu Glu Ala Gln Ile
1               5                   10                  15

Gln Gln Glu Lys Asn Met Tyr Glu Leu Gln Lys Leu Asn Ser Trp Asp
                20                  25                  30

Val Phe Gly
        35

(2) INFORMATION FOR SEQ ID NO:72:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:72:

Phe Leu Glu Glu Asn Ile Thr Ala Leu Leu Glu Ala Gln Ile Gln
1               5                   10                  15

Gln Glu Lys Asn Met Tyr Glu Leu Gln Lys Leu Asn Ser Trp Asp Val
            20                  25                  30

Phe Gly Asn
        35

(2) INFORMATION FOR SEQ ID NO:73:

(i) SEQUENCE CHARACTERISTICS:
      (A) LENGTH: 34 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label= A
        /note= "Preceeding this amino acid, there may be an
        amino group, a hydrophobic group, an acetyl group, a
        9-fluorenylmethoxycarbonyl group, or a macromolecular
        carrier group."

(ix) FEATURE:
      (A) NAME/KEY: Modified-site
      (B) LOCATION: 48
      (D) OTHER INFORMATION: /label= B
        /note= "Following this amino acid, there may be a
        carboxyl group, an amido group, a T-butyloxycarbonyl
        group, or a macromolecular carrier group."

(xi) SEQUENCE DESCRIPTION: SEQ ID NO:73:

Leu His Arg Ile Asp Leu Gly Pro Pro Ile Ser Leu Glu Arg Leu Asp
1               5                   10                  15

Val Gly Thr Asn Leu Gly Asn Ala Ile Ala Lys Leu Glu Ala Lys Glu
            20                  25                  30

Leu Leu (2) INFORMATION FOR SEQ ID NO:74:

(i) SEQUENCE CHARACTERISTICS:
      (A) LENGTH: 34 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label= A
        /note= "Preceeding this amino acid, there may be an
        amino group, a hydrophobic group, an ace
        tyl group, a 9-fluorenylmethoxycarbonyl group, or a
        macromolecular carrier group."

(ix) FEATURE:
      (A) NAME/KEY: Modified-site
      (B) LOCATION: 48
      (D) OTHER INFORMATION: /label= B
        /note= "Following this amino acid, there may be a
        carboxyl group, an amido group, a T-butyloxycarbonyl
        grow up, or a macromolecular carrier group.
        "SEQUENCE DESCRIPTION: SEQ ID NO:74:

His Arg Ile Asp Leu Gly Pro Pro Ile Ser Leu Glu Arg Leu Asp Val

```
             1               5                  10                 15
Gly Thr Asn Leu Gly Asn Ala Ile Ala Lys Leu Glu Ala Lys Glu Leu
             20                 25                 30
Leu Glu
```

NFORMATION FOR SEQ ID NO:75:

(i) SEQUENCE CHARACTERISTICS:
        (A) LENGTH: 34 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            car
            rier group."URE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:75:

```
ArgIle Asp Leu Gly Pro Pro Ile Ser Leu Glu Arg Leu Asp Val Gly
               5                  10                 15
Thr Asn Leu Gly Asn Ala Ile Ala Lys Leu Glu Ala Lys Glu Leu Leu
             20                 25                 30
Glu Ser
```

(2) INFORMATION FOR SEQ ID NO:76:

(i) SEQUENCE CHARACTERISTICS:
        (A) LENGTH: 34 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:76:

```
Ile Asp Leu Gly Pro Pro Ile Ser Leu Glu Arg Leu Asp Val Gly Thr
1              5                  10                 15
Asn Leu Gly Asn Ala Ile Ala Lys Leu Glu Ala Lys Glu Leu Leu Glu
             20                 25                 30
```

Ser Ser (2) INFORMATION FOR SEQ ID NO:77:

(i) SEQUENCE CHARACTERISTICS:
        (A) LENGTH: 34 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:77:

```
Asp Leu Gly Pro Pro Ile Ser Leu Glu Arg Leu Asp Val Gly Thr Asn
1               5                   10                  15

Leu Gly Asn Ala Ile Ala Lys Leu Glu Ala Lys Glu Leu Leu Glu Ser
            20                  25                  30

Ser Asp
```

(2) INFORMATION FOR SEQ ID NO:78:

(i) SEQUENCE CHARACTERISTICS:
        (A) LENGTH: 34 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:78:

```
Leu Gly Pro Pro Ile Ser Leu Glu Arg Leu Asp Val Gly Thr Asn Leu
1               5                   10                  15

Gly Asn Ala Ile Ala Lys Leu Glu Ala Lys Glu Leu Leu Glu Ser Ser
            20                  25                  30

Asp Gln
```

(2) INFORMATION FOR SEQ ID NO:79:

(i) SEQUENCE CHARACTERISTICS:
       (A) LENGTH: 34 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION: /label= A
           /note= "Preceeding this amino acid, there may be an
           amino group, a hydrophobic group, an acetyl group, a
           9-fluorenylmethoxycarbonyl group, or a macromolecular
           carrier group."

(ix) FEATURE:
       (A) NAME/KEY: Modified-site
       (B) LOCATION: 48
       (D) OTHER INFORMATION: /label= B
           /note= "Following this amino acid, there may be a
           carboxyl group, an amido group, a T-butyloxycarbonyl
           group, or a macromolecular carrier group."

(xi) SEQUENCE DESCRIPTION: SEQ ID NO:79:

Gly Pro Pro Ile Ser Leu Glu Arg Leu Asp Val Gly Thr Asn Leu Gly
1               5                   10                  15

Asn Ala Ile Ala Lys Leu Glu Ala Lys Glu Leu Leu Glu Ser Ser Asp
                20                  25                  30

Gln Ile (2) INFORMATION FOR SEQ ID NO:80:

(i) SEQUENCE CHARACTERISTICS:
       (A) LENGTH: 34 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION: /label= A
           /note= "Preceeding this amino acid, there may be an
           amino group, a hydrophobic group, an acetyl group, a
           9-fluorenylmethoxycarbonyl group, or a macromolecular
           carrier group."

(ix) FEATURE:
       (A) NAME/KEY: Modified-site
       (B) LOCATION: 48
       (D) OTHER INFORMATION: /label= B
           /note= "Following this amino acid, there may be a
           carboxyl group, an amido group, a T-butyloxycarbonyl
           group, or a macromolecular carrier group."

(xi) SEQUENCE DESCRIPTION: SEQ ID NO:80:

Pro Pro Ile Ser Leu Glu Arg Leu Asp Val Gly Thr Asn Leu Gly Asn
1               5                   10                  15

Ala Ile Ala Lys Leu Glu Ala Lys Glu Leu Leu Glu Ser Ser Asp Gln
                20                  25                  30

Ile Leu (2) INFORMATION FOR SEQ ID NO:81:

```
        (i) SEQUENCE CHARACTERISTICS:
            (A) LENGTH: 34 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, a hydrophobic group, an acetyl group, a
                9-fluorenylmethoxycarbonyl group, or a macromolecular
                carrier group."

(ix) FEATURE:
            (A) NAME/KEY: Modified-site
            (B) LOCATION: 48
            (D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:81:

Pro Ile Ser Leu Glu Arg Leu Asp Val Gly Thr Asn Leu Gly Asn Ala
1               5                  10                  15

Ile Ala Lys Leu Glu Ala Lys Glu Leu Leu Glu Ser Ser Asp Gln Ile
            20                  25                  30

Leu Arg (2) INFORMATION FOR SEQ ID NO:82:

(i) SEQUENCE CHARACTERISTICS:
            (A) LENGTH: 34 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, a hydrophobic group, an acetyl group, a
                9-fluorenylmethoxycarbonyl group, or a macromolecular
                carrier group."

(ix) FEATURE:
            (A) NAME/KEY: Modified-site
            (B) LOCATION: 48
            (D) OTHER INFORMATION: /label= B
                /note= "Following this amino acid, there may be a
                carboxyl group, an amido group, a T-butyloxycarbonyl
                group, or a macromolecular carrier group."

(xi) SEQUENCE DESCRIPTION: SEQ ID NO:82:

Ser Leu Glu Arg Leu Asp Val Gly Thr Asn Leu Gly Asn Ala Ile Ala
1               5                  10                  15

Lys Leu Glu Ala Lys Glu Leu Leu Glu Ser Ser Asp Gln Ile Leu Arg
            20                  25                  30

Ser Met (2) INFORMATION FOR SEQ ID NO:83:

(i) SEQUENCE CHARACTERISTICS:
            (A) LENGTH: 34 amino acids
            (B) TYPE: amino acid
```

```
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, a hydrophobic group, an acetyl group, a
            9-fluorenylmethoxycarbonyl group, or a macromolecular
            carrier group."

(ix) FEATURE:
        (A) NAME/KEY: Modified-site
        (B) LOCATION: 48
        (D) OTHER INFORMATION: /label= B
            /note= "Following this amino acid, there may be a
            carboxyl group, an amido group, a T-butyloxycarbonyl
            group, or a macromolecular carrier group."

(xi) SEQUENCE DESCRIPTION: SEQ ID NO:83:

Leu Glu Arg Leu Asp Val Gly Thr Asn Leu Gly Asn Ala Ile Ala Lys
 1               5                  10                  15

Leu Glu Ala Lys Glu Leu Leu Glu Ser Ser Asp Gln Ile Leu Arg Ser
             20                  25                  30

Met Lys (2) INFORMATION FOR SEQ ID NO:84:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:84:

Met Lys Gln Leu Glu Asp Lys Val Glu Glu Leu Leu Ser Lys Asn Tyr
 1               5                  10                  15

His Leu Glu Asn Glu Val Ala Arg Leu Lys Lys Leu
             20                  25

(2) INFORMATION FOR SEQ ID NO:85:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:85:

Thr Asp Thr Leu Gln Ala Glu Thr Asp Gln Leu Glu Asp Glu Lys Ser
 1               5                  10                  15

Ala Leu Gln Thr Glu Ile Ala Asn Leu Leu Lys Glu
             20                  25

(2) INFORMATION FOR SEQ ID NO:86:

(i) SEQUENCE CHARACTERISTICS:
        (A) LENGTH: 28 amino acids
        (B) TYPE: amino acid
        (C) STRANDEDNESS:
        (D) TOPOLOGY: unknown
```

(ii) MOLECULE TYPE: peptide (xi) SEQUENCE DESCRIPTION: SEQ ID NO:86:

Ile Ala Arg Leu Glu Glu Lys Val Lys Thr Leu Lys Ala Gln Asn Ser
1               5                   10                  15

Glu Leu Ala Ser Thr Ala Asn Met Leu Arg Glu Gln
            20                  25

(2) INFORMATION FOR SEQ ID NO:87:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:87:

Glu Gln Lys Leu Ile Ser Glu Glu Asp Leu Leu Arg Lys Arg Arg Glu
1               5                   10                  15

Gln Leu Lys His Lys Leu Glu Gln Leu Arg Asn Ser
            20                  25

(2) INFORMATION FOR SEQ ID NO:88:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:88:

Ile Glu Lys Thr Asn Glu Lys Phe His Gln Ile Glu Lys Glu Phe Ser
1               5                   10                  15

Glu Val Glu Gly Arg Ile Gln Asp Leu Glu Lys Tyr
            20                  25

(2) INFORMATION FOR SEQ ID NO:89:

(i) SEQUENCE CHARACTERISTICS:
        (A) LENGTH: 38 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:89:

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
            35

(2) INFORMATION FOR SEQ ID NO:90:

(i) SEQUENCE CHARACTERISTICS:
        (A) LENGTH: 338 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:90:

| Phe | Leu | Gly | Phe | Leu | Gly | Ala | Ala | Gly | Ser | Thr | Met | Gly | Ala | Arg | Ser |
|---|---|---|---|---|---|---|---|---|---|---|---|---|---|---|---|
| 1 | | | | 5 | | | | | 10 | | | | | 15 | |

| Met | Thr | Leu | Thr | Val | Gln | Ala | Arg | Gln | Leu | Leu | Ser | Gly | Ile | Val | Gln |
|---|---|---|---|---|---|---|---|---|---|---|---|---|---|---|---|
| | | | 20 | | | | | 25 | | | | | 30 | | |

| Gln | Gln | Asn | Asn | Leu | Leu | Arg | Ala | Ile | Glu | Ala | Gln | Gln | His | Leu | Leu |
|---|---|---|---|---|---|---|---|---|---|---|---|---|---|---|---|
| | | | 35 | | | | | 40 | | | | | 45 | | |

| Gln | Leu | Thr | Val | Trp | Gly | Ile | Lys | Gln | Leu | Gln | Ala | Arg | Ile | Leu | Ala |
|---|---|---|---|---|---|---|---|---|---|---|---|---|---|---|---|
| | 50 | | | | | 55 | | | | | 60 | | | | |

| Val | Glu | Arg | Tyr | Leu | Lys | Asp | Gln | Gln | Leu | Leu | Gly | Ile | Trp | Gly | Cys |
|---|---|---|---|---|---|---|---|---|---|---|---|---|---|---|---|
| 65 | | | | | 70 | | | | | 75 | | | | | 80 |

| Ser | Gly | Lys | Leu | Ile | Cys | Thr | Thr | Ala | Val | Pro | Trp | Asn | Ala | Ser | Trp |
|---|---|---|---|---|---|---|---|---|---|---|---|---|---|---|---|
| | | | | 85 | | | | | 90 | | | | | 95 | |

| Ser | Asn | Lys | Ser | Leu | Glu | Gln | Ile | Trp | Asn | Asn | Met | Thr | Trp | Met | Glu |
|---|---|---|---|---|---|---|---|---|---|---|---|---|---|---|---|
| | | | 100 | | | | | 105 | | | | | 110 | | |

| Trp | Asp | Arg | Glu | Ile | Asn | Asn | Tyr | Thr | Ser | Leu | Ile | His | Ser | Leu | Ile |
|---|---|---|---|---|---|---|---|---|---|---|---|---|---|---|---|
| | | | 115 | | | | | 120 | | | | | 125 | | |

| Glu | Glu | Ser | Gln | Asn | Gln | Gln | Glu | Lys | Asn | Glu | Gln | Glu | Leu | Leu | Glu |
|---|---|---|---|---|---|---|---|---|---|---|---|---|---|---|---|
| | 130 | | | | | 135 | | | | | 140 | | | | |

| Leu | Asp | Lys | Trp | Ala | Ser | Leu | Trp | Asn | Trp | Phe | Asn | Ile | Thr | Asn | Trp |
|---|---|---|---|---|---|---|---|---|---|---|---|---|---|---|---|
| 145 | | | | | 150 | | | | | 155 | | | | | 160 |

| Leu | Trp | Tyr | Ile | Lys | Ile | Phe | Ile | Met | Ile | Val | Gly | Gly | Leu | Val | Gly |
|---|---|---|---|---|---|---|---|---|---|---|---|---|---|---|---|
| | | | | 165 | | | | | 170 | | | | | 175 | |

| Leu | Arg | Ile | Val | Phe | Ala | Val | Leu | Ser | Ile | Val | Asn | Arg | Val | Arg | Gln |
|---|---|---|---|---|---|---|---|---|---|---|---|---|---|---|---|
| | | | 180 | | | | | 185 | | | | | 190 | | |

| Gly | Tyr | Ser | Pro | Leu | Ser | Phe | Gln | Thr | His | Leu | Pro | Thr | Pro | Arg | Gly |
|---|---|---|---|---|---|---|---|---|---|---|---|---|---|---|---|
| | | | 195 | | | | | 200 | | | | | 205 | | |

| Pro | Asp | Arg | Pro | Glu | Gly | Ile | Glu | Glu | Glu | Gly | Gly | Glu | Arg | Asp | Arg |
|---|---|---|---|---|---|---|---|---|---|---|---|---|---|---|---|
| | 210 | | | | | 215 | | | | | 220 | | | | |

| Asp | Arg | Ser | Ile | Arg | Leu | Val | Asn | Gly | Ser | Leu | Ala | Leu | Ile | Trp | Asp |
|---|---|---|---|---|---|---|---|---|---|---|---|---|---|---|---|
| 225 | | | | | 230 | | | | | 235 | | | | | 240 |

| Asp | Leu | Arg | Ser | Leu | Cys | Leu | Phe | Ser | Tyr | His | Arg | Leu | Arg | Asp | Leu |
|---|---|---|---|---|---|---|---|---|---|---|---|---|---|---|---|
| | | | | 245 | | | | | 250 | | | | | 255 | |

| Leu | Leu | Ile | Val | Thr | Arg | Ile | Val | Glu | Leu | Leu | Gly | Arg | Arg | Gly | Trp |
|---|---|---|---|---|---|---|---|---|---|---|---|---|---|---|---|
| | | | 260 | | | | | 265 | | | | | 270 | | |

| Glu | Ala | Leu | Lys | Tyr | Trp | Trp | Asn | Leu | Leu | Gln | Tyr | Trp | Ser | Gln | Glu |
|---|---|---|---|---|---|---|---|---|---|---|---|---|---|---|---|
| | | | 275 | | | | | 280 | | | | | 285 | | |

| Leu | Lys | Asn | Ser | Ala | Val | Ser | Leu | Leu | Asn | Ala | Thr | Ala | Ile | Ala | Val |
|---|---|---|---|---|---|---|---|---|---|---|---|---|---|---|---|
| | 290 | | | | | 295 | | | | | 300 | | | | |

| Ala | Glu | Gly | Thr | Asp | Arg | Val | Ile | Glu | Val | Val | Gln | Gly | Ala | Cys | Arg |
|---|---|---|---|---|---|---|---|---|---|---|---|---|---|---|---|
| 305 | | | | | 310 | | | | | 315 | | | | | 320 |

| Ala | Ile | Arg | His | Ile | Pro | Arg | Arg | Ile | Arg | Gln | Gly | Leu | Glu | Arg | Ile |
|---|---|---|---|---|---|---|---|---|---|---|---|---|---|---|---|
| | | | | 325 | | | | | 330 | | | | | 335 | |

Leu Leu (2) INFORMATION FOR SEQ ID NO:91:

(i) SEQUENCE CHARACTERISTICS:
        (A) LENGTH: 437 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:91:

```
Phe Leu Gly Phe Leu Gly Val Gly Ser Ala Ile Ala Ser Gly Val
1               5                   10                  15

Ala Val Ser Lys Val Leu His Leu Glu Gly Glu Val Asn Lys Ile Lys
            20                  25                  30

Ser Ala Leu Leu Ser Thr Asn Lys Ala Val Val Ser Leu Ser Asn Gly
            35                  40                  45

Val Ser Val Leu Thr Ser Lys Val Leu Asp Leu Lys Asn Tyr Ile Asp
50                  55                  60

Lys Gln Leu Leu Pro Ile Val Asn Lys Gln Ser Cys Ser Ile Ser Asn
65                  70                  75                  80

Ile Glu Thr Val Ile Glu Phe Gln Gln Lys Asn Asn Arg Leu Leu Glu
                85                  90                  95

Ile Thr Arg Glu Phe Ser Val Asn Ala Gly Val Thr Thr Pro Val Ser
            100                 105                 110

Thr Met Leu Thr Asn Ser Glu Leu Leu Ser Leu Ile Asn Asp Met Pro
            115                 120                 125

Ile Thr Asn Asp Gln Lys Lys Leu Met Ser Asn Asn Val Gln Ile Val
130                 135                 140

Arg Gln Gln Ser Tyr Ser Ile Met Ser Ile Ile Lys Glu Glu Val Leu
145                 150                 155                 160

Ala Tyr Val Val Gln Leu Pro Leu Tyr Gly Val Ile Asp Thr Pro Cys
            165                 170                 175

Trp Lys Leu His Thr Ser Pro Leu Cys Thr Thr Asn Thr Lys Glu Gly
            180                 185                 190

Ser Asn Ile Cys Leu Thr Arg Thr Asp Arg Gly Trp Tyr Cys Asp Asn
            195                 200                 205

Ala Gly Ser Val Ser Phe Phe Pro Gln Ala Glu Thr Cys Lys Val Gln
            210                 215                 220

Ser Asn Arg Val Phe Cys Asp Thr Met Asn Ser Leu Thr Leu Pro Ser
225                 230                 235                 240

Glu Ile Asn Leu Cys Asn Val Asp Ile Phe Asn Pro Lys Tyr Asp Cys
            245                 250                 255

Lys Ile Met Thr Ser Lys Thr Asp Val Ser Ser Ser Val Ile Thr Ser
            260                 265                 270

Leu Gly Ala Ile Val Ser Cys Tyr Gly Lys Thr Lys Cys Thr Ala Ser
            275                 280                 285

Asn Lys Asn Arg Gly Ile Ile Lys Thr Phe Ser Asn Gly Cys Asp Tyr
            290                 295                 300

Val Ser Asn Lys Gly Met Asp Thr Val Ser Val Gly Asn Thr Leu Tyr
305                 310                 315                 320

Tyr Val Asn Lys Gln Glu Gly Lys Ser Leu Tyr Val Lys Gly Glu Pro
            325                 330                 335

Ile Ile Asn Phe Tyr Asp Pro Leu Val Phe Pro Ser Asp Glu Phe Asp
            340                 345                 350

Ala Ser Ile Ser Gln Val Asn Glu Lys Ile Asn Gln Ser Leu Ala Phe
            355                 360                 365

Ile Arg Lys Ser Asp Glu Leu Leu His Asn Val Asn Ala Gly Lys Ser
            370                 375                 380

Thr Thr Asn Ile Met Ile Thr Thr Ile Ile Val Ile Ile Val Ile
385                 390                 395                 400

Leu Leu Ser Leu Ile Ala Val Gly Leu Leu Leu Tyr Cys Lys Ala Arg
```

```
                         405                 410                 415
Ser Thr Pro Val Thr Leu Ser Lys Asp Gln Leu Ser Gly Ile Asn Asn
                420                 425                 430
Ile Ala Phe Ser Asn
            435
```

(2) INFORMATION FOR SEQ ID NO:92:

(i) SEQUENCE CHARACTERISTICS:
        (A) LENGTH: 328 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:92:

```
Phe Leu Gly Phe Leu Gly Ala Ala Gly Thr Ala Met Gly Ala Ala Ala
1                   5                  10                  15
Thr Ala Leu Thr Val Gln Ser Gln His Leu Leu Ala Gly Ile Leu Gln
                20                  25                  30
Gln Gln Lys Asn Leu Leu Ala Ala Val Glu Ala Gln Gln Gln Met Leu
            35                  40                  45
Lys Leu Thr Ile Trp Gly Val Lys Asn Leu Asn Ala Arg Val Thr Ala
50                  55                  60
Leu Glu Lys Tyr Leu Glu Asp Gln Ala Arg Leu Asn Ala Trp Gly Cys
65                  70                  75                  80
Ala Trp Lys Gln Val Cys His Thr Thr Val Pro Trp Gln Trp Asn Asn
                85                  90                  95
Arg Thr Pro Asp Trp Asn Asn Met Thr Trp Leu Glu Trp Glu Arg Gln
            100                 105                 110
Ile Ser Tyr Leu Glu Gly Asn Ile Thr Thr Gln Leu Glu Glu Ala Arg
        115                 120                 125
Ala Gln Glu Glu Lys Asn Leu Asp Ala Tyr Gln Lys Leu Ser Ser Trp
130                 135                 140
Ser Asp Phe Trp Ser Trp Phe Asp Phe Ser Lys Trp Leu Asn Ile Leu
145                 150                 155                 160
Lys Ile Gly Phe Leu Asp Val Leu Gly Ile Ile Gly Leu Arg Leu Leu
                165                 170                 175
Tyr Thr Val Tyr Ser Cys Ile Ala Arg Val Arg Gln Gly Tyr Ser Pro
            180                 185                 190
Leu Ser Pro Gln Ile His Ile His Pro Trp Lys Gly Gln Pro Asp Asn
        195                 200                 205
Ala Glu Gly Pro Gly Glu Gly Asp Lys Arg Lys Asn Ser Ser Glu
210                 215                 220
Pro Trp Gln Lys Glu Ser Gly Thr Ala Glu Trp Lys Ser Asn Trp Cys
225                 230                 235                 240
Lys Arg Leu Thr Asn Trp Cys Ser Ile Ser Ile Trp Leu Tyr Asn
                245                 250                 255
Ser Cys Leu Thr Leu Leu Val His Leu Arg Ser Ala Phe Gln Tyr Ile
            260                 265                 270
Gln Tyr Gly Leu Gly Glu Leu Lys Ala Ala Ala Gln Glu Ala Val Val
        275                 280                 285
Ala Leu Ala Arg Leu Ala Gln Asn Ala Gly Tyr Gln Ile Trp Leu Ala
290                 295                 300
Cys Arg Ser Ala Tyr Arg Ala Ile Ile Asn Ser Pro Arg Arg Val Arg
```

-continued

```
305                 310                 315                 320
Gln Gly Leu Glu Gly Ile Leu Asn
                325

(2) INFORMATION FOR SEQ ID NO:93:

(i) SEQUENCE CHARACTERISTICS:
        (A) LENGTH: 438 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:93:

Phe Ala Gly Val Val Leu Ala Gly Val Ala Leu Gly Val Ala Thr Ala
1               5                   10                  15

Ala Gln Ile Thr Ala Gly Ile Ala Leu His Gln Ser Asn Leu Asn Ala
            20                  25                  30

Gln Ala Ile Gln Ser Leu Arg Thr Ser Leu Glu Gln Ser Asn Lys Ala
        35                  40                  45

Ile Glu Glu Ile Arg Glu Ala Thr Gln Glu Thr Val Ile Ala Val Gln
50                  55                  60

Gly Val Gln Asp Tyr Val Asn Asn Glu Leu Val Pro Ala Met Gln His
65                  70                  75                  80

Met Ser Cys Glu Leu Val Gly Gln Arg Leu Gly Leu Arg Leu Leu Arg
                85                  90                  95

Tyr Tyr Thr Glu Leu Leu Ser Ile Phe Gly Pro Ser Leu Arg Asp Pro
            100                 105                 110

Ile Ser Ala Glu Ile Ser Ile Gln Ala Leu Ile Tyr Ala Leu Gly Gly
        115                 120                 125

Glu Ile His Lys Ile Leu Glu Lys Leu Gly Tyr Ser Gly Ser Asp Met
130                 135                 140

Ile Ala Ile Leu Glu Ser Arg Gly Ile Lys Thr Lys Ile Thr His Val
145                 150                 155                 160

Asp Leu Pro Gly Lys Phe Ile Ile Leu Ser Ile Ser Tyr Pro Thr Leu
                165                 170                 175

Ser Glu Val Lys Gly Val Ile Val His Arg Leu Glu Ala Val Ser Tyr
            180                 185                 190

Asn Ile Gly Ser Gln Glu Trp Tyr Thr Thr Val Pro Arg Tyr Ile Ala
        195                 200                 205

Thr Asn Gly Tyr Leu Ile Ser Asn Phe Asp Glu Ser Ser Cys Val Phe
210                 215                 220

Val Ser Glu Ser Ala Ile Cys Ser Gln Asn Ser Leu Tyr Pro Met Ser
225                 230                 235                 240

Pro Leu Leu Gln Gln Cys Ile Arg Gly Asp Thr Ser Ser Cys Ala Arg
                245                 250                 255

Thr Leu Val Ser Gly Thr Met Gly Asn Lys Phe Ile Leu Ser Lys Gly
            260                 265                 270

Asn Ile Val Ala Asn Cys Ala Ser Ile Leu Cys Lys Cys Tyr Ser Thr
        275                 280                 285

Ser Thr Ile Ile Asn Gln Ser Pro Asp Lys Leu Leu Thr Phe Ile Ala
290                 295                 300

Ser Asp Thr Cys Pro Leu Val Glu Ile Asp Gly Ala Thr Ile Gln Val
305                 310                 315                 320

Gly Gly Arg Gln Tyr Pro Asp Met Val Tyr Glu Gly Lys Val Ala Leu
```

-continued

```
                      325                 330                 335
Gly Pro Ala Ile Ser Leu Asp Arg Leu Asp Val Gly Thr Asn Leu Gly
                340                 345                 350

Asn Ala Leu Lys Lys Leu Asp Asp Ala Lys Val Leu Ile Asp Ser Ser
            355                 360                 365

Asn Gln Ile Leu Glu Thr Val Arg Arg Ser Ser Phe Asn Phe Gly Ser
        370                 375                 380

Leu Leu Ser Val Pro Ile Leu Ser Cys Thr Ala Leu Ala Leu Leu Leu
385                 390                 395                 400

Leu Ile Tyr Cys Cys Lys Arg Arg Tyr Gln Gln Thr Leu Lys Gln His
                405                 410                 415

Thr Lys Val Asp Pro Ala Phe Lys Pro Asp Leu Thr Gly Thr Ser Lys
                420                 425                 430

Ser Tyr Val Arg Ser Leu
                435
```

(2) INFORMATION FOR SEQ ID NO:94:

(i) SEQUENCE CHARACTERISTICS:
        (A) LENGTH: 436 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:94:

```
Phe Ile Gly Ala Ile Gly Ser Val Ala Leu Gly Val Ala Thr Ala
1                   5                  10                  15

Ala Gln Ile Thr Ala Ala Ser Ala Leu Ile Gln Ala Asn Gln Asn Ala
                20                  25                  30

Ala Asn Ile Leu Arg Leu Lys Glu Ser Ile Thr Ala Thr Ile Glu Ala
            35                  40                  45

Val His Glu Val Thr Asp Gly Leu Ser Gln Leu Ala Val Ala Val Gly
        50                  55                  60

Lys Met Gln Gln Phe Val Asn Asp Gln Phe Asn Asn Thr Ala Gln Glu
65                  70                  75                  80

Leu Asp Cys Ile Lys Ile Thr Gln Gln Val Gly Val Glu Leu Asn Leu
                85                  90                  95

Tyr Leu Thr Glu Leu Thr Thr Val Phe Gly Pro Gln Ile Thr Ser Pro
                100                 105                 110

Ala Leu Thr Gln Leu Thr Ile Gln Ala Leu Tyr Asn Ala Gly Gly Asn
            115                 120                 125

Met Asp Tyr Leu Leu Thr Lys Leu Gly Val Gly Asn Asn Gln Leu Ser
        130                 135                 140

Ser Leu Ile Gly Ser Gly Leu Ile Thr Gly Asn Pro Ile Leu Tyr Asp
145                 150                 155                 160

Ser Gln Thr Gln Leu Leu Gly Ile Gln Val Thr Leu Pro Ser Val Gly
                165                 170                 175

Asn Leu Asn Asn Met Arg Ala Thr Tyr Leu Glu Thr Leu Ser Val Ser
            180                 185                 190

Thr Thr Lys Gly Phe Ala Ser Ala Leu Val Pro Lys Val Val Thr Gln
        195                 200                 205

Val Gly Ser Val Ile Glu Glu Leu Asp Thr Ser Tyr Cys Ile Glu Thr
    210                 215                 220

Asp Leu Asp Leu Tyr Cys Thr Arg Ile Val Thr Phe Pro Met Ser Pro
```

```
                      225                 230                 235                 240

Gly Ile Tyr Ser Cys Leu Asn Gly Asn Thr Ser Ala Cys Met Tyr Ser
                245                 250                 255

Lys Thr Glu Gly Ala Leu Thr Thr Pro Tyr Met Thr Leu Lys Gly Ser
                260                 265                 270

Val Ile Ala Asn Cys Lys Met Thr Thr Cys Arg Cys Ala Asp Pro Pro
                275                 280                 285

Gly Ile Ile Ser Gln Asn Tyr Gly Glu Ala Val Ser Leu Ile Asp Arg
                290                 295                 300

His Ser Cys Asn Val Leu Ser Leu Asp Gly Ile Thr Leu Arg Leu Ser
305                 310                 315                 320

Gly Glu Phe Asp Ala Thr Tyr Gln Lys Asn Ile Ser Ile Leu Asp Ser
                325                 330                 335

Gln Val Ile Val Thr Gly Asn Leu Asp Ile Ser Thr Glu Leu Gly Asn
                340                 345                 350

Val Asn Asn Ser Ile Ser Asn Ala Leu Asp Lys Leu Glu Glu Ser Asn
                355                 360                 365

Ser Lys Leu Asp Lys Val Asn Val Lys Leu Thr Ser Thr Ser Ala Leu
                370                 375                 380

Ile Thr Tyr Ile Ala Leu Thr Ala Ile Ser Leu Val Cys Gly Ile Leu
385                 390                 395                 400

Ser Leu Val Leu Ala Cys Tyr Leu Met Tyr Lys Gln Lys Ala Gln Gln
                405                 410                 415

Lys Thr Leu Leu Trp Leu Gly Asn Asn Thr Leu Gly Gln Met Arg Ala
                420                 425                 430

Thr Thr Lys Met
                435

(2) INFORMATION FOR SEQ ID NO:95:

(i) SEQUENCE CHARACTERISTICS:
        (A) LENGTH: 430 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:95:

Phe Phe Gly Gly Val Ile Gly Thr Ile Ala Leu Gly Val Ala Thr Ser
1               5                   10                  15

Ala Gln Ile Thr Ala Ala Val Ala Leu Val Glu Ala Lys Gln Ala Arg
                20                  25                  30

Ser Asp Ile Glu Lys Leu Lys Glu Ala Ile Arg Asp Thr Asn Lys Ala
                35                  40                  45

Val Gln Ser Val Gln Ser Ser Ile Gly Asn Leu Ile Val Ala Ile Lys
            50                  55                  60

Ser Val Gln Asp Tyr Val Asn Lys Glu Ile Val Pro Ser Ile Ala Arg
65                  70                  75                  80

Leu Gly Cys Glu Ala Ala Gly Leu Gln Leu Gly Ile Ala Leu Thr Gln
                85                  90                  95

His Tyr Ser Glu Leu Thr Asn Ile Phe Gly Asp Asn Ile Gly Ser Leu
                100                 105                 110

Gln Glu Lys Gly Ile Lys Leu Gln Gly Ile Ala Ser Leu Tyr Arg Thr
                115                 120                 125

Asn Ile Thr Glu Ile Phe Thr Thr Ser Thr Val Asp Lys Tyr Asp Ile
```

-continued

```
            130                 135                 140
Tyr Asp Leu Leu Phe Thr Glu Ser Ile Lys Val Arg Val Ile Asp Val
145                 150                 155                 160
Asp Leu Asn Asp Tyr Ser Ile Thr Leu Gln Val Arg Leu Pro Leu Leu
                165                 170                 175
Thr Arg Leu Leu Asn Thr Gln Ile Tyr Arg Val Asp Ser Ile Ser Tyr
                180                 185                 190
Asn Ile Gln Asn Arg Glu Trp Tyr Ile Pro Leu Pro Ser His Ile Met
                195                 200                 205
Thr Lys Gly Ala Phe Leu Gly Gly Ala Asp Val Lys Glu Cys Ile Glu
        210                 215                 220
Ala Phe Ser Ser Tyr Ile Cys Pro Ser Asp Pro Gly Phe Val Leu Asn
225                 230                 235                 240
His Glu Met Glu Ser Cys Leu Ser Gly Asn Ile Ser Gln Cys Pro Arg
                245                 250                 255
Thr Val Val Lys Ser Asp Ile Val Pro Arg Tyr Ala Phe Val Asn Gly
                260                 265                 270
Gly Val Val Ala Asn Cys Ile Thr Thr Thr Cys Thr Cys Asn Gly Ile
        275                 280                 285
Gly Asn Arg Ile Asn Gln Pro Pro Asp Gln Gly Val Lys Ile Ile Thr
        290                 295                 300
His Lys Glu Cys Asn Thr Ile Gly Ile Asn Gly Met Leu Phe Asn Thr
305                 310                 315                 320
Asn Lys Glu Gly Thr Leu Ala Phe Tyr Thr Pro Asn Asp Ile Thr Leu
                325                 330                 335
Asn Asn Ser Val Ala Leu Asp Pro Ile Asp Ile Ser Ile Glu Leu Asn
                340                 345                 350
Lys Ala Lys Ser Asp Leu Glu Glu Ser Lys Glu Trp Ile Arg Arg Ser
        355                 360                 365
Asn Gln Lys Leu Asp Ser Ile Gly Asn Trp His Gln Ser Ser Thr Thr
        370                 375                 380
Ile Ile Ile Val Leu Ile Met Ile Ile Ile Leu Phe Ile Ile Asn Val
385                 390                 395                 400
Thr Ile Ile Ile Ile Ala Val Lys Tyr Tyr Arg Ile Gln Lys Arg Asn
                405                 410                 415
Arg Val Asp Gln Asn Asp Lys Pro Tyr Val Leu Thr Asn Lys
                420                 425                 430
```

(2) INFORMATION FOR SEQ ID NO:96:

(i) SEQUENCE CHARACTERISTICS:
        (A) LENGTH: 221 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:96:

```
Gly Leu Phe Gly Ala Ile Ala Gly Phe Ile Glu Asn Gly Trp Glu Gly
1               5                   10                  15
Met Ile Asp Gly Trp Tyr Gly Phe Arg His Gln Asn Ser Glu Gly Thr
                20                  25                  30
Gly Gln Ala Ala Asp Leu Lys Ser Thr Gln Ala Ala Ile Asp Gln Ile
        35                  40                  45
Asn Gly Lys Leu Asn Arg Val Ile Glu Lys Thr Asn Glu Lys Phe His
```

-continued

```
                50                    55                    60
Gln Ile Glu Lys Glu Phe Ser Glu Val Glu Gly Arg Ile Gln Asp Leu
 65                    70                    75                    80

Glu Lys Tyr Val Glu Asp Thr Lys Ile Asp Leu Trp Ser Tyr Asn Ala
                85                    90                    95

Glu Leu Leu Val Ala Leu Glu Asn Gln His Thr Ile Asp Leu Thr Asp
                100                   105                   110

Ser Glu Met Asn Lys Leu Phe Glu Lys Thr Arg Arg Gln Leu Arg Glu
                115                   120                   125

Asn Ala Glu Glu Met Gly Asn Gly Cys Phe Lys Ile Tyr His Lys Cys
130                   135                   140

Asp Asn Ala Cys Ile Glu Ser Ile Arg Asn Gly Thr Tyr Asp His Asp
145                   150                   155                   160

Val Tyr Arg Asp Glu Ala Leu Asn Asn Arg Phe Gln Ile Lys Gly Val
                165                   170                   175

Glu Leu Lys Ser Gly Tyr Lys Asp Trp Ile Leu Trp Ile Ser Phe Ala
                180                   185                   190

Ile Ser Cys Phe Leu Leu Cys Val Val Leu Leu Gly Phe Ile Met Trp
                195                   200                   205

Ala Cys Gln Arg Gly Asn Ile Arg Cys Asn Ile Cys Ile
210                   215                   220
```

(2) INFORMATION FOR SEQ ID NO:97:

(i) SEQUENCE CHARACTERISTICS:
        (A) LENGTH: 46 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:97:

```
Tyr Thr Ser Val Ile Thr Ile Glu Leu Ser Asn Ile Lys Glu Asn Lys
 1                 5                   10                    15

Cys Asn Gly Ala Lys Val Lys Leu Ile Lys Gln Glu Leu Asp Lys Tyr
                20                    25                    30

Lys Asn Ala Val Thr Glu Leu Gln Leu Leu Met Gln Ser Thr
                35                    40                    45
```

(2) INFORMATION FOR SEQ ID NO:98:

(i) SEQUENCE CHARACTERISTICS:
        (A) LENGTH: 54 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:98:

```
Ala Ser Gly Val Ala Val Ser Lys Val Leu His Leu Glu Gly Glu Val
 1                 5                   10                    15

Asn Lys Ile Ala Leu Leu Ser Thr Asn Lys Ala Val Val Ser Leu Ser
                20                    25                    30

Asn Gly Val Ser Val Leu Thr Ser Lys Val Leu Asp Leu Lys Asn Tyr
                35                    40                    45

Ile Asp Lys Gln Leu Leu
 50
```

(2) INFORMATION FOR SEQ ID NO:99:

(i) SEQUENCE CHARACTERISTICS:
        (A) LENGTH: 53 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:99:

```
Gly Glu Pro Ile Ile Asn Phe Tyr Asp Pro Leu Val Phe Pro Ser Asp
 1               5                  10                  15

Glu Phe Asp Ala Ser Ile Ser Gln Val Asn Glu Lys Ile Asn Gln Ser
            20                  25                  30

Leu Ala Phe Ile Arg Lys Ser Asp Glu Leu Leu His Asn Val Asn Ala
        35                  40                  45

Gly Lys Ser Thr Thr
        50
```

(2) INFORMATION FOR SEQ ID NO:100:

(i) SEQUENCE CHARACTERISTICS:
        (A) LENGTH: 70 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:100:

```
Gly Thr Ile Ala Leu Gly Val Ala Thr Ser Ala Gln Ile Thr Ala Ala
 1               5                  10                  15

Val Ala Leu Val Glu Ala Lys Gln Ala Arg Ser Asp Ile Glu Lys Leu
            20                  25                  30

Lys Glu Ala Ile Arg Asp Thr Asn Lys Ala Val Gln Ser Val Gln Ser
        35                  40                  45

Ser Ile Gly Asn Leu Ile Val Ala Ile Lys Ser Val Gln Asp Tyr Val
    50                  55                  60

Asn Lys Glu Ile Val Pro
 65              70
```

(2) INFORMATION FOR SEQ ID NO:101:

(i) SEQUENCE CHARACTERISTICS:
        (A) LENGTH: 56 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:101:

```
Tyr Thr Pro Asn Asp Ile Thr Leu Asn Asn Ser Val Ala Leu Asp Pro
 1               5                  10                  15

Ile Asp Ile Ser Ile Glu Leu Asn Lys Ala Lys Ser Asp Leu Glu Glu
            20                  25                  30

Ser Lys Glu Trp Ile Arg Arg Ser Asn Gln Lys Leu Asp Ser Ile Gly
        35                  40                  45

Asn Trp His Gln Ser Ser Thr Thr
        50                  55
```

-continued (2) INFORMATION FOR SEQ ID NO:102:

(i) SEQUENCE CHARACTERISTICS:
        (A) LENGTH: 249 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:102:

```
Arg Asn Lys Arg Gly Val Phe Val Leu Gly Phe Leu Gly Phe Leu Ala
 1               5                  10                  15

Thr Ala Gly Ser Ala Met Gly Ala Ala Ser Xaa Xaa Xaa Xaa Ala Gln
            20                  25                  30

Ser Arg Thr Leu Leu Ala Gly Ile Val Gln Gln Gln Gln Gln Leu Leu
        35                  40                  45

Asp Val Val Lys Arg Gln Gln Glu Leu Leu Arg Leu Thr Val Trp Gly
    50                  55                  60

Thr Lys Asn Leu Gln Thr Arg Val Thr Ala Ile Glu Lys Tyr Leu Lys
 65                  70                  75                  80

Asp Gln Ala Gln Leu Asn Ala Trp Gly Cys Ala Phe Arg Gln Val Cys
                 85                  90                  95

His Thr Thr Val Pro Trp Pro Asn Ala Ser Leu Thr Pro Asp Trp Asn
            100                 105                 110

Asn Asp Thr Trp Gln Glu Trp Glu Arg Lys Val Asp Phe Leu Glu Glu
        115                 120                 125

Asn Ile Thr Ala Leu Leu Glu Glu Ala Gln Ile Gln Gln Glu Lys Asn
    130                 135                 140

Met Tyr Glu Leu Gln Lys Leu Asn Ser Trp Asp Val Phe Gly Asn Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Ile Tyr Ile Val Met Leu
            180                 185                 190

Ala Lys Leu Arg Gln Gly Tyr Arg Pro Val Phe Ser Ser Pro Pro Ser
        195                 200                 205

Tyr Phe Gln Xaa Thr His Thr Gln Gln Asp Pro Ala Leu Pro Thr Arg
    210                 215                 220

Glu Gly Lys Glu Gly Asp Gly Gly Glu Gly Gly Gly Asn Ser Ser Trp
225                 230                 235                 240

Pro Trp Gln Ile Glu Tyr Ile His Phe
                245
```

(2) INFORMATION FOR SEQ ID NO:103:

(i) SEQUENCE CHARACTERISTICS:
        (A) LENGTH: 856 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:103:

```
Met Thr Arg Arg Arg Val Leu Ser Val Val Leu Leu Ala Ala Leu
 1               5                  10                  15

Ala Cys Arg Leu Gly Ala Gln Thr Pro Glu Gln Pro Ala Pro Ala
            20                  25                  30
```

-continued

```
Thr Thr Val Gln Pro Thr Ala Thr Arg Gln Gln Thr Ser Phe Pro Phe
        35                  40                  45

Arg Val Cys Glu Leu Ser Ser His Gly Asp Leu Phe Arg Phe Ser Ser
 50                  55                  60

Asp Ile Gln Cys Pro Ser Phe Gly Thr Arg Glu Asn His Thr Glu Gly
65                   70                  75                  80

Leu Leu Met Val Phe Lys Asp Asn Ile Ile Pro Tyr Ser Phe Lys Val
            85                  90                  95

Arg Ser Tyr Thr Lys Ile Val Thr Asn Ile Leu Ile Tyr Asn Gly Trp
            100                 105                 110

Tyr Ala Asp Ser Val Thr Asn Arg His Glu Glu Lys Phe Ser Val Asp
        115                 120                 125

Ser Tyr Glu Thr Asp Gln Met Asp Thr Ile Tyr Gln Cys Tyr Asn Ala
    130                 135                 140

Val Lys Met Thr Lys Asp Gly Leu Thr Arg Val Tyr Val Asp Arg Asp
145                 150                 155                 160

Gly Val Asn Ile Thr Val Asn Leu Lys Pro Thr Gly Gly Leu Ala Asn
                165                 170                 175

Gly Val Arg Arg Tyr Ala Ser Gln Thr Glu Leu Tyr Asp Ala Pro Gly
            180                 185                 190

Trp Leu Ile Trp Thr Tyr Arg Thr Arg Thr Thr Val Asn Cys Leu Ile
        195                 200                 205

Thr Asp Met Met Ala Lys Ser Asn Ser Pro Phe Asp Phe Val Thr
210                 215                 220

Thr Thr Gly Gln Thr Val Glu Met Ser Pro Phe Tyr Asp Gly Lys Asn
225                 230                 235                 240

Lys Glu Thr Phe His Glu Arg Ala Asp Ser Phe His Val Arg Thr Asn
            245                 250                 255

Tyr Lys Ile Val Asp Tyr Asp Asn Arg Gly Thr Asn Pro Gln Gly Glu
                260                 265                 270

Arg Arg Ala Phe Leu Asp Lys Gly Thr Tyr Thr Leu Ser Trp Lys Leu
            275                 280                 285

Glu Asn Arg Thr Ala Tyr Cys Pro Leu Gln His Trp Gln Thr Phe Asp
290                 295                 300

Ser Thr Ile Ala Thr Glu Thr Gly Lys Ser Ile His Phe Val Thr Asp
305                 310                 315                 320

Glu Gly Thr Ser Ser Phe Val Thr Asn Thr Thr Val Gly Ile Glu Leu
                325                 330                 335

Pro Asp Ala Phe Lys Cys Ile Glu Glu Gln Val Asn Lys Thr His Glu
            340                 345                 350

Lys Tyr Glu Ala Val Gln Asp Arg Tyr Thr Lys Gly Gln Glu Ala Ile
        355                 360                 365

Thr Tyr Phe Ile Thr Ser Gly Leu Leu Leu Ala Trp Leu Pro Leu
    370                 375                 380

Thr Pro Arg Ser Leu Ala Thr Val Lys Asn Leu Thr Glu Leu Thr Thr
385                 390                 395                 400

Pro Thr Ser Ser Pro Pro Ser Ser Pro Pro Ala Pro Ser Ala
            405                 410                 415

Ala Arg Gly Ser Thr Pro Ala Ala Val Leu Arg Arg Arg Arg Asp
            420                 425                 430

Ala Gly Asn Ala Thr Thr Pro Val Pro Pro Thr Ala Pro Gly Lys Ser
            435                 440                 445

Leu Gly Thr Leu Asn Asn Pro Ala Thr Val Gln Ile Gln Phe Ala Tyr
```

```
            450                 455                 460
Asp Ser Leu Arg Arg Gln Ile Asn Arg Met Leu Gly Asp Leu Ala Arg
465                 470                 475                 480

Ala Trp Cys Leu Glu Gln Lys Arg Gln Asn Met Val Leu Arg Glu Leu
                485                 490                 495

Thr Lys Ile Asn Pro Thr Thr Val Met Ser Ile Tyr Gly Lys Ala
                500                 505             510

Val Ala Ala Lys Arg Leu Gly Asp Val Ile Ser Val Ser Gln Cys Val
            515                 520                 525

Pro Val Asn Gln Ala Thr Val Thr Leu Arg Lys Ser Met Arg Val Pro
        530                 535                 540

Gly Ser Glu Thr Met Cys Tyr Ser Arg Pro Leu Val Ser Phe Ser Phe
545                 550                 555                 560

Ile Asn Asp Thr Lys Thr Tyr Glu Gly Gln Leu Gly Thr Asp Asn Glu
                565                 570                 575

Ile Phe Leu Thr Lys Lys Met Thr Glu Val Cys Gln Ala Thr Ser Gln
                580                 585                 590

Tyr Tyr Phe Gln Ser Gly Asn Glu Ile His Val Tyr Asn Asp Tyr His
            595                 600                 605

His Phe Lys Thr Ile Glu Leu Asp Gly Ile Ala Thr Leu Gln Thr Phe
        610                 615                 620

Ile Ser Leu Asn Thr Ser Leu Ile Glu Asn Ile Asp Phe Ala Ser Leu
625                 630                 635                 640

Glu Leu Tyr Ser Arg Asp Glu Gln Arg Ala Ser Asn Val Phe Asp Leu
                645                 650                 655

Glu Gly Ile Phe Arg Glu Tyr Asn Phe Gln Ala Gln Asn Ile Ala Gly
                660                 665                 670

Leu Arg Lys Asp Leu Asp Asn Ala Val Ser Asn Gly Arg Asn Gln Phe
            675                 680                 685

Val Asp Gly Leu Gly Glu Leu Met Asp Ser Leu Gly Ser Val Gly Gln
        690                 695                 700

Ser Ile Thr Asn Leu Val Ser Thr Val Gly Gly Leu Phe Ser Ser Leu
705                 710                 715                 720

Val Ser Gly Phe Ile Ser Phe Phe Lys Asn Pro Phe Gly Gly Met Leu
                725                 730                 735

Ile Leu Val Leu Val Ala Gly Val Val Ile Leu Val Ile Ser Leu Thr
            740                 745                 750

Arg Arg Thr Arg Gln Met Ser Gln Gln Pro Val Gln Met Leu Tyr Pro
        755                 760                 765

Gly Ile Asp Glu Leu Ala Gln Gln His Ala Ser Gly Glu Gly Pro Gly
770                 775                 780

Ile Asn Pro Ile Ser Lys Thr Glu Leu Gln Ala Ile Met Leu Ala Leu
785                 790                 795                 800

His Glu Gln Asn Gln Glu Gln Lys Arg Ala Ala Gln Arg Ala Ala Gly
                805                 810                 815

Pro Ser Val Ala Ser Arg Ala Leu Gln Ala Ala Arg Asp Arg Phe Pro
            820                 825                 830

Gly Leu Arg Arg Arg Arg Tyr His Asp Pro Glu Thr Ala Ala Ala Leu
        835                 840                 845

Leu Gly Glu Ala Glu Thr Glu Phe
    850                 855
```

(2) INFORMATION FOR SEQ ID NO:104:

(i) SEQUENCE CHARACTERISTICS:
        (A) LENGTH: 245 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:104:

Met Met Asp Pro Asn Ser Thr Ser Glu Asp Val Lys Phe Thr Pro Asp
1               5                  10                  15

Pro Tyr Gln Val Pro Phe Val Gln Ala Phe Asp Gln Ala Thr Arg Val
                20                  25                  30

Tyr Gln Asp Leu Gly Gly Pro Ser Gln Ala Pro Leu Pro Cys Val Leu
            35                  40                  45

Trp Pro Val Leu Pro Glu Pro Leu Pro Gln Gly Gln Leu Thr Ala Tyr
        50                  55                  60

His Val Ser Thr Ala Pro Thr Gly Ser Trp Phe Ser Ala Pro Gln Pro
65                  70                  75                  80

Ala Pro Glu Asn Ala Tyr Gln Ala Tyr Ala Ala Pro Gln Leu Phe Pro
                85                  90                  95

Val Ser Asp Ile Thr Gln Asn Gln Gln Thr Asn Gln Ala Gly Gly Glu
            100                 105                 110

Ala Pro Gln Pro Gly Asp Asn Ser Thr Val Gln Thr Ala Ala Ala Val
        115                 120                 125

Val Phe Ala Cys Pro Gly Ala Asn Gln Gly Gln Gln Leu Ala Asp Ile
    130                 135                 140

Gly Val Pro Gln Pro Ala Pro Val Ala Ala Pro Ala Arg Arg Thr Arg
145                 150                 155                 160

Lys Pro Gln Gln Pro Glu Ser Leu Glu Glu Cys Asp Ser Glu Leu Glu
                165                 170                 175

Ile Lys Arg Tyr Lys Asn Arg Val Ala Ser Arg Lys Cys Arg Ala Lys
            180                 185                 190

Phe Lys Gln Leu Leu Gln His Tyr Arg Glu Val Ala Ala Ala Lys Ser
        195                 200                 205

Ser Glu Asn Asp Arg Leu Arg Leu Leu Leu Lys Gln Met Cys Pro Ser
210                 215                 220

Leu Asp Val Asp Ser Ile Ile Pro Arg Thr Pro Asp Val Leu His Glu
225                 230                 235                 240

Asp Leu Leu Asn Phe
            245

(2) INFORMATION FOR SEQ ID NO:105:

(i) SEQUENCE CHARACTERISTICS:
        (A) LENGTH: 438 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:105:

Phe Ala Gly Val Val Leu Ala Gly Ala Ala Leu Gly Val Ala Thr Ala
1               5                   10                  15

Ala Gln Ile Thr Ala Gly Ile Ala Leu His Gln Ser Met Leu Asn Ser
                20                  25                  30

Gln Ala Ile Asp Asn Leu Arg Ala Ser Leu Glu Thr Thr Asn Gln Ala

```
                35                  40                  45
Ile Glu Ala Ile Arg Gln Ala Gly Gln Glu Met Ile Leu Ala Val Gln
 50                  55                  60

Gly Val Gln Asp Tyr Ile Asn Asn Glu Leu Ile Pro Ser Met Asn Gln
 65                  70                  75                  80

Leu Ser Cys Asp Leu Ile Gly Gln Lys Leu Gly Leu Lys Leu Leu Arg
                 85                  90                  95

Tyr Tyr Thr Glu Ile Leu Ser Leu Phe Gly Pro Ser Leu Arg Asp Pro
                100                 105                 110

Ile Ser Ala Glu Ile Ser Ile Gln Ala Leu Ser Tyr Ala Leu Gly Gly
                115                 120                 125

Asp Ile Asn Lys Val Leu Glu Lys Leu Gly Tyr Ser Gly Gly Asp Leu
130                 135                 140

Leu Gly Ile Leu Glu Ser Arg Gly Ile Lys Ala Arg Ile Thr His Val
145                 150                 155                 160

Asp Thr Glu Ser Tyr Phe Ile Val Leu Ser Ile Ala Tyr Pro Thr Leu
                165                 170                 175

Ser Glu Ile Lys Gly Val Ile Val His Arg Leu Glu Gly Val Ser Tyr
                180                 185                 190

Asn Ile Gly Ser Gln Glu Trp Tyr Thr Thr Val Pro Lys Tyr Val Ala
                195                 200                 205

Thr Gln Gly Tyr Leu Ile Ser Asn Phe Asp Glu Ser Ser Cys Thr Phe
210                 215                 220

Met Pro Glu Gly Thr Val Cys Ser Gln Asn Ala Leu Tyr Pro Met Ser
225                 230                 235                 240

Pro Leu Leu Gln Glu Cys Leu Arg Gly Ser Thr Lys Ser Cys Ala Arg
                245                 250                 255

Thr Leu Val Ser Gly Ser Phe Gly Asn Arg Phe Ile Leu Ser Gln Gly
                260                 265                 270

Asn Leu Ile Ala Asn Cys Ala Ser Ile Leu Cys Lys Cys Tyr Thr Thr
                275                 280                 285

Gly Thr Ile Ile Asn Gln Asp Pro Asp Lys Ile Leu Thr Tyr Ile Ala
                290                 295                 300

Ala Asp His Cys Pro Val Val Glu Val Asn Gly Val Thr Ile Gln Val
305                 310                 315                 320

Gly Ser Arg Arg Tyr Pro Asp Ala Val Tyr Leu His Arg Ile Asp Leu
                325                 330                 335

Gly Pro Pro Ile Ser Leu Glu Arg Leu Asp Val Gly Thr Asn Leu Gly
                340                 345                 350

Asn Ala Ile Ala Lys Leu Glu Asp Ala Lys Glu Leu Leu Glu Ser Ser
                355                 360                 365

Asp Gln Ile Leu Arg Ser Met Lys Gly Leu Ser Ser Thr Ser Ile Val
370                 375                 380

Tyr Ile Leu Ile Ala Val Cys Leu Gly Gly Leu Ile Gly Ile Pro Ala
385                 390                 395                 400

Leu Ile Cys Cys Cys Arg Gly Arg Cys Asn Lys Lys Gly Glu Gln Val
                405                 410                 415

Gly Met Ser Arg Pro Gly Leu Lys Pro Asp Leu Thr Gly Thr Ser Lys
                420                 425                 430

Ser Tyr Val Arg Ser Leu
                435

(2) INFORMATION FOR SEQ ID NO:106:
```

```
    (i) SEQUENCE CHARACTERISTICS:
         (A) LENGTH: 389 amino acids
         (B) TYPE: amino acid
         (C) STRANDEDNESS:
         (D) TOPOLOGY: unknown (ii) MOLECULE TYPE: protein (xi) SEQUENCE DESCRIPTION: SEQ ID NO:106:

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Gly Thr Val Asn Pro Val Leu
    130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Ser Thr Gly Pro Cys Arg Thr Cys Met
        275                 280                 285

Thr Thr Ala Gln Gly Thr Ser Met Tyr Pro Ser Cys Cys Cys Thr Lys
290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Val Ile Trp Met Met Trp Tyr Trp Gly Pro Ser Leu
        355                 360                 365
```

-continued

```
Tyr Ser Ile Leu Ser Pro Phe Leu Pro Leu Pro Ile Phe Phe Cys
    370             375             380

Leu Trp Val Tyr Ile
385
```

(2) INFORMATION FOR SEQ ID NO:107:

(i) SEQUENCE CHARACTERISTICS:
        (A) LENGTH: 192 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:107:

```
Ala Ile Gln Leu Ile Pro Leu Phe Val Gly Leu Gly Ile Thr Thr Ala
1               5                   10                  15

Val Ser Thr Gly Ala Ala Gly Leu Gly Val Ser Ile Thr Gln Tyr Thr
            20                  25                  30

Lys Leu Ser His Gln Leu Ile Ser Asp Val Gln Ala Ile Ser Ser Thr
        35                  40                  45

Ile Gln Asp Leu Gln Asp Gln Val Asp Ser Leu Ala Glu Val Val Leu
    50                  55                  60

Gln Asn Arg Arg Gly Leu Asp Leu Leu Thr Ala Glu Gln Gly Gly Ile
65                  70                  75                  80

Cys Leu Ala Leu Gln Glu Lys Cys Cys Phe Tyr Ala Asn Lys Ser Gly
                85                  90                  95

Ile Val Arg Asp Lys Ile Lys Asn Leu Gln Asp Asp Leu Glu Arg Arg
            100                 105                 110

Arg Arg Gln Leu Ile Asp Asn Pro Phe Trp Thr Ser Phe His Gly Phe
        115                 120                 125

Leu Pro Tyr Val Met Pro Leu Leu Gly Pro Leu Leu Cys Leu Leu Leu
    130                 135                 140

Val Leu Ser Phe Gly Pro Ile Ile Phe Asn Lys Leu Met Thr Phe Ile
145                 150                 155                 160

Lys His Gln Ile Glu Ser Ile Gln Ala Lys Pro Ile Gln Val His Tyr
                165                 170                 175

His Arg Leu Glu Gln Glu Asp Ser Gly Gly Ser Tyr Leu Thr Leu Thr
            180                 185                 190
```

(2) INFORMATION FOR SEQ ID NO:108:

(i) SEQUENCE CHARACTERISTICS:
        (A) LENGTH: 154 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:108:

```
Met Lys Ala Gln Lys Gly Phe Thr Leu Ile Glu Leu Met Ile Val Val
1               5                   10                  15

Ala Ile Ile Gly Ile Leu Ala Ala Ile Ala Ile Pro Gln Tyr Gln Asp
            20                  25                  30

Tyr Thr Ala Arg Thr Gln Val Thr Arg Ala Val Ser Glu Val Ser Ala
        35                  40                  45

Leu Lys Thr Ala Ala Glu Ser Ala Ile Leu Glu Gly Lys Glu Ile Val
```

```
            50                  55                  60
Ser Ser Ala Thr Pro Lys Asp Thr Gln Tyr Asp Ile Gly Phe Thr Glu
65                  70                  75                  80

Ser Thr Leu Leu Asp Gly Ser Gly Lys Ser Gln Ile Gln Val Thr Asp
                85                  90                  95

Asn Gln Asp Gly Thr Val Glu Leu Val Ala Thr Leu Gly Lys Ser Ser
            100                 105                 110

Gly Ser Ala Ile Lys Gly Ala Val Ile Thr Val Ser Arg Lys Asn Asp
            115                 120                 125

Gly Val Trp Asn Cys Lys Ile Thr Lys Thr Pro Thr Ala Trp Lys Pro
130                 135                 140

Asn Tyr Ala Pro Ala Asn Cys Pro Lys Ser
145                 150
```

(2) INFORMATION FOR SEQ ID NO:109:

(i) SEQUENCE CHARACTERISTICS:
        (A) LENGTH: 167 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:109:

```
Met Asn Thr Leu Gln Lys Gly Phe Thr Leu Ile Glu Leu Met Ile Val
1                   5                   10                  15

Ile Ala Ile Val Gly Ile Leu Ala Ala Val Ala Leu Pro Ala Tyr Gln
                20                  25                  30

Asp Tyr Thr Ala Arg Ala Gln Val Ser Glu Ala Ile Leu Leu Ala Glu
            35                  40                  45

Gly Gln Lys Ser Ala Val Thr Glu Tyr Tyr Leu Asn His Gly Ile Trp
50                  55                  60

Pro Lys Asp Asn Thr Ser Ala Gly Val Ala Ser Ser Ser Ile Lys
65                  70                  75                  80

Gly Lys Tyr Val Lys Glu Val Lys Val Glu Asn Gly Val Val Thr Ala
                85                  90                  95

Thr Met Asn Ser Ser Asn Val Asn Lys Glu Ile Gln Gly Lys Lys Leu
            100                 105                 110

Ser Leu Trp Ala Lys Arg Gln Asp Gly Ser Val Lys Trp Phe Cys Gly
        115                 120                 125

Gln Pro Val Thr Arg Asn Ala Lys Asp Asp Thr Val Thr Ala Asp Ala
130                 135                 140

Thr Gly Asn Asp Gly Lys Ile Asp Thr Lys His Leu Pro Ser Thr Cys
145                 150                 155                 160

Arg Asp Asn Phe Asp Ala Ser
                165
```

(2) INFORMATION FOR SEQ ID NO:110:

(i) SEQUENCE CHARACTERISTICS:
        (A) LENGTH: 213 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:110:

```
Met Lys Lys Thr Leu Leu Gly Ser Leu Ile Leu Leu Ala Phe Ala Gly
1               5                   10                  15

Asn Val Gln Ala Asp Ile Asn Thr Glu Thr Ser Gly Lys Val Thr Phe
                20                  25                  30

Phe Gly Lys Val Val Glu Asn Thr Cys Lys Val Lys Thr Glu His Lys
            35                  40                  45

Asn Leu Ser Val Val Leu Asn Asp Val Gly Lys Asn Ser Leu Ser Thr
    50                  55                  60

Lys Val Asn Thr Ala Met Pro Thr Pro Phe Thr Ile Thr Leu Gln Asn
65                  70                  75                  80

Cys Asp Pro Thr Thr Ala Asn Gly Thr Ala Asn Lys Ala Asn Lys Val
                85                  90                  95

Gly Leu Tyr Phe Tyr Ser Trp Lys Asn Val Asp Lys Glu Asn Asn Phe
                100                 105                 110

Thr Leu Lys Asn Glu Gln Thr Thr Ala Asp Tyr Ala Thr Asn Val Asn
            115                 120                 125

Ile Gln Leu Met Glu Ser Asn Gly Thr Lys Ala Ile Ser Val Val Gly
    130                 135                 140

Lys Glu Thr Glu Asp Phe Met His Thr Asn Asn Asn Gly Val Ala Leu
145                 150                 155                 160

Asn Gln Thr His Pro Asn Asn Ala His Ile Ser Gly Ser Thr Gln Leu
                165                 170                 175

Thr Thr Gly Thr Asn Glu Leu Pro Leu His Phe Ile Ala Gln Tyr Tyr
                180                 185                 190

Ala Thr Asn Lys Ala Thr Ala Gly Lys Val Gln Ser Ser Val Asp Phe
                195                 200                 205

Gln Ile Ala Tyr Glu
        210
```

(2) INFORMATION FOR SEQ ID NO:111:

(i) SEQUENCE CHARACTERISTICS:
        (A) LENGTH: 234 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:111:

```
Met Asn Lys Lys Leu Leu Met Asn Phe Phe Ile Val Ser Pro Leu Leu
1               5                   10                  15

Leu Ala Thr Thr Ala Thr Asp Phe Thr Pro Val Pro Leu Ser Ser Asn
                20                  25                  30

Gln Ile Ile Lys Thr Ala Lys Ala Ser Thr Asn Asp Asn Ile Lys Asp
            35                  40                  45

Leu Leu Asp Trp Tyr Ser Ser Gly Ser Asp Thr Phe Thr Asn Ser Glu
    50                  55                  60

Val Leu Asp Asn Ser Leu Gly Ser Met Arg Ile Lys Asn Thr Asp Gly
65                  70                  75                  80

Ser Ile Ser Leu Ile Ile Phe Pro Ser Pro Tyr Tyr Ser Pro Ala Phe
                85                  90                  95

Thr Lys Gly Glu Lys Val Asp Leu Asn Thr Lys Arg Thr Lys Lys Ser
            100                 105                 110

Gln His Thr Ser Glu Gly Thr Tyr Ile His Phe Gln Ile Ser Gly Val
            115                 120                 125
```

```
Thr Asn Thr Glu Lys Leu Pro Thr Pro Ile Glu Leu Pro Leu Lys Val
    130                 135                 140

Lys Val His Gly Lys Asp Ser Pro Leu Lys Tyr Gly Pro Lys Phe Asp
145                 150                 155                 160

Lys Lys Gln Leu Ala Ile Ser Thr Leu Asp Phe Glu Ile Arg His Gln
                165                 170                 175

Leu Thr Gln Ile His Gly Leu Tyr Arg Ser Ser Asp Lys Thr Gly Gly
            180                 185                 190

Tyr Trp Lys Ile Thr Met Asn Asp Gly Ser Thr Tyr Gln Ser Asp Leu
        195                 200                 205

Ser Lys Lys Phe Glu Tyr Asn Thr Glu Lys Pro Pro Ile Asn Ile Asp
    210                 215                 220

Glu Ile Lys Thr Ile Glu Ala Glu Ile Asn
225                 230
```

(2) INFORMATION FOR SEQ ID NO:112:

(i) SEQUENCE CHARACTERISTICS:
        (A) LENGTH: 257 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:112:

```
Met Lys Lys Thr Ala Phe Ile Leu Leu Leu Phe Ile Ala Leu Thr Leu
1               5                   10                  15

Thr Thr Ser Pro Leu Val Asn Gly Ser Glu Lys Ser Glu Glu Ile Asn
                20                  25                  30

Glu Lys Asp Leu Arg Lys Lys Ser Glu Leu Gln Arg Asn Ala Leu Ser
            35                  40                  45

Asn Leu Arg Gln Ile Tyr Tyr Tyr Asn Glu Lys Ala Ile Thr Glu Asn
        50                  55                  60

Lys Glu Ser Asp Asp Gln Phe Leu Glu Asn Thr Leu Leu Phe Lys Gly
65                  70                  75                  80

Phe Phe Thr Gly His Pro Trp Tyr Asn Asp Leu Leu Val Asp Leu Gly
                85                  90                  95

Ser Lys Asp Ala Thr Asn Lys Tyr Lys Gly Lys Lys Val Asp Leu Tyr
            100                 105                 110

Gly Ala Tyr Tyr Gly Tyr Gln Cys Ala Gly Gly Thr Pro Asn Lys Thr
        115                 120                 125

Ala Cys Met Tyr Gly Gly Val Thr Leu His Asp Asn Asn Arg Leu Thr
130                 135                 140

Glu Glu Lys Lys Val Pro Ile Asn Leu Trp Ile Asp Gly Lys Gln Thr
145                 150                 155                 160

Thr Val Pro Ile Asp Lys Val Lys Thr Ser Lys Lys Glu Val Thr Val
                165                 170                 175

Gln Glu Leu Asp Leu Gln Ala Arg His Tyr Leu His Gly Lys Phe Gly
            180                 185                 190

Leu Tyr Asn Ser Asp Ser Phe Gly Gly Lys Val Gln Arg Gly Leu Ile
        195                 200                 205

Val Phe His Ser Ser Glu Gly Ser Thr Val Ser Tyr Asp Leu Phe Asp
    210                 215                 220

Ala Gln Gly Gln Tyr Pro Asp Thr Leu Leu Arg Ile Tyr Arg Asp Asn
225                 230                 235                 240
```

-continued

```
Lys Thr Ile Asn Ser Glu Asn Leu His Ile Asp Leu Tyr Leu Tyr Thr
                245                 250                 255
Thr
```

(2) INFORMATION FOR SEQ ID NO:113:

(i) SEQUENCE CHARACTERISTICS:
        (A) LENGTH: 257 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:113:

```
Met Lys Lys Thr Ala Phe Thr Leu Leu Leu Phe Ile Ala Leu Thr Leu
1               5                   10                  15
Thr Thr Ser Pro Leu Val Asn Gly Ser Glu Lys Ser Glu Glu Ile Asn
                20                  25                  30
Glu Lys Asp Leu Arg Lys Lys Ser Glu Leu Gln Gly Thr Ala Leu Gly
                35                  40                  45
Asn Leu Lys Gln Ile Tyr Tyr Tyr Asn Glu Lys Ala Lys Thr Glu Asn
            50                  55                  60
Lys Glu Ser His Asp Gln Phe Leu Gln His Thr Ile Leu Phe Lys Gly
65                  70                  75                  80
Phe Phe Thr Asp His Ser Trp Tyr Asn Asp Leu Leu Val Asp Phe Asp
                85                  90                  95
Ser Lys Asp Ile Val Asp Lys Tyr Lys Gly Lys Lys Val Asp Leu Tyr
                100                 105                 110
Gly Ala Tyr Tyr Gly Tyr Gln Cys Ala Gly Gly Thr Pro Asn Lys Thr
                115                 120                 125
Ala Cys Met Tyr Gly Gly Val Thr Leu His Asp Asn Asn Arg Leu Thr
                130                 135                 140
Glu Glu Lys Lys Val Pro Ile Asn Leu Trp Leu Asp Gly Lys Gln Asn
145                 150                 155                 160
Thr Val Pro Leu Glu Thr Val Lys Thr Asn Lys Lys Asn Val Thr Val
                165                 170                 175
Gln Glu Leu Asp Leu Gln Ala Arg Arg Tyr Leu Gln Glu Lys Tyr Asn
                180                 185                 190
Leu Tyr Asn Ser Asp Val Phe Asp Gly Lys Val Gln Arg Gly Leu Ile
                195                 200                 205
Val Phe His Thr Ser Thr Glu Pro Ser Val Asn Tyr Asp Leu Phe Gly
                210                 215                 220
Ala Gln Gly Gln Tyr Ser Asn Thr Leu Leu Arg Ile Tyr Arg Asp Asn
225                 230                 235                 240
Lys Thr Ile Asn Ser Glu Asn Met His Ile Asp Ile Tyr Leu Tyr Thr
                245                 250                 255
Ser
```

(2) INFORMATION FOR SEQ ID NO:114:

(i) SEQUENCE CHARACTERISTICS:
        (A) LENGTH: 254 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:114:

```
Met Lys Asn Ile Thr Phe Ile Phe Phe Ile Leu Leu Ala Ser Pro Leu
1               5                   10                  15

Tyr Ala Asn Gly Asp Arg Leu Tyr Arg Ala Asp Ser Arg Pro Pro Asp
            20                  25                  30

Glu Ile Lys Arg Phe Arg Ser Leu Met Pro Arg Gly Asn Glu Tyr Phe
        35                  40                  45

Asp Arg Gly Thr Gln Met Asn Ile Asn Leu Tyr Asp His Ala Arg Gly
    50                  55                  60

Thr Gln Thr Gly Phe Val Arg Tyr Asp Asp Gly Tyr Val Ser Thr Ser
65                  70                  75                  80

Leu Ser Leu Arg Ser Ala His Leu Ala Gly Gln Tyr Ile Leu Ser Gly
                85                  90                  95

Tyr Ser Leu Thr Ile Tyr Ile Val Ala Asn Met Phe Asn Val Asn
                100                 105                 110

Asp Val Ile Ser Val Tyr Ser Pro His Pro Tyr Glu Gln Glu Val Ser
            115                 120                 125

Ala Leu Gly Gly Ile Pro Tyr Ser Gln Ile Tyr Gly Trp Tyr Arg Val
    130                 135                 140

Asn Phe Gly Val Ile Asp Glu Arg Leu His Arg Asn Arg Glu Tyr Arg
145                 150                 155                 160

Asp Arg Tyr Tyr Arg Asn Leu Asn Ile Ala Pro Ala Glu Asp Gly Tyr
                165                 170                 175

Arg Leu Ala Gly Phe Pro Pro Asp His Gln Ala Trp Arg Glu Glu Pro
            180                 185                 190

Trp Ile His His Ala Pro Gln Gly Cys Gly Asp Ser Ser Arg Thr Ile
        195                 200                 205

Thr Gly Asp Thr Cys Asn Glu Glu Thr Gln Asn Leu Ser Thr Ile Tyr
    210                 215                 220

Leu Arg Glu Tyr Gln Ser Lys Val Lys Arg Gln Ile Phe Ser Asp Tyr
225                 230                 235                 240

Gln Ser Glu Val Asp Ile Tyr Asn Arg Ile Arg Asp Glu Leu
                245                 250
```

(2) INFORMATION FOR SEQ ID NO:115:

(i) SEQUENCE CHARACTERISTICS:
        (A) LENGTH: 380 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:115:

```
Met Met Phe Ser Gly Phe Asn Ala Asp Tyr Glu Ala Ser Ser Ser Arg
1               5                   10                  15

Cys Ser Ser Ala Ser Pro Ala Gly Asp Ser Leu Ser Tyr Tyr His Ser
            20                  25                  30

Pro Ala Asp Ser Phe Ser Ser Met Gly Ser Pro Val Asn Ala Gln Asp
        35                  40                  45

Phe Cys Thr Asp Leu Ala Val Ser Ser Ala Asn Phe Ile Pro Thr Val
    50                  55                  60

Thr Ala Ile Ser Thr Ser Pro Asp Leu Gln Trp Leu Val Gln Pro Ala
65                  70                  75                  80

Leu Val Ser Ser Val Ala Pro Ser Gln Thr Arg Ala Pro His Pro Phe
```

```
                    85                  90                  95
Gly Val Pro Ala Pro Ser Ala Gly Ala Tyr Ser Arg Ala Gly Val Val
                100                 105                 110
Lys Thr Met Thr Gly Gly Arg Ala Gln Ser Ile Gly Arg Arg Gly Lys
                115                 120                 125
Val Glu Gln Leu Ser Pro Glu Glu Glu Lys Arg Arg Ile Arg Arg
                130                 135                 140
Glu Arg Asn Lys Met Ala Ala Lys Cys Arg Asn Arg Arg Glu
145                 150                 155                 160
Leu Thr Asp Thr Leu Gln Ala Glu Thr Asp Gln Leu Glu Asp Glu Lys
                165                 170                 175
Ser Ala Leu Gln Thr Glu Ile Ala Asn Leu Leu Lys Glu Lys Glu Lys
                180                 185                 190
Leu Glu Phe Ile Leu Ala Ala His Arg Pro Ala Cys Lys Ile Pro Asp
                195                 200                 205
Asp Leu Gly Phe Pro Glu Glu Met Ser Val Ala Ser Leu Asp Leu Thr
                210                 215                 220
Gly Gly Leu Pro Glu Val Ala Thr Pro Glu Ser Glu Glu Ala Phe Thr
225                 230                 235                 240
Leu Pro Leu Leu Asn Asp Pro Glu Pro Lys Pro Ser Val Glu Pro Val
                245                 250                 255
Lys Ser Ile Ser Ser Met Glu Leu Lys Thr Glu Pro Phe Asp Asp Phe
                260                 265                 270
Leu Phe Pro Ala Ser Ser Arg Pro Ser Gly Ser Glu Thr Ala Arg Ser
                275                 280                 285
Val Pro Asp Met Asp Leu Ser Gly Ser Phe Tyr Ala Leu Pro Leu Leu
                290                 295                 300
Asn Asp Pro Glu Pro Lys Pro Ser Val Glu Pro Val Lys Ser Ile Ser
305                 310                 315                 320
Ser Met Glu Leu Lys Thr Glu Pro Phe Asp Asp Phe Leu Phe Pro Ala
                325                 330                 335
Ser Ser Arg Pro Ser Gly Ser Glu Thr Ala Arg Ser Val Pro Asp Met
                340                 345                 350
Asp Leu Ser Gly Ser Phe Tyr Ala Gly Ser Ser Asn Glu Pro Ser
                355                 360                 365
Ser Asp Ser Leu Ser Ser Pro Thr Leu Leu Ala Leu
                370                 375                 380

(2) INFORMATION FOR SEQ ID NO:116:

(i) SEQUENCE CHARACTERISTICS:
        (A) LENGTH: 607 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:116:

Ser Gly Trp Glu Ser Tyr Tyr Lys Thr Glu Gly Asp Glu Glu Ala Glu
1                   5                   10                  15
Glu Glu Gln Glu Glu Asn Leu Glu Ala Ser Gly Asp Tyr Lys Tyr Ser
                20                  25                  30
Gly Arg Asp Ser Leu Ile Phe Leu Val Asp Ala Ser Lys Ala Met Phe
                35                  40                  45
Glu Ser Gln Ser Glu Asp Glu Leu Thr Pro Phe Asp Met Ser Ile Gln
```

-continued

```
                50                  55                  60
Cys Ile Gln Ser Val Tyr Ile Ser Lys Ile Ile Ser Asp Arg Asp
65                  70                  75                  80

Leu Leu Ala Val Val Phe Tyr Gly Thr Glu Lys Asp Lys Asn Ser Val
                85                  90                  95

Asn Phe Lys Asn Ile Tyr Val Leu Gln Glu Leu Asp Asn Pro Gly Ala
                100                 105                 110

Lys Arg Ile Leu Glu Leu Asp Gln Phe Lys Gly Gln Gln Gly Gln Lys
                115                 120                 125

Arg Phe Gln Asp Met Met Gly His Gly Ser Asp Tyr Ser Leu Ser Glu
                130                 135                 140

Val Leu Trp Val Cys Ala Asn Leu Phe Ser Asp Val Gln Phe Lys Met
145                 150                 155                 160

Ser His Lys Arg Ile Met Leu Phe Thr Asn Glu Asp Asn Pro His Gly
                165                 170                 175

Asn Asp Ser Ala Lys Ala Ser Arg Ala Arg Thr Lys Ala Gly Asp Leu
                180                 185                 190

Arg Asp Thr Gly Ile Phe Leu Asp Leu Met His Leu Lys Lys Pro Gly
                195                 200                 205

Gly Phe Asp Ile Ser Leu Phe Tyr Arg Asp Ile Ser Ile Ala Glu
                210                 215                 220

Asp Glu Asp Leu Arg Val His Phe Glu Glu Ser Ser Lys Leu Glu Asp
225                 230                 235                 240

Leu Leu Arg Lys Val Arg Ala Lys Glu Thr Arg Lys Arg Ala Leu Ser
                245                 250                 255

Arg Leu Lys Leu Lys Leu Asn Lys Asp Ile Val Ile Ser Val Gly Ile
                260                 265                 270

Tyr Asn Leu Val Gln Lys Ala Leu Lys Pro Pro Ile Lys Leu Tyr
                275                 280                 285

Arg Glu Thr Asn Glu Pro Val Lys Thr Lys Thr Arg Thr Phe Asn Thr
                290                 295                 300

Ser Thr Gly Gly Leu Leu Leu Pro Ser Asp Thr Lys Arg Ser Gln Ile
305                 310                 315                 320

Tyr Gly Ser Arg Gln Ile Ile Leu Glu Lys Glu Glu Thr Glu Glu Leu
                325                 330                 335

Lys Arg Phe Asp Asp Pro Gly Leu Met Leu Met Gly Phe Lys Pro Leu
                340                 345                 350

Val Leu Leu Lys Lys His His Leu Arg Pro Ser Leu Phe Val Tyr Pro
                355                 360                 365

Glu Glu Ser Leu Val Ile Gly Ser Ser Thr Leu Phe Ser Ala Leu Leu
                370                 375                 380

Ile Lys Cys Leu Glu Lys Glu Val Ala Ala Leu Cys Arg Tyr Thr Pro
385                 390                 395                 400

Arg Arg Asn Ile Pro Pro Tyr Phe Val Ala Leu Val Pro Gln Glu Glu
                405                 410                 415

Glu Leu Asp Asp Gln Lys Ile Gln Val Thr Pro Pro Gly Phe Gln Leu
                420                 425                 430

Val Phe Leu Pro Phe Ala Asp Asp Lys Arg Lys Met Pro Phe Thr Glu
                435                 440                 445

Lys Ile Met Ala Thr Pro Glu Gln Val Gly Lys Met Lys Ala Ile Val
                450                 455                 460

Glu Lys Leu Arg Phe Thr Tyr Arg Ser Asp Ser Phe Glu Asn Pro Val
465                 470                 475                 480
```

```
Leu Gln Gln His Phe Arg Asn Leu Glu Ala Leu Ala Leu Asp Leu Met
             485                 490                 495

Glu Pro Glu Gln Ala Val Asp Leu Thr Leu Pro Lys Val Glu Ala Met
             500                 505                 510

Asn Lys Arg Leu Gly Ser Leu Val Asp Glu Phe Lys Glu Leu Val Tyr
             515                 520                 525

Pro Pro Asp Tyr Asn Pro Glu Gly Lys Val Thr Lys Arg Lys His Asp
             530                 535                 540

Asn Glu Gly Ser Gly Ser Lys Arg Pro Lys Val Glu Tyr Ser Glu Glu
545                 550                 555                 560

Glu Leu Lys Thr His Ile Ser Lys Gly Thr Leu Gly Lys Phe Thr Val
             565                 570                 575

Pro Met Leu Lys Glu Ala Cys Arg Ala Tyr Gly Leu Lys Ser Gly Leu
             580                 585                 590

Lys Lys Gln Glu Leu Leu Glu Ala Leu Thr Lys His Phe Gln Asp
             595                 600                 605

(2) INFORMATION FOR SEQ ID NO:117:

(i) SEQUENCE CHARACTERISTICS:
        (A) LENGTH: 462 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:117:

Gly Gly Gly Ala Leu Ser Pro Gln His Ser Ala Val Thr Gln Gly Ser
1               5                   10                  15

Ile Ile Lys Asn Lys Glu Gly Met Asp Ala Lys Ser Leu Thr Ala Trp
             20                  25                  30

Ser Arg Thr Leu Val Thr Phe Lys Asp Val Phe Val Asp Phe Thr Arg
             35                  40                  45

Glu Glu Trp Lys Leu Leu Asp Thr Ala Gln Gln Ile Val Tyr Arg Asn
50                  55                  60

Val Met Leu Glu Asn Tyr Lys Asn Leu Val Ser Leu Gly Tyr Gln Leu
65                  70                  75                  80

Thr Lys Pro Asp Val Ile Leu Arg Leu Glu Lys Gly Glu Glu Pro Trp
             85                  90                  95

Leu Val Glu Arg Glu Ile His Gln Glu Thr His Pro Asp Ser Glu Thr
             100                 105                 110

Ala Phe Glu Ile Lys Ser Ser Val Ser Ser Arg Ser Ile Phe Lys Asp
             115                 120                 125

Lys Gln Ser Cys Asp Ile Lys Met Glu Gly Met Ala Arg Asn Asp Leu
             130                 135                 140

Trp Tyr Leu Ser Leu Glu Glu Val Trp Lys Cys Arg Asp Gln Leu Asp
145                 150                 155                 160

Lys Tyr Gln Glu Asn Pro Glu Arg His Leu Arg His Gln Leu Ile His
             165                 170                 175

Thr Gly Glu Lys Pro Tyr Glu Cys Lys Glu Cys Gly Lys Ser Phe Ser
             180                 185                 190

Arg Ser Ser His Leu Ile Gly His Gln Lys Thr His Thr Gly Glu Glu
             195                 200                 205

Pro Tyr Glu Cys Lys Glu Cys Gly Lys Ser Phe Ser Trp Phe Ser His
             210                 215                 220
```

```
Leu Val Thr His Gln Arg Thr His Thr Gly Asp Lys Leu Tyr Thr Cys
225                 230                 235                 240

Asn Gln Cys Gly Lys Ser Phe Val His Ser Ser Arg Leu Ile Arg His
            245                 250                 255

Gln Arg Thr His Thr Gly His Lys Pro Tyr Glu Cys Pro Glu Cys Gly
            260                 265                 270

Lys Ser Phe Arg Gln Ser Thr His Leu Ile Leu His Gln Arg Thr His
        275                 280                 285

Val Arg Val Arg Pro Tyr Glu Cys Asn Glu Cys Gly Lys Ser Tyr Ser
    290                 295                 300

Gln Arg Ser His Leu Val Val His His Arg Ile His Thr Gly Leu Lys
305                 310                 315                 320

Pro Phe Glu Cys Lys Asp Cys Gly Lys Cys Phe Ser Arg Ser Ser His
            325                 330                 335

Leu Tyr Ser His Gln Arg Thr His Thr Gly Glu Lys Pro Tyr Glu Cys
            340                 345                 350

His Asp Cys Gly Lys Ser Phe Ser Gln Ser Ser Ala Leu Ile Val His
            355                 360                 365

Gln Arg Ile His Thr Gly Glu Lys Pro Tyr Glu Cys Cys Gln Cys Gly
370                 375                 380

Lys Ala Phe Ile Arg Lys Asn Asp Leu Ile Lys His Gln Arg Ile His
385                 390                 395                 400

Val Gly Ala Glu Thr Tyr Lys Cys Asn Gln Cys Gly Ile Ile Phe Ser
                405                 410                 415

Gln Asn Ser Pro Phe Ile Val His Gln Ile Ala His Thr Gly Glu Gln
            420                 425                 430

Phe Leu Thr Cys Asn Gln Cys Gly Thr Ala Leu Val Asn Thr Ser Asn
            435                 440                 445

Leu Ile Gly Tyr Gln Thr Asn His Ile Arg Glu Asn Ala Tyr
450                 455                 460
```

(2) INFORMATION FOR SEQ ID NO:118:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:118:

```
Pro Asp Ala Val Tyr Leu His Arg Ile Asp Leu Gly Pro Pro Ile Ser
1               5                   10                  15

Leu Glu Arg Leu Asp Val Gly Thr Asn Leu Gly Asn Ala Ile Ala Lys
            20                  25                  30

Leu Glu Asp
        35
```

(2) INFORMATION FOR SEQ ID NO:119:

(i) SEQUENCE CHARACTERISTICS:
        (A) LENGTH: 34 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:119:

Leu Glu Arg Leu Asp Val Gly Thr Asn Leu Gly Asn Ala Ile Ala Lys
1               5                   10                  15

Leu Glu Ala Lys Glu Leu Leu Glu Ser Ser Asp Gln Ile Leu Arg Ser
                20                  25                  30

Met Lys (2) INFORMATION FOR SEQ ID NO:120:

(i) SEQUENCE CHARACTERISTICS:
        (A) LENGTH: 47 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:120:

Thr Trp Gln Glu Trp Glu Arg Lys Val Asp Phe Leu Glu Glu Asn Ile
1               5                   10                  15

Thr Ala Leu Leu Glu Glu Ala Gln Ile Gln Gln Glu Lys Asn Met Tyr
                20                  25                  30

Glu Leu Gln Lys Leu Asn Ser Trp Asp Val Phe Gly Asn Trp Phe
            35                  40                  45

(2) INFORMATION FOR SEQ ID NO:121:

(i) SEQUENCE CHARACTERISTICS:
        (A) LENGTH: 42 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:121:

Ile Glu Leu Ser Asn Ile Lys Glu Asn Lys Cys Asn Gly Thr Asp Ala
1               5                   10                  15

Lys Val Lys Leu Ile Lys Gln Glu Leu Asp Lys Tyr Lys Asn Ala Val
                20                  25                  30

Thr Glu Leu Gln Leu Leu Met Gln Ser Thr
            35                  40

(2) INFORMATION FOR SEQ ID NO:122:

(i) SEQUENCE CHARACTERISTICS:
        (A) LENGTH: 27 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:122:

Val Ser Lys Gly Tyr Ser Ala Leu Arg Thr Gly Trp Tyr Thr Ser Val
1               5                   10                  15

Ile Thr Ile Glu Leu Ser Asn Ile Lys Glu Asn
                20                  25

(2) INFORMATION FOR SEQ ID NO:123:

(i) SEQUENCE CHARACTERISTICS:
        (A) LENGTH: 13 amino acids
        (B) TYPE: amino acid (C) STRANDEDNESS:
        (D) TOPOLOGY: unknown (ii) MOLECULE TYPE: peptide (xi) SEQUENCE DESCRIPTION: SEQ ID NO:123:

Ala Phe Ile Arg Lys Ser Asp Glu Leu Leu His Asn Val
1               5                   10

(2) INFORMATION FOR SEQ ID NO:124:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 17
        (D) OTHER INFORMATION: /product= "OTHER"
            /note= "X represents U, the standard designation for
            C-abu, a modified cysteine."

(xi) SEQUENCE DESCRIPTION: SEQ ID NO:124:

Tyr Thr Ser Val Ile Thr Ile Glu Leu Ser Asn Ile Lys Glu Asn Lys
1               5                   10                  15

Xaa Asn Gly Thr Asp Ala Lys Val Lys Leu Ile Lys Gln Glu Leu Asp
            20                  25                  30

Lys Tyr Lys
        35

(2) INFORMATION FOR SEQ ID NO:125:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 16
        (D) OTHER INFORMATION: /product= "OTHER"
            /note= "X represents U, the standard designation for
            C-abu, a modified cysteine."

(xi) SEQUENCE DESCRIPTION: SEQ ID NO:125:

Thr Ser Val Ile Thr Ile Glu Leu Ser Asn Ile Lys Glu Asn Lys Xaa
1               5                   10                  15

Asn Gly Thr Asp Ala Lys Val Lys Leu Ile Lys Gln Glu Leu Asp Lys
            20                  25                  30

Tyr Lys Asn
        35

(2) INFORMATION FOR SEQ ID NO:126:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide

```
    (ix) FEATURE:
         (A) NAME/KEY: Modified-site
         (B) LOCATION: 15
         (D) OTHER INFORMATION: /product= "OTHER"
             /note= "X represents U, the standard designation for
             C-abu, a modified cysteine."

(xi) SEQUENCE DESCRIPTION: SEQ ID NO:126:

Ser Val Ile Thr Ile Glu Leu Ser Asn Ile Lys Glu Asn Lys Xaa Asn
1               5                   10                  15

Gly Thr Asp Ala Lys Val Lys Leu Ile Lys Gln Glu Leu Asp Lys Tyr
            20                  25                  30

Lys Asn Ala
        35

(2) INFORMATION FOR SEQ ID NO:127:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 8
         (D) OTHER INFORMATION: /product= "OTHER"
             /note= "X represents U, the standard designation for
             C-abu, a modified cysteine."

(xi) SEQUENCE DESCRIPTION: SEQ ID NO:127:

Ser Asn Ile Lys Glu Asn Lys Xaa Asn Gly Thr Asp Ala Lys Val Lys
1               5                   10                  15

Leu Ile Lys Gln Glu Leu Asp Lys Tyr Lys Asn Ala Val Thr Glu Leu
            20                  25                  30

Gln Leu Leu
        35

(2) INFORMATION FOR SEQ ID NO:128:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 5
         (D) OTHER INFORMATION: /product= "OTHER"
             /note= "X represents U, the standard designation for
             C-abu, a modified cysteine."

(xi) SEQUENCE DESCRIPTION: SEQ ID NO:128:

Lys Glu Asn Lys Xaa Asn Gly Thr Asp Ala Lys Val Lys Leu Ile Lys
1               5                   10                  15

Gln Glu Leu Asp Lys Tyr Lys Asn Ala Val Thr Glu Leu Gln Leu Leu
            20                  25                  30

Met Gln Ser
        35

(2) INFORMATION FOR SEQ ID NO:129:
```

```
        (i) SEQUENCE CHARACTERISTICS:
            (A) LENGTH: 36 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 31
            (D) OTHER INFORMATION: /product= "OTHER"
                /note= "X represents U, the standard designation for
                C-abu, a modified cysteine."

(xi) SEQUENCE DESCRIPTION: SEQ ID NO:129:

Ala Val Ser Lys Gly Tyr Leu Ser Ala Leu Arg Thr Gly Trp Tyr Thr
 1               5                  10                  15

Ser Val Ile Thr Ile Glu Leu Ser Asn Ile Lys Glu Asn Lys Xaa Asn
                20                  25                  30

Gly Thr Asp Ala
            35

(2) INFORMATION FOR SEQ ID NO:130:

(i) SEQUENCE CHARACTERISTICS:
            (A) LENGTH: 27 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:130:

Val Val Ser Leu Ser Asn Gly Val Ser Val Leu Thr Ser Lys Val Leu
 1               5                  10                  15

Asp Leu Lys Asn Tyr Ile Asp Lys Gln Leu Leu
                20                  25

(2) INFORMATION FOR SEQ ID NO:131:

(i) SEQUENCE CHARACTERISTICS:
            (A) LENGTH: 28 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:131:

Leu Leu Ser Thr Asn Lys Ala Val Val Ser Leu Ser Asn Gly Val Ser
 1               5                  10                  15

Val Leu Thr Ser Lys Val Leu Asp Leu Lys Asn Tyr
                20                  25

(2) INFORMATION FOR SEQ ID NO:132:

(i) SEQUENCE CHARACTERISTICS:
            (A) LENGTH: 28 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:132:

Val Leu His Leu Glu Gly Glu Val Asn Lys Ile Lys Ser Ala Leu Leu
 1               5                  10                  15
```

Ser Thr Asn Lys Ala Val Val Ser Leu Ser Asn Gly
            20                  25

(2) INFORMATION FOR SEQ ID NO:133:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:133:

Leu Leu Ser Thr Asn Lys Ala Val Val Ser Leu Ser Asn Gly Val Ser
1               5                   10                  15

Val Leu Thr Ser Lys Val Leu Asp Leu Lys Asn Tyr
            20                  25

(2) INFORMATION FOR SEQ ID NO:134:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:134:

Ala Ser Gly Val Ala Val Ser Lys Val Leu His Leu Glu Gly Glu Val
1               5                   10                  15

Asn Lys Ile Lys Ser Ala Leu Leu Ser Thr Asn Lys Ala Val Val Ser
            20                  25                  30

Leu Ser Asn Gly Val
            35

(2) INFORMATION FOR SEQ ID NO:135:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:135:

Val Leu His Leu Glu Gly Glu Val Asn Lys Ile Lys Ser Ala Leu Leu
1               5                   10                  15

Ser Thr Asn Lys Ala Val Val Ser Leu Ser Asn Gly Val Ser Val Leu
            20                  25                  30

Thr Ser Lys
        35

(2) INFORMATION FOR SEQ ID NO:136:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:136:

Asn Asp Gln Lys Lys Leu Met Ser Asn Asn Val Gln Ile Val Arg Gln
1               5                   10                  15

Gln Ser Tyr Ser Ile Met Ser Ile Ile Lys Glu Glu
            20                  25

(2) INFORMATION FOR SEQ ID NO:137:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:137:

Ser Ile Ser Asn Ile Glu Thr Val Ile Glu Phe Gln Gln Lys Asn Asn
1               5                   10                  15

Arg Leu Leu Glu Ile Thr Arg Glu Phe Ser Val Asn Ala Gly Val Thr
            20                  25                  30

Thr Pro Val Ser
        35

(2) INFORMATION FOR SEQ ID NO:138:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:138:

Pro Ile Ile Asn Phe Tyr Asp Pro Leu Val Phe Pro Ser Asp Glu Phe
1               5                   10                  15

Asp Ala Ser Ile Ser Gln Val Asn Glu Lys Ile Asn Gln Ser Leu Ala
            20                  25                  30

Phe Ile Arg
        35

(2) INFORMATION FOR SEQ ID NO:139:

(i) SEQUENCE CHARACTERISTICS:
        (A) LENGTH: 29 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:139:

Arg Met Lys Gln Leu Glu Asp Lys Val Glu Glu Leu Leu Ser Lys Leu
1               5                   10                  15

Ala Phe Ile Arg Lys Ser Asp Glu Leu Leu His Asn Val
            20                  25

(2) INFORMATION FOR SEQ ID NO:140:

(i) SEQUENCE CHARACTERISTICS:
        (A) LENGTH: 19 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:140:

```
Ala Phe Ile Arg Lys Ser Asp Glu Leu Leu His Asn Val Asn Ala Gly
1               5                   10                  15

Lys Ser Thr
```

(2) INFORMATION FOR SEQ ID NO:141:

(i) SEQUENCE CHARACTERISTICS:
        (A) LENGTH: 19 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:141:

```
Phe Asp Ala Ser Ile Ser Gln Val Asn Glu Lys Ile Asn Gln Ser Leu
1               5                   10                  15

Ala Phe Ile
```

(2) INFORMATION FOR SEQ ID NO:142:

(i) SEQUENCE CHARACTERISTICS:
        (A) LENGTH: 21 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:142:

```
Ser Leu Ala Phe Ile Arg Lys Ser Asp Glu Leu Leu His Asn Val Asn
1               5                   10                  15

Ala Gly Lys Ser Thr
                20
```

(2) INFORMATION FOR SEQ ID NO:143:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:143:

```
Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys
```

(2) INFORMATION FOR SEQ ID NO:144:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:144:

```
Ala Ser Ile Ser Gln Val Asn Glu Lys Ile Asn Gln Ser Leu Ala Phe
1               5                   10                  15

Ile Arg Lys Ser Asp Glu Leu Leu His Asn Val Asn Ala Gly Lys Ser
                20                  25                  30

Thr
```

(2) INFORMATION FOR SEQ ID NO:145:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:145:

```
Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Ala Gly
                20                  25                  30

Lys Ser Thr
        35
```

(2) INFORMATION FOR SEQ ID NO:146:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:146:

```
Ala Thr Ser Ala Gln Ile Thr Ala Ala Val Ala Leu Val Glu Ala Lys
1               5                   10                  15

Gln Ala Arg Ser Asp Ile Glu Lys Leu Lys Glu Ala
                20                  25
```

(2) INFORMATION FOR SEQ ID NO:147:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:147:

```
Ala Ala Val Ala Leu Val Glu Ala Lys Gln Ala Arg Ser Asp Ile Glu
1               5                   10                  15

Lys Leu Lys Glu Ala Ile Arg Asp Thr Asn Lys Ala Val Gln Ser Val
                20                  25                  30

Gln Ser Ser
        35
```

(2) INFORMATION FOR SEQ ID NO:148:

(i) SEQUENCE CHARACTERISTICS:
        (A) LENGTH: 35 amino acids
        (B) TYPE: amino acid
        (C) STRANDEDNESS:

(D) TOPOLOGY: unknown (ii) MOLECULE TYPE: peptide (xi) SEQUENCE DESCRIPTION: SEQ ID NO:148:

Ala Lys Gln Ala Arg Ser Asp Ile Glu Lys Leu Lys Glu Ala Ile Arg
1               5                   10                  15

Asp Thr Asn Lys Ala Val Gln Ser Val Gln Ser Ser Ile Gly Asn Leu
            20                  25                  30

Ile Val Ala
        35

(2) INFORMATION FOR SEQ ID NO:149:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:149:

Ile Arg Asp Thr Asn Lys Ala Val Gln Ser Val Gln Ser Ser Ile Gly
1               5                   10                  15

Asn Leu Ile Val Ala Ile Lys Ser Val Gln Asp Tyr
            20                  25

(2) INFORMATION FOR SEQ ID NO:150:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:150:

Ala Val Gln Ser Val Gln Ser Ser Ile Gly Asn Leu Ile Val Ala Ile
1               5                   10                  15

Lys Ser Val Gln Asp Tyr Val Asn Lys Glu Ile Val
            20                  25

(2) INFORMATION FOR SEQ ID NO:151:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:151:

Leu Lys Glu Ala Ile Arg Asp Thr Asn Lys Ala Val Gln Ser Val Gln
1               5                   10                  15

Ser Ser Ile Gly Asn Leu Ile Val Ala Ile Lys Ser
            20                  25

(2) INFORMATION FOR SEQ ID NO:152:

(i) SEQUENCE CHARACTERISTICS:
        (A) LENGTH: 13 amino acids
        (B) TYPE: amino acid
        (C) STRANDEDNESS:

(D) TOPOLOGY: unknown (ii) MOLECULE TYPE: peptide (xi) SEQUENCE DESCRIPTION: SEQ ID NO:152:

Glu Trp Ile Arg Arg Ser Asn Gln Lys Leu Asp Ser Ile
1               5                   10

(2) INFORMATION FOR SEQ ID NO:153:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:153:

Ile Asp Ile Ser Ile Glu Leu Asn Lys Ala Lys Ser Asp Leu Glu Glu
1               5                   10                  15

Ser Lys Glu Trp Ile Lys Lys Ser Asn Gln Lys Leu Asp Ser Ile Gly
            20                  25                  30

Asn Trp His
        35

(2) INFORMATION FOR SEQ ID NO:154:

(i) SEQUENCE CHARACTERISTICS:
        (A) LENGTH: 29 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:154:

Arg Met Lys Gln Leu Glu Asp Lys Val Glu Glu Leu Leu Ser Lys Leu
1               5                   10                  15

Glu Trp Ile Arg Arg Ser Asn Gln Lys Leu Asp Ser Ile
            20                  25

(2) INFORMATION FOR SEQ ID NO:155:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:155:

Asp Gln Gln Ile Lys Gln Tyr Lys Arg Leu Leu Asp Arg Leu Ile Ile
1               5                   10                  15

Pro Leu Tyr Asp Gly Leu Arg Gln Lys Asp Val Ile Val Ser Asn Gln
            20                  25                  30

Glu Ser Asn
        35

(2) INFORMATION FOR SEQ ID NO:156:

(i) SEQUENCE CHARACTERISTICS:
        (A) LENGTH: 36 amino acids
        (B) TYPE: amino acid
        (C) STRANDEDNESS:

(D) TOPOLOGY: unknown (ii) MOLECULE TYPE: peptide (xi) SEQUENCE DESCRIPTION: SEQ ID NO:156:

```
Tyr Ser Glu Leu Thr Asn Ile Phe Gly Asp Asn Ile Gly Ser Leu Gln
1               5                   10                  15

Glu Lys Gly Ile Lys Leu Gln Gly Ile Ala Ser Leu Tyr Arg Thr Asn
            20                  25                  30

Ile Thr Glu Ile
        35
```

(2) INFORMATION FOR SEQ ID NO:157:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:157:

```
Thr Ser Ile Thr Leu Gln Val Arg Leu Pro Leu Leu Thr Arg Leu Leu
1               5                   10                  15

Asn Thr Gln Ile Tyr Arg Val Asp Ser Ile Ser Tyr Asn Ile Gln Asn
            20                  25                  30

Arg Glu Trp Tyr
        35
```

(2) INFORMATION FOR SEQ ID NO:158:

(i) SEQUENCE CHARACTERISTICS:
        (A) LENGTH: 57 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:158:

```
Asn Lys Ser Leu Glu Gln Ile Trp Asn Asn Met Thr Trp Met Glu Trp
1               5                   10                  15

Asp Arg Glu Ile Asn Asn Tyr Thr Ser Leu Ile His Ser Leu Ile Glu
            20                  25                  30

Glu Gln Asn Gln Gln Glu Lys Asn Glu Gln Glu Leu Leu Glu Leu Asp
        35                  40                  45

Lys Trp Ala Ser Leu Trp Asn Trp Phe
        50              55
```

(2) INFORMATION FOR SEQ ID NO:159:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:159:

```
Trp Met Glu Trp Asp Arg Glu Ile Asn Asn Tyr Thr Ser Leu Ile Gly
1               5                   10                  15

Ser Leu Ile Glu Glu Ser Gln Asn Gln Gln Glu Lys Asn Glu Gln Glu
```

```
                    20                  25                  30

Leu Leu Glu
        35

(2) INFORMATION FOR SEQ ID NO:160:

(i) SEQUENCE CHARACTERISTICS:
        (A) LENGTH: 49 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:160:

Tyr Thr Ser Leu Ile His Ser Leu Ile Glu Glu Ser Gln Asn Gln Gln
1               5                  10                  15

Glu Lys Asn Glu Gln Glu Leu Leu Glu Leu Asp Lys Trp Ala Ser Leu
                20                  25                  30

Trp Asn Trp Phe Asn Ile Thr Asn Trp Leu Trp Leu Ile Lys Ile Phe
            35                  40                  45

Ile (2) INFORMATION FOR SEQ ID NO:161:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:161:

Glu Ala Ala Ala Arg Glu Ala Ala Ala Arg Glu Ala Ala Ala Arg Leu
1               5                  10                  15

Glu Leu Asp Lys Trp Ala Ser Leu Trp Asn Trp Phe
                20                  25

(2) INFORMATION FOR SEQ ID NO:162:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:162:

Arg Met Lys Gln Leu Glu Asp Lys Val Glu Glu Leu Leu Ser Lys Leu
1               5                  10                  15

Glu Leu Asp Lys Trp Ala Ser Leu Trp Asn Trp Phe
                20                  25

(2) INFORMATION FOR SEQ ID NO:163:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:163:
```

Phe Trp Asn Trp Leu Ser Ala Trp Lys Asp Leu Glu Leu Lys Ser Leu
1               5                   10                  15

Leu Glu Glu Val Lys Asp Glu Leu Gln Lys Met Arg
            20                  25

(2) INFORMATION FOR SEQ ID NO:164:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:164:

Arg Met Lys Gln Leu Glu Asp Lys Val Glu Glu Leu Leu Ser Lys Asn
1               5                   10                  15

Tyr His Leu Glu Asn Glu Leu Glu Leu Asp Lys Trp Ala Ser Leu Trp
            20                  25                  30

Asn Trp Phe
        35

(2) INFORMATION FOR SEQ ID NO:165:

(i) SEQUENCE CHARACTERISTICS:
        (A) LENGTH: 30 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:165:

Phe Trp Asn Trp Leu Ser Ala Trp Lys Asp Leu Glu Leu Tyr Pro Gly
1               5                   10                  15

Ser Leu Glu Leu Asp Lys Trp Ala Ser Leu Trp Asn Trp Phe
            20                  25                  30

(2) INFORMATION FOR SEQ ID NO:166:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:166:

Cys Leu Glu Leu Asp Lys Trp Ala Ser Leu Trp Asn Trp Phe Cys
1               5                   10                  15

(2) INFORMATION FOR SEQ ID NO:167:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:167:

Cys Leu Glu Leu Asp Lys Trp Ala Ser Leu Ala Asn Trp Phe Cys
1               5                   10                  15

(2) INFORMATION FOR SEQ ID NO:168:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:168:

```
Cys Leu Glu Leu Asp Lys Trp Ala Ser Leu Trp Asn Phe Phe Cys
1               5                   10                  15
```

(2) INFORMATION FOR SEQ ID NO:169:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:169:

```
Leu Glu Leu Asp Lys Trp Ala Ser Leu Ala Asn Ala Phe
1               5                   10
```

(2) INFORMATION FOR SEQ ID NO:170:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:170:

```
Leu Glu Leu Asp Lys Trp Ala Ser Leu Phe Asn Phe Phe
1               5                   10
```

(2) INFORMATION FOR SEQ ID NO:171:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:171:

```
Leu Glu Leu Asp Lys Trp Ala Ser Leu Trp Asn Ala Phe
1               5                   10
```

(2) INFORMATION FOR SEQ ID NO:172:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:172:

```
Leu Glu Leu Asp Lys Trp Ala Ser Leu Trp Asn Trp Ala
```

1    5         10

(2) INFORMATION FOR SEQ ID NO:173:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:173:

Leu Glu Leu Asp Lys Trp Ala Ser Ala Trp Asn Trp Phe
1                5                  10

(2) INFORMATION FOR SEQ ID NO:174:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:174:

Leu Glu Leu Asp Lys Ala Ala Ser Leu Trp Asn Trp Phe
1                5                  10

(2) INFORMATION FOR SEQ ID NO:175:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:175:

Leu Lys Leu Asp Lys Trp Ala Ser Leu Trp Asn Trp Phe
1                5                  10

(2) INFORMATION FOR SEQ ID NO:176:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:176:

Leu Glu Leu Lys Lys Trp Ala Ser Leu Trp Asn Trp Phe
1                5                  10

(2) INFORMATION FOR SEQ ID NO:177:

(i) SEQUENCE CHARACTERISTICS:
        (A) LENGTH: 39 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:177:

```
Cys Gly Gly Tyr Thr Ser Leu Ile His Ser Leu Ile Glu Glu Ser Gln
1               5                   10                  15

Asn Gln Gln Glu Lys Asn Glu Gln Glu Leu Leu Glu Leu Asp Lys Trp
                20                  25                  30

Ala Ser Leu Trp Asn Trp Phe
            35
```

(2) INFORMATION FOR SEQ ID NO:178:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:178:

```
Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
                20                  25                  30

Trp Asn Ala Phe
            35
```

(2) INFORMATION FOR SEQ ID NO:179:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:179:

```
Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
                20                  25                  30

Ala Asn Trp Phe
            35
```

(2) INFORMATION FOR SEQ ID NO:180:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:180:

```
Tyr Thr Ser Leu Ile His Ser Leu Ile Glu Glu Ser Gln Asn Gln Gln
1               5                   10                  15

Glu Lys Asn Glu Gln Gln Leu Leu Glu Leu Asp Lys Trp Ala Ser Leu
                20                  25                  30

Trp Asn Trp Phe
            35
```

(2) INFORMATION FOR SEQ ID NO:181:

(i) SEQUENCE CHARACTERISTICS:

(A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:181:

Tyr Thr Ser Leu Ile His Ser Leu Ile Glu Glu Ser Gln Asn Gln Gln
1               5                   10                  15

Glu Lys Asn Glu Gln Glu Leu Leu Gln Leu Asp Lys Trp Ala Ser Leu
            20                  25                  30

Trp Asn Trp Phe
        35

(2) INFORMATION FOR SEQ ID NO:182:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:182:

Tyr Thr Ser Leu Ile His Ser Leu Ile Glu Glu Ser Gln Asn Gln Gln
1               5                   10                  15

Glu Lys Asn Gln Gln Glu Leu Leu Gln Leu Asp Lys Trp Ala Ser Leu
            20                  25                  30

Trp Asn Trp Phe
        35

(2) INFORMATION FOR SEQ ID NO:183:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:183:

Tyr Thr Ser Leu Ile Gln Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

(2) INFORMATION FOR SEQ ID NO:184:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:184:

Tyr Thr Ser Leu Ile His Ser Leu Ile Glu Glu Ser Gln Gln Gln Gln
1               5                   10                  15

Glu Lys Asn Glu Gln Glu Leu Leu Glu Leu Asp Lys Trp Ala Ser Leu

```
                    20                  25                  30

Trp Asn Trp Phe
        35

(2) INFORMATION FOR SEQ ID NO:185:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:185:

Tyr Thr Ser Leu Ile His Ser Leu Ile Glu Glu Ser Gln Asn Gln Gln
1               5                  10                  15

Glu Lys Asn Glu Gln Glu Leu Leu Glu Leu Asn Lys Trp Ala Ser Leu
                20                  25                  30

Trp Asn Trp Phe
        35

(2) INFORMATION FOR SEQ ID NO:186:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:186:

Tyr Thr Ser Leu Ile His Ser Leu Ile Glu Gln Ser Gln Asn Gln Gln
1               5                  10                  15

Glu Lys Asn Glu Gln Glu Leu Leu Glu Leu Asp Lys Trp Ala Ser Leu
                20                  25                  30

Trp Asn Trp Phe
        35

(2) INFORMATION FOR SEQ ID NO:187:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:187:

Tyr Thr Ser Leu Ile His Ser Leu Ile Gln Glu Ser Gln Asn Gln Gln
1               5                  10                  15

Glu Lys Asn Glu Gln Glu Leu Leu Glu Leu Asp Lys Trp Ala Ser Leu
                20                  25                  30

Trp Asn Trp Phe
        35

(2) INFORMATION FOR SEQ ID NO:188:

(i) SEQUENCE CHARACTERISTICS:
        (A) LENGTH: 36 amino acids
        (B) TYPE: amino acid
        (C) STRANDEDNESS:
        (D) TOPOLOGY: unknown
```

(ii) MOLECULE TYPE: peptide (xi) SEQUENCE DESCRIPTION: SEQ ID NO:188:

Tyr Thr Ser Leu Ile His Ser Leu Ile Gln Gln Ser Gln Asn Gln Gln
1               5                  10                  15

Gln Lys Asn Gln Gln Gln Leu Leu Gln Leu Asp Lys Trp Ala Ser Leu
            20                  25                  30

Trp Asn Trp Phe
        35

(2) INFORMATION FOR SEQ ID NO:189:

(i) SEQUENCE CHARACTERISTICS:
         (A) LENGTH: 36 amino acids
         (B) TYPE: amino acid
         (C) STRANDEDNESS:
         (D) TOPOLOGY: unknown (ii) MOLECULE TYPE: peptide (xi) SEQUENCE DESCRIPTION: SEQ ID NO:189:

Tyr Thr Ser Leu Ile His Ser Leu Ile Glu Glu Ser Gln Asn Gln Gln
1               5                  10                  15

Glu Lys Asn Glu Gln Glu Leu Leu Glu Leu Asp Lys Trp Ala Ser Leu
            20                  25                  30

Ala Asn Ala Ala
        35

(2) INFORMATION FOR SEQ ID NO:190:

(i) SEQUENCE CHARACTERISTICS:
         (A) LENGTH: 36 amino acids
         (B) TYPE: amino acid
         (C) STRANDEDNESS:
         (D) TOPOLOGY: unknown (ii) MOLECULE TYPE: peptide (xi) SEQUENCE DESCRIPTION: SEQ ID NO:190:

Tyr Thr Ser Leu Ile His Ser Leu Ile Glu Glu Ser Gln Asn Gln Gln
1               5                  10                  15

Glu Lys Asn Glu Gln Gln Leu Leu Glu Leu Asp Lys Trp Ala Ser Leu
            20                  25                  30

Trp Asn Trp Phe
        35

(2) INFORMATION FOR SEQ ID NO:191:

(i) SEQUENCE CHARACTERISTICS:
         (A) LENGTH: 36 amino acids
         (B) TYPE: amino acid
         (C) STRANDEDNESS:
         (D) TOPOLOGY: unknown (ii) MOLECULE TYPE: peptide (xi) SEQUENCE DESCRIPTION: SEQ ID NO:191:

Tyr Thr Ser Leu Ile Gln Ser Leu Ile Glu Glu Ser Gln Asn Gln Gln
1               5                  10                  15

Glu Lys Asn Glu Gln Gln Leu Leu Glu Leu Asp Lys Trp Ala Ser Leu
            20                  25                  30

Trp Asn Trp Phe
        35

(2) INFORMATION FOR SEQ ID NO:192:

(i) SEQUENCE CHARACTERISTICS:
       (A) LENGTH: 36 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO:192:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Phe Asn Phe Phe
        35

(2) INFORMATION FOR SEQ ID NO:193:

(i) SEQUENCE CHARACTERISTICS:
       (A) LENGTH: 36 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO:193:

Tyr Thr Ser Leu Ile His Ser Leu Ile Glu Glu Ser Gln Asn Leu Gln
1               5                   10                  15

Glu Lys Asn Glu Gln Glu Leu Leu Glu Leu Asp Lys Trp Ala Ser Leu
            20                  25                  30

Trp Asn Trp Phe
        35

(2) INFORMATION FOR SEQ ID NO:194:

(i) SEQUENCE CHARACTERISTICS:
       (A) LENGTH: 36 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO:194:

Tyr Thr Ser Leu Ile His Ser Leu Ile Glu Glu Ser Gln Asn Gln Gln
1               5                   10                  15

Glu Lys Leu Glu Gln Glu Leu Leu Glu Leu Asp Lys Trp Ala Ser Leu
            20                  25                  30

Trp Asn Trp Phe
        35

(2) INFORMATION FOR SEQ ID NO:195:

(i) SEQUENCE CHARACTERISTICS:
       (A) LENGTH: 36 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO:195:

```
Tyr Thr Ser Leu Ile His Ser Leu Ile Glu Glu Ser Gln Asn Gln Gln
1               5                   10                  15

Glu Lys Asn Glu Gln Glu Leu Leu Glu Phe Asp Lys Trp Ala Ser Leu
            20                  25                  30

Trp Asn Trp Phe
        35

(2) INFORMATION FOR SEQ ID NO:196:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:196:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Pro Ala Ser Leu
            20                  25                  30

Trp Asn Trp Phe
        35

(2) INFORMATION FOR SEQ ID NO:197:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:197:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Pro
            20                  25                  30

Trp Asn Trp Phe
        35

(2) INFORMATION FOR SEQ ID NO:198:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:198:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Ser Phe
        35

(2) INFORMATION FOR SEQ ID NO:199:
```

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:199:

Leu Leu Asp Asn Phe Glu Ser Thr Trp Glu Gln Ser Lys Glu Leu Trp
1               5                  10                  15

Glu Gln Gln Glu Ile Ser Ile Gln Asn Leu His Lys Ser Ala Leu Gln
                20                  25                  30

Glu Tyr Trp Asn
            35

(2) INFORMATION FOR SEQ ID NO:200:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:200:

Leu Ser Asn Leu Leu Gln Ile Ser Asn Asn Ser Asp Glu Trp Leu Glu
1               5                  10                  15

Ala Leu Glu Ile Glu His Glu Lys Trp Lys Leu Thr Gln Trp Gln Ser
                20                  25                  30

Tyr Glu Gln Phe
            35

(2) INFORMATION FOR SEQ ID NO:201:

(i) SEQUENCE CHARACTERISTICS:
        (A) LENGTH: 63 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:201:

Met Thr Leu Thr Val Gln Ala Arg Gln Leu Leu Ser Gly Ile Val Gln
1               5                  10                  15

Gln Gln Asn Asn Leu Leu Arg Ala Ile Glu Ala Gln Gln His Leu Leu
                20                  25                  30

Gln Leu Thr Val Trp Gly Ile Lys Gln Leu Gln Ala Arg Ile Leu Ala
            35                  40                  45

Val Glu Arg Tyr Leu Lys Asp Gln Gln Leu Leu Gly Ile Trp Gly
        50                  55                  60

(2) INFORMATION FOR SEQ ID NO:202:

(i) SEQUENCE CHARACTERISTICS:
        (A) LENGTH: 45 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:202:

```
Ser Glu Leu Glu Ile Lys Arg Tyr Lys Asn Arg Val Ala Ser Arg Lys
1               5                   10                  15

Cys Arg Ala Lys Phe Gln Leu Leu Gln His Tyr Arg Glu Val Ala Ala
                20                  25                  30

Ala Lys Ser Ser Glu Asn Asp Arg Leu Arg Leu Leu Leu
            35                  40                  45
```

(2) INFORMATION FOR SEQ ID NO:203:

(i) SEQUENCE CHARACTERISTICS:
        (A) LENGTH: 45 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:203:

```
Ala Ser Arg Lys Cys Arg Ala Lys Phe Lys Gln Leu Leu Gln His Tyr
1               5                   10                  15

Arg Glu Val Ala Ala Ala Lys Ser Ser Glu Asn Asp Arg Leu Arg Leu
                20                  25                  30

Leu Leu Lys Gln Met Cys Pro Ser Leu Asp Val Asp Ser
            35                  40                  45
```

(2) INFORMATION FOR SEQ ID NO:204:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:204:

```
Leu Leu Gln His Tyr Arg Glu Val Ala Ala Ala Lys Ser Ser Glu Asn
1               5                   10                  15

Asp Arg Leu Arg Leu Leu Leu Lys Gln Met Cys Pro Ser Leu Asp Val
                20                  25                  30

Asp Ser Ile
        35
```

(2) INFORMATION FOR SEQ ID NO:205:

(i) SEQUENCE CHARACTERISTICS:
        (A) LENGTH: 45 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:205:

```
Leu Gln His Tyr Arg Glu Val Ala Ala Ala Lys Ser Ser Glu Asn Asp
1               5                   10                  15

Arg Leu Arg Leu Leu Leu Lys Gln Met Cys Pro Ser Leu Asp Val Asp
                20                  25                  30

Ser Ile Ile Pro Arg Thr Pro Asp Val Leu His Glu Asp
            35                  40                  45
```

(2) INFORMATION FOR SEQ ID NO:206:

(i) SEQUENCE CHARACTERISTICS:

(A) LENGTH: 35 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:206:

Ser Ser Glu Asn Asp Arg Leu Arg Leu Leu Lys Gln Met Cys Pro
1               5                  10                  15

Ser Leu Asp Val Asp Ser Ile Ile Pro Arg Thr Pro Asp Val Leu His
            20                  25                  30

Glu Asp Leu
        35

(2) INFORMATION FOR SEQ ID NO:207:

(i) SEQUENCE CHARACTERISTICS:
            (A) LENGTH: 37 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:207:

Ser Glu Asn Asp Arg Leu Arg Leu Leu Lys Gln Met Cys Pro Ser
1               5                  10                  15

Leu Asp Val Asp Ser Ile Ile Pro Arg Thr Pro Asp Val Leu His Glu
            20                  25                  30

Asp Leu Leu Asn Phe
        35

(2) INFORMATION FOR SEQ ID NO:208:

(i) SEQUENCE CHARACTERISTICS:
            (A) LENGTH: 46 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:208:

Pro Leu Leu Val Leu Gln Ala Gly Phe Phe Leu Leu Thr Arg Ile Leu
1               5                  10                  15

Thr Ile Pro Gln Ser Leu Asp Ser Trp Trp Thr Ser Leu Asn Phe Leu
            20                  25                  30

Gly Gly Thr Thr Val Cys Leu Gly Gln Asn Ser Gln Ser Pro
        35                  40                  45

(2) INFORMATION FOR SEQ ID NO:209:

(i) SEQUENCE CHARACTERISTICS:
            (A) LENGTH: 57 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:209:

Pro Gly Tyr Arg Trp Met Cys Leu Arg Arg Phe Ile Ile Phe Leu Phe
1               5                  10                  15

Ile Leu Leu Leu Cys Leu Ile Phe Leu Leu Val Leu Leu Asp Tyr Gln

```
                        20                  25                  30
Gly Met Leu Pro Val Cys Pro Leu Ile Pro Gly Ser Ser Thr Ser Thr
                        35                  40                  45
Gly Pro Cys Arg Thr Cys Met Thr Thr
 50                  55
```

(2) INFORMATION FOR SEQ ID NO:210:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 37
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:210:

```
Xaa Thr Ser Val Ile Thr Ile Glu Leu Ser Asn Ile Lys Glu Asn Lys
 1                   5                  10                  15
Cys Asn Gly Thr Asp Ala Lys Val Lys Leu Ile Lys Gln Glu Leu Asp
                    20                  25                  30
Lys Tyr Lys Asn Xaa
                35
```

(2) INFORMATION FOR SEQ ID NO:211:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 37
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or carbohydrates.

(xi) SEQUENCE DESCRIPTION: SEQ ID NO:211:

Xaa Ser Val Ile Thr Ile Glu Leu Ser Asn Ile Lys Glu Asn Lys Cys
1               5                   10                  15

Asn Gly Thr Asp Ala Lys Val Lys Leu Ile Lys Gln Glu Leu Asp Lys
                20                  25                  30

Tyr Lys Asn Ala Xaa
            35

(2) INFORMATION FOR SEQ ID NO:212:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 37
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:212:

Xaa Val Ile Thr Ile Glu Leu Ser Asn Ile Lys Glu Asn Lys Cys Asn
1               5                   10                  15

Gly Thr Asp Ala Lys Val Lys Leu Ile Lys Gln Glu Leu Asp Lys Tyr
                20                  25                  30

Lys Asn Ala Val Xaa
            35

(2) INFORMATION FOR SEQ ID NO:213:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site

```
          (B) LOCATION: 35
          (D) OTHER INFORMATION:/note="Xaa may represent a carboxyl
              group; an amido group; a T-butyloxycarbonyl group; a
              macromolecular carrier group including but not limited
              to lipid-fatty acid conjugates, polyethylene glycol, or
              carbohydrates.

(xi) SEQUENCE DESCRIPTION: SEQ ID NO:213:

Xaa Val Ala Val Ser Lys Val Leu His Leu Glu Gly Glu Val Asn Lys
 1               5                  10                  15

Ile Ala Leu Leu Ser Thr Asn Lys Ala Val Val Ser Leu Ser Asn Gly
             20                  25                  30

Val Ser Xaa
         35

(2) INFORMATION FOR SEQ ID NO:214:

(i) SEQUENCE CHARACTERISTICS:
          (A) LENGTH: 35 amino acids
          (B) TYPE: amino acid
          (C) STRANDEDNESS:
          (D) TOPOLOGY: unknown (ii) MOLECULE TYPE: peptide (ix) FEATURE:
          (A) NAME/KEY: Modified-site
          (B) LOCATION: 1
          (D) OTHER INFORMATION:/note="Xaa may represent an amino
              group, a hydrophobic group, including but not limited
              to carbobenzoxyl, dansyl, or T-butyloxycarbonyl; an
              acetyl group; a 9-fluorenylmethoxy-carbonyl (FMOC) group;
              a macromolecular carrier group including but not limited
              to lipid-fatty acid conjugates, polyethylene glycol, or
              carbohydrates.

(ix) FEATURE:
          (A) NAME/KEY: Modified-site
          (B) LOCATION: 35
          (D) OTHER INFORMATION:/note="Xaa may represent a carboxyl
              group; an amido group; a T-butyloxycarbonyl group; a
              macromolecular carrier group including but not limited
              to lipid-fatty acid conjugates, polyethylene glycol, or
              carbohydrates.

(xi) SEQUENCE DESCRIPTION: SEQ ID NO:214:

Xaa Ala Val Ser Lys Val Leu His Leu Glu Gly Glu Val Asn Lys Ile
 1               5                  10                  15

Ala Leu Leu Ser Thr Asn Lys Ala Val Val Ser Leu Ser Asn Gly Val
             20                  25                  30

Ser Val Xaa
         35

(2) INFORMATION FOR SEQ ID NO:215:

(i) SEQUENCE CHARACTERISTICS:
          (A) LENGTH: 35 amino acids
          (B) TYPE: amino acid
          (C) STRANDEDNESS:
          (D) TOPOLOGY: unknown (ii) MOLECULE TYPE: peptide (ix) FEATURE:
          (A) NAME/KEY: Modified-site
          (B) LOCATION: 1
          (D) OTHER INFORMATION:/note="Xaa may represent an amino
              group, a hydrophobic group, including but not limited
              to carbobenzoxyl, dansyl, or T-butyloxycarbonyl; an
              acetyl group; a 9-fluorenylmethoxy-carbonyl (FMOC) group;
              a macromolecular carrier group including but not limited
```

```
            to lipid-fatty acid conjugates, polyethylene glycol, or
            carbohydrates.

(ix) FEATURE:
        (A) NAME/KEY: Modified-site
        (B) LOCATION: 35
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:215:

Xaa Val Ser Lys Val Leu His Leu Glu Gly Glu Val Asn Lys Ile Ala
 1               5                  10                  15

Leu Leu Ser Thr Asn Lys Ala Val Val Ser Leu Ser Asn Gly Val Ser
             20                  25                  30

Val Leu Xaa
         35

(2) INFORMATION FOR SEQ ID NO:216:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 35
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:216:

Xaa Ser Lys Val Leu His Leu Glu Gly Glu Val Asn Lys Ile Ala Leu
 1               5                  10                  15

Leu Ser Thr Asn Lys Ala Val Val Ser Leu Ser Asn Gly Val Ser Val
             20                  25                  30

Leu Thr Xaa
         35

(2) INFORMATION FOR SEQ ID NO:217:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
```

(D) OTHER INFORMATION:/note="Xaa may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.

(ix) FEATURE:
    (A) NAME/KEY: Modified-site
    (B) LOCATION: 35
    (D) OTHER INFORMATION:/note="Xaa may represent a carboxyl group; an amido group; a T-butyloxycarbonyl group; a macromolecular carrier group including but not limited to lipid-fatty acid conjugates, polyethylene glycol, or carbohydrates.

(xi) SEQUENCE DESCRIPTION: SEQ ID NO:217:

```
Xaa Lys Val Leu His Leu Glu Gly Glu Val Asn Lys Ile Ala Leu Leu
1               5                   10                  15

Ser Thr Asn Lys Ala Val Val Ser Leu Ser Asn Gly Val Ser Val Leu
                20                  25                  30

Thr Ser Xaa
        35
```

(2) INFORMATION FOR SEQ ID NO:218:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.

(ix) FEATURE:
        (A) NAME/KEY: Modified-site
        (B) LOCATION: 35
        (D) OTHER INFORMATION:/note="Xaa may represent a carboxyl group; an amido group; a T-butyloxycarbonyl group; a macromolecular carrier group including but not limited to lipid-fatty acid conjugates, polyethylene glycol, or carbohydrates.

(xi) SEQUENCE DESCRIPTION: SEQ ID NO:218:

```
Xaa Leu Glu Gly Glu Val Asn Lys Ile Ala Leu Leu Ser Thr Asn Lys
1               5                   10                  15

Ala Val Val Ser Leu Ser Asn Gly Val Ser Val Leu Thr Ser Lys Val
                20                  25                  30

Leu Asp Xaa
        35
```

(2) INFORMATION FOR SEQ ID NO:219:

(i) SEQUENCE CHARACTERISTICS:
        (A) LENGTH: 35 amino acids
        (B) TYPE: amino acid
        (C) STRANDEDNESS:
        (D) TOPOLOGY: unknown -continued

```
    (ii) MOLECULE TYPE: peptide (ix) FEATURE:
         (A) NAME/KEY: Modified-site
         (B) LOCATION: 1
         (D) OTHER INFORMATION:/note="Xaa may represent an amino
             group, a hydrophobic group, including but not limited
             to carbobenzoxyl, dansyl, or T-butyloxycarbonyl; an
             acetyl group; a 9-fluorenylmethoxy-carbonyl (FMOC) group;
             a macromolecular carrier group including but not limited
             to lipid-fatty acid conjugates, polyethylene glycol, or
             carbohydrates.

(ix) FEATURE:
         (A) NAME/KEY: Modified-site
         (B) LOCATION: 35
         (D) OTHER INFORMATION:/note="Xaa may represent a carboxyl
             group; an amido group; a T-butyloxycarbonyl group; a
             macromolecular carrier group including but not limited
             to lipid-fatty acid conjugates, polyethylene glycol, or
             carbohydrates.

(xi) SEQUENCE DESCRIPTION: SEQ ID NO:219:

Xaa Gly Glu Val Asn Lys Ile Ala Leu Leu Ser Thr Asn Lys Ala Val
 1               5                  10                  15

Val Ser Leu Ser Asn Gly Val Ser Val Leu Thr Ser Lys Val Leu Asp
            20                  25                  30

Leu Lys Xaa
        35

(2) INFORMATION FOR SEQ ID NO:220:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION:/note="Xaa may represent an amino
             group, a hydrophobic group, including but not limited
             to carbobenzoxyl, dansyl, or T-butyloxycarbonyl; an
             acetyl group; a 9-fluorenylmethoxy-carbonyl (FMOC) group;
             a macromolecular carrier group including but not limited
             to lipid-fatty acid conjugates, polyethylene glycol, or
             carbohydrates.

(ix) FEATURE:
         (A) NAME/KEY: Modified-site
         (B) LOCATION: 35
         (D) OTHER INFORMATION:/note="Xaa may represent a carboxyl
             group; an amido group; a T-butyloxycarbonyl group; a
             macromolecular carrier group including but not limited
             to lipid-fatty acid conjugates, polyethylene glycol, or
             carbohydrates.

(xi) SEQUENCE DESCRIPTION: SEQ ID NO:220:

Xaa Glu Val Asn Lys Ile Ala Leu Leu Ser Thr Asn Lys Ala Val Val
 1               5                  10                  15

Ser Leu Ser Asn Gly Val Ser Val Leu Thr Ser Lys Val Leu Asp Leu
            20                  25                  30

Lys Asn Xaa
        35

(2) INFORMATION FOR SEQ ID NO:221:

(i) SEQUENCE CHARACTERISTICS:
```

(A) LENGTH: 35 amino acids
                    (B) TYPE: amino acid
                    (C) STRANDEDNESS:
                    (D) TOPOLOGY: unknown (ii) MOLECULE TYPE: peptide (ix) FEATURE:
                    (A) NAME/KEY: Modified-site
                    (B) LOCATION: 1
                    (D) OTHER INFORMATION:/note="Xaa may represent an amino
                        group, a hydrophobic group, including but not limited
                        to carbobenzoxyl, dansyl, or T-butyloxycarbonyl; an
                        acetyl group; a 9-fluorenylmethoxy-carbonyl (FMOC) group;
                        a macromolecular carrier group including but not limited
                        to lipid-fatty acid conjugates, polyethylene glycol, or
                        carbohydrates.

(ix) FEATURE:
                    (A) NAME/KEY: Modified-site
                    (B) LOCATION: 35
                    (D) OTHER INFORMATION:/note="Xaa may represent a carboxyl
                        group; an amido group; a T-butyloxycarbonyl group; a
                        macromolecular carrier group including but not limited
                        to lipid-fatty acid conjugates, polyethylene glycol, or
                        carbohydrates.

(xi) SEQUENCE DESCRIPTION: SEQ ID NO:221:

Xaa Val Asn Lys Ile Ala Leu Leu Ser Thr Asn Lys Ala Val Val Ser
 1               5                  10                  15

Leu Ser Asn Gly Val Ser Val Leu Thr Ser Lys Val Leu Asp Leu Lys
             20                  25                  30

Asn Tyr Xaa
         35

(2) INFORMATION FOR SEQ ID NO:222:

(i) SEQUENCE CHARACTERISTICS:
                (A) LENGTH: 35 amino acids
                (B) TYPE: amino acid
                (C) STRANDEDNESS:
                (D) TOPOLOGY: unknown (ii) MOLECULE TYPE: peptide (ix) FEATURE:
                (A) NAME/KEY: Modified-site
                (B) LOCATION: 1
                (D) OTHER INFORMATION:/note="Xaa may represent an amino
                    group, a hydrophobic group, including but not limited
                    to carbobenzoxyl, dansyl, or T-butyloxycarbonyl; an
                    acetyl group; a 9-fluorenylmethoxy-carbonyl (FMOC) group;
                    a macromolecular carrier group including but not limited
                    to lipid-fatty acid conjugates, polyethylene glycol, or
                    carbohydrates.

(ix) FEATURE:
                (A) NAME/KEY: Modified-site
                (B) LOCATION: 35
                (D) OTHER INFORMATION:/note="Xaa may represent a carboxyl
                    group; an amido group; a T-butyloxycarbonyl group; a
                    macromolecular carrier group including but not limited
                    to lipid-fatty acid conjugates, polyethylene glycol, or
                    carbohydrates.

(xi) SEQUENCE DESCRIPTION: SEQ ID NO:222:

Xaa Asn Lys Ile Ala Leu Leu Ser Thr Asn Lys Ala Val Val Ser Leu
 1               5                  10                  15

Ser Asn Gly Val Ser Val Leu Thr Ser Lys Val Leu Asp Leu Lys Asn
             20                  25                  30

Tyr Ile Xaa
         35

(2) INFORMATION FOR SEQ ID NO:223:

(i) SEQUENCE CHARACTERISTICS:
       (A) LENGTH: 35 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION:/note="Xaa may represent an amino
           group, a hydrophobic group, including but not limited
           to carbobenzoxyl, dansyl, or T-butyloxycarbonyl; an
           acetyl group; a 9-fluorenylmethoxy-carbonyl (FMOC) group;
           a macromolecular carrier group including but not limited
           to lipid-fatty acid conjugates, polyethylene glycol, or
           carbohydrates.

(ix) FEATURE:
       (A) NAME/KEY: Modified-site
       (B) LOCATION: 35
       (D) OTHER INFORMATION:/note="Xaa may represent a carboxyl
           group; an amido group; a T-butyloxycarbonyl group; a
           macromolecular carrier group including but not limited
           to lipid-fatty acid conjugates, polyethylene glycol, or
           carbohydrates.

(xi) SEQUENCE DESCRIPTION: SEQ ID NO:223:

Xaa Lys Ile Ala Leu Leu Ser Thr Asn Lys Ala Val Val Ser Leu Ser
 1               5                  10                  15

Asn Gly Val Ser Val Leu Thr Ser Lys Val Leu Asp Leu Lys Asn Tyr
            20                  25                  30

Ile Asp Xaa
        35

(2) INFORMATION FOR SEQ ID NO:224:

(i) SEQUENCE CHARACTERISTICS:
       (A) LENGTH: 35 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION:/note="Xaa may represent an amino
           group, a hydrophobic group, including but not limited
           to carbobenzoxyl, dansyl, or T-butyloxycarbonyl; an
           acetyl group; a 9-fluorenylmethoxy-carbonyl (FMOC) group;
           a macromolecular carrier group including but not limited
           to lipid-fatty acid conjugates, polyethylene glycol, or
           carbohydrates.

(ix) FEATURE:
       (A) NAME/KEY: Modified-site
       (B) LOCATION: 35
       (D) OTHER INFORMATION:/note="Xaa may represent a carboxyl
           group; an amido group; a T-butyloxycarbonyl group; a
           macromolecular carrier group including but not limited
           to lipid-fatty acid conjugates, polyethylene glycol, or
           carbohydrates.

(xi) SEQUENCE DESCRIPTION: SEQ ID NO:224:

Xaa Ile Ala Leu Leu Ser Thr Asn Lys Ala Val Val Ser Leu Ser Asn
 1               5                  10                  15

```
Gly Val Ser Val Leu Thr Ser Lys Val Leu Asp Leu Lys Asn Tyr Ile
            20                  25                  30

Asp Lys Xaa
        35
```

(2) INFORMATION FOR SEQ ID NO:225:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.

(ix) FEATURE:
        (A) NAME/KEY: Modified-site
        (B) LOCATION: 35
        (D) OTHER INFORMATION:/note="Xaa may represent a carboxyl group; an amido group; a T-butyloxycarbonyl group; a macromolecular carrier group including but not limited to lipid-fatty acid conjugates, polyethylene glycol, or carbohydrates.

(xi) SEQUENCE DESCRIPTION: SEQ ID NO:225:

```
Xaa Ala Leu Leu Ser Thr Asn Lys Ala Val Val Ser Leu Ser Asn Gly
 1               5                  10                  15

Val Ser Val Leu Thr Ser Lys Val Leu Asp Leu Lys Asn Tyr Ile Asp
            20                  25                  30

Lys Gln Xaa
        35
```

(2) INFORMATION FOR SEQ ID NO:226:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.

(ix) FEATURE:
        (A) NAME/KEY: Modified-site
        (B) LOCATION: 35
        (D) OTHER INFORMATION:/note="Xaa may represent a carboxyl group; an amido group; a T-butyloxycarbonyl group; a macromolecular carrier group including but not limited to lipid-fatty acid conjugates, polyethylene glycol, or carbohydrates.

(xi) SEQUENCE DESCRIPTION: SEQ ID NO:226:

Xaa Val Ala Val Ser Lys Val Leu His Leu Glu Gly Glu Val Asn Lys
1               5                   10                  15

Ile Ala Leu Leu Ser Thr Asn Lys Ala Val Val Ser Leu Ser Asn Gly
                20                  25                  30

Val Ser Xaa
        35

(2) INFORMATION FOR SEQ ID NO:227:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 35
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:227:

Xaa Ala Val Ser Lys Val Leu His Leu Glu Gly Glu Val Asn Lys Ile
1               5                   10                  15

Ala Leu Leu Ser Thr Asn Lys Ala Val Val Ser Leu Ser Asn Gly Val
                20                  25                  30

Ser Val Xaa
        35

(2) INFORMATION FOR SEQ ID NO:228:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 35
        (D) OTHER INFORMATION:/note="Xaa may represent a carboxyl group; an amido group; a T-butyloxycarbonyl group; a
macromolecular carrier group including but not limited
to lipid-fatty acid conjugates, polyethylene glycol, or
carbohydrates.

(xi) SEQUENCE DESCRIPTION: SEQ ID NO:228:

Xaa Val Ser Lys Val Leu His Leu Glu Gly Glu Val Asn Lys Ile Ala
1               5                   10                  15

Leu Leu Ser Thr Asn Lys Ala Val Val Ser Leu Ser Asn Gly Val Ser
            20                  25                  30

Val Leu Xaa
        35

(2) INFORMATION FOR SEQ ID NO:229:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 35
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:229:

Xaa Ser Lys Val Leu His Leu Glu Gly Glu Val Asn Lys Ile Ala Leu
1               5                   10                  15

Leu Ser Thr Asn Lys Ala Val Val Ser Leu Ser Asn Gly Val Ser Val
            20                  25                  30

Leu Thr Xaa
        35

(2) INFORMATION FOR SEQ ID NO:230:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
    (A) NAME/KEY: Modified-site
    (B) LOCATION: 35
    (D) OTHER INFORMATION:/note="Xaa may represent a carboxyl
        group; an amido group; a T-butyloxycarbonyl group; a
        macromolecular carrier group including but not limited
        to lipid-fatty acid conjugates, polyethylene glycol, or
        carbohydrates.

(xi) SEQUENCE DESCRIPTION: SEQ ID NO:230:

Xaa Lys Val Leu His Leu Glu Gly Glu Val Asn Lys Ile Ala Leu Leu
1               5                   10                  15

Ser Thr Asn Lys Ala Val Val Ser Leu Ser Asn Gly Val Ser Val Leu
            20                  25                  30

Thr Ser Xaa
        35

(2) INFORMATION FOR SEQ ID NO:231:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 35
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:231:

Xaa Leu Glu Gly Glu Val Asn Lys Ile Ala Leu Leu Ser Thr Asn Lys
1               5                   10                  15

Ala Val Val Ser Leu Ser Asn Gly Val Ser Val Leu Thr Ser Lys Val
            20                  25                  30

Leu Asp Xaa
        35

(2) INFORMATION FOR SEQ ID NO:232:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 35
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:232:

Xaa Gly Glu Val Asn Lys Ile Ala Leu Leu Ser Thr Asn Lys Ala Val
 1               5                  10                  15

Val Ser Leu Ser Asn Gly Val Ser Val Leu Thr Ser Lys Val Leu Asp
            20                  25                  30

Leu Lys Xaa
        35

(2) INFORMATION FOR SEQ ID NO:233:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 35
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:233:

Xaa Glu Val Asn Lys Ile Ala Leu Leu Ser Thr Asn Lys Ala Val Val
 1               5                  10                  15

Ser Leu Ser Asn Gly Val Ser Val Leu Thr Ser Lys Val Leu Asp Leu
            20                  25                  30

Lys Asn Xaa
        35

(2) INFORMATION FOR SEQ ID NO:234:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
                  (A) NAME/KEY: Modified-site
                  (B) LOCATION: 1
                  (D) OTHER INFORMATION:/note="Xaa may represent an amino
                      group, a hydrophobic group, including but not limited
                      to carbobenzoxyl, dansyl, or T-butyloxycarbonyl; an
                      acetyl group; a 9-fluorenylmethoxy-carbonyl (FMOC) group;
                      a macromolecular carrier group including but not limited
                      to lipid-fatty acid conjugates, polyethylene glycol, or
                      carbohydrates.

(ix) FEATURE:
                  (A) NAME/KEY: Modified-site
                  (B) LOCATION: 35
                  (D) OTHER INFORMATION:/note="Xaa may represent a carboxyl
                      group; an amido group; a T-butyloxycarbonyl group; a
                      macromolecular carrier group including but not limited
                      to lipid-fatty acid conjugates, polyethylene glycol, or
                      carbohydrates.

(xi) SEQUENCE DESCRIPTION: SEQ ID NO:234:

Xaa Val Asn Lys Ile Ala Leu Leu Ser Thr Asn Lys Ala Val Val Ser
 1               5                  10                  15

Leu Ser Asn Gly Val Ser Val Leu Thr Ser Lys Val Leu Asp Leu Lys
            20                  25                  30

Asn Tyr Xaa
        35

(2) INFORMATION FOR SEQ ID NO:235:

(i) SEQUENCE CHARACTERISTICS:
            (A) LENGTH: 35 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION:/note="Xaa may represent an amino
                group, a hydrophobic group, including but not limited
                to carbobenzoxyl, dansyl, or T-butyloxycarbonyl; an
                acetyl group; a 9-fluorenylmethoxy-carbonyl (FMOC) group;
                a macromolecular carrier group including but not limited
                to lipid-fatty acid conjugates, polyethylene glycol, or
                carbohydrates.

(ix) FEATURE:
            (A) NAME/KEY: Modified-site
            (B) LOCATION: 35
            (D) OTHER INFORMATION:/note="Xaa may represent a carboxyl
                group; an amido group; a T-butyloxycarbonyl group; a
                macromolecular carrier group including but not limited
                to lipid-fatty acid conjugates, polyethylene glycol, or
                carbohydrates.

(xi) SEQUENCE DESCRIPTION: SEQ ID NO:235:

Xaa Asn Lys Ile Ala Leu Leu Ser Thr Asn Lys Ala Val Val Ser Leu
 1               5                  10                  15

Ser Asn Gly Val Ser Val Leu Thr Ser Lys Val Leu Asp Leu Lys Asn
            20                  25                  30

Tyr Ile Xaa
        35

(2) INFORMATION FOR SEQ ID NO:236:

(i) SEQUENCE CHARACTERISTICS:
            (A) LENGTH: 35 amino acids
            (B) TYPE: amino acid (C) STRANDEDNESS:
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION:/note="Xaa may represent an amino
             group, a hydrophobic group, including but not limited
             to carbobenzoxyl, dansyl, or T-butyloxycarbonyl; an
             acetyl group; a 9-fluorenylmethoxy-carbonyl (FMOC) group;
             a macromolecular carrier group including but not limited
             to lipid-fatty acid conjugates, polyethylene glycol, or
             carbohydrates.

(ix) FEATURE:
         (A) NAME/KEY: Modified-site
         (B) LOCATION: 35
         (D) OTHER INFORMATION:/note="Xaa may represent a carboxyl
             group; an amido group; a T-butyloxycarbonyl group; a
             macromolecular carrier group including but not limited
             to lipid-fatty acid conjugates, polyethylene glycol, or
             carbohydrates.

(xi) SEQUENCE DESCRIPTION: SEQ ID NO:236:

Xaa Lys Ile Ala Leu Leu Ser Thr Asn Lys Ala Val Val Ser Leu Ser
 1               5                  10                  15

Asn Gly Val Ser Val Leu Thr Ser Lys Val Leu Asp Leu Lys Asn Tyr
            20                  25                  30

Ile Asp Xaa
        35

(2) INFORMATION FOR SEQ ID NO:237:

(i) SEQUENCE CHARACTERISTICS:
         (A) LENGTH: 35 amino acids
         (B) TYPE: amino acid
         (C) STRANDEDNESS:
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION:/note="Xaa may represent an amino
             group, a hydrophobic group, including but not limited
             to carbobenzoxyl, dansyl, or T-butyloxycarbonyl; an
             acetyl group; a 9-fluorenylmethoxy-carbonyl (FMOC) group;
             a macromolecular carrier group including but not limited
             to lipid-fatty acid conjugates, polyethylene glycol, or
             carbohydrates.

(ix) FEATURE:
         (A) NAME/KEY: Modified-site
         (B) LOCATION: 35
         (D) OTHER INFORMATION:/note="Xaa may represent a carboxyl
             group; an amido group; a T-butyloxycarbonyl group; a
             macromolecular carrier group including but not limited
             to lipid-fatty acid conjugates, polyethylene glycol, or
             carbohydrates.

(xi) SEQUENCE DESCRIPTION: SEQ ID NO:237:

Xaa Ile Ala Leu Leu Ser Thr Asn Lys Ala Val Val Ser Leu Ser Asn
 1               5                  10                  15

Gly Val Ser Val Leu Thr Ser Lys Val Leu Asp Leu Lys Asn Tyr Ile
            20                  25                  30

Asp Lys Xaa
        35

-continued (2) INFORMATION FOR SEQ ID NO:238:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa may represent an amino
            group, a hydrophobic group, including but not limited
            to carbobenzoxyl, dansyl, or T-butyloxycarbonyl; an
            acetyl group; a 9-fluorenylmethoxy-carbonyl (FMOC) group;
            a macromolecular carrier group including but not limited
            to lipid-fatty acid conjugates, polyethylene glycol, or
            carbohydrates.

(ix) FEATURE:
        (A) NAME/KEY: Modified-site
        (B) LOCATION: 35
        (D) OTHER INFORMATION:/note="Xaa may represent a carboxyl
            group; an amido group; a T-butyloxycarbonyl group; a
            macromolecular carrier group including but not limited
            to lipid-fatty acid conjugates, polyethylene glycol, or
            carbohydrates.

(xi) SEQUENCE DESCRIPTION: SEQ ID NO:238:

```
Xaa Ala Leu Leu Ser Thr Asn Lys Ala Val Val Ser Leu Ser Asn Gly
 1               5                  10                  15

Val Ser Val Leu Thr Ser Lys Val Leu Asp Leu Lys Asn Tyr Ile Asp
            20                  25                  30

Lys Gln Xaa
        35
```

(2) INFORMATION FOR SEQ ID NO:239:

(i) SEQUENCE CHARACTERISTICS:
        (A) LENGTH: 49 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 49
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:239:

```
Xaa Pro Leu Leu Val Leu Gln Ala Gly Phe Phe Leu Leu Thr Arg Ile
 1               5                  10                  15

Leu Thr Ile Pro Gln Ser Leu Asp Ser Trp Trp Thr Ser Leu Asn Phe
            20                  25                  30

Leu Gly Gly Gly Thr Thr Val Cys Leu Gly Gln Asn Ser Gln Ser Pro
        35                  40                  45

Xaa
```

(2) INFORMATION FOR SEQ ID NO:240:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:240:

```
Xaa Pro Leu Leu Val Leu Gln Ala Gly Phe Phe Leu Leu Thr Arg Ile
 1               5                  10                  15

Leu Thr Ile Pro Gln Ser Leu Asp Ser Trp Trp Thr Ser Leu Asn Phe
             20                  25                  30

Leu Gly Gly Thr Xaa
         35
```

(2) INFORMATION FOR SEQ ID NO:241:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:241:

```
Xaa Leu Leu Val Leu Gln Ala Gly Phe Phe Leu Leu Thr Arg Ile Leu
 1               5                  10                  15

Thr Ile Pro Gln Ser Leu Asp Ser Trp Trp Thr Ser Leu Asn Phe Leu
             20                  25                  30

Gly Gly Thr Thr Xaa
         35
```

(2) INFORMATION FOR SEQ ID NO:242:

(i) SEQUENCE CHARACTERISTICS:

(A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:242:

Xaa Leu Val Leu Gln Ala Gly Phe Phe Leu Leu Thr Arg Ile Leu Thr
1               5                   10                  15

Ile Pro Gln Ser Leu Asp Ser Trp Trp Thr Ser Leu Asn Phe Leu Gly
            20                  25                  30

Gly Thr Thr Val Xaa
        35

(2) INFORMATION FOR SEQ ID NO:243:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:243:

Xaa Leu Gln Ala Gly Phe Phe Leu Leu Thr Arg Ile Leu Thr Ile Pro
1               5                   10                  15

Gln Ser Leu Asp Ser Trp Trp Thr Ser Leu Asn Gly Leu Gly Gly Thr
            20                  25                  30

Thr Val Cys Leu Xaa
        35

(2) INFORMATION FOR SEQ ID NO:244:

(i) SEQUENCE CHARACTERISTICS:
        (A) LENGTH: 37 amino acids
        (B) TYPE: amino acid
        (C) STRANDEDNESS:
        (D) TOPOLOGY: unknown

```
    (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:244:

Xaa Gln Ala Gly Phe Phe Leu Leu Thr Arg Ile Leu Thr Ile Pro Gln
1               5                   10                  15

Ser Leu Asp Ser Trp Trp Thr Ser Leu Asn Phe Leu Gly Gly Thr Thr
            20                  25                  30

Val Cys Leu Gly Xaa
            35

(2) INFORMATION FOR SEQ ID NO:245:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:245:

Xaa Ala Gly Phe Phe Leu Leu Thr Arg Ile Leu Thr Ile Pro Gln Ser
1               5                   10                  15

Leu Asp Ser Trp Trp Thr Ser Leu Asn Phe Leu Gly Gly Thr Thr Val
            20                  25                  30

Cys Leu Gly Gln Xaa
            35

(2) INFORMATION FOR SEQ ID NO:246:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
```

(D) OTHER INFORMATION:/note="Xaa comprises an amino group,
                an acetyl group, a 9-fluorenylmethoxy-carbonyl group,
                a hydrophobic group, or a macromolecule carrier group.

(ix) FEATURE:
            (A) NAME/KEY: Modified-site
            (B) LOCATION: 37
            (D) OTHER INFORMATION:/note="Xaa comprises a carboxyl group,
                an amido group, a hydrophobic group, or a macromolecular
                carrier group for an effective period of time so that no
                infection of the cell by the virus occurs.

(xi) SEQUENCE DESCRIPTION: SEQ ID NO:246:

Xaa Gly Phe Phe Leu Leu Thr Arg Ile Leu Thr Ile Pro Gln Ser Leu
 1               5                  10                  15

Asp Ser Trp Trp Thr Ser Leu Asn Phe Leu Gly Gly Thr Thr Val Cys
            20                  25                  30

Leu Gly Gln Asn Xaa
            35

(2) INFORMATION FOR SEQ ID NO:247:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:247:

Xaa Phe Phe Leu Leu Thr Arg Ile Leu Thr Ile Pro Gln Ser Leu Asp
 1               5                  10                  15

Ser Trp Trp Thr Ser Leu Asn Phe Leu Gly Gly Thr Thr Val Cys Leu
            20                  25                  30

Gly Gln Asn Ser Xaa
            35

(2) INFORMATION FOR SEQ ID NO:248:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:

(A) NAME/KEY: Modified-site
                (B) LOCATION: 37
                (D) OTHER INFORMATION:/note="Xaa comprises a carboxyl group,
                    an amido group, a hydrophobic group, or a macromolecular
                    carrier group for an effective period of time so that no
                    infection of the cell by the virus occurs.

(xi) SEQUENCE DESCRIPTION: SEQ ID NO:248:

Xaa Phe Leu Leu Thr Arg Ile Leu Thr Ile Pro Gln Ser Leu Asp Ser
 1               5                  10                  15

Trp Trp Thr Ser Leu Asn Phe Leu Gly Gly Thr Thr Val Cys Leu Gly
            20                  25                  30

Gln Asn Ser Gln Xaa
            35

(2) INFORMATION FOR SEQ ID NO:249:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:249:

Xaa Leu Leu Thr Arg Ile Leu Thr Ile Pro Gln Ser Leu Asp Ser Trp
 1               5                  10                  15

Trp Thr Ser Leu Asn Phe Leu Gly Gly Thr Thr Val Cys Leu Gly Gln
            20                  25                  30

Asn Ser Gln Ser Xaa
            35

(2) INFORMATION FOR SEQ ID NO:250:

(i) SEQUENCE CHARACTERISTICS:
        (A) LENGTH: 59 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 59
        (D) OTHER INFORMATION:/note="Xaa comprises a carboxyl group,
            an amido group, a hydrophobic group, or a macromolecular
            carrier group for an effective period of time so that no infection of the cell by the virus occurs.

(xi) SEQUENCE DESCRIPTION: SEQ ID NO:250:

```
Xaa Pro Gly Tyr Arg Trp Met Cys Leu Arg Arg Phe Ile Ile Phe Leu
 1               5                  10                  15

Phe Ile Leu Leu Leu Cys Leu Ile Phe Leu Leu Val Leu Leu Asp Tyr
                20                  25                  30

Gln Gly Met Leu Pro Val Cys Pro Leu Ile Pro Gly Ser Ser Thr Ser
            35                  40                  45

Thr Gly Pro Cys Arg Thr Cys Met Thr Thr Xaa
    50                  55
```

(2) INFORMATION FOR SEQ ID NO:251:

(i) SEQUENCE CHARACTERISTICS:
      (A) LENGTH: 37 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION:/note="Xaa comprises an amino group,
          an acetyl group, a 9-fluorenylmethoxy-carbonyl group,
          a hydrophobic group, or a macromolecule carrier group.

(ix) FEATURE:
      (A) NAME/KEY: Modified-site
      (B) LOCATION: 37
      (D) OTHER INFORMATION:/note="Xaa comprises a carboxyl group,
          an amido group, a hydrophobic group, or a macromolecular
          carrier group for an effective period of time so that no
          infection of the cell by the virus occurs.

(xi) SEQUENCE DESCRIPTION: SEQ ID NO:251:

```
Xaa Pro Gly Tyr Arg Trp Met Cys Leu Arg Arg Phe Ile Ile Phe Leu
 1               5                  10                  15

Phe Ile Leu Leu Leu Cys Leu Ile Phe Leu Leu Val Leu Leu Asp Tyr
                20                  25                  30

Gln Gly Met Leu Xaa
            35
```

(2) INFORMATION FOR SEQ ID NO:252:

(i) SEQUENCE CHARACTERISTICS:
      (A) LENGTH: 37 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION:/note="Xaa comprises an amino group,
          an acetyl group, a 9-fluorenylmethoxy-carbonyl group,
          a hydrophobic group, or a macromolecule carrier group.

(ix) FEATURE:
      (A) NAME/KEY: Modified-site
      (B) LOCATION: 37
      (D) OTHER INFORMATION:/note="Xaa comprises a carboxyl group,
          an amido group, a hydrophobic group, or a macromolecular
          carrier group for an effective period of time so that no
          infection of the cell by the virus occurs.

(xi) SEQUENCE DESCRIPTION: SEQ ID NO:252:

Xaa Gly Tyr Arg Trp Met Cys Leu Arg Arg Phe Ile Ile Phe Leu Phe
1               5                   10                  15

Ile Leu Leu Leu Cys Leu Ile Phe Leu Leu Val Leu Leu Asp Tyr Gln
            20                  25                  30

Gly Met Leu Pro Xaa
        35

(2) INFORMATION FOR SEQ ID NO:253:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:253:

Xaa Tyr Arg Trp Met Cys Leu Arg Arg Phe Ile Ile Phe Leu Phe Ile
1               5                   10                  15

Leu Leu Leu Cys Leu Ile Phe Leu Leu Val Leu Leu Asp Tyr Gln Gly
            20                  25                  30

Met Leu Pro Val Xaa
        35

(2) INFORMATION FOR SEQ ID NO:254:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:254:

Xaa Arg Trp Met Cys Leu Arg Arg Phe Ile Ile Phe Leu Phe Ile Leu
1               5                   10                  15

Leu Leu Cys Leu Ile Phe Leu Leu Val Leu Leu Asp Tyr Gln Gly Met
            20                  25                  30

Leu Pro Val Cys Xaa
        35

(2) INFORMATION FOR SEQ ID NO:255:

(i) SEQUENCE CHARACTERISTICS:
        (A) LENGTH: 37 amino acids
        (B) TYPE: amino acid
        (C) STRANDEDNESS:
        (D) TOPOLOGY: unknown -continued

```
    (ii) MOLECULE TYPE: peptide (ix) FEATURE:
         (A) NAME/KEY: Modified-site
         (B) LOCATION: 1
         (D) OTHER INFORMATION:/note="Xaa comprises an amino group,
             an acetyl group, a 9-fluorenylmethoxy-carbonyl group,
             a hydrophobic group, or a macromolecule carrier group.

(ix) FEATURE:
         (A) NAME/KEY: Modified-site
         (B) LOCATION: 37
         (D) OTHER INFORMATION:/note="Xaa comprises a carboxyl group,
             an amido group, a hydrophobic group, or a macromolecular
             carrier group for an effective period of time so that no
             infection of the cell by the virus occurs.

(xi) SEQUENCE DESCRIPTION: SEQ ID NO:255:

Xaa Trp Met Cys Leu Arg Arg Phe Ile Ile Phe Leu Phe Ile Leu Leu
1               5                  10                  15

Leu Cys Leu Ile Phe Leu Leu Val Leu Leu Asp Tyr Gln Gly Met Leu
            20                  25                  30

Pro Val Cys Pro Xaa
            35

(2) INFORMATION FOR SEQ ID NO:256:

(i) SEQUENCE CHARACTERISTICS:
         (A) LENGTH: 37 amino acids
         (B) TYPE: amino acid
         (C) STRANDEDNESS:
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION:/note="Xaa comprises an amino group,
             an acetyl group, a 9-fluorenylmethoxy-carbonyl group,
             a hydrophobic group, or a macromolecule carrier group.

(ix) FEATURE:
         (A) NAME/KEY: Modified-site
         (B) LOCATION: 37
         (D) OTHER INFORMATION:/note="Xaa comprises a carboxyl group,
             an amido group, a hydrophobic group, or a macromolecular
             carrier group for an effective period of time so that no
             infection of the cell by the virus occurs.

(xi) SEQUENCE DESCRIPTION: SEQ ID NO:256:

Xaa Met Cys Leu Arg Arg Phe Ile Ile Phe Leu Phe Ile Leu Leu Leu
1               5                  10                  15

Cys Leu Ile Phe Leu Leu Val Leu Leu Asp Tyr Gln Gly Met Leu Pro
            20                  25                  30

Val Cys Pro Ile Xaa
            35

(2) INFORMATION FOR SEQ ID NO:257:

(i) SEQUENCE CHARACTERISTICS:
         (A) LENGTH: 37 amino acids
         (B) TYPE: amino acid
         (C) STRANDEDNESS:
         (D) TOPOLOGY: unknown (ii) MOLECULE TYPE: peptide (ix) FEATURE:
         (A) NAME/KEY: Modified-site
         (B) LOCATION: 1
```

(D) OTHER INFORMATION:/note="Xaa comprises an amino group,
                an acetyl group, a 9-fluorenylmethoxy-carbonyl group,
                a hydrophobic group, or a macromolecule carrier group.

(ix) FEATURE:
         (A) NAME/KEY: Modified-site
         (B) LOCATION: 37
         (D) OTHER INFORMATION:/note="Xaa comprises a carboxyl group,
             an amido group, a hydrophobic group, or a macromolecular
             carrier group for an effective period of time so that no
             infection of the cell by the virus occurs.

(xi) SEQUENCE DESCRIPTION: SEQ ID NO:257:

Xaa Cys Leu Arg Arg Phe Ile Ile Phe Leu Phe Ile Leu Leu Leu Cys
 1               5                  10                  15

Leu Ile Phe Leu Leu Val Leu Leu Asp Tyr Gln Gly Met Leu Pro Val
            20                  25                  30

Cys Pro Leu Ile Xaa
            35

(2) INFORMATION FOR SEQ ID NO:258:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION:/note="Xaa comprises an amino group,
             an acetyl group, a 9-fluorenylmethoxy-carbonyl group,
             a hydrophobic group, or a macromolecule carrier group.

(ix) FEATURE:
         (A) NAME/KEY: Modified-site
         (B) LOCATION: 37
         (D) OTHER INFORMATION:/note="Xaa comprises a carboxyl group,
             an amido group, a hydrophobic group, or a macromolecular
             carrier group for an effective period of time so that no
             infection of the cell by the virus occurs.

(xi) SEQUENCE DESCRIPTION: SEQ ID NO:258:

Xaa Leu Arg Arg Phe Ile Ile Phe Leu Phe Ile Leu Leu Leu Cys Leu
 1               5                  10                  15

Ile Phe Leu Leu Val Leu Leu Asp Tyr Gln Gly Met Leu Pro Val Cys
            20                  25                  30

Pro Leu Ile Pro Xaa
            35

(2) INFORMATION FOR SEQ ID NO:259:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION:/note="Xaa comprises an amino group,
             an acetyl group, a 9-fluorenylmethoxy-carbonyl group,
             a hydrophobic group, or a macromolecule carrier group.

(ix) FEATURE:

(A) NAME/KEY: Modified-site
(B) LOCATION: 37
(D) OTHER INFORMATION:/note="Xaa comprises a carboxyl group,
    an amido group, a hydrophobic group, or a macromolecular
    carrier group for an effective period of time so that no
    infection of the cell by the virus occurs.

(xi) SEQUENCE DESCRIPTION: SEQ ID NO:259:

```
Xaa Arg Arg Phe Ile Ile Phe Leu Phe Ile Leu Leu Leu Cys Leu Ile
 1               5                  10                  15

Phe Leu Leu Val Leu Leu Asp Tyr Gln Gly Met Leu Pro Val Cys Pro
            20                  25                  30

Leu Ile Pro Gly Xaa
            35
```

(2) INFORMATION FOR SEQ ID NO:260:

(i) SEQUENCE CHARACTERISTICS:
       (A) LENGTH: 37 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION:/note="Xaa comprises an amino group,
           an acetyl group, a 9-fluorenylmethoxy-carbonyl group,
           a hydrophobic group, or a macromolecule carrier group.

(ix) FEATURE:
       (A) NAME/KEY: Modified-site
       (B) LOCATION: 37
       (D) OTHER INFORMATION:/note="Xaa comprises a carboxyl group,
           an amido group, a hydrophobic group, or a macromolecular
           carrier group for an effective period of time so that no
           infection of the cell by the virus occurs.

(xi) SEQUENCE DESCRIPTION: SEQ ID NO:260:

```
Xaa Arg Phe Ile Ile Phe Leu Phe Ile Leu Leu Leu Cys Leu Ile Phe
 1               5                  10                  15

Leu Leu Val Leu Leu Asp Tyr Gln Gly Met Leu Pro Val Cys Pro Leu
            20                  25                  30

Ile Pro Gly Ser Xaa
            35
```

(2) INFORMATION FOR SEQ ID NO:261:

(i) SEQUENCE CHARACTERISTICS:
       (A) LENGTH: 37 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION:/note="Xaa comprises an amino group,
           an acetyl group, a 9-fluorenylmethoxy-carbonyl group,
           a hydrophobic group, or a macromolecule carrier group.

(ix) FEATURE:
       (A) NAME/KEY: Modified-site
       (B) LOCATION: 37
       (D) OTHER INFORMATION:/note="Xaa comprises a carboxyl group,
           an amido group, a hydrophobic group, or a macromolecular
           carrier group for an effective period of time so that no infection of the cell by the virus occurs.

(xi) SEQUENCE DESCRIPTION: SEQ ID NO:261:

Xaa Phe Ile Ile Phe Leu Phe Ile Leu Leu Leu Cys Leu Ile Phe Leu
1               5                   10                  15

Leu Val Leu Leu Asp Tyr Gln Gly Met Leu Pro Val Cys Pro Leu Ile
            20                  25                  30

Gly Gly Ser Ser Xaa
            35

(2) INFORMATION FOR SEQ ID NO:262:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:262:

Xaa Ile Ile Phe Leu Phe Ile Leu Leu Leu Cys Leu Ile Phe Leu Leu
1               5                   10                  15

Val Leu Leu Asp Tyr Gln Gly Met Leu Pro Val Cys Pro Leu Ile Pro
            20                  25                  30

Gly Ser Ser Thr Xaa
            35

(2) INFORMATION FOR SEQ ID NO:263:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:263:

Xaa Ile Phe Leu Phe Ile Leu Leu Leu Cys Leu Ile Phe Leu Leu Val

-continued

```
1               5                   10                  15
Leu Leu Asp Tyr Gln Gly Met Leu Pro Val Cys Pro Leu Ile Pro Gly
                20                  25                  30
Ser Ser Thr Ser Xaa
            35
```

(2) INFORMATION FOR SEQ ID NO:264:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:264:

```
Xaa Phe Leu Phe Ile Leu Leu Leu Cys Leu Ile Phe Leu Leu Val Leu
 1               5                   10                  15
Leu Asp Tyr Gln Gly Met Leu Pro Val Cys Pro Leu Ile Pro Gly Ser
                20                  25                  30
Ser Thr Ser Thr Xaa
            35
```

(2) INFORMATION FOR SEQ ID NO:265:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:265:

```
Xaa Leu Phe Ile Leu Leu Leu Cys Leu Ile Phe Leu Leu Val Leu Leu
 1               5                   10                  15
Asp Tyr Gln Gly Met Leu Pro Val Cys Pro Leu Ile Pro Gly Ser Ser
                20                  25                  30
```

Thr Ser Thr Gly Xaa
        35

(2) INFORMATION FOR SEQ ID NO:266:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:266:

Xaa Phe Ile Leu Leu Leu Cys Leu Ile Phe Leu Leu Val Leu Leu Asp
1               5                   10                  15

Tyr Gln Gly Met Leu Pro Val Cys Pro Leu Ile Pro Gly Ser Ser Thr
            20                  25                  30

Ser Thr Gly Pro Xaa
        35

(2) INFORMATION FOR SEQ ID NO:267:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:267:

Xaa Ile Leu Leu Leu Cys Leu Ile Phe Leu Leu Val Leu Leu Asp Tyr
1               5                   10                  15

Gln Gly Met Leu Pro Val Cys Pro Leu Ile Pro Gly Ser Ser Thr Ser
            20                  25                  30

Thr Gly Pro Cys Xaa
        35

(2) INFORMATION FOR SEQ ID NO:268:

```
    (i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:268:

Xaa Leu Leu Leu Cys Leu Ile Phe Leu Leu Val Leu Leu Asp Tyr Gln
 1               5                  10                  15

Gly Met Leu Pro Val Cys Pro Leu Ile Pro Gly Ser Ser Thr Ser Thr
            20                  25                  30

Gly Pro Cys Arg Xaa
         35

(2) INFORMATION FOR SEQ ID NO:269:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION:/note="Xaa comprises an amino group,
            an acetyl group, a 9-fluorenylmethoxy-carbonyl group,
            a hydrophobic group, or a macromolecule carrier group.

(ix) FEATURE:
        (A) NAME/KEY: Modified-site
        (B) LOCATION: 37
        (D) OTHER INFORMATION:/note="Xaa comprises a carboxyl group,
            an amido group, a hydrophobic group, or a macromolecular
            carrier group for an effective period of time so that no
            infection of the cell by the virus occurs.

(xi) SEQUENCE DESCRIPTION: SEQ ID NO:269:

Xaa Leu Leu Cys Leu Ile Phe Leu Leu Val Leu Leu Asp Tyr Gln Gly
 1               5                  10                  15

Met Leu Pro Val Cys Pro Leu Ile Pro Gly Ser Ser Thr Ser Thr Gly
            20                  25                  30

Pro Cys Arg Thr Xaa
         35

(2) INFORMATION FOR SEQ ID NO:270:

(i) SEQUENCE CHARACTERISTICS:
        (A) LENGTH: 37 amino acids
        (B) TYPE: amino acid
        (C) STRANDEDNESS:
```

(D) TOPOLOGY: unknown (ii) MOLECULE TYPE: peptide (ix) FEATURE:
            (A) NAME/KEY: Modified-site
            (B) LOCATION: 1
            (D) OTHER INFORMATION:/note="Xaa comprises an amino group,
                an acetyl group, a 9-fluorenylmethoxy-carbonyl group,
                a hydrophobic group, or a macromolecule carrier group.

(ix) FEATURE:
            (A) NAME/KEY: Modified-site
            (B) LOCATION: 37
            (D) OTHER INFORMATION:/note="Xaa comprises a carboxyl group,
                an amido group, a hydrophobic group, or a macromolecular
                carrier group for an effective period of time so that no
                infection of the cell by the virus occurs.

(xi) SEQUENCE DESCRIPTION: SEQ ID NO:270:

Xaa Leu Cys Leu Ile Phe Leu Leu Val Leu Leu Asp Tyr Gln Gly Met
 1               5                  10                  15

Leu Pro Val Cys Pro Leu Ile Pro Gly Ser Ser Thr Ser Thr Gly Pro
            20                  25                  30

Cys Arg Thr Cys Xaa
        35

(2) INFORMATION FOR SEQ ID NO:271:

(i) SEQUENCE CHARACTERISTICS:
            (A) LENGTH: 37 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION:/note="Xaa comprises an amino group,
                an acetyl group, a 9-fluorenylmethoxy-carbonyl group,
                a hydrophobic group, or a macromolecule carrier group.

(ix) FEATURE:
            (A) NAME/KEY: Modified-site
            (B) LOCATION: 37
            (D) OTHER INFORMATION:/note="Xaa comprises a carboxyl group,
                an amido group, a hydrophobic group, or a macromolecular
                carrier group for an effective period of time so that no
                infection of the cell by the virus occurs.

(xi) SEQUENCE DESCRIPTION: SEQ ID NO:271:

Xaa Cys Leu Ile Phe Leu Leu Val Leu Leu Asp Tyr Gln Gly Met Leu
 1               5                  10                  15

Pro Val Cys Pro Leu Ile Pro Gly Ser Ser Thr Ser Thr Gly Pro Cys
            20                  25                  30

Arg Thr Cys Met Xaa
        35

(2) INFORMATION FOR SEQ ID NO:272:

(i) SEQUENCE CHARACTERISTICS:
            (A) LENGTH: 37 amino acids
            (B) TYPE: amino acid
            (C) STRANDEDNESS:
            (D) TOPOLOGY: unknown (ii) MOLECULE TYPE: peptide (ix) FEATURE:

-continued

```
            (A) NAME/KEY: Modified-site
            (B) LOCATION: 1
            (D) OTHER INFORMATION:/note="Xaa comprises an amino group,
                  an acetyl group, a 9-fluorenylmethoxy-carbonyl group,
                  a hydrophobic group, or a macromolecule carrier group.

(ix) FEATURE:
            (A) NAME/KEY: Modified-site
            (B) LOCATION: 37
            (D) OTHER INFORMATION:/note="Xaa comprises a carboxyl group,
                  an amido group, a hydrophobic group, or a macromolecular
                  carrier group for an effective period of time so that no
                  infection of the cell by the virus occurs.

(xi) SEQUENCE DESCRIPTION: SEQ ID NO:272:

Xaa Leu Ile Phe Leu Leu Val Leu Leu Asp Tyr Gln Gly Met Leu Pro
 1               5                  10                  15

Val Cys Pro Leu Ile Pro Gly Ser Ser Thr Ser Thr Gly Pro Cys Arg
            20                  25                  30

Thr Cys Met Thr Xaa
            35

(2) INFORMATION FOR SEQ ID NO:273:

(i) SEQUENCE CHARACTERISTICS:
            (A) LENGTH: 37 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION:/note="Xaa comprises an amino group,
                  an acetyl group, a 9-fluorenylmethoxy-carbonyl group,
                  a hydrophobic group, or a macromolecule carrier group.

(ix) FEATURE:
            (A) NAME/KEY: Modified-site
            (B) LOCATION: 37
            (D) OTHER INFORMATION:/note="Xaa comprises a carboxyl group,
                  an amido group, a hydrophobic group, or a macromolecular
                  carrier group for an effective period of time so that no
                  infection of the cell by the virus occurs.

(xi) SEQUENCE DESCRIPTION: SEQ ID NO:273:

Xaa Ile Phe Leu Leu Val Leu Leu Asp Tyr Gln Gly Met Leu Pro Val
 1               5                  10                  15

Cys Pro Leu Ile Pro Gly Ser Ser Thr Ser Thr Gly Pro Cys Arg Thr
            20                  25                  30

Cys Met Thr Thr Xaa
            35
```

What is claimed is:

1. A method for inhibiting transmission of a respiratory syncytial virus to a cell, said method comprising contacting said cell with an effective concentration of an isolated peptide for an effective period of time;
   wherein said isolated peptide comprises an amino acid sequence of a respiratory syncytial virus protein;
   wherein said isolated peptide is identified by one or more of an ALLMOTI5, 107x178'4 and PLZIP sequence search motifs; and
   wherein fusion of the virus to the cell is inhibited.

2. A method for inhibiting transmission of a respiratory syncytial virus to a cell, said method comprising contacting said cell with an effective concentration of an isolated peptide; wherein said isolated peptide has the formula:

X-TSVITIELSNIKENKCNGTDAKVKLIKQELDKYKN-Z;

X-SVITIELSNIKENKCNGTDAKVKLIKQELDKYKNA-Z;

X-VITIELSNIKENKCNGTDAKVKLIKQELDKYKNAV-Z;

X-VAVSKVLHLEGEVNKIALLSTNKAVVSLSNGVS-Z;

X-AVSKVLHLEGEVNKIALLSTNKAVVSLSNGVSV-Z;

X-VSKVLHLEGEVNKIALLSTNKAVVSLSNGVSVL-Z;
X-SKVLHLEGEVNKIALLSTNKAVVSLSNGVSVLT-Z;
X-KVLHLEGEVNKIALLSTNKAVVSLSNGVSVLTS-Z;
X-LEGEVNKIALLSTNKAVVSLSNGVSVLTSKVLD-Z;
X-GEVNKIALLSTNKAVVSLSNGVSVLTSKVLDLK-Z;
X-EVNKIALLSTNKAVVSLSNGVSVLTSKVLDLKN-Z;
X-VNKIALLSTNKAVVSLSNGVSVLTSKVLDLKNY-Z;
X-NKIALLSTNKAVVSLSNGVSVLTSKVLDLKNYI-Z;
X-KIALLSTNKAVVSLSNGVSVLTSKVLDLKNYID-Z;
X-IALLSTNKAVVSLSNGVSVLTSKVLDLKNYIDK-Z;
X-ALLSTNKAVVSLSNGVSVLTSKVLDLKNYIDKQ-Z;
X-VAVSKVLHLEGEVNKIALLSTNKAVVSLSNGVS-Z;
X-AVSKVLHLEGEVNKIALLSTANKVVSLSNGVSV-Z;
X-VSKVLHLEGEVNKIALLSTNKAVVSLSNGVSVL-Z;
X-SKVLHLEGEVNKIALLSTNKAVVSLSNGVSVLT-Z;
X-KVLHLEGEVNKIALLSTNKAVVSLSNGVSVLTS-Z;
X-LEGEVNKIALLSTNKAVVSLSNGVSVLTSKVLD-Z;
X-GEVNKIALLSTNKAVVSLSNGVSVLTSKVLDLK-Z;
X-EVNKIALLSTNKAVVSLSNGVSVLTSKVLDLKN-Z;
X-VNKIALLSTNKAVVSLSNGVSVLTSKVLDLKNY-Z:
X-NKIALLSTNKAVVSLSNGVSVLTSKVLDLKNYI-Z;
X-KIALLSTNKAVVSLSNGVSVLTSKLDLKCNYID-Z; or
X-IALLSTNKAVVSLSNGVSVLTSKVLDLKNYIDK-Z,
(SEQ ID NOS:210–237, respectively);
in which:
amino acid residues are presented by the single-letter code;
X comprises the amino group of said peptide, an acetyl group, a 9-fluorenylmethoxy carbonyl group, a hydrophobic group, or a macromolecule carrier group;
Z comprises the carboxyl group of said peptide, an amido group, a hydrophobic group, or a macromolecular carrier group; and wherein fusion of said virus to said cell is inhibited.

3. The method of claim 2, wherein said peptide has the formula:
X-TSVITIELSNIKENKCNGTDAKVKLIKQELDKYKN-Z (SEQ ID NO:210).

4. The method of claim 2, wherein said peptide has the formula:
X-SVITIELSNIKENKCNGTDAKVKLIKQELDKYKNA-Z (SEQ ID NO:211).

5. The method of claim 2, wherein said peptide has the formula:
X-VITIELSNIKENKCNGTDAKVKLIKQELDKYKNAV-Z (SEQ ID NO:212).

6. The method of claim 2, wherein said peptide has the formula:
X-VAVSKVLHLEGEVNKIALLSTNKAVVSLSNGVS-Z (SEQ ID NO:213).

7. The method of claim 2, wherein said peptide has the formula:
X-AVSKVLHLEGEVNKIALLSTNKAVVSLSNGVSV-Z (SEQ ID NO:214).

8. The method of claim 2, wherein said peptide has the formula:
X-VSKVLHLEGEVNKIALLSTNKAVVSLSNGVSVL-Z (SEQ ID NO:215).

9. The method of claim 2, wherein said peptide has the formula:
X-SKVLHLEGEVNKIALLSTNKAVVSLSNGVSVLT-Z (SEQ ID NO:216).

10. The method of claim 2, wherein said peptide has the formula:
X-KVLHLEGEVNKIALLSTNKAVVSLSNGVSVLTS-Z (SEQ ID NO:217).

11. The method of claim 2, wherein said peptide has the formula:
X-LEGEVNKIALLSTNKAVVSLSNGVSVLTSKVLD-Z (SEQ ID NO:218).

12. The method of claim 2, wherein said peptide has the formula:
X-GEVNKIALLSTNKAVVSLSNGVSVLTSKVLDLK-Z (SEQ ID NO:219).

13. The method of claim 2, wherein said peptide has the formula:
X-EVNKIALLSTNKAVVSLSNGVSVLTSKVLDLKN-Z (SEQ ID NO:220).

14. The method of claim 2, wherein said peptide has the formula:
X-VNKIALLSTNKAVVSLSNGVSVLTSKVLDLKNY-Z (SEQ ID NO:221).

15. The method of claim 2, wherein said peptide has the formula:
X-NKIALLSTNKAVVSLSNGVSVLTSKVLDLKNYI-Z (SEQ ID NO:222).

16. The method of claim 2, wherein said peptide has the formula:
X-KIALLSTNKAVVSLSNGVSVLTSKVLDLKNYID-Z (SEQ ID NO:223).

17. The method of claim 2, wherein said peptide has the formula:
X-IALLSTNKAVVSLSNGVSVLTSKVLDLKNYIDK-Z (SEQ ID NO:224).

18. The method of claim 2, wherein said peptide has the formula:
X-ALLSTNKAVVSLSNGVSVLTSKVLDLKNYIDKQ-Z (SEQ ID NO:225).

19. The method of claim 2, wherein said peptide has the formula:
X-VAVSKVLHLEGEVNKIALLSTNKAVVSLSNGVS-Z (SEQ ID NO:226).

20. The method of claim 2, wherein said peptide has the formula:
X-AVSKVLHLEGEVNKIALLSTNKAVVSLSNGVSV-Z (SEQ ID NO:227).

21. The method of claim 2, wherein said peptide has the formula:

X-VSKVLHLEGEVNKIALLSTNKAVVSLSNGVSVL-Z (SEQ ID NO:228).

22. The method of claim 2, wherein said peptide has the formula:
X-SKVLHLEGEVNKIALLSTNKAVVSLSNGVSVLT-Z (SEQ ID NO:229).

23. The method of claim 2, wherein said peptide has the formula:
X-KVLHLEGEVNKIALLSTNKAVVSLSNGVSVLTS-Z (SEQ ID NO:230).

24. The method of claim 2, wherein said peptide has the formula:
X-LEGEVNKIALLSTNKAVVSLSNGVSVLTSKVLD-Z (SEQ ID NO:231).

25. The method of claim 2, wherein said peptide has the formula:
X-GEVNKIALLSTNKAVVSLSNGVSVLTSKVLDLK-Z (SEQ ID NO:232).

26. The method of claim 2, wherein said peptide has the formula:
X-EVNKIALLSTNKAVVSLSNGVSVLTSKVLDLKN-Z (SEQ ID NO:233).

27. The method of claim 2, wherein said peptide has the formula:
X-VNKIALLSTNKAVVSLSNGVSVLTSKVLDLKNY-Z (SEQ ID NO:234).

28. The method of claim 2, wherein said peptide has the formula:
X-NKIALLSTNKAVVSLSNGVSVLTSKVLDLKNYI-Z (SEQ ID NO:235).

29. The method of claim 2, wherein said peptide has the formula:
X-KIALLSTNKAVVSLSNGVSVLTSKVLDLKNYID-Z (SEQ ID NO:236).

30. The method of claim 2, wherein said peptide has the formula:
X-IALLSTNKAVVSLSNGVSVLTSKVLDLKNYIDK-Z (SEQ ID NO:237).

31. The method of claim 1, wherein said peptide is 28 amino acid residues in length and is identified by the ALLMOTI5 motif.

32. The method of claim 1, wherein said peptide is 35 amino acid residues in length and is identified by the ALLMOTI5 motif.

33. The method of claim 1, wherein said peptide is 28 amino acid residues in length and is identified by the 107×178×4 motif.

34. The method of claim 1, wherein said peptide is 35 amino acid residues in length and is identified by the 107×178×4 motif.

35. The method of claim 1, wherein said peptide is identified by a PLZIP motif.

36. The method of claim 2 wherein X is a macromolecular carrier group.

37. The method of claim 36 wherein the macromolecular carrier group X is a peptide group.

38. The method of claim 37 wherein said peptide group is 2 to 50 respiratory syncytial virus protein amino acid residues amino to said isolated peptide.

39. The method of claim 2 wherein Z is a macromolecular carrier group.

40. The method of claim 39 wherein the macromolecular carrier group Z is a peptide group.

41. The method of claim 40 wherein said peptide group is about 2 to about 50 respiratory syncytial virus protein amino acid residues carboxy to said isolated peptide.

42. The method of claim 41 wherein X is a macromolecular carrier group, said macromolecular carrier group X being a peptide group of 2 to 50 respiratory syncytial virus protein amino acid residues amino to said isolated peptide.

43. A method for inhibiting transmission of a respiratory syncytial virus to a cell, said method comprising contacting the cell with an effective concentration of an isolated peptide for an effective period of time;
wherein said peptide consists of an amino acid sequence of a respiratory syncytial virus protein;
wherein said peptide is identified by one or more of an ALLMOTI5, 107×178×4 and PLZIP sequence search motifs; and
wherein fusion of the virus to the cell in inhibited.

44. A method for inhibiting transmission of a respiratory syncytial virus to a cell, said method comprising contacting the cell with an effective concentration of an isolated peptide for an effective period of time;
wherein said peptide consists of an amino acid sequence of a respiratory syncytial virus protein;
wherein said peptide is identified by one or more of an ALLMOTI5, 107×178×4 and PLZIP sequence search motifs;
wherein said peptide further comprises an amino terminal X, and a carboxy terminal Z in which X comprises the amino group of said peptide, an acetyl group, a 9-fluorenylmethoxy- carbonyl group, a hydrophobic group or a macromolecular carrier group, and Z comprises the carboxyl group of said peptide, an amido group, a hydrophobic group or a macromolecular carrier group; and
wherein fusion of the virus to the cell in inhibited.

* * * * *

UNITED STATES PATENT AND TRADEMARK OFFICE
CERTIFICATE OF CORRECTION

PATENT NO.     : 6,479,055 B1
DATED          : November 12, 2002
INVENTOR(S)    : Barney et al.

It is certified that error appears in the above-identified patent and that said Letters Patent is hereby corrected as shown below:

<u>Title page,</u>
Item [75], Inventor, remove the following information, "Dani Paul Bolognesi; Thomas James Matthews; Carl T. Wild, all of Durham;" and also remove "Alphonse J. Langlois, Durham." The Inventor infomation should read
-- Shawn O'Lin Barney, Cary; Dennis Michael Lambert, Cary; Stephen Robert Petteway, Cary, all of NC (US) --.
Item [74], *Attorney, Agent of Firm*, "Pennie & Edmonds LLP" should read
-- Pennie & Edmonds LLP; M. Bud Nelson --.

<u>Column 1317,</u>
Line 63, "107x178'4" should read -- 107x178x4 --;
Line 65, "the virus" should read -- said virus --;
Line 65, "the cell" should read -- said cell --.

<u>Column 1322,</u>
Lines 22 and 29, "the cell" should read -- said cell -- in each of the two occurences;
Line 29, "the virus" should read -- said virus --;
Lines 32 and 48, should read -- said cell -- in each of the two occurrences;
Line 48, "the virus" should read -- said virus --.

Signed and Sealed this

Eighth Day of July, 2003

JAMES E. ROGAN
*Director of the United States Patent and Trademark Office*